US011857519B2

(12) United States Patent
Crew et al.

(10) Patent No.: US 11,857,519 B2
(45) Date of Patent: Jan. 2, 2024

(54) COMPOUNDS AND METHODS FOR THE TARGETED DEGRADATION OF ENHANCER OF ZESTE HOMOLOG 2 POLYPEPTIDE

(71) Applicant: Arvinas Operations, Inc., New Haven, CT (US)

(72) Inventors: Andrew P. Crew, Chester, CT (US); Lawrence B. Snyder, Killingworth, CT (US); Jing Wang, Milford, CT (US); Hanqing Dong, Madison, CT (US); Yimin Qian, Plainsboro, NJ (US); Michael Berlin, Flemington, NJ (US)

(73) Assignee: Arvinas Operations, Inc., New Haven, CT (US)

( * ) Notice: Subject to any disclaimer, the term of this patent is extended or adjusted under 35 U.S.C. 154(b) by 137 days.

(21) Appl. No.: 17/354,941

(22) Filed: Jun. 22, 2021

(65) Prior Publication Data
US 2022/0378726 A1   Dec. 1, 2022

Related U.S. Application Data

(63) Continuation of application No. 15/851,053, filed on Dec. 21, 2017, now Pat. No. 11,191,741.
(60) Provisional application No. 62/438,998, filed on Dec. 24, 2016.

(51) Int. Cl.
| A61K 31/166 | (2006.01) |
| A61K 31/405 | (2006.01) |
| A61K 47/54 | (2017.01) |
| A61P 35/00 | (2006.01) |
| A61K 38/45 | (2006.01) |
| C12N 9/10 | (2006.01) |
| A61K 31/351 | (2006.01) |
| C07D 471/04 | (2006.01) |
| C07D 401/14 | (2006.01) |
| C07D 405/14 | (2006.01) |
| C07D 405/12 | (2006.01) |
| C07D 417/14 | (2006.01) |
| C07D 409/14 | (2006.01) |
| A61K 47/55 | (2017.01) |

(52) U.S. Cl.
CPC .......... *A61K 31/166* (2013.01); *A61K 31/351* (2013.01); *A61K 31/405* (2013.01); *A61K 38/45* (2013.01); *A61K 47/545* (2017.08); *A61K 47/55* (2017.08); *A61K 47/555* (2017.08); *A61P 35/00* (2018.01); *C07D 401/14* (2013.01); *C07D 405/12* (2013.01); *C07D 405/14* (2013.01); *C07D 409/14* (2013.01); *C07D 417/14* (2013.01); *C07D 471/04* (2013.01); *C12N 9/1007* (2013.01); *C12Y 201/01043* (2013.01)

(58) Field of Classification Search
CPC .................................................. A61K 31/166
See application file for complete search history.

(56) References Cited

U.S. PATENT DOCUMENTS

| 6,306,663 | B1 | 10/2001 | Kenten et al. |
| 6,670,348 | B1 | 12/2003 | Rosen et al. |
| 7,030,141 | B2 | 4/2006 | Bigge et al. |
| 7,041,298 | B2 | 5/2006 | Deshaies et al. |
| 7,208,157 | B2 | 4/2007 | Sakamoto et al. |
| 7,244,851 | B2 | 7/2007 | Cohen et al. |
| 7,345,081 | B2 | 3/2008 | Cohen et al. |
| 7,419,975 | B2 | 9/2008 | Palermo et al. |
| 7,517,906 | B2 | 4/2009 | Condon et al. |
| 7,915,293 | B2 | 3/2011 | Ramesh |
| 9,500,653 | B2 | 11/2016 | Crews et al. |
| 9,632,089 | B2 | 4/2017 | Crews et al. |
| 11,191,741 | B2 * | 12/2021 | Crew ................... A61K 31/351 |
| 2006/0128632 | A1 | 6/2006 | Sharma et al. |
| 2008/0051432 | A1 | 2/2008 | Zhang |
| 2008/0214501 | A1 | 9/2008 | Zhengying et al. |
| 2008/0269140 | A1 | 10/2008 | Wang et al. |
| 2010/0203012 | A1 | 8/2010 | Laurent et al. |
| 2011/0195043 | A1 | 8/2011 | Sun et al. |

(Continued)

FOREIGN PATENT DOCUMENTS

| CN | 1844118 A | 10/2006 |
| CN | 103688176 A | 3/2014 |

(Continued)

OTHER PUBLICATIONS

Venkatesh, J.Pharm. Sci.89, 145-54, 2000.*
West, Solid State Chemistry and Its Applications, john Wiley & Sons, 1984.*

(Continued)

*Primary Examiner* — Nizal S Chandrakumar
(74) *Attorney, Agent, or Firm* — McCarter & English, LLP; Michael J. DeGrazia; James M. Alburger

(57) ABSTRACT

The present disclosure relates to bifunctional compounds, which find utility as modulators of enhancer of zeste homolog 2 (target protein). In particular, the present disclosure is directed to bifunctional compounds, which contain on one end a Von Hippel-Lindau, cereblon, Inhibitors of Apoptosis Proteins or mouse double-minute homolog 2 ligand which binds to the respective E3 ubiquitin ligase and on the other end a moiety which binds the target protein, such that the target protein is placed in proximity to the ubiquitin ligase to effect degradation (and inhibition) of target protein. The present disclosure exhibits a broad range of pharmacological activities associated with degradation/inhibition of target protein. Diseases or disorders that result from aggregation or accumulation of the target protein are treated or prevented with compounds and compositions of the present disclosure.

16 Claims, 1 Drawing Sheet

(56) References Cited

U.S. PATENT DOCUMENTS

| | | |
|---|---|---|
| 2012/0270800 A1 | 10/2012 | Verdine et al. |
| 2014/0235629 A1 | 8/2014 | Bartberger et al. |
| 2014/0243372 A1 | 8/2014 | Rew |
| 2014/0302523 A1 | 10/2014 | Crews et al. |
| 2014/0356322 A1 | 12/2014 | Crews et al. |
| 2015/0119435 A1 | 4/2015 | Crews et al. |
| 2015/0291562 A1 | 10/2015 | Crew et al. |
| 2015/0344473 A1 | 10/2015 | Du et al. |
| 2016/0022642 A1 | 1/2016 | Crews et al. |
| 2016/0045607 A1 | 2/2016 | Crew et al. |
| 2016/0058872 A1 | 3/2016 | Crew et al. |
| 2016/0136230 A1 | 5/2016 | Campos et al. |
| 2016/0214972 A1 | 7/2016 | Jin et al. |
| 2016/0243247 A1 | 8/2016 | Bradner et al. |
| 2016/0272639 A1 | 9/2016 | Crew et al. |
| 2016/0368911 A1 | 12/2016 | Campos et al. |
| 2017/0008904 A1 | 1/2017 | Crew et al. |
| 2017/0037004 A1 | 2/2017 | Crew et al. |
| 2017/0065719 A1 | 3/2017 | Qian et al. |
| 2017/0121321 A1 | 5/2017 | Crews et al. |
| 2017/0281784 A1 | 10/2017 | Wang et al. |
| 2017/0307614 A1 | 10/2017 | Crews et al. |
| 2017/0327469 A1 | 11/2017 | Crew et al. |
| 2018/0015087 A1 | 1/2018 | Liu et al. |
| 2018/0072711 A1 | 3/2018 | Crew et al. |
| 2018/0099940 A1 | 4/2018 | Crew et al. |
| 2018/0125821 A1 | 5/2018 | Crew et al. |
| 2018/0147202 A1 | 5/2018 | Crew et al. |
| 2018/0155322 A1 | 6/2018 | Crew et al. |
| 2018/0177750 A1 | 6/2018 | Crew et al. |
| 2018/0179183 A1 | 6/2018 | Crew et al. |
| 2018/0193470 A1 | 7/2018 | Crew et al. |
| 2018/0215731 A1 | 8/2018 | Crew et al. |
| 2018/0228907 A1 | 8/2018 | Crew et al. |
| 2018/0237418 A1 | 8/2018 | Crew et al. |
| 2018/0256586 A1 | 9/2018 | Crew et al. |
| 2019/0135796 A1 | 5/2019 | Bradner et al. |

FOREIGN PATENT DOCUMENTS

| | | |
|---|---|---|
| EP | 2985285 | 2/2016 |
| JP | A 2004-525889 | 8/2004 |
| JP | A 2010-502627 | 1/2010 |
| RU | 2008112221 A | 10/2009 |
| RU | 2448101 C2 | 4/2012 |
| RU | 2011121567 A | 10/2012 |
| RU | 2012138709 A | 3/2014 |
| WO | WO 1998/003502 | 1/1998 |
| WO | WO 2000/066119 | 11/2000 |
| WO | WO 2002/066512 | 8/2002 |
| WO | WO 2002/100845 | 12/2002 |
| WO | WO 2005/097791 | 10/2005 |
| WO | WO 2006/069063 | 6/2006 |
| WO | WO 2006/113942 | 10/2006 |
| WO | WO 2007/101347 | 9/2007 |
| WO | WO 2007/106670 | 9/2007 |
| WO | WO 2007/130626 | 11/2007 |
| WO | WO 2008/011392 | 1/2008 |
| WO | WO 2008/014236 | 1/2008 |
| WO | WO 2008/109057 | 9/2008 |
| WO | WO 2008/128121 | 10/2008 |
| WO | WO 2008/128171 | 10/2008 |
| WO | WO 2008/134679 | 11/2008 |
| WO | WO 2009/015254 | 1/2009 |
| WO | WO 2009/060292 | 5/2009 |
| WO | WO 2010/107485 | 9/2010 |
| WO | WO 2010/141805 | 12/2010 |
| WO | WO 2011/008260 | 1/2011 |
| WO | WO 2012/003281 | 1/2012 |
| WO | WO 2012/040389 | 3/2012 |
| WO | WO 2012/040527 | 3/2012 |
| WO | WO 2012/068589 | 5/2012 |
| WO | WO 2012/078559 | 6/2012 |
| WO | WO 2012/090104 | 7/2012 |
| WO | WO 2012/142504 | 10/2012 |
| WO | WO 2013/071035 | 5/2013 |
| WO | WO 2013/071039 | 5/2013 |
| WO | WO 2013/106643 | 7/2013 |
| WO | WO 2013/106646 | 7/2013 |
| WO | WO 2013106643 | * 7/2013 | ........... C07D 413/12 |
| WO | WO 2013/155464 | 10/2013 |
| WO | WO 2013/170147 | 11/2013 |
| WO | WO 2013/173441 | 11/2013 |
| WO | WO 2013/175417 | 11/2013 |
| WO | WO 2013173441 | * 11/2013 | ......... A61K 31/4439 |
| WO | WO 2013/178570 | 12/2013 |
| WO | WO 2014/011712 | 1/2014 |
| WO | WO 2014/020502 | 2/2014 |
| WO | WO 2014/025759 | 2/2014 |
| WO | WO 2014/038606 | 3/2014 |
| WO | WO 2014/047024 | 3/2014 |
| WO | WO 2014/055461 | 4/2014 |
| WO | WO 2014/074658 | 5/2014 |
| WO | WO 2014/100065 | 6/2014 |
| WO | WO 2014/100071 | 6/2014 |
| WO | WO 2014/107713 | 7/2014 |
| WO | WO 2014/108452 | 7/2014 |
| WO | WO 2014/123418 | 8/2014 |
| WO | WO 2014/134201 | 9/2014 |
| WO | WO 2014/151863 | 9/2014 |
| WO | WO 2015/000868 | 1/2015 |
| WO | WO 2015/006524 | 1/2015 |
| WO | WO 2015/077193 | 5/2015 |
| WO | WO 2015/160845 | 10/2015 |
| WO | WO 2016/118666 | 7/2016 |
| WO | WO 2016/146985 | 9/2016 |
| WO | WO 2016/169989 | 10/2016 |
| WO | WO 2016/172134 | 10/2016 |
| WO | WO 2016/197114 | 12/2016 |
| WO | WO 2017/011590 | 1/2017 |
| WO | WO 2017/030814 | 2/2017 |
| WO | WO 2017/079267 | 5/2017 |
| WO | WO 2017/161119 | 9/2017 |
| WO | WO 2017/185036 | 10/2017 |
| WO | WO 2017/197051 | 11/2017 |
| WO | WO 2018/081530 | 5/2018 |

OTHER PUBLICATIONS

Wolff, Burger's medicinal Chemistry and Drug Discovery, vol. 1, Principles and Practice, John Wiley & sons, New York, 1997.*

Tinworth, Med. Chem. Commun., 2016, 7, 2206-2216.*

Abraham, R.T., "Phosphatidylinositol 3-kinase related kinases", (1996), Current Opinion in Immunology. 8 (3) 412-418.

Ahn, et al., "HIF-1alpha peptide derivatives with modifications at the hydroxyproline residue as activators of HIF-1alpha", Bioorg Med Chem Lett. 19(15), 2009, 4403-4405.

Ardecky, RJ, et al., "Design, synthesis and evaluation of inhibitor of apoptosis protein (IAP) antagonists that are highly selective for the BIR2 domain of XIAP", Bioorg. Med. Chem., 23(14): 4253-4257 (2013).

Asano M, et al., "Design, sterioselective synthesis, and biological evaluation of novel tri-cyclic compounds as inhibitor of apoptosis proteins (IAP) antagonists", Bioorg. Med. Chem., 21(18): 5725-5737 (2013).

Bargagna-Mohan, et al., "Use of PROTACS as molecular probes of angiogenesis", Bioorg Med Chem Left. 15(11) 2005, 2724-2727.

Bondeson, et al., (2017) "Targeted Protein Degradation by Small Molecules." *Annu Rev Pharmacol Toxicol* 57:107-123.

Bondeson, et al., "Catalytic in vivo protein knockdown by small-molecule PROTACS", National Chem Biol. 11(8) Aug. 2015, 611-617.

Buckley, et al., "HaloPROTACS: use of small molecule PROTACS to induce degradation of HaloTag fusion proteins", ACS Chem Biol. 10(8), 2015, 1831-1837.

Buckley, et al., "Small-molecule inhibitors of the interaction between the E3 ligase VHL and HIF1a", Angew Chem Int Ed Engl.51(46), Oct. 12, 2012, 11463-11467.

Buckley, et al., "Targeting the von Hippel-Lindau E3 ubiquitin ligase using small molecules to disrupt the VHL/HIF-1α interaction", Journal of the American Chemical Society, Feb. 27, 2012, 134(10): 4465-4468.

(56) References Cited

OTHER PUBLICATIONS

Burslem, et al., (2017) "Small-Molecule Modulation of Protein Homeostasis." *Chem Rev* 117(17):11269-11301.
Cannon, J.G., Chapter Nineteen in Burger's Medicinal Chemistry and Drug Discovery, Fifth Editions, vol. 1: Principles and Practice, Wiley-Interscience 1995, pp. 783-802, 784.
Capitosti, S., et al., "Thalidomide analogues demonstrate dual inhibition of both angiogenesis and prostate cancer", Bioorganic & Medicinal Chemistry 12, (2004) 327-336.
Carmony, KC, et al., "PROTAC-Induced Proteolytic Targeting", Methods Mol. Biol., 2012, vol. 832, pp. 627-638.
CAS Registry No. 1004933-70-3, which entered STN on Feb. 21, 2008.
CAS Registry No. 871986-52-6 entered STN Jan. 16, 2006.
Chene, P., et al., "Inhibiting the p53-MDM2 interaction: an important target for cancer therapy" Nat. Rev. Cancer (2003), 3, 102-109.
Cohen, F, et al., "Orally bioavailable antagonists of inhibitor of apoptosis proteins based on an azabicyclooctane scaffold", J. Med. Chem., 52(6), 1723-1730 (2009).
Cohen, F. et al., "Antagonists of inhibitors of apoptosis proteins based on thiazole amide isosteres", Bioorg. Med. Chem. Lett., 20(7), 2229-2233 (2010).
Contino-Pepin, Christiane, et al., "Preliminary biological evaluations of new thalidomide analogues for multiple sclerosis application", Bioorganic & Medicinal Chemistry Letter 19 (2009), 878-881.
Corson, et al., "Design and applications of bifunctional small molecules: why two heads are better than one", ACS Chemical Biology vol. 3 No. 11, pp. 677-692; Nov. 21, 2008.
Crews, C. M., "Targeting the undruggable proteome: the small molecules of my dreams", *Chem Biol* 17, 551-555, doi:S1074-5521(10)00196-1 [pii] 10.1016/j.chembiol.2010.05.011 (2010).
Cromm, et al., (2017) "Targeted Protein Degradation: from Chemical Biology to Drug Discovery." *Cell Chem Biol* 24(9):1181-1190.
Cyrus, et al., "Jostling for position: optimizing linker location in the design of estrogen receptor-targeting PROTACs", Chem Med Chem. 5(7), Jul. 5, 2010, 979-985.
Cyrus, K. et al., "Impact of Linker Length on the Activity of PROTACs," Mol. Biosyst., 2011, vol. 7, No. 2, pp. 359-364.
Cyrus, K. et al., "Two-Headed PROTAC: An Effective New Tool for Targeted Protein Degradation," Chembiochem., 2010, vol. 11, pp. 1531-1534.
Di, J et al. "Reactivation of p53 by inhibiting Mdm2 E3 Ligase: a novel antitumor approach", Current Cancer Drug Targets (2011), 11(8), 987-994.
Ding, Q, et al., "Discovery of RG7388, a potent and selective p53-MDM2 inhibitor in clinical development", J Med Chem. Jul. 25 2013; 56(14):5979-83. doi: 10.1021/jm400487c. Epub Jul. 16, 2013. PubMed PMID: 23808545 (J. Med. Chem. (2013) 56, 5979-5983 Ding, et al).
Dixon, S. J. et al., "Identifying druggable disease-modifying gene products",. *Curr Opin Chem Biol* 13, 549-555, doi:S1367-5931(09)00107-0 [pii] 10.1016/j.cbpa.2009.08.003 (2009).
Fischer, et al., "Structure of the DDB1-DRBN E3 Ubiquitin ligase in complex with thalidomide", Nature, vol. 000, pp. 1-5 (2014).
Flygare, J.A., et al. "Small-molecule pan-IAP antagonists: a patent review", Expert Opin. Ther. Pat., 20 (2), 251-267 ( 2010).
Gadd, M.S., et al., "Structural basis of PROTAC cooperative recognition for selective protein degradation", Nat Chem Biol 13, 514-521 (2017).
Galdeano, et al., "Structure-guided design and optimization of small molecules targeting the protein-protein interaction between the von hippel-lindau (VHL) E3 ubiquitin ligase and the Hypoxia inducible factor (HIF) alpha subunit with in vitro nanomolar affinities", Journal Med Chem, Aug. 2014, vol. 57, pp. 8657-8663.
Golub, et al., "Molecular classification of cancer: class discovery and class prediction by gene expression monitoring", Science 286, 531-537 (1991).
Gosink, M et al., "Redirecting the specificity of ubiquitination by modifying ubiquitin-conjugating enzymes", Pro. Natl. Acad Sci, vol. 92, pp. 9117-9121, 1995.
Haupt, Y. et al., "Mdm2 promotes the rapid degradation of p53", Nature 387, 296-299 (1997).
Hennessy, EJ, et al., "Discovery of aminopiperidine-based Smac mimetics as IAP antagonists", Bioorg. Med. Chem. Lett., 22(4), 1690-1694 (2012).
Hines, J., et al., "Posttranslational protein knockdown coupled to receptor tyrosine kinase activation with phosphoPROTACs", Proc Natl Acad Sci USA 110, 8942-8947 (2013).
Hird, AW, et al., "Structure-based design and synthesis of tricyclic IAP (Inhibitors of Apoptosis Proteins) inhibitors", Bioorg. Med. Chem. Lett., 24(7): 1820-1824 (2014).
Hon, et al., "Structural basis for the recognition of hydroxyproline in HIf-1 alpha by pVHL", Nature 417, Jun. 27, 2002, 975-978.
Huang, et al., (2016) "Drugging the undruggables: exploring the ubiquitin system for drug development." *Cell Res* 26(4):484-498.
Hughes, et al., (2017) "Molecular recognition of ternary complexes: a new dimension in the structure-guided design of chemical degraders." *Essays Biochem* 61(5):505-516.
Ivan, M., et al., "HIFa Targeted for VHL-Mediated Destruction by Proline Hydroxylation: Implications for O2 Sensing", Science, vol. 292, No. 5516, pp. 464-468, 2001.
Jang, E.R. et al., "Targeted Degradation of Proteins by PROTACs," Curr. Protoc. Chem. Biol., 2010, vol. 2, No. 2, pp. 71-87.
Kim, K.S., "Discovery of tetrahydroisoquinoline-based bivalent heterodimeric IAP antagonists", Bioorg. Med. Chem. Lett. 24(21), 5022-5029 (2014).
Knott, Edward (1955). "Compounds containing sulphur chromophores. Part I. The action of bases on heterocyclic sulphide quarternary salts", Journal of The Chemical Society (resumed). 10.1039/jr9550000916. 949-954) (USPTO summary attached).
Kronke, et al, "Lenalidomide Causes Selective Degradation of IKZF1 and IKZF3 in Multiple Myeloma Cells", Science 343, 301-305 (2014).
Kuntz, K.W. et al., "The importance of being me: magic methyls, methyltransferase inhibitors, and the discovery of tazemetostat", in the Journal of Medicinal Chemistry 2016, 59, 1556-1564.
Lai, A.C., et al., "Modular PROTAC Design for the Degradation of Oncogenic BCR-ABL", Angew Chem Int Ed Engl 55, 807-810 (2016).
Lai, et al., (2017) "Induced protein degradation: an emerging drug discovery paradigm." *Nat Rev Drug Discov* 16(2):101-114.
Lala, et al., "Role of nitric oxide in tumor progression: Lessons from experimental tumors", Cancer and Metastasis Reviews 17:91-106 (1998).
Lebraud, H., et al., "Protein Degradation by In-Cell Self-Assembly of Proteolysis Targeting Chimeras", ACS Central Science, 2, 927-934 (2016).
Lee, et al., "Targeted Degradation of the Aryl Hydrocarbon Receptor by the PROTAC Approach: A Useful Chemical Genetic Tool", ChemBioChem vol. 8, Issue 17, pp. 2058-2062, Nov. 23, 2007.
Levine, et al., Targeting the androgen receptor with steroid conjugates, J. Med. Chem., vol. 57., No. 20. pp. 8224-8237, (2014).
Li, Yan, et al., "Single polymer-drug conjugate carrying two drugs for fixed-dose co-delivery", Medicinal Chemistry, 2014, vol. 4(10): 676-683.
Liu, K., et al., "Design and biological characterization of hybrid compounds of curcumin and thalidomide for multiple myeloma", Org. Biomol. Chem. 2013, 11, 4757-4763.
Lopez-Girona, A. et al., Cereblon is a direct protein target for immunomodulatory and antiproliferative activities of lenalidomide and pomalidomide, Leukemia 26: 2326-2335, 2012).
Lu, et al., "Hijacking the E3 ubiquitin ligase cereblon to efficiently target BRD4", Chem Biol 22(6), 2015, 755-763.
Lu, et al., "The myeloma drug lenalidomide promotes the cereblon-dependent destruction of ikaros proteins", Science 343, 305-309 (2014).
Maniaci C, et al. (2017) "Homo-PROTACs: bivalent small-molecule dimerizers of the VHL E3 ubiquitin ligase to induce self-degradation." *Nat Commun* 8(1):830 1-13.

(56) References Cited

OTHER PUBLICATIONS

Mannhold, R., et al., "IAP antagonists: promising candidates for cancer therapy", Drug Discov. Today, 15 (5-6), 210-219 (2010).
MEDLINE Plus Trusted Health Information for You, www.nlm.nih.gov/medlineplus/cancer.html_pp. 1-10, (2007).
Min, Jung-hyun, et al., "Structure of an HIV-1-alpha-pVHL complex: hydroxyproline recognition in signaling", Jun. 7, 2002, 296: 1886-1889.
Miyazaki, M., et al., "Discovery of DS-5272 as a promising candidate: a potent and orally active p53-MDM2 interaction inhibitor", Bioorg. Med. Chem. Lett. (2015) 23, 2360-2367.
Muller, G., et al., "Amino- Substituted Thalodomide Analogs: Potent Inhibitors of TNF-α_0 Production", Bioorganic & Medicinal Chemistry Letters 9 (1999) 1625-1630.
Nasveschuk, C. G., et al., Discovery and Optimization of Tetramethylpiperidinyl Benzamides as Inhibitors of EZH2, ACS Med. Chem. Lett. 2014, 5, 378-383 (Jan. 14, 2014.
Ndubaku, C, et al., "Antagonism of c-IAP and XIAP proteins is required for efficient induction of cell death by small-molecule IAP antagonists", ACS Chem Biol. Jul. 17, 2009;4(7):557-566.
Neklesa, T.K., et al., "Chemical biology: Greasy tags for protein removal", Nature 487, 308-309 (2012).
Neklesa, Targeted protein degradation by PROTACs. Pharmacology & Therapeutics 174, 138-144 (2017).
Nikolovska-Coleska, et al., "Interaction of a cyclic, Bivalent Smac Mimetic with the X-linked inhibitor of apoptosis protein", Biochemistry, 2008, 47(37), pp. 9811-9824.
Ohoka, N. et al. SNIPER(TACC3) induces cytoplasmic vacuolization and sensitizes cancer cells to Bortezomib. Cancer Sci. 108, 1032-1041 (2017).
Oost, T.K. et al., "Discovery of potent antagonists of the antiapoptotic protein XIAP for the treatment of cancer", Journal of Medicinal Chemistry 2004, 47, 4417-4426.
Ottis P, et al. (2017) "Assessing Different E3 Ligases for Small Molecule Induced Protein Ubiquitination and Degradation." *ACS Chem Biol* 12(10):2570-2578.
Ottis, et al., (2017) "Proteolysis-Targeting Chimeras: Induced Protein Degradation as a Therapeutic Strategy." *ACS Chem Biol* 12(4):892-898.
Perez, HL,"Discovery of potent heterodimeric antagonists of inhibitor of apoptosis proteins (IAPs) with sustained antitumor activity", J. Med. Chem. 58(3), 1556-1562 (2015).
Puppala, D. et al., "Development of an Aryl Hydrocarbon Receptor Antagonist Using the Proteolysis-Targeting chimeric Molecules Approach: A Potential Tool for Chemoprevention," Mol. Pharmacol., 2008, vol. 73, No. 4, pp. 1064-1071.
Raina, et al., (2017) "Targeted protein knockdown using small molecule degraders." *Curr Opin Chem Biol* 39:46-53.
Raina, K., et al., "PROTAC-induced BET protein degradation as a therapy for castration-resistant prostate cancer", Proc Natl Acad Sci USA 113, 7124-7129 (2016).
Remillard D, et al. (2017) "Degradation of the BAF Complex Factor BRD9 by Heterobifunctional Ligands." *Angew Chem Int Ed Engl* 56(21):5738-5743.
Rew, Y, et al., "Discovery of AM-7209, a potent and selective 4-amidobenzoic acid inhibitor of the MDM2-p53 interaction", J Med Chem. Dec. 26, 2014;57(24):10499-10511. doi: 10.1021/jm501550p. Epub Dec. 4, 2014. PubMed PMID: 25384157. (J. Med. Chem. (2014) 57, 10499-10511 Rew, et al.).
Rodriguez-Gonzalez, et al., "Targeting steroid hormone receptors for ubiquitination and degradation in breast and prostate cancer", Oncogene. 27(57), Dec. 4, 2008, 7201-7211.
Rotili, D., et al., "Photoactivable peptides for identifying enzyme-substrate and protein-protein interactions", Chem Commun (Carob) 47(5), Feb. 2011, 1488-1490.
Ruchelman, A., et al., "Isosteric analogs of lenalidominde and pomalidomide: Synthesis and biological activity", Bioorganic & Medicinal Chemistry Letters 23 (2013) 360-365.

Sakamoto, et al., "Development of Protacs to target cancer-promoting proteins for ubiquitination and degradation", Mol Cell Proteomics. 2(12), Dec. 2003, 1350-1358.
Sakamoto, et al., "Protacs: chimeric molecules that target proteins to the Skp 1—Cullin-F box complex for ubiquitination and degradation", Proc Natl Acad Sci U S A.98(15), Jul. 17, 2001, 8554-8559.
Salami, J. & Crews, C. M. Waste disposal-An attractive strategy for cancer therapy. Science 355, 1163-1167 (2017).
Schiedel, M., et al., "Chemically Induced Degradation of Sirtuin 2 (Sirt2) by a Proteolysis Targeting Chimera (PROTAC) Based on Sirtuin Rearranging Ligands (SirReals)", J Med Chem. (2017), 61:482-491.
Schneekloth, et al., "Chemical Genetic Control of Protein Levels: Selective in Vivo Targeted Degradation", J Am Chem Soc. 126(12), Mar. 31, 2004, 3748-3754.
Schneekloth, et al., Targeted intracellular protein degradation induced by a small molecule: En route to chemical proteomics, Bioorg. Med. Chem. Lett. 18 (2008) 5904-5908.
Smith, et al., "Targeted Intracellular Protein Degradation Induced by a Small Molecule: En Route to Ghemical Proteomics", Bioorg Med Chem Lett. 18(22), Nov. 15, 2008, 5904-5908.
Stewart, Scott G., et al., "Efforts toward elucidating Thalidomide's molecular target: An Expedient Synthesis of the first Thalidomide Biotin Analogue" Org. Biomol., Chem., 2010, 8, 4059-4062.
STN transcript excerpt Nov. 24, 2017.
Stoppler, Melissa Conrad., Endometriosis [online], "Endometriosis Definition and Facts" URL http://www.medicinenet.com/endometriosis/article.htm, retrieved on Apr. 5, 2017.
Stoppler, Melissa Conrad., Endometriosis [online], "What about surgery for Endometriosis?" URL http://www.medicinenet.com/endometriosis/article.htm, retrieved on Apr. 5, 2017.
Sun, D, et al., "Discovery of AMG 232, a potent, selective, and orally bioavailable MDM2-p53 inhibitor in clinical development", J Med Chem. Feb. 27, 2014;57(4):1454-72. doi: 10.1021/jm401753e. Epub Feb. 5, 2014. PubMed PMID: 24456472.
Sun, et al., "Potent bivalent Smac mimetics: effect of the linker on binding to inhibitor apoptosis proteins (IAPs) and anticancer activity", J. Med. Chem. 53, 3306-3318 (2011).
Suzuki et al. "Severe impairment of interleukin-1 and toll-like receptor signaling in mice lacking IRAK-4", Nature, 416(6882), 2002, 750-756.
Toure, et al., (2016) "Small-Molecule PROTACS: New Approaches to Protein Degradation." *Angew Chem Int Ed Engl* 55(6):1966-1973.
Turk, B. E., "Binding of thalidomide to alpha 1-acid glycoprotein may be involved in its inhibition of tumor necrosis factor alpha production", Proc. Natl. Acad. Sci. U.S.A. 1996, 93, 7552-7556.
Vamos M., et al., "Expedient synthesis of highly potent antagonists of inhibitor of apoptosis proteins (IAPs) with unique selectivity for ML-IAP", ACS Chem. Biol., 8(4), 725-732 (2013).
Van Molle, et al., "Dissecting fragment-based lead discovery at the von Hippel-Lindau protein:hypoxia inducible factor 1a protein-protein interface", Chem Biol. 19(10), Oct. 26, 2012, 1300-1312.
Vassilev, et al., "In vivo activation of the p53 pathway by small-molecule antagonists of MDM2", Science 303, Feb. 6, 2004, 844-848.
Vazquez, A. et al., "The genetics of the p53 pathway, apoptosis and cancer therapy", Nat. Rev. Drug. Dis., 7, 979-982 (2008).
Venkatesh , S., et al., Role of the Development Scientist in Compound Lead Selection and Optimization, Journal of Pharm Sciences, vol. 89, No. 2, Feb. 2000, 145-154.
Vu, B. et al. "Discovery of RG7112: a small-molecule MDM2 inhibitor in clinical development", ACS Med. Chem. Lett. (2013) 4, 466-469.
Wang J, et al., "Discovery of novel second mitochondrial-derived activator of caspase mimetics as selective inhibitor or apoptosis protein inhibitors", J. Pharmacol. Exp. Ther., 349(2): 319-29 (2014).
Wang, S., et al. "Small-molecule inhibitors of the MDM2-p53 protein-protein interaction (MDM2 inhibitors) in clinical trials for cancer treatment", J. Med. Chem. (2015) 58, 1038-1052.
Wang, S., et al. "Temporal activation of p53 by a specific MDM2 inhibitor is selectively toxic to tumors and leads to complete tumor growth inhabitation", PNAS USA (2008) 105, 3933-3938.

(56) References Cited

OTHER PUBLICATIONS

West, Solid State Chemistry and Its Applications, John Wiley & Sons, 1984, Chapter 10, 358 and 365.
Winter, et al., "Phthalimide Conjugation as a strategy for in vivo target protein degradation", Science, 2015 vol. 348 (6241), pp. 1376-1381 [Pub online: May 21, 2015].
Wolff, Burger's Medicinal Chemistry and Drug Discovery, vol. 1., Principles and Practive, John Wiley & Sons, New York, 1997, 975-977.
Yang, X., et al., Structure-Activity Relationship Studies for Enhancer of Zeste Homologue 2 (EZH2) and Enhancer of Zeste Homologue 1 (EZH1) , J. Med Chem. Aug. 25, 2016, 59(16): 7617-7633.
Zengerle, et al., "Selective Small Molecule Induced Degradation of the BET Bromodomain Protein BRD4" ACS Chemical Biology, Jun. 2, 2015, vol. 10, pp. 1770-1777.
Zhang B.et al., "Small-molecule MDM2-p53 inhibitors: recent advances", Future Med. Chem. (2015) 7, 631-645.
Zhang, D. et al., "Targeted Degradation of Proteins by Small Molecules: A Novel Tool for Functional Proteomics," comb Chem. High Throughput Screen., 2004, vol. 7, No. 7, pp. 689-697.
Zhang, Lidan, et al., Design, Synthesis and biological evaluation of novel 1-methyl-3-oxo-2,3,5,6,7,8-hexahydroisoquinolins as potential EZH2 inhibitors, RSC ADV., Mar. 2015, vol. 5, pp. 25967-25978.
Zhou, B., et al. "Discovery of a Small-Molecule Degrader of Bromodomain and Extra-Terminal (BET) Proteins with Picomolar Cellular Potencies and Capable of Achieving Tumor Regression", J Med Chem. 61(2), 462-481 (2018) (DOI:10.1021/acs.jmedchem. 6b01816) (2017).

\* cited by examiner

COMPOUNDS AND METHODS FOR THE TARGETED DEGRADATION OF ENHANCER OF ZESTE HOMOLOG 2 POLYPEPTIDE

CROSS-REFERENCE TO RELATED APPLICATIONS

The present disclosure is a continuation of U.S. patent application Ser. No. 15/851,053, filed 21 Dec. 2017, Published as U.S. Patent Application Publication No. 2018/0177750 A1, which claims priority to and the benefit of U.S. Provisional Application No. 62/438,998, filed 24 Dec. 2016, titled COMPOUNDS AND METHODS FOR THE TARGETED DEGRADATION OF ENHANCER OF ZESTE HOMOLOG 2 POLYPEPTIDE, each of which are incorporated herein by reference in its entirety for all purposes.

INCORPORATION BY REFERENCE

U.S. patent application Ser. No. 15/230,354, filed on Aug. 5, 2016; and U.S. patent application Ser. No. 15/206,497 filed 11 Jul. 2016; and U.S. patent application Ser. No. 15/209,648 filed 13 Jul. 2016; and U.S. patent application Ser. No. 15/730,728, filed on Oct. 11, 2017; and U.S. patent application Ser. No. 14/686,640, filed on Apr. 14, 2015, published as U.S. Patent Application Publication No. 2015/0291562; and U.S. patent application Ser. No. 14/792,414, filed on Jul. 6, 2015, published as U.S. Patent Application Publication No. 2016/0058872; and U.S. patent application Ser. No. 14/371,956, filed on Jul. 11, 2014, published as U.S. Patent Application Publication No. 2014/0356322; and U.S. patent application Ser. No. 15/074,820, filed on Mar. 18, 2016, published as U.S. Patent Application Publication No. 2016/0272639, are incorporated herein by reference in their entirety. Furthermore, all references cited herein are incorporated by reference herein in their entirety.

FIELD OF THE INVENTION

The description provides bifunctional compounds comprising a target protein binding moiety and a E3 ubiquitin ligase binding moiety, and associated methods of use. The bifunctional compounds are useful as modulators of targeted ubiquitination, especially with respect to enhancer of zeste homolog 2 protein (EZH2), which is degraded and/or otherwise inhibited by bifunctional compounds according to the present disclosure.

BACKGROUND

Most small molecule drugs bind enzymes or receptors in tight and well-defined pockets. On the other hand, protein-protein interactions are notoriously difficult to target using small molecules due to their large contact surfaces and the shallow grooves or flat interfaces involved. E3 ubiquitin ligases (of which hundreds are known in humans) confer substrate specificity for ubiquitination, and therefore, are more attractive therapeutic targets than general proteasome inhibitors due to their specificity for certain protein substrates. The development of ligands of E3 ligases has proven challenging, in part due to the fact that they must disrupt protein-protein interactions. However, recent developments have provided specific ligands which bind to these ligases. For example, since the discovery of nutlins, the first small molecule E3 ligase inhibitors, additional compounds have been reported that target E3 ligases but the field remains underdeveloped. For example, since the discovery of Nutlins, the first small molecule E3 ligase mouse double minute 2 homolog (MDM2) inhibitors, additional compounds have been reported that target MDM2 (i.e., human double minute 2 or HDM2) E3 ligases (J. Di, et al. *Current Cancer Drug Targets* (2011), 11(8), 987-994).

Tumor suppressor gene p53 plays an important role in cell growth arrest and apoptosis in response to DNA damage or stress (A. Vazquez, et al. *Nat. Rev. Drug. Dis.* (2008), 7, 979-982), and inactivation of p53 has been suggested as one of the major pathway for tumor cell survival (A. J. Levine, et al. *Nature* (2000), 408, 307-310). In cancer patients, about 50% were found with p53 mutation (M. Hollstein, et al. *Science* (1991), 233, 49-53), while patients with wild type p53 were often found p53 down regulation by MDM2 through the protein-protein interaction of p53 and MDM2 (P. Chene, et al. *Nat. Rev. Cancer* (2003), 3, 102-109). Under normal cell condition without oncogenic stress signal, MDM2 keeps p53 at low concentration. In response to DNA damage or cellular stress, p53 level increases, and that also causes increase in MDM2 due to the feedback loop from p53/MDM2 auto regulatory system. In other words, p53 regulates MDM2 at the transcription level, and MDM2 regulates p53 at its activity level (A. J. Levine, et al. *Genes Dev.* (1993) 7, 1126-1132).

Several mechanisms can explain p53 down regulation by MDM2. First, MDM2 binds to N-terminal domain of p53 and blocks expression of p53-responsive genes (J. Momand, et al. *Cell* (1992), 69, 1237-1245). Second, MDM2 shuttles p53 from nucleus to cytoplasm to facilitate proteolytic degradation (J. Roth, et al. *EMBO J.* (1998), 17, 554-564). Lastly, MDM2 carries intrinsic E3 ligase activity of conjugating ubiquitin to p53 for degradation through ubiquitin-dependent 26s proteasome system (UPS) (Y. Haupt, et al. *Nature* (1997) 387, 296-299). As such, because MDM2 functions as E3 ligase, recruiting MDM2 to a disease causing protein and effectuating its ubiquitination and degradation is an approach of high interest for drug discovery.

One E3 ligase with exciting therapeutic potential is the von Hippel-Lindau (VHL) tumor suppressor, the substrate recognition subunit of the E3 ligase complex VCB, which also consists of elongins B and C, Cul2 and Rbx1. The primary substrate of VHL is Hypoxia Inducible Factor 1α (HIF-1α), a transcription factor that upregulates genes such as the pro-angiogenic growth factor VEGF and the red blood cell inducing cytokine erythropoietin in response to low oxygen levels. The first small molecule ligands of Von Hippel Lindau (VHL) to the substrate recognition subunit of the E3 ligase were generated, and crystal structures were obtained confirming that the compound mimics the binding mode of the transcription factor HIF-1α, the major substrate of VHL.

Cereblon is a protein that in humans is encoded by the CRBN gene. CRBN orthologs are highly conserved from plants to humans, which underscores its physiological importance. Cereblon forms an E3 ubiquitin ligase complex with damaged DNA binding protein 1 (DDB1), Cullin-4A (CUL4A), and regulator of cullins 1 (ROC1). This complex ubiquitinates a number of other proteins. Through a mechanism which has not been completely elucidated, cereblon ubquitination of target proteins results in increased levels of fibroblast growth factor 8 (FGF8) and fibroblast growth factor 10 (FGF10). FGF8 in turn regulates a number of developmental processes, such as limb and auditory vesicle formation. The net result is that this ubiquitin ligase complex is important for limb outgrowth in embryos. In the absence of cereblon, DDB1 forms a complex with DDB2 that functions as a DNA damage-binding protein.

Inhibitors of Apoptosis Proteins (IAPs) are a protein family involved in suppressing apoptosis, i.e. cell death. The human IAP family includes 8 members, and numerous other organisms contain IAP homologs. IAPs contain an E3 ligase specific domain and baculoviral IAP repeat (BIR) domains that recognize substrates, and promote their ubiquitination. IAPs promote ubiquitination and can directly bind and inhibit caspases. Caspases are proteases (e.g. caspase-3, caspase-7 and caspace-9) that implement apoptosis. As such, through the binding of caspases, IAPs inhibit cell death. However, pro-apoptotic stimuli can result in the release of mitochondrial proteins DIABLO (also known as second mitochondria-derived activator of caspases or SMAC) and HTRA2 (also known as Omi). Binding of DIABLO and HTRA2 appears to block IAP activity.

SMAC interacts with essentially all known IAPs including XIAP, c-IAP1, c-IAP2, NIL-IAP, Bruce, and survivin. The first four amino acids (AVPI) of mature SMAC bind to a portion of IAPs, which is believed to be essential for blocking the anti-apoptotic effects of IAPs.

Bifunctional compounds such as those that are described in U.S. Patent Application Publications 2015-0291562 and 2014-0356322 (incorporated herein by reference), function to recruit endogenous proteins to an E3 ubiquitin ligase for degradation. In particular, the publications describe bifunctional or proteolysis targeting chimeric (PROTAC) compounds, which find utility as modulators of targeted ubiquitination of a variety of polypeptides and other proteins, which are then degraded and/or otherwise inhibited by the bifunctional compounds.

An ongoing need exists in the art for effective treatments for disease associated with overexpression or aggregation of enhancer of zeste homolog 2 (EZH2). However, non-specific effects, and the inability to target and modulate EXH2, remain as obstacles to the development of effective treatments. As such, small-molecule therapeutic agents that target EZH2 and that leverage or potentiate VHL's, cereblon's, MDM2's, and IAPs' substrate specificity would be very useful.

SUMMARY

The present disclosure describes bifunctional compounds which function to recruit endogenous proteins to an E3 ubiquitin ligase for degradation, and methods of using the same. In particular, the present disclosure provides bifunctional or proteolysis targeting chimeric (PROTAC) compounds, which find utility as modulators of targeted ubiquitination of a variety of polypeptides and other proteins, which are then degraded and/or otherwise inhibited by the bifunctional compounds as described herein. An advantage of the compounds provided herein is that a broad range of pharmacological activities is possible, consistent with the degradation/inhibition of targeted polypeptides from virtually any protein class or family. In addition, the description provides methods of using an effective amount of the compounds as described herein for the treatment or amelioration of a disease condition, such as cancer, e.g., breast cancer, prostate cancer, bladder cancer, uterine cancer, renal cancer, melanoma, and/or lymphoma.

As such, in one aspect the disclosure provides bifunctional or PROTAC compounds, which comprise an E3 ubiquitin ligase binding moiety (i.e., a ligand for an E3 ubiquitin ligase or "ULM" group), and a moiety that binds a target protein (i.e., a protein/polypeptide targeting ligand or "PTM" group) such that the target protein/polypeptide is placed in proximity to the ubiquitin ligase to effect degradation (and inhibition) of that protein, such as enhancer of zeste homolog 2 (EZH2). In a preferred embodiment, the ULM (ubiquitination ligase modulator) can be Von Hippel-Lindau E3 ubiquitin ligase (VHL) binding moiety (VLM), or a cereblon E3 ubiquitin ligase binding moiety (CLM), or a mouse double minute 2 homolog (MDM2) E3 ubiquitin ligase binding moiety (MLM), or an IAP E3 ubiquitin ligase binding moiety (i.e., a "ILM"), or a combination thereof. For example, the structure of the bifunctional compound can be depicted as:

The respective positions of the PTM and ULM moieties (e.g., VLM, CLM, MLM or ILM) as well as their number as illustrated herein is provided by way of example only and is not intended to limit the compounds in any way. As would be understood by the skilled artisan, the bifunctional compounds as described herein can be synthesized such that the number and position of the respective functional moieties can be varied as desired.

In certain embodiments, the bifunctional compound further comprises a chemical linker ("L"). In this example, the structure of the bifunctional compound can be depicted as:

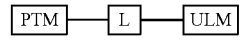

wherein PTM is a protein/polypeptide targeting moiety, L is a linker, e.g., a bond or a chemical group coupling PTM to ULM, and ULM is a IAP E3 ubiquitin ligase binding moiety, or a Von Hippel-Lindau E3 ubiquitin ligase (VHL) binding moiety (VLM), or a cereblon E3 ubiquitin ligase binding moiety (CLM), or a mouse double minute 2 homolog (MDM2) E3 ubiquitin ligase binding moiety (MLM).

For example, the structure of the bifunctional compound can be depicted as:

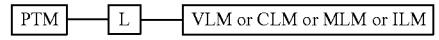

wherein: PTM is a protein/polypeptide targeting moiety; "L" is a linker (e.g. a bond or a chemical linker group) coupling the PTM and at least one of VLM, CLM, MLM, ILM, or a combination thereof; VLM is Von Hippel-Lindau E3 ubiquitin ligase binding moiety that binds to VHL E3 ligase; CLM is cereblon E3 ubiquitin ligase binding moiety that binds to cereblon; MLM is an MDM2 E3 ubiquitin ligase binding moiety; and ILM is a IAP binding moiety which binds to IAP.

In certain preferred embodiments, the ILM is an AVPI tetrapeptide fragment. As such, in certain additional embodiments, the ILM of the bifunctional compound comprises the amino acids alanine (A), valine (V), proline (P), and isoleucine (I) or their unnatural mimetics, respectively. In additional embodiments, the amino acids of the AVPI tetrapeptide fragment are connected to each other through amide bonds (i.e., —C(O)NH— or —NHC(O)—).

In certain embodiments, the compounds as described herein comprise multiple independently selected ULMs, multiple PTMs, multiple chemical linkers or a combination thereof.

In certain embodiments, ILM comprises chemical moieties such as those described herein.

In additional embodiments, VLM can be hydroxyproline or a derivative thereof. Furthermore, other contemplated VLMs are included in U.S. Patent Application Publication No. 2014/03022523, which as discussed above, is incorporated herein in its entirety.

In an embodiment, the CLM comprises a chemical group derived from an imide, a thioimide, an amide, or a thioamide. In a particular embodiment, the chemical group is a phthalimido group, or an analog or derivative thereof. In a certain embodiment, the CLM is thalidomide, lenalidomide, pomalidomide, analogs thereof, isosteres thereof, or derivatives thereof. Other contemplated CLMs are described in U.S. Patent Application Publication No. 2015/0291562, which is incorporated herein in its entirety.

In certain embodiments, MLM can be nutlin or a derivative thereof. Furthermore, other contemplated MLMs are included in U.S. patent application Ser. No. 15/206,497, filed 11 Jul. 2016, which as discussed above, is incorporated herein in its entirety. In certain additional embodiments, the MLM of the bifunctional compound comprises chemical moieties such as substituted imidazolines, substituted spiroindolinones, substituted pyrrolidines, substituted piperidinones, substituted morpholinones, substituted pyrrolopyrimidines, substituted imidazolopyridines, substituted thiazoloimidazoline, substituted pyrrolopyrrolidinones, and substituted isoquinolinones.

In additional embodiments, the MLM comprises the core structures mentioned above with adjacent bis-aryl substitutions positioned as cis- or trans-configurations.

In certain embodiments, "L" is a bond. In additional embodiments, the linker "L" is a connector with a linear non-hydrogen atom number in the range of 1 to 20. The connector "L" can contain, but not limited to the functional groups such as ether, amide, alkane, alkene, alkyne, ketone, hydroxyl, carboxylic acid, thioether, sulfoxide, and sulfone. The linker can contain aromatic, heteroaromatic, cyclic, bicyclic and tricyclic moieties. Substitution with halogen, such as Cl, F, Br and I can be included in the linker. In the case of fluorine substitution, single or multiple fluorines can be included.

In certain embodiments, VLM is a derivative of trans-3-hydroxyproline, where both nitrogen and carboxylic acid in trans-3-hydroxyproline are functionalized as amides.

In certain embodiments, CLM is a derivative of piperidine-2,6-dione, where piperidine-2,6-dione can be substituted at the 3-position, and the 3-substitution can be bicyclic hetero-aromatics with the linkage as C—N bond or C—C bond. Examples of CLM can be, but not limited to, pomalidomide, lenalidomide and thalidomide and their derivatives.

In an additional aspect, the description provides therapeutic compositions comprising an effective amount of a compound as described herein or salt form thereof, and a pharmaceutically acceptable carrier. The therapeutic compositions modulate protein degradation in a patient or subject, for example, an animal such as a human, and can be used for treating or ameliorating disease states or conditions which are modulated through the degraded protein. In certain embodiments, the therapeutic compositions as described herein may be used to effectuate the degradation of proteins of interest for the treatment or amelioration of a disease, e.g., cancer. In yet another aspect, the present disclosure provides a method of ubiquitinating/degrading a target protein in a cell. In certain embodiments, the method comprises administering a bifunctional compound as described herein comprising an ILM and a PTM, a PTM and a VLM, or a PTM and a CLM, or a PTM and a MLM, preferably linked through a linker moiety, as otherwise described herein, wherein the VLM/ILM/CLM/MLM is coupled to the PTM through a linker to target protein that binds to PTM for degradation. Similarly, the PTM can be coupled to VLM or CLM or MLM or ILM through a linker to target a protein or polypeptide for degradation. Degradation of the target protein will occur when the target protein is placed in proximity to the E3 ubiquitin ligase, thus resulting in degradation/inhibition of the effects of the target protein and the control of protein levels. The control of protein levels afforded by the present disclosure provides treatment of a disease state or condition, which is modulated through the target protein by lowering the level of that protein in the cells of a patient.

In still another aspect, the description provides methods for treating or ameliorating a disease, disorder or symptom thereof in a subject or a patient, e.g., an animal such as a human, comprising administering to a subject in need thereof a composition comprising an effective amount, e.g., a therapeutically effective amount, of a compound as described herein or salt form thereof, and a pharmaceutically acceptable carrier, wherein the composition is effective for treating or ameliorating the disease or disorder or symptom thereof in the subject.

In another aspect, the description provides methods for identifying the effects of the degradation of proteins of interest in a biological system using compounds according to the present disclosure.

The preceding general areas of utility are given by way of example only and are not intended to be limiting on the scope of the present disclosure and appended claims. Additional objects and advantages associated with the compositions, methods, and processes of the present disclosure will be appreciated by one of ordinary skill in the art in light of the instant claims, description, and examples. For example, the various aspects and embodiments of the disclosure may be utilized in numerous combinations, all of which are expressly contemplated by the present description. These additional aspects and embodiments are expressly included within the scope of the present disclosure. The publications and other materials used herein to illuminate the background of the disclosure, and in particular cases, to provide additional details respecting the practice, are incorporated by reference.

BRIEF DESCRIPTION OF THE DRAWINGS

The accompanying drawings, which are incorporated into and form a part of the specification, illustrate several embodiments of the present disclosure and, together with the description, serve to explain the principles of the disclosure. The drawings are only for the purpose of illustrating an embodiment of the disclosure and are not to be construed as limiting the disclosure. Further objects, features and advantages of the disclosure will become apparent from the following detailed description taken in conjunction with the accompanying figures showing illustrative embodiments of the disclosure, in which.

DETAILED DESCRIPTION

The following is a detailed description provided to aid those skilled in the art in practicing the present disclosure. Those of ordinary skill in the art may make modifications and variations in the embodiments described herein without departing from the spirit or scope of the present disclosure. All publications, patent applications, patents, figures and other references mentioned herein are expressly incorporated by reference in their entirety.

Figure 1A:
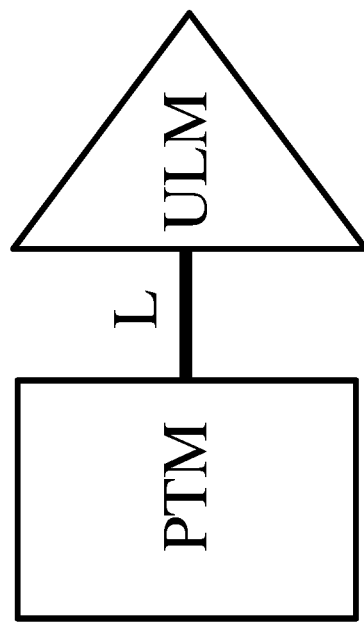
FIGS. 1A and 1B. Illustration of general principle for PROTAC function. (A) Exemplary PROTACs comprise a protein targeting moiety (PTM; darkly shaded rectangle), a ubiquitin ligase binding moiety (ULM; lightly shaded triangle), and optionally a linker moiety (L; black line) coupling or tethering the PTM to the ULM. (B) Illustrates the functional use of the PROTACs as described herein. Briefly, the ULM recognizes and binds to a specific E3 ubiquitin ligase, and the PTM binds and recruits a target protein bringing it into close proximity to the E3 ubiquitin ligase. Typically, the E3 ubiquitin ligase is complexed with an E2 ubiquitin-conjugating protein, and either alone or via the E2 protein catalyzes attachment of ubiquitin (dark circles) to a lysine on the target protein via an isopeptide bond. The poly-ubiquitinated protein (far right) is then targeted for degradation by the proteosomal machinery of the cell.
Figure 1B:
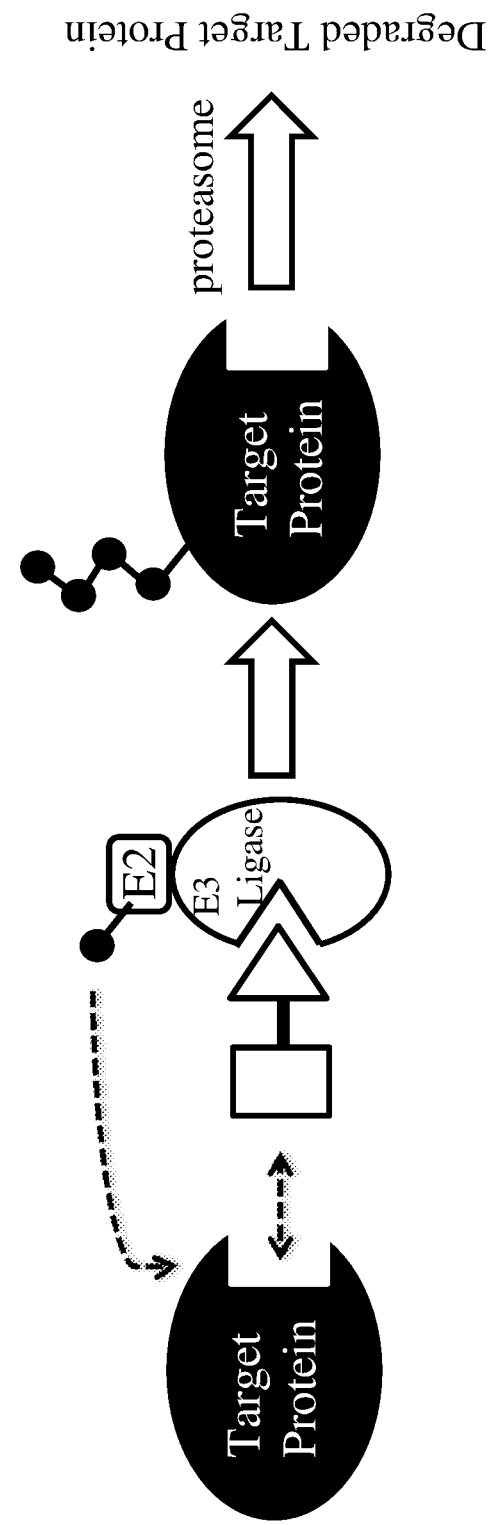

Presently described are compositions and methods that relate to the surprising and unexpected discovery that an E3 ubiquitin ligase protein (e.g., inhibitors of apoptosis proteins (IAP), a Von Hippel-Lindau E3 ubiquitin ligase (VHL), a cereblon E3 ubiquitin ligase, or a mouse double minute 2 homolog (MDM2) E3 ubiquitin ligase) ubiquitinates a target protein once it and the target protein are placed in proximity by a bifunctional or chimeric construct that binds the E3 ubiquitin ligase protein and the target protein (such as enhancer of zeste homolog 2 [EZH2]). Accordingly the present disclosure provides such compounds and compositions comprising an E3 ubiquitin ligase binding moiety ("ULM") coupled to a protein target binding moiety ("PTM"), which result in the ubiquitination of a chosen target protein, which leads to degradation of the target protein by the proteasome (see FIG. 1). The present disclosure also provides a library of compositions and the use thereof.

In certain aspects, the present disclosure provides compounds which comprise a ligand, e.g., a small molecule ligand (i.e., having a molecular weight of below 2,000, 1,000, 500, or 200 Daltons), which is capable of binding to a ubiquitin ligase, such as IAP, VHL, MDM2, or cereblon. The compounds also comprise a moiety that is capable of binding to target protein, in such a way that the target protein is placed in proximity to the ubiquitin ligase to effect degradation (and/or inhibition) of that protein. Small molecule can mean, in addition to the above, that the molecule is non-peptidyl, that is, it is not generally considered a peptide, e.g., comprises fewer than 4, 3, or 2 amino acids. In accordance with the present description, the PTM, ULM or PROTAC molecule can be a small molecule.

Unless otherwise defined, all technical and scientific terms used herein have the same meaning as commonly understood by one of ordinary skill in the art to which this disclosure belongs. The terminology used in the description is for describing particular embodiments only and is not intended to be limiting of the disclosure.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the disclosure. The upper and lower limits of these smaller ranges may independently be included in the smaller ranges is also encompassed within the disclosure, subject to any specifically excluded limit in the stated range. Where the stated range includes one or both of the limits, ranges excluding either both of those included limits are also included in the disclosure.

The following terms are used to describe the present disclosure. In instances where a term is not specifically defined herein, that term is given an art-recognized meaning by those of ordinary skill applying that term in context to its use in describing the present disclosure.

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a nonlimiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, in certain methods described herein that include more than one step or act, the order of the steps or acts of the method is not necessarily limited to the order in which the steps or acts of the method are recited unless the context indicates otherwise.

The terms "co-administration" and "co-administering" or "combination therapy" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent, preferably at effective amounts, at the same time. In certain preferred aspects, one or more of the present compounds described herein, are coadministered in combination with at least one additional bioactive agent, especially including an anticancer agent. In particularly preferred aspects, the co-administration of compounds results in synergistic activity and/or therapy, including anticancer activity.

The term "compound", as used herein, unless otherwise indicated, refers to any specific chemical compound disclosed herein and includes tautomers, regioisomers, geometric isomers, and where applicable, stereoisomers, including optical isomers (enantiomers) and other stereoisomers (diastereomers) thereof, as well as pharmaceutically acceptable salts and derivatives, including prodrug and/or deuterated forms thereof where applicable, in context. Deuterated small molecules contemplated are those in which one or more of the hydrogen atoms contained in the drug molecule have been replaced by deuterium.

Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, in context to prodrug forms of compounds which have been modified to facilitate the administration and delivery of compounds to a site of activity. It is noted that in describing the present compounds, numerous substituents and variables associated with same, among others, are described. It is understood by those of ordinary skill that molecules which are described herein are stable compounds as generally described hereunder. When the bond is shown, both a double bond and single bond are represented or understood within the context of the compound shown and well-known rules for valence interactions.

The term "ubiquitin ligase" refers to a family of proteins that facilitate the transfer of ubiquitin to a specific substrate protein, targeting the substrate protein for degradation. For example, IAP an E3 ubiquitin ligase protein that alone or in combination with an E2 ubiquitin-conjugating enzyme causes the attachment of ubiquitin to a lysine on a target protein, and subsequently targets the specific protein substrates for degradation by the proteasome. Thus, E3 ubiquitin ligase alone or in complex with an E2 ubiquitin conjugating enzyme is responsible for the transfer of ubiquitin to targeted proteins. In general, the ubiquitin ligase is involved in polyubiquitination such that a second ubiquitin is attached to the first; a third is attached to the second, and so forth. Polyubiquitination marks proteins for degradation by the proteasome. However, there are some ubiquitination events that are limited to mono-ubiquitination, in which only a single ubiquitin is added by the ubiquitin ligase to a substrate molecule. Mono-ubiquitinated proteins are not targeted to the proteasome for degradation, but may instead be altered in their cellular location or function, for example, via binding other proteins that have domains capable of binding ubiquitin. Further complicating matters, different lysines on ubiquitin can be targeted by an E3 to make chains. The most common lysine is Lys48 on the ubiquitin chain. This is the lysine used to make polyubiquitin, which is recognized by the proteasome.

The term "patient" or "subject" is used throughout the specification to describe an animal, preferably a human or a domesticated animal, to whom treatment, including prophylactic treatment, with the compositions according to the present disclosure is provided. For treatment of those infections, conditions or disease states which are specific for a specific animal such as a human patient, the term patient refers to that specific animal, including a domesticated animal such as a dog or cat or a farm animal such as a horse, cow, sheep, etc. In general, in the present disclosure, the term patient refers to a human patient unless otherwise stated or implied from the context of the use of the term.

The term "effective" is used to describe an amount of a compound, composition or component which, when used within the context of its intended use, effects an intended result. The term effective subsumes all other effective amount or effective concentration terms, which are otherwise described or used in the present application.

Compounds and Compositions

In one aspect, the description provides compounds comprising an E3 ubiquitin ligase binding moiety ("ULM") that is an IAP E3 ubiquitin ligase binding moiety (an "ILM"), a cereblon E3 ubiquitin ligase binding moiety (a "CLM"), a Von Hippel-Lindae E3 ubiquitin ligase (VHL) binding moiety (VLM), and/or a mouse double minute 2 homologue (MDM2) E3 ubiquitin ligase binding moiety (MLM). In an exemplary embodiment, the ULM is coupled to a target protein binding moiety (PTM) via a chemical linker (L) according to the structure:

PTM-L-ULM     (A)

wherein L is a bond or a chemical linker group, ULM is a E3 ubiquitin ligase binding moiety, and PTM is a target protein binding moiety. The number and/or relative positions of the moieties in the compounds illustrated herein is provided by way of example only. As would be understood by the skilled artisan, compounds described herein can be synthesized with any desired number and/or relative position of the respective functional moieties.

The terms ULM, ILM, VLM, MLM, and CLM are used in their inclusive sense unless the context indicates otherwise. For example, the term ULM is inclusive of all ULMs, including those that bind IAP (i.e., ILMs), MDM2 (i.e., MLM), cereblon (i.e., CLM), and VHL (i.e., VLM). Further, the term ILM is inclusive of all possible IAP E3 ubiquitin ligase binding moieties, the term MLM is inclusive of all possible MDM2 E3 ubiquitin ligase binding moieties, the term VLM is inclusive of all possible VHL binding moieties, and the term CLM is inclusive of all cereblon binding moieties.

In another aspect, the present disclosure provides bifunctional or multifunctional compounds (e.g., PROTACs) useful for regulating protein activity by inducing the degradation of a target protein. In certain embodiments, the compound comprises an ILM or a VLM or a CLM or a MLM coupled, e.g., linked covalently, directly or indirectly, to a moiety that binds a target protein (i.e., a protein targeting moiety or a "PTM"). In certain embodiments, the ILM/VLM/CLM/MLM and PTM are joined or coupled via a chemical linker (L). The ILM binds the IAP E3 ubiquitin ligase, the VLM binds VHL, CLM binds the cereblon E3 ubiquitin ligase, and MLM binds the MDM2 E3 ubiquitin ligase, and the PTM recognizes a target protein and the interaction of the respective moieties with their targets facilitates the degradation of the target protein by placing the target protein in proximity to the ubiquitin ligase protein. An exemplary bifunctional compound can be depicted as:

PTM-ILM     (B)

PTM-CLM     (C)

PTM-VLM     (D)

PTM-MLM     (E)

In certain embodiments, the bifunctional compound further comprises a chemical linker ("L"). For example, the bifunctional compound can be depicted as:

PTM-L-ILM     (F)

PTM-L-CLM     (G)

PTM-L-VLM     (H)

PTM-L-MLM     (I)

wherein the PTM is a protein/polypeptide targeting moiety, the L is a chemical linker, the ILM is a IAP E3 ubiquitin ligase binding moiety, the CLM is a cereblon E3 ubiquitin ligase binding moiety, the VLM is a VHL binding moiety, and the MLM is a MDM2 E3 ubiquitin ligase binding moiety.

In certain embodiments, the ULM (e.g., a ILM, a CLM, a VLM, or a MLM) shows activity or binds to the E3 ubiquitin ligase (e.g., IAP E3 ubiquitin ligase, cereblon E3 ubiquitin ligase, VHL, or MDM2 E3 ubiquitin ligase) with an $IC_{50}$ of less than about 200 µM. The $IC_{50}$ can be determined according to any method known in the art, e.g., a fluorescent polarization assay.

In certain additional embodiments, the bifunctional compounds described herein demonstrate an activity with an $IC_{50}$ of less than about 100, 50, 10, 1, 0.5, 0.1, 0.05, 0.01, 0.005, 0.001 mM, or less than about 100, 50, 10, 1, 0.5, 0.1, 0.05, 0.01, 0.005, 0.001 µM, or less than about 100, 50, 10, 1, 0.5, 0.1, 0.05, 0.01, 0.005, 0.001 nM, or less than about 100, 50, 10, 1, 0.5, 0.1, 0.05, 0.01, 0.005, 0.001 pM.

In certain embodiments, the compounds as described herein comprise multiple PTMs (targeting the same or different protein targets), multiple ULMs, one or more ULMs (i.e., moieties that bind specifically to multiple/different E3 ubiquitin ligase, e.g., VHL, IAP, cereblon, and/or MDM2) or a combination thereof. In any of the aspects or embodiments described herein, the PTMs and ULMs (e.g., ILM, VLM, CLM, and/or MLM) can be coupled directly or via one or more chemical linkers or a combination thereof. In additional embodiments, where a compound has multiple ULMs, the ULMs can be for the same E3 ubiquintin ligase or each respective ULM can bind specifically to a different E3 ubiquitin ligase. In still further embodiments, where a compound has multiple PTMs, the PTMs can bind the same target protein or each respective PTM can bind specifically to a different target protein.

In certain embodiments, where the compound comprises multiple ULMs, the ULMs are identical. In additional embodiments, the compound comprising a plurality of ULMs (e.g., ULM, ULM', etc.), at least one PTM coupled to a ULM directly or via a chemical linker (L) or both. In certain additional embodiments, the compound comprising a plurality of ULMs further comprises multiple PTMs. In still additional embodiments, the PTMs are the same or, optionally, different. In still further embodiments, wherein the PTMs are different, the respective PTMs may bind the same protein target or bind specifically to a different protein target.

In certain embodiments, the compound may comprise a plurality of ULMs and/or a plurality of ULM's. In further embodiments, the compound comprising at least two different ULMs, a plurality of ULMs, and/or a plurality of ULM's further comprises at least one PTM coupled to a ULM or a ULM' directly or via a chemical linker or both. In any of the embodiments described herein, a compound comprising at least two different ILMs can further comprise multiple PTMs. In still additional embodiments, the PTMs are the same or, optionally, different. In still further embodiments, wherein the PTMs are different the respective PTMs may bind the same protein target or bind specifically to a different protein target. In still further embodiments, the PTM itself is a ULM (or ULM'), such as an ILM, a VLM, a CLM, a MLM, an ILM', a VLM', a CLM', and/or a MLM'.

In additional embodiments, the description provides the compounds as described herein including their enantiomers, diastereomers, solvates and polymorphs, including pharmaceutically acceptable salt forms thereof, e.g., acid and base salt forms.

Exemplary ILMs

AVPI Tetrapeptide Fragments

In any of the compounds described herein, the ILM can comprise an alanine-valine-proline-isoleucine (AVPI) tetrapeptide fragment or an unnatural mimetic thereof. In certain embodiments, the ILM is selected from the group consisting of chemical structures represented by Formulas (I), (II), (III), (IV), and (V):

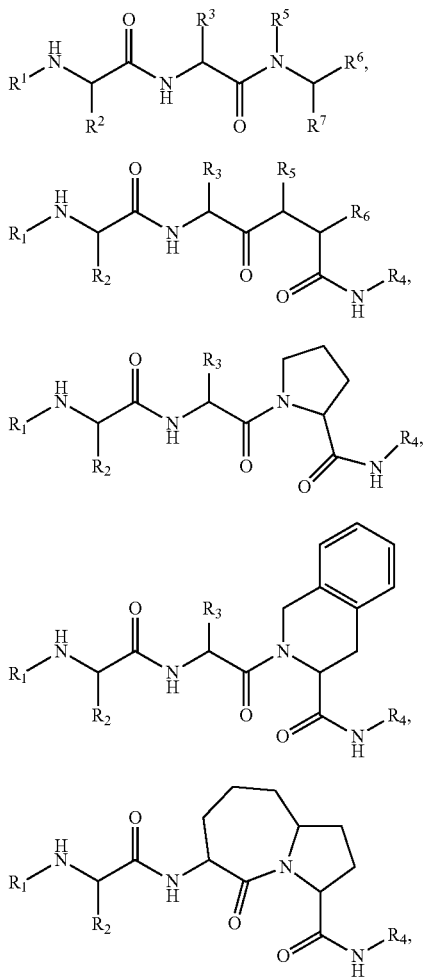

wherein:
- $R^1$ for Formulas (I), (II), (III), (IV), and (V) is selected from H or alkyl;
- $R^2$ for Formulas (I), (II), (III), (IV), and (V) is selected from H or alkyl;
- $R^3$ for Formulas (I), (II), (III), (IV), and (V) is selected from H, alkyl, cycloalkyl and heterocycloalkyl;
- $R^5$ and $R^6$ for Formulas (I), (II), (III), (IV), and (V) are independently selected from H, alkyl, cycloalkyl, heterocycloalkyl, or more preferably, $R^5$ and $R^6$ taken together for Formulas (I), (II), (III), (IV), and (V) form a pyrrolidine or a piperidine ring further optionally fused to 1-2 cycloalkyl, heterocycloalkyl, aryl or heteroaryl rings, each of which can then be further fused to another cycloalkyl, heterocycloalkyl, aryl or heteroaryl ring;
- $R^3$ and $R^5$ for Formulas (I), (II), (III), (IV), and (V) taken together can form a 5-8-membered ring further optionally fused to 1-2 cycloalkyl, heterocycloalkyl, aryl or heteroaryl rings;
- $R^7$ for Formulas (I), (II), (III), (IV), and (V) is selected from cycloalkyl, cycloalkylalkyl, heterocycloalkyl, heterocycloalkylalkyl, aryl, arylalkyl, heteroaryl or heteroarylalkyl, each one further optionally substituted with 1-3 substituents selected from halogen, alkyl, haloalkyl, hydroxyl, alkoxy, cyano, (hetero)cycloalkyl or (hetero)aryl, or $R^7$ is —C(O)NH—$R^4$; and
- $R^4$ is selected from alkyl, cycloalkyl, heterocycloalkyl, cycloalkylalkyl, heterocycloalkylalkyl, aryl, arylalkyl, heteroaryl, heteroarylalkyl, further optionally substituted with 1-3 substituents as described above.

As shown above, P1, P2, P3, and P4 of Formula (II) correlate with A, V, P, and I, respectively, of the AVPI tetrapeptide fragment or an unnatural mimetic thereof. Similarly, each of Formulas (I) and (III) through (V) have portions correlating with A, V, P, and I of the AVPI tetrapeptide fragment or an unnatural mimetic thereof.

In any of the compounds described herein, the ILM can have the structure of Formula (VI), which is a derivative of IAP antagonists described in WO Pub. No. 2008/014236, or an unnatural mimetic thereof:

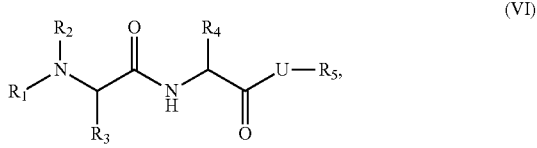

wherein:
- $R_1$ of Formula (VI) is, independently selected from H, $C_1$-$C_4$-alky, $C_1$-$C_4$-alkenyl, $C_1$-$C_4$-alkynyl or $C_3$-$C_{10}$-cycloalkyl which are unsubstituted or substituted;
- $R_2$ of Formula (VI) is, independently selected from H, $C_1$-$C_4$-alkyl, $C_1$-$C_4$-alkenyl, $C_1$-$C_4$-alkynyl or $C_3$-$C_{10}$-cycloalkyl which are unsubstituted or substituted;
- $R_3$ of Formula (VI) is, independently selected from H, —$CF_3$, —$C_2H_5$. $C_1$-$C_4$-alkyl, $C_1$-$C_4$-alkenyl, $C_1$-$C_4$-alkynyl, —$CH_2$—Z or any $R_2$ and $R_3$ together form a heterocyclic ring;
- each Z of Formula (VI) is, independently selected from H, —OH, F, Cl, —$CH_3$, —$CF_3$, —$CH_2Cl$, —$CH_2F$ or —$CH_2OH$;
- $R_4$ of Formula (VI) is, independently selected from $C_1$-$C_{16}$ straight or branched alkyl, $C_1$-$C_{16}$-alkenyl, $C_1$-$C_{16}$-alkynyl, $C_3$-$C_{10}$-cycloalkyl, —$(CH_2)_{0-6}Z_1$, —$(CH_2)_{0-6}$-aryl, and —$(CH_2)_{0-6}$-het, wherein alkyl, cycloalkyl, and phenyl are unsubstituted or substituted;
- $R_5$ of Formula (VI) is, independently selected from H, $C_{1-10}$-alkyl, aryl, phenyl. $C_{3-7}$-cycloalkyl, —$(CH_2)_{1-6}$—$C_{3-7}$-cycloalkyl, —$C_{1-10}$-alkyl-aryl, —$(CH_2)_{0-6}$—$C_{3-7}$-cycloalkyl-$(CH_2)_{0-6}$-phenyl, —$(CH_2)_{0-4}$—CH[$(CH_2)_{1-4}$-phenyl]$_2$, indanyl, —C(O)—$C_{1-10}$-alkyl, —C(O)—$(CH_2)_{1-6}$—$C_{3-7}$-cycloalkyl, —C(O)—$(CH_2)_{0-6}$-phenyl, —$(CH_2)_{0-6}$—C(O)-phenyl, —$(CH_2)_{0-6}$-het, —C(O)—$(CH_2)_{1-6}$-het, or $R_5$ is selected from a residue of an amino acid, wherein the alkyl, cycloalkyl, phenyl, and aryl substituents are unsubstituted or substituted;
- $Z_1$ of Formula (VI) is, independently selected from —N($R_{10}$)—C(O)—$C_{1-10}$-alkyl, —N($R_{10}$)—C(O)—

(CH$_2$)$_{0-6}$—C$_{3-7}$-cycloalkyl, —N(R$_{10}$)—C(O)—(CH$_2$)$_{0-6}$-phenyl, —N(R$_{10}$)—C(O)(CH$_2$)$_{1-6}$-het, —C(O)—N(R$_{11}$)(R$_{12}$), —C(O)—O—C$_{1-10}$-alkyl, —C(O)—O—(CH$_2$)$_{1-6}$—C$_{3-7}$-cycloalkyl, —C(O)—O—(CH$_2$)$_{0-6}$-phenyl, —C(O)—O—(CH$_2$)$_{1-6}$-het, —O—C(O)—C$_{1-10}$-alkyl, —O—C(O)—(CH$_2$)$_{1-6}$—C$_{3-7}$-cycloakyl, —O—C(O)—(CH$_2$)$_{0-6}$-phenyl, —O—C(O)—(CH$_2$)$_{1-6}$-het, wherein alkyl, cycloalkyl, and phenyl are unsubstituted or substituted;

het of Formula (VI) is, independently selected from a 5-7 member heterocyclic ring containing 1-4 heteroatoms selected from N, O, and S, or an 8-12 member fused ring system including at least one 5-7 member heterocyclic ring containing 1, 2, or 3 heteroatoms selected from N, O, and S, which heterocyclic ring or fused ring system is unsubstituted or substituted on a carbon or nitrogen atom;

R$_{10}$ of Formula (VI) is selected from H, —CH$_3$, —CF$_3$, —CH$_2$OH, or —CH$_2$Cl; R$_{11}$ and R$_{12}$ of Formula (VI) are independently selected from H. C$_{1-4}$-alkyl, C$_{3-7}$-cycloalkyl, —(CH$_2$)$_{1-6}$—C$_{3-7}$-cycloakyl, (CH$_2$)$_{0-6}$-phenyl, wherein alkyl, cycloalkyl, and phenyl are unsubstituted or substituted; or R$_{11}$ and R$_{12}$ together with the nitrogen form het, and U of Formula (VI) is, independently, as shown in Formula (VII):

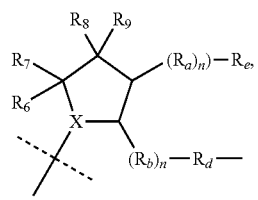

(VII)

wherein:
each n of Formula (VII) is, independently selected from 0 to 5;
X of Formula (VII) is selected from the group —CH and N;
R$_a$ and R$_b$, of Formula (VII) are independently selected from the group O, S. or N atom or C$_{0-8}$-alkyl wherein one or more of the carbon atoms in the alkyl chain are optionally replaced by a heteroatom selected from O, S, or N, and where each alkyl is, independently, either unsubstituted or substituted;
R$_d$ of Formula (VII) is selected from the group Re-Q-(R$_f$)$_p$(R$_g$)$_q$, and Ar$_1$-D-Ar$_2$;
R$_e$ of Formula (VII) is selected from the group H or any R$_c$ and R$_d$ together form a cycloalkyl or het; where if R$_c$ and R$_d$ form a cycloalkyl or het, R$_5$ is attached to the formed ring at a C or N atom;
p and q of Formula (VII) are independently selected from 0 or 1;
R$_e$ of Formula (VII) is selected from the group C$_{1-8}$-alkyl and alkylidene, and each Re is either unsubstituted or substituted;
Q is selected from the group N, O, S, S(O), and S(O)$_2$;
Ar$_1$ and Ar$_2$ of Formula (VII) are independently selected from the group of substituted or unsubstituted aryl and het;

R$_f$ and R$_g$ of Formula (VII) are independently selected from H, —C$_{1-10}$-alkyl, C$_{1-10}$-alkylaryl, —OH, —O—C$_{1-10}$-alkyl, —(CH$_2$)$_{0-6}$—C$_{3-7}$-cycloalkyl, —O—(CH$_2$)$_{0-6}$-aryl, phenyl, aryl, phenyl-phenyl, —(CH$_2$)$_{1-6}$-het, —O—(CH$_2$)$_{1-6}$-het, —OR$_{13}$, —C(O)—R$_{13}$, —C(O)—N(R$_{13}$)(R$_{14}$), —N(R$_{13}$)(R$_{14}$). —S—R$_{13}$, —S(O)—R$_{13}$, —S(O)$_2$—R$_{13}$, —S(O)$_2$—NR$_{13}$R$_{14}$, —NR$_{13}$—S(O)$_2$—R$_{14}$, —S—C$_{1-10}$-alkyl, aryl-C$_{1-4}$-alkyl, or het-C$_{1-4}$-alkyl, wherein alkyl, cycloalkyl, het, and aryl are unsubstituted or substituted, —SO$_2$—C$_{1-2}$-alkyl, —SO$_2$—C$_{1-2}$-alkylphenyl, —O—C$_{1-4}$-alkyl, or any R$_g$ and R$_f$ together form a ring selected from het or aryl;

D of Formula (VII) is selected from the group —CO—, —C(O)—C$_{1-7}$-alkylene or arylene, —CF$_2$—, —O—, —S(O)$_r$ where r is 0-2, 1,3-dioxalane, or C$_{1-7}$-alkyl-OH; where alkyl, alkylene, or arylene are unsubstituted or substituted with one or more halogens. OH, —O—C$_{1-7}$-alkyl, —S—C$_{1-6}$-alkyl, or —CF$_3$; or each D is, independently selected from N(R$_h$);

Rh is selected from the group H, unsubstituted or substituted C$_{1-7}$-alkyl, aryl, unsubstituted or substituted —O—(C$_{1-7}$-cycloalkyl), —C(O)—C$_{1-10}$-alkyl, —C(O)—C$_{0-10}$-alkyl-aryl, —C—O—C$_{01-10}$-alkyl, —C—O—C$_{0-10}$-alkyl-aryl, —SO$_2$—C$_{1-10}$-alkyl, or —SO$_2$—(C$_{0-10}$-alkylaryl);

R$_6$, R$_7$. R$_8$, and R$_9$ of Formula (VII) are, independently, selected from the group H, —C$_{1-10}$-alkyl, —C$_{1-10}$-alkoxy, aryl-C$_{1-10}$-alkoxy, —OH, —O—C$_{1-10}$-alkyl, —(CH$_2$)$_{0-6}$—C$_{3-7}$-cycloalkyl, —O—(CH$_2$)$_{0-6}$-aryl, phenyl, —(CH$_2$)$_{1-6}$-het, —O—(CH$_2$)$_{1-6}$-het, —OR$_{13}$, —C(O)—R$_{13}$, —C(O)—N(R$_{13}$)(R$_{14}$), —N(R$_{13}$)(R$_{14}$), —S—R$_{13}$, —S(O)—R$_{13}$, —S(O)$_2$—R$_{13}$, —S(O)$_2$—NR$_{13}$R$_{14}$, or —NR$_{13}$—S(O)$_2$—R$_{14}$; wherein each alkyl, cycloalkyl, and aryl is unsubstituted or substituted; and any R$_6$, R$_7$, R$_8$, and R$_9$ optionally together form a ring system;

R$_{13}$ and R$_{14}$ of Formula (VII) are independently selected from the group H, C$_{1-10}$-alkyl, —(CH$_2$)$_{0-6}$—C$_{3-7}$-cycloalkyl, —(CH$_2$)$_{0-6}$—(CH)$_{0-1}$-aryl)$_{1-2}$, —C(O)—C$_{1-10}$-alkyl, —C(O)—(CH$_2$)$_{1-6}$—C$_{3-7}$-cycloalkyl, —C(O)—O—(CH$_2$)$_{0-6}$-aryl, —C(O)—(CH$_2$)$_{0-6}$—O-fluorenyl, —C(O)—NH—(CH$_2$)$_{0-6}$-aryl, —C(O)—(CH$_2$)$_{0-6}$-aryl, —C(O)—(CH$_2$)$_{0-6}$-het, —C(S)—C$_{1-10}$-alkyl, —C(S)—(CH$_2$)$_{1-6}$—C$_{3-7}$-cycloalkyl, —C(S)—O—(CH$_2$)$_{0-6}$-aryl, —C(S)—(CH$_2$)$_{0-6}$—O-fluorenyl, —C(S)—NH—(CH$_2$)$_{0-6}$-aryl, —C(S)—(CH$_2$)$_{0-6}$-aryl, or —C(S)—(CH$_2$)$_{1-6}$-het, wherein each alkyl, cycloalkyl, and aryl is unsubstituted or substituted: or any R$_{13}$ and R$_{14}$ together with a nitrogen atom form het;

wherein alkyl substituents of R$_{13}$ and R$_{14}$ of Formula (VII) are unsubstituted or substituted and when substituted, are substituted by one or more substituents selected from C$_{1-10}$-alkyl, halogen, OH, —O—C$_{1-6}$-alkyl, —S—C$_{1-6}$-alkyl, and —CF$_3$; and substituted phenyl or aryl of R$_{13}$ and R$_{14}$ are substituted by one or more substituents selected from halogen, hydroxyl. C$_{1-4}$-alkyl, C$_{1-4}$-alkoxy, nitro, —CN, —O—C(O)—C$_{1-4}$-alkyl, and —C(O)—O—C$_{1-4}$-aryl; or a pharmaceutically acceptable salt or hydrate thereof.

In certain embodiments, the compound further comprises an independently selected second ILM attached to the ILM of Formula (VI), or an unnatural mimetic thereof, by way of at least one additional independently selected linker group. In an embodiment, the second ILM is a derivative of Formula (VI), or an unnatural mimetic thereof. In a certain embodiment, the at least one additional independently selected linker group comprises two additional independently selected linker groups chemically linking the ILM and the second ILM. In an embodiment, the at least one additional linker group for an ILM of the Formula (VI), or an unnatural mimetic thereof, chemically links groups selected from $R_4$ and $R_5$. For example, an ILM of Formula (VI) and a second ILM of Formula (VI), or an unnatural mimetic thereof, can be linked as shown below:

(A)

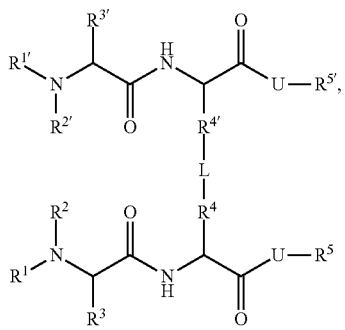

(B)

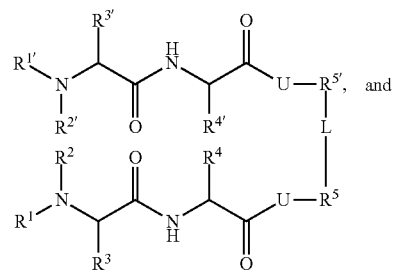

(C)

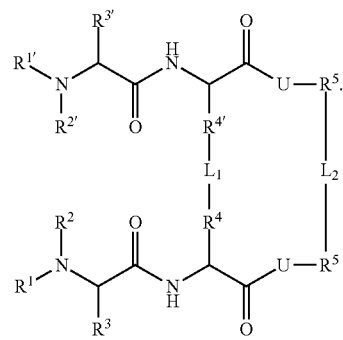

In certain embodiments, the ILM, the at least one additional independently selected linker group L, and the second ILM has a structure selected from the group consisting of:

(A)

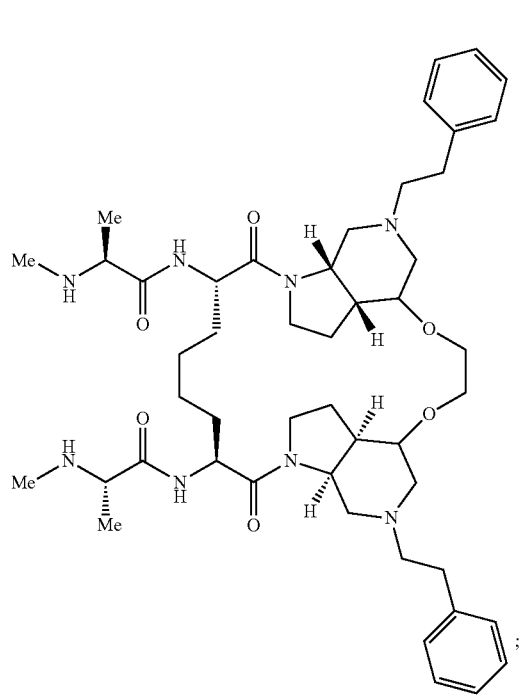

(B)

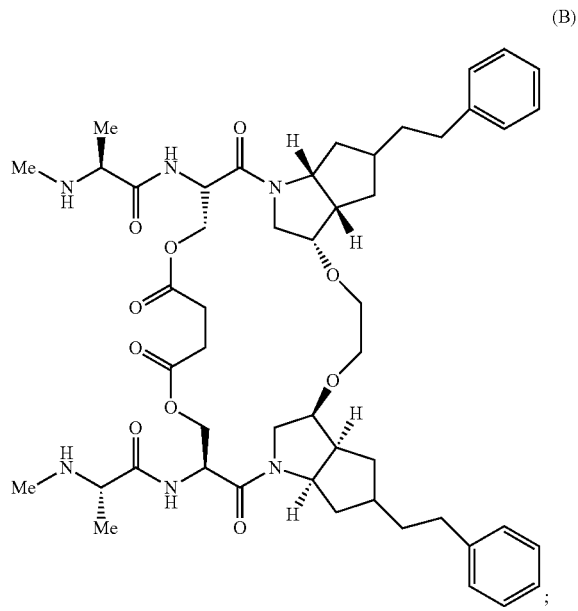

-continued
(C)
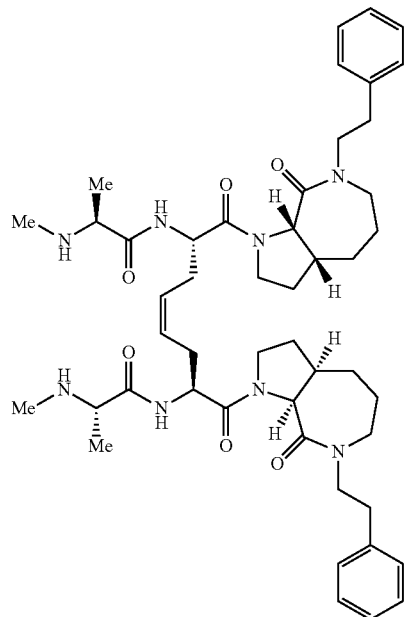
(D)
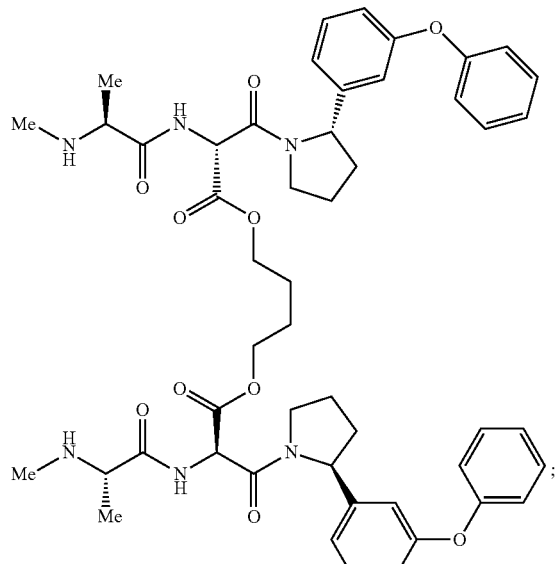
(E)
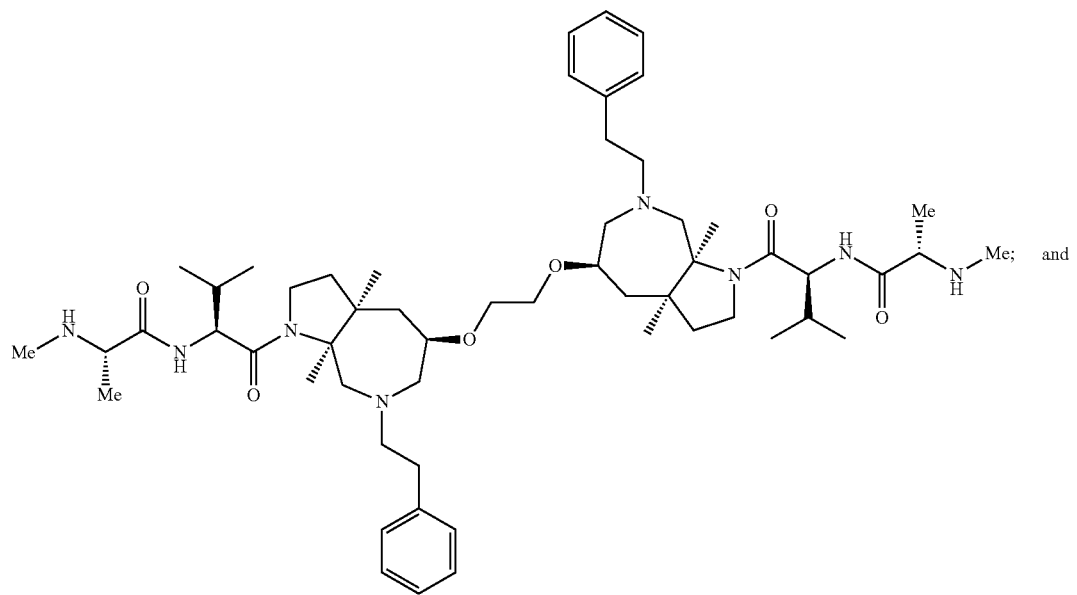
and
(F)
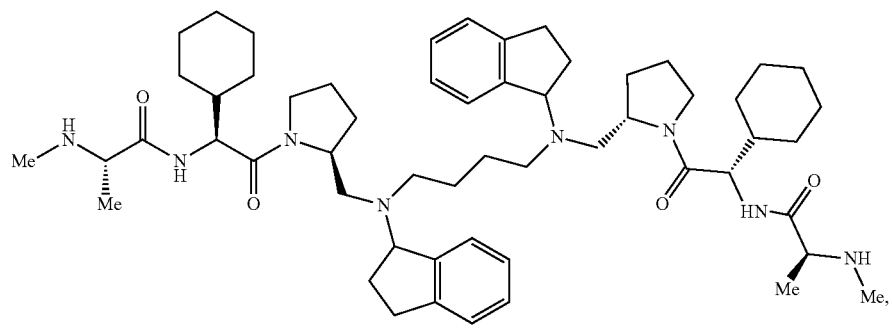

which are derivatives of IAP antagonists described in WO Pub. No. 2008/014236.

In any of the compounds described herein, the ILM can have the structure of Formula (VIII), which is based on the IAP ligands described in Ndubaku, C., et al. Antagonism of c-IAP and XIAP proteins is required for efficient induction of cell death by small-molecule IAP antagonists, *ACS Chem. Biol.*, 557-566, 4 (7) (2009), or an unnatural mimetic thereof:

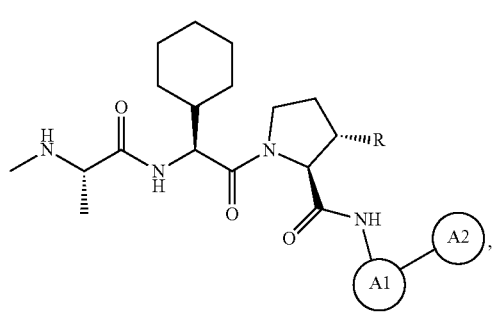

(VIII)

wherein each of A1 and A2 of Formula (VIII) is independently selected from optionally substituted monocyclic, fused rings, aryls and heteroaryls; and R of Formula (VIII) is selected from H or Me.

In a particular embodiment, the linker group L is attached to A1 of Formula (VIII). In another embodiment, the linker group L is attached to A2 of Formula (VIII).

In a particular embodiment, the ILM is selected from the group consisting of

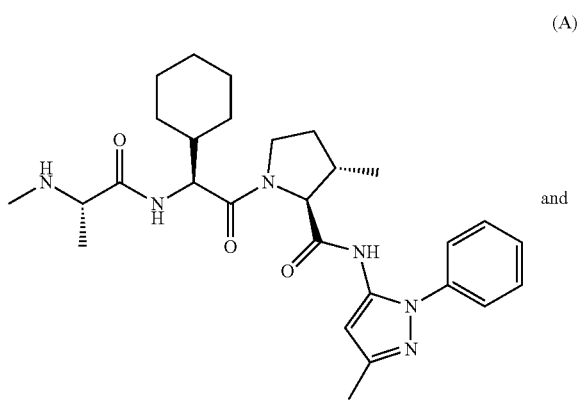

(A)

and (B)

In any of the compounds described herein, the ILM can have the structure of Formula (IX), which is derived from the chemotypes cross-referenced in Mannhold, R., et al. IAP antagonists: promising candidates for cancer therapy, *Drug Discov. Today*, 15 (5-6), 210-9 (2010), or an unnatural mimetic thereof:

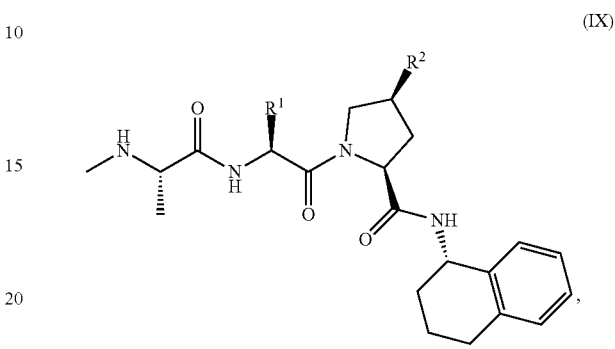

(IX)

wherein $R^1$ is selected from alkyl, cycloalkyl and heterocycloalkyl and, most preferably, from isopropyl, tert-butyl, cyclohexyl and tetrahydropyranyl, and $R^2$ of Formula (IX) is selected from —OPh or H.

In any of the compounds described herein, the ILM can have the structure of Formula (X), which is derived from the chemotypes cross-referenced in Mannhold, R., et al. IAP antagonists: promising candidates for cancer therapy, *Drug Discov. Today*, 15 (5-6), 210-9 (2010), or an unnatural mimetic thereof:

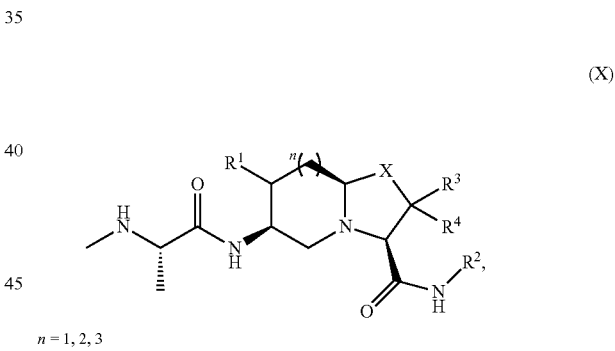

(X)

$n = 1, 2, 3$ wherein:

$R^1$ of Formula (X) is selected from H, —CH$_2$OH, —CH$_2$CH$_2$OH, —CH$_2$NH$_2$, —CH$_2$CH$_2$NH$_2$;

X of Formula (X) is selected from S or CH$_2$;

$R^2$ of Formula (X) is selected from:

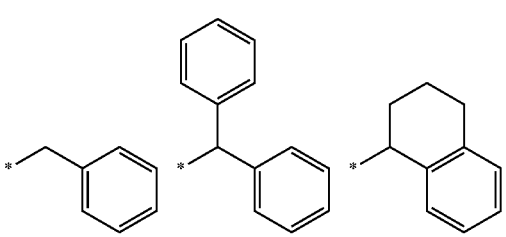

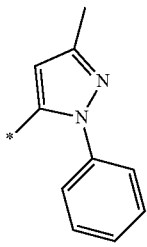

R³ and R⁴ of Formula (X) are independently selected from H or Me

In any of the compounds described herein, the ILM can have the structure of Formula (XI), which is derived from the chemotypes cross-referenced in Mannhold, R., et al. IAP antagonists: promising candidates for cancer therapy, *Drug Discov. Today*, 15 (5-6), 210-9 (2010), or an unnatural mimetic thereof:

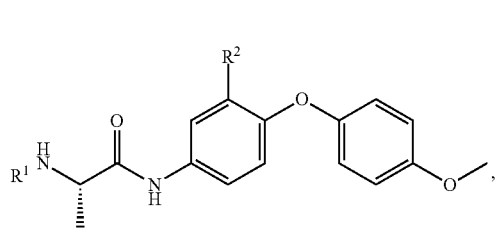

(XI)

wherein $R^1$ of Formula (XI) is selected from H or Me, and $R^2$ of Formula (XI) is selected from H or

In any of the compounds described herein, the ILM can have the structure of Formula (XII), which is derived from the chemotypes cross-referenced in Mannhold, R., et al. IAP antagonists: promising candidates for cancer therapy, *Drug Discov. Today*, 15 (5-6), 210-9 (2010), or an unnatural mimetic thereof:

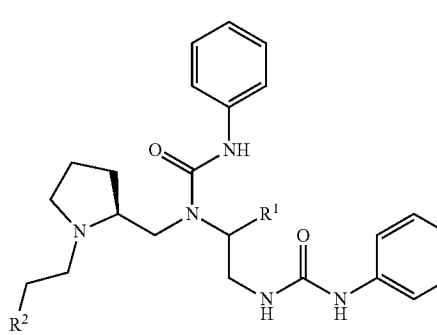

(XII)

wherein:
$R^1$ of Formula (XII) is selected from:

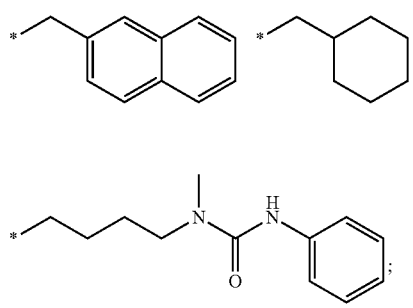

and
$R^2$ of Formula (XII) is selected from:

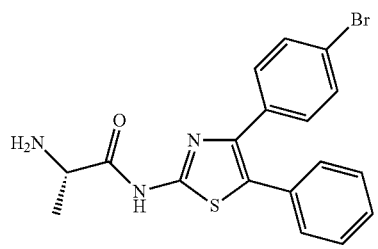

In any of the compounds described herein, the IAP E3 ubiquitin ligase binding moiety is selected from the group consisting of:

-continued
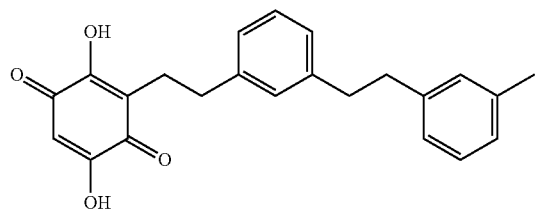
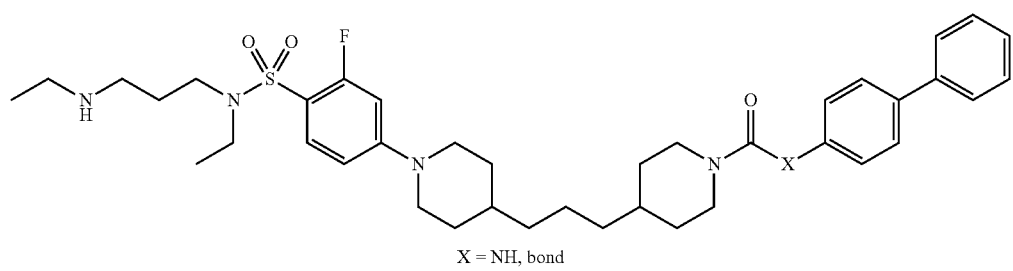
X = NH, bond
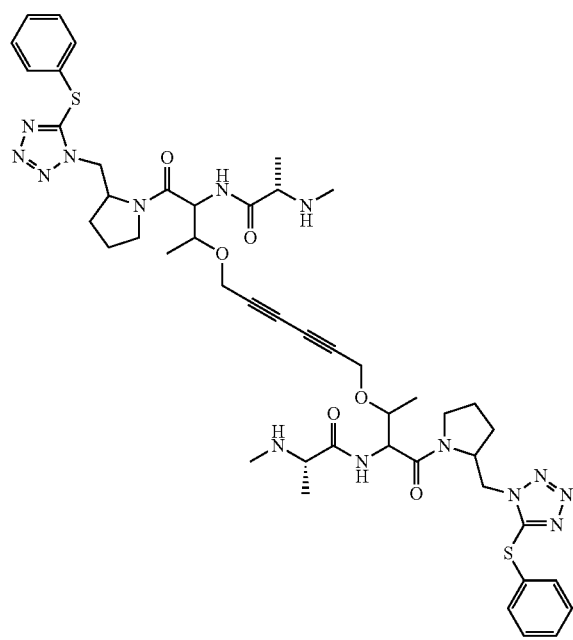

-continued
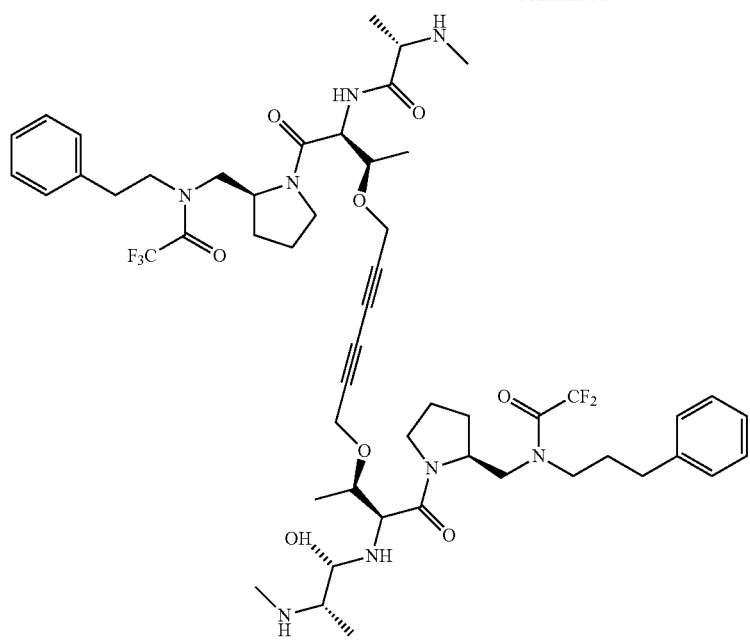
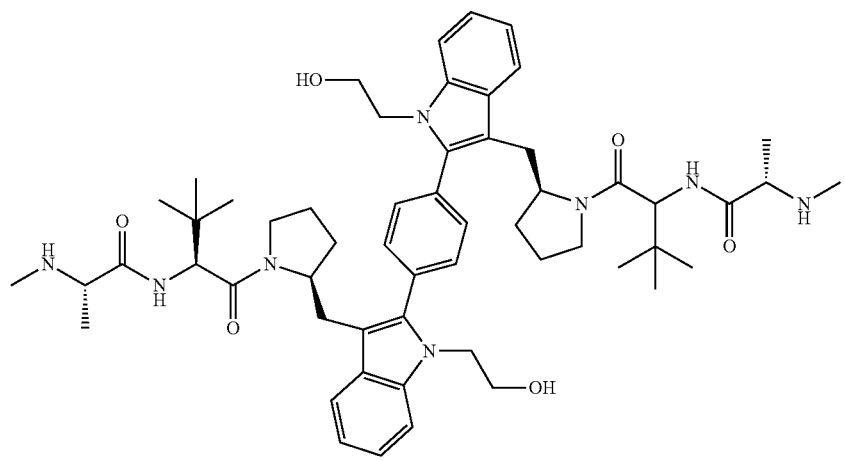
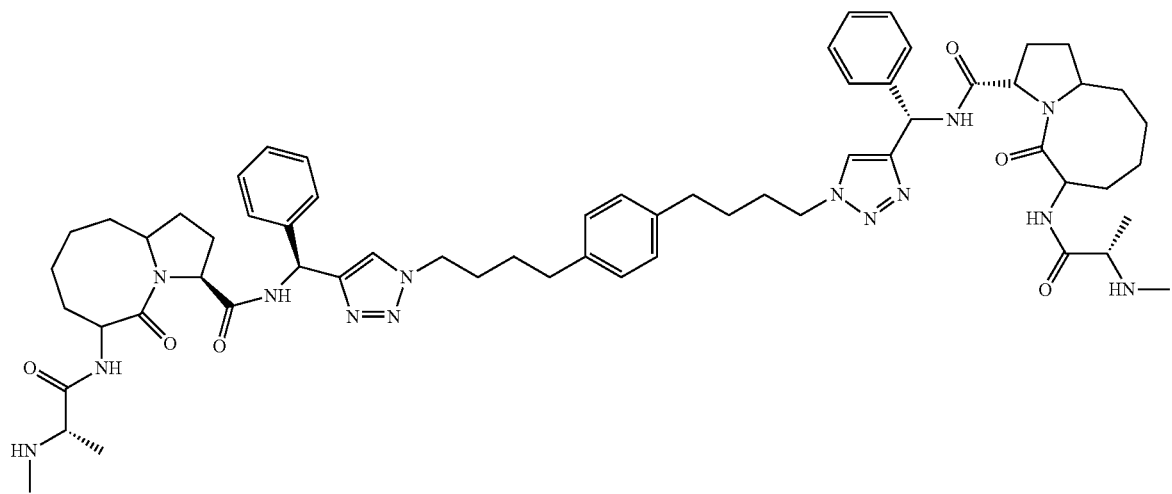

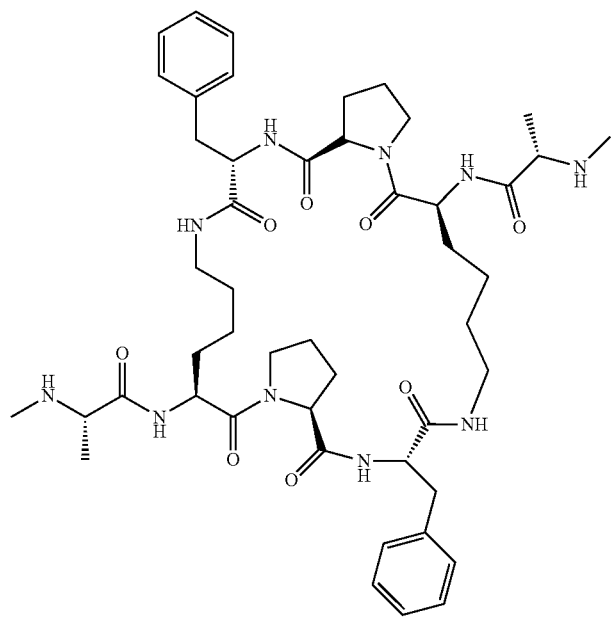
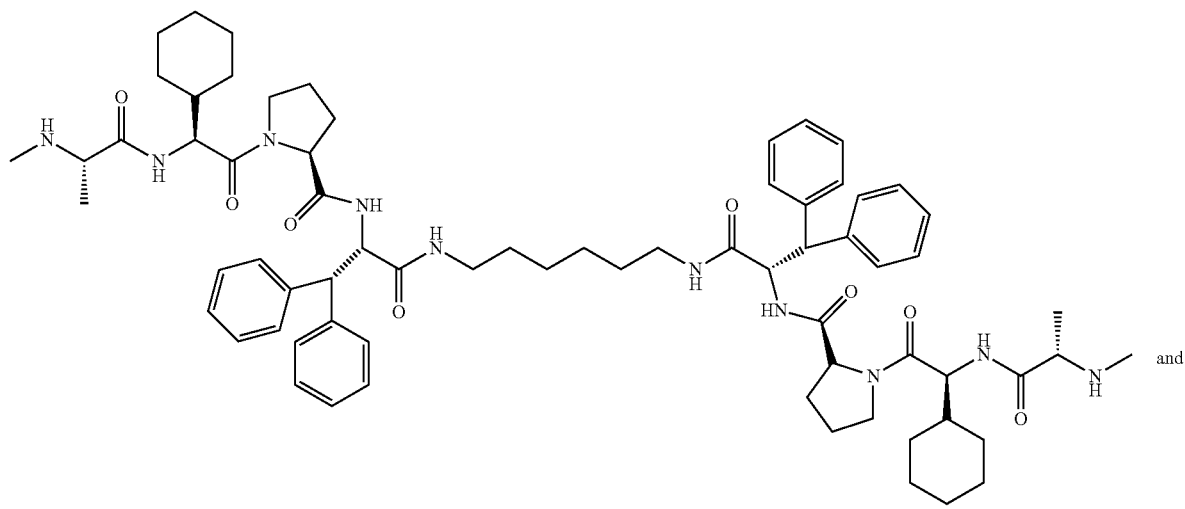
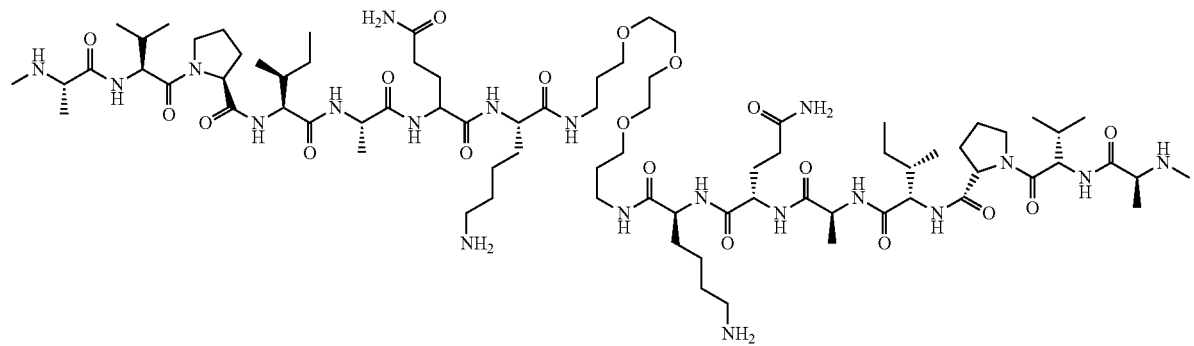

In any of the compounds described herein, the ILM can have the structure of Formula (XIII), which is based on the IAP ligands summarized in Flygare, J. A., et al. Small-molecule pan-IAP antagonists: a patent review, *Expert Opin. Ther. Pat.*, 20 (2), 251-67 (2010), or an unnatural mimetic thereof:

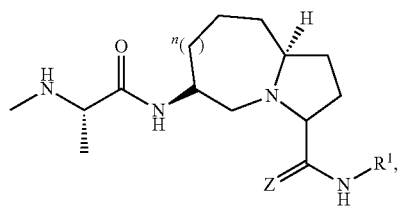

$n$ = 0, 2 or, preferably, 1 wherein:

Z of Formula (XIII) is absent or O;

$R^1$ of Formula (XIII) is selected from:

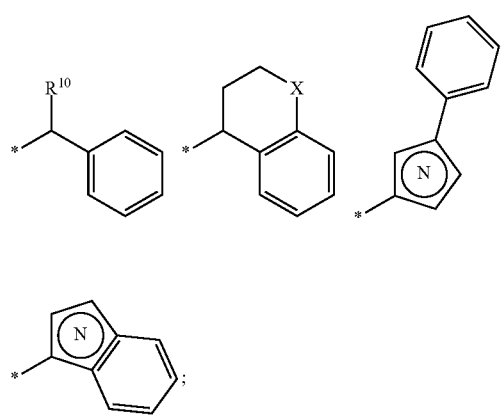

$R^{10}$ of

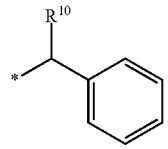

is selected from H, alkyl, or aryl;

X is selected from CH2 and O; and

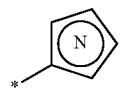

is a nitrogen-containing heteroaryl.

In any of the compounds described herein, the ILM can have the structure of Formula (XIV), which is based on the IAP ligands summarized in Flygare, J. A., et al. Small-molecule pan-IAP antagonists: a patent review, *Expert Opin. Ther. Pat.*, 20 (2), 251-67 (2010), or an unnatural mimetic thereof:

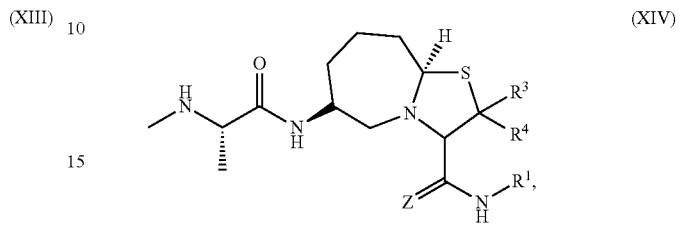

wherein:

Z of Formula (XIV) is absent or O;

$R^3$ and $R^4$ of Formula (XIV) are independently selected from H or Me;

$R^1$ of Formula (XIV) is selected from:

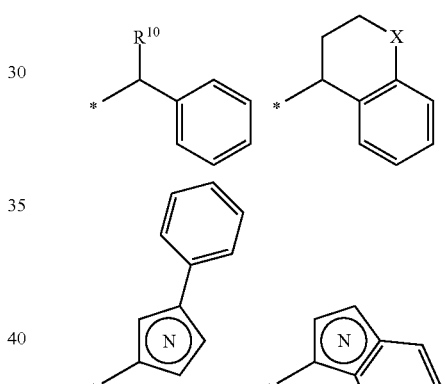

$R^{10}$ of

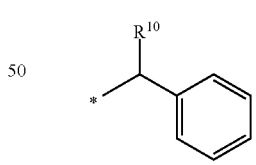

is selected from H, alkyl, or aryl;

X of

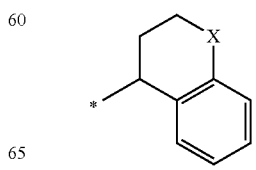

is selected from CH2 and O; and

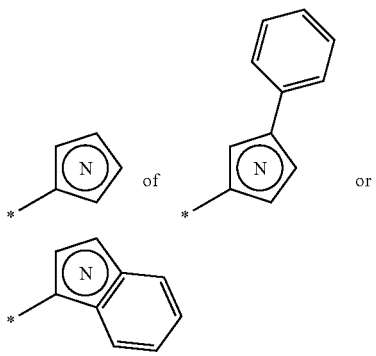

is a nitrogen-containing heteraryl.

In any of the compounds described herein, the ILM is selected from the group consisting of:

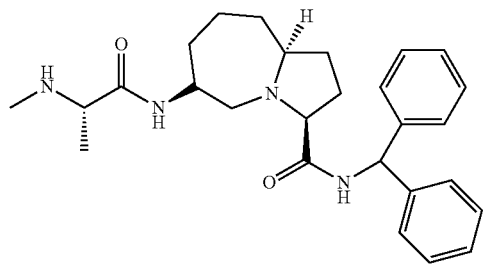

and

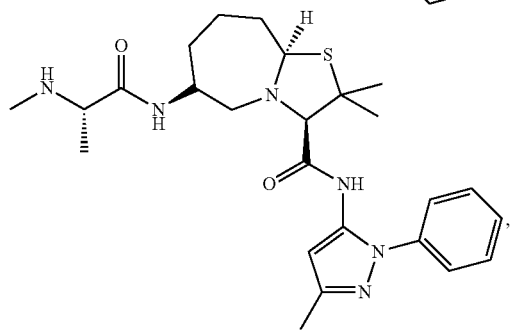

which are derivatives of ligands disclose in US Patent Pub. No. 2008/0269140 and U.S. Pat. No. 7,244,851.

In any of the compounds described herein, the ILM can have the structure of Formula (XV), which was a derivative of the IAP ligand described in WO Pub. No. 2008/128171, or an unnatural mimetic thereof:

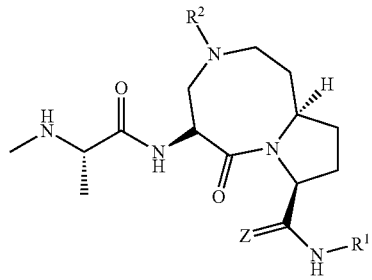

(XV)

wherein:

Z of Formula (XV) is absent or 0;

R$^1$ of Formula (XV) is selected from:

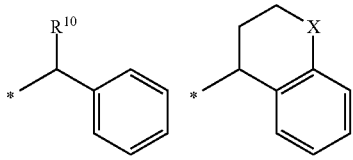

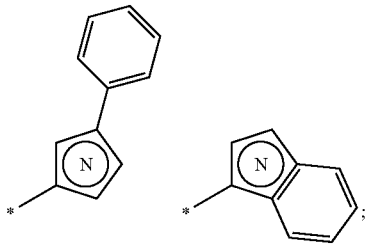

R$^{10}$ of

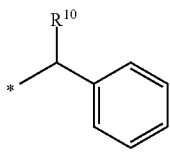

is selected from H, alkyl, or aryl;

X of

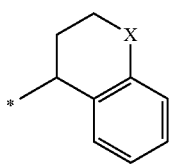

is selected from CH2 and O; and

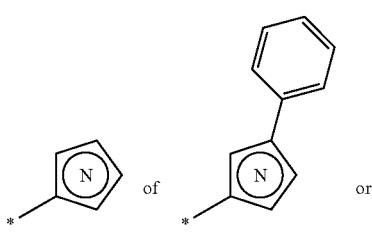

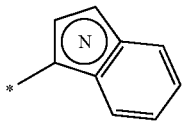

is a nitrogen-containing heteraryl; and
R² of Formula (XV) selected from H, alkyl, or acyl;

In a particular embodiment, the ILM has the following structure:

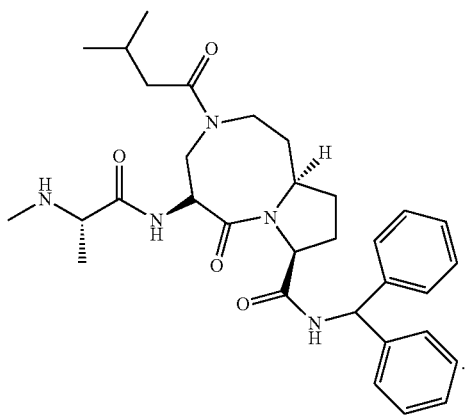

In any of the compounds described herein, the ILM can have the structure of Formula (XVI), which is based on the TAP ligand described in WO Pub. No. 2006/069063, or an unnatural mimetic thereof:

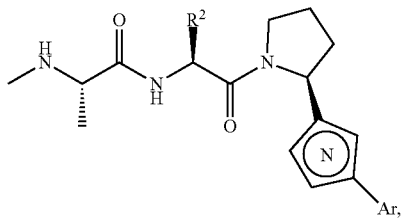

(XVI)

wherein:
R² of Formula (XVI) is selected from alkyl, cycloalkyl and heterocycloalkyl; more preferably, from isopropyl, tert-butyl, cyclohexyl and tetrahydropyranyl, most preferably from cyclohexyl;

of Formula (XVI) is a 5- or 6-membered nitrogen-containing heteraryl; more preferably, 5-membered nitrogen-containing heteraryl, and most preferably thiazole; and Ar of Formula (XVI) is an aryl or a heteroaryl.

In any of the compounds described herein, the ILM can have the structure of Formula (XVII), which is based on the IAP ligands described in Cohen, F. et al., Antagonists of inhibitors of apoptosis proteins based on thiazole amide isosteres, Bioorg. Med. Chem. Lett., 20(7), 2229-33 (2010), or an unnatural mimetic thereof:

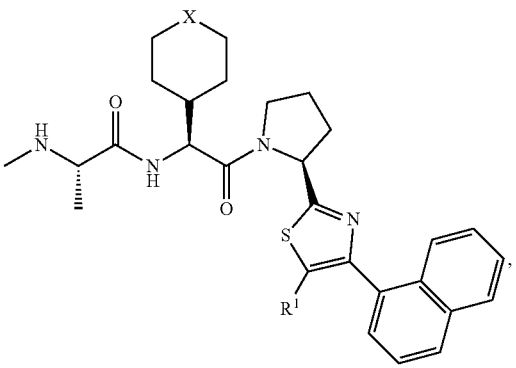

(XVII)

wherein:
R¹ of Formula (XVII) is selected from the group halogen (e.g. fluorine), cyano,

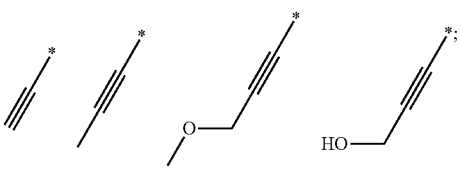

X of Formula (XVII) is selected from the group O or CH2.

In any of the compounds described herein, the ILM can have the structure of Formula (XVIII), which is based on the IAP ligands described in Cohen, F. et al., Antagonists of inhibitors of apoptosis proteins based on thiazole amide isosteres, Bioorg. Med. Chem. Lett., 20(7), 2229-33 (2010), or an unnatural mimetic thereof:

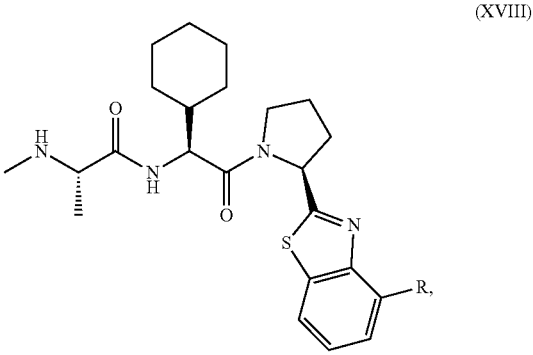

(XVIII)

wherein R of Formula (XVIII) is selected from alkyl, aryl, heteroaryl, arylalkyl, heteroarylalkyl or halogen (in variable substitution position).

In any of the compounds described herein, the ILM can have the structure of Formula (XIX), which is based on the IAP ligands described in Cohen, F. et al., *Antagonists of inhibitors of apoptosis proteins based on thiazole amide isosteres*, Bioorg. Med. Chem. Lett., 20(7), 2229-33 (2010), or an unnatural mimetic thereof:

(XIX)

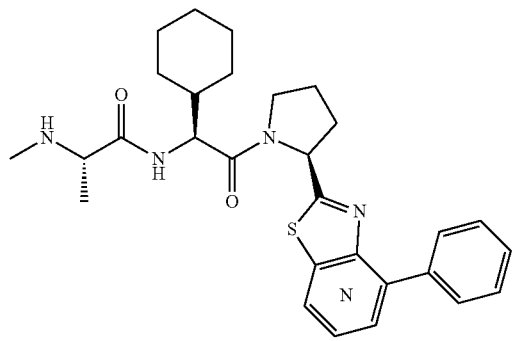

wherein

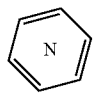

is a 6-member nitrogen heteroaryl.

In a certain embodiment, the ILM of the composition is selected from the group consisting of:

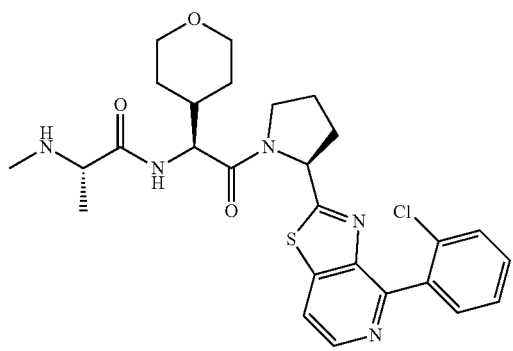

and

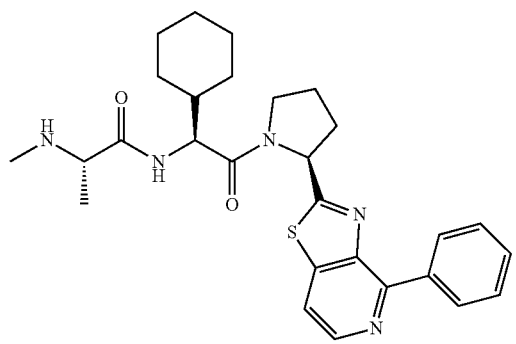

In certain embodiments, the ILM of the composition is selected from the group consisting of:

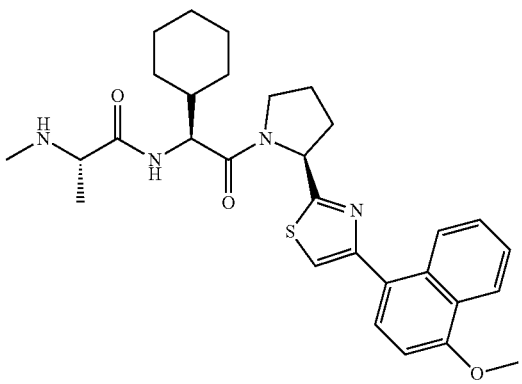

, and

In any of the compounds described herein, the ILM can have the structure of Formula (XX), which is based on the IAP ligands described in WO Pub. No. 2007/101347, or an unnatural mimetic thereof:

(XX)

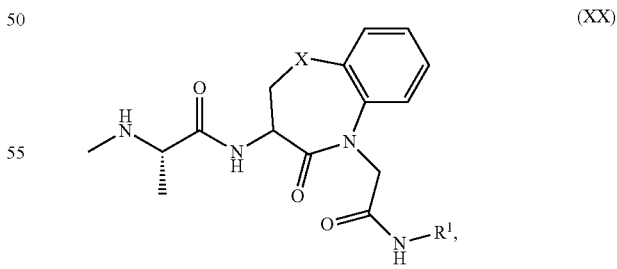

wherein X of Formula (XX) is selected from CH$_2$, O, NH, or S.

In any of the compounds described herein, the ILM can have the structure of Formula (XXI), which is based on the IAP ligands described in U.S. Pat. Nos. 7,345,081 and 7,419,975, or an unnatural mimetic thereof:

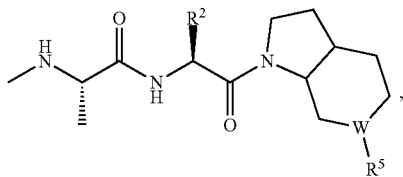
(XXI)
wherein:
R² of Formula (XXI) is selected from:
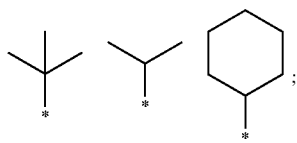
R⁵ of Formula (XXI) is selected from:
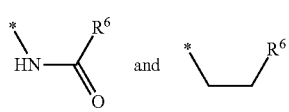
and
W of Formula (XXI) is selected from CH or N; and R⁶ of
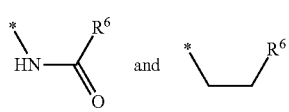
and are independently a mono- or bicyclic fused aryl or heteroaryl.
In certain embodiments, the ILM of the compound is selected from the group consisting of:
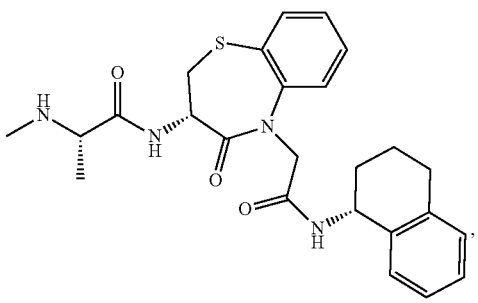
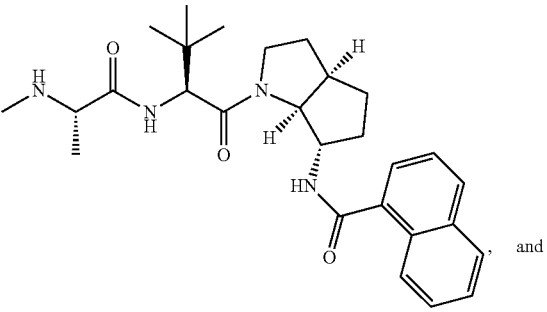
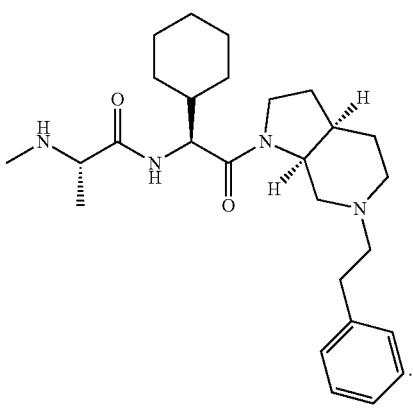

In certain embodiments, the ILM of the compound is selected from the group consisting of:
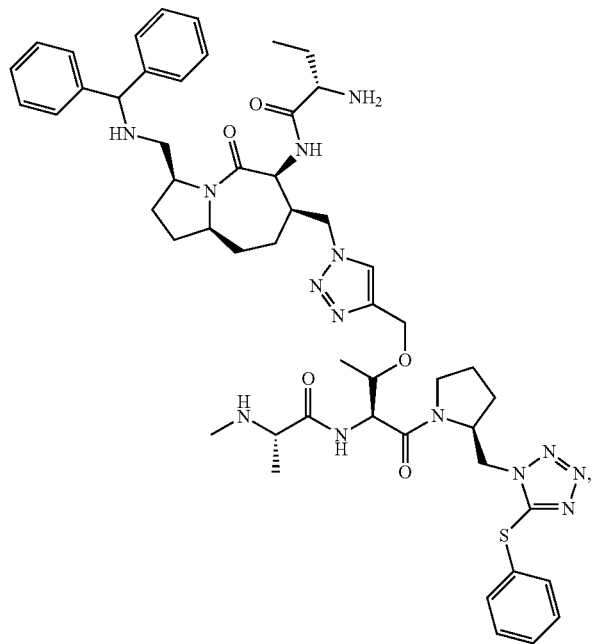
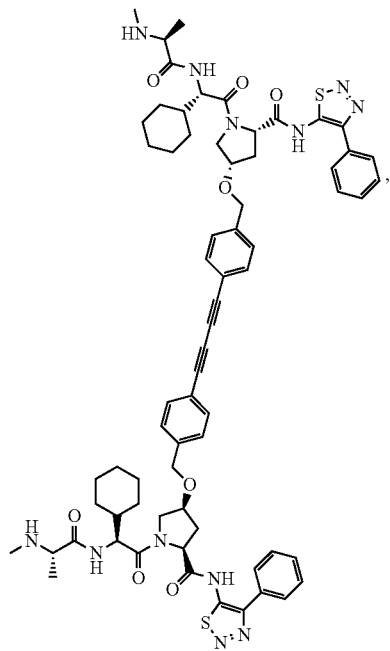
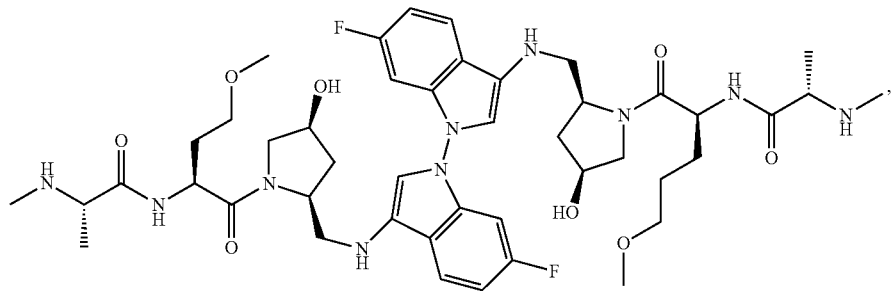

-continued

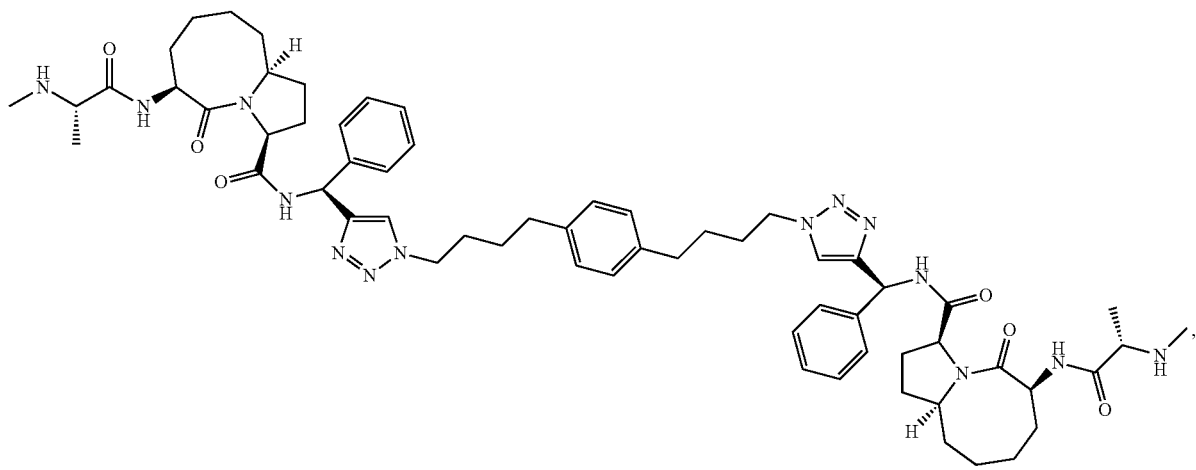

and

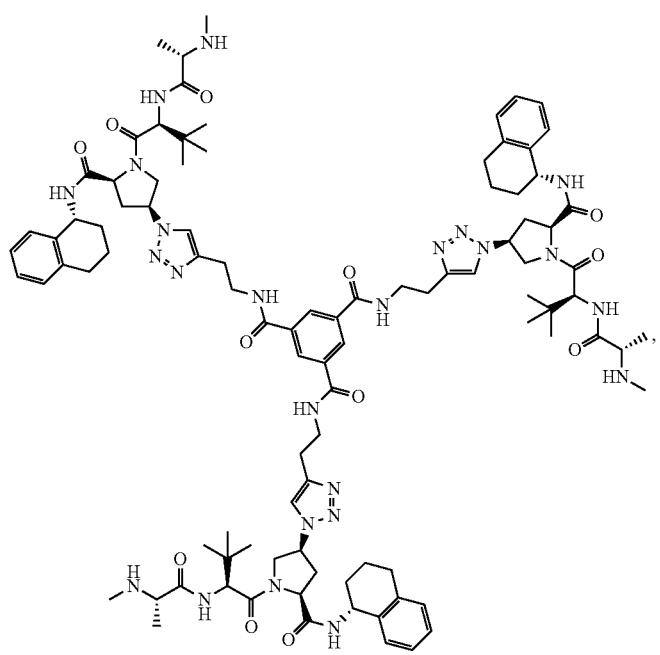

which are described in WO Pub. No. 2009/060292, U.S. Pat. No. 7,517,906, WO Pub. No. 2008/134679, WO Pub. No. 2007/130626, and WO Pub. No. 2008/128121.

In any of the compounds described herein, the ILM can have the structure of Formula (XXII) or (XXIII), which are derived from the IAP ligands described in WO Pub. No. 2015/006524 and Perez H L, *Discovery of potent heterodimeric antagonists of inhibitor of apoptosis proteins (IAPs) with sustained antitumor activity*. J. Med. Chem. 58(3), 1556-62 (2015), or an unnatural mimetic thereof:

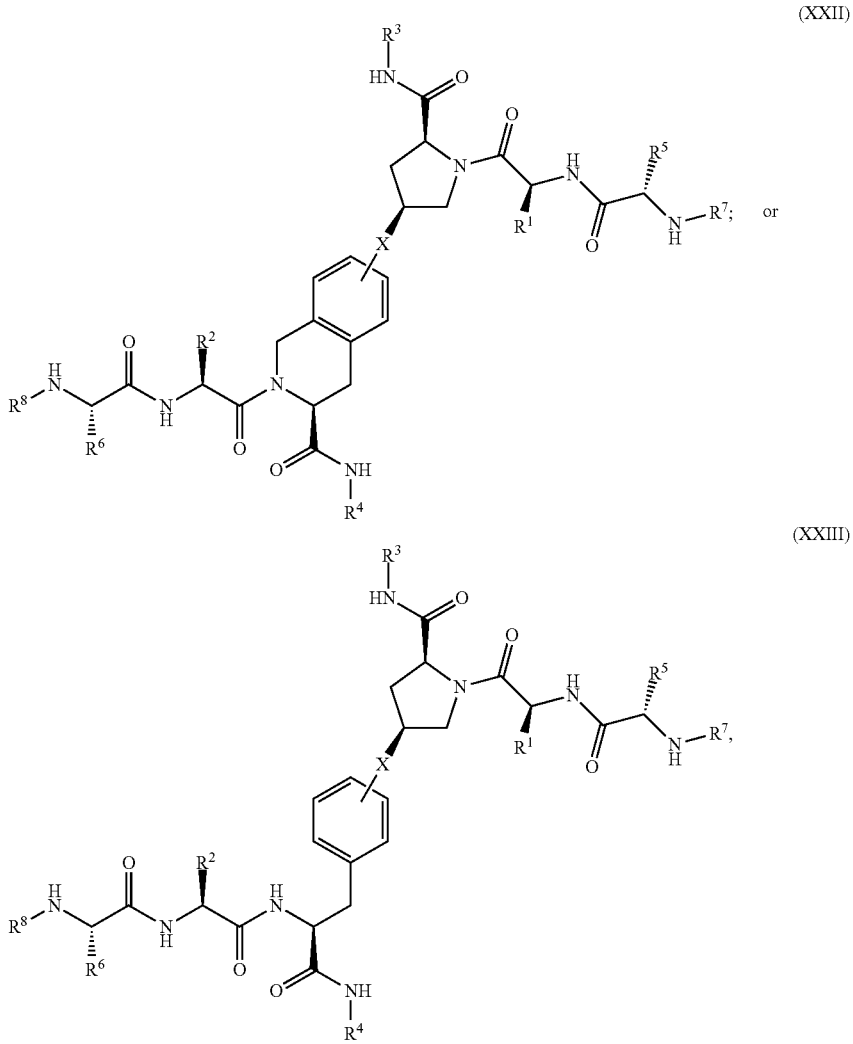

wherein:
R¹ of Formula (XXII) or (XXIII) is optionally substituted alkyl, optionally substituted cycloalkyl, optionally substituted cycloalkylalkyl, optionally substituted heterocyclyl, optionally substituted arylalkyl or optionally substituted aryl;

R² of Formula (XXII) or (XXIII) is optionally substituted alkyl, optionally substituted cycloalkyl, optionally substituted cycloalkylalkyl, optionally substituted heterocyclyl, optionally substituted arylalkyl or optionally substituted aryl;

or alternatively, R¹ and R² of Formula (XXII) or (XXIII) are independently optionally substituted thioalkyl wherein the substituents attached to the S atom of the thioalkyl are optionally substituted alkyl, optionally substituted branched alkyl, optionally substituted heterocyclyl, —(CH$_2$)$_v$COR$^{20}$, —CH$_2$CHR$^{21}$COR$^{22}$ or —CH$_2$R$^{23}$.

wherein:
v is an integer from 1-3;
R$^{20}$ and R$^{22}$ of —(CH$_2$)$_v$COR$^{20}$ and —CH$_2$R$^{23}$ are independently selected from OH, NR$^{24}$R$^{25}$ or OR$^{26}$;
R$^{21}$ of —CH$_2$CHR$^{21}$COR$^2$ is selected from the group NR$^{24}$R$^{25}$.

R$^{23}$ of —CH$_2$R$^{23}$ is selected from optionally substituted aryl or optionally substituted heterocyclyl, where the optional substituents include alkyl and halogen;

R$^{24}$ of NR$^{24}$R$^{25}$ is selected from hydrogen or optionally substituted alkyl;

R$^{25}$ of NR$^{24}$R$^{25}$ is selected from hydrogen, optionally substituted alkyl, optionally substituted branched alkyl, optionally substituted arylalkyl, optionally substituted heterocyclyl, —CH$_2$(OCH$_2$CH$_2$O)$_m$CH$_3$, or a polyamine chain, such as spermine or spermidine;

R$^{26}$ of OR$^{26}$ is selected from optionally substituted alkyl, wherein the optional substituents are OH, halogen or NH$_2$; and m is an integer from 1-8;

R³ and R⁴ of Formula (XXII) or (XXIII) are independently selected from optionally substituted alkyl, optionally substituted cycloalkyl, optionally substituted aryl, optionally substituted arylalkyl, optionally substituted arylalkoxy, optionally substituted heteroaryl, optionally substituted heterocyclyl, optionally substituted heteroarylalkyl or optionally substituted heterocycloalkyl, wherein the substituents are alkyl, halogen or OH;

$R^5$, $R^6$, $R^7$ and $R^8$ of Formula (XXII) or (XXIII) are independently selected from hydrogen, optionally substituted alkyl or optionally substituted cycloalkyl; and X is selected from a bond or a chemical linker group, and/or a pharmaceutically acceptable salt, tautomer or stereoisomer thereof.

In certain embodiments, X is a bond or is selected from the group consisting of:

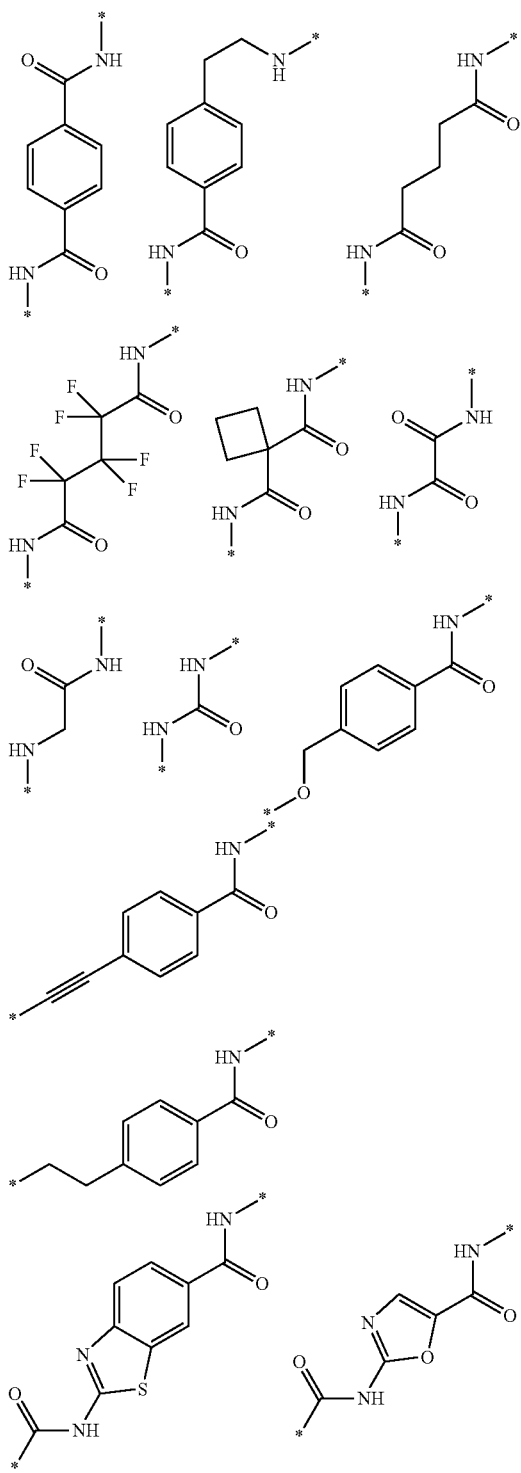

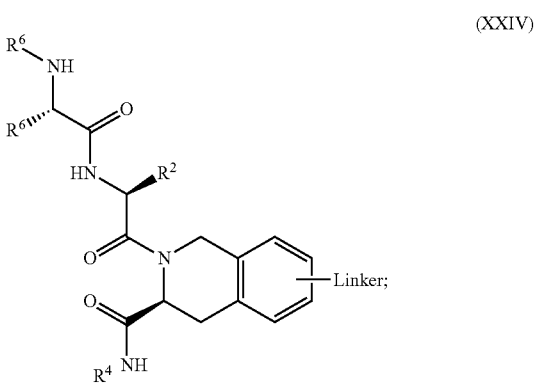

wherein "*" is the point of attachment of a PTM, L or ULM, e.g., an ILM.

In any of the compounds described herein, the ILM can have the structure of Formula (XXIV) or (XXVI), which are derived from the IAP ligands described in WO Pub. No. 2015/006524 and Perez H L, Discovery of potent heterodimeric antagonists of inhibitor of apoptosis proteins (IAPs) with sustained antitumor activity. J. Med. Chem. 58(3), 1556-62 (2015), or an unnatural mimetic thereof, and the chemical linker to linker group L as shown:

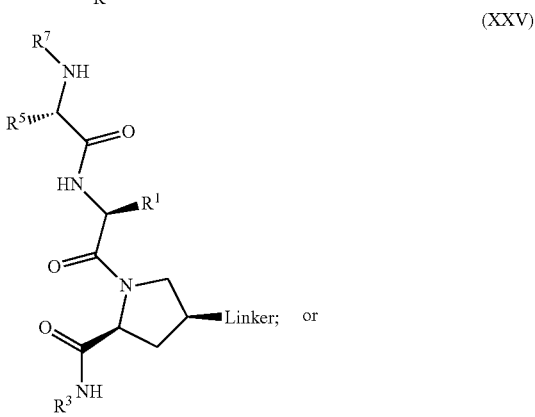

(XXIV)

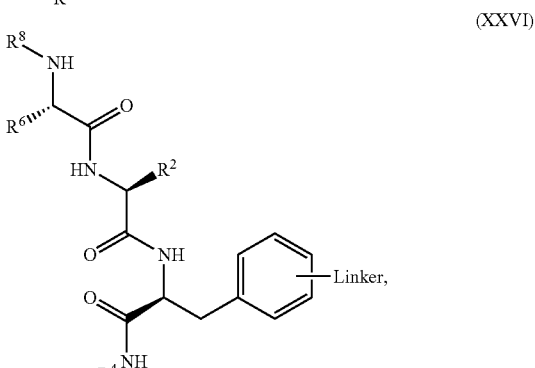

(XXV)

(XXVI)

wherein:

$R^1$ of Formula (XXIV), (XXV) or (XXVI) is selected from optionally substituted alkyl, optionally substituted cycloalkyl, optionally substituted cycloalkylalkyl, optionally substituted heterocyclyl, optionally substituted arylalkyl or optionally substituted aryl;

$R^2$ of Formula (XXIV), (XXV) or (XXVI) is selected from optionally substituted alkyl, optionally substituted cycloalkyl, optionally substituted cycloalkylalkyl, optionally substituted heterocyclyl, optionally substituted arylalkyl or optionally substituted aryl;

or alternatively, $R^1$ and $R^2$ of Formula (XXIV), (XXV) or (XXVI) are independently selected from optionally substituted thioalkyl wherein the substituents attached to the S atom of the thioalkyl are optionally substituted alkyl, optionally substituted branched alkyl, optionally substituted heterocyclyl, —$(CH_2)_vCOR^{20}$, —$CH_2CHR^{21}COR^{22}$ or —$CH_2R^{23}$, wherein:

v is an integer from 1-3;

$R^{20}$ and $R^{22}$ of —$(CH_2)_vCOR^{20}$ and —$CH_2R^{23}$ are independently selected from OH, $NR^{24}R^{25}$ or $OR^{26}$;

$R^{21}$ of —$CH_2CHR^{21}COR^2$ is selected from $NR^{24}R^{25}$;

$R^{23}$ of —$CH_2R^{23}$ is selected from optionally substituted aryl or optionally substituted heterocyclyl, wherein the optional substituents include alkyl and halogen;

$R^{24}$ of $NR^{24}R^{25}$ is selected from hydrogen or optionally substituted alkyl;

$R^{25}$ of $NR^{24}R^{25}$ is selected from hydrogen, optionally substituted alkyl, optionally substituted branched alkyl, optionally substituted arylalkyl, optionally substituted heterocyclyl, —$CH_2(OCH_2CH_2O)_mCH_3$, or a polyamine chain, such as spermine or spermidine;

$R^{26}$ of $OR^{26}$ is selected from optionally substituted alkyl, wherein the optional substituents are OH, halogen or $NH_2$; and m is an integer from 1-8;

$R^3$ and $R^4$ of Formula (XXIV), (XXV) or (XXVI) are independently optionally substituted alkyl, optionally substituted cycloalkyl, optionally substituted aryl, optionally substituted arylalkyl, optionally substituted arylalkoxy, optionally substituted heteroaryl, optionally substituted heterocyclyl, optionally substituted heteroarylalkyl or optionally substituted heterocycloalkyl, wherein the substituents are alkyl, halogen or OH;

$R^5$, $R^6$, $R^7$ and $R^8$ of Formula (XXIV), (XXV) or (XXVI) are independently hydrogen, optionally substituted alkyl or optionally substituted cycloalkyl; and/or a pharmaceutically acceptable salt, tautomer or stereoisomer thereof.

In a particular embodiment, the ILM according to Formulas (XXII) through (XXVI):

$R^7$ and $R^8$ are selected from the H or Me;

$R^5$ and $R^6$ are selected from the group comprising:

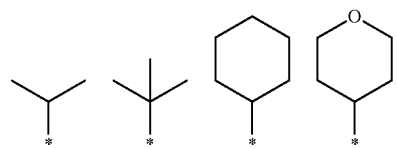

$R^3$ and $R^4$ are selected from the group comprising:

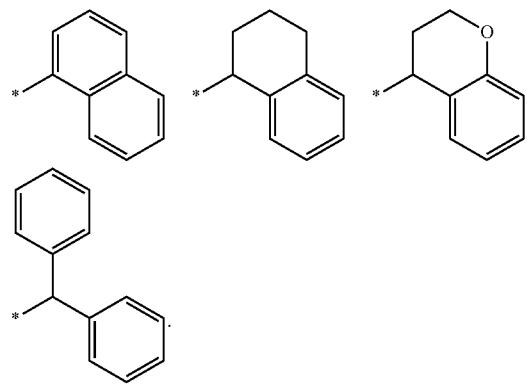

In any of the compounds described herein, the ILM can have the structure of Formula (XXVII) or (XXVII), which are derived from the IAP ligands described in WO Pub. No. 2014/055461 and Kim, K S, *Discovery of tetrahydroisoquinoline-based bivalent heterodimeric IAP antagonists*. Bioorg. Med. Chem. Lett. 24(21), 5022-9 (2014), or an unnatural mimetic thereof:

(XXVII)

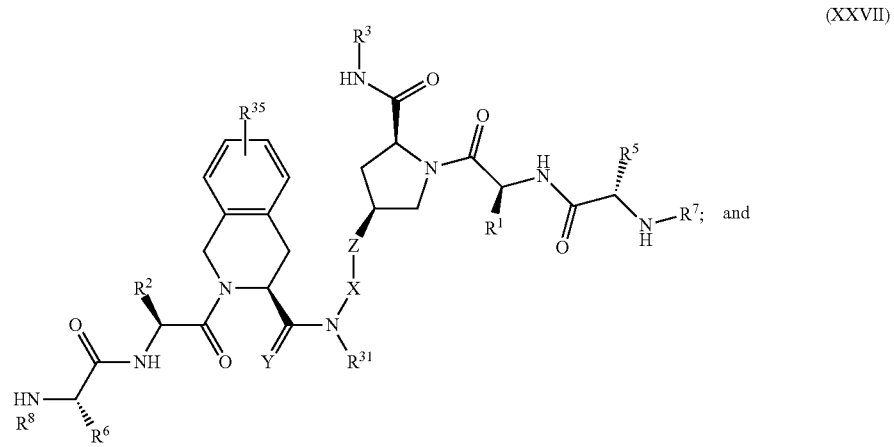

(XXVIII)

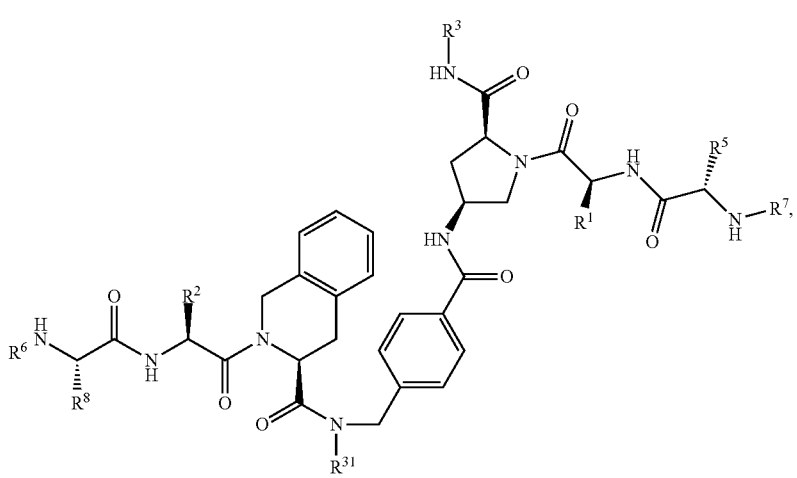

wherein:

$R^{35}$ is 1-2 substituents selected from alkyl, halogen, alkoxy, cyano and haloalkoxy;

$R^1$ of Formula (XXVII) and (XXVIII) is selected from H or an optionally substituted alkyl, optionally substituted cycloalkyl, optionally substituted cycloalkylalkyl, optionally substituted heterocyclyl, optionally substituted arylalkyl or optionally substituted aryl;

$R^2$ of Formula (XXVII) and (XXVIII) is selected from H or an optionally substituted alkyl, optionally substituted cycloalkyl, optionally substituted cycloalkylalkyl, optionally substituted heterocyclyl, optionally substituted arylalkyl or optionally substituted aryl;

or alternatively, $R^1$ and $R^2$ of Formula (XXVII) and (XXVIII) are independently selected from an optionally substituted thioalkyl —$CR^{60}R^{61}SR^{70}$, wherein $R^{60}$ and $R^{61}$ are selected from H or methyl, and $R^{70}$ is selected from an optionally substituted alkyl, optionally substituted branched alkyl, optionally substituted heterocyclyl, —$(CH_2)_vCOR^{20}$, —$CH_2CHR^{21}COR^{22}$ or —$CH_2R^{23}$, wherein:

v is an integer from 1-3;

$R^{20}$ and $R^{22}$ of —$(CH_2)_vCOR^{20}$ and —$CH_2CHR^{21}COR^{22}$ are independently selected from OH, $NR^{24}R^{25}$ or $OR^{26}$;

$R^{21}$ of —$CH_2CHR^{21}COR^{22}$ is selected from $NR^{24}R^{25}$;

$R^{23}$ of —$CH_2R^{23}$ is selected from an optionally substituted aryl or optionally substituted heterocyclyl, where the optional substituents include alkyl and halogen;

$R^{24}$ of $NR^{24}R^{25}$ is selected from hydrogen or optionally substituted alkyl;

$R^{25}$ of $NR^{24}R^{25}$ is selected from hydrogen, optionally substituted alkyl, optionally substituted branched alkyl, optionally substituted arylalkyl, optionally substituted heterocyclyl, —$CH_2CH_2(OCH_2CH_2)_mCH_3$, or a polyamine chain —$[CH_2CH_2(CH_2)_\delta NH]_\psi CH_2CH_2(CH_2)_{\overline{\omega}}NH_2$, such as spermine or spermidine;

wherein $\delta=0-2$, $\psi=1-3$, $\overline{\omega}=0-2$;

$R^{26}$ of $OR^{26}$ is an optionally substituted alkyl, wherein the optional substituents are OH, halogen or $NH_2$; and m is an integer from 1-8, $R^3$ and $R^4$ of Formula (XXVII) and (XXVIII) are independently selected from an optionally substituted alkyl, optionally substituted cycloalkyl, optionally substituted aryl, optionally substituted arylalkyl, optionally substituted arylalkoxy, optionally substituted heteroaryl, optionally substituted heterocyclyl, optionally substituted heteroarylalkyl or optionally substituted heterocycloalkyl, wherein the substituents are alkyl, halogen or OH;

$R^5$, $R^6$, $R^7$ and $R^8$ of Formula (XXVII) and (XXVIII) are independently selected from hydrogen, optionally substituted alkyl or optionally substituted cycloalkyl;

$R^{31}$ of Formulas (XXVII) and (XXVIII) is selected from alkyl, aryl, arylalkyl, heteroaryl or heteroarylalkyl optionally further substituted, preferably selected form the group consisting of:

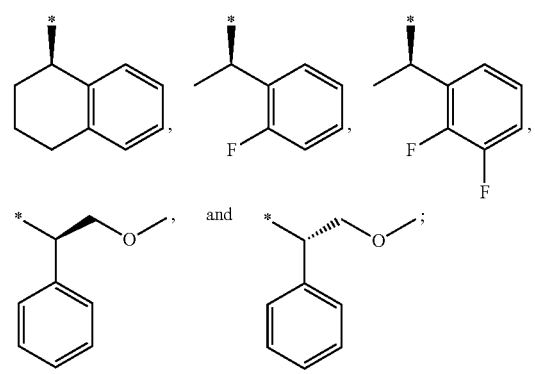

X of Formulas (XXVII) and (XXVIII) is selected from —$(CR^{81}R^{82})_m$—, optionally substituted heteroaryl or heterocyclyl,

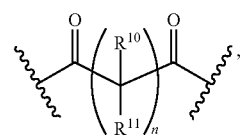

-continued

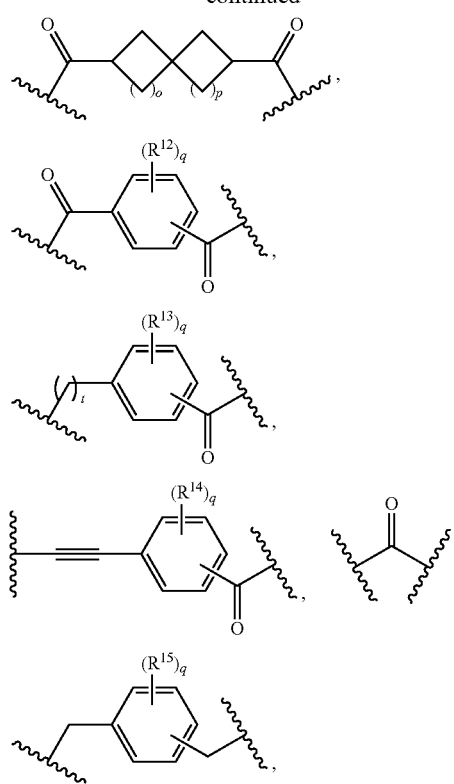

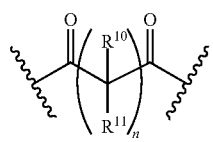

Z of Formulas (XXVII) is selected from C=O, —O—, —NR, —CONH—, —NHCO—, or may be absent;

$R^{81}$ and $R^{82}$ of —$(CR^{81}R^{82})_m$— are independently selected from hydrogen, halogen, alkyl or cycloalkyl, or $R^{81}$ and $R^{82}$ can be taken together to form a carbocyclic ring;

$R^{10}$ and $R^{11}$ of

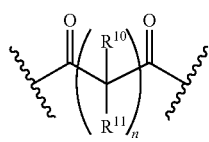

are independently selected from hydrogen, halogen or alkyl;

$R^{12}$, $R^{13}$, $R^{14}$, $R^{15}$ and $R^{16}$ of

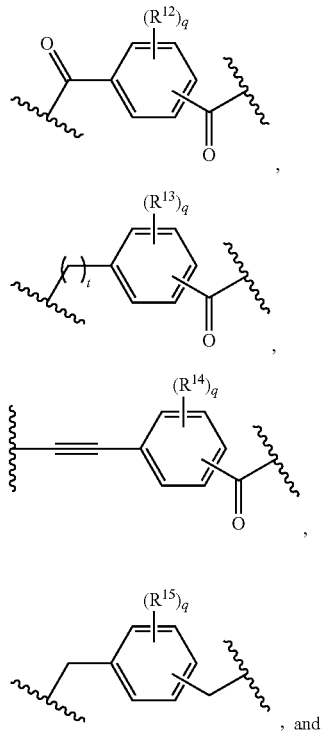

are independently selected from hydrogen, halogen or optionally substituted alkyl or $OR^{17}$;

$R^{17}$ is selected from hydrogen, optionally substituted alkyl or optionally substituted cycloalkyl;

m and n of —$(CR^{21}R^{22})_m$— and

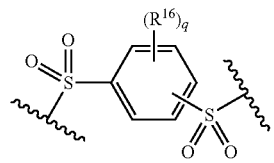

are independently 0, 1, 2, 3, or 4;

and p of

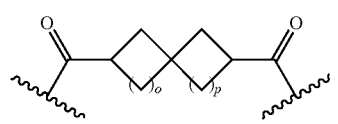

are independently 0, 1, 2 or 3;

q and t of

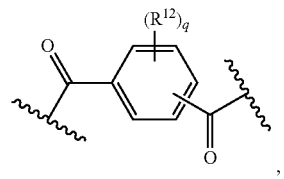,

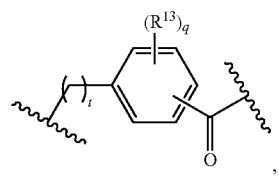,

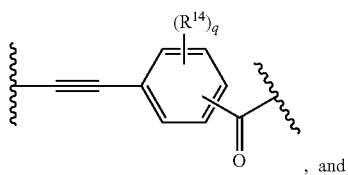, and

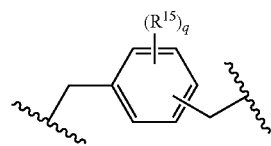

are independently 0, 1, 2, 3, or 4;
r of

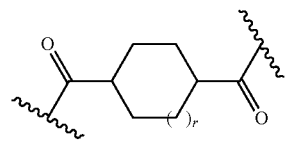

is 0 or 1;

and/or a pharmaceutically acceptable salt, tautomer or stereoisomer thereof.

In any of the compounds described herein, the ILM can have the structure of Formula (XXIX), (XXX), (XXXI), or (XXXII), which are derived from the IAP ligands described in WO Pub. No. 2014/055461 and Kim, K S, *Discovery of tetrahydroisoquinoline-based bivalent heterodimeric IAP antagonists*. Bioorg. Med. Chem. Lett. 24(21), 5022-9 (2014), or an unnatural mimetic thereof, and the chemical linker to linker group L as shown:

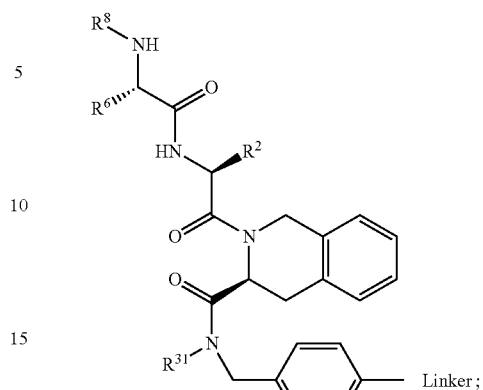 (XXIX)

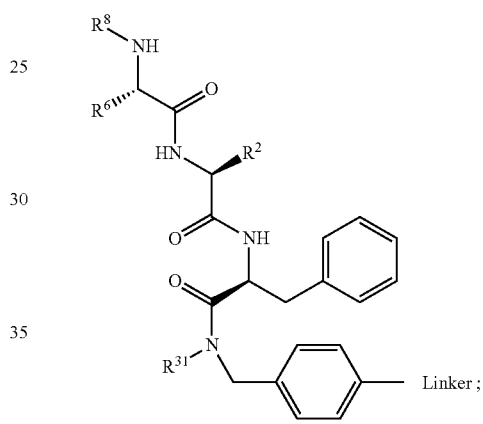 (XXX)

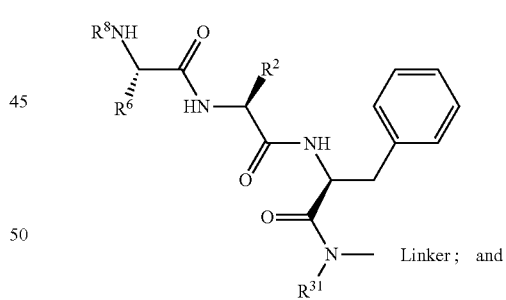 (XXXI)

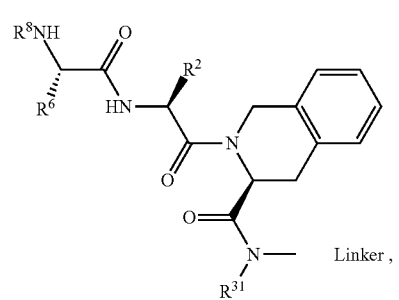 (XXXII)

wherein:
R² of Formula (XXIX) through (XXXII) is selected from H, an optionally substituted alkyl, optionally substituted cycloalkyl, optionally substituted cycloalkylalkyl, optionally substituted heterocyclyl, optionally substituted arylalkyl or optionally substituted aryl;

or alternatively;
R¹ and R² of Formula (XXVII) and (XXVIII) are independently selected from H, an optionally substituted thioalkyl —CR⁶⁰R⁶¹SR⁷⁰ wherein R⁶⁰ and R⁶¹ are selected from H or methyl, and R⁷⁰ is an optionally substituted alkyl, optionally substituted branched alkyl, optionally substituted heterocyclyl, —(CH₂)ᵥCOR²⁰, —CH₂CHR²¹COR²² or —CH₂R²³.

wherein:
v is an integer from 1-3;
R²⁰ and R²² of —(CH₂)ᵥCOR²⁰ and —CH₂CHR²¹COR²² are independently selected from OH, NR²⁴R²⁵ or OR²⁶.
R²¹ of —CH₂CHR²¹COR²² is selected from NR²⁴R²⁵.
R²³ of —CH₂R²³ is selected from an optionally substituted aryl or optionally substituted heterocyclyl, where the optional substituents include alkyl and halogen;
R²⁴ of NR²⁴R²⁵ is selected from hydrogen or optionally substituted alkyl;
R²⁵ of NR²⁴R²⁵ is selected from hydrogen, optionally substituted alkyl, optionally substituted branched alkyl, optionally substituted arylalkyl, optionally substituted heterocyclyl, —CH₂CH₂(OCH₂CH₂)ₘCH₃, or a polyamine chain —[CH₂CH₂(CH₂)δNH]ψCH₂CH₂(CH₂)ψNH₂, such as spermine or spermidine, wherein δ=0-2, ψ=1-3, ω=0-2;
R²⁶ of OR²⁶ is an optionally substituted alkyl, wherein the optional substituents are OH, halogen or NH₂;
m is an integer from 1-8;
R⁶ and R⁸ of Formula (XXIX) through (XXXII) are independently selected from hydrogen, optionally substituted alkyl or optionally substituted cycloalkyl; and R³¹ of Formulas (XXIX) through (XXXII) is selected from alkyl, aryl, arylalkyl, heteroaryl or heteroarylalkyl optionally further substituted, preferably selected form the group consisting of:

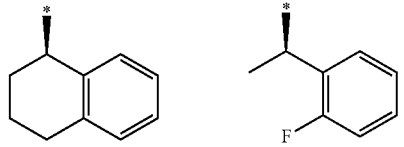

,

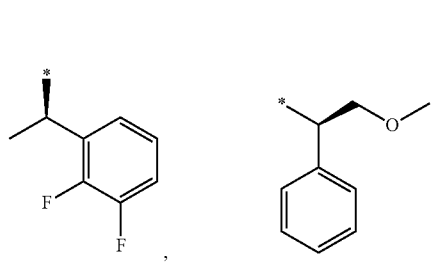

, and

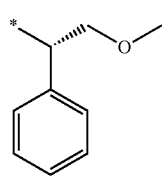

In certain embodiments, the ILM of the compound is:

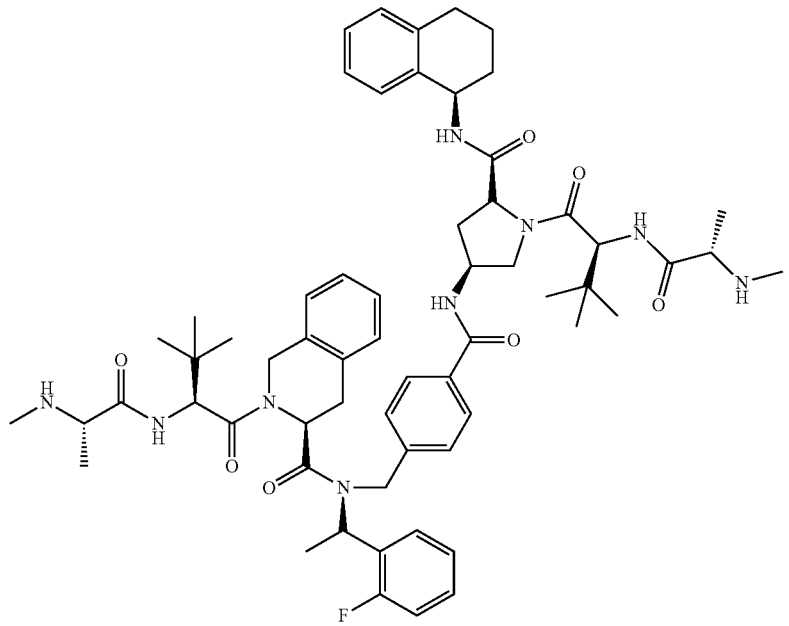

In any of the compounds described herein, the ILM can have the structure of Formula (XXXIII), which are derived from the IAP ligands described in WO Pub. No. 2014/074658 and WO Pub. No. 2013/071035, or an unnatural mimetic thereof:

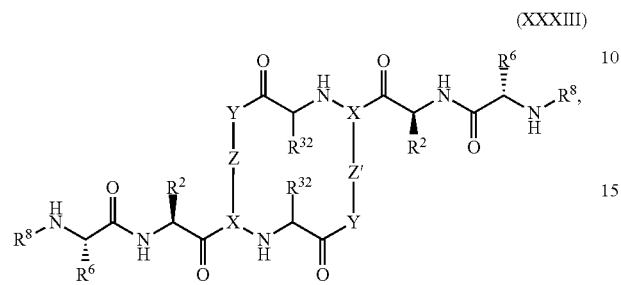

wherein:

R² of Formula (XXXIII) is selected from H, an optionally substituted alkyl, optionally substituted cycloalkyl, optionally substituted cycloalkylalkyl, optionally substituted heterocyclyl, optionally substituted arylalkyl or optionally substituted aryl;

R⁶ and R⁸ of Formula (XXXIII) are independently selected from hydrogen, optionally substituted alkyl or optionally substituted cycloalkyl;

R³² of Formula (XXXIII) is selected from (C1-C4 alkylene)-R³³ wherein R³³ is selected from hydrogen, aryl, heteroaryl or cycloalkyl optionally further substituted;

X of Formula (XXXIII) is selected from:

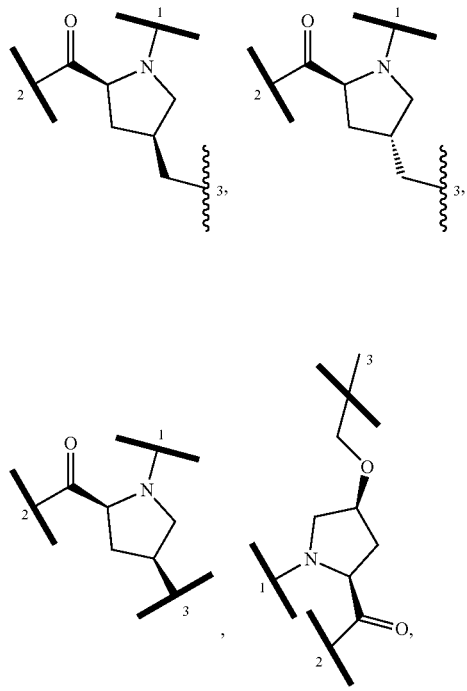

Z and Z' of Formula (XXXIII) are independently selected from:

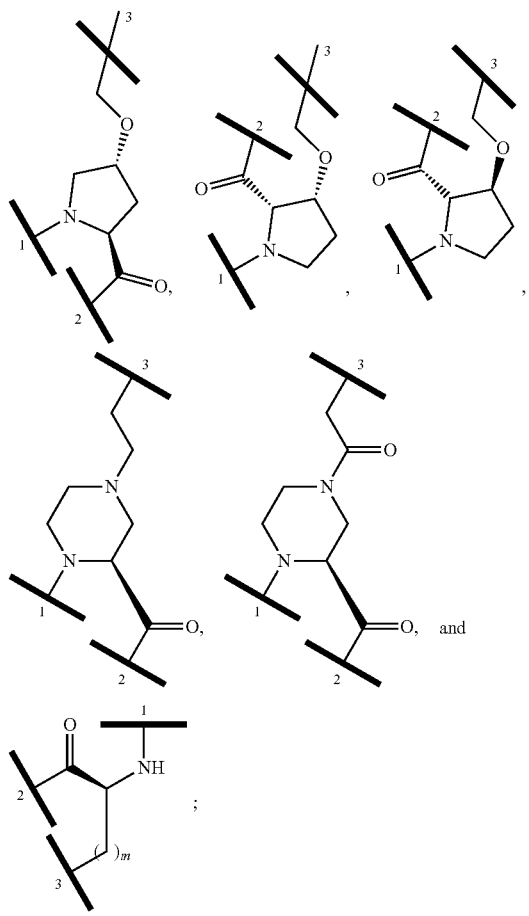

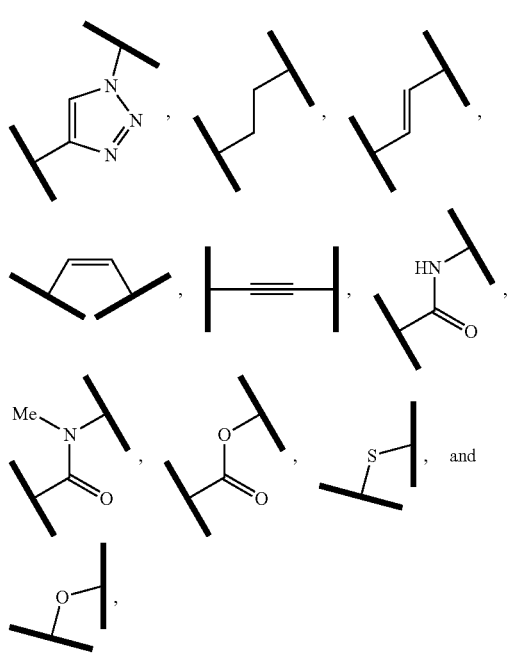

wherein each
represents a point of attachment to the compound, and Z and Z'
cannot both be
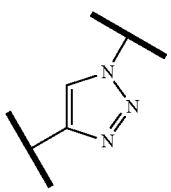
in any given compound;
Y of Formula (XXXIII) is selected from:
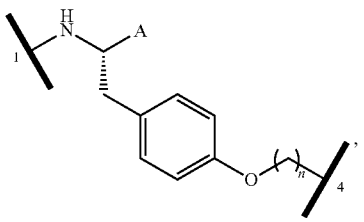
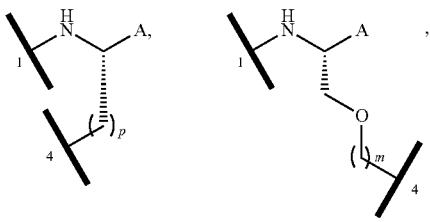
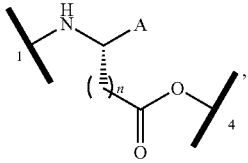
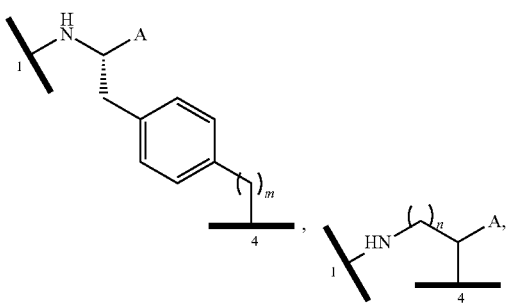
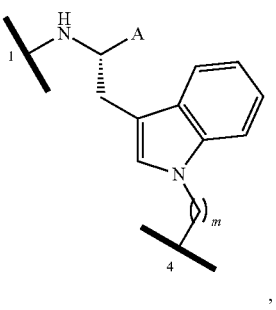
, and
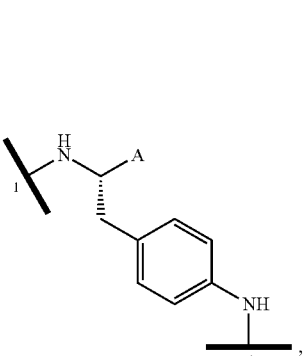
wherein Z and Z' of Formula (XXXIII) are the same and Z is
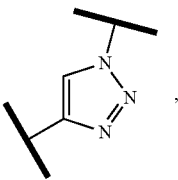
wherein each
represents a point of attachment to the compound, X is selected from:
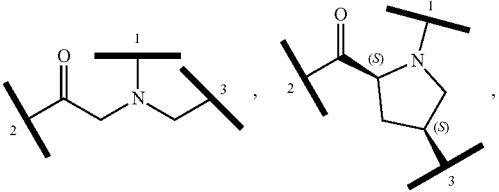

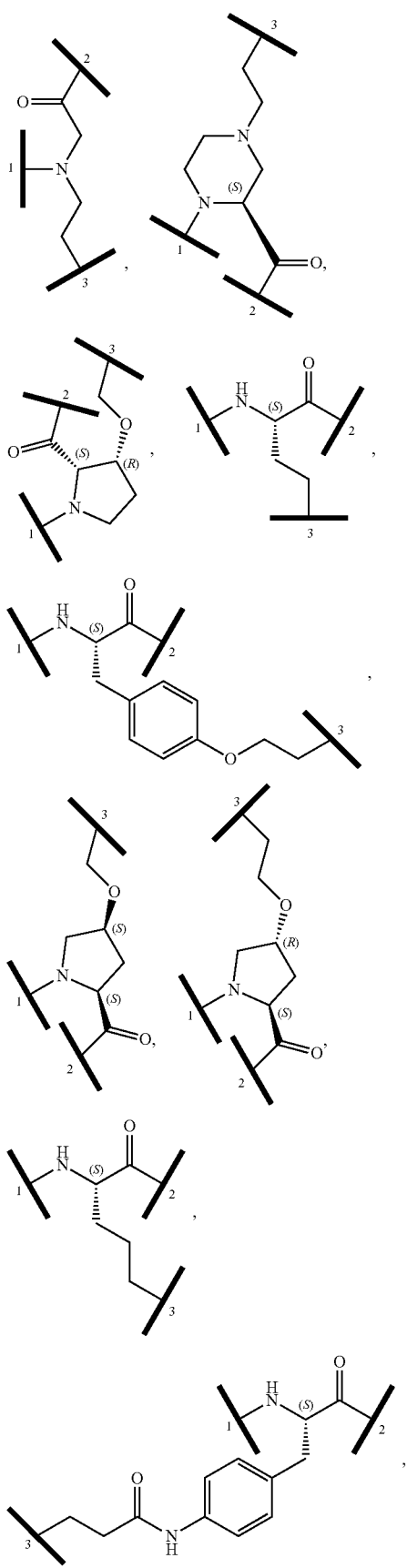
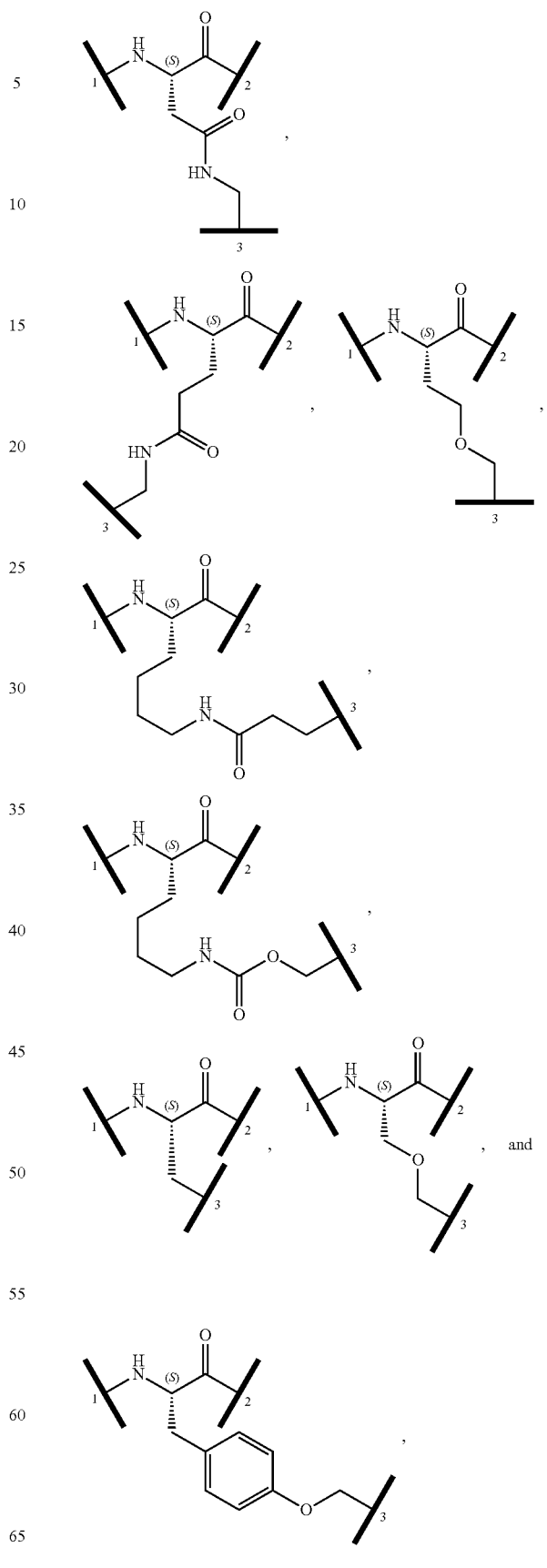

and
Y of Formula (XXXIII) is independently selected from:
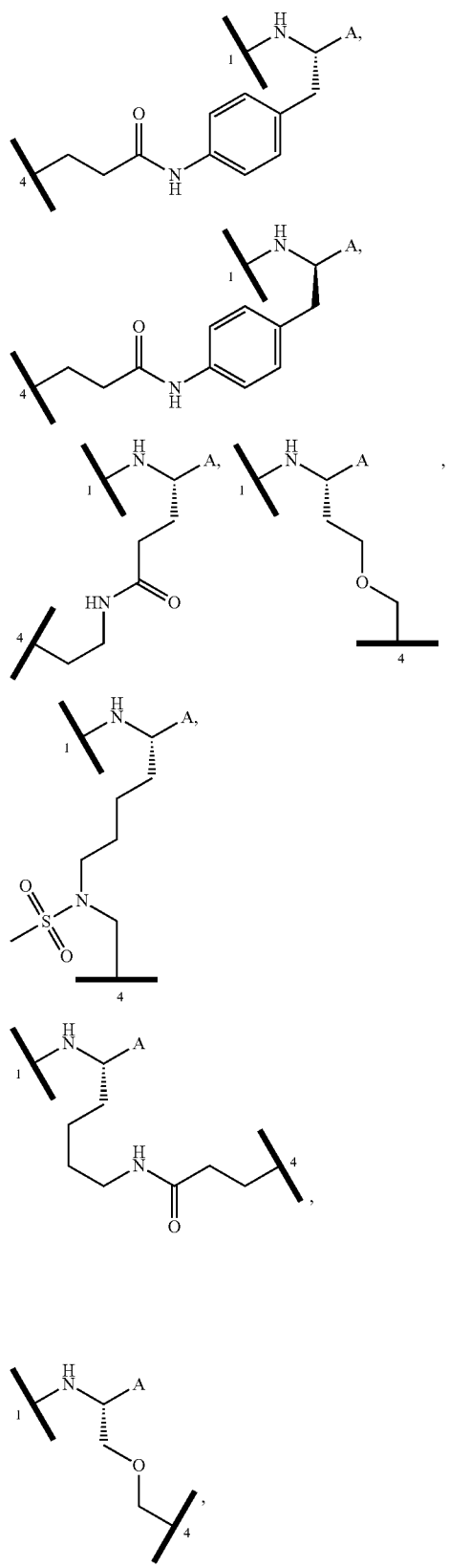
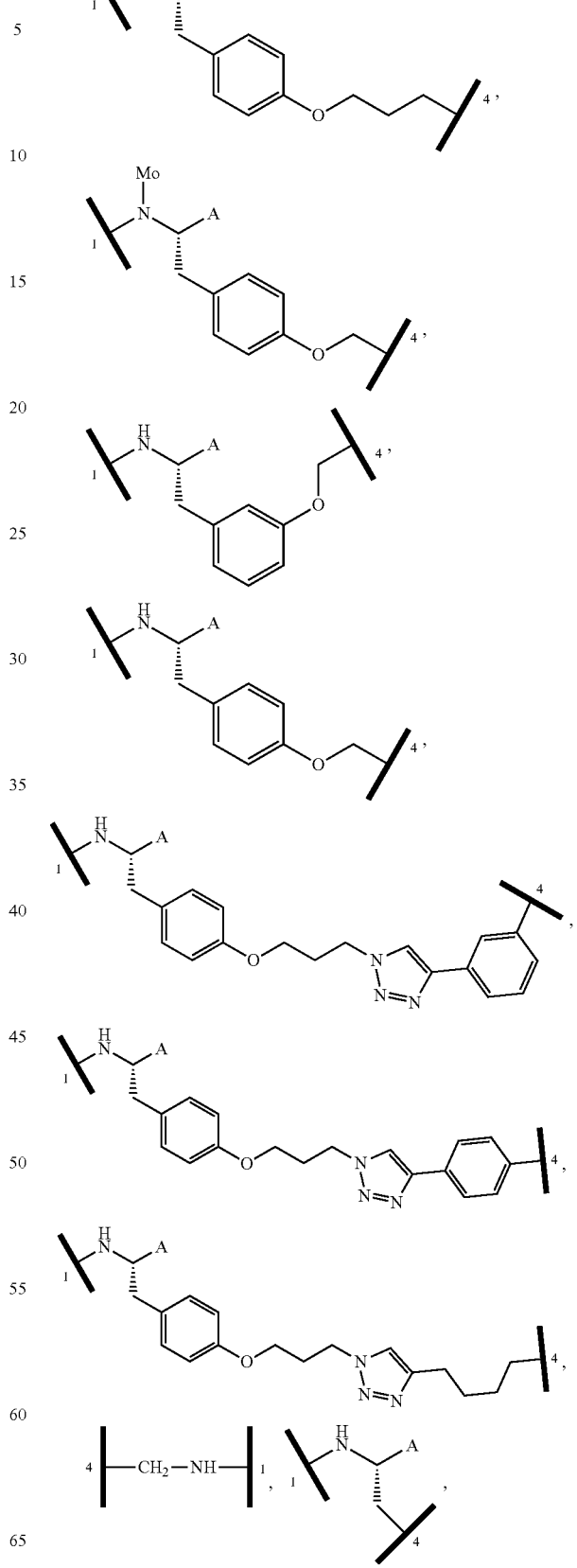

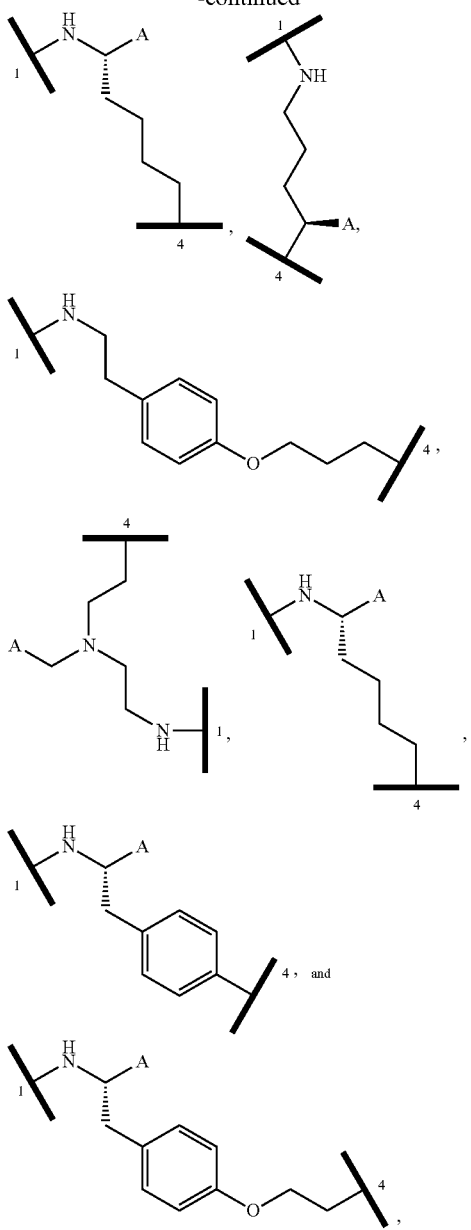

wherein:

represents a point of attachment to a —C=O portion of the compound;

represents a point of attachment to a —NH portion of the compound;

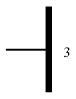

represents a first point of attachment to Z;

represents a second point of attachment to Z;

m is an integer from 0-3;
n is an integer from 1-3;
p is an integer from 0-4; and
A is —C(O)R³;

R³ is selected from —C(O)R³ is OH, NHCN, NHSO₂R¹⁰, NHOR¹¹ or N(R¹²)(R¹³);

R¹⁰ and F¹¹ of NHSO₂R¹⁰ and NHOR¹¹ are independently selected from hydrogen, optionally substituted —C₁-C₄ alkyl, cycloalkyl, aryl, heteroaryl, heterocyclyl or heterocycloalkyl;

R¹² and R¹³ of N(R¹²)(R¹³) are independently selected from hydrogen, —C₁-C₄ alkyl, —(C₁-C₄) alkylene)-NH—(C₁-C₄ alkyl), and —(C₁-C₄ alkylene)-O—(C₁-C₄ hydroxyalkyl), or R¹² and R¹³ taken together with the nitrogen atom to which they are commonly bound to form a saturated heterocyclyl optionally comprising one additional heteroatom selected from N, O and S, and wherein the saturated heterocycle is optionally substituted with methyl.

In any of the compounds described herein, the ILM can have the structure of Formula (XXXIV) or (XXXV), which are derived from the IAP ligands described in WO Pub. No. 2014/047024, or an unnatural mimetic thereof:

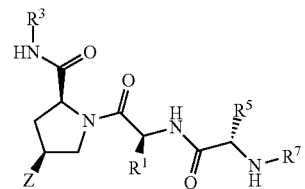

(XXXIV)

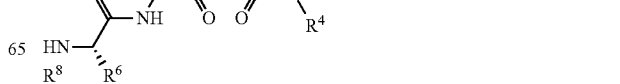

(XXXV)

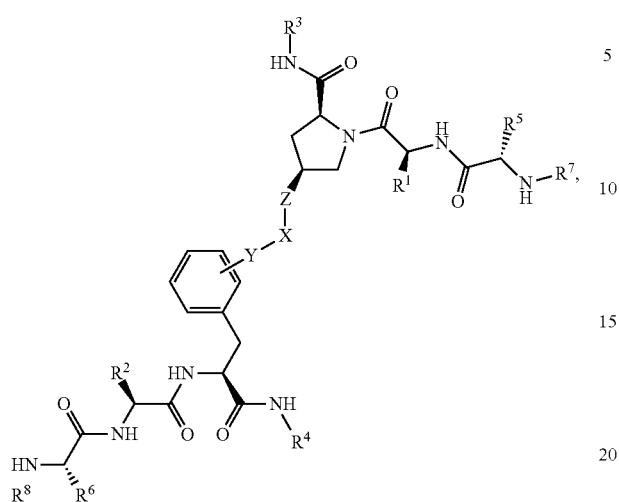

wherein:
X of Formula (XXXIV) or (XXXV) is absent or a group selected from —(CR$^{10}$R$^{11}$)$_m$, optionally substituted heteroaryl or optionally substituted heterocyclyl,

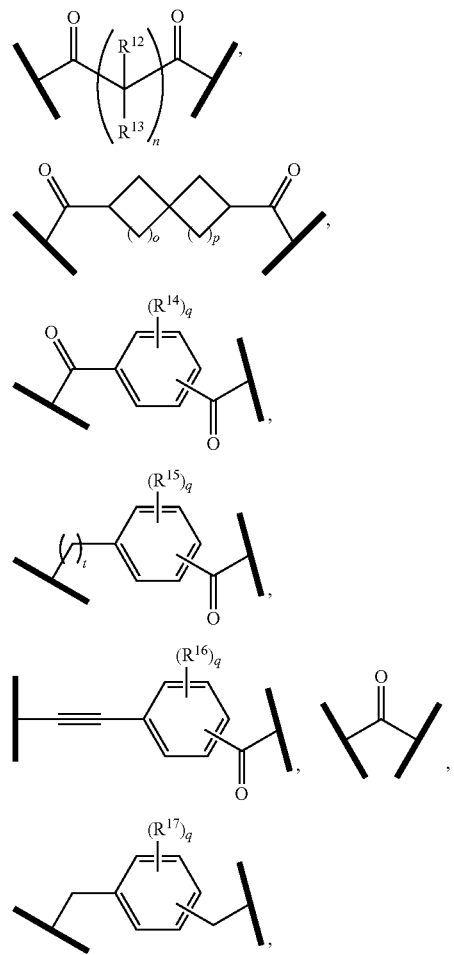

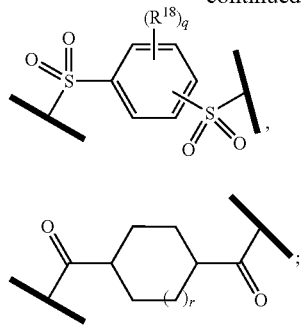

Y and Z of Formula (XXXIV) or (XXXV) are independently selected from C=O, —O—, —NR$^9$—, —CONH—, —NHCO— or may be absent;

R$^1$ and R$^2$ of Formula (XXXIV) or (XXXV) are independently selected from an optionally substituted alkyl, optionally substituted cycloalkyl, optionally substituted cycloalkylalkyl, optionally substituted arylalkyl, optionally substituted aryl, or R$^1$ and R$^2$ of Formula (XXXIV) or (XXXV) are independently selected from optionally substituted thioalkyl wherein the substituents attached to the S atom of the thioalkyl are optionally substituted alkyl, optionally substituted branched alkyl, optionally substituted heterocyclyl, —(CH$_2$)$_v$COR$^{20}$, —CH$_2$CHR$^{21}$COR$^{22}$ or —CH$_2$R$^{23}$; wherein v is an integer from 1-3;

R$^{20}$ and R$^{22}$ of —(CH$_2$)$_v$COR$^{20}$ and —CH$_2$CHR$^{21}$COR$^{22}$ are independently selected from OH, NR$^{24}$R$^{25}$ or OR$^{26}$;

R$^{21}$ of —CH$_2$CHR$^{21}$COR$^{22}$ is selected from NR$^{24}$R$^{25}$;

R$^{23}$ of —CH$_2$R$^{23}$ are selected from an optionally substituted aryl or optionally substituted heterocyclyl, where the optional substituents include alkyl and halogen;

R$^{24}$ of NR$^{24}$R$^{25}$ is selected from hydrogen or optionally substituted alkyl;

R$^{25}$ of NR$^{24}$R$^{25}$ is selected from hydrogen, optionally substituted alkyl, optionally substituted branched alkyl, optionally substituted arylalkyl, optionally substituted heterocyclyl, —CH$_2$(OCH$_2$CH$^{20}$)$_m$CH$_3$, or a polyamine chain;

R$^{26}$ is an optionally substituted alkyl, wherein the optional substituents are OH, halogen or NH$_2$;

m of —(CR$^{10}$R$^{11}$)$_m$ is an integer from 1-8;

R$^3$ and R$^4$ of Formula (XXXIV) or (XXXV) are independently selected from optionally substituted alkyl, optionally substituted cycloalkyl, optionally substituted aryl, optionally substituted arylalkyl, optionally substituted arylalkoxy, optionally substituted heteroaryl, optionally substituted heterocyclyl, optionally substituted heteroarylalkyl or optionally substituted heterocycloalkyl, wherein the substituents are alkyl, halogen or OH;

R$^5$, R$^6$, R$^7$ and R$^8$ of Formula (XXXIV) or (XXXV) are independently selected from hydrogen, optionally substituted alkyl or optionally substituted cycloalkyl;

R$^{10}$ and R$^{11}$ of —(CR$^{10}$R$^{11}$)$_m$ are independently selected from hydrogen, halogen or optionally substituted alkyl;

$R^{12}$ and $R^{13}$ of

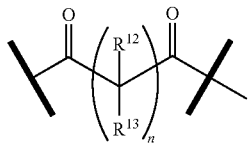

are independently selected from hydrogen, halogen or optionally substituted alkyl, or $R^{12}$ and $R^{13}$ can be taken together to form a carbocyclic ring;

$R^{14}$, $R^{15}$, $R^{16}$, $R^{17}$ and $R^{18}$ of

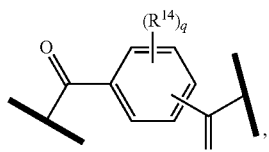

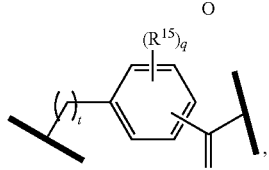

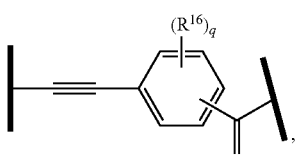

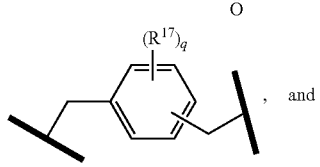, and

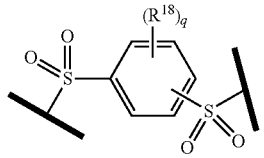

are independently selected from hydrogen, halogen, optionally substituted alkyl or $OR^{19}$;

$R^{19}$ of $OR^{19}$ is selected from hydrogen, optionally substituted alkyl or optionally substituted cycloalkyl;

m and n of —$(CR^{10}R^{11})_m$— are independently 0, 1, 2, 3, or 4;

o and p of —$(CR^{10}R^{11})_m$— are independently 0, 1, 2 or 3;

q of —$(CR^{10}R^{11})_m$— is 0, 1, 2, 3, or 4; r is 0 or 1;

t of —$(CR^{10}R^{11})_m$— is 1, 2, or 3; and/or a pharmaceutically acceptable salt, tautomer or stereoisomer thereof.

In any of the compounds described herein, the ILM can have the structure of Formula (XXXVI), which are derived from the IAP ligands described in WO Pub. No. 2014/025759, or an unnatural mimetic thereof:

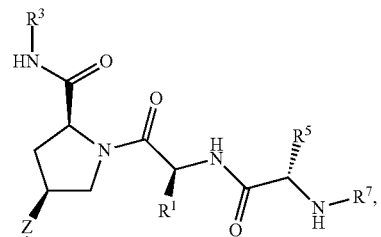

(XXXVI)

where:

A of Formula (XXXVI) is selected from:

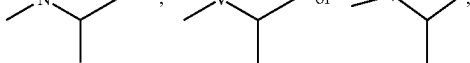

where the dotted line represents an optional double bond;

X of Formula (XXXVI) is selected from: —$(CR^{21}R^{22})_m$—,

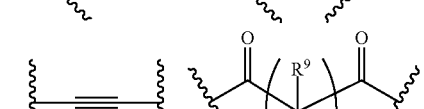

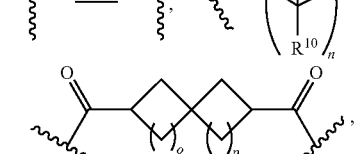

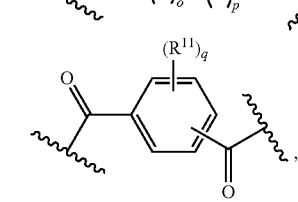

-continued

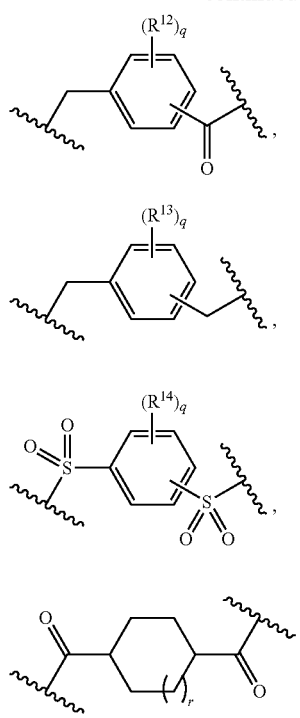

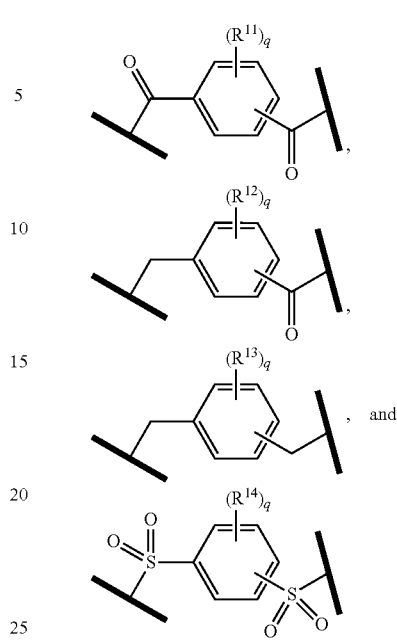

Y and Z of Formula (XXXVI) are independently selected from —O—, —NR$^6$— or are absent;

V of Formula (XXXVI) is selected from —N— or —CH—;

W of Formula (XXXVI) is selected from —CH— or —N—;

R$^1$ of Formula (XXXVI) is selected from an optionally substituted alkyl, optionally substituted cycloalkyl, optionally substituted cycloalkylalkyl, optionally substituted arylalkyl or optionally substituted aryl;

R$^3$ and R$^4$ of Formula (XXXVI) are independently selected from optionally substituted alkyl, optionally substituted cycloalkyl, optionally substituted aryl, optionally substituted heteroaryl, optionally substituted heterocyclyl, optionally substituted arylalkyl, optionally substituted heteroarylalkyl or optionally substituted heterocycloalkyl;

R$^5$, R$^6$, R$^7$ and R$^8$ of Formula (XXIV), (XXV) or (XXVI) are independently selected from hydrogen, optionally substituted alkyl or optionally substituted cycloalkyl, or preferably methyl;

R$^9$ and R$^{10}$ of

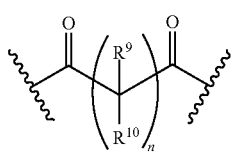

are independently selected from hydrogen, halogen or optionally substituted alkyl, or R$^9$ and R$^{10}$ can be taken together to form a ring;

R$^{11}$, R$^{12}$, R$^{13}$ and R$^{14}$ of

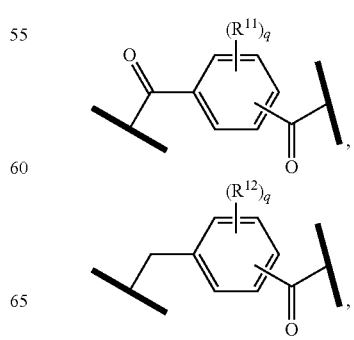

are independently selected from hydrogen, halogen, optionally substituted alkyl or OR$^{15}$;

R$^{15}$ of OR$^{15}$ is selected from hydrogen, optionally substituted alkyl or optionally substituted cycloalkyl;

m and n of —(CR$^{21}$R$^{22}$)$_m$— and

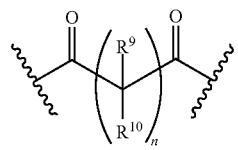

are independently selected from 0, 1, 2, 3, or 4; and p of

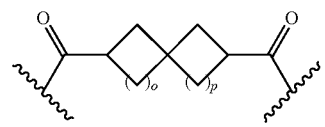

and are independently selected from 0, 1, 2 or 3;

q of

-continued

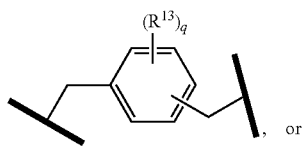, or

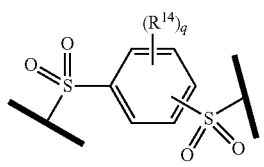

is selected from 0, 1, 2, 3, or 4;
r of

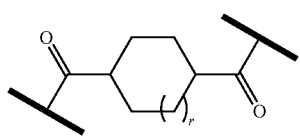

is selected from 0 or 1, and/or or a pharmaceutically acceptable salt, tautomer or stereoisomer thereof.

In any of the compounds described herein, the ILM can have the structure of Formula (XXXVII) or (XXXVIII), which are derived from the IAP ligands described in WO Pub. No. 2014/011712, or an unnatural mimetic thereof:

(XXXVII)

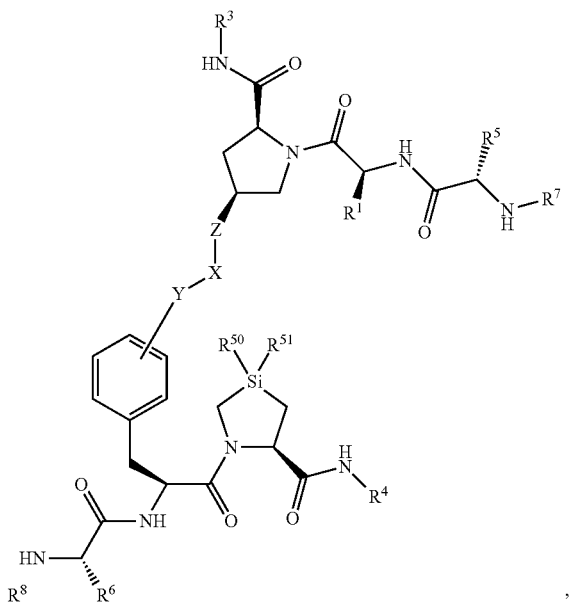

-continued (XXXVIII)

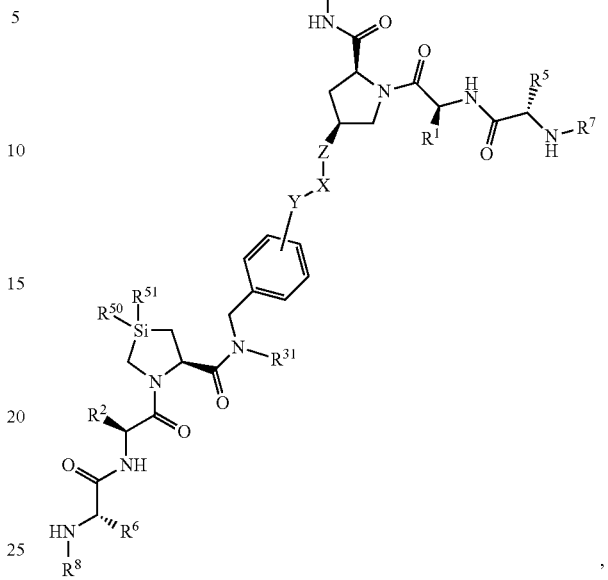

wherein:

X of Formulas (XXXVII) and (XXXVIII) is —(CR$^{16}$R$^{17}$)$_m$—,

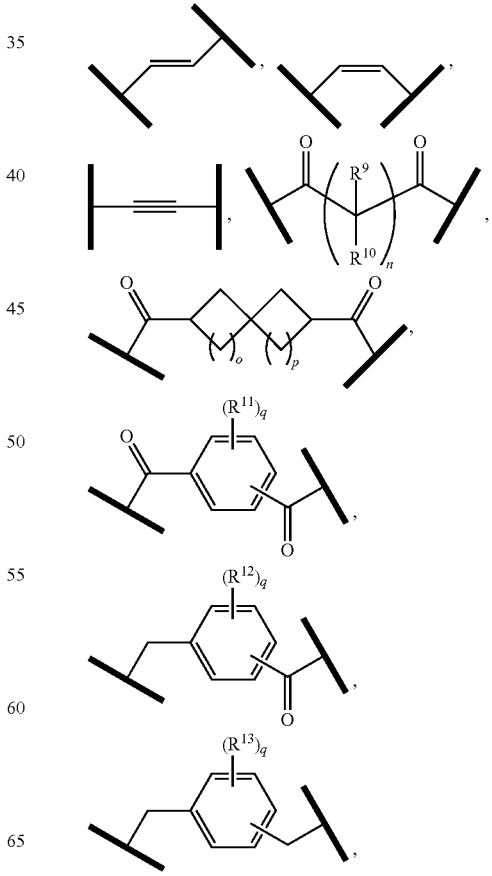

-continued

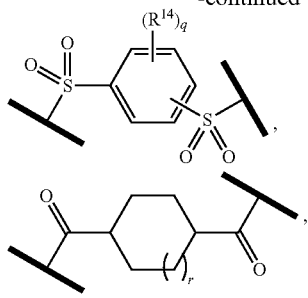

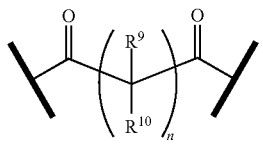

or absent;

Y and Z of Formula (XXXVII) and (XXXVIII) are independently selected from —O—, C=O, NR$^6$ or are absent;

R$^1$ and R$^2$ of Formula (XXXVII) and (XXXVIII) are selected from optionally substituted alkyl, optionally substituted cycloalkyl, optionally substituted alkylaryl or optionally substituted aryl;

R$^3$ and R$^4$ of Formula (XXXVII) and (XXXVIII) are independently selected from optionally substituted alkyl, optionally substituted cycloalkyl, optionally substituted cycloalkylalkyl, optionally substituted arylalkyl or optionally substituted aryl;

R$^5$ and R$^6$ of Formula (XXXVII) and (XXXVIII) are independently selected from optionally substituted alkyl or optionally substituted cycloalkyl;

R$^7$ and R$^8$ of Formula (XXXVII) and (XXXVIII) are independently selected from hydrogen, optionally substituted alkyl or optionally substituted cycloalkyl, or preferably methyl;

R$^9$ and R$^{10}$ of

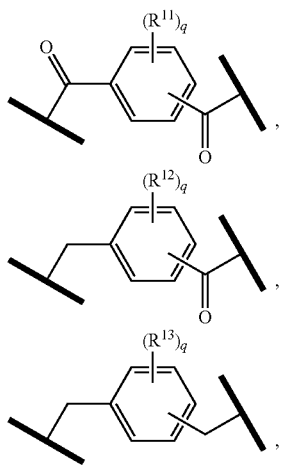

are independently selected from hydrogen, optionally substituted alkyl, or R$^9$ and R$^{10}$ may be taken together to form a ring;

R$^{11}$ to R$^{14}$ of

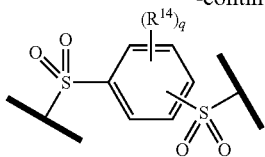

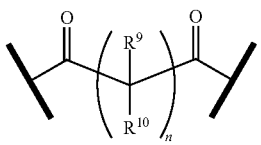

are independently selected from hydrogen, halogen, optionally substituted alkyl or OR$^{15}$;

R$^{15}$ of OR$^{15}$ is selected from hydrogen, optionally substituted alkyl or optionally substituted cycloalkyl;

R$^{16}$ and R$^{17}$ of —(CR$^{16}$R$^{17}$)$_m$— are independently selected from hydrogen, halogen or optionally substituted alkyl;

R$^{50}$ and R$^{51}$ of Formula (XXXVII) and (XXXVIII) are independently selected from optionally substituted alkyl, or R$^{50}$ and R$^{51}$ are taken together to form a ring;

m and n of —(CR$^{16}$R$^{17}$)$_m$— and

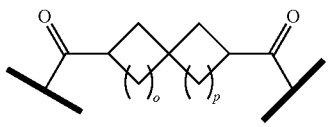

are independently an integer from 0-4;

o and p of

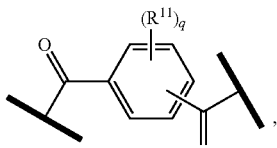

are independently an integer from 0-3;

q of

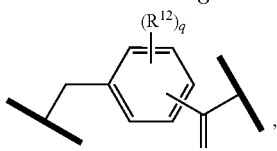

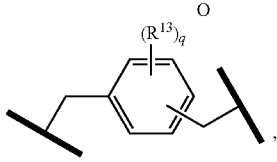

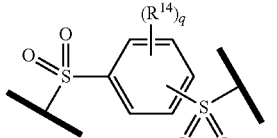

is an integer from 0-4; and
r of

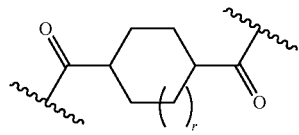

is an integer from 0-1;

or a pharmaceutically acceptable salt, tautomer or stereoisomer thereof.

In an embodiment, $R^1$ and $R^2$ of the ILM of Formula (XXXVII) or (XXXVIII) are t-butyl and $R^3$ and $R^4$ of the ILM of Formula (XXXVII) or (XXXVIII) are tetrahydronaphtalene.

In any of the compounds described herein, the ILM can have the structure of Formula (XXXIX) or (XL), which are derived from the IAP ligands described in WO Pub. No. 2013/071039, or an unnatural mimetic thereof:

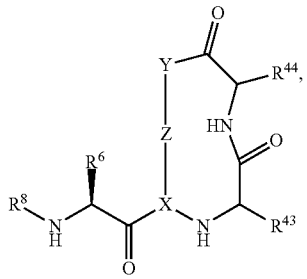

(XXXIX)

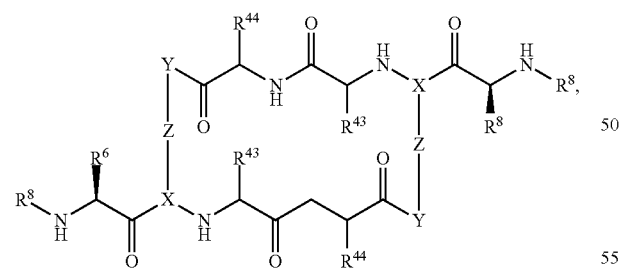

(XL)

wherein:

$R^{43}$ and $R^{44}$ of Formulas (XXXIX) and (XL) are independently selected from hydrogen, alkyl, aryl, arylalkyl, heteroaryl, heteroarylalkyl, cycloalkyl, cycloalkylalkyl further optionally substituted, and $R^6$ and $R^8$ of Formula (XXXIX) and (XL) are independently selected from hydrogen, optionally substituted alkyl or optionally substituted cycloalkyl.

each X of Formulas (XXXIX) and (XL) is independently selected from:

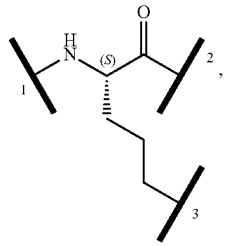

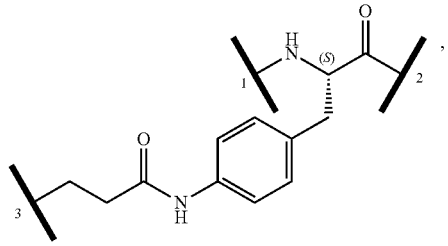

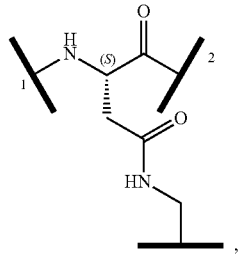

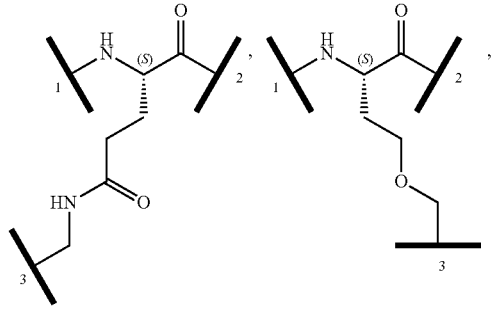

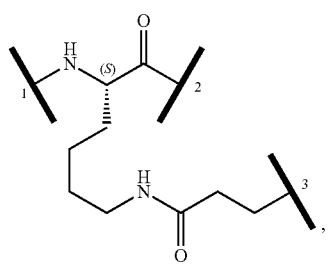

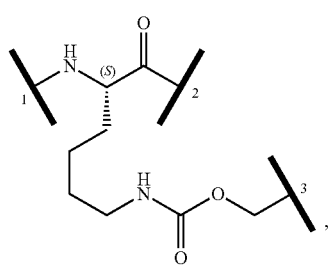

-continued
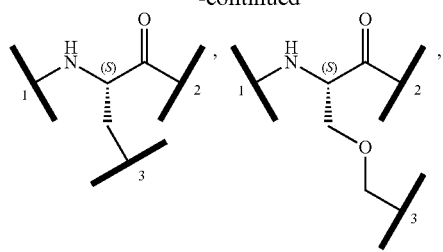
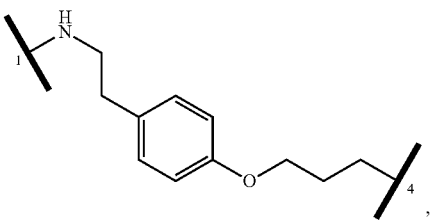
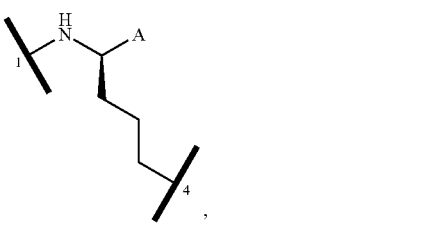

, and

each Z of Formulas (XXXIX) and (XL) is selected from
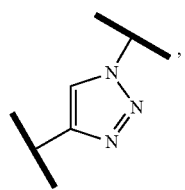
wherein each
represents a point of attachment to the compound; and each Y is selected from:

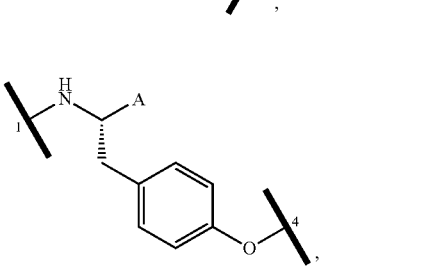

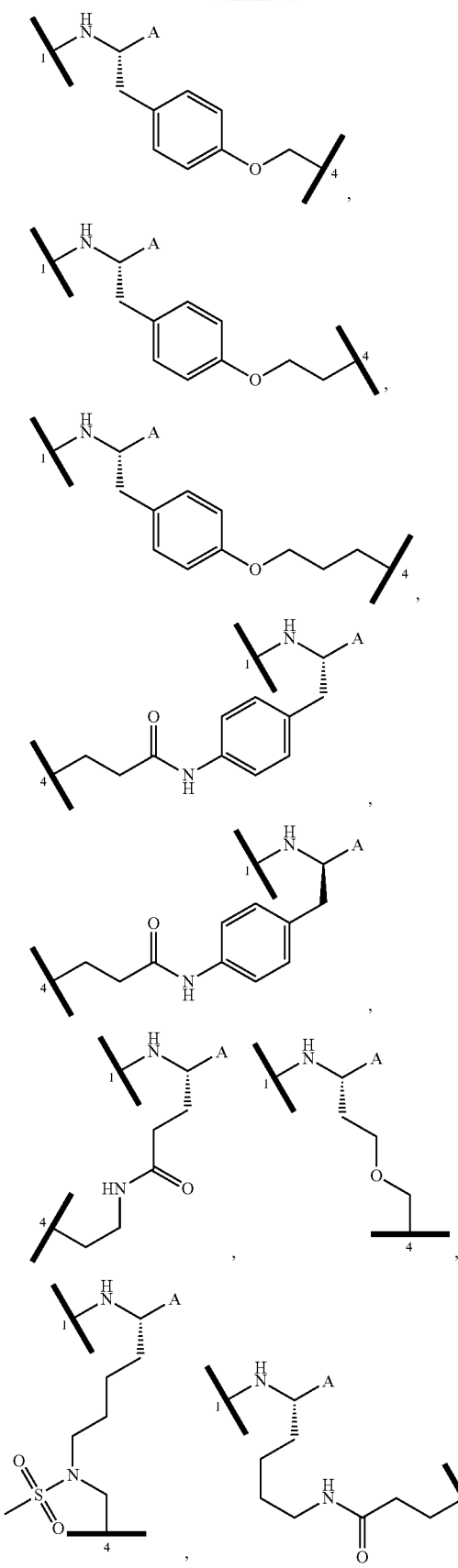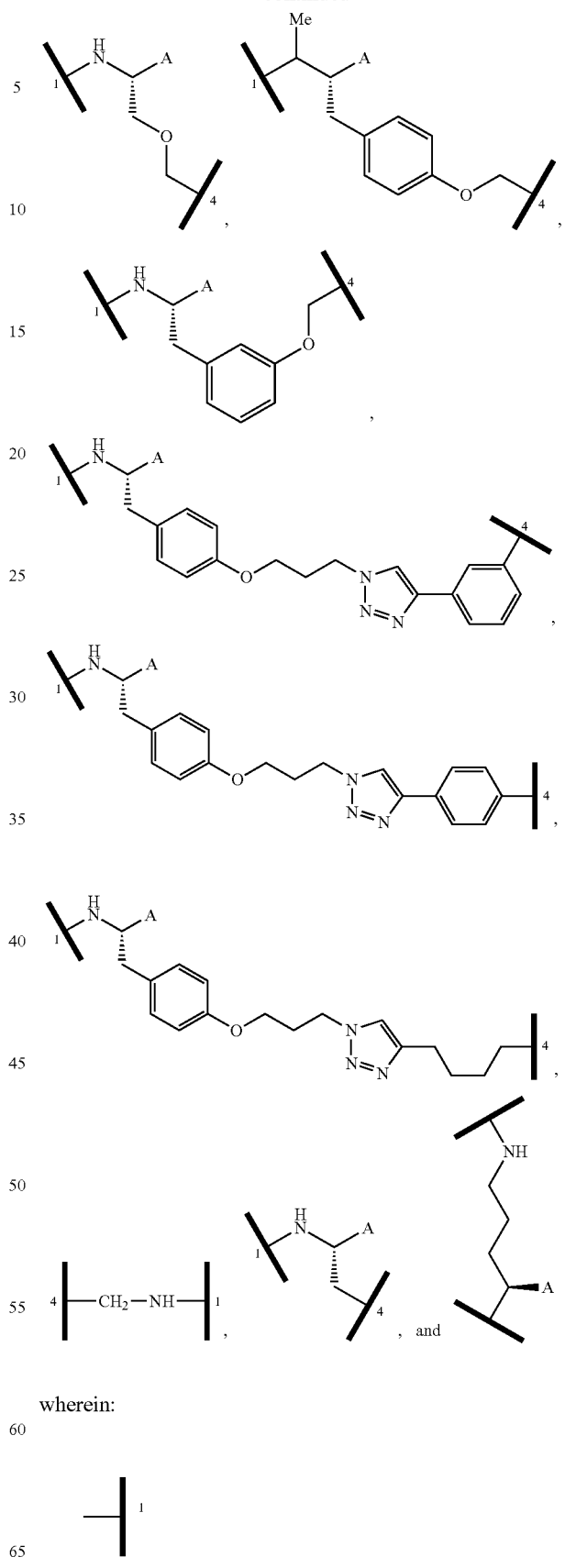
wherein:

represents a point of attachment to a —C=O portion of the compound;

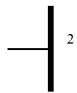

represents a point of attachment to an amino portion of the compound;

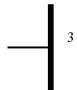

represents a first point of attachment to Z;

represents a second point of attachment to Z; and
A is selected from —C(O)R$^3$ or

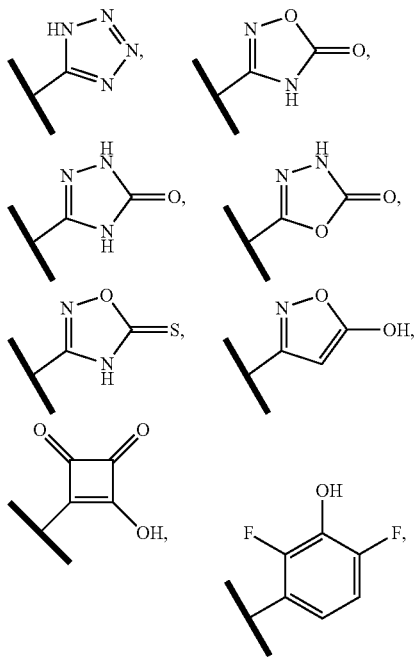

or a tautomeric form of any of the foregoing, wherein:
R$^3$ of —C(O)R$^3$ is selected from OH, NHCN, NHSO$_2$R$^{10}$, NHOR$^{11}$ or N(R$^{12}$)(R$^3$);
R$^{10}$ and R$^{11}$ of NHSO$_2$R$^{10}$ and NHOR$^{11}$ are independently selected from —C$_1$-C$_4$ alkyl, cycloalkyl, aryl, heteroaryl, or heterocycloalkyl, any of which are optionally substituted, and hydrogen;
each of R$^{12}$ and R$^{13}$ of N(R$^{12}$)(R$^{13}$) are independently selected from hydrogen, —C$_1$-C$_4$ alkyl, —(C$_1$-C$_4$ alkylene)-NH—(C$_1$-C$_4$ alkyl), benzyl, —(C$_1$-C$_4$ alkylene)-C(O)OH, —(C$_1$-C$_4$ alkylene)-C(O)CH$_3$, —CH(benzyl)-COOH, —C$_1$-C$_4$ alkoxy, and —(C$_1$-C$_4$ alkylene)-O—(C$_1$-C$_4$ hydroxyalkyl); or R$^{12}$ and R$^{13}$ of N(R$^{12}$)(R$^{13}$) are taken together with the nitrogen atom to which they are commonly bound to form a saturated heterocyclyl optionally comprising one additional heteroatom selected from N, O and S, and wherein the saturated heterocycle is optionally substituted with methyl.

In any of the compounds described herein, the ILM can have the structure of Formula (XLI), which are derived from the IAP ligands described in WO Pub. No. 2013/071039, or an unnatural mimetic thereof:

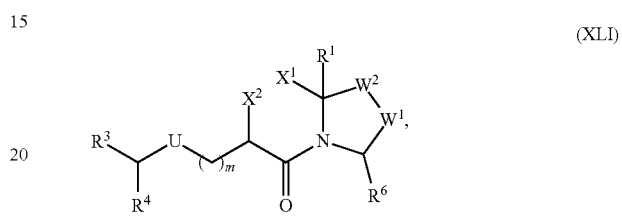

wherein:
W$^1$ of Formula (XLI) is selected from O, S, N—R$^A$, or C(R$^{8a}$)(R$^{8b}$);
W$^2$ of Formula (XLI) is selected from O, S, N—R$^A$, or C(R$^{8c}$)(R$^{8d}$); provided that W$^1$ and W$^2$ are not both O, or both S;
R$^1$ of Formula (XLI) is selected from H, C$_1$-C$_6$alkyl, C$_3$-C$_6$cycloalkyl, —C$_1$-C$_6$alkyl-(substituted or unsubstituted C$_3$-C$_6$cycloalkyl), substituted or unsubstituted aryl, substituted or unsubstituted heteroaryl, —C$_1$-C$_6$alkyl-(substituted or unsubstituted aryl), or —C$_1$-C$_6$alkyl-(substituted or unsubstituted heteroaryl);
when X$^1$ is selected from O, N—R$^A$, S, S(O), or S(O)$_2$, then X$^2$ is C(R$^{2a}$R$^{2b}$);
or:
X$^1$ of Formula (XLI) is selected from CR$^{2c}$R$^{2d}$ and X$^2$ is CR$^{2a}$R$^{2b}$, and R$^{2c}$ and R$^{2a}$ together form a bond;
or:
X$^1$ and X$^2$ of Formula (XLI) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring;
or:
X$^1$ of Formula (XLI) is selected from CH$_2$ and X$^2$ is C=O, C=C(R$^C$)$_2$, or C=NR$^C$; where each R$^c$ is independently selected from H, —CN, —OH, alkoxy, substituted or unsubstituted C$_1$-C$_6$alkyl, substituted or unsubstituted C$_3$-C$_6$cycloalkyl, substituted or unsubstituted C$_2$-C$_5$heterocycloalkyl, substituted or unsubstituted aryl, substituted or unsubstituted heteroaryl, —C$_1$-C$_6$alkyl-(substituted or unsubstituted C$_3$-C$_6$cycloalkyl), —C$_1$-C$_6$alkyl-(substituted or unsubstituted C$_2$-C$_5$heterocycloalkyl), —C$_1$-C$_6$alkyl-(substituted or unsubstituted aryl), or —C$_1$-C$_6$alkyl-(substituted or unsubstituted heteroaryl);
R$^A$ of N—R$^A$ is selected from H, C$_1$-C$_6$alkyl, —C(=O) C$_1$-C$_2$alkyl, substituted or unsubstituted aryl, or substituted or unsubstituted heteroaryl;

$R^{2a}$, $R^{2b}$, $R^{2c}$, $R^{2d}$ of $CR^{2c}R^{2d}$ and $CR^{2a}R^{2b}$ are independently selected from H, substituted or unsubstituted $C_1$-$C_6$alkyl, substituted or unsubstituted $C_1$-$C_6$heteroalkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl) and —C(=O)$R^B$;

$R^B$ of —C(=O)$R^B$ is selected from substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —$NR^D R^E$;

$R^D$ and $R^E$ of $NR^D R^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

m of Formula (XLI) is selected from 0, 1 or 2;

—U— of Formula (XLI) is selected from —NHC(=O)—, —C(=O)NH—, —NHS(=O)$_2$—, —S(=O)$_2$NH—, —NHC(=O)NH—, —NH(C=O)O—, —O(C=O)NH—, or —NHS(=O)$_2$NH—;

$R^3$ of Formula (XLI) is selected from $C_1$-$C_3$alkyl, or $C_1$-$C_3$fluoroalkyl;

$R^4$ of Formula (XLI) is selected from —$NHR^5$, —N($R^5$)2, —N+($R^5$)3 or —$OR^5$; each $R^5$ of —$NHR^5$, —N($R^5$)2, —N+($R^5$)3 and —$OR^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);

or:

$R^3$ and $R^5$ of Formula (XLI) together with the atoms to which they are attached form a substituted or unsubstituted 5-7 membered ring;

or:

$R^3$ of Formula (XLI) is bonded to a nitrogen atom of U to form a substituted or unsubstituted 5-7 membered ring;

$R^6$ of Formula (XLI) is selected from —NHC(=O)$R^7$, —C(=O)NH$R^7$, —NHS(=O)2$R^7$, —S(=O)$_2$NH$R^7$; —NHC(=O)NH$R^7$, —NHS(=O)$_2$NH$R^7$, —($C_1$-$C_3$alkyl)-NHC(=O)$R^7$, —($C_1$-$C_3$alkyl)-C(=O)NH$R^7$, —($C_1$-$C_3$alkyl)-NHS(=O)2$R^7$, —($C_1$-$C_3$alkyl)-S(=O)$_2$NH$R^7$; —($C_1$-$C_3$alkyl)-NHC(=O)NH$R^7$, —($C_1$-$C_3$alkyl)-NHS(=O)2NH$R^7$, substituted or unsubstituted $C_2$-$C_{10}$heterocycloalkyl, or substituted or unsubstituted heteroaryl;

each $R^7$ of —NHC(=O)$R^7$, —C(=O)NH$R^7$, —NHS(=O)2$R^7$, —S(=O)$_2$NH$R^7$; —NHC(=O)NH$R^7$, —NHS(=O)$_2$NH$R^7$, —($C_1$-$C_3$alkyl)-NHC(=O)$R^7$, —($C_1$-$C_3$alkyl)-C(=O)NH$R^7$, —($C_1$-$C_3$alkyl)-NHS(=O)2$R^7$, —($C_1$-$C_3$alkyl)-S(=O)2NH$R^7$; —($C_1$-$C_3$alkyl)-NHC(=O)NH$R^7$, —($C_1$-$C_3$alkyl)-NHS(=O)2NH$R^7$ is independently selected from $C_1$-$C_6$alkyl, $C_1$-$C_6$haloalkyl, $C_1$-$C_6$heteroalkyl, a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted heteroaryl, i-$C_6$alkyl-(substituted or unsubstituted $C_3$-$C_{10}$cycloalkyl), —$C_1$-$C_6$alkyl-(substituted or unsubstituted $C_2$-$C_{10}$heterocycloalkyl, —$C_1$-$C_6$alkyl-(substituted or unsubstituted aryl), —$C_1$-$C_6$alkyl-(substituted or unsubstituted heteroaryl), —(CH$_2$)p-CH(substituted or unsubstituted aryl)2, —(CH$_2$)p-CH(substituted or unsubstituted heteroaryl)2, —(CH$_2$)$_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), or -(substituted or unsubstituted heteroaryl)-(substituted or unsubstituted heteroaryl);

p of $R^7$ is selected from 0, 1 or 2;

$R^{8a}$, $R^{8b}$, $R^{8c}$, and $R^{8d}$ of C($R^{8a}$)($R^{8b}$) and C($R^{8c}$)($R^{8d}$) are independently selected from H, $C_1$-$C_6$alkyl, $C_1$-$C_6$fluoroalkyl, $C_1$-$C_6$ alkoxy, $C_1$-$C_6$heteroalkyl, and substituted or unsubstituted aryl;

or:

$R^{8a}$ and $R^{8d}$ are as defined above, and $R^{8b}$ and $R^{8c}$ together form a bond;

or:

$R^{8a}$ and $R^{8d}$ are as defined above, and $R^{8b}$ and $R^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

$R^{8c}$ and $R^{8d}$ are as defined above, and $R^{8a}$ and $R^{8b}$ together with the atoms to which they are attached form a substituted or unsubstituted saturated, or partially saturated 3-7 membered spirocycle or heterospirocycle comprising 1-3 heteroatoms selected from S, O and N;

or:

$R^{8a}$ and $R^{8b}$ are as defined above, and $R^{8c}$ and $R^{8d}$ together with the atoms to which they are attached form a substituted or unsubstituted saturated, or partially saturated 3-7 membered spirocycle or heterospirocycle comprising 1-3 heteroatoms selected from S, O and N;

where each substituted alkyl, heteroalkyl, fused ring, spirocycle, heterospirocycle, cycloalkyl, heterocycloalkyl, aryl or heteroaryl is substituted with 1-3 $R^9$; and each $R^9$ of $R^{8a}$, $R^{8b}$, $R^{8c}$ and $R^{8d}$ is independently selected from halogen, —OH, —SH, (C=O), CN, $C_1$-$C_4$alkyl, $C_1$-$C_4$fluoroalkyl, $C_1$-$C_4$ alkoxy, $C_1$-$C_4$ fluoroalkoxy, —NH$_2$, —NH($C_1$-$C_4$alkyl), —NH($C_1$-$C_4$alkyl)2, —C(=O)OH, —C(=O)NH$_2$, —C(=O)$C_1$-$C_3$alkyl, —S(=O)$_2$CH$_3$, —NH($C_1$-$C_4$alkyl)-OH, —NH($C_1$-$C_4$alkyl)-O—($C_1$-$C_4$alkyl), —O($C_1$-$C_4$alkyl)-NH$_2$; —O($C_1$-$C_4$alkyl)-NH—($C_1$-$C_4$alkyl), and —O($C_1$-$C_4$alkyl)-N—($C_1$-$C_4$alkyl)$_2$, or two $R^9$ together with the atoms to which they are attached form a methylene dioxy or ethylene dioxy ring substituted or unsubstituted with halogen, —OH, or $C_1$-$C_3$alkyl.

In any of the compounds described herein, the ILM can have the structure of Formula (XLII), which are derived from the IAP ligands described in WO Pub. No. 2013/071039, or an unnatural mimetic thereof:

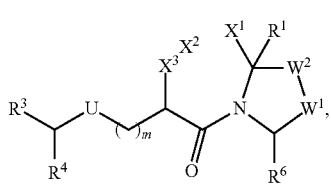

(XLII)

wherein:
W$^1$ of Formula (XLII) is O, S, N—R$^A$, or C(R$^{8a}$)(R$^{8b}$);
W$^2$ of Formula (XLII) is O, S, N—R$^A$, or C(R$^{8c}$)(R$^{8d}$); provided that W$^1$ and W$^2$ are not both O, or both S;
R$^1$ of Formula (XLII) is selected from H, C$_1$-C$_6$alkyl, C$_3$-C$_6$cycloalkyl, —C$_1$-C$_6$alkyl-(substituted or unsubstituted C$_3$-C$_6$cycloalkyl), substituted or unsubstituted aryl, substituted or unsubstituted heteroaryl, —C$_1$-C$_6$alkyl-(substituted or unsubstituted aryl), or —C$_1$-C$_6$alkyl-(substituted or unsubstituted heteroaryl); when X$^1$ of Formula (XLII) is N—R$^A$, then X$^2$ is C=O, or CR$^{2c}$R$^{2d}$, and X$^3$ is CR$^{2a}$R$^{2b}$;
or:
when X$^1$ of Formula (XLII) is selected from S, S(O), or S(O)$_2$, then X$^2$ is CR$^{2c}$R$^{2d}$, and X$^3$ is CR$^{2a}$R$^{2b}$.
or:
when X$^1$ of Formula (XLII) is O, then X$^2$ is CR$^{2c}$R$^{2d}$ and N—R$^A$ and X$^3$ is CR$^{2a}$R$^{2b}$; or:
when X$^1$ of Formula (XLII) is CH$_3$, then X$^2$ is selected from O, N—R$^A$, S, S(O), or S(O)$_2$, and X$^3$ is CR$^{2a}$R$^{2b}$;
when X$^1$ of Formula (XLII) is CR$^{2e}$R$^{2f}$ and X$^2$ is CR$^{2c}$R$^{2d}$, and R$^{2e}$ and R$^{2c}$ together form a bond, and X$^3$ of Formula (VLII) is CR$^{2a}$R$^{2b}$;
or:
X$^1$ and X$^3$ of Formula (XLII) are both CH$_2$ and X$^2$ of Formula (XLII) is C=O, C=C(R$^C$)$_2$, or C=NR$^C$; where each R$^C$ is independently selected from H, —CN, —OH, alkoxy, substituted or unsubstituted C$_1$-C$_6$alkyl, substituted or unsubstituted C$_3$-C$_6$cycloalkyl, substituted or unsubstituted C$_2$-C$_5$heterocycloalkyl, substituted or unsubstituted aryl, substituted or unsubstituted heteroaryl, —C$_1$-C$_6$alkyl-(substituted or unsubstituted C$_3$-C$_6$cycloalkyl), —C$_1$-C$_6$alkyl-(substituted or unsubstituted C$_2$-C$_5$heterocycloalkyl), —C$_1$-C$_6$alkyl-(substituted or unsubstituted aryl), or —C$_1$-C$_6$alkyl-(substituted or unsubstituted heteroaryl);
or:
X$^1$ and X$^2$ of Formula (XLII) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and X$^3$ is CR$^{2a}$R$^{2b}$.
or:
X$^2$ and X$^3$ of Formula (XLII) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and X$^1$ of Formula (VLII) is CR$^{2e}$R$^{2f}$;
R$^A$ of N—R$^A$ is selected from H, C$_1$-C$_6$alkyl, —C(=O) C$_1$-C$_2$alkyl, substituted or unsubstituted aryl, or substituted or unsubstituted heteroaryl;
R$^{2a}$, R$^{2b}$, R$^{2c}$, R$^{2d}$, R$^{2e}$, and R$^{2f}$ of CR$^{2c}$R$^{2d}$, CR$^{2a}$R$^{2b}$ and CR$^{2e}$R$^{2f}$ are independently selected from H, substituted or unsubstituted C$_1$-C$_6$alkyl, substituted or unsubstituted C$_1$-C$_6$heteroalkyl, substituted or unsubstituted C$_3$-C$_6$cycloalkyl, substituted or unsubstituted C$_2$-C$_5$heterocycloalkyl, substituted or unsubstituted aryl, substituted or unsubstituted heteroaryl, —C$_1$-C$_6$alkyl-(substituted or unsubstituted C$_3$-C$_6$cycloalkyl), —C$_1$-C$_6$alkyl-(substituted or unsubstituted C$_2$-C$_5$heterocycloalkyl), —C$_1$-C$_6$alkyl-(substituted or unsubstituted aryl), —C$_1$-C$_6$alkyl-(substituted or unsubstituted heteroaryl) and —C(=O)R$^B$;
R$^B$ of —C(=O)R$^B$ is selected from substituted or unsubstituted C$_1$-C$_6$alkyl, substituted or unsubstituted C$_3$-C$_6$cycloalkyl, substituted or unsubstituted C$_2$-C$_5$heterocycloalkyl, substituted or unsubstituted aryl, substituted or unsubstituted heteroaryl, —C$_1$-C$_6$alkyl-(substituted or unsubstituted C$_3$-C$_6$cycloalkyl), —C$_1$-C$_6$alkyl-(substituted or unsubstituted C$_2$-C$_5$heterocycloalkyl), —C$_1$-C$_6$alkyl-(substituted or unsubstituted aryl), —C$_1$-C$_6$alkyl-(substituted or unsubstituted heteroaryl), or —NR$^D$R$^E$;
R$^D$ and R$^E$ of NR$^D$R$^E$ are independently selected from H, substituted or unsubstituted C$_1$-C$_6$alkyl, substituted or unsubstituted C$_3$-C$_6$cycloalkyl, substituted or unsubstituted C$_2$-C$_5$heterocycloalkyl, substituted or unsubstituted aryl, substituted or unsubstituted heteroaryl, —C$_1$-C$_6$alkyl-(substituted or unsubstituted C$_3$-C$_6$cycloalkyl), —C$_1$-C$_6$alkyl-(substituted or unsubstituted C$_2$-C$_5$heterocycloalkyl), —C$_1$-C$_6$alkyl-(substituted or unsubstituted aryl), or —C$_1$-C$_6$alkyl-(substituted or unsubstituted heteroaryl);
m of Formula (XLII) is selected from 0, 1 or 2;
—U— of Formula (XLII) is selected from —NHC(=O)—, —C(=O)NH—, —NHS(=O)$_2$—, —S(=O)$_2$NH—, —NHC(=O)NH—, —NH(C=O)O—, —O(C=O)NH—, or —NHS(=O)$_2$NH—;
R$^3$ of Formula (XLII) is selected from C$_1$-C$_3$alkyl, or C$_1$-C$_3$fluoroalkyl;
R$^4$ of Formula (XLII) is selected from —NHR$^5$, —N(R$^5$)$_2$, —N+(R$^5$)$_3$ or —OR$^5$;
each R$^5$ of —NHR$^5$, —N(R$^5$)$_2$, —N+(R$^5$)$_3$ and —OR$^5$ is independently selected from H, C$_1$-C$_3$alkyl, C$_1$-C$_3$haloalkyl, C$_1$-C$_3$heteroalkyl and —C$_1$-C$_3$alkyl-(C$_3$-C$_5$cycloalkyl);
or:
R$^3$ and R$^5$ of Formula (XLII) together with the atoms to which they are attached form a substituted or unsubstituted 5-7 membered ring;
or:
R$^3$ of Formula (XLII) is bonded to a nitrogen atom of U to form a substituted or unsubstituted 5-7 membered ring;
R$^6$ of Formula (XLII) is selected from —NHC(=O)R$^7$, —C(=O)NHR$^7$, —NHS(=O)2R$^7$, —S(=O)$_2$NHR$^7$; —NHC(=O)NHR$^7$, —NHS(=O)$_2$NHR$^7$, —(C$_1$-C$_3$alkyl)-NHC(=O)R$^7$, —(C$_1$-C$_3$alkyl)-C(=O)NHR$^7$, —(C$_1$-C$_3$alkyl)-NHS(=O)$_2$R$^7$, —(C$_1$-C$_3$alkyl)-S(=O)$_2$NHR$^7$; —(C$_1$-C$_3$alkyl)-NHC(=O)NHR$^7$, —($C_1$-$C_3$alkyl)-NHS(=O)$_2$NHR$^7$, substituted or unsubstituted $C_2$-$C_{10}$heterocycloalkyl, or substituted or unsubstituted heteroaryl;

each R$^7$ of —NHC(=O)R$^7$, —C(=O)NHR$^7$, —NHS(=O)2R$^7$, —S(=O)$_2$NHR$^7$; —NHC(=O)NHR$^7$, —NHS(=O)$_2$NHR$^7$, —($C_1$-$C_3$alkyl)-NHC(=O)R$^7$, —($C_1$-$C_3$alkyl)-C(=O)NHR$^7$, —($C_1$-$C_3$alkyl)-NHS(=O)2R$^7$, —($C_1$-$C_3$alkyl)-S(=O)2NHR$^7$; —($C_1$-$C_3$alkyl)-NHC(=O)NHR$^7$, —($C_1$-$C_3$alkyl)-NHS(=O)2NHR$^7$ is independently selected from $C_1$-$C_6$alkyl, $C_1$-$C_6$haloalkyl, $C_1$-$C_6$heteroalkyl, a substituted or unsubstituted C3-C10cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted C2-C10heterocycloalkyl, —C1-C6alkyl-(substituted or unsubstituted aryl), —$C_1$-$C_6$alkyl-(substituted or unsubstituted heteroaryl), —(CH2)p-CH(substituted or unsubstituted aryl)2, —(CH$_2$)p-CH(substituted or unsubstituted heteroaryl)2, —(CH$_2$)$_P$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), or -(substituted or unsubstituted heteroaryl)-(substituted or unsubstituted heteroaryl);

p of R$^7$ is selected from 0, 1 or 2;

R$^{8a}$, R$^{8b}$, R$^{8c}$, and R$^{8d}$ of C(R$^{8a}$)(R$^{8b}$) and C(R$^{8c}$)(R$^{8d}$) are independently selected from H, $C_1$-$C_6$alkyl, $C_1$-$C_6$fluoroalkyl, $C_1$-$C_6$ alkoxy, $C_1$-$C_6$heteroalkyl, and substituted or unsubstituted aryl;

or:
R$^{8a}$ and R$^{8d}$ are as defined above, and R$^{8b}$ and R$^{8c}$ together form a bond;

or:
R$^{8a}$ and R$^{8d}$ are as defined above, and R$^{8b}$ and R$^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:
R$^{8c}$ and R$^{8d}$ are as defined above, and R$^{8a}$ and R$^{8b}$ together with the atoms to which they are attached form a substituted or unsubstituted saturated, or partially saturated 3-7 membered spirocycle or heterospirocycle comprising 1-3 heteroatoms selected from S, O and N;

or:
R$^{8a}$ and R$^{8b}$ are as defined above, and R$^{8c}$ and R$^{8d}$ together with the atoms to which they are attached form a substituted or unsubstituted saturated, or partially saturated 3-7 membered spirocycle or heterospirocycle comprising 1-3 heteroatoms selected from S, O and N;

where each substituted alkyl, heteroalkyl, fused ring, spirocycle, heterospirocycle, cycloalkyl, heterocycloalkyl, aryl or heteroaryl is substituted with 1-3 R$^9$; and each R$^9$ of R$^{8a}$, R$^{8b}$, R$^{8c}$ and R$^{8d}$ is independently selected from halogen, —OH, —SH, (C=O), CN, $C_1$-$C_4$alkyl, C1-C4fluoroalkyl, $C_1$-$C_4$ alkoxy, $C_1$-$C_4$ fluoroalkoxy, —NH$_2$, —NH($C_1$-$C_4$alkyl), —NH($C_1$-$C_4$alkyl)$_2$, —C(=O)OH, —C(=O)NH$_2$, —C(=O)$C_1$-$C_3$alkyl, —S(=O)$_2$CH$_3$, —NH($C_1$-$C_4$alkyl)-OH, —NH($C_1$-$C_4$alkyl)-O—($C_1$-$C_4$alkyl), —O($C_1$-$C_4$alkyl)-NH$_2$; —O($C_1$-$C_4$alkyl)-NH—($C_1$-$C_4$alkyl), and —O($C_1$-$C_4$alkyl)-N—($C_1$-$C_4$alkyl)2, or two R$^9$ together with the atoms to which they are attached form a methylene dioxy or ethylene dioxy ring substituted or unsubstituted with halogen, —OH, or $C_1$-$C_3$alkyl.

In any of the compounds described herein, the ILM can have the structure of Formula (XLIII), which is derived from the IAP ligands described in WO Pub. No. 2013/071039, or an unnatural mimetic thereof:

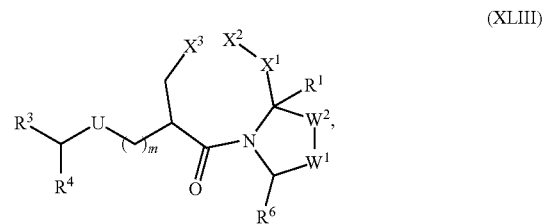

(XLIII)

wherein:
W$^1$ of Formula (XLIII) is selected from O, S, N—R$^A$, or C(R$^{8a}$)(R$^{8b}$);

W$^2$ of Formula (XLIII) is selected from O, S, N—R$^A$, or C(R$^{8c}$)(R$^{8d}$); provided that W$^1$ and W$^2$ are not both 0, or both S;

R$^1$ of Formula (XLIII) is selected from H, $C_1$-$C_6$alkyl, $C_3$-$C_6$cycloalkyl, —$C_1$-$C_6$alkyl-(substituted or unsubstituted $C_3$-$C_6$cycloalkyl), substituted or unsubstituted aryl, substituted or unsubstituted heteroaryl, —$C_1$-$C_6$alkyl-(substituted or unsubstituted aryl), or —$C_1$-$C_6$alkyl-(substituted or unsubstituted heteroaryl);

when X$^1$ of Formula (XLIII) is selected from N—R$^A$, S, S(O), or S(O)$_2$, then X$^2$ of Formula (XLIII) is CR$^{2c}$R$^{2d}$, and X$^3$ of Formula (XLIII) is CR$^{2a}$R$^{2b}$;

or:
when X$^1$ of Formula (XLIII) is O, then X$^2$ of Formula (XLIII) is selected from O, N—R$^A$, S, S(O), or S(O)$_2$, and X$^3$ of Formula (XLIII) is CR$^{2a}$R$^{2b}$;

or:
when X$^1$ of Formula (XLIII) is CR$^{2e}$R$^{2f}$ and X$^2$ of Formula (XLIII) is CR$^{2c}$R$^{2d}$, and R$^{2e}$ and R$^{2c}$ together form a bond, and X$^3$ of Formula (XLIII) is CR$^{2a}$R$^{2b}$;

or:
X$^1$ and X$^2$ of Formula (XLIII) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and X$^3$ of Formula (XLIII) is CR$^{2a}$R$^{2b}$;

or:
X$^2$ and X$^3$ of Formula (XLIII) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and X$^1$ of Formula (VLII) is CR$^{2e}$R$^{2f}$;

$R^A$ of N—$R^A$ is H, $C_1$-$C_6$alkyl, —C(=O)$C_1$-$C_2$alkyl, substituted or unsubstituted aryl, or substituted or unsubstituted heteroaryl;

$R^{2a}$, $R^{2b}$, $R^{2c}$, $R^{2d}$, $R^{2e}$, and $R^{2f}$ of $CR^{2c}R^{2d}$, $CR^{2a}R^{2b}$ and $CR^{2e}R^{2f}$ are independently selected from H, substituted or unsubstituted $C_1$-$C_6$alkyl, substituted or unsubstituted $C_1$-$C_6$heteroalkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl) and —C(=O)$R^B$;

$R^B$ of —C(=O)$R^B$ is substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —$NR^DR^E$;

$R^D$ and $R^E$ of $NR^DR^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

m of Formula (XLIII) is 0, 1 or 2;

—U— of Formula (XLIII) is —NHC(=O)—, —C(=O)NH—, —NHS(=O)$_2$—, —S(=O)$_2$NH—, —NHC(=O)NH—, —NH(C=O)O—, —O(C=O)NH—, or —NHS(=O)$_2$NH—;

$R^3$ of Formula (XLIII) is $C_1$-$C_3$alkyl, or $C_1$-$C_3$fluoroalkyl;

$R^4$ of Formula (XLIII) is —$NHR^5$, —N($R^5$)$_2$, —N+($R^5$)$_3$ or —$OR^5$;

each $R^5$ of —$NHR^5$, —N($R^5$)$_2$, —N+($R^5$)$_3$ and —$OR^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);

or:

$R^3$ and $R^5$ of Formula (XLIII) together with the atoms to which they are attached form a substituted or unsubstituted 5-7 membered ring;

or:

$R^3$ of Formula (XLIII) is bonded to a nitrogen atom of U to form a substituted or unsubstituted 5-7 membered ring;

$R^6$ of Formula (XLIII) is selected from —NHC(=O)$R^7$, —C(=O)NH$R^7$, —NHS(=O)2$R^7$, —S(=O)$_2$NH$R^7$; —NHC(=O)NH$R^7$, —NHS(=O)$_2$NH$R^7$, —($C_1$-$C_3$alkyl)-NHC(=O)$R^7$, —($C_1$-$C_3$alkyl)-C(=O)NH$R^7$, —($C_1$-$C_3$alkyl)-NHS(=O)$_2R^7$, —($C_1$-$C_3$alkyl)-S(=O)$_2$NH$R^7$; —($C_1$-$C_3$alkyl)-NHC(=O)NH$R^7$, —($C_1$-$C_3$alkyl)-NHS(=O)$_2$NH$R^7$, substituted or unsubstituted $C_2$-$C_{10}$heterocycloalkyl, or substituted or unsubstituted heteroaryl;

each $R^7$ of —NHC(=O)$R^7$, —C(=O)NH$R^7$, —NHS(=O)2$R^7$, —S(=O)$_2$NH$R^7$; —NHC(=O)NH$R^7$, —NHS(=O)$_2$NH$R^7$, —($C_1$-$C_3$alkyl)-NHC(=O)$R^7$, —($C_1$-$C_3$alkyl)-C(=O)NH$R^7$, —($C_1$-$C_3$alkyl)-NHS(=O)2$R^7$, —($C_1$-$C_3$alkyl)-S(=O)2NH$R^7$; —($C_1$-$C_3$alkyl)-NHC(=O)NH$R^7$, —($C_1$-$C_3$alkyl)-NHS(=O)2NH$R^7$ is independently selected from $C_1$-$C_6$alkyl, $C_1$-$C_6$haloalkyl, $C_1$-$C_6$heteroalkyl, a substituted or unsubstituted C3-C10cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted C2-C10heterocycloalkyl, —C1-C6alkyl-(substituted or unsubstituted aryl), —$C_1$-$C_6$alkyl-(substituted or unsubstituted heteroaryl), —(CH$_2$)p-CH(substituted or unsubstituted aryl)2, —(CH$_2$)p-CH(substituted or unsubstituted heteroaryl)2, —(CH$_2$)$_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), or -(substituted or unsubstituted heteroaryl)-(substituted or unsubstituted heteroaryl);

p of $R^7$ is 0, 1 or 2;

$R^{8a}$, $R^{8b}$, $R^{8c}$, and $R^{8d}$ of $C(R^{8a})(R^{8b})$ and $C(R^{8c})(R^{8d})$ are independently selected from H, $C_1$-$C_6$alkyl, $C_1$-$C_6$fluoroalkyl, $C_1$-$C_6$ alkoxy, $C_1$-$C_6$heteroalkyl, and substituted or unsubstituted aryl;

or:

$R^{8a}$ and $R^{8d}$ are as defined above, and $R^{8b}$ and $R^{8c}$ together form a bond;

or:

$R^{8a}$ and $R^{8d}$ are as defined above, and $R^{8b}$ and $R^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

$R^{8c}$ and $R^{8d}$ are as defined above, and $R^{8a}$ and $R^{8b}$ together with the atoms to which they are attached form a substituted or unsubstituted saturated, or partially saturated 3-7 membered spirocycle or heterospirocycle comprising 1-3 heteroatoms selected from S, O and N;

or:

$R^{8a}$ and $R^{8b}$ are as defined above, and $R^{8c}$ and $R^{8d}$ together with the atoms to which they are attached form a substituted or unsubstituted saturated, or partially saturated 3-7 membered spirocycle or heterospirocycle comprising 1-3 heteroatoms selected from S, O and N;

where each substituted alkyl, heteroalkyl, fused ring, spirocycle, heterospirocycle, cycloalkyl, heterocycloalkyl, aryl or heteroaryl is substituted with 1-3 $R^9$; and each $R^9$ of $R^{8a}$, $R^{8b}$, $R^{8c}$ and $R^{8d}$ is independently selected from halogen, —OH, —SH, (C=O), CN, $C_1$-$C_4$alkyl, C1-C4fluoroalkyl, $C_1$-$C_4$ alkoxy, $C_1$-$C_4$ fluoroalkoxy, —NH$_2$, —NH($C_1$-$C_4$alkyl), —NH($C_1$-$C_4$alkyl)$_2$, —C(=O)OH, —C(=O)NH$_2$, —C(=O)$C_1$-$C_3$alkyl, —S(=O)$_2$CH$_3$, —NH($C_1$-$C_4$alkyl)-OH, —NH($C_1$-$C_4$alkyl)-O—($C_1$-$C_4$alkyl), —O($C_1$-$C_4$alkyl)-NH2; —O($C_1$-$C_4$alkyl)-NH—($C_1$-$C_4$alkyl), and —O($C_1$-$C_4$alkyl)-N—($C_1$-$C_4$alkyl)$_2$, or two $R^9$ together with the atoms to which they are attached form a methylene dioxy or ethylene dioxy ring substituted or unsubstituted with halogen, —OH, or $C_1$-$C_3$alkyl.

In any of the compounds described herein, the ILM can have the structure of Formula (XLIV), which is derived from the IAP ligands described in WO Pub. No. 2013/071039, or an unnatural mimetic thereof:

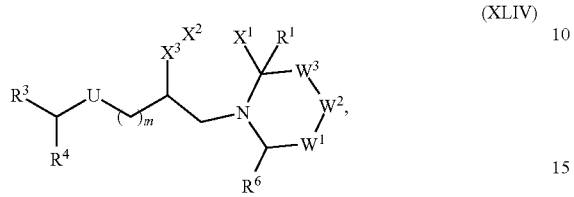

(XLIV)

wherein:
- $W^1$ of Formula (XLIV) is selected from O, S, N—$R^A$, or $C(R^{8a})(R^{8b})$;
- $W^2$ of Formula (XLIV) is selected from O, S, N—$R^A$, or $C(R^{8c})(R^{8d})$; provided that $W^1$ and $W^2$ are not both O, or both S;
- $W^3$ of Formula (XLIV) is selected from O, S, N—$R^A$, or $C(R^{8e})(R^{8f})$, providing that the ring comprising $W^1$, $W^2$, and $W^3$ does not comprise two adjacent oxygen atoms or sulfur atoms;
- $R^1$ of Formula (XLIV) is selected from H, $C_1$-$C_6$alkyl, $C_3$-$C_6$cycloalkyl, —$C_1$-$C_6$alkyl-(substituted or unsubstituted $C_3$-$C_6$cycloalkyl), substituted or unsubstituted aryl, substituted or unsubstituted heteroaryl, —$C_1$-$C_6$alkyl-(substituted or unsubstituted aryl), or —$C_1$-$C_6$alkyl-(substituted or unsubstituted heteroaryl);
- when $X^1$ of Formula (XLIV) is O, then $X^2$ of Formula (XLIV) is selected from $CR^{2c}R^{2d}$ and N—$R^A$, and $X^3$ of Formula (XLIV) is $CR^{2a}R^{2b}$;
- or:
- when $X^1$ of Formula (XLIV) is $CH_2$, then $X^2$ of Formula (XLIV) is selected from O, N—$R^A$, S, S(O), or $S(O)_2$, and $X^3$ of Formula (XLIV) is $CR^{2a}R^{2b}$;
- or:
- when $X^1$ of Formula (XLIV) is $CR^{2e}R^{2f}$ and $X^2$ of Formula (XLIV) is $CR^{2c}R^{2d}$, and $R^{2e}$ and $R^{2c}$ together form a bond, and $X^3$ of Formula (VLIV) is $CR^{2a}R^{2b}$;
- or:
- $X^1$ and $X^3$ of Formula (XLIV) are both $CH_2$ and $X^2$ of Formula (XLII) is C=O, C=C($R^c$)2, or C=$NR^C$; where each $R^C$ is independently selected from H, —CN, —OH, alkoxy, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);
- or:
- $X^1$ and $X^2$ of Formula (XLIV) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^3$ of Formula (XLIV) is $CR^{2a}R^{2b}$;
- or:
- $X^2$ and $X^3$ of Formula (XLIV) are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^1$ of Formula (VLIV) is $CR^{2e}R^{2f}$;
- $R^A$ of N—$R^A$ is selected from H, $C_1$-$C_6$alkyl, —C(=O) $C_1$-$C_2$alkyl, substituted or unsubstituted aryl, or substituted or unsubstituted heteroaryl;
- $R^{2a}$, $R^{2b}$, $R^{2c}$, $R^{2d}$, $R^{2e}$, and $R^{21}$ of $CR^{2c}R^{2d}$, $CR^{2a}R^{2b}$ and $CR^{2e}R^{2f}$ are independently selected from H, substituted or unsubstituted $C_1$-$C_6$alkyl, substituted or unsubstituted $C_1$-$C_6$heteroalkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl) and —C(=O)$R^B$;
- $R^B$ of —C(=O)$R^B$ is selected from substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —$NR^DR^E$;
- $R^D$ and $R^E$ of $NR^DR^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);
- m of Formula (XLIV) is selected from 0, 1 or 2;
- —U— of Formula (XLIV) is selected from —NHC(=O)—, —C(=O)NH—, —NHS(=O)$_2$—, —S(=O)$_2$NH—, —NHC(=O)NH—, —NH(C=O)O—, —O(C=O)NH—, or —NHS(=O)$_2$NH—;
- $R^3$ of Formula (XLIV) is selected from $C_1$-$C_3$alkyl, or $C_1$-$C_3$fluoroalkyl;
- $R^4$ of Formula (XLIV) is selected from —$NHR^5$, —N($R^5$)$_2$, —N+($R^5$)$_3$ or —$OR^5$;
- each $R^5$ of —$NHR^5$, —N($R^5$)$_2$, —N+($R^5$)$_3$ and —$OR^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);
- or:
- $R^3$ and $R^5$ of Formula (XLIV) together with the atoms to which they are attached form a substituted or unsubstituted 5-7 membered ring;

or:
- $R^3$ of Formula (XLIII) is bonded to a nitrogen atom of U to form a substituted or unsubstituted 5-7 membered ring;
- $R^6$ of Formula (XLIII) is selected from —NHC(=O)$R^7$, —C(=O)NH$R^7$, —NHS(=O)2$R^7$, —S(=O)$_2$NH$R^7$; —NHC(=O)NH$R^7$, —NHS(=O)$_2$NH$R^7$, —(C$_1$-C$_3$alkyl)-NHC(=O)$R^7$, —(C$_1$-C$_3$alkyl)-C(=O)NH$R^7$, —(C$_1$-C$_3$alkyl)-NHS(=O)$_2$$R^7$, —(C$_1$-C$_3$alkyl)-S(=O)$_2$NH$R^7$; —(C$_1$-C$_3$alkyl)-NHC(=O)NH$R^7$, —(C$_1$-C$_3$alkyl)-NHS(=O)$_2$NH$R^7$, substituted or unsubstituted C$_2$-C$_{10}$heterocycloalkyl, or substituted or unsubstituted heteroaryl;
- each $R^7$ of —NHC(=O)$R^7$, —C(=O)NH$R^7$, —NHS(=O)2$R^7$, —S(=O)$_2$NH$R^7$; —NHC(=O)NH$R^7$, —NHS(=O)$_2$NH$R^7$, —(C$_1$-C$_3$alkyl)-NHC(=O)$R^7$, —(C$_1$-C$_3$alkyl)-C(=O)NH$R^7$, —(C$_1$-C$_3$alkyl)-NHS(=O)2$R^7$, —(C$_1$-C$_3$alkyl)-S(=O)2NH$R^7$; —(C$_1$-C$_3$alkyl)-NHC(=O)NH$R^7$, —(C$_1$-C$_3$alkyl)-NHS(=O)2NH$R^7$ is independently selected from C$_1$-C$_6$alkyl, C$_1$-C$_6$haloalkyl, C$_1$-C$_6$heteroalkyl, a substituted or unsubstituted C3-C10cycloalkyl, a substituted or unsubstituted C$_2$-C$_{10}$heterocycloalkyl, a substituted or unsubstituted aryl, a substituted or unsubstituted heteroaryl, i-C$_6$alkyl-(substituted or unsubstituted C$_3$-C$_{10}$cycloalkyl), —C$_1$-C$_6$alkyl-(substituted or unsubstituted C2-C10heterocycloalkyl, —C1-C6alkyl-(substituted or unsubstituted aryl), —C$_1$-C$_6$alkyl-(substituted or unsubstituted heteroaryl), —(CH2)p-CH(substituted or unsubstituted aryl)2, —(CH$_2$)p-CH(substituted or unsubstituted heteroaryl)2, —(CH$_2$)$_P$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), or -(substituted or unsubstituted heteroaryl)-(substituted or unsubstituted heteroaryl);
- p of $R^7$ is selected from 0, 1 or 2;
- $R^{8a}$, $R^{8b}$, $R^{8c}$, $R^{8d}$, $R^{8e}$, and $R^{8f}$ of C($R^{8a}$)($R^{8b}$), C($R^{8c}$)($R^{8d}$) and C($R^{8e}$)($R^{8f}$) are independently selected from H, C$_1$-C$_6$alkyl, C$_1$-C$_6$fluoroalkyl, C$_1$-C$_6$ alkoxy, C$_1$-C$_6$heteroalkyl, and substituted or unsubstituted aryl;

or:
- $R^{8a}$, $R^{8d}$, $R^{8e}$, and $R^{8f}$ of C($R^{8a}$)($R^{8b}$), C($R^{8c}$)($R^{8d}$) and C($R^{8e}$)($R^{8f}$) are as defined above, and $R^{8b}$ and $R^{8c}$ together form a bond;

or:
- $R^{8a}$, $R^{8b}$, $R^{8d}$, and $R^{8f}$ of C($R^{8a}$)($R^{8b}$), C($R^{8c}$)($R^{8d}$) and C($R^{8e}$)($R^{8f}$) are as defined above, and $R^{8c}$ and $R^{8e}$ together form a bond;

or:
- $R^{8a}$, $R^{8d}$, $R^{8e}$, and $R^{8f}$ of C($R^{8a}$)($R^{8b}$), C($R^{8c}$)($R^{8d}$) and C($R^{8e}$)($R^{8f}$) are as defined above, and $R^{8b}$ and $R^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:
- $R^{8a}$, $R^{8b}$, $R^{8d}$, and $R^{8f}$ of C($R^{8a}$)($R^{8b}$), C($R^{8c}$)($R^{8d}$) and C($R^{8e}$)($R^{8f}$) are as defined above, and $R^{8c}$ and $R^{8e}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:
- $R^{8c}$, $R^{8d}$, $R^{8e}$, and $R^{8f}$ of C($R^{8c}$)($R^{8d}$) and C($R^{8e}$)($R^{8f}$) are as defined above, and $R^{8a}$ and $R^{8b}$ together with the atoms to which they are attached form a substituted or unsubstituted saturated, or partially saturated 3-7 membered spirocycle or heterospirocycle comprising 1-3 heteroatoms selected from S, O and N;

or:
- $R^{8a}$, $R^{8b}$, $R^{8e}$, and $R^{8f}$ of C($R^{8a}$)($R^{8b}$) and C($R^{8e}$)($R^{8f}$) are as defined above, and $R^{8c}$ and $R^{8d}$ together with the atoms to which they are attached form a substituted or unsubstituted saturated, or partially saturated 3-7 membered spirocycle or heterospirocycle comprising 1-3 heteroatoms selected from S, O and N;

or:
- $R^{8a}$, $R^{8b}$, $R^{8c}$, and $R^{8d}$ of C($R^{8a}$)($R^{8b}$) and C($R^{8c}$)($R^{8d}$) are as defined above, and $R^{8e}$ and $R^{8f}$ together with the atoms to which they are attached form a substituted or unsubstituted saturated, or partially saturated 3-7 membered spirocycle or heterospirocycle comprising 1-3 heteroatoms selected from S, O and N;

or:
- where each substituted alkyl, heteroalkyl, fused ring, spirocycle, heterospirocycle, cycloalkyl, heterocycloalkyl, aryl or heteroaryl is substituted with 1-3 $R^9$; and
- each $R^9$ of $R^{8a}$, $R^{8b}$, $R^{8c}$, $R^{8d}$, $R^{8e}$, and $R^{8f}$ is independently selected from halogen, —OH, —SH, (C=O), CN, C$_1$-C$_4$alkyl, C$_1$-C$_4$fluoroalkyl, C$_1$-C$_4$ alkoxy, C$_1$-C$_4$ fluoroalkoxy, —NH$_2$, —NH(C$_1$-C$_4$alkyl), —NH(C$_1$-C$_4$alkyl)$_2$, —C(=O)OH, —C(=O)NH$_2$, —C(=O)C$_1$-C$_3$alkyl, —S(=O)$_2$CH$_3$, —NH(C$_1$-C$_4$alkyl)-OH, —NH(C$_1$-C$_4$alkyl)-O—(C$_1$-C$_4$alkyl), —O(C$_1$-C$_4$alkyl)-NH2; —O(C$_1$-C$_4$alkyl)-NH—(C$_1$-C$_4$alkyl), and —O(C$_1$-C$_4$alkyl)-N—(C$_1$-C$_4$alkyl)2, or two $R^9$ together with the atoms to which they are attached form a methylene dioxy or ethylene dioxy ring substituted or unsubstituted with halogen, —OH, or C$_1$-C$_3$alkyl.

In any of the compounds described herein, the ILM can have the structure of Formula (XLV), (XLVI) or (XLVII), which is derived from the IAP ligands described in Vamos, M., et al., *Expedient synthesis of highly potent antagonists of inhibitor of apoptosis proteins (IAPs) with unique selectivity for ML-IAP*, ACS Chem. Biol., 8(4), 725-32 (2013), or an unnatural mimetic thereof:

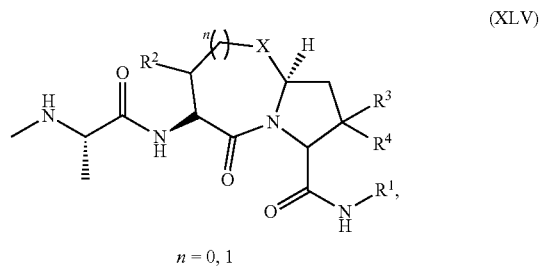

(XLV)

$n = 0, 1$

-continued (XLVI)

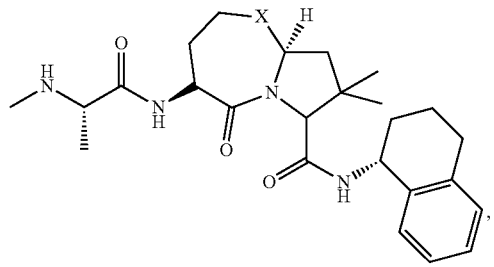

(XLVII)

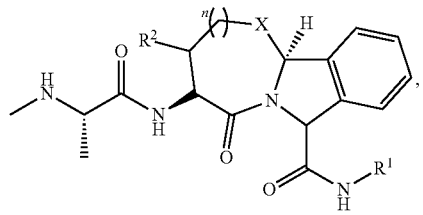

n = 0, 1 wherein:
R², R³ and R⁴ of Formula (XLV) are independently selected from H or ME;
X of Formula (XLV) is independently selected from O or S; and
R¹ of Formula (XLV) is selected from:

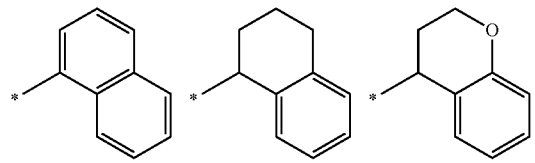

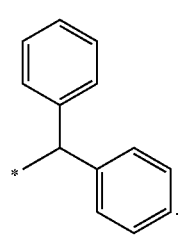

In a particular embodiment, the ILM has a structure according to Formula (XLVIII):

(XLVIII)

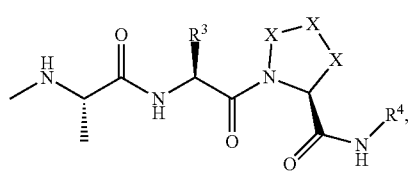

wherein R³ and R⁴ of Formula (XLVIII) are independently selected from H or ME;

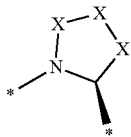

is a 5-member heterocycle selected from:

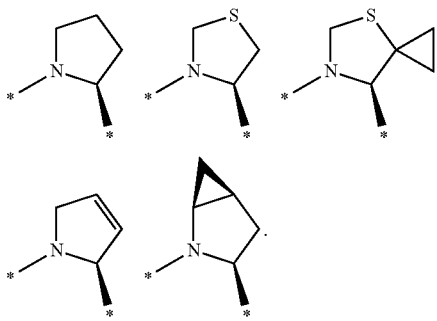

In a particular embodiment, the

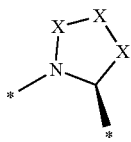

of Formula XLVIII) is

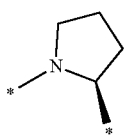

In a particular embodiment, the ILM has a structure and attached to a linker group L as shown below:

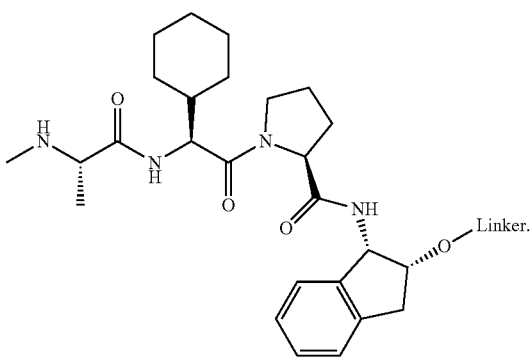

In a particular embodiment, the ILM has a structure according to Formula (XLIX), (L), or (LI):
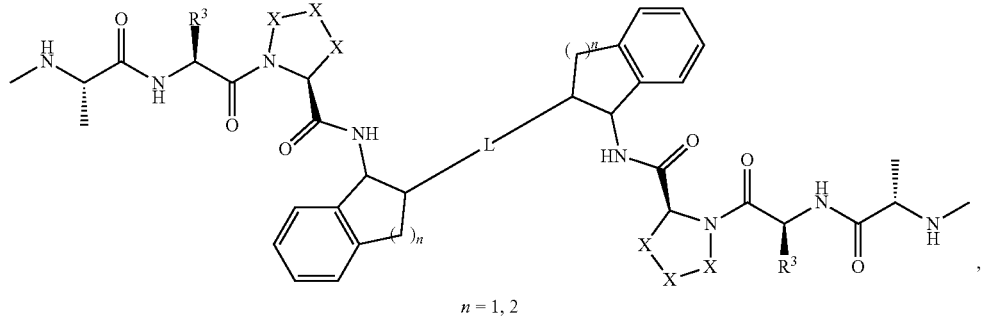
(XLIX)
$n = 1, 2$
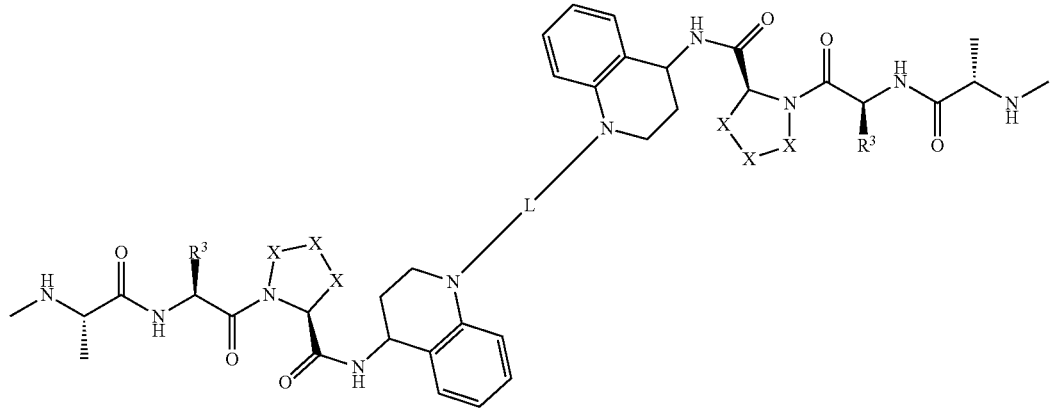
(L)
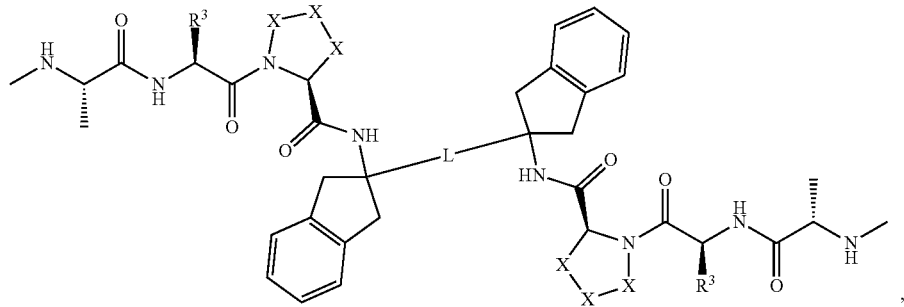
(LI)
wherein:
R³ of Formula (XLIX), (L) or (LI) are independently selected from H or ME;
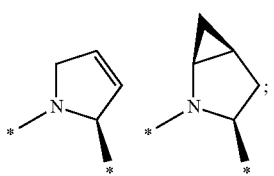
is a 5-member heterocycle selected from:
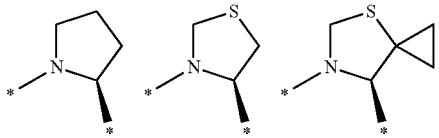

and
L of Formula (XLIX), (L) or (LI) is selected from:
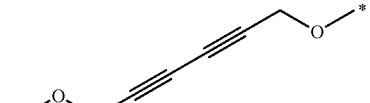
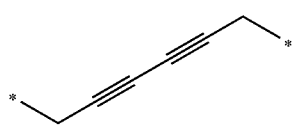
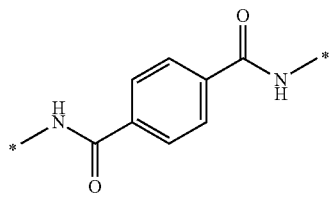
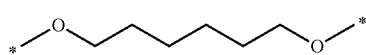
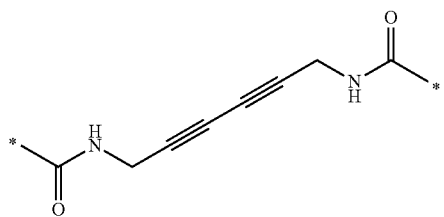
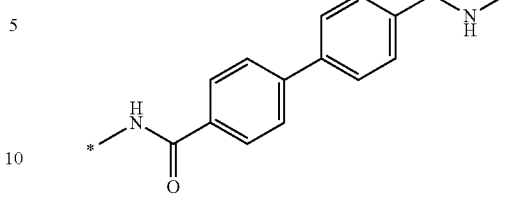
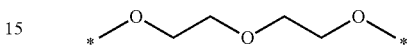
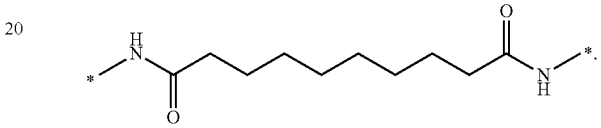
In a particular embodiment, L of Formula (XLIX), (L), or (LI)
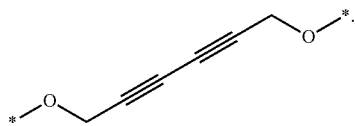
In a particular embodiment, the ILM has a structure according to Formula (LII):
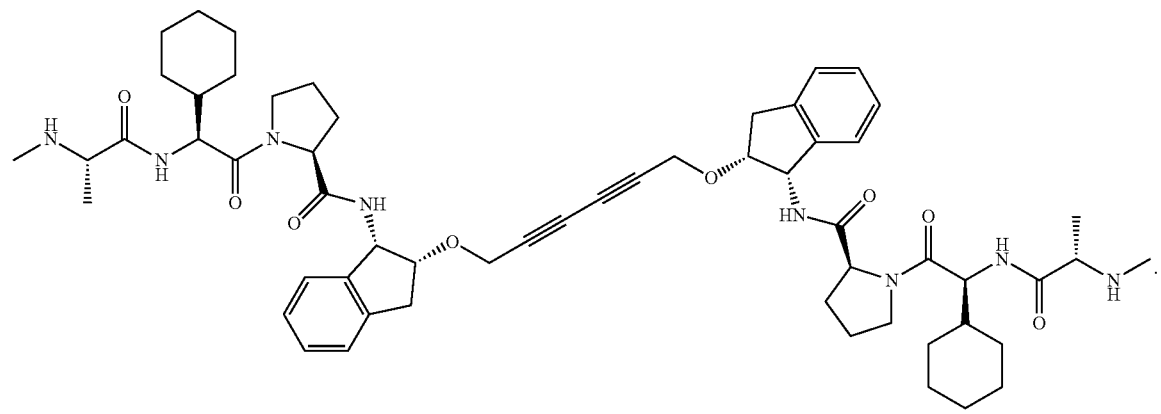

In a particular embodiment, the ILM according to Formula (LII) is chemically linked to the linker group L in the area denoted with

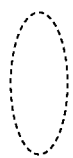

and as shown below:

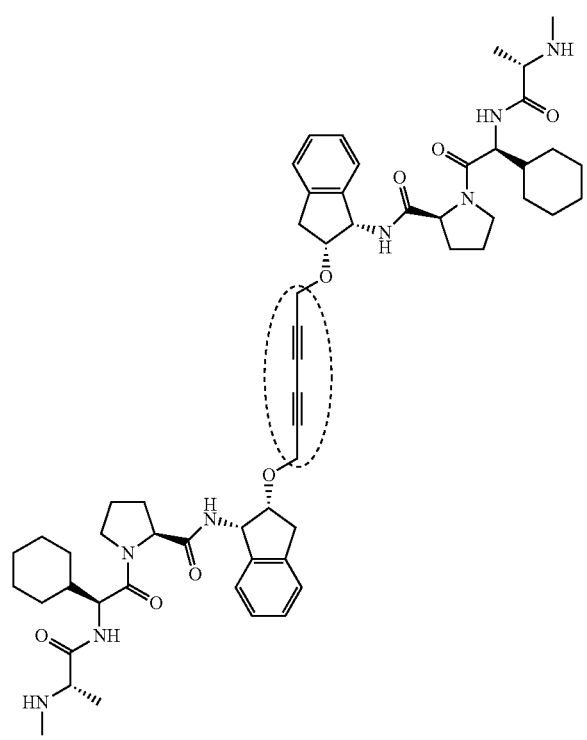 [SMILES: CN[C@@H](C)C(=O)N[C@H](C(=O)N1CCC[C@H]1C(=O)N[C@H]1c2ccccc2C[C@H]1OCC#CC#CCO[C@@H]1Cc2ccccc2[C@@H]1NC(=O)[C@@H]1CCCN1C(=O)[C@@H](NC(=O)[C@H](C)NC)C1CCCCC1)C1CCCCC1]

In any of the compounds described herein, the ILM can have the structure of Formula (LIII) or (LIV), which is based on the TAP ligands described in Hennessy, E J, et al., *Discovery of aminopiperidine-based Smac mimetics as IAP antagonists*, Bioorg. Med. Chem. Lett., 22(4), 1960-4 (2012), or an unnatural mimetic thereof:

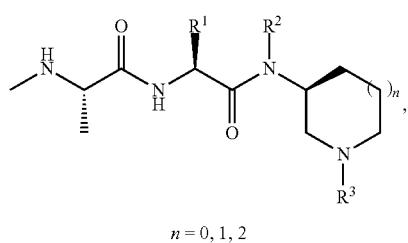

(LIII)

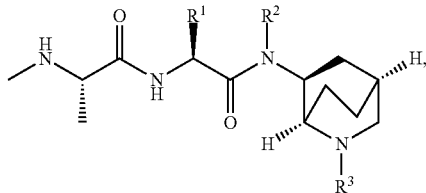

wherein:

R¹ of Formulas (LIII) and (LIV) is selected from:

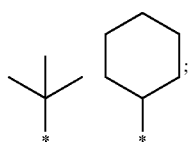

R² of Formulas (LIII) and (LIV) is selected from H or Me;
R³ of Formulas (LIII) and (LIV) is selected from:

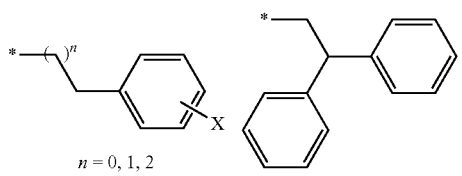

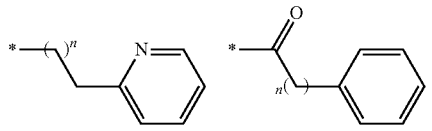

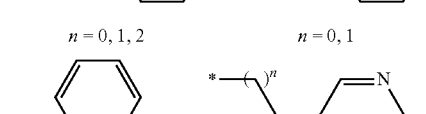

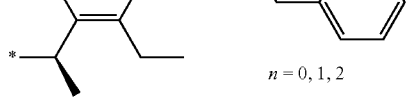

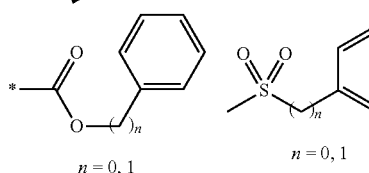

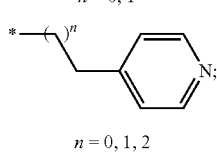

$n = 0, 1, 2$

X of is selected from H, halogen, methyl, methoxy, hydroxy, nitro or trifluoromethyl.

In any of the compounds described herein, the ILM can have the structure of and be chemically linked to the linker as shown in Formula (LV) or (LVI), or an unnatural mimetic thereof:

(LV)
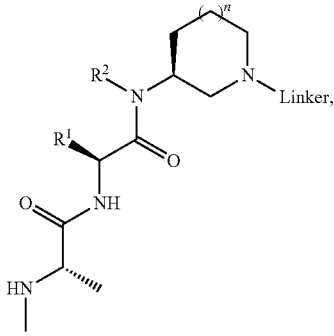

(LVI)
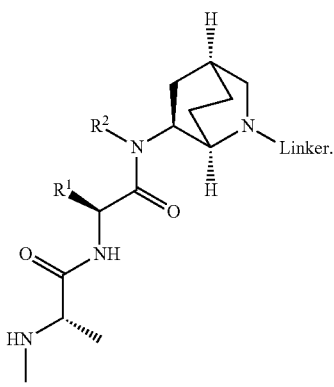

In any of the compounds described herein, the ILM can have the structure of Formula (LVII), which is based on the IAP ligands described in Cohen, F, et al., *Orally bioavailable antagonists of inhibitor of apoptosis proteins based on an azabicyclooctane scaffold*, J. Med. Chem., 52(6), 1723-30 (2009), or an unnatural mimetic thereof:

(LVII)
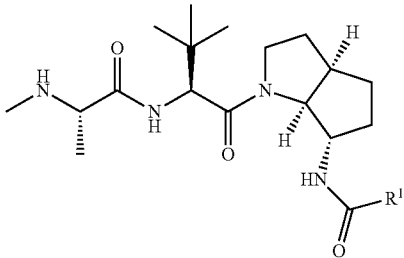

wherein:

$R^1$ of Formulas (LVII) is selected from:

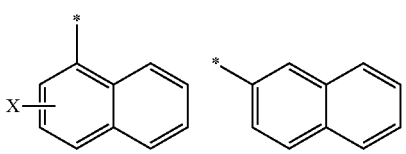

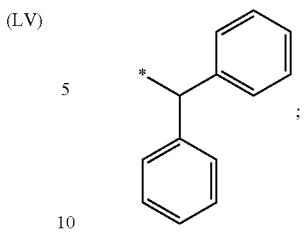

X of

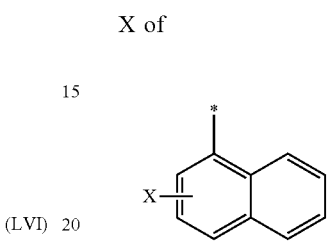

is selected from H, fluoro, methyl or methoxy.

In a particular embodiment, the ILM is represented by the following structure:

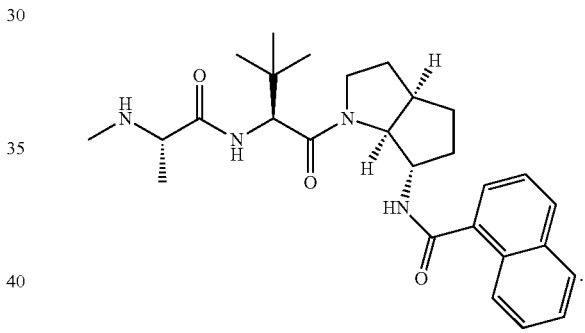

In a particular embodiment, the ILM is selected from the group consisting of, and which the chemical link between the ILM and linker group L is shown:

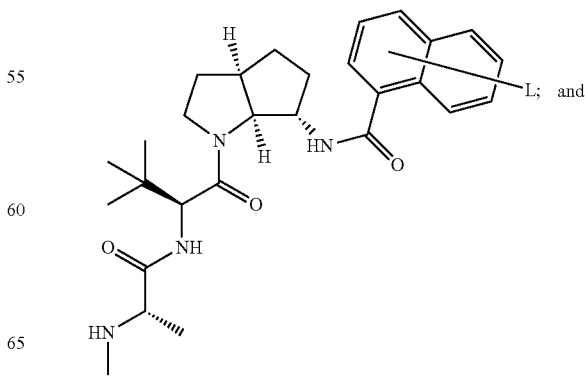

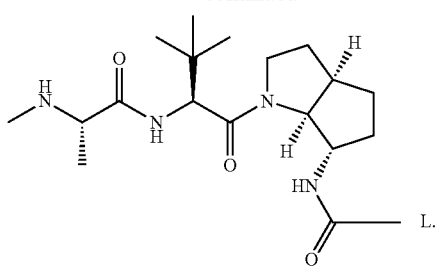

In any of the compounds described herein, the ILM is selected from the group consisting of the structures below, which are based on the IAP ligands described in Asano, M, et al., *Design, sterioselective synthesis, and biological evaluation of novel tri-cyclic compounds as inhibitor of apoptosis proteins (IAP) antagonists*, Bioorg. Med. Chem., 21(18): 5725-37 (2013), or an unnatural mimetic thereof:

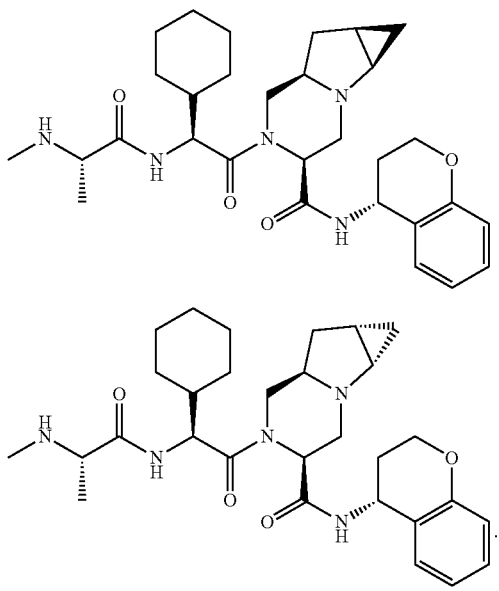

In a particular embodiment, the ILM is selected from the group consisting of, and which the chemical link between the ILM and linker group L is shown:

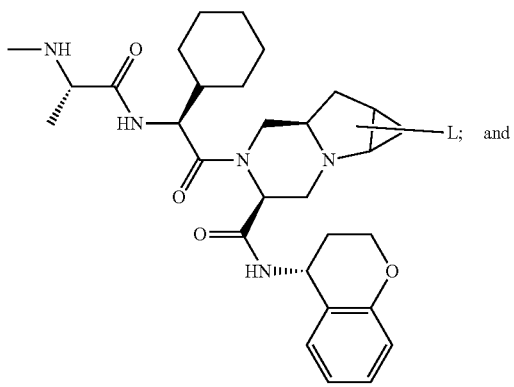

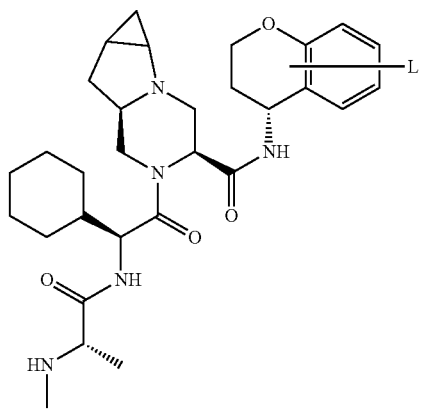

In any of the compounds described herein, the ILM can have the structure of Formula (LVIII), which is based on the IAP ligands described in Asano, M, et al., *Design, sterioselective synthesis, and biological evaluation of novel tri-cyclic compounds as inhibitor of apoptosis proteins (IAP) antagonists*, Bioorg. Med. Chem., 21(18): 5725-37 (2013), or an unnatural mimetic thereof:

(LVIII)

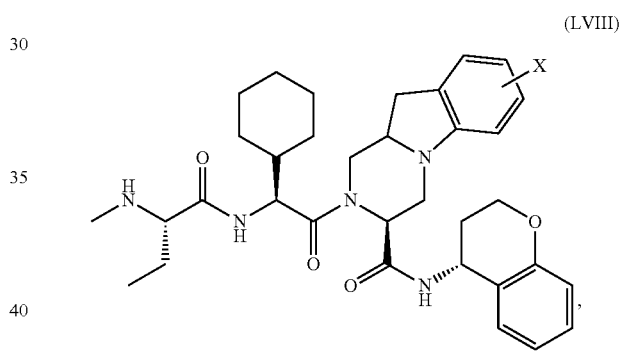

wherein X of Formula (LVIII) is one or two substituents independently selected from H, halogen or cyano.

In any of the compounds described herein, the ILM can have the structure of and be chemically linked to the linker group L as shown in Formula (LIX) or (LX), or an unnatural mimetic thereof:

(LIX)

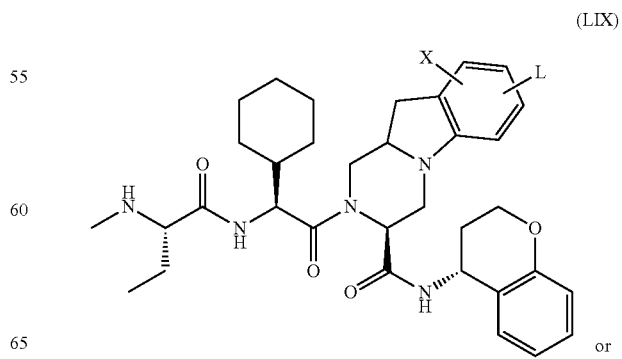

or

-continued

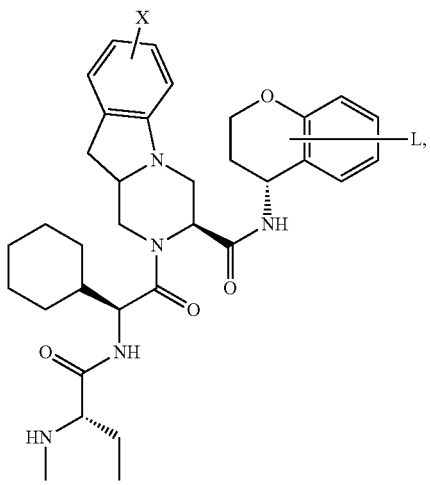
(LX)

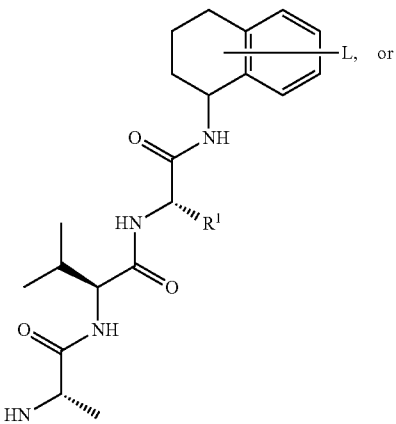
(LXII)

wherein X of Formula (LIX) and (LX) is one or two substituents independently selected from H, halogen or cyano, and; and L of Formulas (LIX) and (LX) is a linker group as described herein.

In any of the compounds described herein, the ILM can have the structure of Formula (LXI), which is based on the IAP ligands described in Ardecky, R J, et al., *Design, synthesis and evaluation of inhibitor of apoptosis (IAP) antagonists that are highly selective for the BIR2 domain of XIAP*, Bioorg. Med. Chem., 23(14): 4253-7 (2013), or an unnatural mimetic thereof:

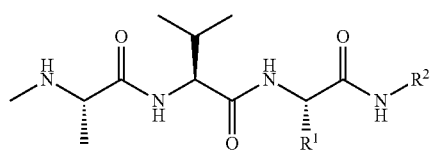
(LXI)

wherein:

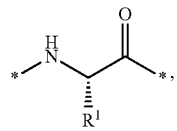

of Formula (LXI) is a natural or unnatural amino acid; and $R^2$ of Formula (LXI) is selected from:

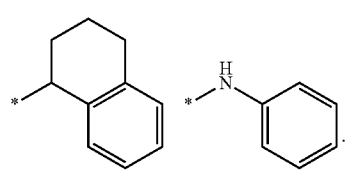

In any of the compounds described herein, the ILM can have the structure of and be chemically linked to the linker group L as shown in Formula (LXII) or (LLXIII), or an unnatural mimetic thereof:

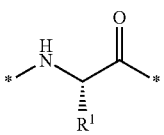

of Formula (LXI) is a natural or unnatural amino acid; and L of Formula (LXI) is a linker group as described herein.

In any of the compounds described herein, the ILM can have the structure selected from the group consisting of, which is based on the IAP ligands described in Wang, J, et al., *Discovery of novel second mitochondrial-derived activator of caspase mimetics as selective inhibitor or apoptosis protein inhibitors*, J. Pharmacol. Exp. Ther., 349(2): 319-29 (2014), or an unnatural mimetic thereof:

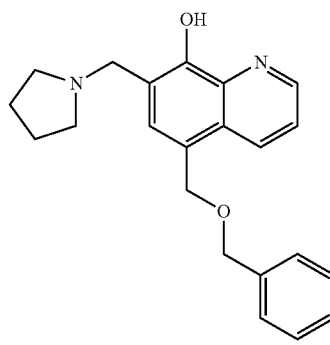
; and

-continued

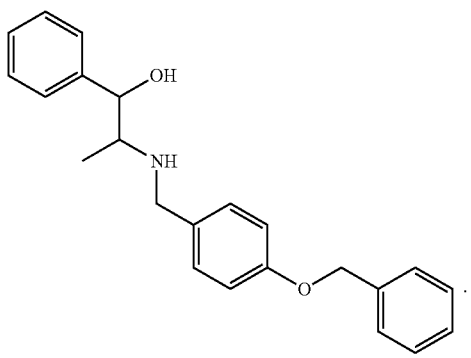

In any of the compounds described herein, the ILM has a structure according to Formula (LXIX), which is based on the IAP ligands described in Hird, A W, et al., Structure-based design and synthesis of tricyclic IAP (*Inhibitors of Apoptosis Proteins*) inhibitors, Bioorg. Med. Chem. Lett., 24(7) 1820-4 (2014), or an unnatural mimetic thereof:

(LXIX)

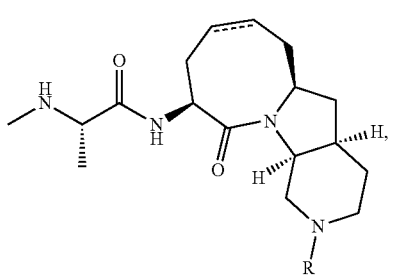

wherein R of Formula LIX is selected from the group consisting of:

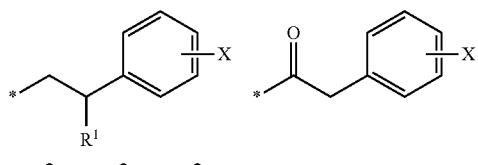

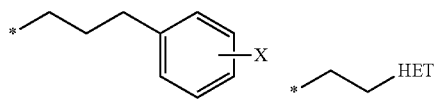

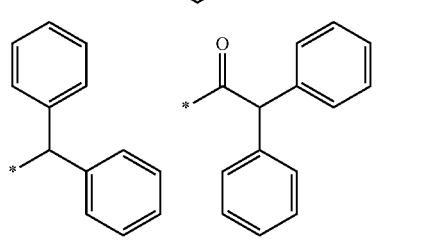

-continued

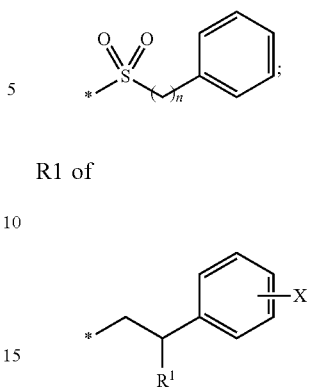

R1 of

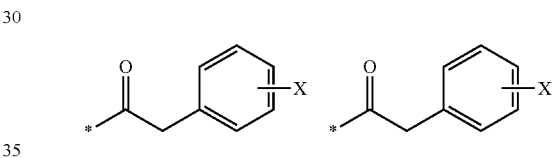

is selected from H or Me;
R2 of

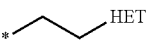

is selected from alkyl or cycloalkyl;
X of is 1-2 substitutents independently selected from halogen, hydroxy, methoxy, nitro and trifluoromethyl
Z of is O or NH;
HET of is mono- or fused bicyclic heteroaryl; and
- - - of Formula (LIX) is an optional double bond.

In a particular embodiment, the ILM of the compound has a chemical structure as represented by:
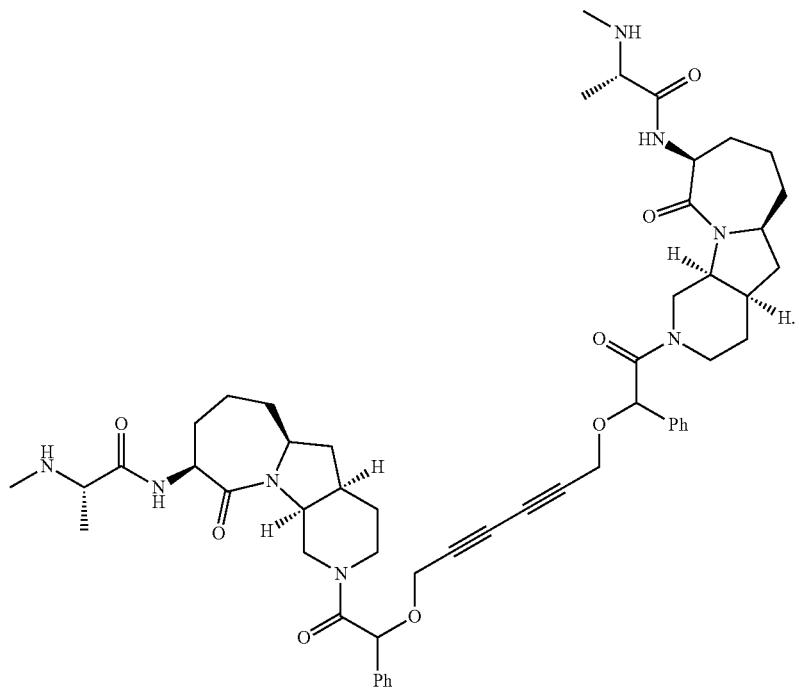
In a particular embodiment, the ILM of the compound has a chemical structure selected from the group consisting of:
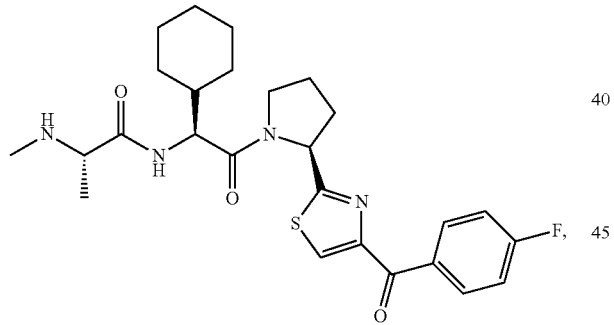
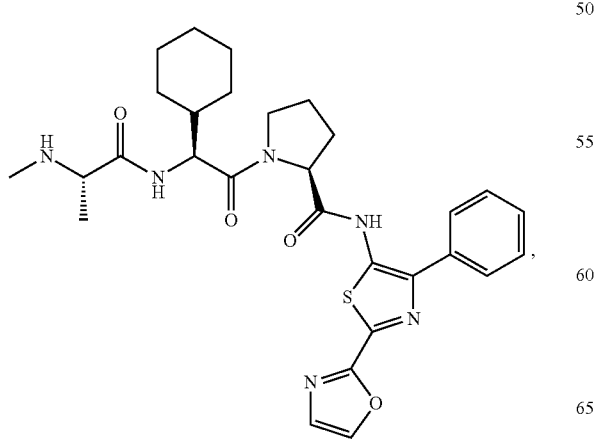
-continued
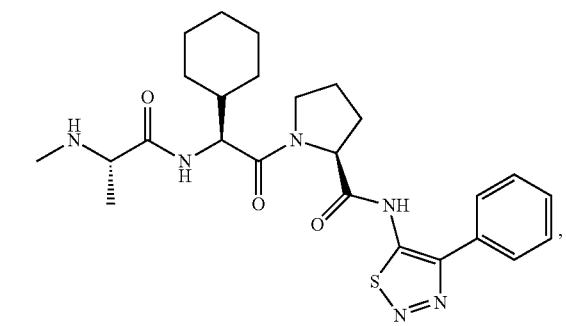
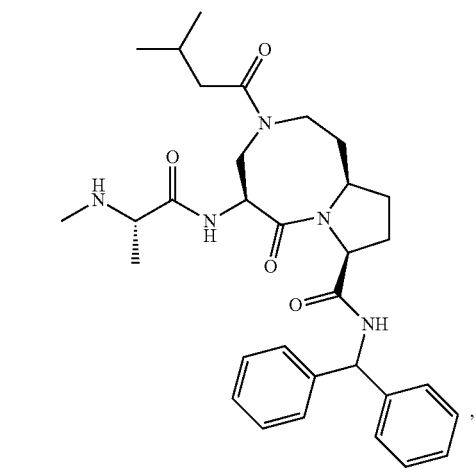

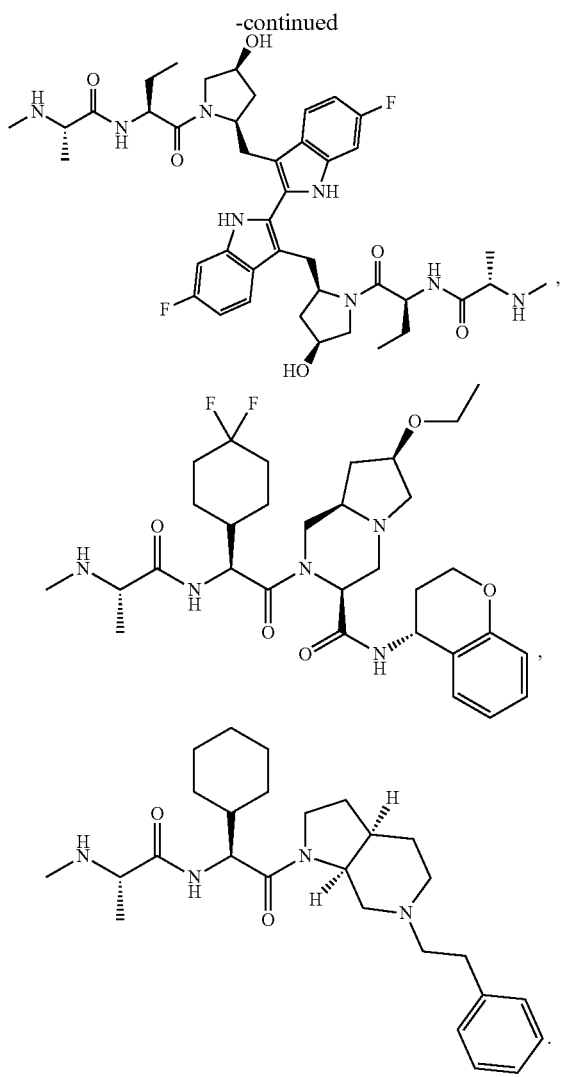

The term "independently" is used herein to indicate that the variable, which is independently applied, varies independently from application to application.

The term "alkyl" shall mean within its context a linear, branch-chained or cyclic fully saturated hydrocarbon radical or alkyl group, preferably a $C_1$-$C_{10}$, more preferably a $C_1$-$C_6$, alternatively a $C_1$-$C_3$ alkyl group, which may be optionally substituted. Examples of alkyl groups are methyl, ethyl, n-butyl, sec-butyl, n-hexyl, n-heptyl, n-octyl, n-nonyl, n-decyl, isopropyl, 2-methylpropyl, cyclopropyl, cyclopropylmethyl, cyclobutyl, cyclopentyl, cyclopentylethyl, cyclohexylethyl and cyclohexyl, among others. In certain embodiments, the alkyl group is end-capped with a halogen group (At, Br, Cl, F, or I). In certain preferred embodiments, compounds according to the present disclosure which may be used to covalently bind to dehalogenase enzymes. These compounds generally contain a side chain (often linked through a polyethylene glycol group) which terminates in an alkyl group which has a halogen substituent (often chlorine or bromine) on its distal end which results in covalent binding of the compound containing such a moiety to the protein.

The term "Alkenyl" refers to linear, branch-chained or cyclic $C_2$-$C_{10}$ (preferably $C_2$-$C_6$) hydrocarbon radicals containing at least one C=C bond.

The term "Alkynyl" refers to linear, branch-chained or cyclic $C_2$-$C_{10}$ (preferably $C_2$-$C_6$) hydrocarbon radicals containing at least one C≡C bond.

The term "alkylene" when used, refers to a —$(CH_2)_n$— group (n is an integer generally from 0-6), which may be optionally substituted. When substituted, the alkylene group preferably is substituted on one or more of the methylene groups with a $C_1$-$C_6$ alkyl group (including a cyclopropyl group or a t-butyl group), but may also be substituted with one or more halo groups, preferably from 1 to 3 halo groups or one or two hydroxyl groups, 0-($C_1$-$C_6$ alkyl) groups or amino acid sidechains as otherwise disclosed herein. In certain embodiments, an alkylene group may be substituted with a urethane or alkoxy group (or other group) which is further substituted with a polyethylene glycol chain (of from 1 to 10, preferably 1 to 6, often 1 to 4 ethylene glycol units) to which is substituted (preferably, but not exclusively on the distal end of the polyethylene glycol chain) an alkyl chain substituted with a single halogen group, preferably a chlorine group. In still other embodiments, the alkylene (often, a methylene) group, may be substituted with an amino acid sidechain group such as a sidechain group of a natural or unnatural amino acid, for example, alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan or tyrosine.

The term "unsubstituted" shall mean substituted only with hydrogen atoms. A range of carbon atoms which includes $C_0$ means that carbon is absent and is replaced with H. Thus, a range of carbon atoms which is $C_0$-$C_6$ includes carbons atoms of 1, 2, 3, 4, 5 and 6 and for $C_0$, H stands in place of carbon.

The term "substituted" or "optionally substituted" shall mean independently (i.e., where more than substituent occurs, each substituent is independent of another substituent) one or more substituents (independently up to five substituents, preferably up to three substituents, often 1 or 2 substituents on a moiety in a compound according to the present disclosure and may include substituents which themselves may be further substituted) at a carbon (or nitrogen) position anywhere on a molecule within context, and includes as substituents hydroxyl, thiol, carboxyl, cyano (C≡N), nitro ($NO_2$), halogen (preferably, 1, 2 or 3 halogens, especially on an alkyl, especially a methyl group such as a trifluoromethyl), an alkyl group (preferably, $C_1$-$C_{10}$, more preferably, $C_1$-$C_6$), aryl (especially phenyl and substituted phenyl for example benzyl or benzoyl), alkoxy group (preferably, $C_1$-$C_6$ alkyl or aryl, including phenyl and substituted phenyl), thioether ($C_1$-$C_6$ alkyl or aryl), acyl (preferably, $C_1$-$C_6$ acyl), ester or thioester (preferably, $C_1$-$C_6$ alkyl or aryl) including alkylene ester (such that attachment is on the alkylene group, rather than at the ester function which is preferably substituted with a $C_1$-$C_6$ alkyl or aryl group), preferably, $C_1$-$C_6$ alkyl or aryl, halogen (preferably, F or $C_1$), amine (including a five- or six-membered cyclic alkylene amine, further including a $C_1$-$C_6$ alkyl amine or a $C_1$-$C_6$ dialkyl amine which alkyl groups may be substituted with one or two hydroxyl groups) or an optionally substituted —N($C_0$-$C_6$ alkyl)C(O)(O—$C_1$-$C_6$ alkyl) group (which may be optionally substituted with a polyethylene glycol chain to which is further bound an alkyl group containing a single halogen, preferably chlorine substituent), hydrazine, amido, which is preferably substituted with one or two $C_1$-$C_6$ alkyl groups (including a carboxamide which is optionally substituted with one or two $C_1$-$C_6$ alkyl groups), alkanol (preferably, $C_1$-$C_6$ alkyl or aryl), or alkanoic acid (preferably, $C_1$-$C_6$ alkyl or aryl). Substituents according to the present disclosure may include, for example —$SiR_1R_2R_3$ groups where each of $R_1$ and $R_2$ is as otherwise described herein and $R_3$ is H or a $C_1$-$C_6$ alkyl group, preferably $R_1$, $R_2$, $R_3$ in this context is a $C_1$-$C_3$ alkyl group (including an isopropyl or t-butyl group). Each of the above-described groups may be linked directly to the substituted moiety or alternatively, the substituent may be linked to the substituted moiety (preferably in the case of an aryl or heteroaryl moiety) through an optionally substituted —$(CH_2)_m$ or alternatively an optionally substituted —$(OCH_2)_m$—, —$(OCH_2CH_2)_m$ or —$(CH_2CH_2O)_m$ group, which may be substituted with any one or more of the above-described substituents. Alkylene groups —$(CH_2)_m$ or —$(CH_2)_n$— groups or other chains such as ethylene glycol chains, as identified above, may be substituted anywhere on the chain. Preferred substituents on alkylene groups include halogen or $C_1$-$C_6$ (preferably $C_1$-$C_3$) alkyl groups, which may be optionally substituted with one or two hydroxyl groups, one or two ether groups (O—$C_1$-$C_6$ groups), up to three halo groups (preferably F), or a sidechain of an amino acid as otherwise described herein and optionally substituted amide (preferably carboxamide substituted as described above) or urethane groups (often with one or two $C_0$-$C_6$ alkyl substituents, which group(s) may be further substituted). In certain embodiments, the alkylene group (often a single methylene group) is substituted with one or two optionally substituted $C_1$-$C_6$ alkyl groups, preferably $C_1$-$C_4$ alkyl group, most often methyl or O-methyl groups or a sidechain of an amino acid as otherwise described herein. In the present disclosure, a moiety in a molecule may be optionally substituted with up to five substituents, preferably up to three substituents. Most often, in the present disclosure moieties which are substituted are substituted with one or two substituents.

The term "substituted" (each substituent being independent of any other substituent) shall also mean within its context of use $C_1$-$C_6$ alkyl, $C_1$-$C_6$ alkoxy, halogen, amido, carboxamido, sulfone, including sulfonamide, keto, carboxy, $C_1$-$C_6$ester (oxyester or carbonylester), $C_1$-$C_6$keto, urethane —O—C(O)—$NR_1R_2$ or —$N(R_1)$—C(O)—O—$R^1$, nitro, cyano and amine (especially including a $C_1$-$C_6$ alkylene-$NR^1R^2$, a mono- or di-$C_1$-$C_6$ alkyl substituted amines which may be optionally substituted with one or two hydroxyl groups). Each of these groups contain unless otherwise indicated, within context, between 1 and 6 carbon atoms. In certain embodiments, preferred substituents will include for example, —NH—, —NHC(O)—, —O—, =O, —$(CH_2)_m$ (here, m and n are in context, 1, 2, 3, 4, 5 or 6), —S—, —S(O)—, $SO_2$— or —NH—C(O)—NH—, —$(CH_2)_n$OH, —$(CH_2)_n$SH, —$(CH_2)_n$COOH, $C_1$-$C_6$ alkyl, —$(CH_2)_n$O—($C_1$-$C_6$ alkyl), —$(CH_2)_n$C(O)—($C_1$-$C_6$ alkyl), —$(CH_2)_n$OC(O)—($C_1$-$C_6$ alkyl), —$(CH_2)_n$C(O)O—($C_1$-$C_6$ alkyl), —$(CH_2)_n$NHC(O)—$R_1$, —$(CH_2)_n$C(O)—$NR_1R_2$, —$(OCH_2)_n$OH, —$(CH_2O)_n$COOH, $C_1$-$C_6$ alkyl, —$(OCH_2)_n$O—($C_1$-$C_6$ alkyl), —$(CH_2O)_n$C(O)—($C_1$-$C_6$ alkyl), —$(OCH_2)_n$NHC(O)—$R_1$, —$(CH_2O)_n$C(O)—$NR_1R_2$, —$S(O)_2$—$R_S$, —S(O)—$R_S$ ($R_S$ is $C_1$-$C_6$ alkyl or a —$(CH_2)_m$—$NR^1R_2$ group), $NO_2$, CN or halogen (F, $C_1$, Br, I, preferably F or $C_1$), depending on the context of the use of the substituent. $R_1$ and $R_2$ are each, within context, H or a $C_1$-$C_6$ alkyl group (which may be optionally substituted with one or two hydroxyl groups or up to three halogen groups, preferably fluorine). The term "substituted" shall also mean, within the chemical context of the compound defined and substituent used, an optionally substituted aryl or heteroaryl group or an optionally substituted heterocyclic group as otherwise described herein. Alkylene groups may also be substituted as otherwise disclosed herein, preferably with optionally substituted $C_1$-$C_6$alkyl groups (methyl, ethyl or hydroxymethyl or hydroxyethyl is preferred, thus providing a chiral center), a sidechain of an amino acid group as otherwise described herein, an amido group as described hereinabove, or a urethane group O—C(O)—$NR_1R_2$ group where $R_1$ and $R_2$ are as otherwise described herein, although numerous other groups may also be used as substituents. Various optionally substituted moieties may be substituted with 3 or more substituents, preferably no more than 3 substituents and preferably with 1 or 2 substituents. It is noted that in instances where, in a compound at a particular position of the molecule substitution is required (principally, because of valency), but no substitution is indicated, then that substituent is construed or understood to be H, unless the context of the substitution suggests otherwise.

The term "aryl" or "aromatic", in context, refers to a substituted (as otherwise described herein) or unsubstituted monovalent aromatic radical having a single ring (e.g., benzene, phenyl, benzyl) or condensed rings (e.g., naphthyl, anthracenyl, phenanthrenyl, etc.) and can be bound to the compound according to the present disclosure at any available stable position on the ring(s) or as otherwise indicated in the chemical structure presented. Other examples of aryl groups, in context, may include heterocyclic aromatic ring systems, "heteroaryl" groups having one or more nitrogen, oxygen, or sulfur atoms in the ring (moncyclic) such as imidazole, furyl, pyrrole, furanyl, thiene, thiazole, pyridine, pyrimidine, pyrazine, triazole, oxazole or fused ring systems such as indole, quinoline, indolizine, azaindolizine, benzofurazan, etc., among others, which may be optionally substituted as described above. Among the heteroaryl groups which may be mentioned include nitrogen-containing heteroaryl groups such as pyrrole, pyridine, pyridone, pyridazine, pyrimidine, pyrazine, pyrazole, imidazole, triazole, triazine, tetrazole, indole, isoindole, indolizine, azaindolizine, purine, indazole, quinoline, dihydroquinoline, tetrahydroquinoline, isoquinoline, dihydroisoquinoline, tetrahydroisoquinoline, quinolizine, phthalazine, naphthyridine, quinoxaline, quinazoline, cinnoline, pteridine, imidazopyridine, imidazotriazine, pyrazinopyridazine, acridine, phenanthridine, carbazole, carbazoline, pyrimidine, phenanthroline, phenacene, oxadiazole, benzimidazole, pyrrolopyridine, pyrrolopyrimidine and pyridopyrimidine; sulfur-containing aromatic heterocycles such as thiophene and benzothiophene; oxygen-containing aromatic heterocycles such as furan, pyran, cyclopentapyran, benzofuran and isobenzofuran; and aromatic heterocycles comprising 2 or more hetero atoms selected from among nitrogen, sulfur and oxygen, such as thiazole, thiadizole, isothiazole, benzoxazole, benzothiazole, benzothiadiazole, phenothiazine, isoxazole, furazan, phenoxazine, pyrazoloxazole, imidazothiazole, thienofuran, furopyrrole, pyridoxazine, furopyridine, furopyrimidine, thienopyrimidine and oxazole, among others, all of which may be optionally substituted.

The term "substituted aryl" refers to an aromatic carbocyclic group comprised of at least one aromatic ring or of multiple condensed rings at least one of which being aromatic, wherein the ring(s) are substituted with one or more substituents. For example, an aryl group can comprise a substituent(s) selected from: —$(CH_2)_n$OH, —$(CH_2)_n$—O—($C_1$-$C_6$)alkyl, —$(CH_2)_n$—O—$(CH_2)_n$—($C_1$-$C_6$)alkyl, —$(CH_2)_n$—C(O)($C_0$-$C_6$) alkyl, —$(CH_2)_n$—C(O)O($C_0$-$C_6$) alkyl, —$(CH_2)_n$—OC(O)($C_0$-$C_6$)alkyl, amine, mono- or di-($C_1$-$C_6$ alkyl) amine wherein the alkyl group on the amine is optionally substituted with 1 or 2 hydroxyl groups or up to three halo (preferably F, $C_1$) groups, OH, COOH, $C_1$-$C_6$ alkyl, preferably CH₃, CF₃, OMe, OCF₃, NO₂, or CN group (each of which may be substituted in ortho-, meta- and/or para-positions of the phenyl ring, preferably para-), an optionally substituted phenyl group (the phenyl group itself is connected/coupled to a PTM group, including a ULM group via a linker group), and/or at least one of F, C₁, OH, COOH, CH₃, CF₃, OMe, OCF₃, NO₂, or CN group (in ortho-, meta- and/or para-positions of the phenyl ring, preferably para-), a naphthyl group, which may be optionally substituted, an optionally substituted heteroaryl, preferably an optionally substituted isoxazole including a methylsubstituted isoxazole, an optionally substituted oxazole including a methylsubstituted oxazole, an optionally substituted thiazole including a methyl substituted thiazole, an optionally substituted isothiazole including a methyl substituted isothiazole, an optionally substituted pyrrole including a methylsubstituted pyrrole, an optionally substituted imidazole including a methylimidazole, an optionally substituted benzimidazole or methoxybenzylimidazole, an optionally substituted oximidazole or methyloximidazole, an optionally substituted diazole group, including a methyldiazole group, an optionally substituted triazole group, including a methylsubstituted triazole group, an optionally substituted pyridine group, including a halo- (preferably, F) or methylsubstitutedpyridine group or an oxapyridine group (where the pyridine group is linked to the phenyl group by an oxygen), an optionally substituted furan, an optionally substituted benzofuran, an optionally substituted dihydrobenzofuran, an optionally substituted indole, indolizine or azaindolizine (2, 3, or 4-azaindolizine), an optionally substituted quinoline, and combinations thereof.

"Carboxyl" denotes the group —C(O)OR, where R is hydrogen, alkyl, substituted alkyl, aryl, substituted aryl, heteroaryl or substituted heteroaryl, whereas these generic substituents have meanings which are identical with definitions of the corresponding groups defined herein.

The term "heteroaryl" or "hetaryl" can mean but is in no way limited to an optionally substituted quinoline (which may be attached to the pharmacophore or substituted on any carbon atom within the quinoline ring), an optionally substituted indole (including dihydroindole), an optionally substituted indolizine, an optionally substituted azaindolizine (2, 3 or 4-azaindolizine) an optionally substituted benzimidazole, benzodiazole, benzoxofuran, an optionally substituted imidazole, an optionally substituted isoxazole, an optionally substituted oxazole (preferably methyl substituted), an optionally substituted diazole, an optionally substituted triazole, a tetrazole, an optionally substituted benzofuran, an optionally substituted thiophene, an optionally substituted thiazole (preferably methyl and/or thiol substituted), an optionally substituted isothiazole, an optionally substituted triazole (preferably a 1,2,3-triazole substituted with a methyl group, a triisopropylsilyl group, an optionally substituted —(CH₂)ₘ—O—C₁-C₆ alkyl group or an optionally substituted —(CH₂)ₘ—C(O)—O—C₁-C₆ alkyl group), an optionally substituted pyridine (2-, 3, or 4-pyridine) or a group according to the chemical structure:

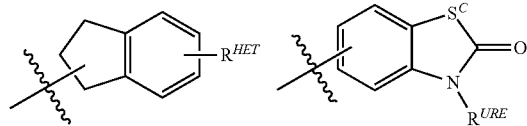

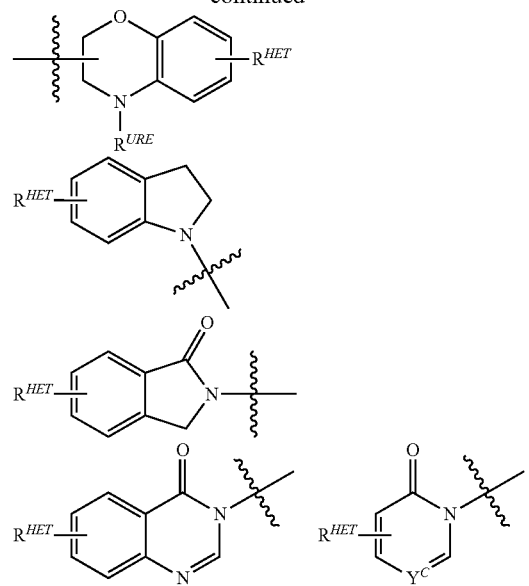

wherein:
$S^c$ is $CHR^{SS}$, $NR^{URE}$, or O;
$R^{HET}$ is H, CN, NO₂, halo (preferably Cl or F), optionally substituted C₁-C₆ alkyl (preferably substituted with one or two hydroxyl groups or up to three halo groups (e.g. CF₃), optionally substituted O(C₁-C₆ alkyl) (preferably substituted with one or two hydroxyl groups or up to three halo groups) or an optionally substituted acetylenic group —C≡C—$R_a$ where $R_a$ is H or a C₁-C₆ alkyl group (preferably C₁-C₃ alkyl);
$R^{SS}$ is H, CN, NO₂, halo (preferably F or C₁), optionally substituted C₁-C₆ alkyl (preferably substituted with one or two hydroxyl groups or up to three halo groups), optionally substituted O—(C₁-C₆ alkyl) (preferably substituted with one or two hydroxyl groups or up to three halo groups) or an optionally substituted —C(O) (C₁-C₆ alkyl) (preferably substituted with one or two hydroxyl groups or up to three halo groups);
$R^{URE}$ is H, a C₁-C₆ alkyl (preferably H or C₁-C₃ alkyl) or a —C(O)(C₁-C₆ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and
$Y^C$ is N or C—$R^{YC}$, where $R^{YC}$ is H, OH, CN, NO₂, halo (preferably Cl or F), optionally substituted C₁-C₆ alkyl (preferably substituted with one or two hydroxyl groups or up to three halo groups (e.g. CF₃), optionally substituted O(C₁-C₆ alkyl) (preferably substituted with one or two hydroxyl groups or up to three halo groups) or an optionally substituted acetylenic group —C≡C—$R_a$ where $R_a$ is H or a C₁-C₆ alkyl group (preferably C₁-C₃ alkyl).

The terms "aralkyl" and "heteroarylalkyl" refer to groups that comprise both aryl or, respectively, heteroaryl as well as alkyl and/or heteroalkyl and/or carbocyclic and/or heterocycloalkyl ring systems according to the above definitions.

The term "arylalkyl" as used herein refers to an aryl group as defined above appended to an alkyl group defined above. The arylalkyl group is attached to the parent moiety through an alkyl group wherein the alkyl group is one to six carbon atoms. The aryl group in the arylalkyl group may be substituted as defined above.

The term "Heterocycle" refers to a cyclic group which contains at least one heteroatom, e.g., N, O or S, and may be aromatic (heteroaryl) or non-aromatic. Thus, the heteroaryl moieties are subsumed under the definition of heterocycle, depending on the context of its use. Exemplary heteroaryl groups are described hereinabove.

Exemplary heterocyclics include: azetidinyl, benzimidazolyl, 1,4-benzodioxanyl, 1,3-benzodioxolyl, benzoxazolyl, benzothiazolyl, benzothienyl, dihydroimidazolyl, dihydropyranyl, dihydrofuranyl, dioxanyl, dioxolanyl, ethyleneurea, 1,3-dioxolane, 1,3-dioxane, 1,4-dioxane, furyl, homopiperidinyl, imidazolyl, imidazolinyl, imidazolidinyl, indolinyl, indolyl, isoquinolinyl, isothiazolidinyl, isothiazolyl, isoxazolidinyl, isoxazolyl, morpholinyl, naphthyridinyl, oxazolidinyl, oxazolyl, pyridone, 2-pyrrolidone, pyridine, piperazinyl, N-methylpiperazinyl, piperidinyl, phthalimide, succinimide, pyrazinyl, pyrazolinyl, pyridyl, pyrimidinyl, pyrrolidinyl, pyrrolinyl, pyrrolyl, quinolinyl, tetrahydrofuranyl, tetrahydropyranyl, tetrahydroquinoline, thiazolidinyl, thiazolyl, thienyl, tetrahydrothiophene, oxane, oxetanyl, oxathiolanyl, thiane among others.

Heterocyclic groups can be optionally substituted with a member selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SOaryl, —SO-heteroaryl, —SO2-alkyl, —SO2-substituted alkyl, —SO2-aryl, oxo (=O), and —SO2-heteroaryl. Such heterocyclic groups can have a single ring or multiple condensed rings. Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxynitrogen containing heterocycles. The term "heterocyclic" also includes bicyclic groups in which any of the heterocyclic rings is fused to a benzene ring or a cyclohexane ring or another heterocyclic ring (for example, indolyl, quinolyl, isoquinolyl, tetrahydroquinolyl, and the like).

The term "cycloalkyl" can mean but is in no way limited to univalent groups derived from monocyclic or polycyclic alkyl groups or cycloalkanes, as defined herein, e.g., saturated monocyclic hydrocarbon groups having from three to twenty carbon atoms in the ring, including, but not limited to, cyclopropyl, cyclobutyl, cyclopentyl, cyclohexyl, cycloheptyl and the like. The term "substituted cycloalkyl" can mean but is in no way limited to a monocyclic or polycyclic alkyl group and being substituted by one or more substituents, for example, amino, halogen, alkyl, substituted alkyl, carbyloxy, carbylmercapto, aryl, nitro, mercapto or sulfo, whereas these generic substituent groups have meanings which are identical with definitions of the corresponding groups as defined in this legend.

"Heterocycloalkyl" refers to a monocyclic or polycyclic alkyl group in which at least one ring carbon atom of its cyclic structure being replaced with a heteroatom selected from the group consisting of N, O, S or P. "Substituted heterocycloalkyl" refers to a monocyclic or polycyclic alkyl group in which at least one ring carbon atom of its cyclic structure being replaced with a heteroatom selected from the group consisting of N, O, S or P and the group is containing one or more substituents selected from the group consisting of halogen, alkyl, substituted alkyl, carbyloxy, carbylmercapto, aryl, nitro, mercapto or sulfo, whereas these generic substituent group have meanings which are identical with definitions of the corresponding groups as defined in this legend.

The term "hydrocarbyl" shall mean a compound which contains carbon and hydrogen and which may be fully saturated, partially unsaturated or aromatic and includes aryl groups, alkyl groups, alkenyl groups and alkynyl groups.

The term "independently" is used herein to indicate that the variable, which is independently applied, varies independently from application to application.

The term "lower alkyl" refers to methyl, ethyl or propyl The term "lower alkoxy" refers to methoxy, ethoxy or propoxy.

In any of the embodiments described herein, the W, X, Y, Z, G, G', R, R', R", Q1-Q4, A, and Rn can independently be covalently coupled to a linker and/or a linker to which is attached one or more PTM, ULM, ILM or ILM' groups.

Exemplary MLMs

In certain additional embodiments, the MLM of the bifunctional compound comprises chemical moieties such as substituted imidazolines, substituted spiro-indolinones, substituted pyrrolidines, substituted piperidinones, substituted morpholinones, substituted pyrrolopyrimidines, substituted imidazolopyridines, substituted thiazoloimidazoline, substituted pyrrolopyrrolidinones, and substituted isoquinolinones.

In additional embodiments, the MLM comprises the core structures mentioned above with adjacent bis-aryl substitutions positioned as cis- or trans-configurations.

In still additional embodiments, the MLM comprises part of structural features as in RG7112, RG7388, SAR405838, AMG-232, AM-7209, DS-5272, MK-8242, and NVP-CGM-097, and analogs or derivatives thereof.

In certain preferred embodiments, MLM is a derivative of substituted imidazoline represented as Formula (A-1), or thiazoloimidazoline represented as Formula (A-2), or spiro indolinone represented as Formula (A-3), or pyrollidine represented as Formula (A-4), or piperidinone/morphlinone represented as Formula (A-5), or isoquinolinone represented as Formula (A-6), or pyrollopyrimidine/imidazolopyridine represented as Formula (A-7), or pyrrolopyrrolidinone/imidazolopyrrolidinone represented as Formula (A-8).

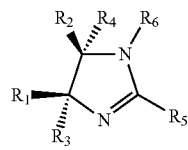

Formula (A-1)

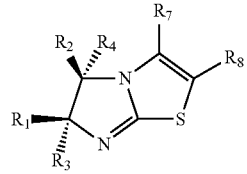

Formula (A-2)

-continued

Formula (A-3)

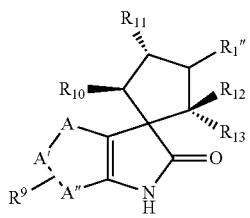

Formula (A-4)

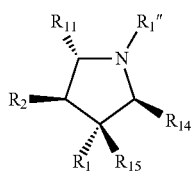

Formula (A-5)

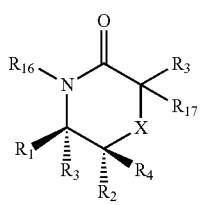

Formula (A-6)

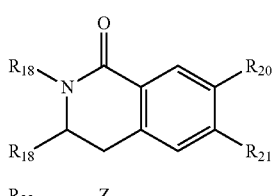

Formula (A-7)

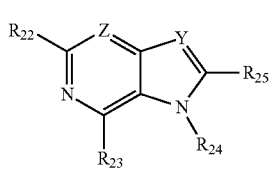

Formula (A-8)

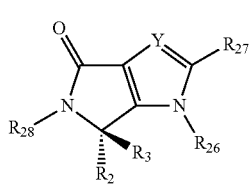

wherein above Formula (A-1) through Formula (A-8),
X of Formula (A-1) through Formula (A-8) is selected from the group consisting of carbon, oxygen, sulfur, sulfoxide, sulfone, and N—$R^a$;
  $R^a$ is independently H or an alkyl group with carbon number 1 to 6;
Y and Z of Formula (A-1) through Formula (A-8) are independently carbon or nitrogen;
A, A' and A" of Formula (A-1) through Formula (A-8) are independently selected from C, N, O or S, can also be one or two atoms forming a fused bicyclic ring, or a 6,5- and 5,5-fused aromatic bicyclic group;
$R_1$, $R_2$ of Formula (A-1) through Formula (A-8) are independently selected from the group consisting of an aryl or heteroaryl group, a heteroaryl group having one or two heteroatoms independently selected from sulfur or nitrogen, wherein the aryl or heteroaryl group can be mono-cyclic or bi-cyclic, or unsubstituted or substituted with one to three substituents independently selected from the group consisting of:
  halogen, —CN, C1 to C6 alkyl group, C3 to C6 cycloalkyl, —OH, alkoxy with 1 to 6 carbons, fluorine substituted alkoxy with 1 to 6 carbons, sulfoxide with 1 to 6 carbons, sulfone with 1 to 6 carbons, ketone with 2 to 6 carbons, amides with 2 to 6 carbons, and dialkyl amine with 2 to 6 carbons;
$R_3$, $R_4$ of Formula (A-1) through Formula (A-8) are independently selected from the group consisting of H, methyl and C1 to C6 alkyl;
$R_5$ of Formula (A-1) through Formula (A-8) is selected from the group consisting of an aryl or heteroaryl group, a heteroaryl group having one or two heteroatoms independently selected from sulfur or nitrogen, wherein the aryl or heteroaryl group can be mono-cyclic or bi-cyclic, or unsubstituted or substituted with one to three substituents independently selected from the group consisting of:
  halogen, —CN, C1 to C6 alkyl group, C3 to C6 cycloalkyl, —OH, alkoxy with 1 to 6 carbons, fluorine substituted alkoxy with 1 to 6 carbons, sulfoxide with 1 to 6 carbons, sulfone with 1 to 6 carbons, ketone with 2 to 6 carbons, amides with 2 to 6 carbons, dialkyl amine with 2 to 6 carbons, alkyl ether (C2 to C6), alkyl ketone (C3 to C6), morpholinyl, alkyl ester (C3 to C6), alkyl cyanide (C3 to C6);
$R_6$ of Formula (A-1) through Formula (A-8) is H or —C(=O)$R^b$, wherein
  $R^b$ of Formula (A-1) through Formula (A-8) is selected from the group consisting of alkyl, cycloalkyl, mono-, di- or tri-substituted aryl or heteroaryl, 4-morpholinyl, 1-(3-oxopiperazunyl), 1-piperidinyl, 4-N—$R^c$-morpholinyl, 4-$R^c$-piperidinyl, and 3-$R^c$-piperidinyl, wherein
  $R^c$ of Formula (A-1) through Formula (A-8) is selected from the group consisting of alkyl, fluorine substituted alkyl, cyano alkyl, hydroxyl-substituted alkyl, cycloalkyl, alkoxyalkyl, amide alkyl, alkyl sulfone, alkyl sulfoxide, alkyl amide, aryl, heteroaryl, mono-, bis- and tri-substituted aryl or heteroaryl, CH2CH2$R^d$, and CH2CH2CH2$R^d$, wherein
  $R^d$ of Formula (A-1) through Formula (A-8) is selected from the group consisting of alkoxy, alkyl sulfone, alkyl sulfoxide, N-substituted carboxamide, —NHC(O)-alkyl, —NH—SO$_2$-alkyl, aryl, substituted aryl, heteroaryl, substituted heteroaryl;
$R_7$ of Formula (A-1) through Formula (A-8) is selected from the group consisting of H, C1 to C6 alkyl, cyclic alkyl, fluorine substituted alkyl, cyano substituted alkyl, 5- or 6-membered hetero aryl or aryl, substituted 5- or 6-membered hetero aryl or aryl;
$R_8$ of Formula (A-1) through Formula (A-8) is selected from the group consisting of —$R^e$—C(O)—
$R^f$, —$R^e$-alkoxy, —$R^e$-aryl, —$R^e$-heteroaryl, and —$R^e$—C(O)—$R^f$—C(O)—$R^g$, wherein:
  $R^e$ of Formula (A-1) through Formula (A-8) is an alkylene with 1 to 6 carbons, or a bond;
  $R^f$ of Formula (A-1) through Formula (A-8) is a substituted 4- to 7-membered heterocycle;
  $R^g$ of Formula (A-1) through Formula (A-8) is selected from the group consisting of aryl, hetero aryl, substituted aryl or heteroaryl, and 4- to 7-membered heterocycle;
$R_9$ of Formula (A-1) through Formula (A-8) is selected from the group consisting of a mono-, bis- or tri-substituent on the fused bicyclic aromatic ring in Formula (A-3), wherein the substitutents are independently selected from the group consisting of halogen, alkene, alkyne, alkyl, unsubstituted or substituted with Cl or F;

$R_{10}$ of Formula (A-1) through Formula (A-8) is selected from the group consisting of an aryl or heteroaryl group, wherein the heteroaryl group can contain one or two heteroatoms as sulfur or nitrogen, aryl or heteroaryl group can be mono-cyclic or bi-cyclic, the aryl or heteroaryl group can be unsubstituted or substituted with one to three substituents, including a halogen, F, $C_1$, —CN, alkene, alkyne, C1 to C6 alkyl group, C1 to C6 cycloalkyl, —OH, alkoxy with 1 to 6 carbons, fluorine substituted alkoxy with 1 to 6 carbons, sulfoxide with 1 to 6 carbons, sulfone with 1 to 6 carbons, ketone with 2 to 6 carbons;

$R_{11}$ of Formula (A-1) through Formula (A-8) is —C(O)—N($R^h$)($R^i$), wherein $R^h$ and $R^i$ are selected from groups consisting of the following:

H, C1 to C6 alkyl, alkoxy substituted alkyl, sulfone substituted alkyl, aryl, heteroaryl, mono-, bis- or tri-substituted aryl or hetero aryl, alkyl carboxylic acid, heteroaryl carboxylic acid, alkyl carboxylic acid, fluorine substituted alkyl carboxylic acid, aryl substituted cycloalkyl, hetero aryl substituted cycloalkyl; wherein $R^h$ and $R^i$ of Formula (A-1) through Formula (A-8) are independently selected from the group consisting of H, connected to form a ring, 4-hydroxycyclohexane; mono- and di-hydroxy substituted alkyl (C3 to C6); 3-hydroxycyclobutane; phenyl-4-carboxylic acid, and substituted phenyl-4-carboxylic acid;

$R_{12}$ and $R_{13}$ of Formula (A-1) through Formula (A-8) are independently selected from H, lower alkyl (C1 to C6), lower alkenyl (C2 to C6), lower alkynyl (C2 to C6), cycloalkyl (4, 5 and 6-membered ring), substituted cycloalkyl, cycloalkenyl, substituted cycloalkenyl, 5- and 6-membered aryl and heteroaryl, $R^{12}$ and $R^{13}$ can be connected to form a 5- and 6-membered ring with or without substitution on the ring;

$R_{14}$ of Formula (A-1) through Formula (A-8) is selected from the group consisting of alkyl, substituted alkyl, alkenyl, substituted alkenyl, aryl, substituted aryl, heteroaryl, substituted heteroaryl, heterocycle, substituted heterocycle, cycloalkyl, substituted cycloalkyl, cycloalkenyl and substituted cycloalkenyl;

$R_{15}$ of Formula (A-1) through Formula (A-8) is CN;

$R_{16}$ of Formula (A-1) through Formula (A-8) is selected from the group consisting of C1-6 alkyl, C1-6 cycloalkyl, C2-6 alkenyl, C1-6 alkyl or C3-6 cycloalkyl with one or multiple hydrogens replaced by fluorine, alkyl or cycloalkyl with one $CH_2$ replaced by S(=O), —S, or —S(=O)$_2$, alkyl or cycloalkyl with terminal $CH_3$ replaced by S(=O)2N(alkyl)(alkyl), —C(=O)N(alkyl)(alkyl), —N(alkyl)S(=O)2(alkyl), —C(=O)2(alkyl), —O(alkyl), C1-6 alkyl or alkyl-cycloalkyl with hydron replaced by hydroxyl group, a 3 to 7 membered cycloalkyl or heterocycloalkyl, optionally containing a —(C=O)— group, or a 5 to 6 membered aryl or heteroaryl group, which heterocycloalkyl or heteroaryl group can contain from one to three heteroatoms independently selected from O, N or S, and the cycloalkyl, heterocycloalkyl, aryl or heteroaryl group can be unsubstituted or substituted with from one to three substituents independently selected from halogen, C1-6 alkyl groups, hydroxylated C1-6 alkyl, C1-6 alkyl containing thioether, ether, sulfone, sulfoxide, fluorine substituted ether or cyano group;

$R_{17}$ of Formula (A-1) through Formula (A-8) is selected from the group consisting of $(CH_2)nC(O)NR^kR^l$, wherein $R^k$ and $R^l$ are independently selected from H, C1-6 alkyl, hydroxylated C1-6 alkyl, C1-6 alkoxy alkyl, C1-6 alkyl with one or multiple hydrogens replaced by fluorine, C1-6 alkyl with one carbon replaced by S(O), S(O)(O), C1-6 alkoxyalkyl with one or multiple hydrogens replaced by fluorine, C1-6 alkyl with hydrogen replaced by a cyano group, 5 and 6 membered aryl or heteroaryl, alkyl aryl with alkyl group containing 1-6 carbons, and alkyl heteroaryl with alkyl group containing 1-6 carbons, wherein the aryl or heteroaryl group can be further substituted;

$R_{18}$ of Formula (A-1) through Formula (A-8) is selected from the group consisting of substituted aryl, heteroaryl, alkyl, cycloalkyl, the substitution is preferably —N(C1-4 alkyl)(cycloalkyl), —N(C1-4 alkyl)alkyl-cycloalkyl, and —N(C1-4 alkyl)[(alkyl)-(heterocycle-substituted)-cycloalkyl];

$R_{19}$ of Formula (A-1) through Formula (A-8) is selected from the group consisting of aryl, heteroaryl, bicyclic heteroaryl, and these aryl or heteroaryl groups can be substituted with halogen, C1-6 alkyl, C1-6 cycloalkyl, $CF_3$, F, CN, alkyne, alkyl sulfone, the halogen substitution can be mon- bis- or tri-substituted;

$R_{20}$ and $R_{21}$ of Formula (A-1) through Formula (A-8) are independently selected from C1-6 alkyl, C1-6 cycloalkyl, C1-6 alkoxy, hydroxylated C1-6 alkoxy, and fluorine substituted C1-6 alkoxy, wherein $R_{20}$ and $R_{21}$ can further be connected to form a 5, 6 and 7-membered cyclic or heterocyclic ring, which can further be substituted;

$R_{22}$ of Formula (A-1) through Formula (A-8) is selected from the group consisting of H, C1-6 alkyl, C1-6 cycloalkyl, carboxylic acid, carboxylic acid ester, amide, reverse amide, sulfonamide, reverse sulfonamide, N-acyl urea, nitrogen-containing 5-membered heterocycle, the 5-membered heterocycles can be further substituted with C1-6 alkyl, alkoxy, fluorine-substituted alkyl, CN, and alkylsulfone;

$R_{23}$ of Formula (A-1) through Formula (A-8) is selected from aryl, heteroaryl, —O-aryl, —O— heteroaryl, —O-alkyl, —O-alkyl-cycloalkyl, —NH-alkyl, —NH-alkyl-cycloalkyl, —N(H)-aryl, —N(H)— heteroaryl, —N(alkyl)-aryl, —N(alkyl)-heteroaryl, the aryl or heteroaryl groups can be substituted with halogen, C1-6 alkyl, hydroxylated C1-6 alkyl, cycloalkyl, fluorine-substituted C1-6 alkyl, CN, alkoxy, alkyl sulfone, amide and sulfonamide;

$R_{24}$ of Formula (A-1) through Formula (A-8) is selected from the group consisting of —$CH_2$—(C1-6 alkyl), —CH2-cycloalkyl, —CH2-aryl, CH2-heteroaryl, where alkyl, cycloalkyl, aryl and heteroaryl can be substituted with halogen, alkoxy, hydoxylated alkyl, cyano-substituted alkyl, cycloalyl and substituted cycloalkyl;

$R_{25}$ of Formula (A-1) through Formula (A-8) is selected from the group consisting of C1-6 alkyl, C1-6 alkyl-cycloalkyl, alkoxy-substituted alkyl, hydroxylated alkyl, aryl, heteroaryl, substituted aryl or heteroaryl, 5,6, and 7-membered nitrogen-containing saturated heterocycles, 5,6-fused and 6,6-fused nitrogen-containing saturated heterocycles and these saturated heterocycles can be substituted with C1-6 alkyl, fluorine-substituted C1-6 alkyl, alkoxy, aryl and heteroaryl group;

$R_{26}$ of Formula (A-1) through Formula (A-8) is selected from the group consisting of C1-6 alkyl, C3-6 cycloalkyl, the alkyl or cycloalkyl can be substituted with —OH, alkoxy, fluorine-substituted alkoxy, fluorine-substituted alkyl, —NH$_2$, —NH-alkyl, NH—C(O)alkyl, —NH—S(O)$_2$-alkyl, and —S(O)$_2$-alkyl;

$R_{27}$ of Formula (A-1) through Formula (A-8) is selected from the group consisting of aryl, heteroaryl, bicyclic heteroaryl, wherein the aryl or heteroaryl groups can be substituted with C1-6 alkyl, alkoxy, NH$_2$, NH-alkyl, halogen, or —CN, and the substitution can be independently mono-, bis- and tri-substitution;

$R_{28}$ of Formula (A-1) through Formula (A-8) is selected from the group consisting of aryl, 5 and 6-membered heteroaryl, bicyclic heteroaryl, cycloalkyl, saturated heterocycle such as piperidine, piperidinone, tetrahydropyran, N-acyl-piperidine, wherein the cycloalkyl, saturated heterocycle, aryl or heteroaryl can be further substituted with —OH, alkoxy, mono-, bis- or tri-substitution including halogen, —CN, alkyl sulfone, and fluorine substituted alkyl groups; and $R^{1'''}$ of Formula (A-1) through Formula (A-8) is selected from the group consisting of alkyl, aryl substituted alkyl, alkoxy substituted alkyl, cycloalkyl, aryl-substituted cycloalkyl, and alkoxy substituted cycloalkyl.

In certain embodiments, the heterocycles in $R^f$ and $R^9$ of Formula (A-1) through Formula (A-8) are substituted pyrrolidine, substituted piperidine, substituted piperazine.

More specifically, non-limiting examples of MLMs include those shown below as well as those 'hybrid' molecules that arise from the combination of 1 or more of the different features shown in the molecules below.

Using MLM in Formula A-1 through A-8, the following PROTACs can be prepared to target a particular protein for degradation, where "L" is a connector (i.e. a linker group), and "PTM" is a ligand binding to a target protein.

In certain embodiments, the description provides a bifunctional molecule comprising a structure selected from the group consisting of:

Formula (A-9)

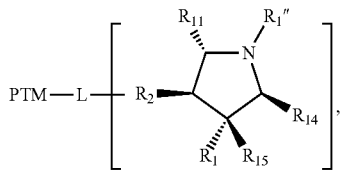

Formula (A-10)

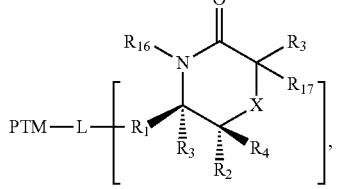

Formula (A-11)

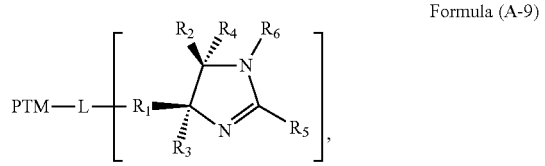

Formula (A-12)

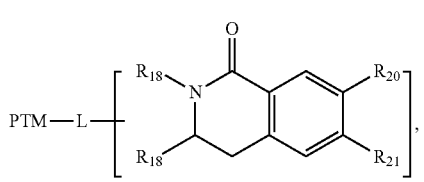

Formula (A-13)

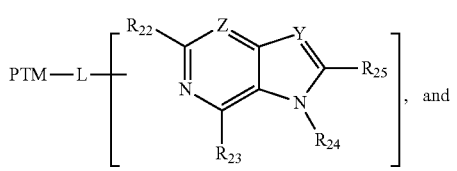

Formula (A-14)

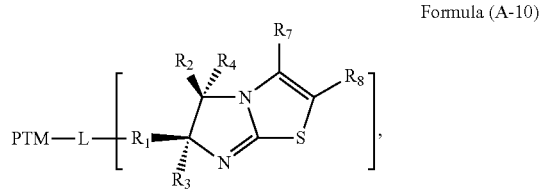

Formula (A-15)

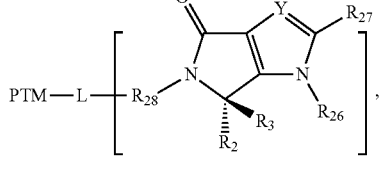

Formula (A-16)

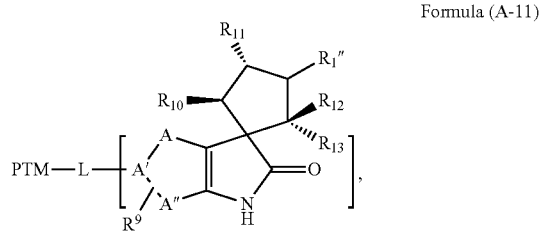

wherein X, $R^a$, Y, Z, A, A', A", $R_1$, $R_2$, $R_3$, $R_4$, $R_5$, $R_6$, $R^b$, $R^c$, $R^d$, $R_7$, $R^e$, $R^f$, $R^g$, $R_9$, $R_{10}$, $R_{11}$, $R_{12}$, $R_{13}$, $R_{14}$, $R_{15}$, $R_{16}$, $R_{17}$, $R^k$, $R^l$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, and $R_{1'''}$ are as defined herein with regard to Formulas (A-1) through (A-8).

In certain embodiments, the description provides bifunctional or chimeric molecules with the structure: PTM-L-MLM, wherein PTM is a protein target binding moiety coupled to an MLM by L, wherein L is a bond (i.e., absent) or a chemical linker. In certain embodiments, the MLM has a structure selected from the group consisting of A-1-1, A-1-2, A-1-3, and A-1-4:

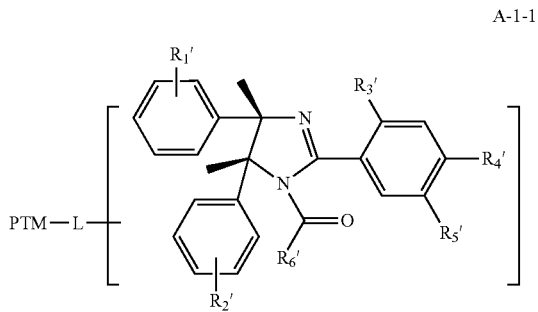

A-1-1

-continued

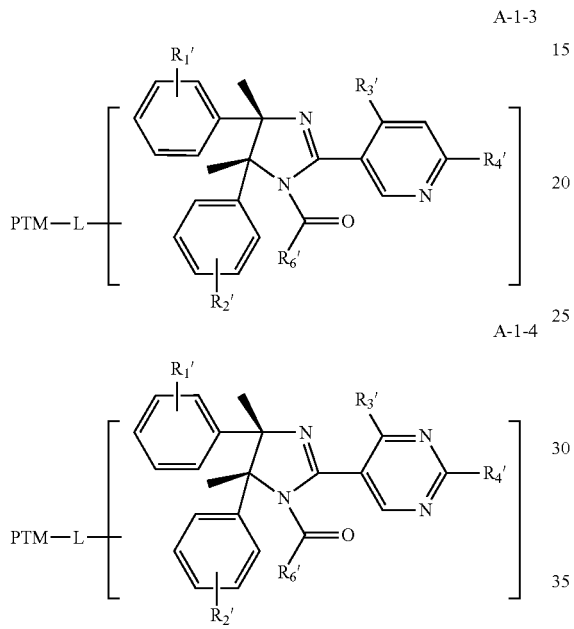

wherein:

R1' and R2' of Formulas A-1-1 through A-1-4 (i.e., A-1-1, A-1-2, A-1-3, and A-1-4) are independently selected from the group consisting of F, Cl, Br, I, acetylene, CN, $CF_3$ and $NO_2$;

R3' is selected from the group consisting of —$OCH_3$, —$OCH_2CH_3$, —$OCH_2CH_2F$, —$OCH_2CH_2OCH_3$, and —$OCH(CH_3)_2$;

R4' of Formulas A-1-1 through A-1-4 is selected from the group consisting of H, halogen, —$CH_3$, —$CF_3$, —$OCH_3$, —$C(CH_3)_3$, —$CH(CH_3)_2$, -cyclopropyl, —CN, —$C(CH_3)_2OH$, —$C(CH_3)_2OCH_2CH_3$, —$C(CH_3)_2CH_2OH$, —$C(CH_3)_2CH_2OCH_2CH_3$, —$C(CH_3)_2CH_2OCH_2CH_2OH$, —$C(CH_3)_2CH_2OCH_2CH_3$, —$C(CH_3)_2CN$, —$C(CH_3)_2C(O)CH_3$, —$C(CH_3)_2C(O)NHCH_3$, —$C(CH_3)_2C(O)N(CH_3)_2$, —$SCH_3$, —$SCH_2CH_3$, —$S(O)_2CH_3$, —$S(O_2)CH_2CH_3$, —$NHC(CH_3)_3$, —$N(CH_3)_2$, pyrrolidinyl, and 4-morpholinyl;

R5' of Formulas A-1-1 through A-1-4 is selected from the group consisting of halogen, -cyclopropyl, —$S(O)_2CH_3$, —$S(O)_2CH_2CH_3$, 1-pyrrolidinyl, —$NH_2$, —$N(CH_3)_2$, and —$NHC(CH_3)_3$; and R6' of Formulas A-1-1 through A-1-4 is selected from the structures presented below where the linker connection point is indicated as "*".

Beside R6' as the point for linker attachment, R4' can also serve as the linker attachment position. In the case that R4' is the linker connection site, linker will be connected to the terminal atom of R4' groups shown above.

In certain embodiments, the linker connection position of Formulas A-1-1 through A-1-4 is at least one of R4' or R6' or both.

In certain embodiments, $R^{6'}$ of Formulas A-1-1 through A-1-4 is independently selected from the group consisting of H,

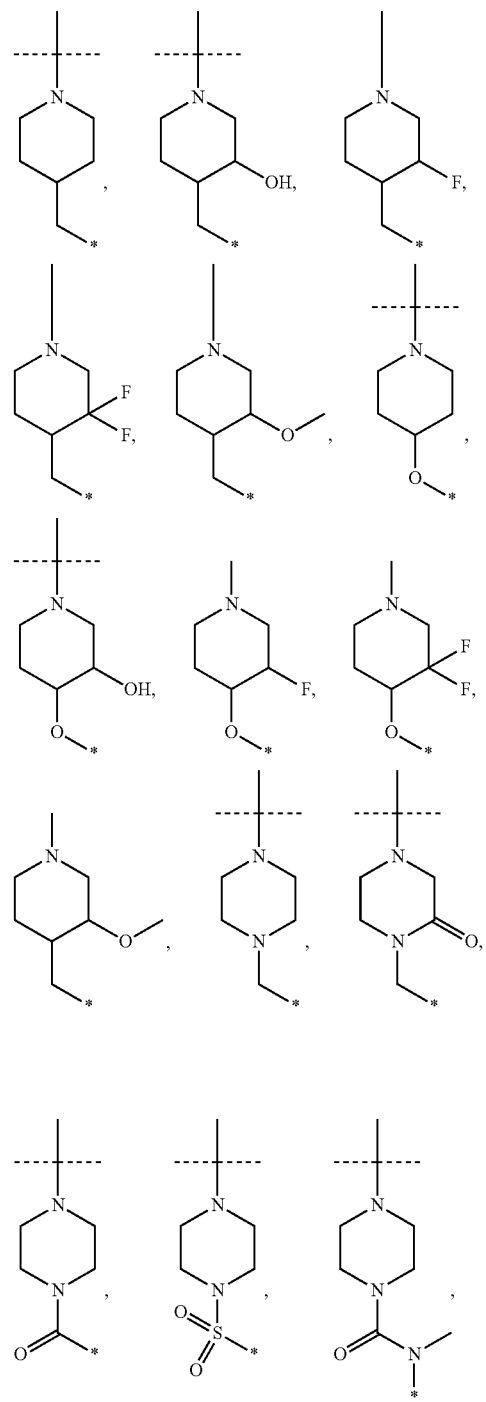

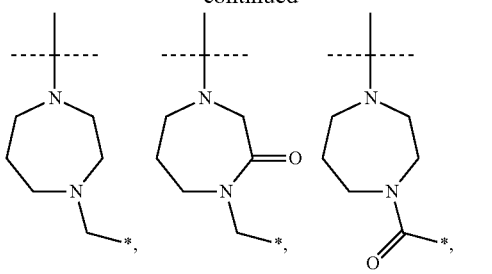
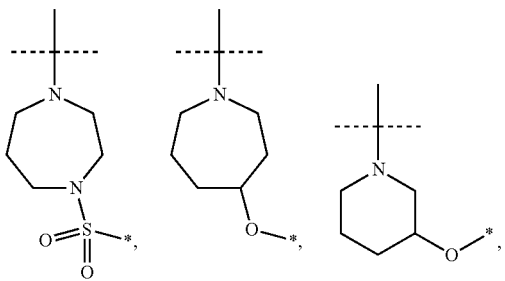
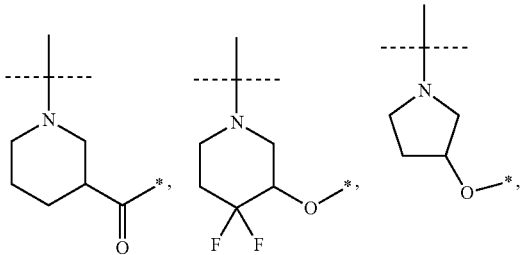
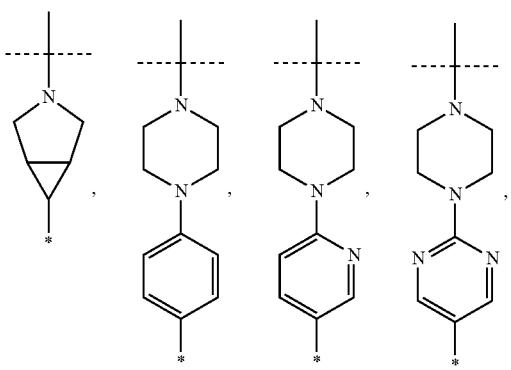
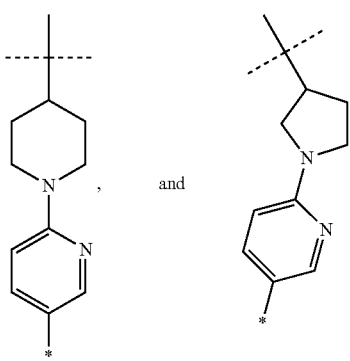

wherein "*" indicates the point of attachment of the linker.

In certain embodiments, the linker of Formula A-4-1 through A-4-6 is attached to at least one of R1', R2', R3', R4', R5', R6', or a combination thereof.

In certain embodiments, the description provides bifunctional or chimeric molecules with the structure: PTM-L-MLM, wherein PTM is a protein target binding moiety coupled to an MLM by L, wherein L is a bond (i.e., absent) or a chemical linker. In certain embodiments, the MLM has a structure selected from the group consisting of A-4-1, A-4-2, A-4-3, A-4-4, A-4-5, and A-4-6:

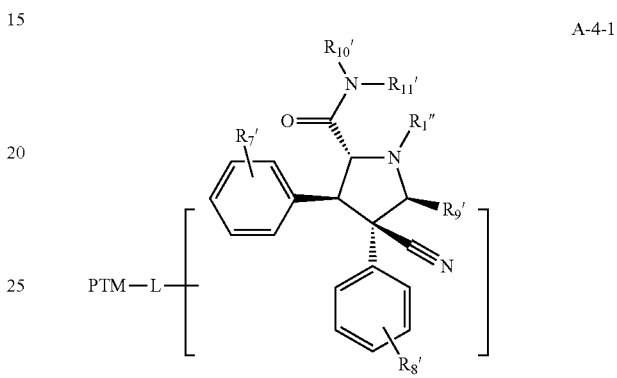

A-4-1

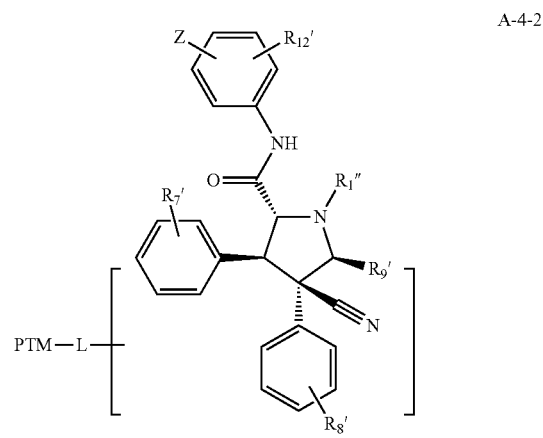

A-4-2

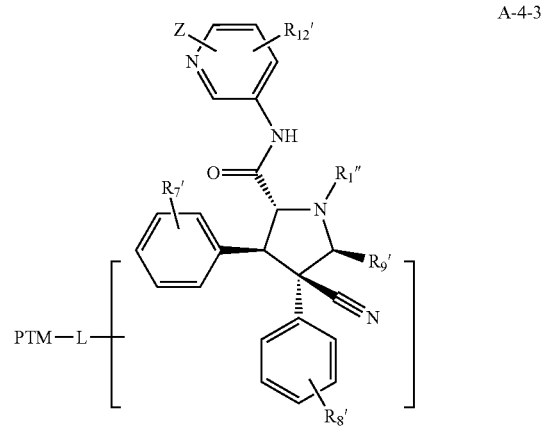

A-4-3

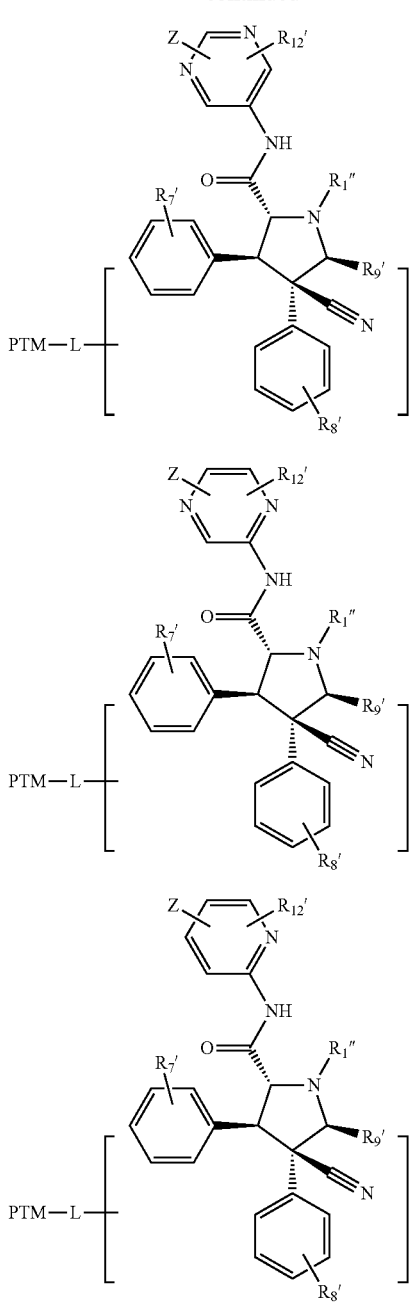

wherein:
- R7' of Formula A-4-1 through A-4-6 (i.e., A-4-1, A-4-2, A-4-3, A-4-4, A-4-5, and A-4-6) is a member selected from the group consisting of halogen, mono-, and di- or tri-substituted halogen;
- R8' of Formula A-4-1 through A-4-6 is selected from the group consisting of H, —F, —Cl, —Br, —I, —CN, —NO$_2$, ethylnyl, cyclopropyl, methyl, ethyl, isopropyl, vinyl, methoxy, ethoxy, isopropoxy, —OH, other C1-6 alkyl, other C1-6 alkenyl, and C1-6 alkynyl, mono-, di- or tri-substituted;
- R9' of Formula A-4-1 through A-4-6 is selected from the group consisting of alkyl, substituted alkyl, alkenyl, substituted alkenyl, alkynyl, substituted alkynyl, aryl, substituted aryl, hetero aryl, substituted heteroaryl, cycloalkyl, substituted cycloalkyl, alkenyl, and substituted cycloalkenyl;
- Z of Formula A-4-1 through A-4-6 is selected from the group consisting of H, —OCH$_3$, —OCH$_2$CH$_3$, and halogen;
- R10' and R11' of Formula A-4-1 through A-4-6 are each independently selected from the group consisting of H, (CH$_2$)$_n$—R', (CH$_2$)$_n$—NR'R", (CH$_2$)$_n$—NR'COR", (CH$_2$)$_n$—NR'SO$_2$R", (CH$_2$)$_n$—COOH, (CH$_2$)$_n$—COOR', (CH)$_n$—CONR'R", (CH$_2$)$_n$—OR', (CH$_2$)$_n$—SR', (CH$_2$)$_n$—SOR', (CH$_2$)$_n$—CH(OH)—R', (CH$_2$)$_n$—COR', (CH$_2$)$_n$—SO$_2$R', (CH$_2$)$_n$—SONR'R", (CH$_2$)$_n$—SO$_2$NR'R", (CH$_2$CH$_2$O)$_m$—(CH$_2$)$_n$—R', (CH$_2$CH$_2$O)$_m$—(CH$_2$)$_n$—OH, (CH$_2$CH$_2$O)$_m$—(CH$_2$)$_n$—OR', (CH$_2$CH$_2$O)$_m$—(CH$_2$)$_n$—NR'R", (CH$_2$CH$_2$O)$_m$(CH$_2$)$_n$—NR'COR", (CH$_2$CH$_2$O)$_m$(CH$_2$)$_n$—NR'SO$_2$R", (CH$_2$CH$_2$O)$_m$(CH$_2$)$_n$—COOH, (CH$_2$CH$_2$O)$_m$(CH$_2$)$_n$—COOR', (CH$_2$CH$_2$O)$_m$—(CH$_2$)$_n$—CONR'R", (CH$_2$CH$_2$O)$_m$—(CH$_2$)$_n$—SO$_2$R', (CH$_2$CH$_2$O)$_m$—(CH$_2$)$_n$—COR', (CH$_2$CH$_2$O)$_m$—(CH$_2$)$_n$—SONR'R", (CH$_2$CH$_2$O)$_m$—(CH$_2$)$_n$—SO$_2$NR'R", (CH$_2$)$_p$—(CH$_2$CH$_2$O)$_m$—(CH$_2$)$_n$R', (CH$_2$)$_p$—(CH$_2$CH$_2$O)$_m$—(CH$_2$)$_n$—OH, (CH$_2$)$_p$—(CH$_2$CH$_2$O)$_m$—(CH$_2$)$_n$—OR', (CH$_2$)$_p$—(CH$_2$CH$_2$O)$_m$—(CH$_2$)$_n$—NR'R", (CH$_2$)$_p$—(CH$_2$CH$_2$O)$_m$—(CH$_2$)$_n$—NR'COR", (CH$_2$)$_p$—(CH$_2$CH$_2$O)$_m$—(CH$_2$)$_n$—NR'SO$_2$R", (CH$_2$)$_p$—(CH$_2$CH$_2$O)$_m$—(CH$_2$)$_n$—COOH, (CH$_2$)$_p$—(CH$_2$CH$_2$O)$_m$—(CH$_2$)$_n$—COOR', (CH$_2$)$_p$—(CH$_2$CH$_2$O)$_m$—(CH$_2$)$_n$—CONR'R", (CH$_2$)$_p$—(CH$_2$CH$_2$O)$_m$—(CH$_2$)$_n$—SO$_2$R', (CH$_2$)$_p$—(CH$_2$CH$_2$O)$_m$—(CH$_2$)$_n$—COR', (CH$_2$)$_p$—(CH$_2$CH$_2$O)$_m$—(CH$_2$)$_n$—SONR'R", (CH$_2$)$_p$—(CH$_2$CH$_2$O)$_m$—(CH$_2$)$_n$—SO$_2$NR'R", Aryl-(CH$_2$)$_n$—COOH, and heteroaryl-alkyl-CO-alkyl-NR'R"m, wherein the alkyl may be substituted with OR', and heteroaryl-(CH$_2$)$_n$-heterocycle wherein the heterocycle may optionally be substituted with alkyl, hydroxyl, COOR' and COR'; wherein R' and R$^{11}$ are selected from H, alkyl, alkyl substituted with halogen, hydroxyl, NH2, NH(alkyl), N(alkyl)2, oxo, carboxy, cycloalkyl and heteroaryl;
- m, n, and p are independently 0 to 6;
- R12' of Formula A-4-1 through A-4-6 is selected from the group consisting of —O-(alkyl), —O-(alkyl)-alkoxy, —C(O)-(alkyl), —C(OH)-alkyl-alkoxy, —C(O)—NH, —C(O)—NH-(alkyl), —C(O)—N-(alkyl)2, —S(O)-(alkyl), S(O)2-(alkyl), —C(O)-(cyclic amine), and —O-aryl-(alkyl), —O-aryl-(alkoxy);
- R1" of Formula A-4-1 through A-4-6 is selected from the group consisting of alkyl, aryl substituted alkyl, alkoxy substituted alkyl, cycloalkyl, aryl-substituted cycloalkyl, and alkoxy substituted cycloalkyl.

In any of the aspects or embodiments described herein, the alkyl, alkoxy or the like can be a lower alkyl or lower alkoxy.

In certain embodiments, the linker connection position of Formula A-4-1 through A-4-6 is at least one of Z, R8', R9', R10', R11", R12", or R1".

The method used to design chimeric molecules as presented in A-1-1 through A-1-4, A-4-1 through A-4-6 can be applied to MLM with formula A-2, A-3, A-5, A-6, A-7 and A-8, wherein the solvent exposed area in the MLM can be connected to linker "L" which will be attached to target protein ligand "PTM", to construct PROTACs.

Exemplary MDM2 binding moieties include, but not limited, the following:

the HDM2/MDM2 inhibitors identified in Vassilev, et al., In vivo activation of the p53 pathway by small-molecule antagonists of MDM2, *SCIENCE* vol:303, pag:844-848 (2004), and Schneekloth, et al., Targeted intracellular protein degradation induced by a small molecule: En route to chemical proteomics, *Bioorg. Med. Chem. Lett.* 18 (2008) 5904-5908, including (or additionally) the compounds nutlin-3, nutlin-2, and nutlin-1 (derivatized) as described below, as well as all derivatives and analogs thereof:

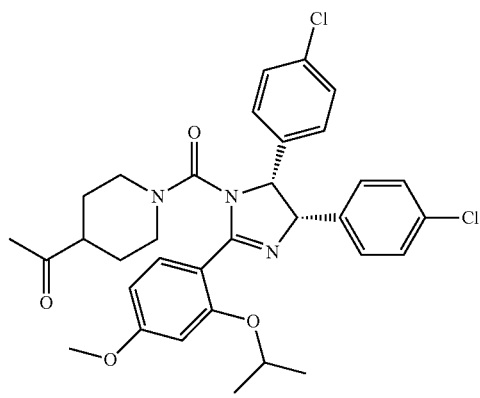

(derivatized where a linker group L or a -(L-MLM) group is attached, for example, via the methoxy group or as a hydroxyl group).

Exemplary CLMs

Neo-Imide Compounds

In one aspect the description provides compounds useful for binding and/or inhibiting cereblon. In certain embodiments, the compound is selected from the group consisting of chemical structures:

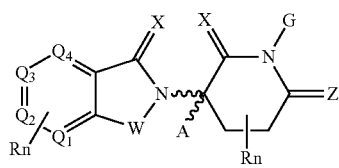
(a)

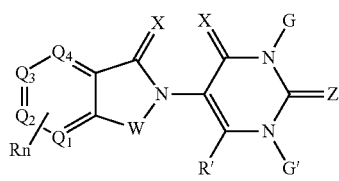
(b)

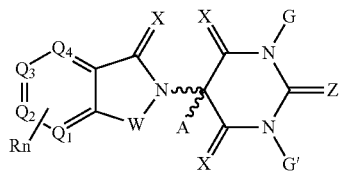
(c)

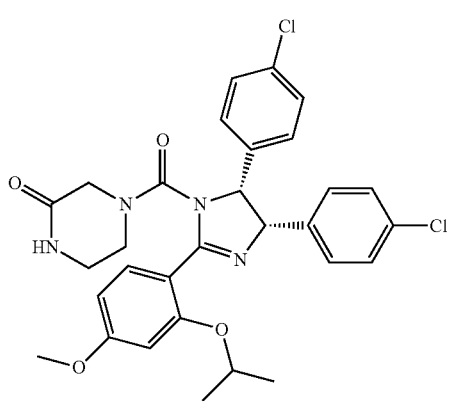 [SMILES: COc1ccc(C2=N[C@@H](c3ccc(Cl)cc3)[C@@H](c3ccc(Cl)cc3)N2C(=O)N2CCNC(=O)C2)c(OC(C)C)c1]

(derivatized where a linker group L or a -(L-MLM) group is attached, for example, at the methoxy group or as a hydroxyl group);

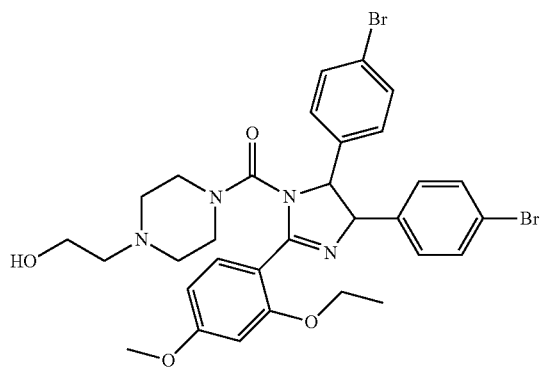 [SMILES: CCOc1cc(OC)ccc1C1=NC(c2ccc(Br)cc2)C(c2ccc(Br)cc2)N1C(=O)N1CCN(CCO)CC1]

(derivatized where a linker group L or a -(L-MLM) group is attached, for example, at the methoxy group or hydroxyl group); and

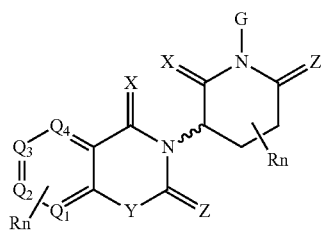
(d)

-continued

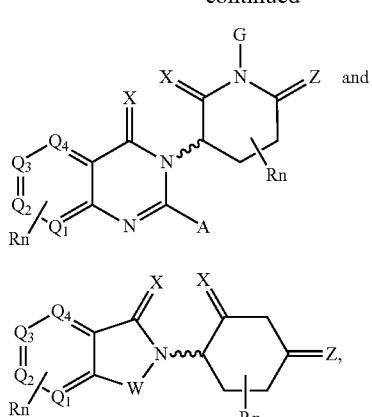
(e)

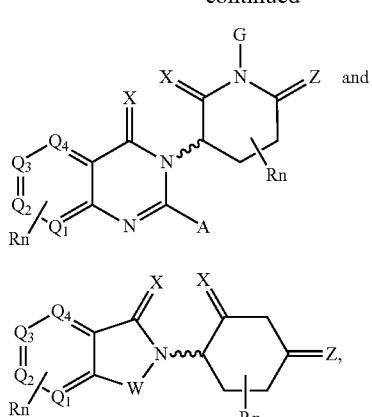
(f)

wherein:
- W of Formulas (a) through (e) is independently selected from the group CH$_2$, CHR, C=O, SO$_2$, NH, and N-alkyl;
- X of Formulas (a) through (e) is independently selected from the group O, S and H$_2$;
- Y of Formulas (a) through (e) is independently selected from the group CH$_2$, —C=CR', NH, N-alkyl, N-aryl, N-hetaryl, N-cycloalkyl, N-heterocyclyl, O, and S;
- Z of Formulas (a) through (e) is independently selected from the group O, and S or H$_2$ except that both X and Z cannot be H$_2$;
- G and G' of Formulas (a) through (e) are independently selected from the group H, alkyl (linear, branched, optionally substituted), OH, R'OCOOR, R'OCONRR", CH$_2$-heterocyclyl optionally substituted with R', and benzyl optionally substituted with R';
- Q1-Q4 of Formulas (a) through (e) represent a carbon C substituted with a group independently selected from R', N or N-oxide;
- A of Formulas (a) through (e) is independently selected from the group H, alkyl (linear, branched, optionally substituted), cycloalkyl, Cl and F;
- R of Formulas (a) through (e) comprises, but is not limited to: —CONR'R", —OR', —NR'R", —SR', —SO$_2$R', —SO$_2$NR'R", —CR'R"—, —CR'NR'R"—, (—CR'O)$_n$R", -aryl, -hetaryl, -alkyl (linear, branched, optionally substituted), -cycloalkyl, -heterocyclyl, —P(O)(OR')R", —P(O)R'R", —OP(O)(OR')R", —OP(O)R'R", —Cl, —F, —Br, —I, —CF$_3$, —CN, —NR'SO$_2$NR'R", —NR'CONR'R", —CONR'COR", —NR'C(=N—CN)NR'R", —C(=N—CN)NR'R", —NR'C(=N—CN)R", —NR'C(=C—NO$_2$)NR'R", —SO$_2$NR'COR", —NO$_2$, —CO$_2$R', —C(C=N—OR')R", —CR'=CR'R", —CCR', —S(C=O)(C=N—R')R", —SF$_5$ and —OCF$_3$
- R' and R" of Formulas (a) through (e) are independently selected from a bond, H, alkyl, cycloalkyl, aryl, heteroaryl, heterocyclic, —C(=O)R, heterocyclyl, each of which is optionally substituted;
- n of Formulas (a) through (e) is an integer from 1-10 (e.g., 1-4);
- ~~~ of Formulas (a) through (e) represents a bond that may be stereospecific ((R) or (S)) or non-stereospecific; and
- R$_n$ of Formulas (a) through (e) comprises 1-4 independent functional groups or atoms.

Exemplary CLMs

In any of the compounds described herein, the CLM comprises a chemical structure selected from the group:

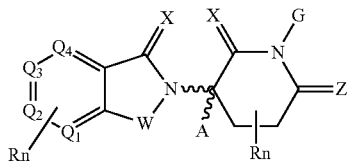
(a)

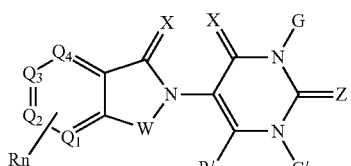
(b)

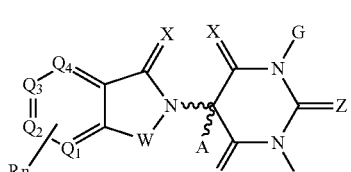
(c)

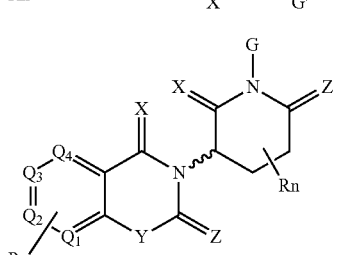
(d)

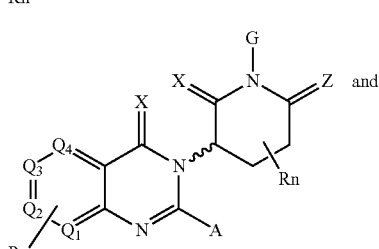
(e)

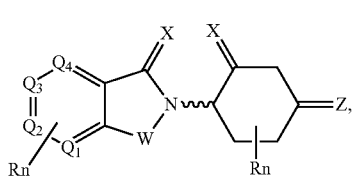
(f)

wherein:
- W of Formulas (a) through (e) is independently selected from the group CH$_2$, CHR, C=O, SO$_2$, NH, and N-alkyl;
- X of Formulas (a) through (e) is independently selected from the group O, S and H2;
- Y of Formulas (a) through (e) is independently selected from the group CH$_2$, —C=CR', NH, N-alkyl, N-aryl, N-hetaryl, N-cycloalkyl, N-heterocyclyl, O, and S;
- Z of Formulas (a) through (e) is independently selected from the group O, and S or H2 except that both X and Z cannot be H2;
- G and G' of Formulas (a) through (e) are independently selected from the group H, alkyl (linear, branched, optionally substituted), OH, R'OCOOR, R'OCONRR", CH$_2$-heterocyclyl optionally substituted with R', and benzyl optionally substituted with R';

Q1-Q4 of Formulas (a) through (e) represent a carbon C substituted with a group independently selected from R', N or N-oxide;

A of Formulas (a) through (e) is independently selected from the group H, alkyl, cycloalkyl, Cl and F;

R of Formulas (a) through (e) comprises, but is not limited to: —CONR'R", —OR', —NR'R", —SR', —SO$_2$R', —SO$_2$NR'R", —CR'R"—, —CR'NR'R"—, -aryl, -hetaryl, -alkyl, -cycloalkyl, -heterocyclyl, —P(O)(OR')R", —P(O)R'R", —OP(O)(OR')R", —OP(O)R'R", —Cl, —F, —Br, —I, —CF3, —CN, —NR'SO$_2$NR'R", —NR'CONR'R", —CONR'COR", —NR'C(=N—CN) NR'R", —C(=N—CN)NR'R", —NR'C(=N—CN)R", —NR'C(=C—NO2)NR'R", —SO$_2$NR'COR", —NO$_2$, —CO2R', —C(C=N—OR')R", —CR'=CR'R", —CCR', —S(C=O)(C=N—R')R", —SF5 and —OCF3

R' and R" of Formulas (a) through (e) are independently selected from a bond, H, alkyl, cycloalkyl, aryl, heteroaryl, heterocyclic, —C(=O)R, heterocyclyl, each of which is optionally substituted;

n of Formulas (a) through (e) is an integer from 1-10 (e.g., 1-4);

~~~ of Formulas (a) through (e) represents a bond that may be stereospecific ((R) or (S)) or non-stereospecific; and Rn of Formulas (a) through (e) comprises 1-4 independent functional groups or atoms, and optionally, one of which is modified to be covalently joined to a PTM, a chemical linker group (L), a ULM, CLM (or CLM') or combination thereof.

In certain embodiments described herein, the CLM or ULM comprises a chemical structure selected from the group:

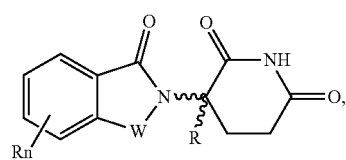

Formula (g)

wherein:
W of Formula (g) is independently selected from the group CH$_2$, C=O, NH, and N-alkyl;
R of Formula (g) is independently selected from a H, methyl, or optionally substituted alkyl (e.g., C1-C6 alkyl (linear, branched, optionally substituted));
~~~ of Formula (g) represents a bond that may be stereospecific ((R) or (S)) or non-stereospecific; and
Rn of Formula (g) comprises 1-4 independently selected functional groups or atoms, and optionally, one of which is modified to be covalently joined to a PTM, a chemical linker group (L), a ULM, CLM (or CLM') or combination thereof.

In any of the embodiments described herein, the W, X, Y, Z, G, G', R, R', R", Q1-Q4, A, and Rn of Formulas (a) through (g) can independently be covalently coupled to a linker and/or a linker to which is attached one or more PTM, ULM, CLM or CLM' groups.

More specifically, non-limiting examples of CLMs include those shown below as well as those "hybrid" molecules that arise from the combination of 1 or more of the different features shown in the molecules below.

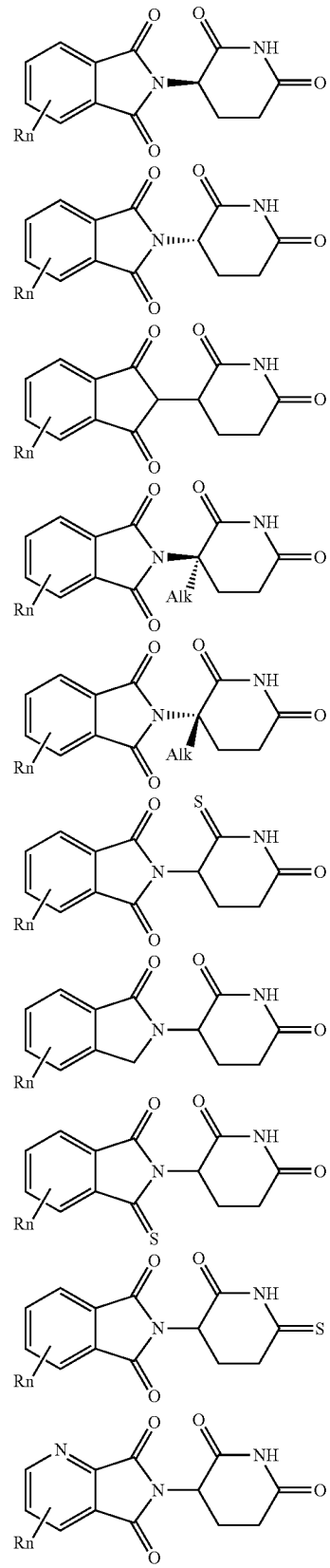

143
-continued
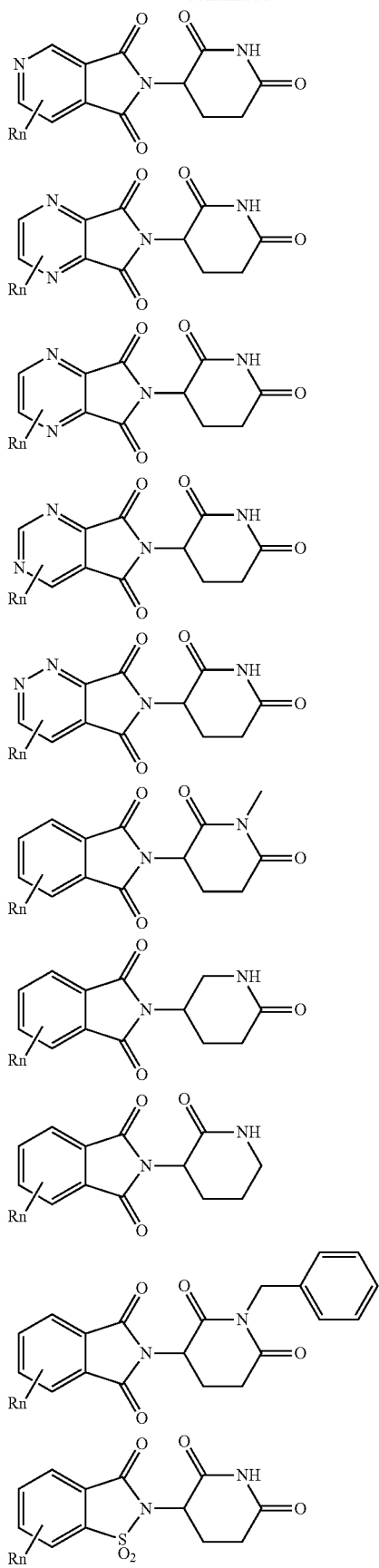
144
-continued
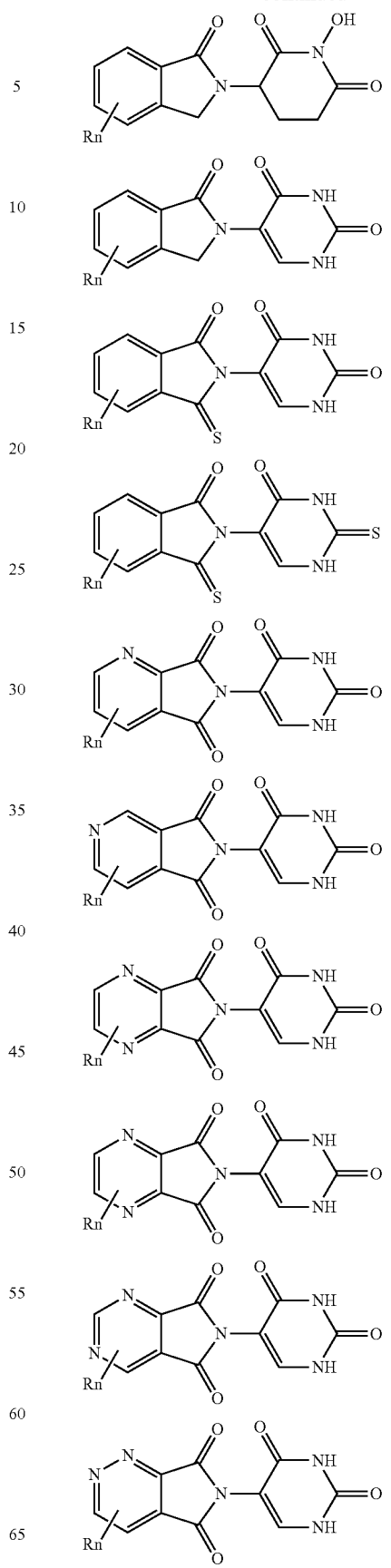

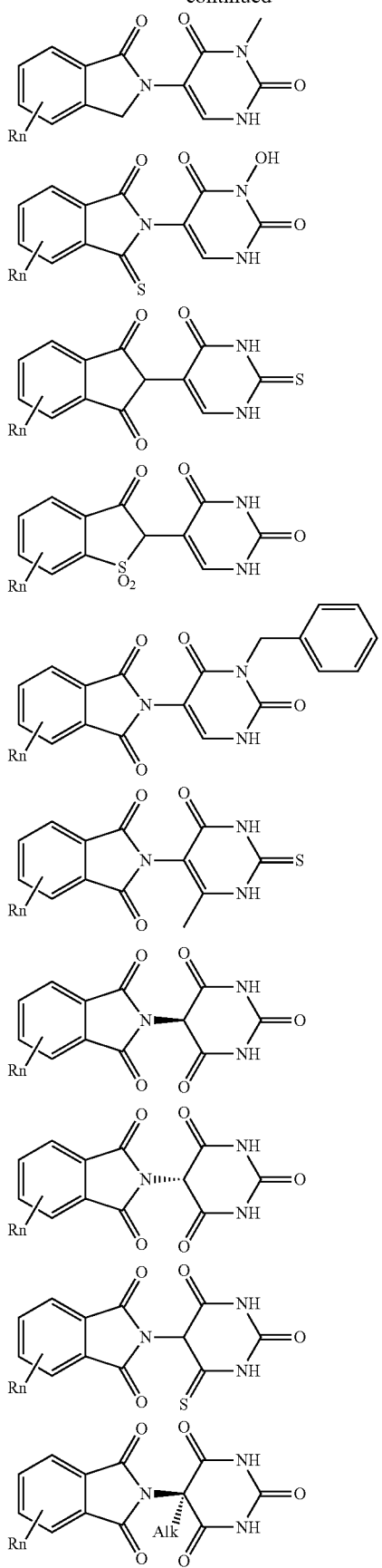
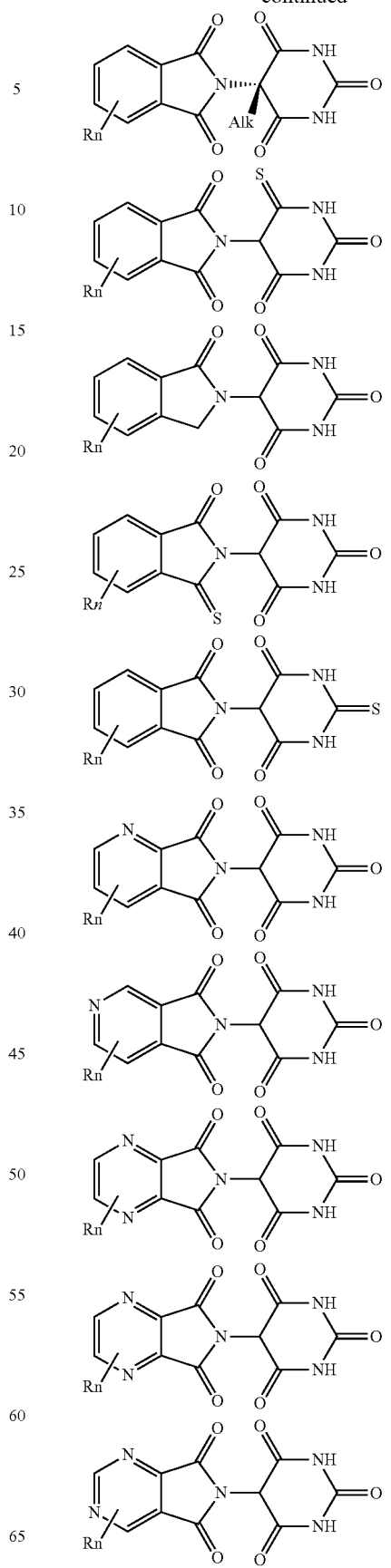

147
-continued
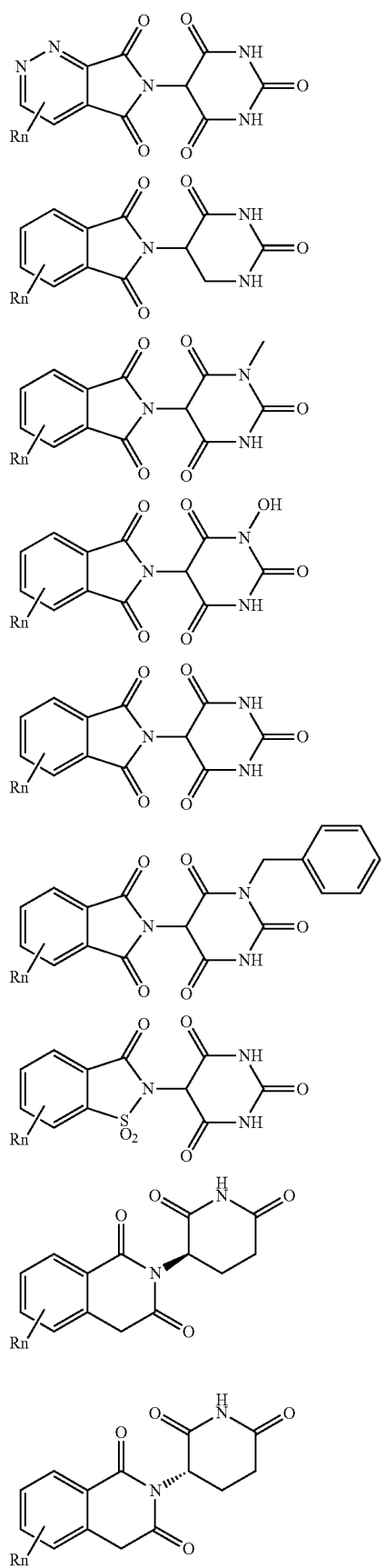
148
-continued
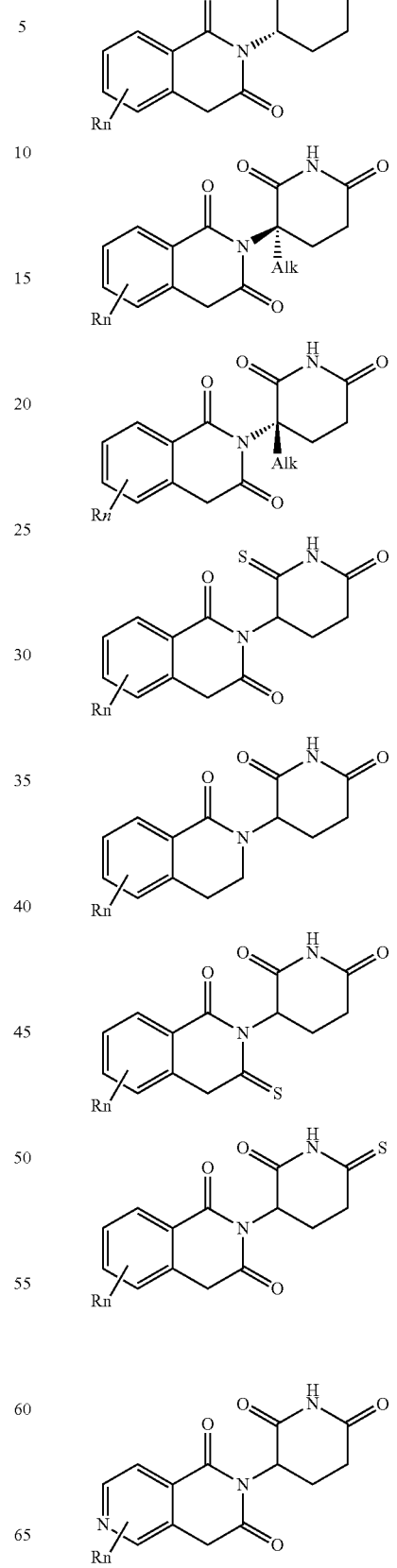

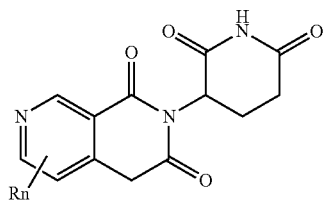
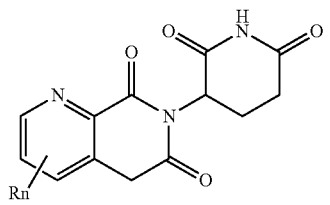
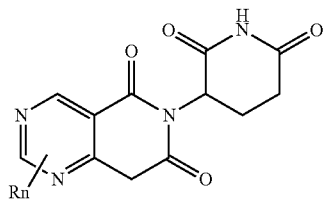
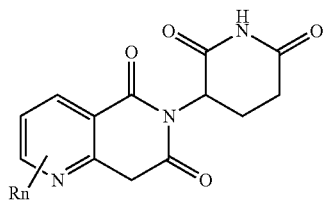
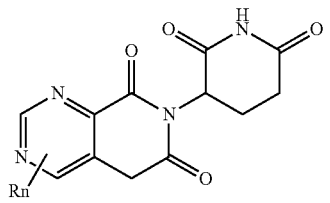
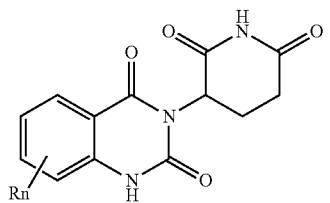
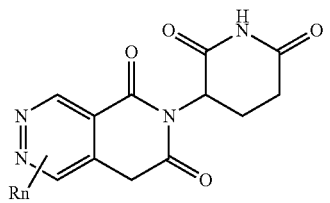
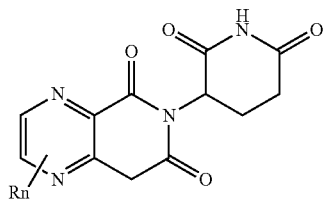
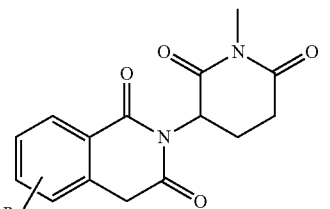
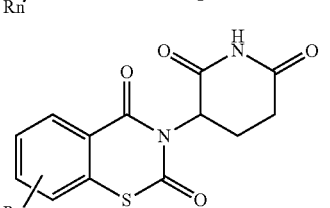
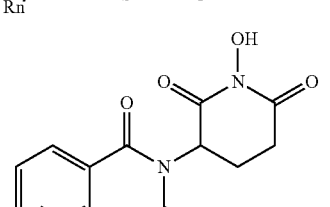
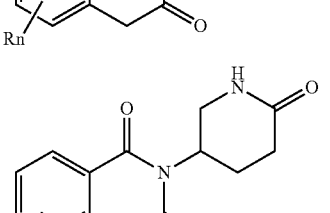
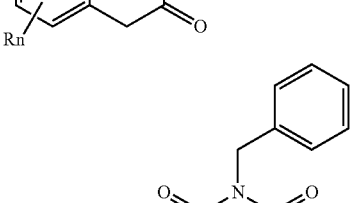
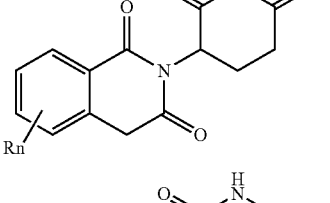
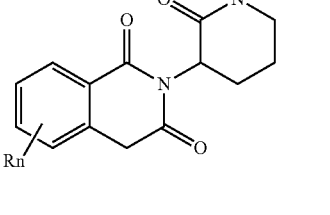
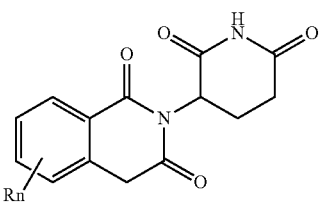

151
-continued
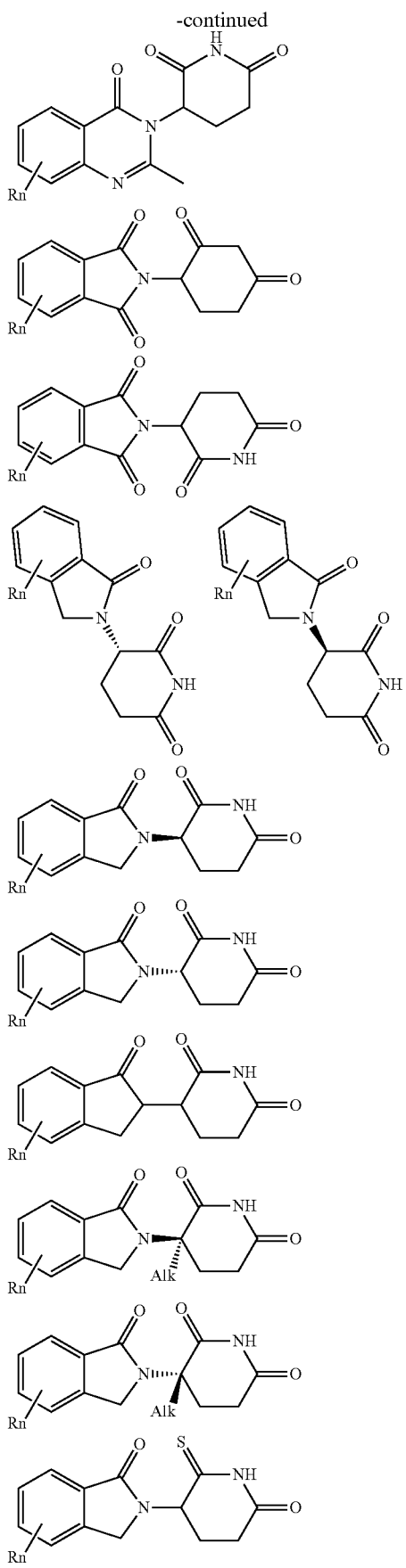
152
-continued
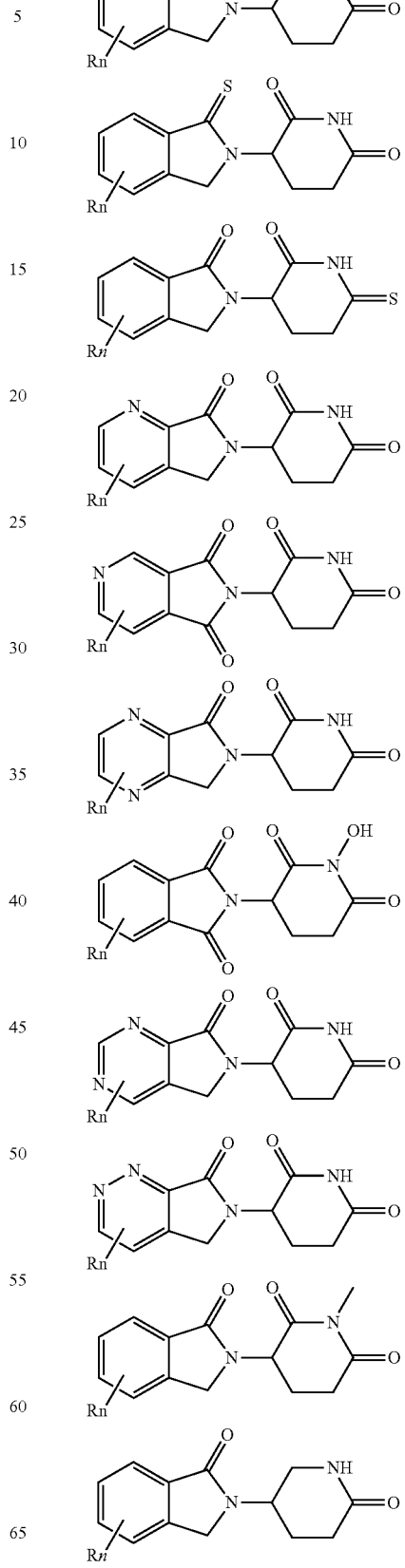

153
-continued
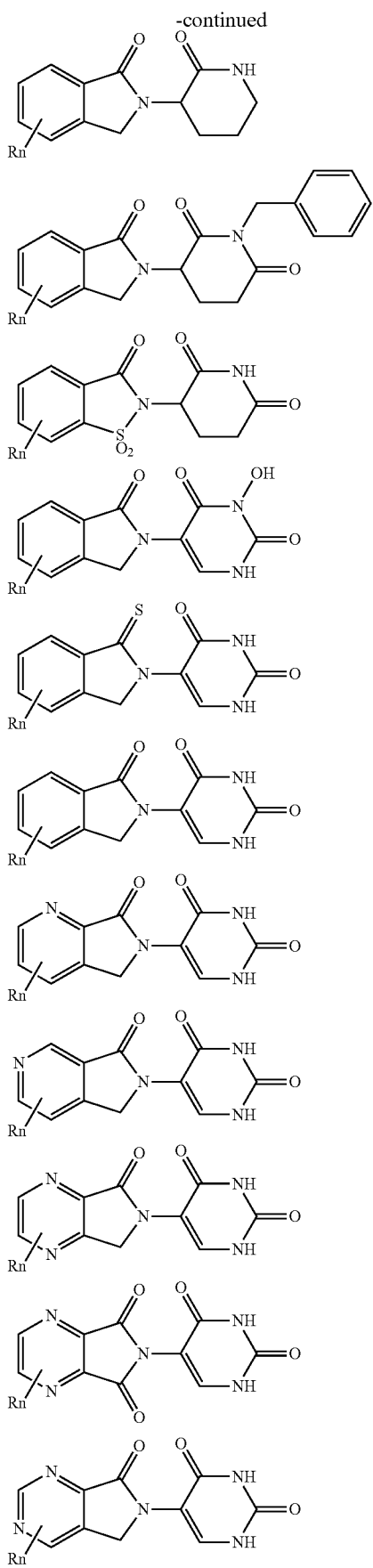
154
-continued
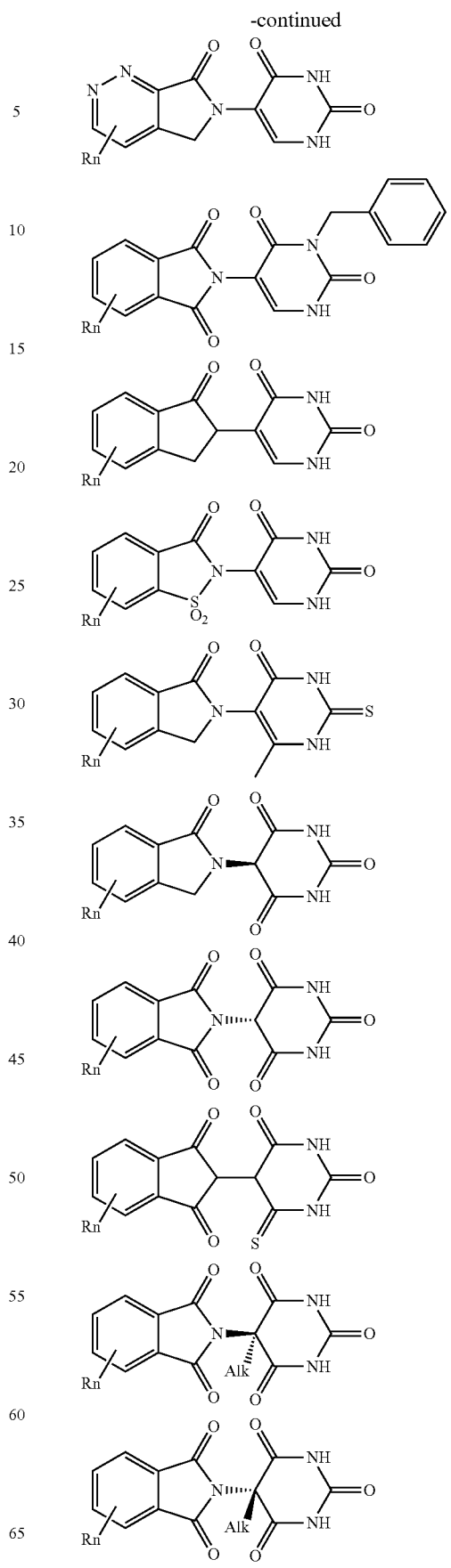

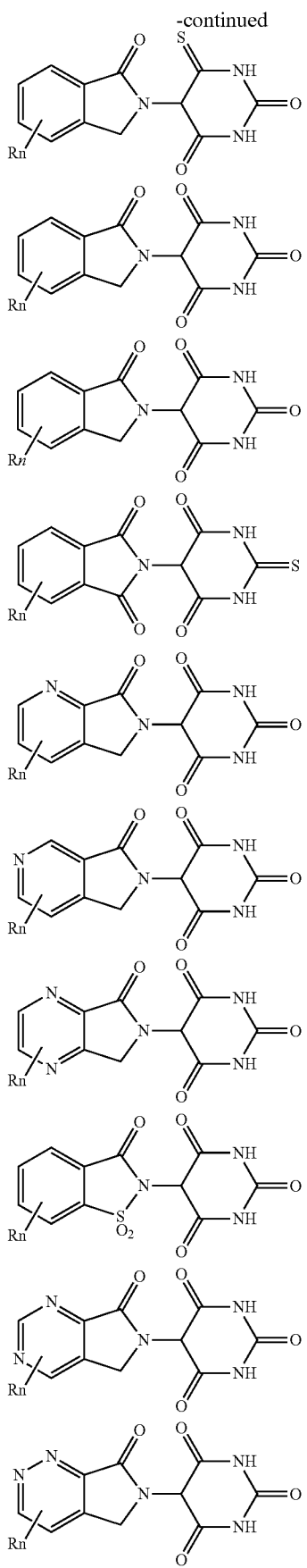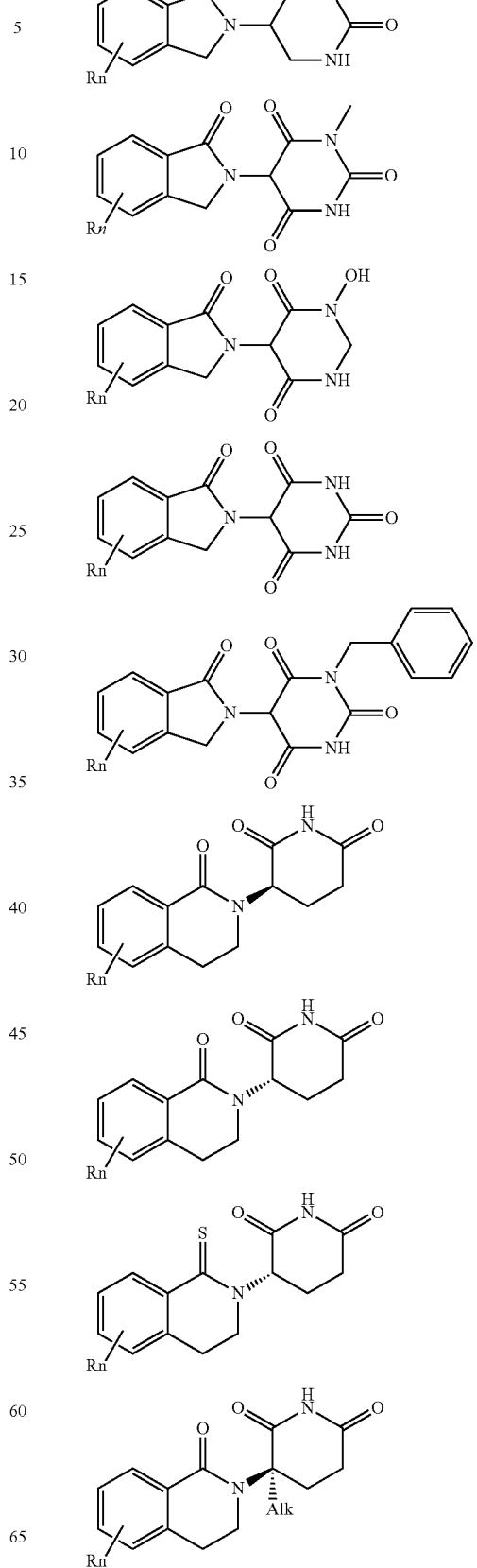

157
-continued
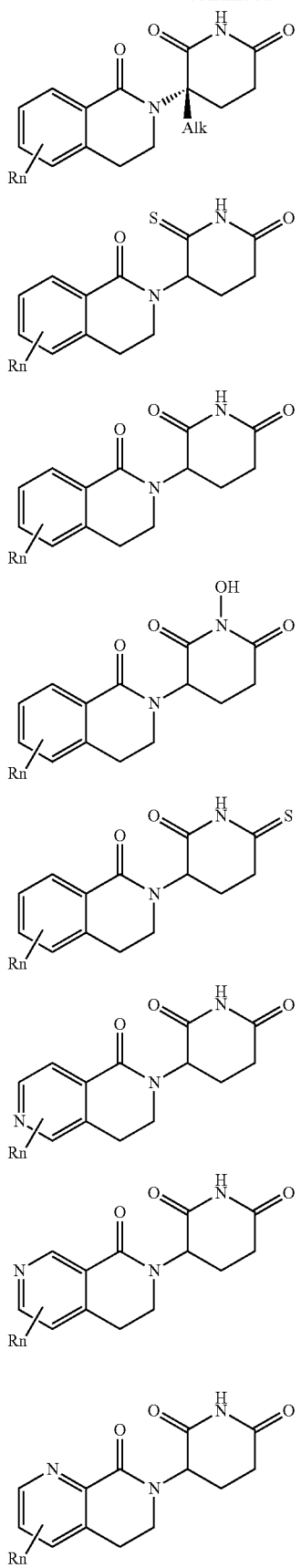
158
-continued
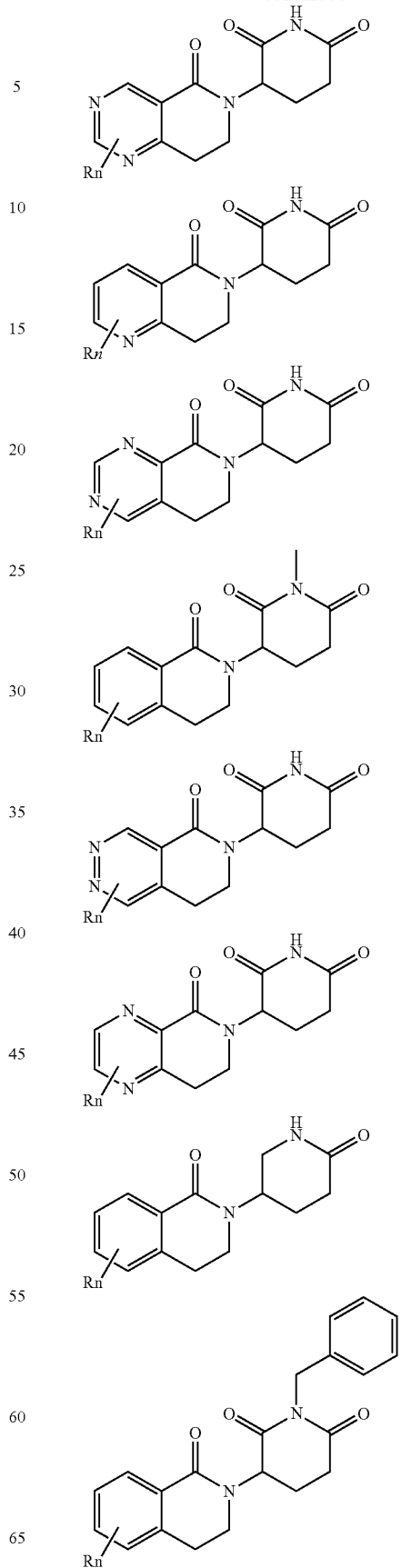

In any of the compounds described herein, the CLM comprises a chemical structure selected from the group:
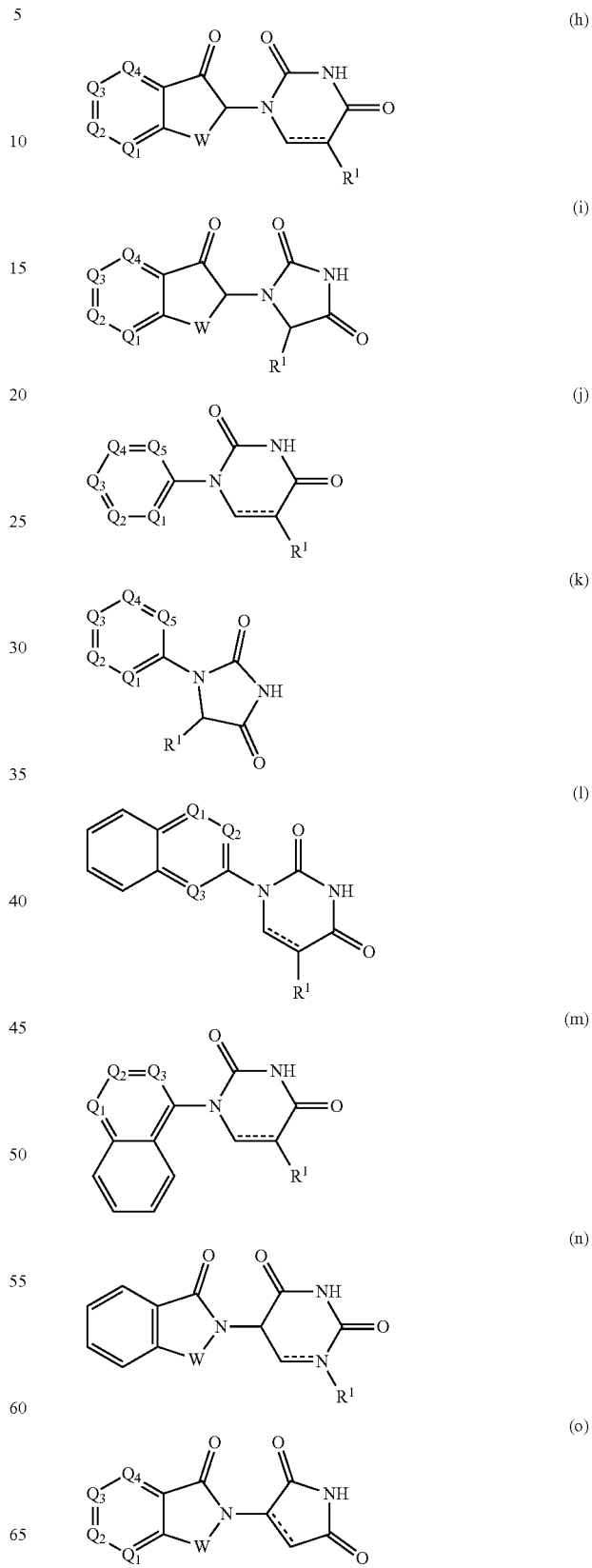

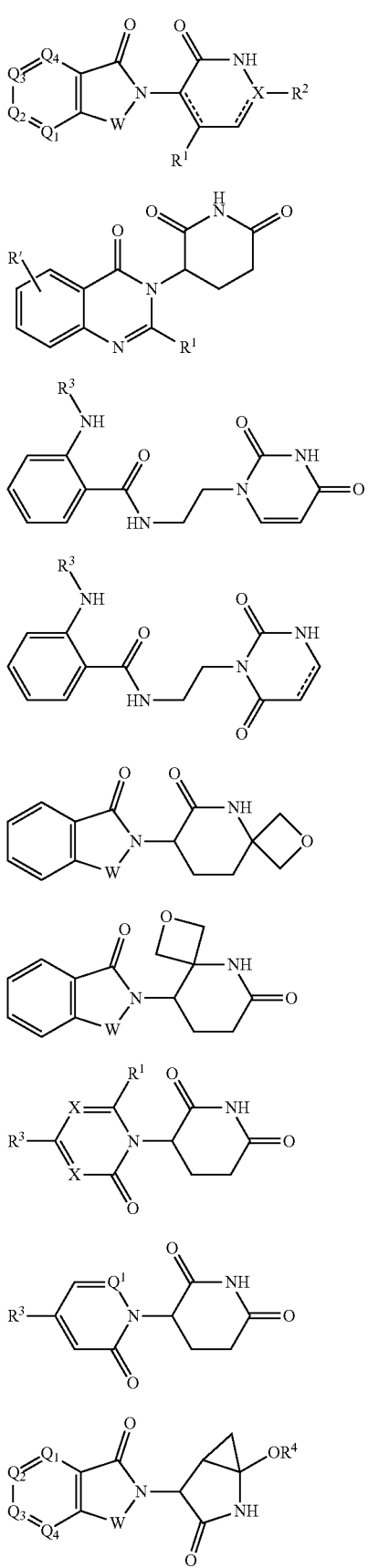

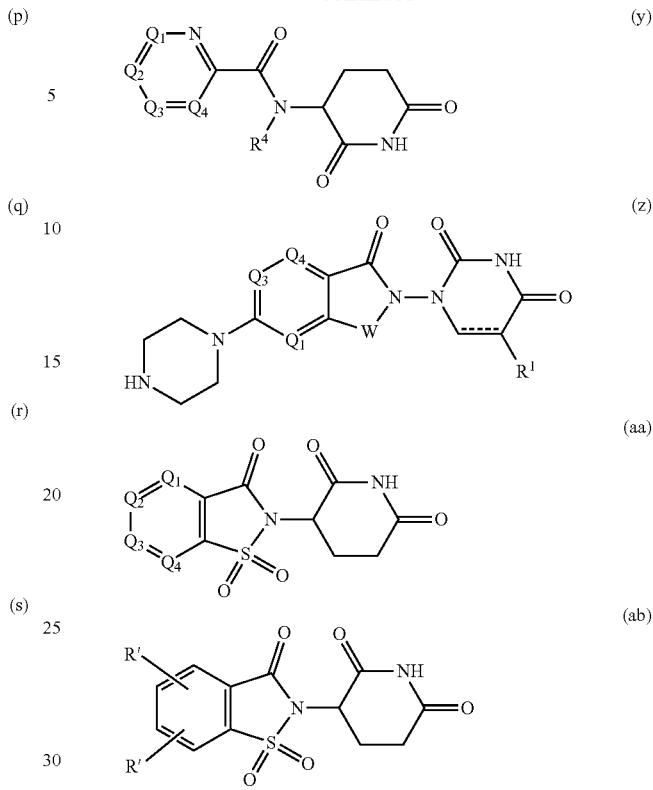

wherein:
W of Formulas (h) through (ab) is independently selected from $CH_2$, CHR, C=O, $SO_2$, NH, and N-alkyl;
$Q_1$, $Q_2$, $Q_3$, $Q_4$, $Q_5$ of Formulas (h) through (ab) are independently represent a carbon C substituted with a group independently selected from R', N or N-oxide;
$R^1$ of Formulas (h) through (ab) is selected from H, CN, C1-C3 alkyl;
$R^2$ of Formulas (h) through (ab) is selected from the group H, CN, C1-C3 alkyl, $CHF_2$, $CF_3$, CHO;
$R^3$ of Formulas (h) through (ab) is selected from H, alkyl, substituted alkyl, alkoxy, substituted alkoxy;
$R^4$ of Formulas (h) through (ab) is selected from H, alkyl, substituted alkyl;
$R^5$ of Formulas (h) through (ab) is H or lower alkyl;
X of Formulas (h) through (ab) is C, CH or N;
R' of Formulas (h) through (ab) is selected from H, halogen, alkyl, substituted alkyl, alkoxy, substituted alkoxy;
R of Formulas (h) through (ab) is H, OH, lower alkyl, lower alkoxy, cyano, halogenated lower alkoxy, or halogenated lower alkyl ⫽ of Formulas (h) through (ab) is a single or double bond; and the CLM is covalently joined to a PTM, a chemical linker group (L), a ULM, CLM (or CLM') or combination thereof.

In any aspect or embodiment described herein, the CLM or CLM' is covalently joined to a PTM, a chemical linker group (L), a ULM, a CLM, a CLM', or a combination thereof via an R group (such as, R, $R^1$, $R^2$, $R^3$, $R^4$ or R'), W, X, or a Q group (such as, $Q_1$, $Q_2$, $Q_3$, $Q_4$, or $Q_5$) of Formulas (h) through (ab).

In any of the embodiments described herein, the CLM or CLM' is covalently joined to a PTM, a chemical linker group (L), a ULM, a CLM, a CLM', or a combination thereof via W, X, R, $R^1$, $R^2$, $R^3$, $R^4$, $R^5$, R', $Q_1$, $Q_2$, $Q_3$, $Q_4$, and $Q_5$ of Formulas (h) through (ab).

In any of the embodiments described herein, the W, X, $R^1$, $R^2$, $R^3$, $R^4$, R', $Q_1$, $Q_2$, $Q_3$, $Q_4$, and $Q_5$ of Formulas (h) through (ab) can independently be covalently coupled to a linker and/or a linker to which is attached to one or more PTM, ULM, ULM', CLM or CLM' groups.

More specifically, non-limiting examples of CLMs include those shown below as well as "hybrid" molecules or compounds that arise from combining 1 or more features of the following compounds:

(ac)
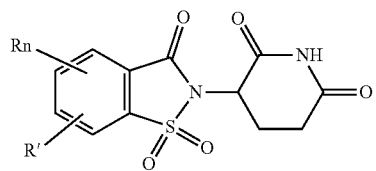

(ad)
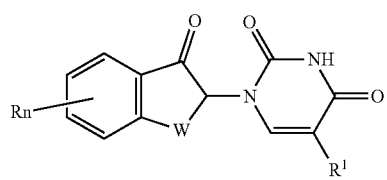

(ae)
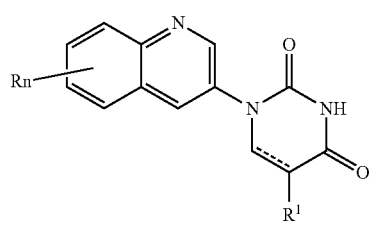

(af)
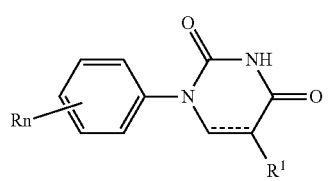

(ag)
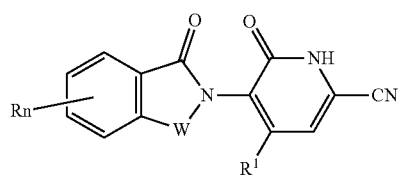

(ah)
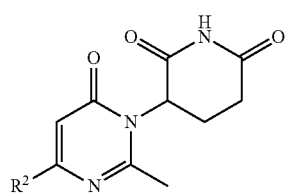

(ai)
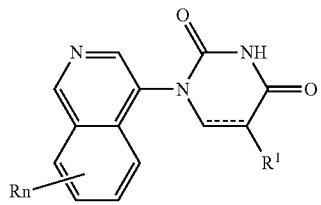

(aj)
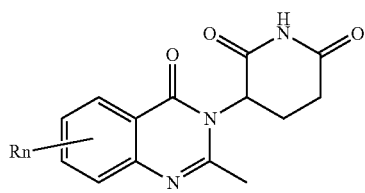

(ak)
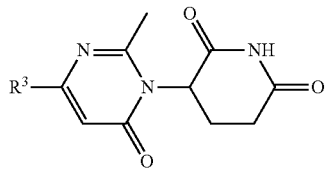

(al)
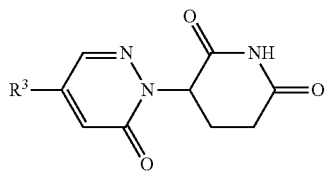

(am)
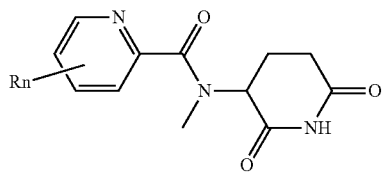

(an)
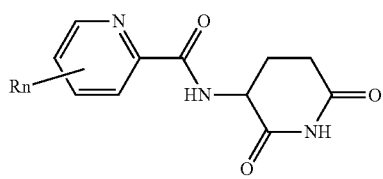

wherein:
W of Formulas (ac) through (an) is independently selected from the group $CH_2$, CHR, C=O, $SO_2$, NH, and N-alkyl;
$R^1$ of Formulas (ac) through (an) is selected from the group H, CN, C1-C3 alkyl;
$R^3$ of Formulas (ac) through (an) is selected from H, alkyl, substituted alkyl, alkoxy, substituted alkoxy;
R of Formulas (ac) through (an) is H;
⇌ is a single or double bond; and
Rn of Formulas (ac) through (an) comprises a functional group or an atom.

In any of the embodiments described herein, the W, $R^1$, $R^2$, $Q_1$, $Q_2$, $Q_3$, $Q_4$, and Rn of Formulas (ac) through (an) can independently be covalently coupled to a linker and/or a linker to which is attached one or more PTM, ULM, ULM', CLM or CLM' groups.

In any of the embodiments described herein, the $R^1$, $R^2$, $Q_1$, $Q_2$, $Q_3$, $Q_4$, and Rn of Formulas (ac) through (an) can independently be covalently coupled to a linker and/or a linker to which is attached one or more PTM, ULM, ULM', CLM or CLM' groups.

In any of the embodiments described herein, the $Q_1$, $Q_2$, $Q_3$, $Q_4$, and Rn of Formulas (ac) through (an) can independently be covalently coupled to a linker and/or a linker to which is attached one or more PTM, ULM, ULM', CLM or CLM' groups.

In any aspect or embodiment described herein, R. of Formulas (ac) through (an) is modified to be covalently joined to the linker group (L), a PTM, a ULM, a second CLM having the same chemical structure as the CLM, a CLM', a second linker, or any multiple or combination thereof.

In any aspect or embodiment described herein, the CLM is selected from:

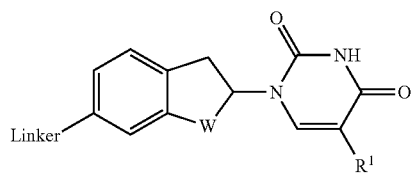

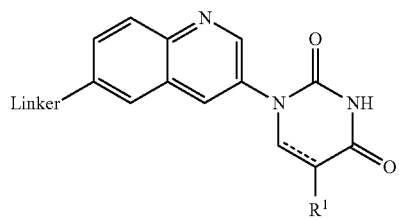

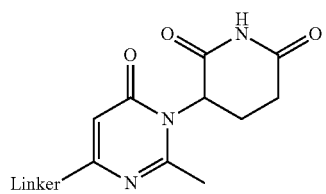

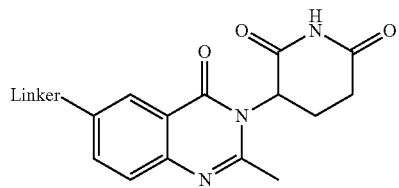

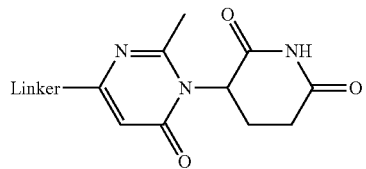

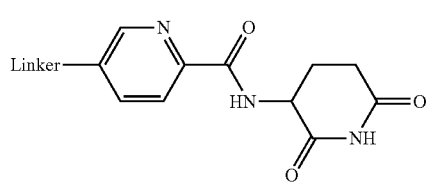

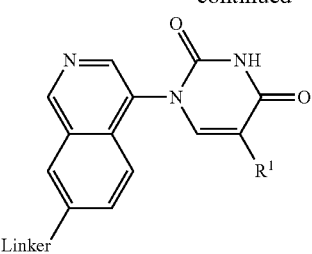

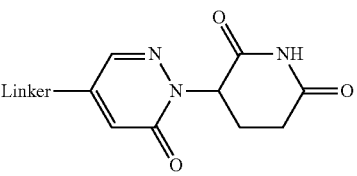

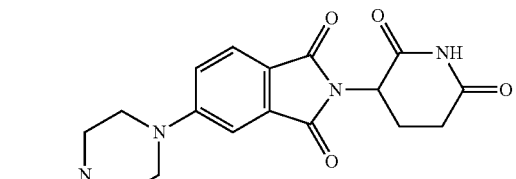

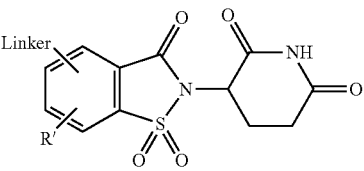

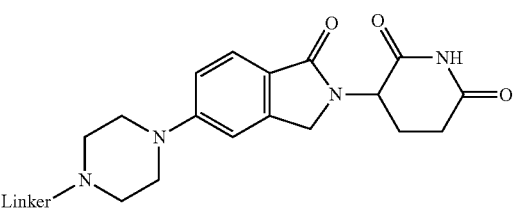

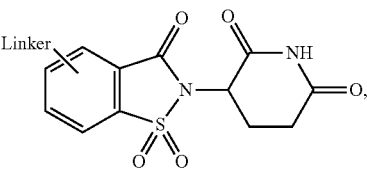

wherein R' is a halogen and $R^1$ is as described above with regard to Formulas (h) through (ab) or (ac) through (an).

In certain cases, the CLM can be imides that bind to cereblon E3 ligase. These imides and linker attachment point can be but not limited to the following structures:

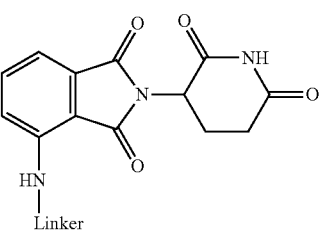

167
-continued

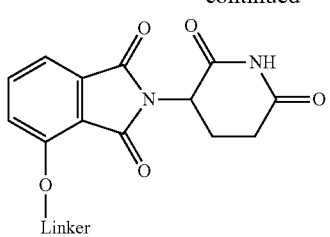

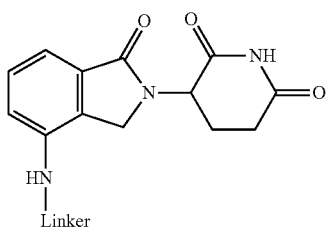

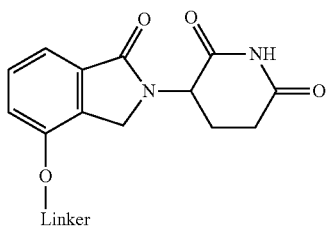

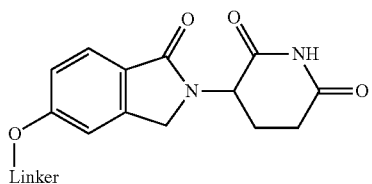

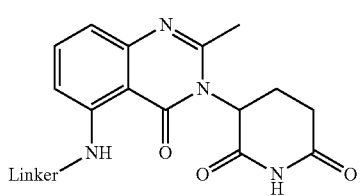

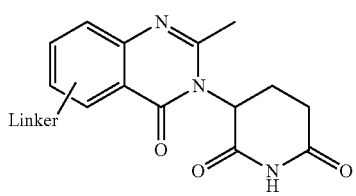

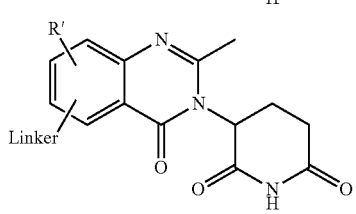

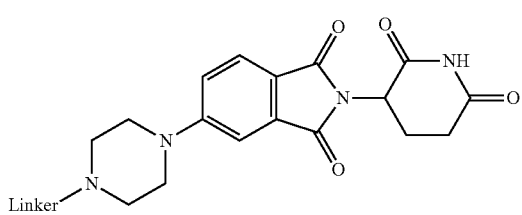

168
-continued

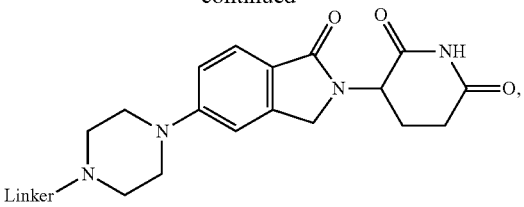

wherein
R' is a halogen.

Exemplary VLMs

In certain embodiments of the compounds as described herein, ULM is VLM and comprises a chemical structure selected from the group ULM-a:

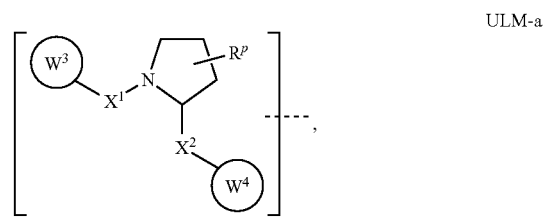

ULM-a wherein:
where a dashed line indicates the attachment of at least one PTM, another ULM or VLM or MLM or ILM or CLM (i.e., ULM' or VLM' or CLM' or ILM' or MLM'), or a chemical linker moiety coupling at least one PTM, a ULM' or a VLM' or a CLM' or a ILM' or a MLM' to the other end of the linker;

$X^1$, $X^2$ of Formula ULM-a are each independently selected from the group of a bond, O, $NR^{Y3}$, $CR^{Y3}R^{Y4}$, C=O, C=S, SO, and $SO_2$;

$R^{Y3}$, $R^{Y4}$ of Formula ULM-a are each independently selected from the group of H, linear or branched $C_{1-6}$ alkyl, optionally substituted by 1 or more halo, optionally substituted $C_{1-6}$ alkoxyl (e.g., optionally substituted by 0-3$R^P$ groups);

$R^P$ of Formula ULM-a is 0, 1, 2, or 3 groups each independently selected from the group H, halo, —OH, $C_{1-3}$ alkyl, C=O;

$W^3$ of Formula ULM-a is selected from the group of an optionally substituted -T-N($R^{1a}R^{1b}$)$X^3$, optionally substituted -T-N($R^{1a}R^{1b}$), optionally substituted -T-Aryl, an optionally substituted -T-Heteroaryl, an optionally substituted T-biheteroaryl, an optionally substituted -T-Heterocycle, an optionally substituted -T-biheterocycle, an optionally substituted —$NR^1$-T-Aryl, an optionally substituted —$NR^1$-T-Heteroaryl or an optionally substituted —$NR^1$-T-Heterocycle;

$X^3$ of Formula ULM-a is C=O, $R^1$, $R^{1a}$, $R^{1b}$;

each of $R^1$, $R^{1a}$, $R^{1b}$ is independently selected from the group consisting of H, linear or branched $C_1$-$C_6$ alkyl group optionally substituted by 1 or more halo or —OH groups, $R^{Y3}$C=O, $R^{Y3}$C=S, $R^{Y3}$SO, $R^{Y3}SO_2$, N($R^{Y3}R^{Y4}$)C=O, N($R^{Y3}R^{Y4}$)C=S, N($R^{Y3}R^{Y4}$)SO, and N($R^{Y3}R^{Y4}$)$SO_2$;

T of Formula ULM-a is covalently bonded to $X^1$ and is selected from the group of an optionally substituted alkyl, —$(CH_2)_n$— group, wherein each one of the methylene groups is optionally substituted with one or two substituents selected from the group of halogen, methyl, a linear or branched $C_1$-$C_6$ alkyl group optionally substituted by 1 or more halogen or —OH groups or an amino acid side chain optionally substituted;

$W^4$ of Formula ULM-a is an optionally substituted —NR1-T-Aryl, an optionally substituted —NR1-T-Heteroaryl group or an optionally substituted —NR1-T-Heterocycle, where —$NR^1$ is covalently bonded to $X^2$ and $R^1$ is H or $CH_3$, preferably H.

In any of the embodiments described herein, T is selected from the group of an optionally substituted alkyl, —$(CH_2)_n$— group, wherein each one of the methylene groups is optionally substituted with one or two substituents selected from the group of halogen, methyl, a linear or branched $C_1$-$C_6$ alkyl group optionally substituted by 1 or more halogen or —OH groups or an amino acid side chain optionally substituted; and n is 0 to 6, often 0, 1, 2, or 3, preferably 0 or 1.

In certain embodiments $W^4$ of Formula ULM-a is

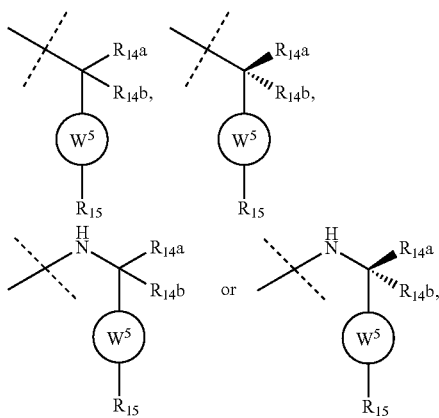

wherein $R_{14a}$, $R_{14b}$, are each independently selected from the group of H, haloalkyl, or optionally substituted alkyl.

In any of the embodiments, $W^5$ of Formula ULM-a is selected from the group of a phenyl or a 5-10 membered heteroaryl, $R_{15}$ of Formula ULM-a is selected from the group of H, halogen, CN, OH, $NO_2$, N $R_{14a}R_{14b}$, $OR_{14a}$, $CONR_{14a}R_{14b}$, $NR_{14a}COR_{14b}$, $SO_2NR_{14a}R_{14b}$, $NR_{14a}SO_2R_{14b}$, optionally substituted alkyl, optionally substituted haloalkyl, optionally substituted haloalkoxy; aryl, heteroaryl, cycloalkyl, or cycloheteroalkyl (each optionally substituted);

In additional embodiments, $W^4$ substituents for use in the present disclosure also include specifically (and without limitation to the specific compound disclosed) the $W^4$ substituents which are found in the identified compounds disclosed herein. Each of these $W^4$ substituents may be used in conjunction with any number of $W^3$ substituents which are also disclosed herein.

In certain additional embodiments, ULM-a, is optionally substituted by 1-3$R^P$ groups in the pyrrolidine moiety. Each $R^P$ is independently H, halo, —OH, C1-3alkyl.

In any of the embodiments described herein, the $W^3$, $W^4$ of Formula ULM-a can independently be covalently coupled to a linker which is attached one or more PTM groups.

and wherein the dashed line indicates the site of attachment of at least one PTM, another ULM (ULM') or a chemical linker moiety coupling at least one PTM or a ULM' or both to ULM.

In certain embodiments, ULM is VHL and is represented by the structure:

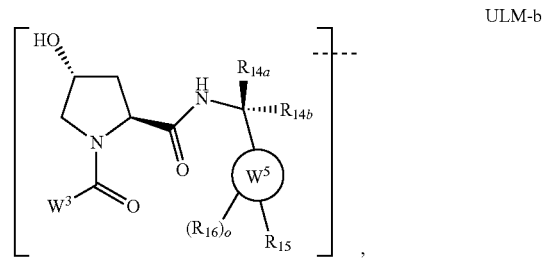

ULM-b wherein:

$W^3$ of Formula ULM-b is selected from the group of an optionally substituted aryl, optionally substituted heteroaryl, or

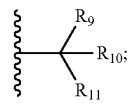

$R_9$ and $R_{10}$ of Formula ULM-b are independently hydrogen, optionally substituted alkyl, optionally substituted cycloalkyl, optionally substituted hydroxyalkyl, optionally substituted heteroaryl, or haloalkyl, or $R_9$, $R_{10}$, and the carbon atom to which they are attached form an optionally substituted cycloalkyl;

$R_{11}$ of Formula ULM-b is selected from the group of an optionally substituted heterocyclic, optionally substituted alkoxy, optionally substituted heteroaryl, optionally substituted aryl,

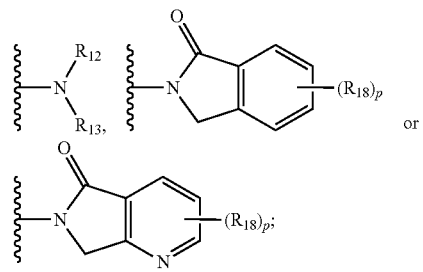

$R_{12}$ of Formula ULM-b is selected from the group of H or optionally substituted alkyl, $R_{13}$ of Formula ULM-b is selected from the group of H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl;

$R_{14a}$, $R_{14b}$ of Formula ULM-b, are each independently selected from the group of H, haloalkyl, or optionally substituted alkyl;

$W^5$ of Formula ULM-b is selected from the group of a phenyl or a 5-10 membered heteroaryl, $R_{15}$ of Formula ULM-b is selected from the group of H, halogen, CN, OH, $NO_2$, N $R_{14a}R_{14b}$, $OR_{14a}$, $CONR_{14a}R_{14b}$, $NR_{14a}COR_{14b}$, $SO_2NR_{14a}R_{14b}$, $NR_{14a}$ SO$_2$R$_{14b}$, optionally substituted alkyl, optionally substituted haloalkyl, optionally substituted haloalkoxy; aryl, heteroaryl, cycloalkyl, or cycloheteroalkyl (optionally substituted);

R$_{16}$ of Formula ULM-b is independently selected from the group of halo, optionally substituted alkyl, optionally substituted haloalkyl, hydroxy, or optionally substituted haloalkoxy;

o of Formula ULM-b is 0, 1, 2, 3, or 4;

R$_{18}$ of Formula ULM-b is independently selected from the group of H, halo, optionally substituted alkoxy, cyano, optionally substituted alkyl, haloalkyl, haloalkoxy or a linker; and p of Formula ULM-b is 0, 1, 2, 3, or 4, and wherein the dashed line indicates the site of attachment of at least one PTM, another ULM (ULM') or a chemical linker moiety coupling at least one PTM or a ULM' or both to ULM.

In certain embodiments, R$_{15}$ of Formula ULM-b is

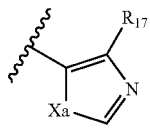

wherein R$_{17}$ is H, halo, optionally substituted C$_{3-6}$cycloalkyl, optionally substituted C$_{1-6}$alkyl, optionally substituted C$_{1-6}$alkenyl, and C$_{1-6}$haloalkyl; and Xa is S or O.

In certain embodiments, R$_{17}$ of Formula ULM-b is selected from the group methyl, ethyl, isopropyl, and cyclopropyl.

In certain additional embodiments, R$_{15}$ of Formula ULM-b is selected from the group consisting of:

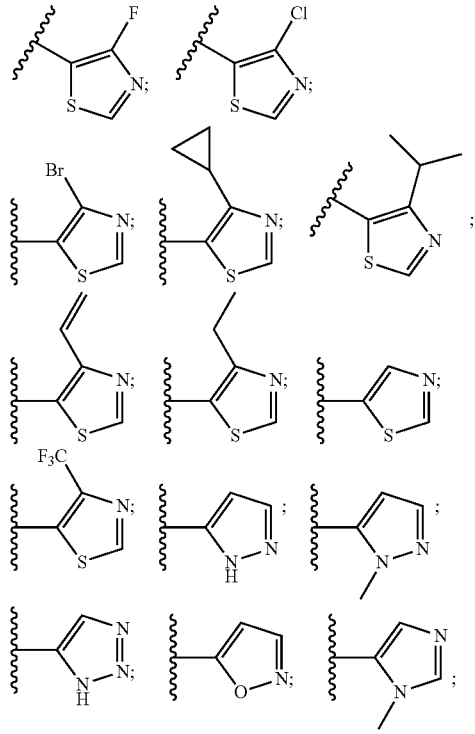

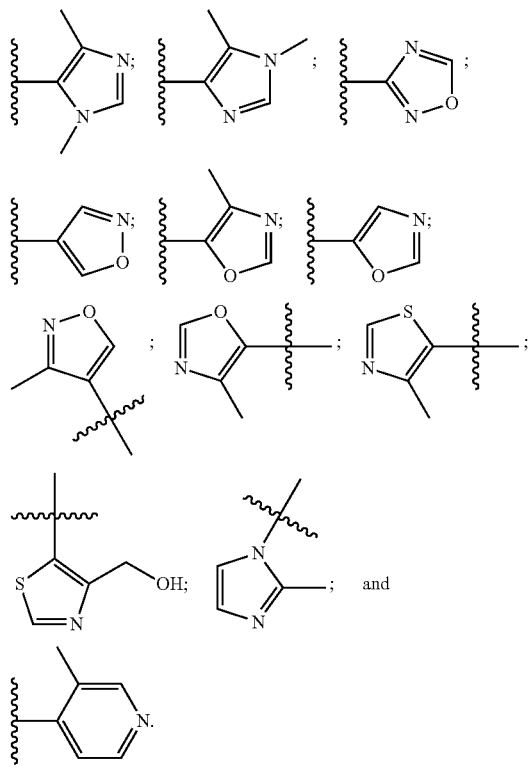

In certain embodiments, R$_{11}$ of Formula ULM-b is selected from the group consisting of:

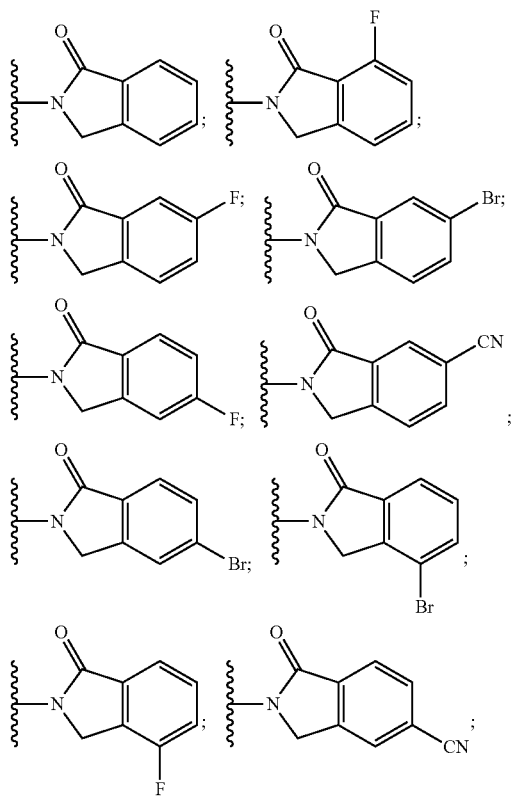

-continued

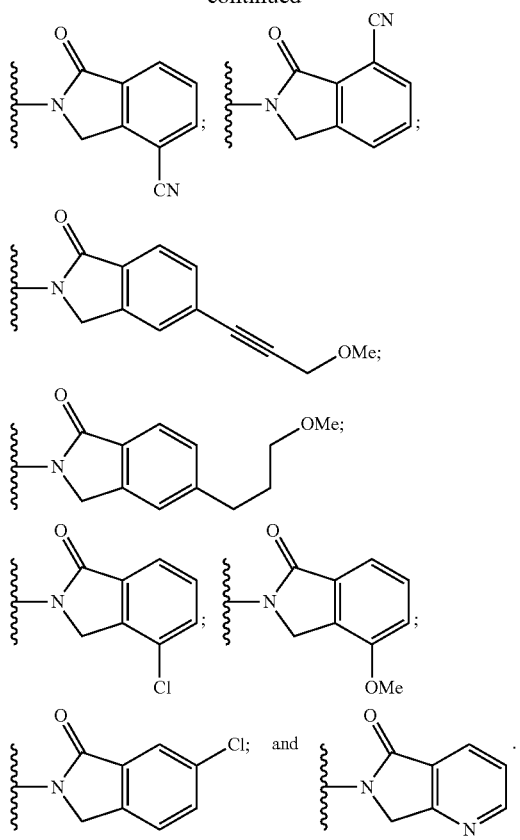

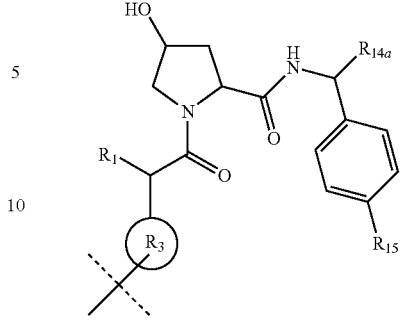

In certain embodiments, ULM has a chemical structure selected from the group of:

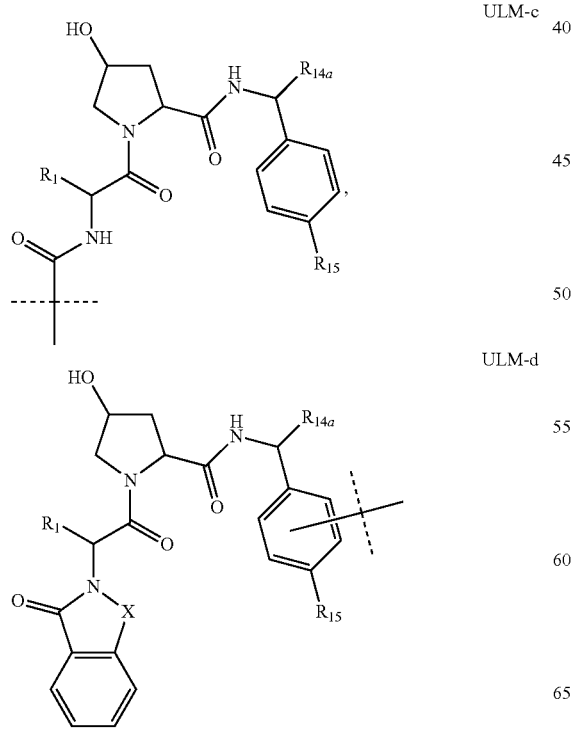

-continued

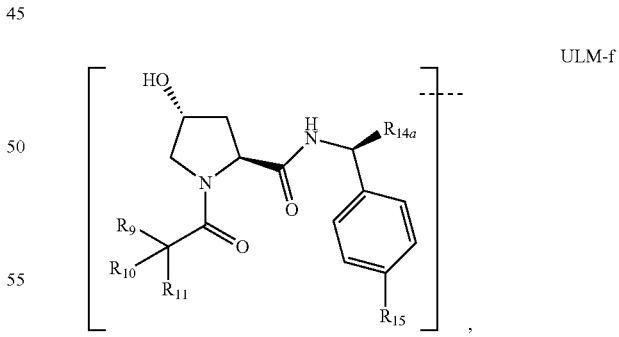

wherein:
$R_1$ of Formulas ULM-c, ULM-d, and ULM-e is H, ethyl, isopropyl, tert-butyl, sec-butyl, cyclopropyl, cyclobutyl, cyclopentyl, or cyclohexyl; optionally substituted alkyl, optionally substituted hydroxyalkyl, optionally substituted heteroaryl, or haloalkyl;

$R_{14a}$ of Formulas ULM-c, ULM-d, and ULM-e is H, haloalkyl, optionally substituted alkyl, methyl, fluoromethyl, hydroxymethyl, ethyl, isopropyl, or cyclopropyl;

$R_{15}$ of Formulas ULM-c, ULM-d, and ULM-e is selected from the group consisting of H, halogen, CN, OH, $NO_2$, optionally substituted heteroaryl, optionally substituted aryl; optionally substituted alkyl, optionally substituted haloalkyl, optionally substituted haloalkoxy, cycloalkyl, or cycloheteroalkyl (each optionally substituted);

X of Formulas ULM-c, ULM-d, and ULM-e is C, $CH_2$, or C=O $R_3$ of Formulas ULM-c, ULM-d, and ULM-e is absent or an optionally substituted 5 or 6 membered heteroaryl; and wherein the dashed line indicates the site of attachment of at least one PTM, another ULM (ULM') or a chemical linker moiety coupling at least one PTM or a ULM' or both to ULM.

In certain embodiments, ULM comprises a group according to the chemical structure:

ULM-f wherein:
$R_{14a}$ of Formula ULM-f is H, haloalkyl, optionally substituted alkyl, methyl, fluoromethyl, hydroxymethyl, ethyl, isopropyl, or cyclopropyl;

$R_9$ of Formula ULM-f is H;

$R_{10}$ of Formula ULM-f is H, ethyl, isopropyl, tert-butyl, sec-butyl, cyclopropyl, cyclobutyl, cyclopentyl, or cyclohexyl;

R₁₁ of Formula ULM-f is

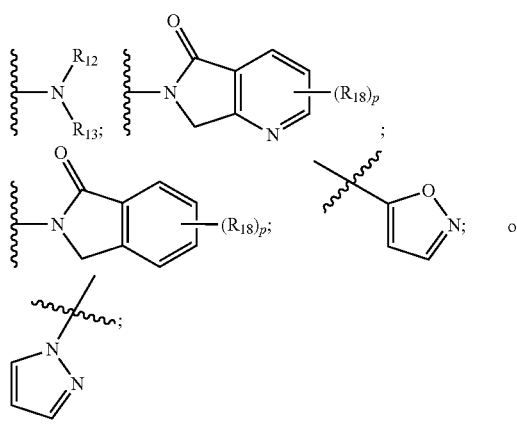

or optionally substituted heteroaryl;
p of Formula ULM-f is 0, 1, 2, 3, or 4;
each R₁₈ of Formula ULM-f is independently halo, optionally substituted alkoxy, cyano, optionally substituted alkyl, haloalkyl, haloalkoxy or a linker;
R₁₂ of Formula ULM-f is H, C=O;
R₁₃ of Formula ULM-f is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl,
R₁₅ of Formula ULM-f is selected from the group consisting of H, halogen, Cl, CN, OH, NO₂, optionally substituted heteroaryl, optionally substituted aryl;

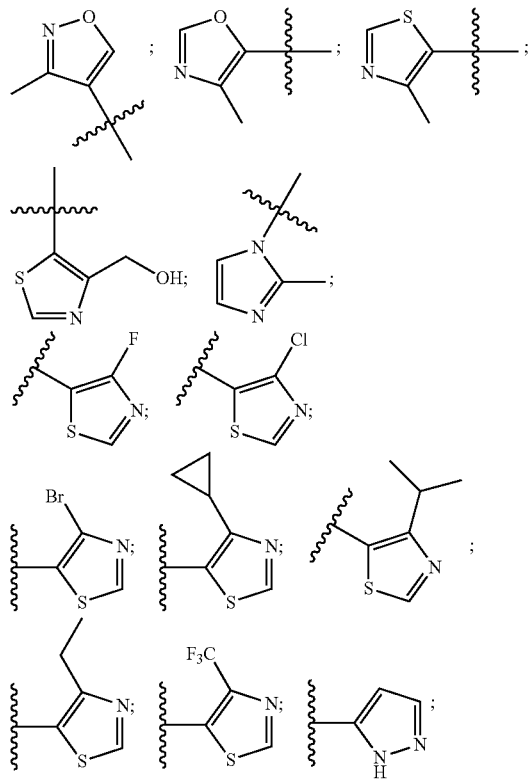

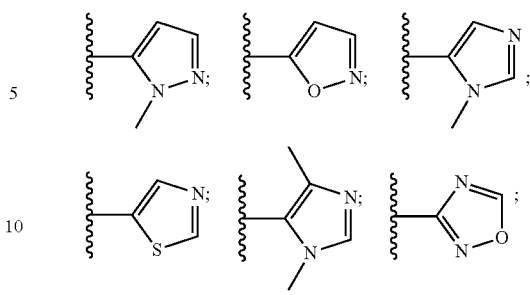

and wherein the dashed line of Formula ULM-f indicates the site of attachment of at least one PTM, another ULM (ULM') or a chemical linker moiety coupling at least one PTM or a ULM' or both to ULM.

In certain embodiments, the ULM is selected from the following structures:

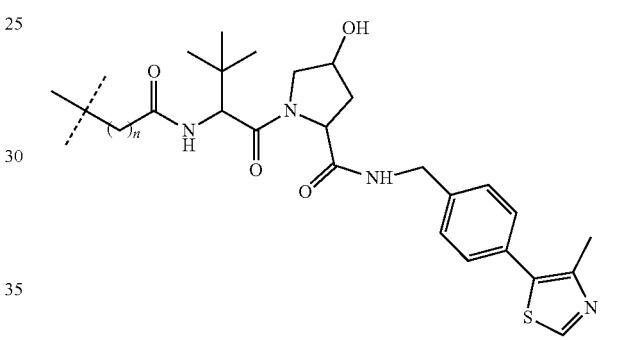

ULM-a2

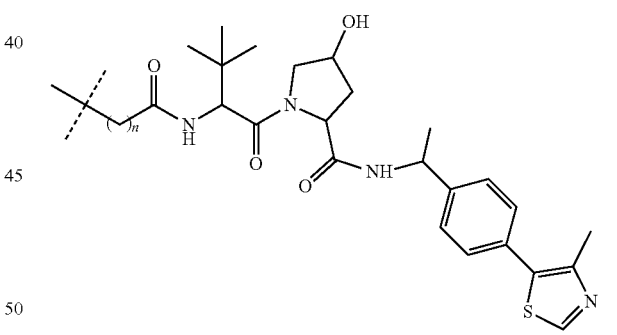

ULM-a3

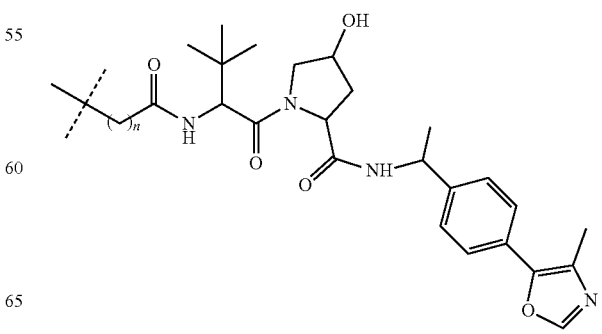

ULM-a4
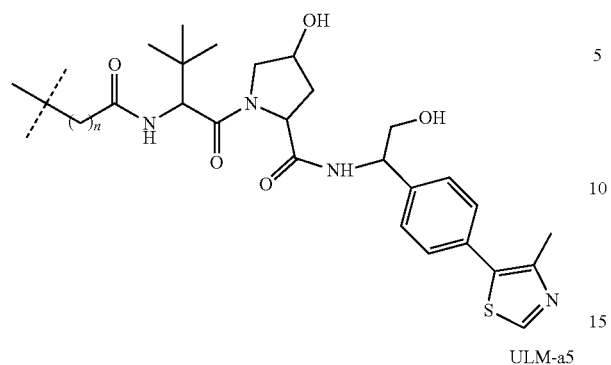
ULM-a5
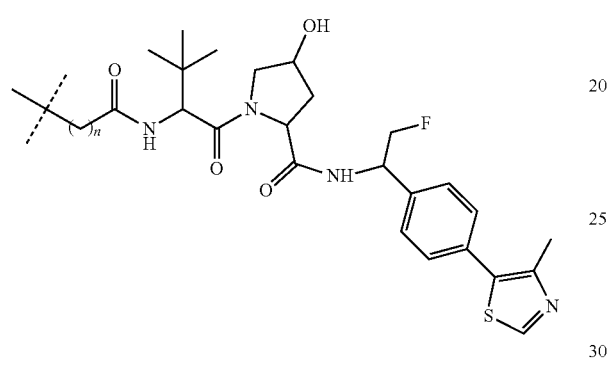
ULM-a6
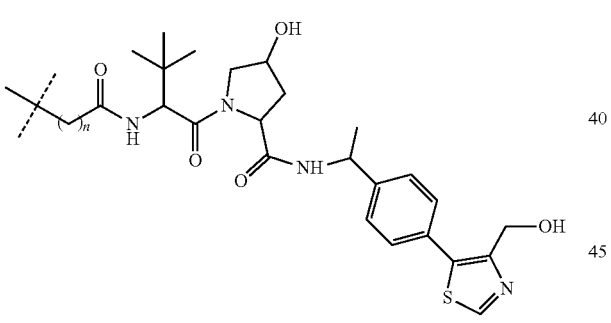
ULM-a7
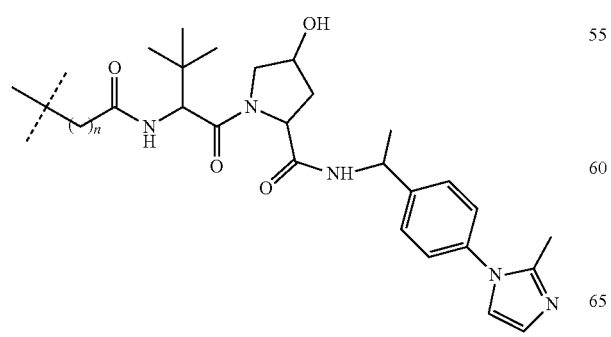
ULM-a8
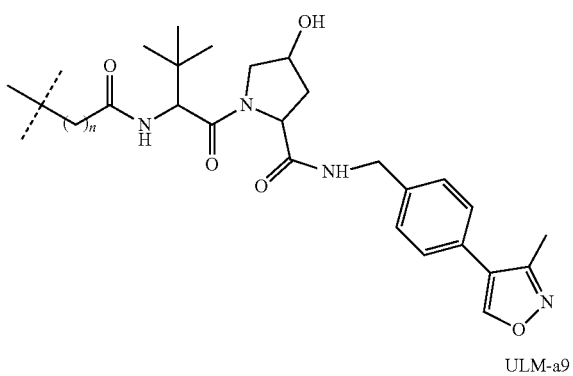
ULM-a9
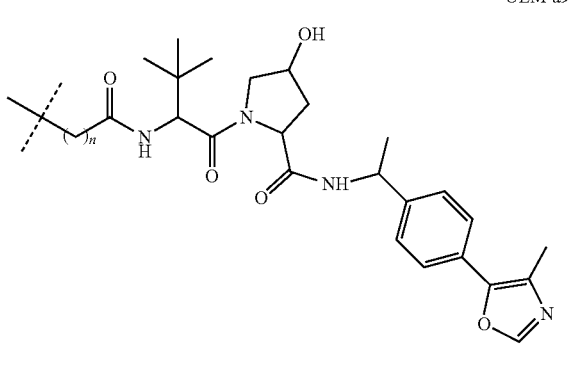
ULM-a10
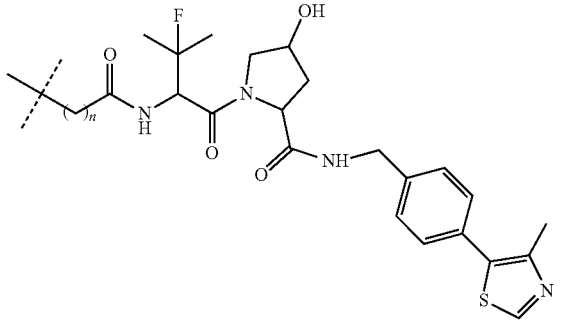
ULM-a11
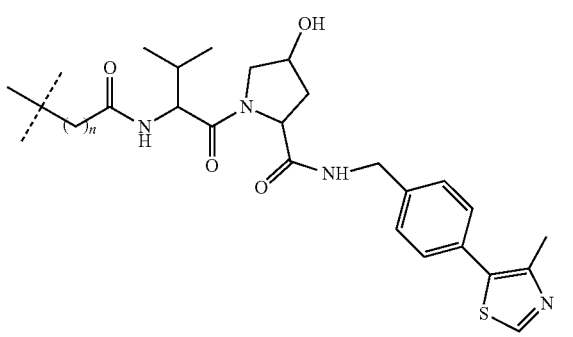

ULM-a12
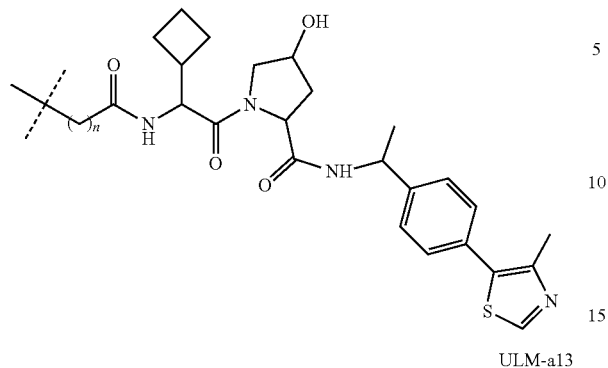
ULM-a13
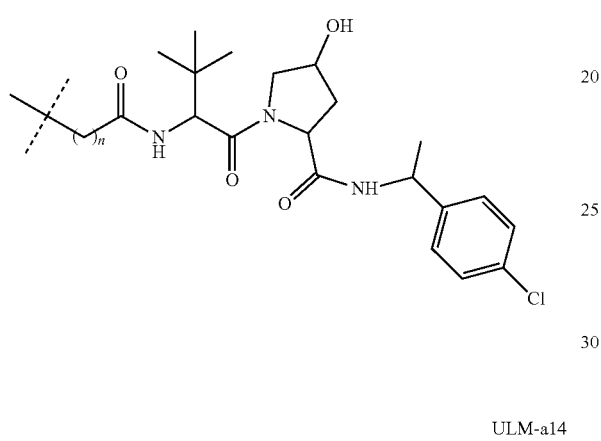
ULM-a14
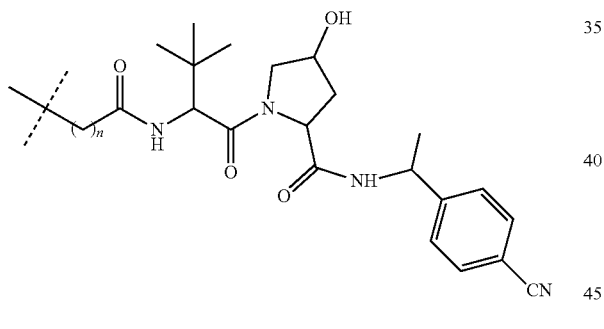
ULM-a15
where n is 0 or 1.
In certain embodiments, the ULM is selected from the following structures:
ULM-b1
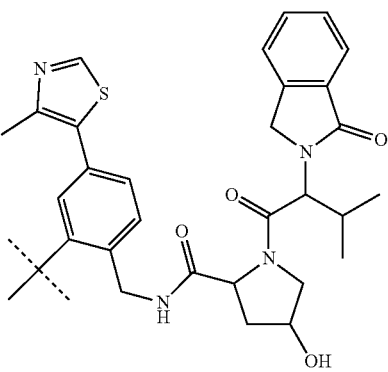
ULM-b2
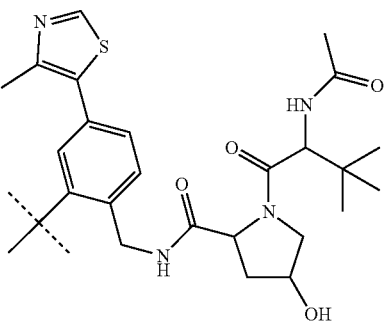
ULM-b3
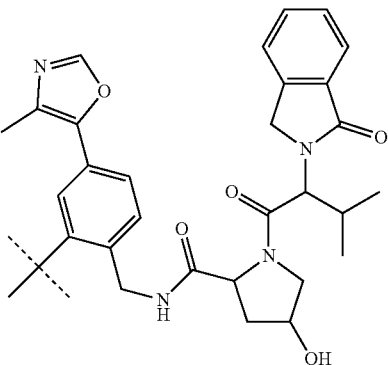
ULM-b4
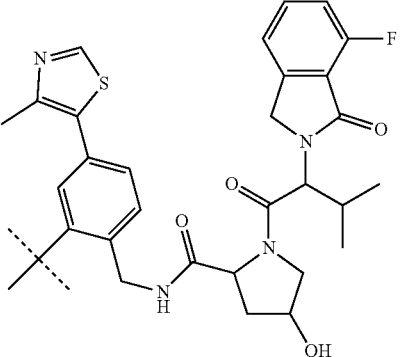

ULM-b5
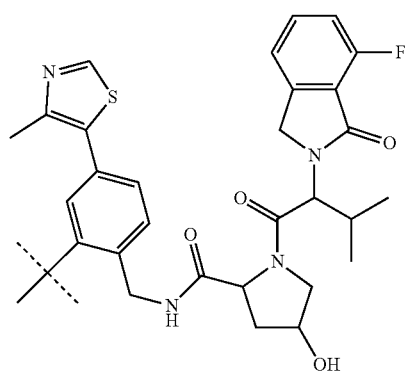
ULM-b6
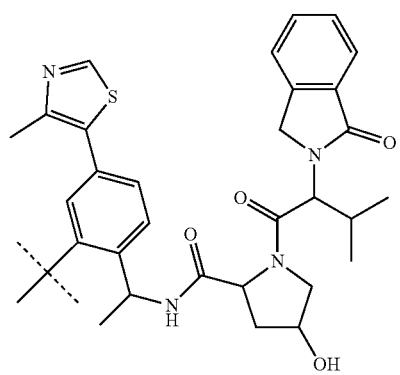
ULM-b7
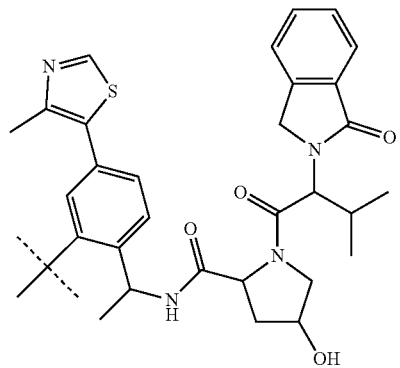
ULM-b8
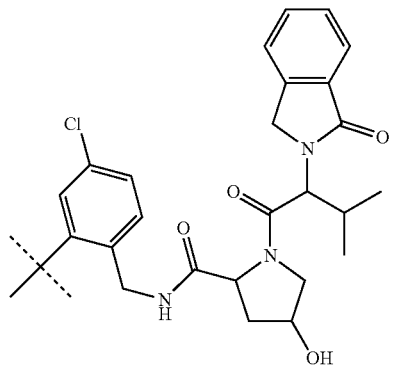
ULM-b9
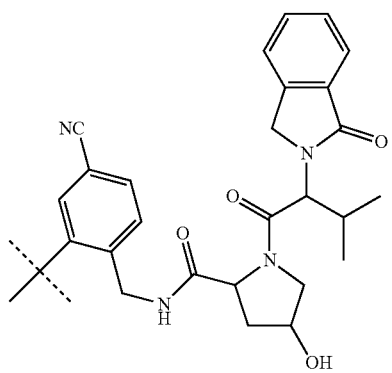
ULM-b10
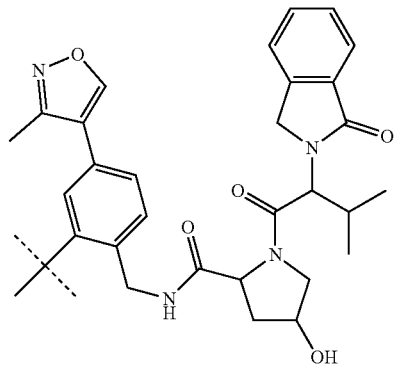
ULM-b11
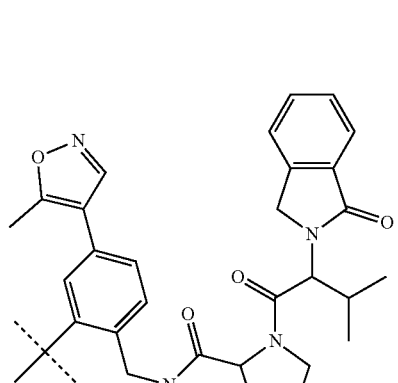
ULM-b12
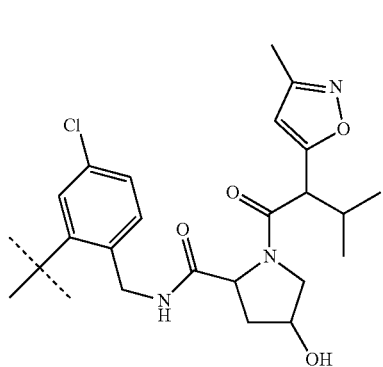

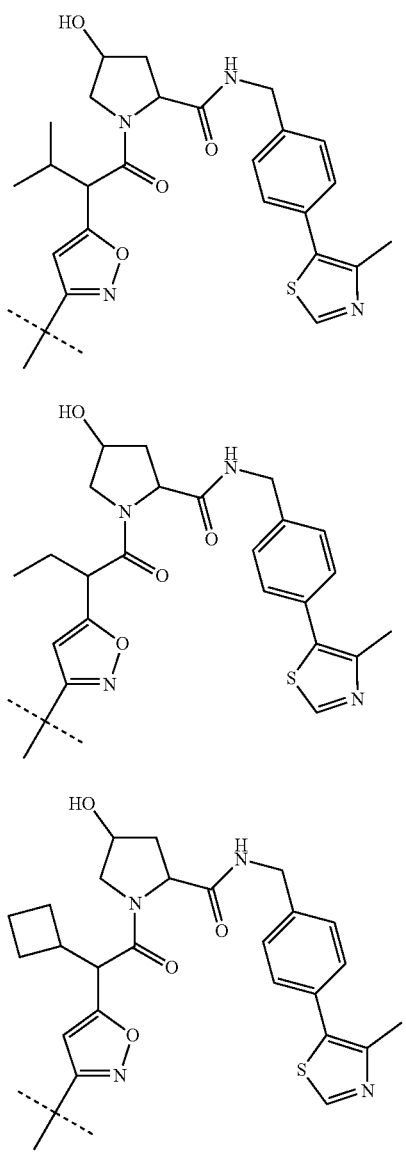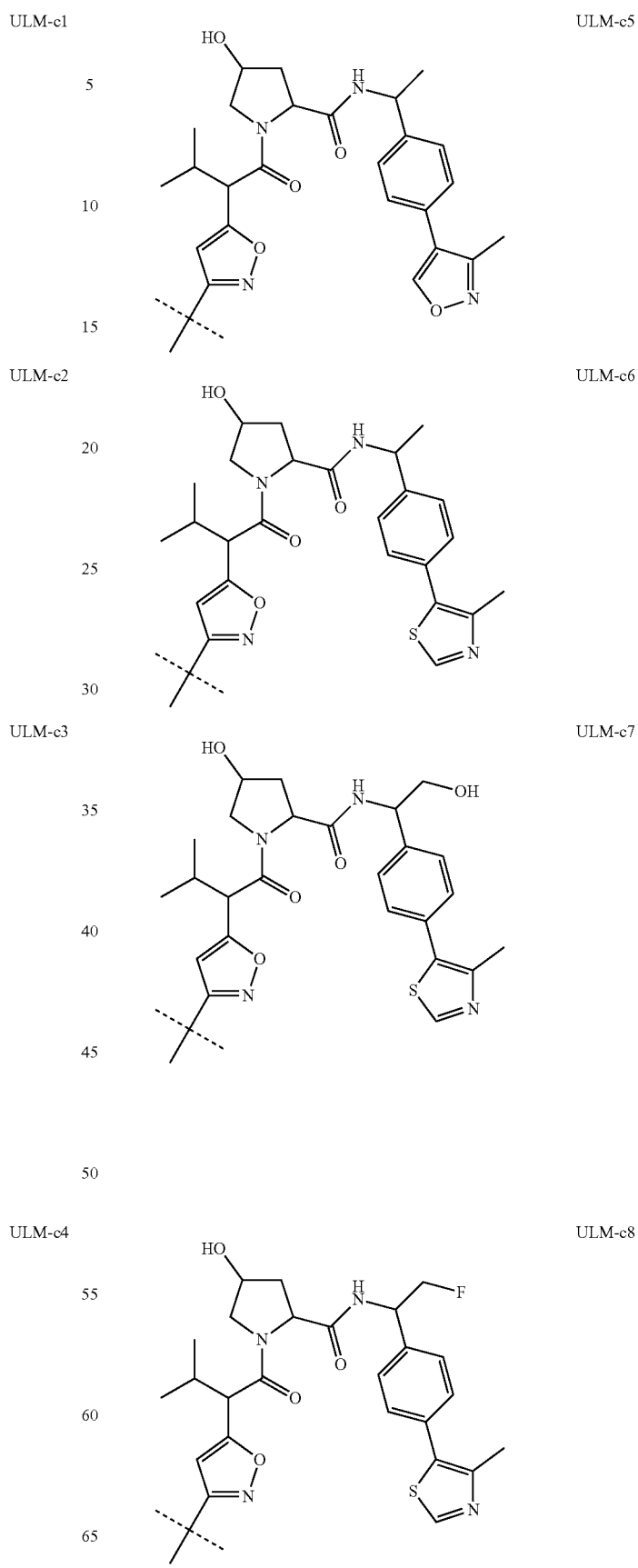

185
-continued

ULM-c9

ULM-c10

ULM-c11

ULM-c12

186
-continued

ULM-c13

ULM-c14

ULM-c15

ULM-d1

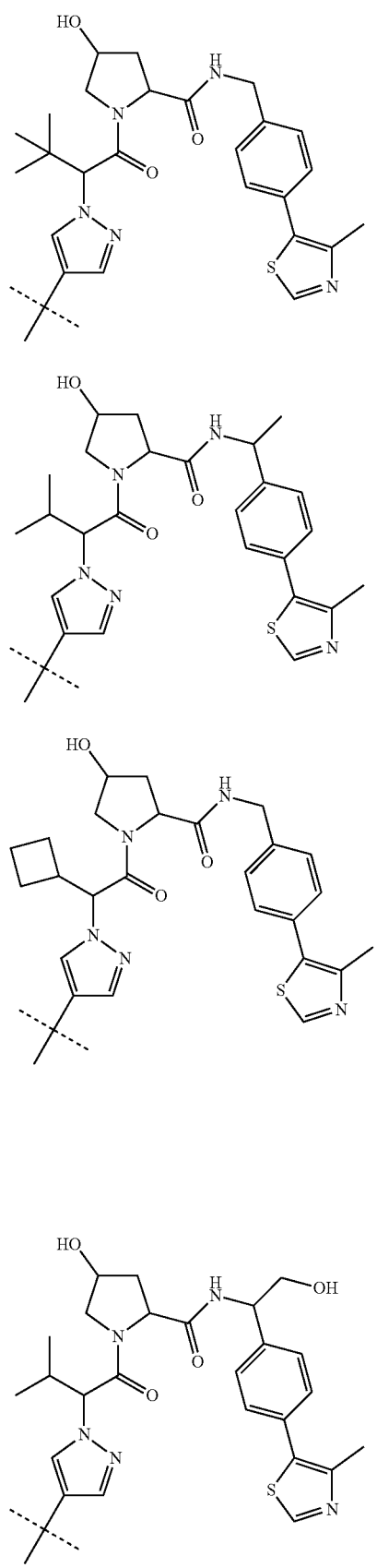
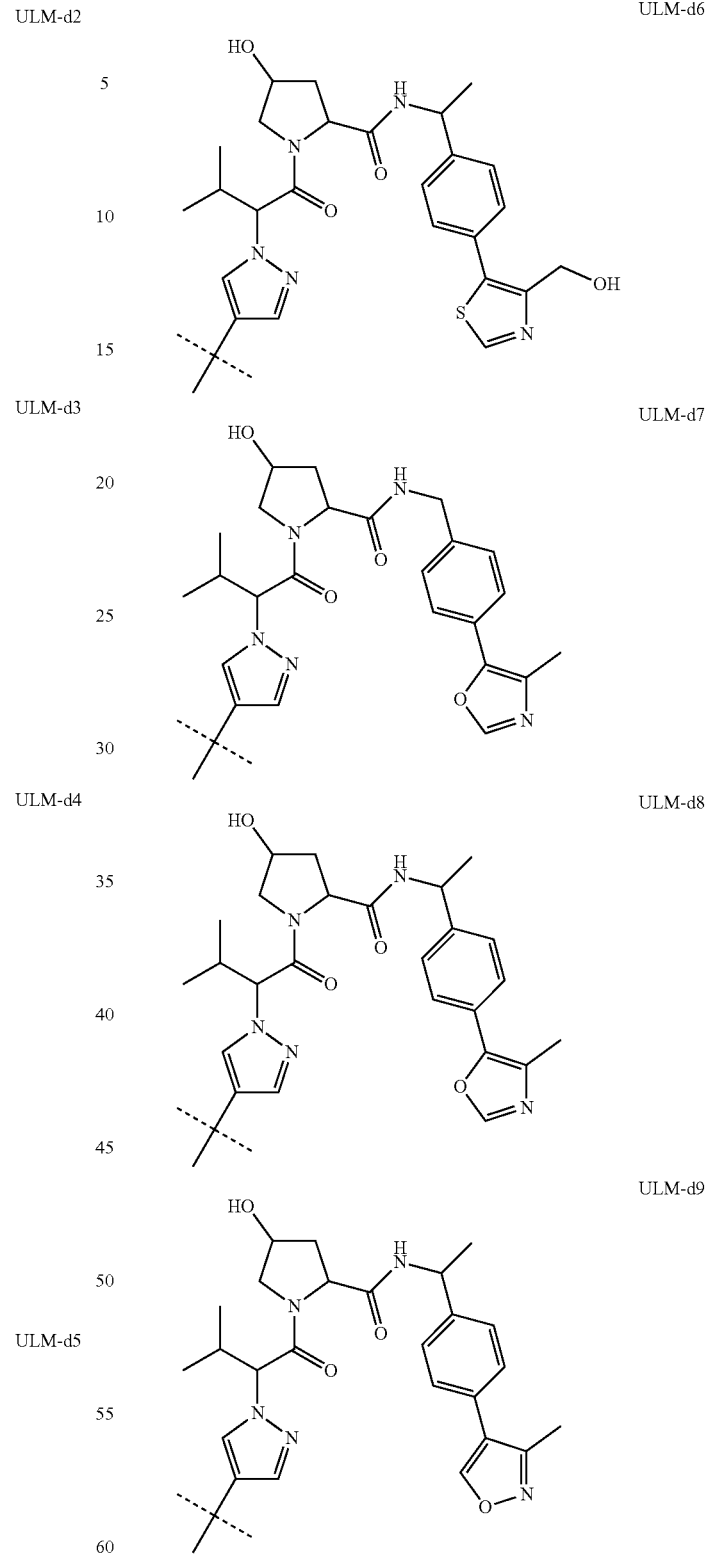
wherein, the phenyl ring in ULM-a1 through ULM-a15, ULM-b1 through ULM-b12, ULM-c1 through ULM-c15 and ULM-d1 through ULM-d9 is optionally substituted with fluorine, lower alkyl and alkoxy groups, and wherein the dashed line indicates the site of attachment of at least one PTM, another ULM (ULM') or a chemical linker moiety coupling at least one PTM or a ULM' or both to ULM-a.

In one embodiment, the phenyl ring in ULM-a1 through ULM-a15, ULM-b1 through ULM-b12, ULM-c1 through ULM-c15 and ULM-d1 through ULM-d9 can be functionalized as the ester to make it a part of the prodrug.

In certain embodiments, the hydroxyl group on the pyrrolidine ring of ULM-a1 through ULM-a15, ULM-b1 through ULM-b12, ULM-c1 through ULM-c15 and ULM-d1 through ULM-d9, respectively, comprises an ester-linked prodrug moiety.

In any of the aspects or embodiments described herein, the ULM and where present, ULM', are each independently a group according to the chemical structure:

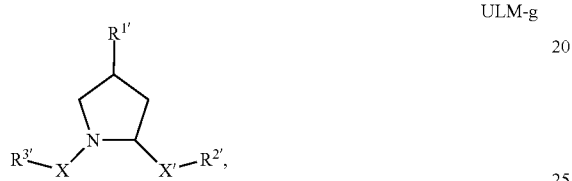

ULM-g wherein:
- $R^{1'}$ of ULM-g is an optionally substituted $C_1$-$C_6$ alkyl group, an optionally substituted $-(CH_2)_n OH$, an optionally substituted $-(CH_2)_n SH$, an optionally substituted $(CH_2)_n-O-(C_1$-$C_6$)alkyl group, an optionally substituted $(CH_2)_n-WCOCW-(C_0$-$C_6$)alkyl group containing an epoxide moiety WCOCW where each W is independently H or a $C_1$-$C_3$ alkyl group, an optionally substituted $-(CH_2)_n COOH$, an optionally substituted $-(CH_2)_n C(O)-(C_1$-$C_6$ alkyl), an optionally substituted $-(CH_2)_n NHC(O)-R_1$, an optionally substituted $-(CH_2)_n C(O)-NR_1R_2$, an optionally substituted $-(CH_2)_n OC(O)-NR_1R_2$, $-(CH_2O)_n H$, an optionally substituted $-(CH_2)_n OC(O)-(C_1$-$C_6$ alkyl), an optionally substituted $-(CH_2)_n C(O)-O-(C_1$-$C_6$ alkyl), an optionally substituted $-(CH_2O)_n COOH$, an optionally substituted $-(OCH_2)_n O-(C_1$-$C_6$ alkyl), an optionally substituted $-(CH_2O)_n C(O)-(C_1$-$C_6$ alkyl), an optionally substituted $-(OCH_2)_n NHC(O)-R_1$, an optionally substituted $-(CH_2O)_n C(O)-NR_1R_2$, $-(CH_2CH_2O)_n H$, an optionally substituted $-(CH_2CH_2O)_n COOH$, an optionally substituted $-(OCH_2CH_2)_n O-(C_1$-$C_6$ alkyl), an optionally substituted $-(CH_2CH_2O)_n C(O)-(C_1$-$C_6$ alkyl), an optionally substituted $-(OCH_2CH_2)_n NHC(O)-R_1$, an optionally substituted $-(CH_2CH_2O)_n C(O)-NR_1R_2$, an optionally substituted $-SO_2R_S$, an optionally substituted $S(O)R_S$, $NO_2$, CN or halogen (F, Cl, Br, I, preferably F or Cl);
- $R_1$ and $R_2$ of ULM-g are each independently H or a $C_1$-$C_6$ alkyl group which may be optionally substituted with one or two hydroxyl groups or up to three halogen groups (preferably fluorine);
- $R_S$ of ULM-g is a $C_1$-$C_6$ alkyl group, an optionally substituted aryl, heteroaryl or heterocycle group or a $-(CH_2)_m NR_1R_2$ group;
- X and X' of ULM-g are each independently C=O, C=S, —S(O), S(O)$_2$, (preferably X and X' are both C=O);
- $R^{2'}$ of ULM-g is an optionally substituted $-(CH_2)_n-(C=O)_u(NR^1)_v(SO_2)_w$alkyl group, an optionally substituted $-(CH_2)_n, -(C=O)_u(NR^1)_v(SO_2)_w NR_{1N}R_{2N}$ group, an optionally substituted $-(CH_2)_n-(C=O)_u(NR^1)_v(SO_2)_w$-Aryl, an optionally substituted $-(CH_2)_n-(C=O)_u(NR_1)_v(SO_2)_w$-Heteroaryl, an optionally substituted $-(CH_2)_n-(C=O)_v NR_1(SO_2)_w$-Heterocycle, an optionally substituted $-NR_1-(CH_2)_n-C(O)_u(NR_1)_v(SO_2)_w$-alkyl, an optionally substituted $-NR^1-(CH_2)_n-C(O)_u(NR_1)_v(SO_2)_w-NR_{1N}R_{2N}$, an optionally substituted $-NR^1-(CH_2)_n-C(O)_u(NR_1)_v(SO_2)_w-NR_1C(O)R_{1N}$, an optionally substituted $-NR^1-(CH_2)_n-(C=O)_u(NR_1)_v(SO_2)_w$-Aryl, an optionally substituted $-NR^1-(CH_2)_n-(C=O)_u(NR_1)_v(SO_2)_w$-Heteroaryl or an optionally substituted $-NR^1-(CH_2)_n-(C=O)_v NR_1(SO_2)_w$-Heterocycle, an optionally substituted $-X^{R2'}$-alkyl group; an optionally substituted $-X^{R2'}$-Aryl group; an optionally substituted $-X^{R2'}$-Heteroaryl group; an optionally substituted $-X^{R2'}$-Heterocycle group; an optionally substituted;
- $R^{3'}$ of ULM-g is an optionally substituted alkyl, an optionally substituted $-(CH_2)_n-(O)_u(NR_1)_v(SO_2)_w$-alkyl, an optionally substituted $-(CH_2)_n-C(O)_u(NR_1)_v(SO_2)_w-NR_{1N}R_{2N}$, an optionally substituted $-(CH_2)_n-C(O)_u(NR_1)_v(SO_2)_w-NR_1C(O)R_{1N}$, an optionally substituted $-(CH_2)_n-C(O)_u(NR_1)_v(SO_2)_w-C(O)NR_1R_2$, an optionally substituted $-(CH_2)_n-C(O)_u(NR_1)_v(SO_2)_w$-Aryl, an optionally substituted $-(CH_2)_n-C(O)_u(NR_1)_v(SO_2)_w$-Heteroaryl, an optionally substituted $-(CH_2)_n-C(O)_u(NR_1)_v(SO_2)_w$-Heterocycle, an optionally substituted $-NR^1-(CH_2)_n-C(O)_u(NR_1)_v(SO_2)_w$-alkyl, an optionally substituted $-NR^1-(CH_2)_n-C(O)_u(NR_1)_v(SO_2)_w-NR_{1N}R_{2N}$, an optionally substituted $-NR^1-(CH_2)_n-C(O)_u(NR_1)_v(SO_2)_w-NR_1C(O)R_1N$, an optionally substituted $-NR^1-(CH_2)_n-C(O)_u(NR_1)_v(SO_2)_w$-Aryl, an optionally substituted $-NR_1-(CH_2)_n-C(O)_u(NR_1)_v(SO_2)_w$-Heteroaryl, an optionally substituted $-NR^1-(CH_2)_n-C(O)_u(NR_1)_v(SO_2)_w$-Heterocycle, an optionally substituted $-O-(CH_2)_n-(C=O)_u(NR^1)_v(SO_2)_w$-alkyl, an optionally substituted $-O-(CH_2)_n-(C=O)_u(NR_1)_v(SO_2)_w-NR_{1N}R_{2N}$, an optionally substituted $-O-(CH_2)_n-(C=O)_u(NR^1)_v(SO_2)_w-NR_1C(O)R_{1N}$, an optionally substituted $-O-(CH_2)_n-(C=O)_u(NR_1)_v(SO_2)_w$-Aryl, an optionally substituted $-O-(CH_2)_n-(C=O)_u(NR_1)_v(SO_2)_w$-Heteroaryl or an optionally substituted $-O-(CH_2)_n-(C=O)_u(NR_1)_v(SO_2)_w$-Heterocycle; $-(CH_2)_n-(V)_{n'}-(CH_2)_n-(V)_{n'}$-alkyl group, an optionally substituted $-(CH_2)_n-(V)_{n'}-(CH_2)_n-(V)_{n'}$-Aryl group, an optionally substituted $-(CH_2)_n-(V)_{n'}-(CH_2)_n-(V)_{n'}$-Heteroaryl group, an optionally substituted $-(CH_2)_n-(V)_{n'}-(CH_2)_n-(V)_{n'}$-Heterocycle group, an optionally substituted $-(CH_2)_n-N(R_1)(C=O)_{m'}-(V)_{n'}$-alkyl group, an optionally substituted $-(CH_2)_n-N(R_1)(C=O)_{m'}-(V)_{n'}$-Aryl group, an optionally substituted $-(CH_2)_n-N(R_1)(C=O)_{m'}-(V)_{n'}$-Heteroaryl group, an optionally substituted $-(CH_2)_n-N(R_1)(C=O)_{m'}-(V)_{n'}$-Heterocycle group, an optionally substituted $-X^{R3'}$-alkyl group; an optionally substituted $-X^{R3'}$-Aryl group; an optionally substituted $-X^{R3'}$-Heteroaryl group; an optionally substituted $-X^{R3'}$-Heterocycle group; an optionally substituted;
- $R_{1N}$ and $R_{2N}$ of ULM-g are each independently H, $C_1$-$C_6$ alkyl which is optionally substituted with one or two hydroxyl groups and up to three halogen groups or an optionally substituted $-(CH_2)_n$-Aryl, $-(CH_2)_n$-Heteroaryl or $-(CH_2)_n$-Heterocycle group;

V of ULM-g is O, S or NR$_1$;
R$_1$ of ULM-g is the same as above;
R$^1$ and R$_1$, of ULM-g are each independently H or a C$_1$-C$_3$ alkyl group;
X$^{R2'}$ and X$^{R3'}$ of ULM-g are each independently an optionally substituted —(CH$_2$)$_n$—, —(CH$_2$)$_n$—CH(X$_v$)=CH(X$_v$)— (cis or trans), —(CH$_2$)$_n$—CH≡CH—, —(CH$_2$CH$_2$O)$_n$— or a C$_3$-C$_6$ cycloalkyl group, where X$_v$ is H, a halo or a C$_1$-C$_3$ alkyl group which is optionally substituted;
each m of ULM-g is independently 0, 1, 2, 3, 4, 5, 6;
each m' of ULM-g is independently 0 or 1;
each n of ULM-g is independently 0, 1, 2, 3, 4, 5, 6;
each n' of ULM-g is independently 0 or 1;
each u of ULM-g is independently 0 or 1;
each v of ULM-g is independently 0 or 1;
each w of ULM-g is independently 0 or 1; and
any one or more of R$^{1'}$, R$^{2'}$, R$^{3'}$, X and X' of ULM-g is optionally modified to be covalently bonded to the PTM group through a linker group when PTM is not ULM', or when PTM is ULM', any one or more of R$^{1'}$, R$^{2'}$, R$^{3'}$, X and X' of each of ULM and ULM' are optionally modified to be covalently bonded to each other directly or through a linker group, or a pharmaceutically acceptable salt, stereoisomer, solvate or polymorph thereof.

In any of the aspects or embodiments described herein, the ULM and when present, ULM', are each independently a group according to the chemical structure:

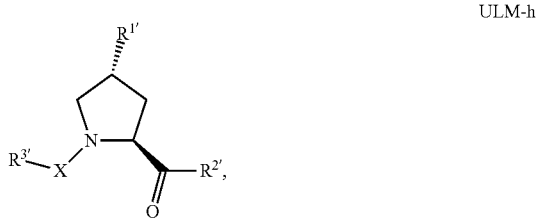

ULM-h wherein:
each of R$^{1'}$, R$^{2'}$ and R$^{3'}$ of ULM-h are the same as above and X is C═O, C═S, —S(O) group or a S(O)$_2$ group, more preferably a C═O group, and
any one or more of R$^{1'}$, R$^{2'}$ and R$^{3'}$ of ULM-h are optionally modified to bind a linker group to which is further covalently bonded to the PTM group when PTM is not ULM', or when PTM is ULM', any one or more of R$^{1'}$, R$^{2'}$, R$^{3'}$ of each of ULM and ULM' are optionally modified to be covalently bonded to each other directly or through a linker group, or
a pharmaceutically acceptable salt, enantiomer, diastereomer, solvate or polymorph thereof.

In any of the aspects or embodiments described herein, the ULM, and when present, ULM', are each independently according to the chemical structure:

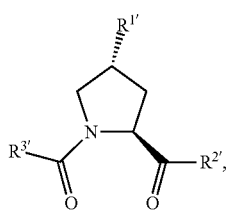

ULM-i wherein:
any one or more of R$^{1'}$, R$^{2'}$ and R$^{3'}$ of ULM-I are optionally modified to bind a linker group to which is further covalently bonded to the PTM group when PTM is not ULM', or when PTM is ULM', any one or more of R$^{1'}$, R$^{2'}$, R$^{3'}$ of each of ULM and ULM' are optionally modified to be covalently bonded to each other directly or through a linker group, or
a pharmaceutically acceptable salt, enantiomer, diastereomer, solvate or polymorph thereof.

In further preferred aspects of the disclosure, R$^{1'}$ of ULM-g through ULM-i is preferably a hydroxyl group or a group which may be metabolized to a hydroxyl or carboxylic group, such that the compound represents a prodrug form of an active compound. Exemplary preferred R$^{1'}$ groups include, for example, —(CH$_2$)$_n$OH, (CH$_2$)$_n$—O—(C$_1$-C$_6$)alkyl group, —(CH$_2$)$_n$COOH, —(CH$_2$O)$_n$H, an optionally substituted —(CH$_2$)$_n$OC(O)—(C$_1$-C$_6$ alkyl), or an optionally substituted —(CH$_2$)$_n$C(O)—O—(C$_1$-C$_6$ alkyl), wherein n is 0 or 1. Where R$^{1'}$ is or contains a carboxylic acid group, a hydroxyl group or an amine group, the hydroxyl group, carboxylic acid group or amine (each of which may be optionally substituted), may be further chemically modified to provide a covalent link to a linker group to which the PTM group (including a ULM' group) is bonded;

X and X', where present, of ULM-g and ULM-h are preferably a C═O, C═S, —S(O) group or a S(O)$_2$ group, more preferably a C═O group;
R$^{2'}$ of ULM-g through ULM-i is preferably an optionally substituted —NR$^1$-T-Aryl, an optionally substituted —NR$^1$-T-Heteroaryl group or an optionally substituted —NR$^1$-T-Heterocycle, where R$^1$ is H or CH$_3$, preferably H and T is an optionally substituted —(CH$_2$)$_n$— group, wherein each one of the methylene groups may be optionally substituted with one or two substituents, preferably selected from halogen, an amino acid side-chain as otherwise described herein or a C$_1$-C$_3$ alkyl group, preferably one or two methyl groups, which may be optionally substituted; and n is 0 to 6, often 0, 1, 2 or 3, preferably 0 or 1. Alternatively, T may also be a —(CH$_2$O)$_n$— group, a —(OCH$_2$)$_n$— group, a —(CH$_2$CH$_2$O)$_n$— group, a —(OCH$_2$CH$_2$)$_n$— group, all of which groups are optionally substituted.

Preferred Aryl groups for R$^{2'}$ of ULM-g through ULM-i include optionally substituted phenyl or naphthyl groups, preferably phenyl groups, wherein the phenyl or naphthyl group is connected to a PTM (including a ULM' group) with a linker group and/or optionally substituted with a halogen (preferably F or Cl), an amine, monoalkyl- or dialkyl amine (preferably, dimethylamine), F, Cl, OH, COOH, C$_1$-C$_6$ alkyl, preferably CH$_3$, CF$_3$, OMe, OCF$_3$, NO$_2$, or CN group (each of which may be substituted in ortho-, meta- and/or para-positions of the phenyl ring, preferably para-), an optionally substituted phenyl group (the phenyl group itself is optionally connected to a PTM group, including a ULM', with a linker group), and/or optionally substituted with at least one of F, Cl, OH, COOH, CH$_3$, CF$_3$, OMe, OCF$_3$, NO$_2$, or CN group (in ortho-, meta- and/or para-positions of the phenyl ring, preferably para-), a naphthyl group, which may be optionally substituted, an optionally substituted heteroaryl, preferably an optionally substituted isoxazole including a methylsubstituted isoxazole, an optionally substituted oxazole including a methylsubstituted oxazole, an optionally substituted thiazole including a methyl substituted thiazole, an optionally substituted isothiazole including a methyl substituted isothiazole, an optionally substituted pyrrole including a methylsubstituted pyrrole, an optionally substituted imidazole including a methylimidazole, an optionally substituted benzimidazole or methoxybenzylimidazole, an optionally substituted oximidazole or methyloximidazole, an optionally substituted diazole group, including a methyldiazole group, an optionally substituted triazole group, including a methylsubstituted triazole group, an optionally substituted pyridine group, including a halo- (preferably, F) or methylsubstitutedpyridine group or an oxapyridine group (where the pyridine group is linked to the phenyl group by an oxygen), an optionally substituted furan, an optionally substituted benzofuran, an optionally substituted dihydrobenzofuran, an optionally substituted indole, indolizine or azaindolizine (2, 3, or 4-azaindolizine), an optionally substituted quinoline, an optionally substituted group according to the chemical structure:

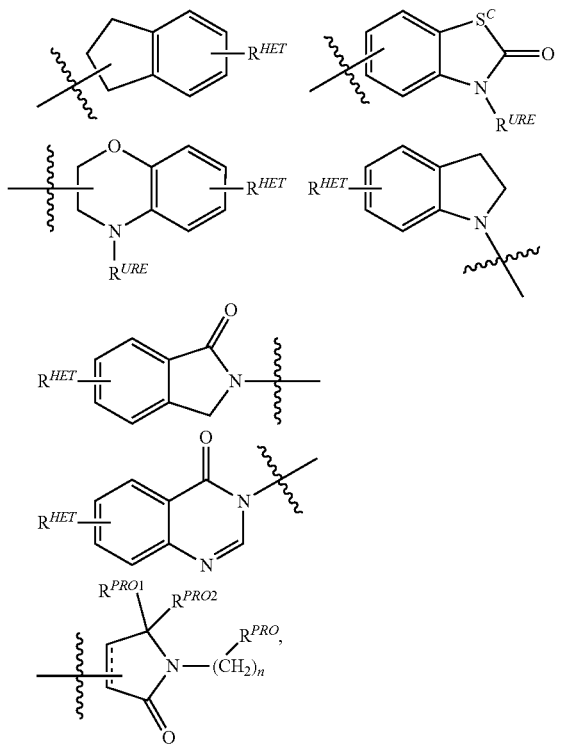

wherein:
$S^c$ of ULM-g through ULM-i is $CHR^{SS}$, $NR^{URE}$, or O;
$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C— $R_a$ where $R_a$ is H or a $C_1$-$C_6$ alkyl group (preferably $C_1$-$C_3$ alkyl);
$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —$C(O)(C_1$-$C_6$alkyl) (preferably substituted with one or two hydroxyl groups or up to three halo groups);

$R^{URE}$ of ULM-g through ULM-i is H, a $C_1$-$C_6$ alkyl (preferably H or $C_1$-$C_3$ alkyl) or a —$C(O)(C_1$-$C_6$ alkyl) each of which groups is optionally substituted with one or two hydroxyl groups or up to three halogen, preferably fluorine groups, or an optionally substituted phenyl group, an optionally substituted heteroaryl, or an optionally substituted heterocycle, preferably for example piperidine, morpholine, pyrrolidine, tetrahydrofuran);
$R^{PRO}$ of ULM-g through ULM-i is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;
$R^{PRO1}$ and $R^{PRO2}$ of ULM-g through ULM-i are each independently H, an optionally substituted $C_1$-$C_3$ alkyl group or together form a keto group; and
each n of ULM-g through ULM-i is independently 0, 1, 2, 3, 4, 5, or 6 (preferably 0 or 1), or an optionally substituted heterocycle, preferably tetrahydrofuran, tetrahydrothiene, piperidine, piperazine or morpholine (each of which groups when substituted, are preferably substituted with a methyl or halo (F, Br, Cl), each of which groups may be optionally attached/coupled to a PTM group (including a ULM' group) via a linker group.
In certain preferred aspects,

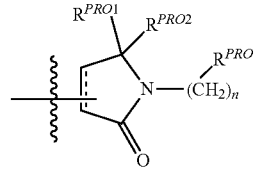

of ULM-g through ULM-i is

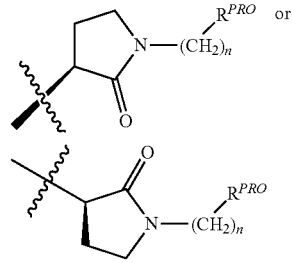

where $R^{PRO}$ and n of ULM-g through ULM-i are the same as above.

Preferred heteroaryl groups for $R^{2'}$ of ULM-g through ULM-i include an optionally substituted quinoline (which may be attached to the pharmacophore or substituted on any carbon atom within the quinoline ring), an optionally substituted indole, an optionally substituted indolizine, an optionally substituted azaindolizine, an optionally substituted benzofuran, including an optionally substituted benzofuran, an optionally substituted isoxazole, an optionally substituted thiazole, an optionally substituted isothiazole, an optionally substituted thiophene, an optionally substituted pyridine (2-, 3-, or 4-pyridine), an optionally substituted imidazole, an optionally substituted pyrrole, an optionally substituted diazole, an optionally substituted triazole, a tetrazole, an optionally substituted oximidazole, or a group according to the chemical structure:

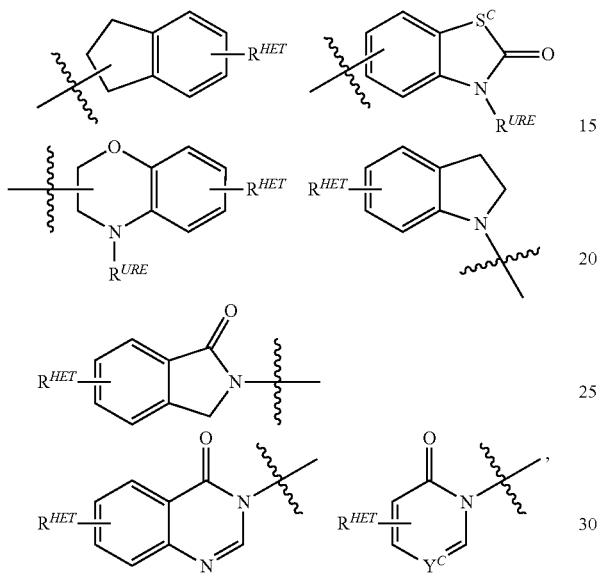

wherein:
- $S^c$ of ULM-g through ULM-i is $CHR^{SS}$, $NR^{U}R^{E}$, or O;
- $R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ of ULM-g through ULM-i is H or a $C_1$-$C_6$ alkyl group (preferably $C_1$-$C_3$ alkyl);
- $R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$alkyl) (preferably substituted with one or two hydroxyl groups or up to three halo groups);
- $R^{URE}$ of ULM-g through ULM-i is H, a $C_1$-$C_6$ alkyl (preferably H or $C_1$-$C_3$ alkyl) or a —C(O)($C_1$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and
- $Y^c$ of ULM-g through ULM-i is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl), each of which groups may be optionally connected/coupled to a PTM group (including a ULM' group) via a linker group.

Preferred heterocycle groups for $R^{2'}$ of ULM-g through ULM-i include tetrahydrofuran, tetrahydrothiene, tetrahydroquinoline, piperidine, piperazine, pyrrollidine, morpholine, oxane or thiane, each of which groups may be optionally substituted, or a group according to the chemical structure:

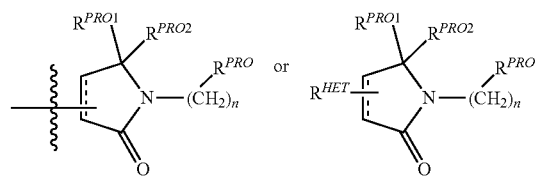

preferably, a

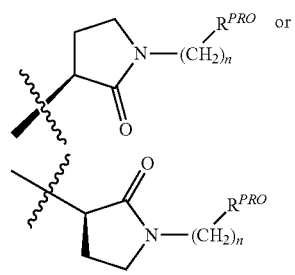

group,
wherein:
- $R^{PRO}$ of ULM-g through ULM-i is H, optionally substituted $C_1$-$C_6$ alkyl or an optionally substituted aryl, heteroaryl or heterocyclic group;
- $R^{PRO1}$ and $R^{PRO2}$ of ULM-g through ULM-i are each independently H, an optionally substituted $C_1$-$C_3$ alkyl group or together form a keto group and
- each n of ULM-g through ULM-i is independently 0, 1, 2, 3, 4, 5, or 6 (often 0 or 1), each of which groups may be optionally connected/coupled to a PTM group (including a ULM' group) via a linker group.

Preferred $R^{2'}$ substituents of ULM-g through ULM-i also include specifically (and without limitation to the specific compound disclosed) the $R^{2'}$ substituents which are found in the identified compounds disclosed herein (which includes the specific compounds which are disclosed in the present specification, and the figures which are attached hereto). Each of these $R^{2'}$ substituents may be used in conjunction with any number of $R^{3'}$ substituents which are also disclosed herein.

$R^{3'}$ of ULM-g through ULM-i is preferably an optionally substituted -T-Aryl, an optionally substituted-T-Heteroaryl, an optionally substituted -T-Heterocycle, an optionally substituted-$NR^1$-T-Aryl, an optionally substituted —$NR^1$-T-Heteroaryl or an optionally substituted-$NR^1$-T-Heterocycle, where $R^1$ is H or a $C_1$-$C_3$ alkyl group, preferably H or $CH_3$, T is an optionally substituted —$(CH_2)_n$— group, wherein each one of the methylene groups may be optionally substituted with one or two substituents, preferably selected from halogen, a $C_1$-$C_3$ alkyl group or the sidechain of an amino acid as otherwise described herein, preferably methyl, which may be optionally substituted; and n is 0 to 6, often 0, 1, 2, or 3 preferably 0 or 1. Alternatively, T may also be a —(CH$_2$O)$_n$— group, a —(OCH$_2$)$_n$— group, a —(CH$_2$CH$_2$O)$_n$— group, a —(OCH$_2$CH$_2$)$_n$— group, each of which groups is optionally substituted.

Preferred aryl groups for $R^{3'}$ of ULM-g through ULM-i include optionally substituted phenyl or naphthyl groups, preferably phenyl groups, wherein the phenyl or naphthyl group is optionally connected/coupled to a PTM group (including a ULM' group) via a linker group and/or optionally substituted with a halogen (preferably F or Cl), an amine, monoalkyl- or dialkyl amine (preferably, dimethylamine), an amido group (preferably a —(CH$_2$)$_m$—NR$_1$C(O)R$_2$ group where m, $R_1$ and $R_2$ are the same as above), a halo (often F or Cl), OH, CH$_3$, CF$_3$, OMe, OCF$_3$, NO$_2$, CN or a S(O)$_2$R$_S$ group (R$_S$ is a $C_1$-$C_6$ alkyl group, an optionally substituted aryl, heteroaryl or heterocycle group or a —(CH$_2$)$_m$NR$_1$R$_2$ group), each of which may be substituted in ortho-, meta- and/or para-positions of the phenyl ring, preferably para-), or an Aryl (preferably phenyl), Heteroaryl or Heterocycle. Preferably said substituent phenyl group is an optionally substituted phenyl group (i.e., the substituent phenyl group itself is preferably substituted with at least one of F, Cl, OH, SH, COOH, CH$_3$, CF$_3$, OMe, OCF$_3$, NO$_2$, CN or a linker group to which is attached a PTM group (including a ULM' group), wherein the substitution occurs in ortho-, meta- and/or para-positions of the phenyl ring, preferably para-), a naphthyl group, which may be optionally substituted including as described above, an optionally substituted heteroaryl (preferably an optionally substituted isoxazole including a methylsubstituted isoxazole, an optionally substituted oxazole including a methylsubstituted oxazole, an optionally substituted thiazole including a methyl substituted thiazole, an optionally substituted pyrrole including a methylsubstituted pyrrole, an optionally substituted imidazole including a methylimidazole, a benzylimidazole or methoxybenzylimidazole, an oximidazole or methyloximidazole, an optionally substituted diazole group, including a methyldiazole group, an optionally substituted triazole group, including a methylsubstituted triazole group, a pyridine group, including a halo-(preferably, F) or methylsubstitutedpyridine group or an oxapyridine group (where the pyridine group is linked to the phenyl group by an oxygen) or an optionally substituted heterocycle (tetrahydrofuran, tetrahydrothiophene, pyrrolidine, piperidine, morpholine, piperazine, tetrahydroquinoline, oxane or thiane. Each of the aryl, heteroaryl or heterocyclic groups may be optionally connected/coupled to a PTM group (including a ULM' group) via a linker group.

Preferred Heteroaryl groups for $R^{3'}$ of ULM-g through ULM-i include an optionally substituted quinoline (which may be attached to the pharmacophore or substituted on any carbon atom within the quinoline ring), an optionally substituted indole (including dihydroindole), an optionally substituted indolizine, an optionally substituted azaindolizine (2, 3 or 4-azaindolizine) an optionally substituted benzimidazole, benzodiazole, benzoxofuran, an optionally substituted imidazole, an optionally substituted isoxazole, an optionally substituted oxazole (preferably methyl substituted), an optionally substituted diazole, an optionally substituted triazole, a tetrazole, an optionally substituted benzofuran, an optionally substituted thiophene, an optionally substituted thiazole (preferably methyl and/or thiol substituted), an optionally substituted isothiazole, an optionally substituted triazole (preferably a 1,2,3-triazole substituted with a methyl group, a triisopropylsilyl group, an optionally substituted —(CH$_2$)$_m$—O—$C_1$-$C_6$ alkyl group or an optionally substituted —(CH$_2$)$_m$—C(O)—O—$C_1$-$C_6$ alkyl group), an optionally substituted pyridine (2-, 3, or 4-pyridine) or a group according to the chemical structure:

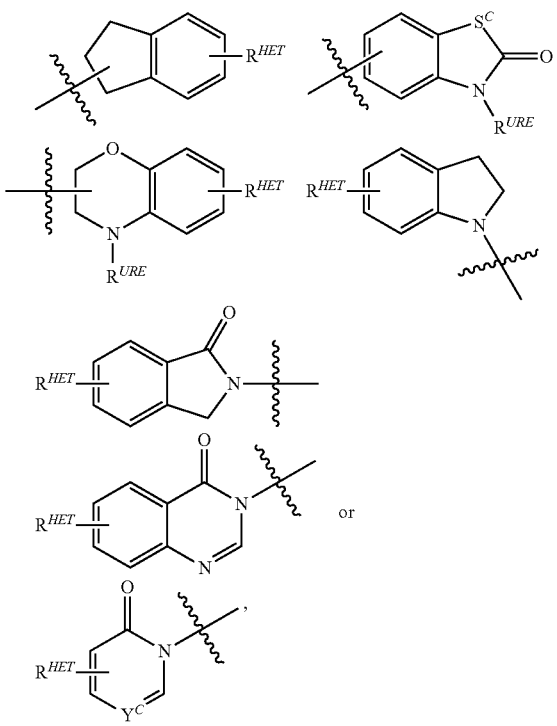

wherein:
$S^c$ of ULM-g through ULM-i is CHR$^{SS}$, NR$^{URE}$, or 0;
$R^{HET}$ of ULM-g through ULM-i is H, CN, NO$_2$, halo (preferably Cl or F), optionally substituted $C_1$-$C_6$ alkyl (preferably substituted with one or two hydroxyl groups or up to three halo groups (e.g. CF$_3$), optionally substituted O($C_1$-$C_6$ alkyl) (preferably substituted with one or two hydroxyl groups or up to three halo groups) or an optionally substituted acetylenic group —C≡C—R$_a$ where R$_a$ is H or a $C_1$-$C_6$ alkyl group (preferably $C_1$-$C_3$ alkyl);
$R^{SS}$ of ULM-g through ULM-i is H, CN, NO$_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$alkyl) (preferably substituted with one or two hydroxyl groups or up to three halo groups);
$R^{URE}$ of ULM-g through ULM-i is H, a $C_1$-$C_6$ alkyl (preferably H or $C_1$-$C_3$ alkyl) or a —C(O)($C_1$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and $Y^C$ of ULM-g through ULM-i is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl). Each of said heteroaryl groups may be optionally connected/coupled to a PTM group (including a ULM' group) via a linker group.

Preferred heterocycle groups for $R^3$ of ULM-g through ULM-i include tetrahydroquinoline, piperidine, piperazine, pyrrollidine, morpholine, tetrahydrofuran, tetrahydrothiophene, oxane and thiane, each of which groups may be optionally substituted or a group according to the chemical structure:

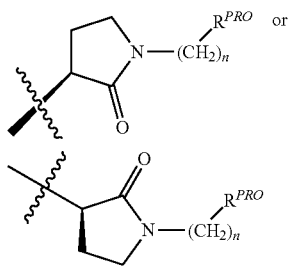

preferably, a

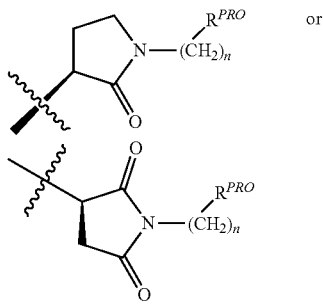

group,
wherein:
  $R^{PRO}$ of ULM-g through ULM-i is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;
  $R^{PRO1}$ and $R^{PRO2}$ of ULM-g through ULM-i are each independently H, an optionally substituted $C_1$-$C_3$ alkyl group or together form a keto group, and
  each n of ULM-g through ULM-i is 0, 1, 2, 3, 4, 5, or 6 (preferably 0 or 1), wherein each of said Heterocycle groups may be optionally connected/coupled to a PTM group (including a ULM' group) via a linker group.

Preferred $R^{3'}$ substituents of ULM-g through ULM-i also include specifically (and without limitation to the specific compound disclosed) the $R^{3'}$ substituents which are found in the identified compounds disclosed herein (which includes the specific compounds which are disclosed in the present specification, and the figures which are attached hereto). Each of these $R^{3'}$ substituents may be used in conjunction with any number of $R^{2'}$ substituents, which are also disclosed herein.

In certain alternative preferred embodiments, $R^{2'}$ of ULM-g through ULM-i is an optionally substituted —$NR_1$—$X^{R2'}$-alkyl group, —$NR_1$—$X^{R2'}$-Aryl group; an optionally substituted —$NR_1$—$X^{R2'}$-HET, an optionally substituted —$NR_1$—$X^{R2'}$-Aryl-HET or an optionally substituted —$NR_1$—$X^{R2'}$-HET-Aryl,
wherein:
  $R_1$ of ULM-g through ULM-i is H or a $C_1$-$C_3$ alkyl group (preferably H);
  $X^{R2'}$ of ULM-g through ULM-i is an optionally substituted —$(CH_2)_n$—, —$(CH_2)_n$—CH($X_v$)=CH($X_t$)— (cis or trans), —$(CH_2)_n$—CH—CH—, —$(CH_2CH_2O)_n$— or a $C_3$-$C_6$ cycloalkyl group; and
  $X_v$ of ULM-g through ULM-i is H, a halo or a $C_1$-$C_3$ alkyl group which is optionally substituted with one or two hydroxyl groups or up to three halogen groups;
  Alkyl of ULM-g through ULM-i is an optionally substituted $C_1$-$C_{10}$ alkyl (preferably a $C_1$-$C_6$ alkyl) group (in certain preferred embodiments, the alkyl group is end-capped with a halo group, often a Cl or Br);
  Aryl of ULM-g through ULM-i is an optionally substituted phenyl or naphthyl group (preferably, a phenyl group); and
  HET of ULM-g through ULM-i is an optionally substituted oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, benzofuran, indole, indolizine, azaindolizine, quinoline (when substituted, each preferably substituted with a $C_1$-$C_3$ alkyl group, preferably methyl or a halo group, preferably F or Cl) or a group according to the chemical structure:

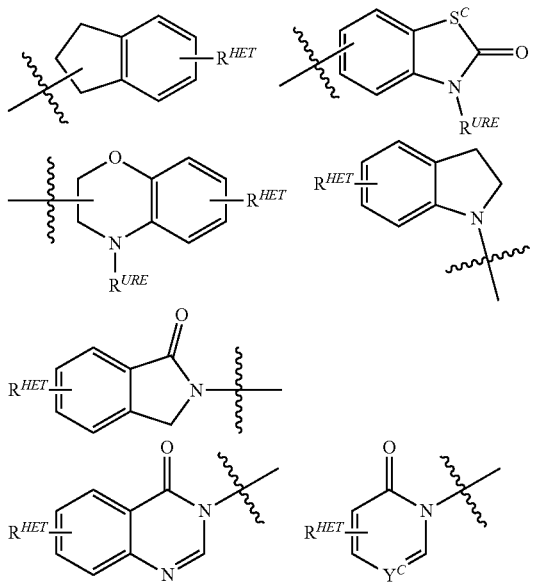

$S^c$ of ULM-g through ULM-i is $CHR^{SS}$, $NR^{URE}$, or O;

$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$alkyl) (preferably substituted with one or two hydroxyl groups or up to three halo groups);

$R^{URE}$ of ULM-g through ULM-i is H, a $C_1$-$C_6$ alkyl (preferably H or $C_1$-$C_3$ alkyl) or a —C(O)($C_1$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted;

$Y^C$ of ULM-g through ULM-i is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{PRO}$ of ULM-g through ULM-i is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;

$R^{PRO1}$ and $R^{PRO2}$ of ULM-g through ULM-i are each independently H, an optionally substituted $C_1$-$C_3$ alkyl group or together form a keto group, and each n of ULM-g through ULM-i is independently 0, 1, 2, 3, 4, 5, or 6 (preferably 0 or 1).

Each of said groups may be optionally connected/coupled to a PTM group (including a ULM' group) via a linker group.

In certain alternative preferred embodiments of the present disclosure, $R^{3'}$ of ULM-g through ULM-i is an optionally substituted —$(CH_2)_n$—$(V)_{n'}$—$(CH_2)_n$—$(V)_{n'}$—$R^{S3'}$ group, an optionally substituted-$(CH_2)_n$—$N(R_1)$ $(C=O)_m$—$(V)_n$—$R^{S3'}$ group, an optionally substituted —$X^{R3'}$-alkyl group, an optionally substituted —$X^{R3'}$-Aryl group; an optionally substituted —$X^{R3'}$-HET group, an optionally substituted —$X^{R3'}$-Aryl-HET group or an optionally substituted —$X^{R3'}$-HET-Aryl group, wherein:

$R^{S3'}$ is an optionally substituted alkyl group ($C_1$-$C_{10}$, preferably $C_1$-$C_6$ alkyl), an optionally substituted Aryl group or a HET group;

$R_1$, is H or a $C_1$-$C_3$ alkyl group (preferably H);

V is O, S or $NR^1$;

$X^{R3'}$ is —$(CH_2)_n$—, —$(CH_2CH_2O)_n$—, —$CH_2)_n$—CH$(X_v)$=CH$(X_v)$— (cis or trans), —$CH_2)_n$—CH≡CH—, or a $C_3$-$C_6$ cycloalkyl group, all optionally substituted;

$X_v$ is H, a halo or a $C_1$-$C_3$ alkyl group which is optionally substituted with one or two hydroxyl groups or up to three halogen groups;

Alkyl is an optionally substituted $C_1$-$C_{10}$alkyl (preferably a $C_1$-$C_6$ alkyl) group (in certain preferred embodiments, the alkyl group is end-capped with a halo group, often a Cl or Br);

Aryl is an optionally substituted phenyl or napthyl group (preferably, a phenyl group); and HET is an optionally substituted oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, benzofuran, indole, indolizine, azaindolizine, quinoline (when substituted, each preferably substituted with a $C_1$-$C_3$ alkyl group, preferably methyl or a halo group, preferably F or Cl), or a group according to the chemical structure:

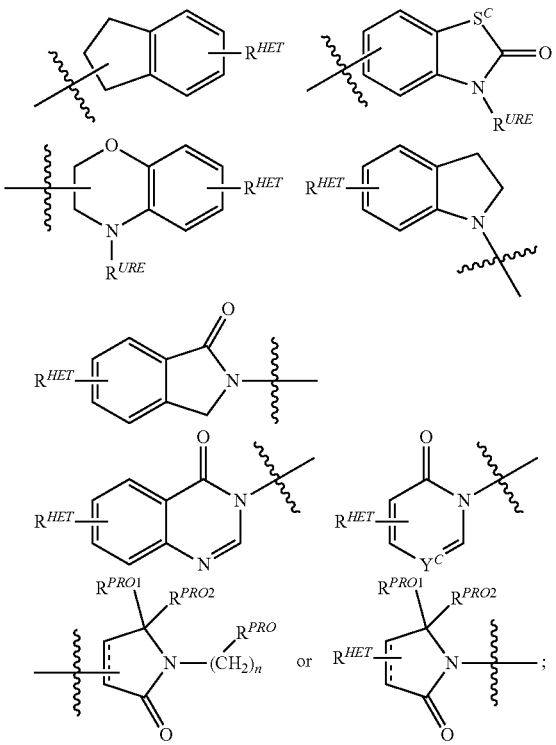

$S^c$ of ULM-g through ULM-i is $CHR^{SS}$, $NR^{URE}$, or O;

$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{SS}$ of ULM-g through ULM-i is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$alkyl) (preferably substituted with one or two hydroxyl groups or up to three halo groups);

$R^{URE}$ of ULM-g through ULM-i is H, a $C_1$-$C_6$ alkyl (preferably H or $C_1$-$C_3$ alkyl) or a —C(O)($C_0$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted;

$Y^C$ of ULM-g through ULM-i is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{PRO}$ of ULM-g through ULM-i is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;

$R^{PRO1}$ and $R^{PRO2}$ of ULM-g through ULM-i are each independently H, an optionally substituted $C_1$-$C_3$ alkyl group or together form a keto group;

each n of ULM-g through ULM-i is independently 0, 1, 2, 3, 4, 5, or 6 (preferably 0 or 1);

each m' of ULM-g through ULM-i is 0 or 1; and each n' of ULM-g through ULM-i is 0 or 1;

wherein each of said compounds, preferably on the alkyl, Aryl or Het groups, is optionally connected/coupled to a PTM group (including a ULM' group) via a linker.

In alternative embodiments, $R^{3'}$ of ULM-g through ULM-i is —$(CH_2)_n$-Aryl, —$(CH_2CH_2O)_n$-Aryl, —$(CH_2)_n$-HET or —$(CH_2CH_2O)_n$-HET, wherein:

said Aryl of ULM-g through ULM-i is phenyl which is optionally substituted with one or two substitutents, wherein said substituent(s) is preferably selected from —$(CH_2)_n$OH, $C_1$-$C_6$ alkyl which itself is further optionally substituted with CN, halo (up to three halo groups), OH, —$(CH_2)_nO(C_1$-$C_6)$alkyl, amine, mono- or di-($C_1$-$C_6$ alkyl) amine wherein the alkyl group on the amine is optionally substituted with 1 or 2 hydroxyl groups or up to three halo (preferably F, $C_1$) groups, or said Aryl group of ULM-g through ULM-i is substituted with —$(CH_2)_n$OH, —$(CH_2)_n$—O—($C_1$-$C_6$)alkyl, —$(CH_2)_n$—O—$(CH_2)_n$—($C_1$-$C_6$)alkyl, —$(CH_2)_n$—C(O)($C_0$-$C_6$) alkyl, —$(CH_2)_n$—C(O)O($C_0$-$C_6$)alkyl, —$(CH_2)_n$—OC(O)($C_0$-$C_6$)alkyl, amine, mono- or di-($C_1$-$C_6$ alkyl) amine wherein the alkyl group on the amine is optionally substituted with 1 or 2 hydroxyl groups or up to three halo (preferably F, $C_1$) groups, CN, $NO_2$, an optionally substituted —$(CH_2)_n$—$(V)_{m'}$—$CH_2)_n$—$(V)_{m'}$—($C_1$-$C_6$)alkyl group, a —$(V)_{m'}$—$(CH_2CH_2O)_n$—$R^{PEG}$ group where V is O, S or $NR_1$, $R_1$, is H or a $C_1$-$C_3$ alkyl group (preferably H) and $R^{PEG}$ is H or a $C_1$-$C_6$ alkyl group which is optionally substituted (including being optionally substituted with a carboxyl group), or said Aryl group of ULM-g through ULM-i is optionally substituted with a heterocycle, including a heteroaryl, selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, benzofuran, indole, indolizine, azaindolizine, (when substituted each preferably substituted with a $C_1$-$C_3$ alkyl group, preferably methyl or a halo group, preferably F or Cl), or a group according to the chemical structure:

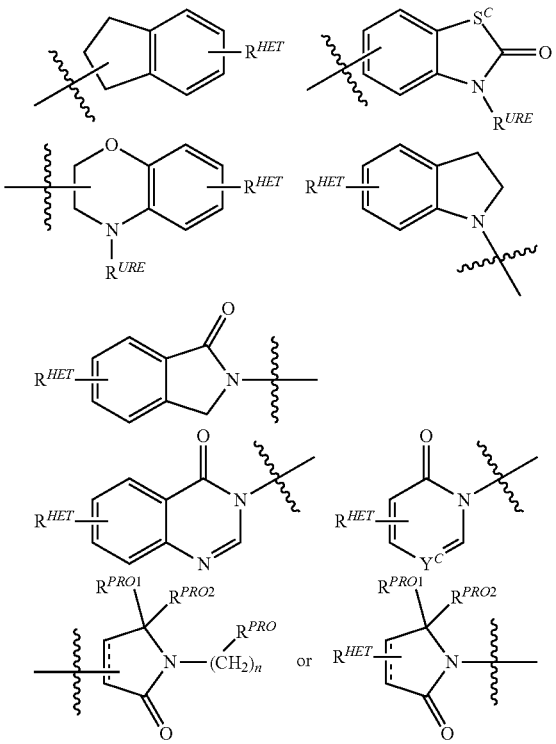

$S^c$ of ULM-g through ULM-i is $CHR^{SS}$, $NR^{URE}$, or O;

$R^{HET}$ of ULM-g through ULM-i is H, CN, $NO_2$, halo (preferably Cl or F), optionally substituted $C_1$-$C_6$ alkyl (preferably substituted with one or two hydroxyl groups or up to three halo groups (e.g. CF$_3$), optionally substituted O(C$_1$-C$_6$ alkyl) (preferably substituted with one or two hydroxyl groups or up to three halo groups) or an optionally substituted acetylenic group —C≡C—R$_a$ where R$_a$ is H or a C$_1$-C$_6$ alkyl group (preferably C$_1$-C$_3$ alkyl);

R$^{SS}$ of ULM-g through ULM-i is H, CN, NO$_2$, halo (preferably F or Cl), optionally substituted C$_1$-C$_6$ alkyl (preferably substituted with one or two hydroxyl groups or up to three halo groups), optionally substituted 0-(C$_1$-C$_6$ alkyl) (preferably substituted with one or two hydroxyl groups or up to three halo groups) or an optionally substituted —C(O)(C$_1$-C$_6$alkyl) (preferably substituted with one or two hydroxyl groups or up to three halo groups);

R$^{URE}$ of ULM-g through ULM-i is H, a C$_1$-C$_6$ alkyl (preferably H or C$_1$-C$_3$ alkyl) or a —C(O)(C$_0$-C$_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted;

Y$^C$ of ULM-g through ULM-i is N or C—R$^{YC}$, where R$^{YC}$ is H, OH, CN, NO$_2$, halo (preferably Cl or F), optionally substituted C$_1$-C$_6$ alkyl (preferably substituted with one or two hydroxyl groups or up to three halo groups (e.g. CF$_3$), optionally substituted O(C$_1$-C$_6$ alkyl) (preferably substituted with one or two hydroxyl groups or up to three halo groups) or an optionally substituted acetylenic group —C≡C—R$_a$ where R$_a$ is H or a C$_1$-C$_6$ alkyl group (preferably C$_1$-C$_3$ alkyl);

R$^{PRO}$ of ULM-g through ULM-i is H, optionally substituted C$_1$-C$_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a C$_1$-C$_3$ alkyl group, preferably methyl or a halo group, preferably F or Cl), benzofuran, indole, indolizine, azaindolizine;

R$^{PRO1}$ and R$^{PRO2}$ of ULM-g through ULM-i are each independently H, an optionally substituted C$_1$-C$_3$ alkyl group or together form a keto group;

HET of ULM-g through ULM-i is preferably oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a C$_1$-C$_3$ alkyl group, preferably methyl or a halo group, preferably F or Cl), benzofuran, indole, indolizine, azaindolizine, or a group according to the chemical structure:

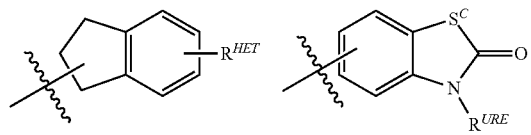

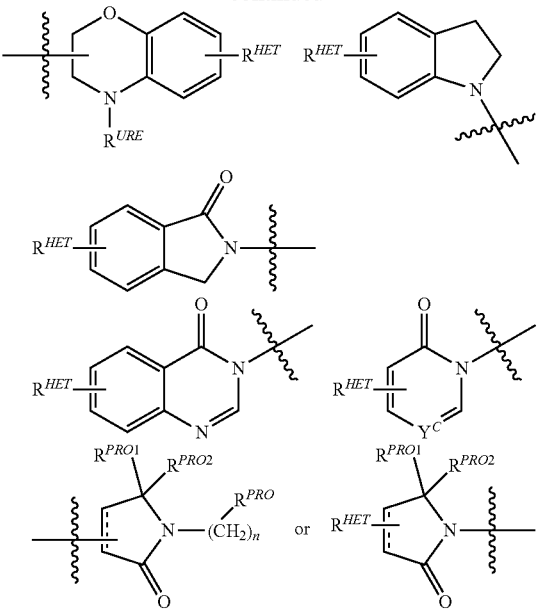

S$^c$ of ULM-g through ULM-i is CHR$^{SS}$, NR$^U$R$^E$, or O;

R$^{HET}$ of ULM-g through ULM-i is H, CN, NO$_2$, halo (preferably Cl or F), optionally substituted C$_1$-C$_6$ alkyl (preferably substituted with one or two hydroxyl groups or up to three halo groups (e.g. CF$_3$), optionally substituted O(C$_1$-C$_6$ alkyl) (preferably substituted with one or two hydroxyl groups or up to three halo groups) or an optionally substituted acetylenic group —C≡C—R$_a$ where R$_a$ is H or a C$_1$-C$_6$ alkyl group (preferably C$_1$-C$_3$ alkyl);

R$^{SS}$ of ULM-g through ULM-i is H, CN, NO$_2$, halo (preferably F or Cl), optionally substituted C$_1$-C$_6$ alkyl (preferably substituted with one or two hydroxyl groups or up to three halo groups), optionally substituted O—(C$_1$-C$_6$ alkyl) (preferably substituted with one or two hydroxyl groups or up to three halo groups) or an optionally substituted —C(O)(C$_1$-C$_6$alkyl) (preferably substituted with one or two hydroxyl groups or up to three halo groups);

R$^{URE}$ of ULM-g through ULM-i is H, a C$_1$-C$_6$ alkyl (preferably H or C$_1$-C$_3$ alkyl) or a —C(O)(C$_0$-C$_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted;

Y$^C$ of ULM-g through ULM-i is N or C—R$^{YC}$, where R$^{YC}$ is H, OH, CN, NO$_2$, halo (preferably Cl or F), optionally substituted C$_1$-C$_6$ alkyl (preferably substituted with one or two hydroxyl groups or up to three halo groups (e.g. CF$_3$), optionally substituted O(C$_1$-C$_6$ alkyl) (preferably substituted with one or two hydroxyl groups or up to three halo groups) or an optionally substituted acetylenic group —C≡C—R$_a$ where R$_a$ is H or a C$_1$-C$_6$ alkyl group (preferably C$_1$-C$_3$ alkyl);

R$^{PRO}$ of ULM-g through ULM-i is H, optionally substituted C$_1$-C$_6$ alkyl or an optionally substituted aryl, heteroaryl or heterocyclic group;

$R^{PRO1}$ and $R^{PRO2}$ of ULM-g through ULM-i are each independently H, an optionally substituted $C_1$-$C_3$ alkyl group or together form a keto group;

each m' of ULM-g through ULM-i is independently 0 or 1; and each n of ULM-g through ULM-i is independently 0, 1, 2, 3, 4, 5, or 6 (preferably 0 or 1), wherein each of said compounds, preferably on said Aryl or HET groups, is optionally connected/coupled to a PTM group (including a ULM' group) via a linker group.

In still additional embodiments, preferred compounds include those according to the chemical structure:

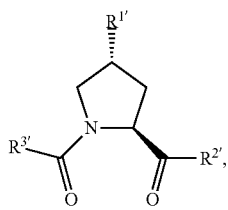

ULM-i wherein:

$R^{1'}$ of ULM-i is OH or a group which is metabolized in a patient or subject to OH;

$R^{2'}$ of ULM-i is a —NH—CH$_2$-Aryl-HET (preferably, a phenyl linked directly to a methyl substituted thiazole);

$R^{3'}$ of ULM-i is a —CHR$^{CR3'}$—NH—C(O)—R$^{3P1}$ group or a —CHR$^{CR3'}$—R$^{3P2}$ group;

$R^{CR3'}$ of ULM-i is a $C_1$-$C_4$ alkyl group, preferably methyl, isopropyl or tert-butyl;

$R^{3P1}$ of ULM-i is $C_1$-$C_3$ alkyl (preferably methyl), an optionally substituted oxetane group (preferably methyl substituted, a —(CH$_2$)$_n$OCH$_3$ group where n is 1 or 2 (preferably 2), or a

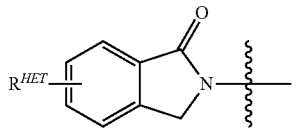

group (the ethyl ether group is preferably meta-substituted on the phenyl moiety), a morpholino group (linked to the carbonyl at the 2- or 3-position;

$R^{3P2}$ of ULM-i is a

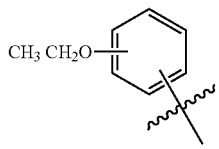

group;

Aryl of ULM-i is phenyl;

HET of ULM-i is an optionally substituted thiazole or isothiazole; and $R^{HET}$ of ULM-i is H or a halo group (preferably H);

or a pharmaceutically acceptable salt, stereoisomer, solvate or polymorph thereof, wherein each of said compounds is optionally connected/coupled to a PTM group (including a ULM' group) via a linker group.

In certain aspects, bifunctional compounds comprising a ubiquitin E3 ligase binding moiety (ULM), wherein ULM is a group according to the chemical structure:

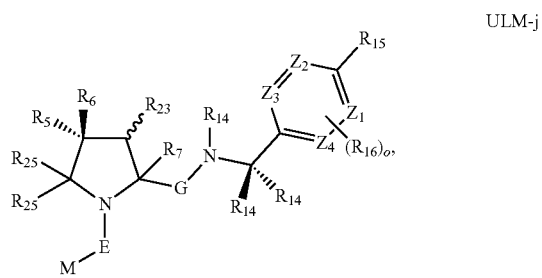

ULM-j wherein:

each $R_5$ and $R_6$ of ULM-j is independently OH, SH, or optionally substituted alkyl or $R_5$, $R_6$, and the carbon atom to which they are attached form a carbonyl;

$R_7$ of ULM-j is H or optionally substituted alkyl;

E of ULM-j is a bond, C=O, or C=S;

G of ULM-j is a bond, optionally substituted alkyl, —COOH or C=J;

J of ULM-j is O or N—R$^8$;

$R_8$ of ULM-j is H, CN, optionally substituted alkyl or optionally substituted alkoxy;

M of ULM-j is optionally substituted aryl, optionally substituted heteroaryl, optionally substituted heterocyclic or

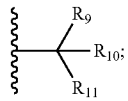

each $R_9$ and $R_{10}$ of ULM-j is independently H; optionally substituted alkyl, optionally substituted cycloalkyl, optionally substituted hydroxyalkyl, optionally substituted thioalkyl, a disulphide linked ULM, optionally substituted heteroaryl, or haloalkyl; or $R_9$, $R_{10}$, and the carbon atom to which they are attached form an optionally substituted cycloalkyl;

$R_{11}$ of ULM-j is optionally substituted heterocyclic, optionally substituted alkoxy, optionally substituted heteroaryl, optionally substituted aryl, or

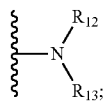

$R_{12}$ of ULM-j is H or optionally substituted alkyl;

$R_{13}$ of ULM-j is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl; optionally substituted (oxoalkyl) carbamate, each $R_{14}$ of ULM-j is independently H, haloalkyl, optionally substituted cycloalkyl, optionally substituted alkyl or optionally substituted heterocycloalkyl;

$R_{15}$ of ULM-j is H, optionally substituted heteroaryl, haloalkyl, optionally substituted aryl, optionally substituted alkoxy, or optionally substituted heterocyclyl;

each $R_{16}$ of ULM-j is independently halo, optionally substituted alkyl, optionally substituted haloalkyl, CN, or optionally substituted haloalkoxy;

each $R_{25}$ of ULM-j is independently H or optionally substituted alkyl; or both $R_{25}$ groups can be taken together to form an oxo or optionally substituted cycloalkyl group;

$R_{23}$ of ULM-j is H or OH;

$Z_1$, $Z_2$, $Z_3$, and $Z_4$ of ULM-j are independently C or N; and of ULM-j is 0, 1, 2, 3, or 4, or a pharmaceutically acceptable salt, stereoisomer, solvate or polymorph thereof.

In certain embodiments, wherein G of ULM-j is C=J, J is O, $R_7$ is H, each $R_{14}$ is H, and o is 0.

In certain embodiments, wherein G of ULM-j is C=J, J is O, $R_7$ is H, each $R_{14}$ is H, $R_{15}$ is optionally substituted heteroaryl, and o is 0. In other instances, E is C=O and M is

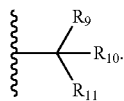

In certain embodiments, wherein E of ULM-j is C=O, $R_{11}$ is optionally substituted heterocyclic or

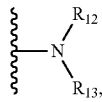

and M is

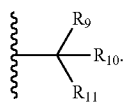

In certain embodiments, wherein E of ULM-j is C=O, M is

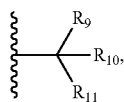

and $R_{11}$ is

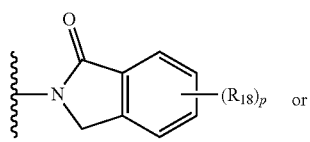 or

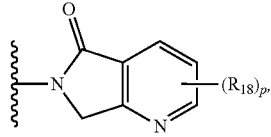

each $R_{18}$ is independently halo, optionally substituted alkoxy, cyano, optionally substituted alkyl, haloalkyl, or haloalkoxy; and p is 0, 1, 2, 3, or 4.

In certain embodiments, ULM and where present, ULM', are each independently a group according to the chemical structure:

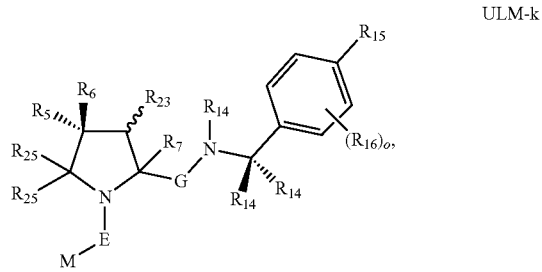

ULM-k wherein:
G of ULM-k is C=J, J is O;
$R_7$ of ULM-k is H;
each $R_{14}$ of ULM-k is H;
o of ULM-k is 0;
$R_{15}$ of ULM-k is

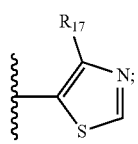

and
$R_{17}$ of ULM-k is H, halo, optionally substituted cycloalkyl, optionally substituted alkyl, optionally substituted alkenyl, and haloalkyl.

In other instances, $R_{17}$ of ULM-k is alkyl (e.g., methyl) or cycloalkyl (e.g., cyclopropyl).

In other embodiments, ULM and where present, ULM', are each independently a group according to the chemical structure:

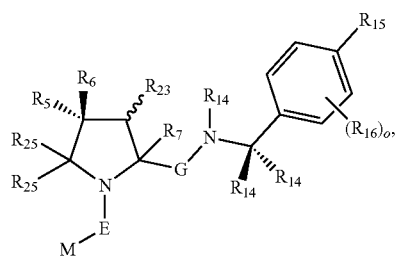

wherein:
G of ULM-k is C=J, J is O;
$R_7$ of ULM-k is H;

each R$_{14}$ of ULM-k is H;
o of ULM-k is O; and
R$_{15}$ of ULM-k is selected from the group consisting of:
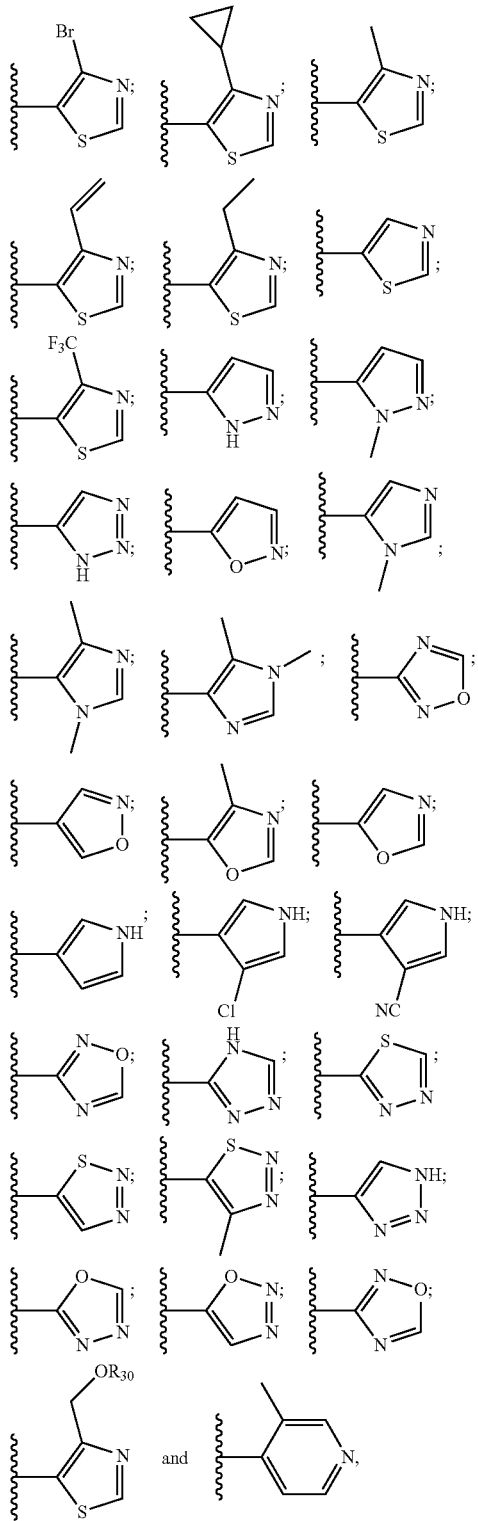
wherein R$_{30}$ of ULM-k is H or an optionally substituted alkyl.
In other embodiments, ULM and where present, ULM', are each independently a group according to the chemical structure:
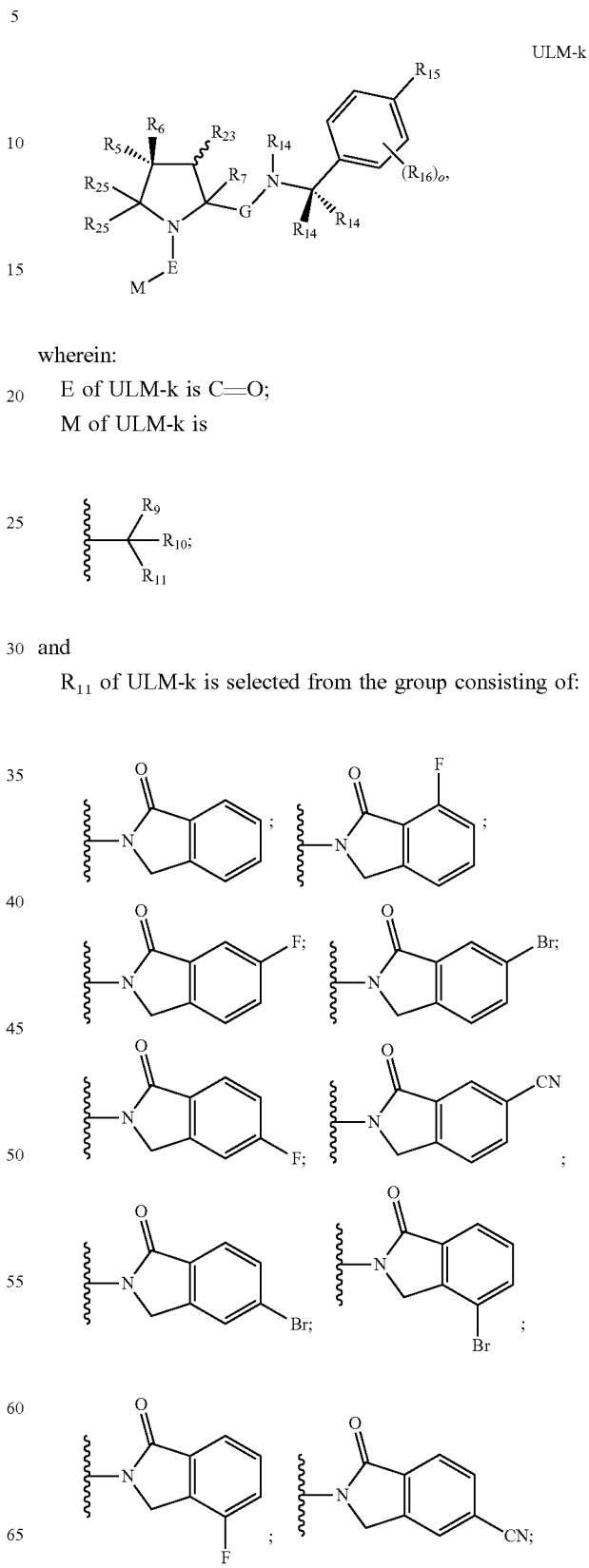
wherein:
E of ULM-k is C=O;
M of ULM-k is
and
R$_{11}$ of ULM-k is selected from the group consisting of:

-continued

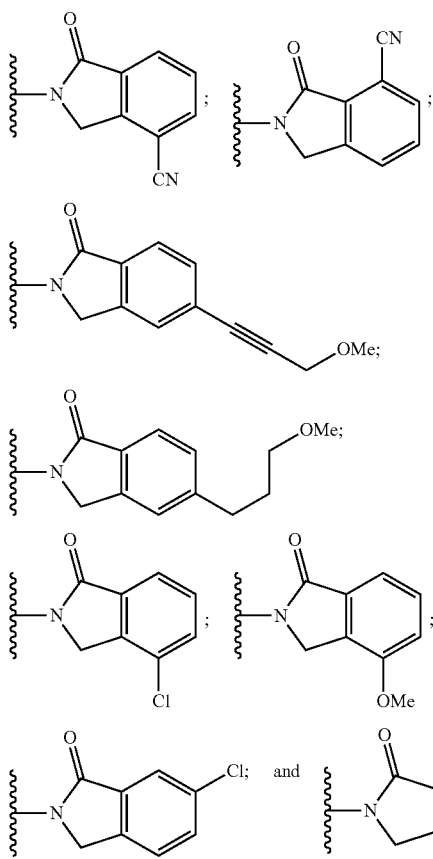

In still other embodiments, a compound of the chemical structure

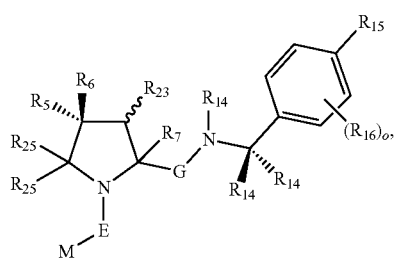

ULM-k wherein E of ULM-k is C=O;

R$_{11}$ of ULM-k is

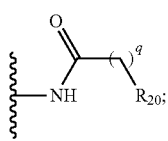

and

M of ULM-k is

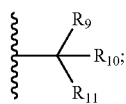

q of ULM-k is 1 or 2;

R$_{20}$ of ULM-k is H, optionally substituted alkyl, optionally substituted cycloalkyl, optionally substituted aryl, or

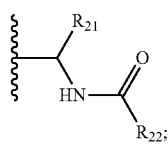

R$_{21}$ of ULM-k is H or optionally substituted alkyl; and

R$_{22}$ of ULM-k is H, optionally substituted alkyl, optionally substituted alkoxy, or haloalkyl.

In any embodiment described herein, R$_{11}$ of ULM-j or ULM-k is selected from the group consisting of:

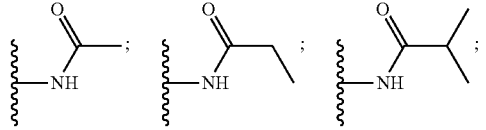

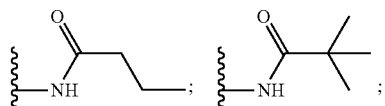

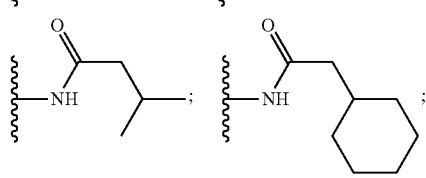

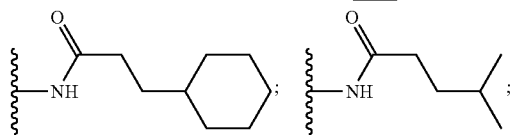

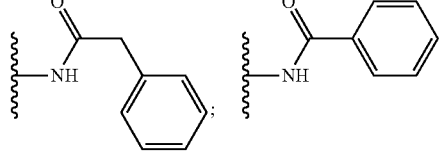

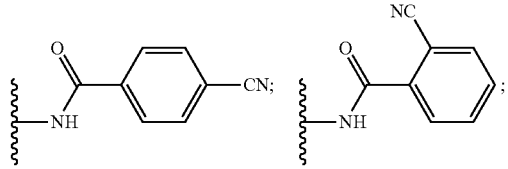

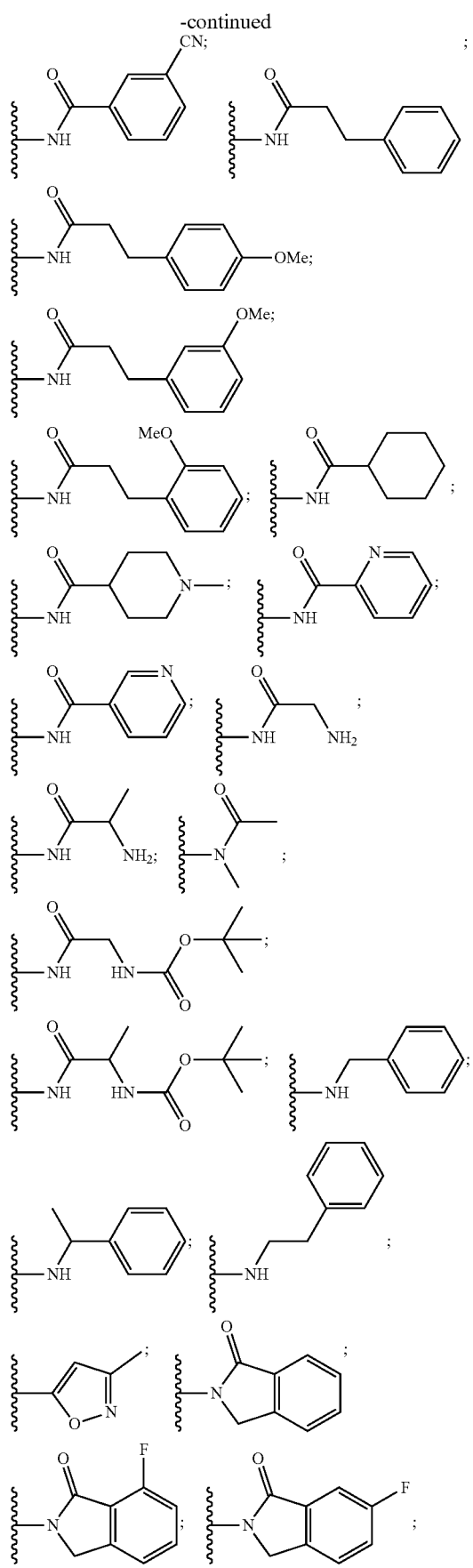
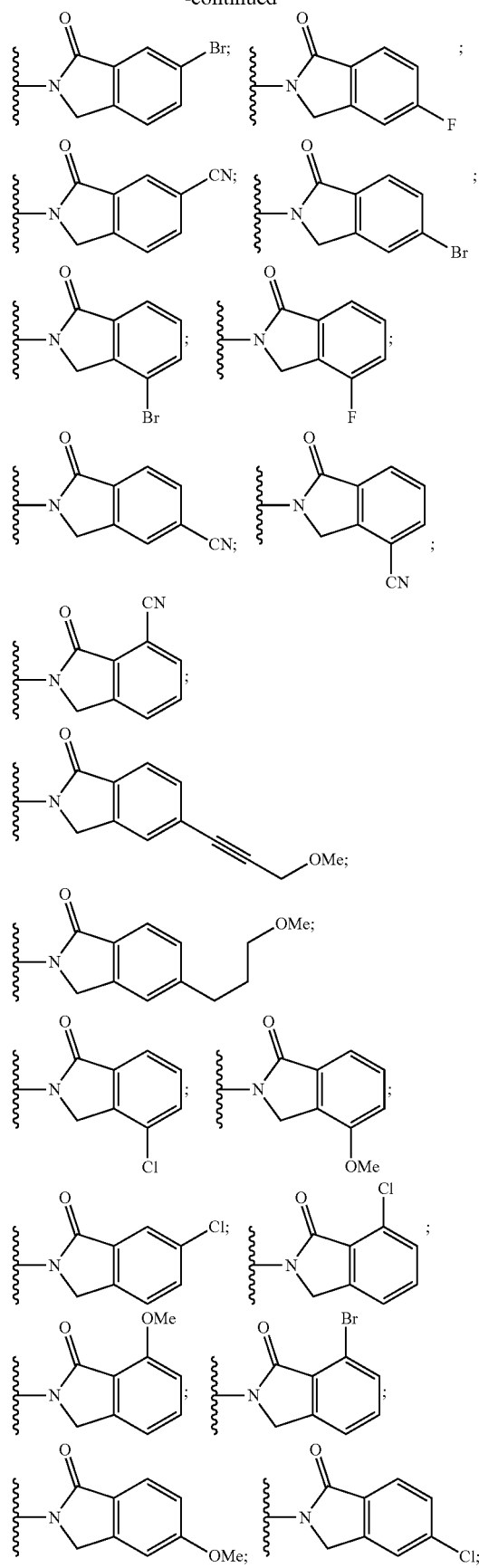

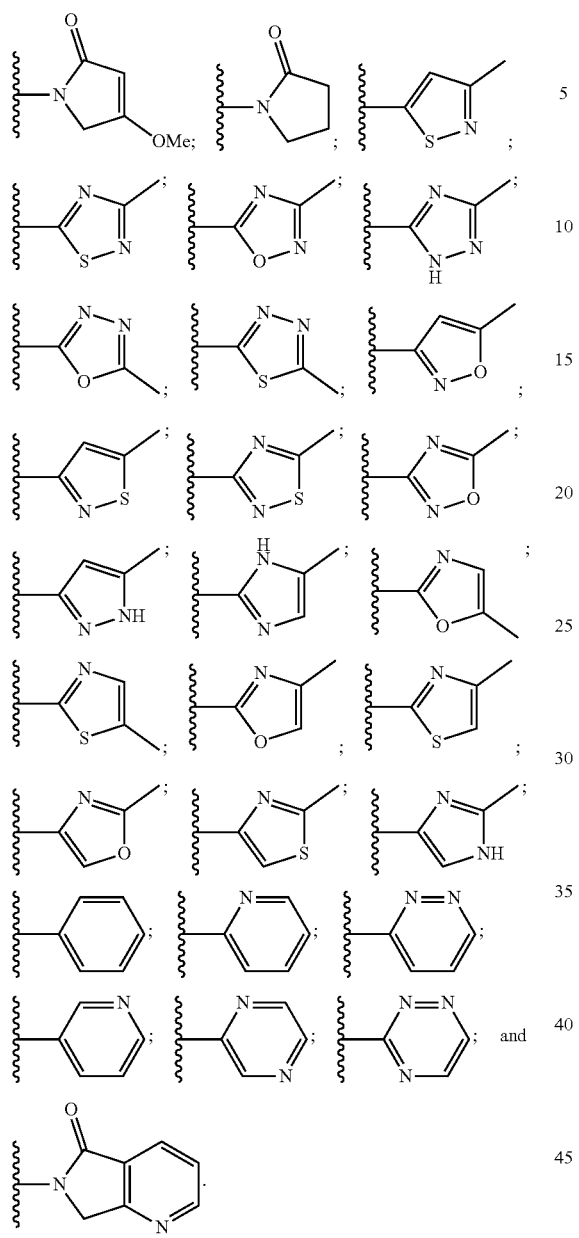
In certain embodiments, $R_{11}$ of ULM-j or ULM-k is selected from the group consisting of:
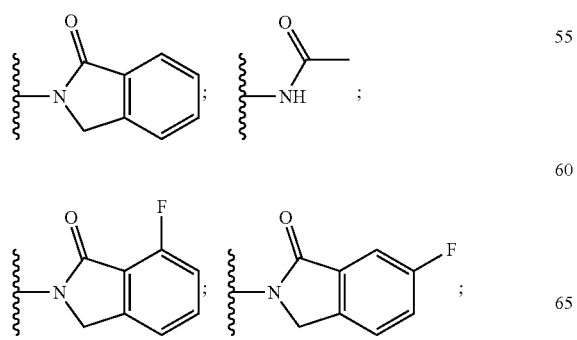
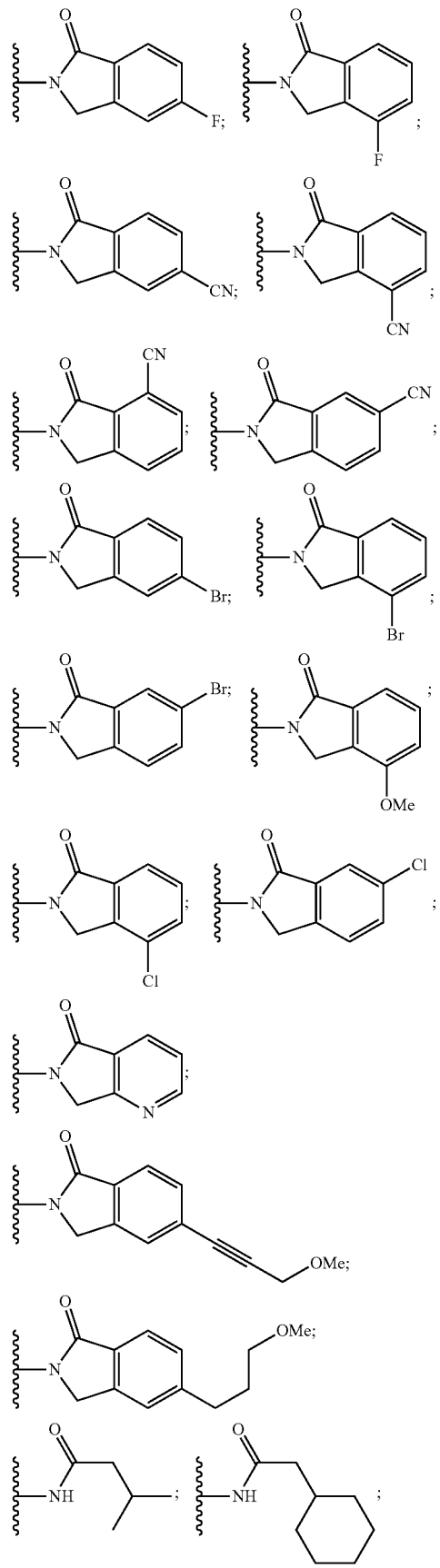

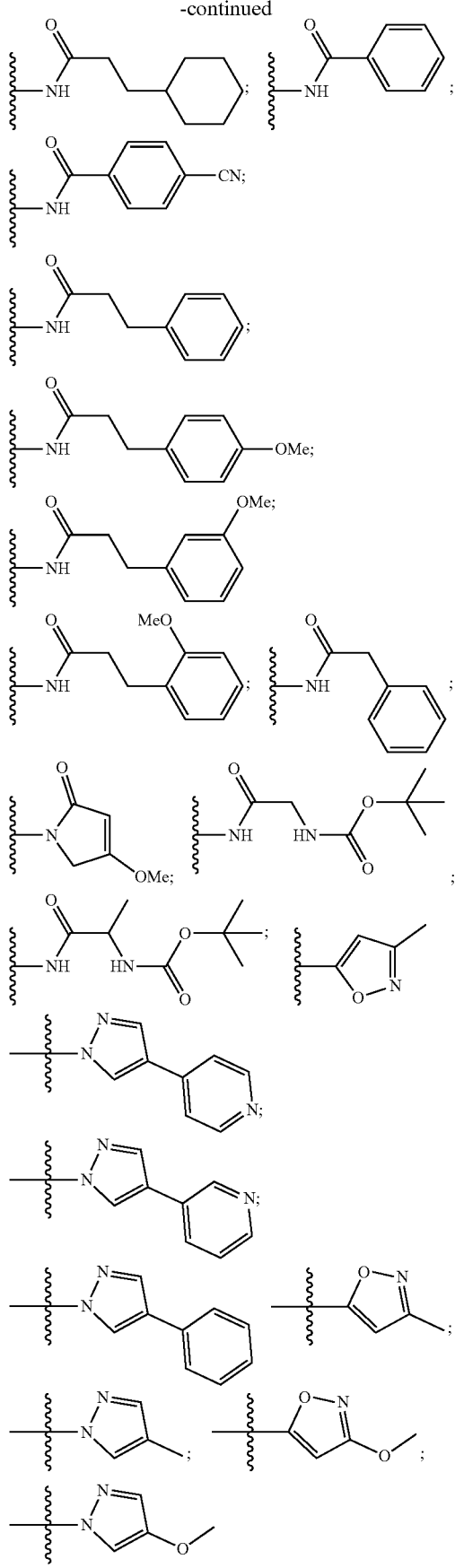

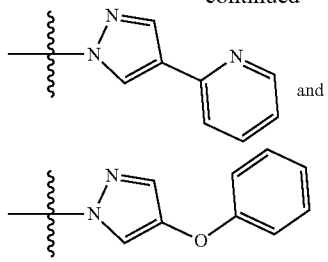

and

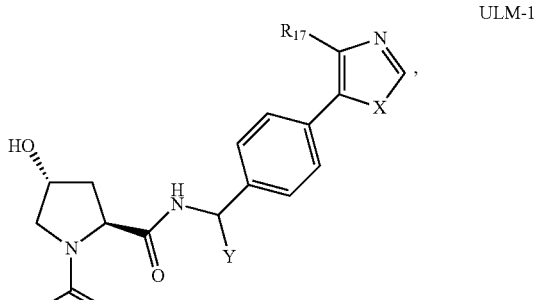

In certain embodiments, ULM (or when present ULM') is a group according to the chemical structure:

ULM-1 wherein:
X of ULM-1 is O or S;
Y of ULM-1 is H, methyl or ethyl;
$R_{17}$ of ULM-1 is H, methyl, ethyl, hydoxymethyl or cyclopropyl;
M of ULM-1 is optionally substituted aryl, optionally substituted heteroaryl, or

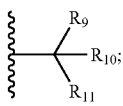

$R^9$ of ULM-1 is H;
$R_{10}$ of ULM-1 is H, optionally substituted alkyl, optionally substituted haloalkyl, optionally substituted heteroaryl, optionally substituted aryl, optionally substituted hydroxyalkyl, optionally substituted thioalkyl or cycloalkyl;
R11 of ULM-1 is optionally substituted heteroaromatic, optionally substituted heterocyclic, optionally substituted aryl or

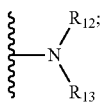

$R_{12}$ of ULM-1 is H or optionally substituted alkyl; and
$R_{13}$ of ULM-1 is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl; optionally substituted (oxoalkyl)carbamate.

In some embodiments, ULM and where present, ULM', are each independently a group according to the chemical structure:

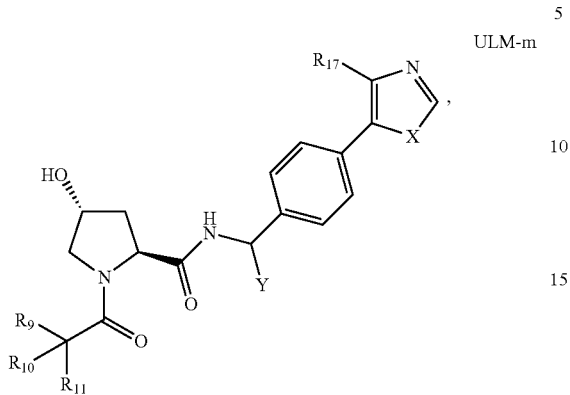

ULM-m wherein:
Y of ULM-m is H, methyol or ethyl
$R_9$ of ULM-m is H;
$R_{10}$ is isopropyl, tert-butyl, sec-butyl, cyclopentyl, or cyclohexyl;
$R_{11}$ of ULM-m is optionally substituted amide, optionally substituted isoindolinone, optionally substituted isooxazole, optionally substituted heterocycles.

In other preferred embodiments of the disclosure, ULM and where present, ULM', are each independently a group according to the chemical structure:

ULM-n wherein:
$R_{17}$ of ULM-n is methyl, ethyl, or cyclopropyl; and
$R_9$, $R_{10}$, and $R_{11}$ of ULM-n are as defined above. In other instances, $R_9$ is H; and
$R_{10}$ of ULM-n is H, alkyl, or cycloalkyl (preferably, isopropyl, tert-butyl, sec-butyl, cyclopentyl, or cyclohexyl).

In any of the aspects or embodiments described herein, the ULM (or when present, ULM') as described herein may be a pharmaceutically acceptable salt, enantiomer, diastereomer, solvate or polymorph thereof. In addition, in any of the aspects or embodiments described herein, the ULM (or when present, ULM') as described herein may be coupled to a PTM directly via a bond or by a chemical linker.

In certain aspects of the disclosure, the ULM moiety is selected from the group consisting of:

223
-continued
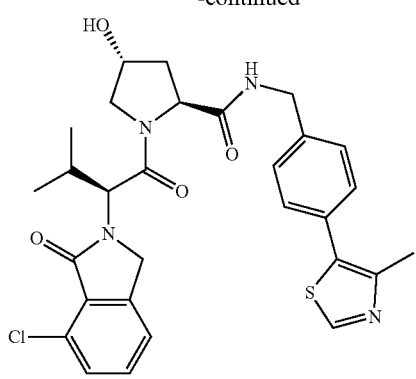
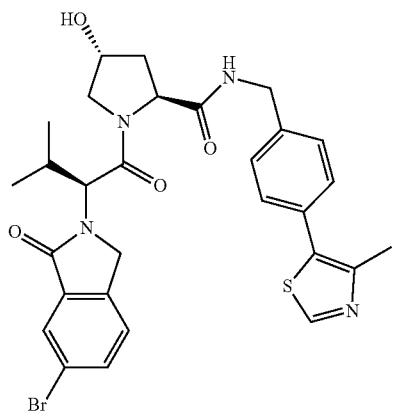
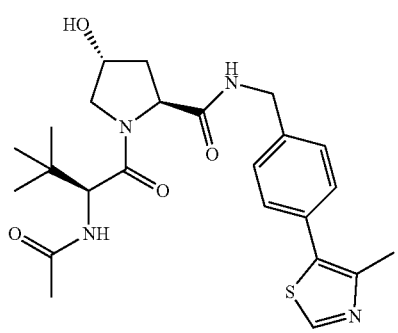
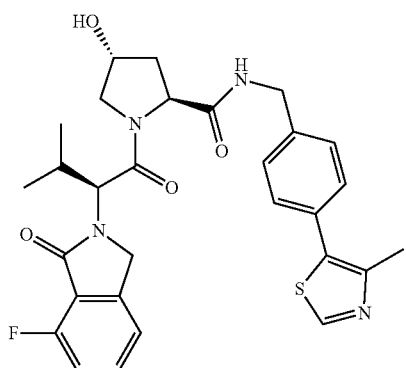
224
-continued
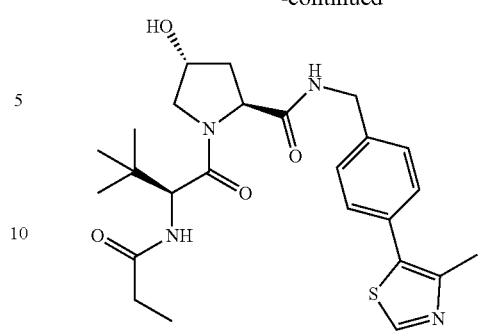
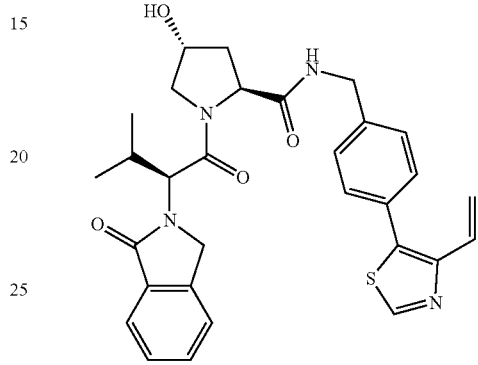
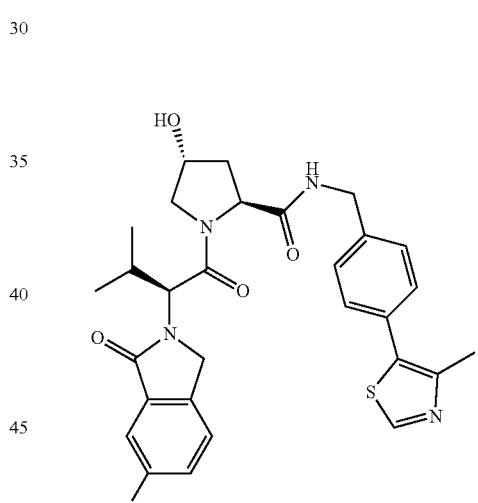
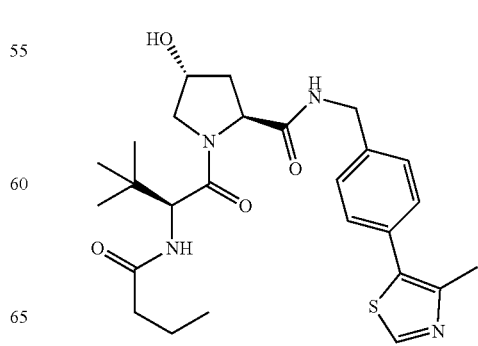

225
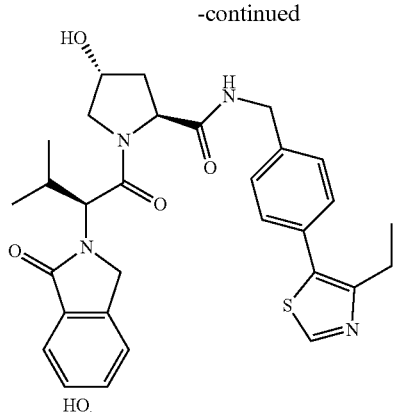
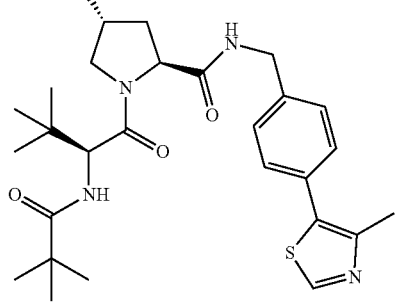
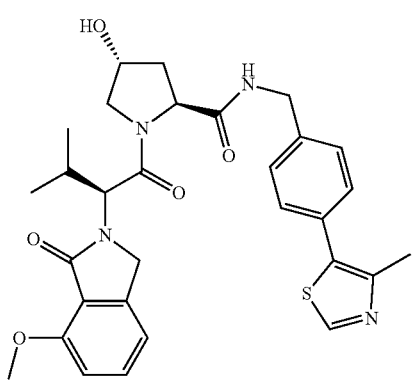
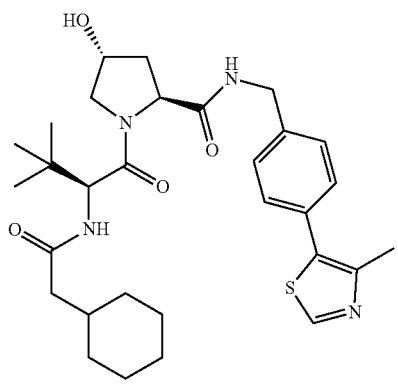
226
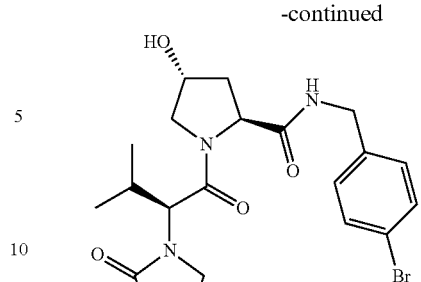
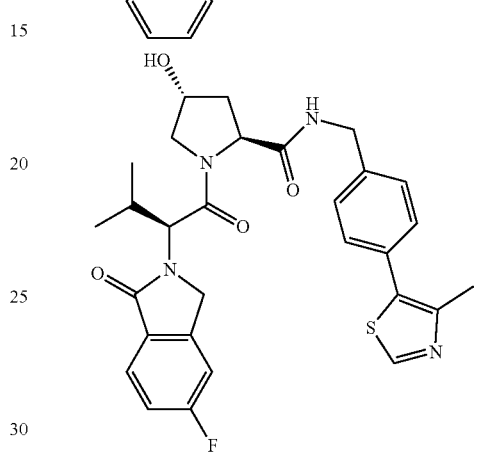
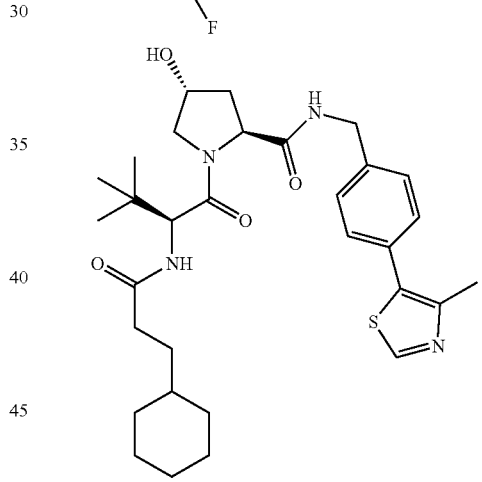
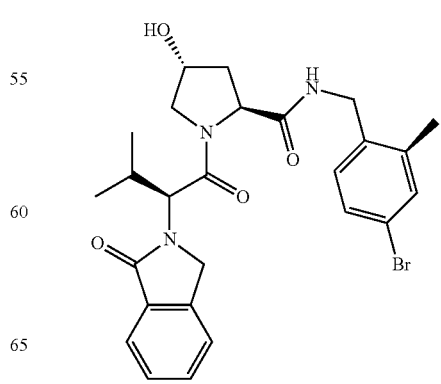

227
-continued
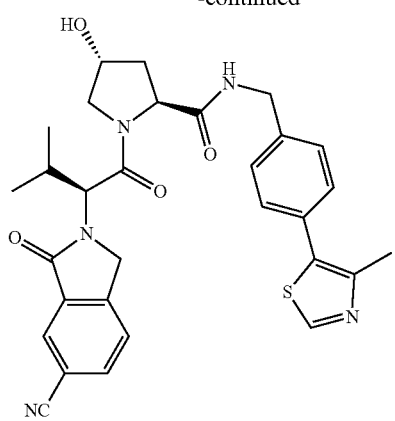
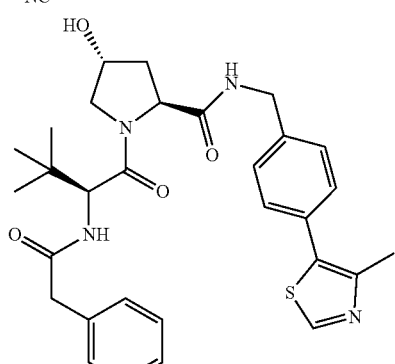
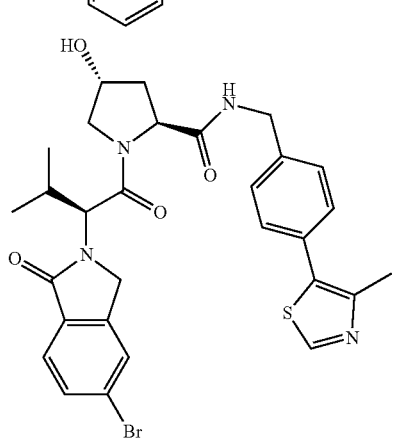
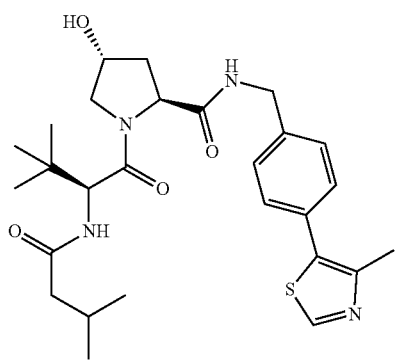
228
-continued
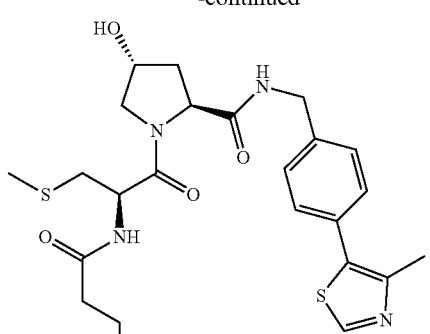
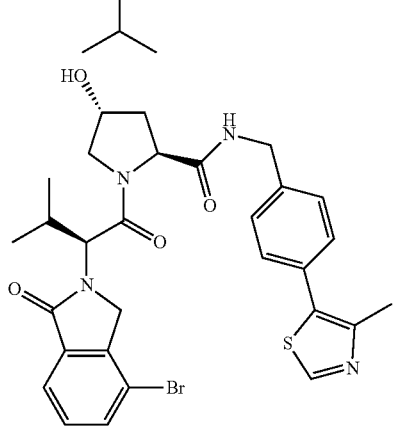
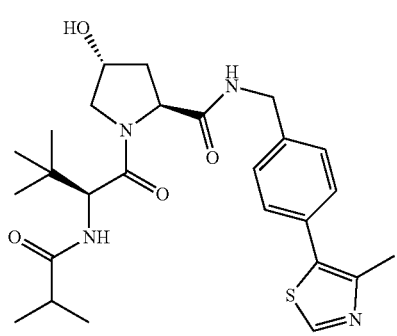
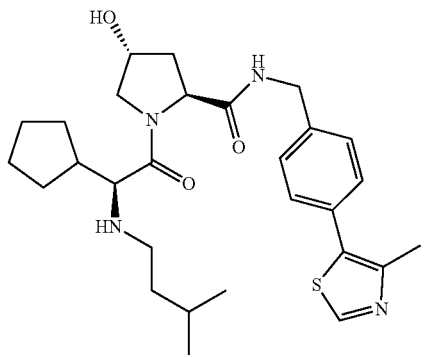

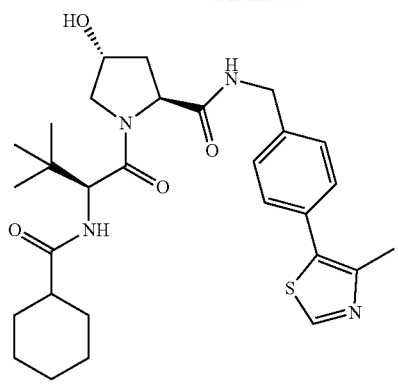
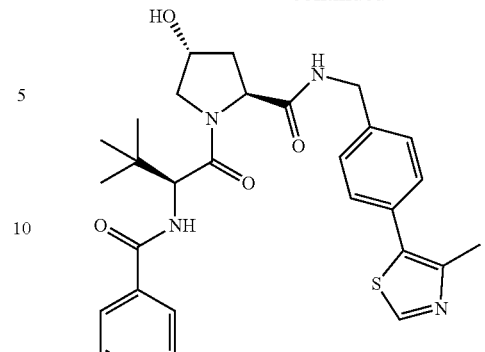
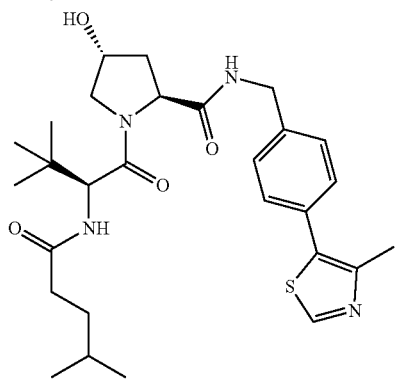
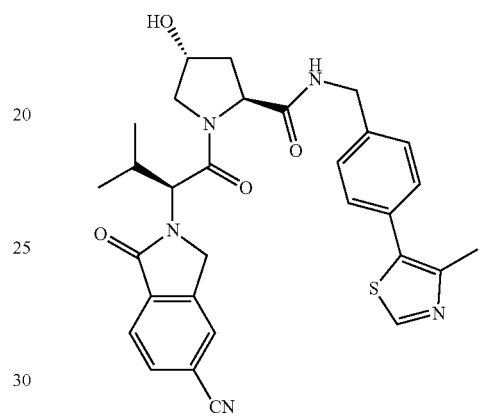
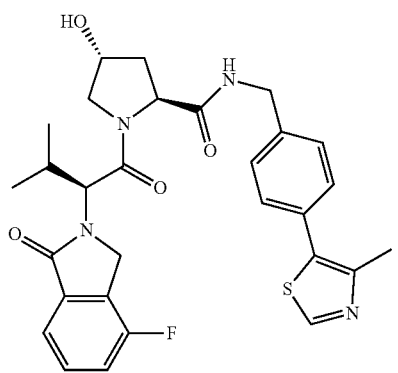
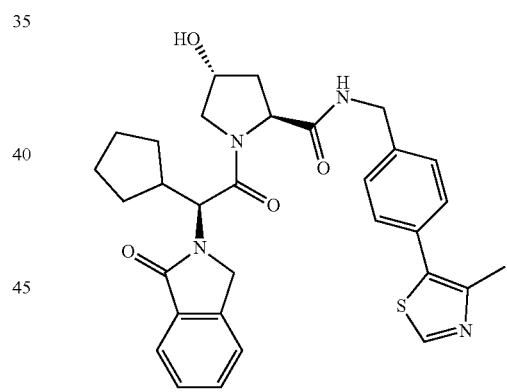
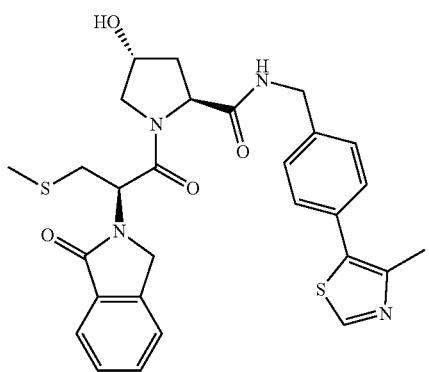
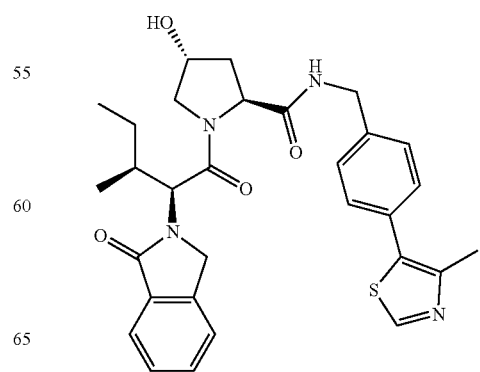

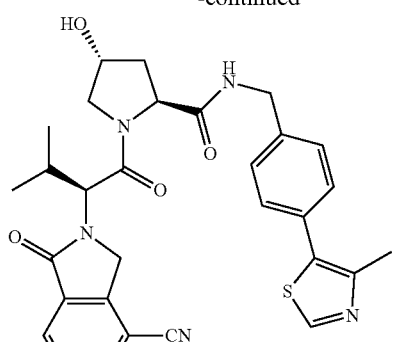
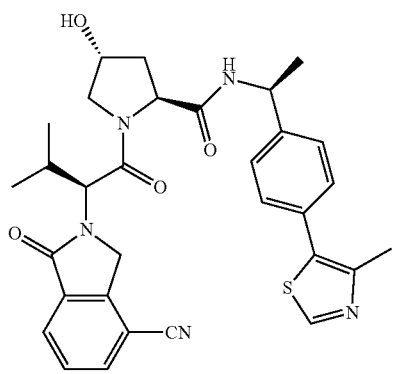
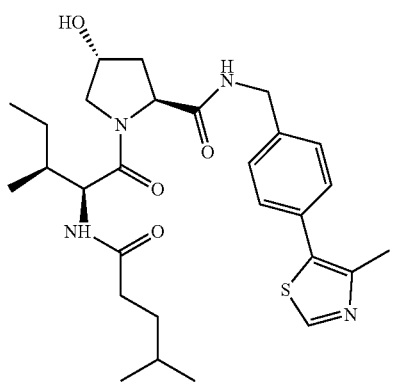
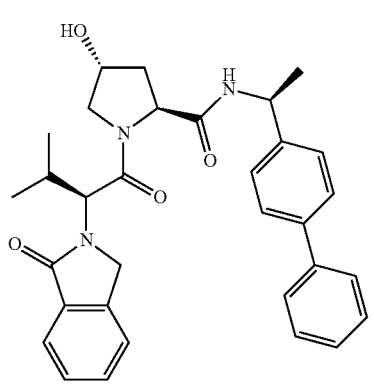
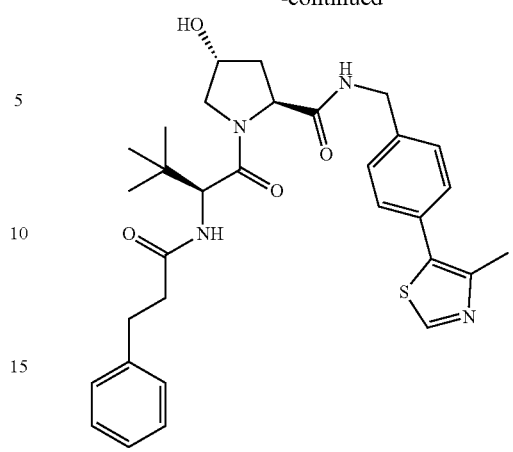
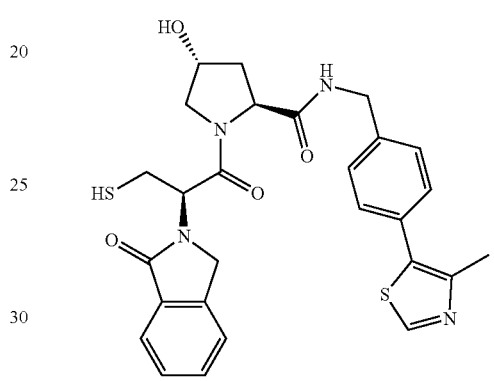
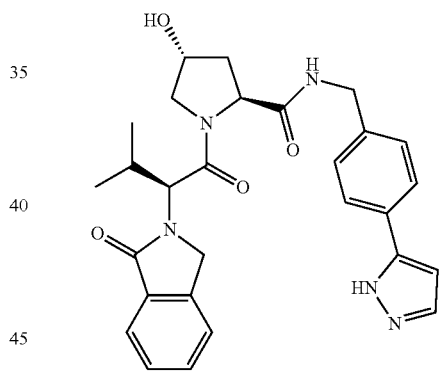
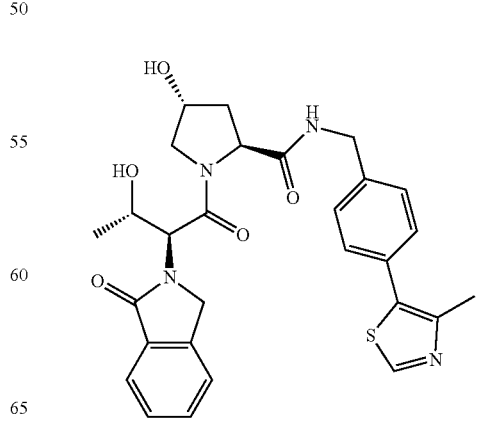

233
-continued
234
-continued
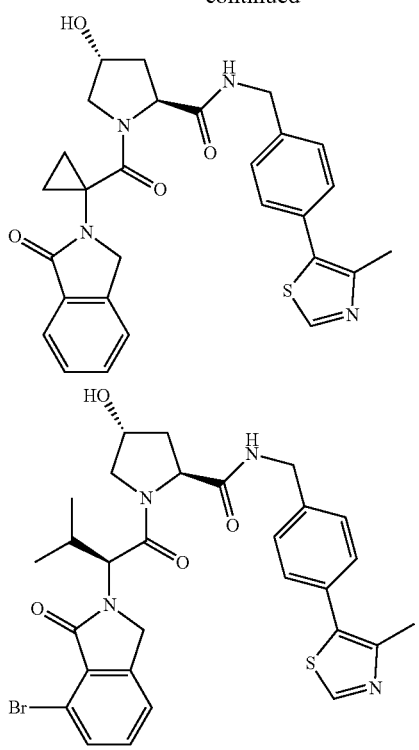
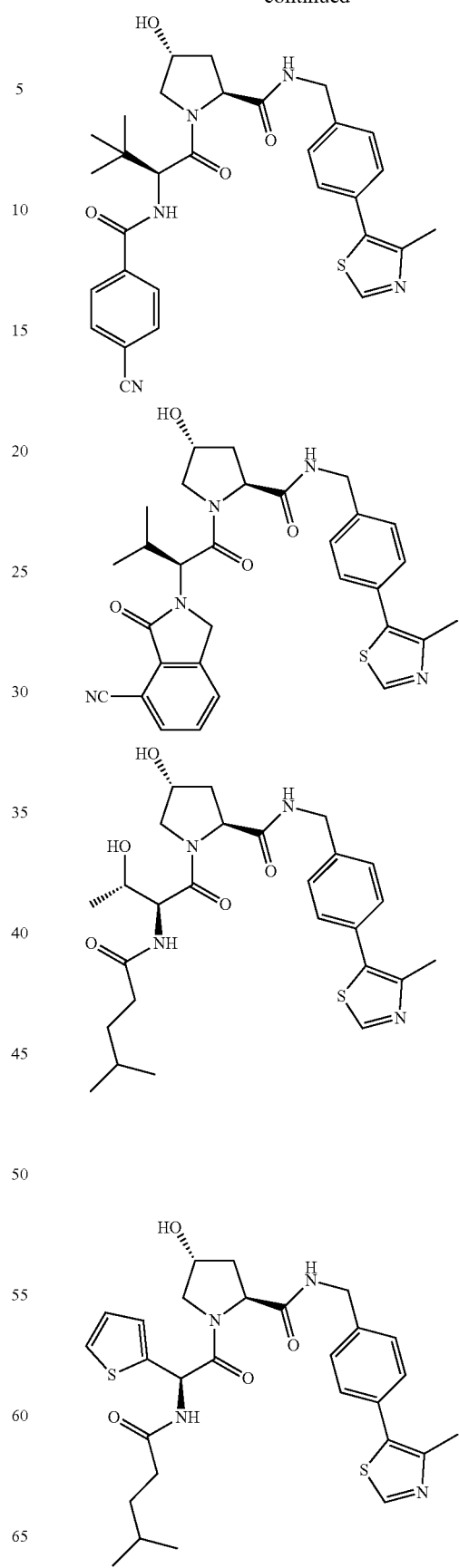

235
-continued
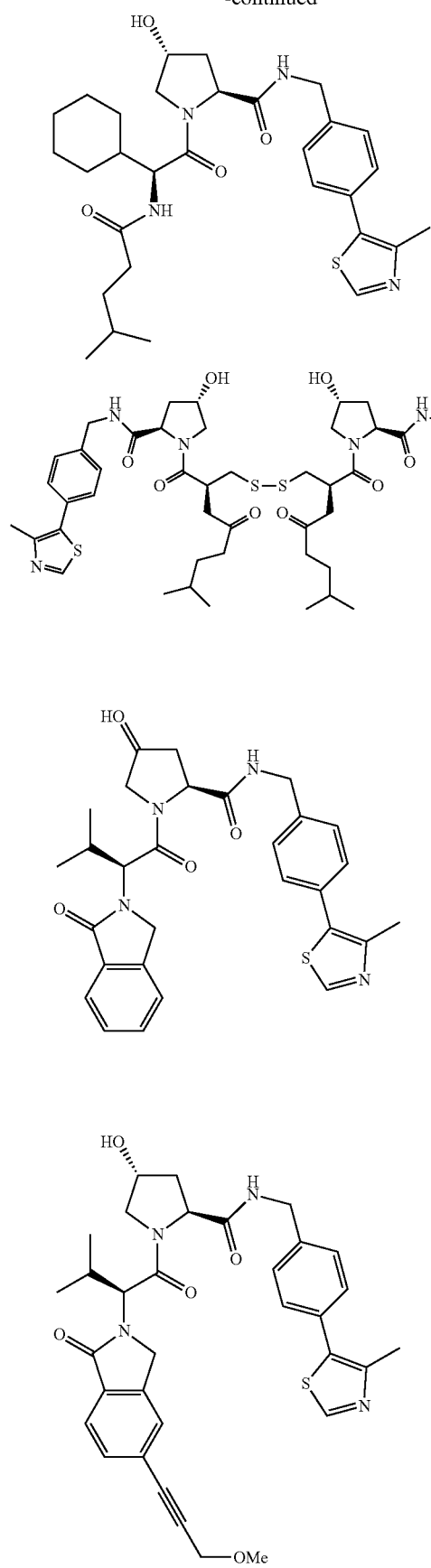
236
-continued
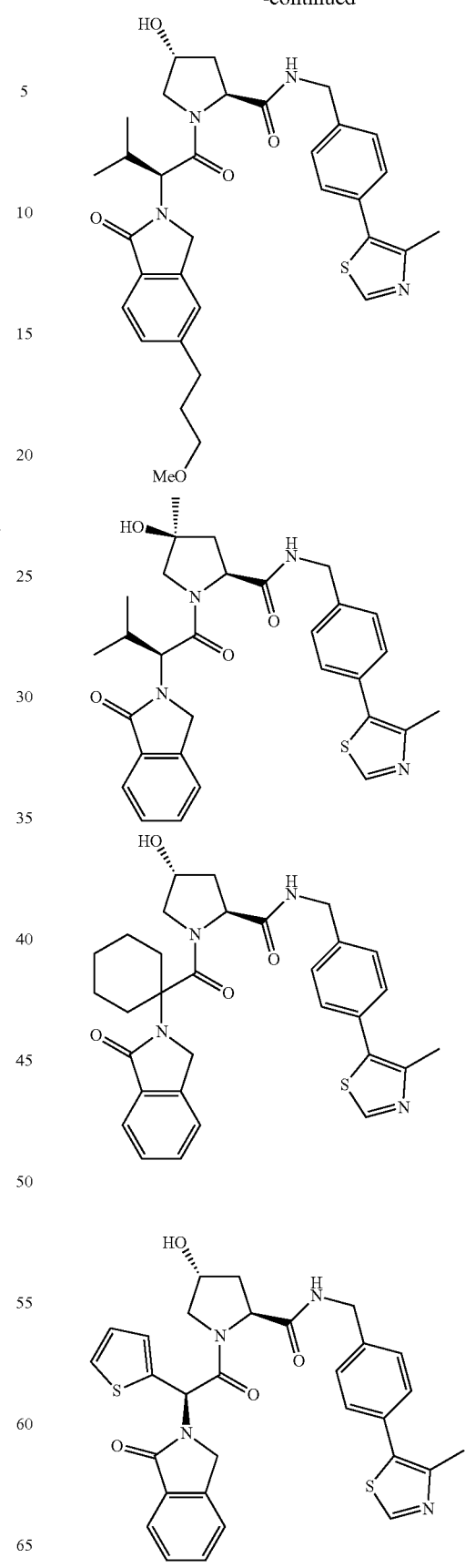

237
-continued
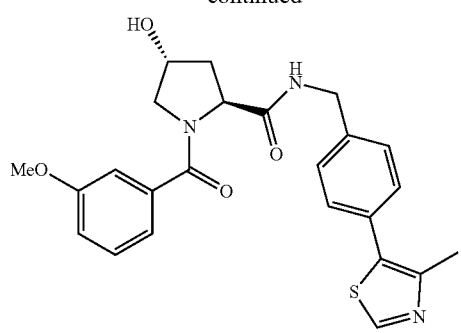
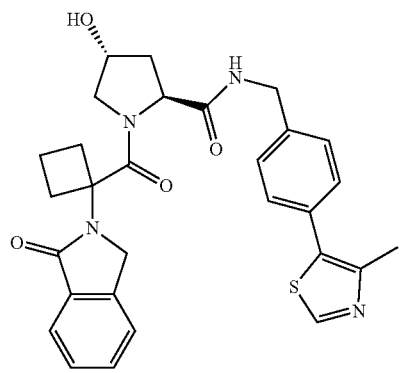
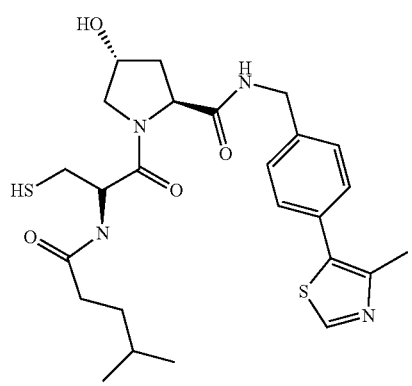
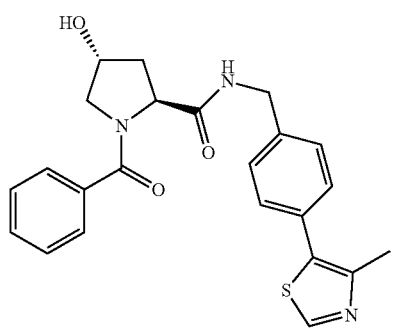
238
-continued
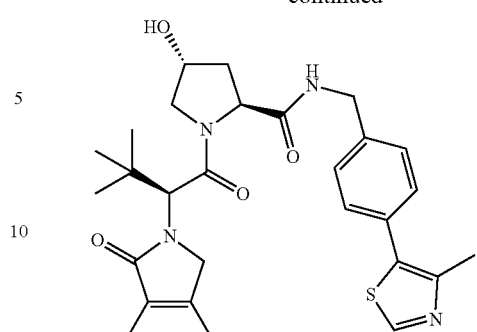
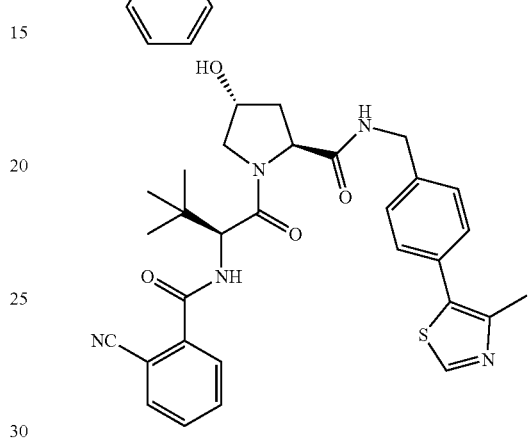
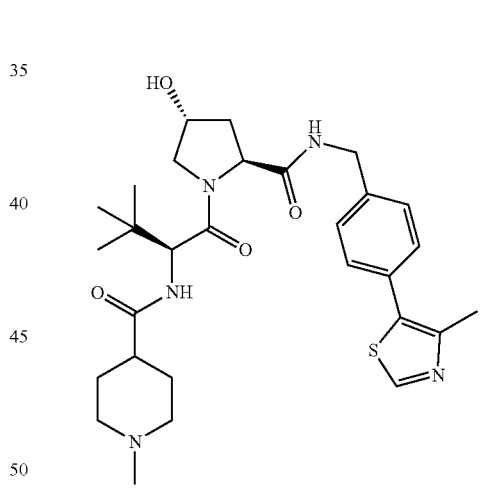
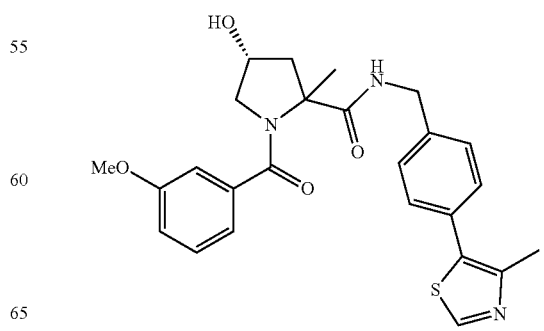

-continued
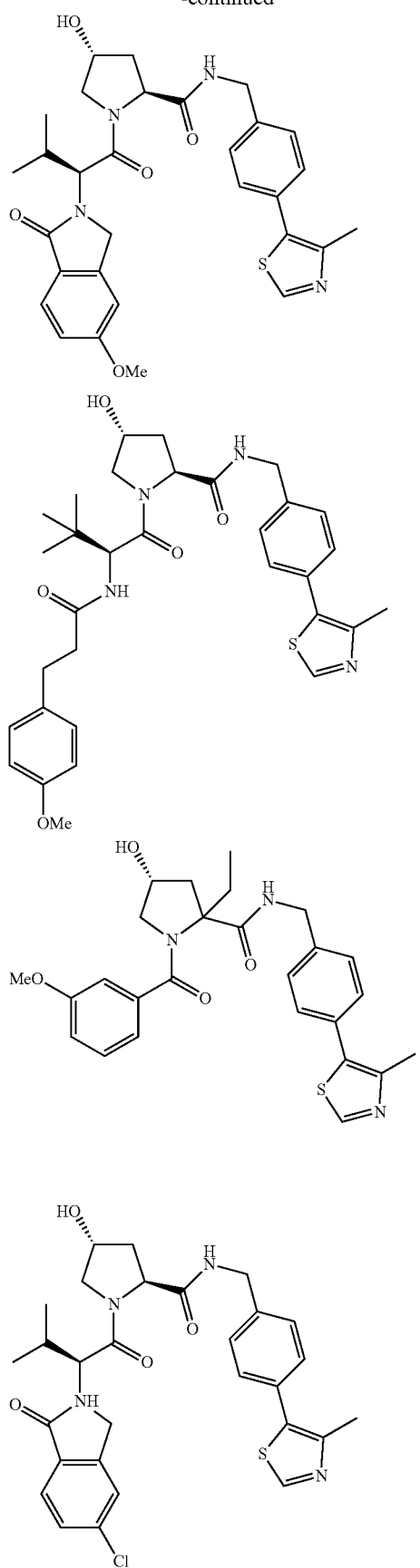
-continued
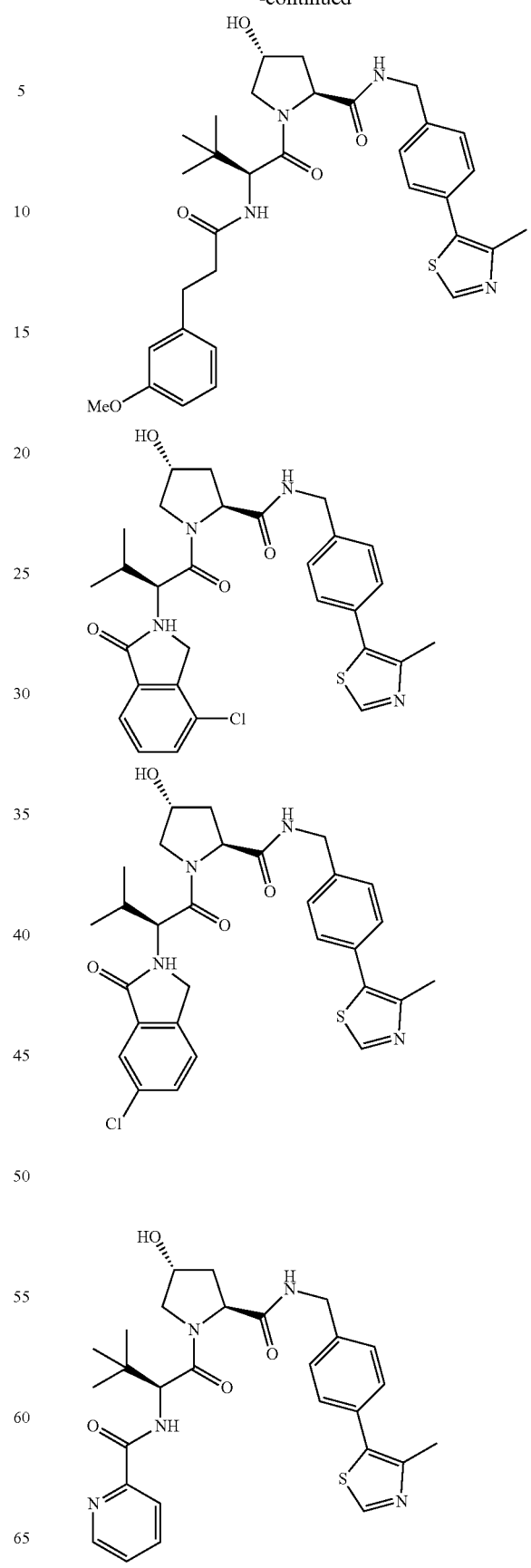

241
-continued
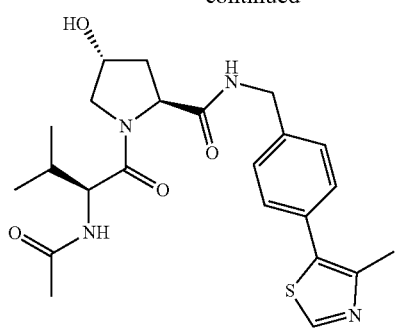
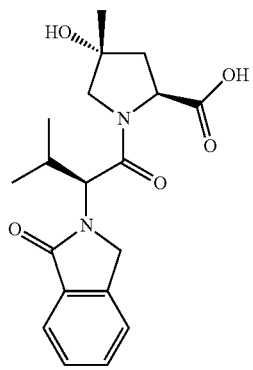
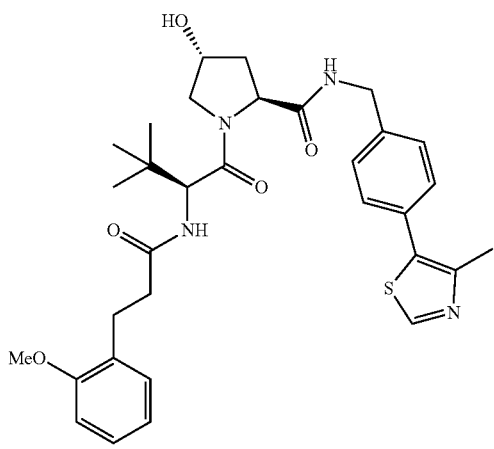
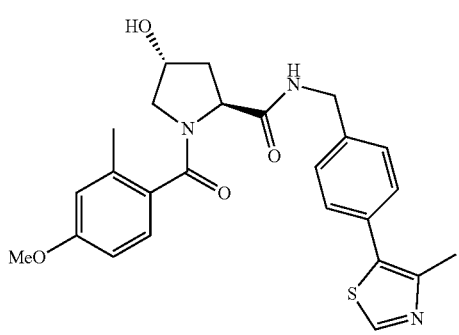
242
-continued
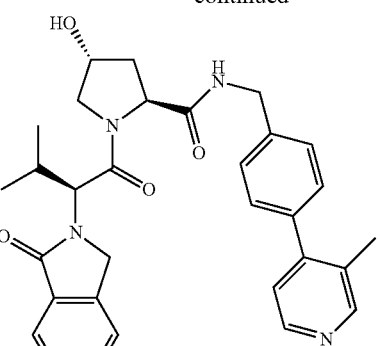
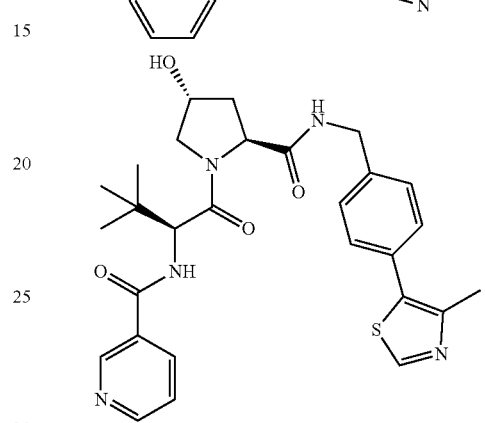
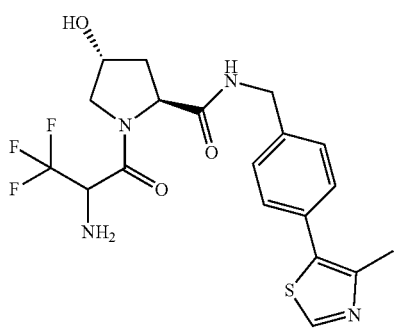
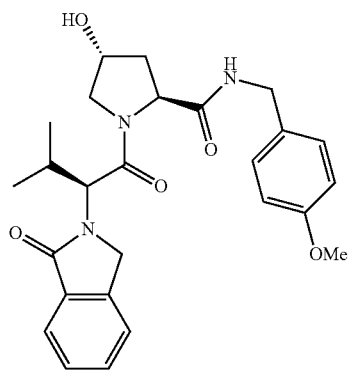

243
-continued
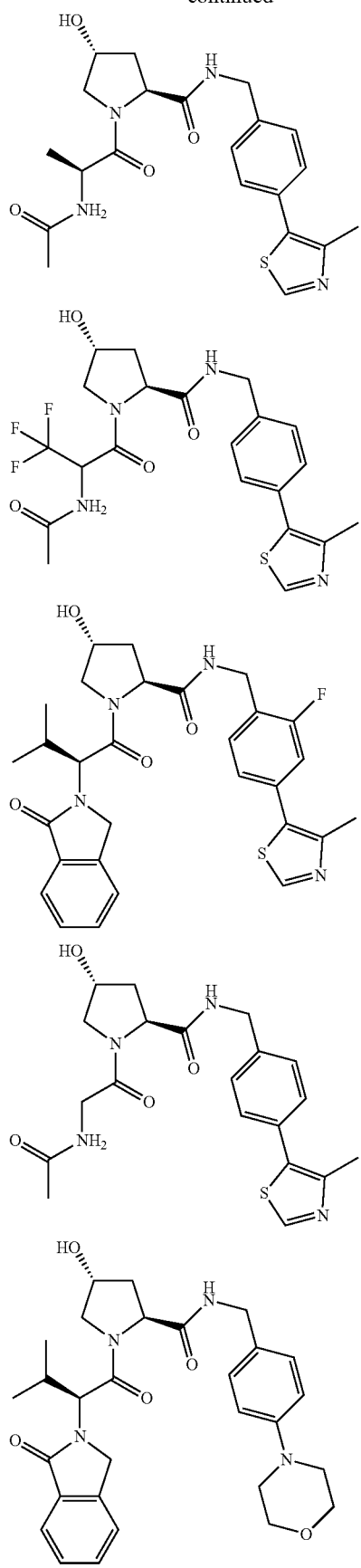
244
-continued
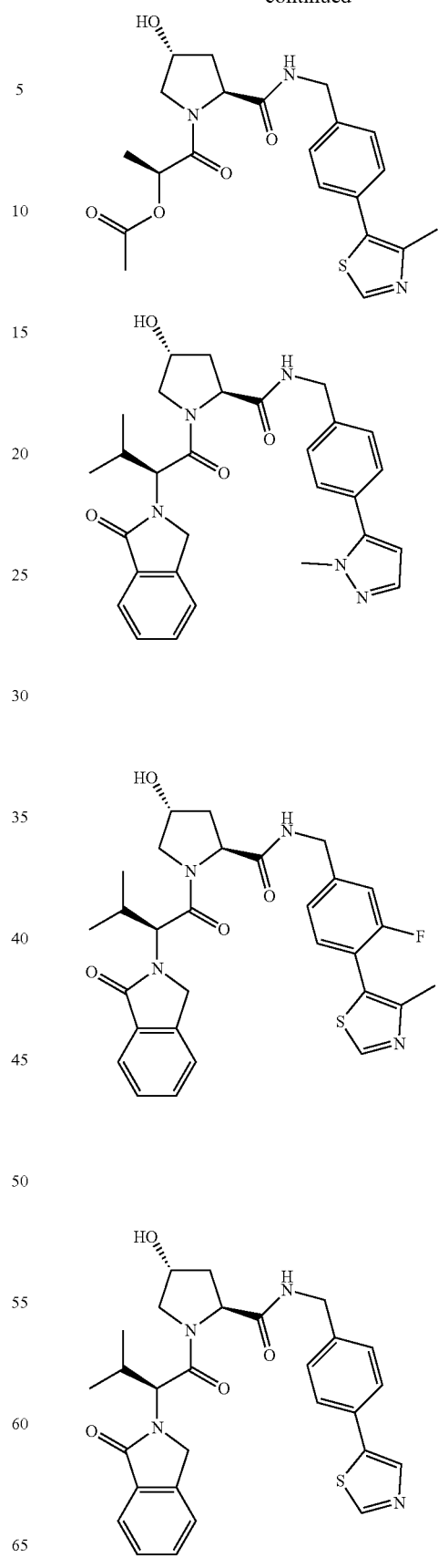

245
-continued
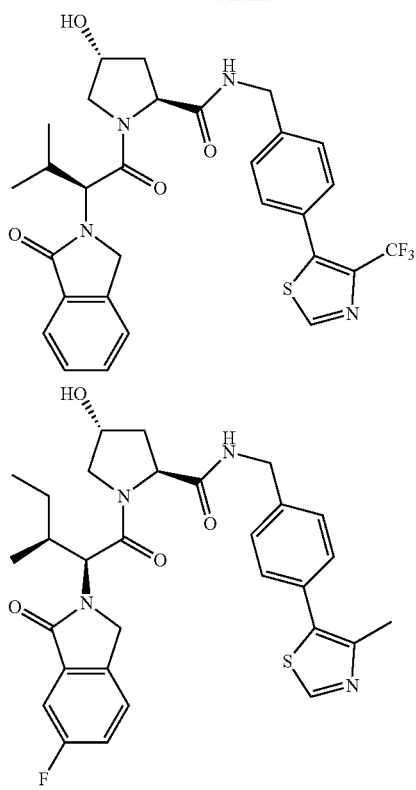
246
-continued
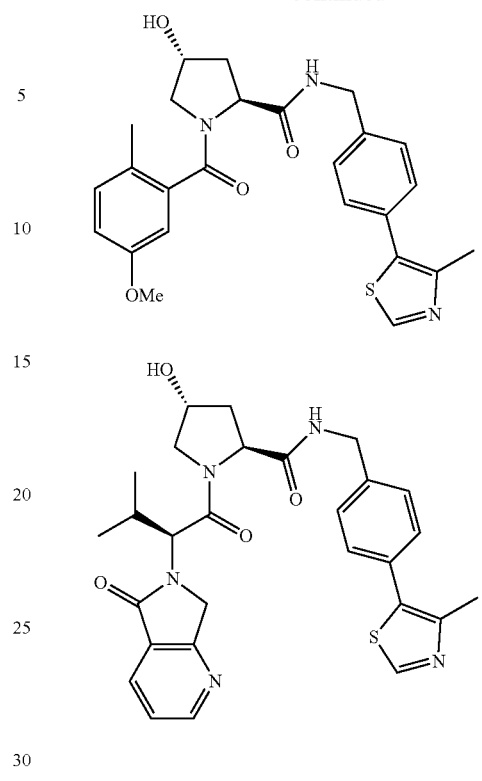
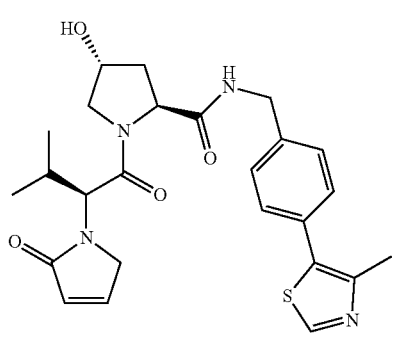
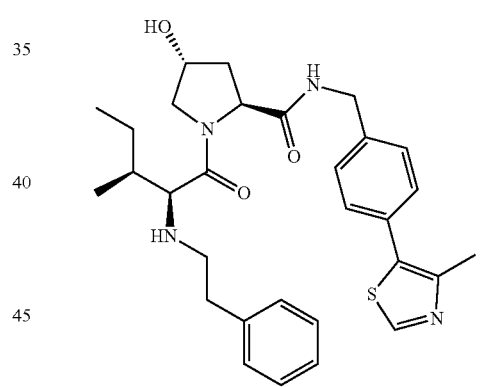
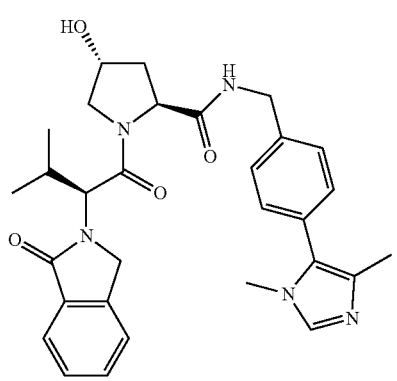
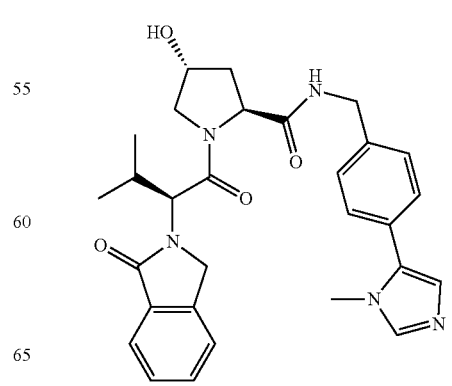

247
-continued
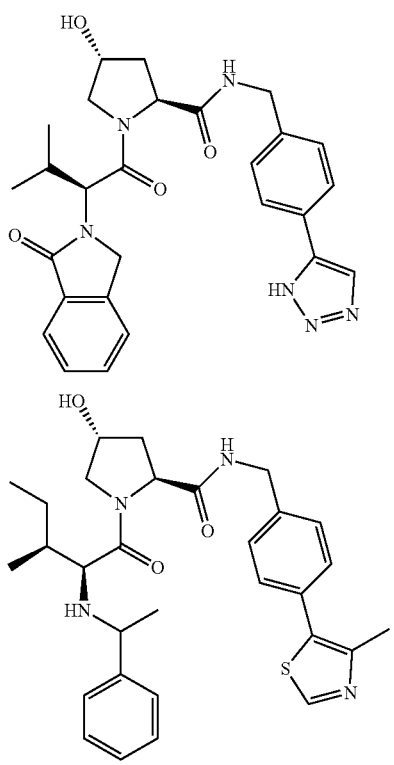
248
-continued
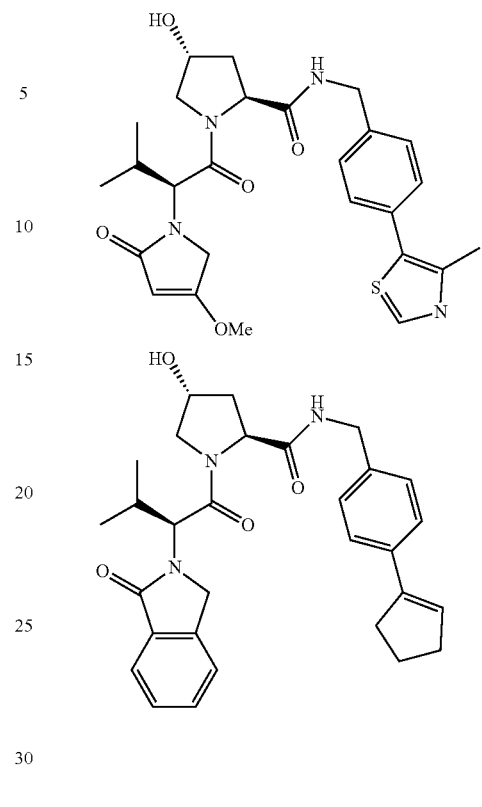
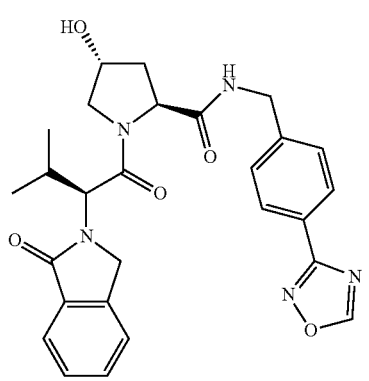
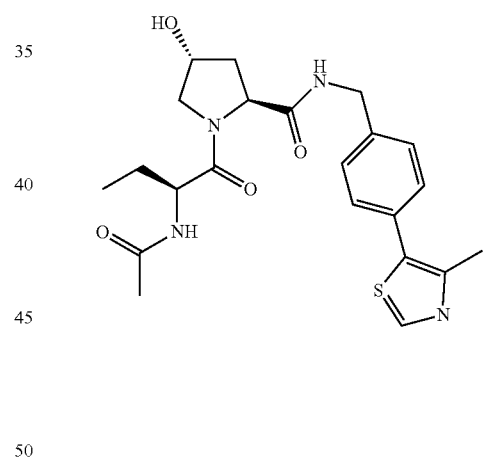
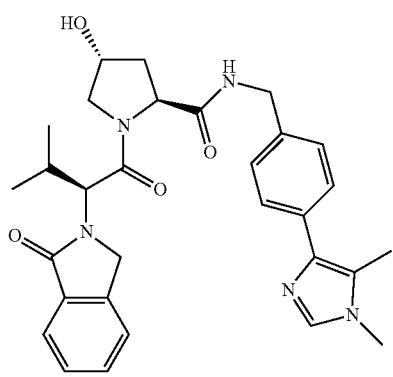
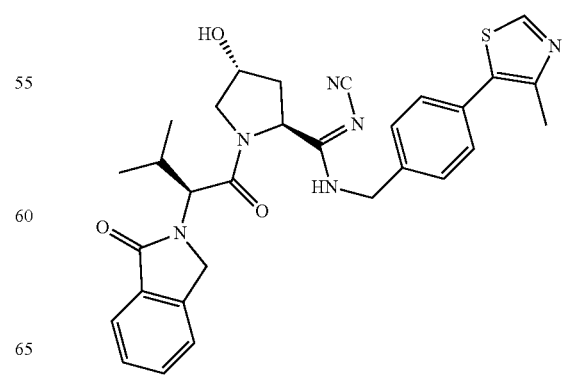

249
-continued
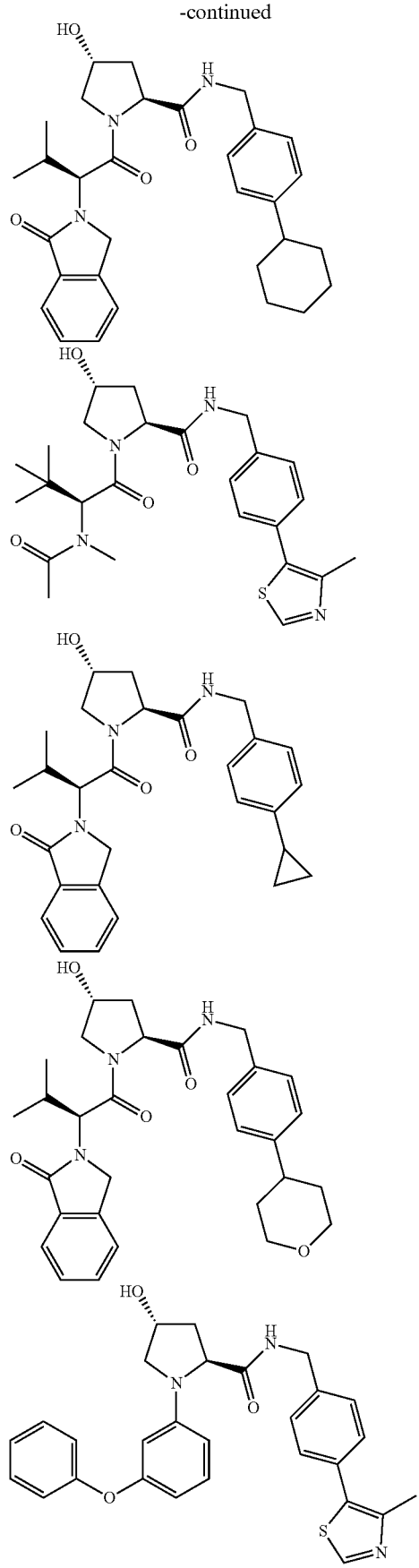
250
-continued
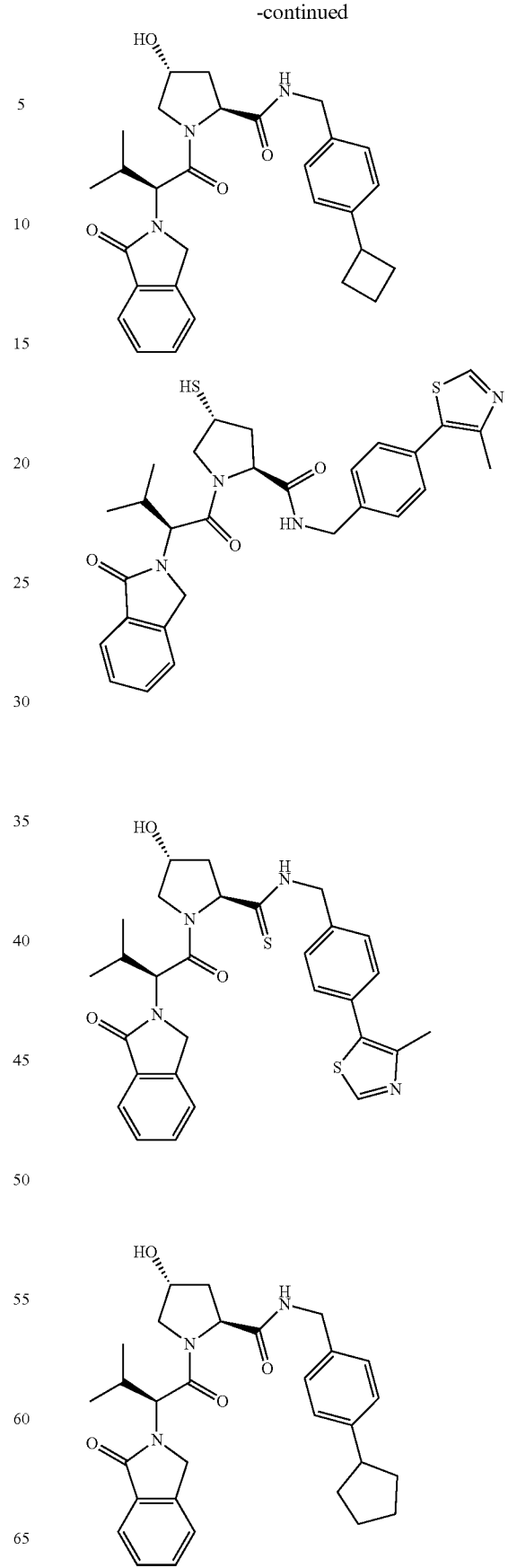

251
-continued
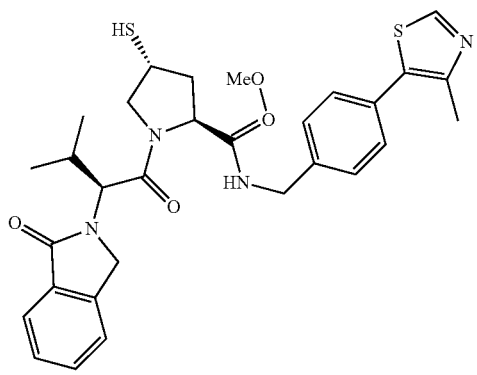
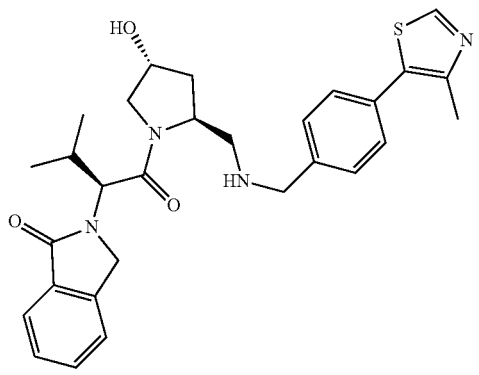
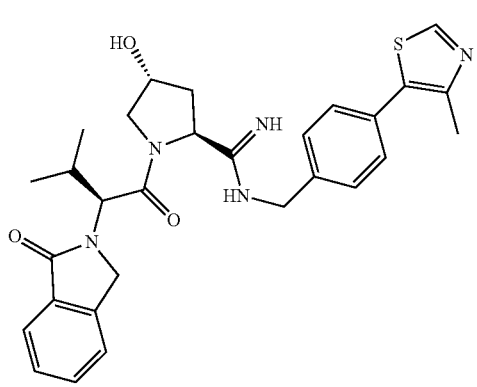
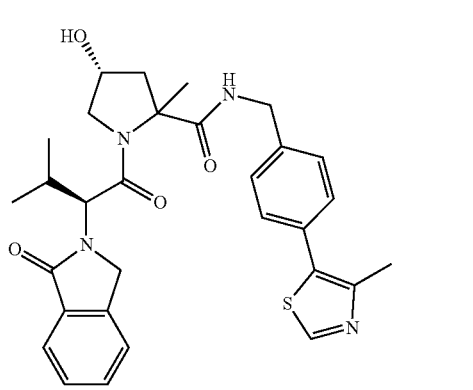
252
-continued
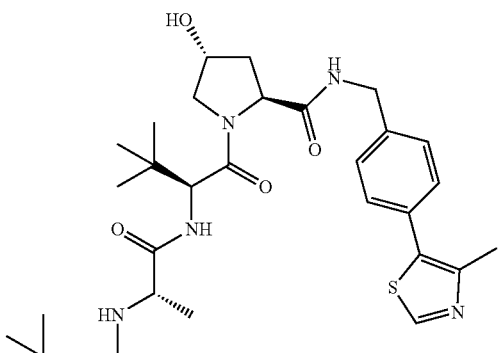
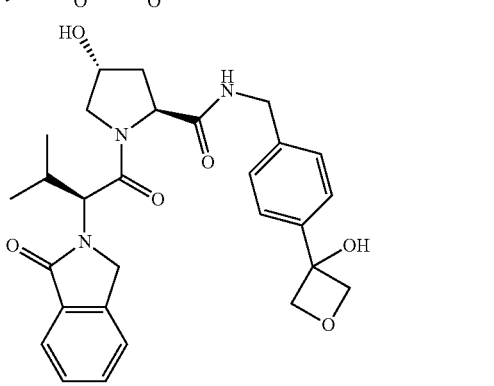
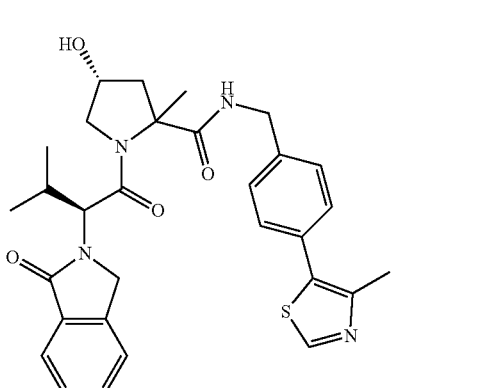
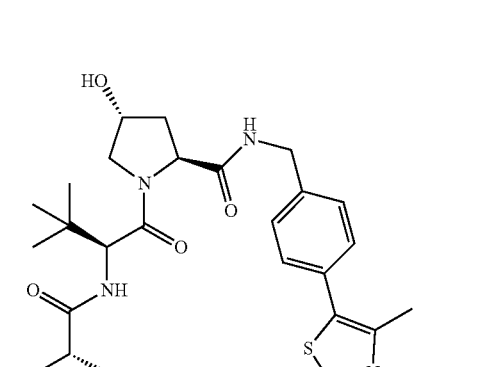

253
-continued
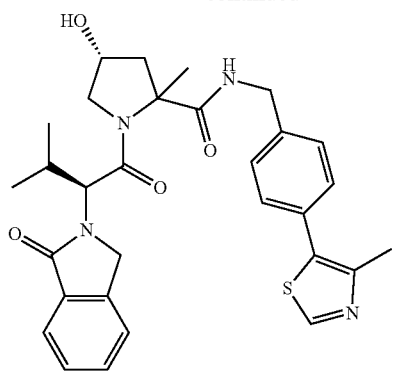
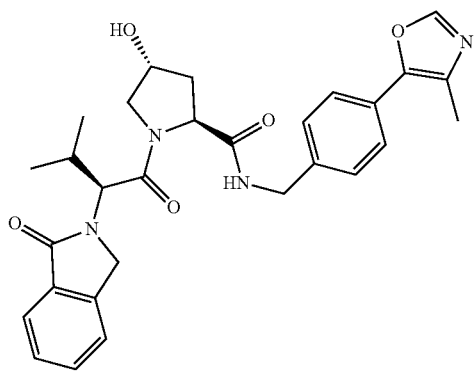
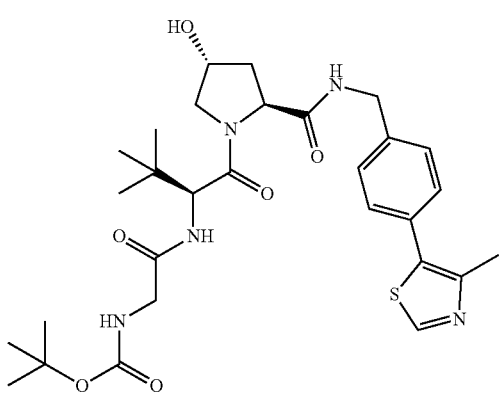
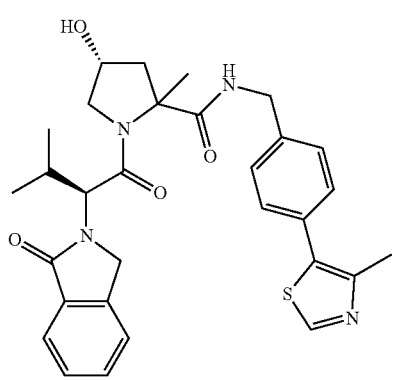
254
-continued
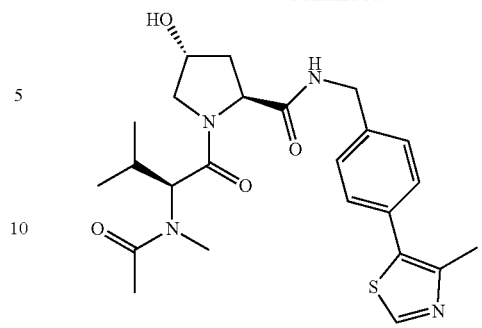
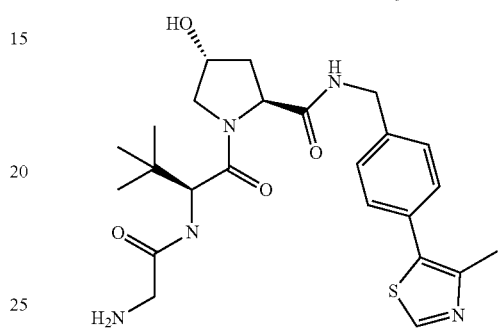
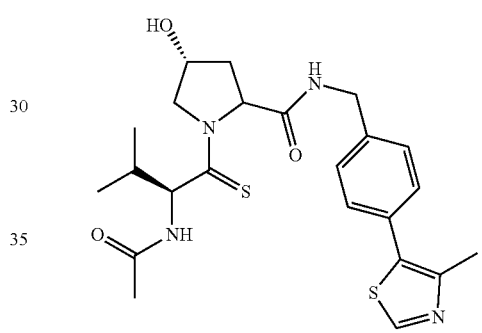
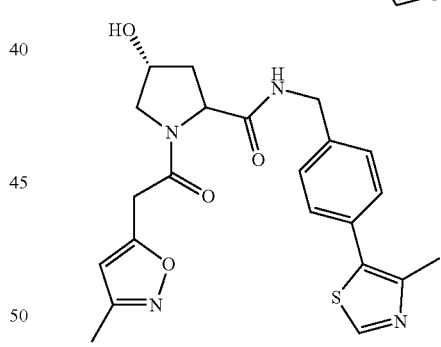
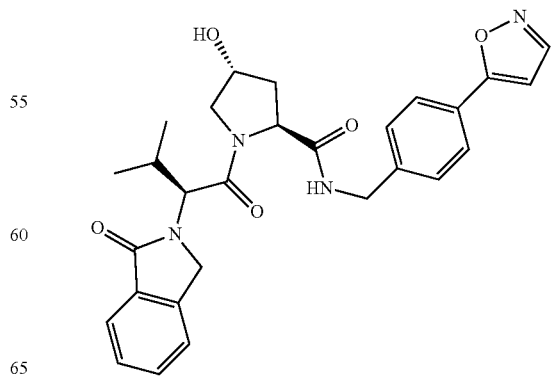

255
-continued
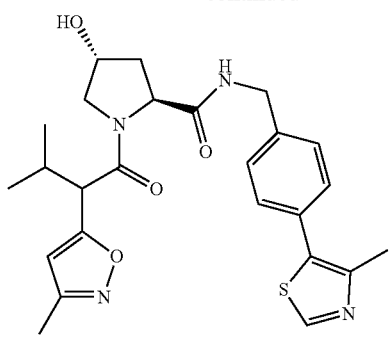
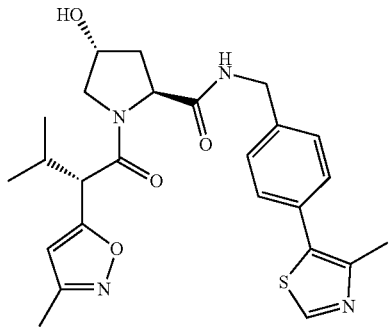
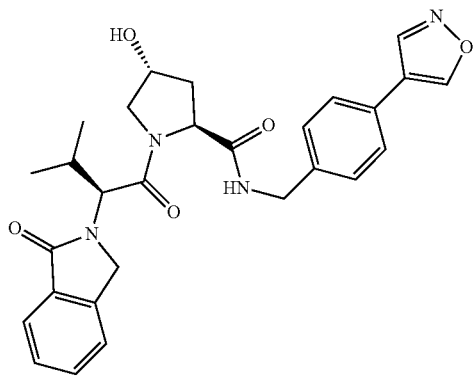
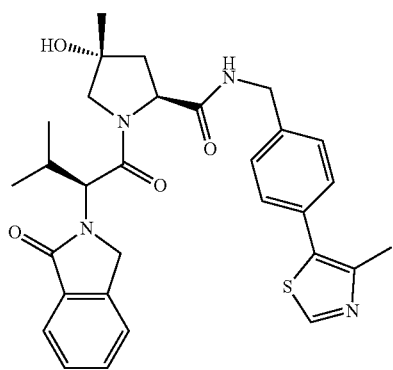
256
-continued
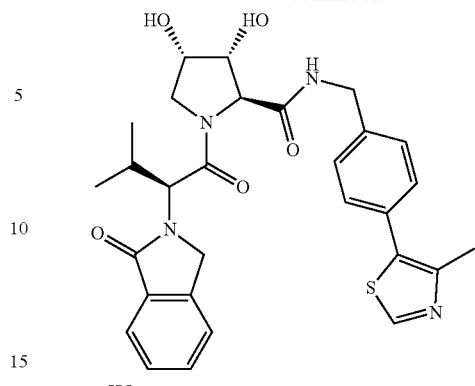
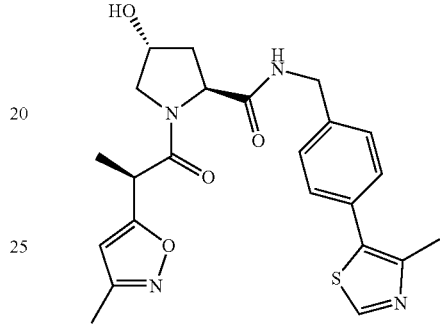
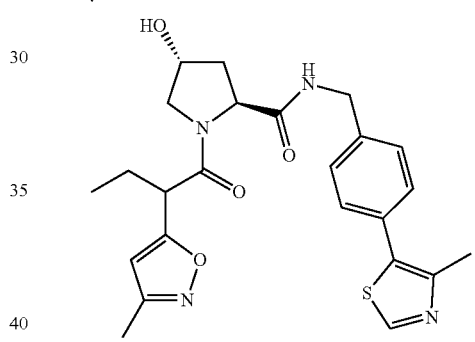
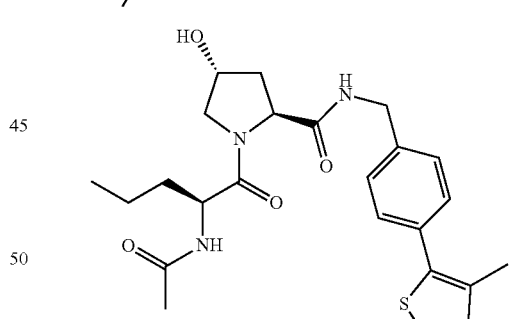
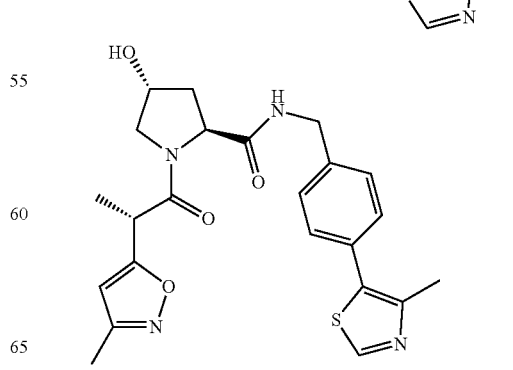

257
-continued
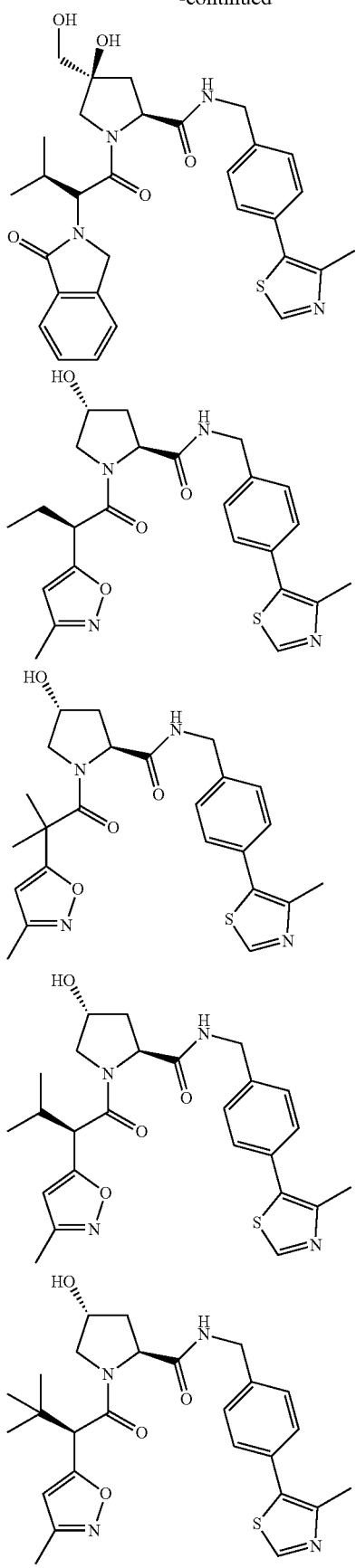
258
-continued
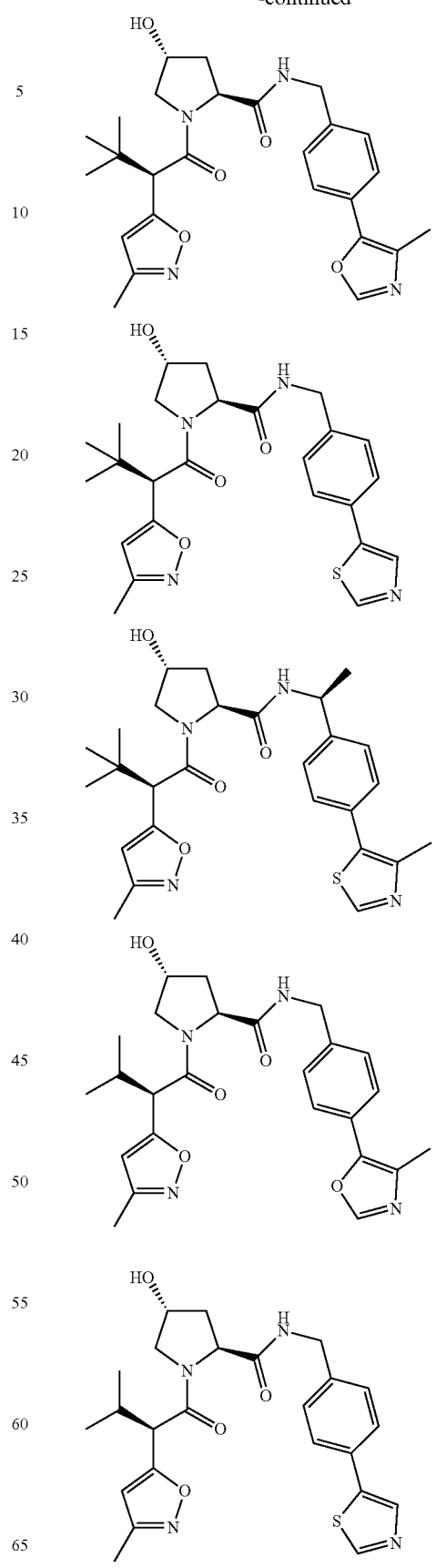

259
-continued
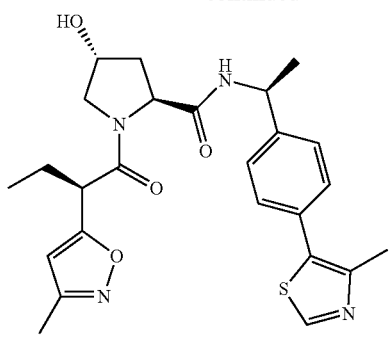
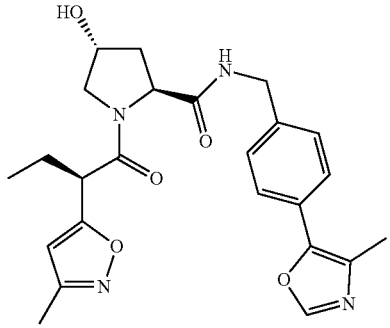
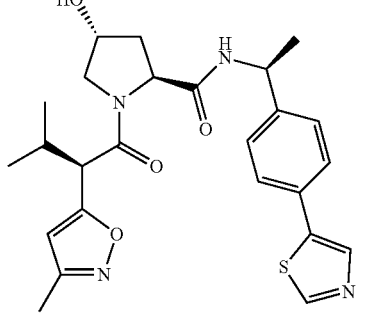
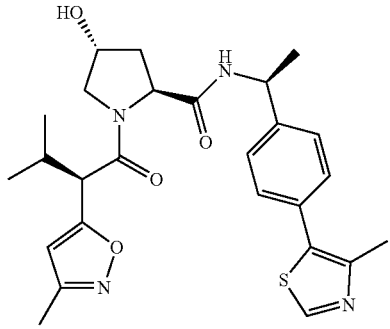
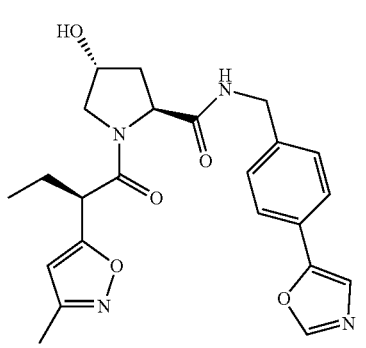
260
-continued
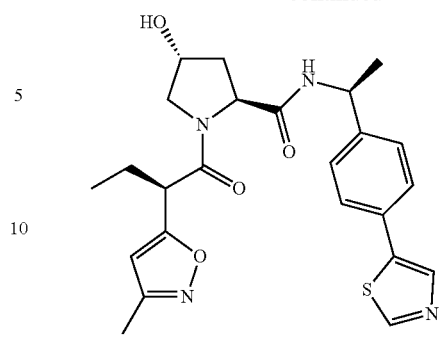
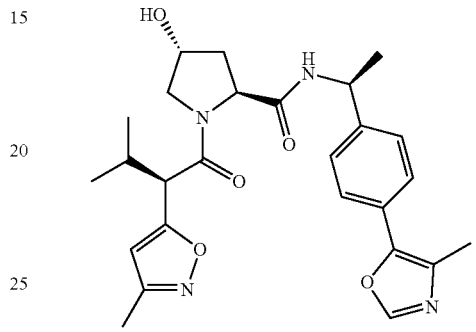
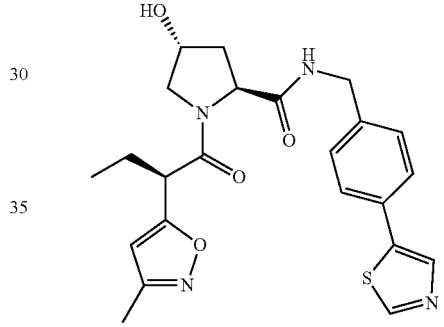
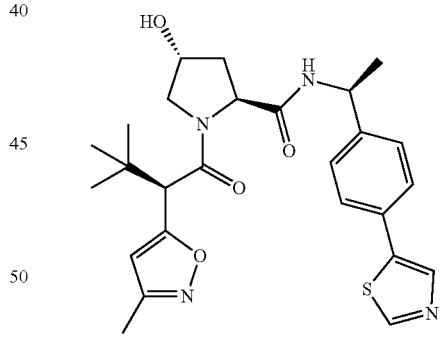
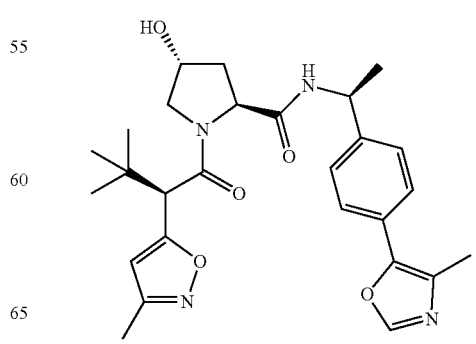

261
-continued
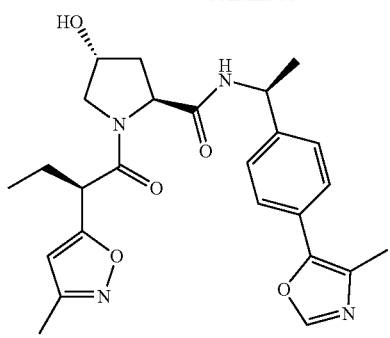
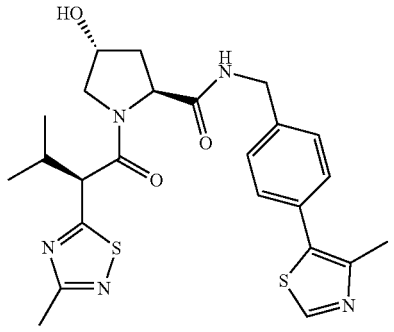
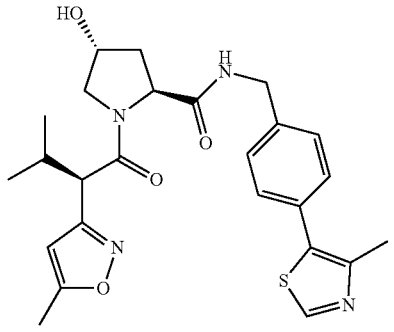
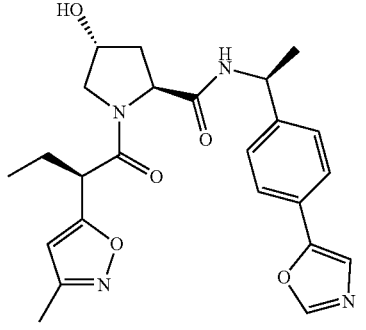
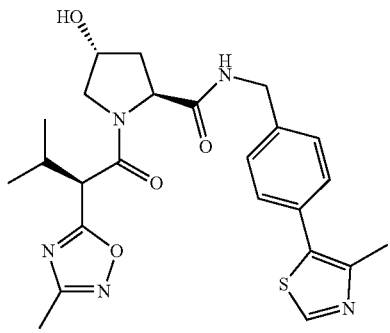
262
-continued
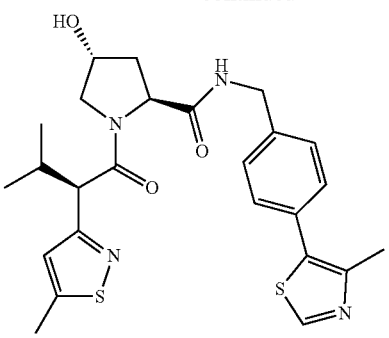
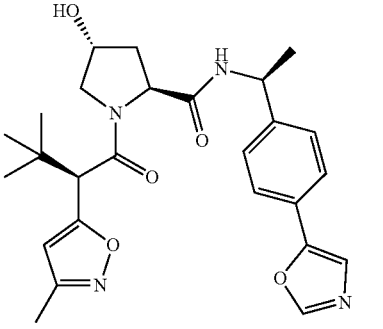
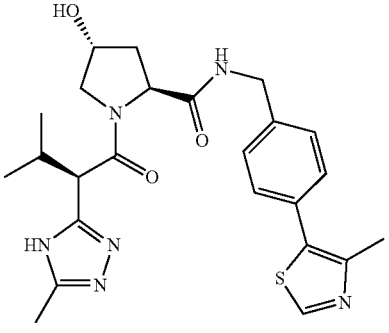
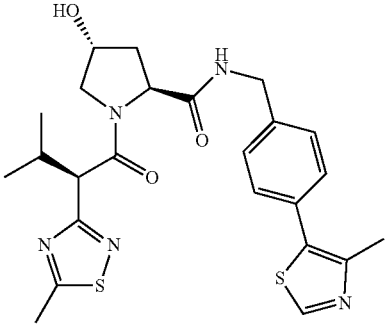
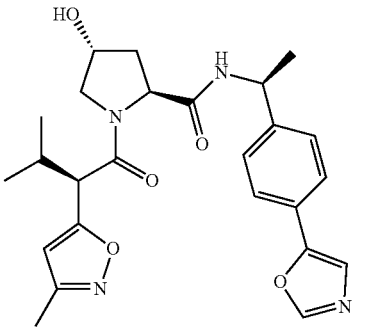

263
-continued
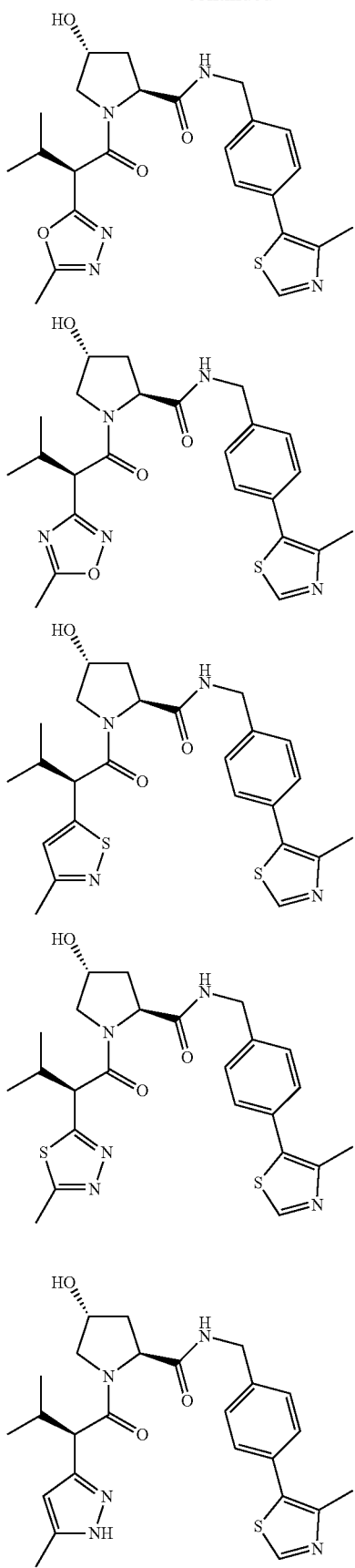
264
-continued
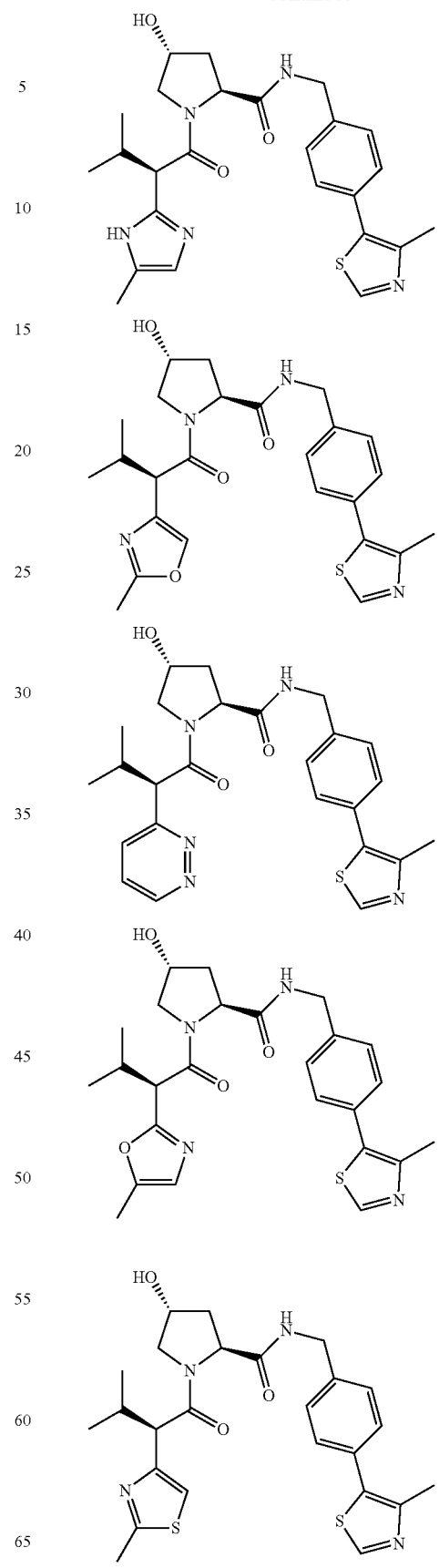

265
-continued
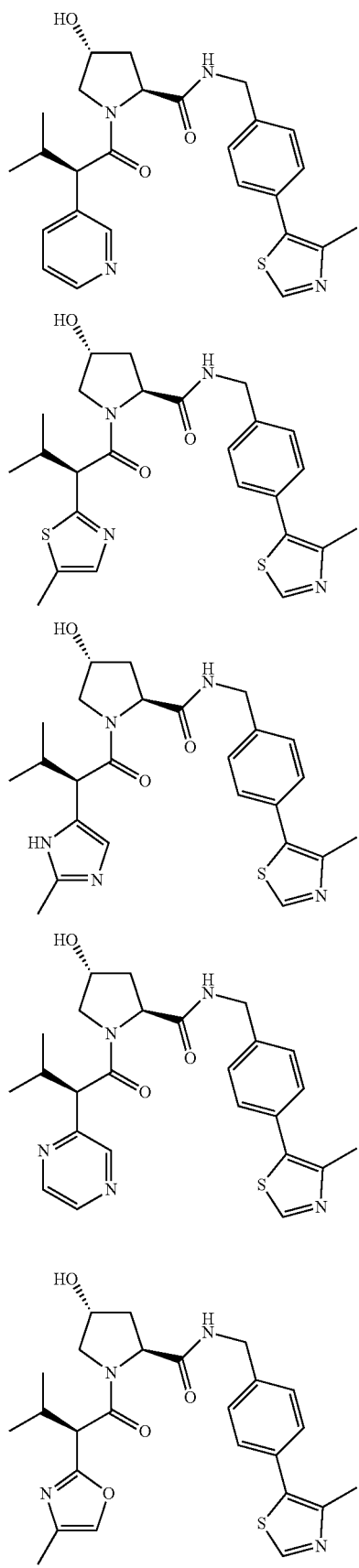
266
-continued
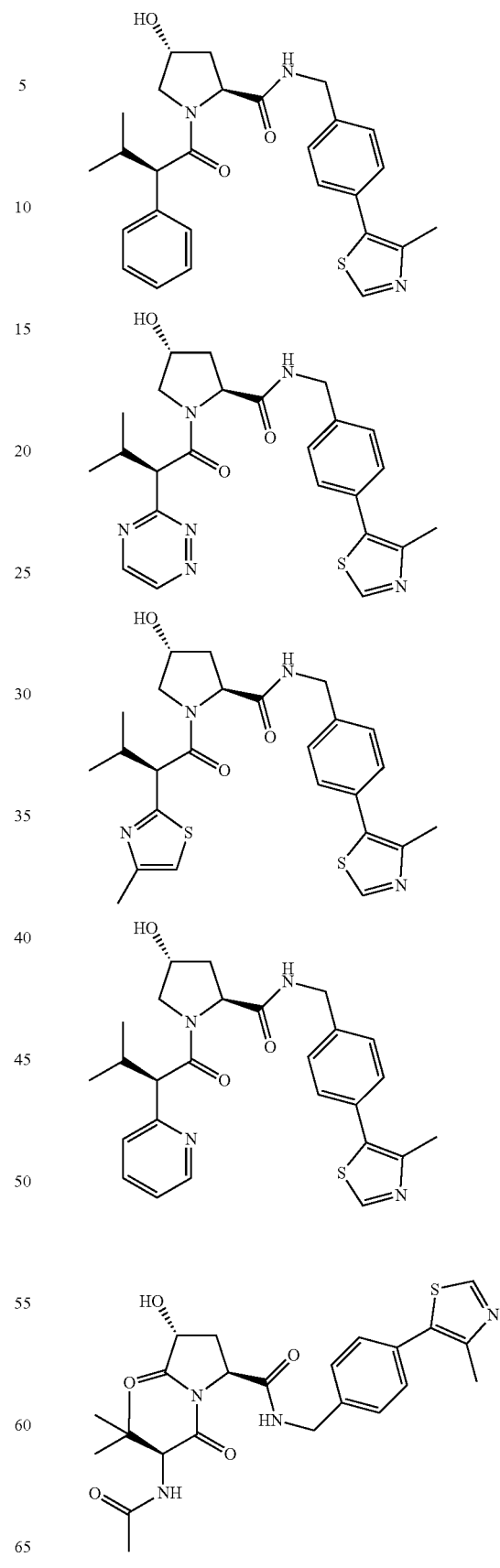

267
-continued
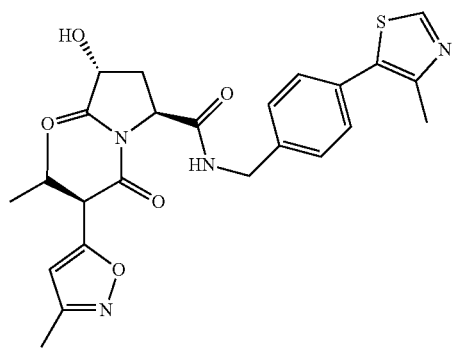
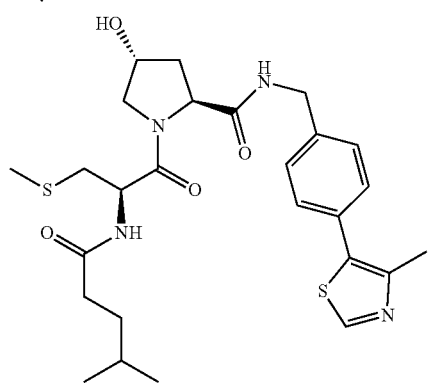
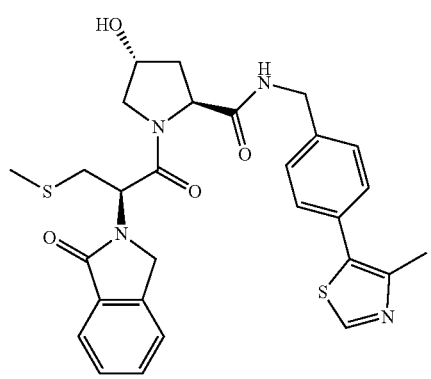
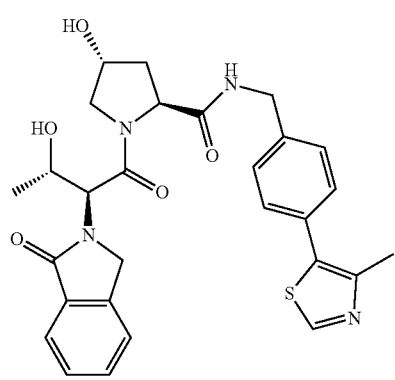
268
-continued
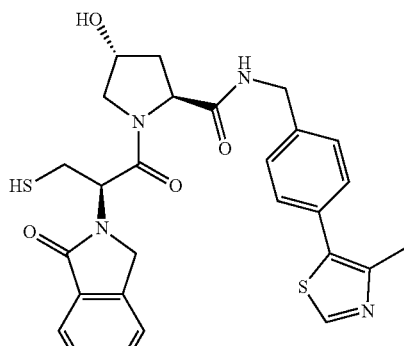
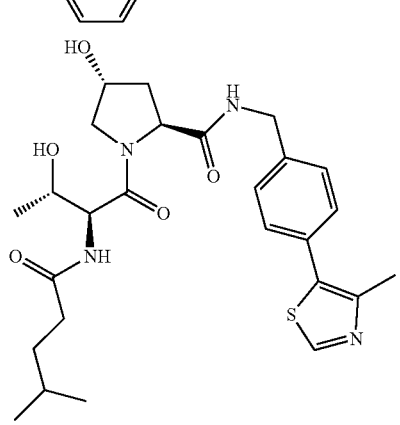
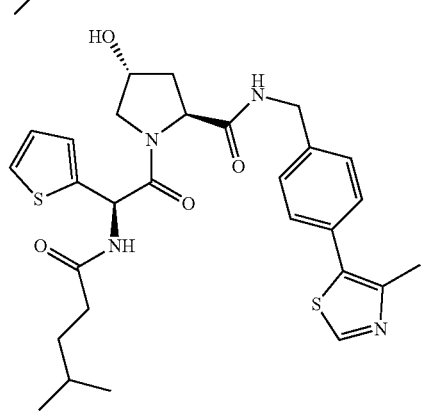
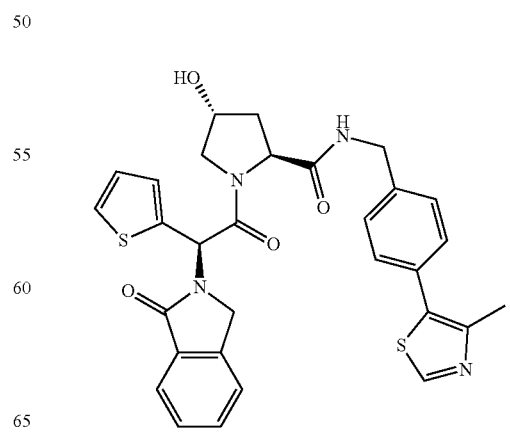

269
-continued
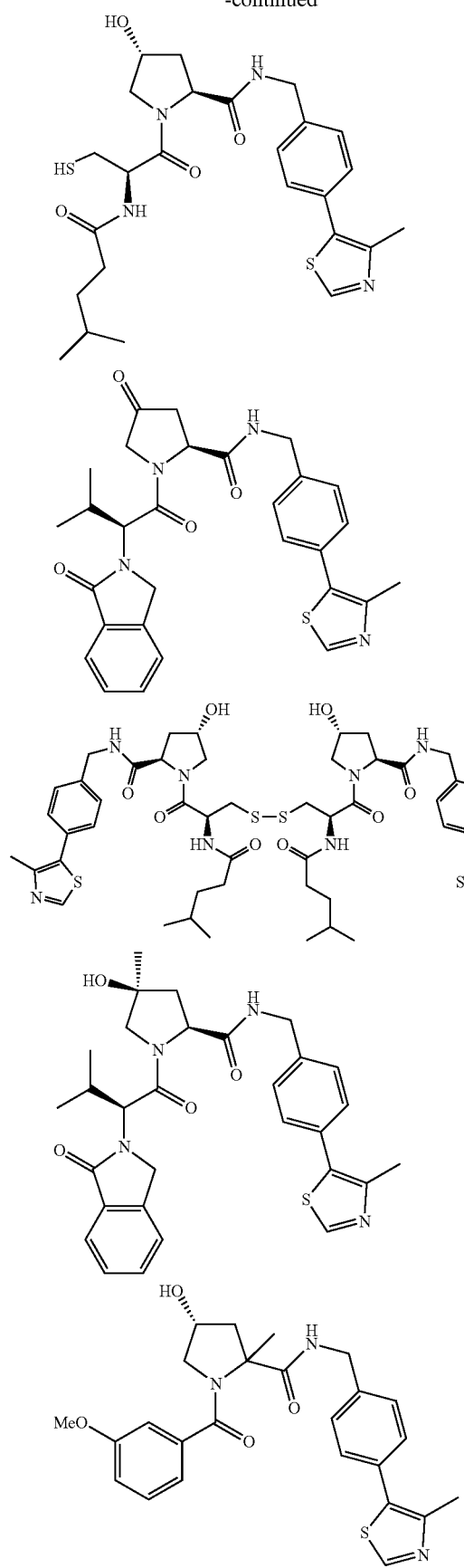
270
-continued
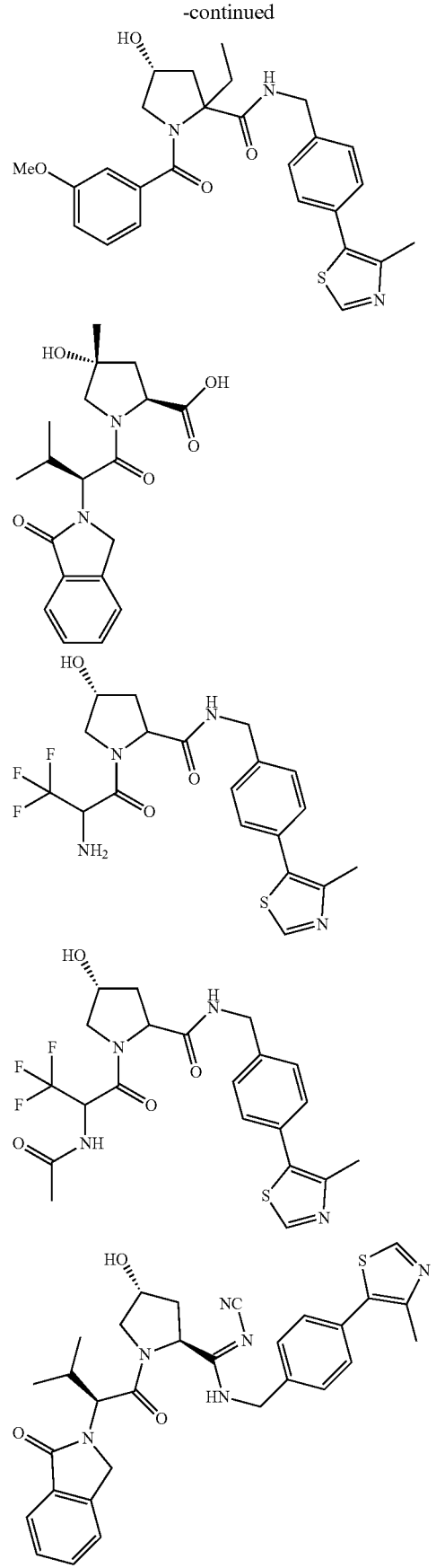

271
-continued
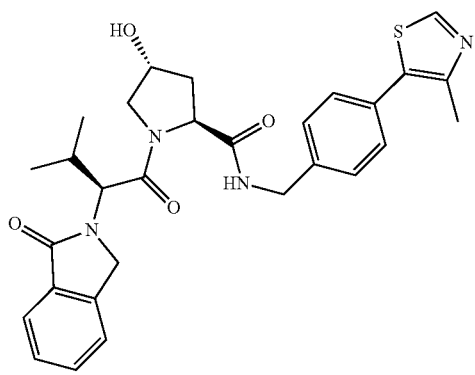
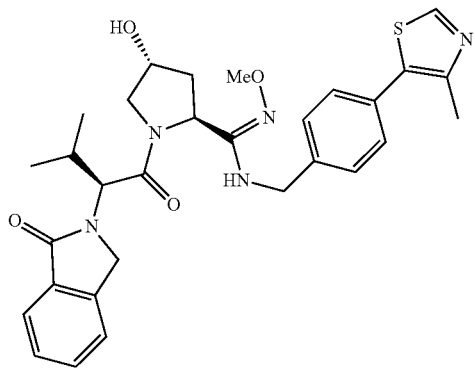
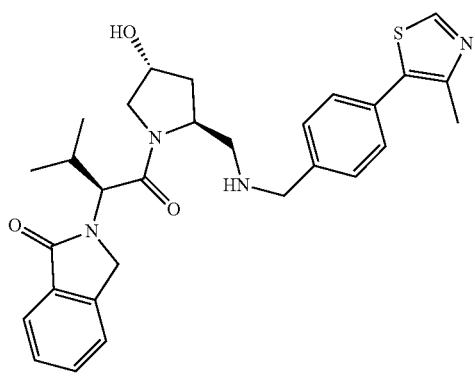
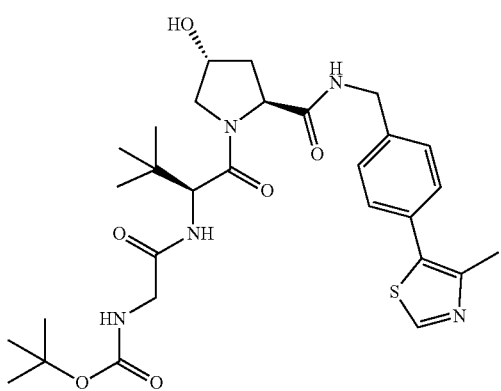
272
-continued
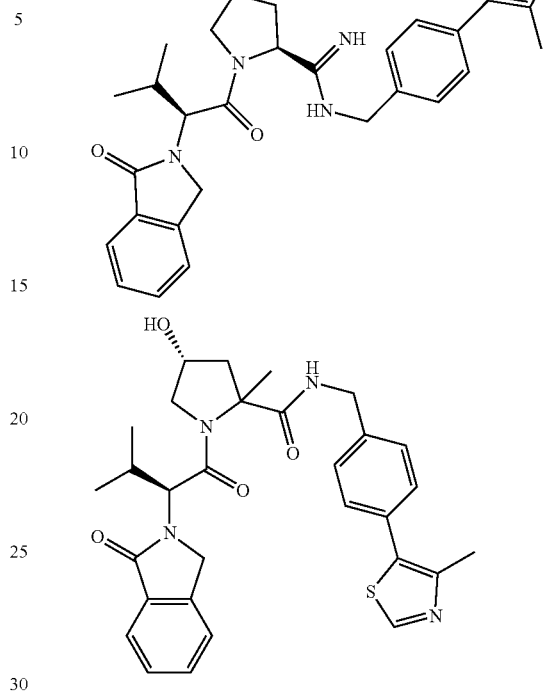
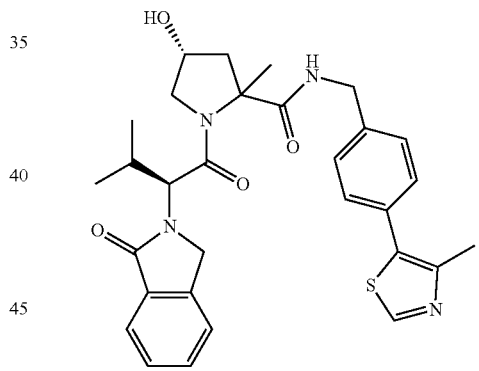
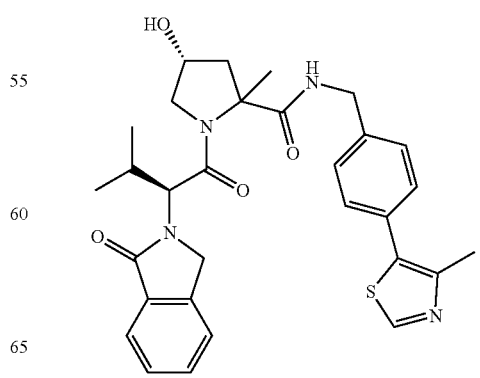

273
-continued
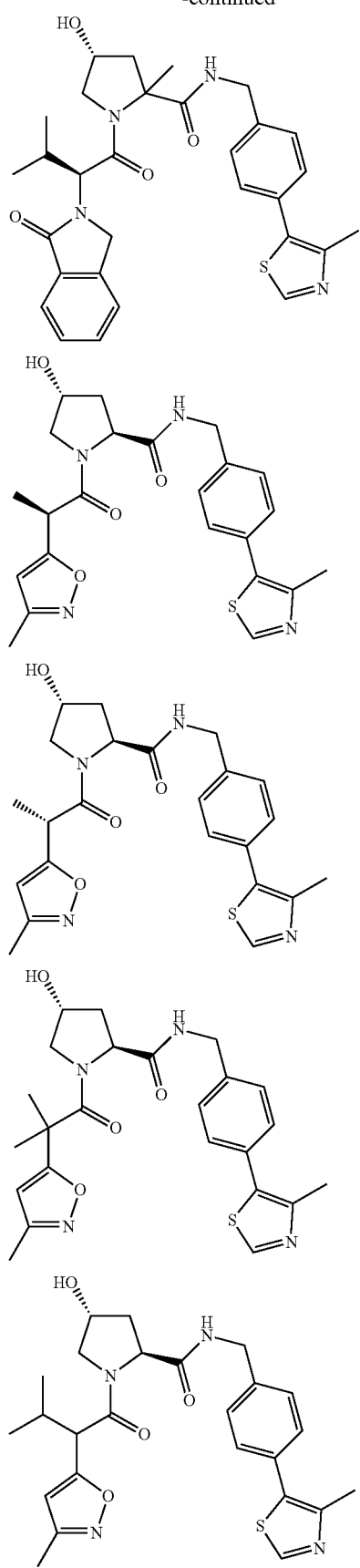
274
-continued
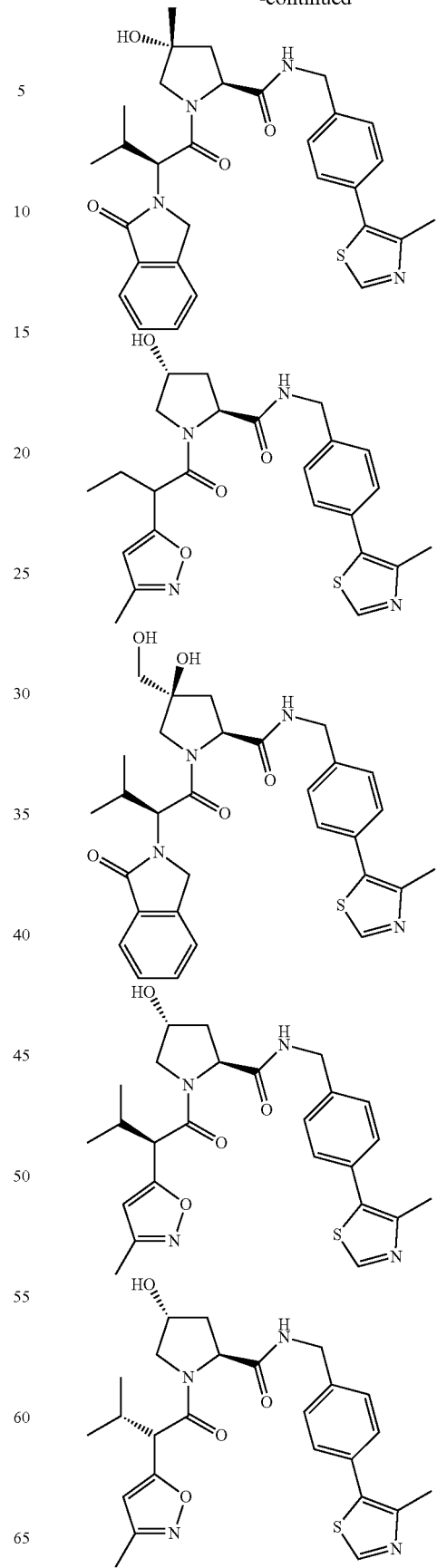

275
-continued
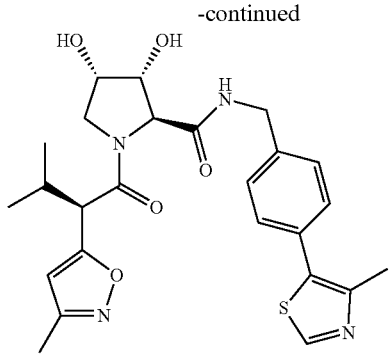
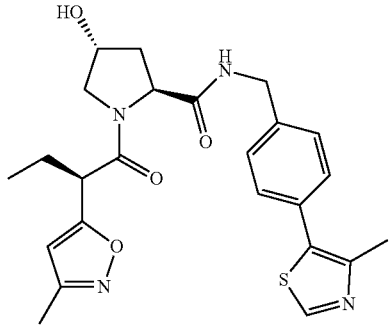
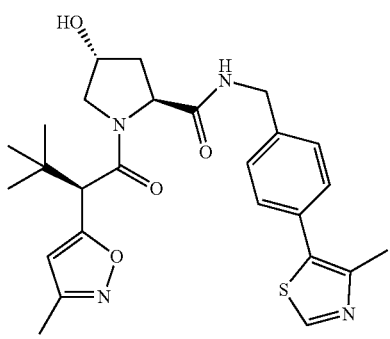
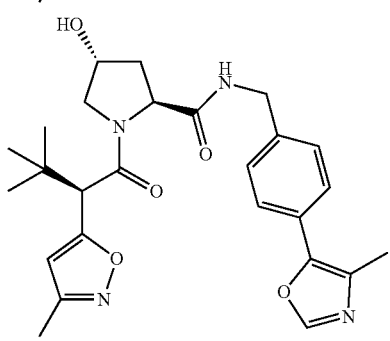
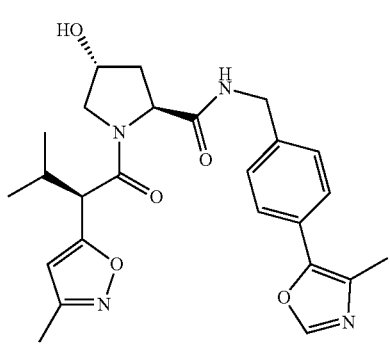
276
-continued
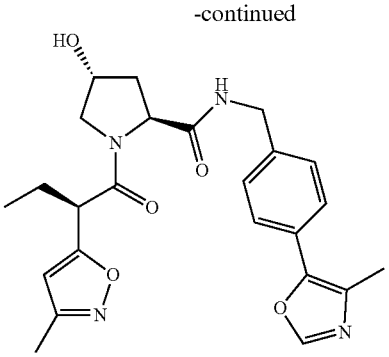
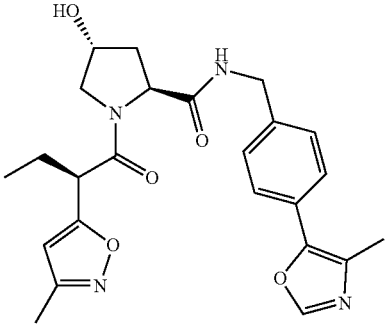
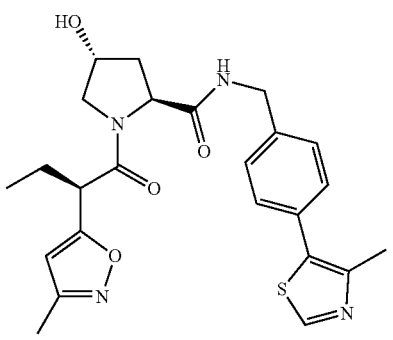
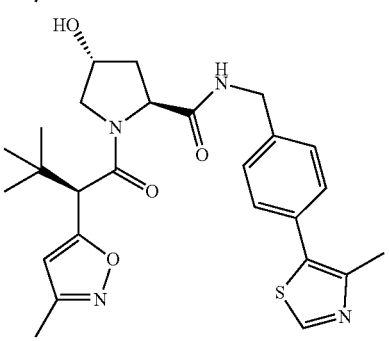
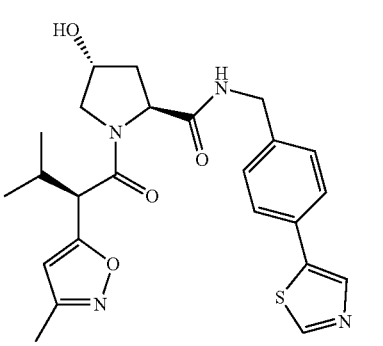

277
-continued
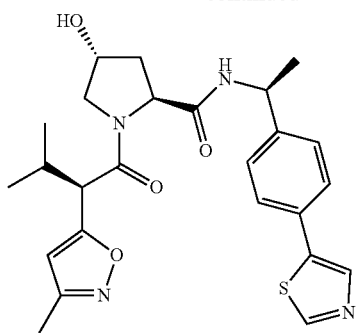
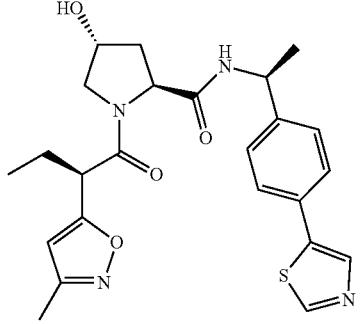
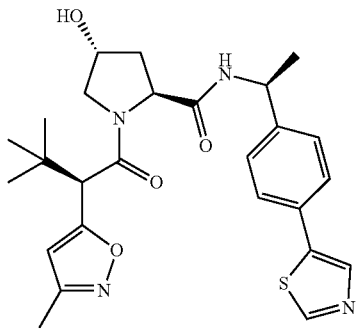
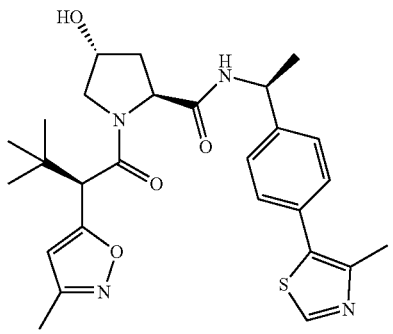
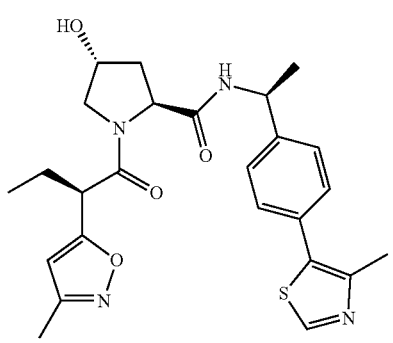
278
-continued
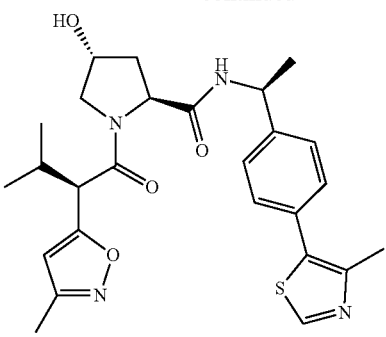
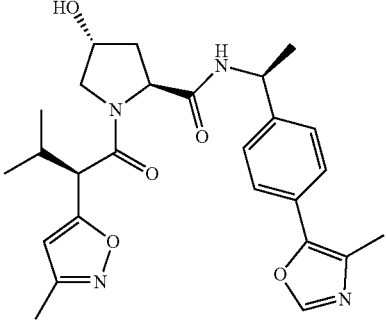
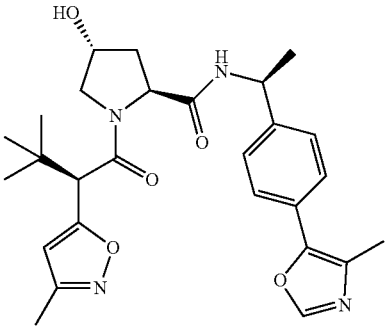
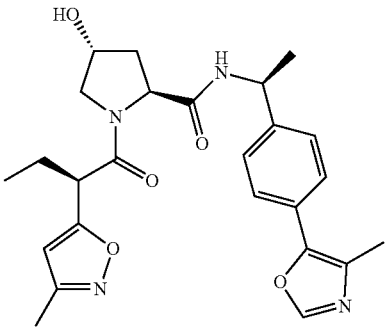
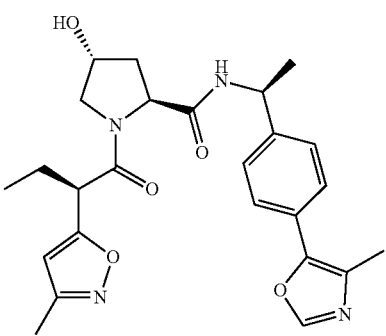

279
-continued
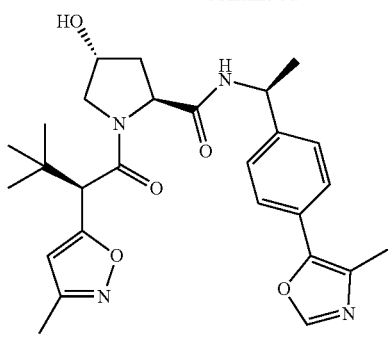
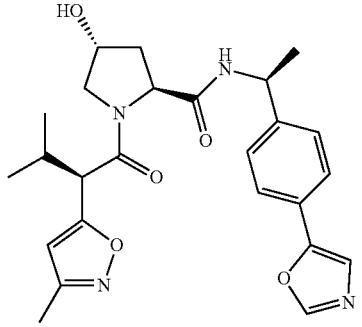
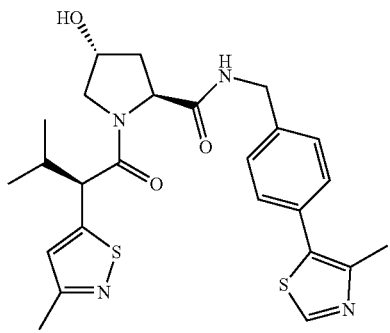
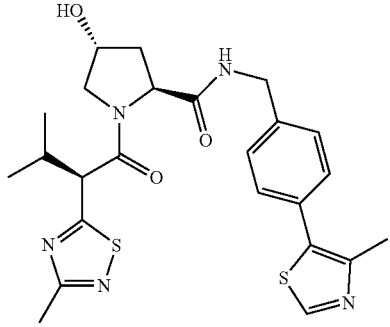
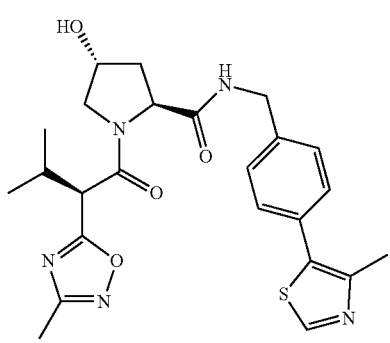
280
-continued
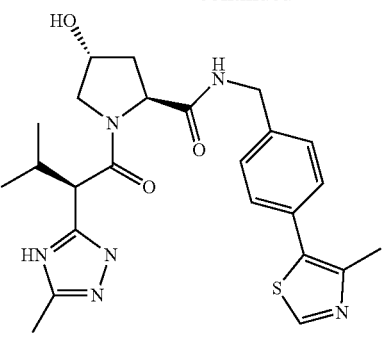
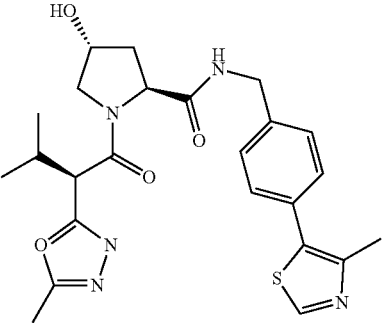
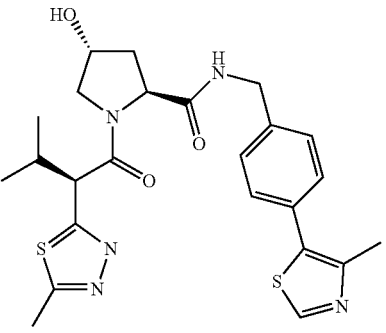
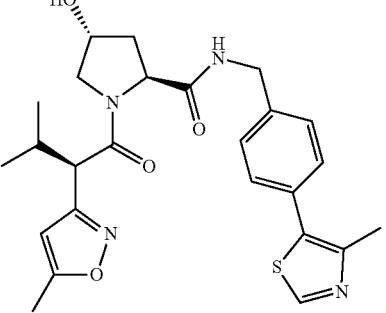
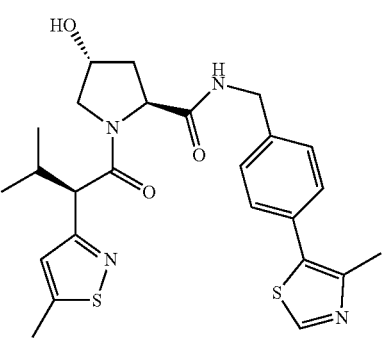

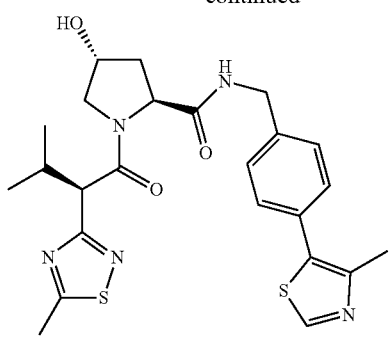
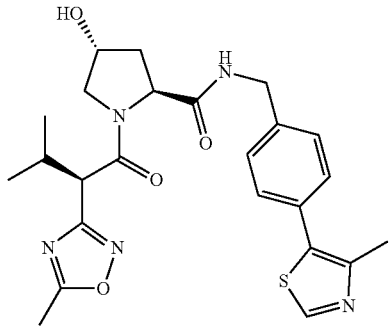
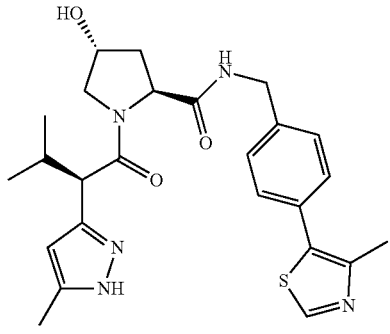
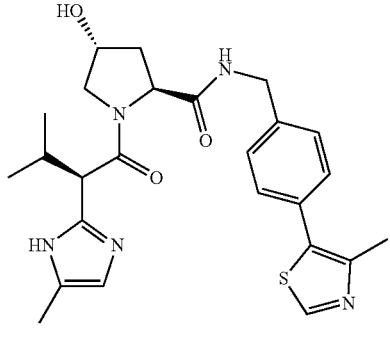
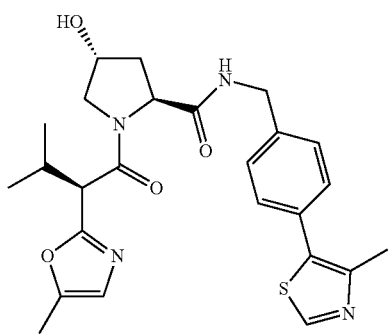
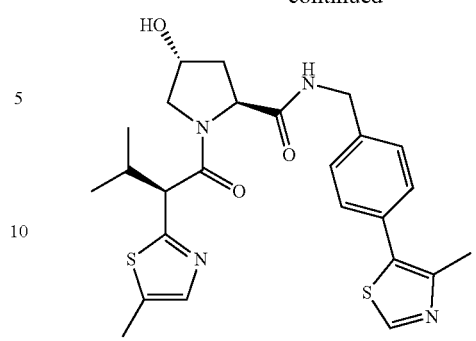
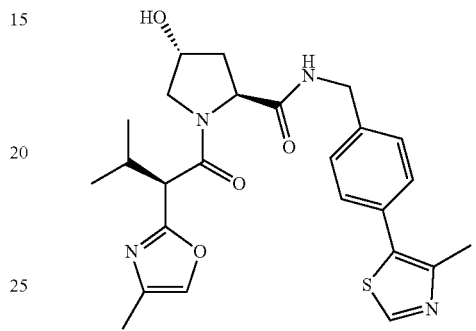
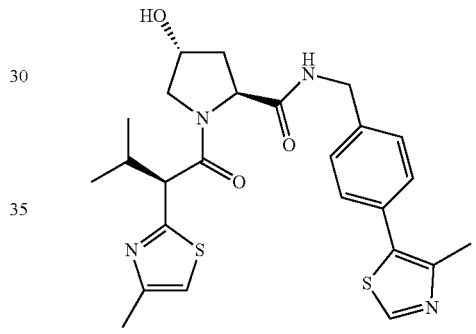
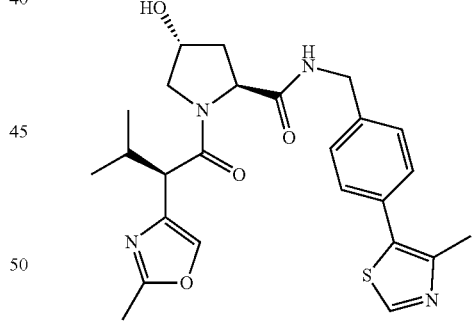
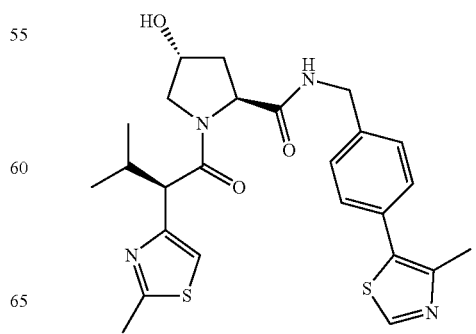

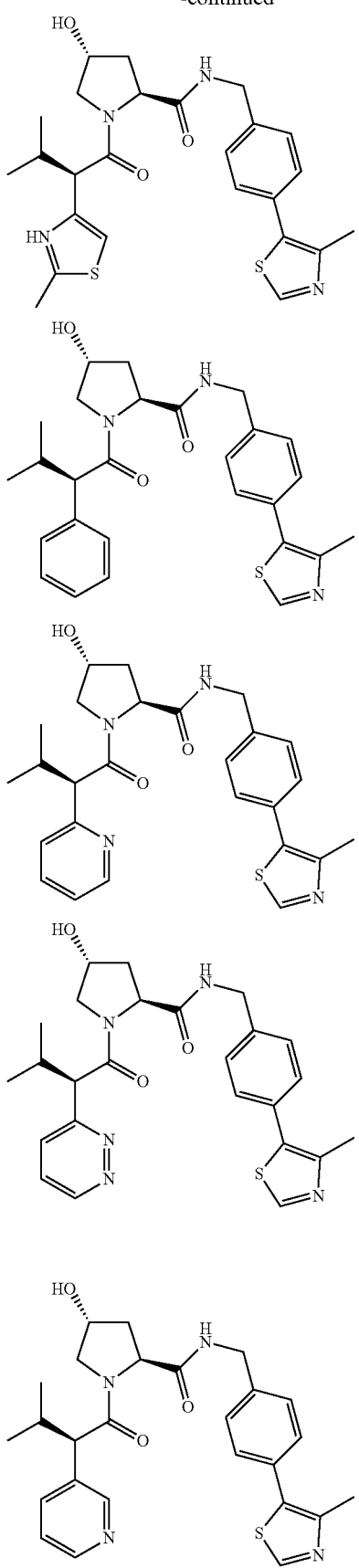
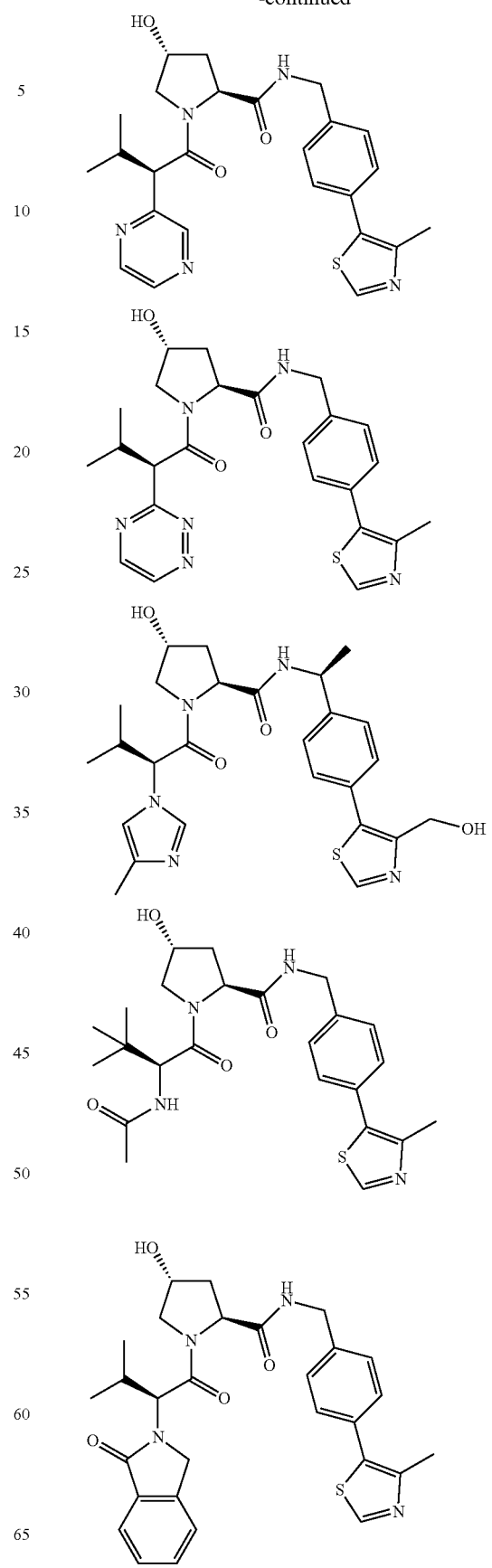

285
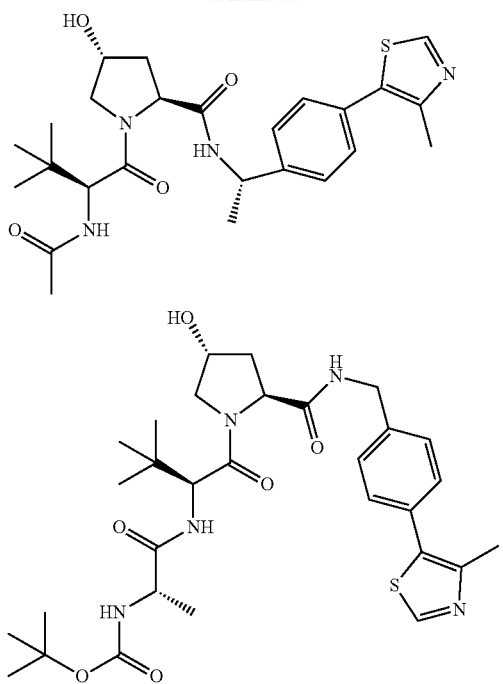
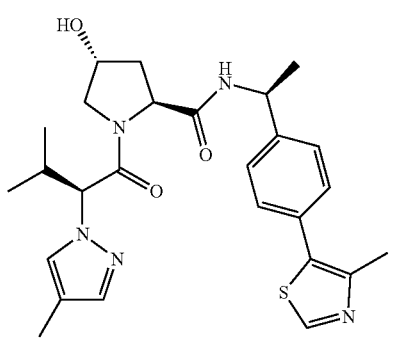
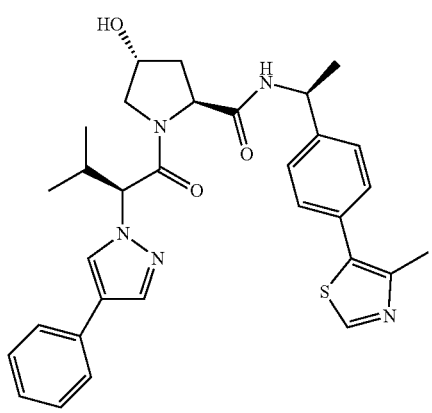
286
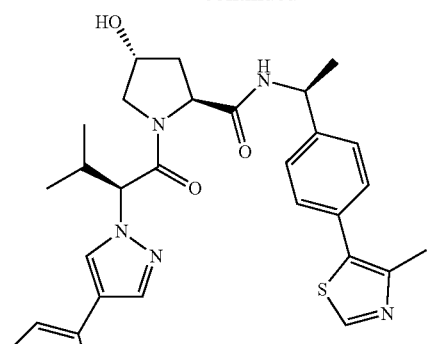
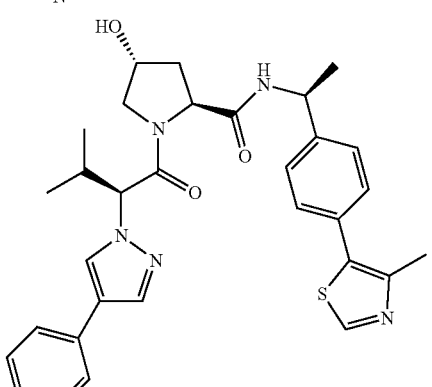
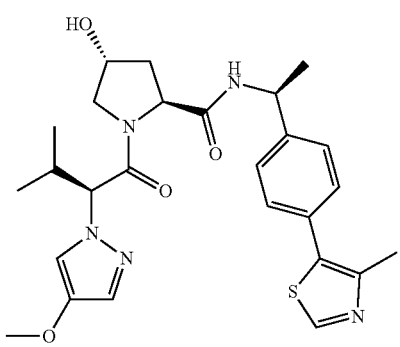
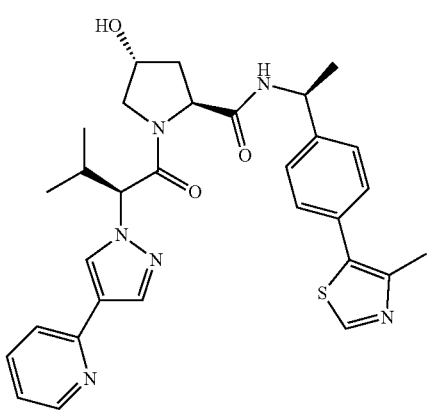

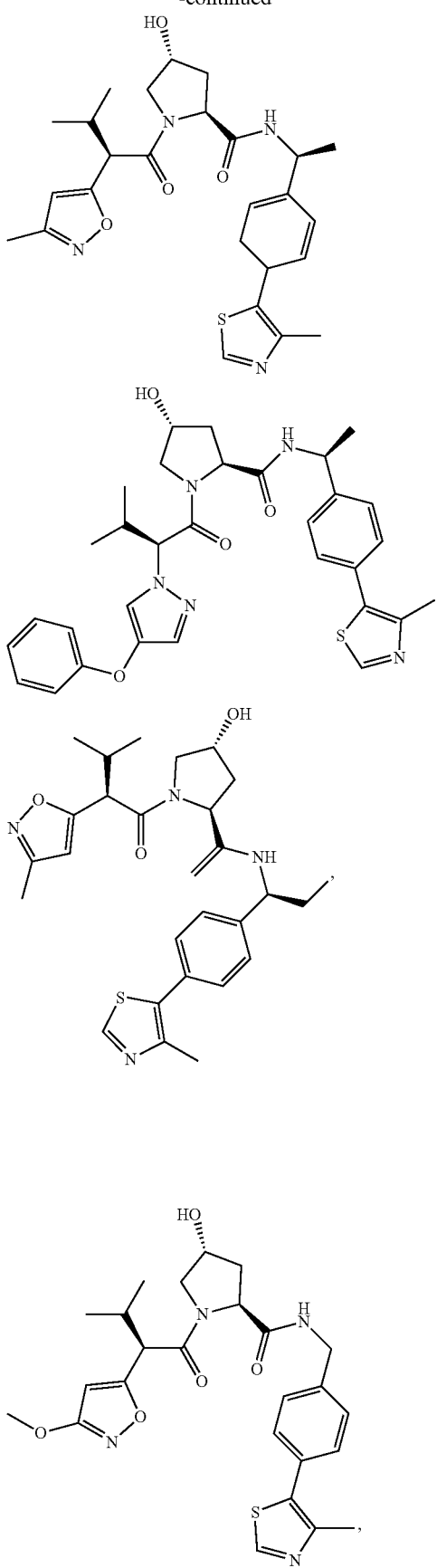

wherein the VLM may be connected to a PTM via a linker, as described herein, at any appropriate location, including, e.g., an aryl, heteroary, phenyl, or phenyl of an indole group, optionally via any appropriate functional group, such as an amine, ester, ether, alkyl, or alkoxy.

Exemplary Linkers

In certain embodiments, the compounds as described herein include one or more PTMs chemically linked or coupled to one or more ULMs (e.g., at least one of CLM, VLM, MLM, ILM, or a combination thereof) via a chemical linker (L). In certain embodiments, the linker group L is a group comprising one or more covalently connected structural units (e.g., -$A^L_1$ ... $A^L_q$- or -$(A^L)_q$-), wherein $A^L_1$ is a group coupled to PTM, and $(A^L)_q$ is a group coupled to ULM.

In certain embodiments, the linker group L is selected from -$(A^L)_q$-:

$(A^L)_q$ is a group which is connected to at least one of a ULM (such as CLM or a VLM), PTM moiety, or a combination thereof;

q of the linker is an integer greater than or equal to 1;

each $A^L$ is independently selected from the group consisting of, a bond, $CR^{L1}R^{L2}$, O, S, SO, $SO_2$, $NR^{L3}$, $SO_2NR^{L3}$, $SONR^{L3}$, $CONR^{L3}$, $NR^{L3}CONR^{L4}$, $NR^{L3}SO_2NR^{L4}$, CO, $CR^{L1}=CR^{L2}$, C≡C, $SiR^{L1}R^{L2}$, $P(O)R^{L1}$, $P(O)OR^{L1}$, $NR^{L3}C(=NCN)NR^{L4}$, $NR^{L3}C(=NCN)$, $NR^{L3}C(=CNO_2)NR^{L4}$, $C_{3-11}$cycloalkyl optionally substituted with 0-6 $R^{L1}$ and/or $R^{L2}$ groups, $C_{5-13}$ spirocycloalkyl optionally substituted with 0-9 $R^{L1}$ and/or $R^{L2}$ groups, $C_{3-11}$ heterocyclyl optionally substituted with 0-6 $R^{L1}$ and/or $R^{L2}$ groups, $C_{5-13}$ spiro-heterocycloalkyl optionally substituted with 0-8 $R^{L1}$ and/or $R^{L2}$ groups, aryl optionally substituted with 0-6

$R^{L1}$ and/or $R^{L2}$ groups, heteroaryl optionally substituted with 0-6 $R^{L1}$ and/or $R^{L2}$ groups, where $R^{L1}$ or $R^{L2}$, each independently are optionally linked to other groups to form cycloalkyl and/or heterocyclyl moiety, optionally substituted with 0-4 $R^{L5}$ groups; and $R^{L1}$, $R^{L2}$, $R^{L3}$, $R^{L4}$ and $R^{L5}$ are, each independently, H, halo, $C_{1-8}$alkyl, $OC^{1-8}$alkyl, $SC_{1-8}$alkyl, $NHC_{1-8}$alkyl, $N(C_{1-8}alkyl)_2$, $C_{3-11}$cycloalkyl, aryl, heteroaryl, $C_{3-11}$heterocyclyl, $OC_{1-8}$cycloalkyl, $SC_{1-8}$cycloalkyl, $NHC_{1-8}$cycloalkyl, $N(C_{1-8}cycloalkyl)_2$, $N(C_{1-8}cycloalkyl)(C_{1-8}alkyl)$, OH, $NH_2$, SH, $SO_2C_{1-8}$alkyl, $P(O)(OC_{1-8}alkyl)(C_{1-8}alkyl)$, $P(O)(OC_{1-8}alkyl)_2$, $CC-C_{1-8}$alkyl, CCH, $CH=CH(C_{1-8}alkyl)$, $C(C_{1-8}alkyl)=CH(C_{1-8}alkyl)$, $C(C_{1-8}alkyl)=C(C_{1-8}alkyl)_2$, $Si(OH)_3$, $Si(C_{1-8}alkyl)_3$, $Si(OH)(C_{1-8}alkyl)_2$, $COC_{1-8}$alkyl, $CO_2H$, halogen, CN, $CF_3$, $CHF_2$, $CH_2F$, $NO_2$, $SF_5$, $SO_2NHC_{1-8}$alkyl, $SO_2N(C_{1-8}alkyl)_2$, $SONHC_{1-8}$alkyl, $SON(C_{1-8}alkyl)_2$, $CONHC_{1-8}$alkyl, $CON(C_{1-8}alkyl)_2$, $N(C_{1-8}alkyl)CONH(C_{1-8}alkyl)$, $N(C_{1-8}alkyl)CON(C_{1-8}alkyl)_2$, $NHCONH(C_{1-8}alkyl)$, $NHCON(C_{1-8}alkyl)_2$, $NHCONH_2$, $N(C_{1-8}alkyl)SO_2NH(C_{1-8}alkyl)$, $N(C_{1-8}alkyl) SO_2N(C_{1-8}alkyl)_2$, NH $SO_2NH(C_{1-8}alkyl)$, NH $SO_2N(C_{1-8}alkyl)_2$, NH $SO_2NH_2$.

In certain embodiments, q of the linker is an integer greater than or equal to 0. In certain embodiments, q is an integer greater than or equal to 1.

In certain embodiments, e.g., where q of the linker is greater than 2, $A^L_q$ is a group which is connected to ULM, and $A^L_1$ and $A^L_q$ are connected via structural units of the linker (L).

In certain embodiments, e.g., where q of the linker is 2, $A^L_q$ is a group which is connected to $A^L_1$ and to a ULM.

In certain embodiments, e.g., where q of the linker is 1, the structure of the linker group L is -$A^L_1$-, and $A^L_1$ is a group which is connected to a ULM moiety and a PTM moiety.

In certain embodiments, the linker (L) comprises a group represented by a general structure selected from the group consisting of:

—NR(CH₂)ₙ-(lower alkyl)-, —NR(CH₂)ₙ-(lower alkoxyl)-, —NR(CH₂)ₙ-(lower alkoxyl)-OCH₂—, —NR(CH₂)ₙ-(lower alkoxyl)-(lower alkyl)-OCH₂—, —NR(CH₂)ₙ-(cycloalkyl)-(lower alkyl)-OCH₂—, —NR(CH₂)ₙ-(hetero cycloalkyl)-, —NR(CH₂CH₂O)ₙ-(lower alkyl)-O—CH₂—, —NR(CH₂CH₂O)ₙ-(hetero cycloalkyl)-O—CH₂—, —NR(CH₂CH₂O)ₙ-Aryl-O—CH₂—, —NR(CH₂CH₂O)ₙ-(hetero aryl)-O—CH₂—, —NR(CH₂CH₂O)ₙ-(cyclo alkyl)-O-(hetero aryl)-O—CH₂—, —NR(CH₂CH₂O)ₙ-(cyclo alkyl)-O-Aryl-O—CH₂—, —NR(CH₂CH₂O)ₙ-(lower alkyl)-NH-Aryl-O—CH₂—, —NR(CH₂CH₂O)ₙ-(lower alkyl)-O-Aryl-CH₂, —NR(CH₂CH₂O)ₙ-cycloalkyl-O-Aryl-, —NR(CH₂CH₂O)ₙ-cycloalkyl-O-(hetero aryl)l-, —NR(CH₂CH₂O)ₙ-(cycloalkyl)-O-(heterocycle)-CH₂, —NR(CH₂CH₂O)ₙ-(heterocycle)-(heterocycle)-CH₂, —N(R¹R²)-(heterocycle)-CH₂; where n of the linker can be 0 to 10;

R of the linker can be H, lower alkyl;

R1 and R2 of the linker can form a ring with the connecting N.

In any aspect or embodiment described herein, the linker (L) comprises a group represented by a structure selected from the group consisting of:

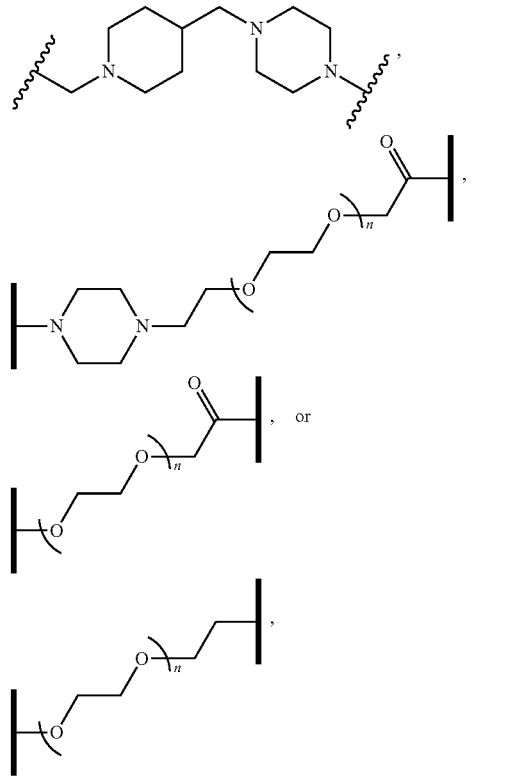

wherein n is 0, 1, 2, 3, 4, 5, 6, 7, 8, 9, or 10.

In certain embodiments, the linker (L) comprises a group represented by a general structure selected from the group consisting of:

—N(R)—(CH₂)ₘ—O(CH₂)ₙ—O(CH₂)ₒ—O(CH₂)ₚ—O(CH₂)ᵩ—O(CH₂)ᵣ—OCH₂—, —O—(CH₂)ₘ—O(CH₂)ₙ—O(CH₂)ₒ—O(CH₂)ₚ—O(CH₂)ᵩ—O(CH₂)ᵣ—OCH₂—, —O—(CH₂)ₘ—O(CH₂)ₙ—O(CH₂)ₒ—O(CH₂)ₚ—O(CH₂)ᵩ—O(CH₂)ᵣ—O—; —N(R)—(CH₂)ₘ—O(CH₂)ₙ—O(CH₂)ₒ—O(CH₂)ₚ—O(CH₂)ᵩ—O(CH₂)ᵣ—O—; —(CH₂)ₘ—O(CH₂)ₙ—O(CH₂)ₒ—O(CH₂)ₚ—O(CH₂)ᵩ—O(CH₂)ᵣ—O—; —(CH₂)ₘ—O(CH₂)ₙ—O(CH₂)ₒ—O(CH₂)ₚ—O(CH₂)ᵩ—O(CH₂)ᵣ—OCH₂—;

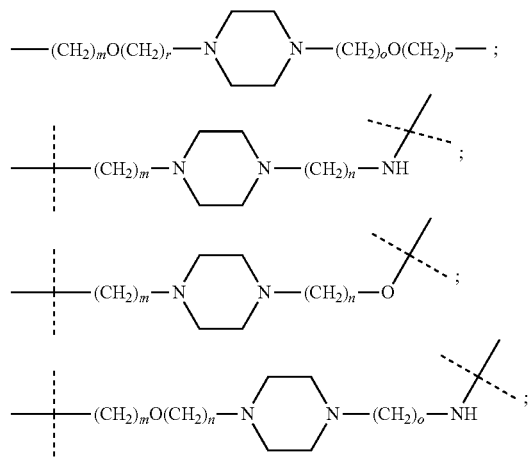

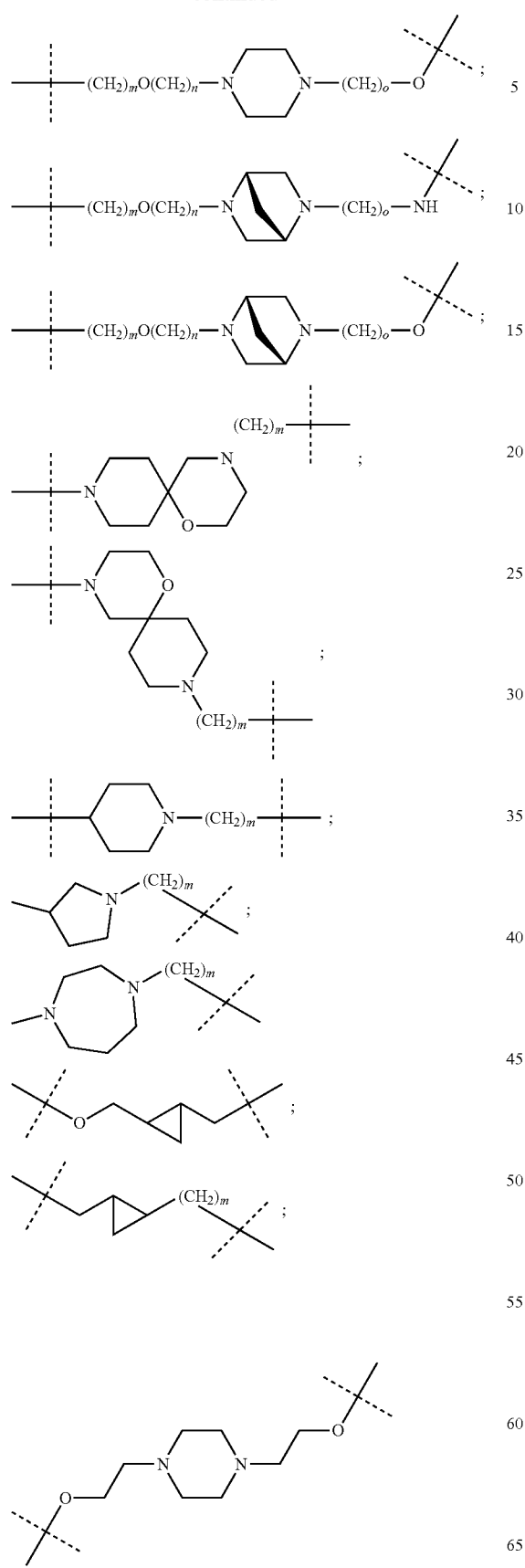
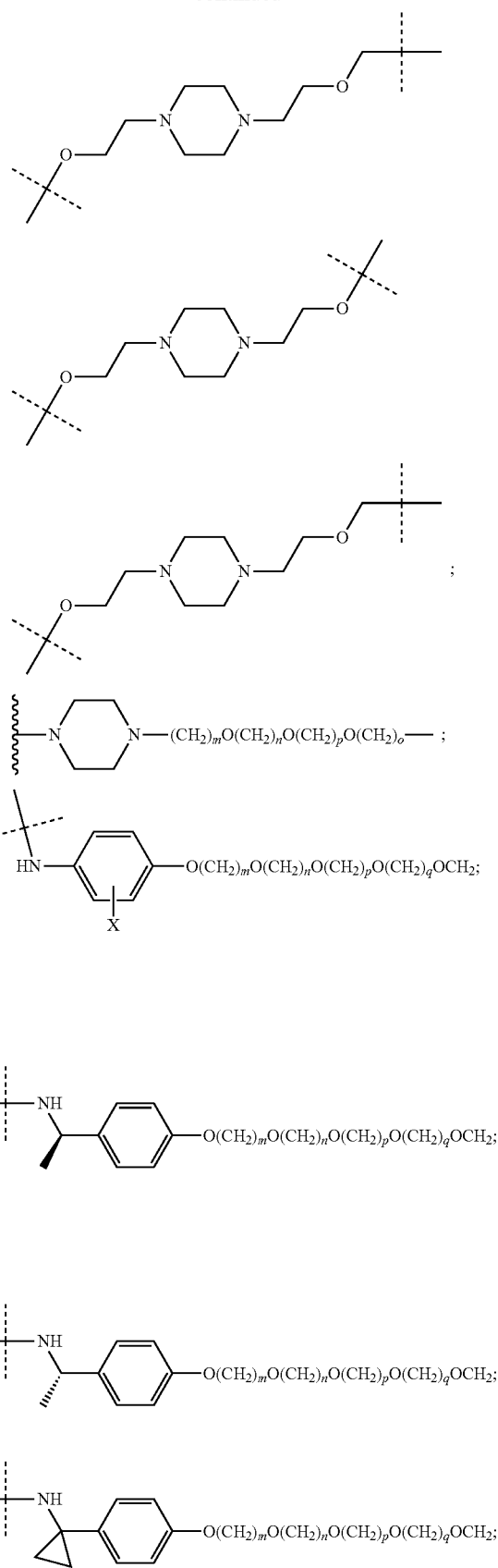

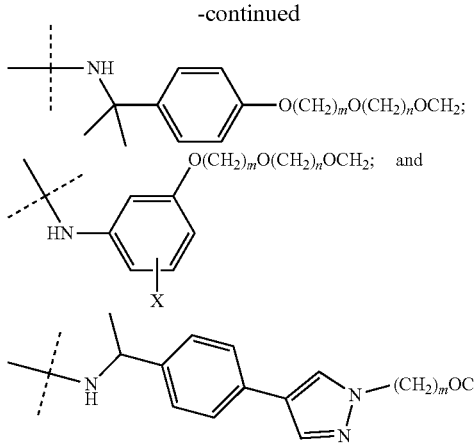
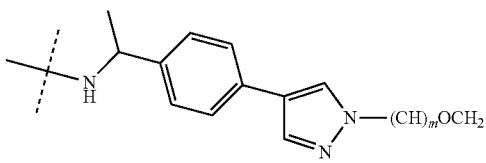
wherein
m, n, o, p, q, and r of the linker are independently 0, 1, 2, 3, 4, 5, 6;
when the number is zero, there is no N—O or O—O bond
R of the linker is H, methyl and ethyl;
X of the linker is H and F
where m of the linker can be 2, 3, 4, 5
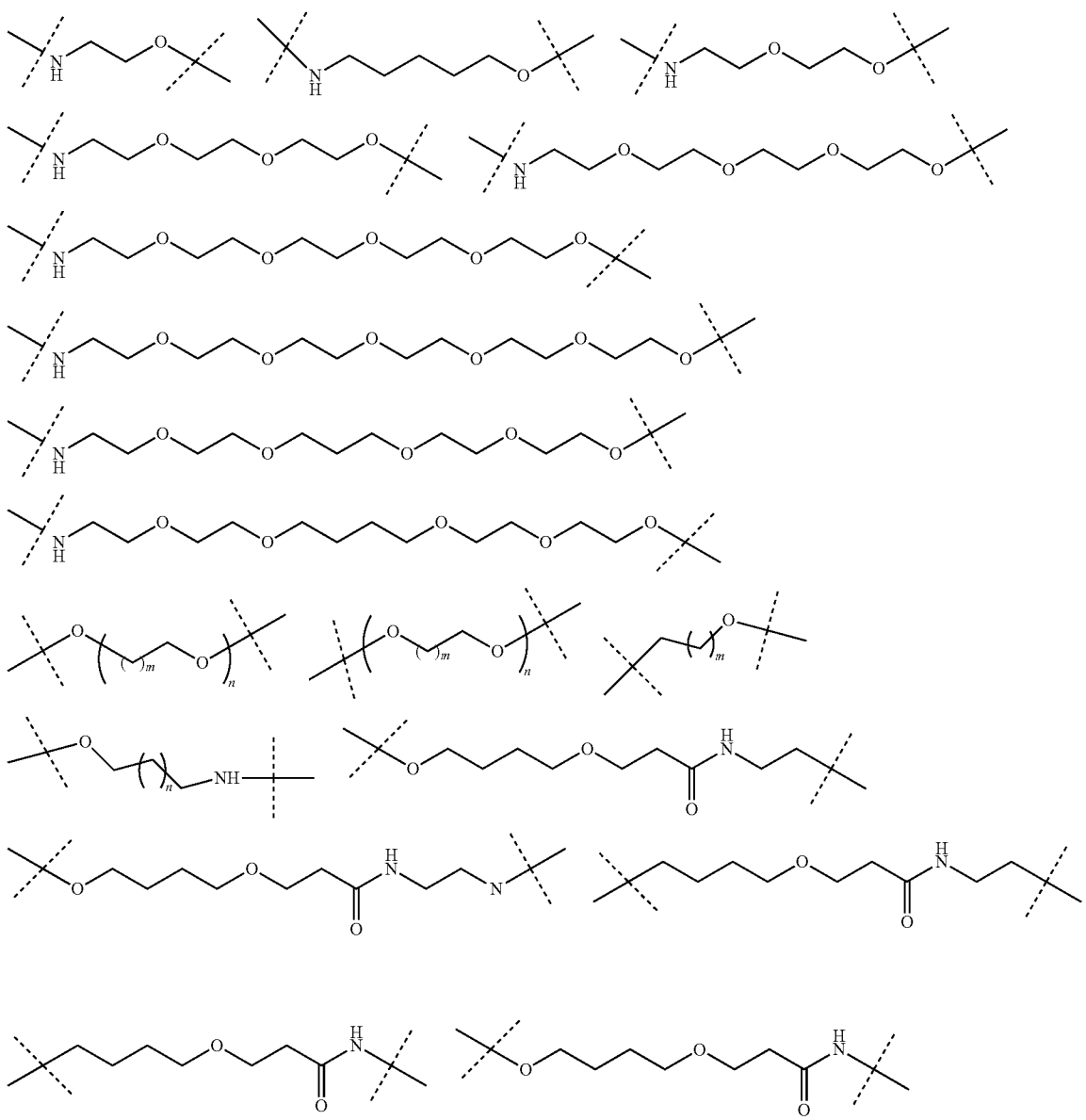

-continued
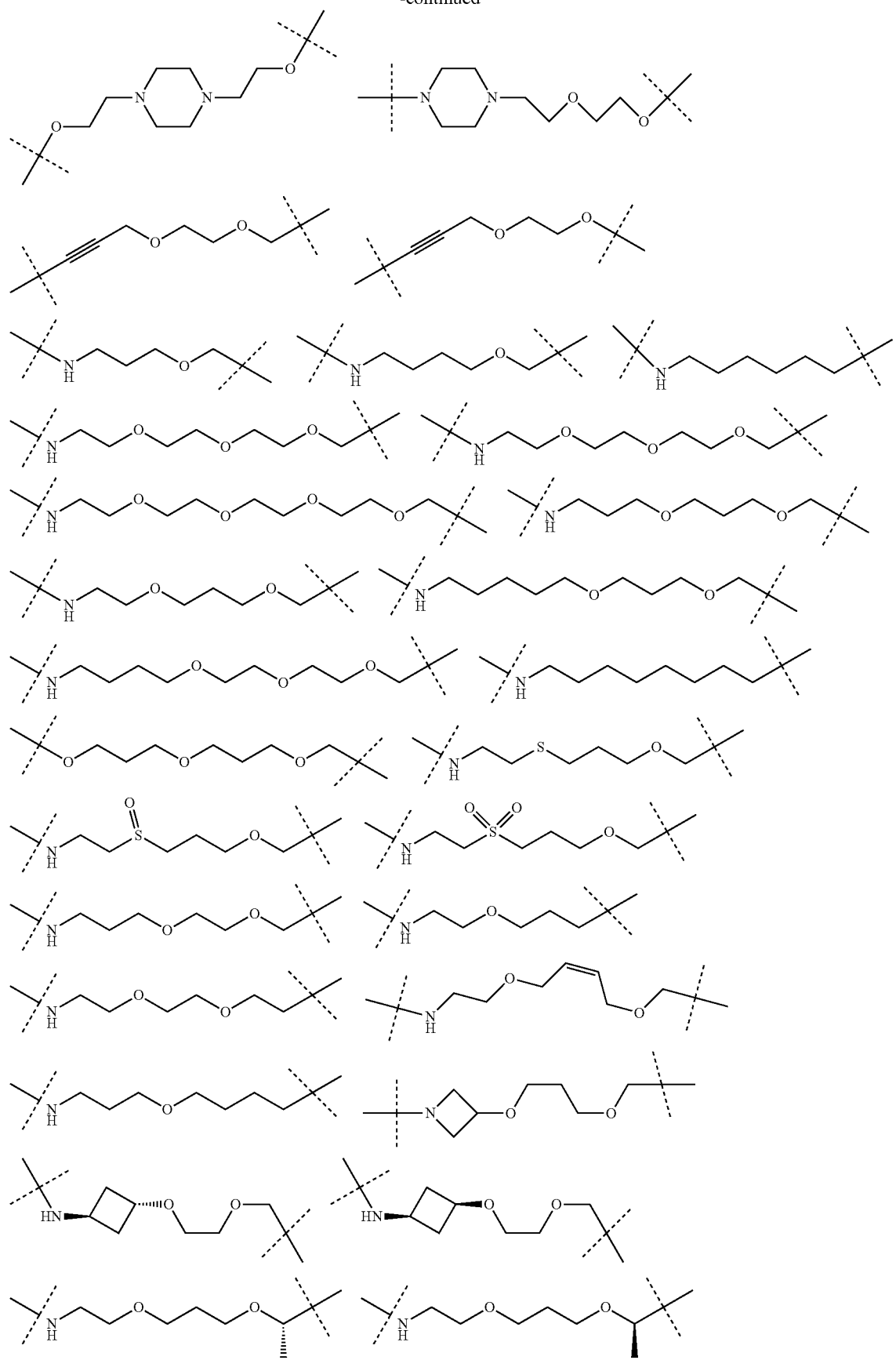

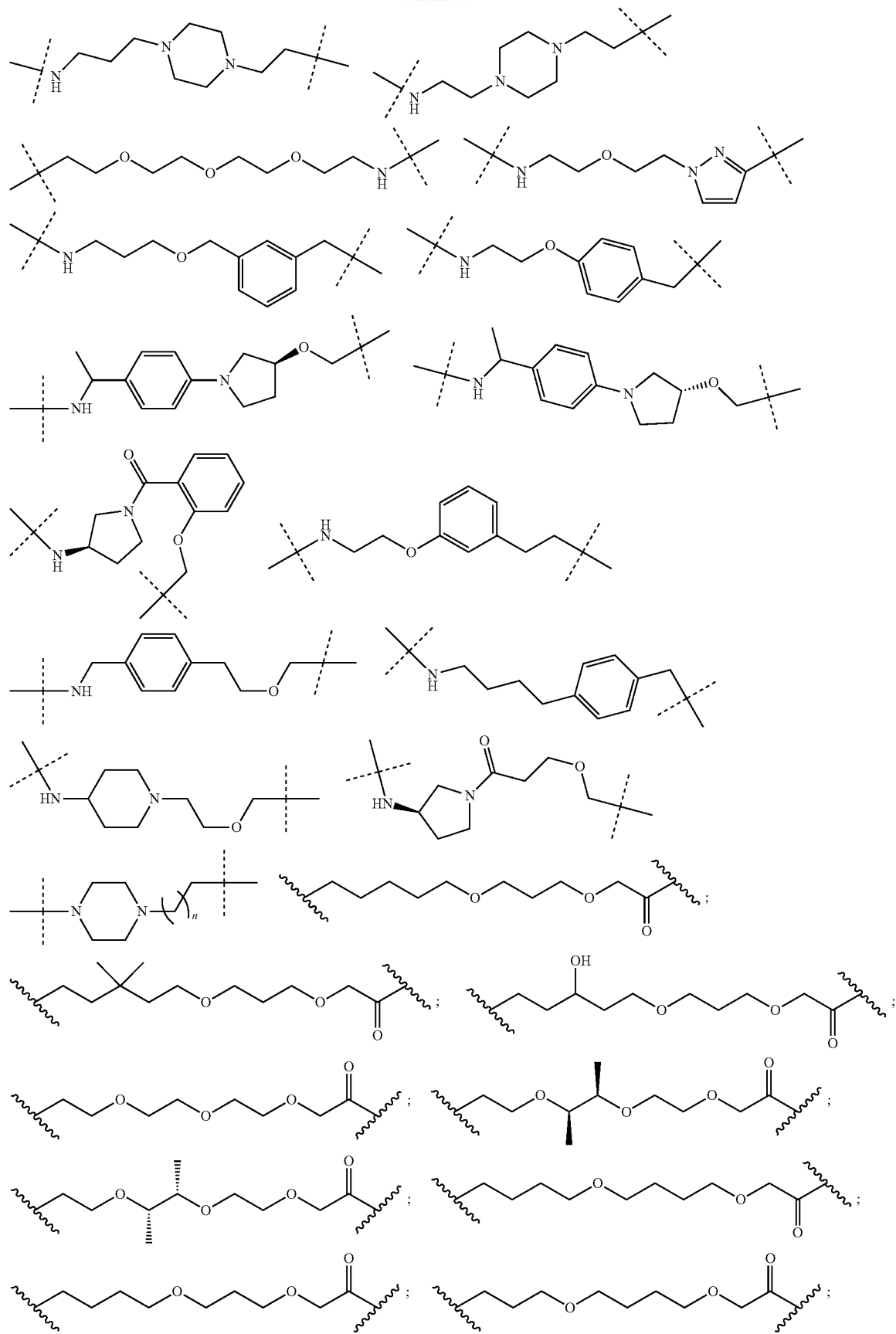

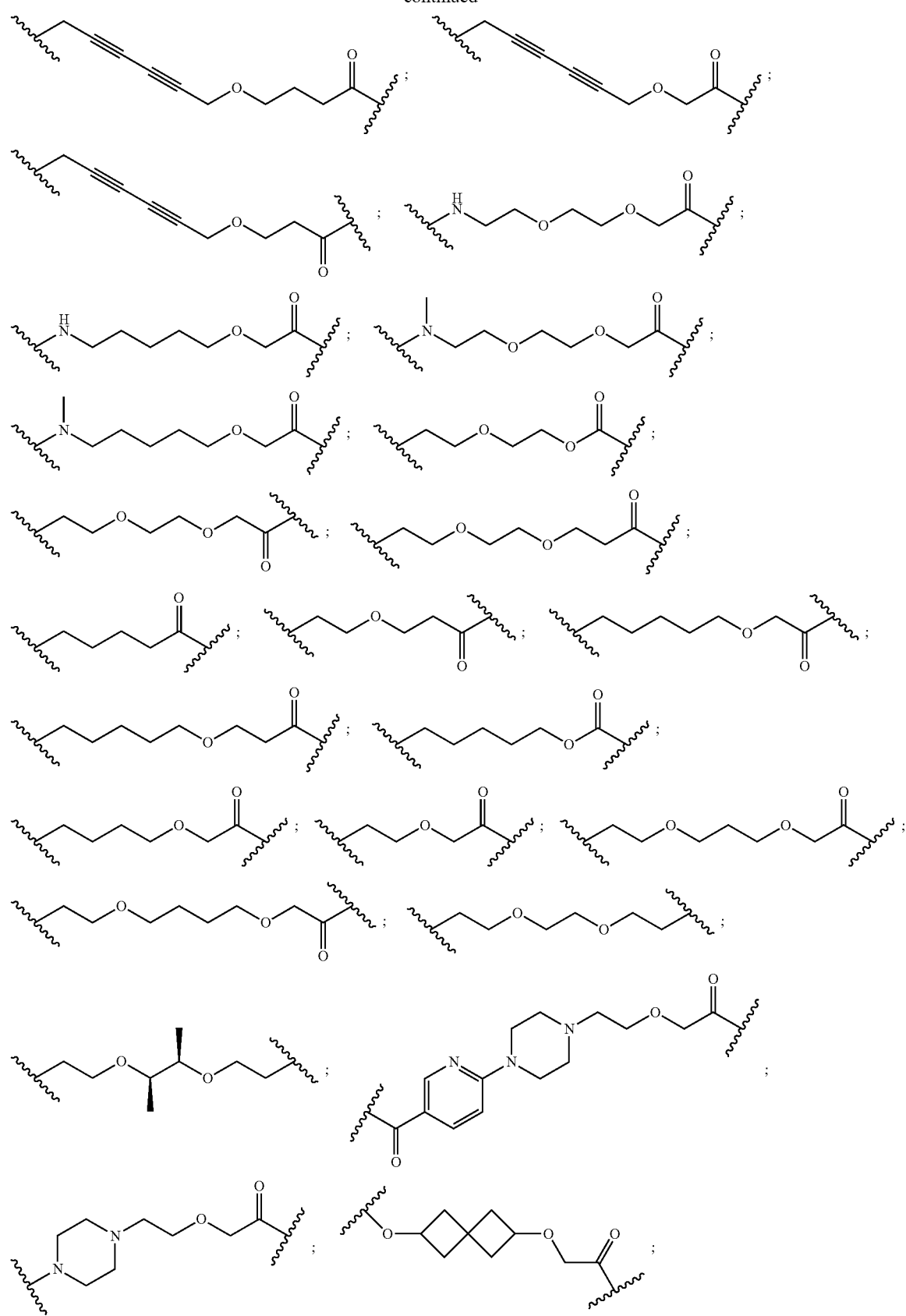

301
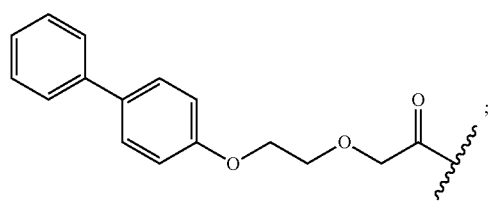
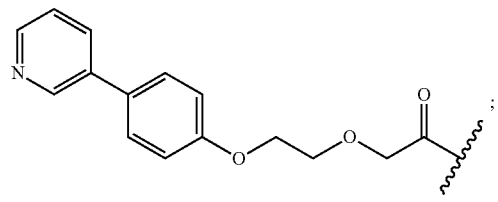
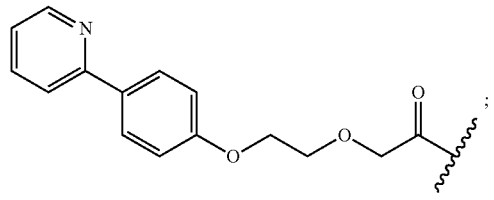
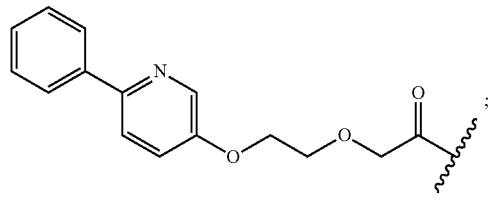
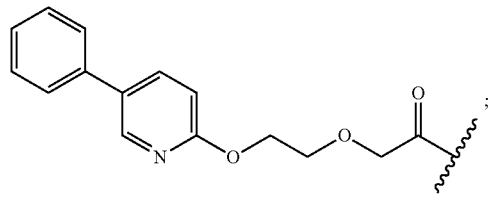
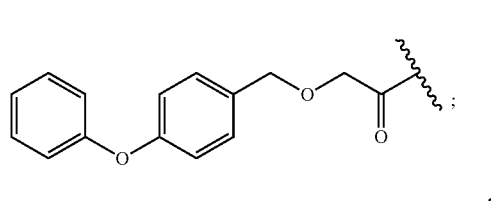
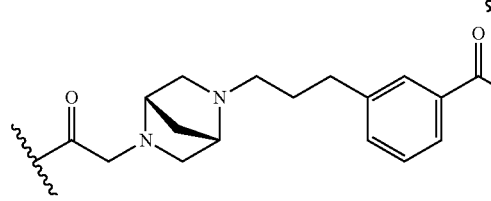
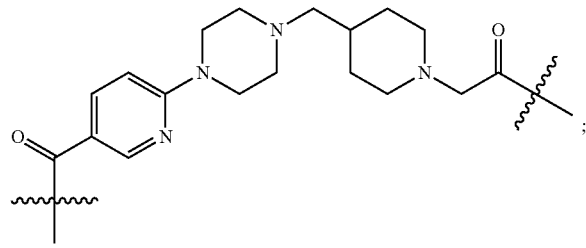
302
-continued
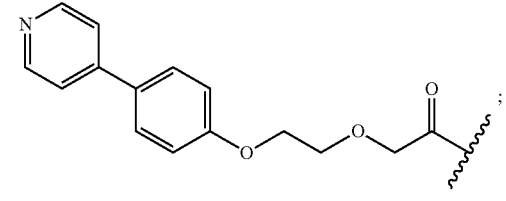
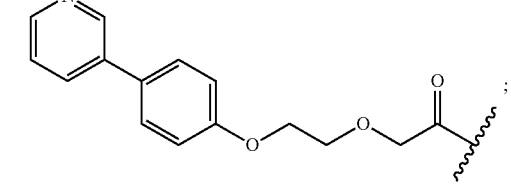
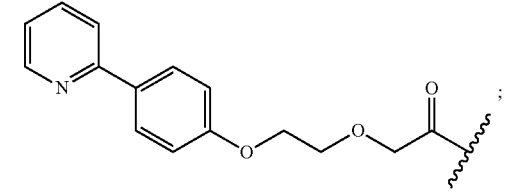
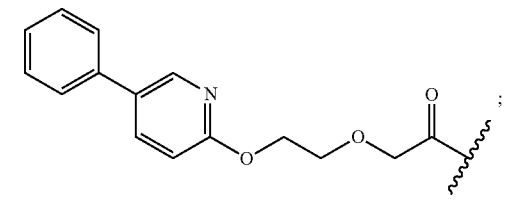
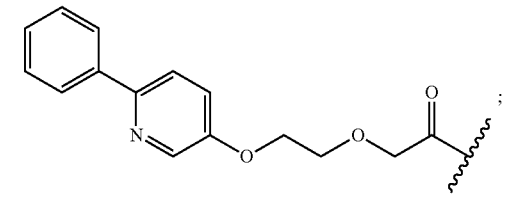
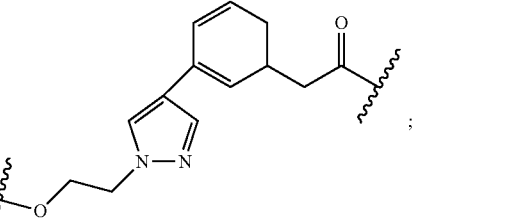
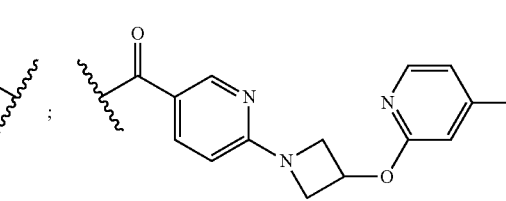
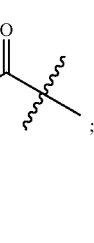

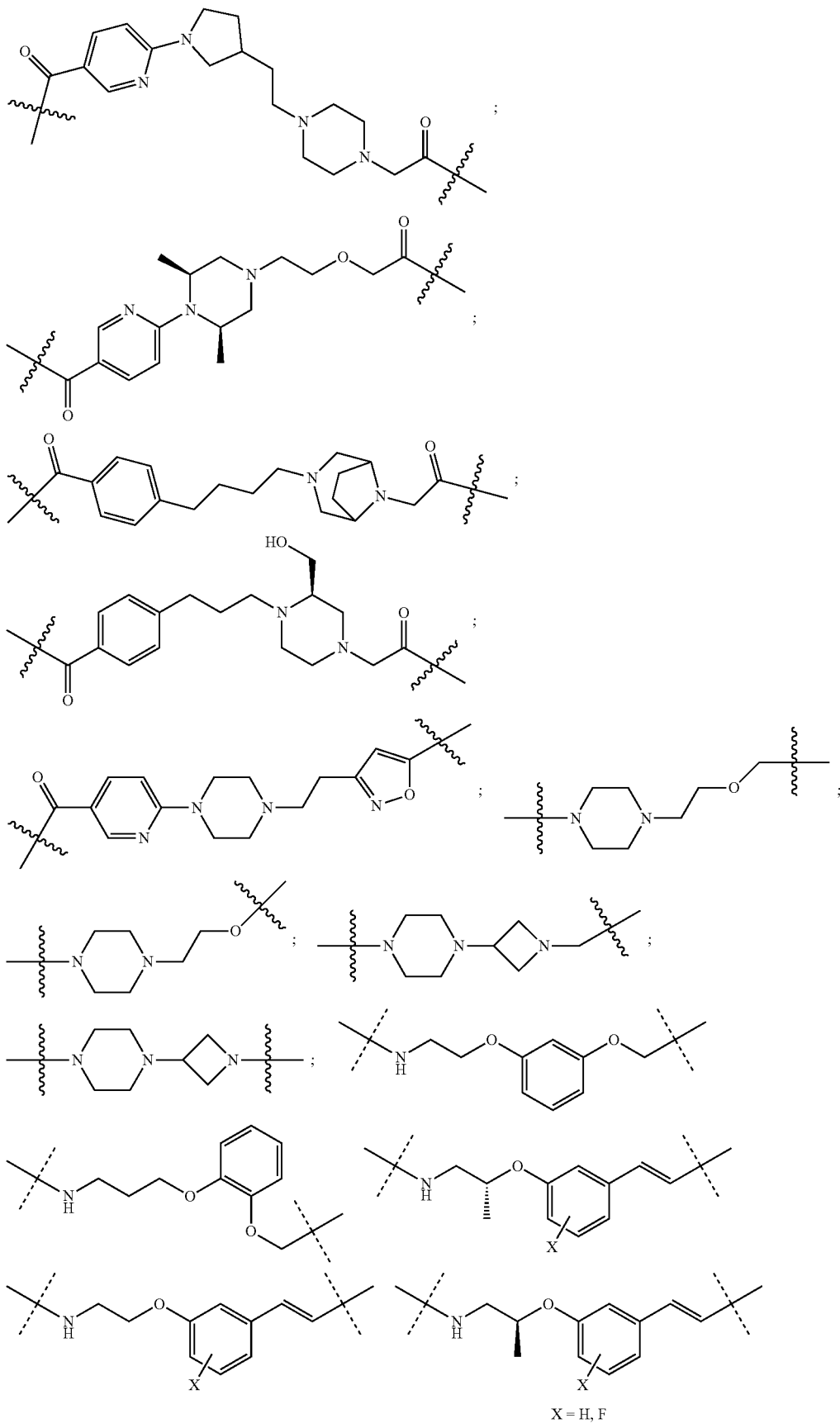

-continued
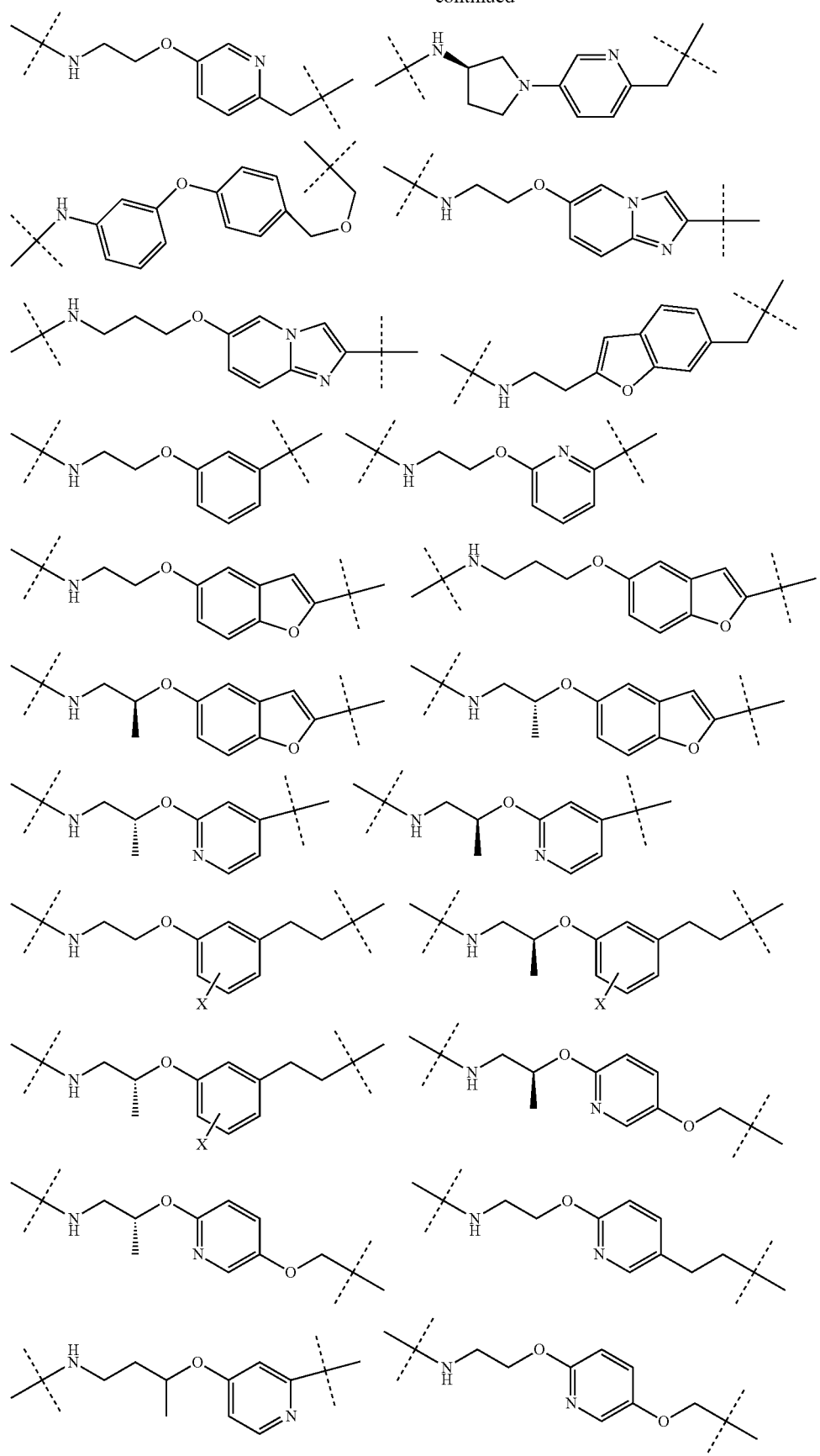

-continued
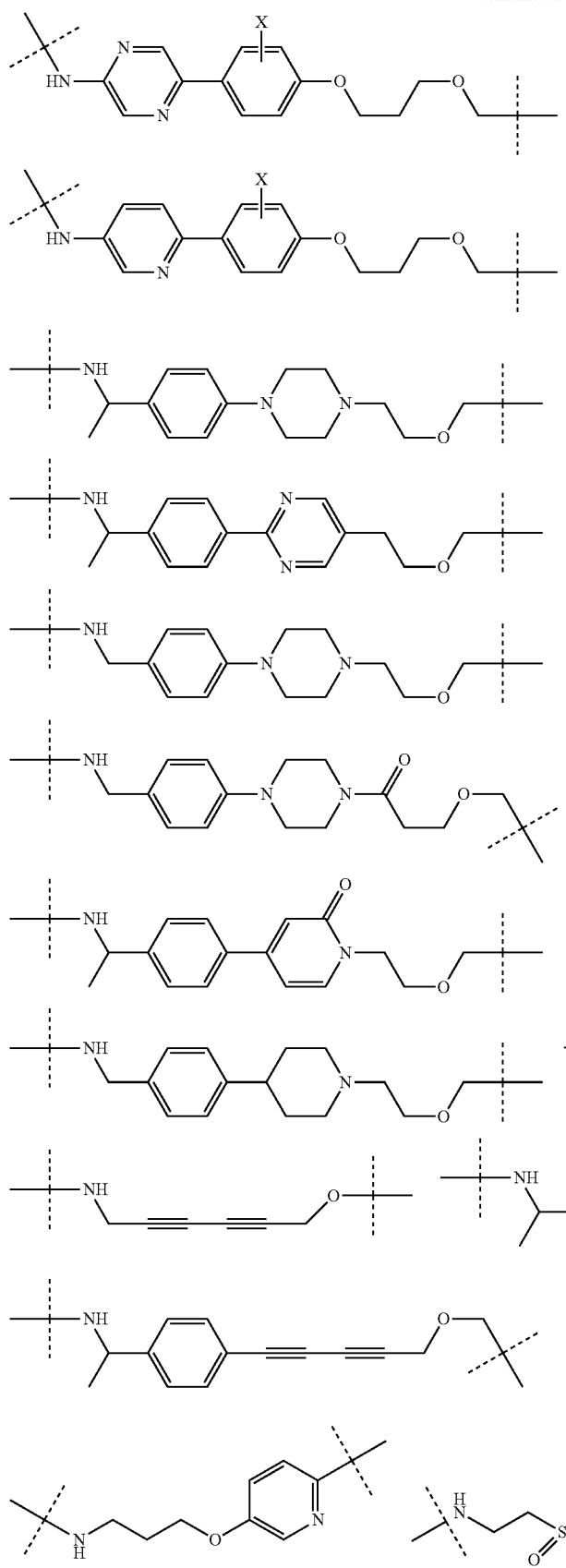

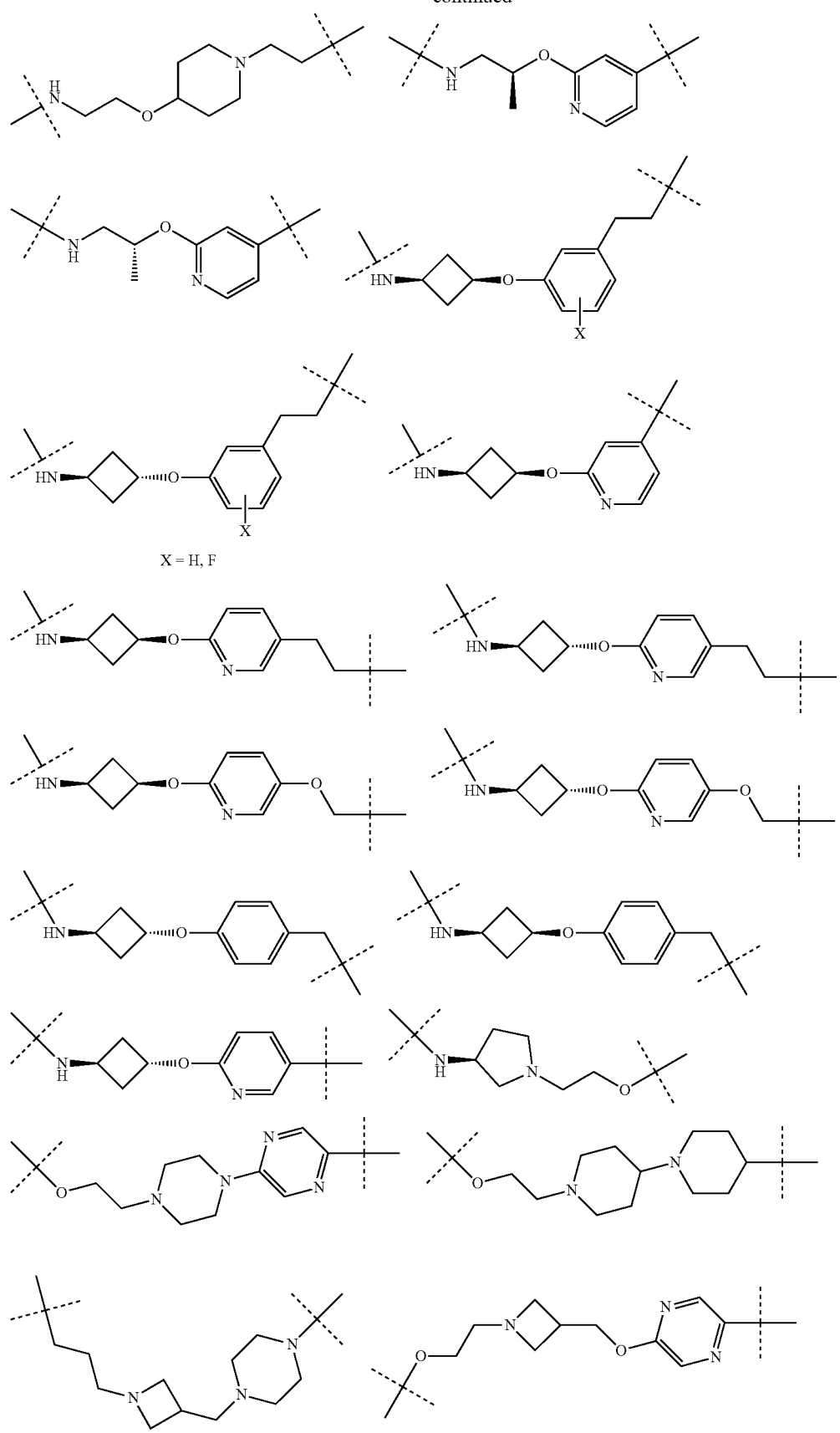

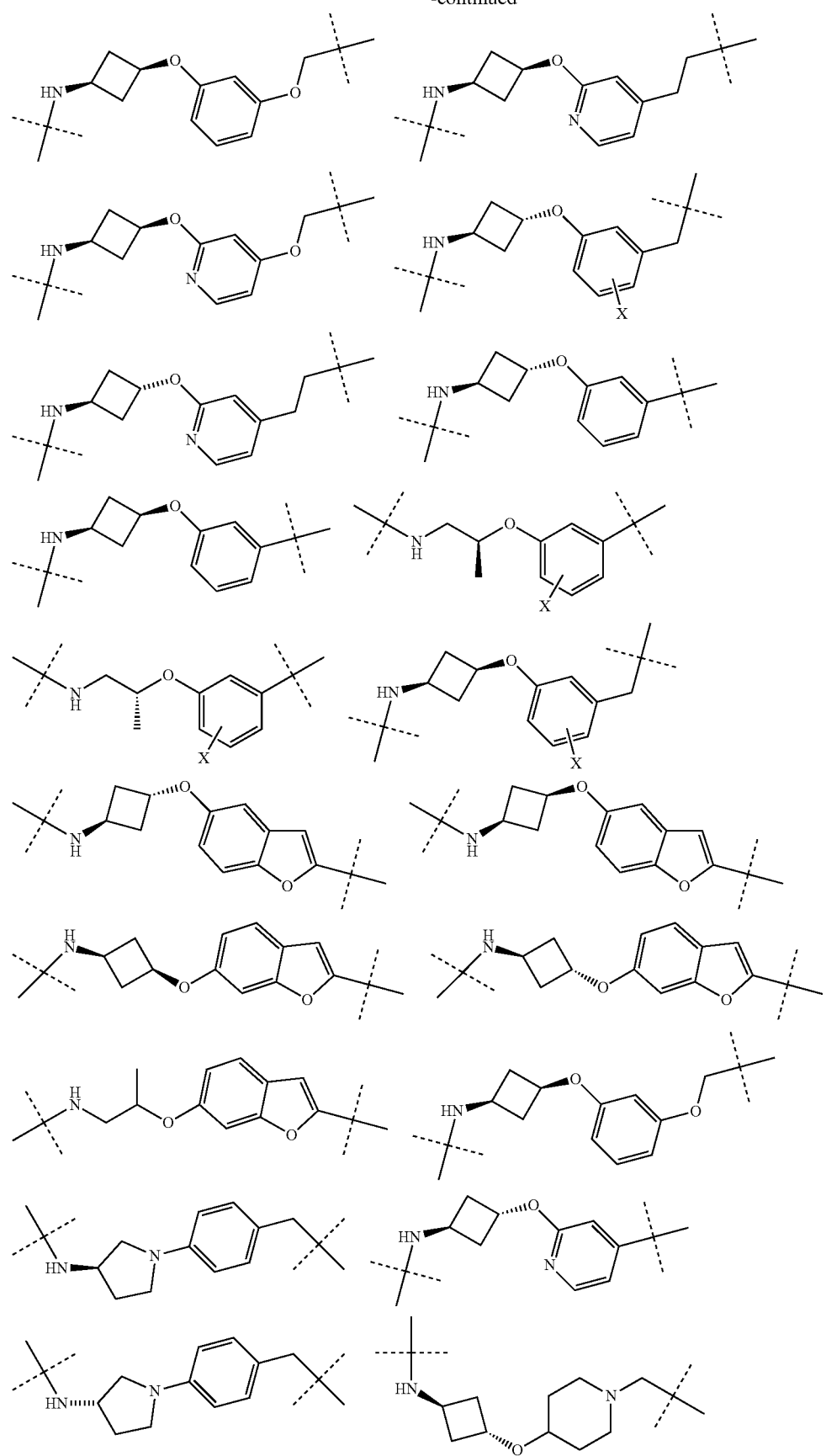

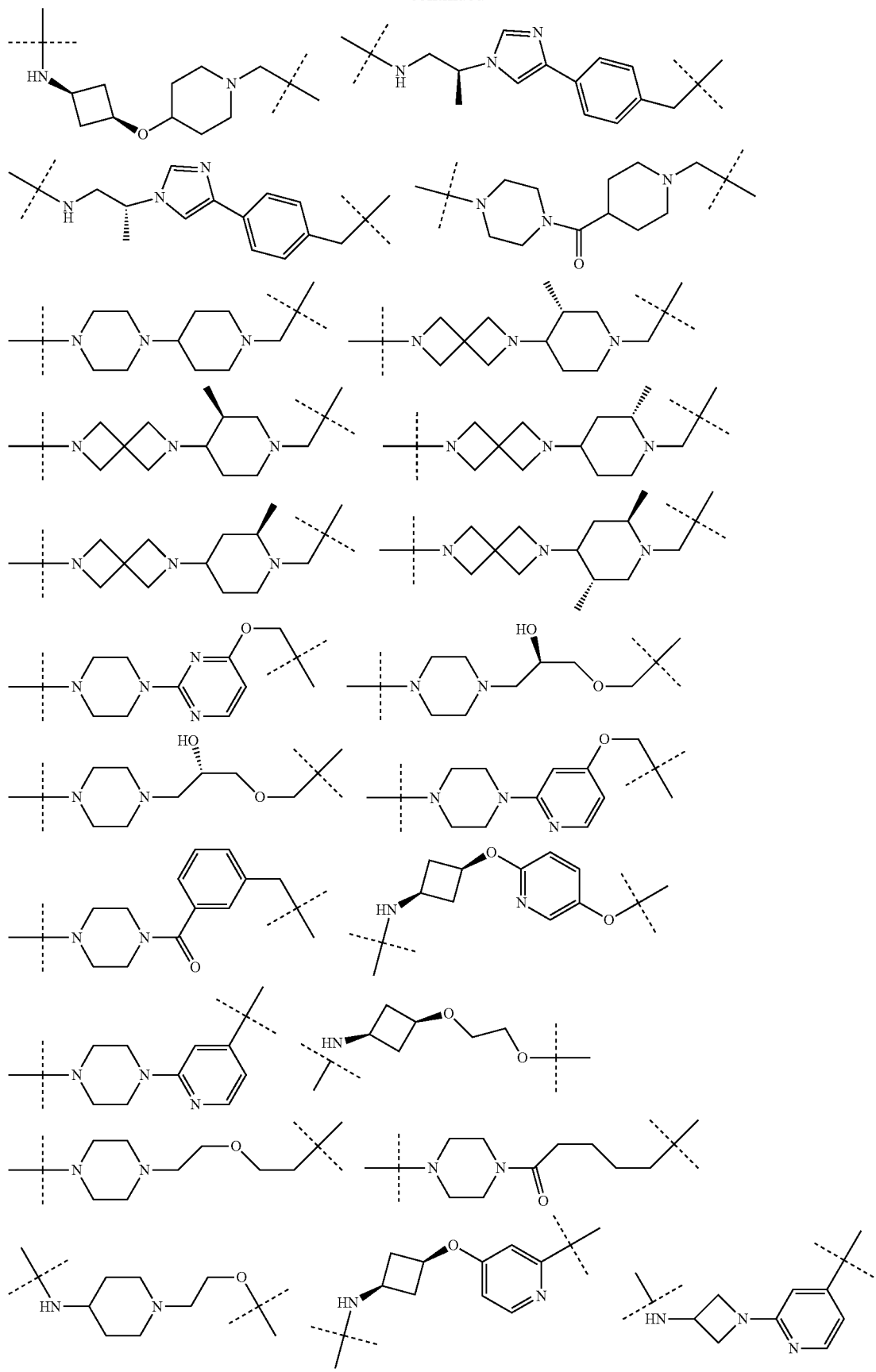

-continued
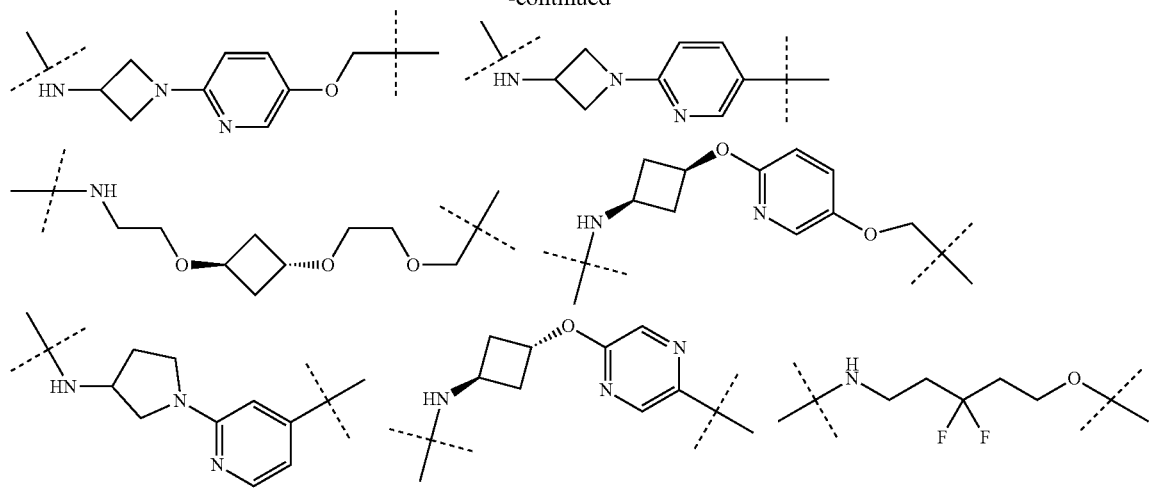
wherein each n and m of the linker can independently be 0, 1, 2, 3, 4, 5, 6.
In any aspect or embodiment described herein, the linker (L) is selected from the group consisting of:
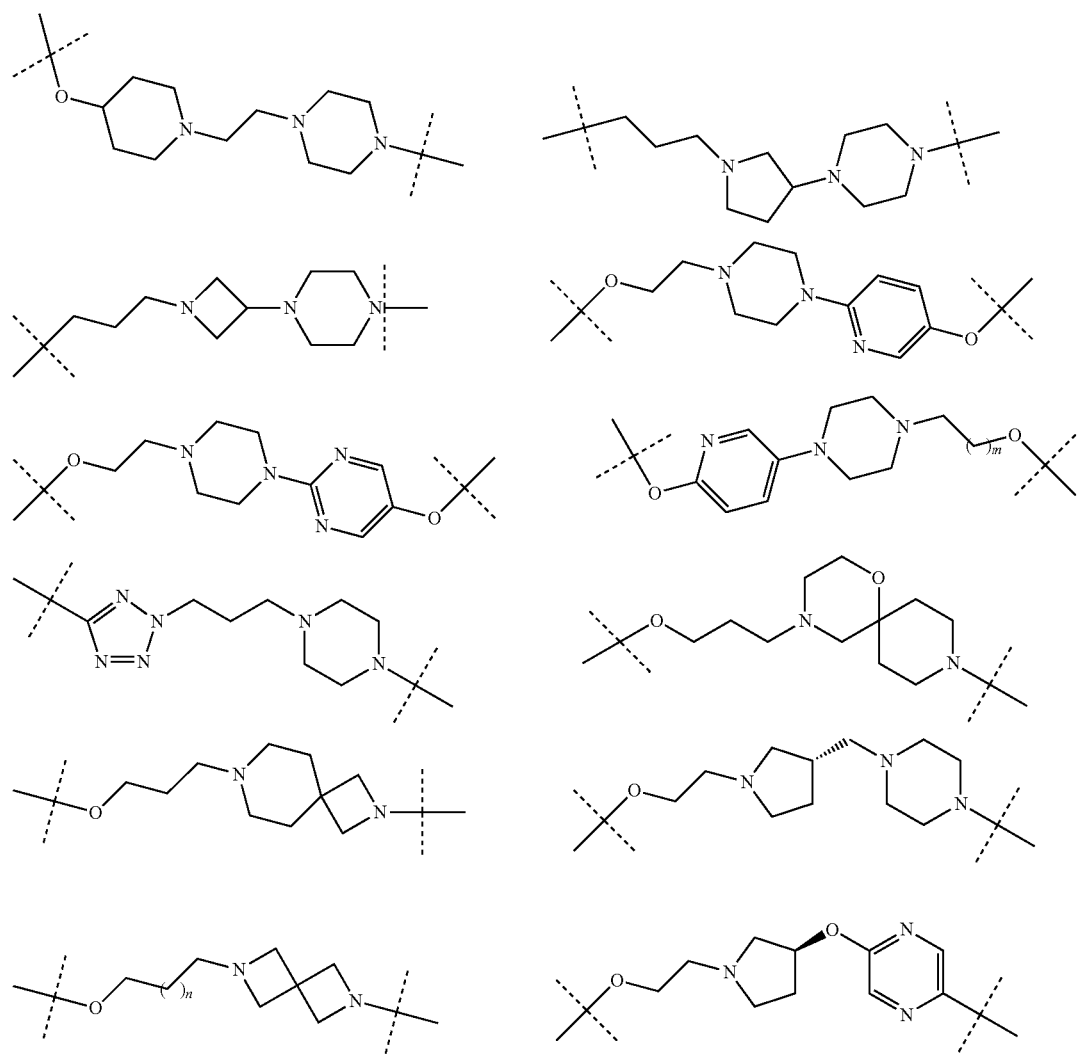

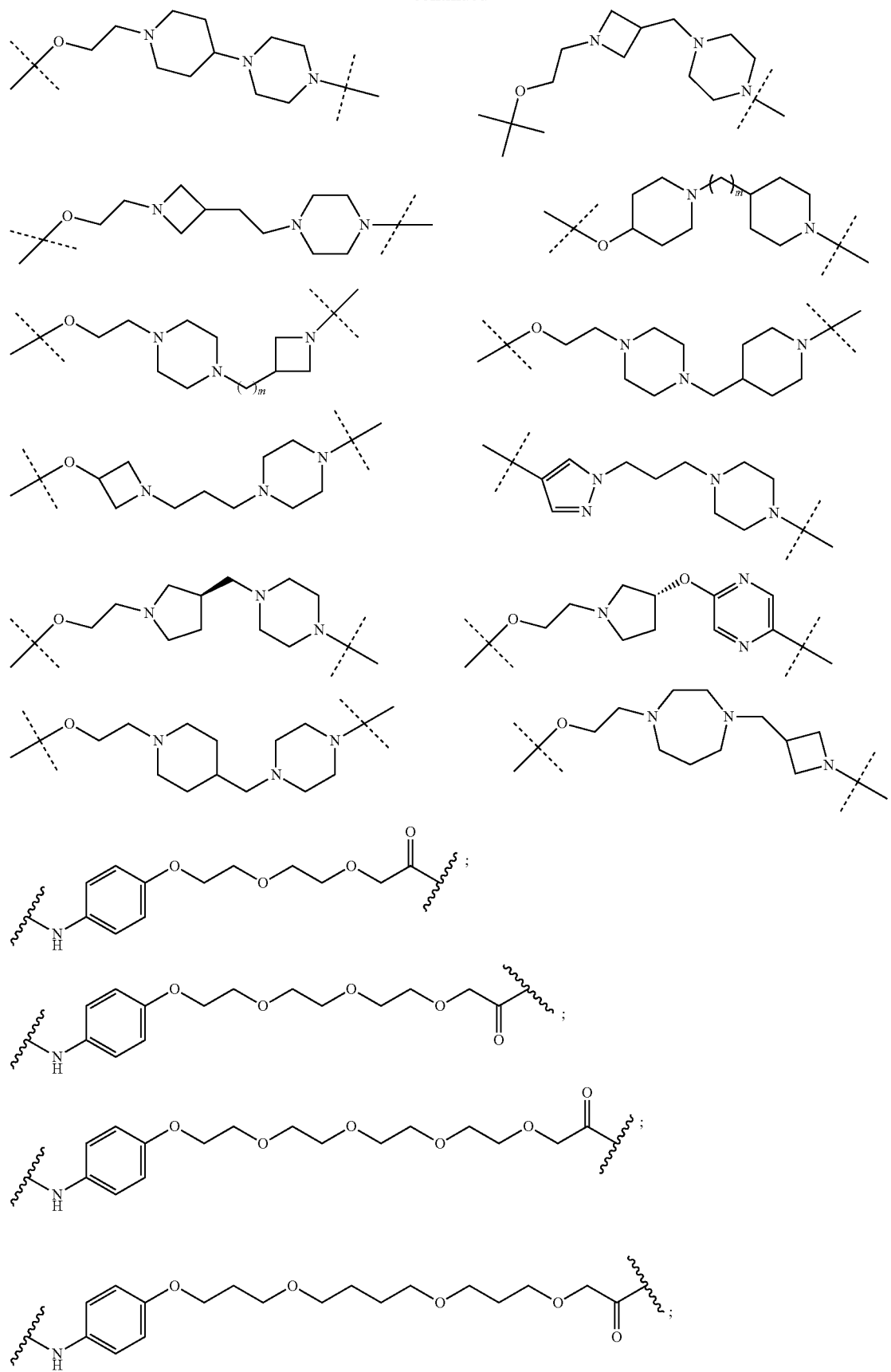

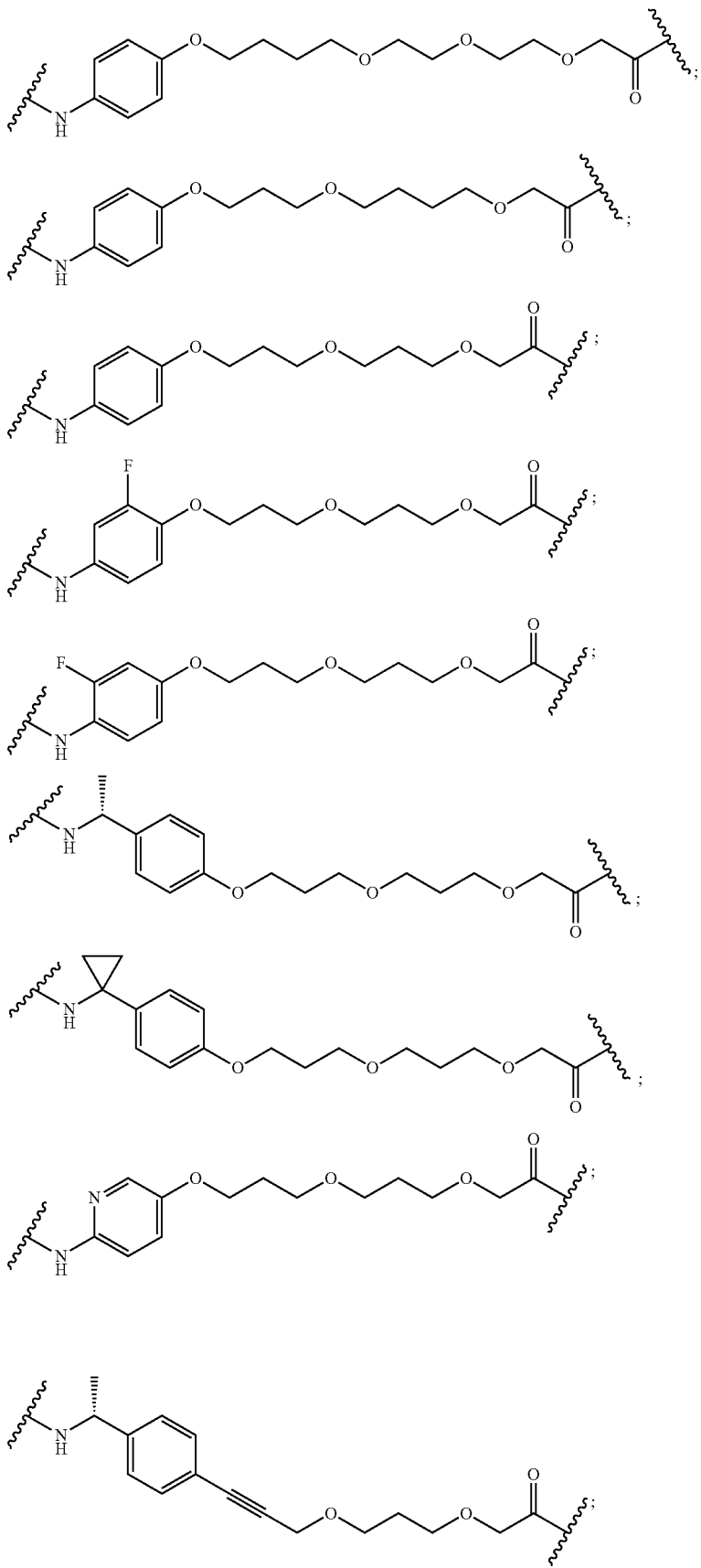

321
322
-continued
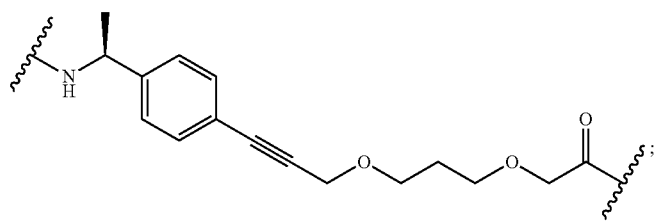
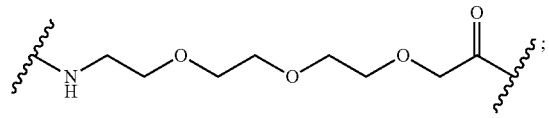
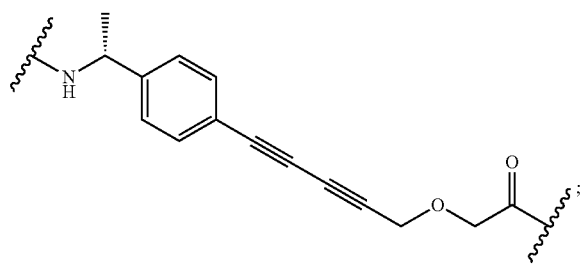
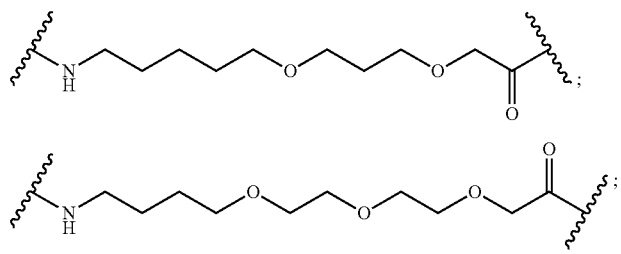
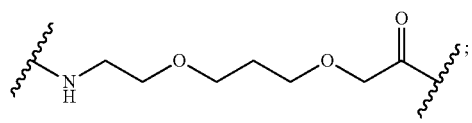
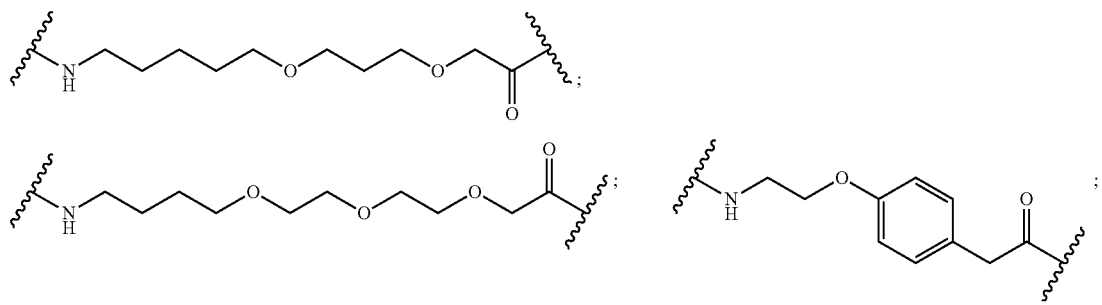
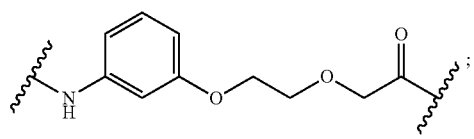
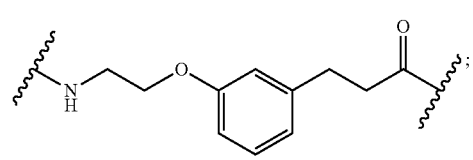
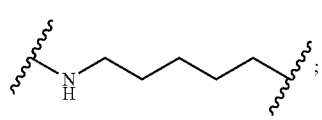
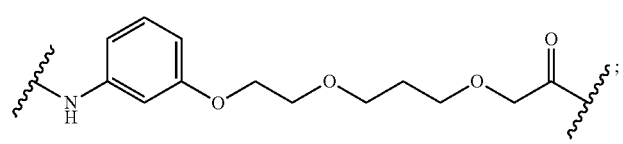
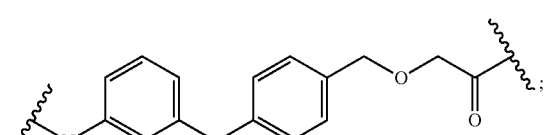
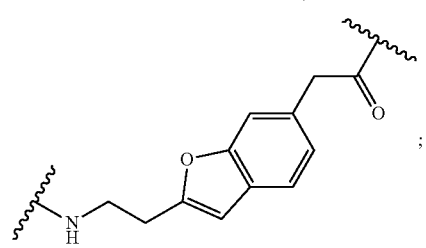
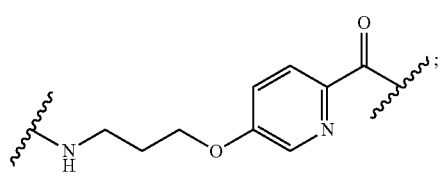
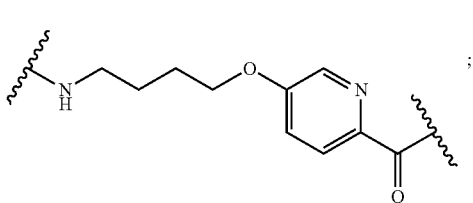

-continued
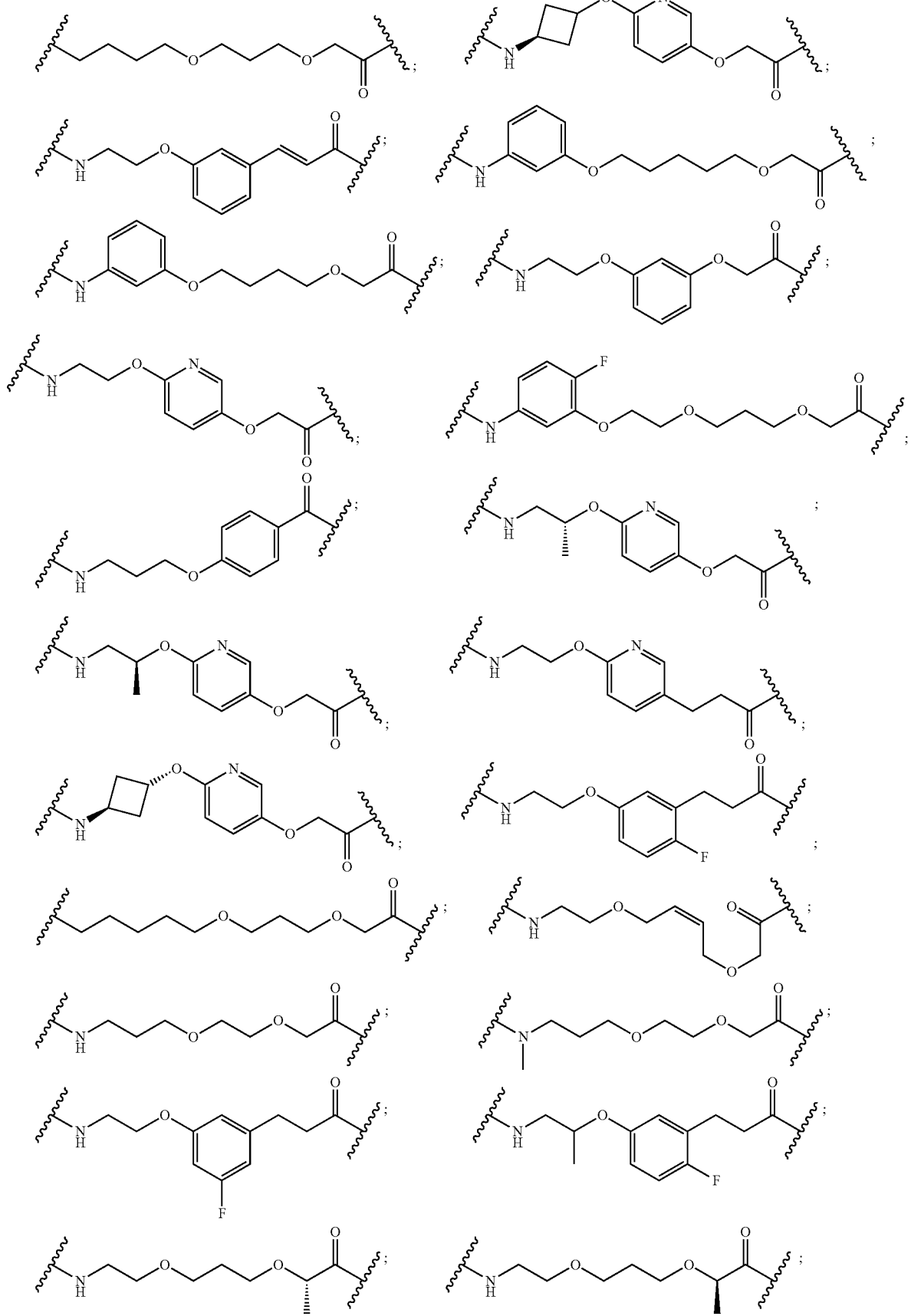

325
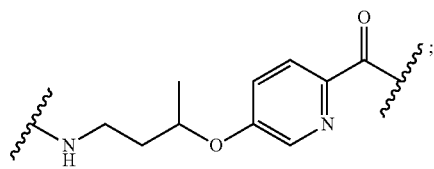
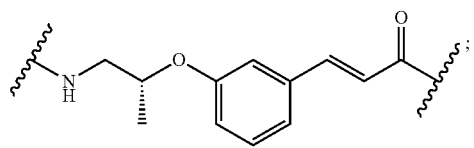
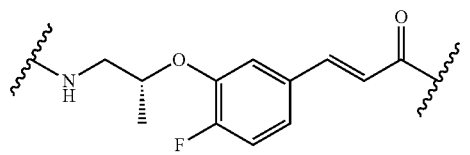
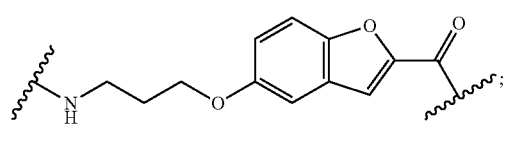
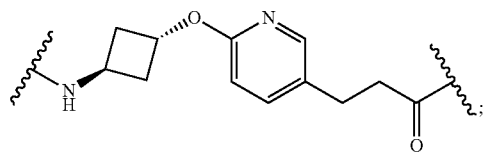
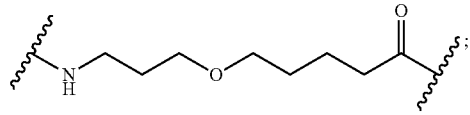
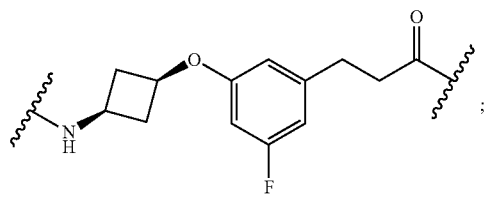
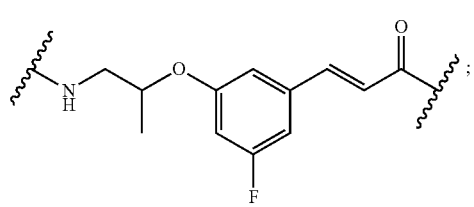
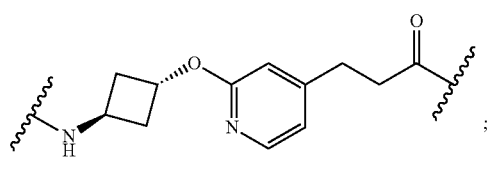
326
-continued
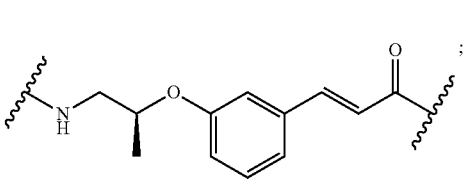
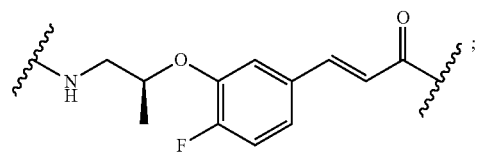
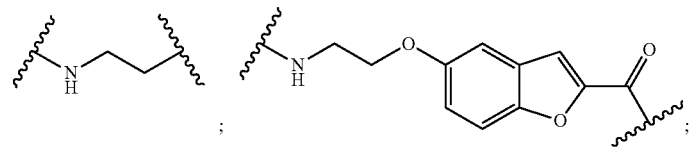
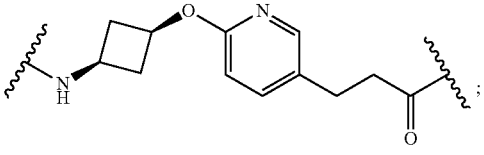
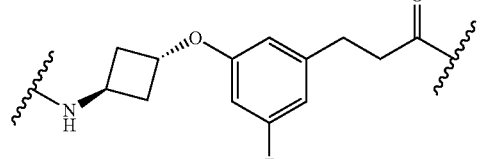
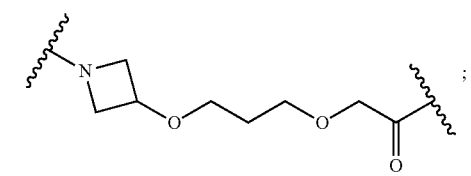
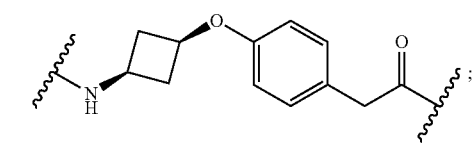
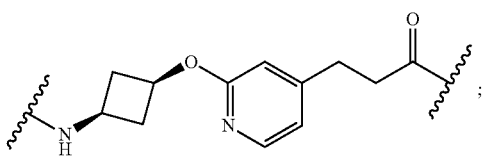
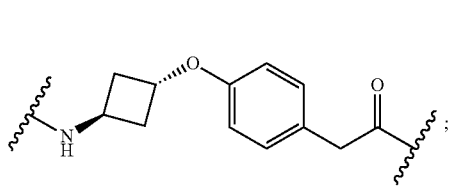

327 328
-continued
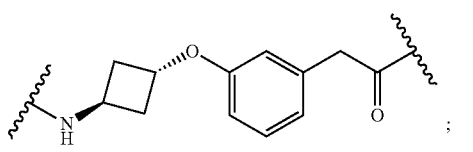 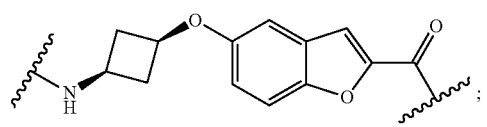
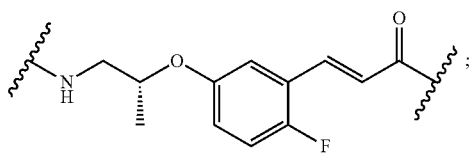 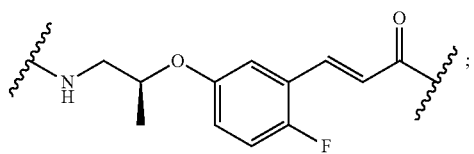
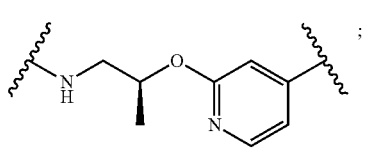 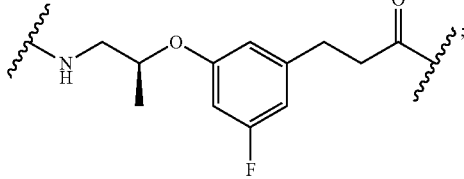
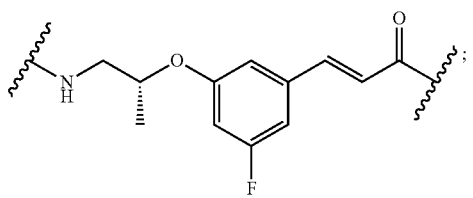 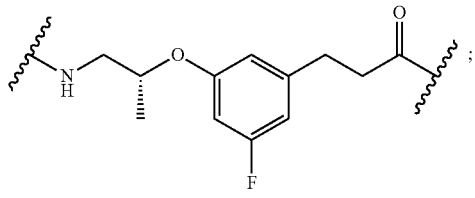
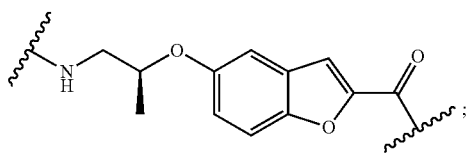 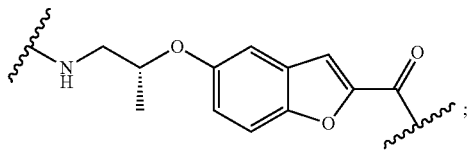
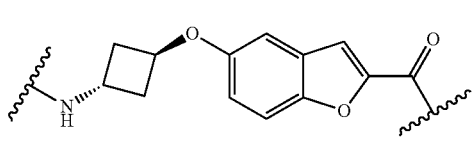 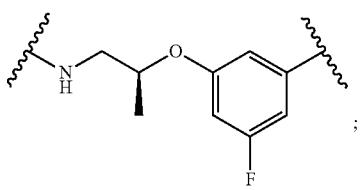
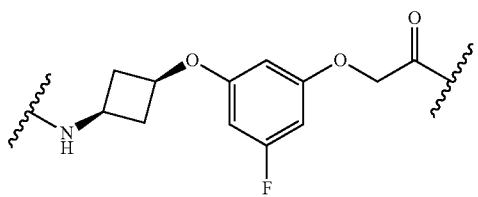 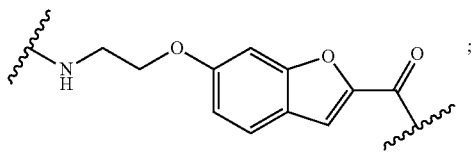
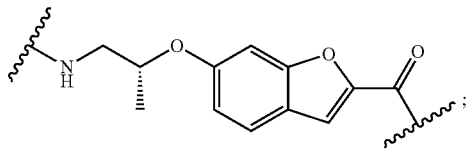 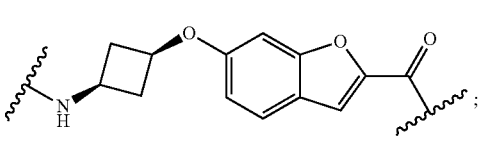
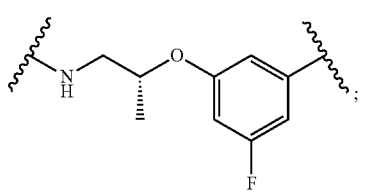 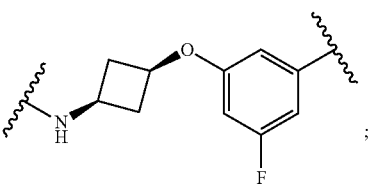

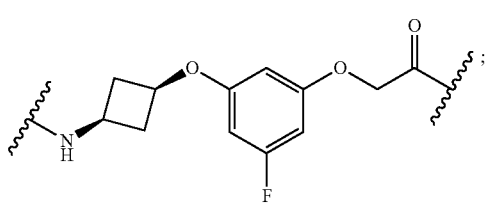
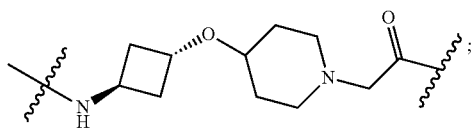
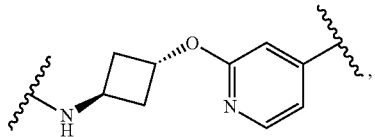
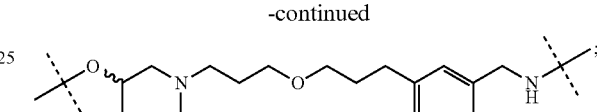
wherein each m and n are independently 0, 1, 2, 3, 4, 5, or 6.
In any aspect or embodiment described herein, the linker (L) is selected from the group consisting of:
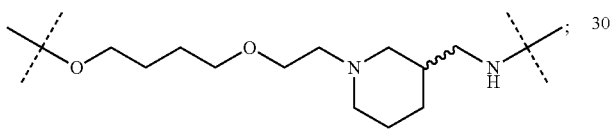
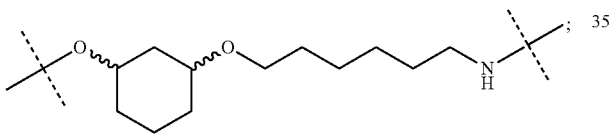
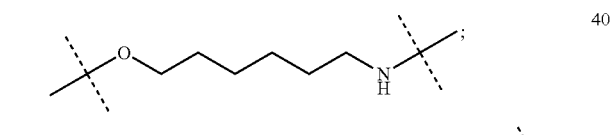
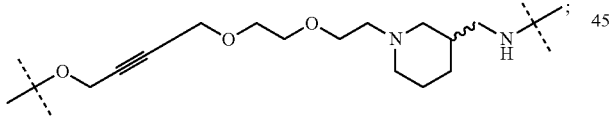
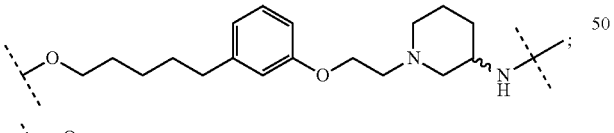
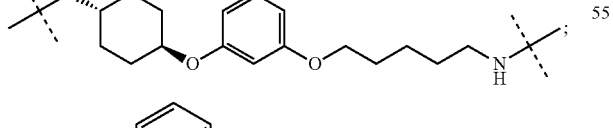
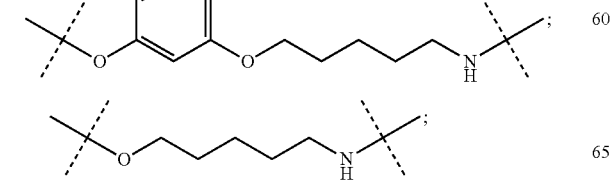
-continued
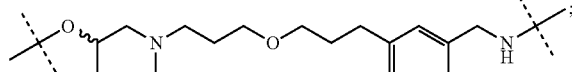
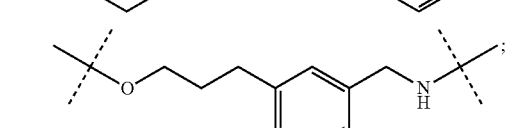
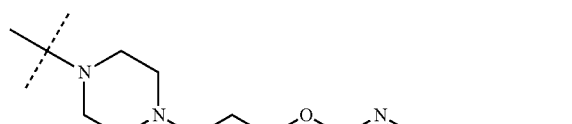
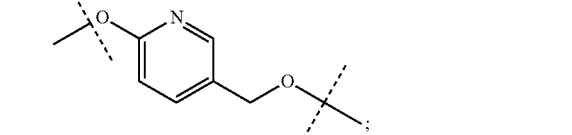
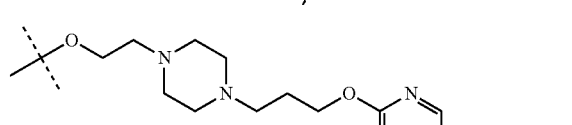
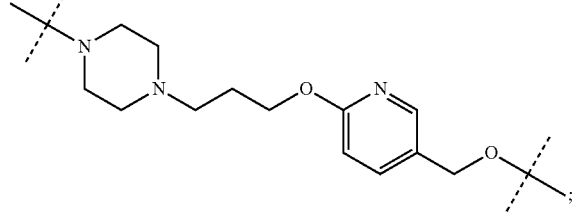

331
-continued
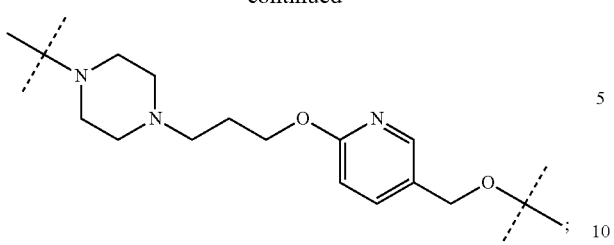
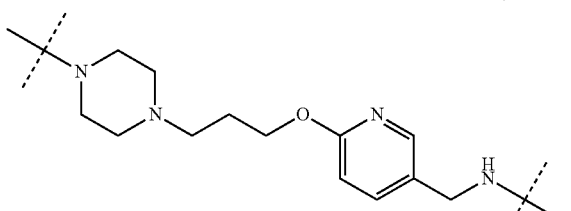
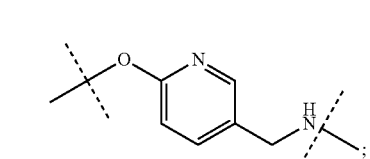
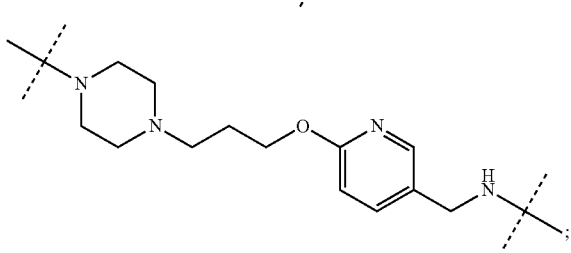
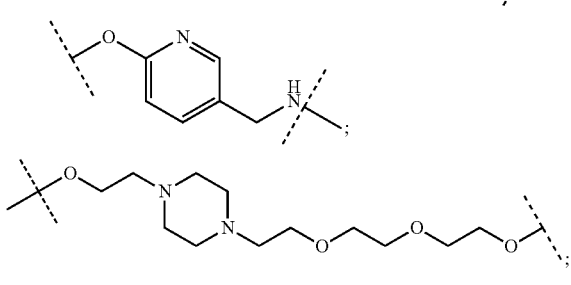
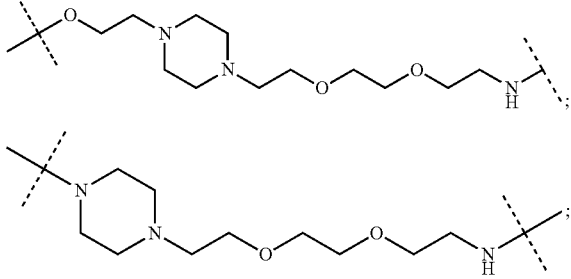
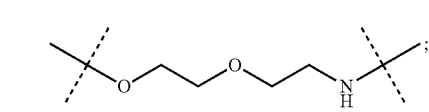
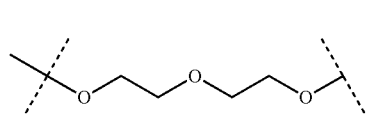
332
-continued
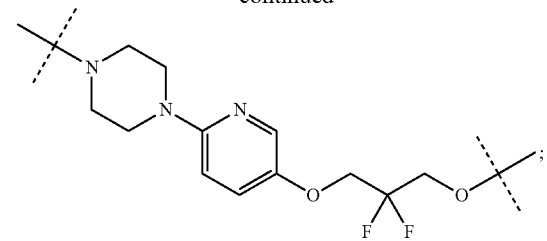
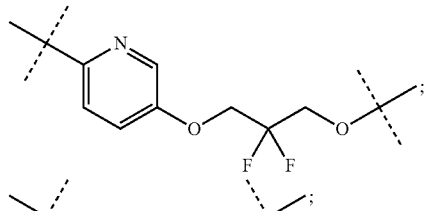
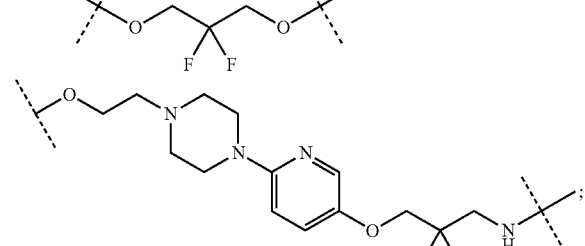
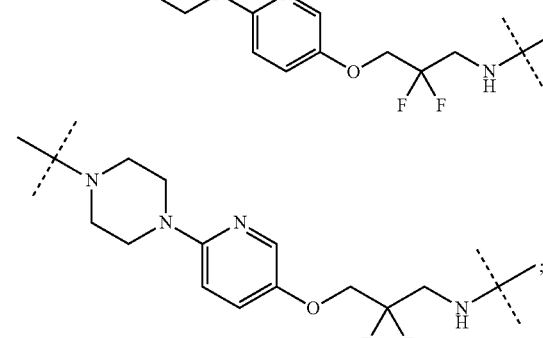
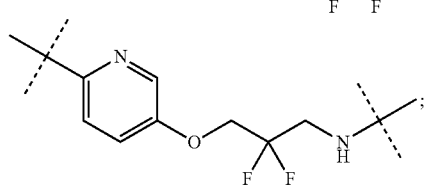
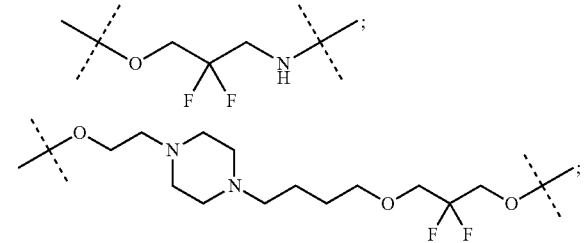
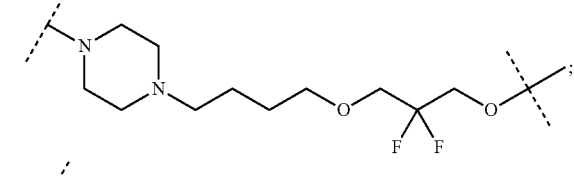
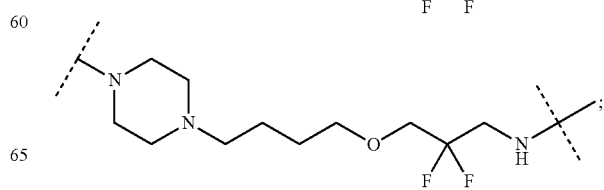

333
-continued
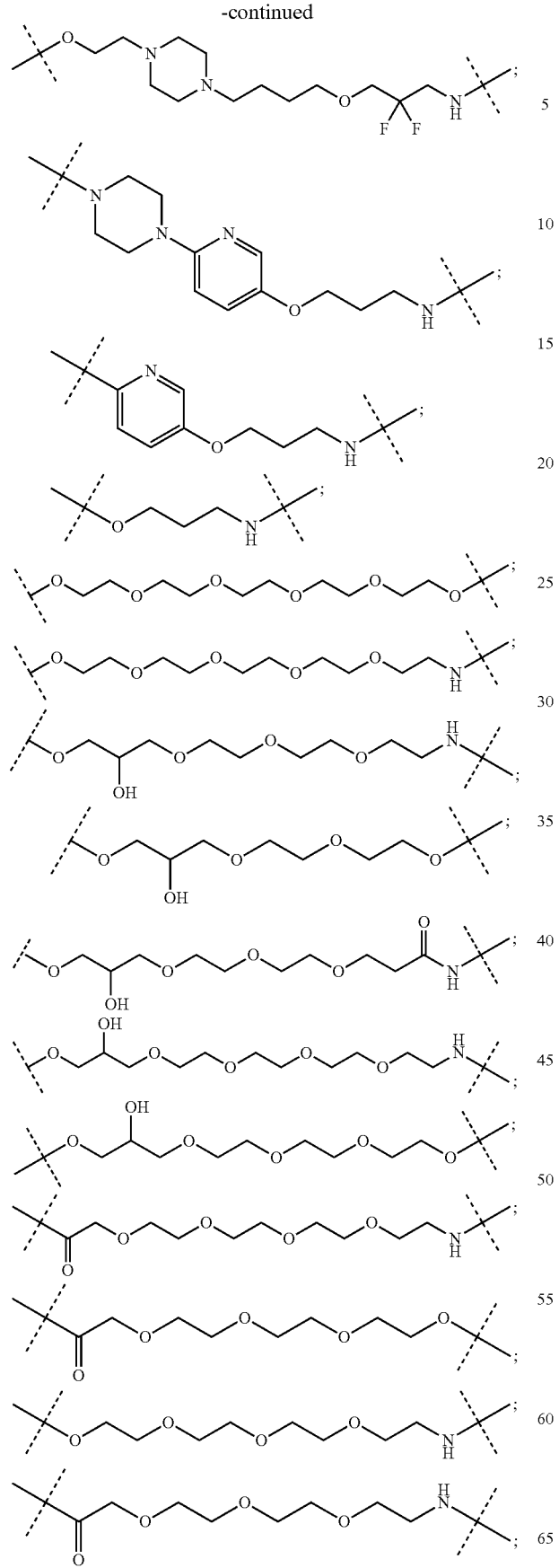
334
-continued
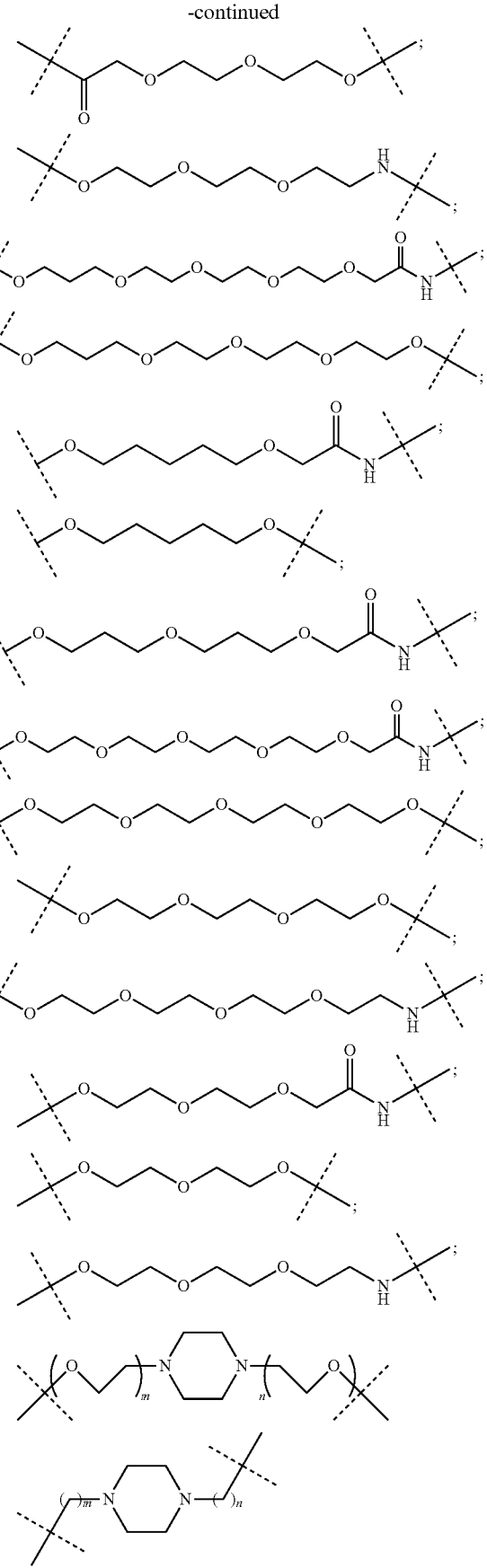

335
-continued
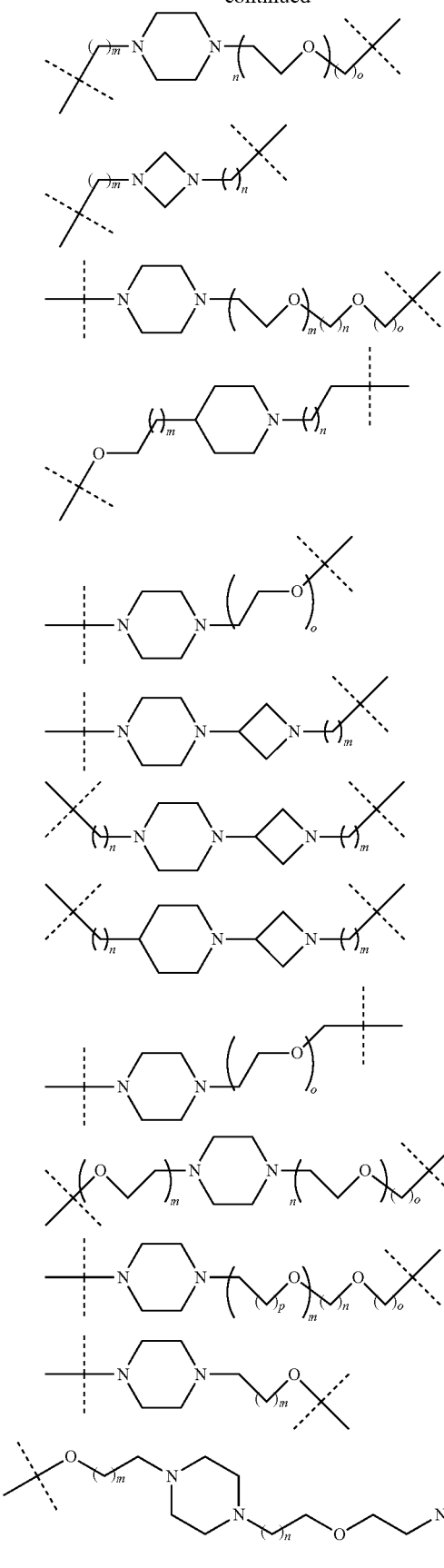
336
-continued
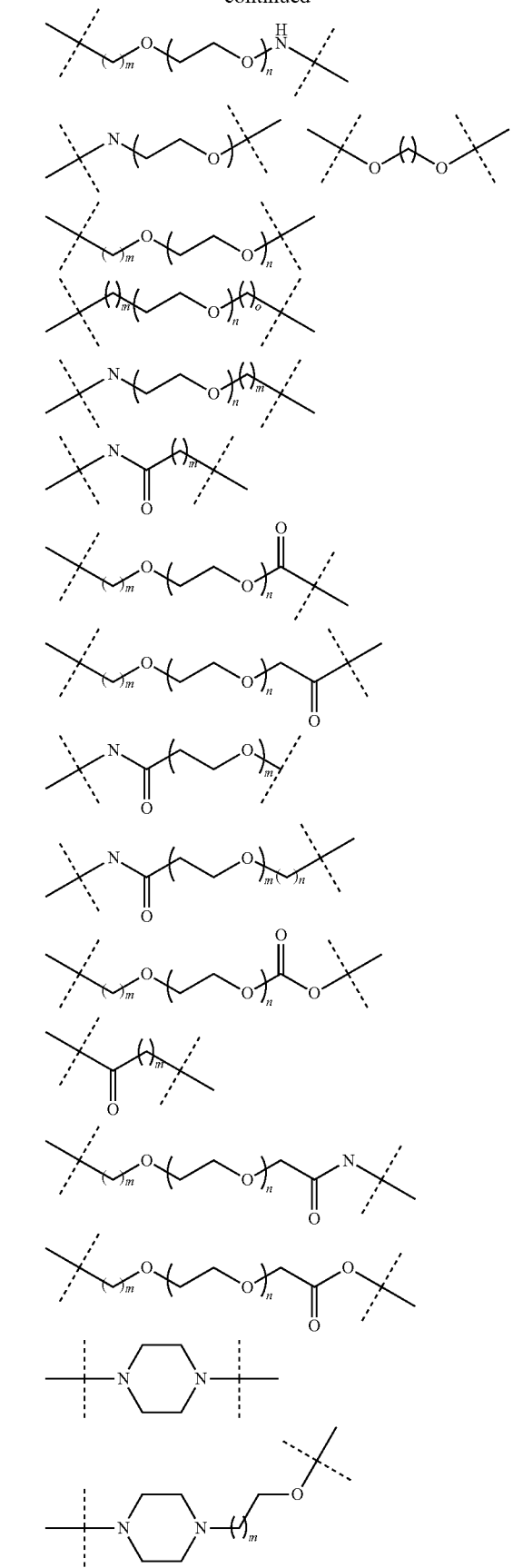

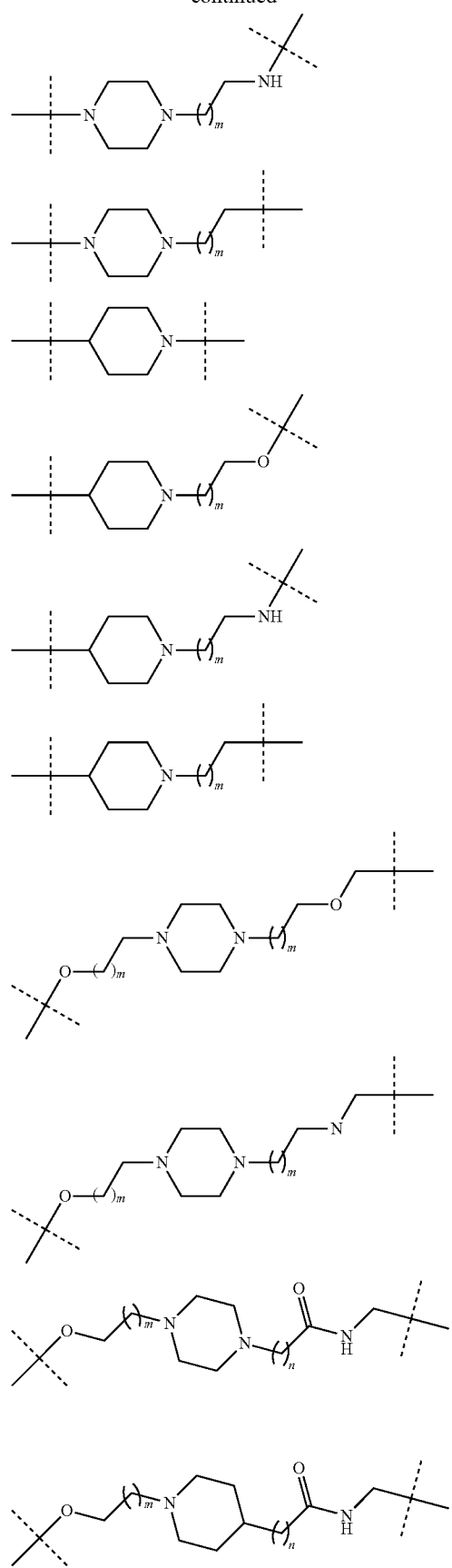
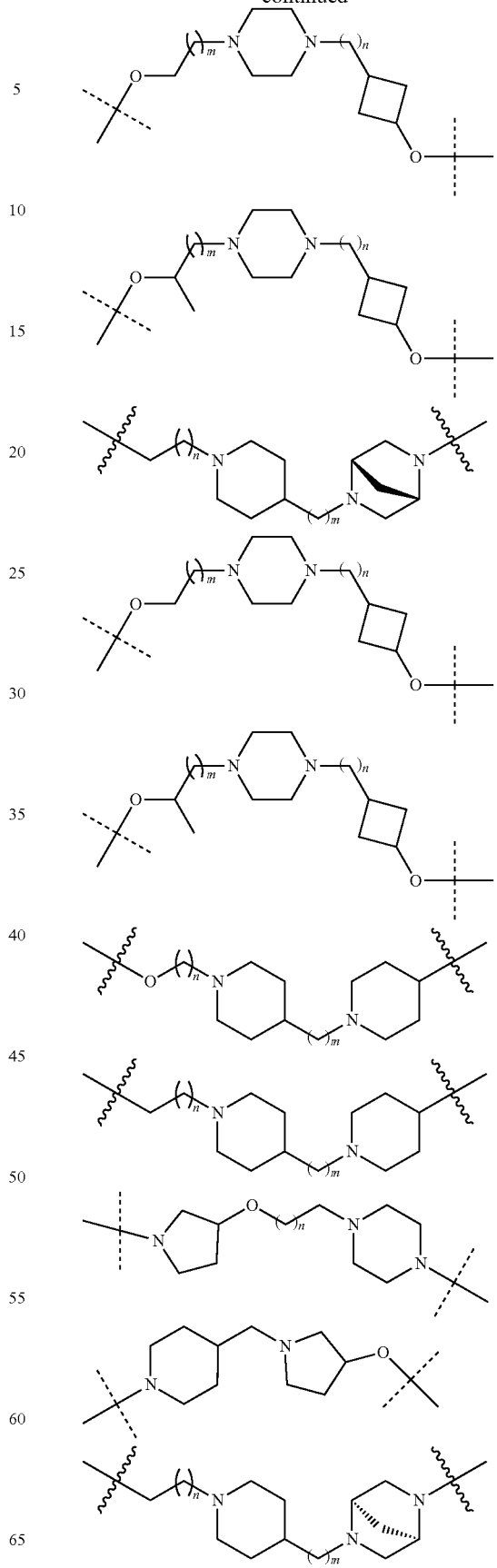

339
-continued
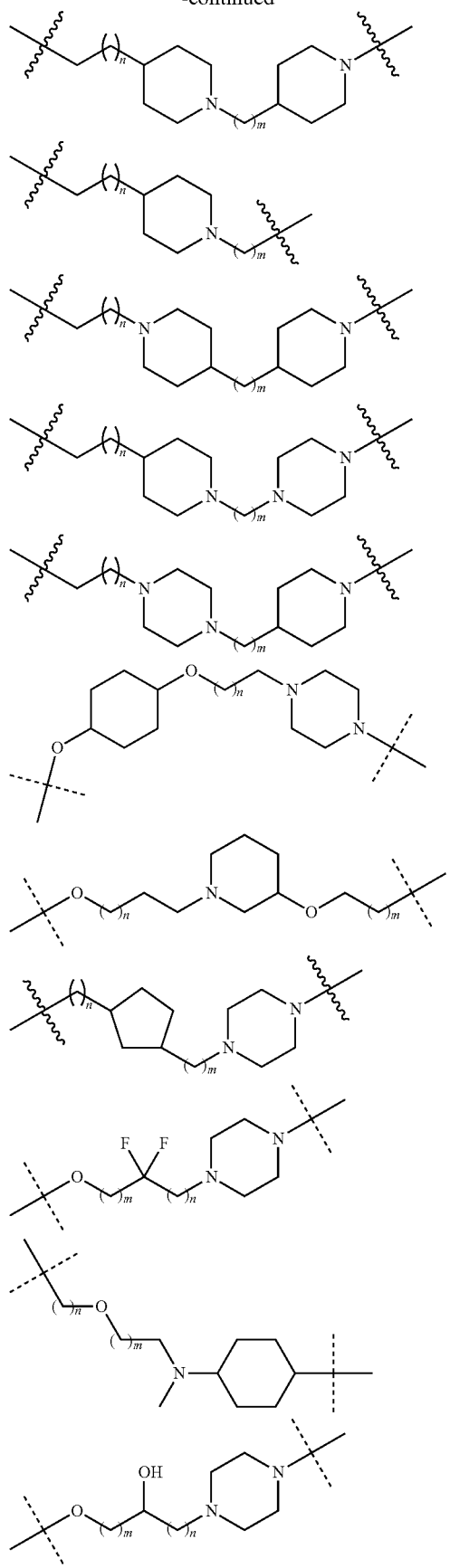
340
-continued
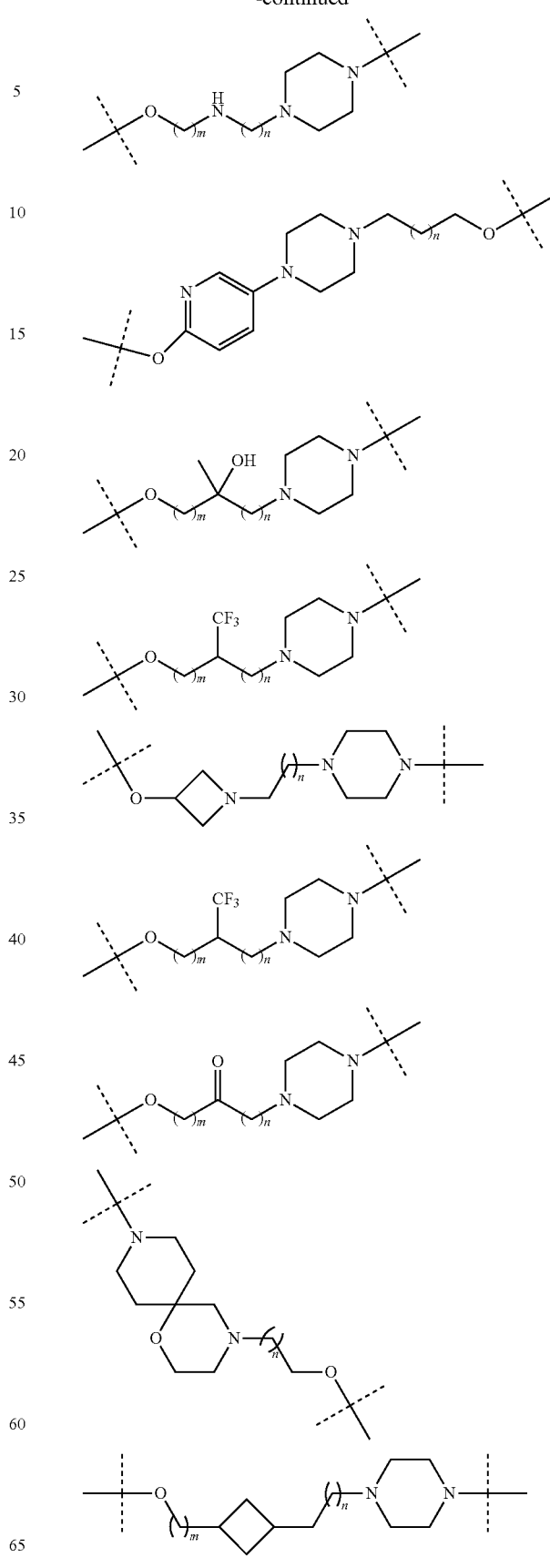

341
-continued
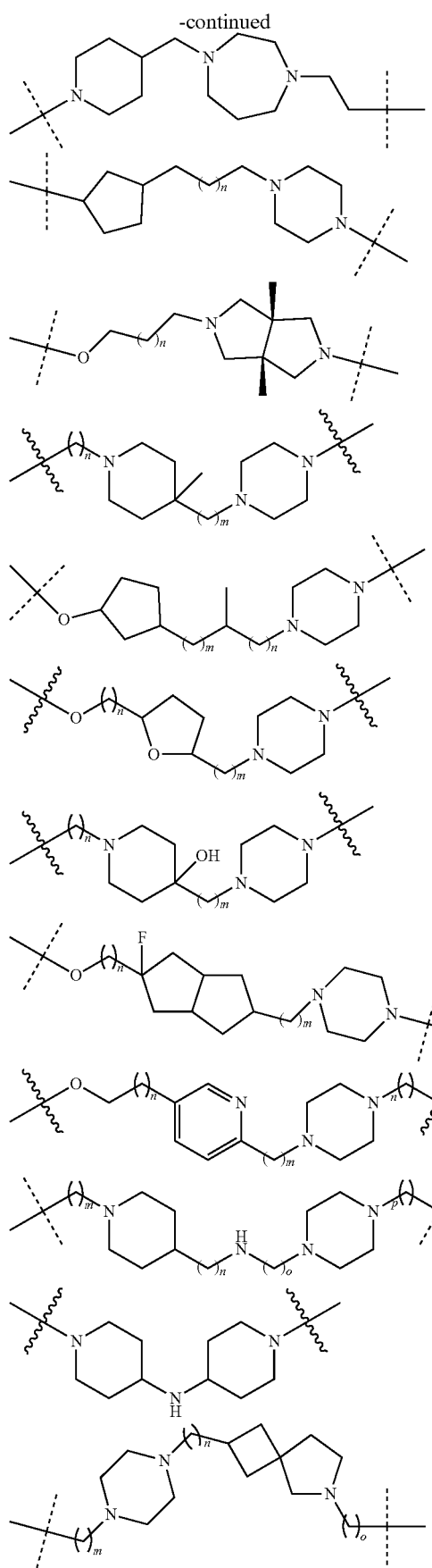
342
-continued
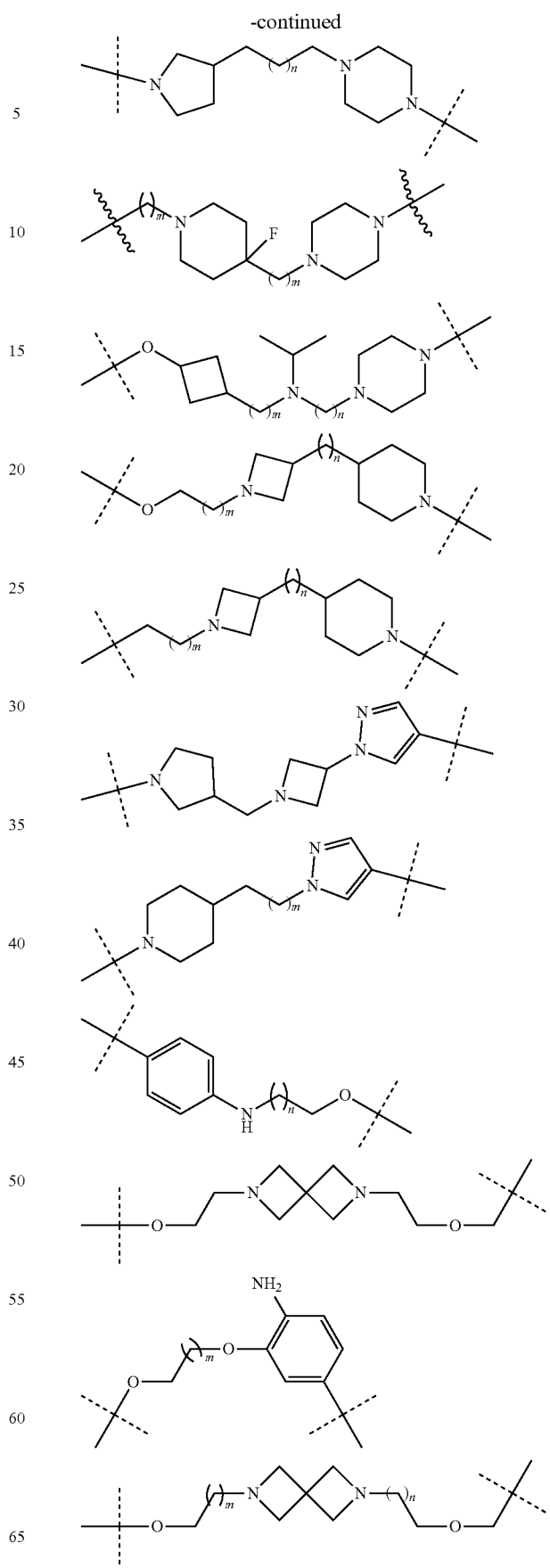

-continued

-continued
| 345 | 346 |
|---|---|
| 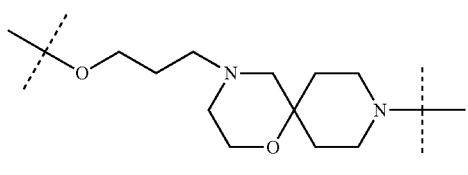 | 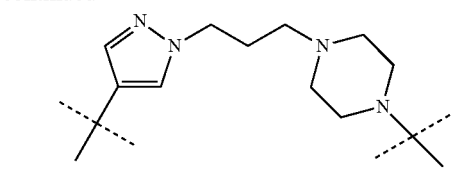 |
| 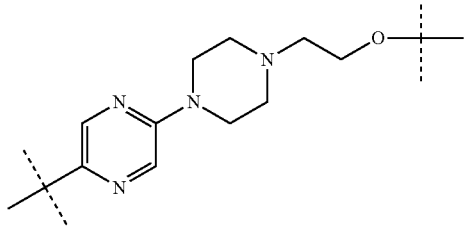 | 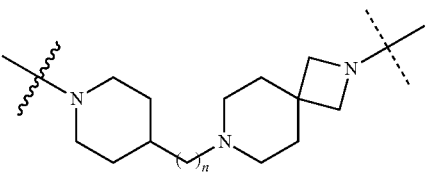 |
| 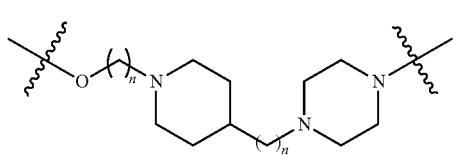 | 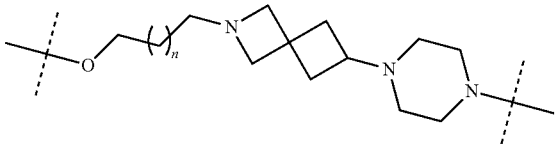 |
| 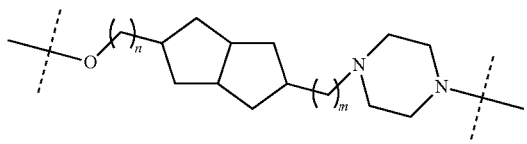 | 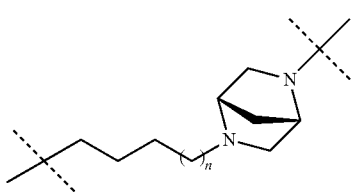 |
| 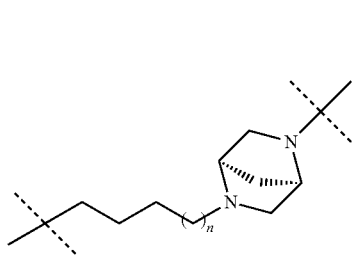 | 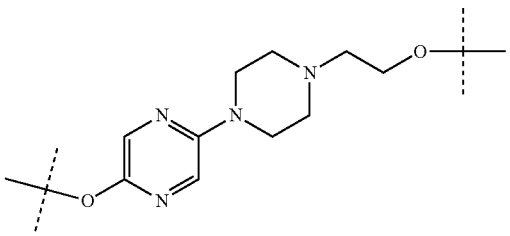 |
| 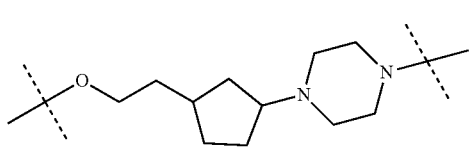 | 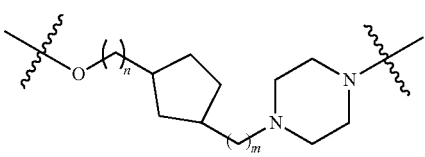 |
| 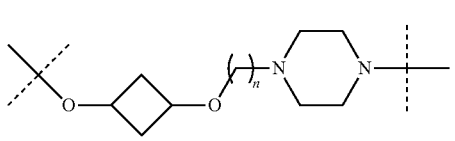 | 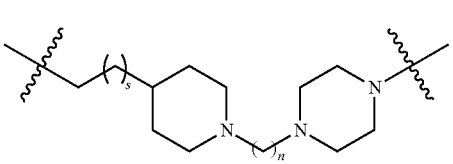 |
| 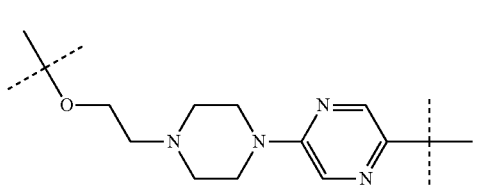 | 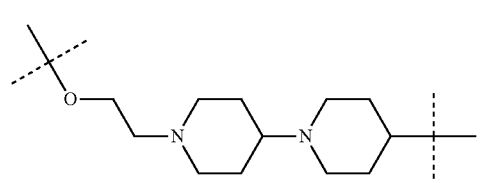 |
| 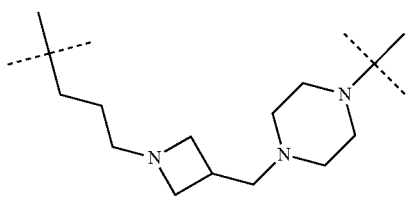 | 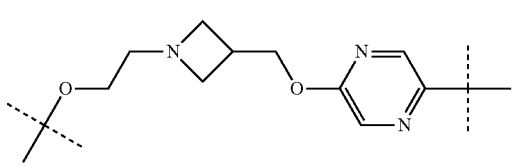 |

-continued
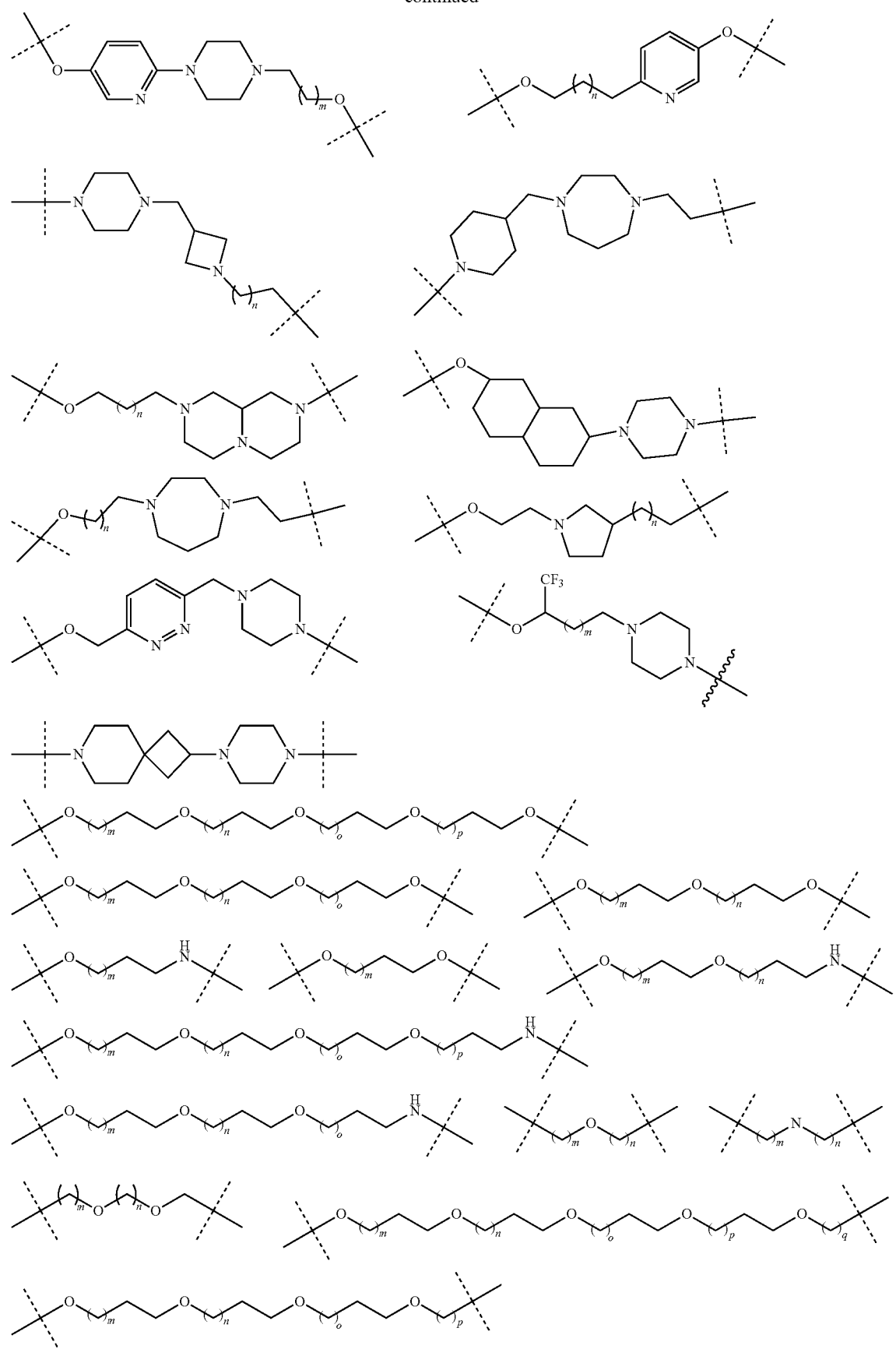

-continued
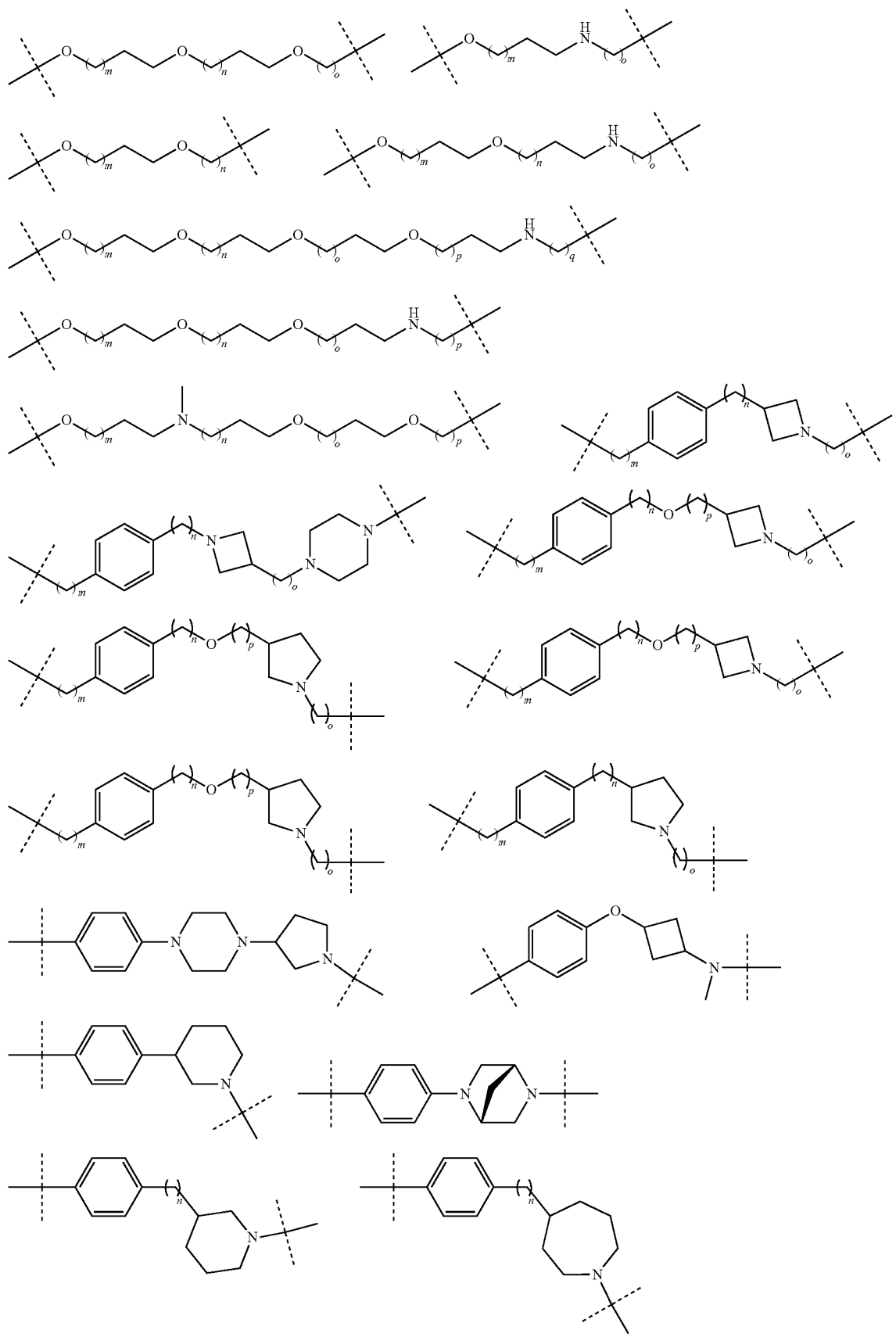

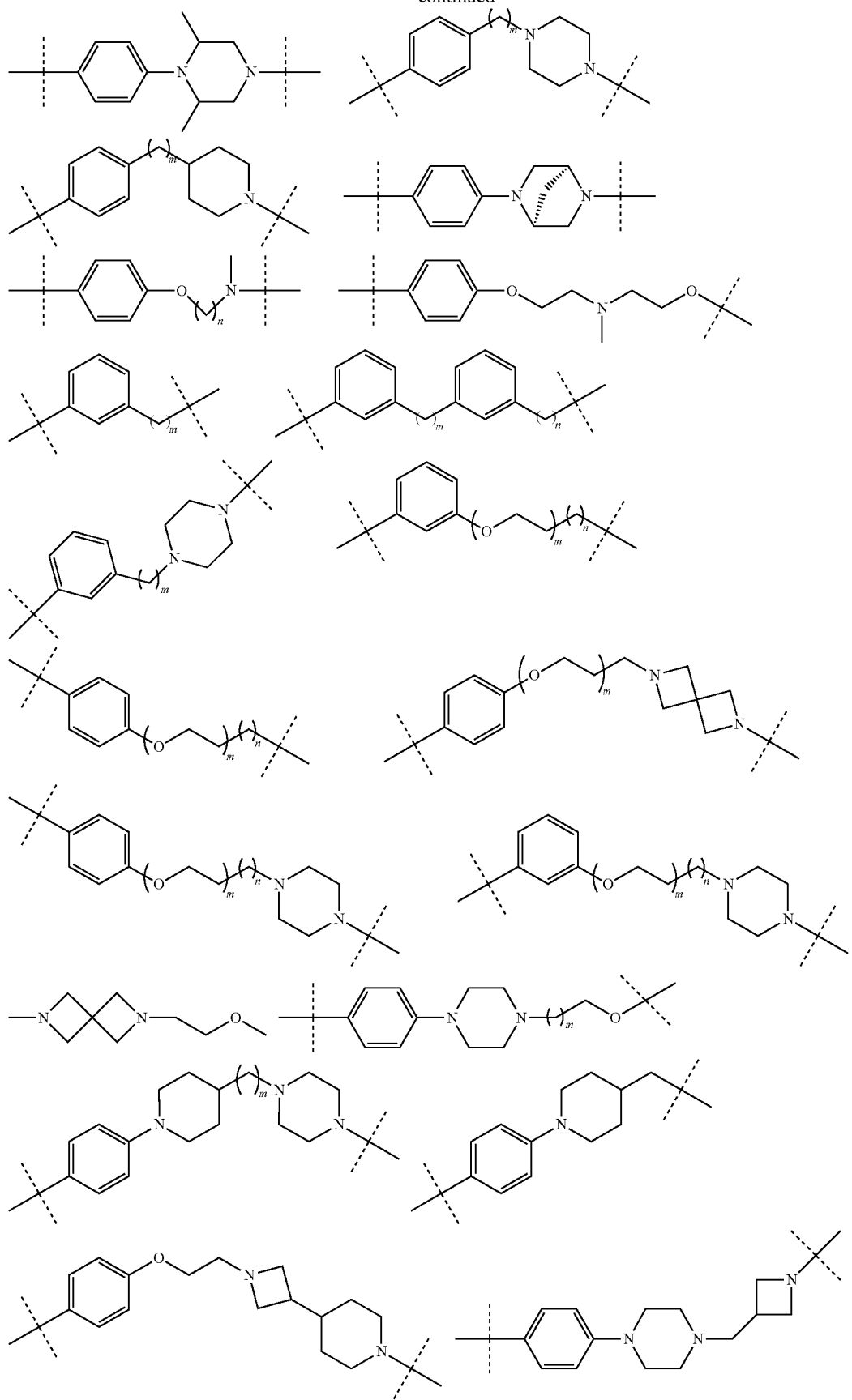

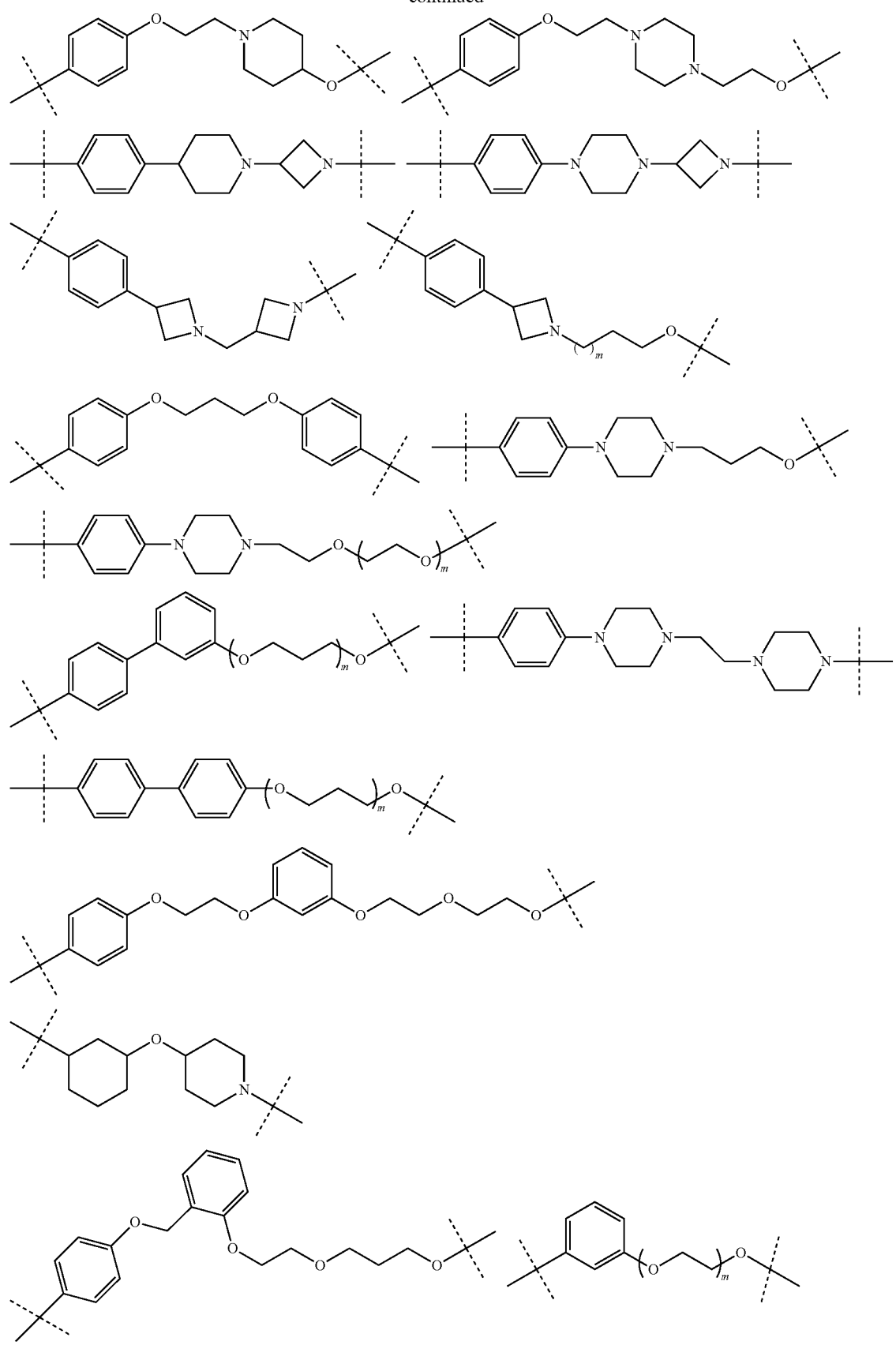

355 356
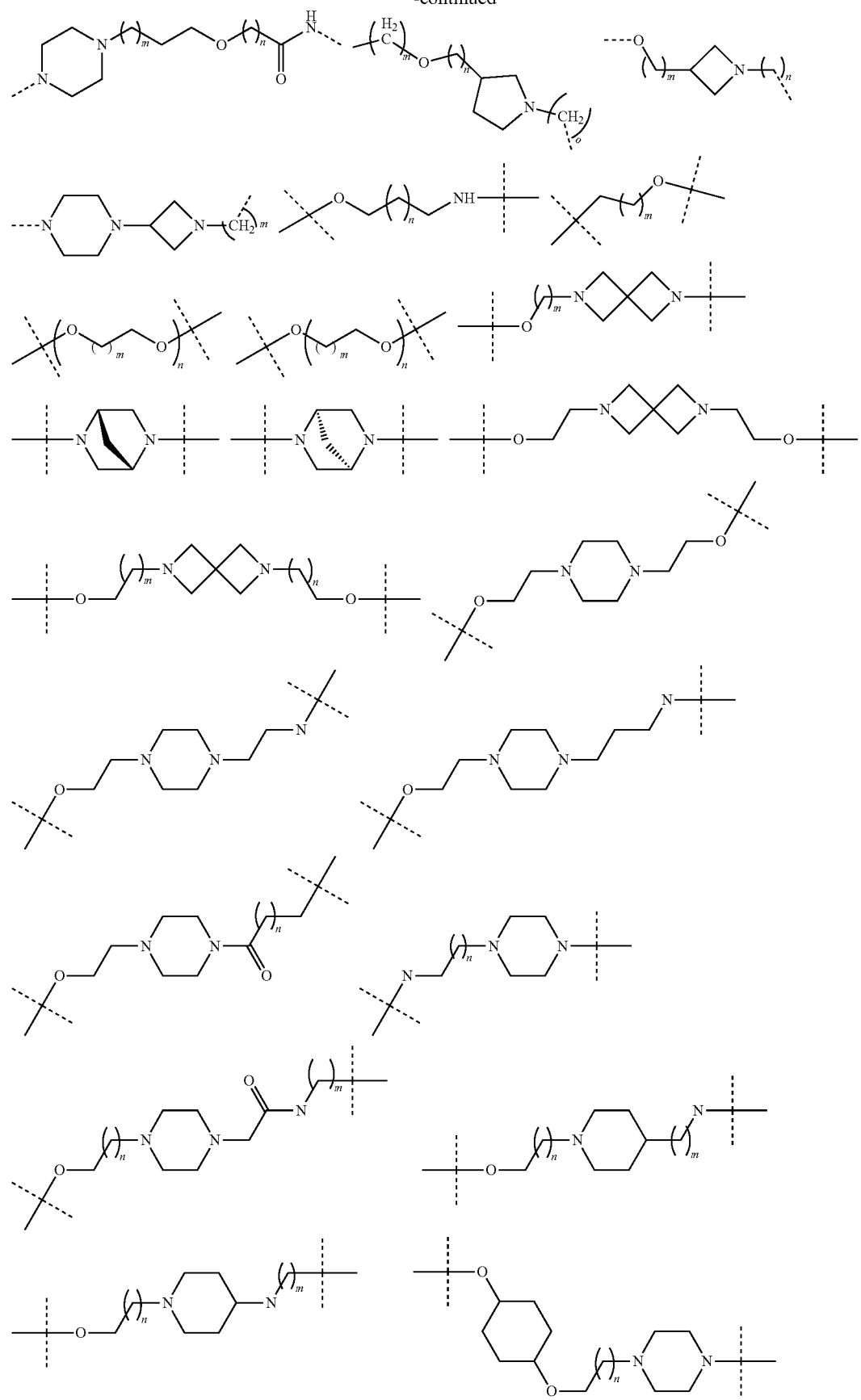

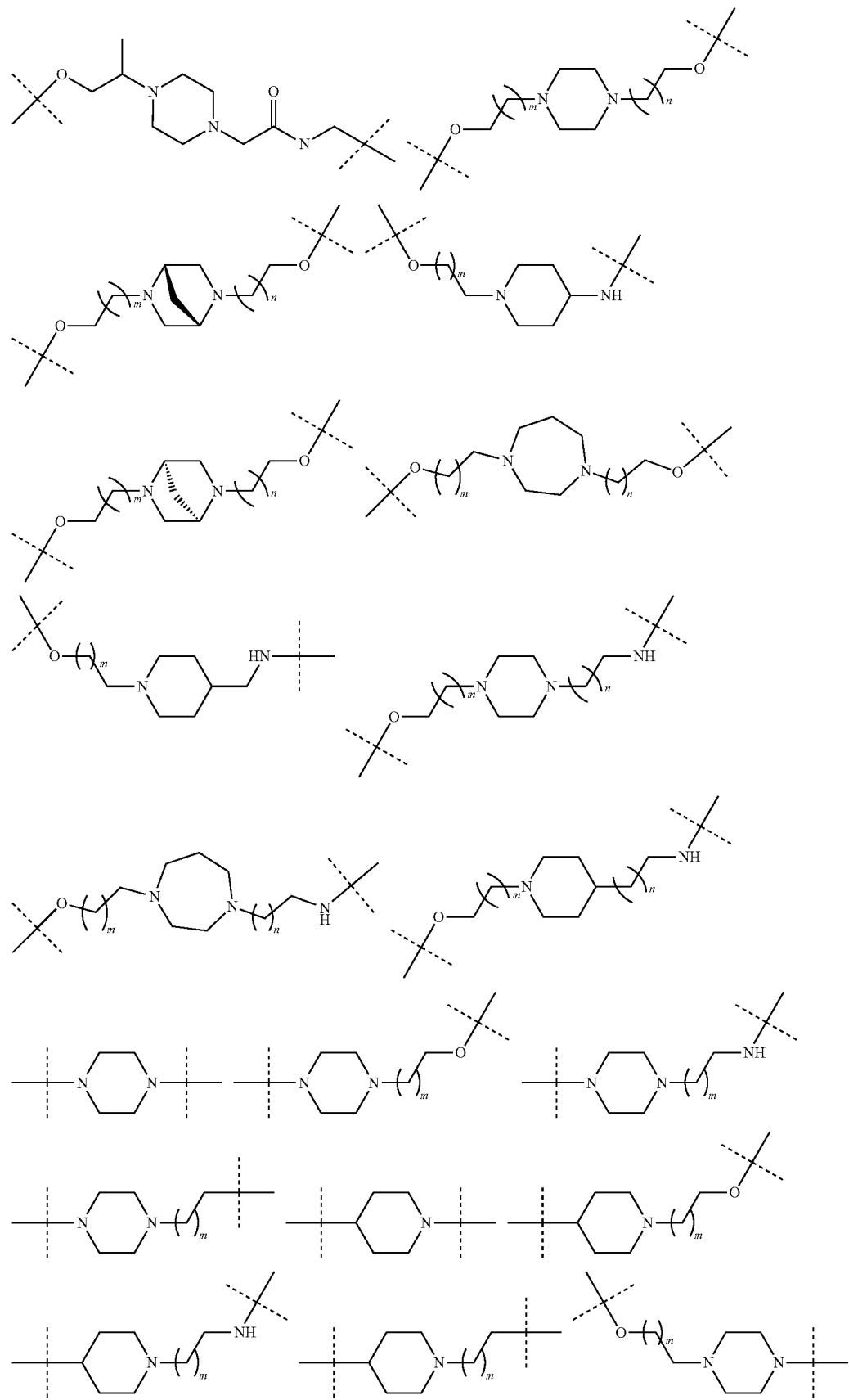

-continued
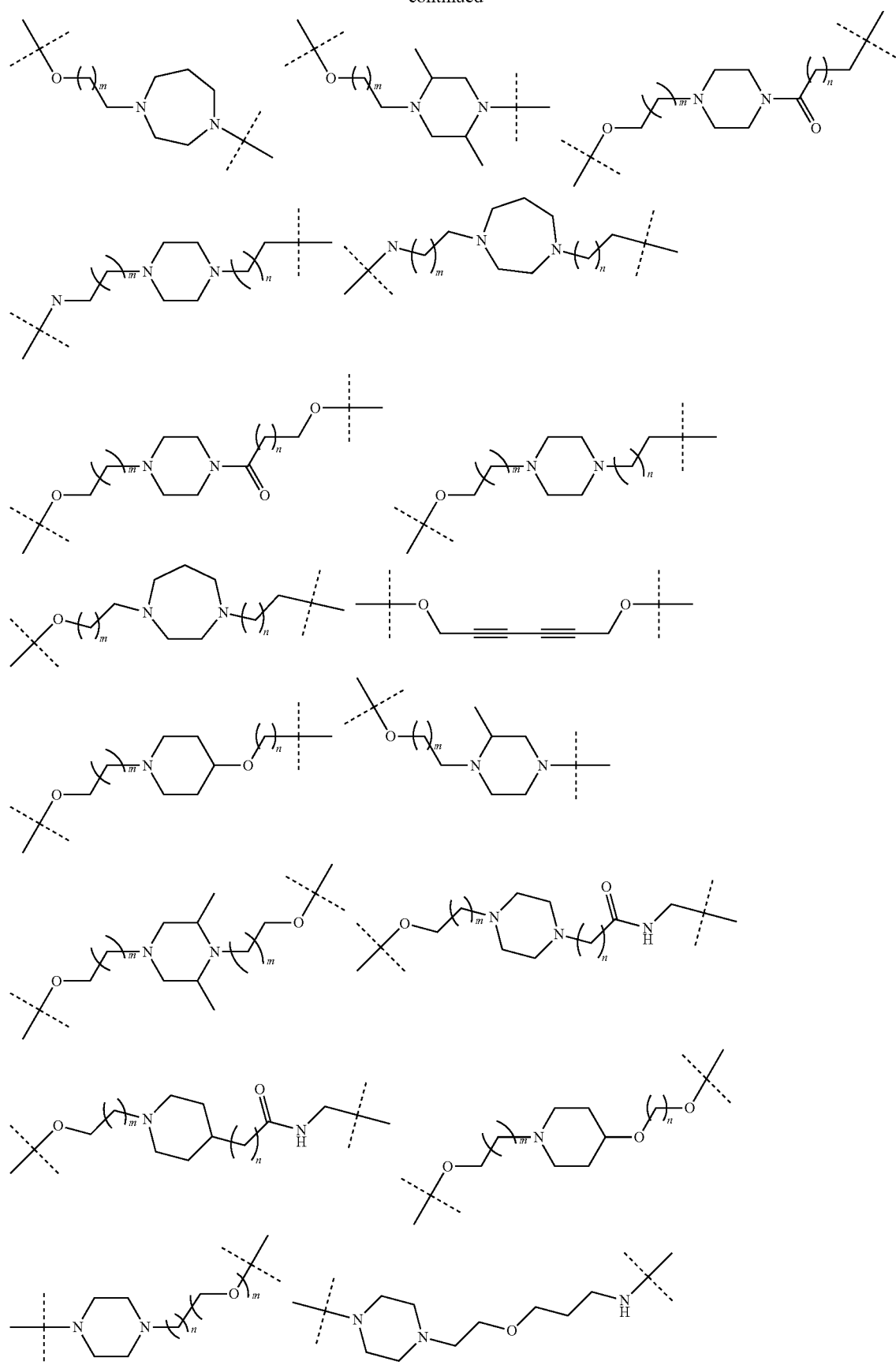

-continued
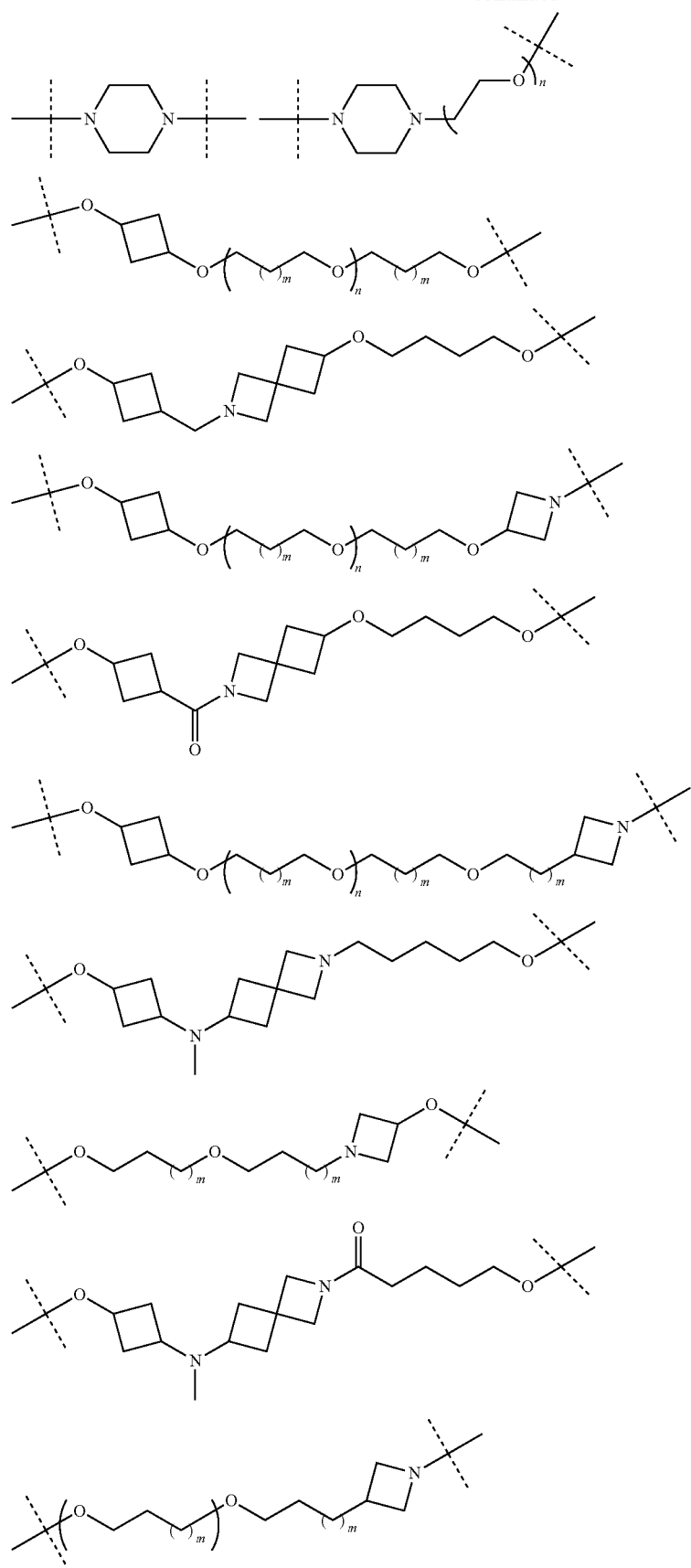

-continued
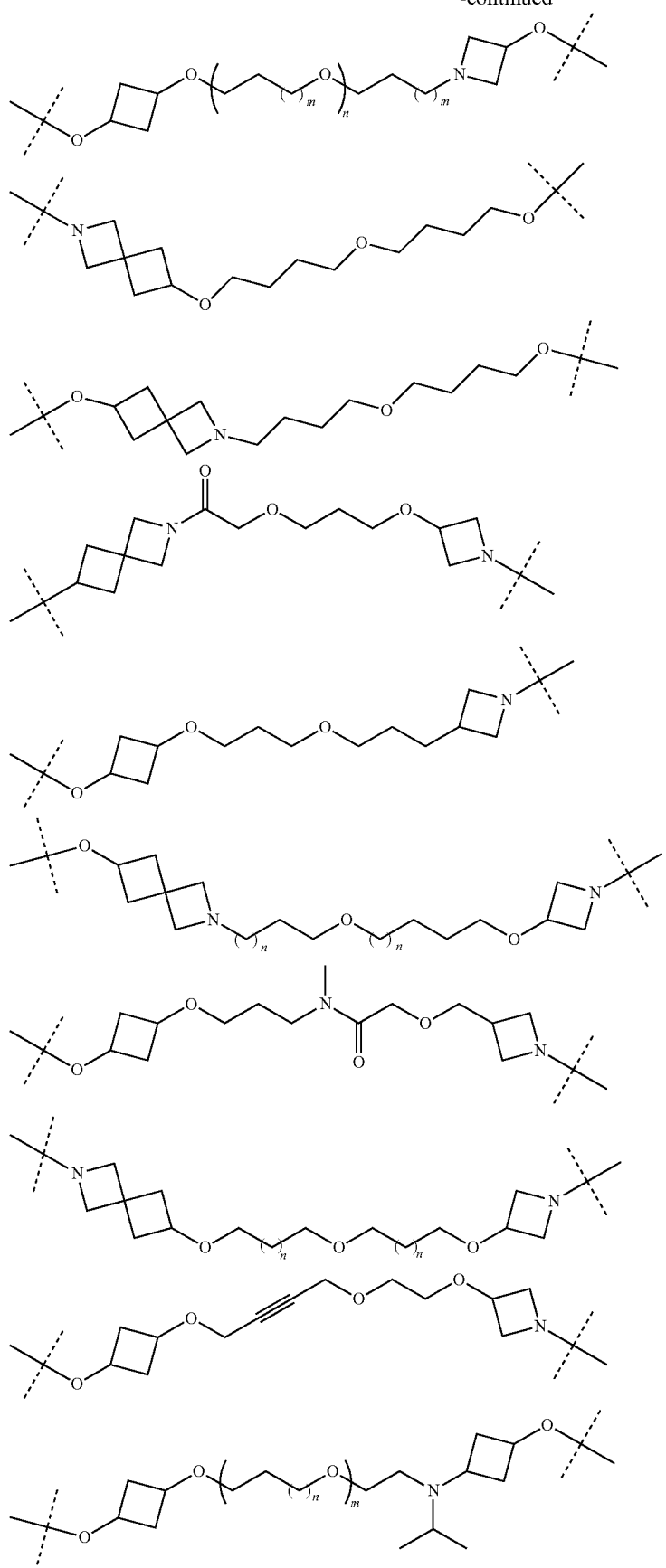

-continued
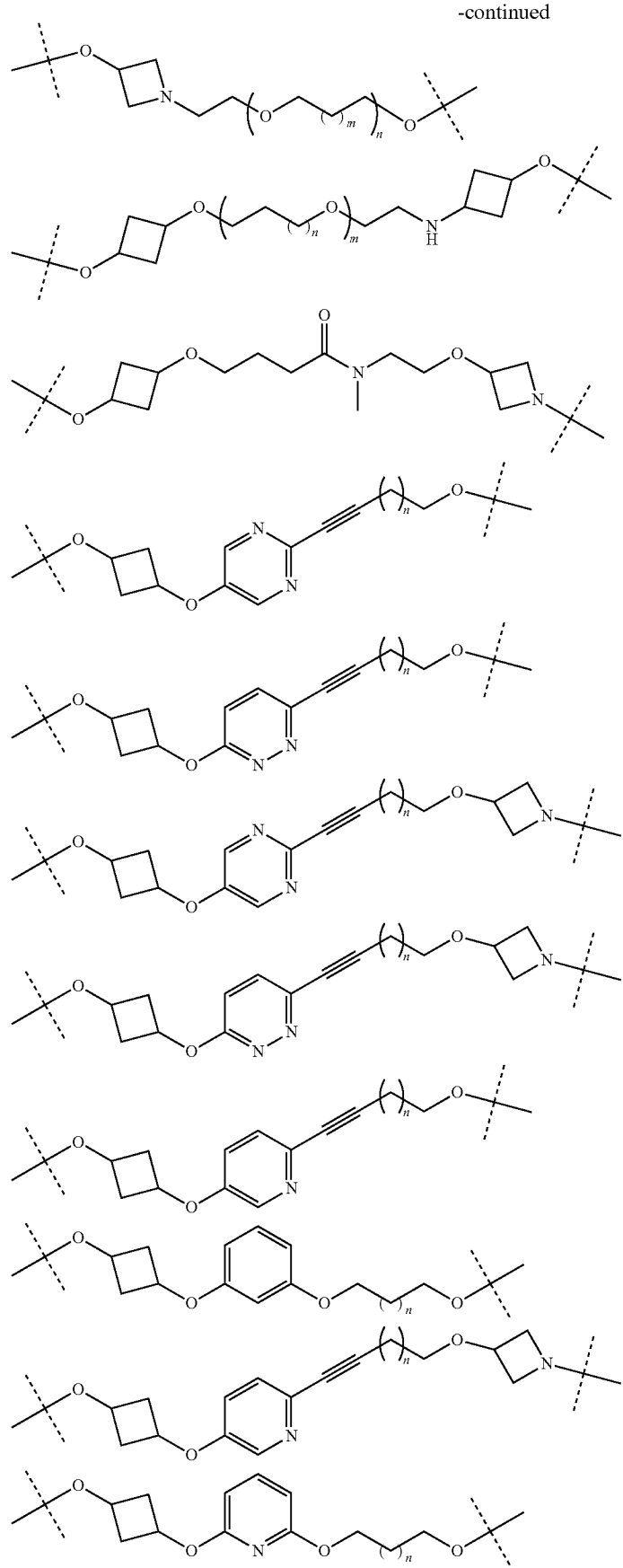

-continued
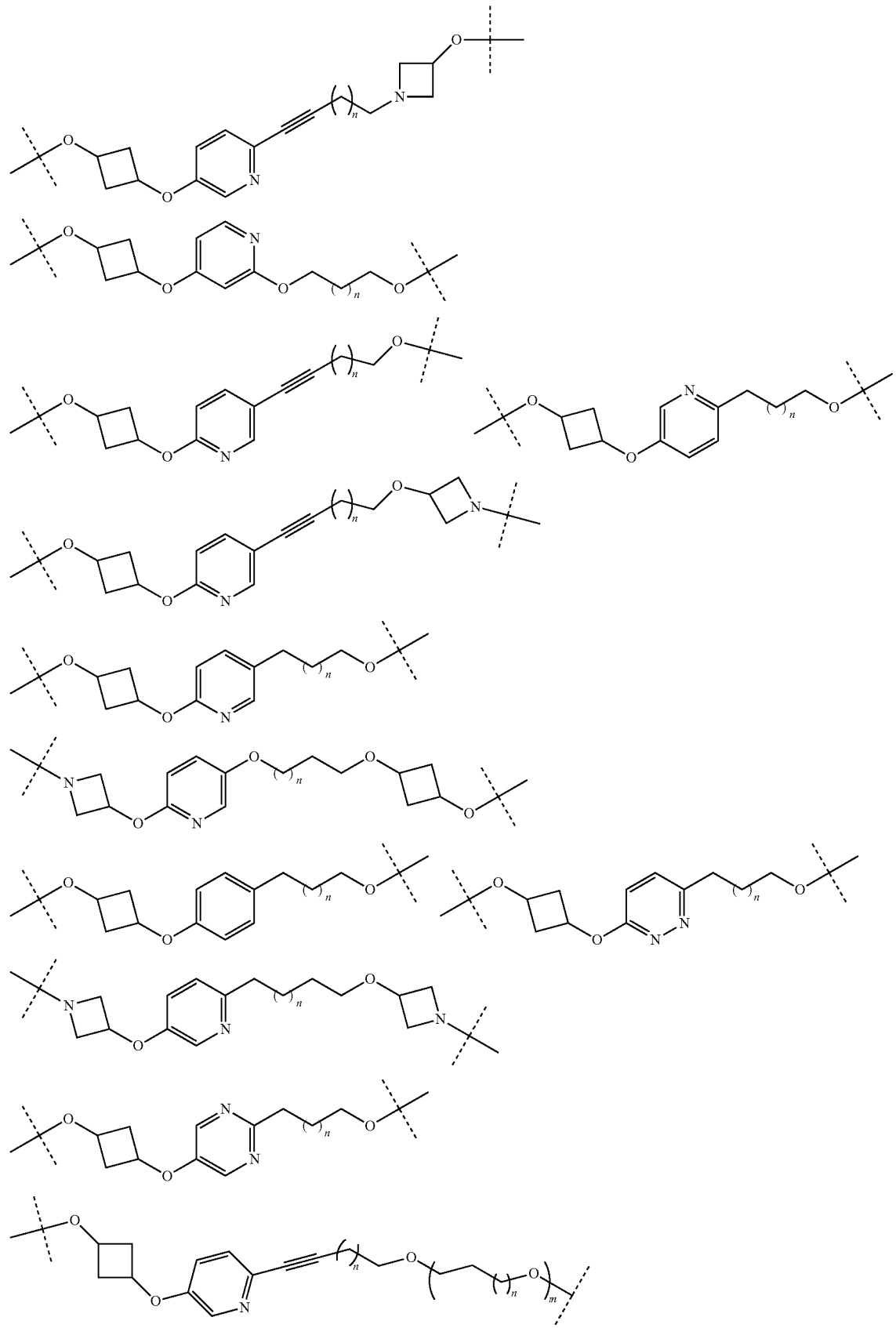

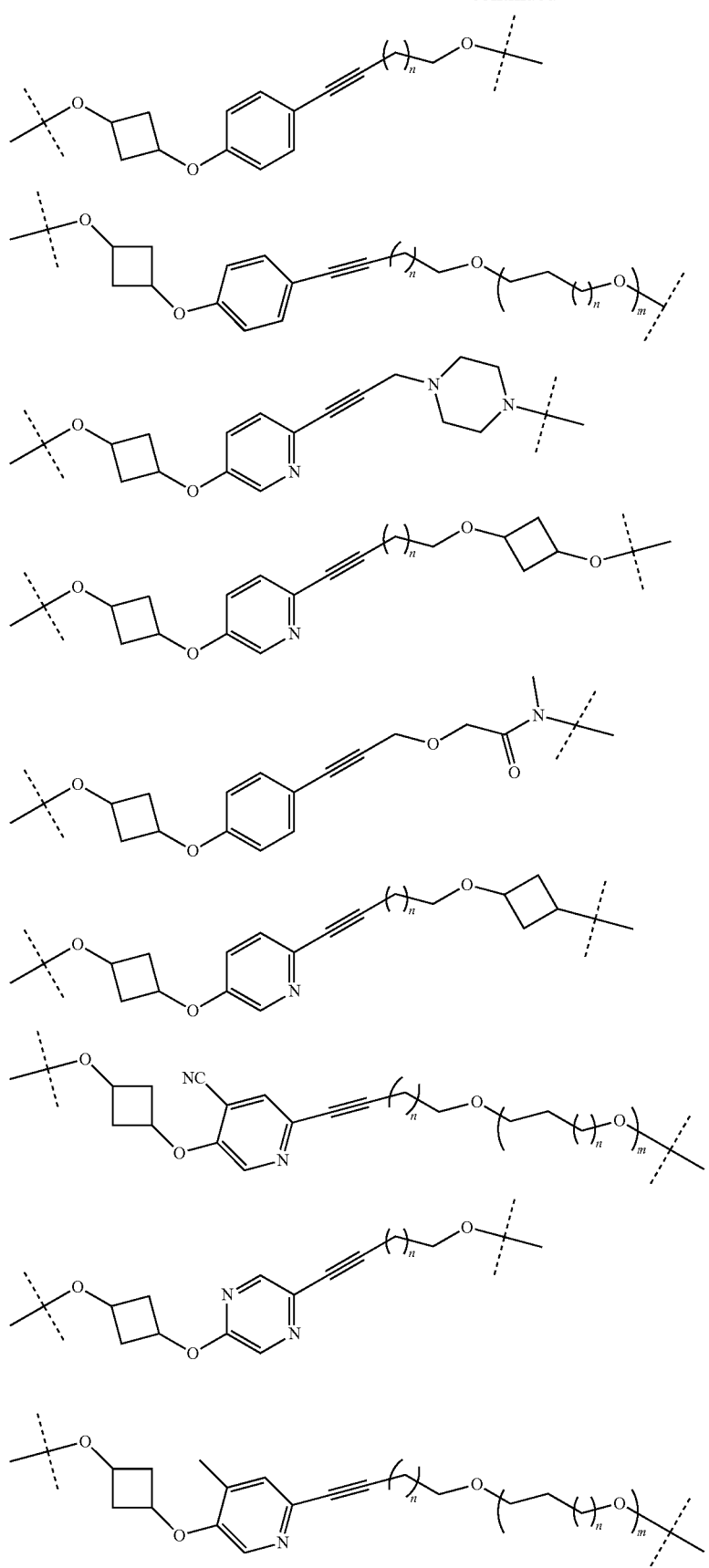

-continued
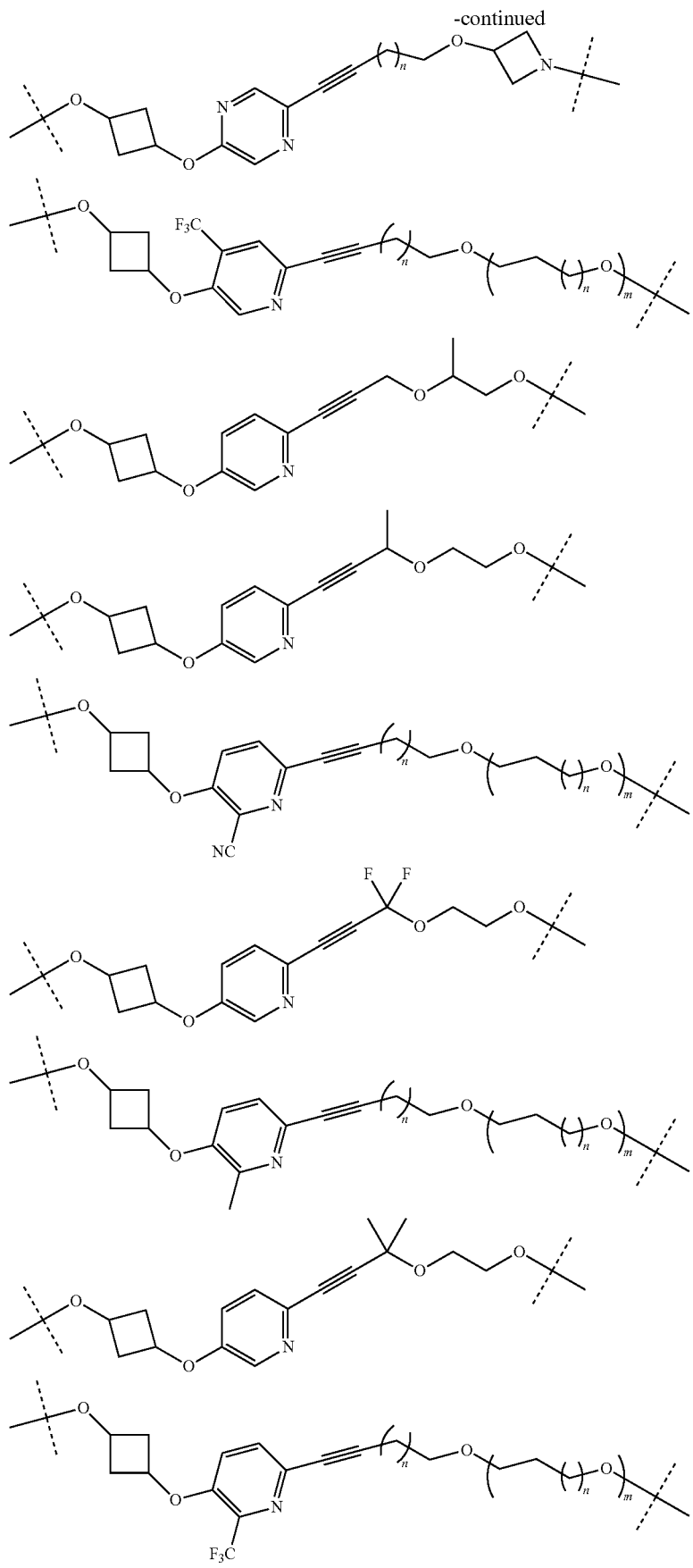

-continued
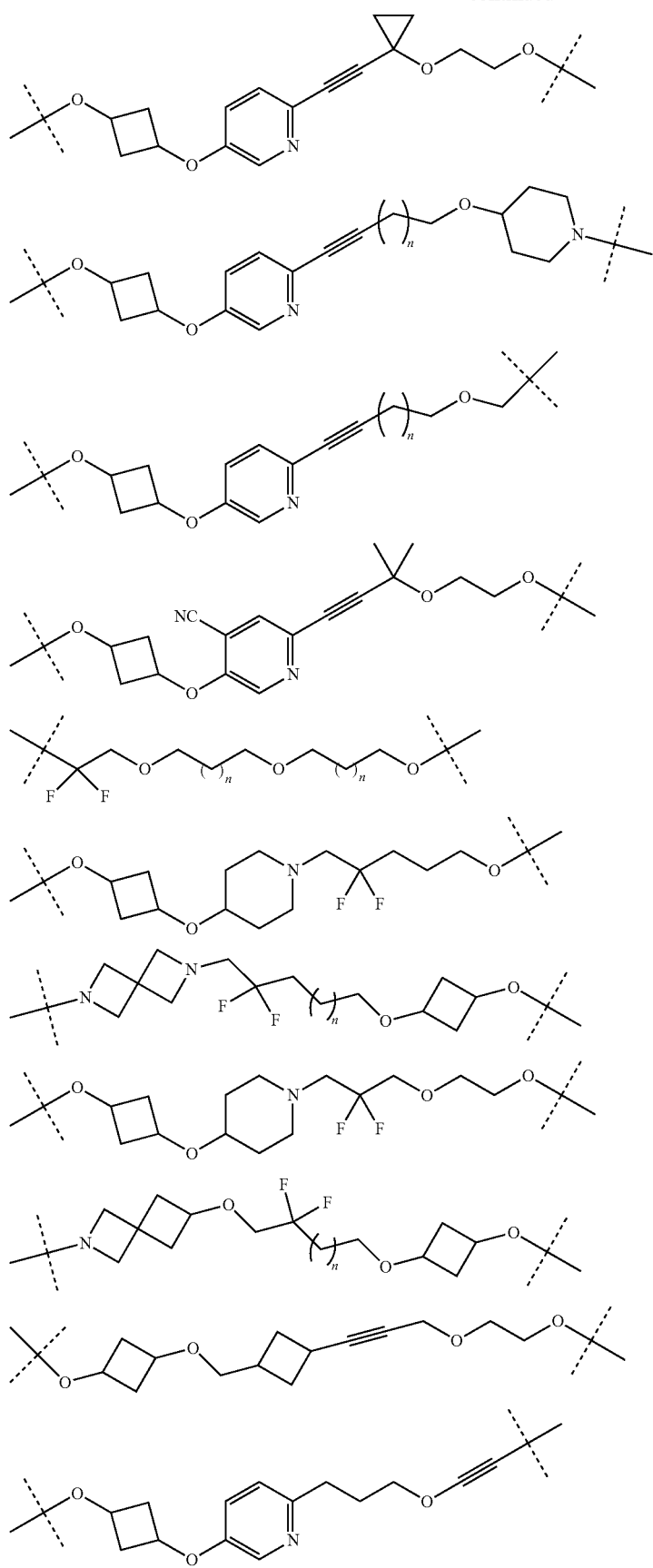

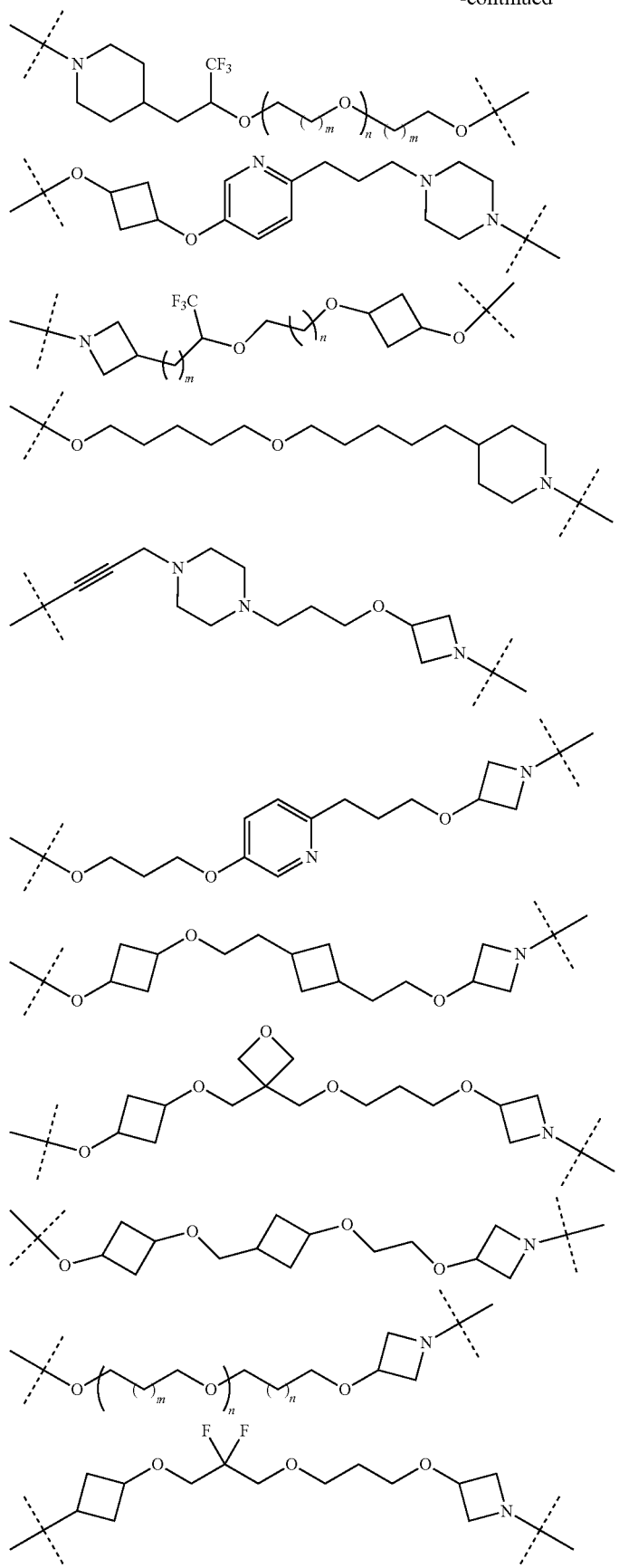

-continued
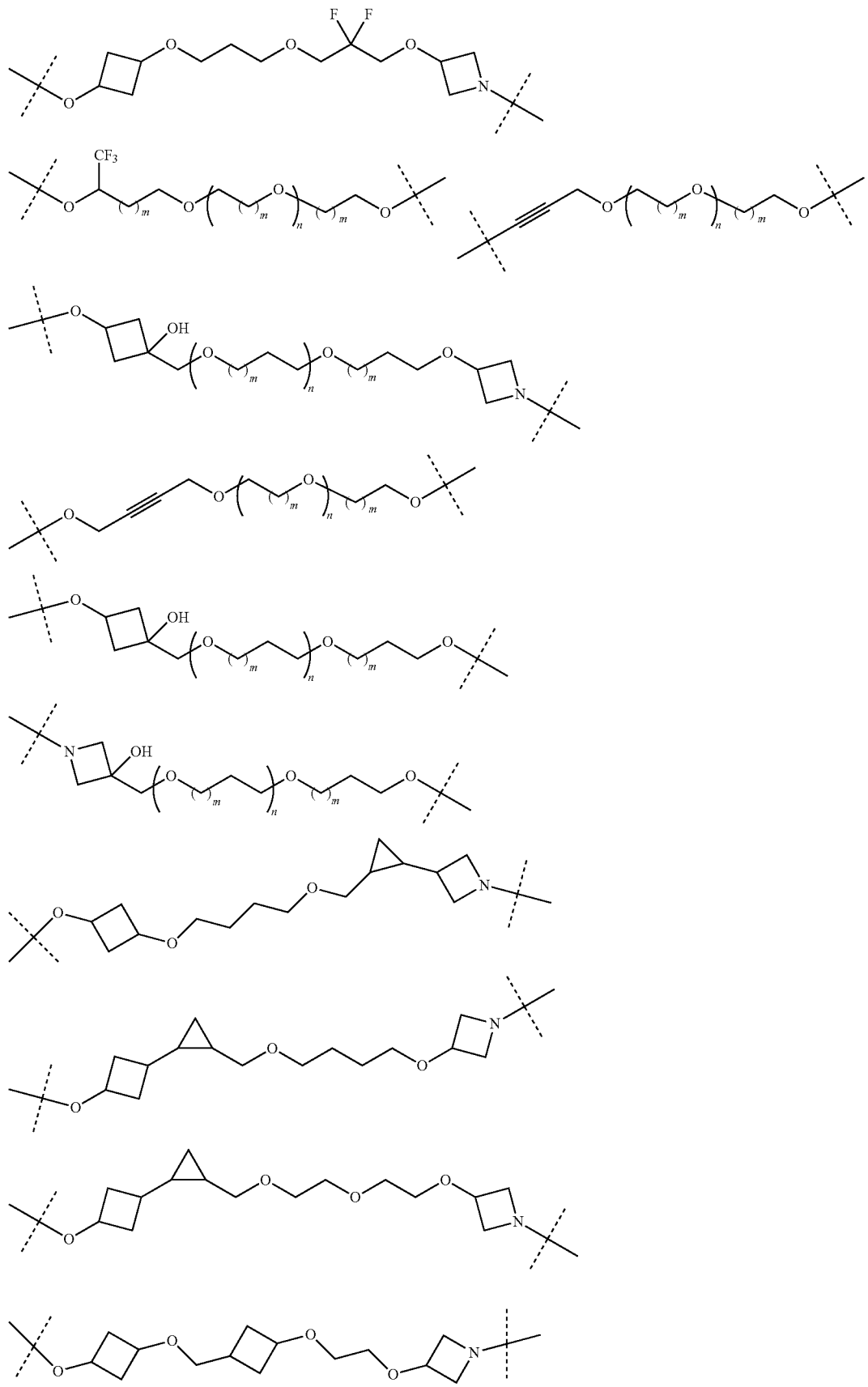

-continued
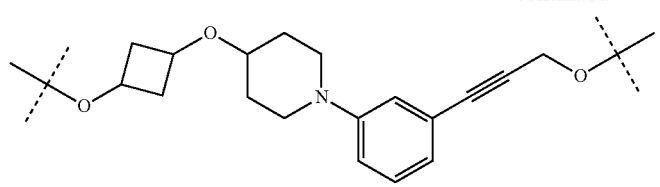
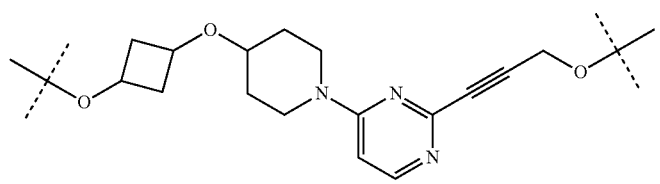
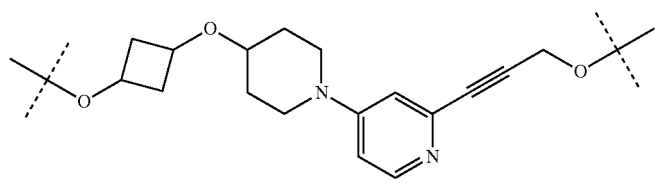
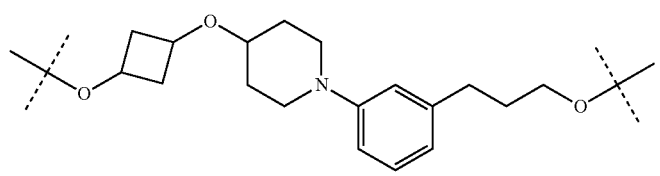
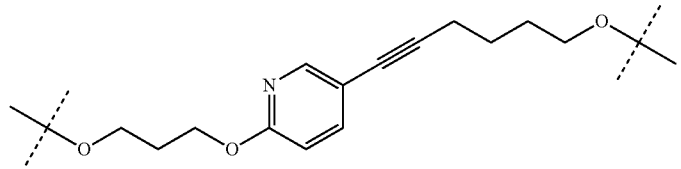
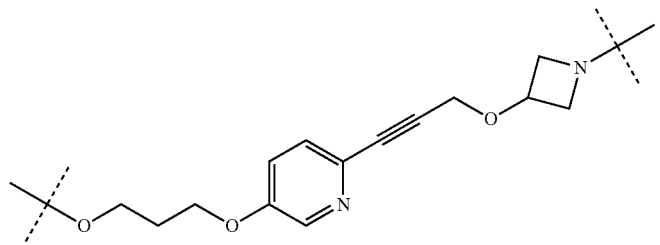

-continued
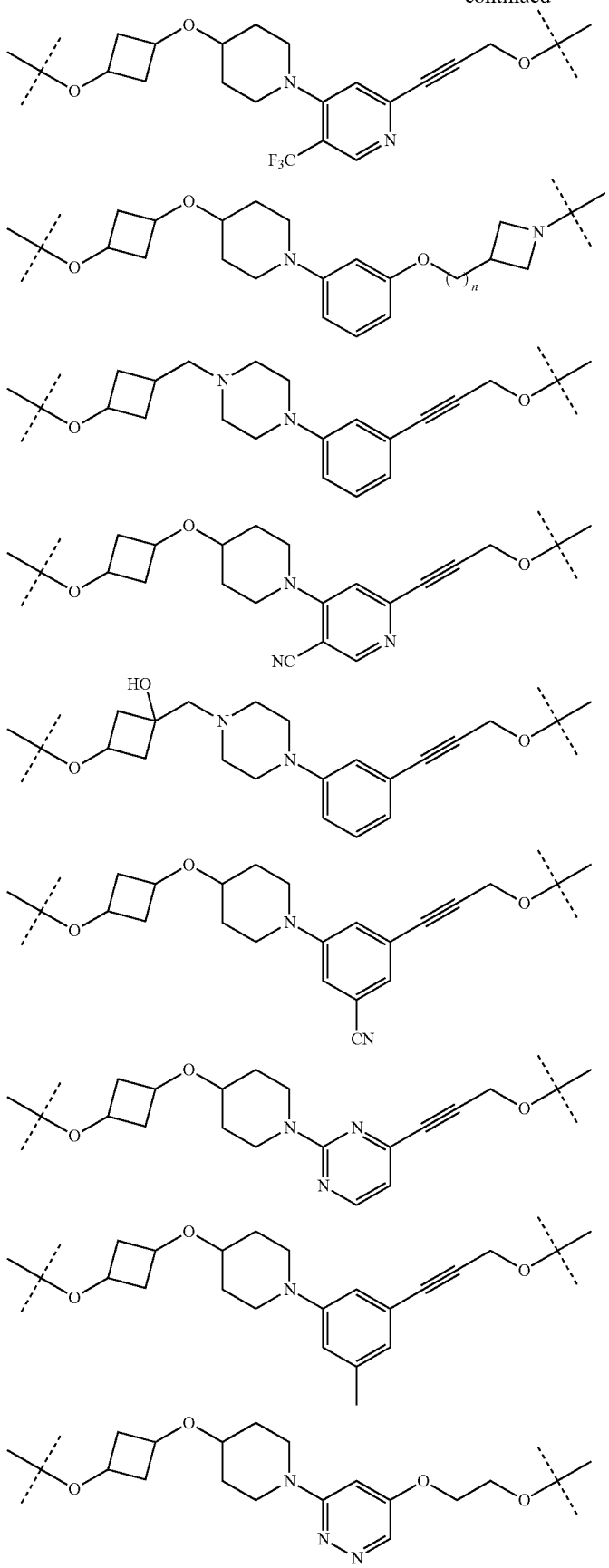

-continued
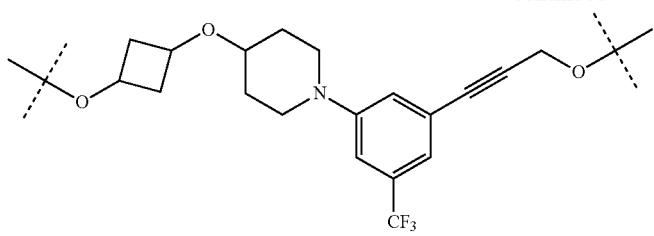
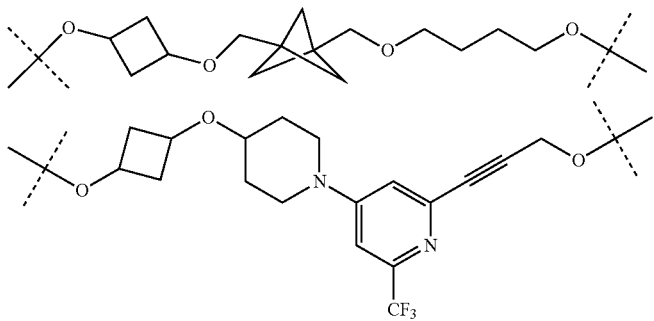
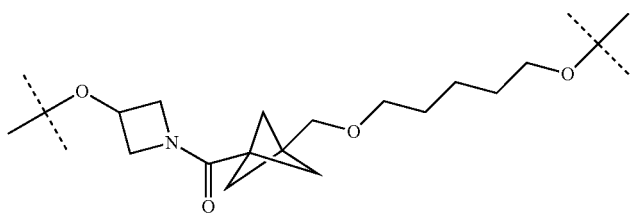
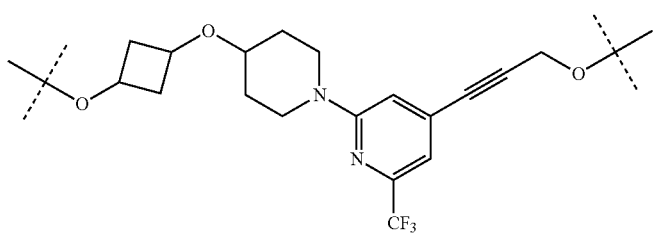
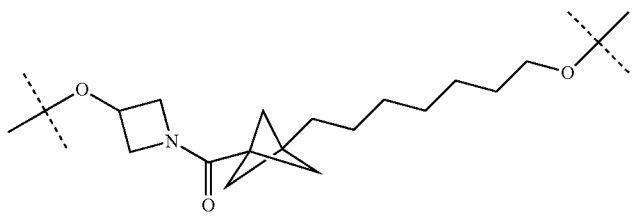
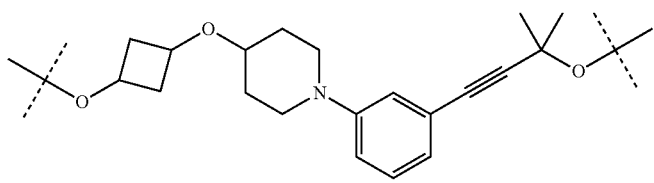
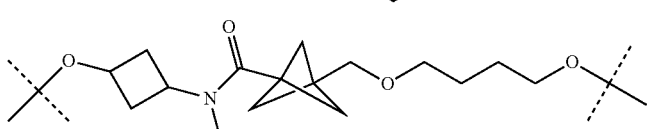
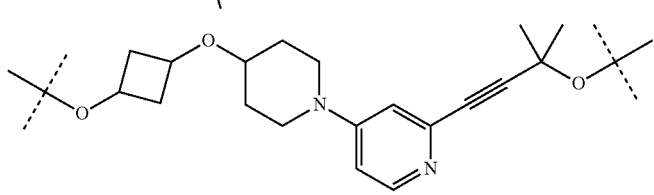

-continued
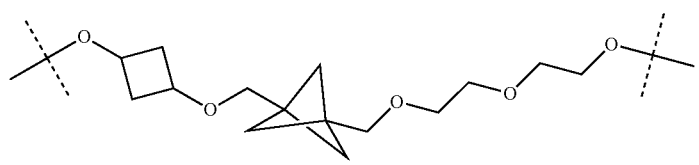
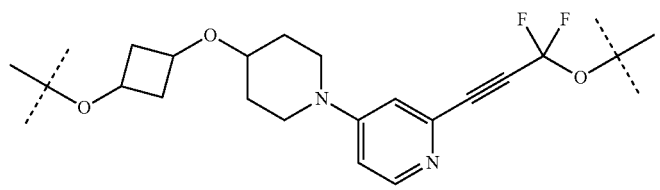
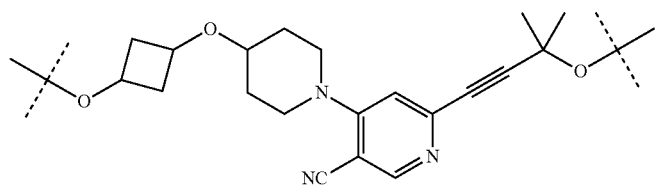
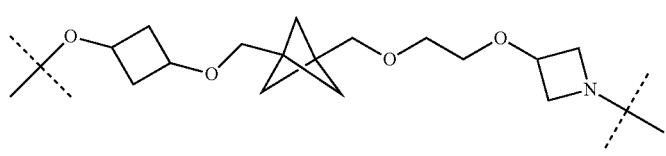
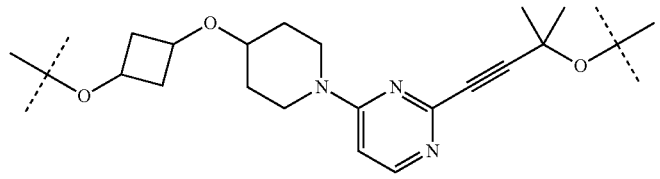
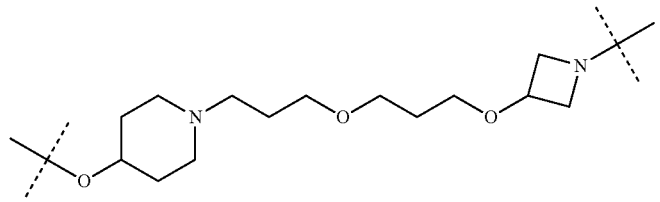
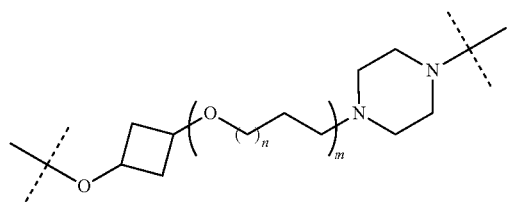
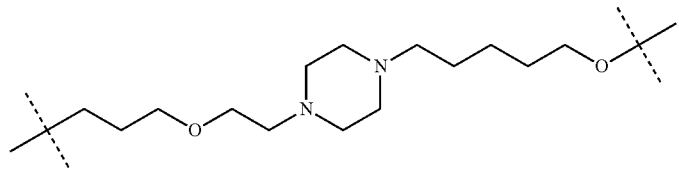

-continued
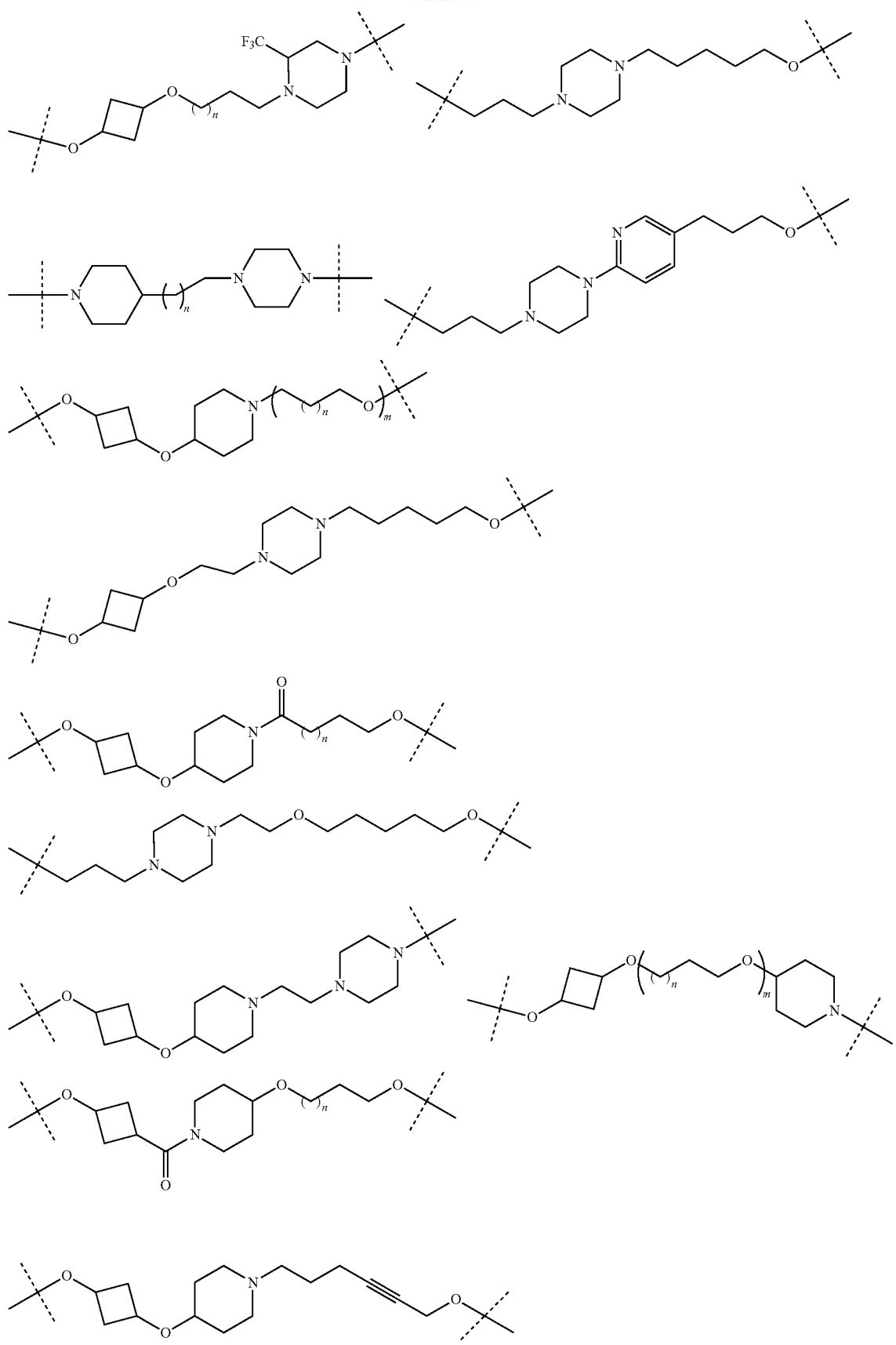

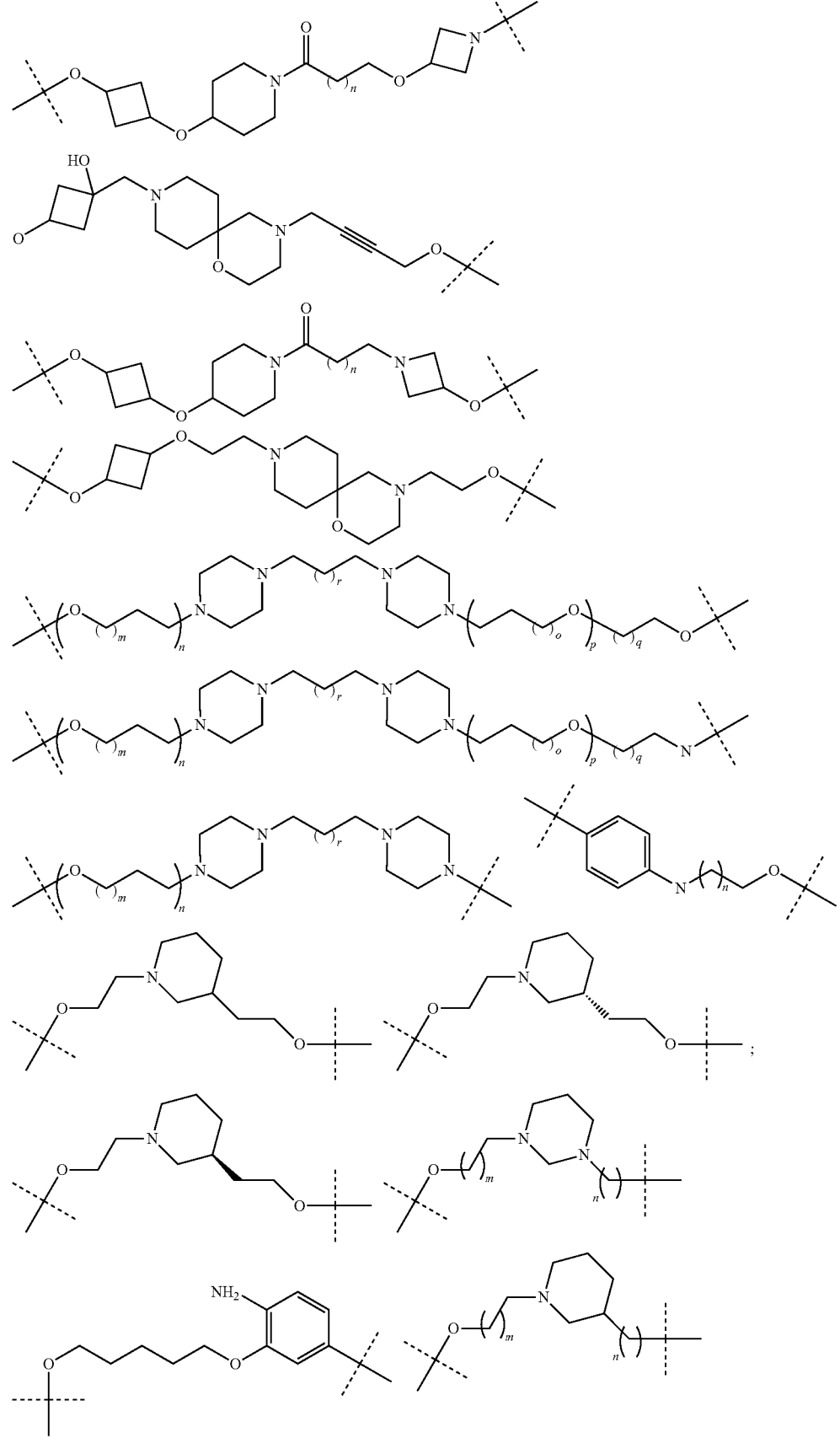

-continued
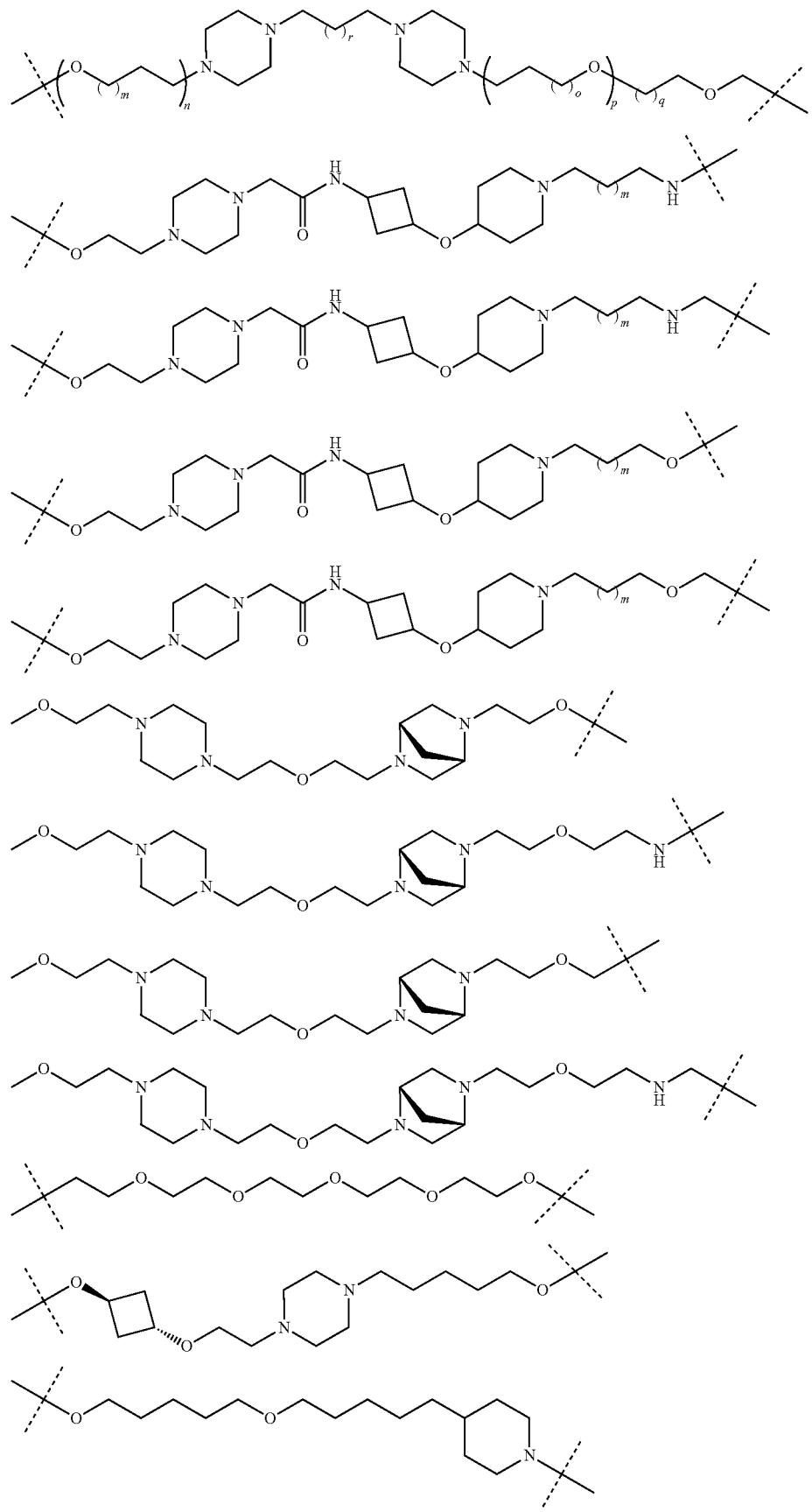

-continued
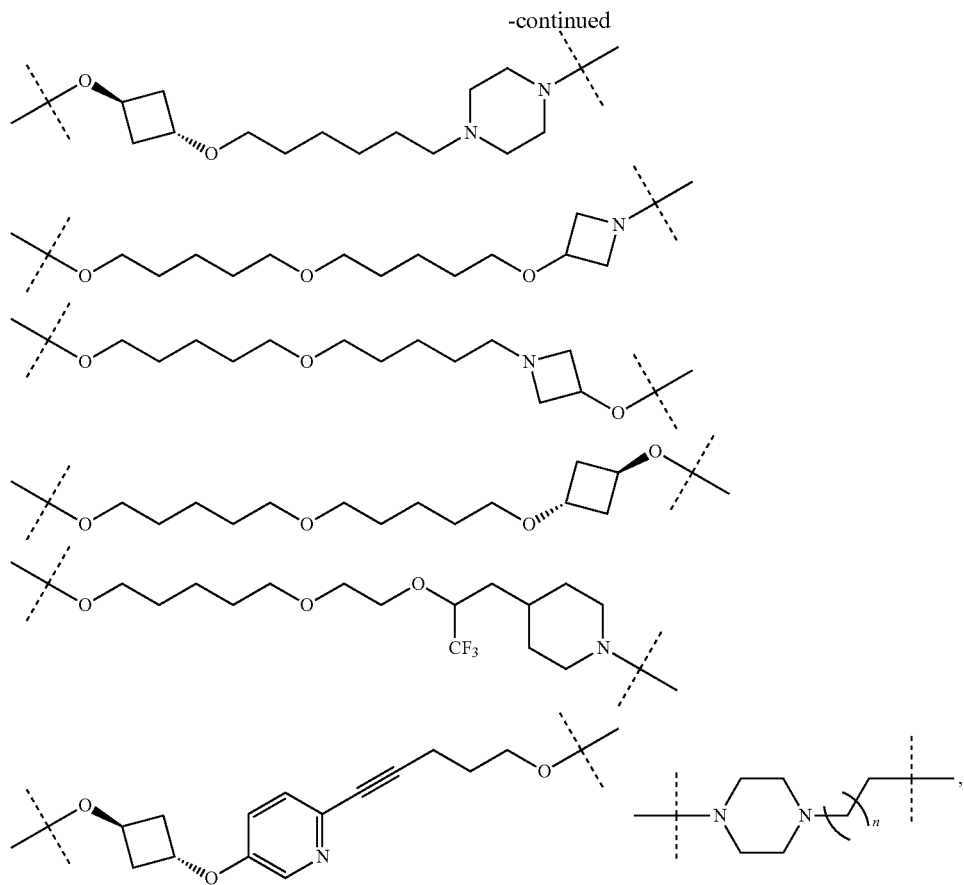
wherein each m, n, o, p, q, and r is independently 0, 1, 2, 3, 4, 5, 6, or 7.
In any aspect or embodiment described herein, L is selected from the group consisting of:
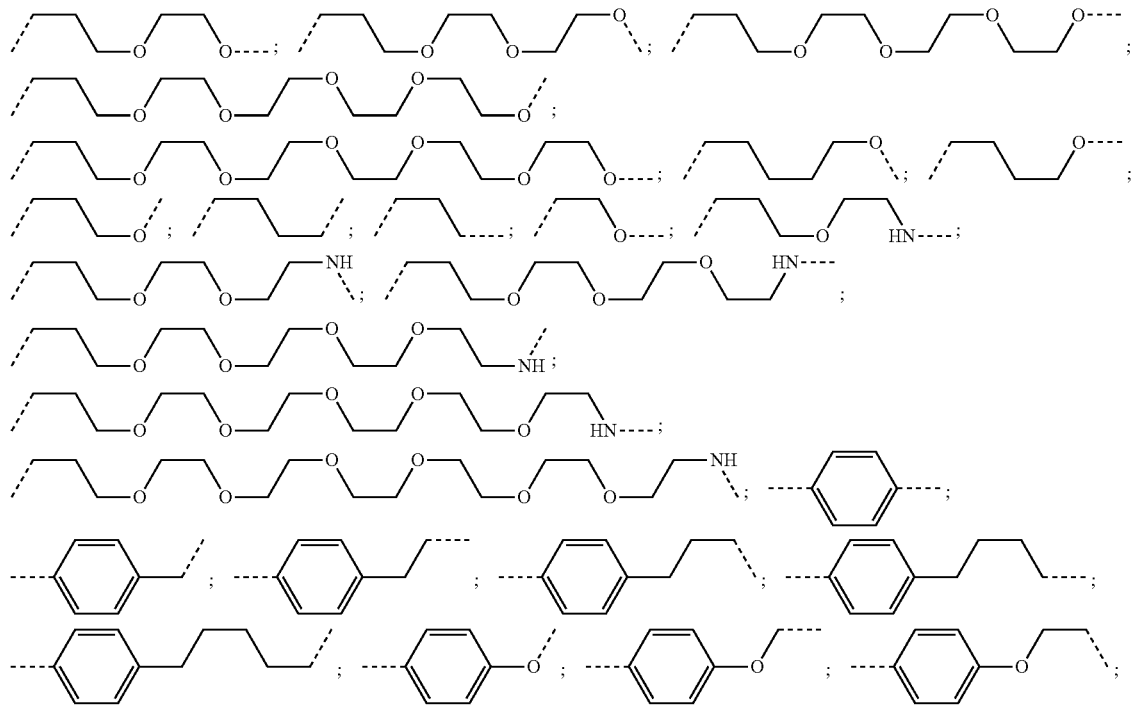

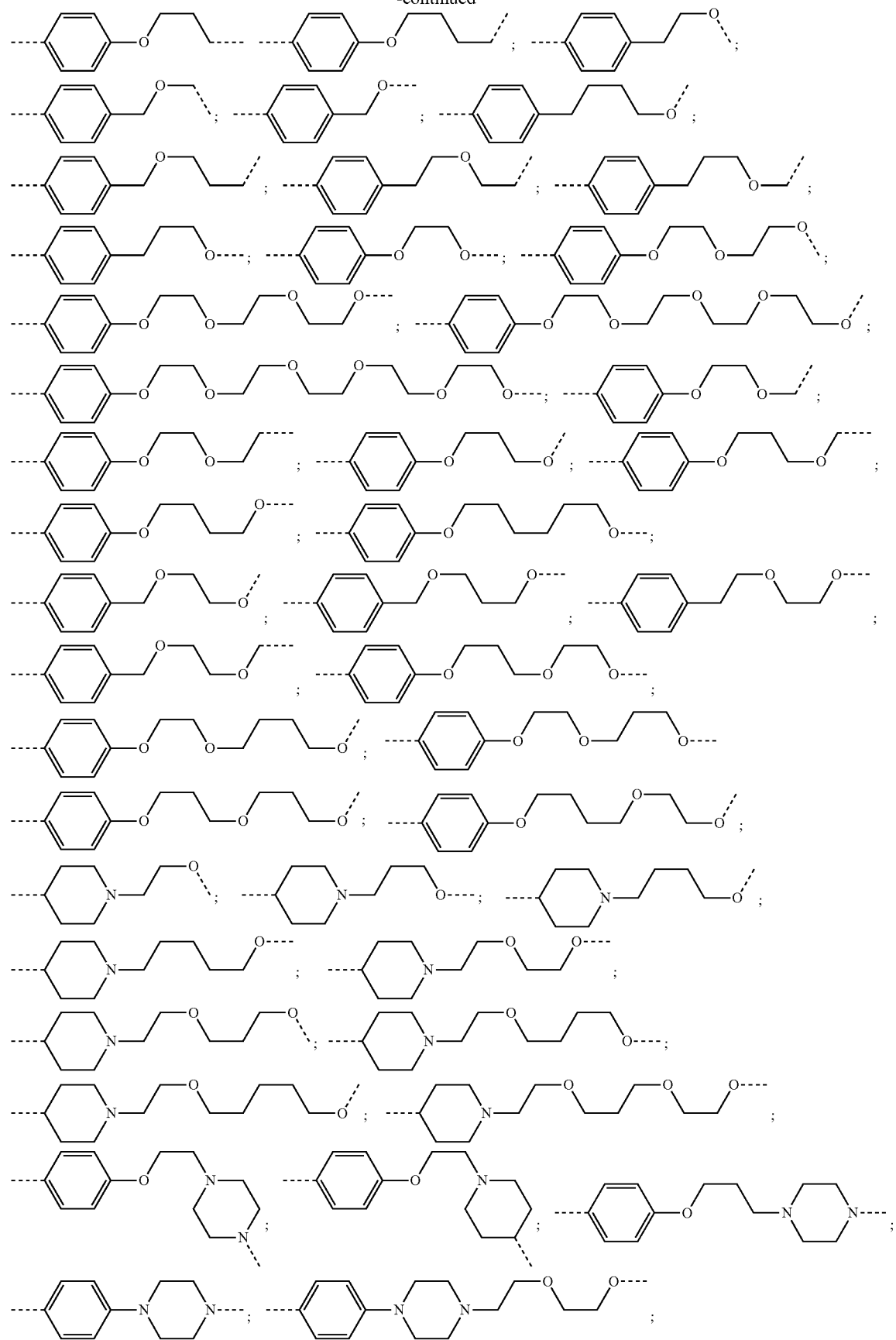

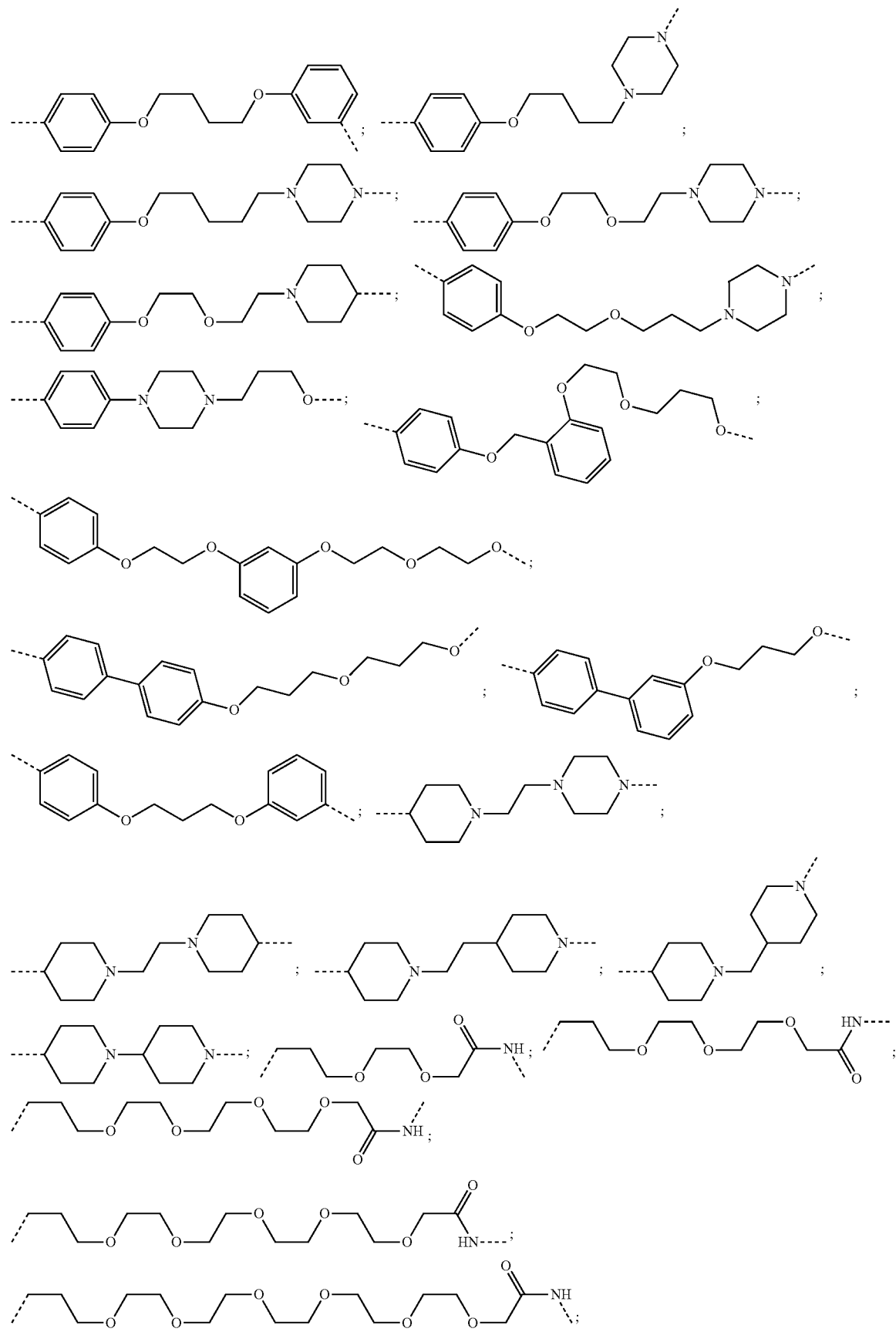

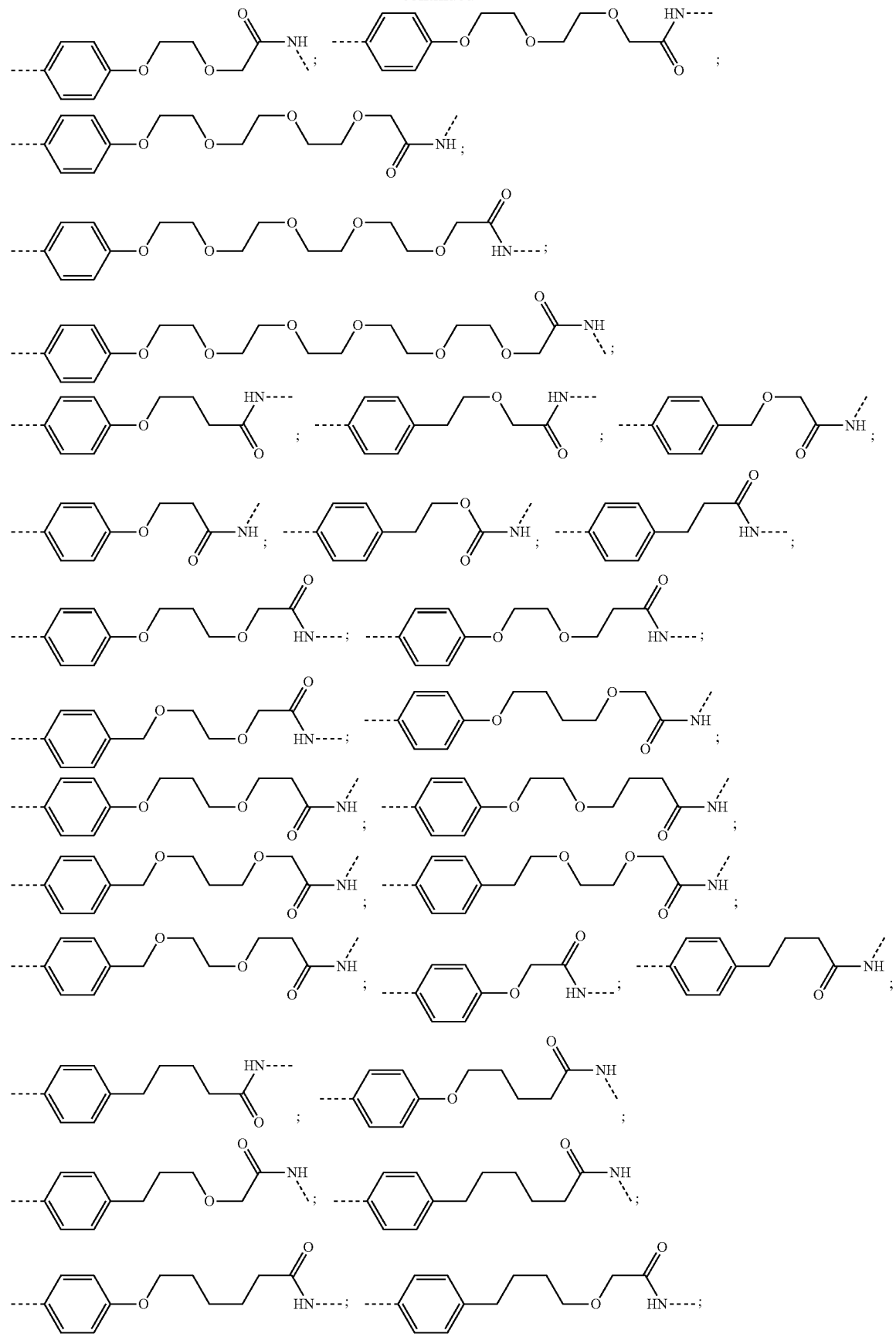

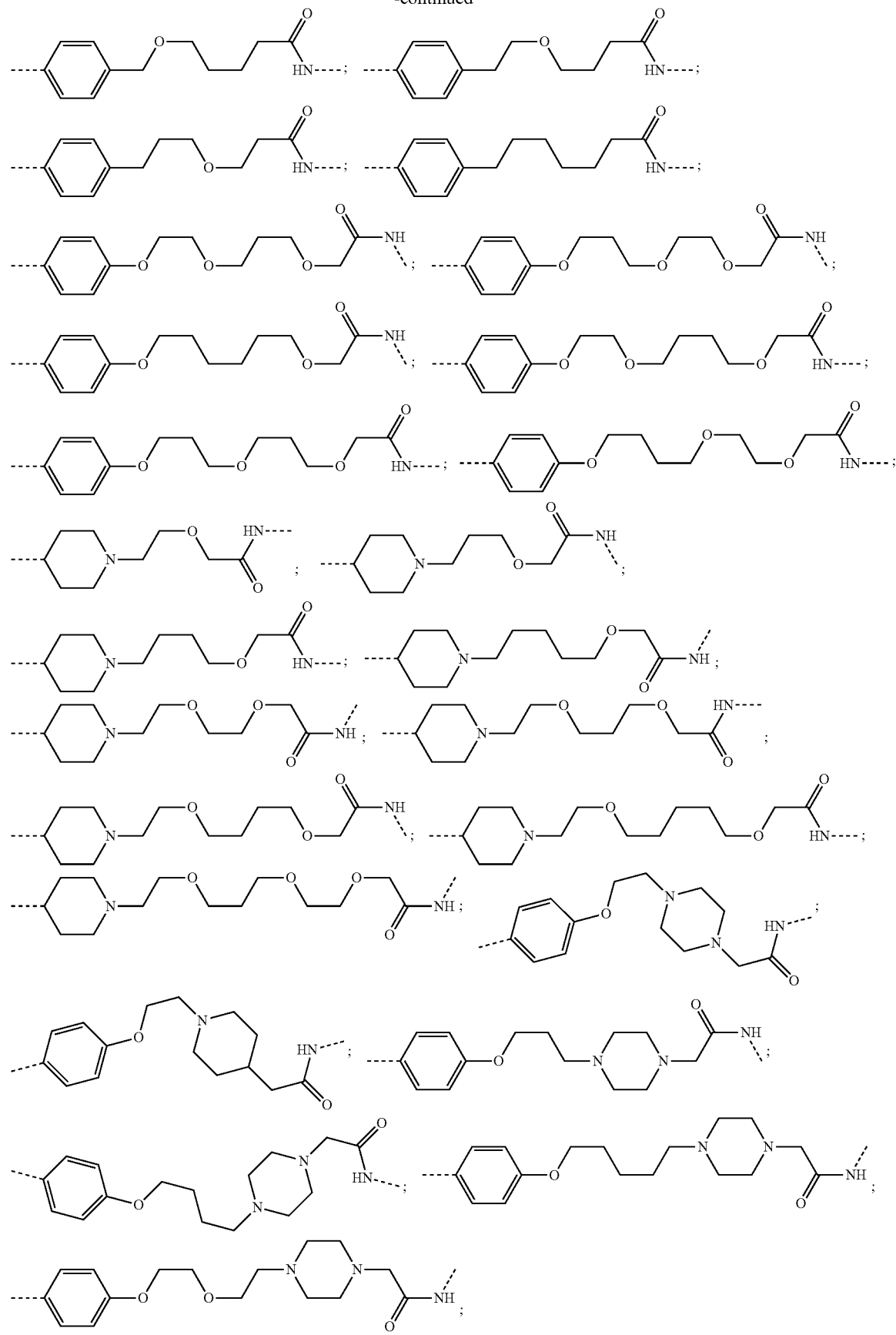

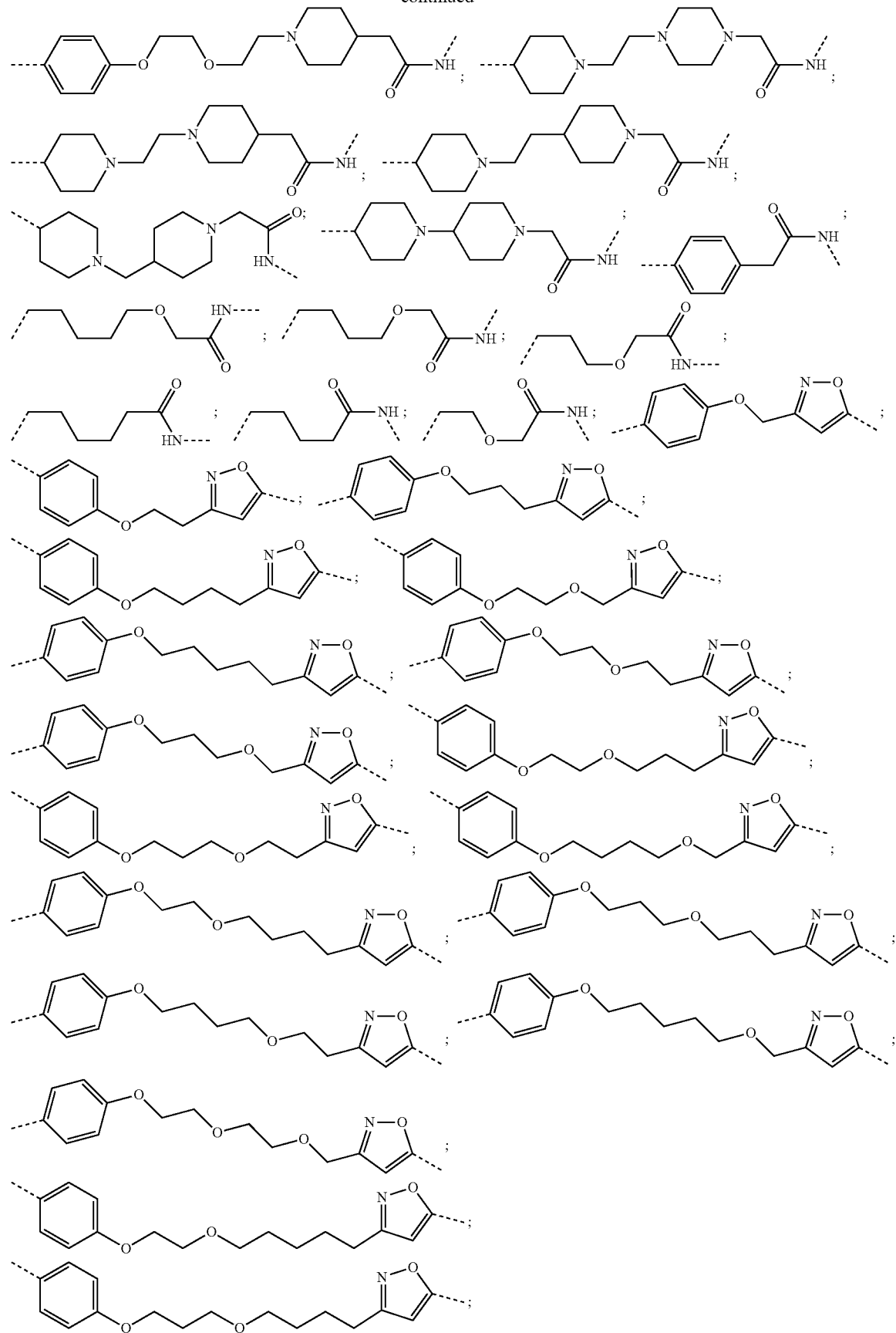

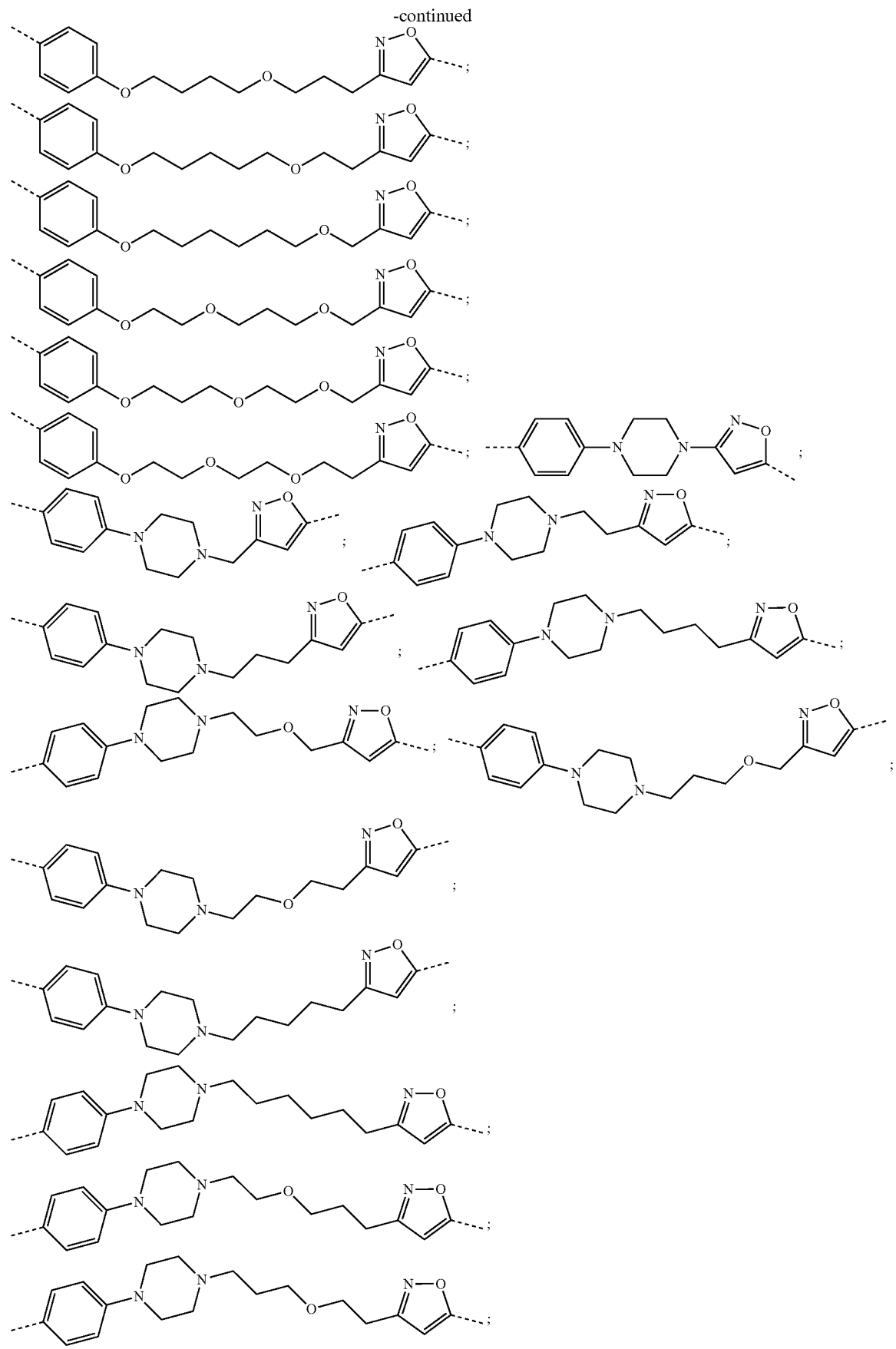

-continued
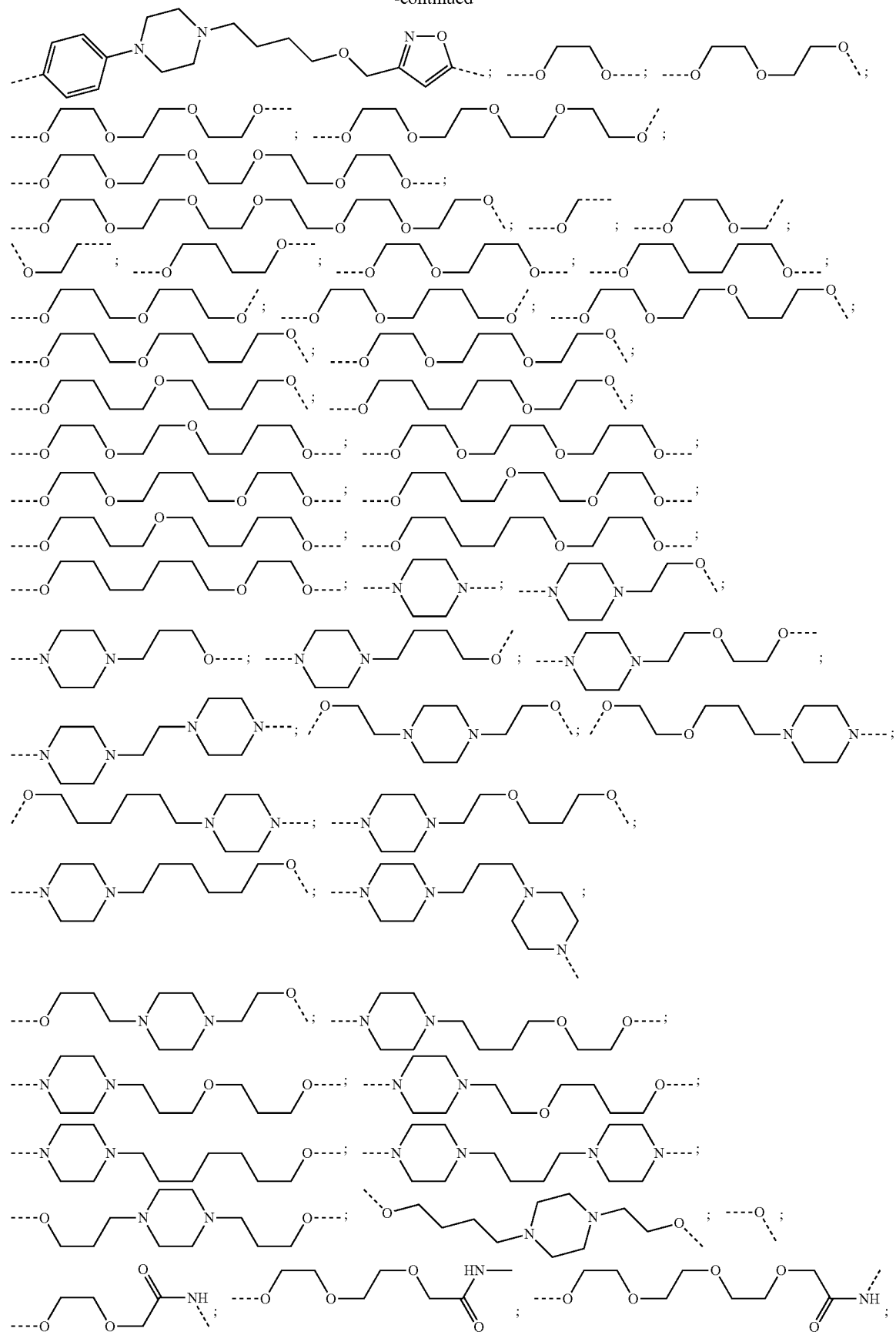

-continued


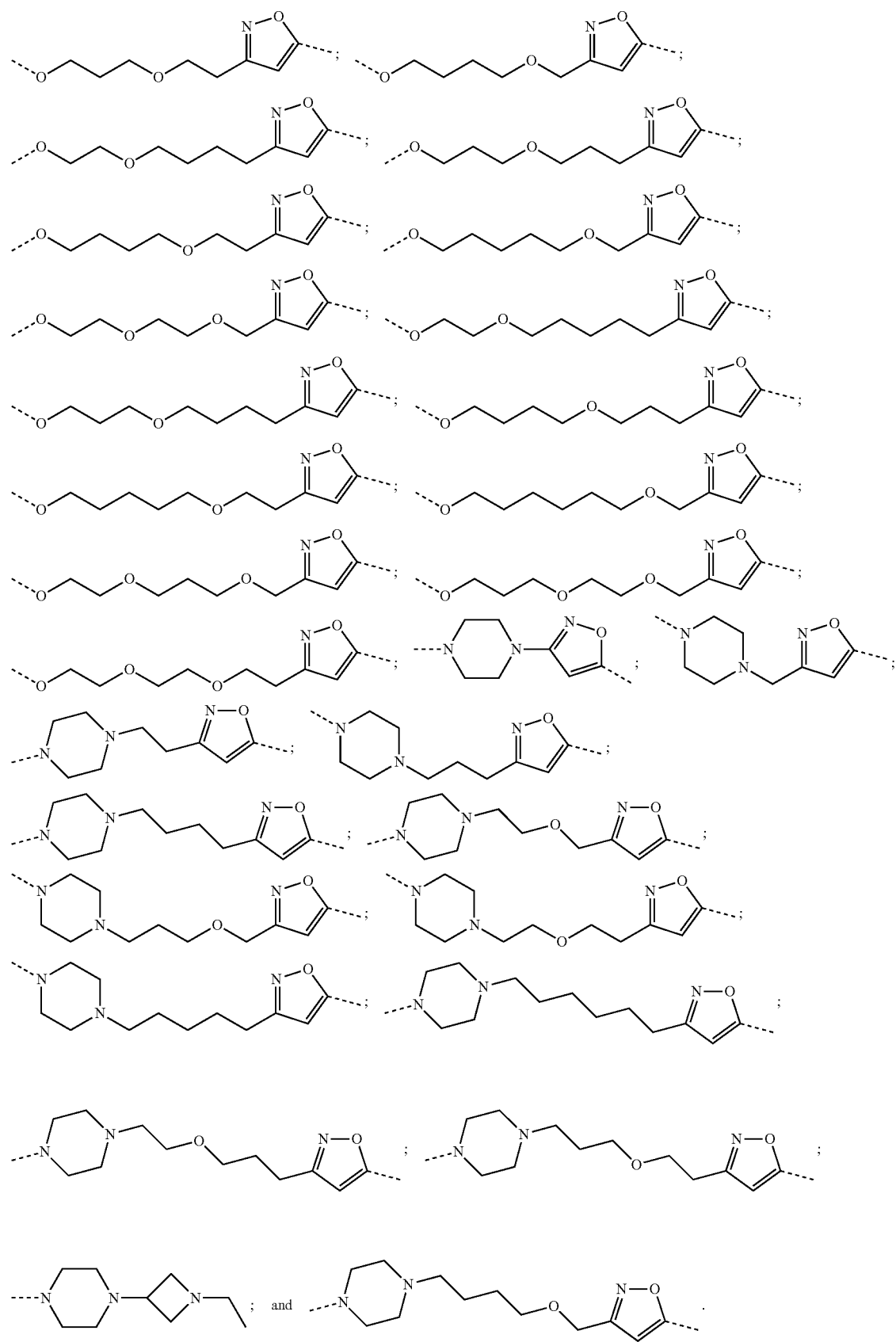

In additional embodiments, the linker (L) comprises a structure selected from, but not limited to the structure shown below, where a dashed line indicates the attachment point to the PTM or ULM moieties.

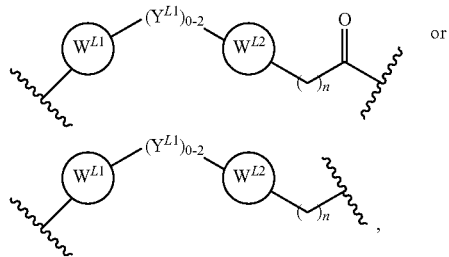

wherein:
$W^{L1}$ and $W^{L2}$ are each independently a 4-8 membered ring with 0-4 heteroatoms, optionally substituted with $R^Q$, each $R^Q$ is independently a H, halo, OH, CN, $CF_3$, $C_1$-$C_6$ alkyl (linear, branched, optionally substituted), $C_1$-$C_6$ alkoxy (linear, branched, optionally substituted), or 2 $R^Q$ groups taken together with the atom they are attached to, form a 4-8 membered ring system containing 0-4 heteroatoms;
$Y^{L1}$ is each independently a bond, $C_1$-$C_6$ alkyl (linear, branched, optionally substituted) and optionally one or more C atoms are replaced with O; or $C_1$-$C_6$ alkoxy (linear, branched, optionally substituted);
n is 0-10; and
a dashed line indicates the attachment point to the PTM or ULM moieties.

In additional embodiments, the linker (L) comprises a structure selected from, but not limited to the structure shown below, where a dashed line indicates the attachment point to the PTM or ULM moieties.

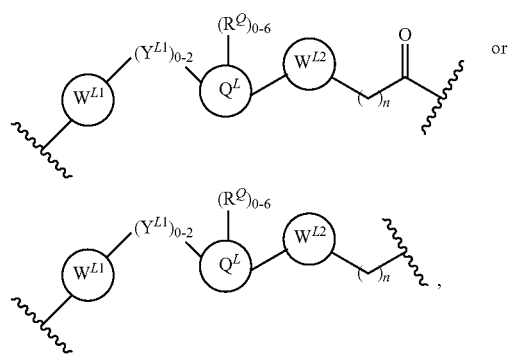

wherein:
$W^{L1}$ and $W^{L2}$ are each independently aryl, heteroaryl, cyclic, heterocyclic, $C_{1-6}$ alkyl, bicyclic, biaryl, biheteroaryl, or biheterocyclic, each optionally substituted with $R^Q$, each $R^Q$ is independently a H, halo, OH, CN, $CF_3$, hydroxyl, nitro, C≡CH, $C_{2-6}$ alkenyl, $C_{2-6}$ alkynyl, $C_1$-$C_6$ alkyl (linear, branched, optionally substituted), $C_1$-$C_6$ alkoxy (linear, branched, optionally substituted), $OC_{1-3}$alkyl (optionally substituted by 1 or more —F), OH, $NH_2$, $NR^{Y1}R^{Y2}$, CN, or 2 $R^Q$ groups taken together with the atom they are attached to, form a 4-8 membered ring system containing 0-4 heteroatoms;

$Y^{L1}$ is each independently a bond, $NR^{YL1}$, O, S, $NR^{YL2}$, $CR^{YL1}R^{YL2}$, C=O, C=S, SO, $SO_2$, $C_1$-$C_6$alkyl (linear, branched, optionally substituted) and optionally one or more C atoms are replaced with O; $C_1$-$C_6$ alkoxy (linear, branched, optionally substituted);

$Q^L$ is a 3-6 membered alicyclic or aromatic ring with 0-4 heteroatoms, optionally bridged, optionally substituted with 0-6 $R^Q$, each $R^Q$ is independently H, $C_{1-6}$ alkyl (linear, branched, optionally substituted by 1 or more halo, $C_{1-6}$ alkoxyl), or 2 $R^Q$ groups taken together with the atom they are attached to, form a 3-8 membered ring system containing 0-2 heteroatoms);

$R^{YL1}$, $R^{YL2}$ are each independently H, OH, $C_{1-6}$ alkyl (linear, branched, optionally substituted by 1 or more halo, $C_{1-6}$ alkoxyl), or $R^1$, $R^2$ together with the atom they are attached to, form a 3-8 membered ring system containing 0-2 heteroatoms);

n is 0-10; and a dashed line indicates the attachment point to the PTM or ULM moieties.

In additional embodiments, the linker group is optionally substituted (poly)ethyleneglycol having between 1 and about 100 ethylene glycol units, between about 1 and about 50 ethylene glycol units, between 1 and about 25 ethylene glycol units, between about 1 and 10 ethylene glycol units, between 1 and about 8 ethylene glycol units and 1 and 6 ethylene glycol units, between 2 and 4 ethylene glycol units, or optionally substituted alkyl groups interdispersed with optionally substituted, O, N, S, P or Si atoms. In certain embodiments, the linker is substituted with an aryl, phenyl, benzyl, alkyl, alkylene, or heterocycle group. In certain embodiments, the linker may be asymmetric or symmetrical.

In any of the embodiments of the compounds described herein, the linker group may be any suitable moiety as described herein. In one embodiment, the linker is a substituted or unsubstituted polyethylene glycol group ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycol units.

In another embodiment, the present disclosure is directed to a compound which comprises a PTM group as described above, which binds to a target protein (e.g., EZH2) or polypeptide, which is ubiquitinated by an ubiquitin ligase and is chemically linked directly to the ULM group or through a linker moiety L, or PTM is alternatively a ULM' group which is also a ubiquitin ligase binding moiety, which may be the same or different than the ULM group as described above and is linked directly to the ULM group directly or through the linker moiety; and L is a linker moiety as described above which may be present or absent and which chemically (covalently) links ULM to PTM, or a pharmaceutically acceptable salt, enantiomer, stereoisomer, solvate or polymorph thereof.

In certain embodiments, the linker group L is a group comprising one or more covalently connected structural units independently selected from the group consisting of:

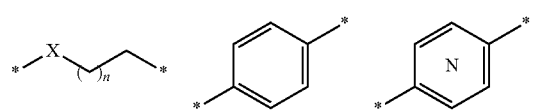

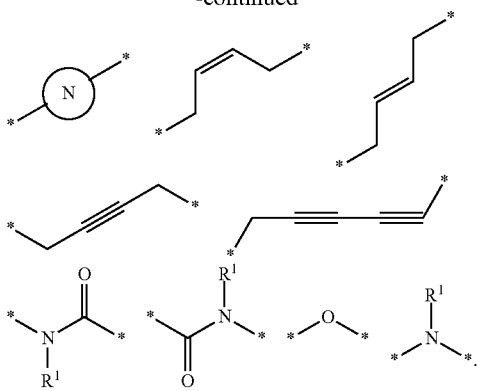

The X is selected from the group consisting of O, N, S, S(O) and SO$_2$; n is integer from 1-5, 5; R$^{L1}$ is hydrogen or alkyl,

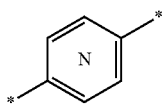

is a mono- or bicyclic aryl or heteroaryl optionally substituted with 1-3 substituents selected from alkyl, halogen, haloalkyl, hydroxy, alkoxy or cyano;

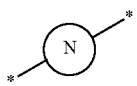

is a mono- or bicyclic cycloalkyl or a heterocycloalkyl optionally substituted with 1-3 substituents selected from alkyl, halogen, haloalkyl, hydroxy, alkoxy or cyano; and the phenyl ring fragment can be optionally substituted with 1, 2 or 3 substituents selected from the group consisting of alkyl, halogen, haloalkyl, hydroxy, alkoxy and cyano. In an embodiment, the linker group L comprises up to 10 covalently connected structural units, as described above.

Although the ULM group and PTM group may be covalently linked to the linker group through any group which is appropriate and stable to the chemistry of the linker, in preferred aspects of the present disclosure, the linker is independently covalently bonded to the ULM group and the PTM group preferably through an amide, ester, thioester, keto group, carbamate (urethane), carbon or ether, each of which groups may be inserted anywhere on the ULM group and PTM group to provide maximum binding of the ULM group on the ubiquitin ligase and the PTM group on the target protein to be degraded. (It is noted that in certain aspects where the PTM group is a ULM group, the target protein for degradation may be the ubiquitin ligase itself). In certain preferred aspects, the linker may be linked to an optionally substituted alkyl, alkylene, alkene or alkyne group, an aryl group or a heterocyclic group on the ULM and/or PTM groups.

Exemplary PTMs

In preferred aspects of the disclosure, the PTM group is a group, which binds to target proteins. Targets of the PTM group are numerous in kind and are selected from proteins that are expressed in a cell such that at least a portion of the sequences is found in the cell and may bind to a PTM group. The term "protein" includes oligopeptides and polypeptide sequences of sufficient length that they can bind to a PTM group according to the present disclosure. Any protein in a eukaryotic system or a microbial system, including a virus, bacteria or fungus, as otherwise described herein, are targets for ubiquitination mediated by the compounds according to the present disclosure. Preferably, the target protein is a eukaryotic protein, such as EZH2.

PTM groups according to the present disclosure include, for example, any moiety which binds to a protein specifically (binds to a target protein) and includes the following non-limiting examples of small molecule target protein moieties: histone-lysine N-methyltransferase, Hsp90 inhibitors, kinase inhibitors, EZH2 inhibitors, HDM2 & MDM2 inhibitors, compounds targeting Human BET Bromodomain-containing proteins, HDAC inhibitors, human lysine methyltransferase inhibitors, angiogenesis inhibitors, nuclear hormone receptor compounds, immunosuppressive compounds, and compounds targeting the aryl hydrocarbon receptor (AHR), among numerous others. The compositions described below exemplify some of the members of small molecule target protein binding moieties. Such small molecule target protein binding moieties also include pharmaceutically acceptable salts, enantiomers, solvates and polymorphs of these compositions, as well as other small molecules that may target a protein of interest. These binding moieties are linked to the ubiquitin ligase binding moiety preferably through a linker in order to present a target protein (to which the protein target moiety is bound) in proximity to the ubiquitin ligase for ubiquitination and degradation.

Any protein, which can bind to a protein target moiety or PTM group and acted on or degraded by a ubiquitin ligase is a target protein according to the present disclosure. In general, target proteins may include, for example, structural proteins, receptors, enzymes, cell surface proteins, proteins pertinent to the integrated function of a cell, including proteins involved in catalytic activity, aromatase activity, motor activity, helicase activity, metabolic processes (anabolism and catrabolism), antioxidant activity, proteolysis, biosynthesis, proteins with kinase activity, oxidoreductase activity, transferase activity, hydrolase activity, lyase activity, isomerase activity, ligase activity, enzyme regulator activity, signal transducer activity, structural molecule activity, binding activity (protein, lipid carbohydrate), receptor activity, cell motility, membrane fusion, cell communication, regulation of biological processes, development, cell differentiation, response to stimulus, behavioral proteins, cell adhesion proteins, proteins involved in cell death, proteins involved in transport (including protein transporter activity, nuclear transport, ion transporter activity, channel transporter activity, carrier activity, permease activity, secretion activity, electron transporter activity, pathogenesis, chaperone regulator activity, nucleic acid binding activity, transcription regulator activity, extracellular organization and biogenesis activity, translation regulator activity. Proteins of interest can include proteins from eurkaryotes and prokaryotes including humans as targets for drug therapy, other animals, including domesticated animals, microbials for the determination of targets for antibiotics and other antimicrobials and plants, and even viruses, among numerous others.

The present disclosure may be used to treat a number of disease states and/or conditions, including any disease state and/or condition in which proteins are dysregulated and where a patient would benefit from the degradation of proteins.

In an additional aspect, the description provides therapeutic compositions comprising an effective amount of a compound as described herein or salt form thereof, and a pharmaceutically acceptable carrier, additive or excipient, and optionally an additional bioactive agent. The therapeutic compositions modulate protein degradation in a patient or subject, for example, an animal such as a human, and can be used for treating or ameliorating disease states or conditions which are modulated through the degraded protein. In certain embodiments, the therapeutic compositions as described herein may be used to effectuate the degradation of proteins of interest for the treatment or amelioration of a disease, e.g., cancer. In certain additional embodiments, the disease is breast cancer, prostate cancer, bladder cancer, uterine cancer, renal cancer, melanoma, and/or lymphoma.

In alternative aspects, the present disclosure relates to a method for treating a disease state or ameliorating the symptoms of a disease or condition in a subject in need thereof by degrading a protein or polypeptide through which a disease state or condition is modulated comprising administering to said patient or subject an effective amount, e.g., a therapeutically effective amount, of at least one compound as described hereinabove, optionally in combination with a pharmaceutically acceptable carrier, additive or excipient, and optionally an additional bioactive agent, wherein the composition is effective for treating or ameliorating the disease or disorder or symptom thereof in the subject. The method according to the present disclosure may be used to treat a large number of disease states or conditions including cancer, by virtue of the administration of effective amounts of at least one compound described herein. The disease state or condition may be a disease caused by a microbial agent or other exogenous agent such as a virus, bacteria, fungus, protozoa or other microbe or may be a disease state, which is caused by overexpression of a protein, which leads to a disease state and/or condition.

In another aspect, the description provides methods for identifying the effects of the degradation of proteins of interest in a biological system using compounds according to the present disclosure.

The term "target protein" is used to describe a protein or polypeptide, which is a target for binding to a compound according to the present disclosure and degradation by ubiquitin ligase hereunder. Such small molecule target protein binding moieties also include pharmaceutically acceptable salts, enantiomers, solvates and polymorphs of these compositions, as well as other small molecules that may target a protein of interest. These binding moieties are linked to at least one ULM group (e.g. VLM, CLM, ILM, and/or MLM) through at least one linker group L.

Target proteins, which may be bound to the protein target moiety and degraded by the ligase to which the ubiquitin ligase binding moiety is bound, include any protein or peptide, including fragments thereof, analogues thereof, and/or homologues thereof. Target proteins include proteins and peptides having any biological function or activity including structural, regulatory, hormonal, enzymatic, genetic, immunological, contractile, storage, transportation, and signal transduction. In certain embodiments, the target proteins include structural proteins, receptors, enzymes, cell surface proteins, proteins pertinent to the integrated function of a cell, including proteins involved in catalytic activity, aromatase activity, motor activity, helicase activity, metabolic processes (anabolism and catabolism), antioxidant activity, proteolysis, biosynthesis, proteins with kinase activity, oxidoreductase activity, transferase activity, hydrolase activity, lyase activity, isomerase activity, ligase activity, enzyme regulator activity, signal transducer activity, structural molecule activity, binding activity (protein, lipid carbohydrate), receptor activity, cell motility, membrane fusion, cell communication, regulation of biological processes, development, cell differentiation, response to stimulus, behavioral proteins, cell adhesion proteins, proteins involved in cell death, proteins involved in transport (including protein transporter activity, nuclear transport, ion transporter activity, channel transporter activity, carrier activity, permease activity, secretion activity, electron transporter activity, pathogenesis, chaperone regulator activity, nucleic acid binding activity, transcription regulator activity, extracellular organization and biogenesis activity, translation regulator activity. Proteins of interest can include proteins from eurkaryotes and prokaryotes, including microbes, viruses, fungi and parasites, including humans, microbes, viruses, fungi and parasites, among numerous others, as targets for drug therapy, other animals, including domesticated animals, microbials for the determination of targets for antibiotics and other antimicrobials and plants, and even viruses, among numerous others.

More specifically, a number of drug targets for human therapeutics represent protein targets to which protein target moiety may be bound and incorporated into compounds according to the present disclosure. These include proteins which may be used to restore function in numerous polygenic diseases, including for example EZH2, B7.1 and B7, TINFRlm, TNFR2, NADPH oxidase, BclIBax and other partners in the apotosis pathway, $C_5a$ receptor, HMG-CoA reductase, PDE V phosphodiesterase type, PDE IV phosphodiesterase type 4, PDE I, PDEII, PDEIII, squalene cyclase inhibitor, CXCR1, CXCR2, nitric oxide (NO) synthase, cyclo-oxygenase 1, cyclo-oxygenase 2, 5HT receptors, dopamine receptors, G Proteins, i.e., Gq, histamine receptors, 5-lipoxygenase, tryptase serine protease, thymidylate synthase, purine nucleoside phosphorylase, GAPDH trypanosomal, glycogen phosphorylase, Carbonic anhydrase, chemokine receptors, JAW STAT, RXR and similar, HIV 1 protease, HIV 1 integrase, influenza, neuramimidase, hepatitis B reverse transcriptase, sodium channel, multi drug resistance (MDR), protein P-glycoprotein (and MRP), tyrosine kinases, CD23, CD124, tyrosine kinase p56 lck, CD4, CD5, IL-2 receptor, IL-1 receptor, TNF-alphaR, ICAM1, Cat+channels, VCAM, VLA-4 integrin, selectins, CD40/CD40L, newokinins and receptors, inosine monophosphate dehydrogenase, p38 MAP Kinase, RaslRaflMEWERK pathway, interleukin-1 converting enzyme, caspase, HCV, NS3 protease, HCV NS3 RNA helicase, glycinamide ribonucleotide formyl transferase, rhinovirus 3C protease, herpes simplex virus-1 (HSV-I), protease, cytomegalovirus (CMV) protease, poly (ADP-ribose) polymerase, cyclin dependent kinases, vascular endothelial growth factor, oxytocin receptor, microsomal transfer protein inhibitor, bile acid transport inhibitor, 5 alpha reductase inhibitors, angiotensin 11, glycine receptor, noradrenaline reuptake receptor, endothelin receptors, neuropeptide Y and receptor, estrogen receptors, androgen receptors, adenosine receptors, adenosine kinase and AMP deaminase, purinergic receptors (P2Y1, P2Y2, P2Y4, P2Y6, P2X1-7), farnesyltransferases, geranylgeranyl transferase, TrkA a receptor for NGF, beta-amyloid, tyrosine kinase Flk-IIKDR, vitronectin receptor, integrin receptor, Her-21 neu, telomerase inhibition, cytosolic phospholipaseA2 and EGF receptor tyrosine kinase. Additional protein targets include, for example, ecdysone 20-monooxygenase, ion channel of the GABA gated chloride channel, acetylcholinesterase, voltage-sensitive sodium channel protein, calcium release channel, and chloride channels. Still further target proteins include Acetyl-CoA carboxylase, adenylosuccinate synthetase, protoporphyrinogen oxidase, and enolpyruvylshikimate-phosphate synthase.

These various protein targets may be used in screens that identify compound moieties which bind to the protein and by incorporation of the moiety into compounds according to the present disclosure, the level of activity of the protein may be altered for therapeutic end result.

The term "protein target moiety" or PTM is used to describe a small molecule which binds to a target protein or other protein or polypeptide of interest and places/presents that protein or polypeptide in proximity to an ubiquitin ligase such that degradation of the protein or polypeptide by ubiquitin ligase may occur. Non-limiting examples of small molecule target protein binding moieties include EZH2 inhibitors, Hsp90 inhibitors, kinase inhibitors, MDM2 inhibitors, compounds targeting Human BET Bromodomain-containing proteins, HDAC inhibitors, human lysine methyltransferase inhibitors, angiogenesis inhibitors, immunosuppressive compounds, and compounds targeting the aryl hydrocarbon receptor (AHR), among numerous others. The compositions described below exemplify some of the members of the small molecule target proteins.

Exemplary protein target moieties according to the present disclosure include, haloalkane halogenase inhibitors, EZH2 inhibitors, Hsp90 inhibitors, kinase inhibitors, MDM2 inhibitors, compounds targeting Human BET Bromodomain-containing proteins, HDAC inhibitors, human lysine methyltransferase inhibitors, angiogenesis inhibitors, immunosuppressive compounds, and compounds targeting the aryl hydrocarbon receptor (AHR).

The compositions described below exemplify some of the members of these types of small molecule target protein binding moieties. Such small molecule target protein binding moieties also include pharmaceutically acceptable salts, enantiomers, solvates and polymorphs of these compositions, as well as other small molecules that may target a protein of interest. References which are cited herein below are incorporated by reference herein in their entirety.

In any aspect or embodiment described herein, the PTM or EZH2 binding moiety (EBM) is represented by Formula PTM-I, PTM-II, PTM-III, PTM-IVa, PTM-IVb, PTM-V, or PTM-VI:

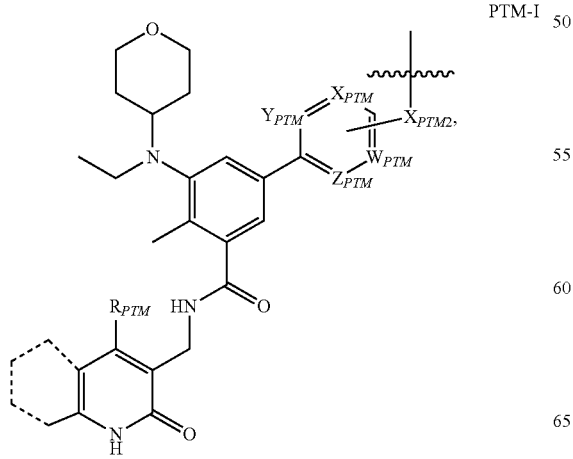

PTM-I

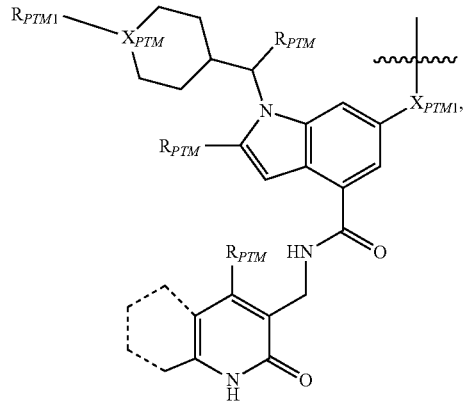

PTM-II

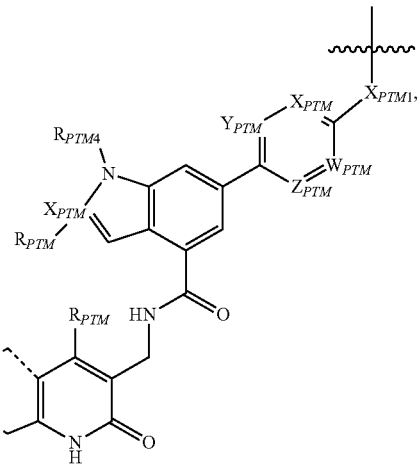

PTM-III

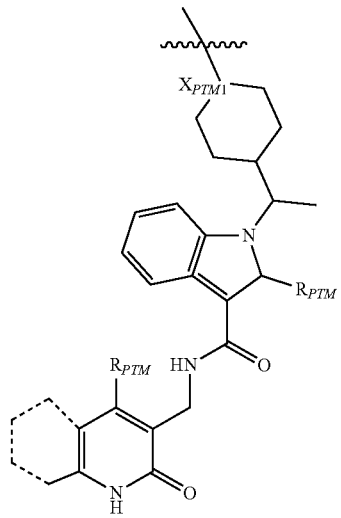

PTM-Iva

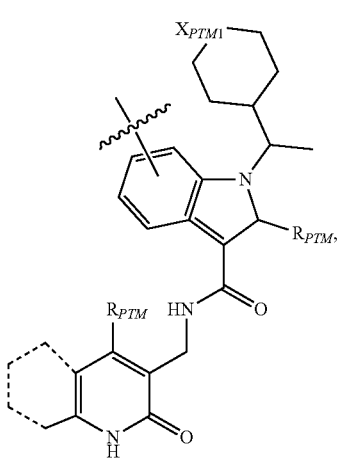

PTM-IVb

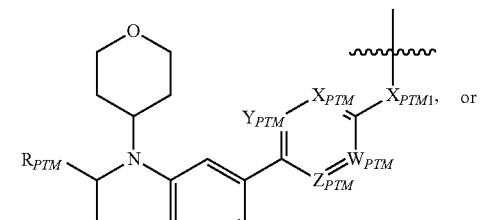

PTM-V

PTM-VI wherein:
each $W_{PTM}$, $X_{PTM}$, $Y_{PTM}$, and $Z_{PTM}$ is independently chosen from C or N, wherein no more than two of $W_{PTM}$, $X_{PTM}$, $Y_{PTM}$, and $Z_{PTM}$ is N;
$X_{PTM1}$ is absent, NH, O, heterocycle (e.g., a 4-6 member heterocyclic, such as a heterocyclic group with 1-3 N-substitutions);
$X_{PTM2}$ is absent, $CH_2$, NH, O, heterocycle (e.g., a 4-6 member heterocyclic, such as a heterocyclic group with 1-3 N-substitutions), heteroaryl (e.g., a 4-6 member heteroaryl, such as a heteroaryl group with 1-3 N-substitutions), or $CH_2$-heteroaryl (e.g., a 4-6 member heteroaryl, such as a heteroaryl group with 1-3 N-substitutions);
$R_{PTM}$ is absent, H, short chain alkyl (linear, branched, optionally substituted), methoxy, or ethoxy;
$R_{PTM1}$ is an absent, alkyl, halogen, haloalkyl, or alkoxy;
$R_{PTM2}$ and $R_{PTM3}$ are independently a halogen, CN, alkoxy (e.g., methoxy or ethoxy);

$R_{PTM4}$ is a alkyl (linear, branched, optionally substituted) or a 4-6 member cyclicalkyl (e.g., 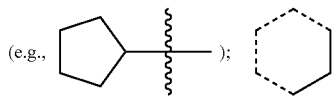 );

is an optionally substituted $C_1$-$C_4$ alkyl that is optionally cyclized to the adjacent carbon of the pyridinyl ring to which it is attached; and ━━━ indicates a covalent linkage to at least one of a linker (L), a ULM, a ULM', a VLM, a VLM', a CLM, a CLM', an ILM, an ILM', a MLM, a MLM', or a combination thereof.

In certain embodiments, the

◯ is a methyl group.

In any aspect or embodiment described herein, the PTM is selected from the group consisting of:

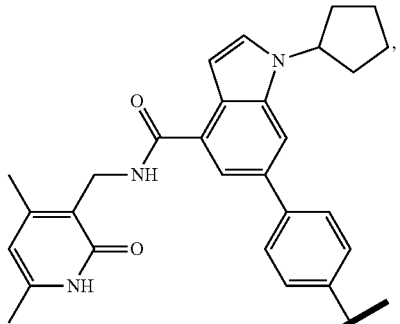

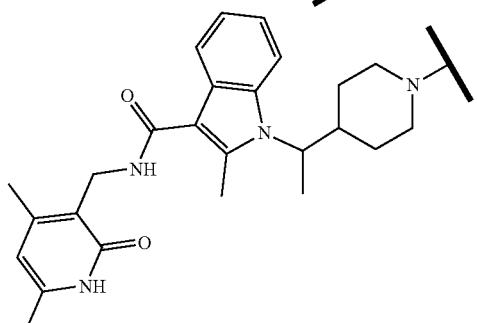

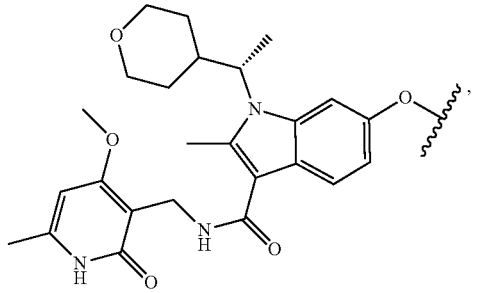

425
-continued
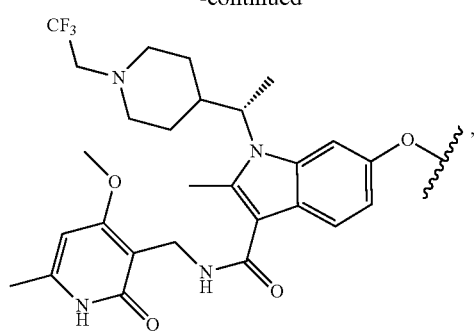
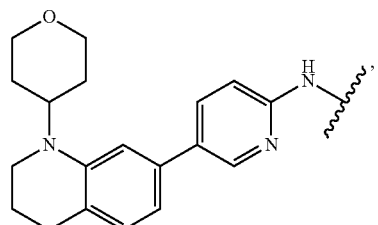
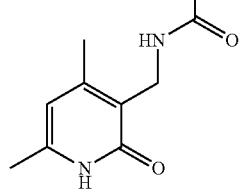
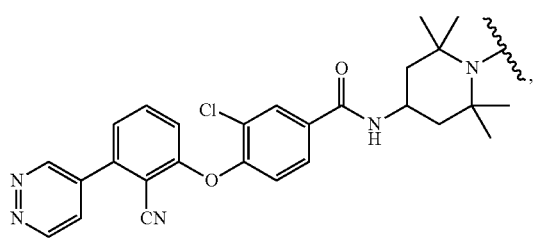
426
-continued
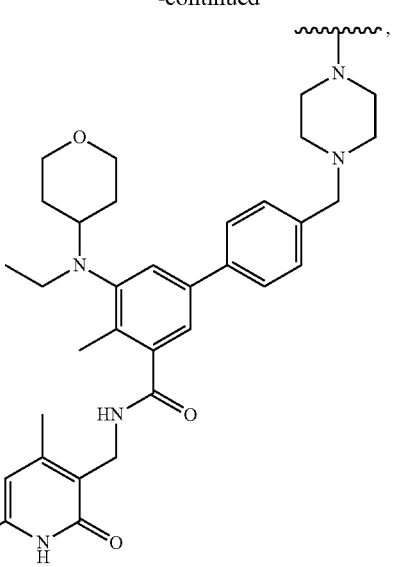
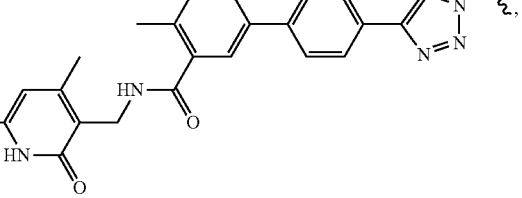
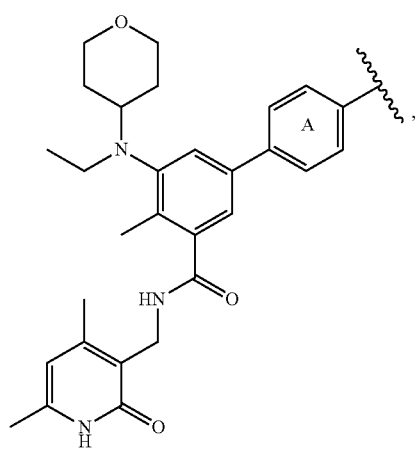
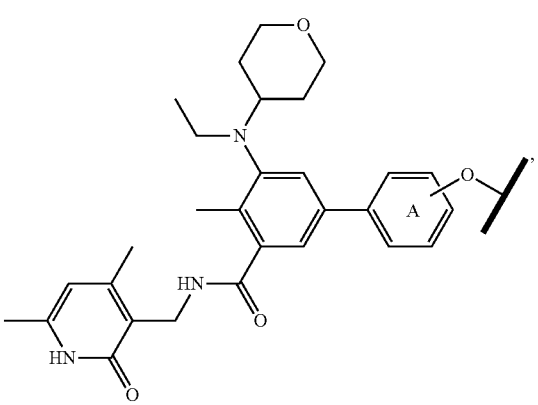

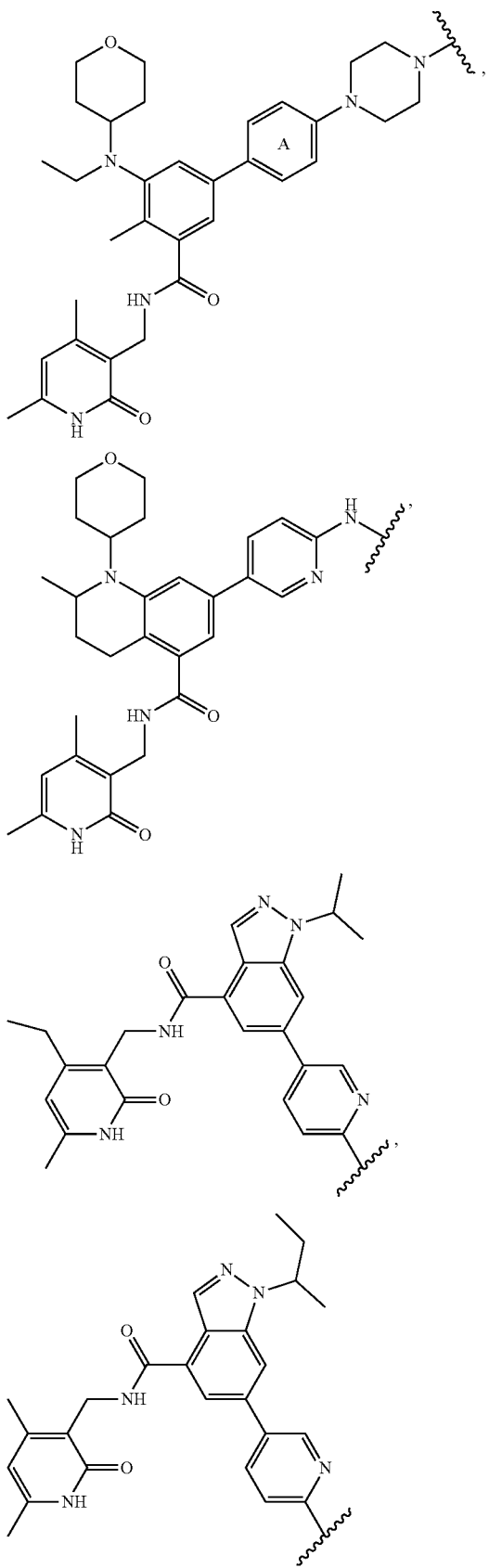

or a combination thereof, wherein

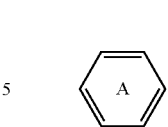

may be N-substituted.

Therapeutic Compositions

Pharmaceutical compositions comprising combinations of an effective amount of at least one bifunctional compound as described herein, and one or more of the compounds otherwise described herein, all in effective amounts, in combination with a pharmaceutically effective amount of a carrier, additive or excipient, represents a further aspect of the present disclosure.

The present disclosure includes, where applicable, the compositions comprising the pharmaceutically acceptable salts, in particular, acid or base addition salts of compounds as described herein. The acids which are used to prepare the pharmaceutically acceptable acid addition salts of the aforementioned base compounds useful according to this aspect are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3 naphthoate)]salts, among numerous others.

Pharmaceutically acceptable base addition salts may also be used to produce pharmaceutically acceptable salt forms of the compounds or derivatives according to the present disclosure. The chemical bases that may be used as reagents to prepare pharmaceutically acceptable base salts of the present compounds that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (eg, calcium, zinc and magnesium), ammonium or water-soluble amine addition salts such as N-methylglucamine-(meglumine), and the lower alkanolammonium and other base salts of pharmaceutically acceptable organic amines, among others.

The compounds as described herein may, in accordance with the disclosure, be administered in single or divided doses by the oral, parenteral or topical routes. Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal, sublingual and suppository administration, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient. Administration of compounds according to the present disclosure as sprays, mists, or aerosols for intra-nasal, intra-tracheal or pulmonary administration may also be used. The present disclosure therefore also is directed to pharmaceutical compositions comprising an effective amount of compound as described herein, optionally in combination with a pharmaceutically acceptable carrier, additive or excipient. Compounds according to the present disclosure may be administered in immediate release, intermediate release or sustained or controlled release forms. Sustained or controlled release forms are preferably administered orally, but also in suppository and transdermal or other topical forms. Intramuscular injections in liposomal form may also be used to control or sustain the release of compound at an injection site.

The compositions as described herein may be formulated in a conventional manner using one or more pharmaceutically acceptable carriers and may also be administered in controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions as described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions as described herein may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1, 3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions as described herein may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions as described herein may be administered in the form of suppositories for rectal administration. These can be prepared by mixing the agent with a suitable non-irritating excipient, which is solid at room temperature but liquid at rectal temperature and therefore will melt in the rectum to release the drug. Such materials include cocoa butter, beeswax and polyethylene glycols.

The pharmaceutical compositions as described herein may also be administered topically. Suitable topical formulations are readily prepared for each of these areas or organs. Topical application for the lower intestinal tract can be effected in a rectal suppository formulation (see above) or in a suitable enema formulation. Topically-acceptable transdermal patches may also be used.

For topical applications, the pharmaceutical compositions may be formulated in a suitable ointment containing the active component suspended or dissolved in one or more carriers. Carriers for topical administration of the compounds of this disclosure include, but are not limited to, mineral oil, liquid petrolatum, white petrolatum, propylene glycol, polyoxyethylene, polyoxypropylene compound, emulsifying wax and water. In certain preferred aspects of the disclosure, the compounds may be coated onto a stent which is to be surgically implanted into a patient in order to inhibit or reduce the likelihood of occlusion occurring in the stent in the patient.

Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions as described herein may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compound in a pharmaceutical composition as described herein that may be combined with the carrier materials to produce a single dosage form will vary depending upon the host and disease treated, the particular mode of administration. Preferably, the compositions should be formulated to contain between about 0.05 milligram to about 750 milligrams or more, more preferably about 1 milligram to about 600 milligrams, and even more preferably about 10 milligrams to about 500 milligrams of active ingredient, alone or in combination with at least one other compound according to the present disclosure.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

A patient or subject in need of therapy using compounds according to the methods described herein can be treated by administering to the patient (subject) an effective amount of the compound according to the present disclosure including pharmaceutically acceptable salts, solvates or polymorphs, thereof optionally in a pharmaceutically acceptable carrier or diluent, either alone, or in combination with other known erythopoiesis stimulating agents as otherwise identified herein.

These compounds can be administered by any appropriate route, for example, orally, parenterally, intravenously, intradermally, subcutaneously, or topically, including transdermally, in liquid, cream, gel, or solid form, or by aerosol form.

The active compound is included in the pharmaceutically acceptable carrier or diluent in an amount sufficient to deliver to a patient a therapeutically effective amount for the desired indication, without causing serious toxic effects in the patient treated. A preferred dose of the active compound for all of the herein-mentioned conditions is in the range from about 10 ng/kg to 300 mg/kg, preferably 0.1 to 100 mg/kg per day, more generally 0.5 to about 25 mg per kilogram body weight of the recipient/patient per day. A typical topical dosage will range from 0.01-5% wt/wt in a suitable carrier.

The compound is conveniently administered in any suitable unit dosage form, including but not limited to one containing less than 1 mg, 1 mg to 3000 mg, preferably 5 to 500 mg of active ingredient per unit dosage form. An oral dosage of about 25-250 mg is often convenient.

The active ingredient is preferably administered to achieve peak plasma concentrations of the active compound of about 0.00001-30 mM, preferably about 0.1-30 µM. This may be achieved, for example, by the intravenous injection of a solution or formulation of the active ingredient, optionally in saline, or an aqueous medium or administered as a bolus of the active ingredient. Oral administration is also appropriate to generate effective plasma concentrations of active agent.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound or its prodrug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable salts thereof can also be mixed with other active materials that do not impair the desired action, or with materials that supplement the desired action, such as erythropoietin stimulating agents, including EPO and darbapoietin alfa, among others. In certain preferred aspects of the disclosure, one or more compounds according to the present disclosure are coadministered with another bioactive agent, such as an erythropoietin stimulating agent or a would healing agent, including an antibiotic, as otherwise described herein.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension.

Therapeutic Methods

In an additional aspect, the description provides therapeutic compositions comprising an effective amount of a compound as described herein or salt form thereof, and a pharmaceutically acceptable carrier. The therapeutic compositions modulate protein degradation in a patient or subject, for example, an animal such as a human, and can be used for treating or ameliorating disease states or conditions which are modulated through the degraded protein.

The terms "treat", "treating", and "treatment", etc., as used herein, refer to any action providing a benefit to a patient for which the present compounds may be administered, including the treatment of any disease state or condition which is modulated through the protein to which the present compounds bind. Disease states or conditions, including cancer, which may be treated using compounds according to the present disclosure are set forth hereinabove.

The description provides therapeutic compositions as described herein for effectuating the degradation of proteins of interest for the treatment or amelioration of a disease, e.g., cancer. In certain additional embodiments, the disease is multiple myeloma. As such, in another aspect, the description provides a method of ubiquitinating/degrading a target protein in a cell. In certain embodiments, the method comprises administering a bifunctional compound as described herein comprising, e.g., a ULM and a PTM, preferably linked through a linker moiety, as otherwise described herein, wherein the ULM is coupled to the PTM and wherein the ULM recognizes a ubiquitin pathway protein (e.g., an ubiquitin ligase, such as an E3 ubiquitin ligase including cereblon, VHL, IAP, and/or MDM2) and the PTM recognizes the target protein such that degradation of the target protein will occur when the target protein is placed in proximity to the ubiquitin ligase, thus resulting in degradation/inhibition of the effects of the target protein and the control of protein levels. The control of protein levels afforded by the present disclosure provides treatment of a disease state or condition, which is modulated through the target protein by lowering the level of that protein in the cell, e.g., cell of a patient. In certain embodiments, the method comprises administering an effective amount of a compound as described herein, optionally including a pharmaceutically acceptable excipient, carrier, adjuvant, another bioactive agent or combination thereof.

In additional embodiments, the description provides methods for treating or ameliorating a disease, disorder or symptom thereof in a subject or a patient, e.g., an animal such as a human, comprising administering to a subject in need thereof a composition comprising an effective amount, e.g., a therapeutically effective amount, of a compound as described herein or salt form thereof, and a pharmaceutically acceptable excipient, carrier, adjuvant, another bioactive agent or combination thereof, wherein the composition is effective for treating or ameliorating the disease or disorder or symptom thereof in the subject.

In another aspect, the description provides methods for identifying the effects of the degradation of proteins of interest in a biological system using compounds according to the present disclosure.

In another embodiment, the present disclosure is directed to a method of treating a human patient in need for a disease state or condition modulated through a protein where the degradation of that protein will produce a therapeutic effect in the patient, the method comprising administering to a patient in need an effective amount of a compound according to the present disclosure, optionally in combination with another bioactive agent. The disease state or condition may be a disease caused by a microbial agent or other exogenous agent such as a virus, bacteria, fungus, protozoa or other microbe or may be a disease state, which is caused by overexpression of a protein, which leads to a disease state and/or condition The term "disease state or condition" is used to describe any disease state or condition wherein protein dysregulation (i.e., the amount of protein expressed in a patient is elevated) occurs and where degradation of one or more proteins in a patient may provide beneficial therapy or relief of symptoms to a patient in need thereof. In certain instances, the disease state or condition may be cured.

Disease states or conditions which may be treated using compounds according to the present disclosure include, for example, asthma, autoimmune diseases such as multiple sclerosis, various cancers, ciliopathies, cleft palate, diabetes, heart disease, hypertension, inflammatory bowel disease, mental retardation, mood disorder, obesity, refractive error, infertility, Angelman syndrome, Canavan disease, Coeliac disease, Charcot-Marie-Tooth disease, Cystic fibrosis, Duchenne muscular dystrophy, Haemochromatosis, Haemophilia, Klinefelter's syndrome, Neurofibromatosis, Phenylketonuria, Polycystic kidney disease, (PKD1) or 4 (PKD2) Prader-Willi syndrome, Sickle-cell disease, Tay-Sachs disease, Turner syndrome.

The term "neoplasia" or "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascitic and solid tumors. Exemplary cancers which may be treated by the present compounds either alone or in combination with at least one additional anti-cancer agent include squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas. Additional cancers which may be treated using compounds according to the present disclosure include, for example, T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL and Philadelphia chromosome positive CML.

In any aspect or embodiment described herein, the disease state or condition is selected from breast cancer, prostate cancer, bladder cancer, uterine cancer, renal cancer, melanoma, and/or lymphoma.

The term "bioactive agent" is used to describe an agent, other than a compound according to the present disclosure, which is used in combination with the present compounds as an agent with biological activity to assist in effecting an intended therapy, inhibition and/or prevention/prophylaxis for which the present compounds are used. Preferred bioactive agents for use herein include those agents which have pharmacological activity similar to that for which the present compounds are used or administered and include for example, anti-cancer agents, antiviral agents, especially including anti-HIV agents and anti-HCV agents, antimicrobial agents, antifungal agents, etc.

The term "additional anti-cancer agent" is used to describe an anti-cancer agent, which may be combined with compounds according to the present disclosure to treat cancer. These agents include, for example, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhbitor, a c-MET inhibitor, a PARP inhibitor, a Cdk inhibitor, an EGFR TK inhibitor, an IGFR-TK inhibitor, an anti-HGF antibody, a PI3 kinase inhibitor, an AKT inhibitor, an mTORC1/2 inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR1 KRX-0402, lucanthone, LY317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5′-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES(diethylstilbestrol), estradiol, estrogen, conjugated estrogen, bevacizumab, IMC-1C11, CHIR-258); 3-[5-(methylsulfonylpiperadinemethyl)-indolyl-quinolone, vatalanib, AG-013736, AVE-0005, goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, Bacillus Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gleevec, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779, 450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof.

The term "anti-HIV agent" or "additional anti-HIV agent" includes, for example, nucleoside reverse transcriptase inhibitors (NRTI), other non-nucloeoside reverse transcriptase inhibitors (i.e., those which are not representative of the present disclosure), protease inhibitors, fusion inhibitors, among others, exemplary compounds of which may include, for example, 3TC (Lamivudine), AZT (Zidovudine), (−)-FTC, ddI (Didanosine), ddC (zalcitabine), abacavir (ABC), tenofovir (PMPA), D-D4FC (Reverset), D4T (Stavudine), Racivir, L-FddC, L-FD4C, NVP (Nevirapine), DLV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), LPV (Lopinavir), fusion inhibitors such as T20, among others, fuseon and mixtures thereof, including anti-HIV compounds presently in clinical trials or in development.

Other anti-HIV agents which may be used in coadministration with compounds according to the present disclosure include, for example, other NNRTI's (i.e., other than the NNRTI's according to the present disclosure) may be selected from the group consisting of nevirapine (BI-R6-587), delavirdine (U-90152S/T), efavirenz (DMP-266), UC-781 (N-[4-chloro-3-(3-methyl-2-butenyloxy)phenyl]-2methyl3-furancarbothiamide), etravirine (TMC125), Trovirdine (Ly300046.HCl), MKC-442 (emivirine, coactinon), HI-236, HI-240, HI-280, HI-281, rilpivirine (TMC-278), MSC-127, HBY 097, DMP266, Baicalin (TJN-151) ADAM-II (Methyl 3',3'-dichloro-4',4"-dimethoxy-5',5"-bis (methoxycarbonyl)-6,6-diphenylhexenoate), Methyl 3-Bromo-5-(1-5-bromo-4-methoxy-3-(methoxycarbonyl) phenyl)hept-1-enyl)-2-methoxybenzoate (Alkenyldiarylmethane analog, Adam analog), (5-chloro-3-(phenylsulfinyl)-2'-indolecarboxamide), AAP-BHAP (U-104489 or PNU-104489), Capravirine (AG-1549, S-1153), atevirdine (U-87201E), aurin tricarboxylic acid (SD-095345), 1-[(6-cyano-2-indolyl)carbonyl]-4-[3-(isopropylamino)-2-pyridinyl]piperazine, 1-[5-[[N-(methyl)methylsulfonylamino]-2-indolylcarbonyl-4-[3-(isopropylamino)-2-pyridinyl] piperazine, 1-[3-(Ethylamino)-2-[pyridinyl]-4-[(5-hydroxy-2-indolyl)carbonyl]piperazine, 1-[(6-Formyl-2-indolyl) carbonyl]-4-[3-(isopropylamino)-2-pyridinyl]piperazine, 1-[[5-(Methylsulfonyloxy)-2-indoyly)carbonyl]-4-[3-(isopropylamino)-2-pyridinyl]piperazine, U88204E, Bis(2-nitrophenyl)sulfone (NSC 633001), Calanolide A (NSC675451), Calanolide B, 6-Benzyl-5-methyl-2-(cyclohexyloxy)pyrimidin-4-one (DABO-546), DPC 961, E-EBU, E-EBU-dm, E-EPSeU, E-EPU, Foscarnet (Foscavir), HEPT (1-[(2-Hydroxyethoxy)methyl]-6-(phenylthio)thymine), HEPT-M (1-[(2-Hydroxyethoxy)methyl]-6-(3-methylphenyl)thio)thymine), HEPT-S(1-[(2-Hydroxyethoxy)methyl]-6-(phenylthio)-2-thiothymine), Inophyllum P, L-737,126, Michellamine A (NSC650898), Michellamine B (NSC649324), Michellamine F, 6-(3,5-Dimethylbenzyl)-1-[(2-hydroxyethoxy)methyl]-5-isopropyluracil, 6-(3,5-Dimethylbenzyl)-1-(ethyoxymethyl)-5-isopropyluracil, NPPS, E-BPTU (NSC 648400), Oltipraz (4-Methyl-5-(pyrazinyl)-3H-1,2-dithiole-3-thione), N-{2-(2-Chloro-6-fluorophenethyl]-N'-(2-thiazolyl)thiourea (PETT Cl, F derivative), N-{2-(2,6-Difluorophenethyl]-N'-[2-(5-bromopyridyl)]thiourea {PETT derivative), N-{2-(2,6-Difluorophenethyl]-N'-[2-(5-methylpyridyl)]thiourea {PETT Pyridyl derivative), N-[2-(3-Fluorofuranyl)ethyl]-N'-[2-(5-chloropyridyl)]thiourea, N-[2-(2-Fluoro-6-ethoxyphenethyl)]-N'-[2-(5-bromopyridyl)]thiourea, N-(2-Phenethyl)-N'-(2-thiazolyl)thiourea (LY-73497), L-697,639, L-697,593, L-697,661, 3-[2-(4,7-Difluorobenzoxazol-2-yl)ethyl}-5-ethyl-6-methyl (pypridin-2(1H)-thione (2-Pyridinone Derivative), 3-[[(2-Methoxy-5,6-dimethyl-3-pyridyl)methyl]amine]-5-ethyl-6-methyl(pypridin-2(1H)-thione, R82150, R82913, R87232, R88703, R89439 (Loviride), R90385, S-2720, Suramin Sodium, TBZ (Thiazolobenzimidazole, NSC 625487), Thiazoloisoindol-5-one, (+)(R)-9b-(3,5-Dimethylphenyl-2,3-dihydrothiazolo[2,3-a]isoindol-5(9bH)-one, Tivirapine (R86183), UC-38 and UC-84, among others.

The term "pharmaceutically acceptable salt" is used throughout the specification to describe, where applicable, a salt form of one or more of the compounds described herein which are presented to increase the solubility of the compound in the gastic juices of the patient's gastrointestinal tract in order to promote dissolution and the bioavailability of the compounds. Pharmaceutically acceptable salts include those derived from pharmaceutically acceptable inorganic or organic bases and acids, where applicable. Suitable salts include those derived from alkali metals such as potassium and sodium, alkaline earth metals such as calcium, magnesium and ammonium salts, among numerous other acids and bases well known in the pharmaceutical art. Sodium and potassium salts are particularly preferred as neutralization salts of the phosphates according to the present disclosure.

The term "pharmaceutically acceptable derivative" is used throughout the specification to describe any pharmaceutically acceptable prodrug form (such as an ester, amide other prodrug group), which, upon administration to a patient, provides directly or indirectly the present compound or an active metabolite of the present compound.

General Synthetic Approach

The synthetic realization and optimization of the bifunctional molecules as described herein may be approached in a step-wise or modular fashion. For example, identification of compounds that bind to the target molecules can involve high or medium throughput screening campaigns if no suitable ligands are immediately available. It is not unusual for initial ligands to require iterative design and optimization cycles to improve suboptimal aspects as identified by data from suitable in vitro and pharmacological and/or ADMET assays. Part of the optimization/SAR campaign would be to probe positions of the ligand that are tolerant of substitution and that might be suitable places on which to attach the linker chemistry previously referred to herein. Where crystallographic or NMR structural data are available, these can be used to focus such a synthetic effort.

In a very analogous way, one can identify and optimize ligands for an E3 Ligase, i.e. ULMs/ILMs/VLMs/CLMs/ILMs.

With PTMs and ULMs (e.g. ILMs, VLMs, CLMs, and/or ILMs) in hand, one skilled in the art can use known synthetic methods for their combination with or without a linker moiety. Linker moieties can be synthesized with a range of compositions, lengths and flexibility and functionalized such that the PTM and ULM groups can be attached sequentially to distal ends of the linker. Thus a library of bifunctional molecules can be realized and profiled in in vitro and in vivo pharmacological and ADMET/PK studies. As with the PTM and ULM groups, the final bifunctional molecules can be subject to iterative design and optimization cycles in order to identify molecules with desirable properties.

Compounds of the present disclosure [e.g., the general Formula PTM-I] may be prepared by methods known in the art of organic synthesis as set forth in the specific Examples described in this application. In all of the methods, it is well understood that protecting groups for sensitive or reactive groups may be employed where necessary in accordance with general principles of chemistry. Protecting groups are manipulated according to standard methods of organic synthesis (T. W. Green and P. G. M. Wuts (1999) Protective Groups in Organic Synthesis, 3$^{rd}$ edition, John Wiley & Sons). These groups are removed at a convenient stage of the compound synthesis using methods that are readily apparent to those skilled in the art. The selection of processes as well as the reaction conditions and order of their execution shall be consistent with the preparation of compounds of the present disclosure, including compounds of Formula PTM-I. Schemes described below illustrate the general methods of preparing compounds with the structure featured as Formula PTM-I.

General Synthetic Scheme 1
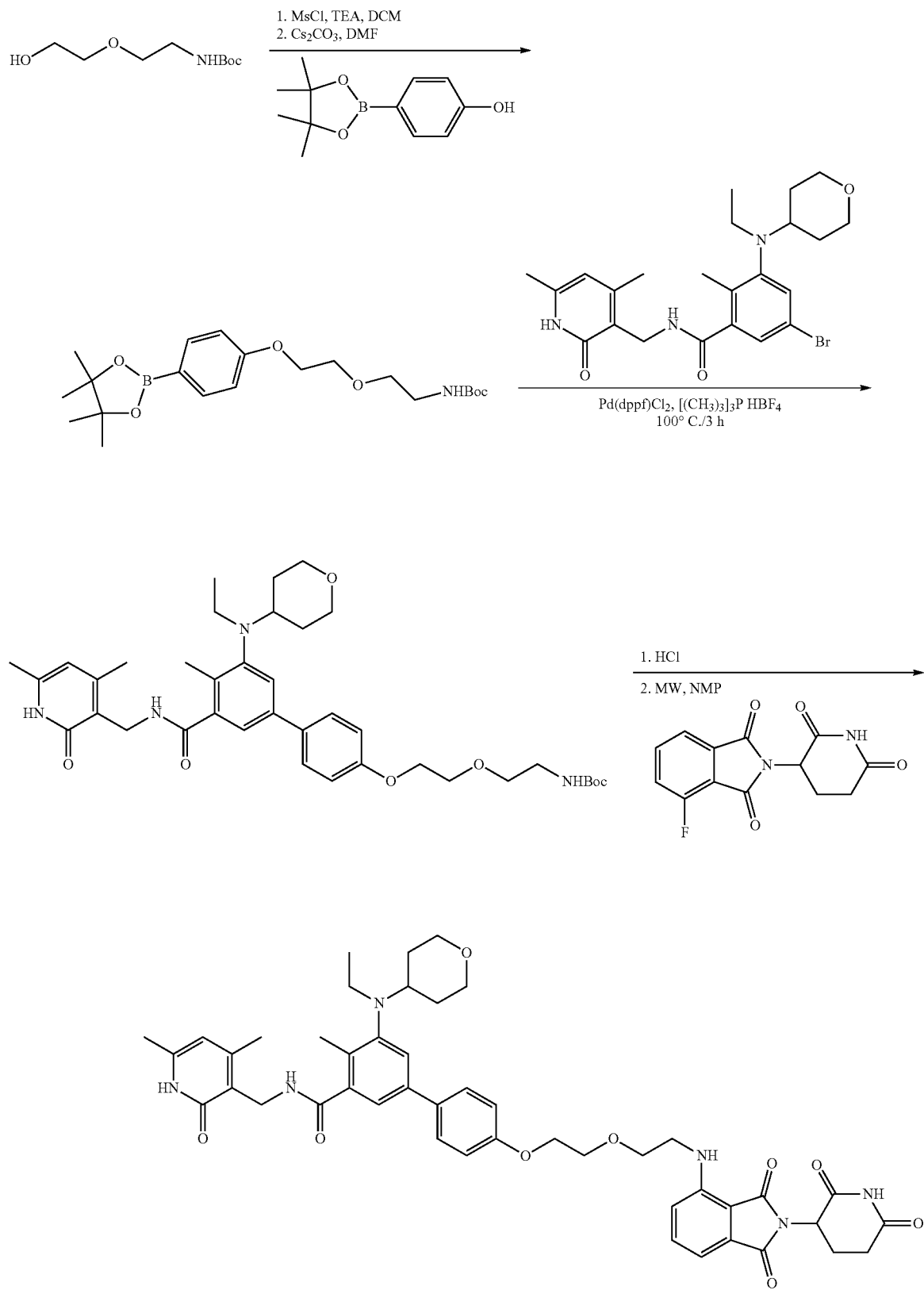

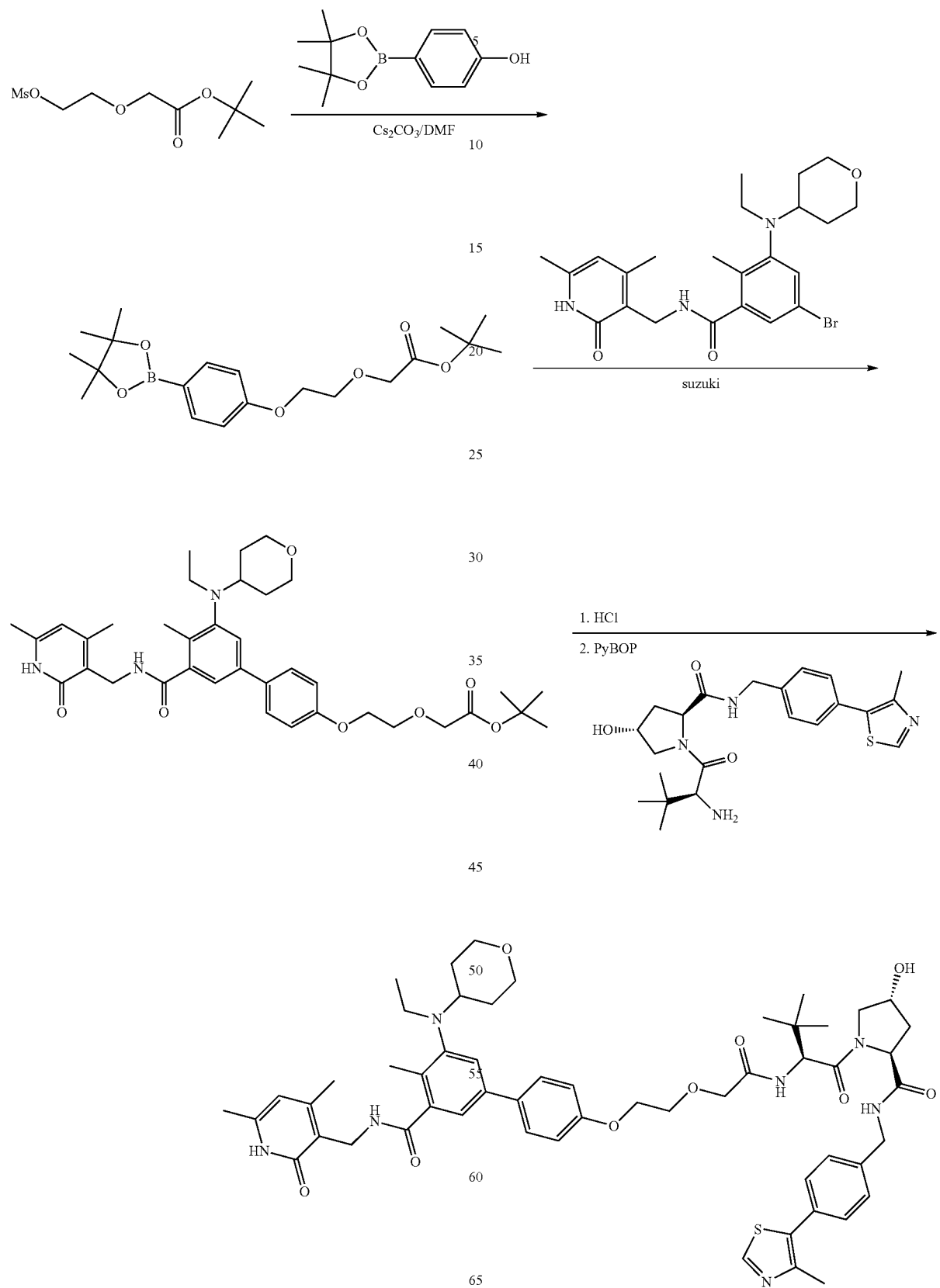
General Synthetic Scheme 2

General Synthetic Scheme 3
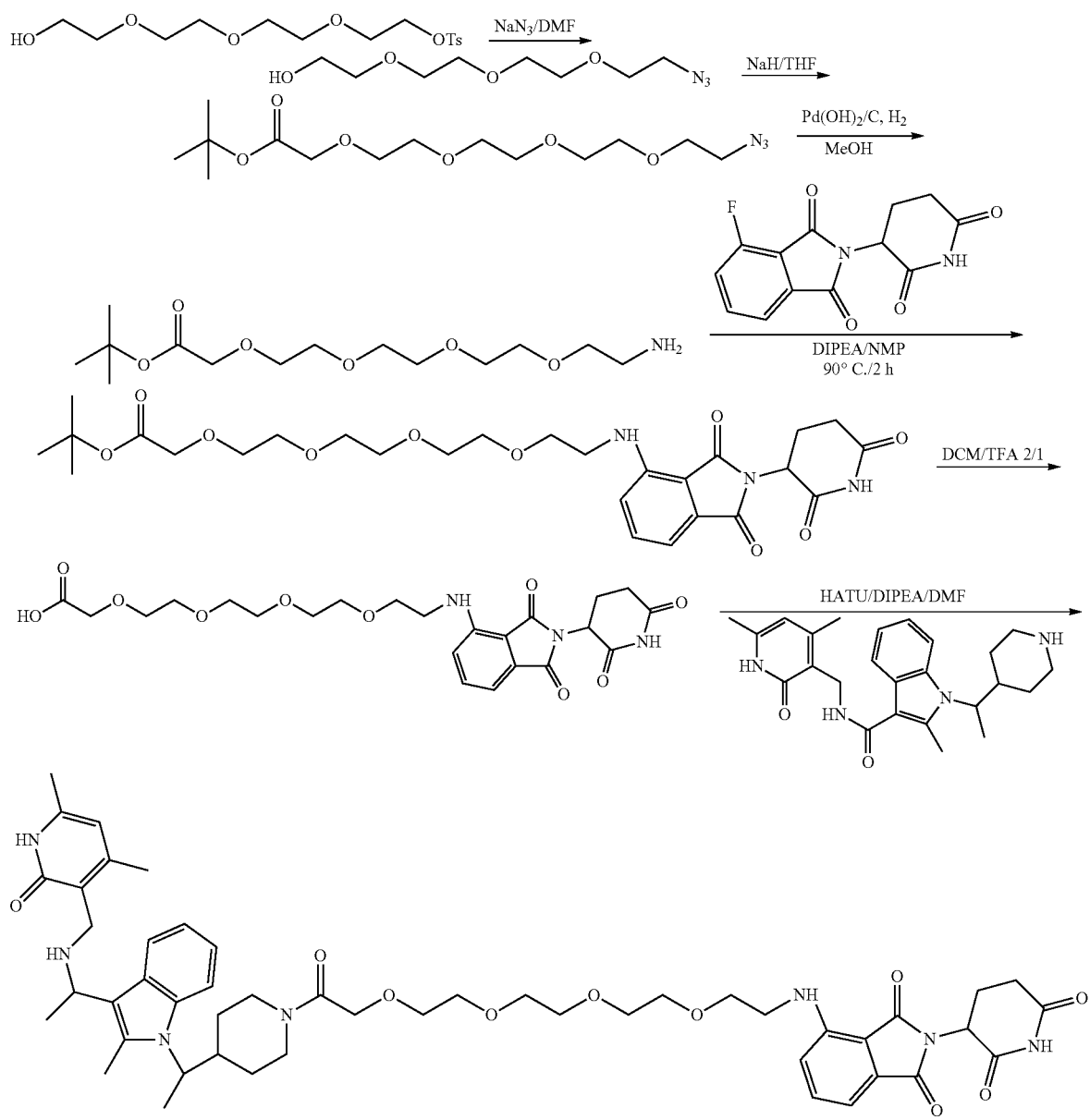
General Synthetic Scheme 4
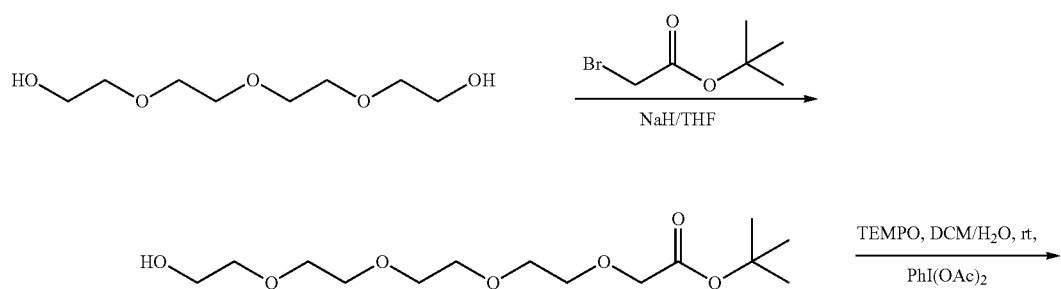

445  446
-continued
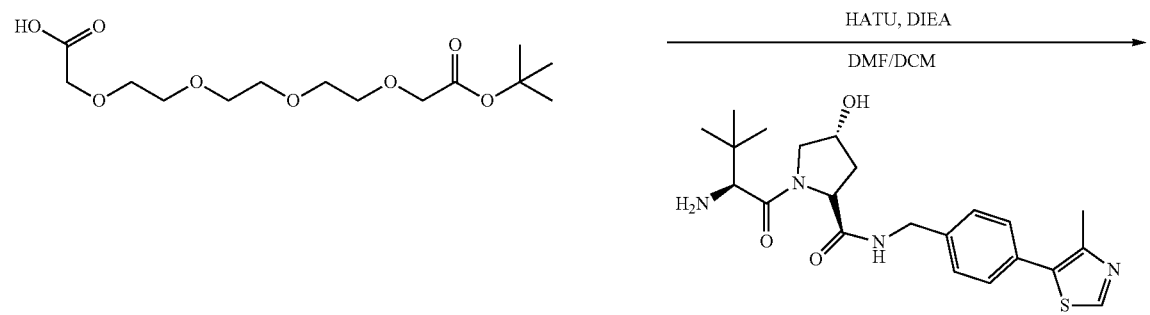
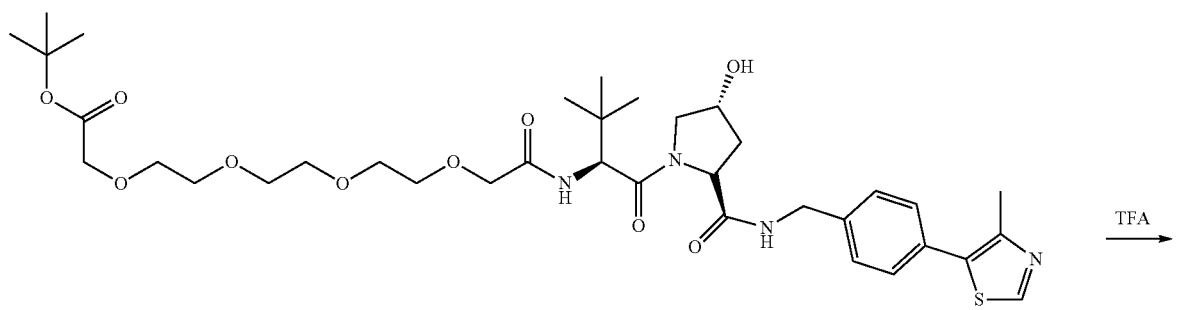
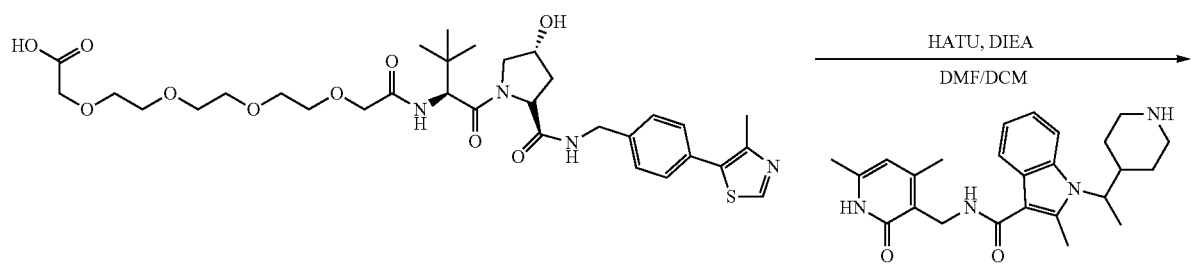
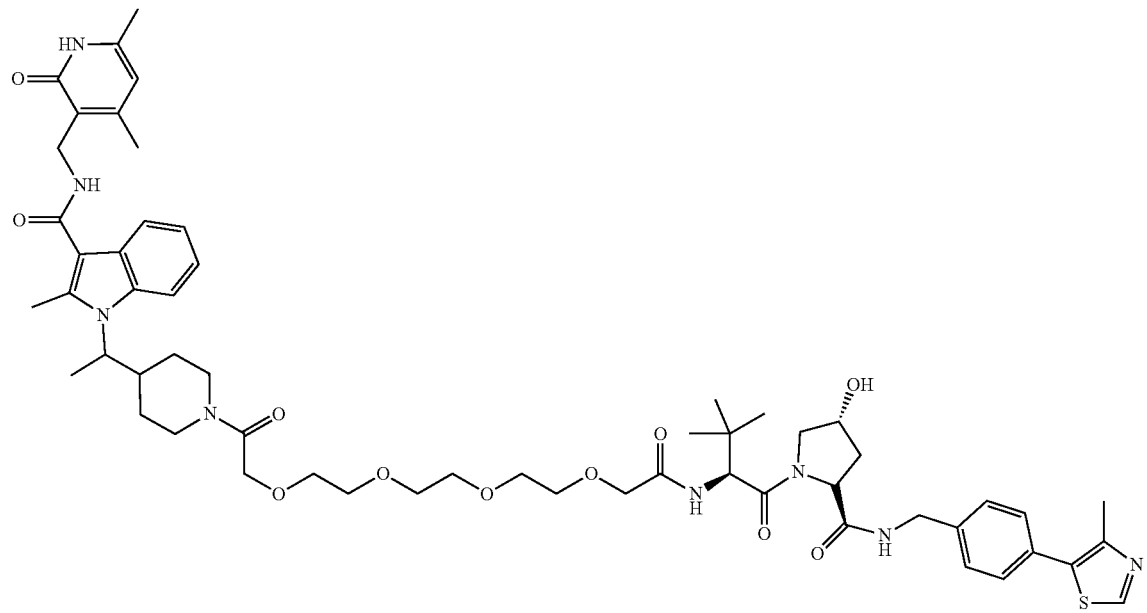

General Synthetic Scheme 5
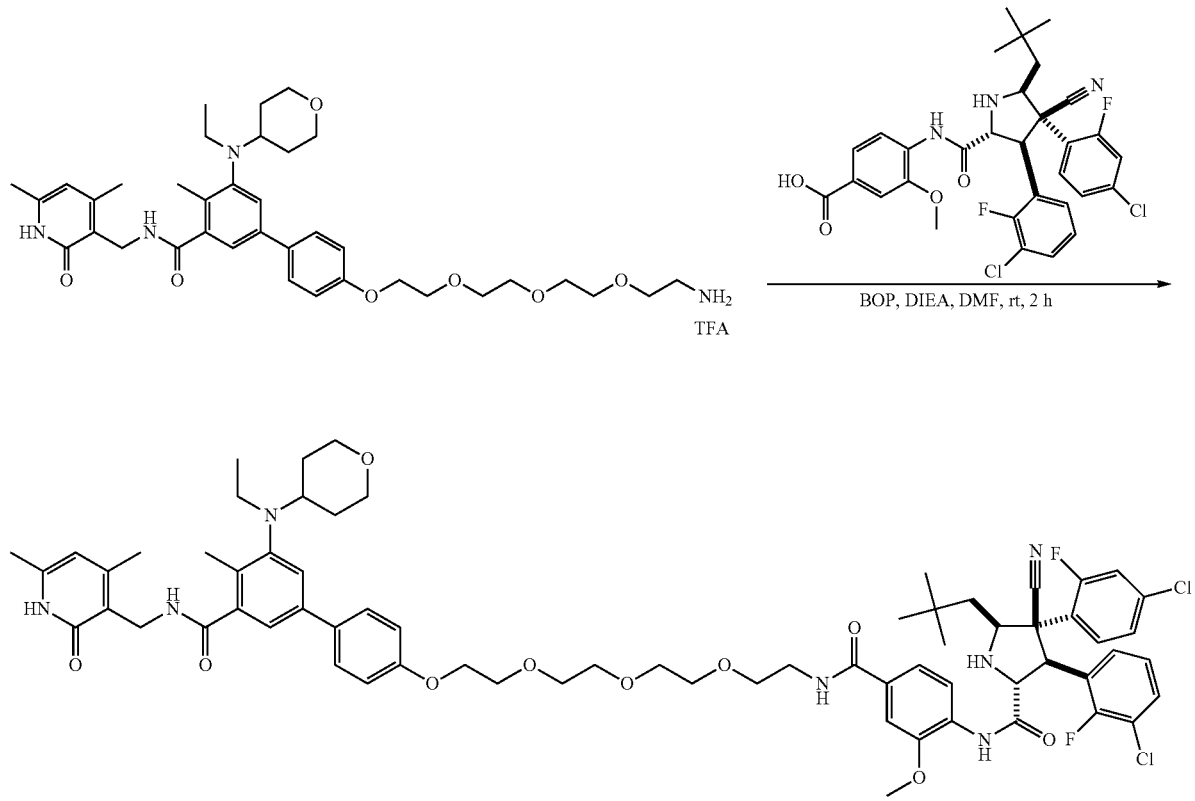
General Synthetic Scheme 6
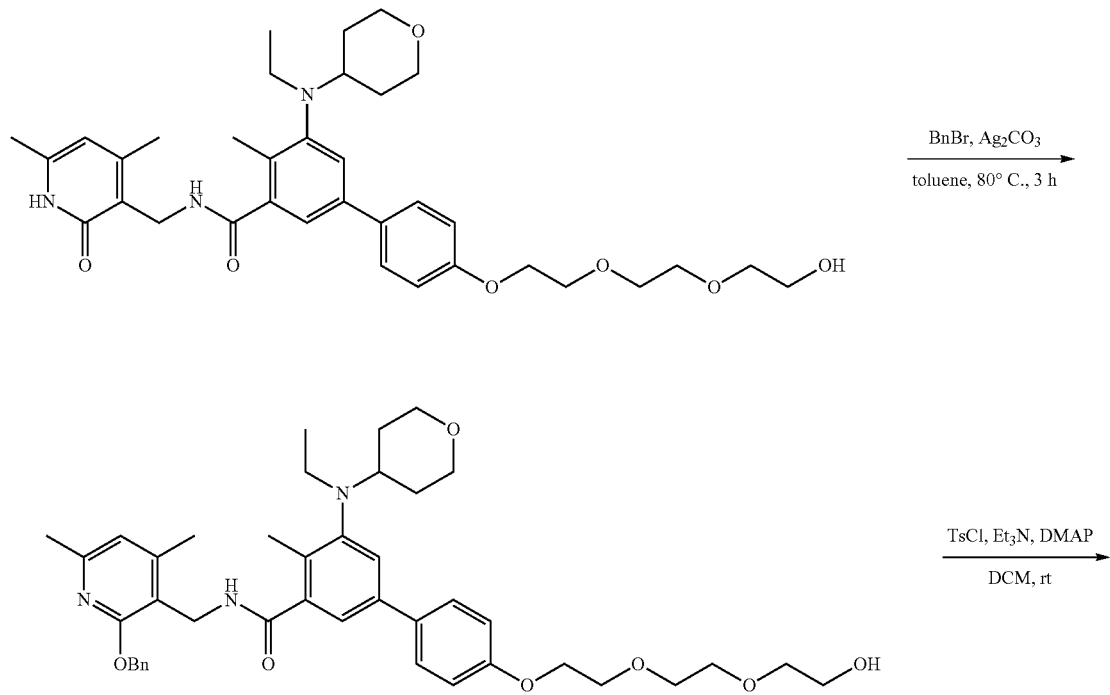

449 450
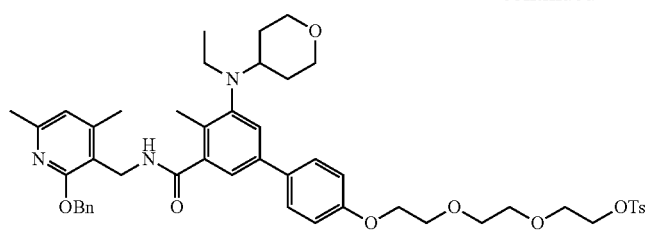 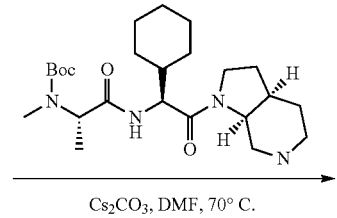
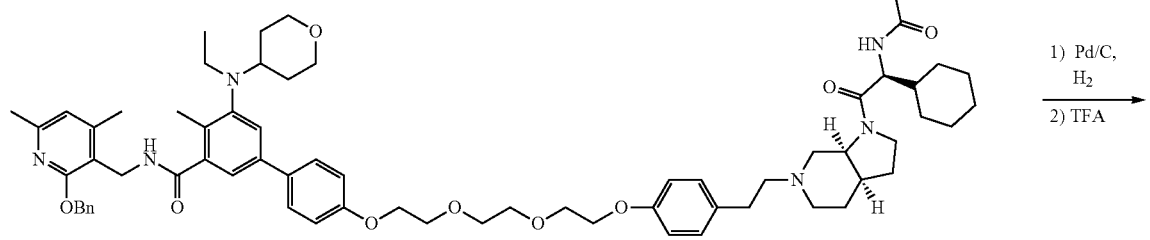
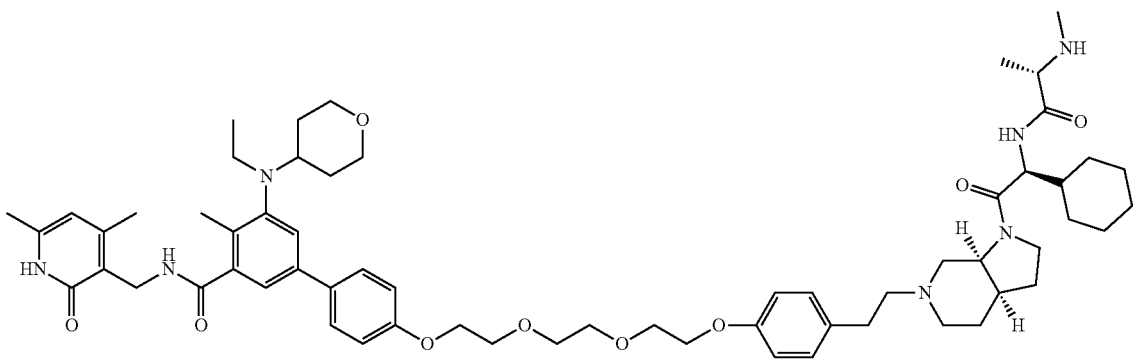
45
General Synthetic Scheme 7
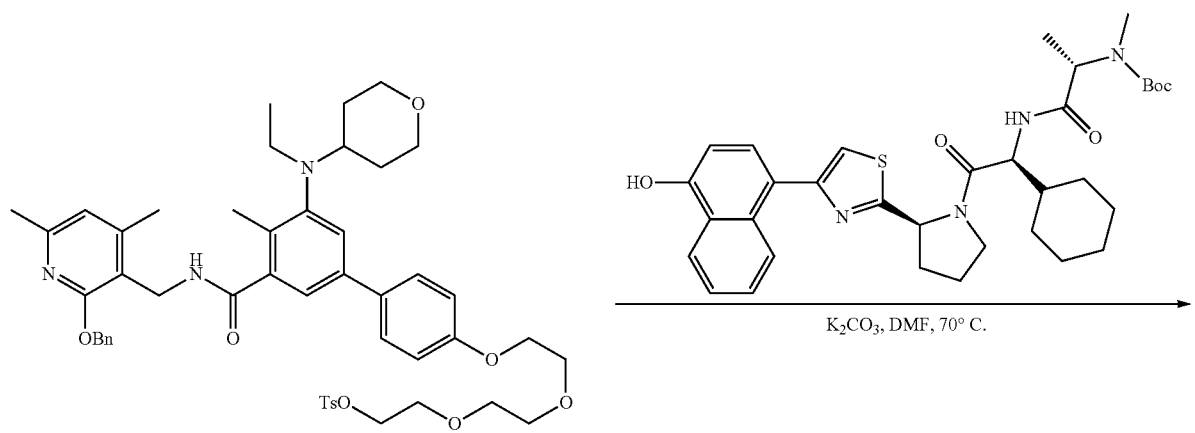

451 452
-continued
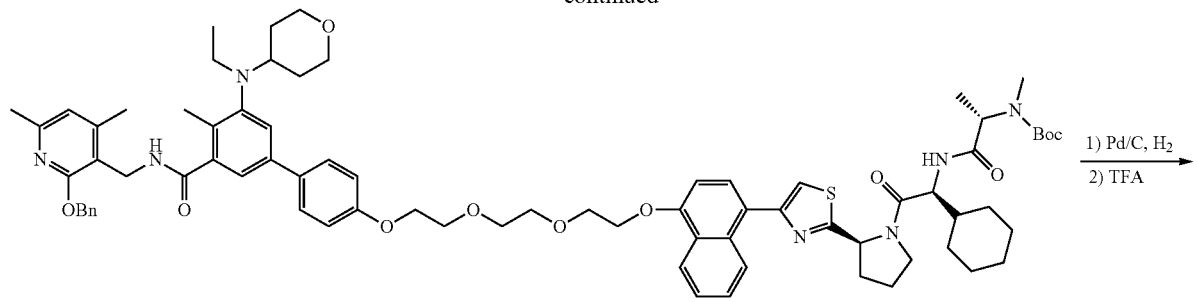
1) Pd/C, H₂
2) TFA
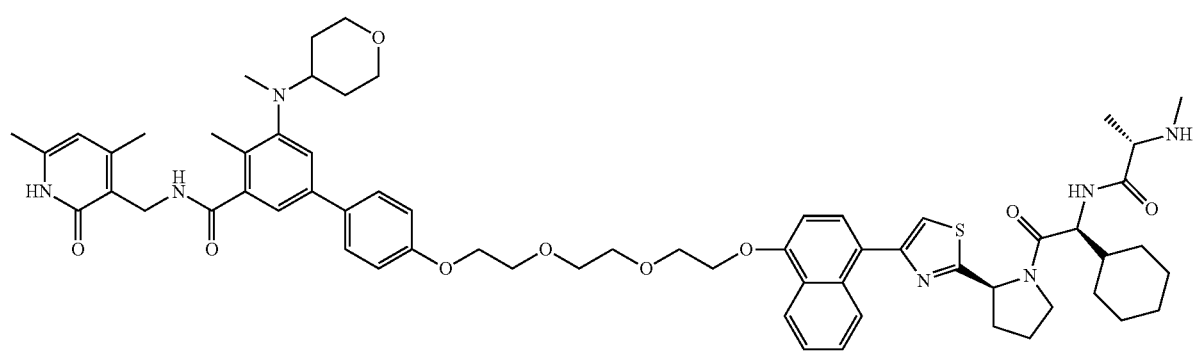
General Synthetic Scheme 8
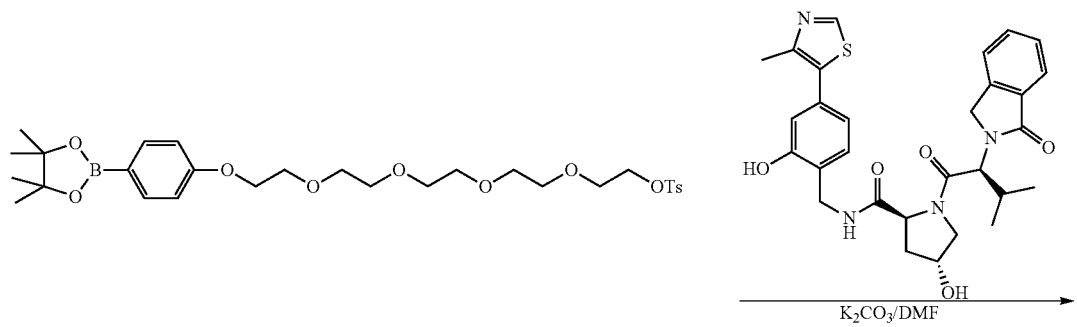
K₂CO₃/DMF
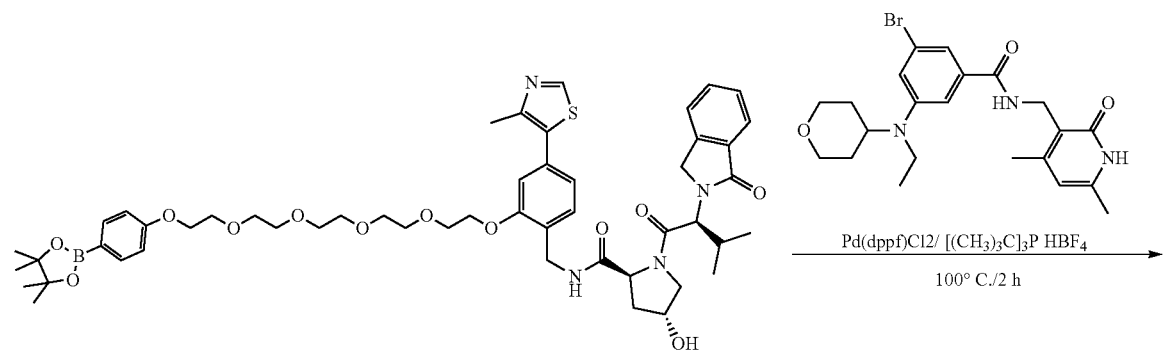
Pd(dppf)Cl2/ [(CH₃)₃C]₃P HBF₄
100° C./2 h

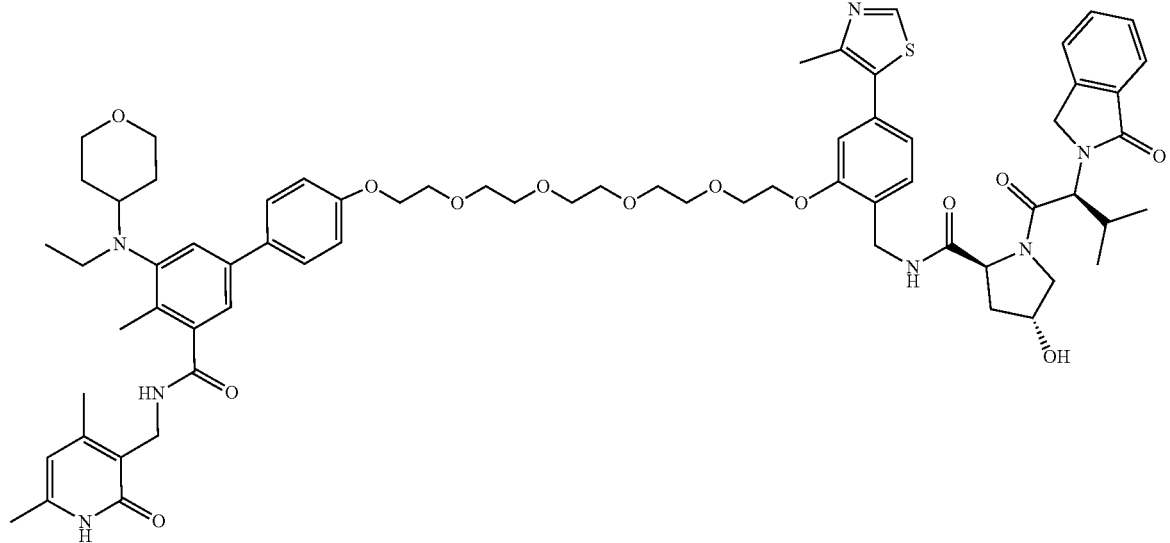
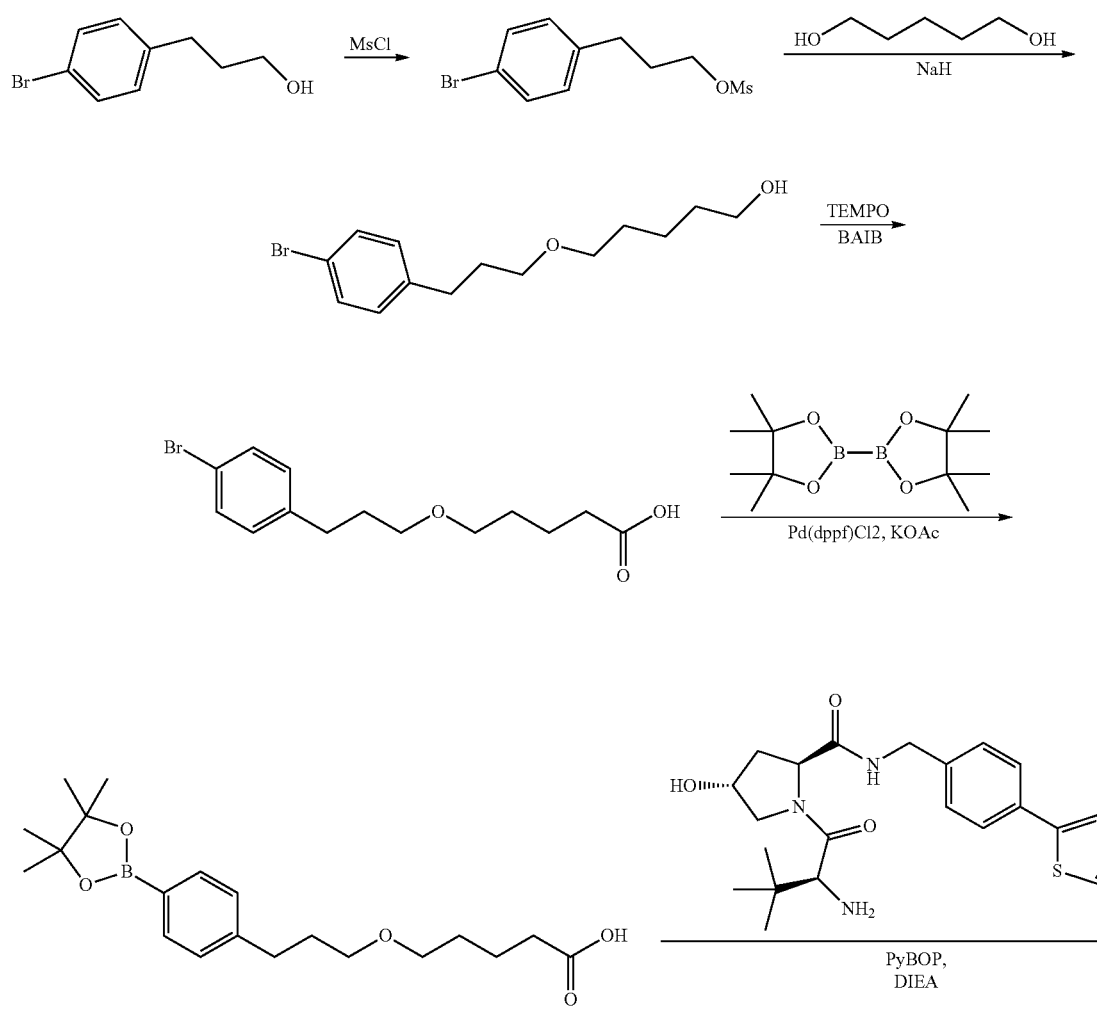
General Synthetic Scheme 9

455 456
-continued
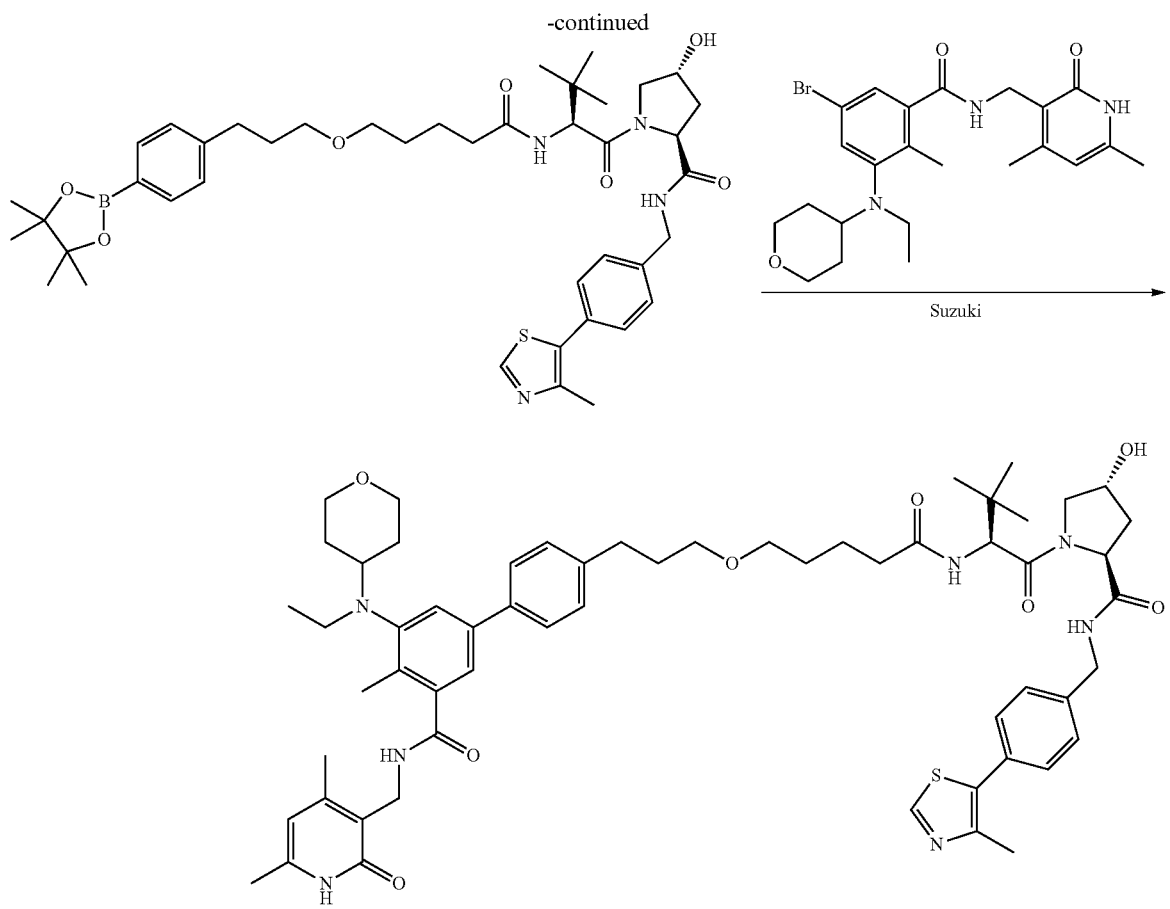
Suzuki
General Synthetic Scheme 10
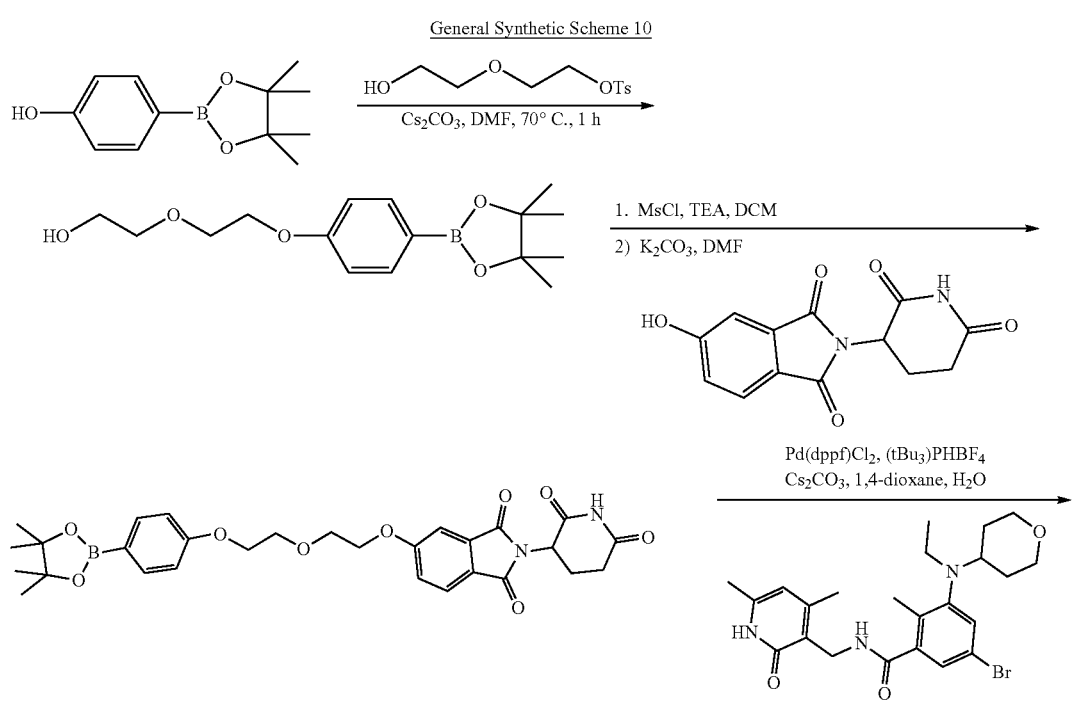

-continued
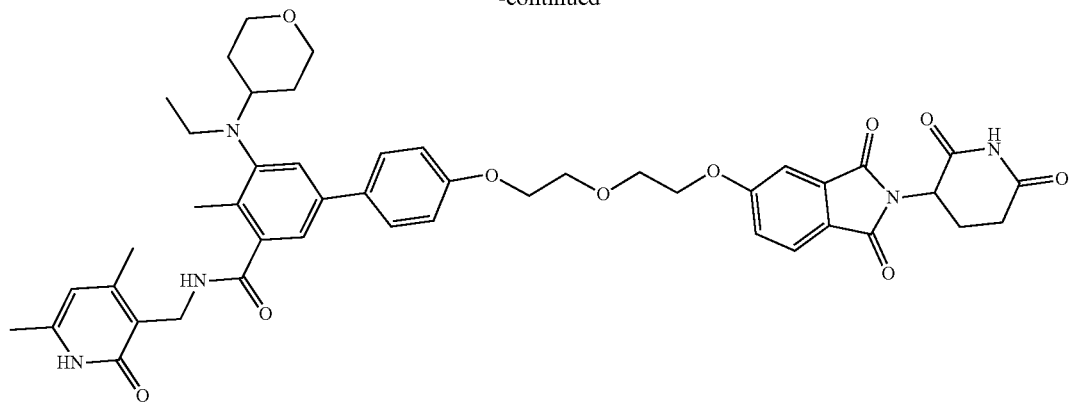
General Synthetic Scheme 11
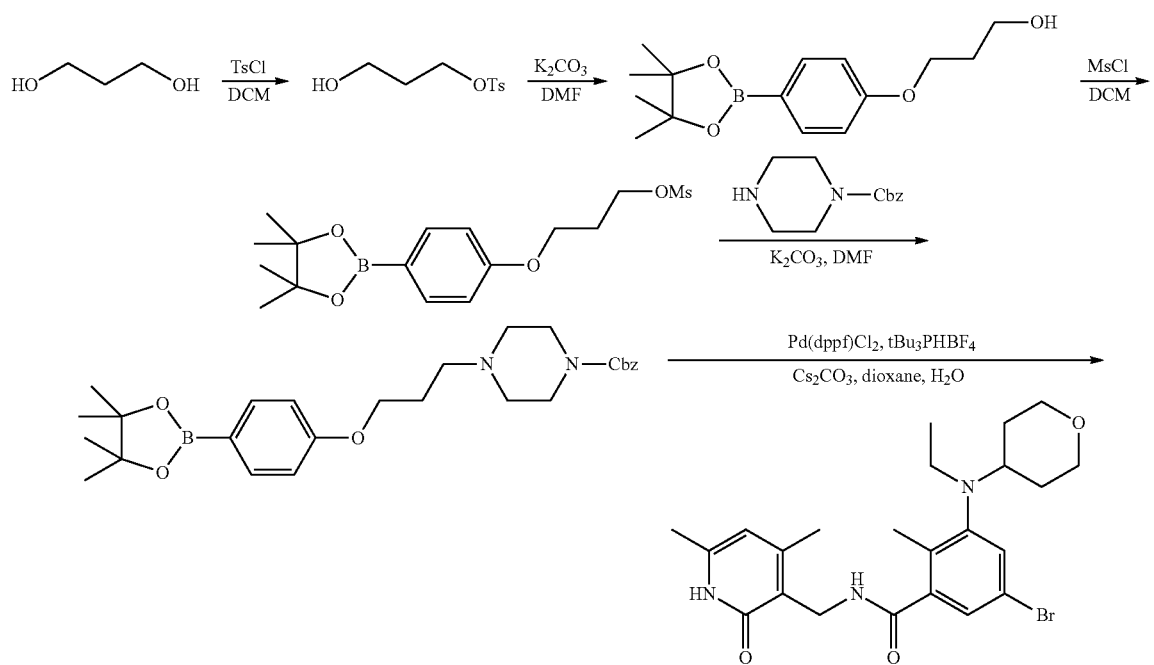
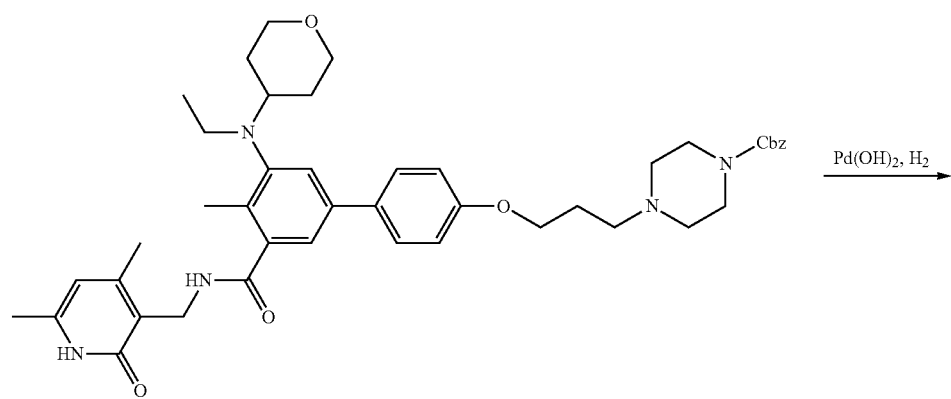

459
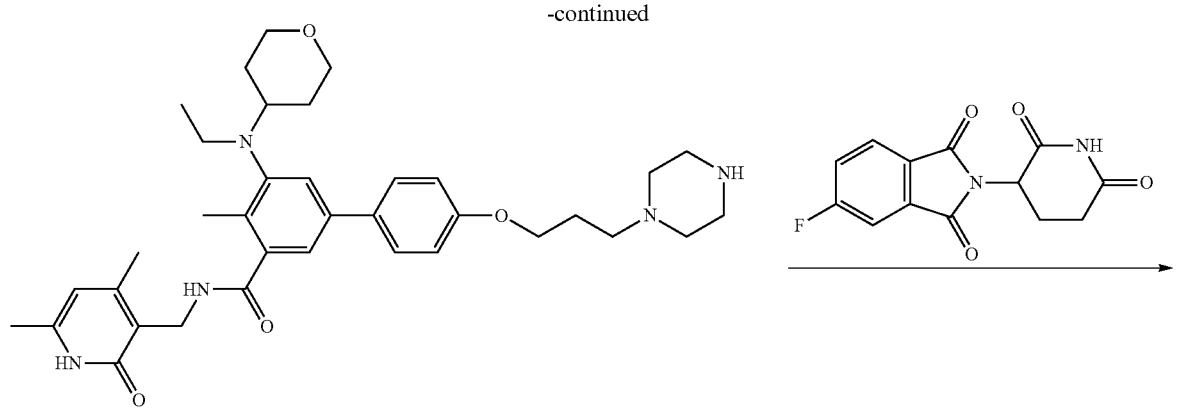
460
-continued
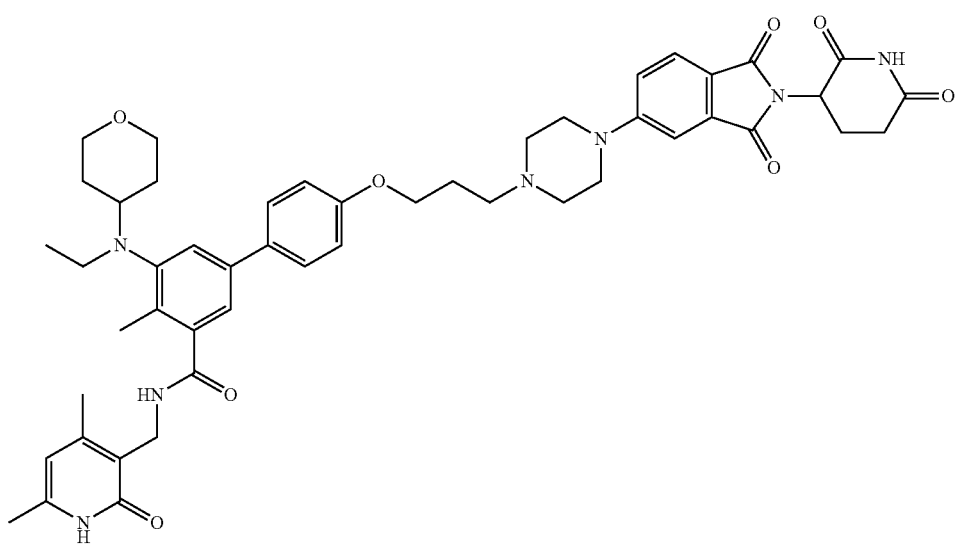
General Synthetic Scheme 12
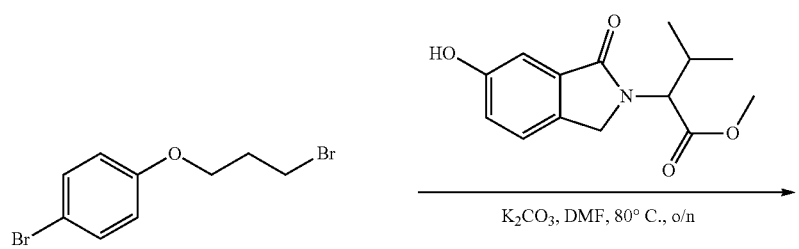
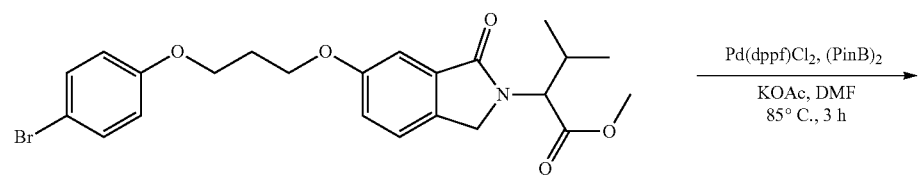

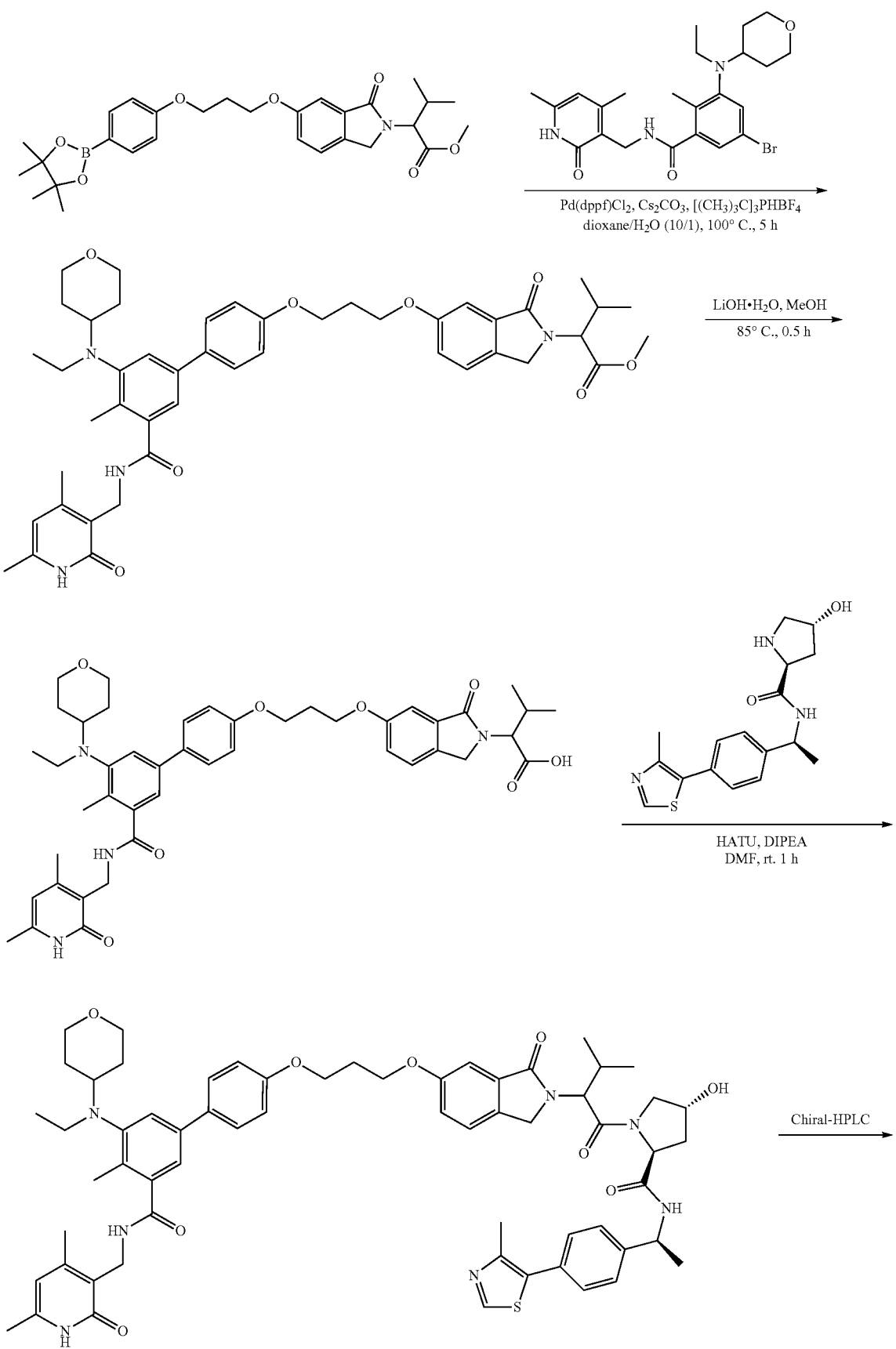
-continued 463
464
-continued
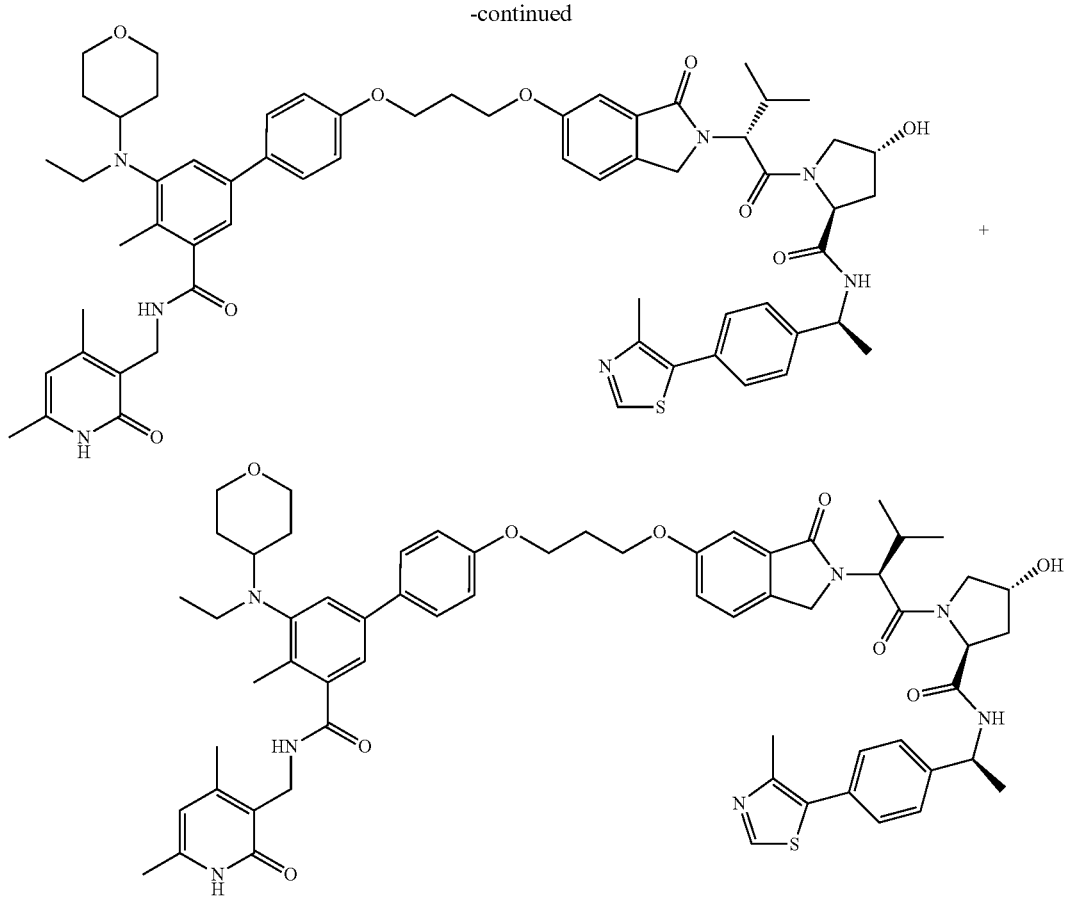
General Synthetic Scheme 13
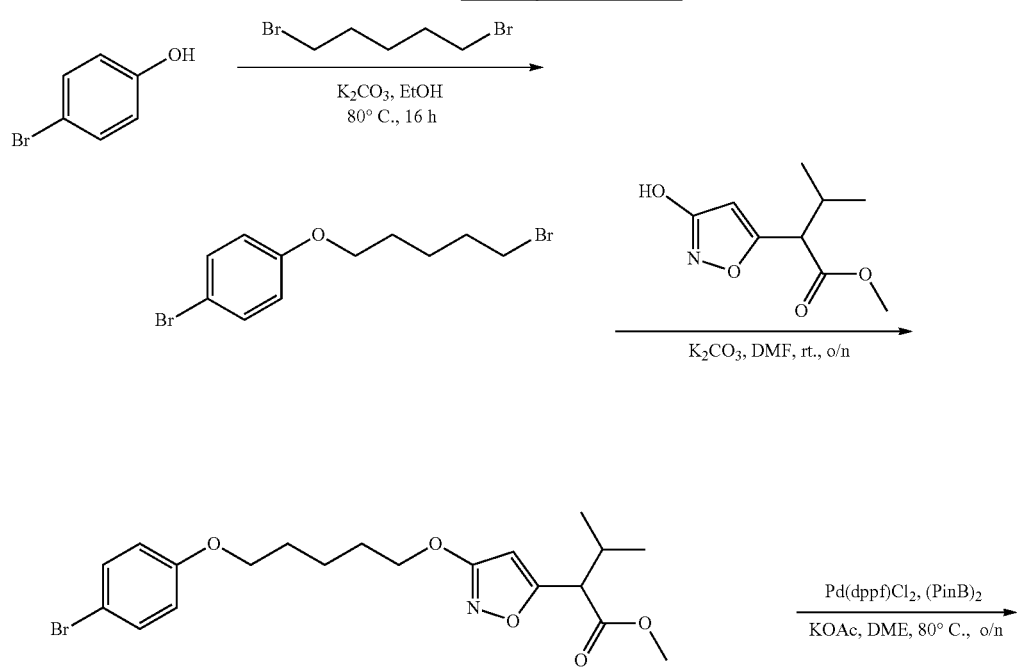

465 466
-continued
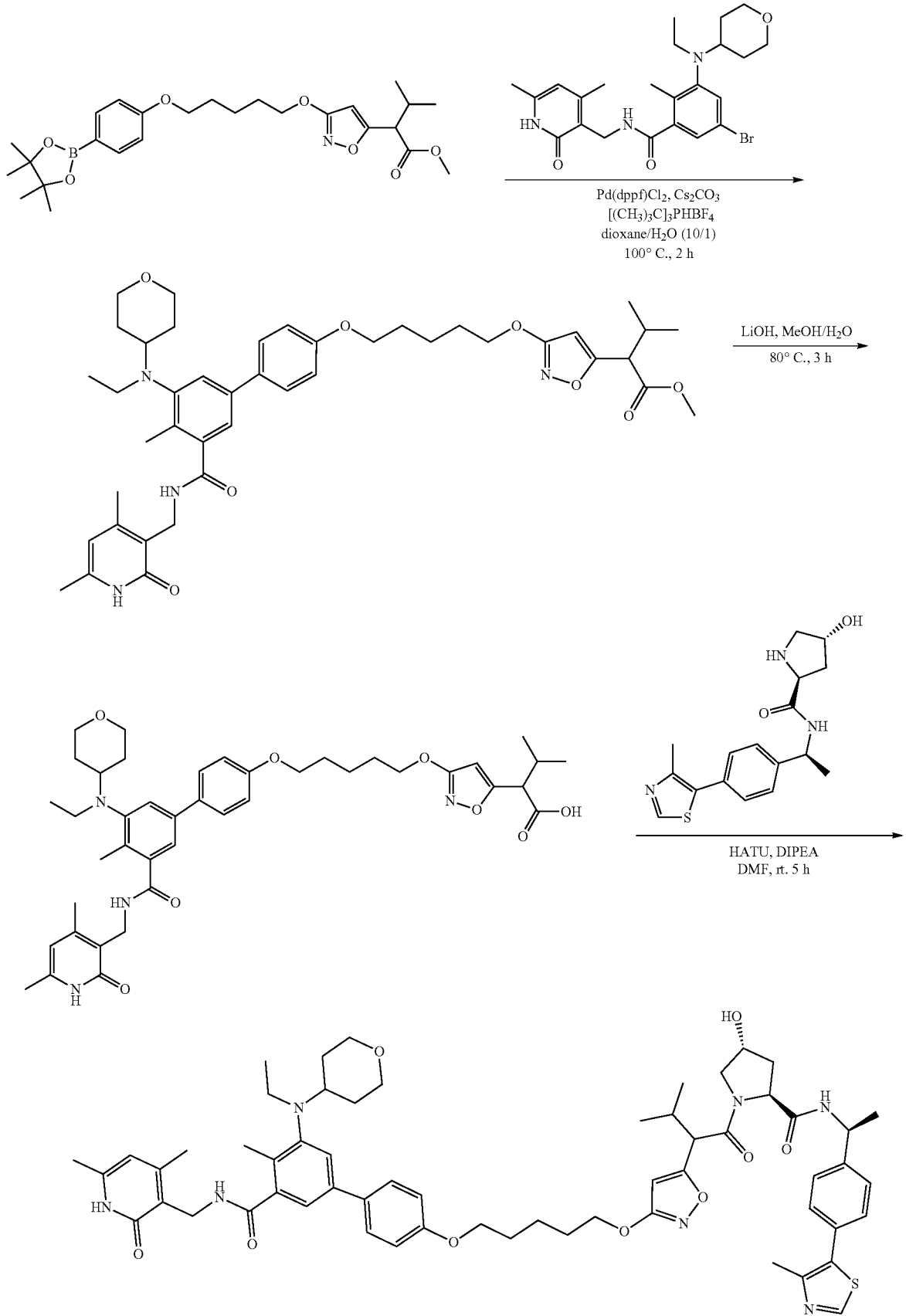

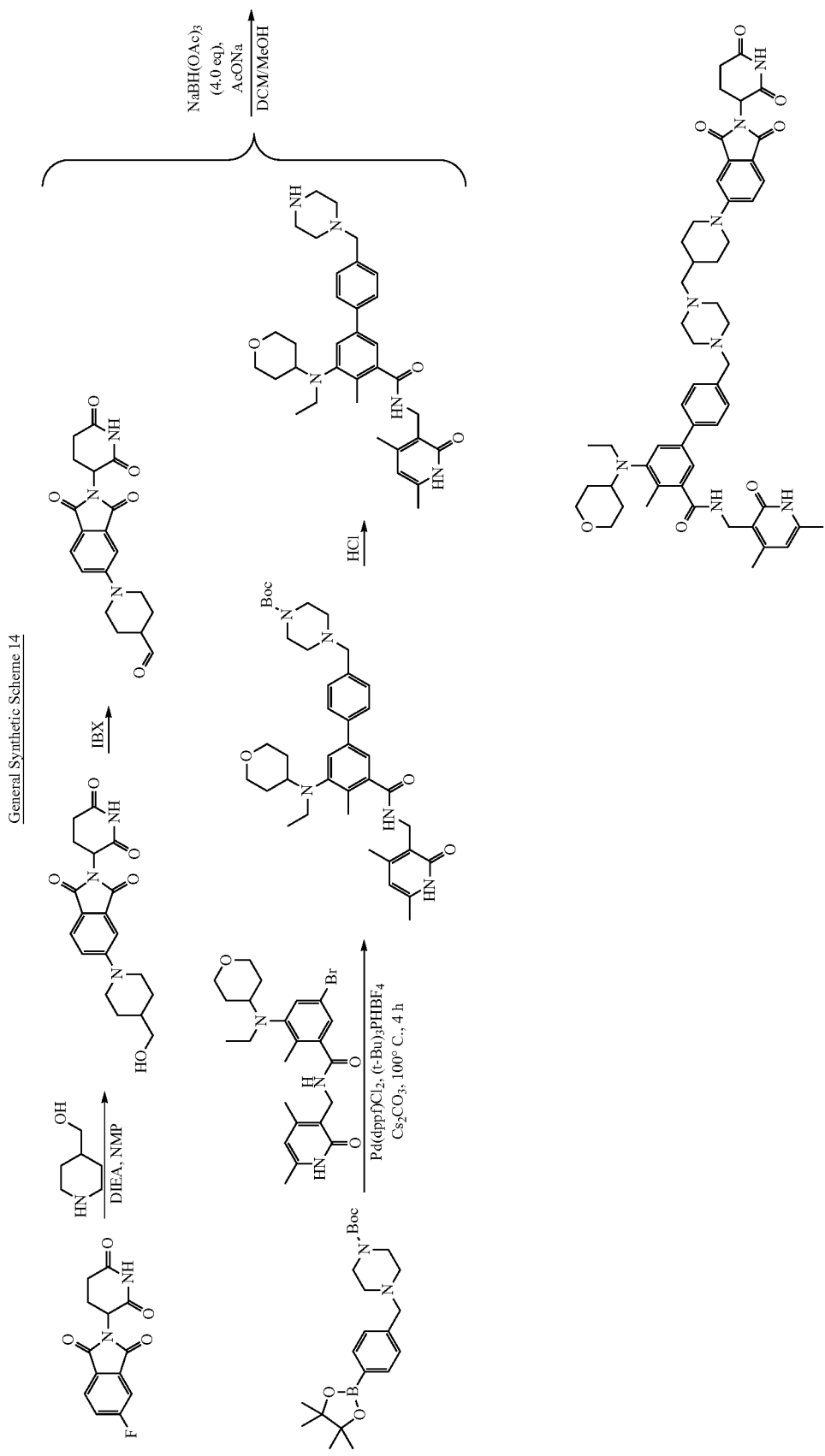

Example Synthesis of Exemplary Compound 104

Step 1. The Synthesis of 1-bromo-4-(5-bromopentyloxy)benzene (2)

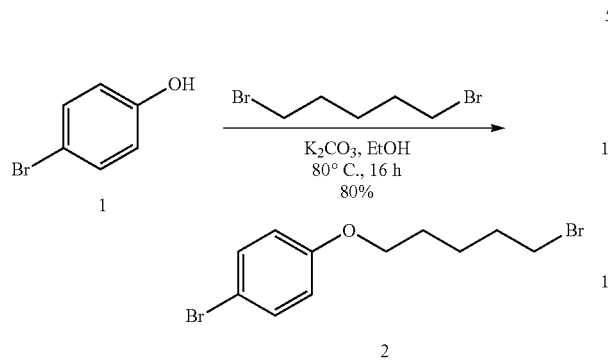

To a solution of 4-bromophenol (3.0 g, 17.4 mmol) in ethanol (20 mL) was added potassium carbonate (3.6 g, 26.2 mmol) and 1,5-dibromopentane (6.6 g, 28.7 mmol). The mixture was heated to 80° C. for 16 hours under nitrogen. After cooling to room temperature, the mixture was extracted with ethyl acetate (20 mL×3). The combined organic phase was dried over anhydrous sodium sulfate, filtered, and concentrated in vacuo and purified by silica gel (petroleum ether/ethyl acetate=50:1) to give compound 1-bromo-4-(6-bromohexyloxy)benzene (4.52 g, 80% yield) as a white solid.

Step 2. The synthesis of methyl 2-(3-(5-(4-bromophenoxy)pentyloxy)isoxazol-5-yl)-3-methylbutanoate (3)

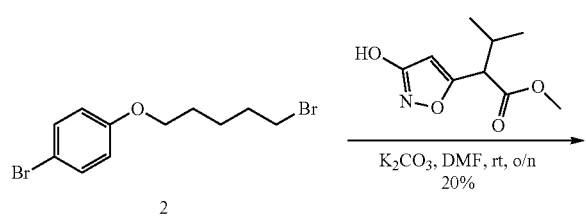

To a solution of 1-bromo-4-(5-bromopentyloxy)benzene (1.4 g, 4.3 mmol) in N,N-dimethylformamide (10 mL) was added methyl 2-(3-hydroxyisoxazol-5-yl)-3-methylbutanoate (700 mg, 4.4 mmol) and potassium carbonate (1.4 g, 10.5 mmol). The mixture was stirred at room temperature overnight. Water (15 mL) was added to the reaction mixture, and extracted with ethyl acetate (15 mL×3). The organic layer was washed with brine (15 mL×3). The combined organic phases were dried over anhydrous sodium sulfate and concentrated in vacuo and purified by Pre-TLC (petroether/ethyl acetate=10:1) to give compound methyl 2-(3-(5-(4-bromophenoxy)pentyloxy)isoxazol-5-yl)-3-methylbutanoate (300 mg, 20% yield) as light oil.

LCMS (Agilent LCMS 1200-6120, Column: Waters X-Bridge C18 (30 mm×4.6 mm×3.5 μm); Column Temperature: 40° C.; Flow Rate: 2.0 mL/min; Mobile Phase: from 90% [water+10 mM $NH_4HCO_3$] and 10% [$CH_3CN$] to 5% [water+10 mM $NH_4HCO_3$] and 95% [$CH_3CN$] in 0.5 min, then under this condition for 1.5 min, finally changed to 90% [water+10 mM $NH_4HCO_3$] and 10% [$CH_3CN$] in 0.1 min and under this condition for 0.5 min). Purity is 63.97%, Rt=1.387 min.; MS Calcd.: 440.33; MS Found: 440.0 $[M+H]^+$.

Step 3. The synthesis of methyl 3-methyl-2-(3-(5-(4-(4,4,5,5-tetramethyl-1,3,2-dioxaborolan-2-yl)phenoxy)pentyloxy)isoxazol-5-yl)butanoate (4)

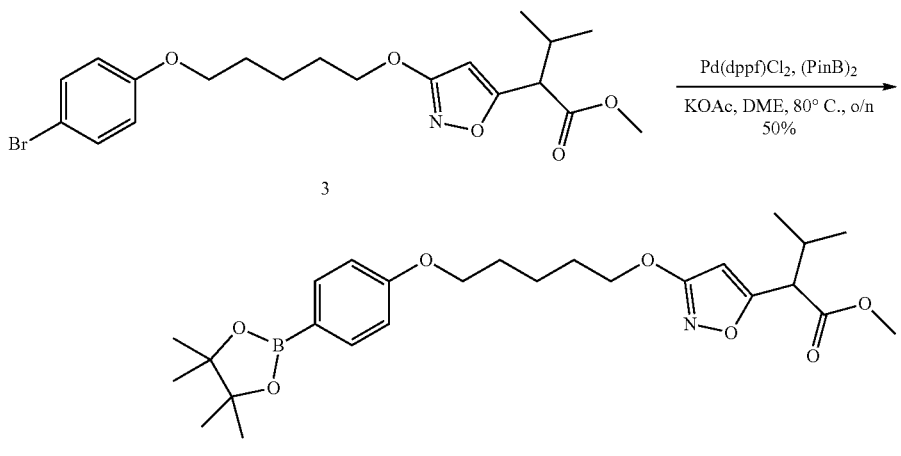

To a solution of methyl 2-(3-(5-(4-bromophenoxy)pentyloxy)isoxazol-5-yl)-3-methylbutanoate (200 mg, 0.46 mmol) in 1,2-Dimethoxyethane (10 mL) was added 4,4,4',4',5,5,5',5'-octamethyl-2,2'-bi(1,3,2-dioxaborolane) (278 mg, 1.1 mmol), potassium acetate (129 mg, 1.3 mmol) and [1,1'-Bis(diphenylphosphino)ferrocene]dichloropalladium (II) (65 mg, 0.10 mmol). The reaction mixture was stirred at 80° C. overnight under nitrogen. Water (10 mL) was added to the mixture and extracted with ethyl acetate (5 mL×3). The combined organic layer was washed with brine (10 mL×2), dried over anhydrous sodium sulfate, filtered and concentrated in vacuo and purified by pre-TLC (petroether/ethyl acetate=10:1) to give methyl 3-methyl-2-(3-(5-(4-(4,4,5,5-tetramethyl-1,3,2-dioxaborolan-2-yl)phenoxy)pentyloxy)isoxazol-5-yl)butanoate (110 mg, 50% yield) as light oil.

Step 4. The synthesis of methyl 2-(3-(5-(3'-((4,6-dimethyl-2-oxo-1,2-dihydropyridin-3-yl)methylcarbamoyl)-5'-(ethyl(tetrahydro-2H-pyran-4-yl)amino)-4'-methylbiphenyl-4-yloxy)pentyloxy)isoxazol-5-yl)-3-methylbutanoate (5)

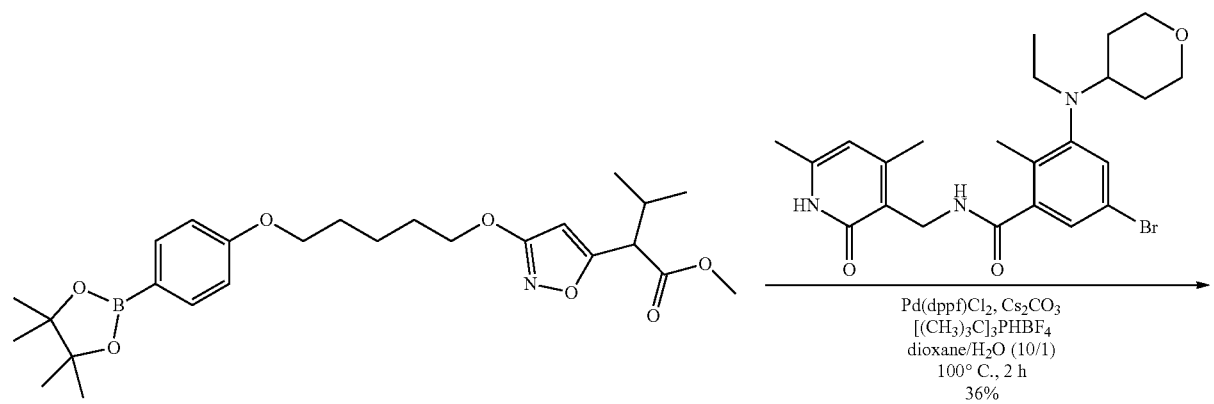

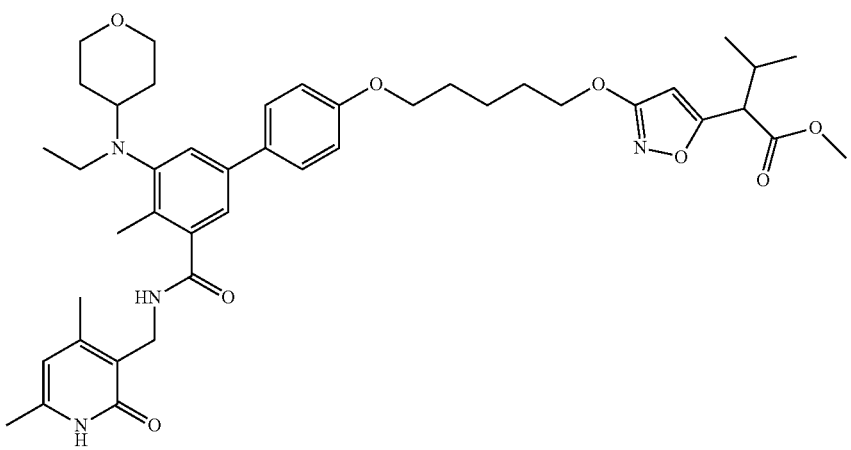

To a solution of methyl 3-methyl-2-(3-(6-(4-(4,4,5,5-tetramethyl-1,3,2-dioxaborolan-2-yl)phenoxy)hexyloxy)isoxazol-5-yl)butanoate (200 mg, 0.41 mmol) and 5-bromo-N-((4,6-dimethyl-2-oxo-1,2-dihydropyridin-3-yl)methyl)-3-(ethyl(tetrahydro-2H-pyran-4-yl)amino)-2-methylbenzamide (220 mg, 0.45 mmol) in dioxane (5 mL) and H₂O (0.5 mL) was added cesium carbonate (450 mg, 1.38 mmol), Tri-tert-butylphosphine tetrafluoroborate (40 mg, 0.14 mmol), [1,1'-Bis(diphenylphosphino)ferrocene]dichloropalladium(II) (46 mg, 0.06 mmol), stirred at 100° C. for 2 hours under nitrogen. The mixture was quenched with water (10 mL) and extracted with dichloromethane/methanol (10:1) (10 mL×3), and the combined organic layer was washed with brine (5 mL×2), dried over anhydrous sodium sulfate, filtered and concentrated in vacuo and purified by pre-TLC (dichloromethane/methanol=15:1) to give methyl 2-(3-(5-(3'-((4,6-dimethyl-2-oxo-1,2-dihydropyridin-3-yl)methylcarbamoyl)-5'-(ethyl(tetrahydro-2H-pyran-4-yl)amino)-4'-methylbiphenyl-4-yloxy)pentyloxy)isoxazol-5-yl)-3-methylbutanoate (110 mg, 36% yield) as a yellow solid.

LCMS (Agilent LCMS 1200-6120, Column: Waters X-Bridge C18 (50 mm×4.6 mm×3.5 μm); Column Temperature: 40° C.; Flow Rate: 2.0 mL/min; Mobile Phase: from 90% [(total 10 mM AcONH₄) water/CH₃CN=900/100 (v/v)] and 10% [(total 10 mM AcONH₄) water/CH₃CN=100/900 (v/v)] to 10% [(total 10 mM AcONH₄) water/CH₃CN=900/100 (v/v)] and 90% [(total 10 mM AcONH₄) water/CH₃CN=100/900 (v/v)] in 1.6 min, then under this condition for 2.4 min, finally changed to 90% [(total 10 mM AcONH₄) water/CH₃CN=900/100 (v/v)] and 10% [(total 10 mM AcONH₄) water/CH₃CN=100/900 (v/v)] in 0.1 min and under this condition for 0.7 min). Purity is 76.61%, Rt=1.275 min.; MS Calcd.: 756.93; MS Found: 757.3[M+H]⁺.

Step 5. The synthesis of 2-(3-(5-(3'-((4,6-dimethyl-2-oxo-1,2-dihydropyridin-3-yl)methylcarbamoyl)-5'-(ethyl(tetrahydro-2H-pyran-4-yl)amino)-4'-methylbiphenyl-4-yloxy)pentyloxy)isoxazol-5-yl)-3-methylbutanoic acid (6)

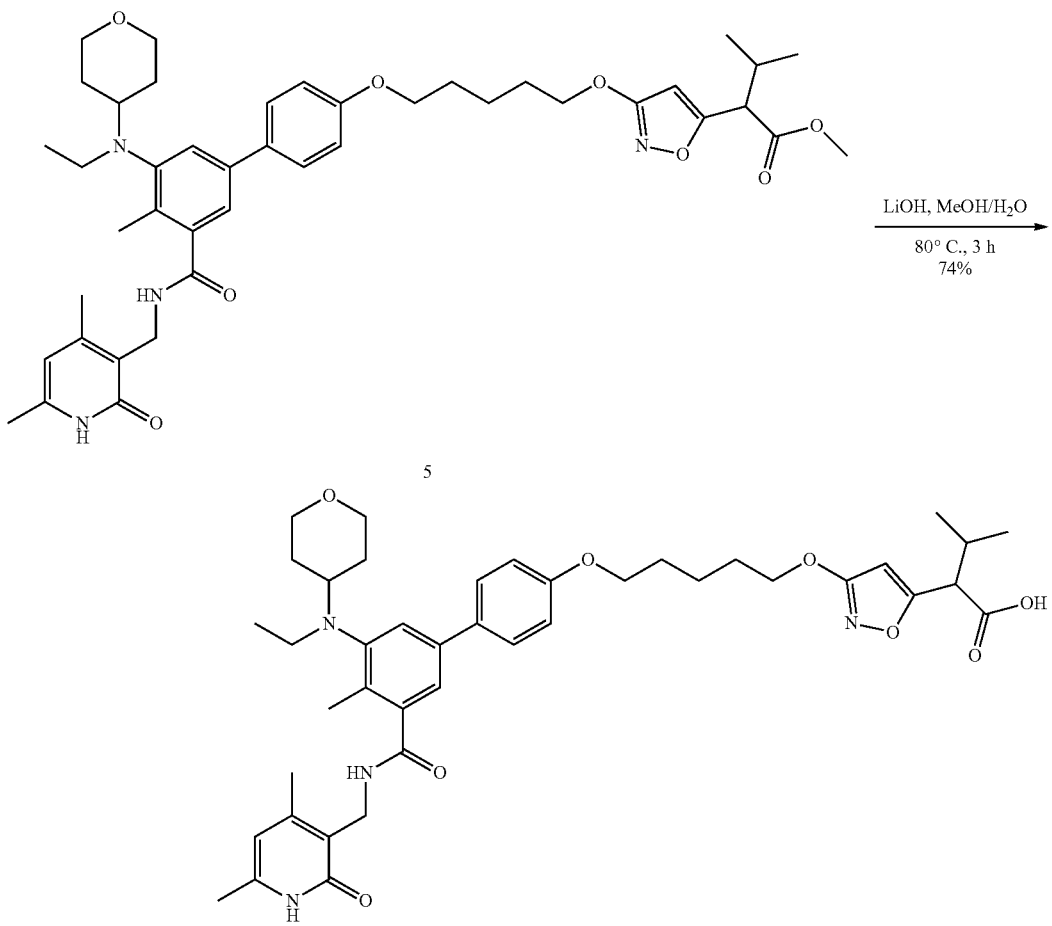

To a solution of methyl 2-(3-(5-(3'-((4,6-dimethyl-2-oxo-1,2-dihydropyridin-3-yl)methylcarbamoyl)-5'-(ethyl(tetrahydro-2H-pyran-4-yl)amino)-4'-methylbiphenyl-4-yloxy)pentyloxy)isoxazol-5-yl)-3-methylbutanoate (110 mg, 0.115 mmol) dissolved in methanol (5 mL) was added lithium hydroxide (40 mg, 1.6 mmol), and heated to 80° C. for 3 h. The reaction mixture solvent was concentrated in vacuo, water was added to the mixture and neutralized by hydrochloric acid (1 M), then extracted with ethyl acetate (5 mL×3). The combined organic phases were dried over anhydrous sodium sulfate, filtered, and concentrated in vacuo and purified by pre-TLC (dichloromethane/methanol=10:1) to give compound 2-(3-(5-(3'-((4,6-dimethyl-2-oxo-1,2-dihydropyridin-3-yl)methylcarbamoyl)-5'-(ethyl(tetrahydro-2H-pyran-4-yl)amino)-4'-methylbiphenyl-4-yloxy)pentyloxy)isoxazol-5-yl)-3-methylbutanoic acid (80 mg, 74% yield) as pale yellow oil.

LCMS (Agilent LCMS 1200-6120, Column: Waters X-Bridge C18 (30 mm×4.6 mm×3.5 μm); Column Temperature: 40° C.; Flow Rate: 2.0 mL/min; Mobile Phase: from 90% [water+10 mM $NH_4HCO_3$] and 10% [$CH_3CN$] to 5% [water+10 mM $NH_4HCO_3$] and 95% [$CH_3CN$] in 0.5 min, then under this condition for 1.5 min, finally changed to 90% [water+10 mM $NH_4HCO_3$] and 10% [$CH_3CN$] in 0.1 min and under this condition for 0.5 min.). Purity is 72.34%, Rt=0.946 min.; MS Calcd.: 742.90; MS Found: 743.3[M+H]$^+$.

Step 6. The synthesis of (2S,4R)-1-(2-(3-(5-(3'-((4,6-dimethyl-2-oxo-1,2-dihydropyridin-3-yl)methylcarbamoyl)-5'-(ethyl(tetrahydro-2H-pyran-4-yl)amino)-4'-methylbiphenyl-4-yloxy)pentyloxy)isoxazol-5-yl)-3-methylbutanoyl)-4-hydroxy-N—((S)-1-(4-(4-methylthiazol-5-yl)phenyl)ethyl)pyrrolidine-2-carboxamide (Compound 104)

To a solution of 2-(3-(5-(3'-((4,6-dimethyl-2-oxo-1,2-dihydropyridin-3-yl)methylcarbamoyl)-5'-(ethyl(tetrahydro-2H-pyran-4-yl)amino)-4'-methylbiphenyl-4-yloxy)pentyloxy)isoxazol-5-yl)-3-methylbutanoic acid (80 mg, 0.1 mmol), (2S,4R)-4-hydroxy-N—((S)-1-(4-(4-methylthiazol-5-yl)phenyl)ethyl)pyrrolidine-2-carboxamide (40 mg, 0.12 mmol) in N,N-dimethylformamide (2 mL) was added HATU (46 mg, 1.12 mmol) and ethyldiisopropylamine (40 mg, 0.3 mmol), and stirred at room temperature for 5 hours. The reaction mixture was quenched with water (5.0 mL) and extracted with dichloromethane/methanol=10:1 (5 mL×3). The organic layer was washed with brine (10 mL×2). The combined organic phases were dried over anhydrous sodium sulfate, filtered, concentrated in vacuo and purified by pre-HPLC to give (2S,4R)-1-(2-(3-(5-(3'-((4,6-dimethyl-2-oxo-1,2-dihydropyridin-3-yl)methylcarbamoyl)-5'-(ethyl(tetrahydro-2H-pyran-4-yl)amino)-4'-methylbiphenyl-4-yloxy)pentyloxy)isoxazol-5-yl)-3-methylbutanoyl)-4-hydroxy-N—((S)-1-(4-(4-methylthiazol-5-yl)phenyl)ethyl)pyrrolidine-2-carboxamide (32 mg, 28% yield) as pale yellow solid.

LC-MS (Agilent LCMS 1200-6120, Column: Waters X-Bridge C18 (50 mm×4.6 mm×3.5 μm); Column Tempera-

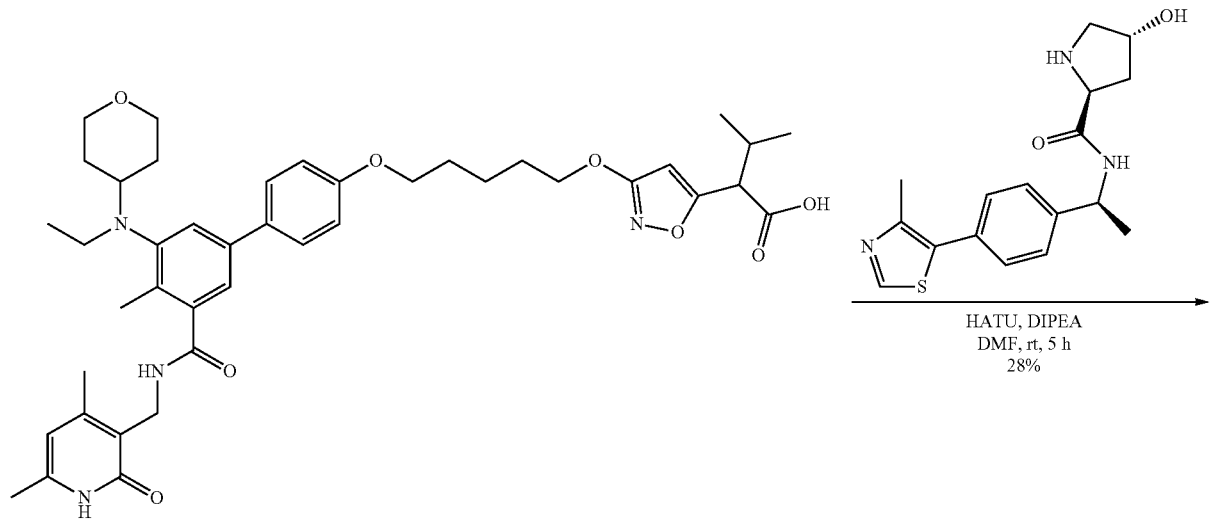

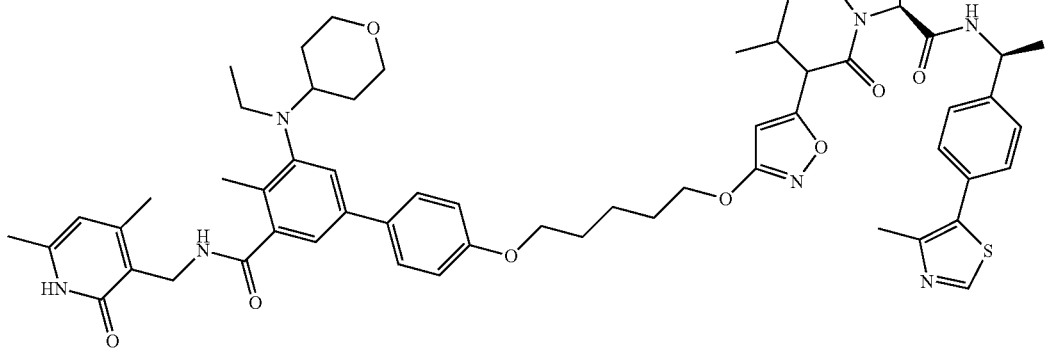

Compound 104 ture: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 3.0 min, then under this condition for 1.0 min, finally changed to 95% [water+10 mM NH$_4$HCO$_3$] and 5% [CH$_3$CN] in 0.1 min and under this condition for 0.7 min). Purity is 98.28%, Rt=2.796 min; MS/2 Calcd.: 1056.32; MS Found: 1057.4 [M+H]$^+$.

HPLC (Agilent HPLC 1200, Column: Waters X-Bridge C18 (150 mm×4.6 mm×3.5 m); Column Temperature: 40° C.; Flow Rate: 1.0 mL/min; Mobile Phase: from 95% [water+10 mM NH$_4$HCO$_3$] and 5% [CH$_3$CN] to 0% [water+ 10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min). Purity is 91.56%, Rt=9.494 min.

$^1$H NMR (400 MHz, CDCl$_3$) δ 0.86-0.88 (6H, m), 1.01-1.03 (3H, m), 1.35-1.42 (4H, m), 1.63-1.69 (5H, brs), 1.82-1.84 (4H, brs), 1.95-1.98 (1H, m), 2.12-2.19 (3H, m), 2.34 (3H, d, J=5.6 Hz), 2.40-2.41 (4H, m), 2.52 (3H, d, J=3.2 Hz), 2.88 (1H, s), 2.96 (1H, s), 2.97-3.11 (3H, m), 3.28-3.34 (2H, m), 3.44-3.66 (3H, m), 3.70 (1H, s), 3.78-4.03 (5H, m), 4.18-4.23 (2H, m), 4.36-4.50 (1H, m), 4.56-4.79 (3H, m), 4.93-5.07 (1H, m), 5.81 (1H, d, J=9.6 Hz), 5.91 (1H, d, J=14.4 Hz), 6.90 (2H, d, J=8.0 Hz), 7.06-7.21 (2H, m), 7.27-7.41 (8H, m), 7.79-8.01 (1H, m), 8.67 (1H, d, J=2.8 Hz).

Chemical Formula: C$_{59}$H$_{73}$N$_7$O$_9$S, Molecular Weight: 1056.32.

Total H count from HNMR data: 73.

Example Synthesis of Exemplary Compound 107

Step 1. The synthesis of methyl 2-(3-(4-(4-bromophenoxy)butoxy)isoxazol-5-yl)-3-methylbutanoate

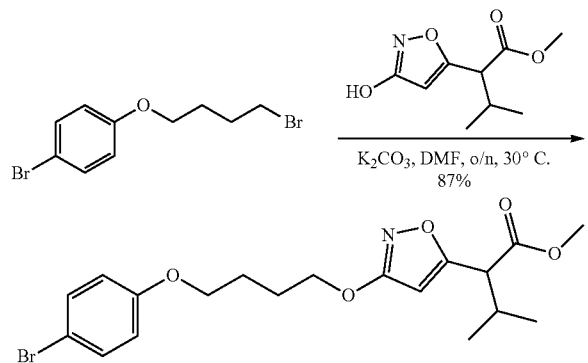

A mixture of 1-bromo-4-(4-bromobutoxy)benzene (200 mg, 0.65 mmol), methyl 2-(6-hydroxy-1-oxoisoindolin-2-yl)-3-methylbutanoate (130 mg, 0.65 mmol) and potassium carbonate (176 mg, 1.3 mmol) in N,N-dimethylformamide (5 mL) was stirred at 30° C. overnight. After cooling, it was diluted with water (20 mL) and extracted with ethyl acetate (10 mL×3). The combined organic layers were washed by brine (20 mL), dried over anhydrous sodium sulfate, filtered and concentrated in vacuo. The residue was purified by column chromatography on silica (petroleum ether/ethyl acetate=5/1) to give methyl 2-(3-(4-(4-bromophenoxy)butoxy)isoxazol-5-yl)-3-methylbutanoate (240 mg, 87% yield) as yellow oil.

LC-MS (Agilent LCMS 1200-6120, Column: Waters X-Bridge C18 (30 mm×4.6 mm×3.5 μm); Column Temperature: 40° C.; Flow Rate: 1.5 mL/min; Mobile Phase: from 90% [water+10 mM NH$_4$HCO$_3$] and 10% [CH$_3$CN] to 5% [water+10 mM NH$_4$HCO$_3$] and 95% [CH$_3$CN] in 0.5 min, then under this condition for 1.5 min, finally changed to 90% [water+10 mM NH$_4$HCO$_3$] and 10% [CH$_3$CN] in 0.1 min and under this condition for 0.5 min). Purity is 96.96%, Rt=1.718 min; MS Calcd.: 425.1; MS Found: 426.8 [M+H]$^+$.

Step 2. The synthesis of methyl 3-methyl-2-(3-(4-(4-(4,4,5,5-tetramethyl-1,3,2-dioxaborolan-2-yl) phenoxy)butoxy)isoxazol-5-yl)butanoate

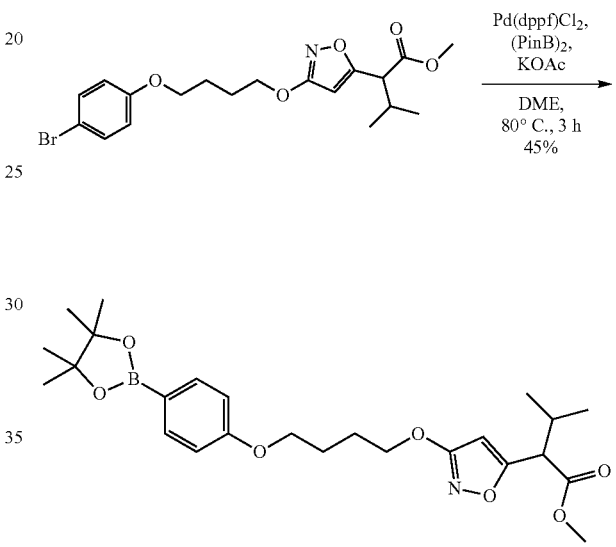

A mixture of methyl 2-(3-(4-(4-bromophenoxy)butoxy) isoxazol-5-yl)-3-methylbutanoate (240 mg, 0.56 mmol), [1,1'-bis(diphenylphosphino)ferrocene]dichloropalladium (II) (24 mg, 0.03 mmol), bis(pinacolato)diboron (571.8 mg, 2.25 mmol) and potassium acetate (164.8 mg, 1.68 mmol) in dimethoxyethane (5 mL) was stirred at 80° C. for 3 hours under nitrogen. After cooling, it was diluted with water (20 mL) and extracted with ethyl acetate (10 mL×3). The combined organic layers were washed by brine (20 mL), dried over anhydrous sodium sulfate, filtered and concentrated in vacuo. The residue was purified by column chromatography on silica (petroleum ether/ethyl acetate=2/1) to give methyl 3-methyl-2-(3-(4-(4-(4,4,5,5-tetramethyl-1,3,2-dioxaborolan-2-yl)phenoxy)butoxy)isoxazol-5-yl)butanoate (120 mg, 45% yield) as yellow oil.

LC-MS (Agilent LCMS 1200-6120, Column: Waters X-Bridge C18 (30 mm×4.6 mm×3.5 μm); Column Temperature: 40° C.; Flow Rate: 2.0 mL/min; Mobile Phase: from 90% [water+10 mM NH$_4$HCO$_3$] and 10% [CH$_3$CN] to 5% [water+10 mM NH$_4$HCO$_3$] and 95% [CH$_3$CN] in 0.5 min, then under this condition for 1.5 min, finally changed to 90% [water+10 mM NH$_4$HCO$_3$] and 10% [CH$_3$CN] in 0.1 min and under this condition for 0.5 min). Purity is 70.55%, Rt=1.383 min; MS Calcd.: 473.3; MS Found: 474.3 [M+H]$^+$.

Step 3. The synthesis of methyl 2-(3-(4-(3'-((4,6-dimethyl-2-oxo-1,2-dihydropyridin-3-yl)methylcarbamoyl)-5'-(ethyl(tetrahydro-2H-pyran-4-yl)amino)-4'-methylbiphenyl-4-yloxy)butoxy)isoxazol-5-yl)-3-methylbutanoate

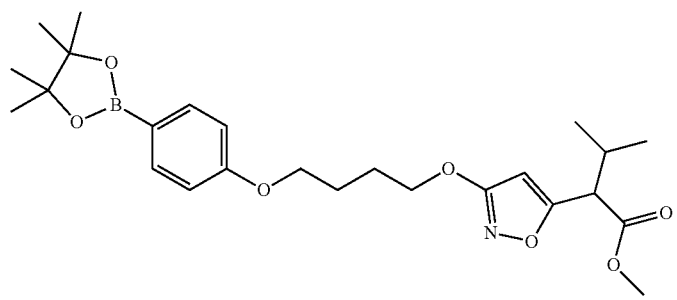
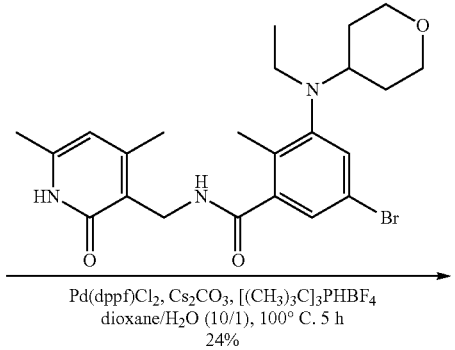

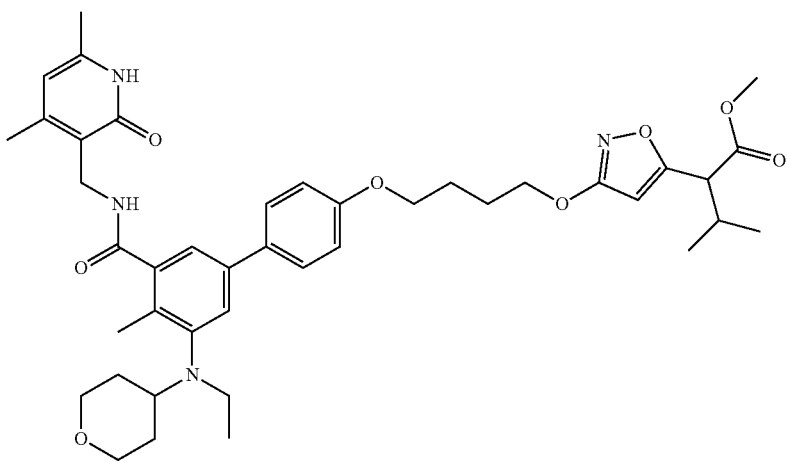

A mixture of methyl 3-methyl-2-(3-(4-(4-(4,4,5,5-tetramethyl-1,3,2-dioxaborolan-2-yl)phenoxy)butoxy)isoxazol-5-yl)butanoate (120 mg, 0.25 mmol), 5-bromo-N-((4,6-dimethyl-2-oxo-1,2-dihydropyridin-3-yl)methyl)-3-(ethyl(tetrahydro-2H-pyran-4-yl)amino)-2-methylbenzamide (120 mg, 0.25 mmol), cesium carbonate (203 mg, 0.63 mmol), [1,1'-bis(diphenylphosphino)ferrocene]dichloropalladium(II) (12 mg, 0.02 mmol) and tri-tert-butylphosphine tetrafluoroborate (24 mg, 0.08 mmol) in 1,4-dioxane/water (5 mL, v/v=10/1) was stirred at 100° C. for 5 hours under nitrogen. After cooling, it was diluted with water (15 mL) and extracted with dichloromethane (10 mL×3). The combined organic layers were washed by brine (20 mL), dried over anhydrous sodium sulfate, filtered and concentrated in vacuo. The residue was purified by Prep-HPLC to give methyl 2-(3-(4-(3'-((4,6-dimethyl-2-oxo-1,2-dihydropyridin-3-yl)methylcarbamoyl)-5'-(ethyl(tetrahydro-2H-pyran-4-yl)amino)-4'-methylbiphenyl-4-yloxy)butoxy)isoxazol-5-yl)-3-methylbutanoate (45 mg, 24% yield) as a white solid.

Step 4. The synthesis of 2-(3-(4-(3'-((4,6-dimethyl-2-oxo-1,2-dihydropyridin-3-yl)methylcarbamoyl)-5'-(ethyl(tetrahydro-2H-pyran-4-yl)amino)-4'-methylbiphenyl-4-yloxy)butoxy)isoxazol-5-yl)-3-methylbutanoic acid

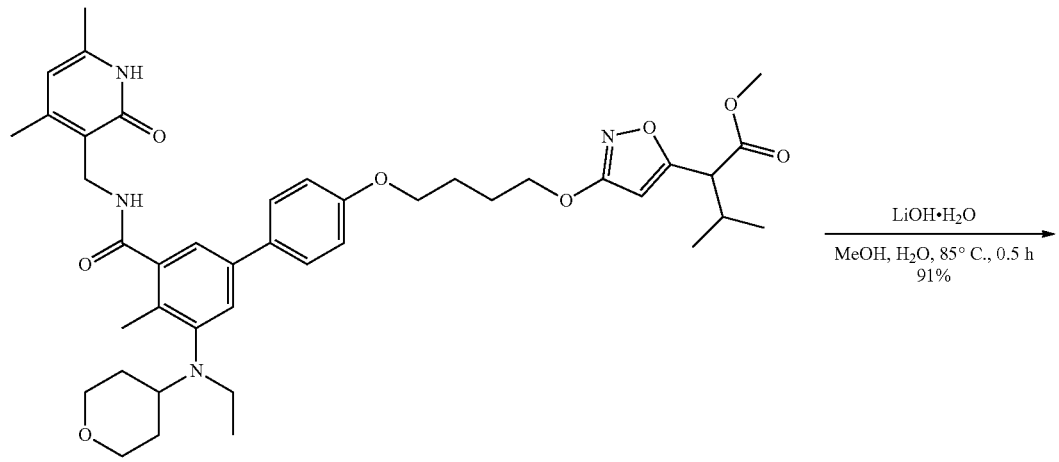

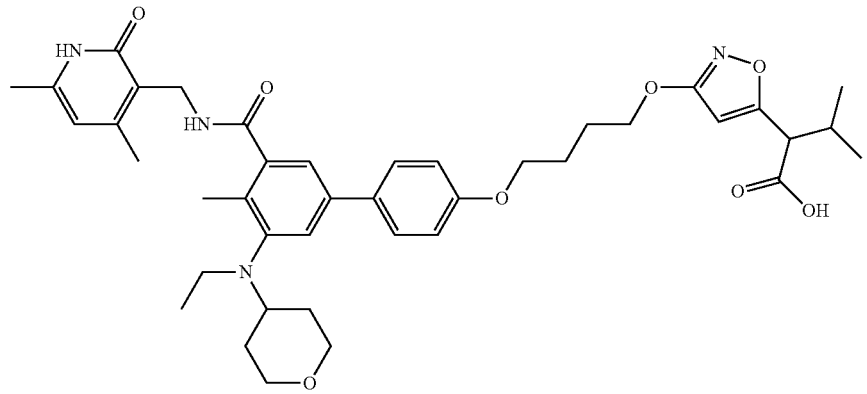

To a solution of methyl 2-(3-(4-(3'-((4,6-dimethyl-2-oxo-1,2-dihydropyridin-3-yl)methylcarbamoyl)-5'-(ethyl(tetrahydro-2H-pyran-4-yl)amino)-4'-methylbiphenyl-4-yloxy)butoxy)isoxazol-5-yl)-3-methylbutanoate (45 mg, 0.06 mmol) in methanol (2 mL) was added lithium hydroxide hydrate (13 mg, 0.30 mmol) and water (1 mL), then it was stirred at 85° C. for 30 minutes. After cooling, the reaction mixture was diluted by water (10 mL) and extracted by dichloromethane (20 mL×3). The combined organic layers were washed by brine (20 mL), dried over anhydrous sodium sulfate, filtered and concentrated in vacuo. The residue was purified by Prep-TLC to give 2-(3-(4-(3'-((4,6-dimethyl-2-oxo-1,2-dihydropyridin-3-yl)methylcarbamoyl)-5'-(ethyl(tetrahydro-2H-pyran-4-yl)amino)-4'-methylbiphenyl-4-yloxy)butoxy)isoxazol-5-yl)-3-methylbutanoic acid (40 mg, 91% yield) as a white solid.

LC-MS (Agilent LCMS 1200-6120, Column: Waters X-Bridge C18 (50 mm×4.6 mm×3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min). Purity is 85.58%, Rt=1.555 min; MS Calcd.: 728.4; MS Found: 729.4 [M+H]$^+$.

Step 5. The synthesis of (2S,4R)-1-(2-(3-(4-(3'-((4,6-dimethyl-2-oxo-1,2-dihydropyridin-3-yl)methyl-carbamoyl)-5'-(ethyl(tetrahydro-2H-pyran-4-yl)amino)-4'-methylbiphenyl-4-yloxy)butoxy)isoxazol-5-yl)-3-methylbutanoyl)-4-hydroxy-N—((S)-1-(4-(4-methylthiazol-5-yl)phenyl)ethyl)pyrrolidine-2-carboxamide

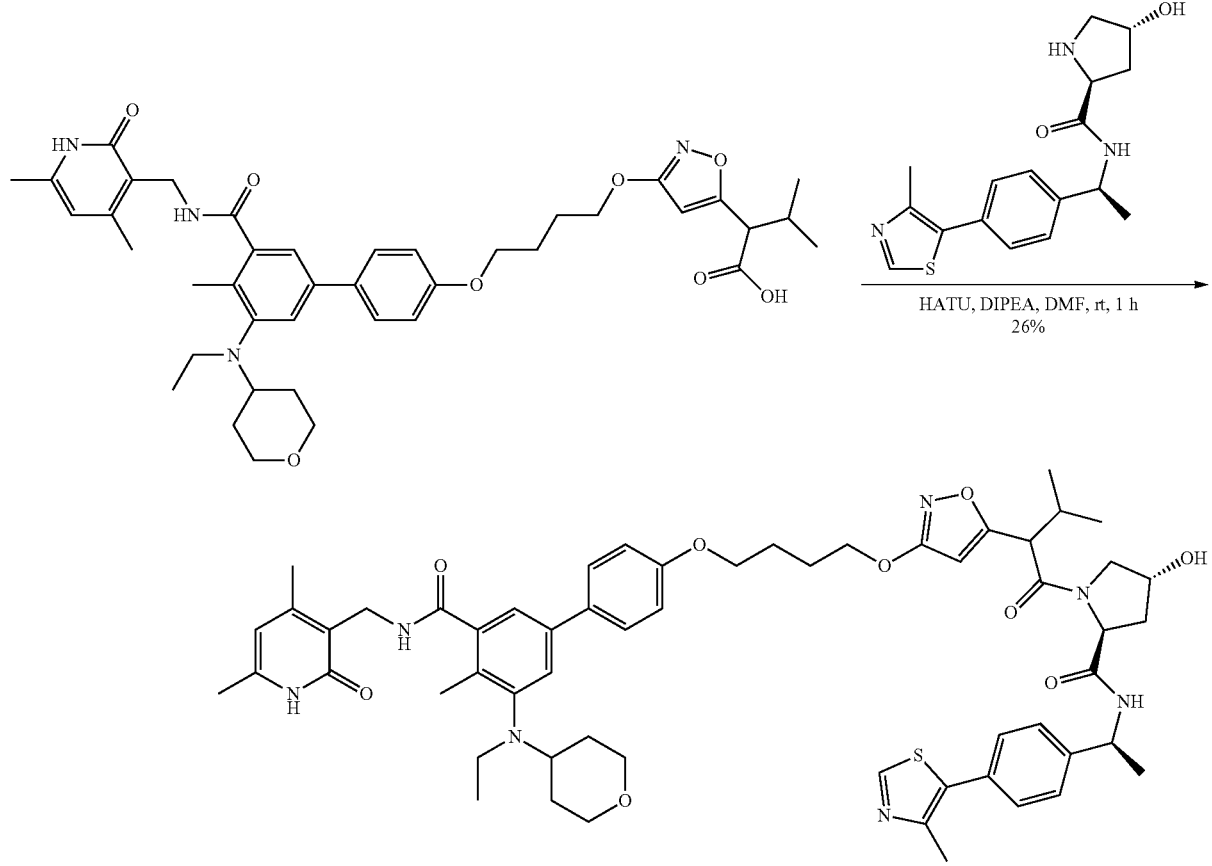

A mixture of 2-(3-(4-(3'-((4,6-dimethyl-2-oxo-1,2-dihydropyridin-3-yl)methylcarbamoyl)-5'-(ethyl(tetrahydro-2H-pyran-4-yl)amino)-4'-methylbiphenyl-4-yloxy)butoxy)isoxazol-5-yl)-3-methylbutanoic acid (40 mg, 0.06 mmol), (2S,4R)-4-hydroxy-N—((S)-1-(4-(4-methylthiazol-5-yl)phenyl)ethyl)pyrrolidine-2-carboxamide (18 mg, 0.06 mmol), 0-(7-azabenzotriazole-1-yl)-N,N,N',N'-tetramethyluronium hexamluorophosphate (30 mg, 0.08 mmol) and ethyldiisopropylamine (14 mg, 0.11 mmol) in N,N-dimethylformamide (2 mL) was stirred at room temperature for an hour. It was diluted with water (10 mL) and extracted with dichloromethane (10 mL×3). The combined organic layers were washed by brine (10 mL), dried over anhydrous sodium sulfate, filtered and concentrated in vacuo. The residue was purified by Prep-HPLC to give (2S,4R)-1-(2-(3-(4-(3'-((4,6-dimethyl-2-oxo-1,2-dihydropyridin-3-yl)methylcarbamoyl)-5'-(ethyl(tetrahydro-2H-pyran-4-yl)amino)-4'-methylbiphenyl-4-yloxy)butoxy)isoxazol-5-yl)-3-methylbutanoyl)-4-hydroxy-N—((S)-1-(4-(4-methylthiazol-5-yl)phenyl)ethyl)pyrrolidine-2-carboxamide (15 mg, 26% yield) as a white solid.

LC-MS (Agilent LCMS 1200-6120, Column: Waters X-Bridge C18 (50 mm×4.6 mm×3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 3.0 min, then under this condition for 1.0 min, finally changed to 95% [water+10 mM $NH_4HCO_3$] and 5% [$CH_3CN$] in 0.1 min and under this condition for 0.7 min). Purity is 96.77%, Rt=2.714 min; MS Calcd.: 1041.5; MS Found: 1042.4 $[M+H]^+$.

HPLC (Agilent HPLC 1200, Column: Waters X-Bridge C18 (150 mm×4.6 mm×3.5 μm); Column Temperature: 40° C.; Flow Rate: 1.0 mL/min; Mobile Phase: from 95% [water+10 mM $NH_4HCO_3$] and 5% [$CH_3CN$] to 0% [water+ 10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min). Purity is 94.25%, Rt=9.196 min.

$^1$H NMR (400 MHz, $CDCl_3$) δ 0.89-0.91 (3H, m), 1.01-1.04 (3H, m), 1.26-1.43 (6H, m), 1.66 (6H, m), 1.95-1.98 (5H, m), 2.13-2.19 (3H, m), 2.33-2.35 (3H, m), 2.40-2.41 (3H, m), 2.51-2.52 (3H, m), 3.00-3.11 (4H, m), 3.29-3.34 (2H, m), 3.51-3.64 (3H, m), 3.93-4.05 (4H, m), 4.27 (2H, m), 4.32-4.50 (1H, m), 4.57-4.80 (3H, m), 4.92-5.08 (1H, m), 5.80-5.94 (2H, m), 6.89-6.91 (2H, m), 7.12-7.18 (2H, m), 7.28-7.44 (8H, m), 7.53-7.83 (1H, m), 8.67 (1H, m).

Chemical Formula: $C_{58}H_{71}N_7O_9S$, Molecular Weight: 1042.29.

Total H count from HNMR data: 71.

Example Synthesis of Exemplary Compound 99

Step 1. The Synthesis of
2-(4-bromobenzyloxy)ethanol

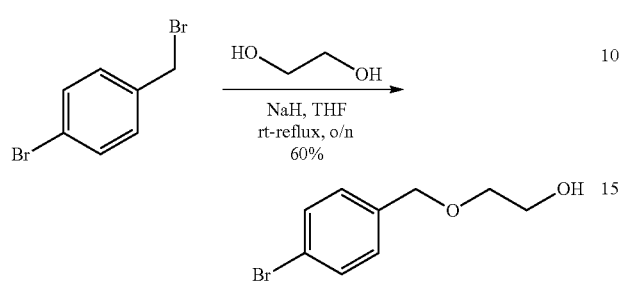

To the solution of ethylene glycol (1.0 g, 16.1 mmol) in tetrahydrofuran (20 mL) was added sodium hydride (1.3 g, 32.2 mmol, 60% in mineral oil) at room temperature and the mixture was stirred for 30 minutes. To the mixture above was added a solution of 1-bromo-4-(bromomethyl)benzene (400 mg, 1.6 mmol) in tetrahydrofuran (10 mL) and the reaction mixture was refluxed overnight. After cooling to room temperature, the mixture was poured into saturated ammonium chloride (30 mL) and extracted with dichloromethane (30 mL×3). The organic phase was concentrated in vacuo and the residue was purified by silica gel (dichloromethane/methanol=20/1) to give 2-(4-bromobenzyloxy)ethanol (221 mg, 60% yield) as colorless oil.

Agilent LCMS 1200-6120, Column: Waters X-Bridge C18 (50 mm*4.6 mm*3.5 m); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 3.0 min, then under this condition for 1.0 min, finally changed to 95% [water+10 mM $NH_4HCO_3$] and 5% [$CH_3CN$] in 0.1 min and under this condition for 0.7 min. Purity is 88.9%, Rt=1.588 min; MS Calcd.: 229.9; MS Found: 248.2 $[M+NH_4]^+$.

Chemical Formula: $C_{13}H_{19}Br_2O_2$, Molecular Weight: 231.09.

Route for methyl (S)-2-(6-hydroxy-1-oxoisoindolin-2-yl)-3-methylbutanoate

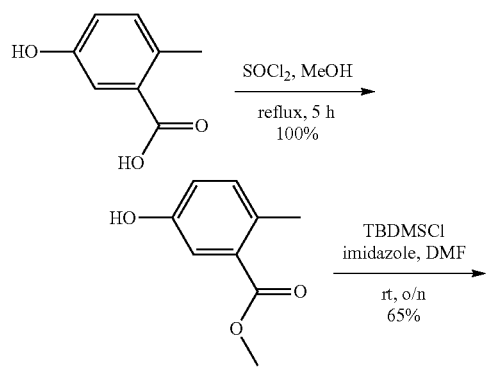

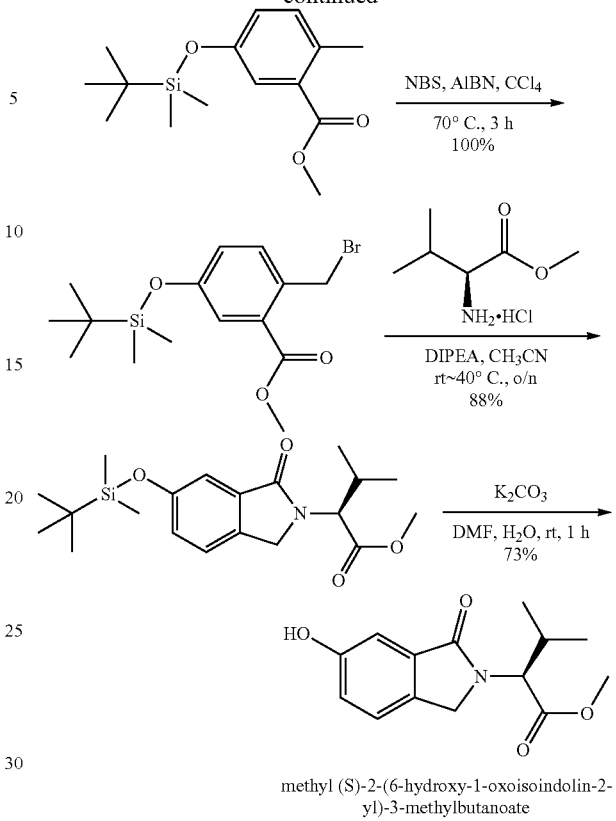

methyl (S)-2-(6-hydroxy-1-oxoisoindolin-2-yl)-3-methylbutanoate

Step 2. The synthesis of methyl
5-hydroxy-2-methylbenzoate

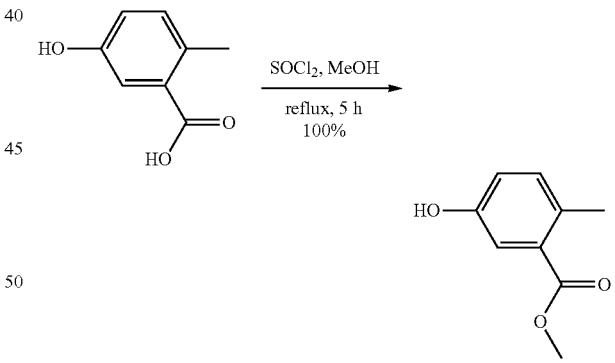

To a solution of 5-hydroxy-2-methylbenzoic acid (10.0 g, 65.7 mmol) in methanol (200 mL) was added thionyl chloride (5 mL). After stirred at 85° C. for 5 hours, the solvent was removed in vacuo to give methyl 5-hydroxy-2-methylbenzoate (10.9 g, 100% yield) as a pale yellow solid, which was used to next step without further purification.

LC-MS (Agilent LCMS 1200-6120, Column: Waters X-Bridge C18 (30 mm×3 mm×2.5 µm); Column Temperature: 40° C.; Flow Rate: 1.5 mL/min; Mobile Phase: from 95% [water+10 mM $NH_4HCO_3$] and 5% [$CH_3CN+10$ mM $NH_4HCO_3$] to 5% [water+10 mM $NH_4HCO_3$] and 95% [$CH_3CN+10$ mM $NH_4HCO_3$] in 1.5 min, then under this condition for 0.5 min, finally changed to 95% [water+10 mM NH$_4$HCO$_3$] and 5% [CH$_3$CN+10 mM NH$_4$HCO$_3$] in 0.1 min and under this condition for 0.5 min). Purity is 98.56%, Rt=1.052 min; MS Calcd.: 166.1; MS Found: 167.1 [M+H]$^+$.

Step 3. The synthesis of methyl 5-(tert-butyldimethylsilyloxy)-2-methylbenzoate

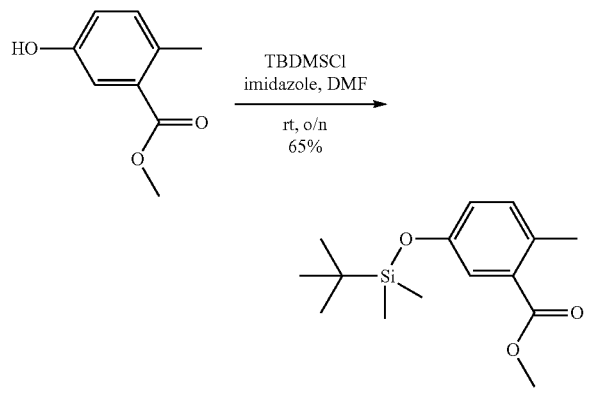

To a solution of methyl 5-hydroxy-2-methylbenzoate (10.9 g, 65.7 mmol) in N,N-dimethylformamide (100 mL) was added imidazole (8.95 g, 131 mmol) and tert-butyldimethylsilyl chloride (11.9 g, 78.8 mmol) at 0° C., and the mixture was agitated at 0° C. for 1 hour. The mixture was warmed up to room temperature for overnight. The reaction mixture was added to ice water (200 mL), and extracted with ethyl acetate (100 mL×3). The organic layer was washed with cold water (50 mL) and brine (50 mL). The combined organic phases were dried over anhydrous sodium sulfate, filtered, and concentrated in vacuo to give methyl 5-(tert-butyldimethylsilyloxy)-2-methylbenzoate (12.0 g, 65%) as pale yellow oil, and used to next step without further purification.

Step 4. The synthesis of methyl 2-(bromomethyl)-5-(tert-butyldimethylsilyloxy)benzoate

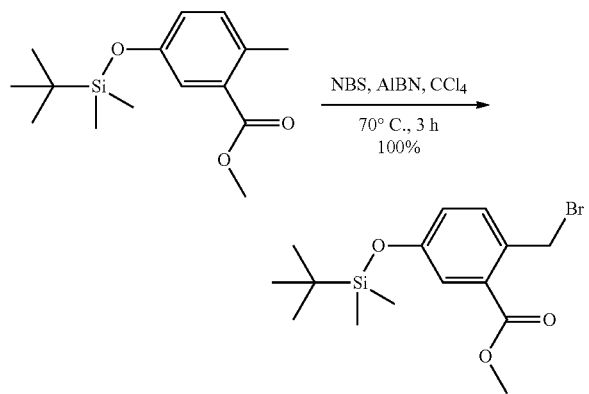

To a solution of compound methyl 5-(tert-butyldimethylsilyloxy)-2-methylbenzoate (11.0 g, 39.2 mmol) in carbon tetrachloride (120 mL) was added 1-bromopyrrolidine-2,5-dione (6.98 g, 39.2 mmol) and benzoyl peroxide (0.475 g, 1.96 mmol). After the reaction mixture was heated to 70° C. for 3 hours. The reaction mixture was cooled down and washed by sodium sulfite solution (100 mL×2, 50% saturated concentration), water (100 mL) and brine (100 mL). The organic layer was dried over anhydrous sodium sulfate, filtered, and concentrated in vacuo to give methyl 2-(bromomethyl)-5-(tert-butyldimethylsilyloxy)benzoate (14.1 g, 100%) as light brown oil, and used to next step without further purification LC-MS (Agilent LCMS 1200-6120, Column: Waters X-Bridge C18 (30 mm×3 mm×2.5 µm); Column Temperature: 40° C.; Flow Rate: 1.5 mL/min; Mobile Phase: from 95% [water+10 mM NH$_4$HCO$_3$] and 5% [CH$_3$CN+10 mM NH$_4$HCO$_3$] to 5% [water+10 mM NH$_4$HCO$_3$] and 95% [CH$_3$CN+10 mM NH$_4$HCO$_3$] in 1.5 min, then under this condition for 0.5 min, finally changed to 95% [water+10 mM NH$_4$HCO$_3$] and 5% [CH$_3$CN+10 mM NH$_4$HCO$_3$] in 0.1 min and under this condition for 0.5 min). Purity is 69.62%, Rt=1.820 min; MS Calcd.: 358.1; MS Found: 279.1 [M−Br+H]$^+$.

Step 5. The synthesis of (S)-methyl 2-(6-(tert-butyldimethylsilyloxy)-1-oxoisoindolin-2-yl)-3-methylbutanoate

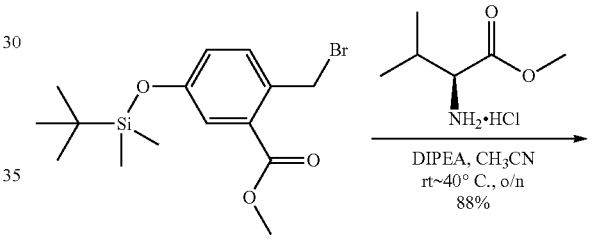

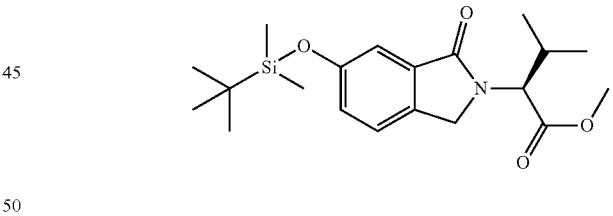

To a solution of methyl 2-(bromomethyl)-5-(tert-butyldimethylsilyloxy)benzoate (14.1 g, 39.2 mmol) in acetonitrile (150 mL) was added (S)-methyl 2-amino-3-methylbutanoate hydrochloride (6.57 g, 39.2 mmol). To the mixture was added ethyldiisopropylamine (10.1 g, 78.4 mmol) through an addition funnel over 10 minutes and the mixture was stirred at room temperature for 1 hour before heating to 40° C. overnight. The reaction mixture was concentrated in vacuo. The residue was stirred in ethyl acetate (200 mL) and washed with hydrochloric acid (1N, 50 mL), sodium bicarbonate (sat. 50 mL) and brine (50 mL). The organic layers was dried over anhydrous sodium sulfate, filtered, and concentrated in vacuo to give crude (S)-methyl 2-(6-(tert-butyldimethylsilyloxy)-1-oxoisoindolin-2-yl)-3-methylbutanoate (13.0 g, 88%) as brown oil, and used to next step without further purification.

Step 6. The synthesis of (S)-methyl 2-(6-hydroxy-1-oxoisoindolin-2-yl)-3-methylbutanoate

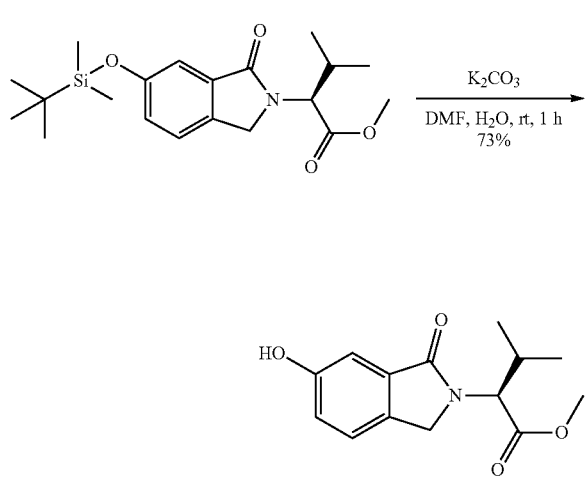

To a stirred cold solution of (S)-methyl 2-(6-(tert-butyldimethylsilyloxy)-1-oxoisoindolin-2-yl)-3-methylbutanoate (13.0 g, 34.4 mmol) in N,N-dimethylformamide (50 mL) and water (5 mL), was added potassium carbonate (9.50 g, 68.9 mmol) by portions over 5 minutes. The resulting reaction mixture was stirred at room temperature for 1 hour. The reaction mixture was cooled in an ice bath. To the mixture, hydrochloric acid (12M, 43.1 mmol) was added slowly. After the addition, acetonitrile (100 mL) was added to the mixture and stirred at room temperature for 10 minutes and filtered. The filtrate was concentrated and purified by silica gel (petroether/ethyl acetate=2:1) to give (S)-methyl 2-(6-hydroxy-1-oxoisoindolin-2-yl)-3-methylbutanoate (6.60 g, 73%) as a pale yellow solid.

$^1$H NMR (400 MHz, DMSO-$d_6$) δ 0.81 (3H, d, J=6.8 Hz), 0.97 (3H, d, J=6.8 Hz), 2.23-2.33 (1H, m), 3.66 (3H, s), 4.37-4.47 (2H, m), 4.55 (1H, d, J=10.4 Hz), 7.02-7.04 (2H, m), 7.40-7.42 (1H, m), 9.82 (1H, s).

Chemical Formula: $C_{14}H_{17}NO_4$, Molecular Weight: 263.29

Total H count from HNMR data: 17.

Step 7. The synthesis of (S)-methyl 2-(6-(2-(4-bromobenzyloxy)ethoxy)-1-oxoisoindolin-2-yl)-3-methylbutanoate

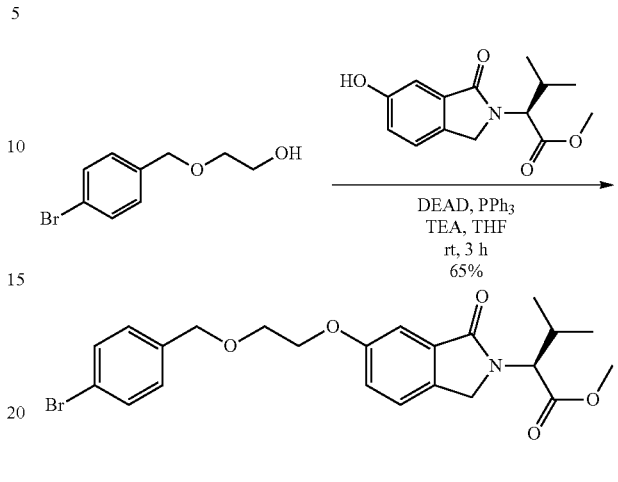

To the mixture of 2-(4-bromobenzyloxy)ethanol (100 mg, 0.43 mmol), (S)-methyl 2-(6-hydroxy-1-oxoisoindolin-2-yl)-3-methylbutanoate (113 mg, 0.43 mmol), triphenylphosphine (113 mg, 0.43 mmol) and triethylamine (43 mg, 0.43 mmol) in dry tetrahydrofuran (10 mL) was added diethyl azodicarboxylate (75 mg, 0.43 mmol) at room temperature under nitrogen atmosphere and the mixture was stirred for 2 hours. The mixture was concentrated in vacuo and the residue was purified by silica gel (petroleum ether/ethyl acetate=10/1) to give (S)-methyl 2-(6-(2-(4-bromobenzyloxy)ethoxy)-1-oxoisoindolin-2-yl)-3-methylbutanoate (133 mg, 65% yield) as yellow oil.

Agilent LCMS 1200-6120, Column: Waters X-Bridge C18 (50 mm*4.6 mm*3.5 m); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 3.0 min, then under this condition for 1.0 min, finally changed to 95% [water+10 mM $NH_4HCO_3$] and 5% [$CH_3CN$] in 0.1 min and under this condition for 0.7 min. Purity is 65.4%, Rt=2.085 min; MS Calcd.: 475.1; MS Found: 476.2 [M+H]$^+$.

Chemical Formula: $C_{23}H_{26}BrNO_5$, Molecular Weight: 476.36.

Step 8. The synthesis of (S)-methyl 3-methyl-2-(1-oxo-6-(2-(4-(4,4,5,5-tetramethyl-1,3,2-dioxaborolan-2-yl)benzyloxy)ethoxy)isoindolin-2-yl)butanoate

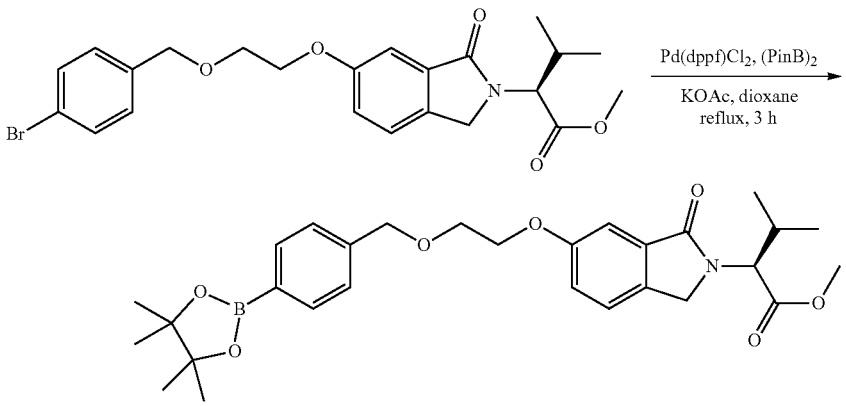

The mixture of (S)-methyl 2-(6-(2-(4-bromobenzyloxy)ethoxy)-1-oxoisoindolin-2-yl)-3-methylbutanoate (100 mg, 0.21 mmol), 4,4,4',4',5,5,5',5'-octamethyl-2,2'-bi(1,3,2-dioxaborolane) (53 mg, 0.21 mmol), 1,1'-bis(diphenylphosphino)ferrocene palladium dichloride (26 mg, 0.04 mmol) and potassium carbonate (21 mg, 0.42 mmol) in dioxane (5 mL) was refluxed for 3 hours. The reaction mixture was used for the next step directly without further purification.

Step 9. The synthesis of (S)-methyl 2-(6-(2-((3'-((4,6-dimethyl-2-oxo-1,2-dihydropyridin-3-yl)methylcarbamoyl)-5'-(ethyl(tetrahydro-2H-pyran-4-yl)amino)-4'-methylbiphenyl-4-yl)methoxy)ethoxy)-1-oxoisoindolin-2-yl)-3-methylbutanoate (5 mL, 10/1) was heated at 100° C. for 5 hours. After cooling to room temperature, the mixture was poured into water (30 mL) and extracted with dichloromethane (30 mL×3). The organic phase was concentrated in vacuo and the residue was purified by silica gel (dichloromethane/methanol=20/1) to give (S)-methyl 2-(6-(2-((3'-((4,6-dimethyl-2-oxo-1,2-dihydropyridin-3-yl)methylcarbamoyl)-5'-(ethyl(tetrahydro-2H-pyran-4-yl)amino)-4'-methylbiphenyl-4-yl)methoxy)ethoxy)-1-oxoisoindolin-2-yl)-3-methylbutanoate (83 mg, 50% yield) as brown oil.

Agilent LCMS 1200-6120, Column: Waters X-Bridge C18 (30 mm*4.6 mm*3.5 μm); Column Temperature: 40° C.; Flow Rate: 2.0 mL/min; Mobile Phase: from 90% [water+10 mM NH$_4$HCO$_3$] and 10% [CH$_3$CN] to 5% [water+10 mM NH$_4$HCO$_3$] and 95% [CH$_3$CN] in 0.5 min, then

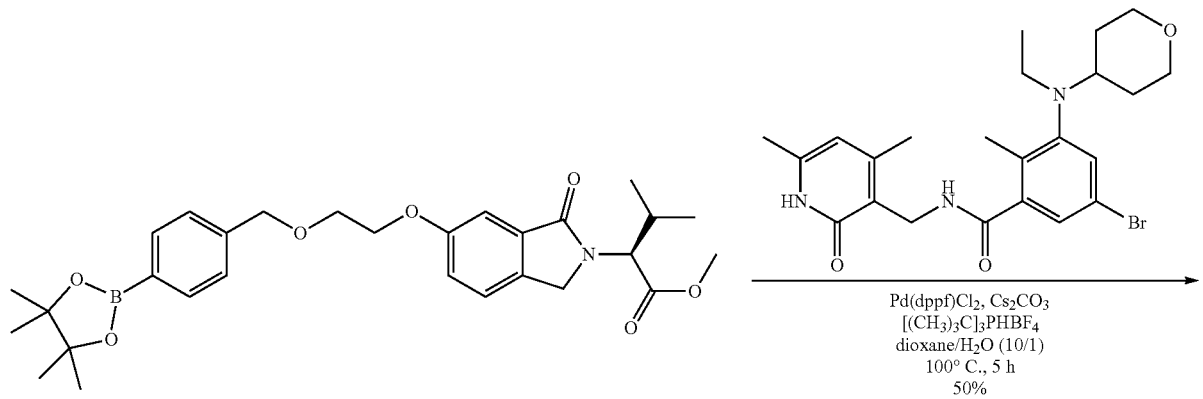

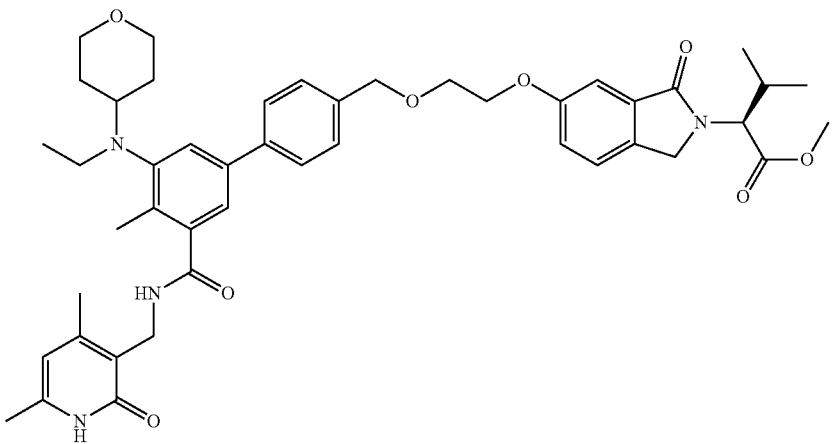

The mixture of crude (S)-methyl 3-methyl-2-(1-oxo-6-(2-(4-(4,4,5,5-tetramethyl-1,3,2-dioxaborolan-2-yl)benzyloxy)ethoxy)isoindolin-2-yl)butanoate (110 mg, 0.21 mmol), 5-bromo-N-((4,6-dimethyl-2-oxo-1,2-dihydropyridin-3-yl)methyl)-3-(ethyl(tetrahydro-2H-pyran-4-yl)amino)-2-methylbenzamide (100 mg, 0.21 mmol), 1,1'-bis(diphenylphosphino)ferrocene palladium dichloride (26 mg, 0.04 mmol) and cesium carbonate (136 mg, 0.42 mmol) in dioxane/water under this condition for 1.5 min, finally changed to 90% [water+10 mM NH$_4$HCO$_3$] and 10% [CH$_3$CN] in 0.1 min and under this condition for 0.5 min. Purity is 41.7%, Rt=1.463 min; MS Calcd.: 792.4; MS Found: 794.3 [M+H]$^+$.

Chemical Formula: C$_{46}$H$_{56}$N$_4$O$_8$, Molecular Weight: 792.96.

Step 10. The synthesis of (S)-2-(6-(2-((3'-((4,6-dimethyl-2-oxo-1,2-dihydropyridin-3-yl)methylcarbamoyl)-5'-(ethyl(tetrahydro-2H-pyran-4-yl)amino)-4'-methylbiphenyl-4-yl)methoxy)ethoxy)-1-oxoisoindolin-2-yl)-3-methylbutanoic acid

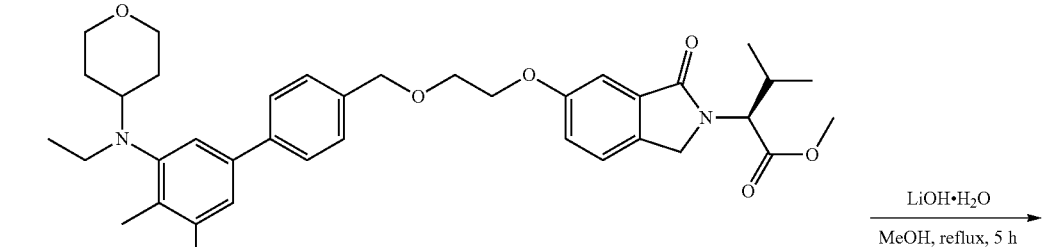

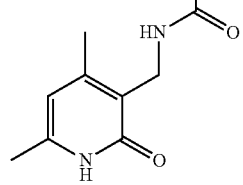

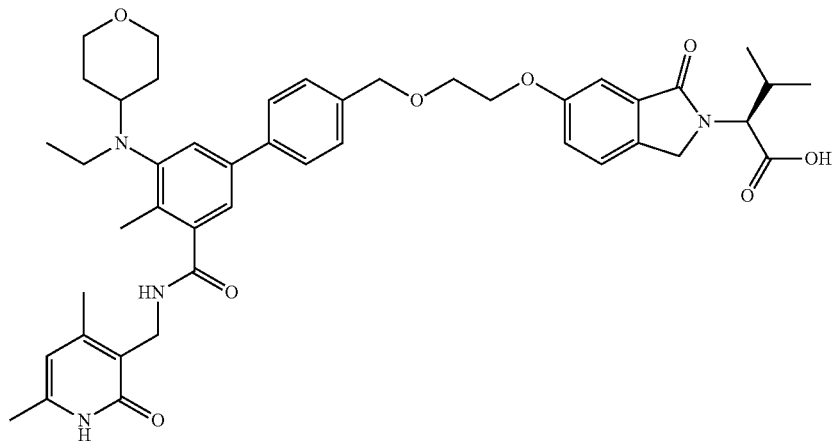

The mixture of (S)-methyl 2-(6-(2-((3'-((4,6-dimethyl-2-oxo-1,2-dihydropyridin-3-yl)methylcarbamoyl)-5'-(ethyl(tetrahydro-2H-pyran-4-yl)amino)-4'-methylbiphenyl-4-yl)methoxy)ethoxy)-1-oxoisoindolin-2-yl)-3-methylbutanoate (80 mg, 0.1 mmol) and lithium hydroxide monohydrate (42 mg, 1.0 mmol) in methanol (10 mL) was refluxed for 5 hours. The reaction mixture was concentrated in vacuo and the residue was redissolved in water (10 mL). The pH value of solution was adjusted to 5-6 with hydrochloride acid (1.0 N) and extracted with dichloromethane (20 mL×3). The combined organic solvent was concentrated and the residue was purified by silica gel (dichloromethane/methanol=20/1) to give (S)-2-(6-(2-((3'-((4,6-dimethyl-2-oxo-1,2-dihydropyridin-3-yl)methylcarbamoyl)-5'-(ethyl(tetrahydro-2H-pyran-4-yl)amino)-4'-methylbiphenyl-4-yl)methoxy)ethoxy)-1-oxoisoindolin-2-yl)-3-methylbutanoic acid (62 mg, 80% yield) as a brown solid.

Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% TFA] and 5% [$CH_3CN$+0.05% TFA] to 0% [water+0.05% TFA] and 100% [$CH_3CN$+0.05% TFA] in 1.6 min, then under this condition for 1.4 min, finally changed to 95% [water+0.05% TFA] and 5% [$CH_3CN$+0.05% TFA] in 0.05 min and under this condition for 0.7 min. Purity is 53.3%, Rt=1.516 min; MS Calcd.: 778.4; MS Found: 779.4 [M+H]$^+$.

Chemical Formula: $C_{24}H_{19}IN_4O_2S$, Molecular Weight: 778.93.

Step 11. The synthesis of (2S,4R)-1-((S)-2-(6-(2-((3'-((4,6-dimethyl-2-oxo-1,2-dihydropyridin-3-yl)methylcarbamoyl)-5'-(ethyl(tetrahydro-2H-pyran-4-yl)amino)-4'-methylbiphenyl-4-yl)methoxy)ethoxy)-1-oxoisoindolin-2-yl)-3-methylbutanoyl)-4-hydroxy-N—((S)-1-(4-(4-methylthiazol-5-yl)phenyl)ethyl)pyrrolidine-2-carboxamide then changed to 5% [water+10 mM NH₄HCO₃] and 95% [CH₃CN] in 0.2 min and under this condition for 3.8 min; Flow rate: 20 mL/min; Column temperature: room temperature] to give (2S,4R)-1-((S)-2-(6-(2-((3'-((4,6-dimethyl-2-oxo-1,2-dihydropyridin-3-yl)methylcarbamoyl)-5'-(ethyl(tetrahydro-2H-pyran-4-yl)amino)-4'-methylbiphenyl-4-yl)methoxy)ethoxy)-1-oxoisoindolin-2-yl)-3-methylbutanoyl)-

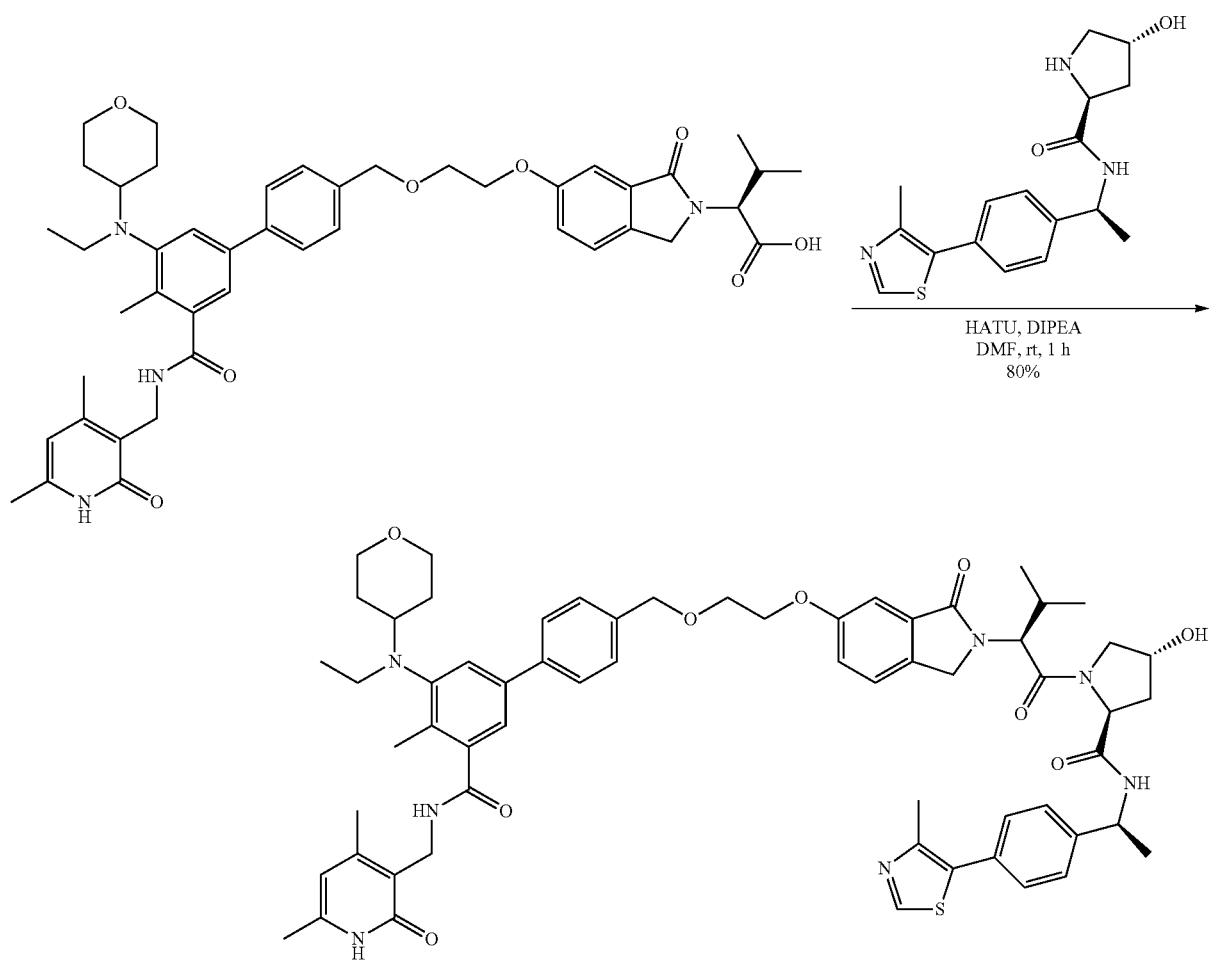

The mixture of (S)-2-(6-(2-((3'-((4,6-dimethyl-2-oxo-1,2-dihydropyridin-3-yl)methylcarbamoyl)-5'-(ethyl(tetrahydro-2H-pyran-4-yl)amino)-4'-methylbiphenyl-4-yl)methoxy)ethoxy)-1-oxoisoindolin-2-yl)-3-methylbutanoic acid (60 mg, 0.08 mmol), (2S,4R)-4-hydroxy-N—((S)-1-(4-(4-methylthiazol-5-yl)phenyl)ethyl)pyrrolidine-2-carboxamide (26 mg, 0.08 mmol), 1-[bis(dimethylamino)methylene]-1H-1,2,3-triazolo[4,5-b]pyridinium 3-oxid hexafluorophosphate (46 mg, 0.12 mmol) and ethyldiisopropylamine (31 mg, 0.24 mmol) in N,N-dimethylformamide (5 mL) was stirred at room temperature for 1 hour. The reaction mixture was poured into water (15 mL) and extracted with dichloromethane (20 mL×3). The combined organic solvent was concentrated in vacuo and the residue was purified by pre-HPLC [Gilson-GX281; Column: Waters X-Bridge C18: 100 mm*30 mm 5 m; Mobile Phase: from 65% [water+10 mM NH₄HCO₃] and 35% [CH₃CN] to 45% [water+10 mM NH₄HCO₃] and 55% [CH₃CN] in 8 min, 4-hydroxy-N—((S)-1-(4-(4-methylthiazol-5-yl)phenyl)ethyl)pyrrolidine-2-carboxamide (70 mg, 80% yield) as a pale yellow solid.

Agilent LCMS 1200-6120, Column: Waters X-Bridge C18 (50 mm*4.6 mm*3.5 m); Column Temperature: 40° C.; Flow Rate: 2.0 mL/min; Mobile Phase: from 95% [water+10 mM NH₄HCO₃] and 5% [CH₃CN] to 0% [water+10 mM NH₄HCO₃] and 100% [CH₃CN] in 3.0 min, then under this condition for 1.0 min, finally changed to 95% [water+10 mM NH₄HCO₃] and 5% [CH₃CN] in 0.1 min and under this condition for 0.7 min. Purity is 14.0%, Rt=2.604 min; MS Calcd.: 1091.5; MS Found: 547.0 [M/2+H]⁺.

Agilent HPLC 1200, Column: Waters X-Bridge C18 (150 mm*4.6 mm*3.5 m); Column Temperature: 40° C.; Flow Rate: 1.0 mL/min; Mobile Phase: from 95% [water+10 mM NH₄HCO₃] and 5% [CH₃CN] to 0% [water+10 mM NH₄HCO₃] and 100% [CH₃CN] in 10 min, then under this condition for 5 min, finally changed to 95% [water+10 mM NH₄HCO₃] and 5% [CH₃CN] in 0.1 min and under this condition for 5 min; Purity is 94.4%, Rt=9.055 min.

¹H NMR (400 MHz, DMSO-d₆) δ 0.68-0.73 (3H, m), 0.81-0.84 (3H, m), 0.95-0.98 (4H, m), 1.34-1.38 (3H, m), 1.51-1.53 (2H, m), 1.64-1.67 (2H, m), 1.75-1.79 (1H, m), 2.10 (3H, s), 2.20 (3H, s), 2.24 (3H, s), 2.45 (3H, s), 3.08-3.11 (2H, m), 3.22-3.27 (3H, m), 3.65-3.73 (2H, m), 3.80-3.83 (5H, m), 4.23-4.25 (2H, m), 4.28-4.29 (2H, m), 4.33-4.38 (2H, m), 4.44-4.50 (2H, m), 4.56 (2H, s), 4.67-4.70 (1H, m), 4.90-4.94 (1H, m), 5.08-5.09 (1H, m), 5.85 (1H, s), 7.20-7.22 (3H, m), 7.35-7.37 (2H, m), 7.40-7.46 (5H, m), 7.51-7.53 (2H, m), 7.60-7.62 (2H, m), 8.22 (1H, t, J=4.8 Hz), 8.43 (1H, d, J=7.2 Hz), 8.99 (1H, s), 11.4 (1H, d, J=4.8 Hz).

Chemical Formula: $C_{62}H_{73}N_7O_9S$, Molecular Weight: 1092.35.

Total H count from HNMR data: 73.

Example Synthesis of Exemplary Compound 51

Step 1.
2-hydroxy-4-(4-methylthiazol-5-yl)benzonitrile

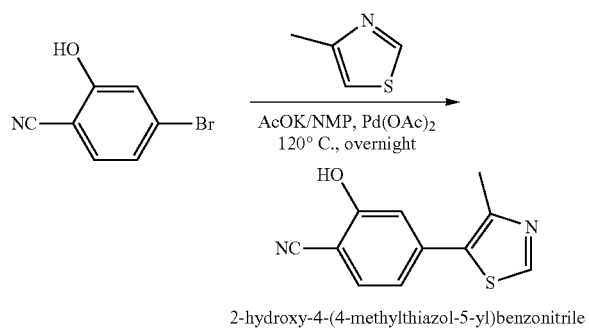

2-hydroxy-4-(4-methylthiazol-5-yl)benzonitrile

Into a 500-ml-3-necked round-bottom flash with an inert atmosphere of nitrogen, 4-bromo-2-hydroxybenzonitrile (26 g, 131.3 mmol, 1.00 equiv), DMA (300 ml), 4-methylthiazole (26, 262.6 mmol, 2.00 equiv), KOAc (26 g, 262.6 mmol, 2.00 equiv), Pd(OAc)₂ (884.3 mg, 3.94 mmol, 0.03 equiv). The resulting solution was stirred for 5 hour at 150° C. The reaction was then quenched by the addition of 1000 mL of water. The resulting mixture was washed with 3×500 mL of ethyl acetate and the organic layers combined, and the organic layers was washed with 3×500 mL of H₂O. The mixture was dried over anhydrous sodium sulfate and concentrated under vacuum. The residue was applied onto a silica gel column with ethyl acetate/petroleum ether (1:1). This resulted in 14.4 g (66.66 mmol, 50.77%) of 2-hydroxy-4-(4-methylthiazol-5-yl) benzonitrile as a yellow solid.

¹HNMR (400 MHz, DMSO-d6): δ 2.49 (s, 3H), 7.08 (d, J=8.0 Hz, 1H), 7.13 (s, 1H), 7.71 (d, J=8.0 Hz, 1H), 9.07 (s, 1H), 11.35 (s, 1H).

Step 2.
2-(aminomethyl)-5-(4-methylthiazol-5-yl)phenol

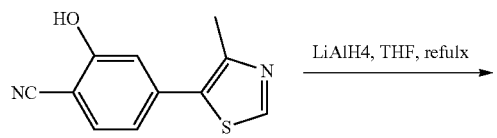

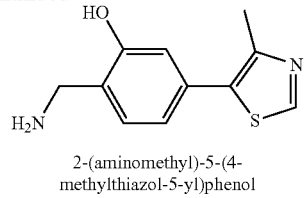

2-(aminomethyl)-5-(4-methylthiazol-5-yl)phenol

Into a 1000-ml-3-necked round-bottom flash purged and maintained with an inert atmosphere of nitrogen, was placed a solution of 2-hydroxy-4-(4-methylthiazol-5-yl) benzonitrile (14.4 g, 66.66 mmol) in THF 400 ml. This was followed by the addition of LiAlH₄ (6.34 g, 166.67 mmol, 2.50 equiv) in several batches at 0° C. The resulting mixture was filtered and the filter cake was washed with 10% MeOH in DCM for four times. The combined filtrates were concentrated to afford the crude 2-(aminomethyl)-5-(4-methylthiazol-5-yl) phenol 10.4 g (47.27 mmol, 71% yield). It was used to next step without further purification.

¹HNMR (400 MHz, DMSO-d6): δ 2.40 (s, 3H), 3.62 (br, 1H), 6.33 (d, J=6.0 Hz, 1H), 6.56 (s, 1H), 6.96 (d, J=7.6 Hz, 1H), 8.82 (s, 1H).

Step 3. (S)-3-methyl-2-(1-oxoisoindolin-2-yl)butanoic acid

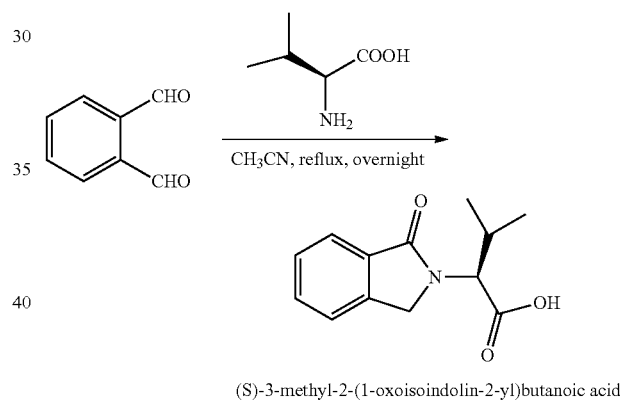

(S)-3-methyl-2-(1-oxoisoindolin-2-yl)butanoic acid (S)-2-amino-3-methylbutanoic acid (43.7 g, 373 mmol) was added to a solution of phthalaldehyde (50 g, 373 mmol) in acetonitrile (1000 mL). The resulting mixture was refluxed for overnight. The reaction mixture was cooled to room temperature then filtered and dried to afford (S)-3-methyl-2-(1-oxoisoindolin-2-yl)butanoic acid (72 g, 83%).

Step 4, methyl (2S,4R)-4-hydroxy-1-((S)-3-methyl-2-(1-oxoisoindolin-2-yl)butanoyl)pyrrolidine-2-carboxylate

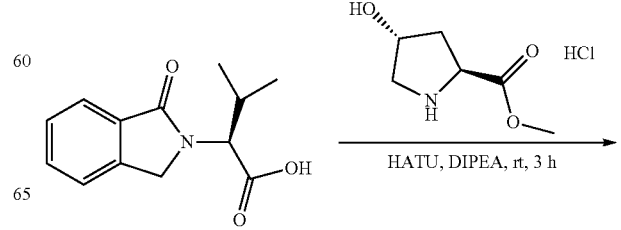

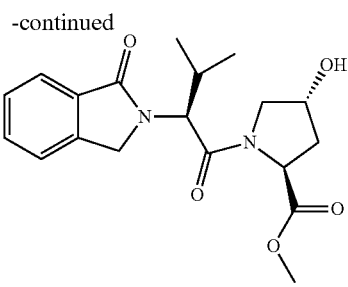

methyl (2S,4R)-4-hydroxy-1-((S)-3-methyl-2-(1-oxoisoindolin-2-yl)butanoyl)pyrrolidine-2-carboxylate A solution of (S)-3-methyl-2-(1-oxoisoindolin-2-yl) butanoic acid (5 g, 21.44 mmol), (2S,4R)-methyl 4-hydroxy-pyrrolidine-2-carboxylate, HCl (4.67 g, 25.7 mmol) DIPEA (8.98 ml, 51.4 mmol) in DMF (Volume: 30 ml) was added HATU (9.78 g, 25.7 mmol) at 0° C., The resulting mixture was stirred at room temperature for 2 hours. The mixture was partitioned between EtOAc and water. The organic phase was washed with water, brine and dried over anhydrous Na$_2$SO$_4$. The residue was purified with column chromatography to afford methyl (2S,4R)-4-hydroxy-1-((S)-3-methyl-2-(1-oxoisoindolin-2-yl)butanoyl)pyrrolidine-2-carboxylate (5.41 g, 70%).

$^1$HNMR (400 MHz, CDCl$_3$): δ 0.84 (d, J=5.6 Hz, 3H), 1.09 (d, J=5.2 Hz, 3H), 2.00 (m, 1H), 2.31-2.41 (m, 2H), 3.76 (s, 3H), 3.84 (d, J=11.2 Hz, 1H), 4.30-4.38 (m, 2H), 4.56-4.71 (m, 3H), 4.78 (m, 1H), 7.27-7.42 (m, 3H), 7.69 (d, J=7.2 Hz, 1H).

Step 5. (2S,4R)-4-hydroxy-1-((S)-3-methyl-2-(1-oxoisoindolin-2-yl)butanoyl)pyrrolidine-2-carboxylic acid

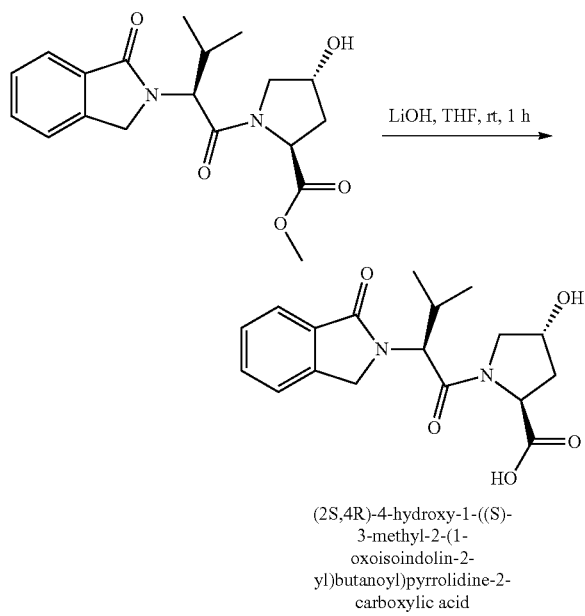

(2S,4R)-4-hydroxy-1-((S)-3-methyl-2-(1-oxoisoindolin-2-yl)butanoyl)pyrrolidine-2-carboxylic acid A solution of (2S,4R)-methyl 4-hydroxy-1-((S)-3-methyl-2-(1-oxoisoindolin-2-yl) butanoyl) pyrrolidine-2-carboxylate (5 g, 13.87 mmol) in Water (Volume: 50 ml), THF (Volume: 100 ml), was added lithium hydroxide, H$_2$O (1.164 g, 27.7 mmol), at 0° C. The reaction was stirred at room temperature for 2 hours. The reaction mixture was acidified with 1N HCl to pH 1-2, and extracted with EtOAc. The combined organic layer was washed with brine, dried over Na$_2$SO$_4$ and concentrated to afford (2S,4R)-4-hydroxy-1-((S)-3-methyl-2-(1-oxoisoindolin-2-yl)butanoyl)pyrrolidine-2-carboxylic acid (4.42 g, 92%).

$^1$HNMR (400 MHz, CDCl$_3$): δ 0.87 (d, J=6.4 Hz, 3H), 1.05 (d, J=5.6 Hz, 3H), 2.21 (m, 1H), 2.31 (m, 1H), 2.43 (m, 1H), 3.80 (d, J=6.4 Hz, 1H), 4.37-4.44 (m, 2H), 4.55 (s, 1H), 4.64 (t, J=8.0 Hz, 7.6 Hz, 1H), 4.73 (d, J=17.6 Hz, 1H), 4.83 (d, J=10.8 Hz, 1H), 7.38-7.42 (m, 2H), 7.49 (d, J=7.2 Hz, 1H), 7.74 (d, J=7.6 Hz, 1H).

Step 6. (2S,4R)-4-hydroxy-N-(2-hydroxy-4-(4-methylthiazol-5-yl)benzyl)-1-((S)-3-methyl-2-(1-oxoisoindolin-2-yl)butanoyl)pyrrolidine-2-carboxamide

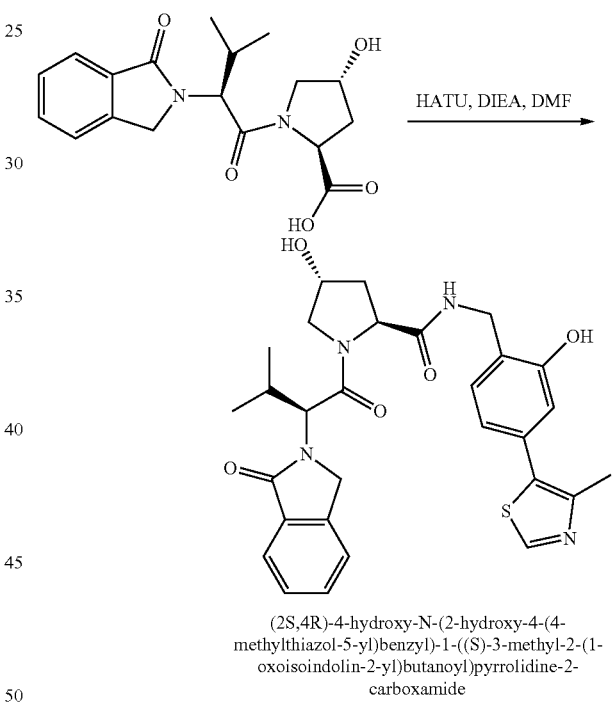

(2S,4R)-4-hydroxy-N-(2-hydroxy-4-(4-methylthiazol-5-yl)benzyl)-1-((S)-3-methyl-2-(1-oxoisoindolin-2-yl)butanoyl)pyrrolidine-2-carboxamide To a solution of (2S,4R)-4-hydroxy-1-((S)-3-methyl-2-(1-oxoisoindolin-2-yl)butanoyl)pyrrolidine-2-carboxylic acid (6.00 g, 27.27 mmol, 1.10 equiv), 2-(aminomethyl)-5-(4-methylthiazol-5-yl)phenol (8.58 g, 24.79 mmol, 1.00 equiv), EDCI (5.70 g, 29.75 mmol, 1.20 equiv), HOBT (4.02 g, 29.75 mmol, 1.20 equiv) in CH$_2$Cl$_2$ (100 mL), was added Et$_3$N (6.0 g, 10.75 mmol). The resulting solution was stirred at room temperature for 1 hour. The mixture was partitioned between CH$_2$Cl$_2$ and water. The organic phase was washed with water, brine and dried over anhydrous Na$_2$SO$_4$. The residue was purified with column chromatography to give (2S,4R)-4-hydroxy-N-(2-hydroxy-4-(4-methylthiazol-5-yl) benzyl)-1-((S)-3-methyl-2-(1-oxoisoindolin-2-yl)butanoyl) pyrrolidine-2-carboxamide (6.3 g, 11.49 mmol, 46.3% yield)

¹HNMR (400 MHz, CDCl₃): δ 0.81 (d, J=6.4 Hz, 3H), 0.86 (d, J=6.8 Hz, 3H), 1.96-2.01 (m, 1H), 2.34-2.40 (m, 1H), 2.44-2.53 (m, 4H), 3.63 (dd, J=3.6, 12.0 Hz 1H), 4.27-4.2 (m, 1H), 4.38-4.43 (m, 2H), 4.53 (s, 2H), 4.68-4.71 (m, 3H), 6.91 (d, J=8.0 Hz, 1H), 7.01 (s, 1H), 7.13 (d, J=7.6 Hz, 1H), 7.42-7.44 (m, 2H), 7.52 (d, J=7.2 Hz, 1H), 7.78 (d, J=7.2 Hz, 1H), 8.01 (s, 1H), 8.66 (s, 1H), 9.20 (br, H). LC-MS (ESI): calcd. 548.21; Found, 549.3 (M+H).

Step 7. 4-(Benzyloxy)butan-1-ol

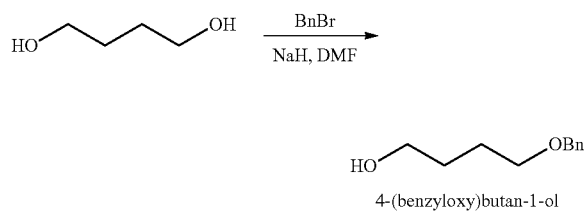

4-(benzyloxy)butan-1-ol

To a solution of 5-(benzyloxy)pentan-1-ol (50 g, 0.56 mol) in DMF (400 ml) was added NaH (17.7 g, 0.44 mol) in batches at 0° C. After stirring for 30 minutes, BnBr (66 g, 0.39 mol) was added dropwise at 0° C. The resulting suspension was stirred at 20° C. for 30 minutes. Then it was heated to 50° C. for another 2 hours. The reaction was quenched with water (500 mL) and extracted with of EA (1 L). The organic phase was washed with brine. The combined organic layers were dried over anhydrous Na₂SO₄. The solvent was removed under vacuum to afford crude desired product 4-(benzyloxy)butan-1-ol (60 g crude, 100% yield), which was used in next step directly.

¹H NMR: (400 MHz, DMSO): δ 7.28-7.35 (m, 5H), 4.46 (s, 2H), 4.21 (t, J=6.8 Hz, 2H), 3.46 (t, J=6.8 Hz, 2H), 3.15 (s, 3H), 1.61-1.76 (m, 4H).

Chemical Formula: C₁₁H₁₆O₂; Molecular Weight: 180.24
Total H count from ¹HNMR data: 18

Step 8. 3-(4-(Benzyloxy)butoxy)propan-1-ol

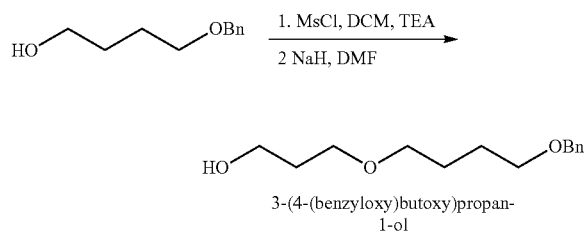

3-(4-(benzyloxy)butoxy)propan-1-ol

To a solution of 4-(benzyloxy)butan-1-ol (12 g, 66.6 mmol) and TEA (20 g, 199.9 mmol) in DCM (120 mL) was added MsCl (11.5 g, 100 mmol) dropwise at 0° C. The resulting solution was stirred at 20° C. for 30 minutes. The reaction was quenched with water and was washed with brine. The organic phase was dried over anhydrous sodium sulfate. The solvent was removed under vacuum to afford crude desired product (15 g crude), which was used in next step directly.

To a solution of above crude desired product (15 g, 58.1 mmol) in THF (150 ml) were added propane-1,3-diol (11 g, 145 mmol) and NaH (3.72 g, 93 mmol) at 0° C. The resulting solution was heated to 80° C. for 16 hours. The reaction was quenched with water and extracted with EA (200 mL). The organic phase was washed with brine. The combined organic layers were dried over anhydrous sodium sulfate and concentrated to afford crude desired product 3-(4-(Benzyloxy)butoxy)propan-1-ol (17 g crude, 100% yield in two steps), which was used in next step directly.

¹H NMR: (400 MHz, DMSO): δ 7.27-7.36 (m, 5H), 4.44 (s, 2H), 4.23 (t, J=6.4 Hz, 2H), 3.38 (m, 7H), 3.15 (s, 3H), 1.89 (m, 2H), 1.56 (m, 4H).

Chemical Formula: C₁₄H₂₂O₃; Molecular Weight: 238.32.

Total H count from ¹HNMR data: 25.

Step 9. 2-(4-(3-(4-(Benzyloxy)butoxy)propoxy)phenyl)-4,4,5,5-tetramethyl-1,3,2-dioxaborolane

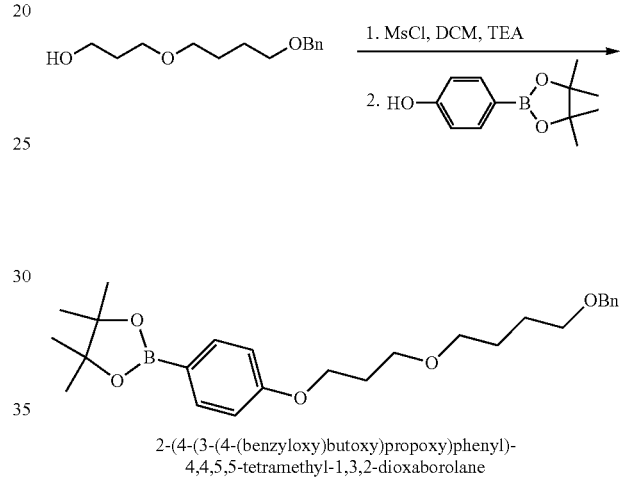

2-(4-(3-(4-(benzyloxy)butoxy)propoxy)phenyl)-4,4,5,5-tetramethyl-1,3,2-dioxaborolane To a solution of 3-(4-(Benzyloxy)butoxy)propan-1-ol (1 g, 4.2 mmol) and TEA (848 mg, 8.4 mmol) in DCM (20 mL) was added MsCl (722 mg, 6.3 mmol) dropwise at 0° C. The resulting solution was stirred at 20° C. for 30 minutes. The reaction was quenched with water and washed with brine. The organic layer was dried over anhydrous sodium sulfate. The solvent was removed under vacuum to afford crude desired product (1.2 g crude), which was used in next step directly. To a solution of above crude desired product (600 mg, 1.90 mmol) in dry DMF (6 ml) were added Cs₂CO₃ (1.24 g, 3.79 mmol) and 4-(4,4,5,5-tetramethyl-1,3, 2-dioxaborolan-2-yl)phenol (420 mg, 1.90 mmol) subsequently. The resulting solution was heated to 80° C. for 2 hours. The reaction was diluted with EA (30 mL) and washed with brine. The organic phase was dried over anhydrous sodium sulfate and concentrated under vacuum. The residue was purified with a column to afford 2-(4-(3-(4-(Benzyloxy)butoxy)propoxy)phenyl)-4,4,5,5-tetramethyl-1,3,2-dioxaborolane (EA:PE=1:10) (500 mg, 54% yield in two steps).

¹H NMR: (400 MHz, CDCl₃): δ 7.73 (d, J=8.4 Hz, 2H), 7.32 (m, 5H), 6.88 (d, J=8.8 Hz, 2H), 4.49 (s, 2H), 4.08 (t, J=6.4 Hz, 2H), 3.57 (t, J=6.0 Hz, 2H), 3.47 (m, 4H), 2.03 (m, 2H), 1.67 (m, 4H), 1.33 (s, 12H).

Chemical Formula: C₂₆H₃₇BO₅; Molecular Weight: 440.38.

Total H count from ¹HNMR data: 37.

Step 10. 4-(3-(4-(4,4,5,5-tetramethyl-1,3,2-dioxaborolan-2-yl)phenoxy)propoxy)butan-1-ol

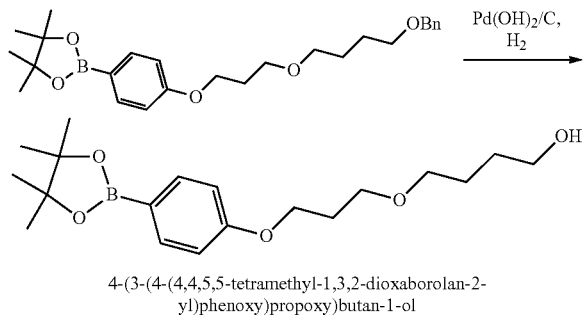

4-(3-(4-(4,4,5,5-tetramethyl-1,3,2-dioxaborolan-2-yl)phenoxy)propoxy)butan-1-ol

To a solution of 2-(4-(3-(4-(Benzyloxy)butoxy)propoxy)phenyl)-4,4,5,5-tetramethyl-1,3,2-dioxaborolane (500 mg, 1.14 mmol) in MeOH (30 mL) was added Pd(OH)$_2$/C (250 mg). The resulting mixture was stirred at 20° C. for 2 hours under H$_2$ at 1 atm. The mixture was filtered through a Celite pad, and the filtrate was concentrated to afford 4-(3-(4-(4,4,5,5-tetramethyl-1,3,2-dioxaborolan-2-yl)phenoxy)propoxy)butan-1-ol (340 mg, 85% yield), which was used in next step directly.

Step 11. (2S,4R)-4-Hydroxy-1-((S)-3-methyl-2-(1-oxoisoindolin-2-yl)butanoyl)-N-(4-(4-methylthiazol-5-yl)-2-(4-(3-(4-(4,4,5,5-tetramethyl-1,3,2-dioxaborolan-2-yl)phenoxy)propoxy)butoxy)benzyl)pyrrolidine-2-carboxamide

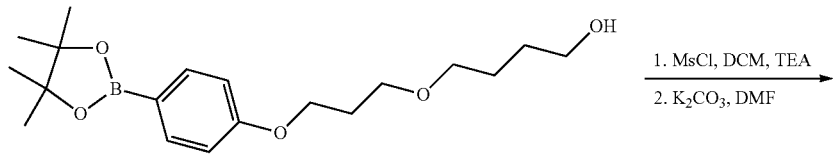

To a solution of 4-(3-(4-(4,4,5,5-tetramethyl-1,3,2-dioxaborolan-2-yl)phenoxy)butan-1-ol (170 mg, 0.51 mmol) and TEA (155 mg, 1.53 mmol) in DCM (10 mL) was added MsCl (117 mg, 1.02 mmol) dropwise at 0° C. The resulting solution was stirred at 20° C. for 30 minutes. The reaction was quenched with water and washed with brine. The organic layer was dried over anhydrous sodium sulfate. The solvent was removed under vacuum to afford crude desired product (260 mg crude, 100% yield), which was used in next step directly.

To a solution of above crude desired product (260 mg, 0.61 mmol) in dry DMF (4 ml), was added K$_2$CO$_3$ (168 mg, 1.21 mmol) and (2S,4R)-4-hydroxy-N-(2-hydroxy-4-(4-methylthiazol-5-yl)benzyl)-1-((S)-3-methyl-2-(1-oxoisoindolin-2-yl)butanoyl)pyrrolidine-2-carboxamide (332 mg, 0.61 mmol) subsequently. The resulting solution was stirred at 70° C. overnight. The reaction was diluted EA with (30 mL) and washed with brine. The organic phase was dried over anhydrous sodium sulfate and concentrated under vacuum. The residue was purified by TLC to afford (2S, 4R)-4-Hydroxy-1-((S)-3-methyl-2-(1-oxoisoindolin-2-yl)butanoyl)-N-(4-(4-methylthiazol-5-yl)-2-(4-(3-(4-(4,4,5,5-tetramethyl-1,3,2-dioxaborolan-2-yl)phenoxy)propoxy)butoxy)benzyl)pyrrolidine-2-carboxamide (DCM:MeOH=20:1) (90 mg, yield=21%).

$^1$HNMR: (400 MHz, DMSO): δ 8.98 (s, 1H), 8.35 (m, 1H), 7.71 (d, J=7.2 Hz, 2H), 7.58 (m, 4H), 7.48 (m, 1H), 7.32 (d, J=7.2 Hz, 1H), 7.00 (m, 2H), 6.91 (d, J=8.4 Hz, 2H), 5.07 (d, J=4.0 Hz, 1H), 4.71 (m, 1H), 4.15-4.60 (m, 6H), 4.05 (m, 8H), 3.60-3.80 (m, 2H), 3.40-3.55 (m, 4H), 2.46 (s, 3H), 2.35 (m, 1H), 1.65-2.10 (m, 9H), 1.26 (s, 12H), 1.07 (s, 2H), 0.96 (d, J=6.4 Hz, 3H), 0.72 (d, J=6.4 Hz, 3H).

Chemical Formula: C$_{48}$H$_{61}$BN$_4$O$_9$S; Molecular Weight: 880.90.

Total H count from $^1$HNMR data: 69.

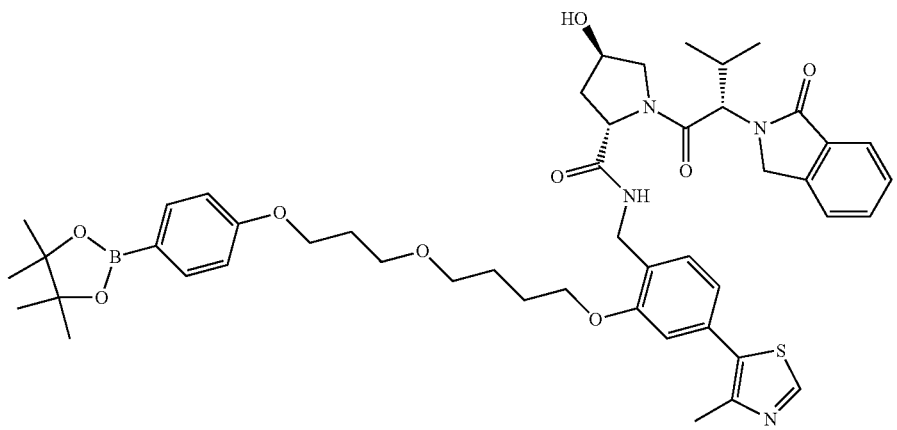

(2S,4R)-4-hydroxy-1-((S)-3-methyl-2-(1-oxoisoindolin-2-yl)butanoyl)-N-(4-(4-methylthiazol-5-yl)-2-(4-(3-(4-(4,4,5,5-tetramethyl-1,3,2-dioxaborolan-2-yl)phenoxy)propoxy)butoxy)benzyl)pyrrolidine-2-carboxamide

Step 12. 5-Bromo-2-methyl-3-nitrobenzoic acid

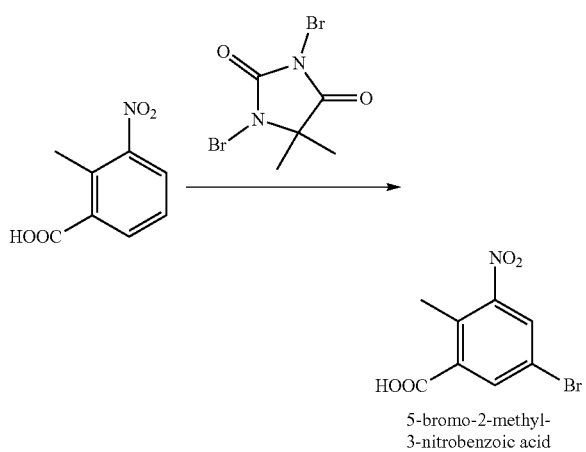

To stirred solution of 2-methyl-3-nitrobenzoic acid (10 g, 55 mmol) in conc. $H_2SO_4$ (40 mL), 1,3-dibromo-5,5-dimethyl-2,4-imidazolidinedione (9 g, 32 mmol) was added portion wise at room temperature and reaction was stirred at room temperature for 5 hours. Then the reaction mass was poured on an ice cold water. Solid was filtered, and the resulting residue was washed with water and dried under vacuum to afford 5-Bromo-2-methyl-3-nitrobenzoic acid (12 g, 84%) as a light yellow solid.

$^1$H NMR: (400 MHz, DMSO-$d_6$): δ 8.28 (d, J=2.0 Hz, 1H), 8.13 (d, J=2.0 Hz, 1H), 2.51 (s, 3H).

Chemical Formula: C8H6BrNO4; Molecular Weight: 260.04.

Total H count from $^1$HNMR data: 5.

Step 13. Methyl 5-bromo-2-methyl-3-nitrobenzoate

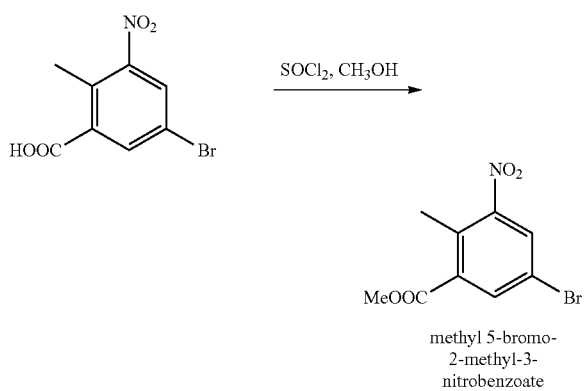

A mixture of 5-bromo-2-methyl-3-nitrobenzoic acid (12 g, 41 mmol) in $SOCl_2$/MeOH (v:v=1:10) (250 mL) was heated to reflux overnight. The reaction mixture was cooled and concentrated. The residue was dissolved in 300 mL of EA. The organic layer was washed sequentially with sat. aq. $NaHCO_3$ and brine, dried over $Na_2SO_4$, and concentrated. The residue was purified by chromatography (silica gel, PE:EA (20:1, v:v)) to afford Methyl 5-bromo-2-methyl-3-nitrobenzoate (11 g, yield: 87%).

$^1$H NMR: (400 MHz, CDCl$_3$): δ 8.12 (d, J=2.0 Hz, 1H), 7.97 (d, J=2.0 Hz, 1H), 3.95 (s, 3H), 2.57 (s, 3H).

Chemical Formula: C9H8BrNO4; Molecular Weight: 272.96.

Total H count from $^1$HNMR data: 8.

Step 14. Methyl 3-amino-5-bromo-2-methylbenzoate

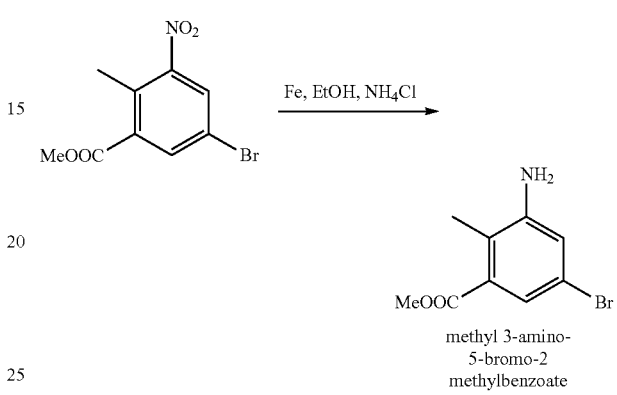

methyl 3-amino-5-bromo-2 methylbenzoate

To a stirred solution of methyl 3-bromo-5-nitrobenzoate (11 g, 40 mmol) in ethanol (100 mL), was added NH$_4$Cl solution (13 g in 50 mL water, 240 mmol) followed by Fe powder (20 g, 360 mmol). The resulting reaction was stirred at 80° C. for 2-3 hours. Then the reaction mixture was filtered and the filtrate was concentrated till dryness to give a solid which was dissolved in sat. sodium bicarbonate solution. Aqueous layer was extracted with ethyl acetate (3×100 mL). The combined organic layers were dried over sodium sulfate and concentrated to afford the desired compound methyl 3-amino-5-bromo-2-methylbenzoate (8.1 g, 83%).

$^1$H NMR: (400 MHz, CDCl$_3$): δ 7.33 (s, 1H), 6.94 (s, 1H), 3.87 (s, 3H), 3.79 (br, 2H), 2.28 (s, 3H).

Chemical Formula: C9H10BrNO2; Molecular Weight: 242.99.

Total H count from $^1$HNMR data: 10.

Step 15. Methyl 5-bromo-2-methyl-3-((tetrahydro-2H-pyran-4-yl) amino) benzoate

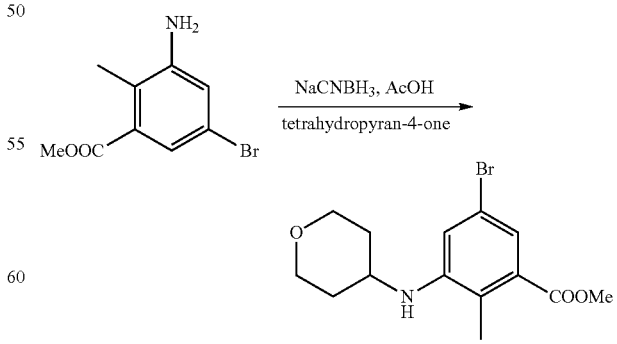

methyl 5-bromo-2-methyl-3-((tetrahydro-2H-pyran-4-yl) amino)benzoate

To a solution of methyl 3-amino-5-bromo-2-methylbenzoate (2 g, 8.2 mmol) in DCM (20 mL), and acetic acid (2.5 g, 40 mol) was added dihydro-2H-pyran-4(3H)-one (1.2 g, mol 12 mmol) at 25° C. After 2.5 h, NaCNBH₃ was added into the reaction in portions and the mixture was stirred overnight. The reaction was quenched with a solution of sodium hydroxide (1.6 g, 40 mmol) in water (50 mL). After stirring for 10 minutes at ambient temperature, the organic layer was washed with water (2×50 mL), dried (Na₂SO₄) and concentrated. The crude product was purified by silica gel chromatography eluting with 5-20% ethyl acetate in petroleum to afford Methyl 5-bromo-2-methyl-3-((tetrahydro-2H-pyran-4-yl) amino) benzoate (1.3 g, 50%) as a light yellow oil.

¹H NMR: (400 MHz, DMSO-d₆): δ 6.97 (s, 1H), 6.93 (s, 1H), 4.99 (d, J=8.0 Hz, 1H), 3.87 (d, d, J=10.80 Hz, 2H), 3.80 (s, 3H), 3.60 (br, 1H), 3.44 (t, J=11.6 Hz, 3H), 2.15 (s, 3H), 1.84 (d, J=12.4 Hz, 2H), 1348-1.57 (m, 2H).

Chemical Formula: C14H18BrNO3; Molecular Weight: 328.2.

Total H count from ¹HNMR data: 18.

Step 16. Methyl 5-bromo-3-[ethyl(oxan-4-yl)amino]-2-methylbenzoate

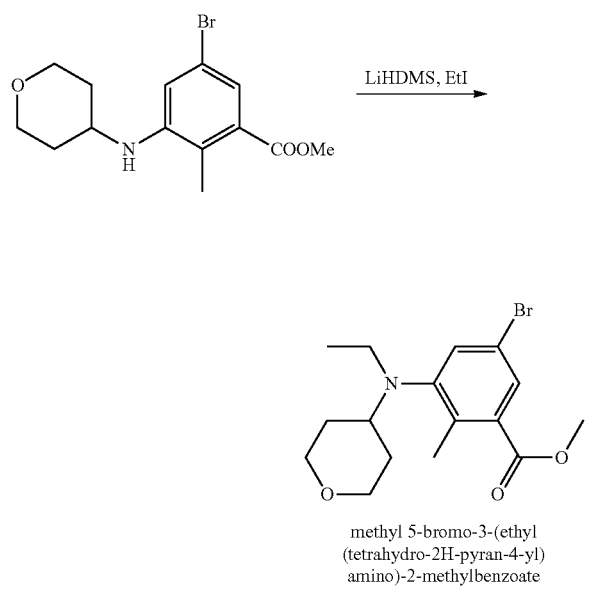

methyl 5-bromo-3-(ethyl(tetrahydro-2H-pyran-4-yl)amino)-2-methylbenzoate

To a stirred solution of methyl 5-bromo-2-methyl-3-[(oxan-4-yl)amino]benzoate (1 g, 119 mmol) in THF (20 mL) was added LiHDMS (1.0 M, 2.0 eq, THF) at 0° C. After 30 minutes, EtI (4.0 eq) was added into the mixture at 0° C. Then reaction mixture was stirred at room temperature for 3 hours. Saturated NaHCO₃ was added and the mixture was separated. The aqueous layer was extracted with CH₂Cl₂ and the combined organic layers were concentrated in vacuo to afford methyl 5-bromo-3-[ethyl(oxan-4-yl)amino]-2-methylbenzoate (1.2 g crude) which was used into next step without further purification.

Chemical Formula: C16H22BrNO3; Molecular Weight: 356.25.

Step 17. 5-Bromo-3-(ethyl(tetrahydro-2H-pyran-4-yl)amino)-2-methylbenzoic acid

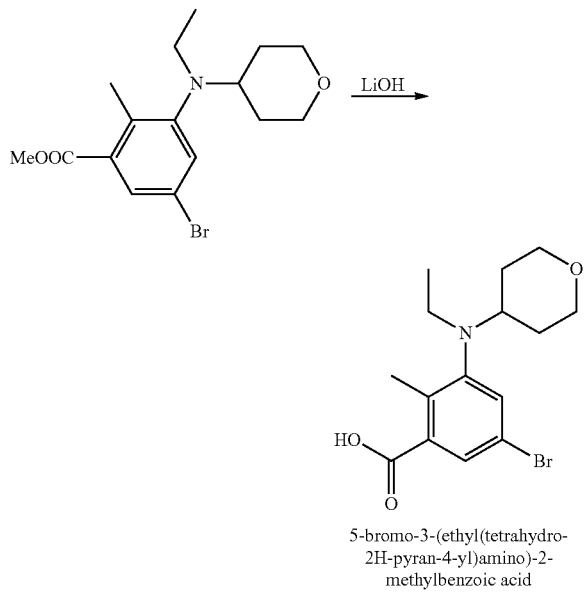

5-bromo-3-(ethyl(tetrahydro-2H-pyran-4-yl)amino)-2-methylbenzoic acid

To a stirred solution of 5-bromo-3-(ethyl(tetrahydro-2H-pyran-4-yl)amino)-2-methylbenzoate (1.2 g, crude) in ethanol (15 mL) was added LiOH (0.3 g, 10 mmol) and the resulting mixture was stirred at 60° C. for 1 hours. Upon the completion of the reaction as determined by TLC, the solvent was removed under reduced pressure and the residue was acidified with 1N HCl until pH-5, and it was concentrated. The crude product was purified by silica gel chromatography eluting with 5-10% (CH₃OH/DCM) to afford 5-Bromo-3-(ethyl(tetrahydro-2H-pyran-4-yl)amino)-2-methylbenzoic acid (0.7 g, 70%) as a light yellow oil.

¹H NMR: (400 MHz, CDCl₃): δ 7.88 (s, 1H), 7.42 (s, 1H), 3.98 (d, J=11.2 Hz, 2H), 3.34 (t, J=11.2 Hz, 2H), 3.03-3.09 (m, 2H), 2.95-3.00 (m, 1H), 2.52 (s, 3H), 1.64-1.73 (m, 4H), 0.88 (t, J=6.8 Hz, 3H).

Chemical Formula: C15H20BrNO3; Molecular Weight: 342.23.

Total H count from ¹HNMR data: 19.

Step 18. 5-Bromo-N-((4,6-dimethyl-2-oxo-1,2-dihydropyridin-3-yl)methyl)-3-(ethyl(tetrahydro-2H-pyran-4-yl)amino)-2-methylbenzamide

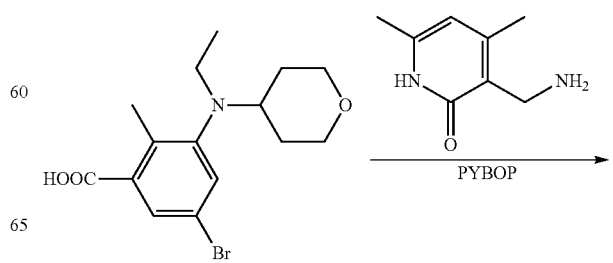

-continued

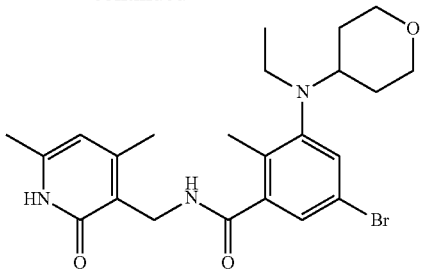

5-bromo-N-((4,6-dimethyl-2-oxo-1,2-dihydropyridin-3-yl)methyl)-3-(ethyl(tetrahydro-2H-pyran-4-yl)amino)-2-methylbenzamide 5-Bromo-3-(ethyl(tetrahydro-2H-pyran-4-yl)amino)-2-methylbenzoic acid (0.5 g, 1.5 mmol) was dissolved in DMF (5 mL), and 3-(amino methyl)-4,6-dimethylpyridin-2(1H)-one (0.45 g, 2.9 mmol) and DIEA (0.84 g, 5.8 mmol) were added. The reaction mixture was stirred at room temperature for 15 minutes, and then PYBOP (1.6 g, 3.0 mmol) was added. The mixture was stirred at room temperature for 3 hours. Upon the completion of the reaction as determined by TLC, the reaction mixture was poured onto an ice-cold water (150 mL). The mixture was stirred for another 10 minutes and the solid was collected by filtration. The solid was washed with water (50 mL) and dried by air. Then the solid was slurried in 5% MeOH in DCM solution to afford desired product 5-Bromo-N-((4,6-dimethyl-2-oxo-1,2-dihydropyridin-3-yl)methyl)-3-(ethyl(tetrahydro-2H-pyran-4-yl)amino)-2-methylbenzamide as a solid (200 mg, 30%).

$^1$H NMR: (DMSO-$d_6$, 400 MHz) δ 11.46 (s, 1H), 8.21 (s, 1H), 7.31 (s, 1H), 7.09 (s, 1H), 5.86 (s, 1H), 4.26 (d, J=4.4 Hz, 2H), 3.83 (d, J=9.60 Hz, 2H), 3.20-3.27 (m, 2H), 3.00-3.02 (m, 3H), 2.19 (s, 3H), 2.15 (s, 3H), 2.11 (s, 3H), 1.48-1.62 (m, 4H), 0.78 (t, J=6.8 Hz, 3H).

Chemical Formula: C23H30BrN3O3; Molecular Weight: 476.41.

Total H count from $^1$HNMR data: 30.

Step 19. (2S,4R)—N-(2-(4-(3-((3'-(((4,6-Dimethyl-2-oxo-1,2-dihydropyridin-3-yl)methyl)carbamoyl)-5'-(ethyl(tetrahydro-2H-pyran-4-yl)amino)-4'-methyl-[1,1'-biphenyl]-4-yl)oxy)propoxy)butoxy)-4-(4-methylthiazol-5-yl)benzyl)-4-hydroxy-1-((S)-3-methyl-2-(1-oxoisoindolin-2-yl)butanoyl)pyrrolidine-2-carboxamide

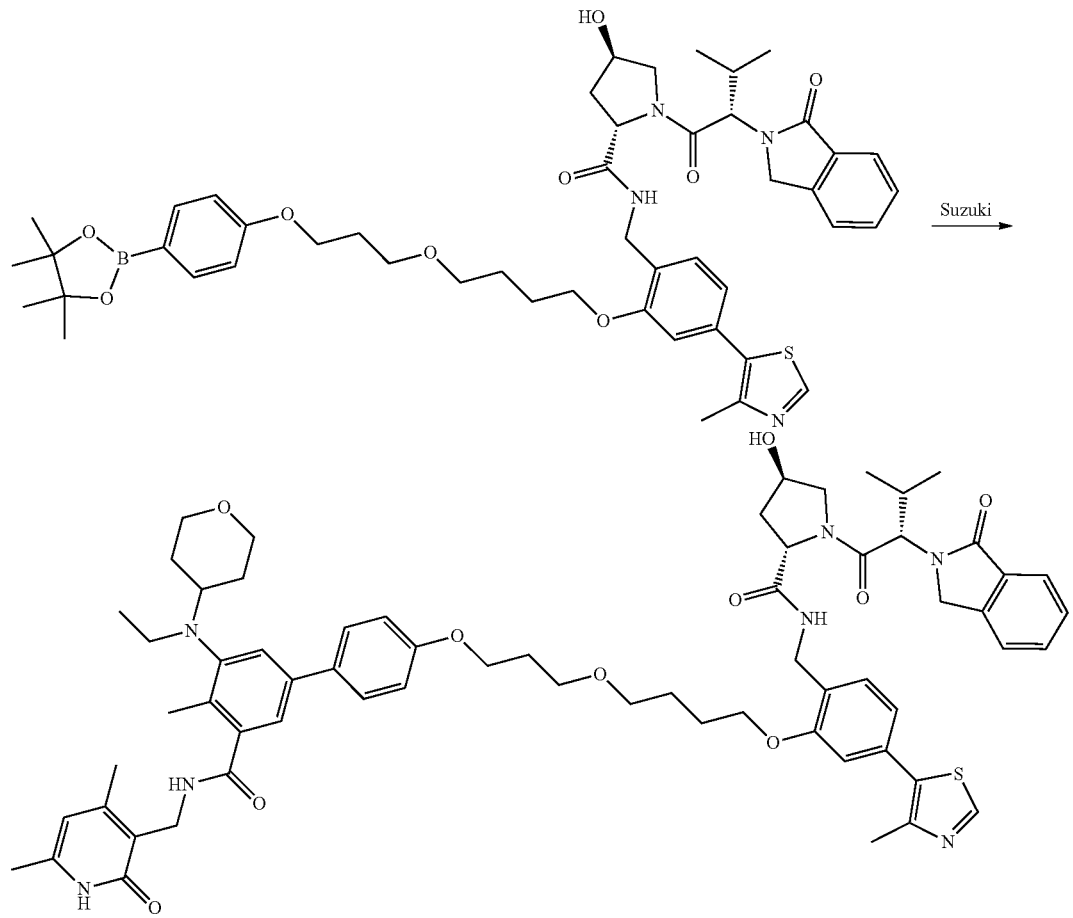

(2S,4R)-N-(2-(4-(3-((3'-(((4,6-dimethyl-2-oxo-1,2-dihydropyridin-3-yl)methyl)carbamoyl)-5'-(ethyl(tetrahydro-2H-pyran-4-yl)amino)-4'-methyl-[1,1'-biphenyl]-4-yl)oxy)propoxy)butoxy)-4-(4-methylthiazol-5-yl)benzyl)-4-hydroxy-1-((S)-3-methyl-2-(1-oxoisoindolin-2-yl)butanoyl)pyrrolidine-2-carboxamide To a solution of 5-Bromo-N-((4,6-dimethyl-2-oxo-1,2-dihydropyridin-3-yl)methyl)-3-(ethyl(tetrahydro-2H-pyran-4-yl)amino)-2-methylbenzamide (43 mg, 0.091 mmol) and (2S,4R)-4-Hydroxy-1-((S)-3-methyl-2-(1-oxoisoindolin-2-yl)butanoyl)-N-(4-(4-methylthiazol-5-yl)-2-(4-(3-(4-(4,4,5,5-tetramethyl-1,3,2-dioxaborolan-2-yl)phenoxy)propoxy)butoxy)benzyl)pyrrolidine-2-carboxamide (80 mg, 0.091 mmol) in dioxane (5 mL)/H$_2$O (0.5 mL) were added Cs$_2$CO$_3$ (74 mg, 0.227 mmol), Pd(dppf)C$_{12}$ (26 mg, 0.036 mmol) and tri-tert-butylphosphine tetrafluoroborate (21 mg, 0.073 mmol) subsequently. After stirring at 100° C. for 2 hours under nitrogen atmosphere, the reaction mixture was diluted with ethyl acetate (30 mL), and the organic layer was washed with brine (20 mL×3). The organic phase was dried over anhydrous sodium sulfate and concentrated under vacuum. The residue was purified by prep-TLC (DCM/MeOH 19/1) first and then by prep-HPLC to afford the desired product (2S,4R)—N-(2-(4-(3-((3'-(((4,6-Dimethyl-2-oxo-1,2-dihydropyridin-3-yl)methyl)carbamoyl)-5'-(ethyl(tetrahydro-2H-pyran-4-yl)amino)-4'-methyl-[1,1'-biphenyl]-4-yl)oxy)propoxy)butoxy)-4-(4-methylthiazol-5-yl)benzyl)-4-hydroxy-1-((S)-3-methyl-2-(1-oxoisoindolin-2-yl)butanoyl)pyrrolidine-2-carboxamide (34 mg, 32% yield).

$^1$H NMR: (400 MHz, MeOD): δ 8.74 (s, 1H), 7.67 (d, J=8.0 Hz, 1H), 7.28-7.55 (m, 7H), 7.15 (s, 1H), 6.82 (m, 4H), 5.98 (s, 1H), 4.30-4.53 (m, 10H), 3.97 (t, J=6.4 Hz, 4H), 3.80 (m, 4H), 3.54 (t, J=6.0 Hz, 2H), 3.47 (t, J=6.0 Hz, 2H), 3.25 (m, 1H), 3.04 (m, 6H), 2.36 (s, 3H), 2.28 (s, 3H), 2.21 (s, 3H), 2.12 (s, 3H), 1.45-2.10 (m, 16H), 0.92 (d, J=6.4 Hz, 3H), 0.78 (t, J=7.2 Hz, 3H), 0.70 (d, J=6.8 Hz, 3H).

Chemical Formula: C$_{65}$H$_{79}$N$_7$O$_{10}$S; Molecular Weight: 1150.43.

Total H count from $^1$HNMR data: 81.

LC-MS: (ES$^+$): m/z 575.9 [M+H]$^+$, t$_R$=4.00 min.

Example Synthesis of Exemplary Compound 43

Step 1. Tert-butyl 2-(2-(2-(4-(4,4,5,5-tetramethyl-1,3,2-dioxaborolan-2-yl)phenoxy)ethoxy)ethoxy)acetate

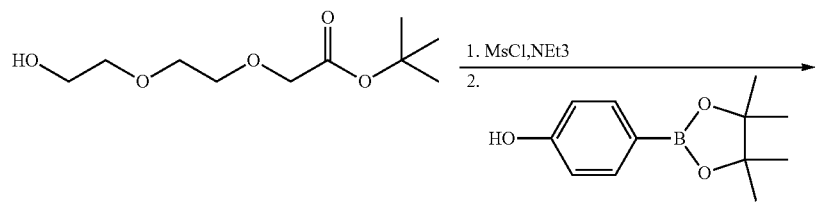

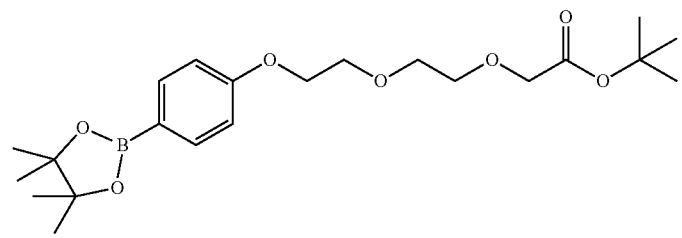

tert-butyl 2-(2-(2-(4-(4,4,5,5-tetramethyl-1,3,2-dioxaborolan-2-yl)phenoxy)ethoxy)ethoxy)acetate To a solution of tert-butyl 2-(2-(2-hydroxyethoxy)ethoxy)acetate (1.0 g, 4.54 mmol) and Et$_3$N (1.37 g, 13.6 mmol) in DCM (15 mL) were added MsCl (779.7 mg, 6.81 mmol) dropwise at 0° C. The resulting solution was stirred at 30° C. for 1 hour. The solvent was evaporated under reduced pressure. The residue was diluted with EA (30 mL), washed with brine twice. The organic phase was dried over Na$_2$SO$_4$, concentrated under reduced pressure. The residue was used for next step without further purification.

A solution of the above intermediate and 4-(4,4,5,5-tetramethyl-1,3,2-dioxaborolan-2-yl)phenol in DMF (10 mL) was added Cs$_2$CO$_3$(2.62 g, 8.04 mmol). The resulting mixture was stirred at 70° C. for 1 hour. After cooling to room temperature, the reaction was diluted with EA (30 mL), washed with brine twice. The organic phase was evaporated under reduced pressure. The residue was purified by silica gel column chromatography on silica gel (PE/EA=8/1) to afford tert-butyl 2-(2-(2-(4-(4,4,5,5-tetramethyl-1,3,2-dioxaborolan-2-yl)phenoxy)ethoxy)ethoxy)acetate (1.6 g, 78.5% yield) as a colorless oil.

Step 2. Tert-butyl 2-(2-(2-((3'-(((4,6-dimethyl-2-oxo-1,2-dihydropyridin-3-yl)methyl)carbamoyl)-5'-(ethyl(tetrahydro-2H-pyran-4-yl)amino)-4'-methyl-[1,1'-biphenyl]-4-yl)oxy)ethoxy)ethoxy)acetate To a solution of tert-butyl 2-(2-(2-(4-(4,4,5,5-tetramethyl-1,3,2-dioxaborolan-2-yl)phenoxy)ethoxy)ethoxy)acetate (400 mg, 0.92 mmol) and 5-bromo-3-(ethyl(tetrahydro-2H-pyran-4-yl)amino)-2-methyl-N-((4-methyl-2-oxo-1,2-dihydropyridin-3-yl)methyl)benzamide (432 mg, 0.92 mmol) in dioxane/H$_2$O (10 mL, 10:1) were added t-Bu$_3$PHBF$_4$(106.3 mg, 0.37 mmol), CsF (557.4 mg, 3.67 mmol), Cy2NMe (5 drops) and Pd$_2$(dba)$_3$ (167.9 mg, 0.18 mmol) subsequently. The resulting mixture was stirred at 100° C. for 2 hours under N$_2$ 1 atm. After cooling to room temperature, the reaction was diluted with EA (30 mL), and the mixture was washed with brine twice. The organic phase was evaporated under reduced pressure. The residue was purified by silica gel column chromatography on silica gel (DCM/MeOH=40/1) to afford tert-butyl-2-(2-(2-((3'-(((4,6-dimethyl-2-oxo-1,2-dihydropyridin-3-yl)methyl) carbamoyl)-5'-(ethyl(tetrahydro-2H-pyran-4-yl)amino)-4'-methyl-[1,1'-biphenyl]-4-yl)oxy)ethoxy)ethoxy)acetate (520 mg, 82.0% yield) as a colorless oil.

LC-MS: (ES$^+$): m/z 693.3 [M+H]$^+$, t$_R$=3.78 min.

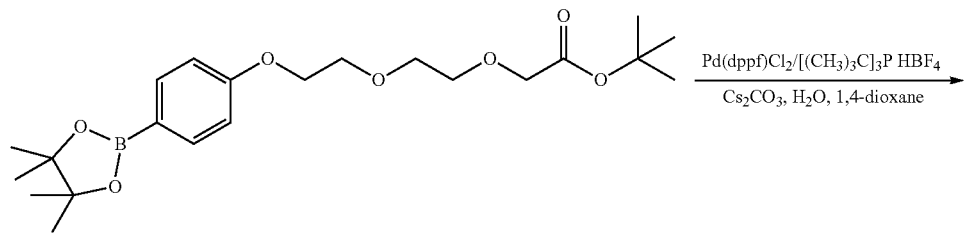

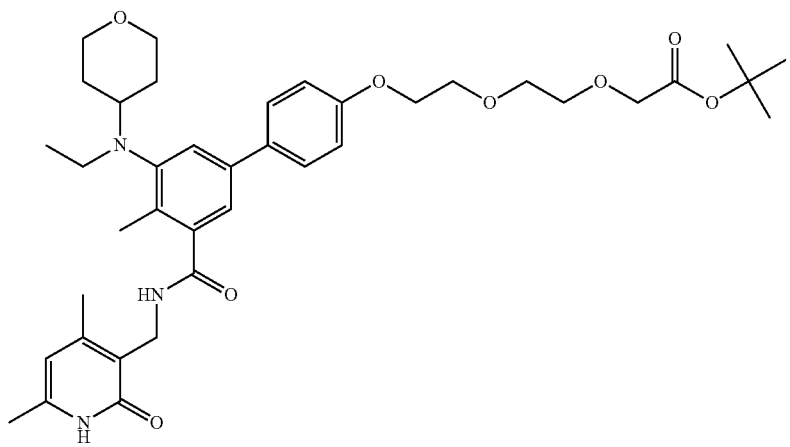

tert-butyl 2-(2-(2-((3'–(((4,6-dimethyl-2-oxo-1,2-dihydropyridin-3-yl)methyl)carbamoyl)-5'-(ethyl(tetrahydro-2H-pyran-4-yl)amino)-4'-methyl-[1,1'-biphenyl]-4-yl)oxy)ethoxy)ethoxy)acetate Step 3. 2-(2-(2-((3'-(((4,6-Dimethyl-2-oxo-1,2-dihydropyridin-3-yl)methyl)carbamoyl)-5'-(ethyl(tetrahydro-2H-pyran-4-yl)amino)-4'-methyl-[1,1'-biphenyl]-4-yl)oxy)ethoxy)ethoxy)acetic acid

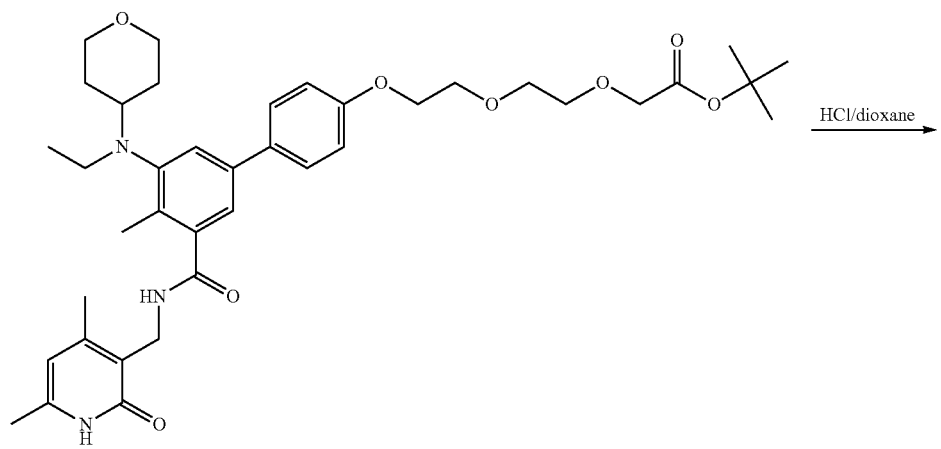

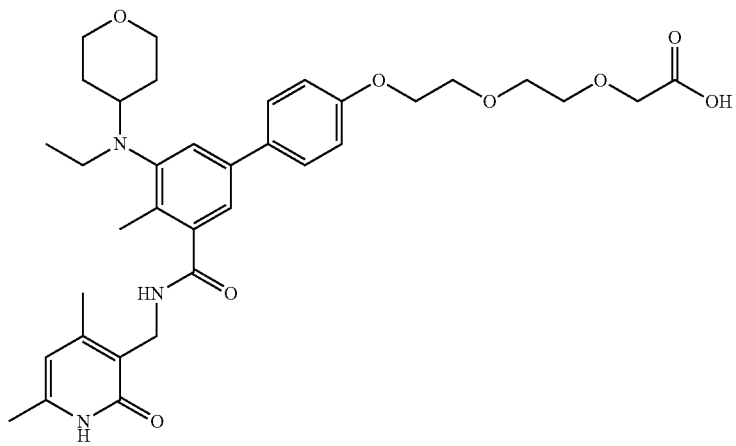

2-(2-(2-((3'-(((4,6-dimethyl-2-oxo-1,2-dihydropyridin-3-yl)methyl)carbamoyl)-5'-(ethyl(tetrahydro-2H-pyran-4-yl)amino)-4'-methyl-[1,1'-biphenyl]-4-yl)oxy)ethoxy)ethoxy)acetic acid To a solution of tert-butyl 2-(2-(2-((3'-(((4,6-dimethyl-2-oxo-1,2-dihydropyridin-3-yl)methyl)carbamoyl)-5'-(ethyl(tetrahydro-2H-pyran-4-yl)amino)-4'-methyl-[1,1'-biphenyl]-4-yl)oxy)ethoxy)ethoxy)acetate (520 mg, 0.75 mmol) in dioxane (10 mL) were HCl(g)/dioxane (6 N, 5 mL). The resulting mixture was stirred at 25° C. for 3 hours. The solvent was removed under vacuum to afford 2-(2-(2-((3'-(((4,6-dimethyl-2-oxo-1,2-dihydropyridin-3-yl)methyl)carbamoyl)-5'-(ethyl(tetrahydro-2H-pyran-4-yl)amino)-4'-methyl-[1,1'-biphenyl]-4-yl)oxy)ethoxy)ethoxy)acetic acid (400 mg. 83.6% yield) as a yellow solid.

LC-MS: (ES$^+$): m/z 636.3 [M+H]$^+$, t$_R$=3.13 min.

Step 4. 2-(2-(2-((3'-(((4,6-Dimethyl-2-oxo-1,2-dihydropyridin-3-yl)methyl)carbamoyl)-5'-(ethyl(tetrahydro-2H-pyran-4-yl)amino)-4'-methyl-[1,1'-biphenyl]-4-yl)oxy)ethoxy)ethoxy)acetic acid ¹HNMR: (400 MHz, CDCl₃) δ 10.53 (br, 2H), 8.67 (s, 1H), 7.41-7.54 (m, 4H), 7.35 (dd, J=17.5, 8.2 Hz, 4H), 7.28 (s, 1H), 7.20 (s, 1H), 6.99 (d, J=8.5 Hz, 2H), 5.90 (s, 1H), 5.01-5.12 (m, 1H), 4.75 (t, J=7.6 Hz, 1H), 4.70 (d, J=8.9 Hz, 1H), 4.62 (dd, J=14.1, 6.4 Hz, 1H), 4.51 (s, 1H), 4.39 (dd,

(2S,4R)-1-((S)-2-(2-(2-(2-((3'-(((4,6-dimethyl-2-oxo-1,2-dihydropyridin-3-yl)methyl)
carbamoyl)-5'-(ethyl(tetrahydro-2H-pyran-4-yl)amino)-4'-methyl-[1,1'-biphenyl]
-4-yl)oxy)ethoxy)ethoxy)acetamido)-3,3-dimethylbutanoyl)-4-hydroxy-N-((S)-1-
(4-(4-methylthiazol-5-yl)phenyl)ethyl)pyrrolidine-2-carboxamide To a solution of 2-(2-(2-((3'-(((4,6-dimethyl-2-oxo-1,2-dihydropyridin-3-yl)methyl) carbamoyl)-5'-(ethyl(tetrahydro-2H-pyran-4-yl)amino)-4'-methyl-[11,1'-biphenyl]-4-yl)oxy)ethoxy)ethoxy)acetic acid (400 mg, 0.60 mmol) in DMF (10 mL) were added (2S,4R)-1-((S)-2-amino-3,3-dimethylbutanoyl)-4-hydroxy-N—((S)-1-(4-(4-methyl-thiazol-5-yl)phenyl)ethyl)pyrrolidine-2-carboxamide hydrochloride (572.2 mg, 1.19 mmol), PyBOP (620.2 mg, 1.19 mmol) and DIPEA (307.4 mg, 2.38 mmol) subsequently. The resulting mixture was stirred at 25° C. for 1.5 hours. The mixture was diluted with EA (30 mL), washed with brine twice. The organic phase was evaporated under reduced pressure. The residue was purified by prep-HPLC to afford (2S,4R)-1-((S)-2-(2-(2-(2-((3'-(((4,6-dimethyl-2-oxo-1,2-dihydropyridin-3-yl)methyl)carbamoyl)-5'-(ethyl(tetrahydro-2H-pyran-4-yl)amino)-4'-methyl-[1,1'-biphenyl]-4-yl)oxy)ethoxy)ethoxy)acetamido)-3,3-dimethylbutanoyl)-4-hydroxy-N—((S)-1-(4-(4-methylthiazol-5-yl)phenyl)ethyl) pyrrolidine-2-carboxamide (100 mg, 15.8% yield) as a white solid.

J=14.3, 5.4 Hz, 1H), 4.31 (s, 1H), 4.19 (d, J=11.1 Hz, 3H), 4.10-3.98 (m, 2H), 3.97-3.83 (m, 5H), 3.75 (d, J=4.2 Hz, 2H), 3.65-3.72 (m, 2H), 3.58 (d, J=8.6 Hz, 1H), 3.31 (s, 2H), 3.08 (d, J=6.8 Hz, 2H), 3.00 (s, 1H), 2.51 (m, 4H), 2.43 (s, 3H), 2.36 (s, 3H), 2.19 (s, 3H), 1.95-2.05 (m, 1H), 1.72 (m, 2H), 1.44 (d, J=6.9 Hz, 3H), 1.07 (s, 9H), 0.87 (t, J=6.9 Hz, 3H).

Chemical Formula: $C_{58}H_{75}N_7O_{10}S$; Molecular Weight: 1062.32.

Total H count from ¹HNMR data: 75.

LC-MS: (ES⁺): m/z 1062.5 [M+H]⁺, $t_R$=3.53 min.

Protein Level Control

This description also provides methods for the control of protein levels with a cell. This is based on the use of compounds as described herein, which are known to interact with a specific target protein such that degradation of a target protein in vivo will result in the control of the amount of protein in a biological system, preferably to a particular therapeutic benefit.

The following examples are used to assist in describing the present disclosure, but should not be seen as limiting the present disclosure in any way.

Assays and Degradation Data

Protocol of the Cellular Assay of Target Protein Degradation (VCaP Cells, ELISA).

For detection Cell Signaling PathScan Sandwich ELISA Catalog #12850 Lot 11 was used. VCaP cells were cultured in ATCC DMEM+ATCC FBS and plated 40,000/well 100 µl/well in RPMI P/S with 5% CSS Omega (bovine) serum into a 96 well plate. The cells were grown for a minimum of 3 days, dosed with compounds in 0.1% DMSO (diluted with 5% CSS) and incubated with aspiration for 4 hours. 100 µl of 1× Cell Signaling lysis buffer #9803 (36 mL $dH_2O$+4 mL Cell Signaling lysis buffer) was added. The incubation was placed on cold room shaker for 10 minutes at speed 8-9. 5 µl to 100 µL of Diluent was transferred to ELISA plate (0.15 µg/mL–0.075 µg/mL) and stored at 4° C. overnight on cold room shaker speed 5 (gentle swirl) and then shaken next morning at 37° C. for 30 minutes. The preparation was washed 4×200 µl with ELISA wash buffer and aspirated with eight-channel aspirator. 100 µl/well of target protein detection antibody was added after, which the preparation was covered and shaken at 37° C. for 1 hour. 100 µl TMB was added, and the mixture was shaken for 5 min while under observation. When TMB turned light blue, 100 µl of Stop solution was added, and the mixture was shaken and read at 450 nM. Also read at 562 nm for background subtraction.

Exemplary compounds (or compounds) are shown in Table 1 below with the associated degradation data shown in Table 2 below.

TABLE 1

Exemplary compounds of the present disclosure

| Ex # | Structure | Mass Spec (M + H)+ unless otherwise noted | Name |
|---|---|---|---|
| 1 | 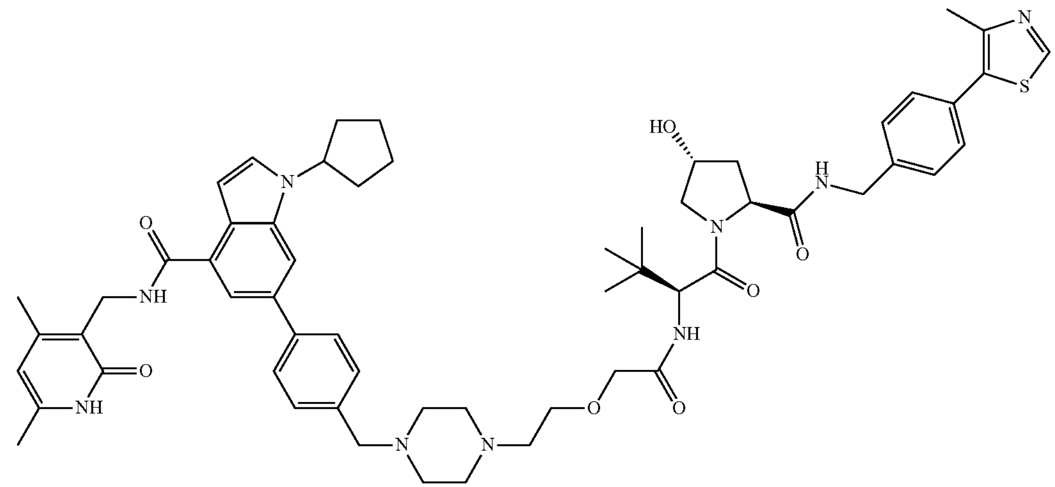 [SMILES: Cc1cc(C)c(CNC(=O)c2cc(-c3ccc(CN4CCN(CCOCC(=O)N[C@H](C(=O)N5C[C@H](O)C[C@H]5C(=O)NCc5ccc(-c6scnc6C)cc5)C(C)(C)C)CC4)cc3)cc3c2ccn3C2CCCC2)c(=O)[nH]1] | | 1-cyclopentyl-N-[(4,6-dimethyl-2-oxo-1,2-dihydropyridin-3-yl)methyl]-6-[4-({4-[2-({[(2S)-1-[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl]carbamoyl}methoxy)ethyl]piperazin-1-yl}methyl)phenyl]-1H-indole-4-carboxamide |
| 2 | 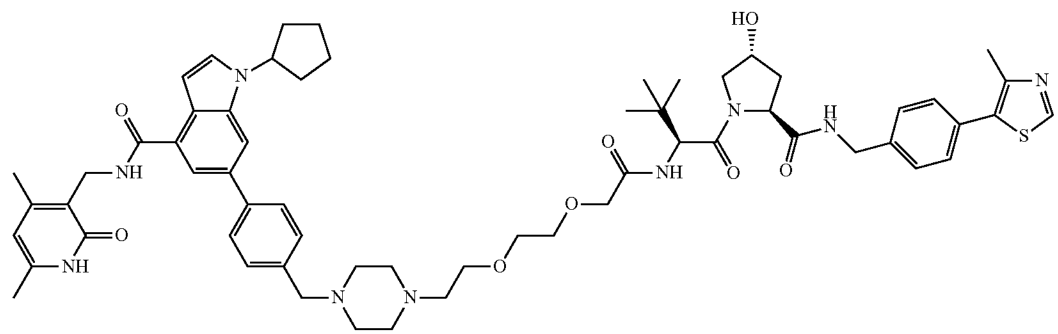 [SMILES: Cc1cc(C)c(CNC(=O)c2cc(-c3ccc(CN4CCN(CCOCCOCC(=O)N[C@H](C(=O)N5C[C@H](O)C[C@H]5C(=O)NCc5ccc(-c6scnc6C)cc5)C(C)(C)C)CC4)cc3)cc3c2ccn3C2CCCC2)c(=O)[nH]1] | 1096.55 | 1-cyclopentyl-N-[(4,6-dimethyl-2-oxo-1,2-dihydropyridin-3-yl)methyl]-6-{4-[(4-{2-[2-({[(2S)-1-[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl]carbamoyl}methoxy)ethoxy]ethyl}piperazin-1-yl)methyl]phenyl}-1H-indole-4-carboxamide |

TABLE 1-continued

Exemplary compounds of the present disclosure

| Ex # | Structure | Mass Spec (M + H)+ unless otherwise noted | Name |
|---|---|---|---|
| 3 | 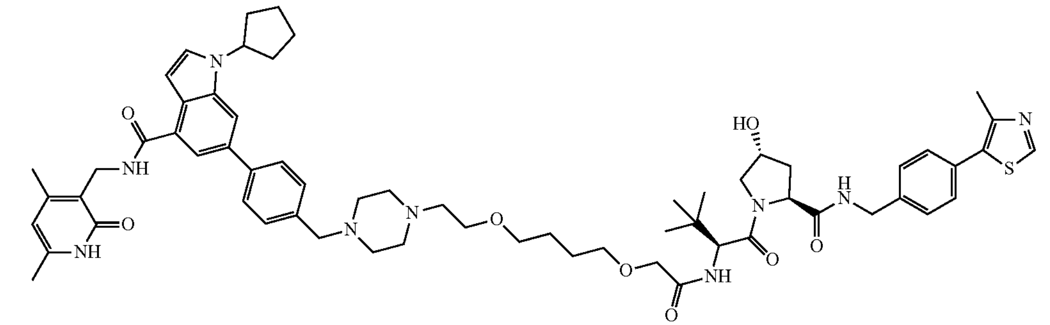 [SMILES: Cc1cc(C)c(CNC(=O)c2cc(-c3ccc(CN4CCN(CCOCCCCOCC(=O)N[C@H](C(=O)N5C[C@H](O)C[C@H]5C(=O)NCc5ccc(-c6scnc6C)cc5)C(C)(C)C)CC4)cc3)cc3c2ccn3C2CCCC2)c(=O)[nH]1] | 1124.58 | 1-cyclopentyl-N-[(4,6-dimethyl-2-oxo-1,2-dihydropyridin-3-yl)methyl]-6-{4-[(2-{4-[(2S)-1-[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl][carbamoyl]methoxy)ethyl]piperazin-1-yl]methyl]phenyl]-1H-indole-4-carboxamide |
| 4 | 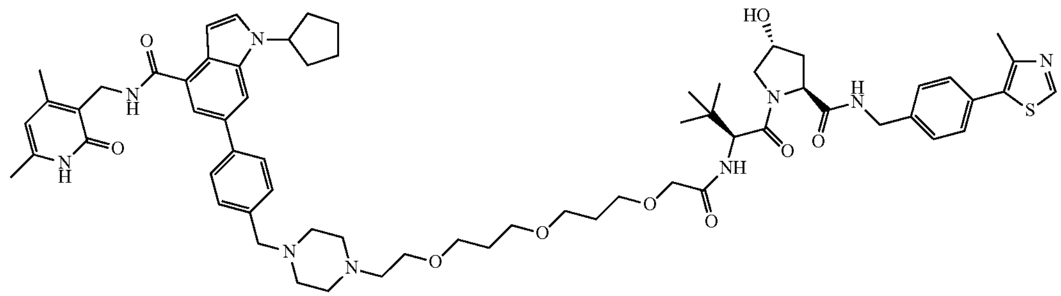 [SMILES: Cc1cc(C)c(CNC(=O)c2cc(-c3ccc(CN4CCN(CCOCCCOCCCOCC(=O)N[C@H](C(=O)N5C[C@H](O)C[C@H]5C(=O)NCc5ccc(-c6scnc6C)cc5)C(C)(C)C)CC4)cc3)cc3c2ccn3C2CCCC2)c(=O)[nH]1] | 1169.61 | 1-cyclopentyl-N-[(4,6-dimethyl-2-oxo-1,2-dihydropyridin-3-yl)methyl]-6-(4-{[4-(2-{3-[3-({[(2S)-1-[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl][carbamoyl]methoxy)propoxy]propoxy}ethyl)piperazin-1-yl]methyl}phenyl)-1H-indole-4-carboxamide |
| 5 | 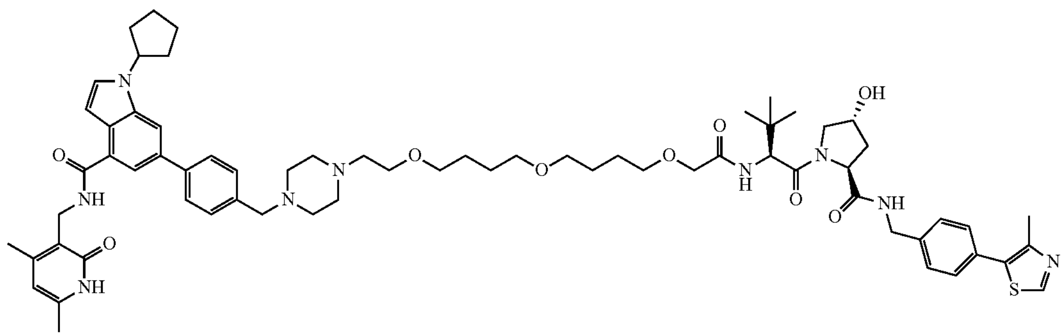 [SMILES: Cc1cc(C)c(CNC(=O)c2cc(-c3ccc(CN4CCN(CCOCCCCOCCCCOCC(=O)N[C@H](C(=O)N5C[C@H](O)C[C@H]5C(=O)NCc5ccc(-c6scnc6C)cc5)C(C)(C)C)CC4)cc3)cc3c2ccn3C2CCCC2)c(=O)[nH]1] | 1196.65 | 1-cyclopentyl-N-[(4,6-dimethyl-2-oxo-1,2-dihydropyridin-3-yl)methyl]-6-(4-{[4-(2-{4-[4-({[(2S)-1-[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl][carbamoyl]methoxy)butoxy]butoxy}ethyl)piperazin-1-yl]methyl}phenyl)-1H-indole-4-carboxamide |

TABLE 1-continued

Exemplary compounds of the present disclosure

| Ex # | Structure | Mass Spec (M + H)+ unless otherwise noted | Name |
|---|---|---|---|
| 6 | 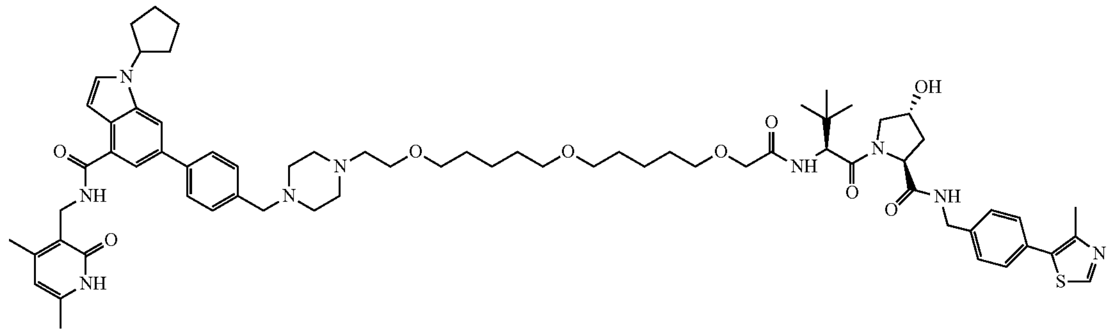 [SMILES: Cc1cc(C)c(CNC(=O)c2cc(-c3ccc(CN4CCN(CCOCCCCCOCCCCCOCC(=O)N[C@H](C(=O)N5C[C@H](O)C[C@H]5C(=O)NCc5ccc(-c6scnc6C)cc5)C(C)(C)C)CC4)cc3)cc3c2ccn3C2CCCC2)c(=O)[nH]1] | 1224.68 | 1-cyclopentyl-N-[(4,6-dimethyl-2-oxo-1,2-dihydropyridin-3-yl)methyl]-6-[4-{(4-{2-[(6-{[5-({[(2S)-1-[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl]carbamoyl}methoxy)pentyl]oxy}pentyl)oxy]ethyl}piperazin-1-yl)methyl]phenyl}-1H-indole-4-carboxamide |
| 7 | 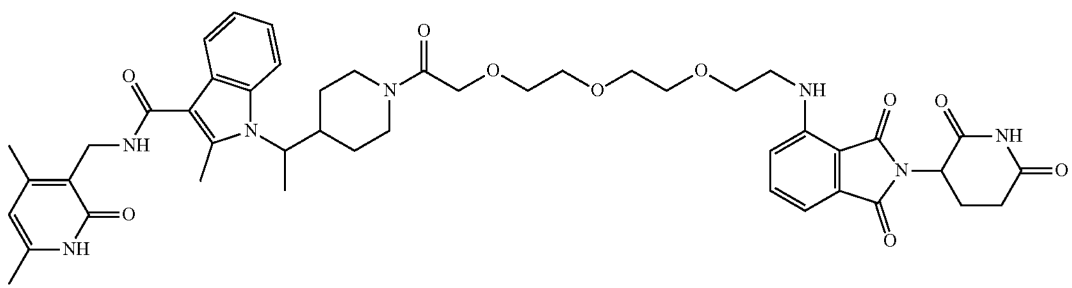 [SMILES: Cc1cc(C)c(CNC(=O)c2c(C)n(C(C)C3CCN(C(=O)COCCOCCOCCNc4cccc5c4C(=O)N(C4CCC(=O)NC4=O)C5=O)CC3)c3ccccc23)c(=O)[nH]1] | (M + Na)+ = 888.4 | N-[(4,6-dimethyl-2-oxo-1,2-dihydropyridin-3-yl)methyl]-1-[1-(1-{2-[2-(2,6-dioxopiperidin-3-yl)-1,3-dioxo-2,3-dihydro-1H-isoindol-4-yl]-4,7,10-trioxa-1-azadodecanoyl}piperidin-4-yl)ethyl]-2-methyl-1H-indole-3-carboxamide |

TABLE 1-continued

Exemplary compounds of the present disclosure

| Ex # | Structure | Mass Spec (M + H)+ unless otherwise noted | Name |
|---|---|---|---|
| 8 | 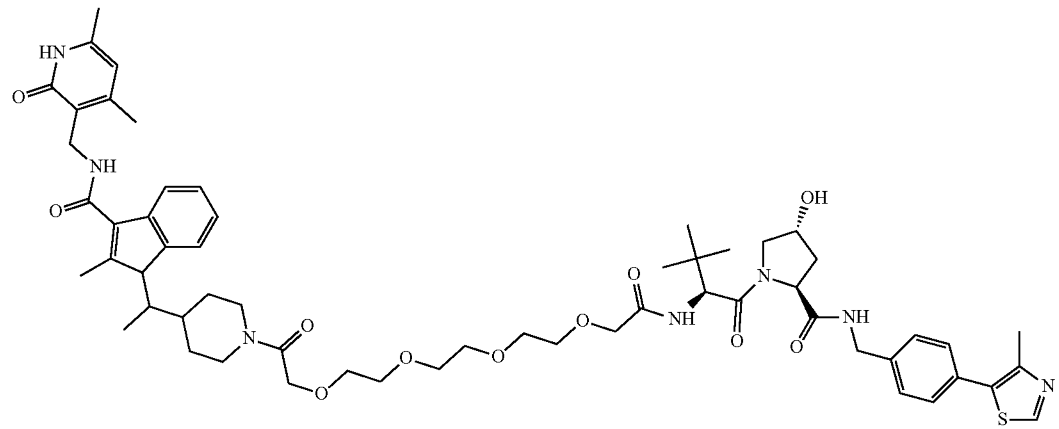 [SMILES: CC1=C(C(=O)NCc2c(C)cc(C)[nH]c2=O)c2ccccc2C1C(C)C1CCN(C(=O)COCCOCCOCCOCC(=O)N[C@H](C(=O)N2C[C@H](O)C[C@H]2C(=O)NCc2ccc(-c3scnc3C)cc2)C(C)(C)C)CC1] | 1081.5 | N-[(4,6-dimethyl-2-oxo-1,2-dihydropyridin-3-yl)methyl]-1-{1-[1-(1-{[(2S)-1-[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl]carbamoyl}-2,5,8,11-tetraoxatridecanoyl)piperidin-4-yl]ethyl}-2-methyl-1H-indole-3-carboxamide |
| 9 | 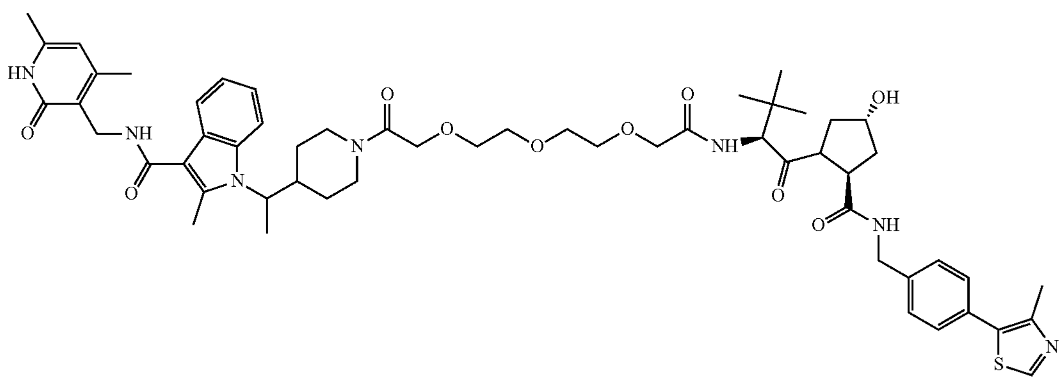 [SMILES: Cc1cc(C)c(CNC(=O)c2c(C)n(C(C)C3CCN(C(=O)COCCOCCOCC(=O)N[C@H](C(=O)C4C[C@H](O)C[C@H]4C(=O)NCc4ccc(-c5scnc5C)cc4)C(C)(C)C)CC3)c3ccccc23)c(=O)[nH]1] | 1037.4 | N-[(4,6-dimethyl-2-oxo-1,2-dihydropyridin-3-yl)methyl]-1-{1-[1-(2-{2-[2-({[(2S)-1-[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl]carbamoyl}methoxy)ethoxy]ethoxy}acetyl)piperidin-4-yl]ethyl}-2-methyl-1H-indole-3-carboxamide |

TABLE 1-continued

Exemplary compounds of the present disclosure

| Ex # | Structure | Mass Spec (M + H)⁺ unless otherwise noted | Name |
|---|---|---|---|
| 10 | 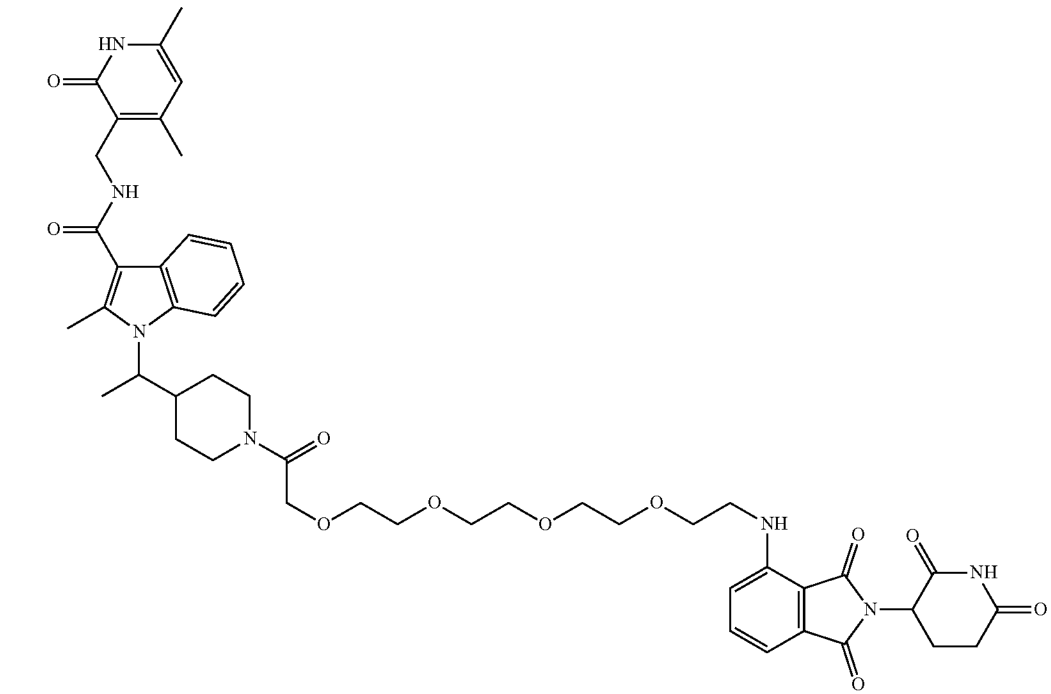 [SMILES: Cc1cc(C)c(CNC(=O)c2c(C)n(C(C)C3CCN(C(=O)COCCOCCOCCOCCNc4cccc5c4C(=O)N(C4CCC(=O)NC4=O)C5=O)CC3)c3ccccc23)c(=O)[nH]1] | (M + 2H)⁺/2 = 455.8 | N-[(4,6-dimethyl-2-oxo-1,2-dihydropyridin-3-yl)methyl]-1-[1-(1-{1-[2-(2,6-dioxopiperidin-3-yl)-1,3-dioxo-2,3-dihydro-1H-isoindol-4-yl]-4,7,10,13-tetraoxa-1-azapentadecanoyl}piperidin-4-yl)ethyl]-2-methyl-1H-indole-3-carboxamide |
| 11 | 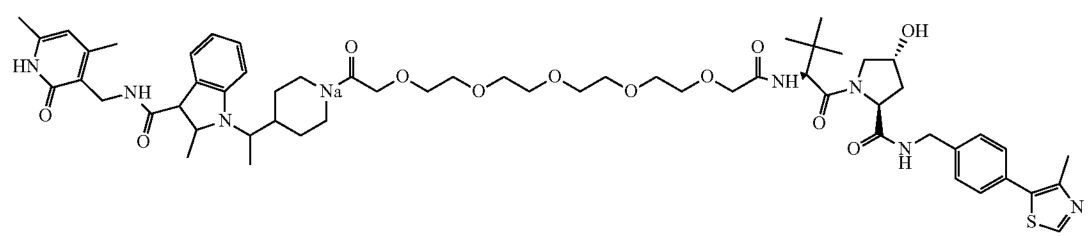 | (M + 2H)⁺/2 = 563.3 | N-[(4,6-dimethyl-2-oxo-1,2-dihydropyridin-3-yl)methyl]-1-{1-[1-(1-{[(2S)-1-[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl]carbamoyl}-2,5,8,11,14-pentaoxahexadecanoyl)piperidin-4-yl]ethyl}-2-methyl-1H-indole-3-carboxamide |

TABLE 1-continued

Exemplary compounds of the present disclosure

| Ex # | Structure | Mass Spec (M + H)+ unless otherwise noted | Name |
|---|---|---|---|
| 12 | 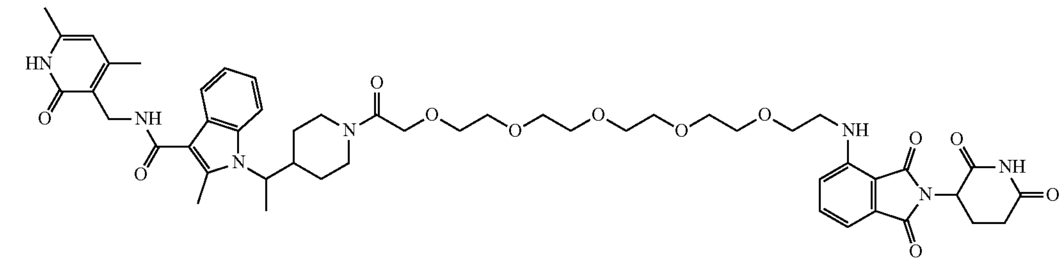 [SMILES: Cc1cc(C)c(CNC(=O)c2c(C)n(C(C)C3CCN(C(=O)COCCOCCOCCOCCOCCNc4cccc5c4C(=O)N(C4CCC(=O)NC4=O)C5=O)CC3)c3ccccc23)c(=O)[nH]1] | 954.4 | N-[(4,6-dimethyl-2-oxo-1,2-dihydropyridin-3-yl)methyl]-1-[1-(1-{1-[2-(2,6-dioxopiperidin-3-yl)-1,3-dioxo-2,3-dihydro-1H-isoindol-4-yl]-4,7,10,13,16-pentaoxa-1-azaoctadecanoyl}piperidin-4-yl)ethyl]-2-methyl-1H-indole-3-carboxamide |
| 13 | 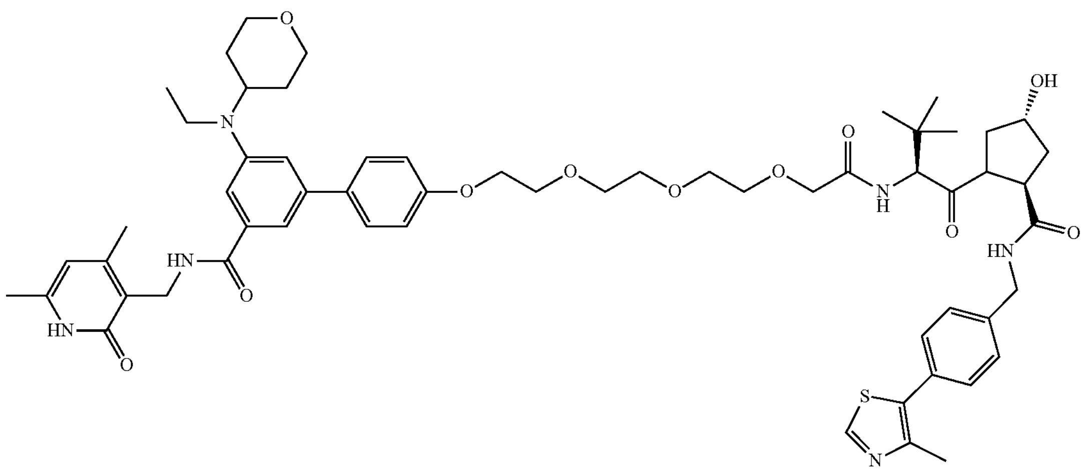 [SMILES: CCN(c1cc(C(=O)NCc2c(C)cc(C)[nH]c2=O)cc(-c2ccc(OCCOCCOCCOCC(=O)N[C@H](C(=O)C3C[C@H](O)C[C@H]3C(=O)NCc3ccc(-c4scnc4C)cc3)C(C)(C)C)cc2)c1)C1CCOCC1] | 1092.6 | (2S,4R)-1-[(2S)-2-{1-[4-(3-{[(4,6-dimethyl-2-oxo-1,2-dihydropyridin-3-yl)methyl]carbamoyl}-5-[ethyl(oxan-4-yl)amino]-4-methylphenyl)phenyl]-1,4,7,10-tetraoxadodecan-12-amido}-3,3-dimethylbutanoyl]-4-hydroxy-N-{[4-(4-methyl-1,3-thiazol-5-yl)phenyl]methyl}pyrrolidine-2-carboxamide |

TABLE 1-continued

Exemplary compounds of the present disclosure

| Ex # | Structure | Mass Spec (M + H)+ unless otherwise noted | Name |
|---|---|---|---|
| 14 | 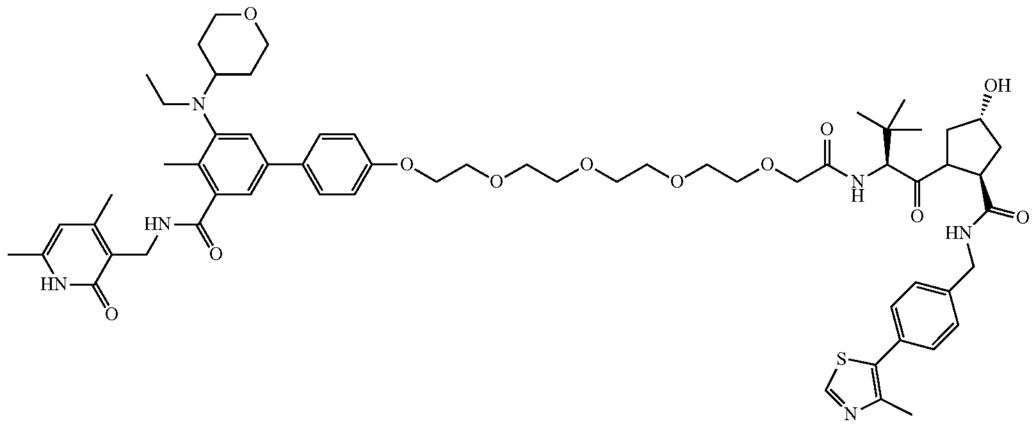 [SMILES: CCN(c1cc(-c2ccc(OCCOCCOCCOCCOCC(=O)N[C@H](C(=O)C3C[C@H](O)C[C@H]3C(=O)NCc3ccc(-c4scnc4C)cc3)C(C)(C)C)cc2)cc(C(=O)NCc2c(C)cc(C)[nH]c2=O)c1C)C1CCOCC1] | 1136.7 | (2S,4R)-1-[(2S)-2-[1-[4-(3-{[(4,6-dimethyl-2-oxo-1,2-dihydropyridin-3-yl)methyl]carbamoyl}-5-[ethyl(oxan-4-yl)amino]-4-methylphenyl)phenyl]-1,4,7,10,13-pentaoxapentadecan-15-amido}-3,3-dimethylbutanoyl]-4-hydroxy-N-{[4-(4-methyl-1,3-thiazol-5-yl)phenyl]methyl}pyrrolidine-2-carboxamide |
| 15 | 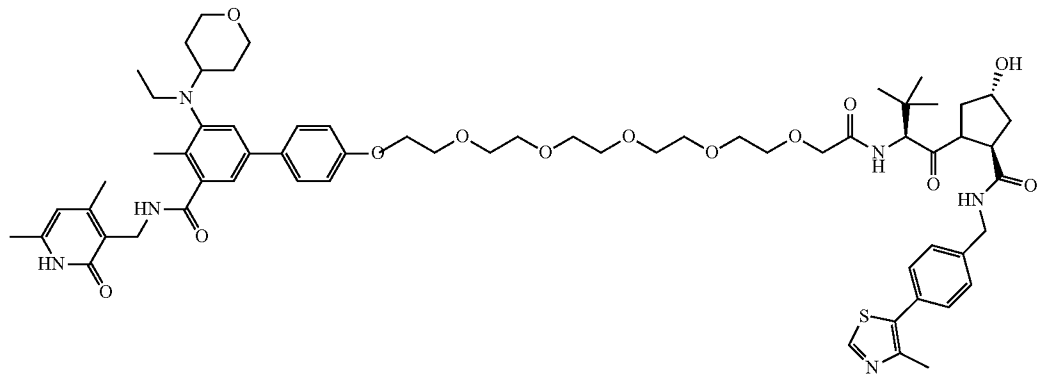 | 1180.8 | (2S,4R)-1-[(2S)-2-[1-[4-(3-{[(4,6-dimethyl-2-oxo-1,2-dihydropyridin-3-yl)methyl]carbamoyl}-5-[ethyl(oxan-4-yl)amino]-4-methylphenyl)phenyl]-1,4,7,10,13,16-hexaoxaoctadecan-18-amido}-3,3-dimethylbutanoyl]-4-hydroxy-N-{[4-(4-methyl-1,3-thiazol-5-yl)phenyl]methyl}pyrrolidine-2-carboxamide |

TABLE 1-continued

Exemplary compounds of the present disclosure

| Ex # | Structure | Mass Spec (M + H)+ unless otherwise noted | Name |
|---|---|---|---|
| 16 | 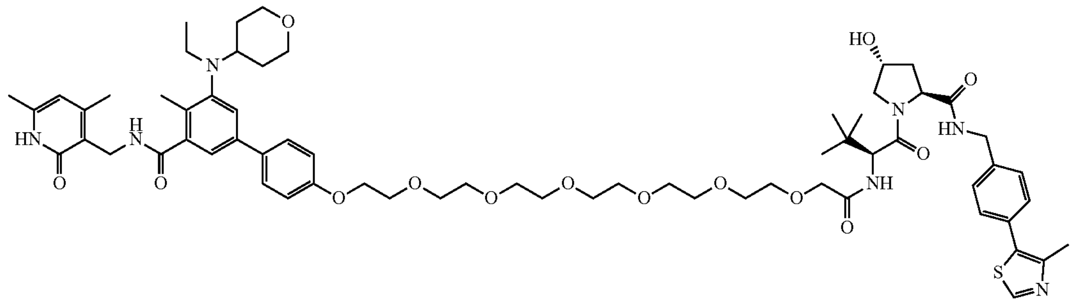 | 1224.8 | (2S,4R)-1-[(2S)-2-[1-[4-(3-{[(4,6-dimethyl-2-oxo-1,2-dihydropyridin-3-yl)methyl]carbamoyl]-5-[ethyl(oxan-4-yl)amino]-4-methylphenyl)phenyl]-1,4,7,10,13,16,19-heptaoxahenicosan-21-amido)-3,3-dimethylbutanoyl]-4-hydroxy-N-{[4-(4-methyl-1,3-thiazol-5-yl)phenyl]methyl}pyrrolidine-2-carboxamide |
| 17 | 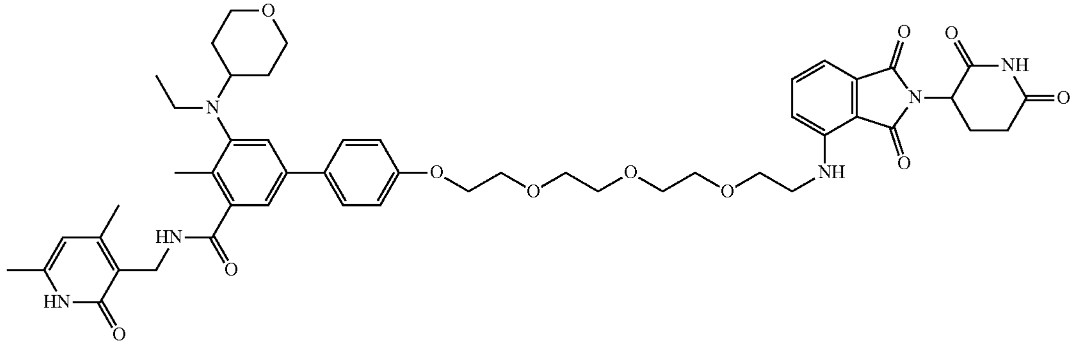 [SMILES: CCN(c1cc(-c2ccc(OCCOCCOCCOCCNc3cccc4c3C(=O)N(C3CCC(=O)NC3=O)C4=O)cc2)cc(C(=O)NCc2c(C)cc(C)[nH]c2=O)c1C)C1CCOCC1] | 921.5 | N-[(4,6-dimethyl-2-oxo-1,2-dihydropyridin-3-yl)methyl]-5-[4-({1-[2-(2,6-dioxopiperidin-3-yl)-1,3-dioxo-2,3-dihydro-1H-isoindol-4-yl]-4,7,10-trioxa-1-azadodecan-12-yl}oxy)phenyl]-3-[ethyl(oxan-4-yl)amino]-2-methylbenzamide |
| 18 | 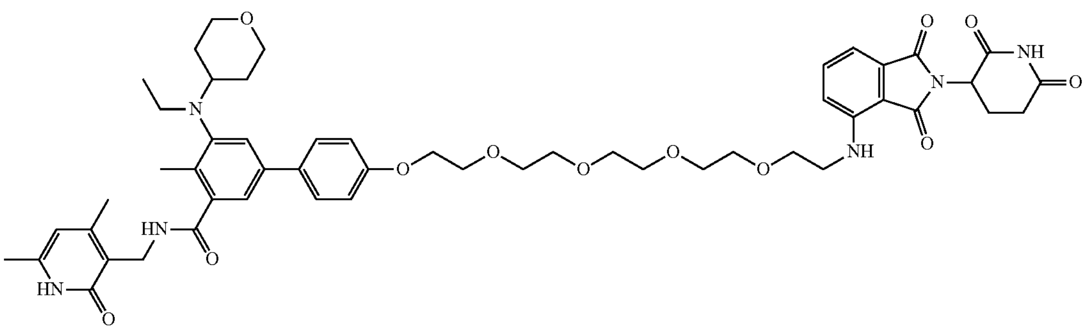 [SMILES: CCN(c1cc(-c2ccc(OCCOCCOCCOCCOCCNc3cccc4c3C(=O)N(C3CCC(=O)NC3=O)C4=O)cc2)cc(C(=O)NCc2c(C)cc(C)[nH]c2=O)c1C)C1CCOCC1] | 965.6 | N-[(4,6-dimethyl-2-oxo-1,2-dihydropyridin-3-yl)methyl]-5-[4-({1-[2-(2,6-dioxopiperidin-3-yl)-1,3-dioxo-2,3-dihydro-1H-isoindol-4-yl]-4,7,10,13-tetraoxa-1-azapentadecan-15-yl}oxy)phenyl]-3-[ethyl(oxan-4-yl)amino]-2-methylbenzamide |

TABLE 1-continued

Exemplary compounds of the present disclosure

| Ex # | Structure | Mass Spec (M + H)+ unless otherwise noted | Name |
|---|---|---|---|
| 19 | 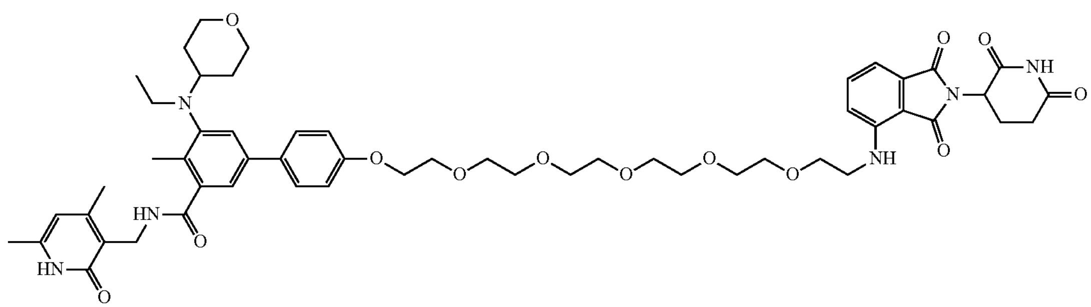 [SMILES: CCN(c1cc(-c2ccc(OCCOCCOCCOCCOCCOCCNc3cccc4c3C(=O)N(C3CCC(=O)NC3=O)C4=O)cc2)cc(C(=O)NCc2c(C)cc(C)[nH]c2=O)c1C)C1CCOCC1] | 1009.3 | N-[(4,6-dimethyl-2-oxo-1,2-dihydropyridin-3-yl)methyl]-5-[4-({1-[2-(2,6-dioxopiperidin-3-yl)-1,3-dioxo-2,3-dihydro-1H-isoindol-4-yl]-4,7,10,13,16-pentaoxa-1-azaoctadecan-18-yl}oxy)phenyl]-3-[ethyl(oxan-4-yl)amino]-2-methylbenzamide |
| 20 | 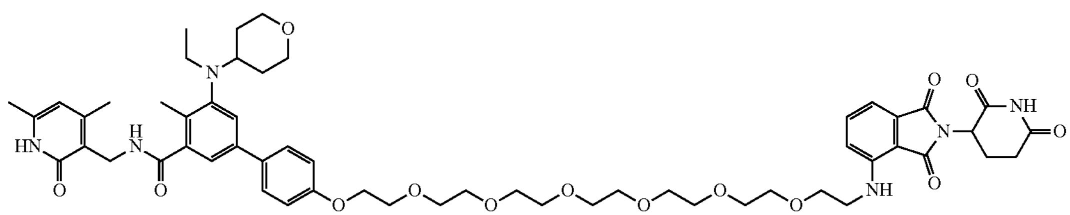 [SMILES: CCN(c1cc(-c2ccc(OCCOCCOCCOCCOCCOCCOCCNc3cccc4c3C(=O)N(C3CCC(=O)NC3=O)C4=O)cc2)cc(C(=O)NCc2c(C)cc(C)[nH]c2=O)c1C)C1CCOCC1] | 1053.6 | N-[(4,6-dimethyl-2-oxo-1,2-dihydropyridin-3-yl)methyl]-5-[4-({1-[2-(2,6-dioxopiperidin-3-yl)-1,3-dioxo-2,3-dihydro-1H-isoindol-4-yl]-4,7,10,13,16,19-hexaoxa-1-azahenicosan-21-yl}oxy)phenyl]-3-[ethyl(oxan-4-yl)amino]-2-methylbenzamide |
| 21 | 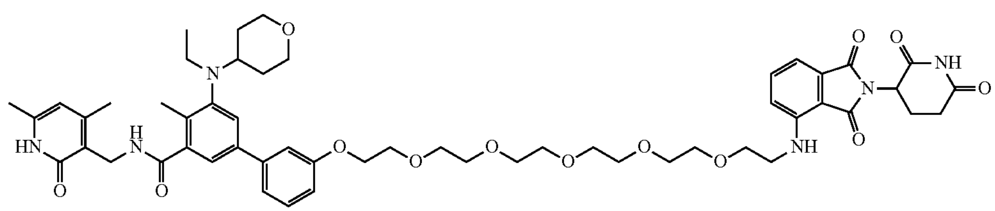 [SMILES: CCN(c1cc(-c2cccc(OCCOCCOCCOCCOCCOCCNc3cccc4c3C(=O)N(C3CCC(=O)NC3=O)C4=O)c2)cc(C(=O)NCc2c(C)cc(C)[nH]c2=O)c1C)C1CCOCC1] | 1009.5 | N-[(4,6-dimethyl-2-oxo-1,2-dihydropyridin-3-yl)methyl]-5-[3-({1-[2-(2,6-dioxopiperidin-3-yl)-1,3-dioxo-2,3-dihydro-1H-isoindol-4-yl]-4,7,10,13,16-pentaoxa-1-azaoctadecan-18-yl}oxy)phenyl]-3-[ethyl(oxan-4-yl)amino]-2-methylbenzamide |

TABLE 1-continued

Exemplary compounds of the present disclosure

| Ex # | Structure | Mass Spec (M + H)+ unless otherwise noted | Name |
|---|---|---|---|
| 22 | 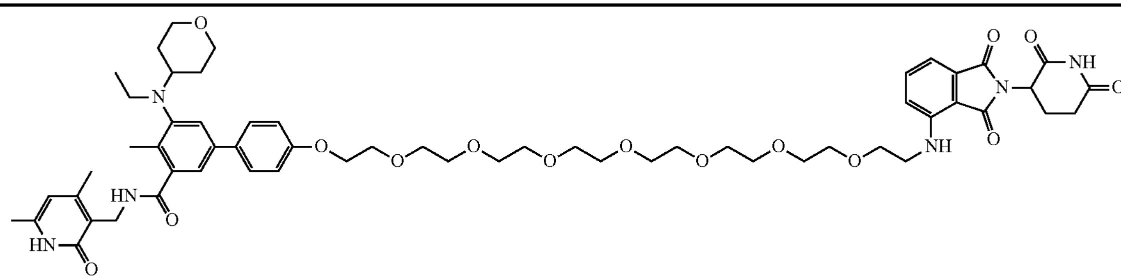 | 1097.6 | N-[(4,6-dimethyl-2-oxo-1,2-dihydropyridin-3-yl)methyl]-5-[4-({1-[2-(2,6-dioxopiperidin-3-yl)-1,3-dioxo-2,3-dihydro-1H-isoindol-4-yl]-4,7,10,13,16,19,22-heptaoxa-1-azatetracosan-24-yl}oxy)phenyl]-3-[ethyl(oxan-4-yl)amino]-2-methylbenzamide |
| 23 | 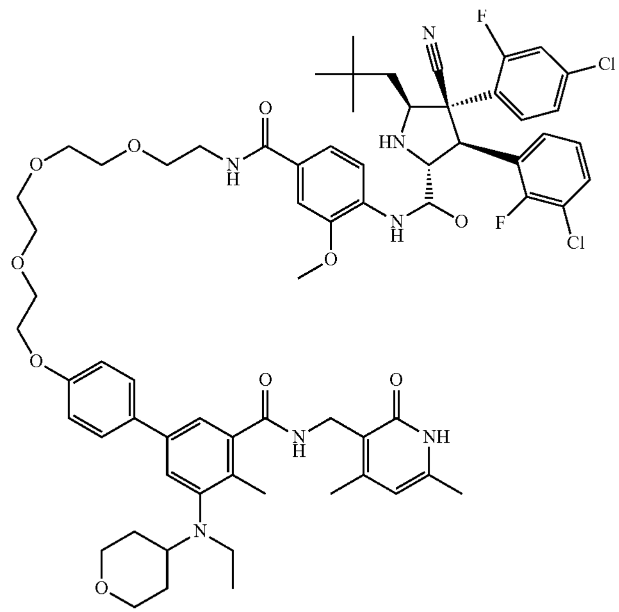 [SMILES: CCN(c1cc(-c2ccc(OCCOCCOCCOCCNC(=O)c3ccc(NC(O)[C@@H]4N[C@@H](CC(C)(C)C)[C@](C#N)(c5ccc(Cl)cc5F)[C@H]4c4cccc(Cl)c4F)c(OC)c3)cc2)cc(C(=O)NCc2c(C)cc(C)[nH]c2=O)c1C)C1CCOCC1] | (M + 2H)+/2 = 571.6 | N-[(4,6-dimethyl-2-oxo-1,2-dihydropyridin-3-yl)methyl]-5-[4-({1-[2-(2,6-dioxopiperidin-3-yl)-1,3-dioxo-2,3-dihydro-1H-isoindol-4-yl]-4,7,10,13,16,19,22,25-octaoxa-1-azaheptacosan-27-yl}oxy)phenyl]-3-[ethyl(oxan-4-yl)amino]-2-methylbenzamide |

TABLE 1-continued

Exemplary compounds of the present disclosure

| Ex # | Structure | Mass Spec (M + H)+ unless otherwise noted | Name |
|---|---|---|---|
| 24 | 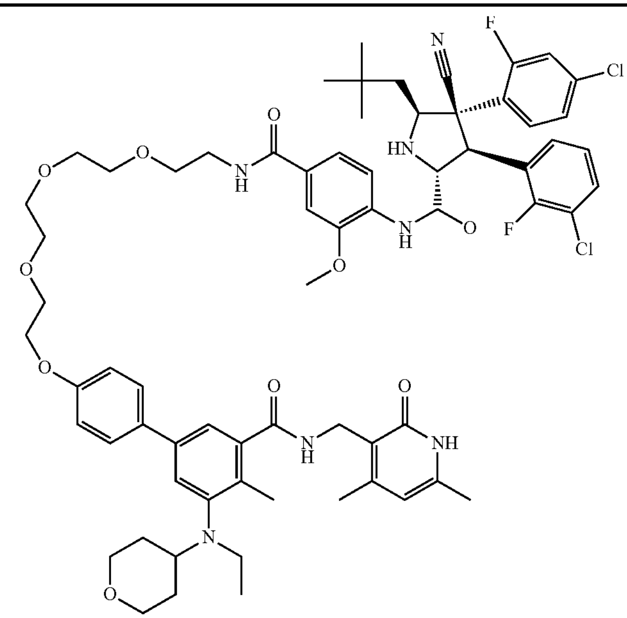 | (M + 3H)+/3 = 421.9 | (2R,3S,4R,5S)-3-(3-chloro-2-fluorophenyl)-4-(4-chloro-2-fluorophenyl)-4-cyano-N-[4-({1-[4-(3-{[(4,6-dimethyl-2-oxo-1,2-dihydropyridin-3-yl)methyl]carbamoyl}-5-[ethyl(oxan-4-yl)amino]-4-methylphenyl)phenyl]-1,4,7,10-tetraoxadodecan-12-yl]carbamoyl)-2-methoxyphenyl]-5-(2,2-dimethylpropyl)pyrrolidine-2-carboxamide |
| 25 | 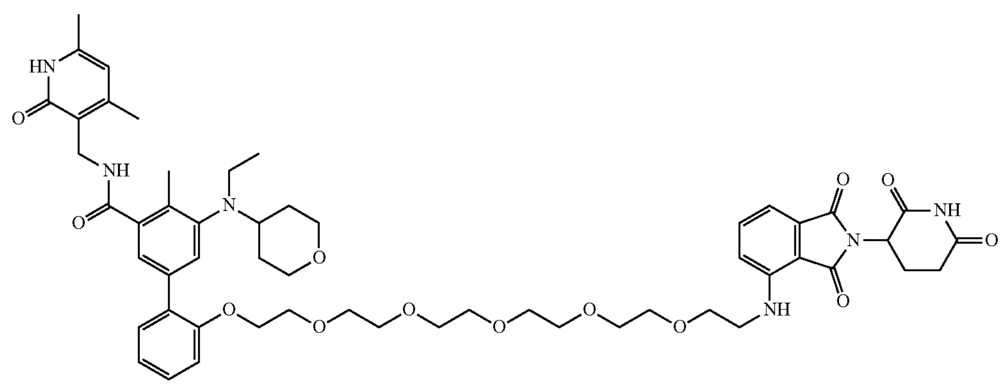 [SMILES: CCN(c1cc(-c2ccccc2OCCOCCOCCOCCOCCOCCNc2cccc3c2C(=O)N(C2CCC(=O)NC2=O)C3=O)cc(C(=O)NCc2c(C)cc(C)[nH]c2=O)c1C)C1CCOCC1] | 1009.6 | N-[(4,6-dimethyl-2-oxo-1,2-dihydropyridin-3-yl)methyl]-5-[2-({1-[2-(2,6-dioxopiperidin-3-yl)-1,3-dioxo-2,3-dihydro-1H-isoindol-4-yl]-4,7,10,13,16-pentaoxa-1-azaoctadecan-18-yl}oxy)phenyl]-3-[ethyl(oxan-4-yl)amino]-2-methylbenzamide |

TABLE 1-continued

Exemplary compounds of the present disclosure

| Ex # | Structure | Mass Spec (M + H)+ unless otherwise noted | Name |
|---|---|---|---|
| 26 | 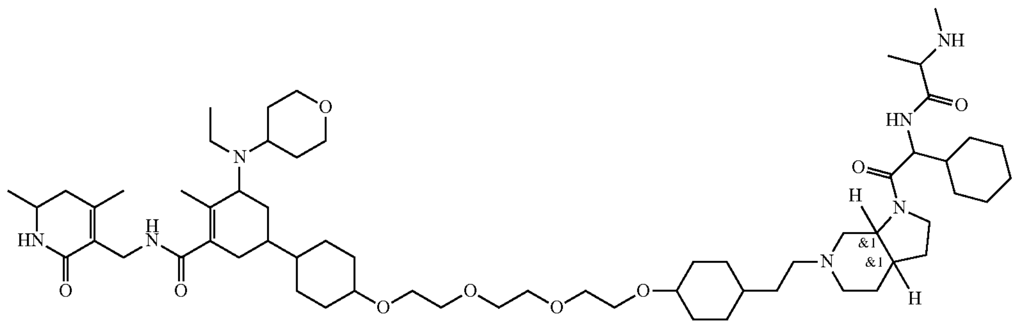 [SMILES: CCN(C1CCOCC1)C1CC(C2CCC(OCCOCCOCCOC3CCC(CCN4CCC5CCN(C(=O)C(NC(=O)C(C)NC)C6CCCCC6)C5C4)CC3)CC2)CC(C(=O)NCC2=C(C)CC(C)NC2=O)=C1C] | 1074.7 | 5-[4-(2-{2-[4-{2-[(3aR,7aS)-1-[(2S)-2-cyclohexyl-2-[(2S)-2-(methylamino)propanamido]acetyl]-octahydro-1H-pyrrolo[2,3-c]pyridin-6-yl]ethyl}phenoxy]ethoxy}ethoxy)phenyl]-N-[(4,6-dimethyl-2-oxo-1,2-dihydropyridin-3-yl)methyl]-3-[ethyl(oxan-4-yl)amino]-2-methylbenzamide |
| 27 | 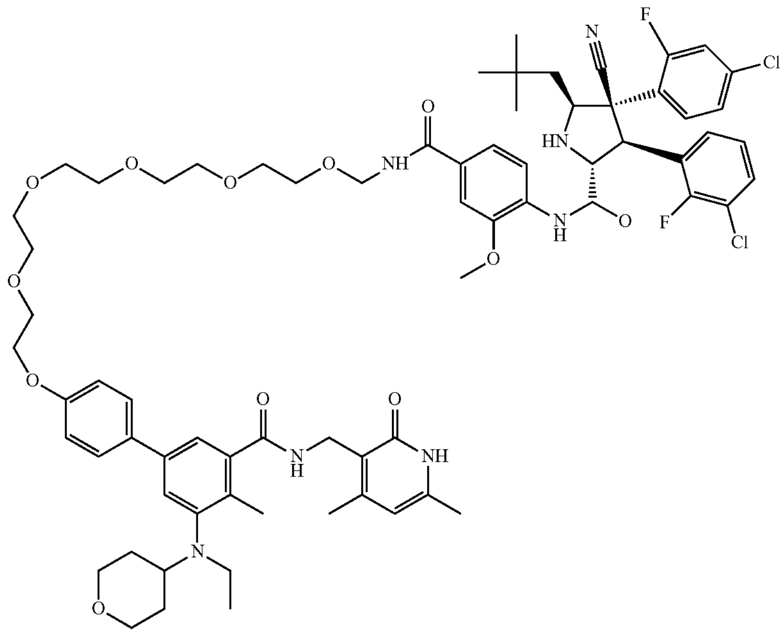 [SMILES: CCN(c1cc(-c2ccc(OCCOCCOCCOCCOCCOCNC(=O)c3ccc(NC(O)[C@@H]4N[C@@H](CC(C)(C)C)[C@](C#N)(c5ccc(Cl)cc5F)[C@H]4c4cccc(Cl)c4F)c(OC)c3)cc2)cc(C(=O)NCc2c(C)cc(C)[nH]c2=O)c1C)C1CCOCC1] | 1351.7 | (2R,3S,4R,5S)-3-(3-chloro-2-fluorophenyl)-4-(4-chloro-2-fluorophenyl)-4-cyano-N-[4-({1-[4-(3-{[(4,6-dimethyl-2-oxo-1,2-dihydropyridin-3-yl)methyl]carbamoyl}-5-[ethyl(oxan-4-yl)amino]-4-methylphenyl)phenyl-1,4,7,10,13,16-hexaoxaoctadecan-18-yl]carbamoyl)-2-methoxyphenyl]-5-(2,2-dimethylpropyl)pyrrolidine-2-carboxamide |

TABLE 1-continued

Exemplary compounds of the present disclosure

| Ex # | Structure | Mass Spec (M + H)+ unless otherwise noted | Name |
|---|---|---|---|
| 28 | 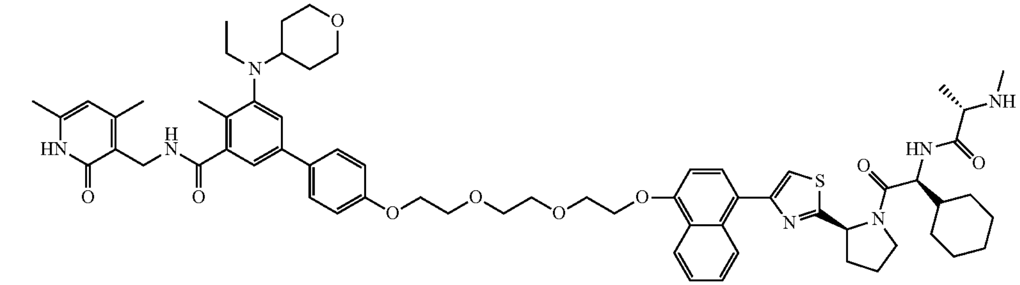 | (M + 3H)+/3 = 375.5 | 5-{4-[2-(2-{2-[(4-{2-[(2S)-1-[(2S)-2-cyclohexyl-2-[(2S)-2-(methylamino)propanamido]acetyl]pyrrolidin-2-yl]-1,3-thiazol-4-yl]naphthalen-1-yl}oxy)ethoxy]ethoxy}phenyl)-N-[(4,6-dimethyl-2-oxo-1,2-dihydropyridin-3-yl)methyl]-3-[ethyl(oxan-4-yl)amino]-2-methylbenzamide |
| 29 | 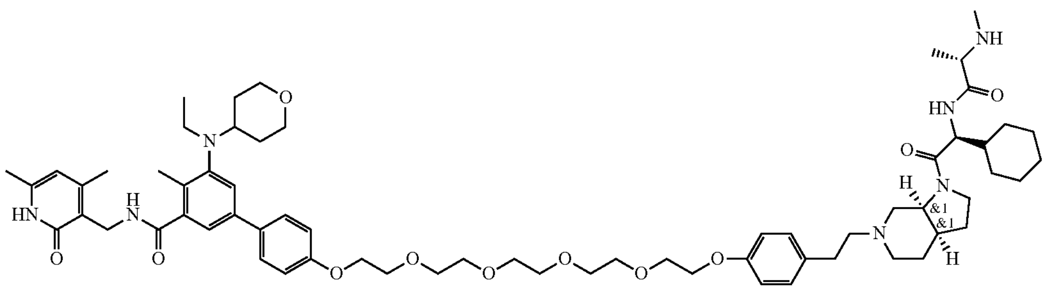 [SMILES: CCN(c1cc(-c2ccc(OCCOCCOCCOCCOCCOc3ccc(CCN4CC[C@@H]5CCN(C(=O)[C@@H](NC(=O)[C@H](C)NC)C6CCCCC6)[C@@H]5C4)cc3)cc2)cc(C(=O)NCc2c(C)cc(C)[nH]c2=O)c1C)C1CCOCC1] | 1162.7 | 5-(4-{[1-(4-{2-[(3aR,7aS)-1-[(2S)-2-cyclohexyl-2-[(2S)-2-(methylamino)propanamido]acetyl]-octahydro-1H-pyrrolo[2,3-c]pyridin-6-yl]ethyl]phenyl)-1,4,7,10,13-pentaoxapentadecan-15-yl]oxy}phenyl)-N-[(4,6-dimethyl-2-oxo-1,2-dihydropyridin-3-yl)methyl]-3-[ethyl(oxan-4-yl)amino]-2-methylbenzamide |
| 30 | 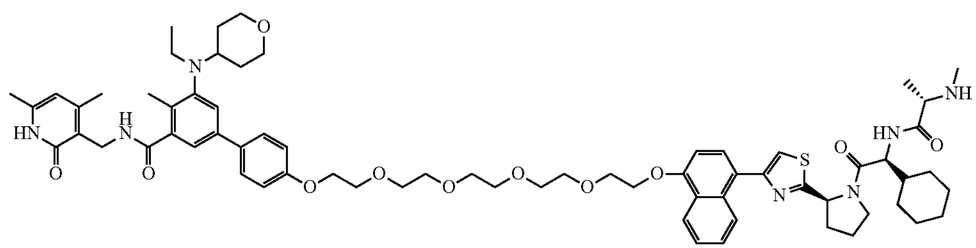 | 1212.6 | 5-(4-{[1-(4-{2-[(2S)-1-[(2S)-2-cyclohexyl-2-[(2S)-2-(methylamino)propanamido]acetyl]pyrrolidin-2-yl]-1,3-thiazol-4-yl}naphthalen-1-yl)-1,4,7,10,13-pentaoxapentadecan-15-yl]oxy}phenyl)-N-[(4,6-dimethyl-2-oxo-1,2-dihydropyridin-3-yl)methyl]-3-[ethyl(oxan-4-yl)amino]-2-methylbenzamide |

TABLE 1-continued
Exemplary compounds of the present disclosure
| Ex # | Structure | Mass Spec (M + H)+ unless otherwise noted | Name |
|---|---|---|---|
| 31 | 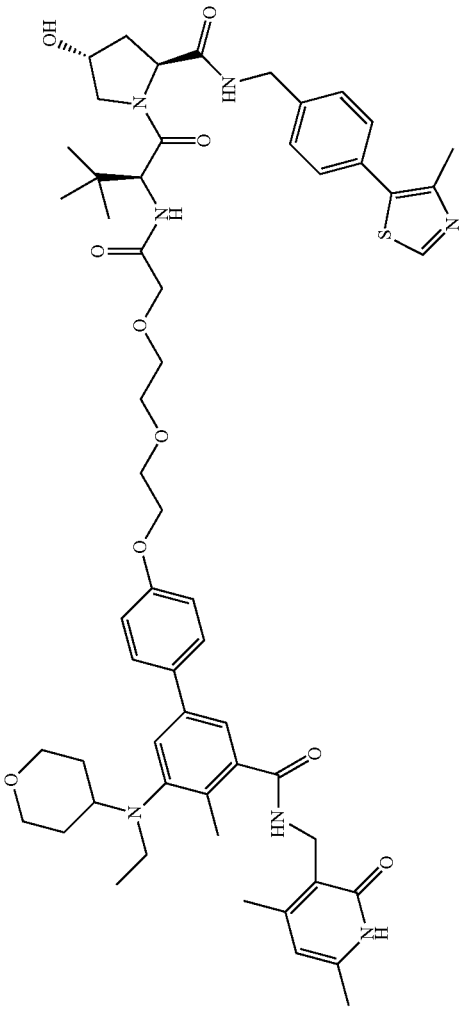 | (M + 2H)+/2 = 525.4 | (2S,4R)-1-[(2S)-2-[2-(2-2-[4-(3-{[(4,6-dimethyl-2-oxo-1,2-dihydropyridin-3-yl)methyl]carbamoyl}-5-[ethyl(oxan-4-yl)amino]-4-methylphenyl)phenoxy]ethoxy}ethoxy)acetamido]-3,3-dimethylbutanoyl]-4-hydroxy-N-{[4-(4-methyl-1,3-thiazol-5-yl)phenyl]methyl}pyrrolidine-2-carboxamide |

TABLE 1-continued

Exemplary compounds of the present disclosure

| Ex # | Structure | Mass Spec (M + H)+ unless otherwise noted | Name |
|---|---|---|---|
| 32 | 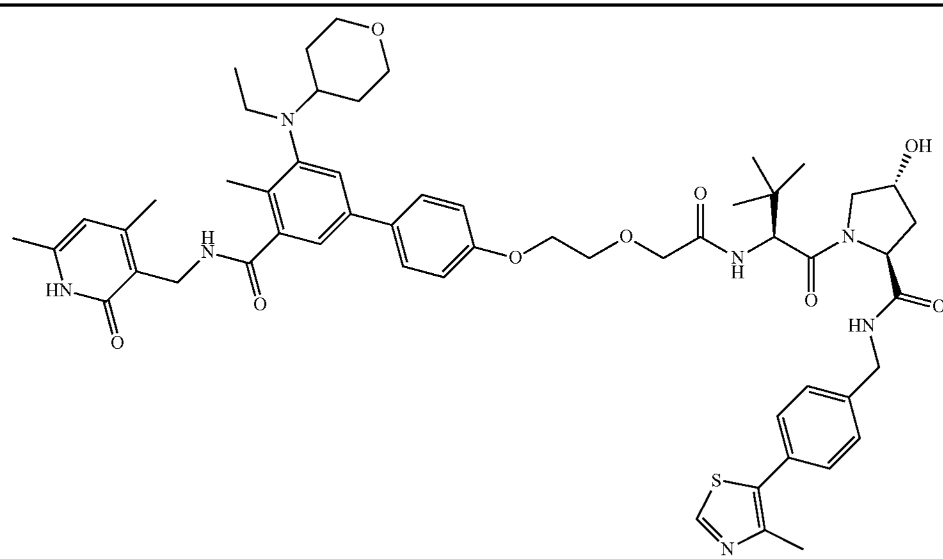 | (M + 3H)+/3 = 335.5 | (2S,4R)-1-[(2S)-2-(2-{2-[4-(3-{[(4,6-dimethyl-2-oxo-1,2-dihydropyridin-3-yl)methyl]carbamoyl}-5-[ethyl(oxan-4-yl)amino]-4-methylphenyl)phenoxy]ethoxy}acetamido)-3,3-dimethylbutanoyl]-4-hydroxy-N-{[4-(4-methyl-1,3-thiazol-5-yl)phenyl]methyl}pyrrolidine-2-carboxamide |
| 33 | 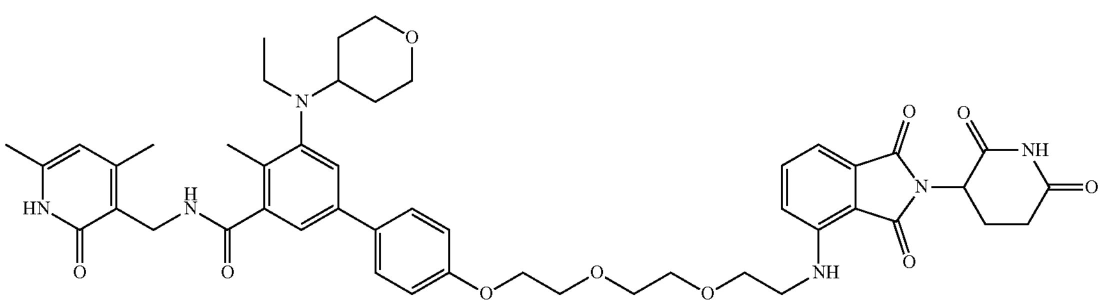 [SMILES: CCN(c1cc(-c2ccc(OCCOCCOCCNc3cccc4c3C(=O)N(C3CCC(=O)NC3=O)C4=O)cc2)cc(C(=O)NCc2c(C)cc(C)[nH]c2=O)c1C)C1CCOCC1] | (M + 2H)+/2 = 439.3 | N-[(4,6-dimethyl-2-oxo-1,2-dihydropyridin-3-yl)methyl]-5-(4-{2-[2-(2-{[2-(2,6-dioxopiperidin-3-yl)-1,3-dioxo-2,3-dihydro-1H-isoindol-4-yl]amino}ethoxy)ethoxy]ethoxy}phenyl)-3-[ethyl(oxan-4-yl)amino]-2-methylbenzamide |

TABLE 1-continued

Exemplary compounds of the present disclosure

| Ex # | Structure | Mass Spec (M + H)+ unless otherwise noted | Name |
|---|---|---|---|
| 34 | 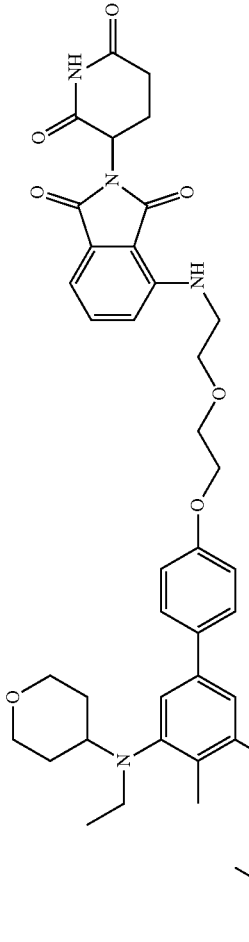 | 833.3 | N-[(4,6-dimethyl-2-oxo-1,2-dihydropyridin-3-yl)methyl]-5-{4-[2-(2-{[2-(2,6-dioxopiperidin-3-yl)-1,3-dioxo-2,3-dihydro-1H-isoindol-4-yl]amino}ethoxy)ethoxy]phenyl}-3-[ethyl(oxan-4-yl)amino]-2-methylbenzamide |
| 35 | 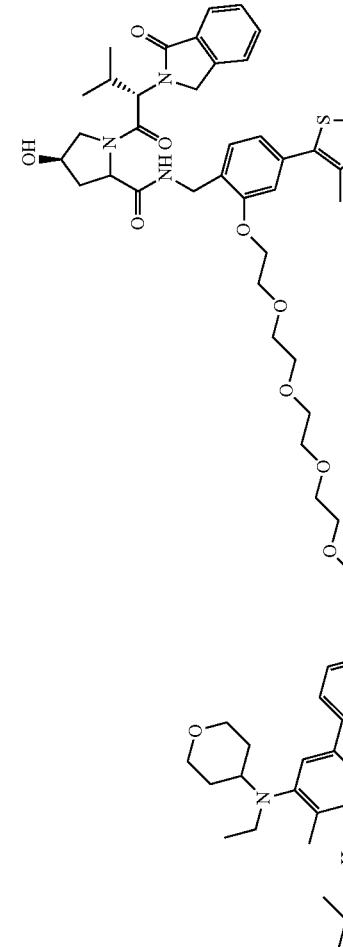 | (M + 2H)+/2 = 620.9 | (2S,4R)-N-{[2-({1-[4-(3-{[(4,6-dimethyl-2-oxo-1,2-dihydropyridin-3-yl)methyl][carbamoyl]-5-[ethyl(oxan-4-yl)amino]-4-methylphenyl)phenyl]-1,4,7,10,13-pentaoxapentadecan-15-yl}oxy)-4-(4-methyl-1,3-thiazol-5-yl)phenyl]methyl}-4-hydroxy-1-[(2S)-3-methyl-2-(1-oxo-2,3-dihydro-1H-isoindol-2-yl)butanoyl]pyrrolidine-2-carboxamide |

TABLE 1-continued
Exemplary compounds of the present disclosure
| Ex # | Structure | Mass Spec (M + H)+ unless otherwise noted | Name |
|---|---|---|---|
| 36 | 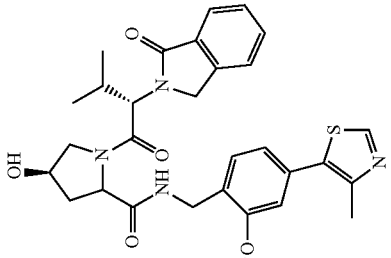 | 1197.4 | (2S,4R)-N-{[2-({1-[4-(3-{[(4,6-dimethyl-2-oxo-1,2-dihydropyridin-3-yl)methyl]carbamoyl}-5-[ethyl(oxan-4-yl)amino]-4-methylphenyl)phenyl]-1,4,7,10-tetraoxadodecan-12-yl}oxy)-4-(4-methyl-1,3-thiazol-5-yl)phenyl]methyl}-4-hydroxy-1-[(2S)-3-methyl-2-(1-oxo-2,3-dihydro-1H-isoindol-2-yl)butanoyl]pyrrolidine-2-carboxamide |

TABLE 1-continued
Exemplary compounds of the present disclosure
| Ex # | Structure | Mass Spec (M + H)+ unless otherwise noted | Name |
|---|---|---|---|
| 37 | 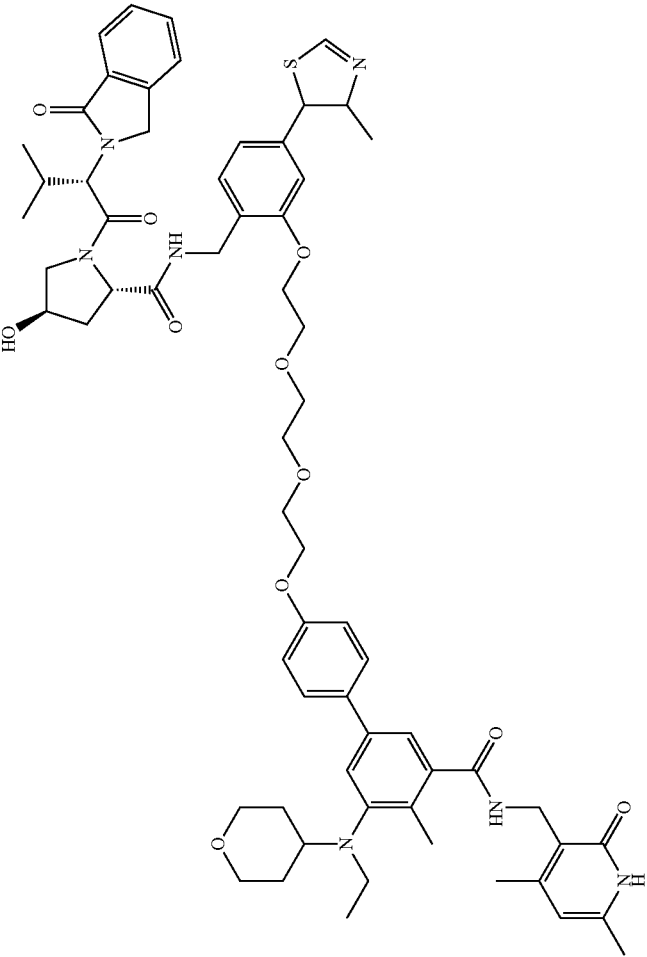 | (M + 2H)+/2 = 576.8 | (2S,4R)-N-({2-[2-(2-{2-[4(3-{[(4,6-dimethyl-2-oxo-1,2-dihydropyridin-3-yl)methyl]carbamoyl}-5-[ethyl(oxan-4-yl)amino]-4-methylphenyl)phenoxy]ethoxy}ethoxy)ethoxy]-4-(4-methyl-1,3-thiazol-5-yl)phenyl}methyl)-4-hydroxy-1-[(2S)-3-methyl-2-(1-oxo-2,3-dihydro-1H-isoindol-2-yl)butanoyl]pyrrolidine-2-carboxamide |

TABLE 1-continued

Exemplary compounds of the present disclosure

| Ex # | Structure | Mass Spec (M + H)+ unless otherwise noted | Name |
|---|---|---|---|
| 38 | 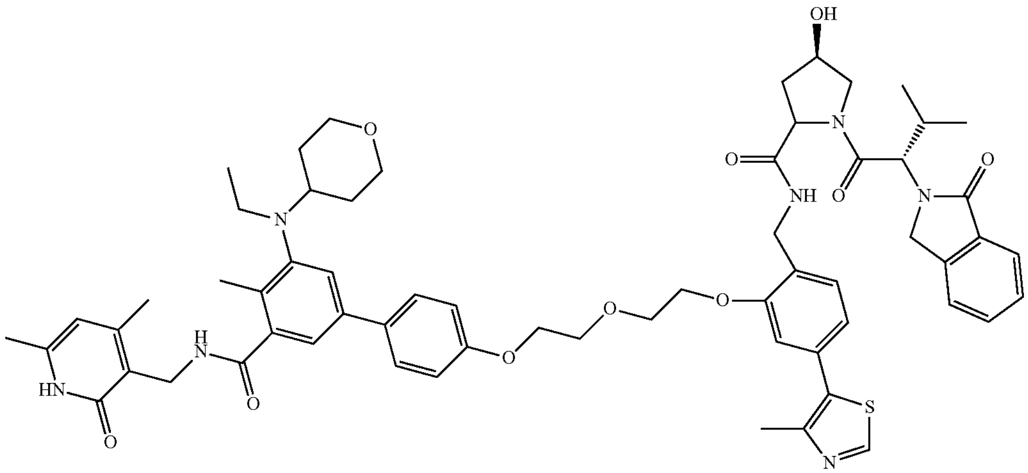 [SMILES: CCN(c1cc(-c2ccc(OCCOCCOc3cc(-c4scnc4C)ccc3CNC(=O)C3C[C@@H](O)CN3C(=O)[C@H](C(C)C)N3Cc4ccccc4C3=O)cc2)cc(C(=O)NCc2c(C)cc(C)[nH]c2=O)c1C)C1CCOCC1] | (M + 2H)+/2 = 555.0 | (2S,4R)-N-{[2-(2-{2-[4-(3-{[(4,6-dimethyl-2-oxo-1,2-dihydropyridin-3-yl)methyl]carbamoyl}-5-[ethyl(oxan-4-yl)amino]-4-methylphenyl)phenoxy]ethoxy}ethoxy)-4-(4-methyl-1,3-thiazol-5-yl)phenyl]methyl}-4-hydroxy-1-[(2S)-3-methyl-2-(1-oxo-2,3-dihydro-1H-isoindol-2-yl)butanoyl]pyrrolidine-2-carboxamide |
| 39 | 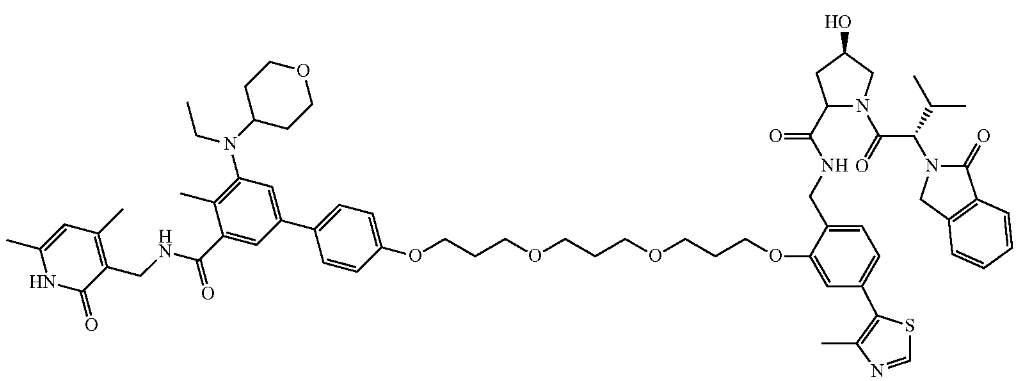 [SMILES: CCN(c1cc(-c2ccc(OCCCOCCCOCCCOc3cc(-c4scnc4C)ccc3CNC(=O)C3C[C@@H](O)CN3C(=O)[C@H](C(C)C)N3Cc4ccccc4C3=O)cc2)cc(C(=O)NCc2c(C)cc(C)[nH]c2=O)c1C)C1CCOCC1] | (M + 2H)+/2 = 576.3 | (2S,4R)-N-({2-[3-(3-{3-[4-(3-{[(4,6-dimethyl-2-oxo-1,2-dihydropyridin-3-yl)methyl]carbamoyl}-5-[ethyl(oxan-4-yl)amino]-4-methylphenyl)phenoxy]propoxy}propoxy)-4-(4-methyl-1,3-thiazol-5-yl)phenyl]methyl}-4-hydroxy-1-[(2S)-3-methyl-2-(1-oxo-2,3-dihydro-1H-isoindol-2-yl)butanoyl]pyrrolidine-2-carboxamide |

TABLE 1-continued

Exemplary compounds of the present disclosure

| Ex # | Structure | Mass Spec (M + H)+ unless otherwise noted | Name |
|---|---|---|---|
| 40 | 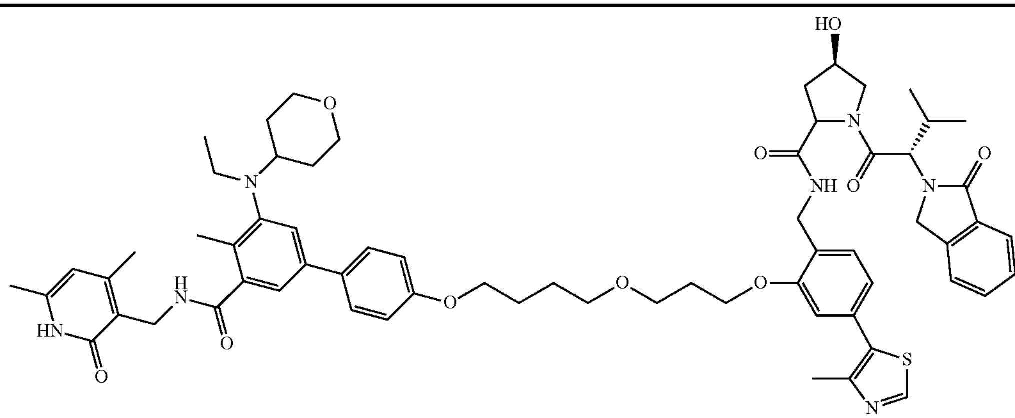 | (M + 2H)+/2 = 576.3 | (2S,4R)-N-{[2-(3-{4-[4-(3-{[(4,6-dimethyl-2-oxo-1,2-dihydropyridin-3-yl)methyl]carbamoyl}-5-[ethyl(oxan-4-yl)amino]-4-methylphenyl)phenoxy]butoxy}-4-methyl-1,3-thiazol-5-yl)phenyl]methyl}-4-hydroxy-1-[(2S)-3-methyl-2-(1-oxo-2,3-dihydro-1H-isoindol-2-yl)butanoyl]pyrrolidine-2-carboxamide |
| 41 | 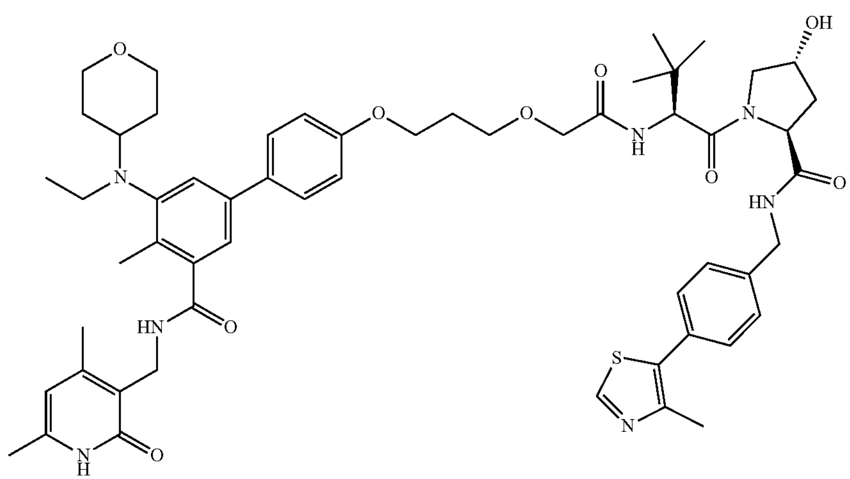 [SMILES: CCN(c1cc(-c2ccc(OCCCOCC(=O)N[C@H](C(=O)N3C[C@H](O)C[C@H]3C(=O)NCc3ccc(-c4scnc4C)cc3)C(C)(C)C)cc2)cc(C(=O)NCc2c(C)cc(C)[nH]c2=O)c1C)C1CCOCC1] | (M + 2H)+/2 = 509.8 | (2S,4R)-1-[(2S)-2-(2-{3-[4-(3-{[(4,6-dimethyl-2-oxo-1,2-dihydropyridin-3-yl)methyl]carbamoyl}-5-[ethyl(oxan-4-yl)amino]-4-methylphenyl)phenoxy]propoxy}acetamido)-3,3-dimethylbutanoyl]-4-hydroxy-N-{[4-(4-methyl-1,3-thiazol-5-yl)phenyl]methyl}pyrrolidine-2-carboxamide |

TABLE 1-continued

Exemplary compounds of the present disclosure

| Ex # | Structure | Mass Spec (M + H)+ unless otherwise noted | Name |
|---|---|---|---|
| 42 | 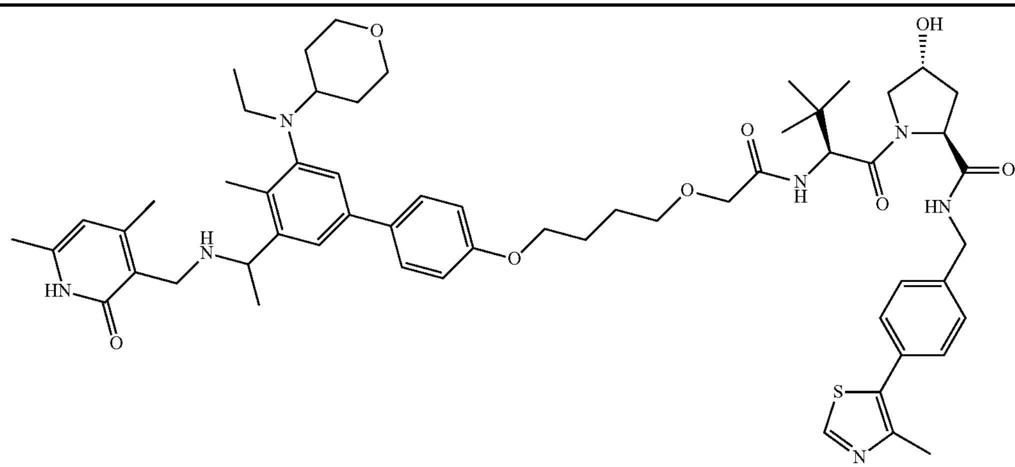 | $(M + 2H)^+/2 = 516.8$ | (2S,4R)-1-[(2S)-2-(2-{4-[4-(3-{[(4,6-dimethyl-2-oxo-1,2-dihydropyridin-3-yl)methyl]carbamoyl}-5-[ethyl(oxan-4-yl)amino]-4-methylphenyl)phenoxy]butoxy}acetamido)-3,3-dimethylbutanoyl]-4-hydroxy-N-{[4-(4-methyl-1,3-thiazol-5-yl)phenyl]methyl}pyrrolidine-2-carboxamide |
| 43 | 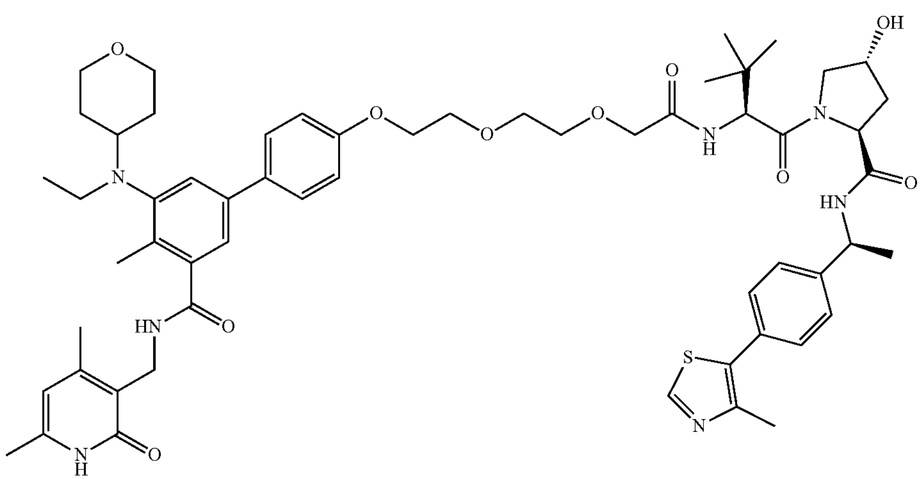 [SMILES: CCN(c1cc(-c2ccc(OCCOCCOCC(=O)N[C@H](C(=O)N3C[C@H](O)C[C@H]3C(=O)N[C@@H](C)c3ccc(-c4scnc4C)cc3)C(C)(C)C)cc2)cc(C(=O)NCc2c(C)cc(C)[nH]c2=O)c1C)C1CCOCC1] | 1062.5 | (2S,4R)-1-[(2S)-2-[2-(2-{2-[4-(3-{[(4,6-dimethyl-2-oxo-1,2-dihydropyridin-3-yl)methyl]carbamoyl}-5-[ethyl(oxan-4-yl)amino]-4-methylphenyl)phenoxy]ethoxy}ethoxy)acetamido]-3,3-dimethylbutanoyl]-4-hydroxy-N-[(1S)-1-[4-(4-methyl-1,3-thiazol-5-yl)phenyl]ethyl]pyrrolidine-2-carboxamide |

TABLE 1-continued
Exemplary compounds of the present disclosure
| Ex # | Structure | Mass Spec (M + H)+ unless otherwise noted | Name |
|---|---|---|---|
| 44 | 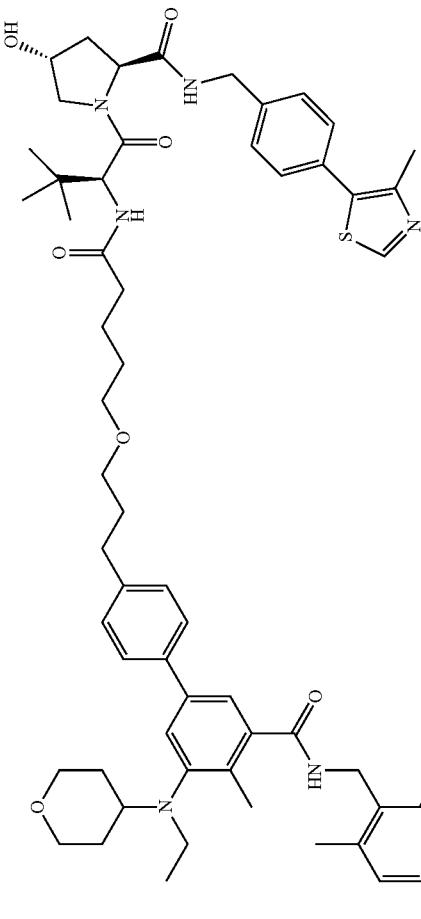 | (M + 3H)+/3 = 349.0 | (2S,4R)-1-[(2S)-2-(5-{3-[4-(3-{[(4,6-dimethyl-2-oxo-1,2-dihydropyridin-3-yl)methyl]carbamoyl}-5-[ethyl(oxan-4-yl)amino]-4-methylphenyl)phenyl]propoxy}pentanamido)-3,3-dimethylbutanoyl]-4-hydroxy-N-{[4-(4-methyl-1,3-thiazol-5-yl)phenyl]methyl}pyrrolidine-2-carboxamide |

TABLE 1-continued

Exemplary compounds of the present disclosure

| Ex # | Structure | Mass Spec (M + H)+ unless otherwise noted | Name |
|---|---|---|---|
| 45 | 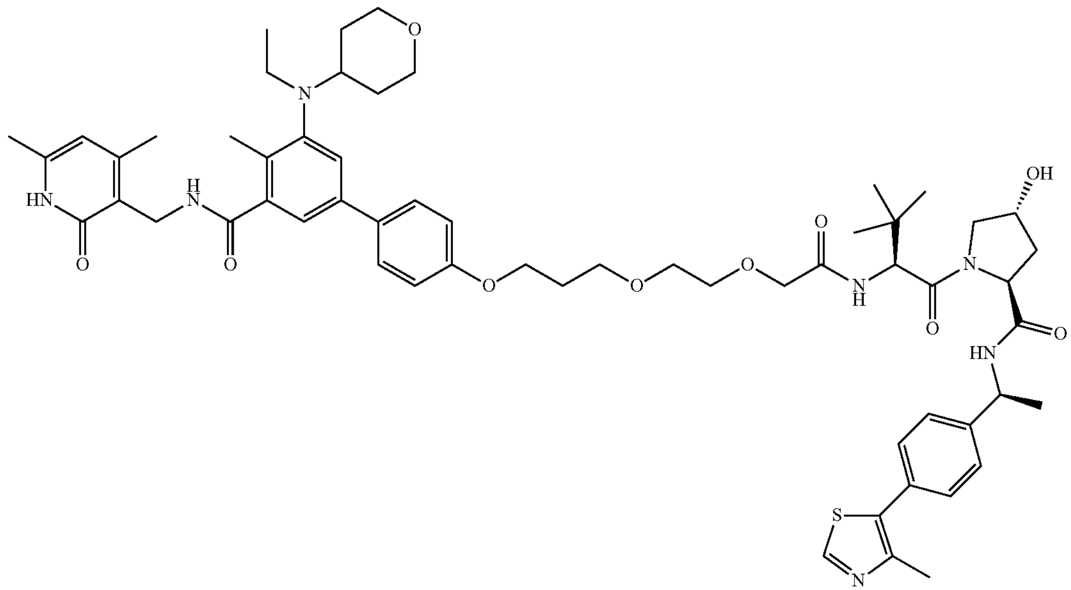 [SMILES: CCN(c1cc(-c2ccc(OCCCOCCOCC(=O)N[C@H](C(=O)N3C[C@H](O)C[C@H]3C(=O)N[C@@H](C)c3ccc(-c4scnc4C)cc3)C(C)(C)C)cc2)cc(C(=O)NCc2c(C)cc(C)[nH]c2=O)c1C)C1CCOCC1] | $(M + 2H)^+/2 = 531.8$ | (2S,4R)-1-[(2S)-2-[2-(2-{3-[4-(3-{[(4,6-dimethyl-2-oxo-1,2-dihydropyridin-3-yl)methyl]carbamoyl}-5-[ethyl(oxan-4-yl)amino]-4-methylphenyl)phenoxy]propoxy}ethoxy)acetamido]-3,3-dimethylbutanoyl]-4-hydroxy-N-{[4-(4-methyl-1,3-thiazol-5-yl)phenyl]methyl}pyrrolidine-2-carboxamide |

TABLE 1-continued

Exemplary compounds of the present disclosure

| Ex # | Structure | Mass Spec (M + H)+ unless otherwise noted | Name |
|---|---|---|---|
| 46 | 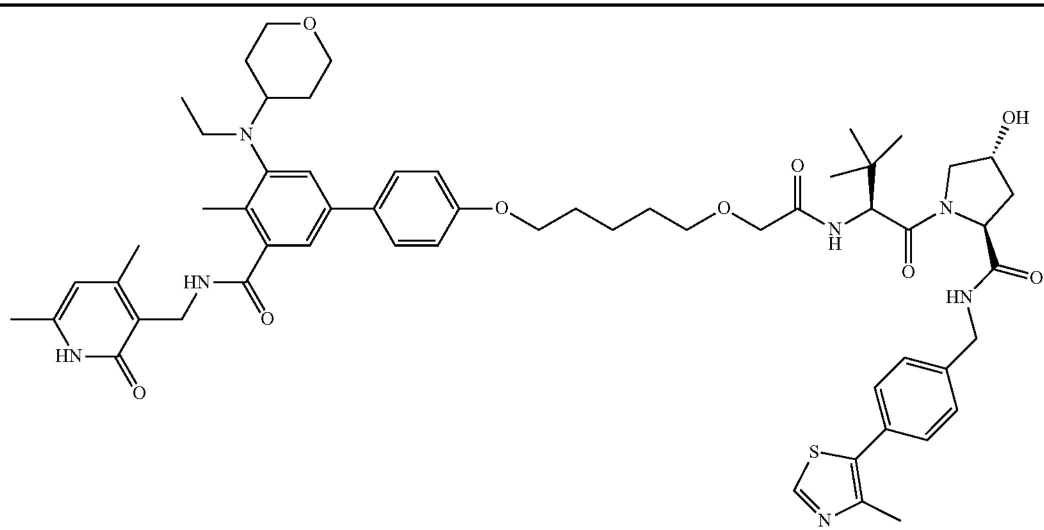 | (M + 2H)+/2 = 523.8 | (2S,4R)-1-[(2S)-2-[2-(3-[4-(3-{[(4,6-dimethyl-2-oxo-1,2-dihydropyridin-3-yl)methyl]carbamoyl}-5-[ethyl(oxan-4-yl)amino]-4-methylphenyl)phenoxy]pentyl}oxy)acetamido]-3,3-dimethylbutanoyl]-4-hydroxy-N-{[4-(4-methyl-1,3-thiazol-5-yl)phenyl]methyl}pyrrolidine-2-carboxamide |
| 47 | 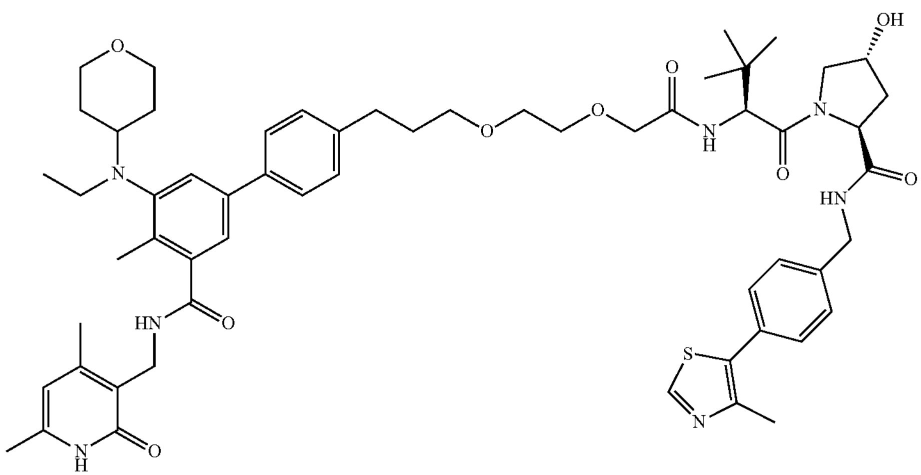 [SMILES: CCN(c1cc(-c2ccc(CCCOCCOCC(=O)N[C@H](C(=O)N3C[C@H](O)C[C@H]3C(=O)NCc3ccc(-c4scnc4C)cc3)C(C)(C)C)cc2)cc(C(=O)NCc2c(C)cc(C)[nH]c2=O)c1C)C1CCOCC1] | (M + 2H)+/2 = 523.9 | (2S,4R)-1-[(2S)-2-[2-(2-{3-[4-(3-{[(4,6-dimethyl-2-oxo-1,2-dihydropyridin-3-yl)methyl]carbamoyl}-5-[ethyl(oxan-4-yl)amino]-4-methylphenyl)phenyl]propoxy}ethoxy)acetamido]-3,3-dimethylbutanoyl]-4-hydroxy-N-{[4-(4-methyl-1,3-thiazol-5-yl)phenyl]methyl}pyrrolidine-2-carboxamide |

TABLE 1-continued

Exemplary compounds of the present disclosure

| Ex # | Structure | Mass Spec (M + H)+ unless otherwise noted | Name |
|---|---|---|---|
| 48 | 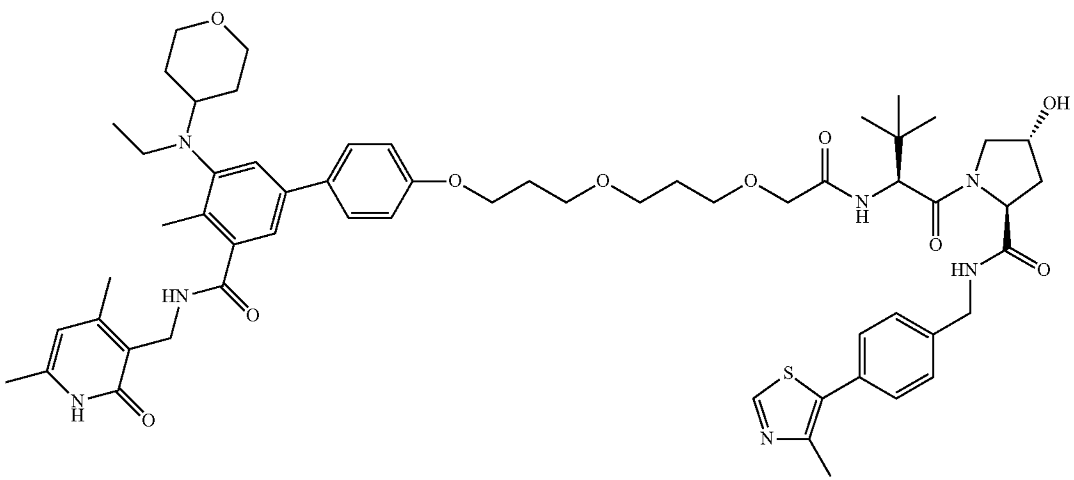 [SMILES: CCN(c1cc(-c2ccc(OCCCOCCCOCC(=O)N[C@H](C(=O)N3C[C@H](O)C[C@H]3C(=O)NCc3ccc(-c4scnc4C)cc3)C(C)(C)C)cc2)cc(C(=O)NCc2c(C)cc(C)[nH]c2=O)c1C)C1CCOCC1] | 1076.4 | (2S,4R)-1-[(2S)-2-[2-(3-{3-[4-(3-{[(4,6-dimethyl-2-oxo-1,2-dihydropyridin-3-yl)methyl]carbamoyl}-5-[ethyl(oxan-4-yl)amino]-4-methylphenyl)phenoxy]propoxy}propoxy)acetamido]-3,3-dimethylbutanoyl]-4-hydroxy-N-{[4-(4-methyl-1,3-thiazol-5-yl)phenyl]methyl}pyrrolidine-2-carboxamide |
| 49 | 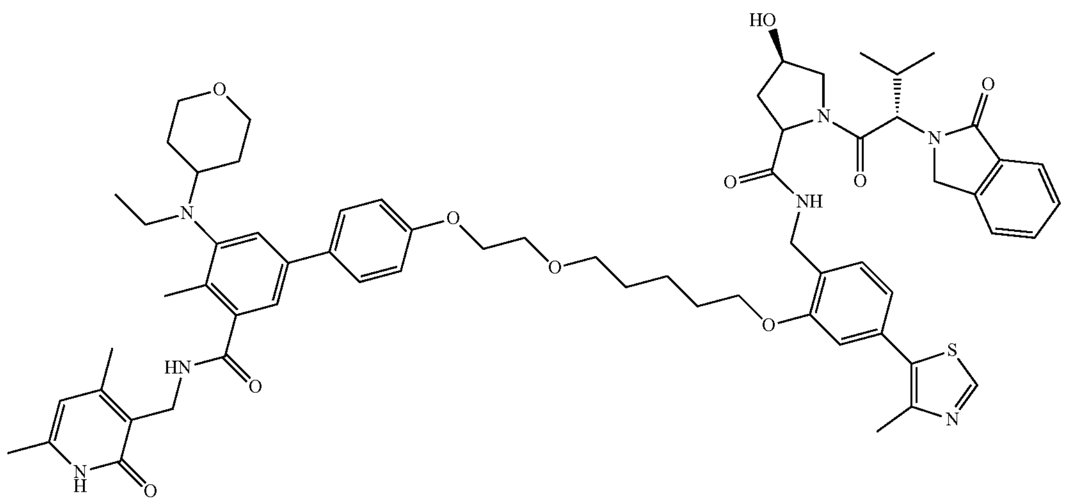 | (M + 2H)+/2 = 576.0 | (2S,4R)-N-({2-[(5-{2-[4-(3-{[(4,6-dimethyl-2-oxo-1,2-dihydropyridin-3-yl)methyl]carbamoyl}-5-[ethyl(oxan-4-yl)amino]-4-methylphenyl)phenoxy]ethoxy}pentyl)oxy]-4-(4-methyl-1,3-thiazol-5-yl)phenyl}methyl)-4-hydroxy-1-[(2S)-3-methyl-2-(1-oxo-2,3-dihydro-1H-isoindol-2-yl)butanoyl]pyrrolidine-2-carboxamide |

TABLE 1-continued
Exemplary compounds of the present disclosure
| Ex # | Structure | Mass Spec (M + H)+ unless otherwise noted | Name |
|---|---|---|---|
| 50 | 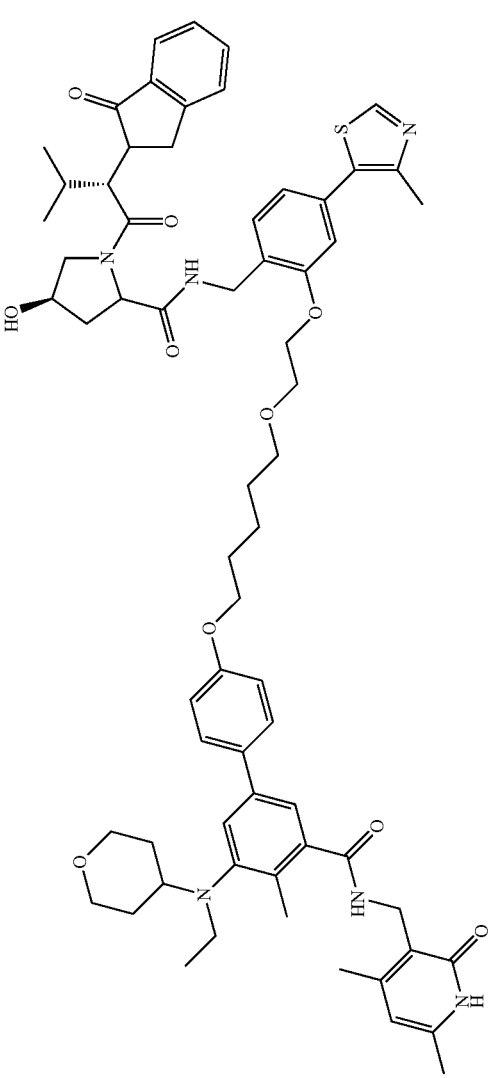 | 1150.4 | (2S,4R)-N-({2-[2-({5-[4-(3-{[(4,6-dimethyl-2-oxo-1,2-dihydropyridin-3-yl)methyl]carbamoyl}-5-[ethyl(oxan-4-yl)amino]-4-methylphenyl)phenoxy]pentyl}oxy)ethoxy]-4-(4-methyl-1,3-thiazol-5-yl)phenyl]methyl)-4-hydroxy-1-[(2S)-3-methyl-2-(1-oxo-2,3-dihydro-1H-isoindol-2-yl)butanoyl]pyrrolidine-2-carboxamide |

TABLE 1-continued

Exemplary compounds of the present disclosure

| Ex # | Structure | Mass Spec (M + H)+ unless otherwise noted | Name |
|---|---|---|---|
| 51 | 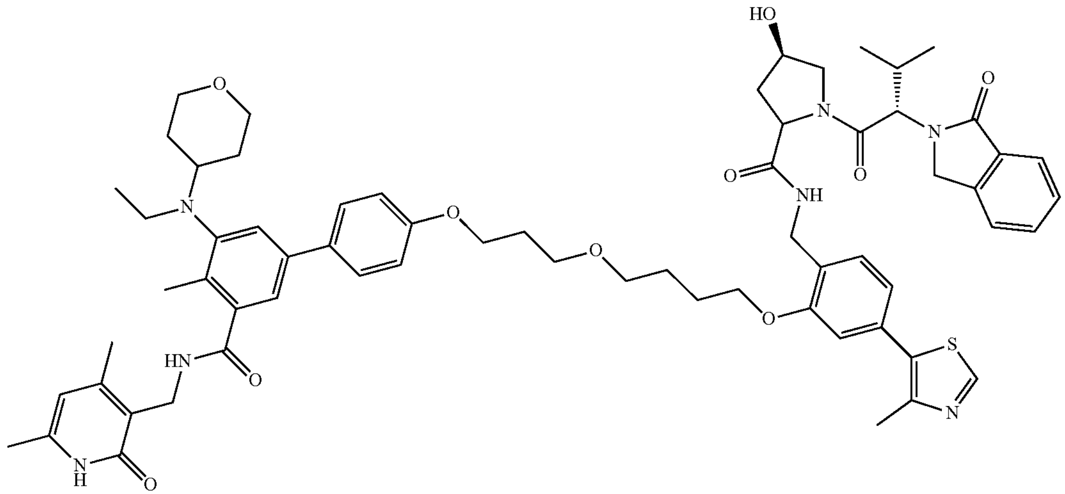 | (M + 2H)+/2 = 575.9 | (2S,4R)-N-{[2-(4-{3-[4-(3-{[(4,6-dimethyl-2-oxo-1,2-dihydropyridin-3-yl)methyl]carbamoyl}-5-[ethyl(oxan-4-yl)amino]-4-methylphenyl)phenoxy]propoxy}butoxy)-4-(4-methyl-1,3-thiazol-5-yl)phenyl]methyl}-4-hydroxy-1-[(2S)-3-methyl-2-(1-oxo-2,3-dihydro-1H-isoindol-2-yl)butanoyl]pyrrolidine-2-carboxamide |
| 52 | 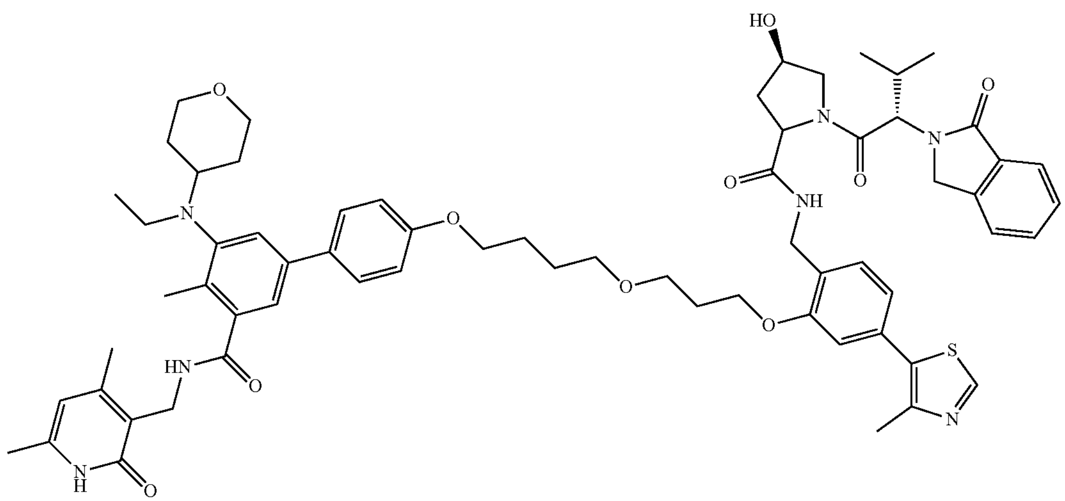 [SMILES: CCN(c1cc(-c2ccc(OCCCOCCCCOc3cc(-c4scnc4C)ccc3CNC(=O)C3C[C@@H](O)CN3C(=O)[C@H](C(C)C)N3Cc4ccccc4C3=O)cc2)cc(C(=O)NCc2c(C)cc(C)[nH]c2=O)c1C)C1CCOCC1] | (M + 2H)+/2 = 575.8 | (2S,4R)-N-{[2-(3-{4-[3-{[(4,6-dimethyl-2-oxo-1,2-dihydropyridin-3-yl)methyl]carbamoyl}-5-[ethyl(oxan-4-yl)amino]-4-methylphenyl)phenoxy]butoxy}propoxy)-4-(4-methyl-1,3-thiazol-5-yl)phenyl]methyl}-4-hydroxy-1-[(2S)-3-methyl-2-(1-oxo-2,3-dihydro-1H-isoindol-2-yl)butanoyl]pyrrolidine-2-carboxamide |

TABLE 1-continued

Exemplary compounds of the present disclosure

| Ex # | Structure | Mass Spec (M + H)+ unless otherwise noted | Name |
|---|---|---|---|
| 53 | 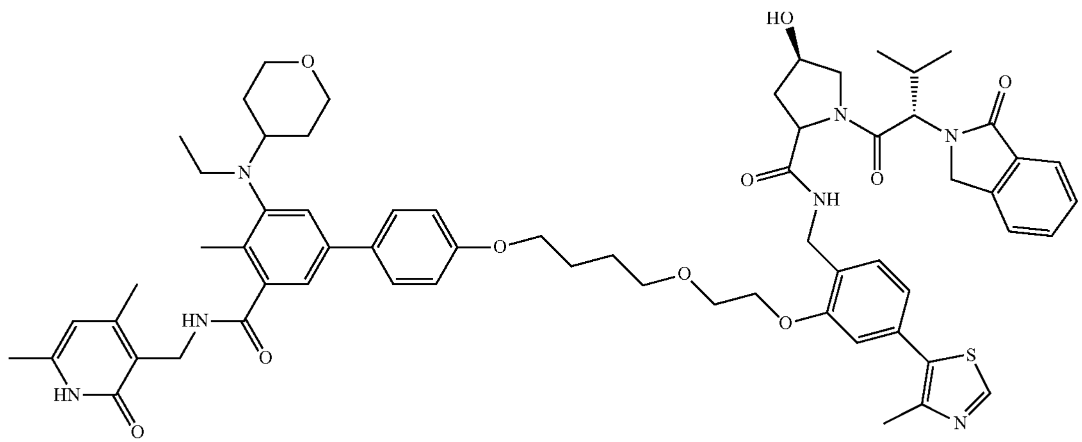 [SMILES: CCN(c1cc(-c2ccc(OCCCCOCCOc3cc(-c4scnc4C)ccc3CNC(=O)C3C[C@@H](O)CN3C(=O)[C@H](C(C)C)N3Cc4ccccc4C3=O)cc2)cc(C(=O)NCc2c(C)cc(C)[nH]c2=O)c1C)C1CCOCC1] | 1136.4 | (2S,4R)-N-{[2-(2-{4-[4-(3-{[(4,6-dimethyl-2-oxo-1,2-dihydropyridin-3-yl)methyl]carbamoyl}-5-[ethyl(oxan-4-yl)amino]-4-methylphenyl)phenoxy]butoxy}ethoxy)-4-(4-methyl-1,3-thiazol-5-yl)phenyl]methyl}-4-hydroxy-1-[(2S)-3-methyl-2-(1-oxo-2,3-dihydro-1H-isoindol-2-yl)butanoyl]pyrrolidine-2-carboxamide |
| 54 | 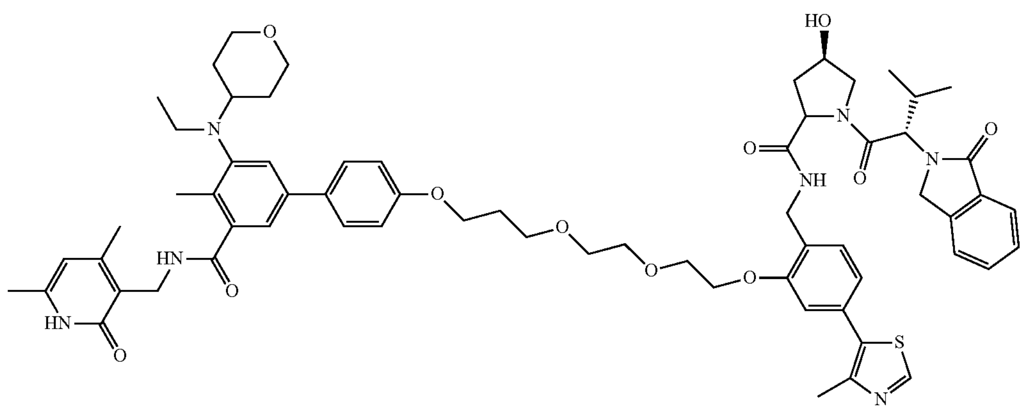 [SMILES: CCN(c1cc(-c2ccc(OCCCOCCOCCOc3cc(-c4scnc4C)ccc3CNC(=O)C3C[C@@H](O)CN3C(=O)[C@H](C(C)C)N3Cc4ccccc4C3=O)cc2)cc(C(=O)NCc2c(C)cc(C)[nH]c2=O)c1C)C1CCOCC1] | (M + 2H)+/2 = 538.8 | (2S,4R)-N-({2-[2-(2-{3-[4-(3-{[(4,6-dimethyl-2-oxo-1,2-dihydropyridin-3-yl)methyl]carbamoyl}-5-[ethyl(oxan-4-yl)amino]-4-methylphenyl)phenoxy]propoxy}ethoxy)ethoxy]-4-(4-methyl-1,3-thiazol-5-yl)phenyl}methyl)-4-hydroxy-1-[(2S)-3-methyl-2-(1-oxo-2,3-dihydro-1H-isoindol-2-yl)butanoyl]pyrrolidine-2-carboxamide |

TABLE 1-continued
Exemplary compounds of the present disclosure
| Ex # | Structure | Mass Spec (M + H)+ unless otherwise noted | Name |
|---|---|---|---|
| 55 | 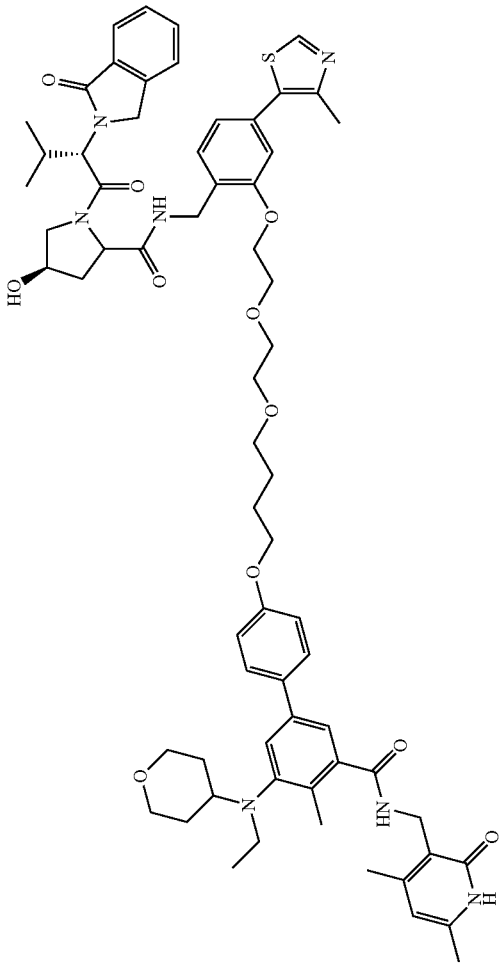 | (M + 2H)+/2 = 590.8 | (2S,4R)-N-({2-[2-(2-{4-[4-(3-{[(4,6-dimethyl-2-oxo-1,2-dihydropyridin-3-yl)methyl]carbamoyl}-5-[ethyl(oxan-4-yl)amino]-4-methylphenyl)phenoxy]butoxy}ethoxy)ethoxy]-4-(4-methyl-1,3-thiazol-5-yl)phenyl}methyl)-4-hydroxy-1-[(2S)-3-methyl-2-(1-oxo-2,3-dihydro-1H-isoindol-2-yl)butanoyl]pyrrolidine-2-carboxamide |

TABLE 1-continued

Exemplary compounds of the present disclosure

| Ex # | Structure | Mass Spec (M + H)+ unless otherwise noted | Name |
|---|---|---|---|
| 56 | 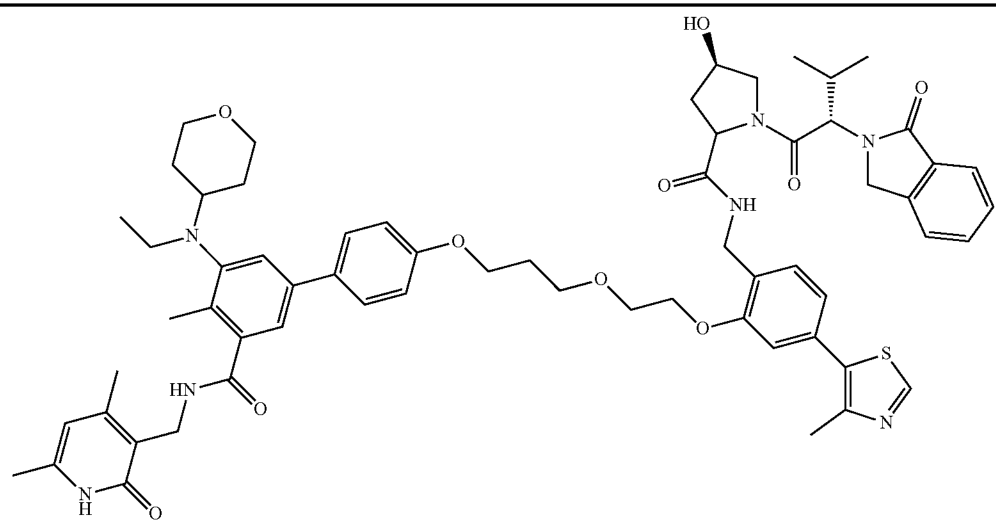 | 1122.4 | (2S,4R)-N-{[2-(2-{3-[4-(3-{[(4,6-dimethyl-2-oxo-1,2-dihydropyridin-3-yl)methyl]carbamoyl}-5-[ethyl(oxan-4-yl)amino]-4-methylphenyl)phenoxy]propoxy}ethoxy)-4-(4-methyl-1,3-thiazol-5-yl)phenyl]methyl}-4-hydroxy-1-[(2S)-3-methyl-2-(1-oxo-2,3-dihydro-1H-isoindol-2-yl)butanoyl]pyrrolidine-2-carboxamide |
| 57 | 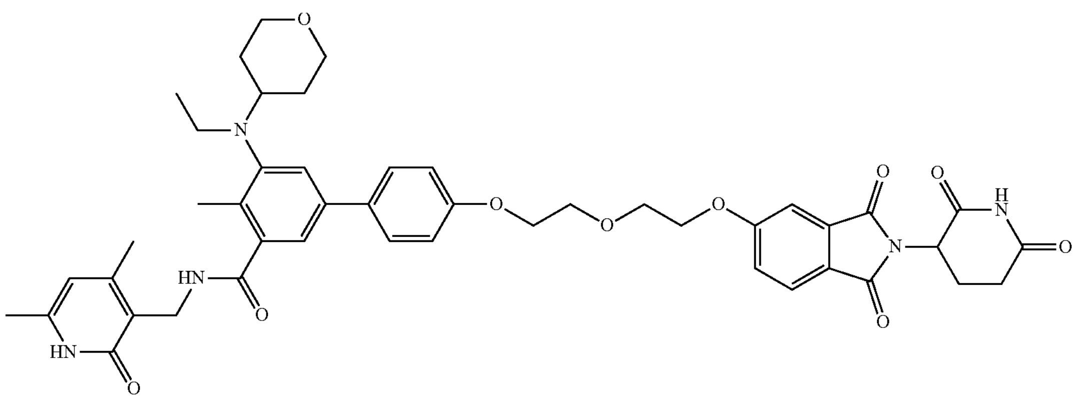 [SMILES: CCN(c1cc(-c2ccc(OCCOCCOc3ccc4c(c3)C(=O)N(C3CCC(=O)NC3=O)C4=O)cc2)cc(C(=O)NCc2c(C)cc(C)[nH]c2=O)c1C)C1CCOCC1] | 834.3 | N-[(4,6-dimethyl-2-oxo-1,2-dihydropyridin-3-yl)methyl]-5-{4-[2-(2-{[2-(2,6-dioxopiperidin-3-yl)-1,3-dioxo-2,3-dihydro-1H-isoindol-5-yl]oxy}ethoxy)ethoxy]phenyl}-3-[ethyl(oxan-4-yl)amino]-2-methylbenzamide |

TABLE 1-continued

Exemplary compounds of the present disclosure

| Ex # | Structure | Mass Spec (M + H)+ unless otherwise noted | Name |
|---|---|---|---|
| 58 | 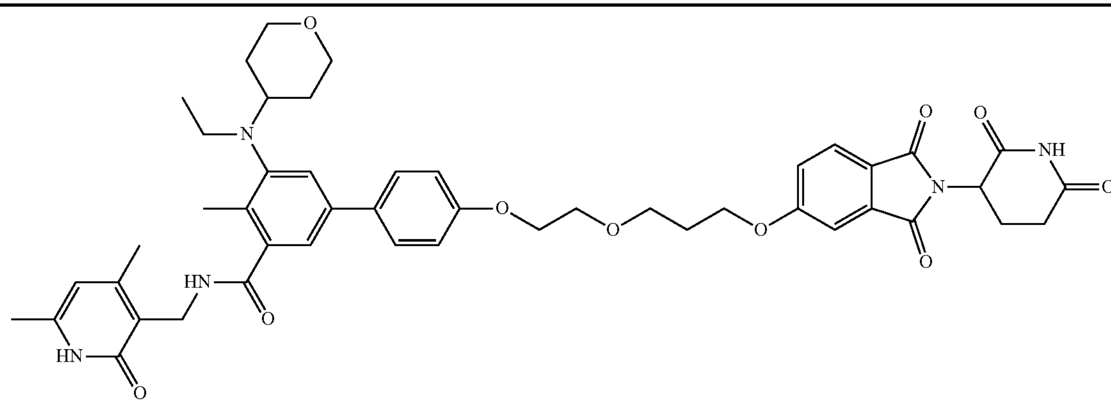 | 848.3 | N-[(4,6-dimethyl-2-oxo-1,2-dihydropyridin-3-yl)methyl]-5-{4-[2-(3-{[2-(2,6-dioxopiperidin-3-yl)-1,3-dioxo-2,3-dihydro-1H-isoindol-5-yl]oxy}propoxy)ethoxy]phenyl}-3-[ethyl(oxan-4-yl)amino]-2-methylbenzamide |
| 59 | 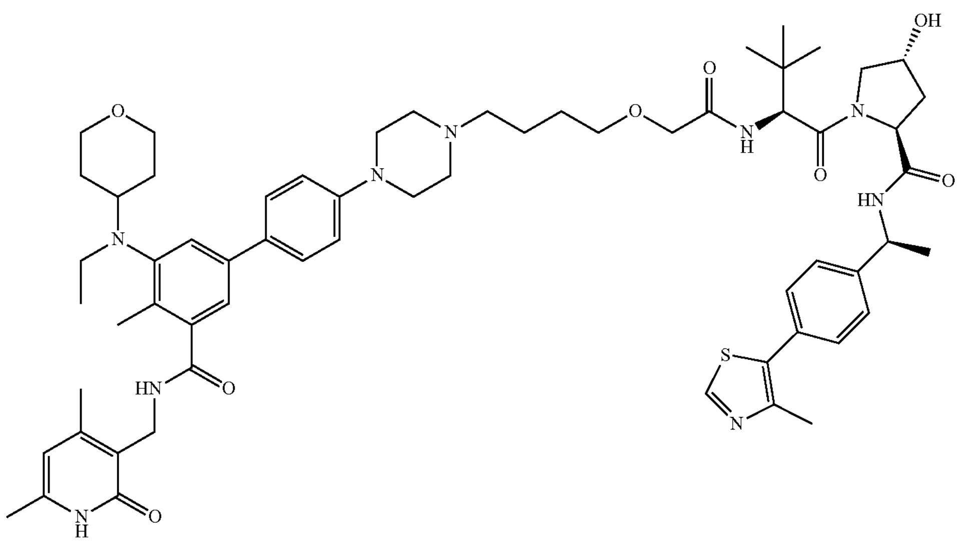 [SMILES: CCN(c1cc(-c2ccc(N3CCN(CCCCOCC(=O)N[C@H](C(=O)N4C[C@H](O)C[C@H]4C(=O)N[C@@H](C)c4ccc(-c5scnc5C)cc4)C(C)(C)C)CC3)cc2)cc(C(=O)NCc2c(C)cc(C)[nH]c2=O)c1C)C1CCOCC1] | 1114.89 | (2S,4R)-1-((S)-2-(2-(4-(4-(3'-(((4,6-dimethyl-2-oxo-1,2-dihydropyridin-3-yl)methyl)carbamoyl)-5'-(ethyl(tetrahydro-2H-pyran-4-yl)amino)-4'-methyl-[1,1'-biphenyl]-4-yl)piperazin-1-yl)butoxy)acetamido)-3,3-dimethylbutanoyl)-4-hydroxy-N-((S)-1-(4-(4-methylthiazol-5-yl)phenyl)ethyl)pyrrolidine-2-carboxamide |

TABLE 1-continued

Exemplary compounds of the present disclosure

| Ex # | Structure | Mass Spec (M + H)+ unless otherwise noted | Name |
|---|---|---|---|
| 60 | 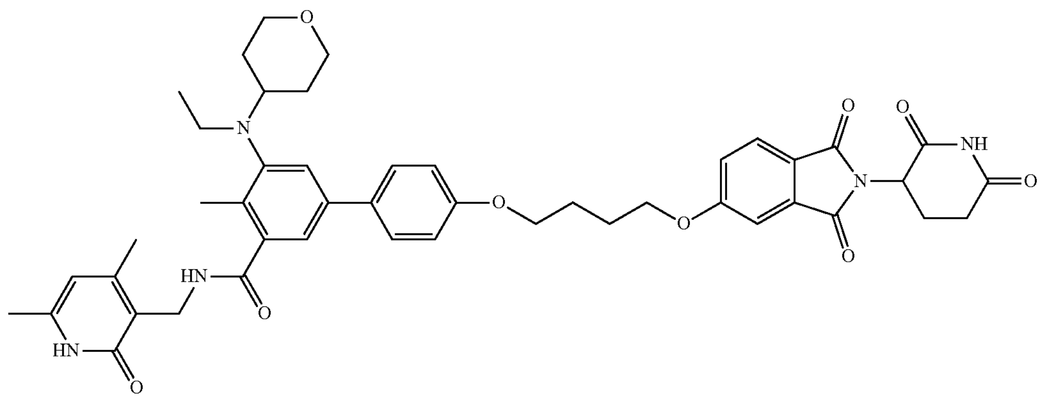 [SMILES: CCN(c1cc(-c2ccc(OCCCCOc3ccc4c(c3)C(=O)N(C3CCC(=O)NC3=O)C4=O)cc2)cc(C(=O)NCc2c(C)cc(C)[nH]c2=O)c1C)C1CCOCC1] | 818.3 | N-[(4,6-dimethyl-2-oxo-1,2-dihydropyridin-3-yl)methyl]-5-[4-(4-{[2-(2,6-dioxopiperidin-3-yl)-1,3-dioxo-2,3-dihydro-1H-isoindol-5-yl]oxy}butoxy)phenyl]-3-[ethyl(oxan-4-yl)amino]-2-methylbenzamide |
| 61 | 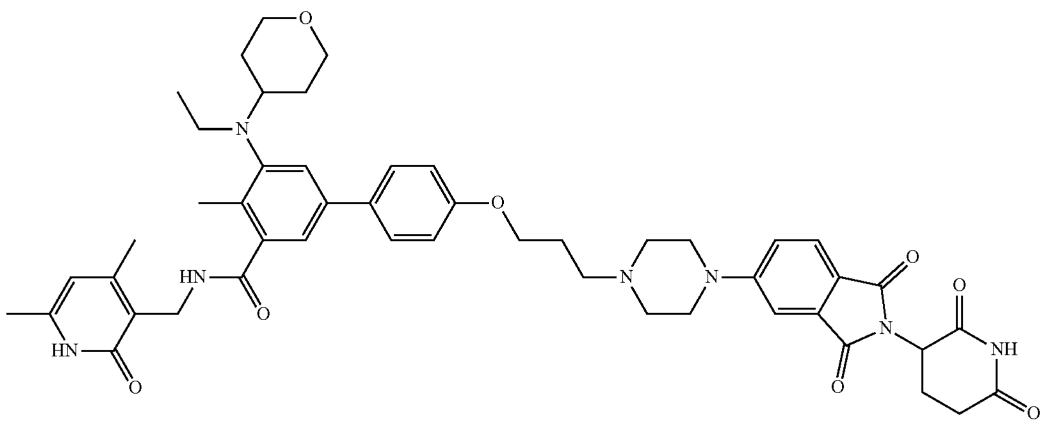 [SMILES: CCN(c1cc(-c2ccc(OCCCN3CCN(c4ccc5c(c4)C(=O)N(C4CCC(=O)NC4=O)C5=O)CC3)cc2)cc(C(=O)NCc2c(C)cc(C)[nH]c2=O)c1C)C1CCOCC1] | (M + 2H)+/2 = 436.9 | N-[(4,6-dimethyl-2-oxo-1,2-dihydropyridin-3-yl)methyl]-5-[4-(3-{4-[2-(2,6-dioxopiperidin-3-yl)-1,3-dioxo-2,3-dihydro-1H-isoindol-5-yl]piperazin-1-yl}propoxy)phenyl]-3-[ethyl(oxan-4-yl)amino]-2-methylbenzamide |

TABLE 1-continued

Exemplary compounds of the present disclosure

| Ex # | Structure | Mass Spec (M + H)+ unless otherwise noted | Name |
|---|---|---|---|
| 62 | 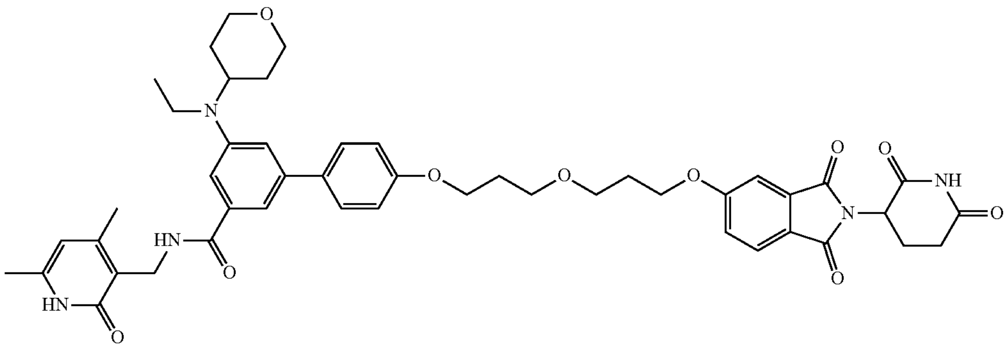 [SMILES: CCN(c1cc(C(=O)NCc2c(C)cc(C)[nH]c2=O)cc(-c2ccc(OCCCOCCCOc3ccc4c(c3)C(=O)N(C3CCC(=O)NC3=O)C4=O)cc2)c1)C1CCOCC1] | 862.3 | N-[(4,6-dimethyl-2-oxo-1,2-dihydropyridin-3-yl)methyl]-5-{4-[3-(3-{[2-(2,6-dioxopiperidin-3-yl)-1,3-dioxo-2,3-dihydro-1H-isoindol-5-yl]oxy}propoxy)propoxy]phenyl}-3-[ethyl(oxan-4-yl)amino]-2-methylbenzamide |
| 63 | 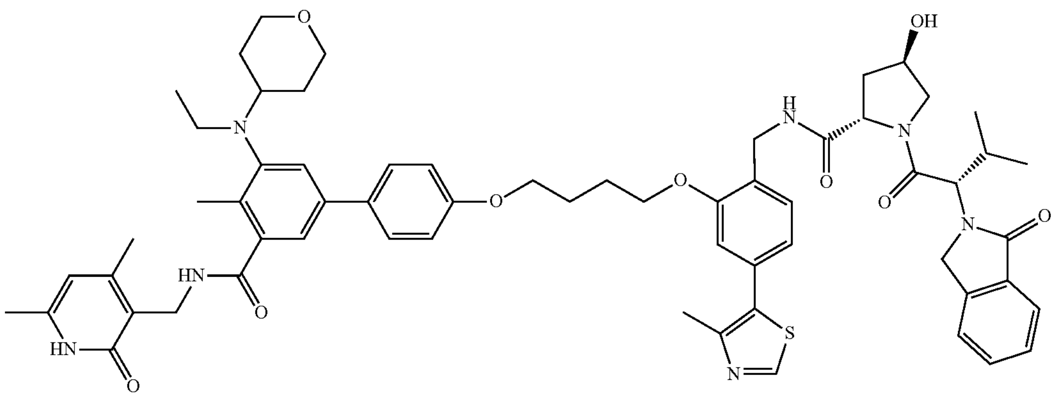 [SMILES: CCN(c1cc(-c2ccc(OCCCCOc3cc(-c4scnc4C)ccc3CNC(=O)[C@@H]3C[C@@H](O)CN3C(=O)[C@H](C(C)C)N3Cc4ccccc4C3=O)cc2)cc(C(=O)NCc2c(C)cc(C)[nH]c2=O)c1C)C1CCOCC1] | (M + 2H)+/2 = 546.9 | (2S,4R)-N-[(2-{4-[4-(3-{[(4,6-dimethyl-2-oxo-1,2-dihydropyridin-3-yl)methyl]carbamoyl}-5-[ethyl(oxan-4-yl)amino]-4-methylphenyl)phenoxy]butoxy}-4-(4-methyl-1,3-thiazol-5-yl)phenyl)methyl]-4-hydroxy-1-[(2S)-3-methyl-2-(1-oxo-2,3-dihydro-1H-isoindol-2-yl)butanoyl]pyrrolidine-2-carboxamide |

TABLE 1-continued

Exemplary compounds of the present disclosure

| Ex # | Structure | Mass Spec (M + H)+ unless otherwise noted | Name |
|---|---|---|---|
| 64 | 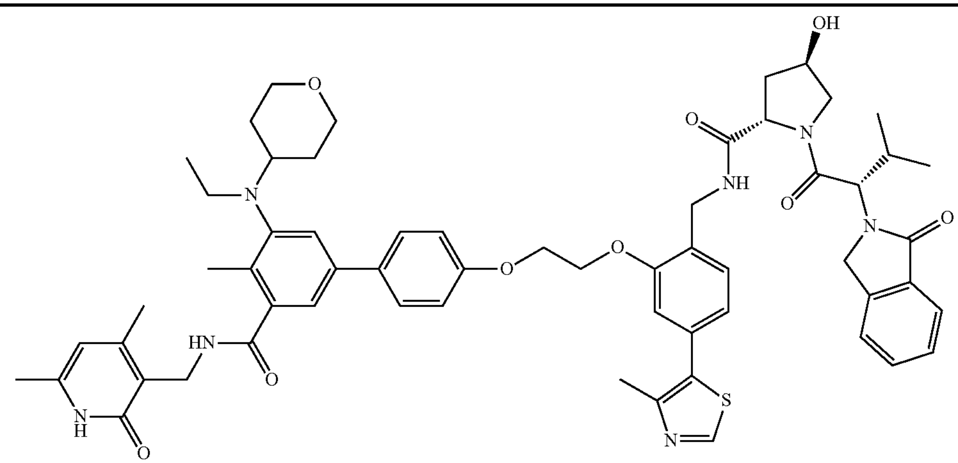 | 1064.4 | N-[(2-{2-[4-(3-{[(4,6-dimethyl-2-oxo-1,2-dihydropyridin-3-yl)methyl]carbamoyl}-5-[ethyl(oxan-4-yl)amino]-4-methylphenyl)phenoxy]ethoxy}-4-(4-methyl-1,3-thiazol-5-yl)phenyl)methyl]-4-hydroxy-1-[3-methyl-2-(1-oxo-2,3-dihydro-1H-isoindol-2-yl)butanoyl]pyrrolidine-2-carboxamide |
| 65 | 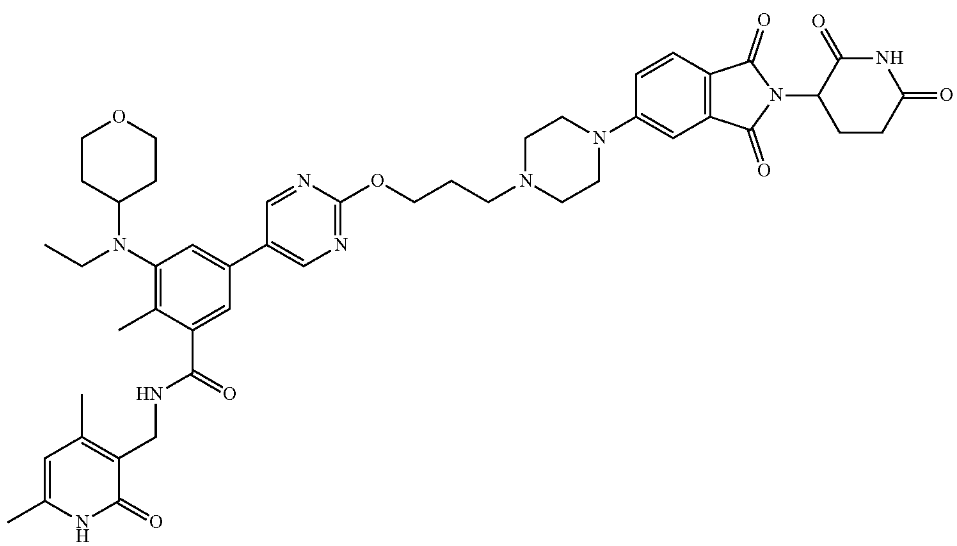 [SMILES: CCN(c1cc(-c2cnc(OCCCN3CCN(c4ccc5c(c4)C(=O)N(C4CCC(=O)NC4=O)C5=O)CC3)nc2)cc(C(=O)NCc2c(C)cc(C)[nH]c2=O)c1C)C1CCOCC1] | | N-((4,6-dimethyl-2-oxo-1,2-dihydropyridin-3-yl)methyl)-5-(2-(3-(4-(2-(2,6-dioxopiperidin-3-yl)-1,3-dioxoisoindolin-5-yl)piperazin-1-yl)propoxy)pyrimidin-5-yl)-3-(ethyl(tetrahydro-2H-pyran-4-yl)amino)-2-methylbenzamide |

TABLE 1-continued
Exemplary compounds of the present disclosure
| Ex # | Structure | Mass Spec (M + H)+ unless otherwise noted | Name |
|---|---|---|---|
| 66 | 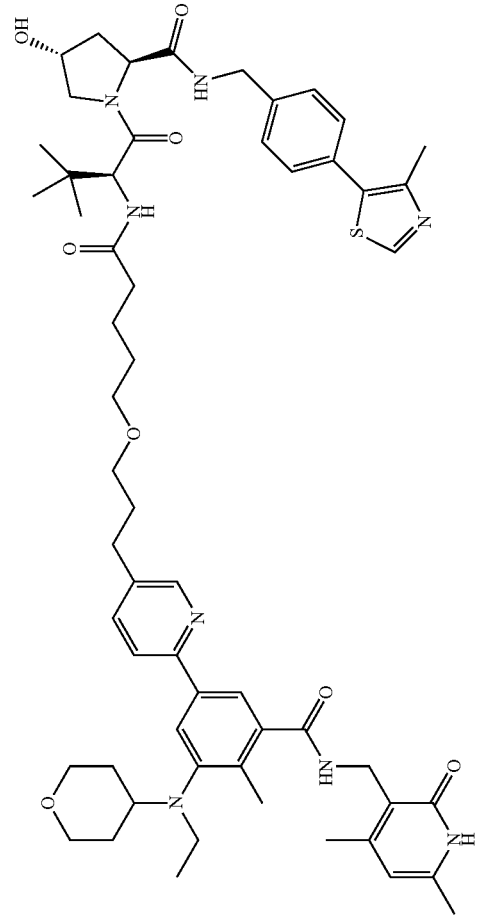 | | (2S,4R)-1-((S)-2-(5-(3-(6-(3-(((4,6-dimethyl-2-oxo-1,2-dihydropyridin-3-yl)methyl)carbamoyl)-5-(ethyl(tetrahydro-2H-pyran-4-yl)amino)-4-methylphenyl)pyridin-3-yl)propoxy)pentanamido)-3,3-dimethylbutanoyl)-4-hydroxy-N-(4-(4-methylthiazol-5-yl)benzyl)pyrrolidine-2-carboxamide |

TABLE 1-continued

Exemplary compounds of the present disclosure

| Ex # | Structure | Mass Spec (M + H)+ unless otherwise noted | Name |
|---|---|---|---|
| 67 | 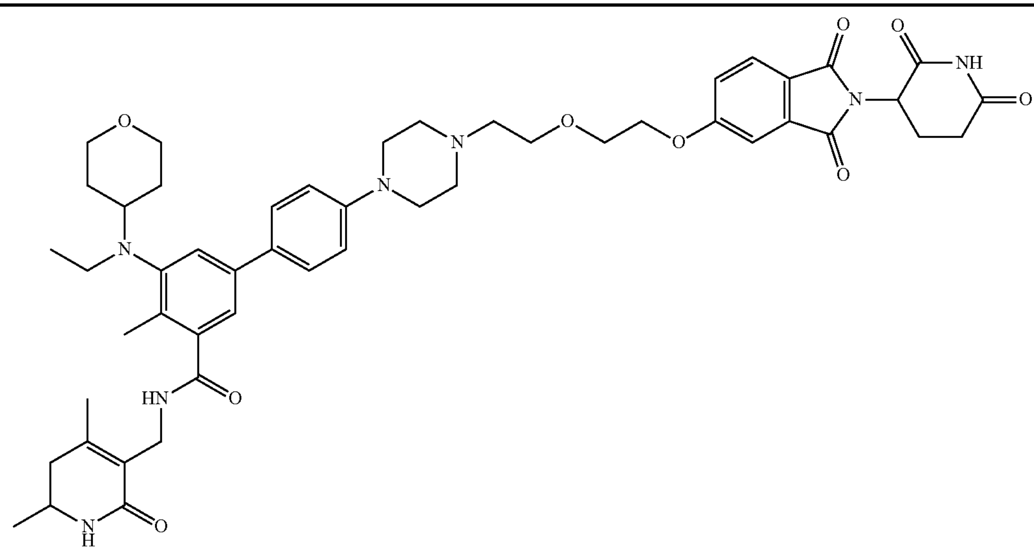 | | N-((4,6-dimethyl-2-oxo-1,2-dihydropyridin-3-yl)methyl)-4'-(4-(2-(2-((2-(2,6-dioxopiperidin-3-yl)-1,3-dioxoisoindolin-5-yl)oxy)ethoxy)ethyl)piperazin-1-yl)-5-(ethyl(tetrahydro-2H-pyran-4-yl)amino)-4-methyl-[1,1'-biphenyl]-3-carboxamide |

TABLE 1-continued

Exemplary compounds of the present disclosure

| Ex # | Structure | Mass Spec (M + H)+ unless otherwise noted | Name |
|---|---|---|---|
| 68 | 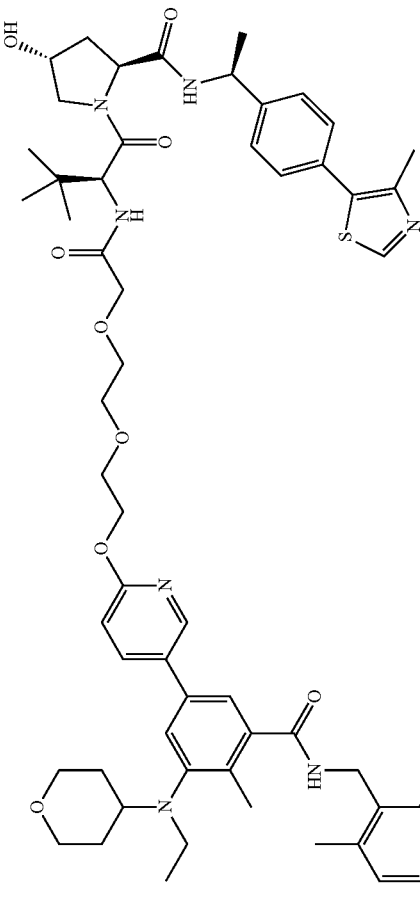 | | (2S,4R)-1-((S)-2-(2-(2-(2-((5-(3-(((4,6-dimethyl-2-oxo-1,2-dihydropyridin-3-yl)methyl)carbamoyl)-5-(ethyl(tetrahydro-2H-pyran-4-yl)amino)-4-methylphenyl)pyridin-2-yl)oxy)ethoxy)ethoxy)acetamido)-3,3-dimethylbutanoyl)-4-hydroxy-N-((S)-1-(4-(4-methylthiazol-5-yl)phenyl)ethyl)pyrrolidine-2-carboxamide |
| 69 | 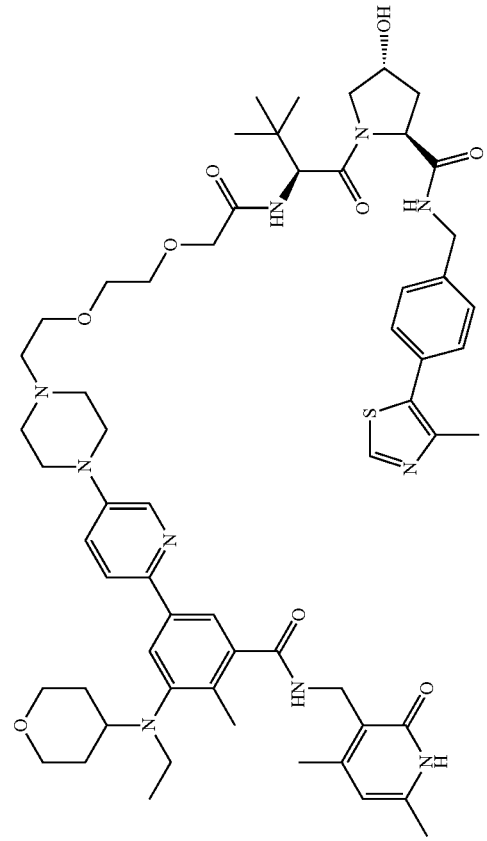 | | (2S,4R)-1-((S)-2-(2-(2-(2-(4-(6-(3-(((4,6-dimethyl-2-oxo-1,2-dihydropyridin-3-yl)methyl)carbamoyl)-5-(ethyl(tetrahydro-2H-pyran-4-yl)amino)-4-methylphenyl)pyridin-3-yl)piperazin-1-yl)ethoxy)ethoxy)acetamido)-3,3-dimethylbutanoyl)-4-hydroxy-N-(4-(4-methylthiazol-5-yl)benzyl)pyrrolidine-2-carboxamide |

TABLE 1-continued

Exemplary compounds of the present disclosure

| Ex # | Structure | Mass Spec (M + H)+ unless otherwise noted | Name |
|---|---|---|---|
| 70 | 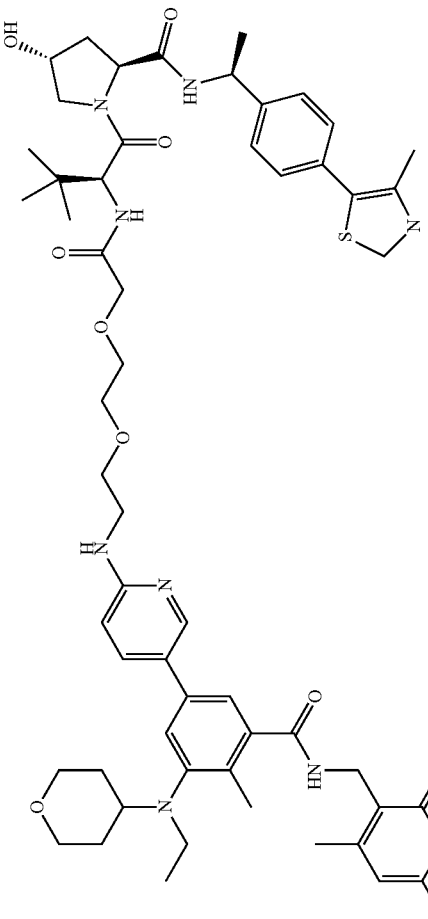 | | (2S,4R)-1-((S)-2-(2-(2-(2-((5-(3-(((4,6-dimethyl-2-oxo-1,2-dihydropyridin-3-yl)methyl)carbamoyl)-5-(ethyl(tetrahydro-2H-pyran-4-yl)amino)-4-methylphenyl)pyridin-2-yl)amino)ethoxy)ethoxy)acetamido)-3,3-dimethylbutanoyl)-4-hydroxy-N-((S)-1-(4-(4-methylthiazol-5-yl)phenyl)ethyl)pyrrolidine-2-carboxamide |
| 71 | 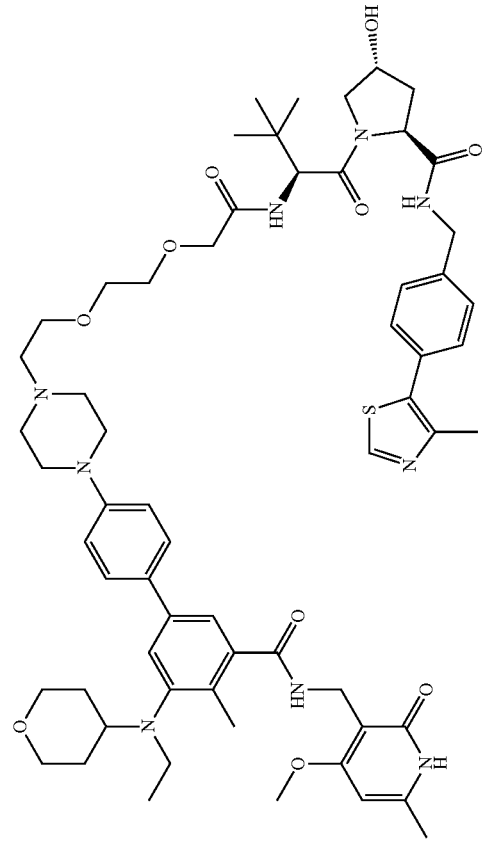 | | (2S,4R)-1-((S)-2-(2-(2-(2-(4-(3'-(((4,6-dimethyl-2-oxo-1,2-dihydropyridin-3-yl)methyl)carbamoyl)-5'-(ethyl(tetrahydro-2H-pyran-4-yl)amino)-4'-methyl-[1,1'-biphenyl]-4-yl)piperazin-1-yl)ethoxy)ethoxy)acetamido)-3,3-dimethylbutanoyl)-4-hydroxy-N-(4-(4-methylthiazol-5-yl)benzyl)pyrrolidine-2-carboxamide |

TABLE 1-continued

Exemplary compounds of the present disclosure

| Ex # | Structure | Mass Spec (M + H)+ unless otherwise noted | Name |
|---|---|---|---|
| 72 | 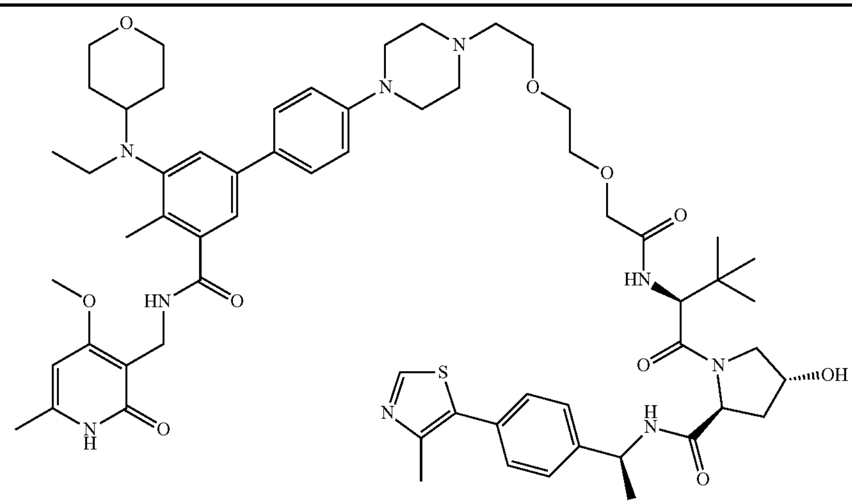 | | (2S,4R)-1-((S)-2-(2-(2-(2-(4-(3'-(((4,6-dimethyl-2-oxo-1,2-dihydropyridin-3-yl)methyl)carbamoyl)-5'-(ethyl(tetrahydro-2H-pyran-4-yl)amino)-4'-methyl-[1,1'-biphenyl]-4-yl)piperazin-1-yl)ethoxy)ethoxy)acetamido)-3,3-dimethylbutanoyl)-4-hydroxy-N-((S)-1-(4-(4-methylthiazol-5-yl)phenyl)ethyl)pyrrolidine-2-carboxamide |
| 73 | 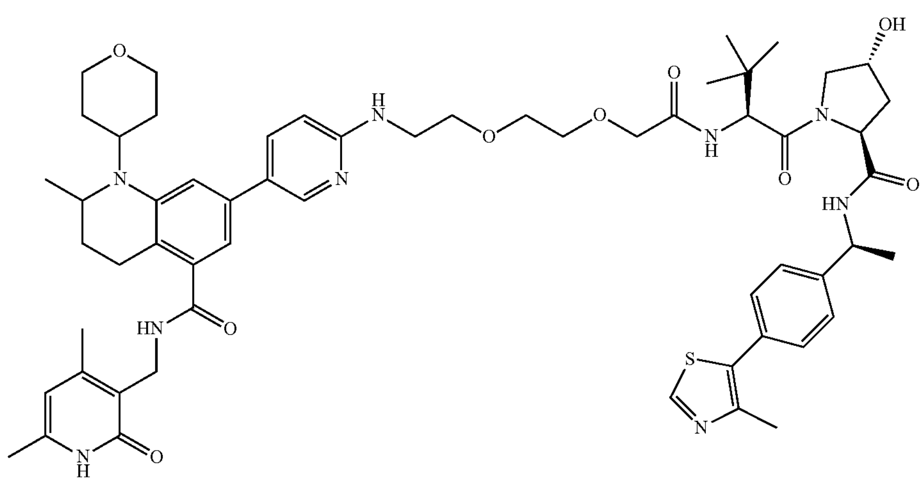 [SMILES: Cc1cc(C)c(CNC(=O)c2cc(-c3ccc(NCCOCCOCC(=O)N[C@H](C(=O)N4C[C@H](O)C[C@H]4C(=O)N[C@@H](C)c4ccc(-c5scnc5C)cc4)C(C)(C)C)nc3)cc3c2CCC(C)N3C2CCOCC2)c(=O)[nH]1] | | N-((4,6-dimethyl-2-oxo-1,2-dihydropyridin-3-yl)methyl)-7-(6-((2-(2-(2-((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-2-oxoethoxy)ethoxy)ethyl)amino)pyridin-3-yl)-2-methyl-1-(tetrahydro-2H-pyran-4-yl)-1,2,3,4-tetrahydroquinoline-5-carboxamide |

TABLE 1-continued
Exemplary compounds of the present disclosure
| Ex # | Structure | Mass Spec (M + H)+ unless otherwise noted | Name |
|---|---|---|---|
| 74 | 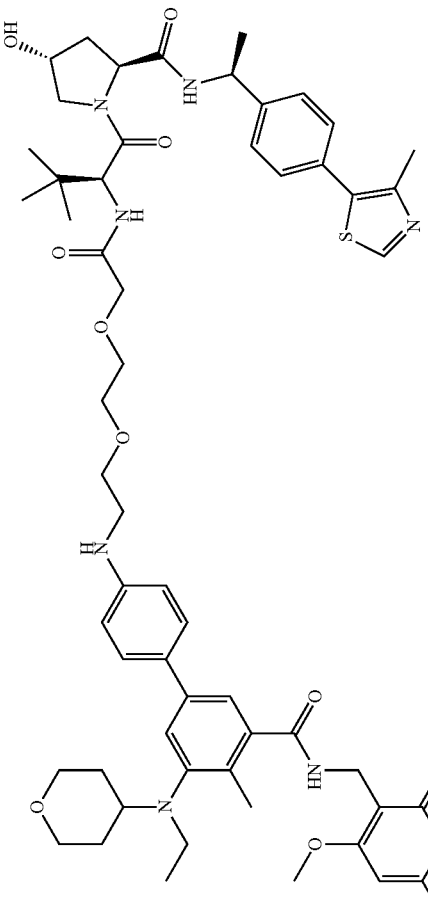 | | (2S,4R)-1-((S)-2-(2-(2-(2-((3'-(ethyl(tetrahydro-2H-pyran-4-yl)amino)-5'-(((4-methoxy-6-methyl-2-oxo-1,2-dihydropyridin-3-yl)methyl)carbamoyl)-4'-methyl-[1,1'-biphenyl]-4-yl)amino)ethoxy)ethoxy)acetamido)-3,3-dimethylbutanoyl)-4-hydroxy-N-((S)-1-(4-(4-methylthiazol-5-yl)phenyl)ethyl)pyrrolidine-2-carboxamide |

TABLE 1-continued
Exemplary compounds of the present disclosure
| Ex # | Structure | Mass Spec (M + H)+ unless otherwise noted | Name |
|---|---|---|---|
| 75 | 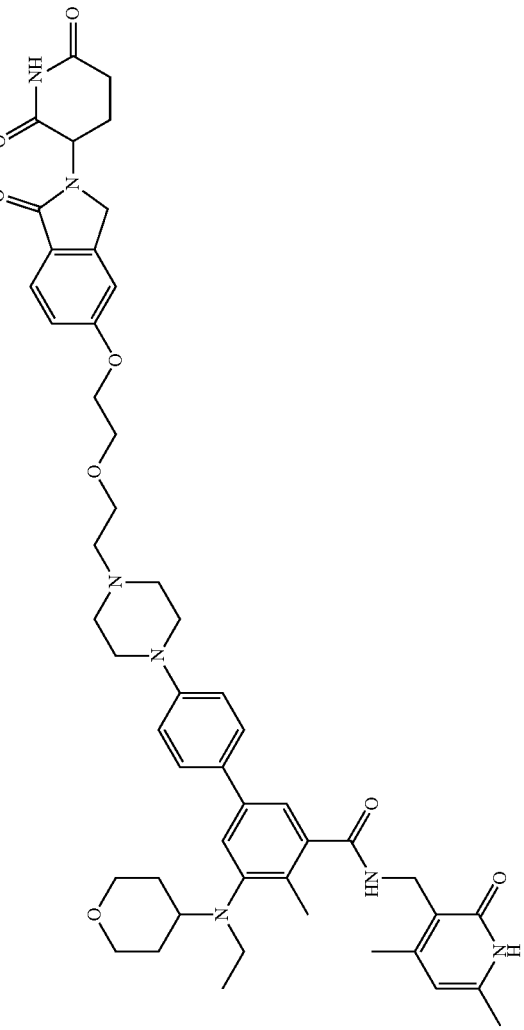 | | N-((4,6-dimethyl-2-oxo-1,2-dihydropyridin-3-yl)methyl)-4'-(4-(2-(2-((2-(2,6-dioxopiperidin-3-yl)-1-oxoisoindolin-5-yl)oxy)ethoxy)ethyl)piperazin-1-yl)-5-(ethyl(tetrahydro-2H-pyran-4-yl)amino)-4-methyl-[1,1'-biphenyl]-3-carboxamide |

TABLE 1-continued
Exemplary compounds of the present disclosure
| Ex # | Structure | Mass Spec (M + H)+ unless otherwise noted | Name |
|---|---|---|---|
| 76 | 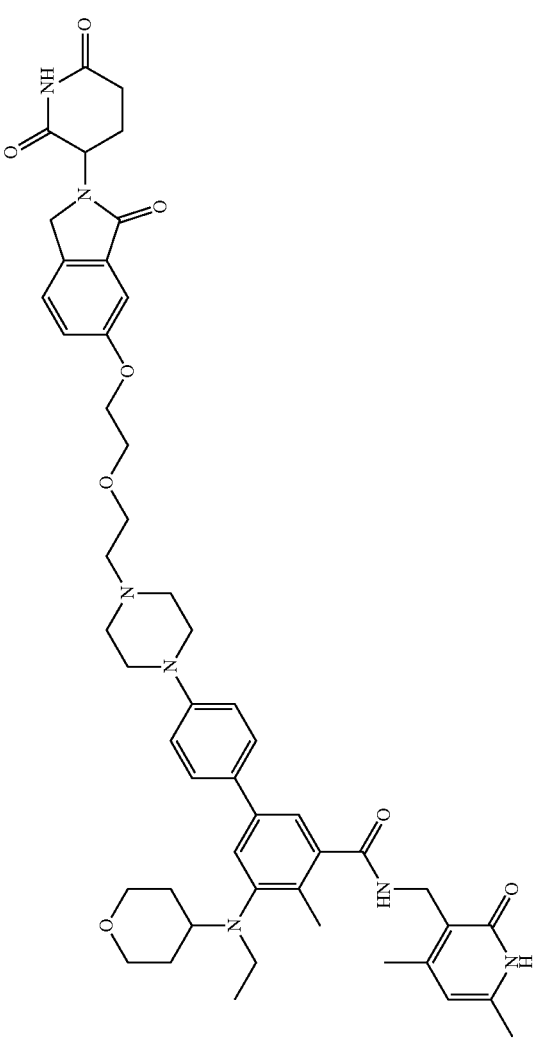 | | N-((4,6-dimethyl-2-oxo-1,2-dihydropyridin-3-yl)methyl)-4'-(4-(2-(2-((2-(2,6-dioxopiperidin-3-yl)-3-oxoisoindolin-5-yl)oxy)ethoxy)ethyl)piperazin-1-yl)-5-(ethyl(tetrahydro-2H-pyran-4-yl)amino)-4-methyl-[1,1'-biphenyl]-3-carboxamide |

TABLE 1-continued

Exemplary compounds of the present disclosure

| Ex # | Structure | Mass Spec (M + H)+ unless otherwise noted | Name |
|---|---|---|---|
| 77 | 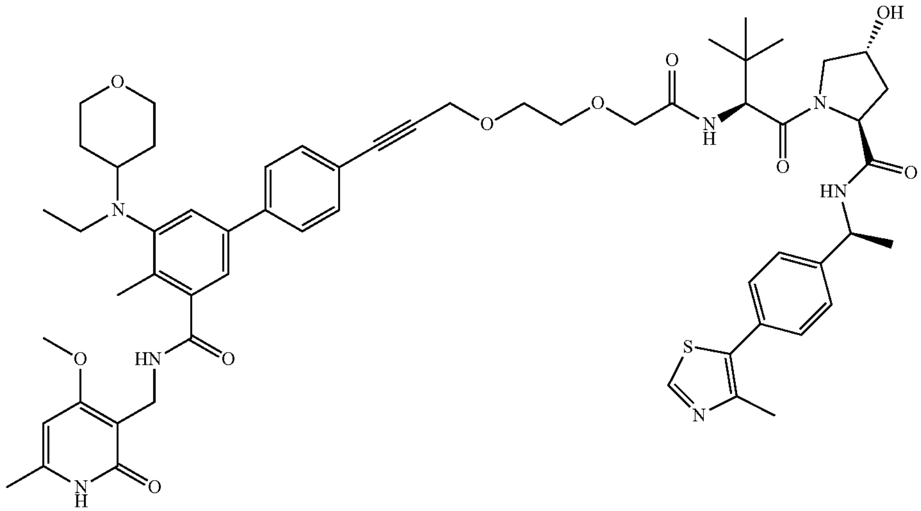 [SMILES: CCN(c1cc(-c2ccc(C#CCOCCOCC(=O)N[C@H](C(=O)N3C[C@H](O)C[C@H]3C(=O)N[C@@H](C)c3ccc(-c4scnc4C)cc3)C(C)(C)C)cc2)cc(C(=O)NCc2c(OC)cc(C)[nH]c2=O)c1C)C1CCOCC1] | | (2S,4R)-1-((S)-2-(2-(2-((3-(3'-(ethyl(tetrahydro-2H-pyran-4-yl)amino)-5'-(((4-methoxy-6-methyl-2-oxo-1,2-dihydropyridin-3-yl)methyl)carbamoyl)-4'-methyl-[1,1'-biphenyl]-4-yl)prop-2-yn-1-yl)oxy)ethoxy)acetamido)-3,3-dimethylbutanoyl)-4-hydroxy-N-((S)-1-(4-(4-methylthiazol-5-yl)phenyl)ethyl)pyrrolidine-2-carboxamide |

TABLE 1-continued

Exemplary compounds of the present disclosure

| Ex # | Structure | Mass Spec (M + H)+ unless otherwise noted | Name |
|---|---|---|---|
| 78 | 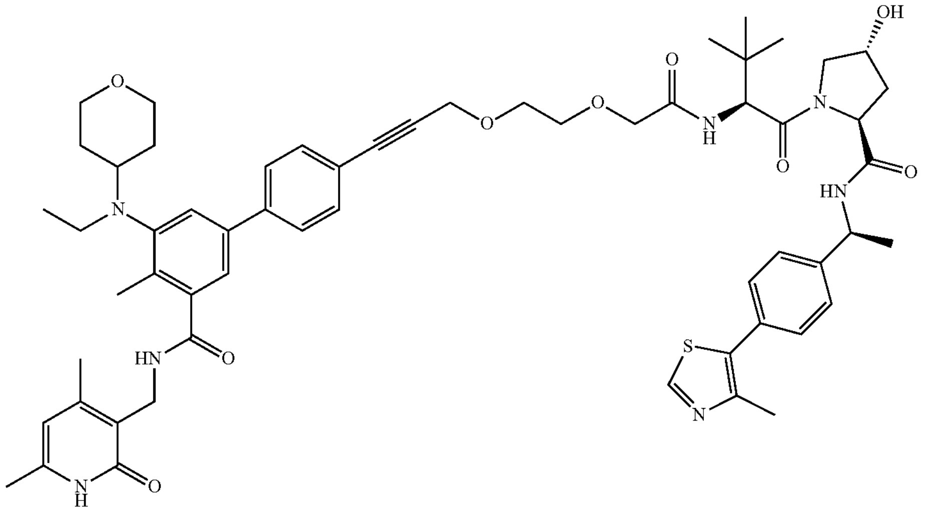 [SMILES: CCN(c1cc(-c2ccc(C#CCOCCOCC(=O)N[C@H](C(=O)N3C[C@H](O)C[C@H]3C(=O)N[C@@H](C)c3ccc(-c4scnc4C)cc3)C(C)(C)C)cc2)cc(C(=O)NCc2c(C)cc(C)[nH]c2=O)c1C)C1CCOCC1] | | (2S,4R)-1-((S)-2-(2-(2-(3-(3'-(((4,6-dimethyl-2-oxo-1,2-dihydropyridin-3-yl)methyl)carbamoyl)-5'-(ethyl(tetrahydro-2H-pyran-4-yl)amino)-4'-methyl-[1,1'-biphenyl]-4-yl)prop-2-yn-1-yl)oxy)ethoxy)acetamido)-3,3-dimethylbutanoyl)-4-hydroxy-N-((S)-1-(4-(4-methylthiazol-5-yl)phenyl)ethyl)pyrrolidine-2-carboxamide |
| 79 | 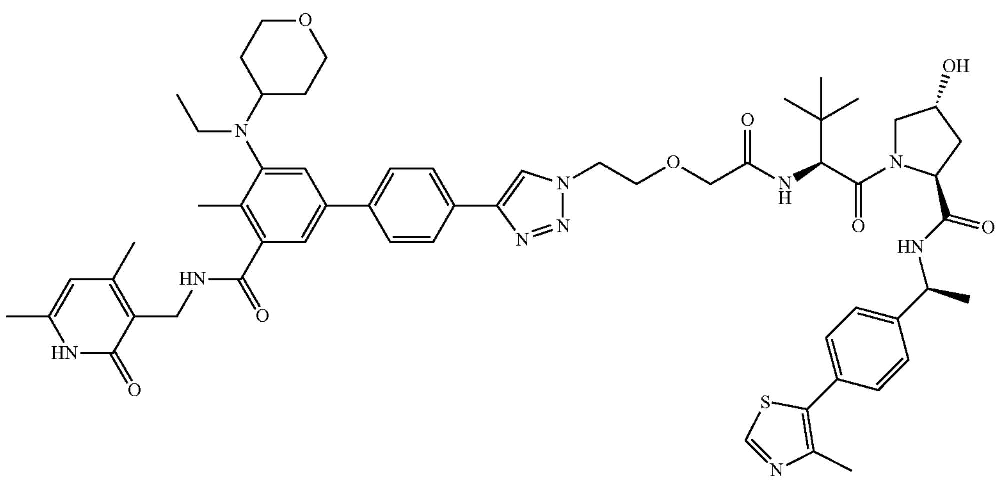 [SMILES: CCN(c1cc(-c2ccc(-c3cn(CCOCC(=O)N[C@H](C(=O)N4C[C@H](O)C[C@H]4C(=O)N[C@@H](C)c4ccc(-c5scnc5C)cc4)C(C)(C)C)nn3)cc2)cc(C(=O)NCc2c(C)cc(C)[nH]c2=O)c1C)C1CCOCC1] | | (2S,4R)-1-((S)-2-(2-(2-(4-(3'-(((4,6-dimethyl-2-oxo-1,2-dihydropyridin-3-yl)methyl)carbamoyl)-5'-(ethyl(tetrahydro-2H-pyran-4-yl)amino)-4'-methyl-[1,1'-biphenyl]-4-yl)-1H-1,2,3-triazol-1-yl)ethoxy)acetamido)-3,3-dimethylbutanoyl)-4-hydroxy-N-((S)-1-(4-(4-methylthiazol-5-yl)phenyl)ethyl)pyrrolidine-2-carboxamide |

TABLE 1-continued

Exemplary compounds of the present disclosure

| Ex # | Structure | Mass Spec (M + H)+ unless otherwise noted | Name |
|---|---|---|---|
| 80 | 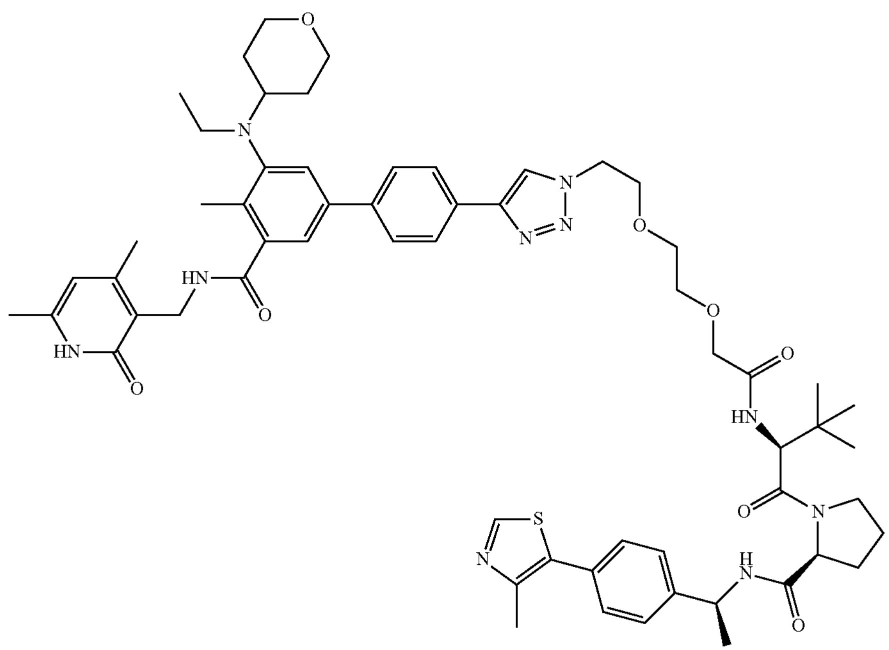 [SMILES: CCN(c1cc(-c2ccc(-c3cn(CCOCCOCC(=O)N[C@H](C(=O)N4CCC[C@H]4C(=O)N[C@@H](C)c4ccc(-c5scnc5C)cc4)C(C)(C)C)nn3)cc2)cc(C(=O)NCc2c(C)cc(C)[nH]c2=O)c1C)C1CCOCC1] | | (2S,4R)-1-((S)-2-(2-(2-(4-(3'-(((4,6-dimethyl-2-oxo-1,2-dihydropyridin-3-yl)methyl)carbamoyl)-5'-(ethyl(tetrahydro-2H-pyran-4-yl)amino)-4'-methyl-[1,1'-biphenyl]-4-yl)-1H-1,2,3-triazol-1-yl)ethoxy)ethoxy)acetamido)-3,3-dimethylbutanoyl)-4-hydroxy-N-((S)-1-(4-(4-methylthiazol-5-yl)phenyl)ethyl)pyrrolidine-2-carboxamide |

TABLE 1-continued

Exemplary compounds of the present disclosure

| Ex # | Structure | Mass Spec (M + H)+ unless otherwise noted | Name |
|---|---|---|---|
| 81 | 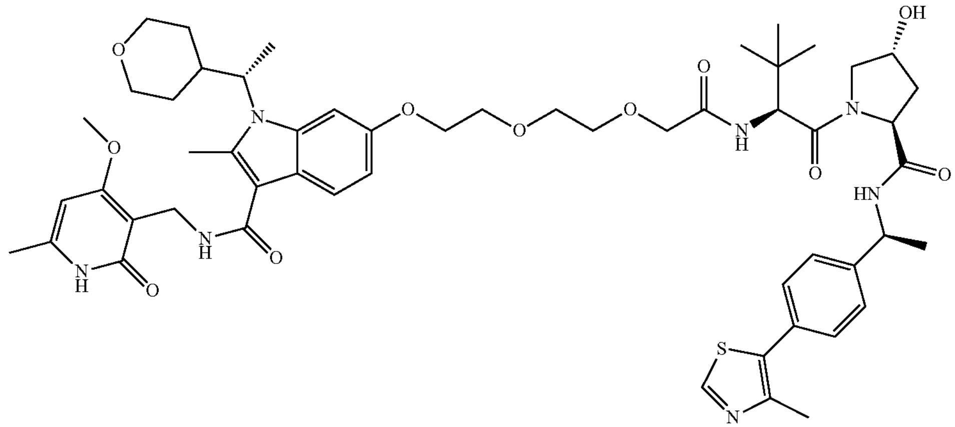 [SMILES: COc1cc(C)[nH]c(=O)c1CNC(=O)c1c(C)n([C@@H](C)C2CCOCC2)c2cc(OCCOCCOCC(=O)N[C@H](C(=O)N3C[C@H](O)C[C@H]3C(=O)N[C@@H](C)c3ccc(-c4scnc4C)cc3)C(C)(C)C)ccc12] | | 6-(2-(2-(2-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-2-oxoethoxy)ethoxy)-N-((4-methoxy-6-methyl-2-oxo-1,2-dihydropyridin-3-yl)methyl)-2-methyl-1-((S)-1-(tetrahydro-2H-pyran-4-yl)ethyl)-1H-indole-3-carboxamide |
| 82 | 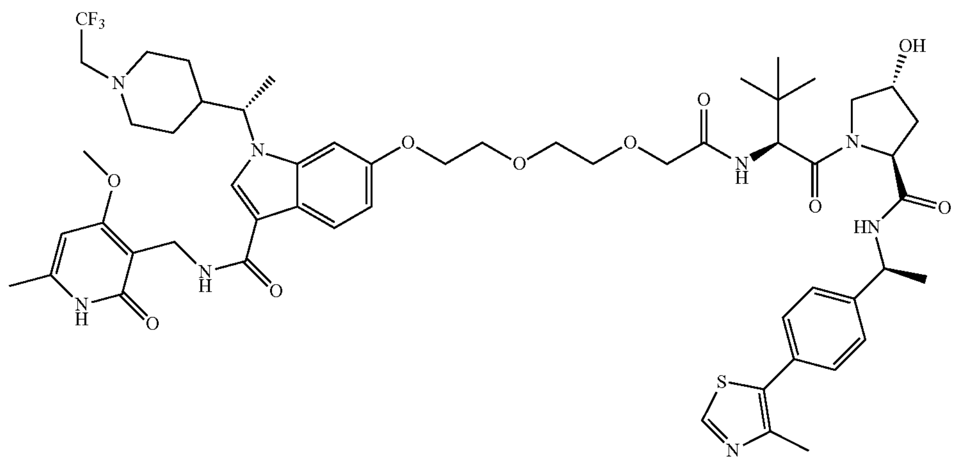 [SMILES: COc1cc(C)[nH]c(=O)c1CNC(=O)c1cn([C@@H](C)C2CCN(CC(F)(F)F)CC2)c2cc(OCCOCCOCC(=O)N[C@H](C(=O)N3C[C@H](O)C[C@H]3C(=O)N[C@@H](C)c3ccc(-c4scnc4C)cc3)C(C)(C)C)ccc12] | | 6-(2-(2-(2-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-2-oxoethoxy)ethoxy)-N-((4-methoxy-6-methyl-2-oxo-1,2-dihydropyridin-3-yl)methyl)-2-methyl-1-((S)-1-(1-(2,2,2-trifluoroethyl)piperidin-4-yl)ethyl)-1H-indole-3-carboxamide |

TABLE 1-continued

Exemplary compounds of the present disclosure

| Ex # | Structure | Mass Spec (M + H)+ unless otherwise noted | Name |
|---|---|---|---|
| 93 | 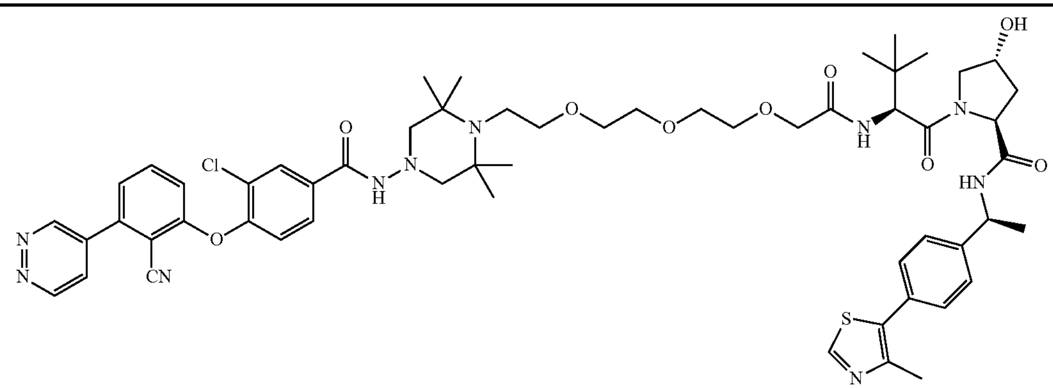 | | (2S,4R)-1-((S)-2-(tert-butyl)-14-(4-(3-chloro-4-(2-cyano-3-(pyridazin-4-yl)phenoxy)benzamido)-2,2,6,6-tetramethylpiperidin-1-yl)-4-oxo-6,9,12-trioxa-3-azatetradecanoyl)-4-hydroxy-N-((S)-1-(4-(4-methylthiazol-5-yl)phenyl)ethyl)pyrrolidine-2-carboxamide |
| 84 | 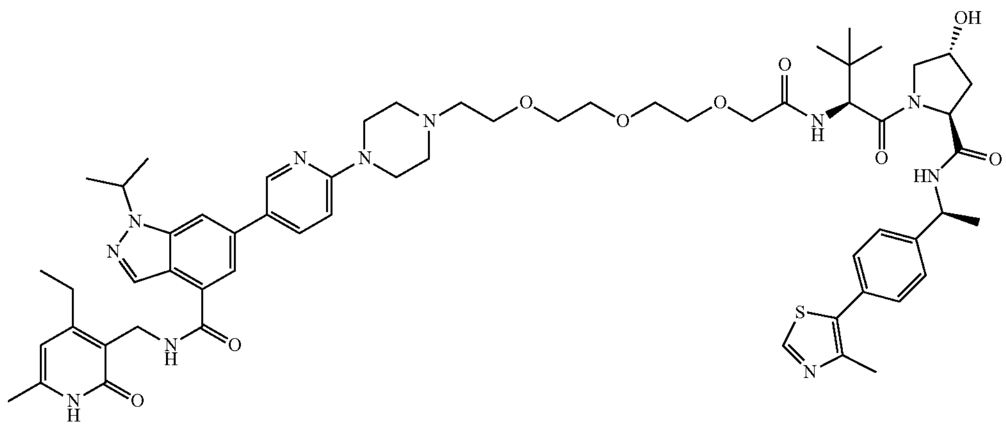 [SMILES: CCc1cc(C)[nH]c(=O)c1CNC(=O)c1cc(-c2ccc(N3CCN(CCOCCOCCOCC(=O)N[C@H](C(=O)N4C[C@H](O)C[C@H]4C(=O)N[C@@H](C)c4ccc(-c5scnc5C)cc4)C(C)(C)C)CC3)nc2)cc2c1cnn2C(C)C] | | N-((4-ethyl-6-methyl-2-oxo-1,2-dihydropyridin-3-yl)methyl)-6-(6-(4-((S)-13-((2S,4R)-4-hydroxy-2-(((S)-1-(4-(4-methylthiazol-5-yl)phenyl)ethyl)carbamoyl)pyrrolidine-1-carbonyl)-14,14-dimethyl-11-oxo-3,6,9-trioxa-12-azapentadecyl)piperazin-1-yl)pyridin-3-yl)-1-isopropyl-1H-indazole-4-carboxamide |

TABLE 1-continued

Exemplary compounds of the present disclosure

| Ex # | Structure | Mass Spec (M + H)+ unless otherwise noted | Name |
|---|---|---|---|
| 85 | 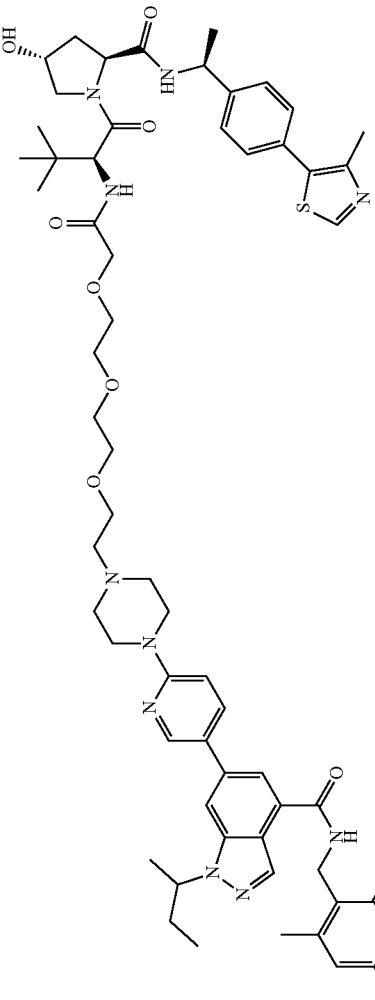 | | 1-((S)-sec-butyl)-N-((4,6-dimethyl-2-oxo-1,2-dihydropyridin-3-yl)methyl)-6-(6-(4-((S)-13-((2S,4R)-4-hydroxy-2-(((S)-1-(4-(4-methylthiazol-5-yl)phenyl)ethyl)carbamoyl)pyrrolidine-1-carbonyl)-14,14-dimethyl-11-oxo-3,6,9-trioxa-12-azapentadecyl)piperazin-1-yl)pyridin-3-yl)-1H-indazole-4-carboxamide |
| 86 | 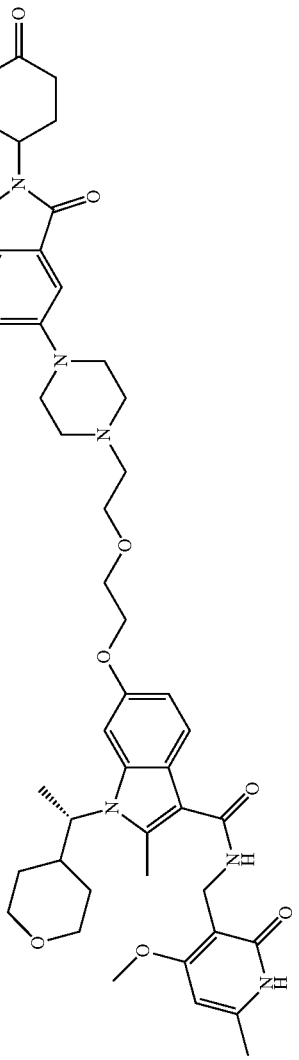 | | 6-(2-(2-(4-(2-(2,6-dioxopiperidin-3-yl)-1,3-dioxoisoindolin-5-yl)piperazin-1-yl)ethoxy)ethoxy)-N-((4-methoxy-6-methyl-2-oxo-1,2-dihydropyridin-3-yl)methyl)-2-methyl-1-((S)-1-(tetrahydro-2H-pyran-4-yl)ethyl)-1H-indole-3-carboxamide |

TABLE 1-continued

Exemplary compounds of the present disclosure

| Ex # | Structure | Mass Spec (M + H)+ unless otherwise noted | Name |
|---|---|---|---|
| 87 | 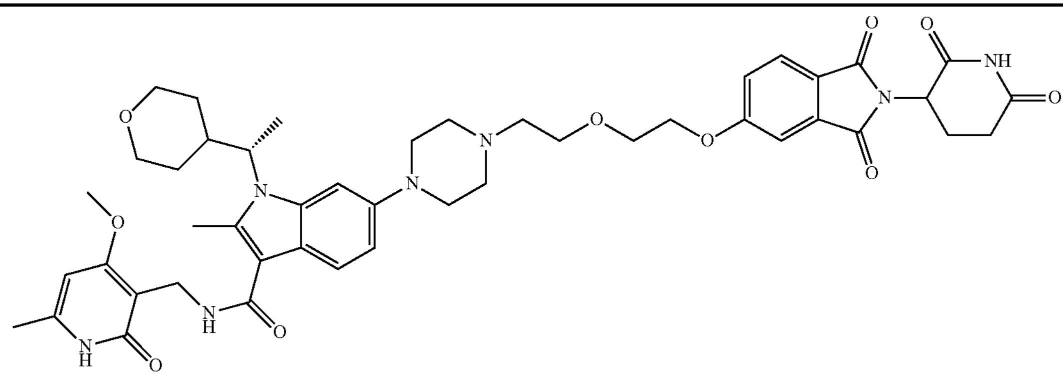 | | 6-(4-(2-(2-((2-(2,6-dioxopiperidin-3-yl)-1,3-dioxoisoindolin-5-yl)oxy)ethoxy)ethyl)piperazin-1-yl)-N-((4-methoxy-6-methyl-2-oxo-1,2-dihydropyridin-3-yl)methyl)-2-methyl-1-((S)-1-(tetrahydro-2H-pyran-4-yl)ethyl)-1H-indole-3-carboxamide |
| 88 | 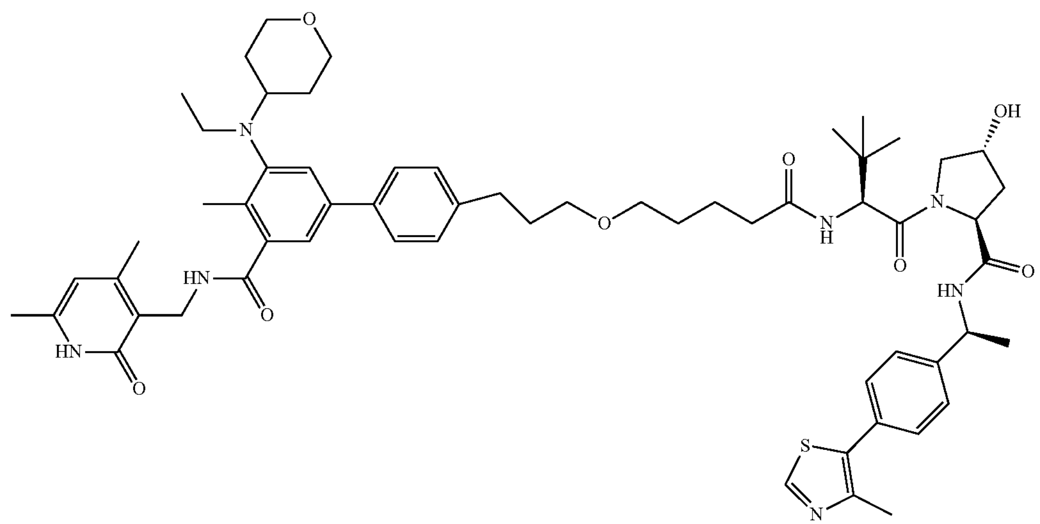 [SMILES: CCN(c1cc(-c2ccc(CCCOCCCCC(=O)N[C@H](C(=O)N3C[C@H](O)C[C@H]3C(=O)N[C@@H](C)c3ccc(-c4scnc4C)cc3)C(C)(C)C)cc2)cc(C(=O)NCc2c(C)cc(C)[nH]c2=O)c1C)C1CCOCC1] | 1058.32 | (2S,4R)-1-((S)-2-(5-(3'-(((4,6-dimethyl-2-oxo-1,2-dihydropyridin-3-yl)methyl)carbamoyl)-5'-(ethyl(tetrahydro-2H-pyran-4-yl)amino)-4'-methyl-[1,1'-biphenyl]-4-yl)propoxy)pentanamido)-3,3-dimethylbutanoyl)-4-hydroxy-N-((S)-1-(4-(4-methylthiazol-5-yl)phenyl)ethyl)pyrrolidine-2-carboxamide |

TABLE 1-continued

Exemplary compounds of the present disclosure

| Ex # | Structure | Mass Spec (M + H)+ unless otherwise noted | Name |
|---|---|---|---|
| 89 | 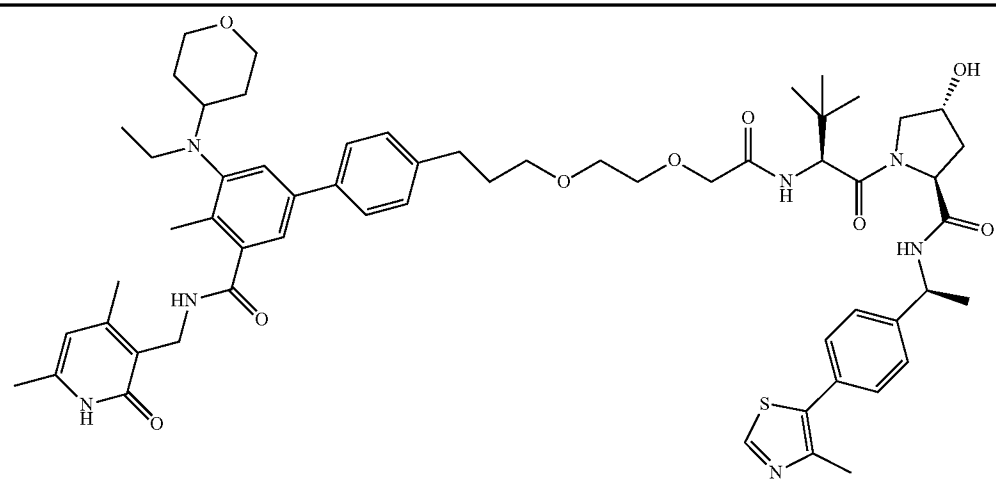 | 1060.29 | (2S,4R)-1-((S)-2-(2-(2-(3-(3-(((4,6-dimethyl-2-oxo-1,2-dihydropyridin-3-yl)methyl)carbamoyl)-5'-(ethyl(tetrahydro-2H-pyran-4-yl)amino)-4'-methyl-[1,1'-biphenyl]-4-yl)propoxy)ethoxy)acetamido)-3,3-dimethylbutanoyl)-4-hydroxy-N-((S)-1-(4-(4-methylthiazol-5-yl)phenyl)ethyl)pyrrolidine-2-carboxamide |
| 90 | 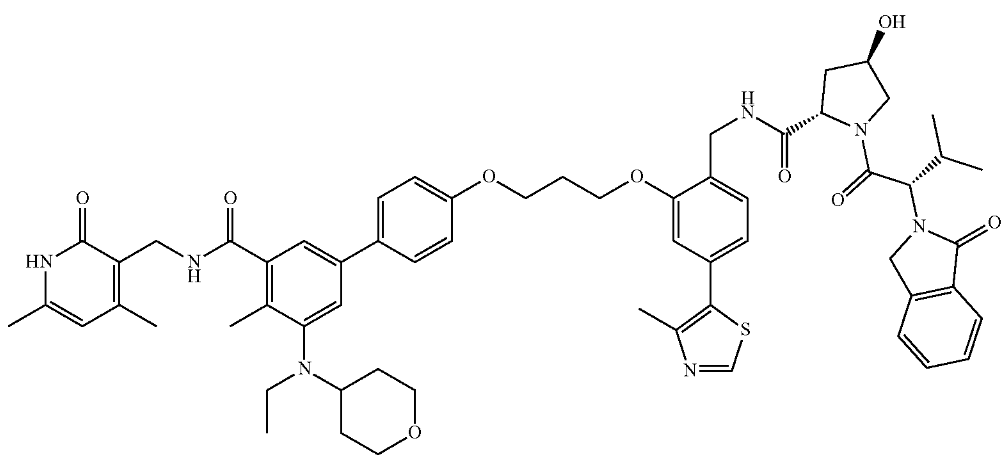 [SMILES: CCN(c1cc(-c2ccc(OCCCOc3cc(-c4scnc4C)ccc3CNC(=O)[C@@H]3C[C@@H](O)CN3C(=O)[C@H](C(C)C)N3Cc4ccccc4C3=O)cc2)cc(C(=O)NCc2c(C)cc(C)[nH]c2=O)c1C)C1CCOCC1] | 1078.12 | (2S,4R)-N-(2-(3-((3'-(((4,6-dimethyl-2-oxo-1,2-dihydropyridin-3-yl)methyl)carbamoyl)-5'-(ethyl(tetrahydro-2H-pyran-4-yl)amino)-4'-methyl-[1,1'-biphenyl]-4-yl)oxy)propoxy)-4-(4-methylthiazol-5-yl)benzyl)-4-hydroxy-1-((S)-3-methyl-2-(1-oxoisoindolin-2-yl)butanoyl)pyrrolidine-2-carboxamide |

TABLE 1-continued

Exemplary compounds of the present disclosure

| Ex # | Structure | Mass Spec (M + H)+ unless otherwise noted | Name |
|---|---|---|---|
| 91 | 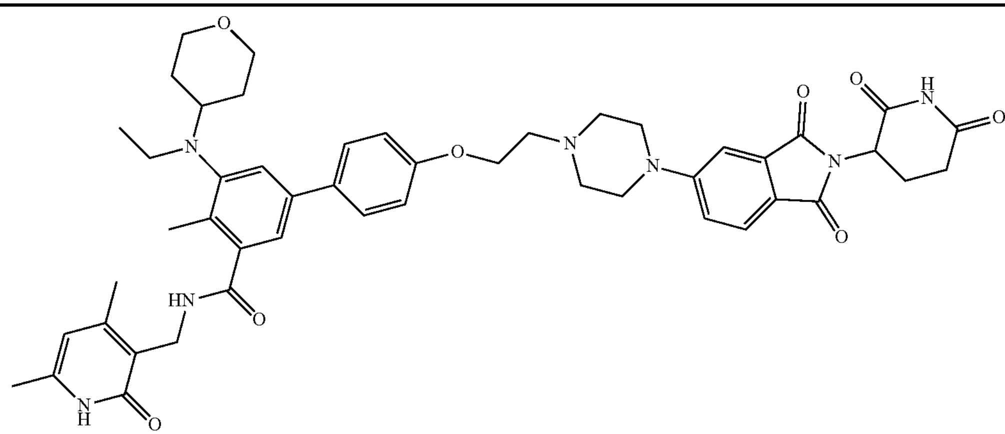 | 858.3 | N-((4,6-dimethyl-2-oxo-1,2-dihydropyridin-3-yl)methyl)-4-(2-(4-(2-(2,6-dioxopiperidin-3-yl)-1,3-dioxoisoindolin-5-yl)piperazin-1-yl)ethoxy)-5-(ethyl(tetrahydro-2H-pyran-4-yl)amino)-4-methyl-[1,1'-biphenyl]-3-carboxamide |
| 92 | 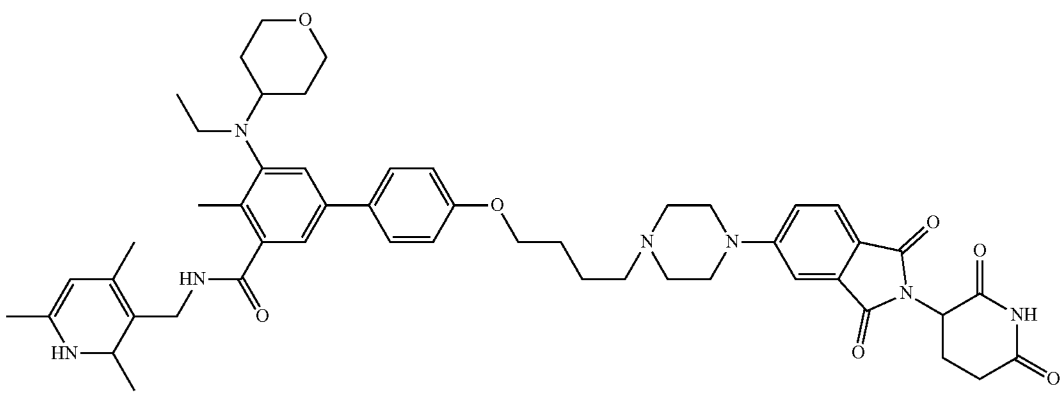 [SMILES: CCN(c1cc(-c2ccc(OCCCCN3CCN(c4ccc5c(c4)C(=O)N(C4CCC(=O)NC4=O)C5=O)CC3)cc2)cc(C(=O)NCC2=C(C)C=C(C)NC2C)c1C)C1CCOCC1] | | N-((4,6-dimethyl-2-oxo-1,2-dihydropyridin-3-yl)methyl)-4-(4-(4-(2-(2,6-dioxopiperidin-3-yl)-1,3-dioxoisoindolin-5-yl)piperazin-1-yl)butoxy)-5-(ethyl(tetrahydro-2H-pyran-4-yl)amino)-4-methyl-[1,1'-biphenyl]-3-carboxamide |

TABLE 1-continued

Exemplary compounds of the present disclosure

| Ex # | Structure | Mass Spec (M + H)+ unless otherwise noted | Name |
|---|---|---|---|
| 93 | 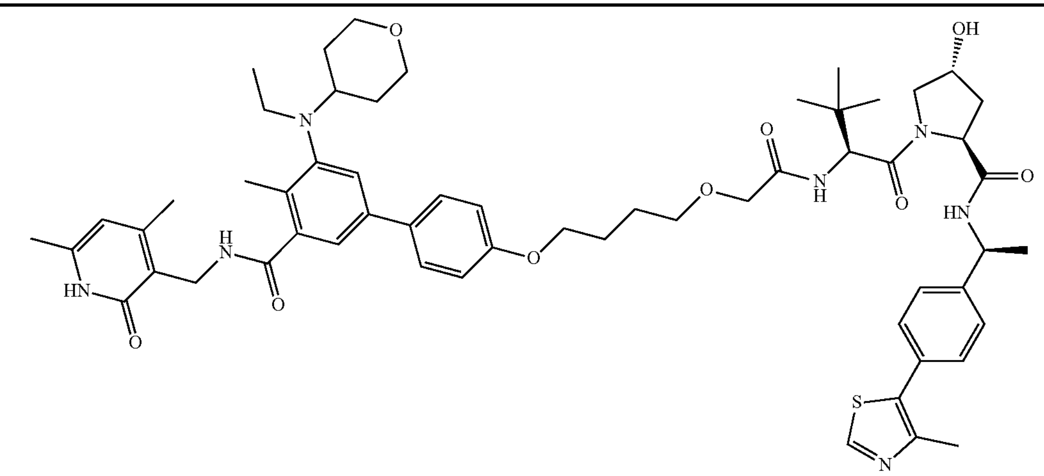 | 523.8 [M/2 + H] | (2S,4R)-1-((S)-2-(2-(4-((3-(((4,6-dimethyl-2-oxo-1,2-dihydropyridin-3-yl)methyl)carbamoyl)-5'-(ethyl(tetrahydro-2H-pyran-4-yl)amino)-4'-methyl-[1,1'-biphenyl]-4-yl)oxy)butoxy)acetamido)-3,3-dimethylbutanoyl)-4-hydroxy-N-((S)-1-(4-(4-methylthiazol-5-yl)phenyl)ethyl)pyrrolidine-2-carboxamide |
| 94 | 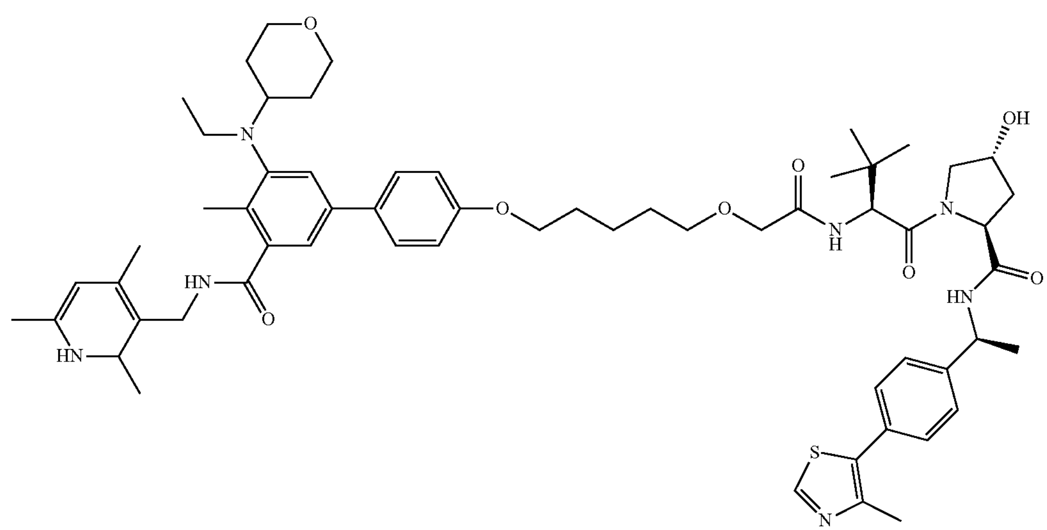 [SMILES: CCN(c1cc(-c2ccc(OCCCCCOCC(=O)N[C@H](C(=O)N3C[C@H](O)C[C@H]3C(=O)N[C@@H](C)c3ccc(-c4scnc4C)cc3)C(C)(C)C)cc2)cc(C(=O)NCC2=C(C)C=C(C)NC2C)c1C)C1CCOCC1] | 1060.5 | (2S,4R)-1-((S)-2-(2-(5-((3'-(((4,6-dimethyl-2-oxo-1,2-dihydropyridin-3-yl)methyl)carbamoyl)-5'-(ethyl(tetrahydro-2H-pyran-4-yl)amino)-4'-methyl-[1,1'-biphenyl]-4-yl)oxy)pentyl)oxy)acetamido)-3,3-dimethylbutanoyl)-4-hydroxy-N-((S)-1-(4-(4-methylthiazol-5-yl)phenyl)ethyl)pyrrolidine-2-carboxamide |

TABLE 1-continued

Exemplary compounds of the present disclosure

| Ex # | Structure | Mass Spec (M + H)+ unless otherwise noted | Name |
|---|---|---|---|
| 95 | 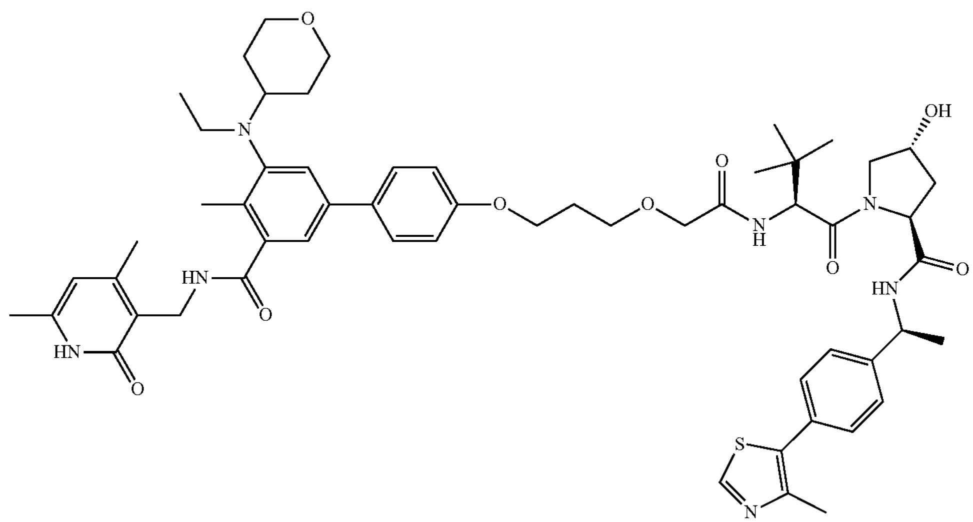 [SMILES: CCN(c1cc(-c2ccc(OCCCOCC(=O)N[C@H](C(=O)N3C[C@H](O)C[C@H]3C(=O)N[C@@H](C)c3ccc(-c4scnc4C)cc3)C(C)(C)C)cc2)cc(C(=O)NCc2c(C)cc(C)[nH]c2=O)c1C)C1CCOCC1] | 1032.4 | (2S,4R)-1-((S)-2-(2-(3-((3'-(((4,6-dimethyl-2-oxo-1,2-dihydropyridin-3-yl)methyl)carbamoyl)-5'-(ethyl(tetrahydro-2H-pyran-4-yl)amino)-4'-methyl-[1,1'-biphenyl]-4-yl)oxy)propoxy)acetamido)-3,3-dimethylbutanoyl)-4-hydroxy-N-((S)-1-(4-(4-methylthiazol-5-yl)phenyl)ethyl)pyrrolidine-2-carboxamide |

TABLE 1-continued

Exemplary compounds of the present disclosure

| Ex # | Structure | Mass Spec (M + H)+ unless otherwise noted | Name |
|---|---|---|---|
| 96 | 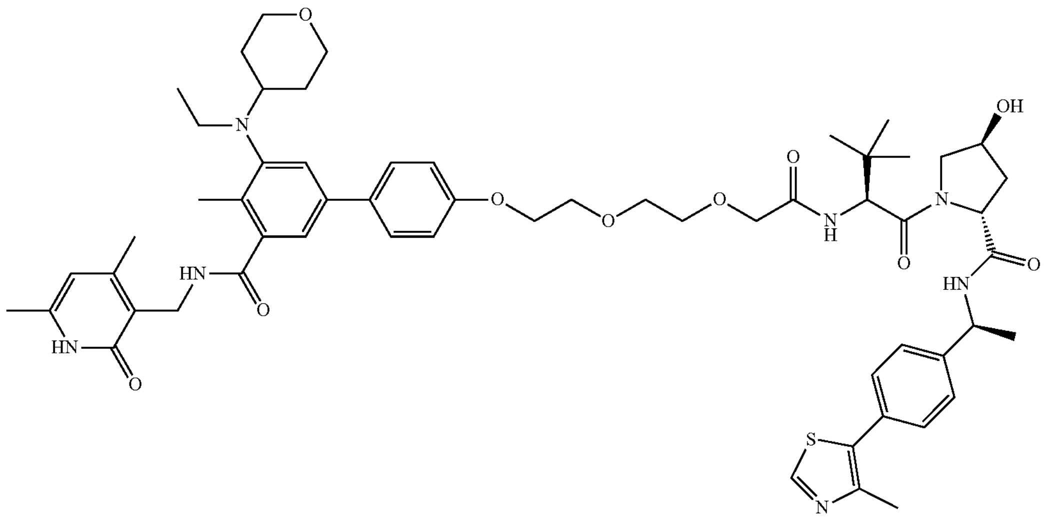 [SMILES: CCN(c1cc(-c2ccc(OCCOCCOCC(=O)N[C@H](C(=O)N3C[C@@H](O)C[C@@H]3C(=O)N[C@@H](C)c3ccc(-c4scnc4C)cc3)C(C)(C)C)cc2)cc(C(=O)NCc2c(C)cc(C)[nH]c2=O)c1C)C1CCOCC1] | | (2R,4S)-1-((S)-2-(2-(2-(2-(((4,6-dimethyl-2-oxo-1,2-dihydropyridin-3-yl)methyl)carbamoyl)-5'-(ethyl(tetrahydro-2H-pyran-4-yl)amino)-4'-methyl-[1,1'-biphenyl]-4-yl)oxy)ethoxy)ethoxy)acetamido)-3,3-dimethylbutanoyl)-4-hydroxy-N-((S)-1-(4-(4-methylthiazol-5-yl)phenyl)ethyl)pyrrolidine-2-carboxamide |
| 97 | 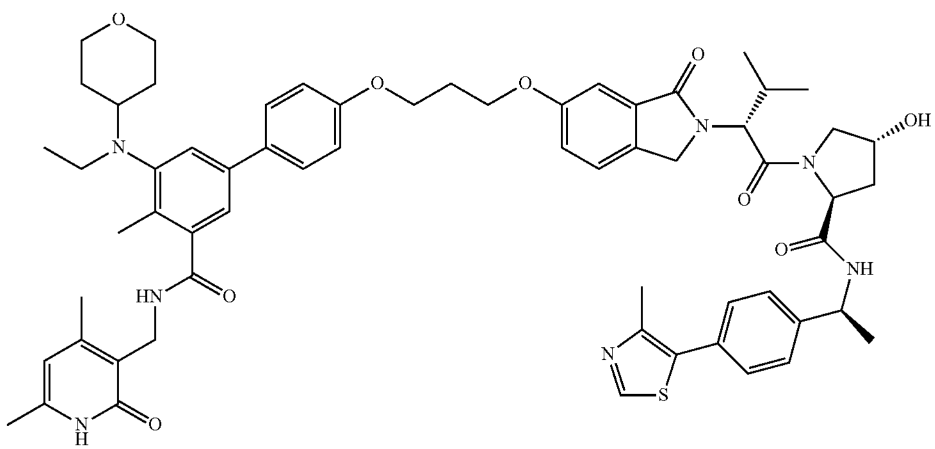 [SMILES: CCN(c1cc(-c2ccc(OCCCOc3ccc4c(c3)C(=O)N([C@@H](C(=O)N3C[C@H](O)C[C@H]3C(=O)N[C@@H](C)c3ccc(-c5scnc5C)cc3)C(C)C)C4)cc2)cc(C(=O)NCc2c(C)cc(C)[nH]c2=O)c1C)C1CCOCC1] | 1092.48 | (2S,4R)-1-((R)-2-(6-(3-((3'-(((4,6-dimethyl-2-oxo-1,2-dihydropyridin-3-yl)methyl)carbamoyl)-5'-(ethyl(tetrahydro-2H-pyran-4-yl)amino)-4'-methyl-[1,1'-biphenyl]-4-yl)oxy)propoxy)-1-oxoisoindolin-2-yl)-3-methylbutanoyl)-4-hydroxy-N-((S)-1-(4-(4-methylthiazol-5-yl)phenyl)ethyl)pyrrolidine-2-carboxamide |

TABLE 1-continued

Exemplary compounds of the present disclosure

| Ex # | Structure | Mass Spec (M + H)+ unless otherwise noted | Name |
|---|---|---|---|
| 98 | 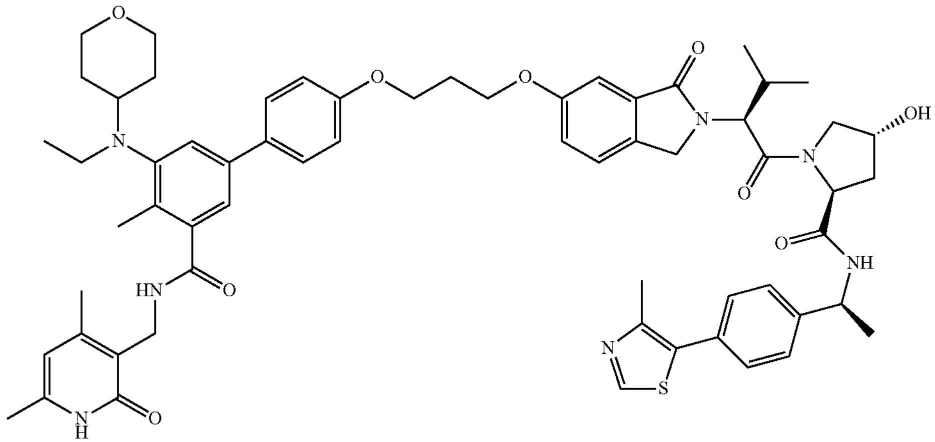 [SMILES: CCN(c1cc(-c2ccc(OCCCOc3ccc4c(c3)C(=O)N([C@H](C(=O)N3C[C@H](O)C[C@H]3C(=O)N[C@@H](C)c3ccc(-c5scnc5C)cc3)C(C)C)C4)cc2)cc(C(=O)NCc2c(C)cc(C)[nH]c2=O)c1C)C1CCOCC1] | 1092.48 | (2S,4R)-1-((S)-2-(6-(3-((3'-(((4,6-dimethyl-2-oxo-1,2-dihydropyridin-3-yl)methyl)carbamoyl)-5'-(ethyl(tetrahydro-2H-pyran-4-yl)amino)-4'-methyl-[1,1'-biphenyl]-4-yl)oxy)propoxy)-1-oxoisoindolin-2-yl)-3-methylbutanoyl)-4-hydroxy-N-((S)-1-(4-(4-methylthiazol-5-yl)phenyl)ethyl)pyrrolidine-2-carboxamide |
| 99 | 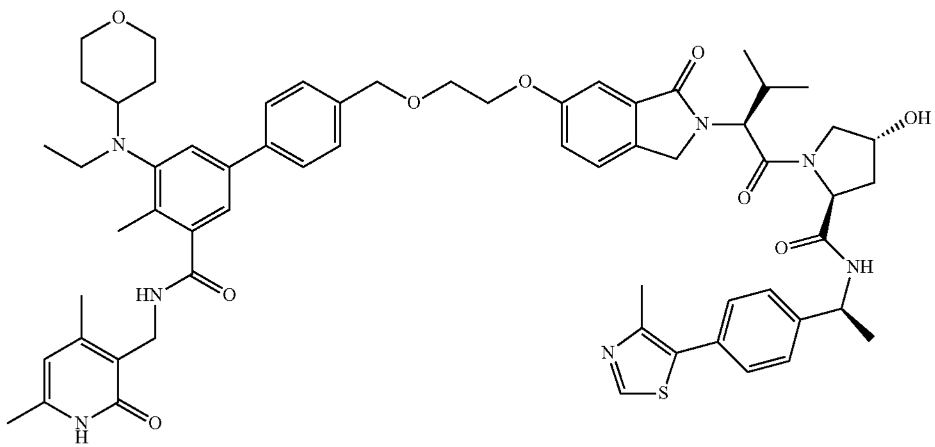 [SMILES: CCN(c1cc(-c2ccc(COCCOc3ccc4c(c3)C(=O)N([C@H](C(=O)N3C[C@H](O)C[C@H]3C(=O)N[C@@H](C)c3ccc(-c5scnc5C)cc3)C(C)C)C4)cc2)cc(C(=O)NCc2c(C)cc(C)[nH]c2=O)c1C)C1CCOCC1] | 1092.48 | (2S,4R)-1-((S)-2-(6-(2-((3'-(((4,6-dimethyl-2-oxo-1,2-dihydropyridin-3-yl)methyl)carbamoyl)-5'-(ethyl(tetrahydro-2H-pyran-4-yl)amino)-4'-methyl-[1,1'-biphenyl]-4-yl)methoxy)ethoxy)-1-oxoisoindolin-2-yl)-3-methylbutanoyl)-4-hydroxy-N-((S)-1-(4-(4-methylthiazol-5-yl)phenyl)ethyl)pyrrolidine-2-carboxamide |

TABLE 1-continued

Exemplary compounds of the present disclosure

| Ex # | Structure | Mass Spec (M + H)+ unless otherwise noted | Name |
|---|---|---|---|
| 100 | 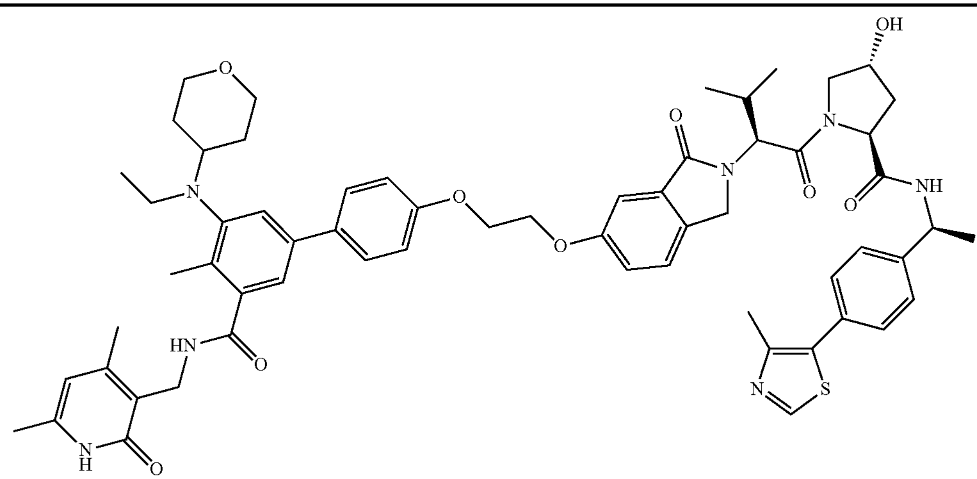 | 1078.47 | (2S,4R)-1-((S)-2-(6-(2-((3-(((4,6-dimethyl-2-oxo-1,2-dihydropyridin-3-yl)methyl)carbamoyl)-5'-(ethyl(tetrahydro-2H-pyran-4-yl)amino)-4'-methyl-[1,1'-biphenyl]-4-yl)oxy)ethoxy)-1-oxoisoindolin-2-yl)-3-methylbutanoyl)-4-hydroxy-N-((S)-1-(4-(4-methylthiazol-5-yl)phenyl)ethyl)pyrrolidine-2-carboxamide |
| 101 | 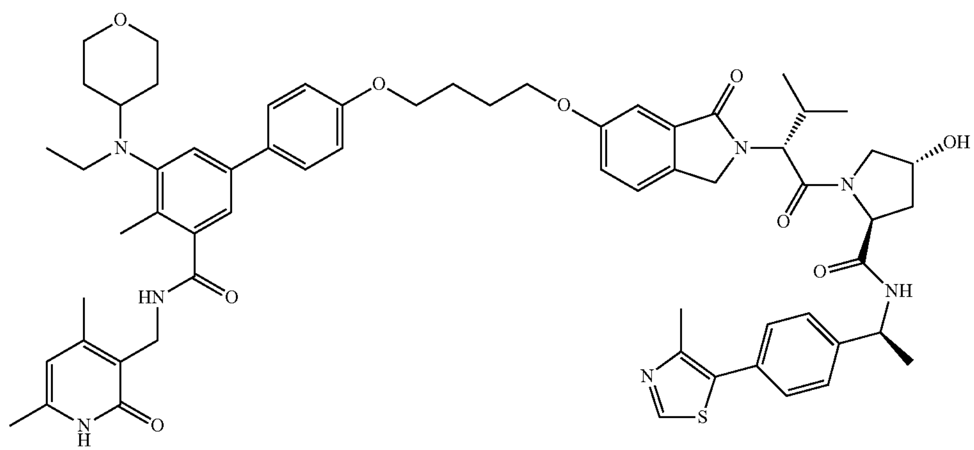 | 1106.49 | (2S,4R)-1-((R)-2-(6-(4-((3'-(((4,6-dimethyl-2-oxo-1,2-dihydropyridin-3-yl)methyl)carbamoyl)-5'-(ethyl(tetrahydro-2H-pyran-4-yl)amino)-4'-methyl-[1,1'-biphenyl]-4-yl)oxy)butoxy)-1-oxoisoindolin-2-yl)-3-methylbutanoyl)-4-hydroxy-N-((S)-1-(4-(4-methylthiazol-5-yl)phenyl)ethyl)pyrrolidine-2-carboxamide |

TABLE 1-continued

Exemplary compounds of the present disclosure

| Ex # | Structure | Mass Spec (M + H)+ unless otherwise noted | Name |
|---|---|---|---|
| 102 | 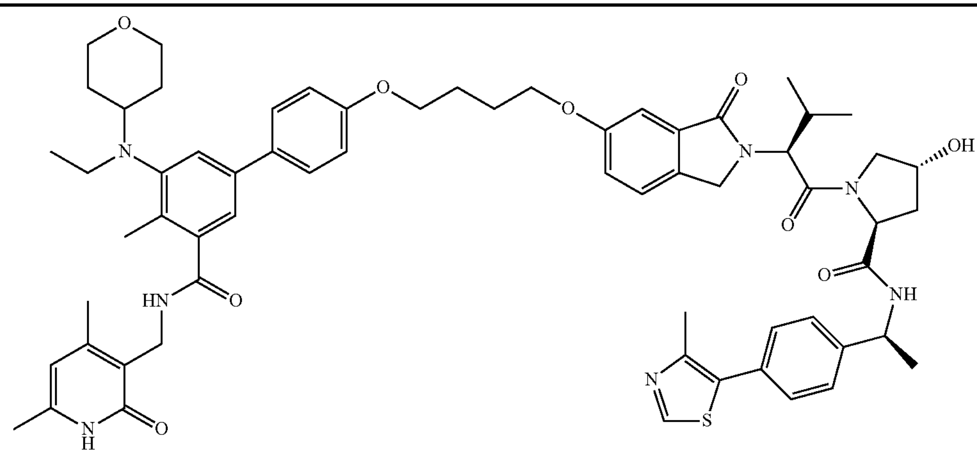 | 1106.49 | (2S,4R)-1-((S)-2-(6-(4-((3-(((4,6-dimethyl-2-oxo-1,2-dihydropyridin-3-yl)methyl)carbamoyl)-5'-(ethyl(tetrahydro-2H-pyran-4-yl)amino)-4'-methyl-[1,1'-biphenyl]-4-yl)oxy)butoxy)-1-oxoisoindolin-2-yl)-3-methylbutanoyl)-4-hydroxy-N-((S)-1-(4-(4-methylthiazol-5-yl)phenyl)ethyl)pyrrolidine-2-carboxamide |
| 103 | 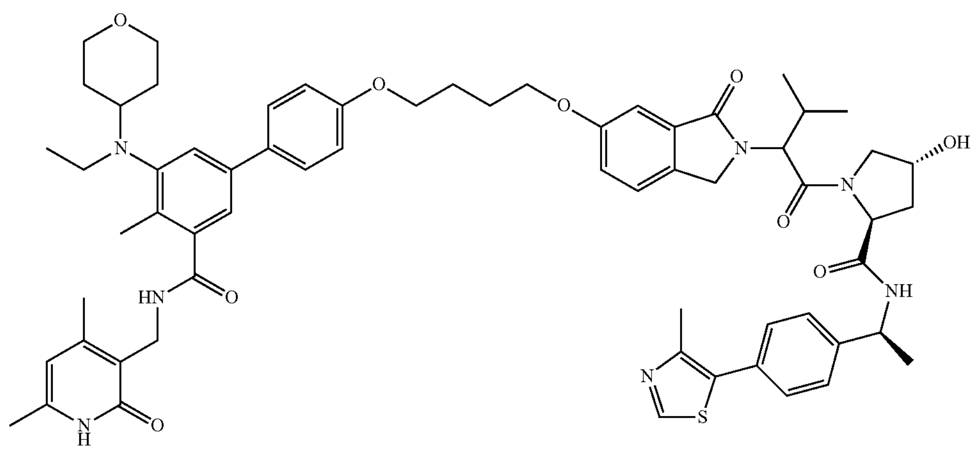 [SMILES: CCN(c1cc(-c2ccc(OCCCCOc3ccc4c(c3)C(=O)N([C@@H](C(=O)N3C[C@H](O)C[C@H]3C(=O)N[C@@H](C)c3ccc(-c5scnc5C)cc3)C(C)C)C4)cc2)cc(C(=O)NCc2c(C)cc(C)[nH]c2=O)c1C)C1CCOCC1] | 1106.49 | (2S,4R)-1-(2-(6-(4-((3'-(((4,6-dimethyl-2-oxo-1,2-dihydropyridin-3-yl)methyl)carbamoyl)-5'-(ethyl(tetrahydro-2H-pyran-4-yl)amino)-4'-methyl-[1,1'-biphenyl]-4-yl)oxy)butoxy)-1-oxoisoindolin-2-yl)-3-methylbutanoyl)-4-hydroxy-N-((S)-1-(4-(4-methylthiazol-5-yl)phenyl)ethyl)pyrrolidine-2-carboxamide |

TABLE 1-continued

Exemplary compounds of the present disclosure

| Ex # | Structure | Mass Spec (M + H)+ unless otherwise noted | Name |
|---|---|---|---|
| 104 | 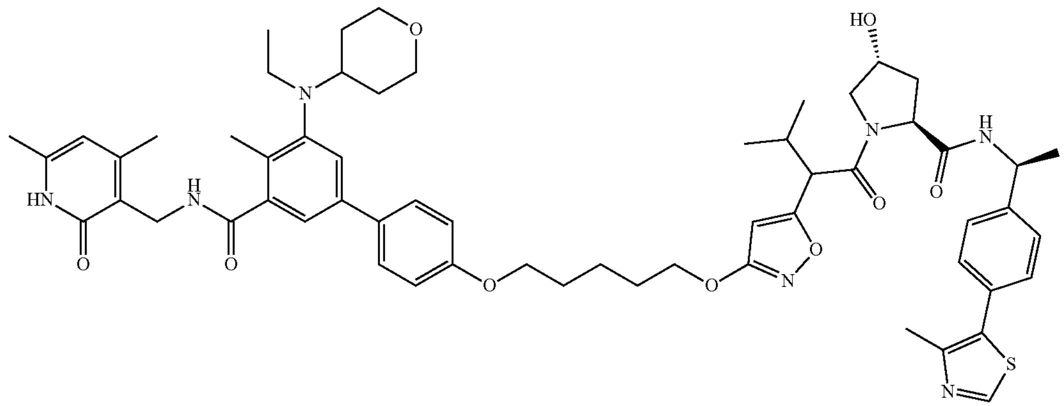 [SMILES: CCN(c1cc(-c2ccc(OCCOCCOc3cc(C(C(=O)N4C[C@H](O)C[C@H]4C(=O)N[C@@H](C)c4ccc(-c5scnc5C)cc4)C(C)C)on3)cc2)cc(C(=O)NCc2c(C)cc(C)[nH]c2=O)c1C)C1CCOCC1] | 1056.47 | (2S,4R)-1-(2-(3-(5-((3'-(((4,6-dimethyl-2-oxo-1,2-dihydropyridin-3-yl)methyl)carbamoyl)-5'-(ethyl(tetrahydro-2H-pyran-4-yl)amino)-4'-methyl-[1,1'-biphenyl]-4-yl)oxy)pentyl)oxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 105 | 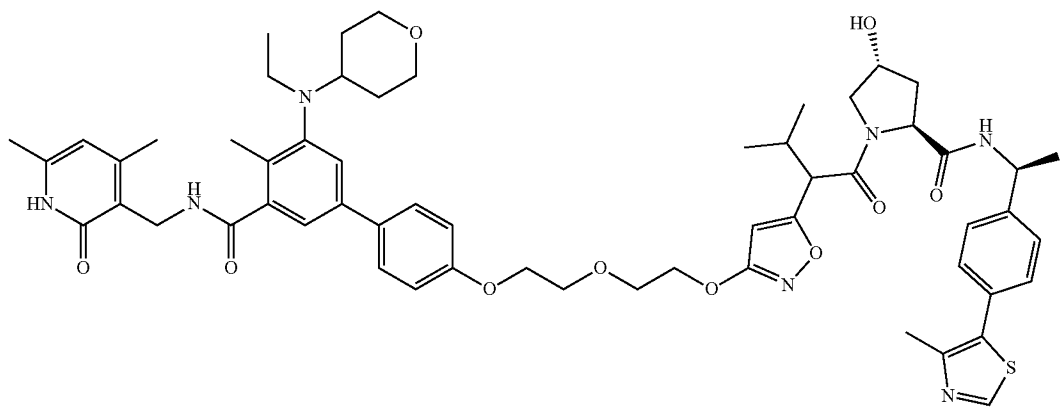 | 1058.45 | (2S,4R)-1-(2-(3-(2-(2-((3'-(((4,6-dimethyl-2-oxo-1,2-dihydropyridin-3-yl)methyl)carbamoyl)-5'-(ethyl(tetrahydro-2H-pyran-4-yl)amino)-4'-methyl-[1,1'-biphenyl]-4-yl)oxy)ethoxy)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1-continued

Exemplary compounds of the present disclosure

| Ex # | Structure | Mass Spec (M + H)+ unless otherwise noted | Name |
|---|---|---|---|
| 106 | 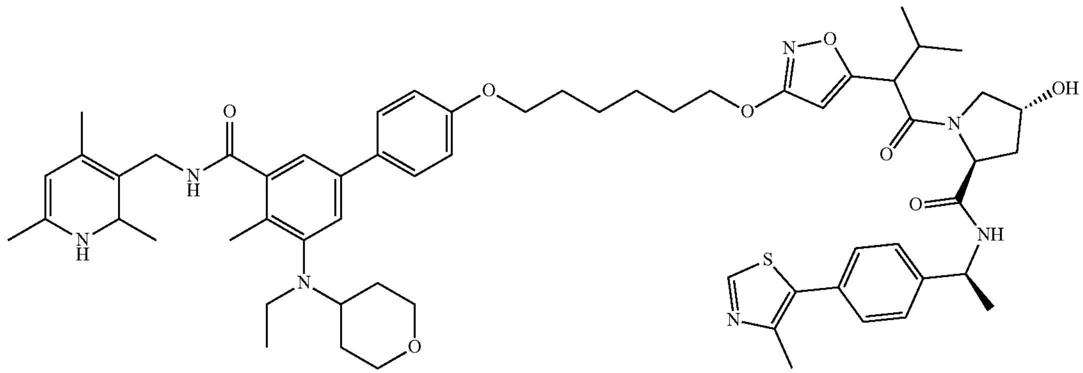 [SMILES: CCN(c1cc(-c2ccc(OCCCCCCOc3cc(C(C(=O)N4C[C@H](O)C[C@H]4C(=O)N[C@@H](C)c4ccc(-c5scnc5C)cc4)C(C)C)on3)cc2)cc(C(=O)NCC2=C(C)C=C(C)NC2C)c1C)C1CCOCC1] | 1070.49 | (2S,4R)-1-(2-(3-((6-((3'-(((4,6-dimethyl-2-oxo-1,2-dihydropyridin-3-yl)methyl)carbamoyl)-5'-(ethyl(tetrahydro-2H-pyran-4-yl)amino)-4'-methyl-[1,1'-biphenyl]-4-yl)oxy)hexyl)oxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 107 | 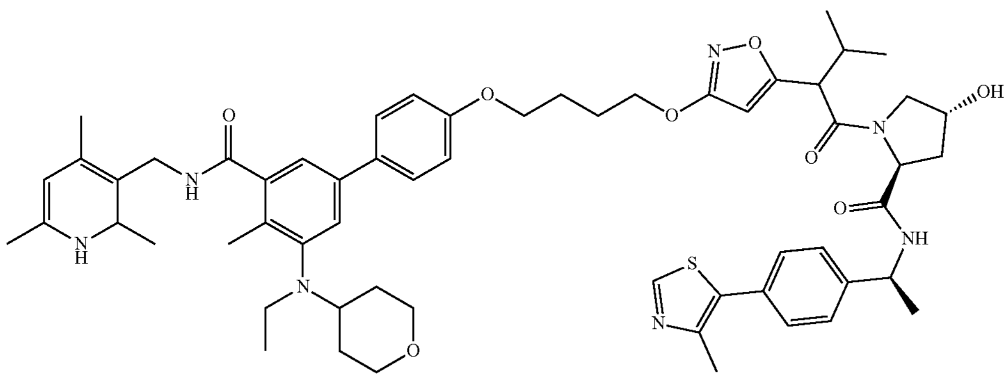 [SMILES: CCN(c1cc(-c2ccc(OCCCCOc3cc(C(C(=O)N4C[C@H](O)C[C@H]4C(=O)N[C@@H](C)c4ccc(-c5scnc5C)cc4)C(C)C)on3)cc2)cc(C(=O)NCC2=C(C)C=C(C)NC2C)c1C)C1CCOCC1] | 1042.46 | (2S,4R)-1-(2-(3-(4-((3'-(((4,6-dimethyl-2-oxo-1,2-dihydropyridin-3-yl)methyl)carbamoyl)-5'-(ethyl(tetrahydro-2H-pyran-4-yl)amino)-4'-methyl-[1,1'-biphenyl]-4-yl)oxy)butoxy)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1-continued

Exemplary compounds of the present disclosure

| Ex # | Structure | Mass Spec (M + H)+ unless otherwise noted | Name |
|---|---|---|---|
| 108 | 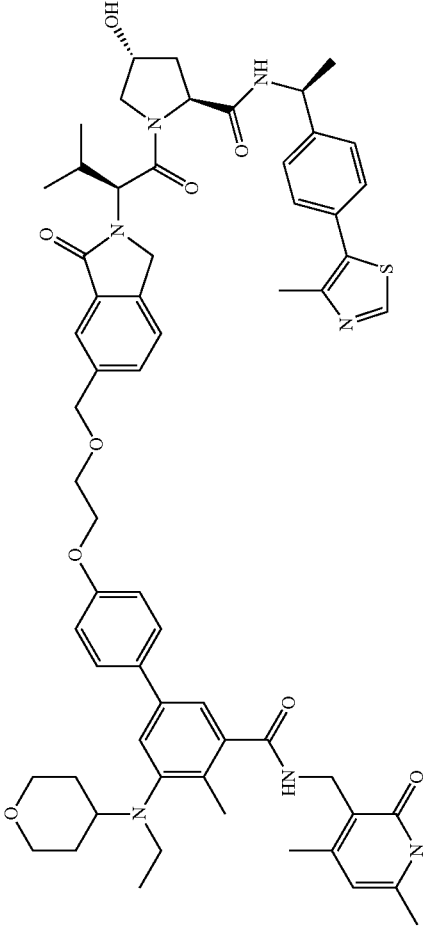 | 1092.37 | (2S,4R)-1-((S)-2-(6-((2-(((3-((4,6-dimethyl-2-oxo-1,2-dihydropyridin-3-yl)methyl)carbamoyl)-5'-(ethyl(tetrahydro-2H-pyran-4-yl)amino)-4'-methyl-[1,1'-biphenyl]-4-yl)oxy)ethoxy)methyl)-1-oxoisoindolin-2-yl)-3-methylbutanoyl)-4-hydroxy-N-((S)-1-(4-(4-methylthiazol-5-yl)phenyl)ethyl)pyrrolidine-2-carboxamide |
| 109 | 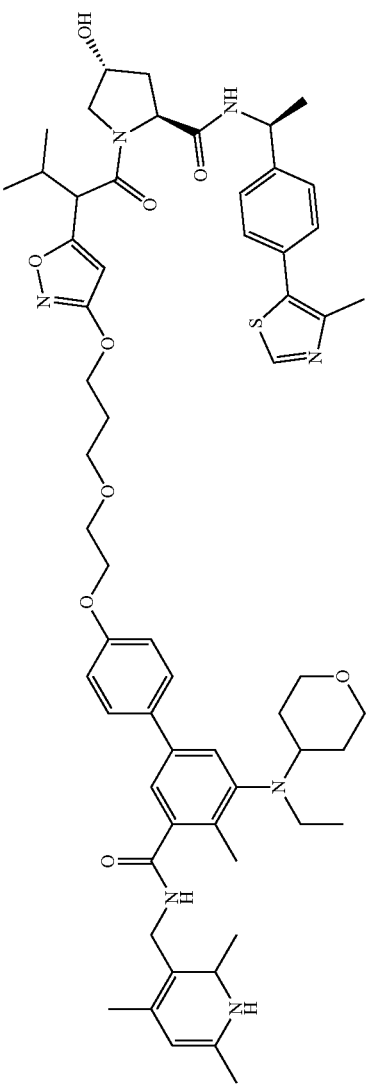 | 1072.38 | (2S,4R)-1-(2-(3-(3-(2-((3-((4,6-dimethyl-2-oxo-1,2-dihydropyridin-3-yl)methyl)carbamoyl)-5'-(ethyl(tetrahydro-2H-pyran-4-yl)amino)-4'-methyl-[1,1'-biphenyl]-4-yl)oxy)ethoxy)propoxy)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1-continued

Exemplary compounds of the present disclosure

| Ex # | Structure | Mass Spec (M + H)+ unless otherwise noted | Name |
|---|---|---|---|
| 110 | 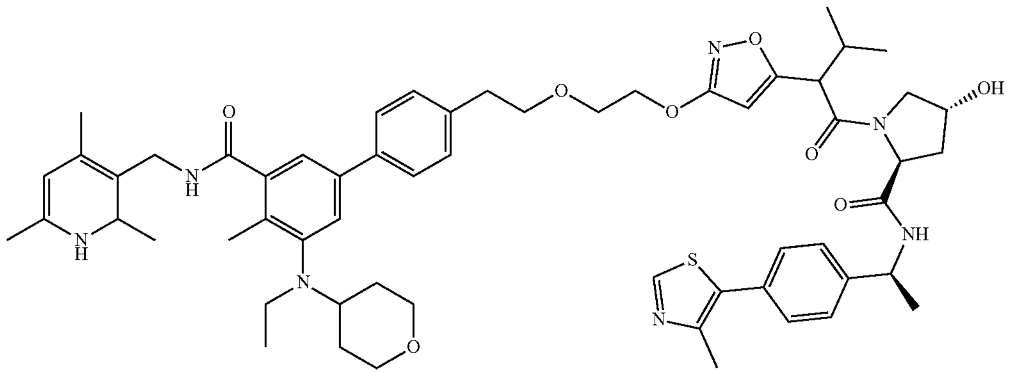 | 1042.37 | (2S,4R)-1-(2-(3-(2-(3'-(((4,6-dimethyl-2-oxo-1,2-dihydropyridin-3-yl)methyl)carbamoyl)-5'-(ethyl(tetrahydro-2H-pyran-4-yl)amino)-4'-methyl-[1,1'-biphenyl]-4-yl)ethoxy)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 111 | 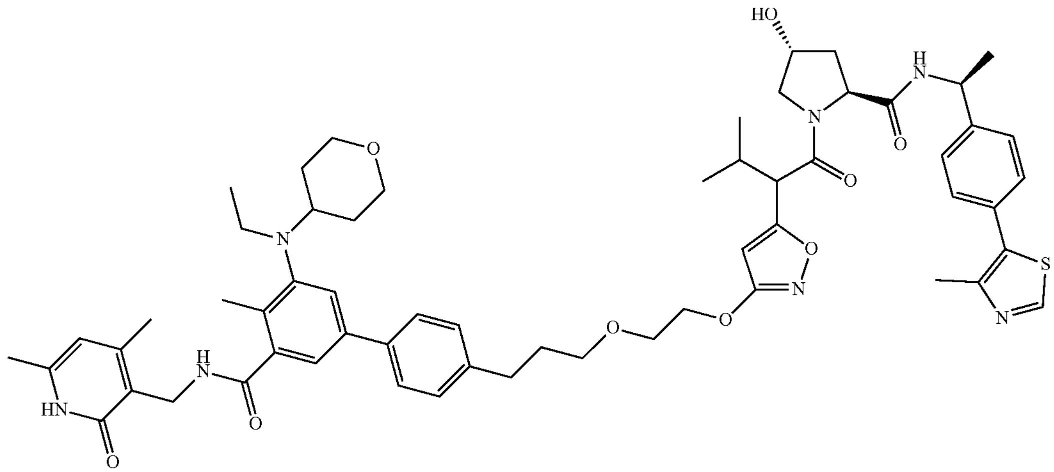 [SMILES: CCN(c1cc(-c2ccc(CCCOCCOc3cc(C(C(=O)N4C[C@H](O)C[C@H]4C(=O)N[C@@H](C)c4ccc(-c5scnc5C)cc4)C(C)C)on3)cc2)cc(C(=O)NCc2c(C)cc(C)[nH]c2=O)c1C)C1CCOCC1] | 1056.39 | (2S,4R)-1-(2-(3-(2-(3'-(((4,6-dimethyl-2-oxo-1,2-dihydropyridin-3-yl)methyl)carbamoyl)-5'-(ethyl(tetrahydro-2H-pyran-4-yl)amino)-4'-methyl-[1,1'-biphenyl]-4-yl)propoxy)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |

TABLE 1-continued

Exemplary compounds of the present disclosure

| Ex # | Structure | Mass Spec (M + H)+ unless otherwise noted | Name |
|---|---|---|---|
| 112 | 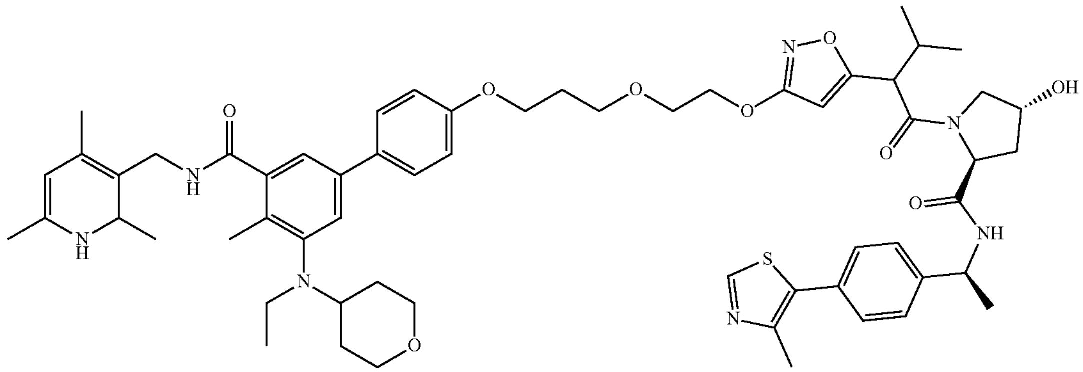 [SMILES: CCN(c1cc(-c2ccc(OCCCOCCOc3cc(C(C(=O)N4C[C@H](O)C[C@H]4C(=O)N[C@@H](C)c4ccc(-c5scnc5C)cc4)C(C)C)on3)cc2)cc(C(=O)NCC2=C(C)C=C(C)NC2C)c1C)C1CCOCC1] | 1072.39 | (2S,4R)-1-(2-(3-(2-(3-(((4,6-dimethyl-2-oxo-1,2-dihydropyridin-3-yl)methyl)carbamoyl)-5'-(ethyl(tetrahydro-2H-pyran-4-yl)amino)-4'-methyl-[1,1'-biphenyl]-4-yl)oxy)propoxy)ethoxy)isoxazol-5-yl)-3-methylbutanoyl)-4-hydroxy-N-((S)-1-(4-(4-methylthiazol-5-yl)phenyl)ethyl)pyrrolidine-2-carboxamide |
| 113 | 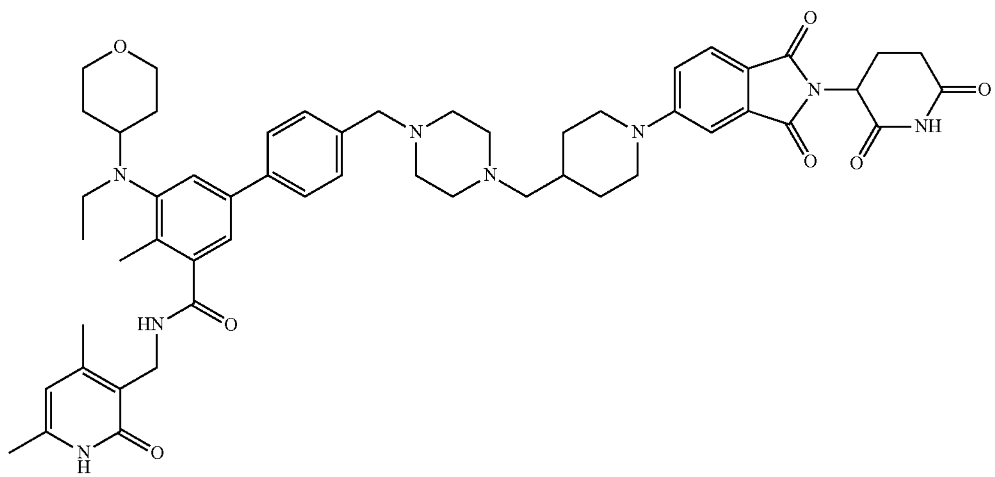 [SMILES: CCN(c1cc(-c2ccc(CN3CCN(CC4CCN(c5ccc6c(c5)C(=O)N(C5CCC(=O)NC5=O)C6=O)CC4)CC3)cc2)cc(C(=O)NCc2c(C)cc(C)[nH]c2=O)c1C)C1CCOCC1] | 925.73 | N-((4,6-dimethyl-2-oxo-1,2-dihydropyridin-3-yl)methyl)-4'-((4-((1-(2-(2,6-dioxopiperidin-3-yl)-1,3-dioxoisoindolin-5-yl)piperidin-4-yl)methyl)piperazin-1-yl)methyl)-5-(ethyl(tetrahydro-2H-pyran-4-yl)amino)-4-methyl-[1,1'-biphenyl]-3-carboxamide |

TABLE 1-continued

Exemplary compounds of the present disclosure

| Ex # | Structure | Mass Spec (M + H)+ unless otherwise noted | Name |
|---|---|---|---|
| 114 | 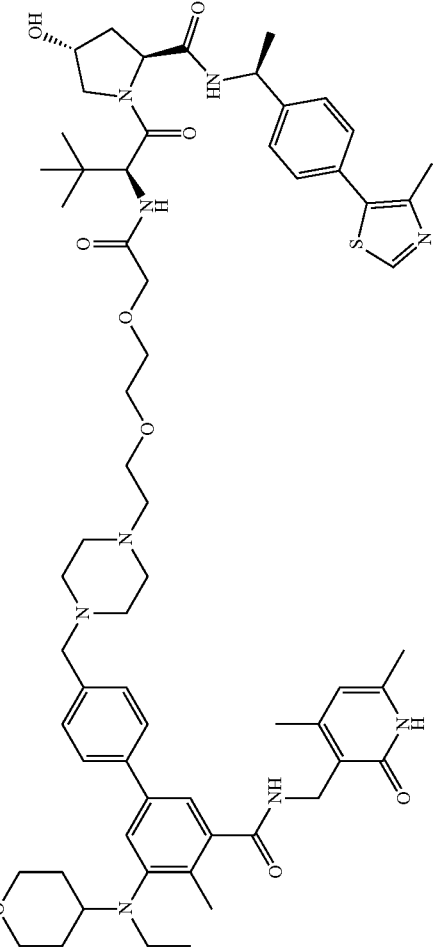 | 1144.90 | (2S,4R)-1-((S)-2-(2-(2-(2-(4-((3'-(((4,6-dimethyl-2-oxo-1,2-dihydropyridin-3-yl)methyl)carbamoyl)-5'-(ethyl(tetrahydro-2H-pyran-4-yl)amino)-4'-methyl-[1,1'-biphenyl]-4-yl)methyl)piperazin-1-yl)ethoxy)ethoxy)acetamido)-3,3-dimethylbutanoyl)-4-hydroxy-N-((S)-1-(4-(4-methylthiazol-5-yl)phenyl)ethyl)pyrrolidine-2-carboxamide |

TABLE 1-continued

Exemplary compounds of the present disclosure

| Ex # | Structure | Mass Spec (M + H)+ unless otherwise noted | Name |
|---|---|---|---|
| 115 | 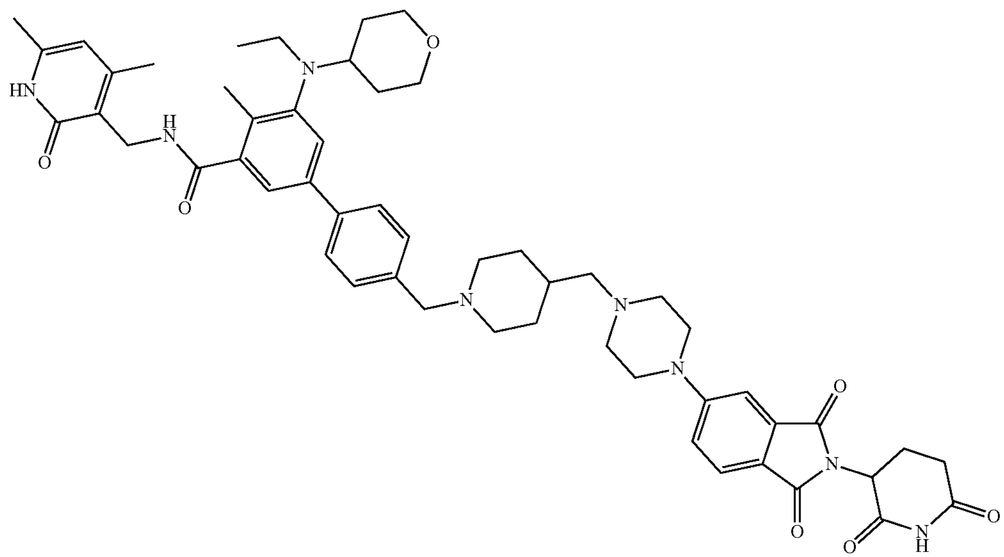 [SMILES: CCN(c1cc(-c2ccc(CN3CCC(CN4CCN(c5ccc6c(c5)C(=O)N(C5CCC(=O)NC5=O)C6=O)CC4)CC3)cc2)cc(C(=O)NCc2c(C)cc(C)[nH]c2=O)c1C)C1CCOCC1] | 925.73 | N-((4,6-dimethyl-2-oxo-1,2-dihydiopyridin-3-yl)methyl)-4'-((4-((4-(2-(2,6-dioxopiperidin-3-yl)-1,3-dioxoisoindolin-5-yl)piperazin-1-yl)methyl)piperidin-1-yl)methyl)-5-(ethyl(tetrahydro-2H-pyran-4-yl)amino)-4-methyl-[1,1'-biphenyl]-3-carboxamide |

TABLE 1-continued
Exemplary compounds of the present disclosure
| Ex # | Structure | Mass Spec (M + H)+ unless otherwise noted | Name |
|---|---|---|---|
| 116 | 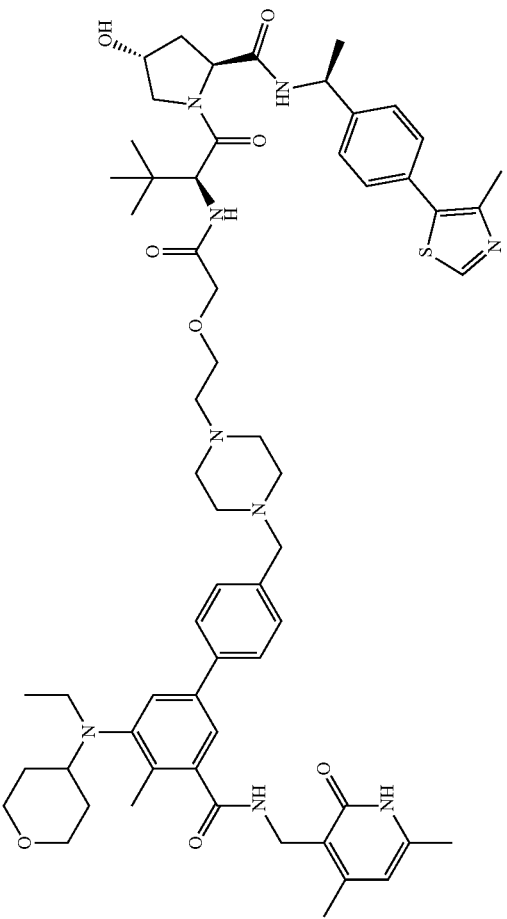 | 1100.86 | (2S,4R)-1-((S)-2-(2-(2-(4-((3'-(((4,6-dimethyl-2-oxo-1,2-dihydropyridin-3-yl)methyl)carbamoyl)-5'-(ethyl(tetrahydro-2H-pyran-4-yl)amino)-4'-methyl-[1,1'-biphenyl]-4-yl)methyl)piperazin-1-yl)ethoxy)acetamido)-3,3-dimethylbutanoyl)-4-hydroxy-N-((S)-1-(4-(4-methylthiazol-5-yl)phenyl)ethyl)pyrrolidine-2-carboxamide |

TABLE 1-continued

Exemplary compounds of the present disclosure

| Ex # | Structure | Mass Spec (M + H)+ unless otherwise noted | Name |
|---|---|---|---|
| 117 | 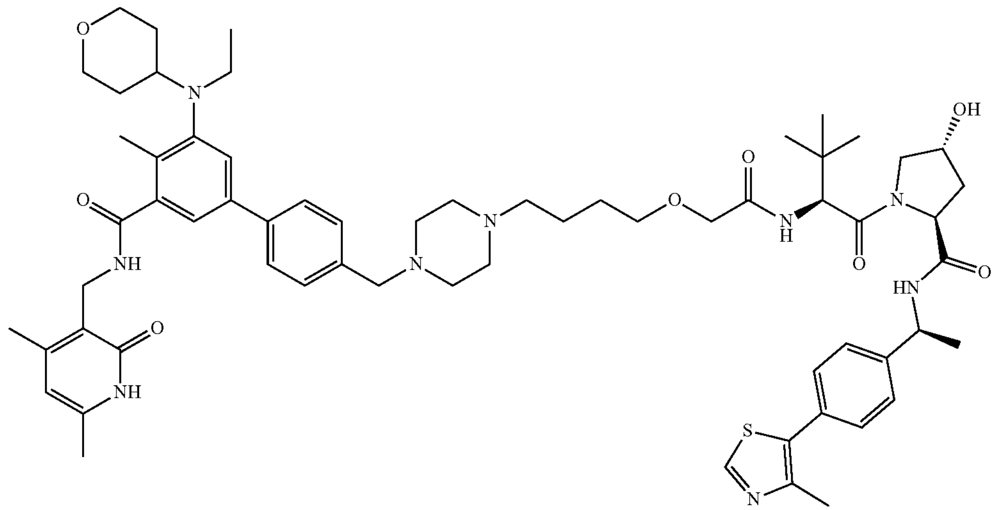 [SMILES: CCN(c1cc(-c2ccc(CN3CCN(CCCCOCC(=O)N[C@H](C(=O)N4C[C@H](O)C[C@H]4C(=O)N[C@@H](C)c4ccc(-c5scnc5C)cc4)C(C)(C)C)CC3)cc2)cc(C(=O)NCc2c(C)cc(C)[nH]c2=O)c1C)C1CCOCC1] | 1128.90 | (2S,4R)-1-((S)-2-(2-(4-(4-(3'-(((4,6-dimethyl-2-oxo-1,2-dihydropyridin-3-yl)methyl)carbamoyl)-5'-(ethyl(tetrahydro-2H-pyran-4-yl)amino)-4'-methyl-[1,1'-biphenyl]-4-yl)methyl)piperazin-1-yl)butoxy)acetamido)-3,3-dimethylbutanoyl)-4-hydroxy-N-((S)-1-(4-(4-methylthiazol-5-yl)phenyl)ethyl)pyrrolidine-2-carboxamide |
| 118 | 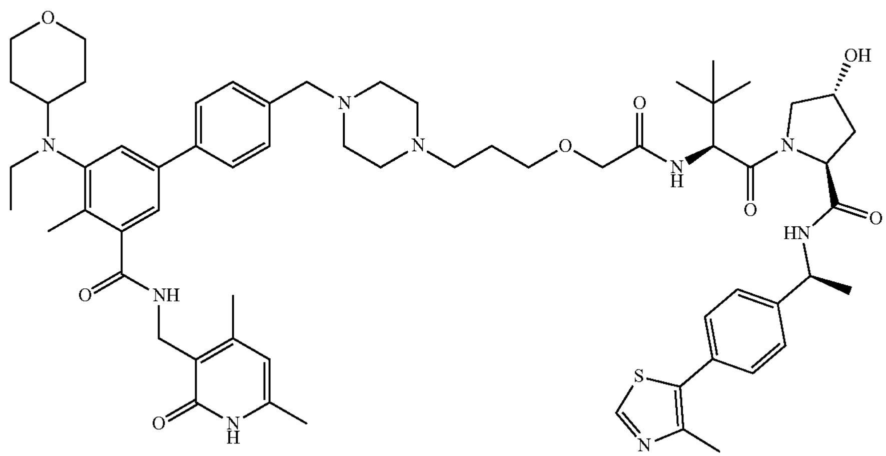 [SMILES: CCN(c1cc(-c2ccc(CN3CCN(CCCOCC(=O)N[C@H](C(=O)N4C[C@H](O)C[C@H]4C(=O)N[C@@H](C)c4ccc(-c5scnc5C)cc4)C(C)(C)C)CC3)cc2)cc(C(=O)NCc2c(C)cc(C)[nH]c2=O)c1C)C1CCOCC1] | 1114.89 | (2S,4R)-1-((S)-2-(2-(3-(4-(4-(3'-(((4,6-dimethyl-2-oxo-1,2-dihydropyridin-3-yl)methyl)carbamoyl)-5'-(ethyl(tetrahydro-2H-pyran-4-yl)amino)-4'-methyl-[1,1'-biphenyl]-4-yl)methyl)piperazin-1-yl)propoxy)acetamido)-3,3-dimethylbutanoyl)-4-hydroxy-N-((S)-1-(4-(4-methylthiazol-5-yl)phenyl)ethyl)pyrrolidine-2-carboxamide |

TABLE 1-continued

Exemplary compounds of the present disclosure

| Ex # | Structure | Mass Spec (M + H)+ unless otherwise noted | Name |
|---|---|---|---|
| 119 | 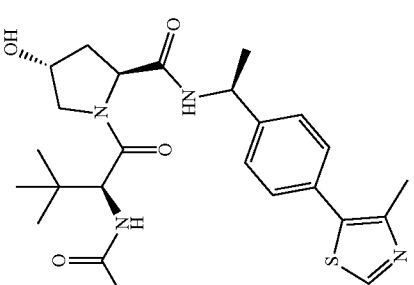 | 1144.90 | (2S,4R)-1-((S)-2-(2-(2-(3-(4-(3'-(((4,6-dimethyl-2-oxo-1,2-dihydropyridin-3-yl)methyl)carbamoyl)-5'-(ethyl(tetrahydro-2H-pyran-4-yl)amino)-4'-methyl-[1,1'-biphenyl]-4-yl)piperazin-1-yl)propoxy)ethoxy)acetamido)-3,3-dimethylbutanoyl)-4-hydroxy-N-((S)-1-(4-(4-methylthiazol-5-yl)phenyl)ethyl)pyrrolidine-2-carboxamide |

The following PROTACs demonstrated target protein degradation when tested under the conditions described above:

The following PROTACs demonstrated target protein degradation when tested under the conditions described above:

TABLE 2

Target protein degradation via Exemplary PROTACs

| Ex # | DC$_{50}$ | 1H NMR | Synthetic Scheme |
|---|---|---|---|
| 1 | B | | |
| 2 | B | | |
| 3 | B | | |
| 4 | B | | |
| 5 | B | | |
| 6 | B | | |
| 7 | B | | 3 |
| 8 | B | | 4 |
| 9 | B | | 4 |
| 10 | B | $^1$HNMR (400 MHz, CDCl$_3$): δ 11.40 (s, 1H), 7.88 (s, 1H), 7.35-7.50 (m, 3H), 7.09 (d, J = 6.8 Hz, 3H), 6.90 (d, J = 8.4 Hz, 1H), 6.51 (s, 1H), 4.88-4.91 (t, 1H), 4.10-4.59 (m, 6H), 3.44-3.68 (m, 16H), 2.65-2.83 (m, 11H), 2.43 (s, 3H), 1.67-2.20 (m, 6H), 1.59-1.61 (m, 4H). | 3 |
| 11 | B | | 4 |
| 12 | B | $^1$HNMR (400 MHz, CDCl$_3$): δ 11.12 (br, 1H), 7.87 (s, 1H), 7.45 (m, 2H), 7.35 (m, 1H), 7.15 (m, 3H), 6.91 (d, J = 8.8 Hz, 1H), 6.51 (s, 1H), 5.92 (s, 1H), 4.90 (m, 1H), 4.52 (m, 3H), 4.09 (m, 3H), 3.53 (m, 20H), 2.75 (m, 8H), 2.43 (s, 3H), 2.20 (s, 3H), 2.10 (m, 3H), 1.60 (m, 5H). | 3 |
| 13 | B | | 2 |
| 14 | B | | 2 |
| 15 | B | | 2 |
| 16 | B | | 2 |
| 17 | B | | 1 |
| 18 | B | | 1 |
| 19 | B | | 1 |
| 20 | B | | 1 |
| 21 | B | H-NMR (300 MHz, CD3OD) δ 7.55-7.43 (m, 2H), 7.32-7.29 (m, 2H), 7.14-7.01 (s, 4H), 6.92-6.89 (m, 1H), 6.10 (s, 1H), 5.01-4.99 (m, 1H), 4.49 (s, 2H), 4.18-4.15 (m, 2H), 3.95-3.78 (m, 4H), 3.75-3.51 (m, 18H), 3.51-3.33 (m, 4H), 3.22-3.01 (m, 3H), 2.89-2.59 (m, 3H), 2.39 (s, 3H), 2.33 (s, 3H), 2.23 (s, 3H), 2.12-2.02 (m, 1H), 1.82-1.55 m, 4H), 0.92-081 (m, 3H) | 1 |
| 22 | B | H-NMR: (300 MHz, CD3OD) δ 7.57-7.50 (m, 3H), 7.43 (s, 1H), 7.29 (s, 1H), 7.10-6.99 (m, 4H), 6.13 (s, 1H), 5.07-4.89 (m, 1H), 4.51 (s, 2H), 4.18-4.15 (m, 2H), 3.95-3.92 (d, J = 11.2 Hz, 2H), 3.88-3.86 (m, 2H), 3.72-3.60 (m, 26H), 3.51-3.48 (m, 2H), 3.45-3.40 (m, 2H), 3.19-3.11 (m, 3H), 2.82-2.72 (m, 3H), 2.41 (s, 3H), 2.33 (s, 3H), 2.25 (s, 3H), 2.09-2.07 (m, 1H), 1.79-1.76 (m, 2H), 1.66-1.64 (m, 2H), 0.93-0.89 (m, 3H) | 1 |
| 23 | B | H-NMR: (400 MHz, CD3OD) δ 7.58-7.50 (m, 3H), 7.43 (s, 1H), 7.29 (s, 1H), 7.11-7.00 (m, 4H), 6.13 (s, 1H), 5.07-5.02 (m, 1H), 4.51 (s, 2H), 4.18-4.16 (m, 2H), 3.95-3.92 (d, J = 10.4 MHz, 2H), 3.88-3.86 (m, 2H), 3.73-3.60 (m, 30H), 3.51-3.49 (m, 2H), 3.41-3.37 (m, 2H), 3.19-3.14 (m, 3H), 2.91-2.67 (m, 3H), 2.41 (s, 3H), 2.33 (s, 3H), 2.56 (s, 3H), 2.11-2.03 (m, 1H), 1.79-1.76 (d, J = 12.4 MHz, 2H), 1.67-1.64 (m, 2H), 0.93-0.90 (m, 3H) | 1 |
| 24 | B | $^1$H NMR (300 MHz, CD$_3$OD) δ11.60 (s, 1H), 10.41 (s, 1H), 8.62-8.55 (m, 1H), 8.33-8.31 (m, 1H), 8.19-8.16 (m, 1H), 7.82-7.80 (m, 1H), 7.60-7.54 (m, 6H), 7.40-7.35 (m, 4H), 7.18 (s, 1H), 7.02-6.99 (m, 2H), 5.85 (s, 1H), 4.61-4.59 (m, 2H), 4.50-4.25 (m, 3H), 4.11-4.10 (m, 2H), 4.08-3.91 (m, 4H), 3.91-3.72 (m, 4H), 3.56-3.54 (m, 10H), 3.42-3.34 (m, 4H), 3.08-3.06 (m, 3H), 2.51-2.49 (m, 6H), 2.10 (s, 3H), 1.75-1.63 (m, 4H), 0.97 (s, 9H). | 5 |
| 25 | B | H-NMR (400 MHz, CD3OD) δ 7.55-7.43 (m, 2H), 7.32-7.22 (m, 3H), 7.14-7.01 (s, 4H), 6.10 (s, 1H), 5.01-4.99 (m, 1H), 4.49 (s, 2H), 4.18-4.15 (m, 2H), 3.95-3.89 (m, 2H), 3.75-3.68 (m, 4H), 3.66-3.50 (m, 18H), 3.22-3.01 (m, 3H), 2.89-2.59 (m, 3H), 2.39 (s, 3H), 2.33 (s, 3H), 2.23 (s, 3H), 2.12-2.02 (m, 3H), 1.82-1.55 m, 4H), 0.91-0.89 (m, 3H) | 1 |
| 26 | B | 1H NMR (400 MHz, CD$_3$OD): δ7.52-7.49 (d, J = 8.8 Hz, 2H), 7.42 (d, J = 1.6 Hz, 1H), 7.29 (s, 1H), 7.09-6.99 (m, 4H), 6.85-6.83 (m, 2H), 6.12 (s, 1H), 4.50 (s, 2H), 4.16-4.14 (m, 3H), 4.09-4.07 (m, 2H), 3.94-3.82 (m, 7H), 3.74 (m, 4H), 3.37-3.32 (m, 3H), 3.16-3.13 (m, 5H), 2.85-2.70 (m, 3H), 2.60-2.50 (m, 2H), 2.33-2.30 (m, 3H), 2.28-2.26 (m, 6H), 2.25 (s, 3H), 2.20-2.00 (m, 4H), 1.88-1.85 (m, 3H), 1.78-1.64 (m, 10H), 1.24-1.21 (d, J = 14.0 Hz, 6H), 1.20-1.00 (m, 2H), 0.92-0.89 (t, J = 7.0 Hz, 3H) | 6 |

TABLE 2-continued

Target protein degradation via Exemplary PROTACs

| Ex # | DC$_{50}$ | 1H NMR | Synthetic Scheme |
|---|---|---|---|
| 27 | B | 1H NMR (400 MHz, CD3OD): δ8.38-8.36 (d, J = 8.4 Hz, 1H), 7.72-7.70 (m, 1H), 7.56-7.47 (m, 4H), 7.45-7.33 (m, 4H), 7.29-7.24 (m, 3H), 7.00-6.98 (d, J = 8.8 Hz, 2H), 6.11 (s, 1H), 4.78-4.75 (d, J = 8.4 Hz, 1H), 4.63-4.61 (d, J = 9.6 Hz, 1H), 4.50 (s, 2H), 4.15-4.12 (m, 2H), 4.09-4.06 (d, J = 9.6 Hz, 1H), 3.99 (s, 3H), 3.94-3.82 (m, 4H), 3.69-3.55 (m, 20H), 3.39-3.36 (m, 2H), 3.16-3.14 (m, 3H), 2.40 (s, 3H), 2.32 (s, 3H), 2.24 (s, 3H), 1.74-1.68 (m, 5H), 1.38-1.35 (m, 1H), 1.04 (s, 9H), 0.92-0.88 (m, 3H) | 5 |
| 28 | B | $^1$H NMR (400 MHz, CD$_3$OD): δ 8.35 (m, 1H), 8.10 (m, 1H), 7.50-7.43 (m, 6H), 7.38 (s, 1H), 7.25 (m, 1H), 6.95-6.92 (m, 3H), 6.09 (s, 1H), 5.50 (m, 1H), 4.60 (m, 1H), 4.48 (s, 2H), 4.34-4.32 (d, J = 4.40 Hz, 2H), 4.10-4.08 (m, 2H), 4.03-4.01 (m, 2H), 3.90-3.76 (m, 10H), 3.32-3.30 (m, 3H), 3.20-3.10 (m, 4H), 2.38 (s, 3H), 2.33-2.30 (d, J = 11.2 Hz, 6H), 2.22-2.16 (m, 4H), 1.80-1.59 (m, 11H), 1.28-1.24 (m, 5H), 1.13-1.11 (m, 4H), 0.88-0.85 (t, J = 7.0 Hz, 3H) | 7 |
| 29 | B | 1H NMR (400 MHz, CD3OD): δ7.60-7.50 (m, 2H), 7.41-7.40 (s, 1H), 7.27 (s, 1H), 7.19-6.98 (m, 4H), 6.90-6.83 (m, 2H), 6.11 (m, 1H), 4.88 (s, 2H), 4.49 (m, 1H), 4.14-4.05 (m, 5H), 4.05-3.79 (m, 7H), 3.70-3.64 (m, 13H), 3.35-3.30 (s, 1H), 3.15-3.00 (m, 4H), 2.80-2.60 (m, 3H), 2.60-2.50 (m, 3H), 2.45-2.35 (m, 3H), 2.30 (s, 6H), 2.24-2.10 (m, 5H), 2.10-1.95 (m, 2H), 1.90-1.50 (m, 14H), 1.40-1.15 (m, 10H), 0.91-0.85 (m, 3H) | 6 |
| 30 | B | 1H NMR (400 MHz, CD3OD): δ 8.40 (m, 1H), 8.10-8.00 (m, 1H), 7.60-7.45 (m, 7H), 7.39 (s, 1H), 7.26 (s, 1H), 6.95-6.93 (m, 3H), 6.09 (s, 1H), 5.50 (s, 1H), 4.60 (m, 1H), 4.48 (s, 2H), 4.32 (m, 2H), 4.08-4.07 (m, 2H), 4.00-3.99 (m, 3H), 3.98-3.90 (m, 3H), 3.78-3.77 (m, 5H), 3.76-3.75 (m, 3H), 3.69-3.60 (m, 10H), 3.30-3.12 (m, 4H), 2.40-2.38 (m, 7H), 2.30 (s, 4H), 2.22 (s, 6H), 2.15-2.00 (m, 2H), 1.90-1.50 (m, 12H), 0.89-0.85 (m, 4H) | 7 |
| 31 | A | $^1$HNMR (400 MHz, MeOD): δ 8.81 (s, 1H), 7.36-7.45 (m, 7H), 6.96 (d, J = 8.8 Hz, 2H), 6.10 (s, 1H), 4.85 (s, 1H), 4.49-4.69 (m, 5H), 4.18-4.19 (d, J = 4.8 Hz, 1H), 4.05-4.17 (m, 4H), 3.75-3.91 (m, 10H), 3.11-3.13 (m, 3H), 2.41 (s, 3H), 2.39 (s, 3H), 2.30 (s, 3H), 2.03-2.23 (m, 7H), 1.50-1.80 (m, 5H), 1.00 (s, 9H), 0.88 (m, 6H). | 2 |
| 32 | B | $^1$H NMR (400 MHz, MeOD): δ 8.77 (s, 1H), 7.32-7.48 (m, 7H), 7.21 (s, 1H), 7.10 (d, J = 8.8 Hz, 2H), 6.10 (s, 1H), 4.73 (s, 1H), 4.49-4.62 (m, 5H), 3.80-4.35 (m, 11H), 2.92-3.11 (m, 3H), 2.47 (s, 3H), 2.39 (s, 3H), 2.35 (s, 3H), 2.30 (s, 3H), 2.10-2.28 (m, 7H), 1.50-1.80 (m, 4H), 1.36 (s, 9H), 0.82-0.93 (m, 3H). | 2 |
| 33 | B | $^1$HNMR (400 MHz, CDCl$_3$): δ 10.98 (s, 1H), 10.75 (s, 1H), 7.46 (m, 4H), 7.27 (m, 1H), 7.20 (s, 1H), 7.08 (d, J = 7.2 Hz, 1H), 6.95 (d, J = 8.8 Hz, 2H), 6.89 (d, J = 8.4 Hz, 1H), 6.60 (m, 1H), 5.92 (s, 1H), 4.80 (m, 2H), 4.51 (d, J = 6.0 Hz, 2H), 4.15-4.30 (m, 2H), 3.65-4.00 (m, 10H), 3.00-3.55 (m, 7H), 2.50-2.75 (m, 3H), 2.42 (s, 3H), 2.38 (s, 3H), 2.20 (s, 3H), 1.90 (m, 1H), 1.75 (m, 3H), 0.89 (m, 3H). | 1 |
| 34 | B | $^1$H NMR (400 MHz, MeOD): δ11.55 (br, 1H), 10.85 (br, 1H), 7.42-7.56 (m, 5H), 7.29 (s, 1H), 7.22 (s, 1H), 7.10 (d, J = 7.2 Hz, 1H), 7.06 (d, J = 28.2 Hz, 2H), 6.95 (m, 1H), 6.71 (m, 1H), 5.91 (s, 1H), 4.92-4.98 (m, 1H), 4.65-4.72 (m, 1H), 4.35-4.41 (m, 1H), 4.19-4.21 (m, 2H), 3.81-3.96 (m, 6H), 3.21-3.47 (m, 4H), 2.83-3.17 (m, 6H), 2.41 (s, 6H), 2.19 (s, 3H), 2.12-2.23 (m, 1H), 1.71 (m, 3H), 0.89 (t, J = 14.0 Hz, 3H). | 1 |
| 35 | B | $^1$H NMR (400 MHz, DMSO): δ 11.42 (s, 1H), 8.90 (s, 1H), 8.29 (s, 1H), 8.10 (s, 1H), 7.54 (d, J = 3.2 Hz, 1H), 7.45-7.55 (m, 5H), 7.27 (d, J = 5.6 Hz, 2H), 7.11 (s, 1H), 6.92-6.98 (m, 4H), 5.78 (s, 1H), 5.02 (s, 1H), 4.67 (d, J = 4.0 Hz, 1H), 4.32-4.51 (m, 3H), 4.22-4.28 (m, 5H), 4.05-4.12 (m, 4H), 3.67-3.72 (m, 8H), 3.46-4.50 (m, 12H), 3.11 (m, 3H), 3.05 (m, 3H), 2.40 (s, 3H), 2.25 (m, 1H), 2.16 (s, 3H), 2.14 (s, 3H), 2.03 (s, 3H), 2.00 (m, 1H), 1.90 (m, 1H), 1.61 (m, 2H), 1.52 (m, 2H), 0.90 (d, J = 6.4 Hz, 3H), 0.75 (t, J = 6.8 Hz, 3H), 0.66 (d, J = 6.8 Hz, 3H). | 8 |
| 36 | B | $^1$HNMR (400 MHz, DMSO): δ 11.45 (s, 1H), 8.99 (s, 1H), 8.38 (t, J = 6.4 Hz, 1H), 8.18 (t, J = 6.4 Hz, 1H), 7.75 (d, J = 4.8 Hz, 1H), 7.60 (m, 5H), 7.40 (m, 2H), 7.15 (s, 1H), 7.02 (m, 4H), 5.88 (s, 1H), 5.12 (s, 1H), 4.72 (d, J = 4.0 Hz, 1H), 4.40 (m, 12H), 3.50 (m, 16H), 3.25 (m, 3H), 3.10 (m, 3H), 2.42 (d, J = 14.4 Hz, 3H), 2.30 (m, 1H), 2.15 (d, J = 10.4 Hz, 3H), 2.15 (s, 3H), 1.90 (m, 2H), 1.50 (m, 4H), 1.00 (d, J = 6.4 Hz, 3H), 0.85 (t, J = 6.8 Hz, 3H), 0.76 (d, J = 6.8 Hz, 3H). | 8 |
| 37 | A | $^1$HNMR (400 MHz, CD3OD): δ 8.84 (s, 1H), 7.81 (t, J = 6.8 Hz, 1H), 7.41-7.53 (m, 7H), 7.24 (s, 1H), 7.03-7.04 (m, 2H), 6.94 (d, J = 8.8 Hz, 2H), 6.08 (s, 1H), 5.12 (s, 1H), 4.45-4.57 (m, | 8 |

TABLE 2-continued

Target protein degradation via Exemplary PROTACs

| Ex # | DC$_{50}$ | 1H NMR | Synthetic Scheme |
|---|---|---|---|
| | | 8H), 4.22-4.24 (m, 2H), 4.09-4.22 (m, 2H), 3.74-3.92 (m, 12H), 3.11-3.13 (m, 3H), 2.47 (s, 3H), 2.38 (s, 3H), 2.31 (m, 3H), 2.22 (s, 3H), 2.15 (m, 13H), 2.04 (m, 1H), 1.60-1.72 (m, 4H), 1.03 (d, J = 6.4 Hz, 3H), 0.88 (t, J = 6.8 Hz, 3H), 0.80 (d, J = 6.8 Hz, 3H). | |
| 38 | B | $^1$H NMR (400 MHz, CD3OD): δ 8.84 (s, 1H), 7.74 (t, J = 6.8 Hz, 1H), 7.38-7.57 (m, 8H), 7.25 (s, 1H), 7.02-7.06 (m, 2H), 6.96 (d, J = 8.8 Hz, 2H), 6.08 (s, 1H), 4.42-4.55 (m, 9H), 4.27 (s, 2H), 4.19 (s, 2H), 3.89-3.99 (m, 9H), 3.12-3.14 (m, 3H), 2.47 (s, 3H), 2.38 (s, 3H), 2.31 (m, 3H), 2.22 (s, 3H), 2.15 (m, 1H), 2.04 (m, 1H), 1.60-1.72 (m, 4H), 1.03 (d, J = 6.4 Hz, 3H), 0.88 (t, J = 6.8 Hz, 3H), 0.80 (d, J = 6.8 Hz, 3H). | 8 |
| 39 | B | 1H NMR (400 MHz, DMSO): δ 11.45 (s, 1H), 8.99 (s, 1H), 8.38 (t, J = 6.4 Hz, 1H), 8.18 (t, J = 6.4 Hz, 1H), 7.75 (d, J = 4.8 Hz, 1H), 7.60 (m, 5H), 7.35 (m, 2H), 7.18 (s, 1H), 6.99 (m, 4H), 5.86 (s, 1H), 5.09 (s, 1H), 4.72 (d, J = 4.0 Hz, 1H), 4.40 (m, 12H), 3.80 (m, 4H), 3.00-3.60 (m, 14H), 2.45 (s, 3H), 2.35 (m, 1H), 2.24 (s, 3H), 2.21 (s, 3H), 2.11 (s, 3H), 1.95 (m, 6H), 1.50-1.80 (m, 6H), 1.30 (d, J = 12.0 Hz, 2H), 0.97 (d, J = 6.8 Hz, 3H), 0.83 (t, J = 6.8 Hz, 3H), 0.74 (t, J = 6.8 Hz, 3H). | 8 |
| 40 | B | $^1$HNMR (400 MHz, DMSO): δ 11.45 (s, 1H), 8.97 (s, 1H), 8.33-8.35 (m, 1H), 8.13-8.15 (m, 1H), 7.70 (t, J = 6.8 Hz, 1H), 7.61 (d, J = 4.0 Hz, 2H), 7.50-7.52 (m, 3H), 7.33 (m, 2H), 7.16 (s, 1H), 6.95-7.02 (m, 4H), 5.85 (s, 1H), 5.08 (s, 1H), 4.71 (d, J = 6.8 Hz, 1H), 4.41-4.52 (m, 3H), 4.31-4.41 (s, 5H), 4.20 (t, J = 4.0 Hz, 2H), 3.98 (t, J = 4.0 Hz, 2H), 3.59-3.78 (m, 4H), 3.47 (t, J = 6.4 Hz, 3H), 3.31 (t, J = 6.4 Hz, 2H), 2.46 (s, 3H), 2.21-2.23 (m, 6H), 2.10 (m, 3H), 1.95-2.00 (m, 3H), 1.64-1.82 (m, 6H), 1.45-1.52 (m, 2H), 0.96 (d, J = 6.4 Hz, 3H), 0.82 (d, J = 6.8 Hz, 3H), 0.73 (t, J = 6.4 Hz, 3H). | 8 |
| 41 | A | $^1$HNMR (400 MHz, MeOD): δ 8.83 (s, 1H), 7.80 (d, J = 8.0 Hz, 1H), 7.44-7.47 (m, 5H), 7.36-7.38 (m, 2H), 7.24 (s, 1H), 7.01 (d, J = 8.0 Hz, 2H), 6.11 (s, 1H), 4.50-4.57 (m, 9H), 4.32-4.35 (m, 1H), 4.17-4.19 (m, 2H), 4.02-4.04 (m, 2H), 3.88-3.92 (m, 3H), 3.78-3.83 (m, 3H), 3.05-3.15 (m, 3H), 2.42 (s, 3H), 2.40 (s, 3H), 2.32 (s, 3H), 2.21-2.24 (m, 4H), 2.10-2.15 (m, 3H), 1.72-1.78 (m, 2H), 1.61-1.69 (m, 2H), 1.03 (s, 9H), 0.89 (t, J = 4.0 Hz, 3H). | 2 |
| 42 | A | $^1$HNMR (400 MHz, CDCl3): δ 10.51 (br, 1H), 8.67 (s, 1H), 7.42 (d, J = 8.4 Hz, 2H), 7.26-7.43 (m, 8H), 7.21 (s, 2H), 6.91 (d, J = 8.4 Hz, 2H), 5.90 (s, 1H), 4.72 (t, J = 6.4 Hz, 1H), 4.52-4.59 (m, 4H), 4.40-4.45 (m, 1H), 4.23-4.28 (m, 1H), 3.91-4.05 (m, 6H), 3.57-3.62 (m, 3H), 3.22-3.28 (m, 2H), 2.95-3.07 (m, 3H), 2.50 (s, 4H), 2.41 (s, 3H), 2.35 (s, 3H), 2.19 (s, 3H), 1.95-2.07 (m, 2H), 1.81-1.87 (m, 4H), 1.62-1.69 (m, 3H), 0.95 (s, 9H), 0.89 (t, J = 6.8 Hz, 3H). | 2 |
| 43 | A | $^1$HNMR (400 MHz, CDCl$_3$) δ 10.53 (br, 2H), 8.67 (s, 1H), 7.41-7.54 (m, 4H), 7.35 (dd, J = 17.5, 8.2 Hz, 4H), 7.28 (s, 1H), 7.20 (s, 1H), 6.99 (d, J = 8.5 Hz, 2H), 5.90 (s, 1H), 5.01-5.12 (m, 1H), 4.75 (t, J = 7.6 Hz, 1H), 4.70 (d, J = 8.9 Hz, 1H), 4.62 (dd, J = 14.1, 6.4 Hz, 1H), 4.51 (s, 1H), 4.39 (dd, J = 14.3, 5.4 Hz, 1H), 4.31 (s, 1H), 4.19 (d, J = 11.1 Hz, 3H), 4.10-3.98 (m, 2H), 3.97-3.83 (m, 5H), 3.75 (d, J = 4.2 Hz, 2H), 3.65-3.72 (m, 2H), 3.58 (d, J = 8.6 Hz, 1H), 3.31 (s, 2H), 3.08 (d, J = 6.8 Hz, 2H), 3.00 (s, 1H), 2.51 (s, 3H), 2.43 (s, 3H), 2.36 (s, 3H), 2.19 (s, 3H), 1.95-2.05 (m, 1H), 1.44 (d, J = 6.9 Hz, 3H), 1.07 (s, 9H), 0.87 (t, J = 6.9 Hz, 3H). | 2 |
| 44 | B | $^1$HNMR (400 MHz, MeOD): δ 8.84 (s, 1H), 7.80 (d, J = 8.0 Hz, 1H), 7.38-7.47 (m, 7H), 7.24-7.29 (m, 3H), 6.09 (s, 1H), 4.62-4.65 (m, 1H), 4.54-4.56 (m, 1H), 4.43-4.48 (m, 3H), 4.32-4.35 (m, 1H), 3.88-3.91 (m, 3H), 3.73-3.75 (m, 1H), 3.65 (s, 1H), 3.40-3.44 (m, 4H), 3.32-3.35 (m, 2H), 3.10-3.14 (m, 3H), 2.65-2.70 (m, 2H), 2.45 (s, 3H), 2.38 (s, 3H), 2.29-2.31 (m, 5H), 2.21-2.23 (m, 4H), 2.16-2.18 (m, 1H), 1.86-1.88 (m, 2H), 1.72-1.78 (m, 4H), 1.61-1.69 (m, 4H), 1.03 (s, 9H), 0.89 (t, J = 4.0 Hz, 3H). | 9 |
| 45 | B | $^1$H NMR (400 MHz, CDCl$_3$): δ 11.13 (br, 1H), 8.60 (s, 1H), 7.32-7.37 (m, 4H), 7.19-7.25 (m, 6H), 7.14 (s, 1H), 6.87 (d, J = 8.0 Hz, 2H), 5.83 (s, 1H), 5.22 (s, 2H), 4.43-4.58 (m, 5H), 4.28-4.33 (m, 1H), 4.18-4.23 (m, 1H), 3.93-4.12 (m, 3H), 3.85-3.89 (m, 4H), 3.53-3.59 (m, 7H), 3.21-3.25 (m, 2H), 2.93-3.02 (m, 3H), 2.43 (s, 3H), 2.30-2.34 (m, 7H), 2.10 (s, 3H), 1.95-1.98 (m, 3H), 1.19 (s, 3H), 0.89 (s, 9H), 0.81 (t, J = 6.8 Hz, 3H). | 2 |

TABLE 2-continued

Target protein degradation via Exemplary PROTACs

| Ex # | DC$_{50}$ | 1H NMR | Synthetic Scheme |
|---|---|---|---|
| 46 | A | ¹HNMR (400 MHz, CDCl$_3$): δ 11.50 (s, 1H), 8.66 (s, 1H), 7.40-7.46 (m, 3H), 7.22-7.33 (m, 9H), 6.89-6.91 (d, J = 8.0 Hz, 2H), 5.89 (s, 1H), 4.71-4.73 (m, 1H), 4.59-4.62 (m, 1H), 4.50-4.56 (m, 3H), 4.26-4.29 (m, 2H), 4.06-4.09 (m, 1), 3.99-4.02 (m, 1H), 3.88-3.96 (m, 5H), 3.49-3.52 (m, 2H), 3.41-3.45 (m, 2H), 3.27-3.30 (m, 2), 3.09-3.13 (m, 3H), 2.49 (s, 3H), 2.39-2.44 (m, 7H), 2.15 (s, 3H), 2.05-2.08 (m, 1H), 1.76-1.80 (m, 2H), 1.63-1.69 (m, 6H), 1.51-1.55 (m, 2H), 0.96 (s, 9H), 0.87-0.90 (t, J = 4.0 Hz, 3H). | 2 |
| 47 | B | ¹HNMR (400 MHz, CDCl3): δ 11.50 (br, 1H), 8.59 (s, 1H), 7.48-7.51 (m, 1H), 7.34 (d, J = 8.0 Hz, 2H), 7.11-7.25 (m, 11H), 5.82 (s, 1H), 4.63 (t, J = 6.4 Hz, 1H), 4.42-4.52 (m, 5H), 4.13-4.18 (m, 1H), 3.92-3.93 (m, 1H), 3.85-3.88 (m, 4H), 3.50-3.60 (m, 5H), 3.37-3.41 (m, 3H), 3.21-3.28 (m, 2H), 2.95-3.05 (m, 3H), 2.62 (t, J = 7.2 Hz, 2H), 2.29-2.41 (m, 10H), 2.08 (s, 3H), 1.82-1.84 (m, 3H), 1.63-1.75 (m, 4H), 0.89 (s, 9H), 0.81 (t, J = 6.8 Hz, 3H). | |
| 48 | A | ¹H NMR (400 MHz, CDCl$_3$): δ 11.03 (br, 1H), 8.68 (s, 1H), 7.43 (d, J = 8.0 Hz, 2H), 7.22-7.35 (m, 8H), 6.92 (d, J = 8.0 Hz, 2H), 5.92 (s, 1H), 4.51-4.69 (m, 5H), 4.27-4.41 (m, 2H), 4.06-4.14 (m, 3H), 3.79-3.95 (m, 4H), 3.52-3.58 (m, 7H), 3.31 (br, 3H), 3.01-3.08 (m, 3H), 2.61 (m, 3H), 2.51 (s, 3H), 2.42 (m, 3H), 2.37 (s, 3H), 2.00-2.03 (m, 3H), 1.84-1.87 (m, 2H), 0.95 (s, 9H), 0.84-0.89 (m, 3H). | 2 |
| 49 | B | ¹H NMR (400 MHz, MeOD): δ 8.85 (s, 1H), 8.38-8.40 (m, 1H), 8.27 (s, 1H), 7.77 (d, J = 8.0 Hz, 1H), 7.38-7.76 (m, 7H), 7.25 (s, 1H), 6.97-7.03 (m, 4H), 6.08 (s, 1H), 4.39-4.63 (m, 10H), 4.06-4.15 (m, 4H), 3.79-3.98 (m, 6H), 3.60-3.63 (m, 2H), 3.34-3.37 (m, 2H), 3.04-3.15 (m, 3H), 2.47 (m, 3H), 2.39-2.44 (m, 1H), 2.38 (s, 3H), 2.30 (s, 3H), 2.22 (s, 3H), 2.15-2.19 (m, 1H), 2.03-2.11 (m, 1H), 1.85-1.92 (m, 2H), 1.61-1.75 (m, 8H), 1.02 (d, J = 8.0 Hz, 3H), 0.86-0.89 (m, 3H), 0.81 (d, J = 8.0 Hz, 3H). | 8 |
| 50 | A | 1H NMR (400 MHz, MeOD) δ 8.86 (s, 1H), 7.54 (d, J = 4.8 Hz, 1H), 7.43-7.46 (m, 2H), 7.39-7.41 (m, 5H), 7.25 (s, 1H), 7.04-7.07 (m, 2H), 6.92 (d, J = 8.8 Hz, 2H), 6.09 (s, 1H), 4.80 (m, 2H), 4.43-4.57 (m, 8H), 4.24 (d, J = 2.8 Hz, 2H), 3.85-3.95 (m, 8H), 3.62 (t, J = 6.8 Hz, 2H), 3.35-3.36 (m, 1H), 3.12-3.14 (m, 3H), 2.49 (s, 3H), 2.46-2.48 (m, 1H), 2.38 (s, 3H), 2.31 (s, 3H), 2.23 (s, 3H), 2.05-2.22 (m, 2H), 1.67-1.76 (m, 10H), 1.03 (d, J = 6.4 Hz, 3H), 0.88 (t, J = 6.8 Hz, 3H), 0.80 (d, J = 6.4 Hz, 3H) | 8 |
| 51 | B | ¹H NMR (400 MHz, MeOD): δ 8.74 (s, 1H), 7.67 (d, J = 8.0 Hz, 1H), 7.28-7.55 (m, 7H), 7.15 (s, 1H), 6.82 (m, 4H), 5.98 (s, 1H), 4.30-4.53 (m, 10H), 3.97 (t, J = 6.4 Hz, 4H), 3.80 (m, 4H), 3.54 (t, J = 6.0 Hz, 2H), 3.47 (t, J = 6.0 Hz, 2H), 3.25 (m, 1H), 3.04 (m, 6H), 2.36 (s, 3H), 2.28 (s, 3H), 2.21 (s, 3H), 2.12 (s, 3H), 1.45-2.10 (m, 16H), 0.92 (d, J = 6.4 Hz, 3H), 0.78 (t, J = 7.2 Hz, 3H), 0.70 (d, J = 6.8 Hz, 3H). | 8 |
| 52 | B | ¹H NMR (400 MHz, CDCl$_3$): δ 8.75 (s, 1H), 7.78-7.79 (m, 1H), 7.52-7.62 (m, 1H), 7.39-7.41 (m, 4H), 7.25-7.33 (m, 9H), 6.92 (m, 1H), 6.87-6.89 (m, 3H), 5.95 (s, 1H), 4.45-4.78 (m, 11H), 4.37-4.41 (m, 2H), 3.94-4.16 (m, 4H), 3.66-3.68 (m, 3H), 3.54-3.55 (m, 2H), 3.32-3.38 (m, 2H), 3.01-3.21 (m, 3H), 2.54 (s, 3H), 2.36-2.42 (m, 10H), 2.13-2.23 (m, 9H), 1.98-2.04 (m, 2H), 1.71-1.86 (m, 12H), 0.86-0.93 (m, 9H) | 8 |
| 53 | B | ¹H NMR (400 MHz, CDCl$_3$) δ 10.79-11.15 (m, 1H), 8.68 (s, 1H), 7.70 (d, J = 6.2 Hz, 1H), 7.47 (d, J = 6.8 Hz, 1H), 7.38 (s, 4H), 7.32 (d, J = 8.0 Hz, 1H), 7.15 (s, 1H), 6.98 (d, J = 7.7 Hz, 1H), 6.83-6.93 (m, 3H), 5.94 (s, 1H), 4.67-4.85 (m, 2H), 4.51 (s, 4H), 4.39 (s, 3H), 4.19 (s, 2H), 3.79-4.04 (m, 6H), 3.64 (d, J = 6.0 Hz, 3H), 3.31 (s, 2H), 3.04 (d, J = 29.7 Hz, 3H), 2.53 (s, 3H), 2.41 (s, 3H), 2.36 (s, 3H), 2.27 (s, 3H), 1.88 (d, J = 5.8 Hz, 3H), 1.81 (d, J = 6.7 Hz, 3H), 1.70 (s, 6H), 0.72-0.96 (m, 9H). | 8 |
| 54 | B | ¹HNMR (400 MHz, MeOD): δ 8.83 (s, 1H), 8.35 (t, J = 5.6 Hz, 1H), 8.26 (m, 1H), 7.75 (d, J = 7.6 Hz, 1H), 7.37-7.58 (m, 8H), 7.24 (s, 1H), 7.00-7.02 (m, 2H), 6.92 (d, J = 8.8 Hz, 2H), 6.07 (s, 1H), 4.42-4.61 (m, 9H), 4.17-4.20 (m, 6H), 3.84-3.98 (m, 6H), 3.63-3.74 (m, 6H), 2.37-2.45 (m, 6H), 2.30 (s, 3H), 2.01-2.21 (m, 4H), 1.97-2.07 (m, 5H), 1.56-1.74 (m, 4H), 1.22-1.28 (m, 2H), 1.02 (d, J = 6.4 Hz, 3H), 0.86 (t, J = 13.6 Hz, 3H), 0.79 (d, J = 6.4 Hz, 3H). | 8 |
| 55 | B | ¹H NMR (400 MHz, CDCl3): δ 11.027 (s, 1H), 8.678 (s, 1H), 7.72 (d, J = 7.6, 1H), 7.49-7.51 (m, 1H), 7.40 (d, J = 7.2, 4H), 7.19-7.32 (m, 6H), 6.97 (d, J = 7.6, 1H), 6.88-6.90 (m, 3H), | 8 |

TABLE 2-continued

Target protein degradation via Exemplary PROTACs

| Ex # | DC$_{50}$ | 1H NMR | Synthetic Scheme |
|---|---|---|---|
| | | 5.91 (s, 1H), 4.73-4.80 (m, 2H), 4.34-4.57 (m, 8H), 4.18-4.21 (m, 2H), 3.92-3.98 (m, 6H), 3.73-3.74 (m, 2H), 3.62-3.65 (m, 3H), 3.51 (t, J = 6.4, 2H), 3.31 (t, J = 10.8, 2H), 3.01-3.09 (m, 3H), 2.52 (s, 3H), 2.36-2.40 (m, 6H), 2.23-2.28 (m, 3H), 1.93-1.98 (m, 1H), 1.79-1.84 (m, 3H), 1.71-1.76 (m, 7H), 0.85-0.94 (m, 10H). | |
| 56 | B | $^1$H NMR (400 MHz, MeOD) δ 8.84-8.87 (m, 1H), 7.76-7.80 (m, 1H), 7.46-7.64 (m, 4H), 7.41-7.45 (m, 1H), 7.38-7.40 (m, 1H), 7.25-7.28 (m, 1H), 7.01-7.07 (m, 2H), 6.90-6.95 (m, 2H), 6.06-6.14 (m, 2H), 4.85-4.88 (m, 1H), 4.62-4.65 (m, 1H), 4.57-4.60 (m, 1H), 4.52-4.56 (m, 1H), 4.43-4.52 (m, 5H), 4.23-4.29 (m, 2H), 4.07-4.14 (m, 2H), 3.85-4.00 (m, 6H), 3.78-3.83 (m, 2H), 3.09-3.18 (m, 3H), 2.48 (s, 3H), 2.40 (s, 3H), 2.33 (s, 2H), 2.24 (s, 3H), 2.12-2.22 (m, 3H), 2.02-2.12 (m, 4H), 1.70-1.81 (m, 3H), 1.57-1.70 (m, 4H), 1.28-1.39 (m, 6H), 1.01-1.05 (m, 2H), 0.87-0.95 (m, 4H), 0.78-0.85 (m, 3H) | 8 |
| 57 | B | $^1$H NMR (400 MHz, MeOD): δ 7.82 (s, 1H), 7.71 (d, J = 8.3 Hz, 2H), 7.60 (d, J = 7.9 Hz, 2H), 7.39 (d, J = 2.0 Hz, 1H), 7.29 (dd, J = 8.3, 2.1 Hz, 1H), 6.98 (d, J = 8.7 Hz, 2H), 6.12 (s, 1H), 5.07 (dd, J = 12.7, 5.5 Hz, 1H), 4.50 (s, 2H), 4.31-4.37 (m, 2H), 4.15-4.21 (m, 2H), 3.89-4.12 (m, 8H), 3.78 (s, 3H), 3.43 (d, J = 39.1 Hz, 3H), 2.57-2.94 (m, 6H), 2.42 (s, 3H), 2.40 (s, 3H), 2.24 (s, 3H), 2.18 (dd, J = 16.0, 10.1 Hz, 1H), 2.00-2.12 (m, 2H), 1.05 (s, 3H). | 10 |
| 58 | A | $^1$H NMR (400 MHz, CDCl$_3$): δ 10.52 (s, 1H), 10.15-10.31 (m, 2H), 7.67 (d, J = 8.3 Hz, 1H), 7.33-7.43 (m, 3H), 7.22 (d, J = 8.1 Hz, 2H), 7.15 (d, J = 8.3 Hz, 1H), 6.81 (d, J = 8.5 Hz, 2H), 5.94 (s, 1H), 4.87 (d, J = 6.9 Hz, 1H), 4.55 (s, 2H), 4.25 (t, J = 6.0 Hz, 2H), 4.09 (d, J = 4.6 Hz, 2H), 3.95 (d, J = 11.7 Hz, 2H), 3.83 (d, J = 4.2 Hz, 2H), 3.75 (t, J = 5.5 Hz, 2H), 3.33 (t, J = 11.0 Hz, 3H), 3.09 (d, J = 7.3 Hz, 2H), 3.01 (s, 1H), 2.64-2.88 (m, 4H), 2.42 (s, 3H), 2.32 (s, 3H), 2.22 (s, 3H), 2.10 (dd, J = 17.3, 11.5 Hz, 4H), 1.63-1.77 (m, 4H), 0.90 (t, J = 6.9 Hz, 3H). | 10 |
| 59 | B | 1H NMR (400 MHz, CDCl3): δ: 8.66 (s, 1H), 7.40-7.42 (m, 4H), 7.33-7.38 (m, 6H), 7.21-7.23 (m, 2H), 6.89 (d, J = 8.4 Hz, 1H), 5.92 (s, 1H), 5.02-5.10 (m, 1H), 4.83 (t, J = 8.0 Hz, 1H), 4.73 (d, J = 8.8 Hz, 1H), 4.49-4.56 (m, 3H), 4.03-4.11 (m, 2H), 3.85-3.97 (m, 4H), 3.57-3.69 (m, 8H), 3.46 (s, 2H), 3.31 (s, 2H), 3.08 (s, 7H), 2.50 (s, 3H), 2.43 (s, 3H), 2.37 (s, 3H), 2.20 (s, 3H), 2.02 (s, 2H), 1.65-1.78 (m, 8H), 1.04 (s, 9H), 0.88 (t, J = 6.4 Hz, 3H). | 2 |
| 60 | A | $^1$HNMR (400 MHz, CDCl$_3$): δ 9.69-9.80 (m, 2H), 7.75 (d, J = 8.4 Hz, 1H), 7.42 (d, J = 8.8 Hz, 2H), 7.32 (s, 1H), 7.14-7.19 (m, 3H), 6.82 (d, J = 8.8 Hz, 2H), 5.93 (s, 1H), 4.91-4.94 (m, 1H), 4.20-4.30 (m, 2H), 4.03-4.10 (m, 2H), 3.96 (d, J = 11.6 Hz, 2H), 3.35-3.23 (m, 2H), 3.05-3.15 (m, 2H), 3.01 (s, 1H), 2.86-3.00 (m, 3H), 2.41 (s, 3H), 2.33 (s, 3H), 2.30 (s, 4H), 2.12-2.15 (m, 1H), 2.02-2.06 (m, 5H), 1.66-1.71 (m, 5H), 0.88-0.91 (m, 3H). | 10 |
| 61 | B | 1HNMR (400 MHz, MeOD): δ 7.67-7.69 (d, J = 8 Hz, 1H), 7.48-7.50 (d, J = 8 Hz, 2H), 7.37-7.40 (d, J = 12 Hz, 1H), 7.23-7.26 (m, 2H), 6.97-7.00 (d, J = 12 Hz, 2H), 611 (s, 1H), 5.04-5.07 (m, 1H), 4.48 (s, 2H), 4.10-4.12 (t, J = 8 Hz, 2H), 3.90-3.93 (m, 2H), 3.49 (s, 4H), 3.38-3.49 (m, 2H), 3.13-3.15 (m, 3H), 2.82-2.85 (m, 1H), 2.65-2.69 (m, 8H), 2.39 (s, 3H), 2.30 (s, 3H), 2.23 (s, 3H), 2.03-2.07 (m, 4H), 1.73-1.76 (m, 2H), 1.62-1.64 (m, 2H), 0.90-0.92 (t, J = 8 Hz, 3H). | 11 |
| 62 | B | $^1$H NMR (400 MHz, CDCl$_3$): δ 10.15-10.24 (m, 1H), 7.65-7.71 (m, 1H), 7.40 (d, J = 8.7 Hz, 2H), 7.32 (s, 1H), 7.22 (s, 1H), 7.09-7.17 (m, 2H), 6.84 (d, J = 8.6 Hz, 2H), 5.96 (s, 1H), 4.85-4.91 (m, 1H), 4.55 (d, J = 6.0 Hz, 2H), 4.18 (s, 2H), 4.03 (s, 2H), 3.92-3.98 (m, 2H), 3.63 (d, J = 5.7 Hz, 3H), 3.27-3.37 (m, 2H), 3.08 (s, 2H), 3.04-2.96 (m, 1H), 2.68-2.89 (m, 4H), 2.43 (s, 3H), 2.31 (s, 3H), 2.24 (s, 3H), 2.07 (d, J = 6.7 Hz, 4H), 1.71 (s, 4H), 0.90 (t, J = 6.9 Hz, 3H). | 10 |
| 63 | B | | 8 |
| 64 | B | 1H NMR (400 MHz, CDCl3) δ 10.87-11.15 (m, 1H), 8.70 (s, 1H), 7.63 (d, J = 7.6 Hz, 1H), 7.46 (d, J = 8.5 Hz, 3H), 7.36 (t, J = 8.5 Hz, 3H), 7.30 (d, J = 9.7 Hz, 3H), 7.01 (d, J = 8.7 Hz, 3H), 6.97 (s, 1H), 6.72 (s, 1H), 5.98 (s, 1H), 4.76-4.86 (m, 2H), 4.74 (s, 1H), 4.28-4.57 (m, 12H), 4.15 (s, 1H), 3.95 (d, J = 10.5 Hz, 2H), 3.50 (d, J = 7.8 Hz, 1H), 3.32 (s, 3H), 3.10 (d, J = 6.8 Hz, 2H), 3.01 (s, 1H), 2.56 (s, 3H), 2.42 (s, 3H), 2.40 (d, J = 4.4 Hz, 3H), 2.38 (s, 3H), 0.97 (d, J = 6.4 Hz, 3H), 0.91 (t, J = 6.9 Hz, 3H), 0.83 (d, J = 6.6 Hz, 3H). | 8 |

TABLE 2-continued

Target protein degradation via Exemplary PROTACs

| Ex # | DC$_{50}$ | 1H NMR | Synthetic Scheme |
|---|---|---|---|
| 65 | | | |
| 66 | | | |
| 67 | | | |
| 68 | | | |
| 69 | | | |
| 70 | | | |
| 71 | | | |
| 72 | | | |
| 73 | | | |
| 74 | | | |
| 75 | | | |
| 76 | | | |
| 77 | | | |
| 78 | | | |
| 79 | | | |
| 80 | | | |
| 81 | | | |
| 82 | | | |
| 83 | | | |
| 84 | | | |
| 85 | | | |
| 86 | | | |
| 87 | | | |
| 88 | A | 1H NMR (400 MHz, MeOD) δ 8.87 (s, 1H), 8.55 (d, J = 7.3 Hz, 1H), 8.30 (s, 1H), 7.85 (d, J = 9.2 Hz, 1H), 7.48 (d, J = 8.0 Hz, 2H), 7.34-7.46 (m, 6H), 7.23-7.32 (m, 3H), 6.11 (s, 1H), 4.96-5.05 (m, 2H), 4.63 (d, J = 8.9 Hz, 1H), 4.57 (t, J = 8.4 Hz, 2H), 4.49 (d, J = 4.7 Hz, 2H), 4.43 (s, 1H), 3.90 (t, J = 12.4 Hz, 3H), 3.71-3.78 (m, 1H), 3.44 (dd, J = 9.9, 6.1 Hz, 4H), 3.37 (d, J = 11.5 Hz, 2H), 3.13 (dd, J = 16.2, 9.6 Hz, 4H), 2.72 (t, J = 7.4 Hz, 2H), 2.47 (s, 3H), 2.39 (s, 3H), 2.32 (s, 4H), 2.24 (s, 3H), 2.17 (d, J = 8.6 Hz, 1H), 1.84-1.99 (m, 4H), 1.54-1.81 (m, 10H), 1.48 (t, J = 8.2 Hz, 3H), 1.04 (s, 9H), 0.90 (t, J = 6.9 Hz, 3H | 2 |
| 89 | A | 1H NMR (400 MHz, MeOD): δ 8.89 (s, 1H), 8.56 (d, J = 9.6 Hz, 1H), 7.69 (d, J = 9.6 Hz, 1H), 7.49-7.53 (m, 3H), 7.31-7.44 (m, 7H), 6.12 (s, 1H), 4.72 (d, J = 9.6 Hz, 1H), 4.59 (t, J = 8 Hz, 1H), 4.51 (s, 3H), 4.46 (s, 2H), 4.08 (d, J = 1.6 Hz, 2H), 3.86-3.94 (m, 3H), 3.75-3.79 (m, 3H), 3.67-3.68 (m, 2H), 3.54-3.57 (m, 2H), 3.19 (s, 3H), 2.77 (d, J = 7.6 Hz, 2H), 2.48 (s, 3H), 2.40 (s, 3H), 2.35 (s, 3H), 2.25 (s, 3H), 2.18-2.21 (m, 1H), 1.94-2.09 (m, 3H), 1.75-1.78 (m, 2H), 1.57-1.69 (m, 3H), 1.45 (d, J = 6.8 Hz, 3H), 1.07 (s, 9H), 0.92 (t, J = 6.8 Hz, 3H). | 2 |
| 90 | B | 1H NMR (400 MHz, MeOD) δ 8.86 (s, 1H), 8.35 (d, J = 48.7 Hz, 1H), 7.74 (d, J = 7.5 Hz, 1H), 7.56-7.62 (m, 1H), 7.52 (d, J = 7.5 Hz, 1H), 7.39-7.50 (m, 4H), 7.37 (s, 1H), 7.25 (s, 1H), 7.02 (dd, J = 15.5, 6.6 Hz, 4H), 6.09 (s, 1H), 4.81 (d, J = 10.9 Hz, 1H), 4.39-4.63 (m, 8H), 4.26 (t, J = 15.2 Hz, 4H), 3.80-4.01 (m, 4H), 3.36 (d, J = 10.9 Hz, 2H), 3.01-3.17 (m, 3H), 2.46 (d, J = 10.4 Hz, 3H), 2.38 (s, 3H), 2.31 (s, 3H), 2.23 (s, 3H), 2.19-2.03 (m, 2H), 1.74 (d, J = 11.5 Hz, 2H), 1.62 (d, J = 11.8 Hz, 2H), 1.01 (d, J = 6.5 Hz, 3H), 0.88 (t, J = 6.9 Hz, 3H), 0.79 (d, J = 6.5 Hz, 3H). | 8 |
| 91 | A | 1H NMR (400 MHz, MeOD) δ 7.68 (d, J = 8.8 Hz, 1H), 7.51 (d, J = 8.4 Hz, 2H), 7.41 (s, 1H), 7.37 (s, 1H), 7.24-7.27 (m, 2H), 7.02 (d, J = 8.4 Hz, 2H), 6.11 (s, 1H), 5.04-5.08 (m, 1H), 4.48 (s, 2H), 4.22 (t, J = 4.8 Hz, 2H), 3.92 (d, J = 10.0 Hz, 2H), 3.35 (s, 4H), 3.30-3.32 (m, 2H), 3.00-3.18 (m, 3H), 2.72-2.91 (m, 9H), 2.39 (s, 3H), 2.31 (s, 3H), 2.24 (s, 3H), 2.10-2.13 (m, 1H), 1.74-1.77 (m, 2H), 1.62-1.65 (m, 2H), 0.88 (t, J = 6.8 Hz, 3H). | 11 |
| 92 | B | 1HNMR (400 MHz, MeOD): δ 7.68-7.70 (d, J = 8 Hz, 1H), 7.50-7.52 (d, J = 8 Hz, 2H), 7.42 (s, 1H), 7.37 (s, 1H), 7.29 (s, 1H), 7.23-7.25 (d, J = 8 Hz, 1H), 6.99-7.01 (d, J = 8 Hz, 2H), 613 (s, 1H), 5.07-5.10 (m, 1H), 4.50 (s, 2H), 4.09-4.10 (t, J = 4 Hz, 2H), 3.92-3.94 (m, 2H), 3.49 (s, 4H), 3.37-3.40 (m, 2H), 3.07-3.15 (m, 3H), 2.78-2.84 (m, 1H), 2.68-2.74 (m, 6H), 2.52-2.54 (m, 2H), 2.41 (s, 3H), 2.32 (s, 3H), 2.26 (s, 3H), 2.07-2.12 (m, 3H), 1.78-1.87 (m, 6H), 1.63-1.75 (m, 2H), 0.90-0.92 (t, J = 8 Hz, 3H). | 11 |
| 93 | A | 1H NMR (400 MHz, CDCl3): δ 11.42 (s, 1H), 8.66 (s, 1H), 7.42 (d, J = 8.4 Hz, 1H), 7.39-7.33 (m, 6H), 7.29-7.22 (m, 4H), 6.91 (d, J = 8.4 Hz, 2H), 5.90 (s, 1H), 5.08-5.02 (m, 1H), 4.78-4.73 (m, 1H), 4.62-4.50 (m, 4H), 4.08-3.93 (m, 7H), 3.78 (s, 1H), 3.68-3.61 (m, 3H), 3.48 (s, 1H), 3.31-3.30 (m, 2H), 3.08-3.07 (m, 3H), 2.51 (s, 4H), 2.40 (s, 3H), 2.34 (s, 3H), 2.15 (s, 3H), 2.08-2.01 (m, 1H), 1.88-1.82 (m, 7H), 1.76 (s, 3H), 1.45 (d, J = 6.8 Hz, 3H), 1.06 (s, 9H), 0.88 (t, J = 6.8 Hz, 3H). | 2 |

TABLE 2-continued

Target protein degradation via Exemplary PROTACs

| Ex # | DC$_{50}$ | 1H NMR | Synthetic Scheme |
|---|---|---|---|
| 94 | A | 1H NMR (400 MHz, MeOD) δ 8.87 (s, 1H), 8.53-8.61 (m, 1H), 8.25-8.31 (m, 1H), 7.53-7.57 (m, 1H), 7.49 (d, J = 8.6 Hz, 2H), 7.41 (t, J = 8.2 Hz, 5H), 7.28 (s, 1H), 6.98 (d, J = 8.6 Hz, 2H), 6.10 (s, 1H), 4.94-5.04 (m, 2H), 4.66-4.73 (m, 1H), 4.52-4.62 (m, 2H), 4.48 (s, 2H), 4.41-4.46 (m, 1H), 4.04 (d, J = 6.2 Hz, 2H), 3.99 (d, J = 7.2 Hz, 2H), 3.81-3.95 (m, 3H), 3.71-3.78 (m, 1H), 3.61 (t, J = 6.0 Hz, 2H), 3.35 (s, 2H), 3.14 (d, J = 6.9 Hz, 4H), 2.47 (s, 3H), 2.38 (s, 3H), 2.31 (s, 3H), 2.23 (s, 3H), 2.17-2.21 (m, 1H), 1.90-1.99 (m, 2H), 1.81-1.90 (m, 2H), 1.73 (s, 4H), 1.63 (d, J = 7.0 Hz, 5H), 1.47 (d, J = 6.9 Hz, 3H), 1.04 (s, 9H), 0.89 (t, J = 6.8 Hz, 3H). | 2 |
| 95 | A | 1H NMR (400 MHz, MeOD): 8.86 (s, 1H), 7.51 (d, J = 8.0 Hz, 2H), 7.37-7.46 (m, 5H), 7.27 (s, 1H), 7.02 (d, J = 8.4 Hz, 2H), 6.12 (s, 1H), 4.72 (d, J = 9.6 Hz, 1H), 4.55-4.60 (m, 1H), 4.61 (s, 3H), 4.08 (s, 2H), 3.85-3.94 (m, 3H), 3.75-3.78 (m, 3H), 3.66-3.68 (m, 2H), 3.54-3.57 (m, 2H), 3.19 (s, 3H), 2.75-2.77 (m, 2H), 2.48 (s, 3H), 2.40 (s, 3H), 2.35 (s, 3H), 2.25 (s, 3H), 2.18-2.21 (m, 1H), 1.94-2.09 (m, 3H), 1.75-1.78 (m, 2H), 1.57-1.69 (m, 3H), 1.45 (d, J = 6.8 Hz, 3H), 1.07 (s, 9H), 0.92 (t, J = 6.8 Hz, 3H). | 2 |
| 96 | B | 1HNMR (400 MHz, MeOD): δ 8.82 (s, 1H), 7.44-7.46 (m, 4H), 7.38-7.39 (m, 3H), 7.25 (s, 1H), 6.94 (d, J = 8.8 Hz, 2H), 6.10 (s, 1H), 4.98-5.00 (m, 1H), 4.53-4.59 (m, 2H), 4.46-4.48 (m, 3H), 4.00-4.09 (m, 4), 3.89-3.92 (m, 3H), 3.65-3.77 (m, 7H), 3.30-3.33 (m, 2), 3.12-3.14 (m, 3), 2.43 (s, 3H), 2.39 (m, 3H), 2.30 (s, 3H), 2.20-2.23 (m, 4H), 2.05-2.08 (m, 1H), 1.72-1.75 (m, 2H), 1.61-1.63 (m, 2H), 1.42 (d, J = 6.8 Hz, 3H), 1.03 (s, 9H), 0.90 (t, J = 6.8 Hz, 3H). | 2 |
| 97 | B | 1H NMR (400 MHz, CDCl3) δ 0.78-0.90 (3H, m), 0.96-1.06 (3H, m), 1.34-1.35 (3H, m), 1.67-1.69 (6H, m), 1.99-2.10 (1H, m), 2.15-2.18 (3H, m), 2.20-2.33 (6H, m), 2.40 (3H, m), 2.45-2.55 (4H, m), 2.96-3.11 (3H, m), 3.28-3.34 (2H, m), 3.64-3.81 (2H, m), 3.90-3.95 (2H, m), 4.17-4.40 (5H, m), 4.50-4.80 (6H, m), 4.94-5.24 (1H, m), 5.88-5.92 (1H, m), 6.92-7.00 (2H, m), 7.06-7.24 (8H, m), 7.28-7.52 (7H, m), 8.67-8.70 (1H, m), 10.48-10.52 (1H, m). | 12 |
| 98 | B | 1H NMR (400 MHz, CDCl3) δ 0.84-0.88 (3H, m), 1.04-1.06 (3H, m), 1.43-1.46 (3H, m), 1.63-1.69 (6H, m), 2.01-2.30 (7H, m), 2.33-2.39 (6H, m), 2.52 (3H, m), 2.95-3.11 (4H, m), 3.23-3.34 (2H, m), 3.65-3.76 (1H, m), 3.90-3.96 (2H, m), 4.12-4.83 (12H, m), 5.03-5.11 (1H, m), 5.87-5.89 (1H, m), 6.85-6.95 (2H, m), 7.08-7.24 (4H, m), 7.29-7.62 (11H, m), 8.67 (1H, m), 10.91-10.92 (1H, m). | 12 |
| 99 | A | 1H NMR (400 MHz, DMSO-d6) δ 0.68-0.73 (3H, m), 0.81-0.84 (3H, m), 0.95-0.98 (4H, m), 1.34-1.38 (3H, m), 1.51-1.53 (2H, m), 1.64-1.67 (2H, m), 1.75-1.79 (1H, m), 2.10 (3H, s), 2.20 (3H, s), 2.24 (3H, s), 2.45 (3H, s), 3.08-3.11 (2H, m), 3.22-3.27 (3H, m), 3.65-3.73 (2H, m), 3.80-3.83 (5H, m), 4.23-4.25 (2H, m), 4.28-4.29 (2H, m), 4.33-4.38 (2H, m), 4.44-4.50 (2H, m), 4.56 (2H, s), 4.67-4.70 (1H, m), 4.90-4.94 (1H, m), 5.08-5.09 (1H, m), 5.85 (1H, s), 7.20-7.22 (3H, m), 7.35-7.37 (2H, m), 7.40-7.46 (5H, m), 7.51-7.53 (2H, m), 7.60-7.62 (2H, m), 8.22 (1H, t, J = 4.8 Hz), 8.43 (1H, d, J = 7.2 Hz), 8.99 (1H, s), 11.4 (1H, d, J = 4.8 Hz). | 12 |
| 100 | A | 1H NMR (400 MHz, CDCl3) δ 0.94 (3H, d, J = 6.8 Hz), 1.05 (3H, d, J = 6.8 Hz), 1.46 (3H, d, J = 6.8 Hz), 1.71 (3H, m), 2.01 (3H, m), 2.22 (3H, s), 2.34 (3H, s), 2.41 (3H, s), 2.49 (1H, d, J = 5.6 Hz), 2.53 (3H, s), 2.99-3.11 (3H, m), 3.32 (2H, m), 3.65 (1H, dd, J = 4.0, 8.0 Hz), 3.96 (2H, m), 4.35-4.41 (6H, m), 4.46-4.55 (4H, m), 4.70 (2H, m), 4.79 (1H, d, J = 11.2 Hz), 5.09 (1H, m), 5.35 (2H, t, J = 4.6 Hz), 5.92 (1H, s), 6.95-7.00 (2H, m), 7.06 (1H, t, J = 4.8 Hz), 7.17-7.20 (2H, m), 7.32-7.43 (10H, m), 7.52-7.53 (2 H, m), 8.67 (1H, s). | 12 |
| 101 | B | 1H NMR (400 MHz, CDCl3) δ 0.86-0.91 (3H, m), 1.06 (3H, d, J = 6.4 Hz), 1.50 (3H, J = 9.6 Hz), 1.67-1.70 (6H, m), 2.00-2.05 (4H, brs), 2.19 (3H, s), 2.29-2.51 (8H, m), 2.53 (3H, s), 3.06-3.11 (3H, m), 3.32 (3H, t, J = 10.8 Hz), 3.74-3.80 (2H, m), 3.93-4.11 (7H, m), 4.28-4.68 (7H, m), 4.78-4.85 (1H, m), 4.97-5.00 (1H, m), 5.91 (1H, s), 6.88-6.90 (2H, m), 7.01-7.23 (6H, m), 7.26-7.46 (7H, m), 8.66 (1H, s), 10.51-10.58 (1H, brs). | 12 |
| 102 | B | 1H NMR (400 MHz, CDCl3) δ 0.91-0.93 (3H, m), 1.05 (3H, d, J = 6.4 Hz), 1.45 (3H, J = 6.8 Hz), 1.68-1.70 (5H, m), 1.99-2.03 (5H, brs), 2.20 (3H, s), 2.34-2.53 (12H, m), 3.00-3.28 (4H, m), 3.28-3.34 (2H, m), 3.67-3.69 (1H, m), 3.93-3.96 (2H, d, J = 11.2 Hz), 4.06-4.07 (4H, m), 4.34-4.53 (5H, m), 4.65-4.68 (2H, m), 4.78 (1H, d, J = 11.2 Hz), 5.06-5.11 (1H, m), 5.90 (1H, s), 6.90 (2H, d, | 12 |

TABLE 2-continued

Target protein degradation via Exemplary PROTACs

| Ex # | DC$_{50}$ | 1H NMR | Synthetic Scheme |
|---|---|---|---|
| | | J = 8.4 Hz), 7.07-7.17 (4H, m), 7.29-7.40 (8H, m), 7.59 (1H, d, J = 7.6 Hz), 8.67 (1H, s), 10.80-10.86 (1H, brs). | |
| 103 | B | | 12 |
| 104 | A | 1H NMR (400 MHz, CDCl3) δ 0.86-0.88 (6 H, m), 1.01-1.03 (3H, m), 1.35-1.42 (4H, m), 1.63-1.69 (5H, brs), 1.82-1.84 (4H, brs), 1.95-1.98 (1H, m), 2.12-2.19 (3H, m), 2.34 (3H, d, J = 5.6 Hz), 2.40-2.41 (4H, m), 2.52 (3H, d, J = 3.2 Hz), 2.88 (1H, s), 2.96 (1H, s), 2.97-3.11 (3H, m), 3.28-3.34 (2H, m), 3.44-3.66 (3H, m), 3.70 (1H, s), 3.78-4.03 (5H, m), 4.18-4.23 (2H, m), 4.36-4.50 (1H, m), 4.56-4.79 (3H, m), 4.93-5.07 (1H, m), 5.81 (1H, d, J = 9.6 Hz), 5.91 (1H, d, J = 14.4 Hz), 6.90 (2H, d, J = 8.0 Hz), 7.06-7.21 (2H, m), 7.27-7.41 (8H, m), 7.79-8.01 (1H, m), 8.67 (1H, d, J = 2.8 Hz). | 13 |
| 105 | A | 1H NMR (400 MHz, CDCl3) δ 0.88-0.90 (3H, m), 0.97-1.01 (3H, m), 1.26-1.42 (6H, m), 1.68-1.70 (5H, m), 1.93-1.99 (1H, m), 2.12-2.18 (3 H, m), 2.34-2.36 (3H, m), 2.40-2.42 (3H, m), 2.52 (3H, m), 2.96-3.59 (9H, m), 3.77-3.96 (7H, m), 4.15-4.19 (2H, m), 4.32-4.80 (6H, m), 4.93-5.06 (1H, m), 5.74-5.95 (2H, m), 6.91-6.94 (2H, m), 7.10-7.24 (2H, m), 7.28-7.42 (8H, m), 7.48-7.89 (1H, m), 8.67 (1H, m). | 13 |
| 106 | A | 1H NMR (400 MHz, CDCl3) δ 0.86-0.92 (6 H, m), 1.02-1.05 (3H, m), 1.33-1.36 (3H, m), 1.50-1.52 (4H, m), 1.70-1.84 (8H, m), 1.99-2.02 (1H, m), 2.17-2.28 (3H, m), 2.33-2.36 (3H, m), 2.41-2.42 (3H, m), 2.52-2.53 (3H, m), 2.98-3.09 (3H, m), 3.29-3.37 (2H, m), 3.46-3.88 (4H, m), 3.94-4.05 (4H, m), 4.19-4.25 (3H, m), 4.42-4.81 (4H, m), 4.93-5.07 (1H, m), 5.34-5.36 (1H, m), 5.81-5.82 (1H, m), 5.91-5.96 (1H, m), 6.91-6.93 (3H, m), 7.12-7.19 (1H, m), 7.29-7.42 (8H, m), 7.58-8.13 (1H, m), 8.67-8.68 (1H, m). | 13 |
| 107 | A | 1H NMR (400 MHz, CDCl3) δ 0.89-0.91 (3H, m), 1.01-1.04 (3H, m), 1.26-1.43 (6H, m), 1.66 (6H, m), 1.95-1.98 (5H, m), 2.13-2.19 (3H, m), 2.33-2.35 (3H, m), 2.40-2.41 (3H, m), 2.51-2.52 (3H, m), 3.00-3.11 (4H, m), 3.29-3.34 (2H, m), 3.51-3.64 (3H, m), 3.93-4.05 (4H, m), 4.27 (2H, m), 4.32-4.50 (1H, m), 4.57-4.80 (3H, m), 4.92-5.08 (1H, m), 5.80-5.94 (2H, m), 6.89-6.91 (2H, m), 7.12-7.18 (2H, m), 7.28-7.44 (8H, m), 7.53-7.83 (1H, m), 8.67 (1H, m). | 13 |
| 108 | B | 1H NMR (400 MHz, CDCl3) δ 0.86-0.91 (3H, m), 0.97 (3H, d, J = 6.8 Hz), 1.01 (3H, d, J = 6.4 Hz), 1.35 (3H, d, J = 6.8 Hz), 1.68-1.71 (4H, m), 1.99-2.03 (2H, m), 2.27 (3H, s), 2.36 (3H, s), 2.42 (3H, s), 2.52 (3H, s), 2.98-3.12 (3H, m), 3.28-3.36 (2H, m), 3.72-3.80 (2H, m), 3.81-3.92 (2H, m), 3.92-3.950 (2H, m), 4.18-4.29 (3H, m), 4.36 (1H, d, J = 8.8 Hz), 4.58-4.61 (1H, m), 4.69 (2H, s), 4.71-4.75 (1 H, m), 4.89-4.93 (1H, dd, J = 4.8, 8.0 Hz), 5.01-5.04 (1H, t, J = 7.2 Hz), 5.30 (3H, s), 5.35 (1H, t, J = 4.6 Hz), 5.94 (1H, s), 6.98 (2H, t, J = 7.0 Hz), 7.17 (1H, s), 7.32-7.38 (7H, m), 7.41 (2H, J = 8.8 Hz), 7.49-7.52 (2H, m), 7.96 (1H, s), 8.32 (1H, d, J = 7.2 Hz), 8.67 (1H, s). | 12 |
| 109 | A | 1H NMR (400 MHz, CDCl3) δ 0.86-0.90 (3H, m), 0.98-0.99 (3H, m), 1.35-1.43 (3H, m), 1.70-1.73 (5H, m), 1.94-2.06 (3H, m), 2.08-2.16 (3H, m), 2.34-2.36 (3H, m), 2.39-2.41 (3H, m), 2.51-2.52 (3H, m), 2.98-3.37 (6H, m), 3.43-3.81 (8H, m), 3.92-3.95 (2H, m), 4.11-4.15 (2H, m), 4.29-4.32 (2H, m), 4.34-4.78 (4H, m), 4.90-5.08 (1H, m), 5.78-5.79 (1H, m), 5.89-5.93 (1H, m), 6.91-6.94 (2H, m), 7.17-7.25 (2H, m), 7.27-7.42 (8H, m), 7.48-7.89 (1H, m), 8.67 (1H, m). | 13 |
| 110 | A | 1H NMR (400 MHz, CDCl3) δ 0.84-0.90 (3H, m), 0.94-1.03 (6H, m), 1.25 (3H, m), 1.30-1.36 (3H, m), 2.16-2.24 (3H, m), 2.34-2.42 (6H, m), 2.49-2.52 (3H, m), 2.91-3.10 (8H, m), 3.24-3.56 (6H, m), 3.75-3.78 (4H, m), 3.93-3.96 (2H, m), 4.29-4.79 (8H, m), 5.82-5.98 (2H, m), 7.00-7.17 (4H, m), 7.30-7.42 (9H, m), 8.65-8.68 (1H, m). | 13 |
| 111 | A | 1H NMR (400 MHz, CDCl3) δ 0.81-0.83 (3H, m), 0.93-0.97 (6H, m), 1.26-1.30 (5H, m), 1.82-1.89 (4H, m), 2.08 (1H, s), 2.19 (2H, s), 2.25-2.27 (4H, m), 2.34-2.35 (4H, m), 2.45 (4H, d, J = 4.4 Hz), 2.63 (2H, brs), 2.91-3.04 (4H, m), 3.22-3.26 (2H, m), 3.35-3.49 (5H, m), 3.66-3.70 (2H, m), 3.75-3.79 (1H, m), 3.86-3.89 (2H, m), 4.16-4.21 (1H, m), 4.24-4.30 (2H, m), 4.33-4.46 (1H, m), 4.52-4.55 (1H, m), 4.64-4.72 (2H, m), 4.83-4.98 (1H, m), 5.78-5.89 (2H, m), 6.93-6.94 (1H, m), 7.09-7.17 (3H, m), 7.21-7.33 (9H, m), 8.60 (1H, d, J = 3.6 Hz). | 13 |
| 112 | A | 1H NMR (400 MHz, CDCl3) δ 0.79-0.91 (6 H, m), 0.94-1.02 (3H, m), 1.31-2.34 (3H, m), 1.65-1.69 (4H, m), 1.93-2.09 (3H, m), 2.15-2.24 (3H, m), 2.30-2.33 (3H, m), 2.41-2.42 (3H, m), 2.51-2.52 (3H, m), 2.96-3.11 (3H, m), 3.25-3.36 (2H, m), | 13 |

TABLE 2-continued

Target protein degradation via Exemplary PROTACs

| Ex # | DC$_{50}$ | 1H NMR | Synthetic Scheme |
|---|---|---|---|
| | | 3.43-3.55 (3H, m), 3.66-3.85 (6H, m), 3.89-3.95 (2H, m), 4.07-4.23 (3H, m), 4.28-4.45 (3H, m), 4.51-4.66 (2H, m), 4.74-4.81 (1H, m), 4.90-5.06 (1H, m), 5.70-5.82 (1H, m), 5.90-5.97 (1H, m), 6.92-6.95 (2H, m), 7.00-7.24 (2H, m), 7.27-7.43 (8H, m), 7.63-8.20 (1H, m), 8.66-8.67 (1H, m). | |
| 113 | B | 1HNMR (400 MHz, MeOD-d4): δ: δ: 7.66 (d, J = 8.4 Hz, 1H), 7.60-7.59 (m, 2H), 7.46 (s, 3H), 7.33 (s, 2H), 7.22-7.19 (m, 1H), 6.12 (s, 1H), 5.06-5.03 (m, 1H), 4.05-4.03 (m, 2H), 3.92 (d, J = 10.8 Hz, 3H), 3.84 (s, 1H), 3.39-3.37 (m, 2H), 3.18-3.14 (m, 4H), 3.10-3.00 (m, 3H), 2.89-2.69 (m, 9H), 2.50 (s, 3H), 2.40 (s, 3H), 2.35 (s, 3H), 2.25 (s, 3H), 2.21-2.19 (m, 1H), 2.17-2.10 (m, 2H), 2.03-2.02 (m, 1H), 1.94-1.91 (m, 3H), 1.77-1.74 (m, 2H), 1.68-1.60 (m, 3H), 0.90 (t, J = 6.8 Hz, 3H). | 14 |
| 114 | A | 1H NMR SL-ARV-LS-011E (400 MHz, CDCl3): δ: 8.60 (s, 1H), 7.07-7.49 (m, 15H), 5.85 (s, 1H), 4.96-5.06 (m, 1H), 4.49-4.63 (m, 2H), 4.37-4.42 (m, 3H), 3.83-4.03 (m, 5H), 3.46-3.67 (m, 8H), 3.44 (s, 2H), 3.41 (s, 3H), 3.24 (t, J = 10.9 Hz, 2H), 2.99-3.04 (m, 2H), 2.93 (d, J = 4.7 Hz, 1H), 2.49-2.62 (m, 5H), 2.45 (s, 3H), 2.34 (s, 3H), 2.29 (s, 3H), 2.12 (s, 3H), 1.80-1.97 (m, 4H), 1.53-1.57 (m, 3H), 1.40 (d, J = 6.9 Hz, 3H), 0.96 (s, 9H), 0.82 (t, J = 6.9 Hz, 3H). | 2 |
| 115 | B | 1HNMR (400 MHz, DMSO-d6): δ: 11.45 (s, 1H), 11.06 (s, 1H), 8.18 (s, 1H), 7.69-7.62 (m, 5H), 7.44 (s, 1H), 7.34 (s, 1H), 7.27 (s, 2H), 5.86 (s, 1H), 5.09-5.06 (m, 1H), 4.36-4.29 (m, 4H), 3.85-3.82 (m, 2H), 3.43 (s, 4H), 3.26-2.85 (m, 11H), 2.68-2.55 (m, 3H), 2.25 (s, 3H), 2.21 (s, 3H), 2.11 (s, 3H), 2.10-2.00 (m, 3H), 1.91-1.88 (m, 3H), 1.68-1.65 (m, 2H), 1.54-1.51 (m, 3H), 1.44-1.38 (m, 2H), 0.95-0.91 (m, 3H). | 14 |
| 116 | A | 1HNMR (400 MHz, CDCl3): δ: 8.68 (s, 1H), 7.24-7.45 (m, 14H), 7.12 (s, 1H), 5.92 (s, 1H), 5.07 (t, J = 8.4 Hz, 1H), 4.70 (t, J = 8.0 Hz, 1H), 4.50-4.58 (m, 4H), 3.93-4.15 (m, 6H), 3.56-3.65 (m, 6H), 3.32 (t, J = 5.6 Hz, 2H), 3.08-3.10 (m, 2H), 2.52-2.66 (m, 8H), 2.42 (s, 3H), 2.35 (s, 3H), 2.20 (s, 3H), 2.00-2.02 (m, 2H), 1.64 (s, 4H), 1.45 (d, J = 6.8 Hz, 4H), 1.05 (s, 9H), 0.87-0.89 (m, 3H). | 2 |
| 117 | A | 1H NMR (400 MHz, CD3OD): δ 8.88 (s, 1H), 7.57-7.59 (m, 2H), 7.38-7.46 (m, 7H), 7.34 (s, 1H), 6.13 (s, 1H), 4.96-5.01 (m, 1H), 4.71 (s, 1H), 4.51-4.58 (m, 9H), 3.82-4.03 (m, 5H), 3.61-3.74 (m, 7H), 3.24-3.26 (m, 2H), 2.71-3.16 (m, 10H), 2.48 (m, 3H), 2.41 (s, 3H), 2.34 (s, 3H), 2.18-2.26 (m, 4H), 1.90-2.09 (m, 2H), 1.49 (d, J = 7.2 Hz, 3H), 1.39 (d, J = 5.6 Hz, 6H), 1.05 (s, 9H), 0.92 (m, 3H). | 2 |
| 118 | A | 1H NMR (400 MHz, CDCl3): δ: 8.83 (s, 1H), 7.55 (d, J = 7.7 Hz, 2H), 7.47 (d, J = 7.8 Hz, 2H), 7.43 (d, J = 7.8 Hz, 1H), 7.37 (s, 4H), 7.26 (s, 4H), 7.18 (d, J = 8.8 Hz, 1H), 6.91 (s, 1H), 6.45 (s, 1H), 5.04-5.11 (m, 1H), 4.73 (t, J = 8.2 Hz, 1H), 4.65 (d, J = 9.2 Hz, 1H), 4.57 (d, J = 5.2 Hz, 2H), 4.48 (s, 1H), 4.21 (m, 2H), 3.91-4.09 (m, 6H), 3.65 (m, 5H), 3.52 (s, 4H), 3.27-3.37 (m, 4H), 3.07-3.20 (m, 3H), 2.61 (s, 3H), 2.52 (s, 3H), 2.43 (s, 3H), 2.36 (s, 3H), 2.33 (s, 1H), 2.12-2.27 (m, 2H), 2.00-2.03 (m, 2H), 1.66-1.73 (m, 4H), 1.03 (s, 9H), 0.88-0.94 (m, 3H). | 2 |
| 119 | B | 1H NMR (400 MHz, CDCl3): δ: 8.67 (s, 1H), 7.22-7.42 (m, 10H), 6.89 (d, J = 4.4 Hz, 2H), 5.92 (s, 1H), 5.45 (s, 1H), 5.02-5.10 (m, 1H), 4.83 (t, J = 8.0 Hz, 1H), 4.73 (d, J = 9.0 Hz, 1H), 4.40-4.64 (m, 3H), 3.91-4.08 (m, 7H), 3.31-3.69 (m, 12H), 3.00-3.09 (m, 6H), 2.50 (s, 3H), 2.43 (s, 3H), 2.37 (s, 3H), 2.20 (s, 3H), 2.03-2.20 (m, 3H), 1.60-1.68 (m, 5H), 1.47 (d, J = 4.0 Hz, 6H), 1.33 (s, 1H), 1.04 (s, 9H). | 2 |

*Protein degradation range at indicated concentration (relative to DMSO control): A = degradation more than 60%; B = degradation between 30% and 60%; C = degradation between 0% and 30%.

Specific Embodiments of the Present Disclosure

The present disclosure encompasses the following specific embodiments. These following embodiments may include all of the features recited in a proceeding embodiment, as specified. Where applicable, the following embodiments may also include the features recited in any proceeding embodiment inclusively or in the alternative.

In certain embodiments, the description provides an EZH2 PROTAC molecules selected from compounds 1-119 of Table 1 or 2, including salts, prodrugs, polymorphs, analogs, derivatives, and deuterated forms thereof.

As such, the description provides a compound comprising the structure of any one of compounds 1-119 (i.e., any compound of Table 1 or 2), including salts, prodrugs, polymorphs, analogs, derivatives, and deuterated forms thereof therapeutic compositions comprising the same, and methods of use as described herein.

In an aspect, the present disclosure provides a bifunctional compound having the chemical structure:

ULM-L-PTM, or a pharmaceutically acceptable salt, enantiomer, stereoisomer, solvate, polymorph or prodrug thereof, wherein: the ULM is a small molecule E3 ubiquitin ligase binding moiety that binds an E3 ubiquitin ligase; the PTM is a small molecule comprising a enhancer of zeste homolog 2 (EZH2) protein targeting moiety; and the L is a bond or a chemical linking moiety connecting the ULM and the PTM.

In any aspect or embodiment described herein, the E3 ubiquitin ligase binding moiety that targets an E3 ubiquitin ligase selected from the group consisting of Von Hippel-Lindau (VLM), cereblon (CLM), mouse double-minute homolog2 (MLM), and IAP (ILM).

In any aspect or embodiment described herein, the PTM or EBM is represented by Formula PTM-I, PTM-II, PTM-III, PTM-IVa, PTM-IVb, PTM-V, or PTM-VI:

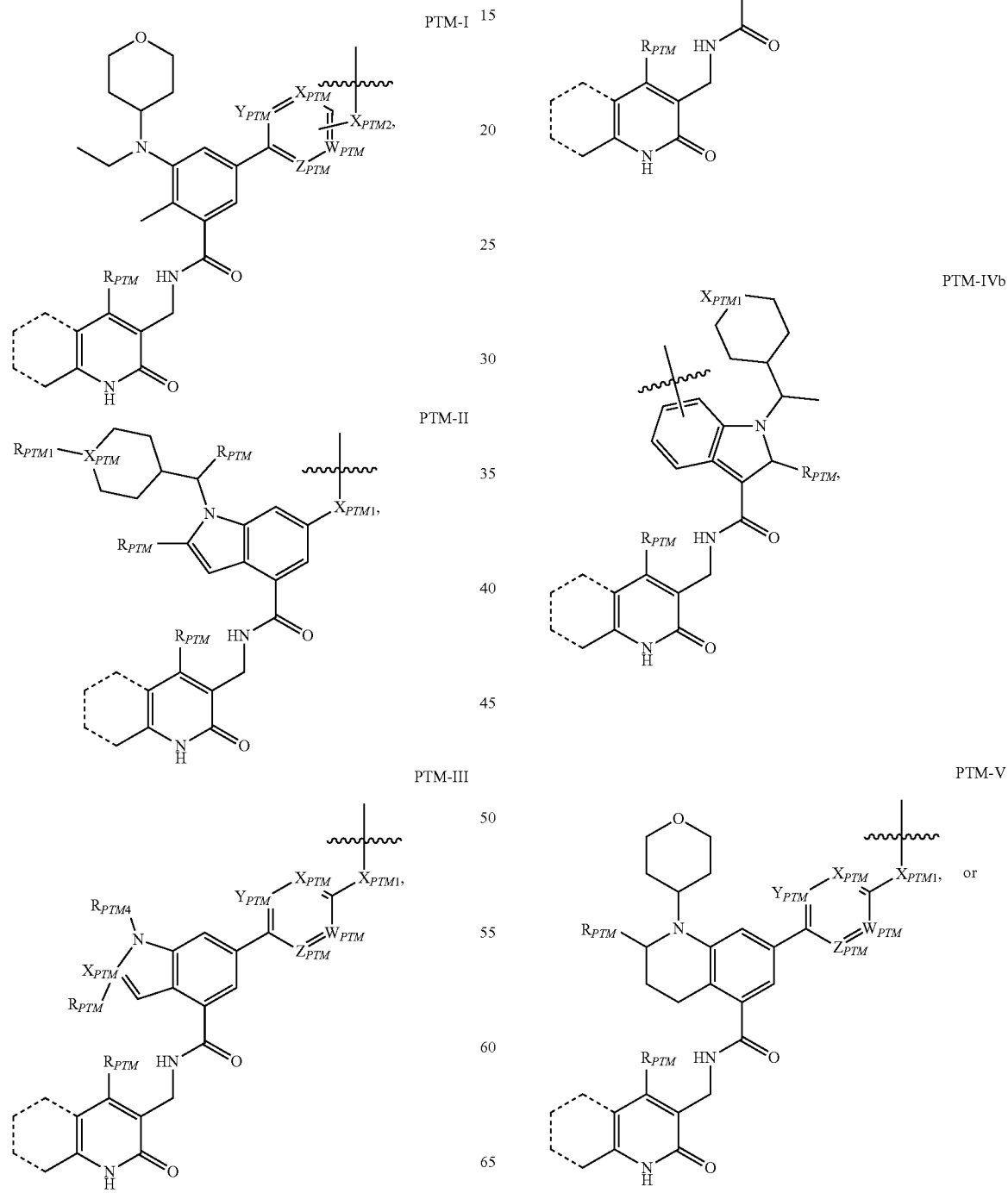

-continued

PTM-VI

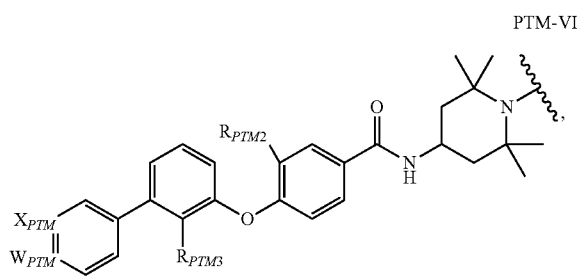

wherein:

$W_{PTM}$, $X_{PTM}$, $Y_{PTM}$, and $Z_{PTM}$ are independently chosen from C or N, wherein no more than two of $W_{PTM}$, $X_{PTM}$, $Y_{PTM}$, and $Z_{PTM}$ is N;

$X_{PTM1}$ is absent, NH, O, heterocycle (e.g., a 4-6 member heterocyclic, such as a heterocyclic group with 1-3 N-substitutions);

$X_{PTM2}$ is absent, $CH_2$, NH, O, heterocycle (e.g., a 4-6 member heterocyclic, such as a heterocyclic group with 1-3 N-substitutions), heteroaryl (e.g., a 4-6 member heteroaryl, such as a heteroaryl group with 1-3 N-substitutions), or $CH_2$-heteroaryl (e.g., a 4-6 member heteroaryl, such as a heteroaryl group with 1-3 N-substitutions);

$R_{PTM}$ is absent, H, short chain alkyl (linear, branched, optionally substituted), methoxy, or ethoxy;

$R_{PTM1}$ is an absent, alkyl, halogen, haloalkyl, or alkoxy;

$R_{PTM2}$ and $R_{PTM3}$ are independently a halogen, CN, alkoxy (e.g., methoxy or ethoxy);

$R_{PTM4}$ is a alkyl (linear, branched, optionally substituted) or a 4-6 member cyclicalkyl

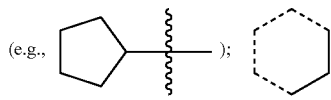

is an optionally substituted $C_1$-$C_4$ alkyl that is optionally cyclized to the adjacent carbon of the pyridinyl ring to which it is attached; and

- - - indicates a covalent linkage to at least one of a linker (L), a ULM, a ULM', a VLM, a VLM', a CLM, a CLM', an ILM, an ILM', a MLM, a MLM', or a combination thereof.

In any aspect or embodiment described herein, the

is a methyl group.

In any aspect or embodiment described herein, the ULM is a Von Hippel-Lindau (VHL) ligase-binding moiety (VLM) with a chemical structure represented by:

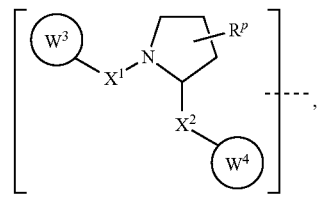

wherein:

$X^1$, $X^2$ are each independently selected from the group of a bond, O, $NR^3$, $CR^{Y3}R^{Y4}$, C=O, C=S, SO, and $SO_2$;

$R^{Y3}$, $R^{Y4}$ are each independently selected from the group of H, linear or branched $C_{1-6}$ alkyl, optionally substituted by 1 or more halo, optionally substituted $C_{1-6}$ alkoxyl (e.g., optionally substituted by 0-3$R^P$ groups);

$R^P$ is 0, 1, 2, or 3 groups each independently selected from the group H, halo, —OH, $C_{1-3}$ alkyl, C=O;

$W^3$ is selected from the group of an optionally substituted -T-N($R^{1a}R^{1b}$)$X^3$, optionally substituted-T-N($R^{1a}R^{1b}$), optionally substituted -T-Aryl, an optionally substituted -T-Heteroaryl, an optionally substituted T-biheteroaryl, an optionally substituted -T-Heterocycle, an optionally substituted -T-biheterocycle, an optionally substituted —$NR^1$-T-Aryl, an optionally substituted —$NR^1$-T-Heteroaryl or an optionally substituted —$NR^1$-T-Heterocycle;

$X^3$ is C=O, $R^1$, $R^{1a}$, $R^{1b}$;

each of $R^1$, $R^{1a}$, $R^{1b}$ is independently selected from the group consisting of H, linear or branched $C_1$-$C_6$ alkyl group optionally substituted by 1 or more halo or —OH groups, $R^{Y3}$C=O, $R^{Y3}$C=S, $R^{Y3}$SO, $R^{Y3}SO_2$, N($R^{Y3}R^{Y4}$)C=O, N($R^{Y3}R^{Y4}$)C=S, N($R^{Y3}R^{Y4}$)SO, and N($R^{Y3}R^{Y4}$)$SO_2$;

T is selected from the group of an optionally substituted alkyl, —$(CH_2)_n$— group, wherein each one of the methylene groups is optionally substituted with one or two substituents selected from the group of halogen, methyl, a linear or branched $C_1$-$C_6$ alkyl group optionally substituted by 1 or more halogen or —OH groups or an amino acid side chain optionally substituted; and n is 0 to 6, $W^4$ is

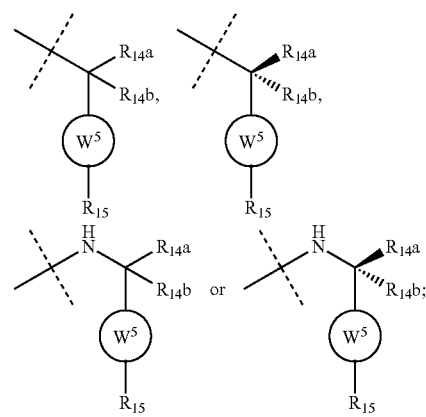

$R_{14a}$, $R_{14b}$, are each independently selected from the group of H, haloalkyl, or optionally substituted alkyl;

$W^5$ is selected from the group of a phenyl or a 5-10 membered heteroaryl, $R_{15}$ is selected from the group of H, halogen, CN, OH, $NO_2$, $NR_{14a}R_{14b}$, $OR_{14a}$, $CONR_{14a}R_{14b}$, $NR_{14a}COR_{14b}$, $SO_2NR_{14a}R_{14b}$, $NR_{14a}SO_2R_{14b}$, optionally substituted alkyl, optionally substituted haloalkyl, optionally substituted haloalkoxy; aryl, heteroaryl, cycloalkyl, or cycloheteroalkyl (each optionally substituted); and the dashed line indicates the site of attachment of at least one PTM, another ULM (ULM') or a chemical linker moiety coupling at least one PTM or a ULM' or both to ULM.

In any aspect or embodiment described herein, the ULM is a Von Hippel-Lindau (VHL) ligase-binding moiety (VLM) with a chemical structure represented by:

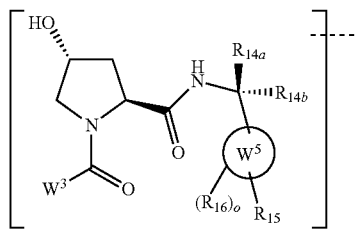

wherein:

$W^3$ is selected from the group of an optionally substituted aryl, optionally substituted heteroaryl, or

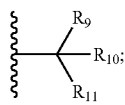

$R_9$ and $R_{10}$ are independently hydrogen, optionally substituted alkyl, optionally substituted cycloalkyl, optionally substituted hydroxyalkyl, optionally substituted heteroaryl, or haloalkyl, or $R_9$, $R_{10}$, and the carbon atom to which they are attached form an optionally substituted cycloalkyl;

$R_{11}$ is selected from the group of an optionally substituted heterocyclic, optionally substituted alkoxy, optionally substituted heteroaryl, optionally substituted aryl,

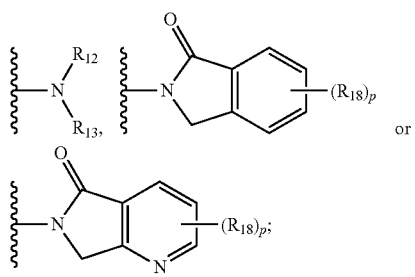

$R_{12}$ is selected from the group of H or optionally substituted alkyl;

$R_{13}$ is selected from the group of H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl;

$R_{14a}$, $R_{14b}$, are each independently selected from the group of H, haloalkyl, or optionally substituted alkyl;

$W^5$ is selected from the group of a phenyl or a 5-10 membered heteroaryl, $R_{15}$ is selected from the group of H, halogen, CN, OH, $NO_2$, $NR_{14a}R_{14b}$, $OR_{14a}$, $CONR_{14a}R_{14b}$, $NR_{14a}COR_{14b}$, $SO_2NR_{14a}R_{14b}$, $NR_{14a}SO_2R_{14b}$, optionally substituted alkyl, optionally substituted haloalkyl, optionally substituted haloalkoxy; aryl, heteroaryl, cycloalkyl, or cycloheteroalkyl (optionally substituted);

$R_{16}$ is independently selected from the group of halo, optionally substituted alkyl, optionally substituted haloalkyl, hydroxy, or optionally substituted haloalkoxy;

o is 0, 1, 2, 3, or 4;

$R_{18}$ is independently selected from the group of H, halo, optionally substituted alkoxy, cyano, optionally substituted alkyl, haloalkyl, haloalkoxy or a linker; and p is 0, 1, 2, 3, or 4, and wherein the dashed line indicates the site of attachment of at least one PTM, another ULM (ULM') or a chemical linker moiety coupling at least one PTM or a ULM' or both to ULM.

The compound of any of the claims 1-5, wherein the ULM has a chemical structure selected from the group of:

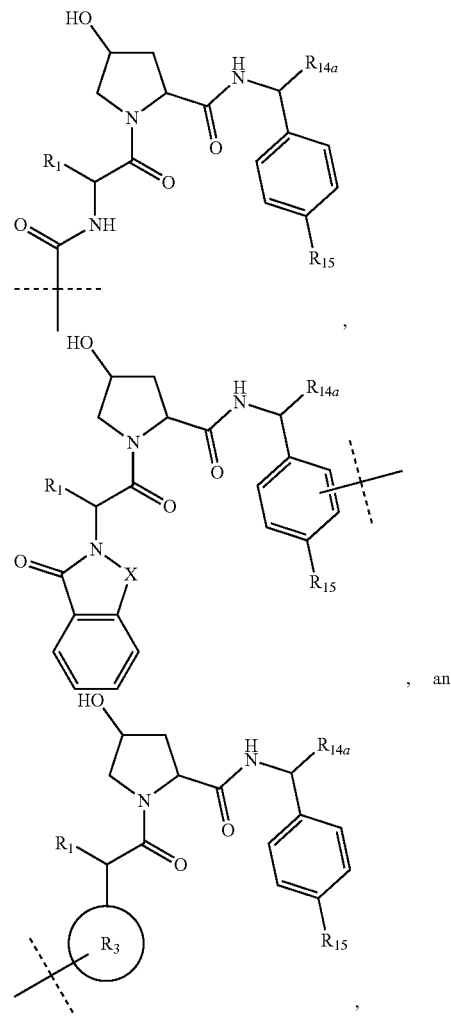

, and wherein:
R₁ is H, ethyl, isopropyl, tert-butyl, sec-butyl, cyclopropyl, cyclobutyl, cyclopentyl, or cyclohexyl; optionally substituted alkyl, optionally substituted hydroxyalkyl, optionally substituted heteroaryl, or haloalkyl;

$R_{14a}$ is H, haloalkyl, optionally substituted alkyl, methyl, fluoromethyl, hydroxymethyl, ethyl, isopropyl, or cyclopropyl;

$R_{15}$ is selected from the group consisting of H, halogen, CN, OH, NO₂, optionally substituted heteroaryl, optionally substituted aryl; optionally substituted alkyl, optionally substituted haloalkyl, optionally substituted haloalkoxy, cycloalkyl, or cycloheteroalkyl (optionally substituted);

X is C, CH₂, or C=O

R³ is absent or an optionally substituted 5 or 6 membered heteroaryl; and the dashed line indicates the site of attachment of at least one PTM, another ULM (ULM') or a chemical linker moiety coupling at least one PTM or a ULM' or both to the ULM.

In any aspect or embodiment described herein, the ULM comprises a group according to the chemical structure:

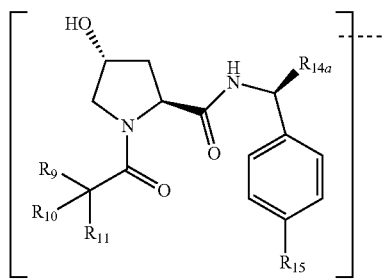

wherein:
$R_{14a}$ is H, haloalkyl, optionally substituted alkyl, methyl, fluoromethyl, hydroxymethyl, ethyl, isopropyl, or cyclopropyl;
R9 is H;
R10 is H, ethyl, isopropyl, tert-butyl, sec-butyl, cyclopropyl, cyclobutyl, cyclopentyl, or cyclohexyl;
R11 is

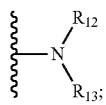

optionally substituted heteroaryl;

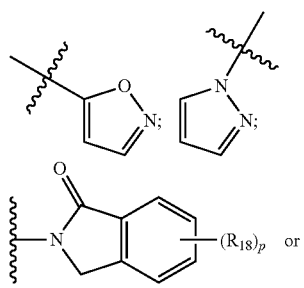

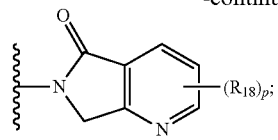

p is 0, 1, 2, 3, or 4; and each $R_{18}$ is independently halo, optionally substituted alkoxy, cyano, optionally substituted alkyl, haloalkyl, haloalkoxy or a linker;

R12 is H, C=O

R13 is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl, $R_{15}$ is selected from the group consisting of H, halogen, Cl, CN, OH, NO₂, optionally substituted heteroaryl, optionally substituted aryl;

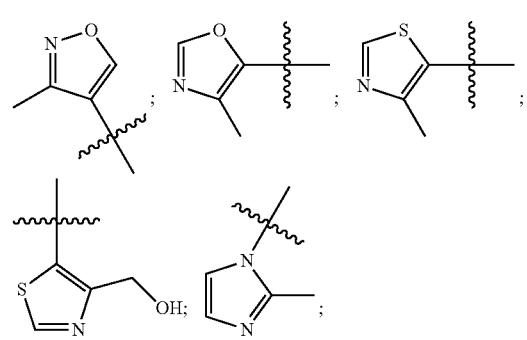

and wherein the dashed line indicates the site of attachment of at least one PTM, another ULM (ULM') or a chemical linker moiety coupling at least one PTM or a ULM' or both to the ULM.

In any aspect or embodiment described herein, the ULM is a cereblon E3 ligase-binding moiety (CLM) selected from the group consisting of a thalidomide, lenalidomide, pomalidomide, analogs thereof, isosteres thereof, or derivatives thereof.

In any aspect or embodiment described herein, the CLM has a chemical structure represented by:

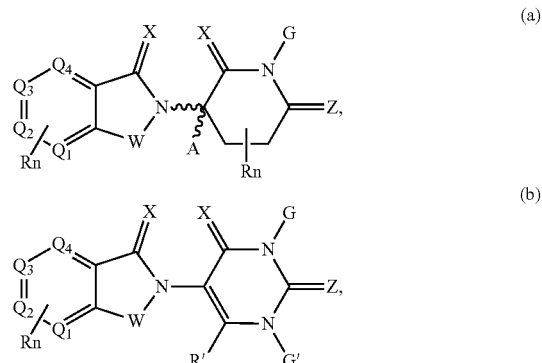

-continued

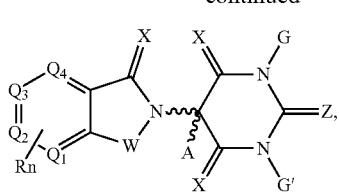

(c)

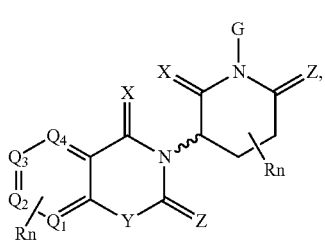

(d)

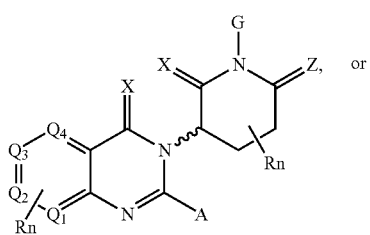

(e) or

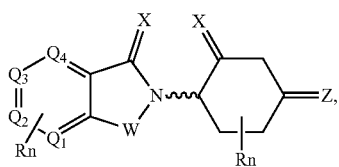

(f)

wherein:
W is selected from the group consisting of CH$_2$, CHR, C=O, SO$_2$, NH, and N-alkyl;
each X is independently selected from the group consisting of O, S, and H$_2$;
Y is selected from the group consisting of CH$_2$, —C=CR', NH, N-alkyl, N-aryl, N-hetaryl, N-cycloalkyl, N-heterocyclyl, O, and S;
Z is selected from the group consisting of O, S, and H$_2$;
G and G' are independently selected from the group consisting of H, alkyl (linear, branched, optionally substituted), OH, R'OCOOR, R'OCONRR", CH$_2$-heterocyclyl optionally substituted with R', and benzyl optionally substituted with R';
Q$_1$, Q$_2$, Q$_3$, and Q$_4$ represent a carbon C substituted with a group independently selected from R', N or N-oxide;
A is independently selected from the group H, alkyl (linear, branched, optionally substituted), cycloalkyl, C$_1$ and F;
R comprises —CONR'R", —OR', —NR'R", —SR', —SO$_2$R', —SO$_2$NR'R", —CR'R"—, —CR'NR'R"—, (—CR'O)$_n$R", -aryl, -hetaryl, -alkyl (linear, branched, optionally substituted), -cycloalkyl, -heterocyclyl, —P(O)(OR')R", —P(O)R'R", —OP(O)(OR')R", —OP(O)R'R", —Cl, —F, —Br, —I, —CF$_3$, —CN, —NR'SO$_2$NR'R", —NR'CONR'R", —CONR'COR", —NR'C(=N—CN)NR'R", —C(=N—CN)NR'R", —NR'C(=N—CN)R", —NR'C(=C—NO$_2$)NR'R", —SO$_2$NR'COR", —NO$_2$, —CO$_2$R', —C(C=N—OR') R", —CR'=CR'R", —CCR', —S(C=O)(C=N—R') R", —SF$_5$ and —OCF$_3$;

R' and R" are independently selected from the group consisting of a bond, H, alkyl, cycloalkyl, aryl, heteroaryl, heterocyclic, —C(=O)R, heterocyclyl, each of which is optionally substituted;
⁓ represents a bond that may be stereospecific ((R) or (S)) or non-stereospecific; and
R$_n$ comprises a functional group or an atom,
wherein n is an integer from 1-10 (e.g., 1-4, 1, 2, 3, 4, 5, 6, 7, 8, 9, or 10), and wherein
when n is 1, R$_n$ is modified to be covalently joined to the linker group (L), and
when n is 2, 3, or 4, then one R$_n$ is modified to be covalently joined to the linker group (L), and any other R$_n$ is optionally modified to be covalently joined to a PTM, a CLM, a second CLM having the same chemical structure as the CLM, a CLM', a second linker, or any multiple or combination thereof.

In any aspect or embodiment described herein, the CLM has a chemical structure represented by:

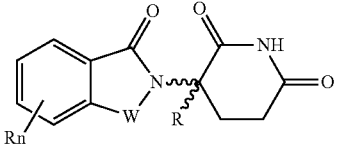

wherein:
W is independently selected from the group CH$_2$, C=O, NH, and N-alkyl;
R is independently selected from a H, methyl, optionally substituted alkyl (e.g., C$_1$-C$_6$ alkyl (linear, branched, optionally substituted));
⁓ represents a bond that may be stereospecific ((R) or (S)) or non-stereospecific; and
Rn comprises 1-4 independently selected functional groups or atoms, and optionally, one of which is modified to be covalently joined to a PTM, a chemical linker group (L), a CLM (or CLM') or combination thereof.

In any aspect or embodiment described herein, the ULM is a (MDM2) binding moiety (MLM) as described in the present disclosure (e.g., the MLM has a chemical moiety selected from the group consisting of a substituted imidazolines, a substituted spiro-indolinones, a substituted pyrrolidines, a substituted piperidinones, a substituted morpholinones, a substituted pyrrolopyrimidines, a substituted imidazolopyridines, a substituted thiazoloimidazoline, a substituted pyrrolopyrrolidinones, and a substituted isoquinolinones).

In any aspect or embodiment described herein, the MLM has a structure selected from the group consisting of:

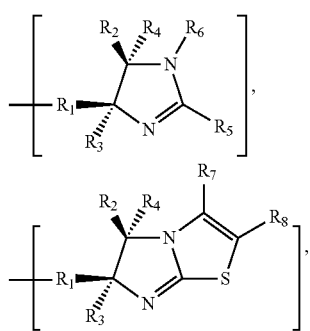

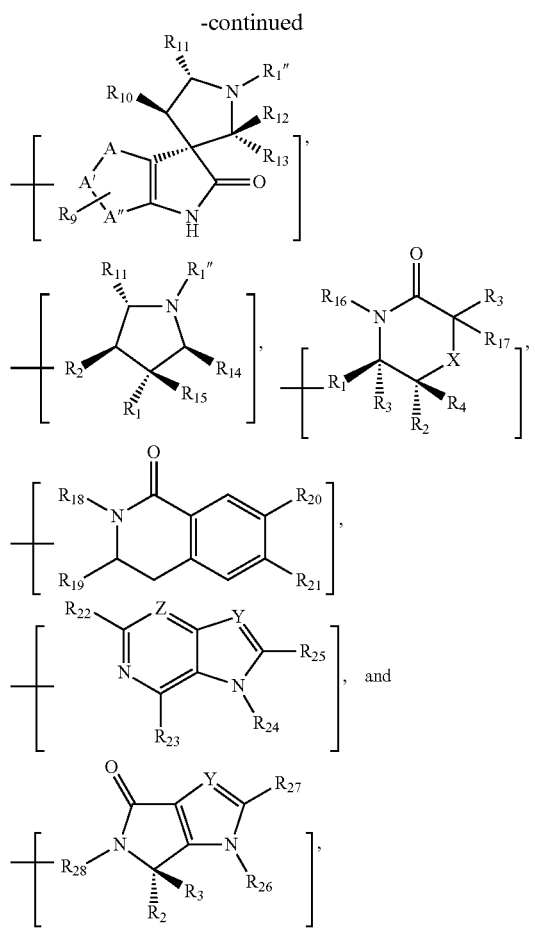

wherein:
- X is selected from the group consisting of carbon, oxygen, sulfur, sulfoxide, sulfone, and N—$R^a$;
- $R^a$ is independently H or an alkyl group with carbon number 1 to 6;
- Y and Z are independently carbon or nitrogen;
- A, A' and A'' are independently selected from C, N, O or S, can also be one or two atoms forming a fused bicyclic ring, or a 6,5- and 5,5-fused aromatic bicyclic group;
- $R_1$, $R_2$ are independently selected from the group consisting of an aryl or heteroaryl group, a heteroaryl group having one or two heteroatoms independently selected from sulfur or nitrogen, wherein the aryl or heteroaryl group can be mono-cyclic or bi-cyclic, or unsubstituted or substituted with one to three substituents independently selected from the group consisting of: halogen, —CN, C1 to C6 alkyl group, C3 to C6 cycloalkyl, —OH, alkoxy with 1 to 6 carbons, fluorine substituted alkoxy with 1 to 6 carbons, sulfoxide with 1 to 6 carbons, sulfone with 1 to 6 carbons, ketone with 2 to 6 carbons, amides with 2 to 6 carbons, and dialkyl amine with 2 to 6 carbons;
- $R_3$, $R_4$ are independently selected from the group consisting of H, methyl and C1 to C6 alkyl;
- $R_5$ is selected from the group consisting of an aryl or heteroaryl group, a heteroaryl group having one or two heteroatoms independently selected from sulfur or nitrogen, wherein the aryl or heteroaryl group can be mono-cyclic or bi-cyclic, or unsubstituted or substituted with one to three substituents independently selected from the group consisting of: halogen, —CN, C1 to C6 alkyl group, C3 to C6 cycloalkyl, —OH, alkoxy with 1 to 6 carbons, fluorine substituted alkoxy with 1 to 6 carbons, sulfoxide with 1 to 6 carbons, sulfone with 1 to 6 carbons, ketone with 2 to 6 carbons, amides with 2 to 6 carbons, dialkyl amine with 2 to 6 carbons, alkyl ether (C2 to C6), alkyl ketone (C3 to C6), morpholinyl, alkyl ester (C3 to C6), alkyl cyanide (C3 to C6);
- $R_6$ is H or —C(=O)$R^b$, wherein
- $R^b$ is selected from the group consisting of alkyl, cycloalkyl, mono-, di- or tri-substituted aryl or heteroaryl, 4-morpholinyl, 1-(3-oxopiperazunyl), 1-piperidinyl, 4-N—$R^c$-morpholinyl, 4-$R^c$-1-piperidinyl, and 3-R'-1-piperidinyl, wherein
- $R^c$ is selected from the group consisting of alkyl, fluorine substituted alkyl, cyano alkyl, hydroxyl-substituted alkyl, cycloalkyl, alkoxyalkyl, amide alkyl, alkyl sulfone, alkyl sulfoxide, alkyl amide, aryl, heteroaryl, mono-, bis- and tri-substituted aryl or heteroaryl, CH2CH2$R^d$, and CH2CH2CH2$R^d$, wherein
- $R^d$ is selected from the group consisting of alkoxy, alkyl sulfone, alkyl sulfoxide, N-substituted carboxamide, —NHC(O)-alkyl, —NH—$SO_2$-alkyl, aryl, substituted aryl, heteroaryl, substituted heteroaryl;
- $R_7$ is selected from the group consisting of H, C1 to C6 alkyl, cyclic alkyl, fluorine substituted alkyl, cyano substituted alkyl, 5- or 6-membered hetero aryl or aryl, substituted 5- or 6-membered hetero aryl or aryl;
- $R_8$ is selected from the group consisting of —$R^e$—C(O)—$R^f$, —$R^e$-alkoxy, —$R^e$-aryl, —$R^e$-heteroaryl, and —$R^e$—C(O)—$R^f$—C(O)—$R^g$, wherein:
- $R^e$ is an alkylene with 1 to 6 carbons, or a bond;
- $R^f$ is a substituted 4- to 7-membered heterocycle;
- $R^g$ is selected from the group consisting of aryl, hetero aryl, substituted aryl or heteroaryl, and 4- to 7-membered heterocycle;
- $R_9$ is selected from the group consisting of a mono-, bis- or tri-substituent on the fused bicyclic aromatic ring in Formula (A-3), wherein the substitutents are independently selected from the group consisting of halogen, alkene, alkyne, alkyl, unsubstituted or substituted with Cl or F;
- $R_{10}$ is selected from the group consisting of an aryl or heteroaryl group, wherein the heteroaryl group can contain one or two heteroatoms as sulfur or nitrogen, aryl or heteroaryl group can be mono-cyclic or bi-cyclic, the aryl or heteroaryl group can be unsubstituted or substituted with one to three substituents, including a halogen, F, Cl, —CN, alkene, alkyne, C1 to C6 alkyl group, C1 to C6 cycloalkyl, —OH, alkoxy with 1 to 6 carbons, fluorine substituted alkoxy with 1 to 6 carbons, sulfoxide with 1 to 6 carbons, sulfone with 1 to 6 carbons, ketone with 2 to 6 carbons;
- $R_{11}$ is —C(O)—N($R^h$)($R^i$), wherein $R^h$ and $R^i$ are selected from groups consisting of the following: H, C1 to C6 alkyl, alkoxy substituted alkyl, sulfone substituted alkyl, aryl, heterol aryl, mono-, bis- or tri-substituted aryl or hetero aryl, alkyl carboxylic acid, heteroaryl carboxylic acid, alkyl carboxylic acid, fluorine substituted alkyl carboxylic acid, aryl substituted cycloalkyl, hetero aryl substituted cycloalkyl; wherein $R^h$ and $R^i$ are independently selected from the group consisting of H, connected to form a ring, 4-hydroxycyclohehexane; mono- and di-hydroxy substituted alkyl (C3 to C6);

3-hydroxycyclobutane; phenyl-4-carboxylic acid, and substituted phenyl-4-carboxylic acid;

$R_{12}$ and $R_{13}$ are independently selected from H, lower alkyl (C1 to C6), lower alkenyl (C2 to C6), lower alkynyl (C2 to C6), cycloalkyl (4, 5 and 6-membered ring), substituted cycloalkyl, cycloalkenyl, substituted cycloalkenyl, 5- and 6-membered aryl and heteroaryl, $R^{12}$ and $R^{13}$ can be connected to form a 5- and 6-membered ring with or without substitution on the ring;

$R_{14}$ is selected from the group consisting of alkyl, substituted alkyl, alkenyl, substituted alkenyl, aryl, substituted aryl, heteroaryl, substituted heteroaryl, heterocycle, substituted heterocycle, cycloalkyl, substituted cycloalkyl, cycloalkenyl and substituted cycloalkenyl;

$R_{15}$ is CN;

$R_{16}$ is selected from the group consisting of C1-6 alkyl, C1-6 cycloalkyl, C2-6 alkenyl, C1-6 alkyl or C3-6 cycloalkyl with one or multiple hydrogens replaced by fluorine, alkyl or cycloalkyl with one $CH_2$ replaced by S(=O), —S, or —S(=O)$_2$, alkyl or cycloalkyl with terminal $CH_3$ replaced by S(=O)2N(alkyl)(alkyl), —C(=O)N(alkyl)(alkyl), —N(alkyl)S(=O)2(alkyl), —C(=O)2(alkyl), —O(alkyl), C1-6 alkyl or alkyl-cycloalkyl with hydron replaced by hydroxyl group, a 3 to 7 membered cycloalkyl or heterocycloalkyl, optionally containing a —(C=O)— group, or a 5 to 6 membered aryl or heteroaryl group, which heterocycloalkyl or heteroaryl group can contain from one to three heteroatoms independently selected from O, N or S, and the cycloalkyl, heterocycloalkyl, aryl or heteroaryl group can be unsubstituted or substituted with from one to three substituents independently selected from halogen, C1-6 alkyl groups, hydroxylated C1-6 alkyl, C1-6 alkyl containing thioether, ether, sulfone, sulfoxide, fluorine substituted ether or cyano group;

$R_{17}$ is selected from the group consisting of $(CH_2)nC(O)NR^kR^l$, wherein $R^k$ and $R^l$ are independently selected from H, C1-6 alkyl, hydroxylated C1-6 alkyl, C1-6 alkoxy alkyl, C1-6 alkyl with one or multiple hydrogens replaced by fluorine, C1-6 alkyl with one carbon replaced by S(O), S(O)(O), C1-6 alkoxyalkyl with one or multiple hydrogens replaced by fluorine, C1-6 alkyl with hydrogen replaced by a cyano group, 5 and 6 membered aryl or heteroaryl, alkyl aryl with alkyl group containing 1-6 carbons, and alkyl heteroaryl with alkyl group containing 1-6 carbons, wherein the aryl or heteroaryl group can be further substituted;

$R_{18}$ is selected from the group consisting of substituted aryl, heteroaryl, alkyl, cycloalkyl, the substitution is preferably —N(C1-4 alkyl)(cycloalkyl), —N(C1-4 alkyl)alkyl-cycloalkyl, and —N(C1-4 alkyl)[(alkyl)-(heterocycle-substituted)-cycloalkyl];

$R_{19}$ is selected from the group consisting of aryl, heteroaryl, bicyclic heteroaryl, and these aryl or heteroaryl groups can be substituted with halogen, C1-6 alkyl, C1-6 cycloalkyl, $CF_3$, F, CN, alkyne, alkyl sulfone, the halogen substitution can be mon- bis- or tri-substituted;

$R_{20}$ and $R_{21}$ are independently selected from C1-6 alkyl, C1-6 cycloalkyl, C1-6 alkoxy, hydroxylated C1-6 alkoxy, and fluorine substituted C1-6 alkoxy, wherein $R_{20}$ and $R_{21}$ can further be connected to form a 5, 6 and 7-membered cyclic or heterocyclic ring, which can further be substituted;

$R_{22}$ is selected from the group consisting of H, C1-6 alkyl, C1-6 cycloalkyl, carboxylic acid, carboxylic acid ester, amide, reverse amide, sulfonamide, reverse sulfonamide, N-acyl urea, nitrogen-containing 5-membered heterocycle, the 5-membered heterocycles can be further substituted with C1-6 alkyl, alkoxy, fluorine-substituted alkyl, CN, and alkylsulfone;

$R_{23}$ is selected from aryl, heteroaryl, —O-aryl, —O-heteroaryl, —O-alkyl, —O-alkyl-cycloalkyl, —NH-alkyl, —NH-alkyl-cycloalkyl, —N(H)-aryl, —N(H)-heteroaryl, —N(alkyl)-aryl, —N(alkyl)-heteroaryl, the aryl or heteroaryl groups can be substituted with halogen, C1-6 alkyl, hydoxylated C1-6 alkyl, cycloalkyl, fluorine-substituted C1-6 alkyl, CN, alkoxy, alkyl sulfone, amide and sulfonamide;

$R_{24}$ is selected from the group consisting of —CH2-(C1-6 alkyl), —CH2-cycloalkyl, -CH2-aryl, CH2-heteroaryl, where alkyl, cycloalkyl, aryl and heteroaryl can be substituted with halogen, alkoxy, hydoxylated alkyl, cyano-substituted alkyl, cycloalyl and substituted cycloalky;

$R_{25}$ is selected from the group consisting of C1-6 alkyl, C1-6 alkyl-cycloalkyl, alkoxy-substituted alkyl, hydroxylated alkyl, aryl, heteroaryl, substituted aryl or heteroaryl, 5,6, and 7-membered nitrogen-containing saturated heterocycles, 5,6-fused and 6,6-fused nitrogen-containing saturated heterocycles and these saturated heterocycles can be substituted with C1-6 alkyl, fluorine-substituted C1-6 alkyl, alkoxy, aryl and heteroaryl group;

$R_{26}$ is selected from the group consisting of C1-6 alkyl, C3-6 cycloalkyl, the alkyl or cycloalkyl can be substituted with —OH, alkoxy, fluorine-substituted alkoxy, fluorine-substituted alkyl, —$NH_2$, —NH-alkyl, NH—C(O)alkyl, —NH—S(O)2-alkyl, and —S(O)2-alkyl;

$R^{27}$ is selected from the group consisting of aryl, heteroaryl, bicyclic heteroaryl, wherein the aryl or heteroaryl groups can be substituted with C1-6 alkyl, alkoxy, NH2, NH-alkyl, halogen, or —CN, and the substitution can be independently mono-, bis- and tri-substitution;

$R_{28}$ is selected from the group consisting of aryl, 5 and 6-membered heteroaryl, bicyclic heteroaryl, cycloalkyl, saturated heterocycle such as piperidine, piperidinone, tetrahydropyran, N-acyl-piperidine, wherein the cycloalkyl, saturated heterocycle, aryl or heteroaryl can be further substituted with —OH, alkoxy, mono-, bis- or tri-substitution including halogen, —CN, alkyl sulfone, and fluorine substituted alkyl groups; and $R_{1''}$ is selected from the group consisting of alkyl, aryl substituted alkyl, alkoxy substituted alkyl, cycloalkyl, aryl-substituted cycloalkyl, and alkoxy substituted cycloalkyl, or a pharmaceutically acceptable salt, enantiomer, stereoisomer, solvate, polymorph or prodrug thereof.

In any aspect or embodiment described herein, the heterocycles in $R^f$ and $R^g$ are independently selected from the group consisting of substituted pyrrolidine, substituted piperidine, and substituted piperizine.

In any aspect or embodiment described herein, the $R_9$ substituents are selected from Cl and F.

In any aspect or embodiment described herein, the $R_{10}$ substituents are selected from H, F and Cl.

In any aspect or embodiment described herein, $R^h$ and $R^i$ are selected from the group consisting of:
(i) $R^h$ is H, and $R^i$ is 4-hydroxycyclohehexane;
(ii) $R^h$ is H, and $R^i$ is mono- and di-hydroxy substituted lower alkyl (C3 to C6);
(iii) $R^h$ is H, and $R^i$ is 3-hydroxycyclobutane; and
(iv) $R^h$ is H, and $R^i$ is phenyl-4-carboxylic acid, substituted phenyl-4-carboxylic acid.

In any aspect or embodiment described herein, the $R_{18}$ substitution is selected from the group consisting of —N(C1-4 alkyl)(cycloalkyl), —N(C1-4 alkyl)alkyl-cycloalkyl, and —N(C1-4 alkyl)[(alkyl)-(heterocycle-substituted)-cycloalkyl].

In any aspect or embodiment described herein, the $R_{28}$ saturated heterocycle is selected from piperidine, piperidinone, tetrahydropyran, and N-acyl-piperidine.

In any aspect or embodiment described herein, the compound has a structure selected from the group consisting of:

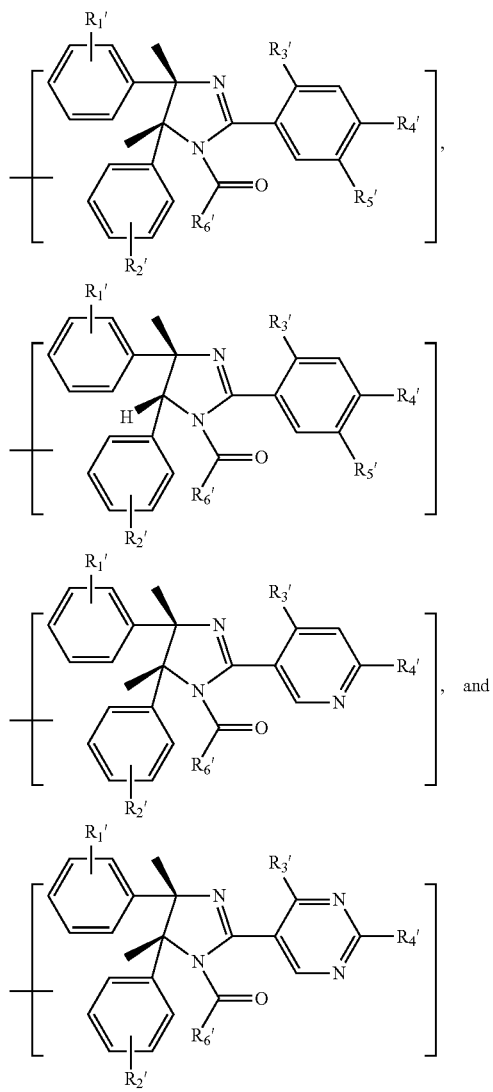

wherein:
R1' and R2' are independently selected from the group consisting of F, Cl, Br, I, acetylene, CN, $CF_3$ and $NO_2$;
R3' is selected from the group consisting of —$OCH_3$, —$OCH_2CH_3$, —$OCH_2CH_2F$, —$OCH_2CH_2OCH_3$, and —$OCH(CH_3)_2$;
R4' and R6' are independently selected from the group consisting of H, halogen, —$CH_3$, —$CF_3$, —$OCH_3$, —$C(CH_3)_3$, —$CH(CH_3)_2$, -cyclopropyl, —CN, —$C(CH_3)_2OH$, —$C(CH_3)_2OCH_2CH_3$, —$C(CH_3)_2CH_2OH$, —$C(CH_3)_2OCH_2CH_3$, —$C(CH_3)_2CH_2CH_2CH_2OH$, $C(CH_3)_2OCH_2CH_3$, —$C(CH_3)_2CN$, —$C(CH_3)_2C(O)CH_3$, —$C(CH_3)_2C(O)NHCH_3$, —$C(CH_3)_2C(O)N(CH_3)_2$, —$SCH_3$, —$SCH_2CH_3$, —$S(O)_2CH_3$, —$S(O_2)CH_2CH_3$, —NHC$(CH_3)_3$, —$N(CH_3)_2$, pyrrolidinyl, and 4-morpholinyl; and R5' is selected from the group consisting of halogen, -cyclopropyl, —$S(O)_2CH_3$, —$S(O)_2CH_2CH_3$, 1-pyrrolidinyl, —$NH_2$, —$N(CH_3)_2$, and —$NHC(CH_3)_3$, or a pharmaceutically acceptable salt, enantiomer, stereoisomer, solvate, polymorph or prodrug thereof.

In any aspect or embodiment described herein, the linker is attached to at least one of R1', R2', R3', R4', R5', R6', or a combination thereof.

In any aspect or embodiment described herein, $R^{6'}$ is independently selected from the group consisting of H,

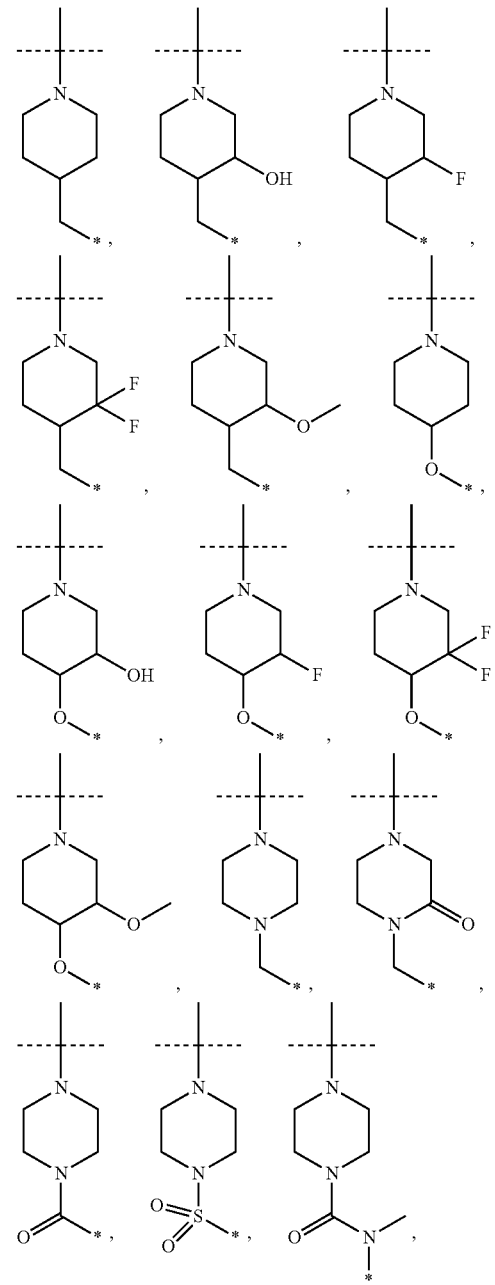

-continued
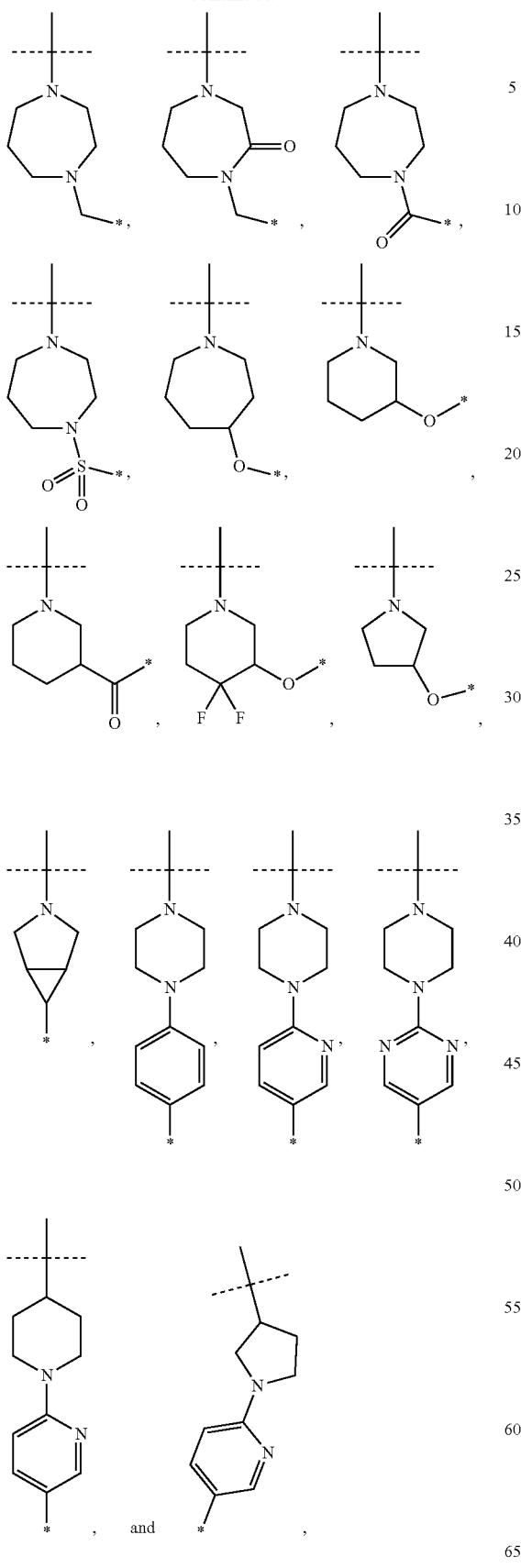
wherein * indicates the point of attachment of the linker.
In any aspect or embodiment described herein, the MLM has a structure selected from the group consisting of:
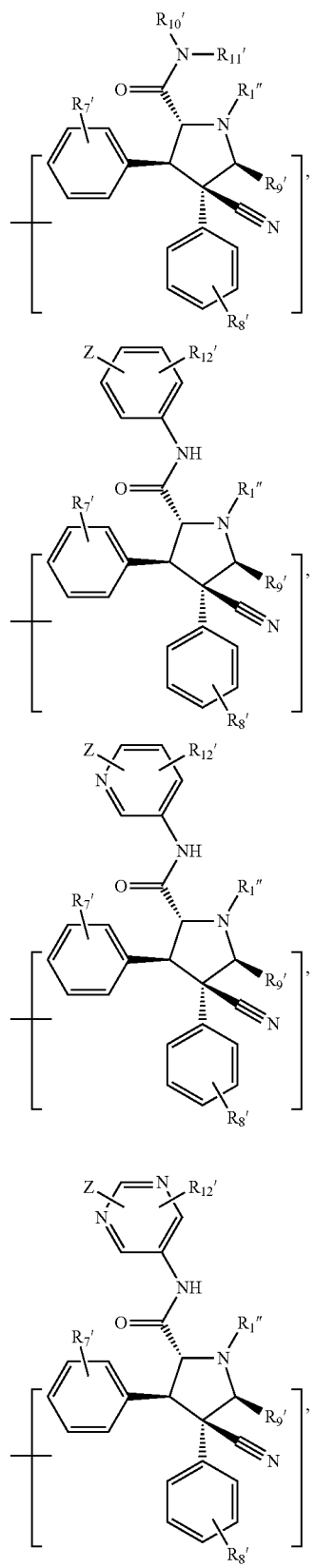

-continued

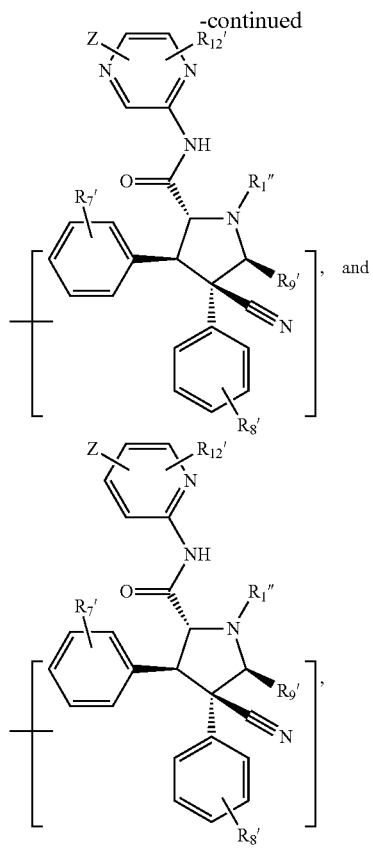

, and wherein
R<sub>7'</sub> is a member selected from the group consisting of halogen, mono-, and di- or tri-substituted halogen;
R<sub>8'</sub> is selected from the group consisting of H, —F, —Cl, —Br, —I, —CN, —NO$_2$, ethylnyl, cyclopropyl, methyl, ethyl, isopropyl, vinyl, methoxy, ethoxy, isopropoxy, —OH, other C1-6 alkyl, other C1-6 alkenyl, and C1-6 alkynyl, mono-, di- or tri-substituted;
R<sub>9'</sub> is selected from the group consisting of alkyl, substituted alkyl, alkenyl, substituted alkenyl, alkynyl, substituted alkynyl, aryl, substituted aryl, hetero aryl, substituted heteroaryl, cycloalkyl, substituted cycloalkyl, alkenyl, and substituted cycloalkenyl;
Z is selected from the group consisting of H, —OCH$_3$, —OCH$_2$CH$_3$, and halogen;
R<sub>10'</sub> and R<sub>11'</sub> are each independently selected from the group consisting of H, (CH$_2$)$_n$—R', (CH$_2$)$_n$—NR'R", (CH$_2$)$_n$—NR'COR", (CH$_2$)$_n$—NR'SO$_2$R", (CH$_2$)$_n$—COOH, (CH$_2$)$_n$—COOR', (CH)$_n$—CONR'R", (CH$_2$)$_n$—OR', (CH$_2$)$_n$—SR', (CH$_2$)$_n$—SOR', (CH$_2$)$_n$—CH(OH)—R', (CH$_2$)$_n$—COR', (CH$_2$)$_n$—SO$_2$R', (CH$_2$)$_n$—SONR'R", (CH$_2$)$_n$—SO$_2$NR'R", (CH$_2$CH$_2$O)$_m$—(CH$_2$)$_n$—R', (CH$_2$CH$_2$O)$_m$—(CH$_2$)$_n$—OH, (CH$_2$CH$_2$O)$_m$—(CH$_2$)$_n$—OR', (CH$_2$CH$_2$O)$_m$—(CH$_2$)$_n$—NR'R", (CH$_2$CH$_2$O)$_m$—(CH$_2$)$_n$—NR'COR", (CH$_2$CH$_2$O)$_m$(CH$_2$)$_n$—NR'SO$_2$R", (CH$_2$CH$_2$O)$_m$(CH$_2$)$_n$—COOH, (CH$_2$CH$_2$O)$_m$(CH$_2$)$_n$—COOR', (CH$_2$CH$_2$O)$_m$—(CH$_2$)$_n$—CONR'R", (CH$_2$CH$_2$O)$_m$—(CH$_2$)$_n$—SO$_2$R', (CH$_2$CH$_2$O)$_m$—(CH$_2$)$_n$—COR', (CH$_2$CH$_2$O)$_m$—(CH$_2$)$_n$—SONR'R", (CH$_2$CH$_2$O)$_m$—(CH$_2$)$_n$—SO$_2$NR'R", (CH$_2$)$_p$—(CH$_2$CH$_2$O)$_m$—(CH$_2$)$_n$R', (CH$_2$)$_p$—(CH$_2$CH$_2$O)$_m$—(CH$_2$)$_n$—OH, (CH$_2$)$_p$—(CH$_2$CH$_2$O)$_m$—(CH$_2$)$_n$—OR', (CH$_2$)$_p$—(CH$_2$CH$_2$O)$_m$—(CH$_2$)$_n$—NR'R", (CH$_2$)$_p$—(CH$_2$CH$_2$O)$_m$—(CH$_2$)$_n$—NR'COR", (CH$_2$)$_p$—(CH$_2$CH$_2$O)$_m$—(CH$_2$)$_n$—NR'SO$_2$R", (CH$_2$)$_p$—(CH$_2$CH$_2$O)$_m$—(CH$_2$)$_n$—COOH, (CH$_2$)$_p$—(CH$_2$CH$_2$O)$_m$—(CH$_2$)$_n$—COOR', (CH$_2$)$_p$—(CH$_2$CH$_2$O)$_m$—(CH$_2$)$_n$—CONR'R", (CH$_2$)$_p$—(CH$_2$CH$_2$O)$_m$—(CH$_2$)$_n$—SO$_2$R', (CH$_2$)$_p$—(CH$_2$CH$_2$O)$_m$—(CH$_2$)$_n$—COR', (CH$_2$)$_p$—(CH$_2$ CH$_2$O)$_m$—(CH$_2$)$_n$—SONR'R", (CH$_2$)$_p$—(CH$_2$ CH$_2$O)$_m$—(CH$_2$)$_n$—SO$_2$NR'R", Aryl-(CH$_2$)$_n$—COOH, and heteroaryl-alkyl-CO-alkyl-NR'R"m, wherein the alkyl may be substituted with OR', and heteroaryl-(CH$_2$)$_n$-heterocycle wherein the heterocycle may optionally be substituted with alkyl, hydroxyl, COOR' and COR'; wherein R' and R" are selected from H, alkyl, alkyl substituted with halogen, hydroxyl, NH$_2$, NH(alkyl), N(alkyl)$_2$, oxo, carboxy, cycloalkyl and heteroaryl;

m, n, and p are independently 0 to 6;

R<sub>12'</sub> is selected from the group consisting of —O-(alkyl), —O-(alkyl)-alkoxy, —C(O)-(alkyl), —C(OH)-alkylalkoxy, —C(O)—NH-(alkyl), —C(O)—N-(alkyl)2, —S(O)-(alkyl), S(O)2-(alkyl), —C(O)-(cyclic amine), and —O-aryl-(alkyl), —O-aryl-(alkoxy); and R<sub>1"</sub> is selected from the group consisting of alkyl, aryl substituted alkyl, alkoxy substituted alkyl, cycloalkyl, aryl-substituted cycloalkyl, and alkoxy substituted cycloalkyl, or a pharmaceutically acceptable salt, enantiomer, stereoisomer, solvate, polymorph or prodrug thereof.

In any aspect or embodiment described herein, the linker is attached to at least one of Z, R<sub>8'</sub>, R<sub>9'</sub>, R<sub>10'</sub>, R<sub>11'</sub>, R<sub>12'</sub>, R<sub>1"</sub>, or a combination thereof.

In any aspect or embodiment described herein, the ULM is a IAP E3 ubiquitin ligase binding moiety (ILM) as described in the present disclosure (e.g., the ILM comprises the amino acids alanine (A), valine (V), proline (P), and isoleucine (I) or their unnatural mimetics).

In any aspect or embodiment described herein, the ULM is a IAP E3 ubiquitin ligase binding moiety (ILM) comprising a AVPI tetrapeptide fragment or derivative thereof.

In any aspect or embodiment described herein, the ILM may have a chemical structure represented by:

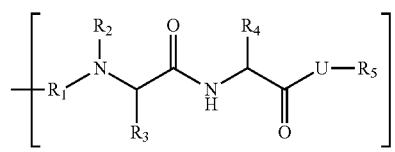

wherein:
PTM is a protein target moiety that binds to a target protein or a target polypeptide;
L is a linker group coupling PTM to the ILM molecule shown;
R$_1$ is, independently, H, C$_1$-C$_4$-alky, Q-Cvalkenyl, C$_1$-C$_4$-alkynyl or C$_3$-C$_{10}$-cycloalkyl which are unsubstituted or substituted;
R$_2$ is, independently, H. C$_1$-C$_4$-alkyl, C$_1$-C$_4$-alkenyl, C$_1$-C$_4$-alkynyl or C$_3$-C$_{10}$-cycloalkyl which are unsubstituted or substituted;

$R_3$ is, independently. H, —$CF_3$, —$C_2H_5$, $C_1$-$C_4$-alkyl. $C_1$-$C_4$-alkenyl, $C_1$-$C_4$-alkynyl, —$CH_2$—Z or any $R_2$ and $R_3$ together form a heterocyclic ring:

Z is, independently. H, —OH, F, Cl—$CH_3$—$CF_3$— $CH_2Cl$—$CH_2F$ or —$CH_2OH$;

$R_4$ is, independently, $C_1$-$C_{16}$ straight or branched alkyl, $C_1$-$C_{16}$-alkenyl. $C_1$-$C_{16}$-alkynyl. $C_3$-$C_{10}$-cycloalkyl, —$(CH_2)_{0-6}$—$Z_1$, —$(CH_2)_{0-6}$-aryl and —$(CH_2)_{0-6}$-het, wherein alkyl, cycloalkyl, and phenyl are unsubstituted or substituted;

$R_5$ is, independently. H. $C_{1-10}$-alkyl, aryl, phenyl, $C_{3-7}$-cycloalkyl, —$(CH_2)_{1-6}$—$C_{3-7}$-cycloalkyl. —$C_{1-10}$-alkyl-aryl, —$(CH_2)_{0-6}$—$C_{3-7}$-cycloalkyl-$(CH_2)_{0-6}$-phenyl, —$(CH_2)_{0-4}$—$CH[(CH_2)_{1-4}$-phenyl$]_2$, indanyl, —C(O)—$C_{1-10}$-alkyl, —C(O)—$(CH_2)_{1-6}$—$C_{3-7}$-cycloalkyl, —C(O)—$(CH_2)_{0-6}$-phenyl, —$(CH_2)_{0-6}$—C(O)-phenyl, —$(CH_2)_{0-6}$-het, —C(O)—$(CH_2)_{1-6}$-het, or $R_5$ is a residue of an amino acid, wherein the alkyl, cycloalkyl, phenyl, and aryl substituents are unsubstituted or substituted;

$Z_1$ is, independently, —$N(R_{10})$—C(O)—$C_{1-10}$-alkyl, —$N(R_{10})$—C(O)—$(CH_2)_{0-6}$—$C_{3-7}$-cycloalkyl, —$N(R_{10})$—C(O)—$(CH_2)_{0-6}$-phenyl, —$N(R_{10})$—C(O)$(CH_2)_{1-6}$-het, —C(O)—$N(R_{11})(R_{12})$, —C(O)—O—$C_{1-10}$-alkyl, —C(O)—O—$(CH_2)_{1-6}$—$C_{3-7}$-cycloalkyl, —C(O)—O—$(CH_2)_{0-6}$-phenyl, —C(O)—O—$(CH_2)_{1-6}$-het, —O—C(O)—$C_{1-10}$-alkyl, —O—C(O)—$(CH_2)_{1-6}$—$C_{3-7}$-cycloalkyl, —O—C(O)—$(CH_2)_{0-6}$-phenyl, —O—C(O)—$(CH_2)_{1-6}$-het, wherein alkyl, cycloalkyl, and phenyl are unsubstituted or substituted;

het is, independently, a 5-7 member heterocyclic ring containing 1-4 heteroatoms selected from N, O. and S, or an 8-12 member fused ring system including at least one 5-7 member heterocyclic ring containing 1, 2, or 3 heteroatoms selected from N, O, and S, which heterocyclic ring or fused ring system is unsubstituted or substituted on a carbon or nitrogen atom;

$R_{10}$ is, independently. H, —$CH_3$, —$CF_3$, —$CH_2OH$, or —$CH_2Cl$;

$R_{11}$ and $R_{12}$ is, independently, H, $C_{1-4}$-alkyl, $C_{3-7}$-cycloalkyl, —$(CH_2)_{1-6}$—$C_{3-7}$-cycloakyl, $(CH_2)_{0-6}$-phenyl, wherein alkyl, cycloalkyl, and phenyl are unsubstituted or substituted; or $R_{11}$ $R_{12}$ together with the nitrogen form het;

U is as shown in structure (11):

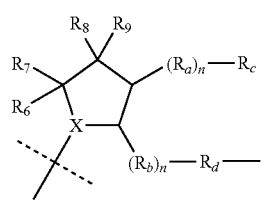

(II)

wherein:
each n is independently 0 to 5;
X is —CH or N;
$R_a$ and $R_b$, are independently selected from the group of an O. S, or N atom or $C_{0-8}$-alkyl wherein one or more of the carbon atoms in the alkyl chain are optionally replaced by a heteroatom selected from O, S. or N, and where each alkyl is, independently, either unsubstituted or substituted;

$R_d$ is selected from: Re-Q-$(R_f)_p(R_g)_q$; and $Ar_1$-D-$Ar_2$ $R_e$ is selected from H or any $R_c$ and $R_d$ together form a cycloalkyl or het; where if $R_c$ and $R_d$ form a cycloalkyl or het. $R_5$ is attached to the formed ring at a C or N atom;

each p and q is, independently. 0 or 1;

$R_e$ is selected from the group of $C_{1-8}$-alkyl or alkylidene, and each $R_c$ is either unsubstituted or substituted; each Q is, independently, N, O, S, S(O), or $S(O)_2$;

each $Ar_1$ and $Ar_2$ is, independently, substituted or unsubstituted aryl or het;

$R_f$ and $R_g$ are independently selected from H, —C1-10-alkyl, $C_{1-10}$-alkylaryl, —OH, —O—$C_{1-10}$-alkyl, —$(CH_2)_{0-6}$—$C_{3-7}$-cycloalky, —O—$(CH_2)_{0-6}$-aryl, phenyl, aryl, phenyl-phenyl, —$(CH_2)_{1-6}$-het, —O—$(CH_2)_{1-6}$-het, —$OR_{13}$, —C(O)—$R_{13}$, —C(O)—$N(R_{13})(R_{14})$, —$N(R_{13})(R_{14})$, —S—$R_{13}$, —S(O)—$R_{13}$, —$S(O)_2$—$R_{13}$, —$S(O)_2$—$NR_{13}R_{14}$, —$NR_{13}$—$S(O)_2$—$R_{14}$, —S—$C_{1-10}$-alkyl, aryl-$C_{1-4}$-alkyl, or het-$C_{1-4}$-alkyl, wherein alkyl, cycloalkyl, het, and aryl are unsubstituted or substituted; —$SO_2$—$C_{1-2}$-alkyl, —$SO_2$—$C_{1-2}$-alkylphenyl, —O—$C_{1-4}$-alkyl, or any $R_g$ and $R_f$ together form a ring selected from het or aryl;

D is selected from the group of —CO—, —C(O)—$C_{1-7}$-alkylene or arylene, —$CF_2$—, —O—, —$S(O)_r$ where r is 0-2, 1,3-dioxalane, or $C_{1-7}$-alkyl-OH, where alkyl, alkylene, or arylene are unsubstituted or substituted with one or more halogens, OH, —O—$C_{1-6}$-alkyl, —S—$C_{1-6}$-alkyl, or —$CF_3$, or each D is, independently, $N(R_h)$ wherein each Rh is, independently, H, unsubstituted or substituted $C_{1-7}$-alkyl, aryl, unsubstituted or substituted —O—($C_{1-7}$-cycloalkyl), —C(O)—$C_{1-10}$-alkyl, —C(O)—$C_{0-10}$-alkyl-aryl, —C—O—$C_{01-10}$-alkyl, —C—O—$C_{0-10}$-alkyl-aryl, —$SO_2$—$C_{1-10}$-alkyl, or —$SO_2$—($C_{0-10}$-alkylaryl);

$R_6$, $R_7$. $R_8$, and $R_9$ are independently selected from the group of H, —$C_{1-10}$-alkyl, —$C_{1-10}$-alkoxy, aryl-$C_{1-10}$-alkoxy, —OH, —O—$C_{1-10}$-alkyl, —$(CH_2)_{0-6}$—$C_{3-7}$-cycloalkyl, —O—$(CH_2)_{0-6}$-aryl, phenyl, —$(CH_2)_{1-6}$-het, —O—$(CH_2)_{1-6}$-het, —$OR_{13}$, —C(O)—$R_{13}$, —C(O)—$N(R_{13})(R_{14})$, —$N(R_{13})(R_{14})$, —S—$R_{13}$, —S(O)—$R_{13}$, —$S(O)_2$—$R_{13}$, —$S(O)_2$—$NR_{13}R_{14}$, or —$NR_{13}$—$S(O)_2$—$R_{14}$, wherein each alkyl, cycloalkyl, and aryl is unsubstituted or substituted; and any $R_6$, $R_7$. $R_8$, and $R_9$ optionally together form a ring system;

$R_{13}$ and $R_{14}$ are independently selected from the group of H, $C_{1-10}$-alkyl, —$(CH_2)_{0-6}$—$C_{3-7}$-cycloalkyl, —$(CH_2)_{0-6}$—(CH)$_{0-1}$-(aryl)$_{1-2}$, —C(O)—$C_{1-10}$-alkyl, —C(O)—$(CH_2)_{1-6}$—$C_{3-7}$-cycloalkyl. —C(O)—O—$(CH_2)_{0-6}$-aryl, —C(O)—$(CH_2)_{0-6}$-O-fluorenyl, —C(O)—NH—$(CH_2)_{0-6}$-aryl, —C(O)—$(CH_2)_{0-6}$-aryl, —C(O)—$(CH_2)_{0-6}$-het, —C(S)—$C_{1-10}$-alkyl, —C(S)—$(CH_2)_{1-6}$—$C_{3-7}$-cycloalkyl, —C(S)—O—$(CH_2)_{0-6}$-aryl, —C(S)—$(CH_2)_{0-6}$-O-fluorenyl, —C(S)—NH—$(CH_2)_{0-6}$-aryl, —C(S)—$(CH_2)_{0-6}$-aryl, or —C(S)—$(CH_2)_{1-6}$-het, wherein each alkyl, cycloalkyl, and aryl is unsubstituted or substituted; or any $R_{13}$ and $R_{14}$ together with a nitrogen atom form het; and wherein alkyl substituents of $R_{13}$ and $R_{14}$ are unsubstituted or substituted and when substituted, are substituted by one or more substituents selected from $C_{1-10}$-alkyl, halogen, OH, —O—$C_{1-6}$-alkyl, —S—$C_{1-6}$-alkyl, and —$CF_3$; and substituted phenyl or aryl of $R_{13}$ and $R_{14}$ are substituted by one or more substituents selected from halogen, hydroxyl. $C_{1-4}$-alkyl, $C_{1-4}$-alkoxy, nitro, —CN, —O—C(O)—$C_{1-4}$-alkyl, and —C(O)—O—$C_{1-4}$-aryl; or a pharmaceutically acceptable salt or hydrate thereof.

In any aspect or embodiment described herein, the AVPI tetrapeptide fragment has a chemical structure represented by a member selected from the group of:

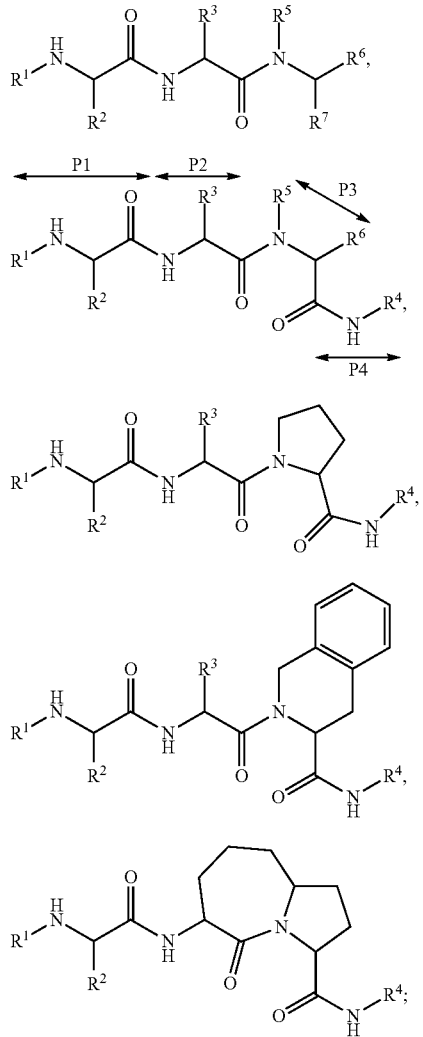

wherein:
- $R^1$ is selected from the group of H and alkyl;
- $R^2$ is selected from the group of H and alkyl;
- $R^3$ is selected from the group of H, alkyl, cycloalkyl and heterocycloalkyl;
- $R^4$ is selected from alkyl, cycloalkyl, heterocycloalkyl, cycloalkylalkyl, heterocycloalkylalkyl, aryl, arylalkyl, heteroaryl, heteroarylalkyl, further optionally substituted with 1-3 substituents selected from halogen, alkyl, haloalkyl, hydroxyl, alkoxy, cyano, (hetero)cycloalkyl or (hetero)aryl, or —C(O)NH—$R^4$, where $R^4$ is selected from alkyl, cycloalkyl, heterocycloalkyl, cycloalkylalkyl, heterocycloalkylalkyl, aryl, arylalkyl, heteroaryl, heteroarylalkyl, further optionally substituted with 1-3 substituents as described above;
- $R^5$ and $R^6$ are independently selected from the group of H, alkyl, cycloalkyl, heterocycloalkyl, aryl, heteroaryl or fused rings; and
- $R^7$ is selected from the group of cycloalkyl, cycloalkylalkyl, heterocycloalkyl, heterocycloalkylalkyl, aryl, arylalkyl, heteroaryl or heteroarylalkyl, each one further optionally substituted with 1-3 substituents selected from halogen, alkyl, haloalkyl, hydroxyl, alkoxy, cyano, (hetero)cycloalkyl or (hetero)aryl, or —C(O)NH—$R^4$, where $R^4$ is selected from alkyl, cycloalkyl, heterocycloalkyl, cycloalkylalkyl, heterocycloalkylalkyl, aryl, arylalkyl, heteroaryl, heteroarylalkyl, further optionally substituted with 1-3 substituents as described above.

In any aspect or embodiment described herein, the $R^5$ and $R^6$ taken together form a pyrrolidine or a piperidine ring optionally fused to 1-2 cycloalkyl, heterocycloalkyl, aryl or heteroaryl rings, each of which can then be further fused to another cycloalkyl, heterocycloalkyl, aryl or heteroaryl ring.

In any aspect or embodiment described herein, the $R^3$ and $R^5$ taken together form a 5-8-membered ring further optionally fused to 1-2 cycloalkyl, heterocycloalkyl, aryl or heteroaryl rings.

In any aspect or embodiment described herein, the ILM is selected from the group consisting of:

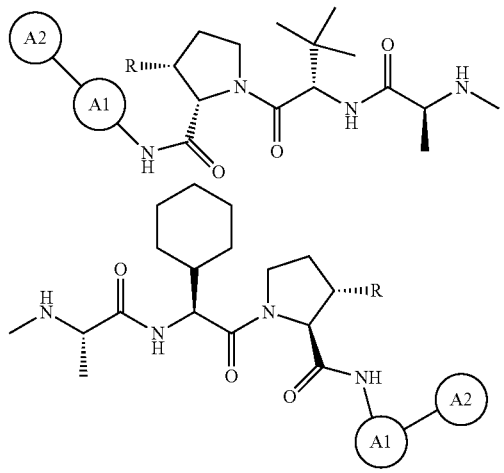

wherein:
- each of A1 and A2 is independently selected from optionally substituted monocyclic, fused rings, aryls and hetoroaryls; and
- R is selected from H or Me.

In any aspect or embodiment described herein, the ILM is selected from the group consisting of:

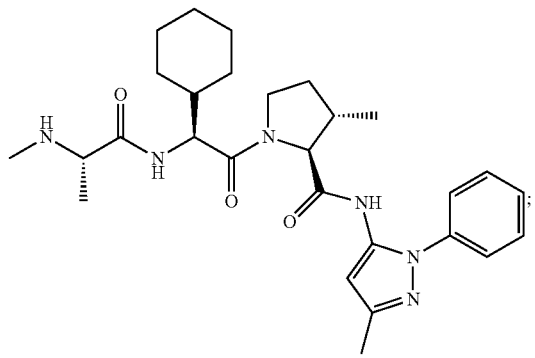

697
-continued
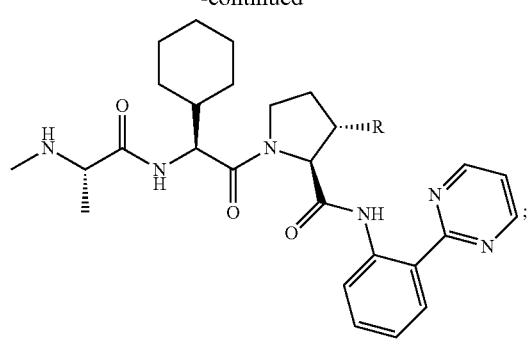
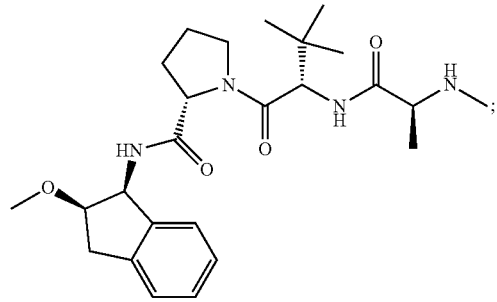
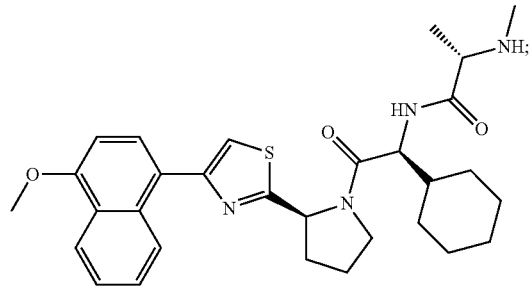
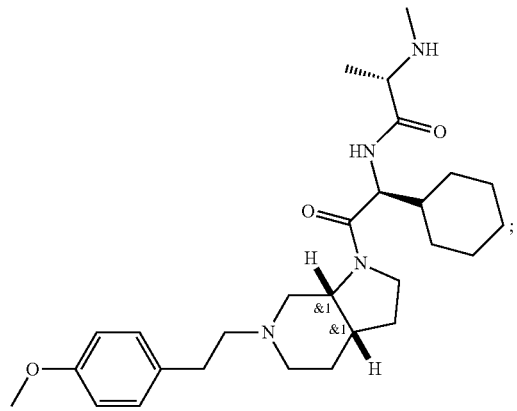
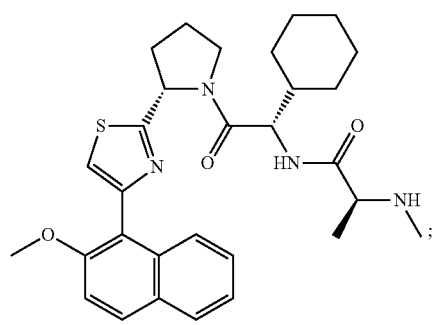
698
-continued
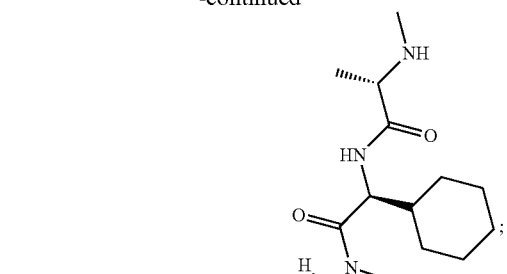
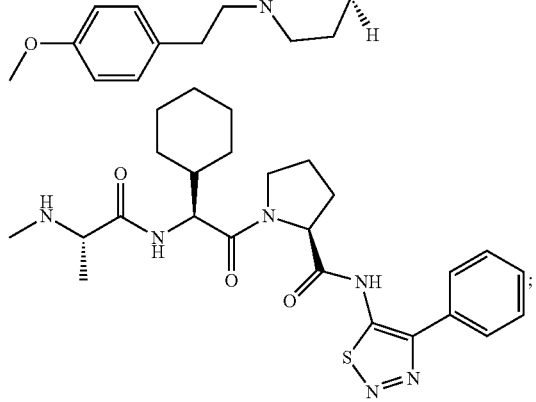
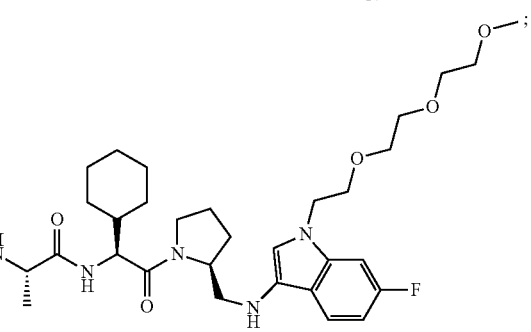
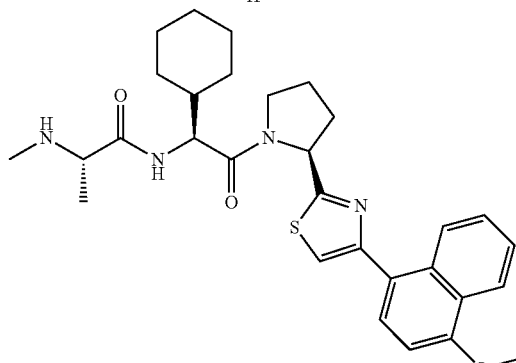
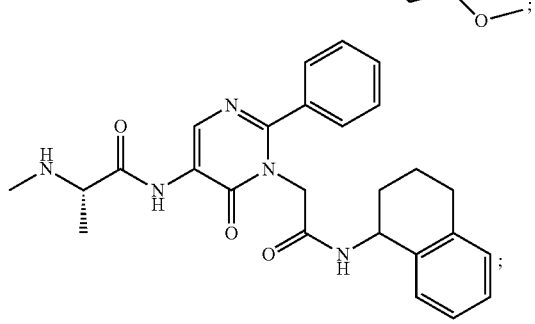

699
-continued
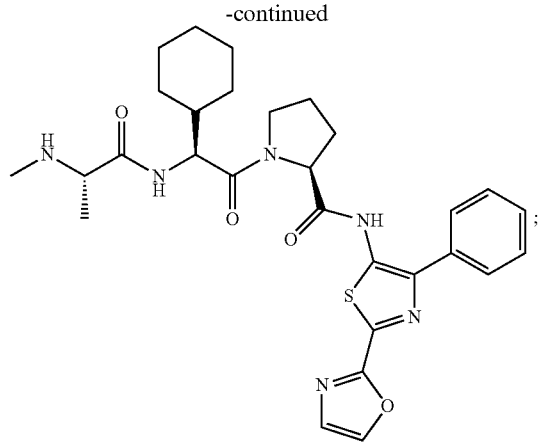
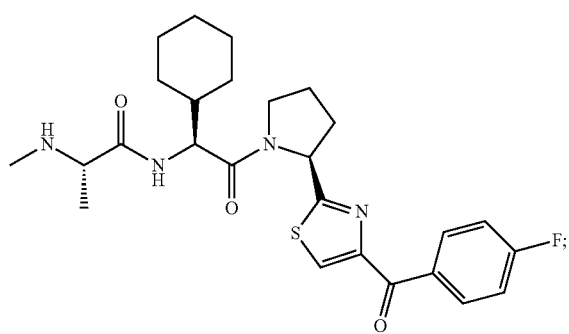
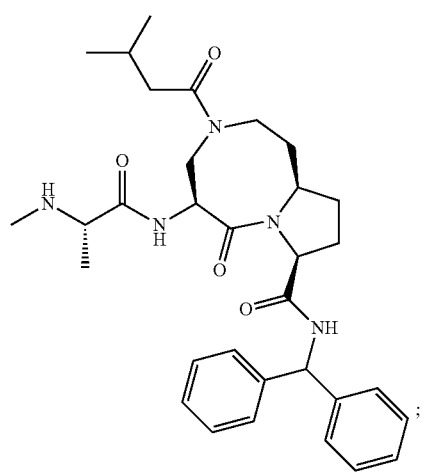
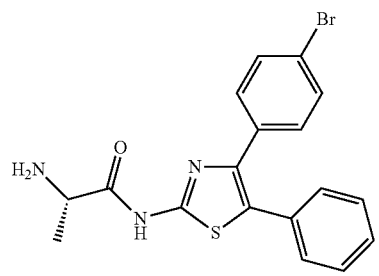
700
-continued
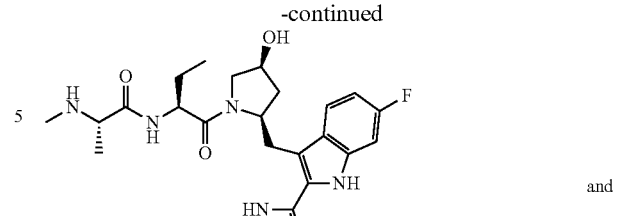
and
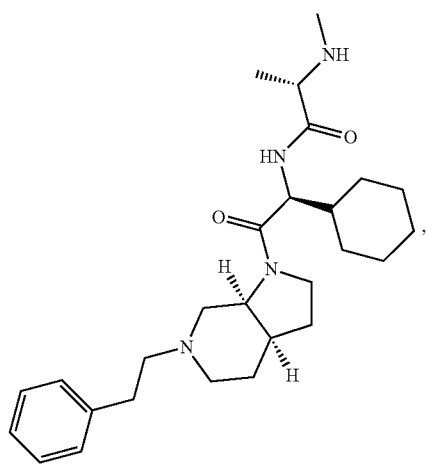
wherein "& 1" means ring junction stereochemistry is cis-, but configuration of either stereocenter is not fixed in the absolute sense.
In any aspect or embodiment described herein, the IAP E3 ubiquitin ligase binding moiety is selected from the group consisting of:
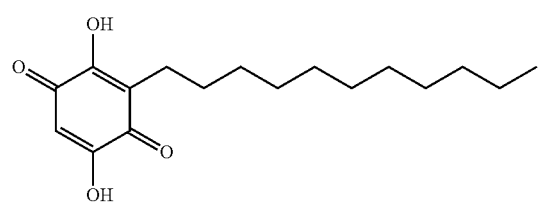

701
702
-continued
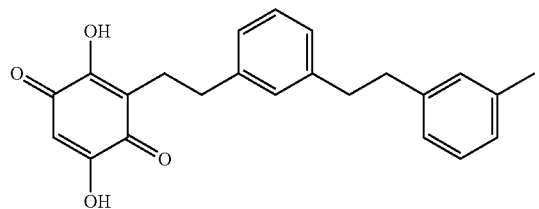
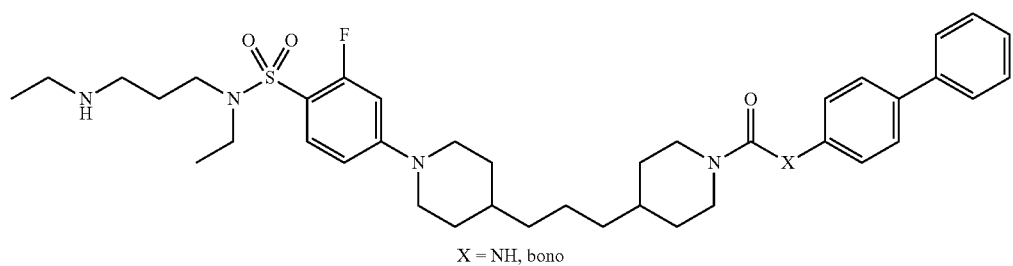
X = NH, bono
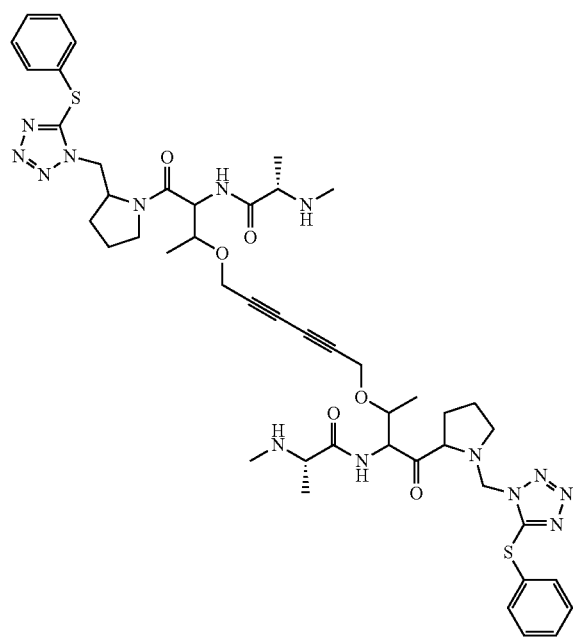

703
-continued
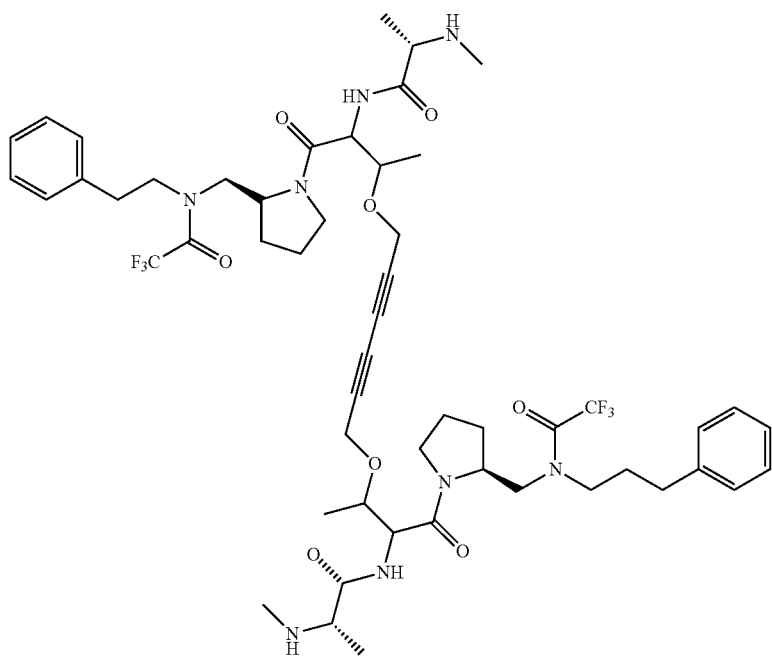
704
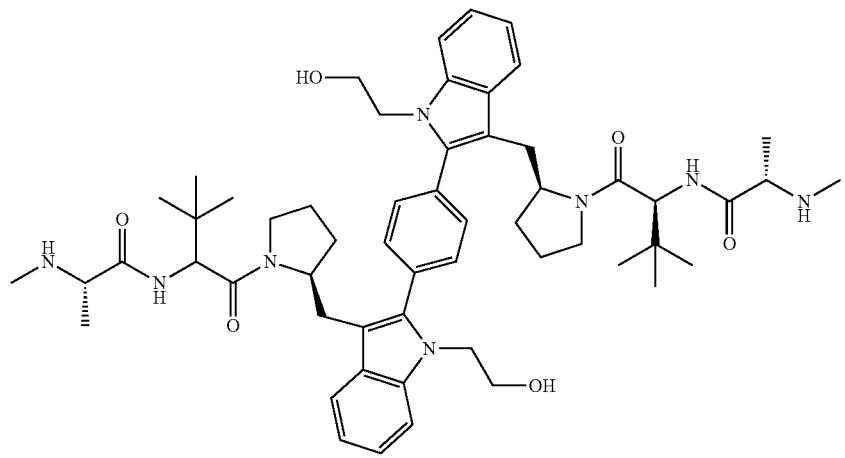
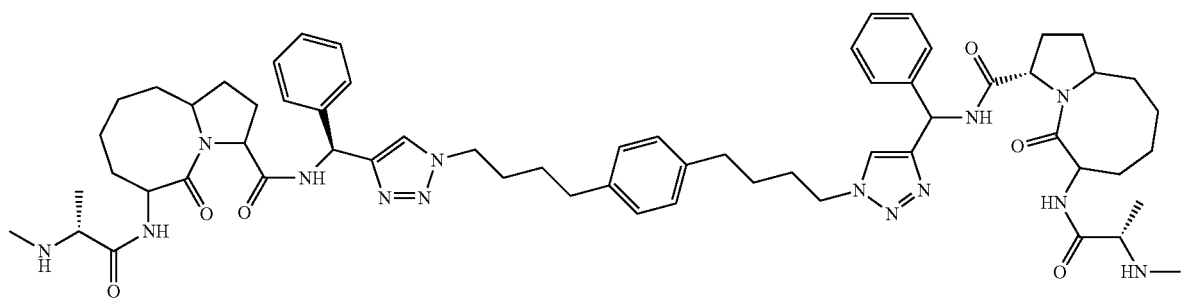

-continued

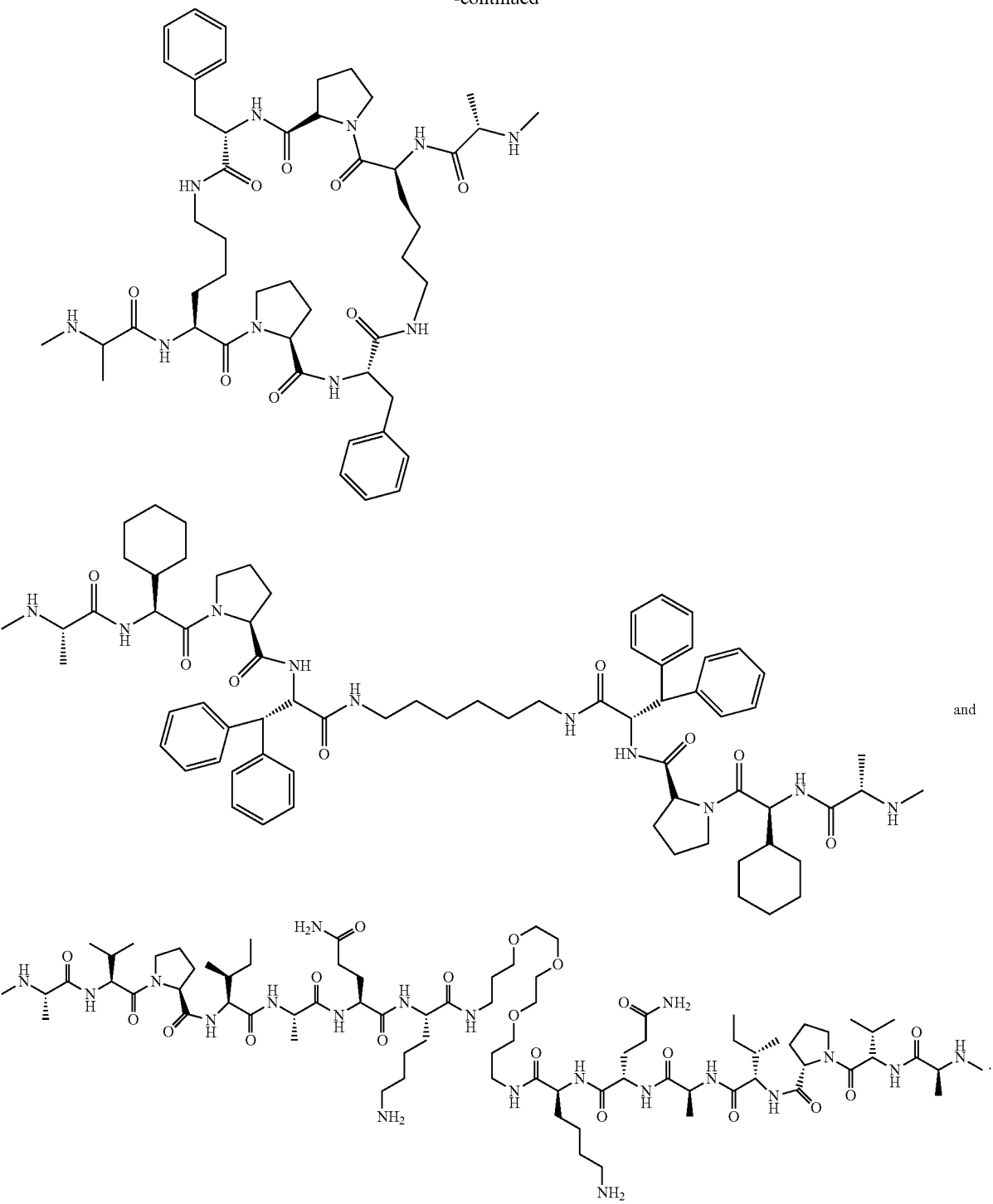

In any aspect or embodiment described herein, the compound further comprises an independently selected second ILM attached to the ILM by way of at least one additional linker group, wherein the second ILM is an AVPI tetrapeptide fragment or an unnatural mimetic thereof and the at least one additional linker chemically links amino acids or unnatural mimetics thereof selected from the group consisting of valine, proline and isoleucine, or unnatural mimetics thereof and wherein at least one of the ILM and the second ILM is chemically linked to the linker group chemically linked to the PTM.

In any aspect or embodiment described herein, the ILM, at least one additional independently selected linker group L, and the second ILM has a structure selected from the group consisting of:

707                                    708
(A)
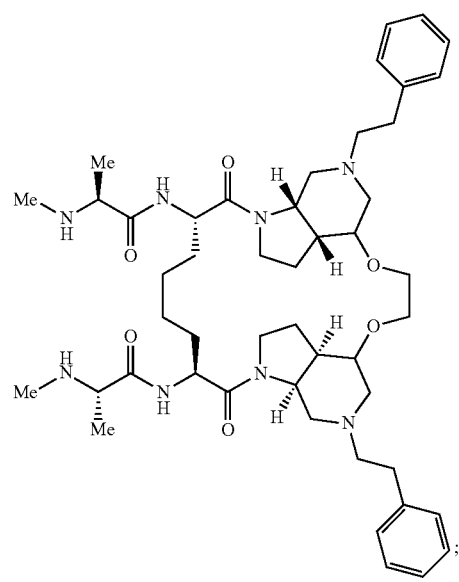
;
(B)
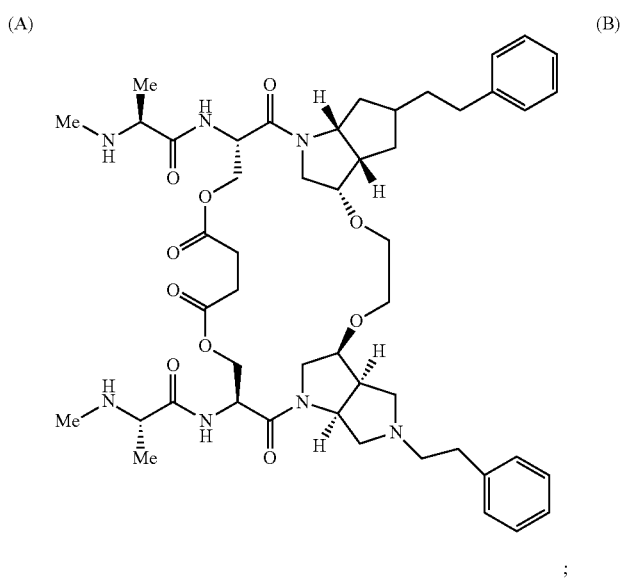
;
(C)
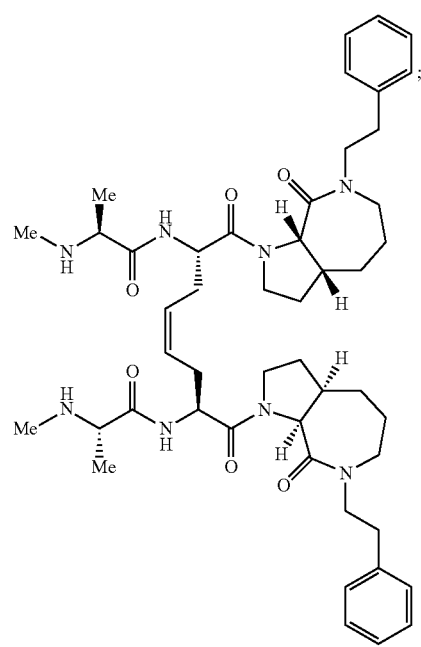
;
(D)
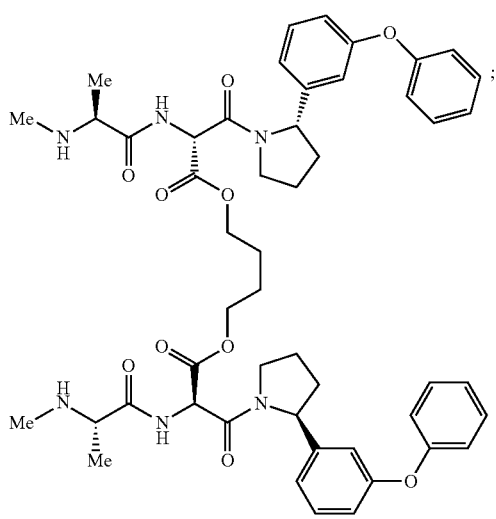
;

-continued
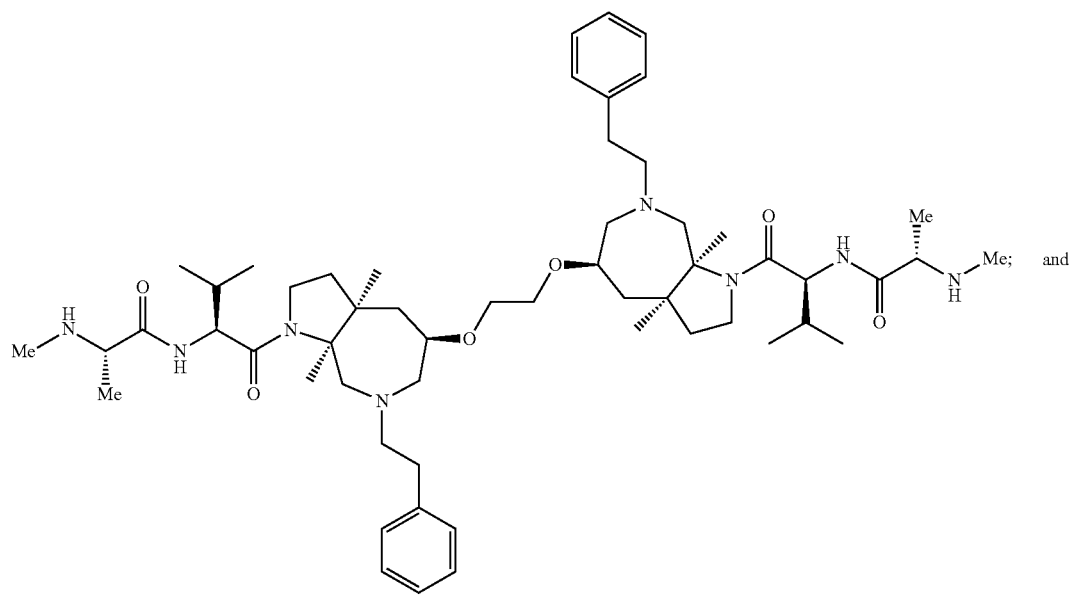
(E)
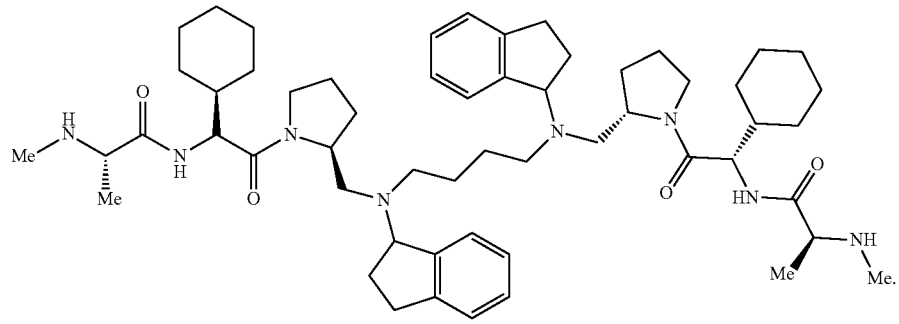
(F)
In any aspect or embodiment described herein, the ULM is selected from the group consisting of:
-continued
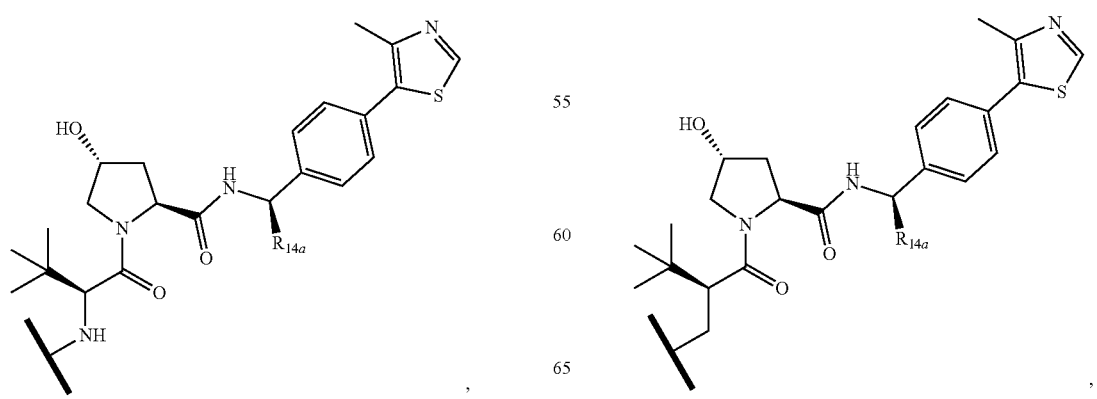

US 11,857,519 B2
| 711 -continued | 712 -continued |
|---|---|
| 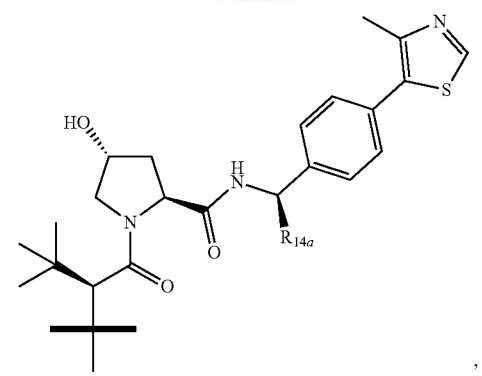 | 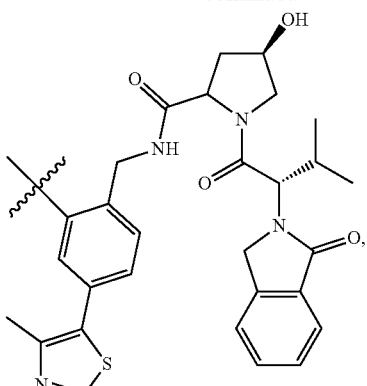 |
| 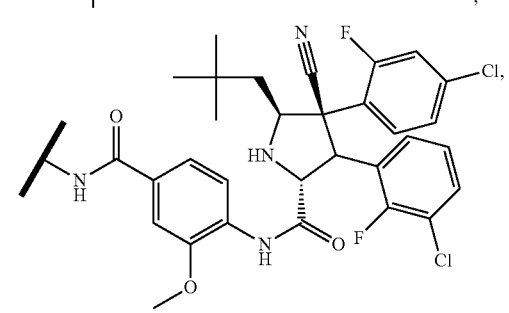 | 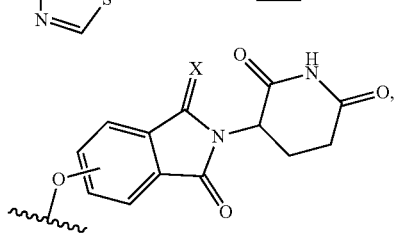 |
| 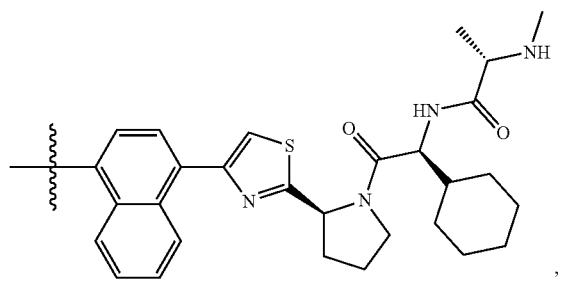 | 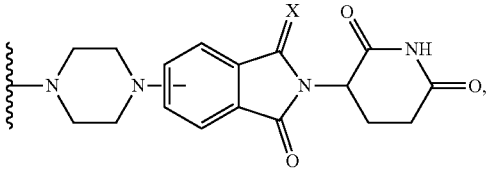 |
| 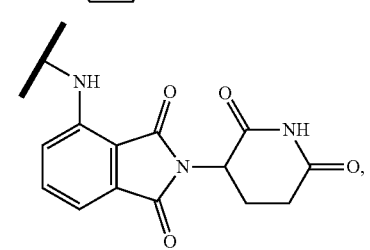 | 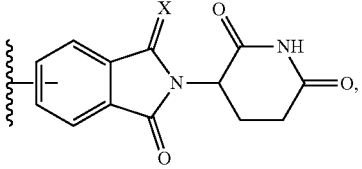 |
| 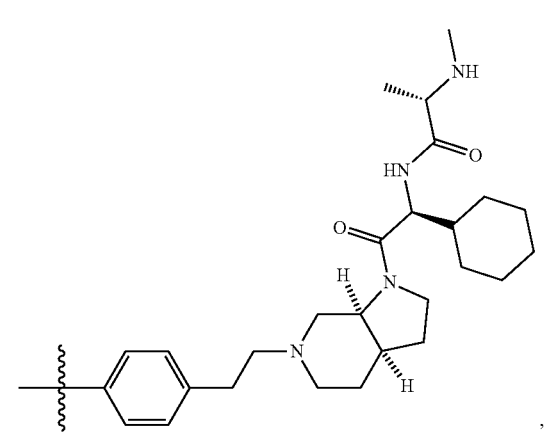 | 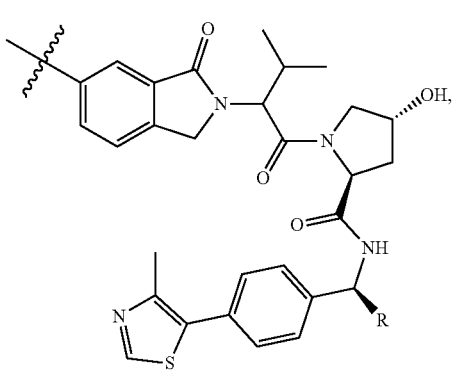 |

713
-continued
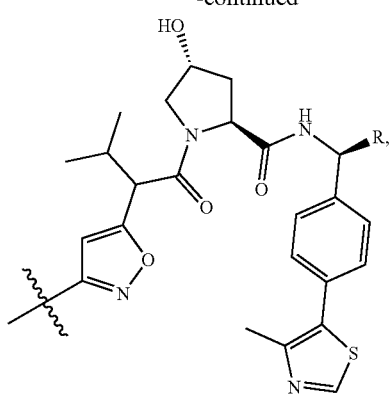
or a combination thereof,
wherein:
R$_{14a}$ is a methyl, ethyl, or hydroxymethy; and
X is O or H$_2$.
In any aspect or embodiment described herein, the PTM is selected from the group consisting of:
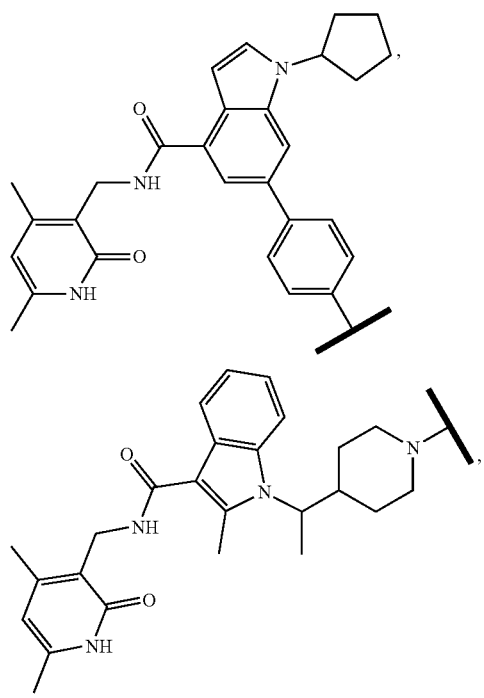
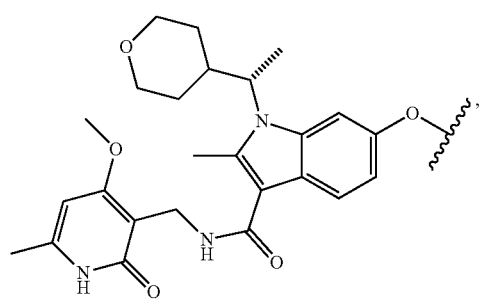
714
-continued
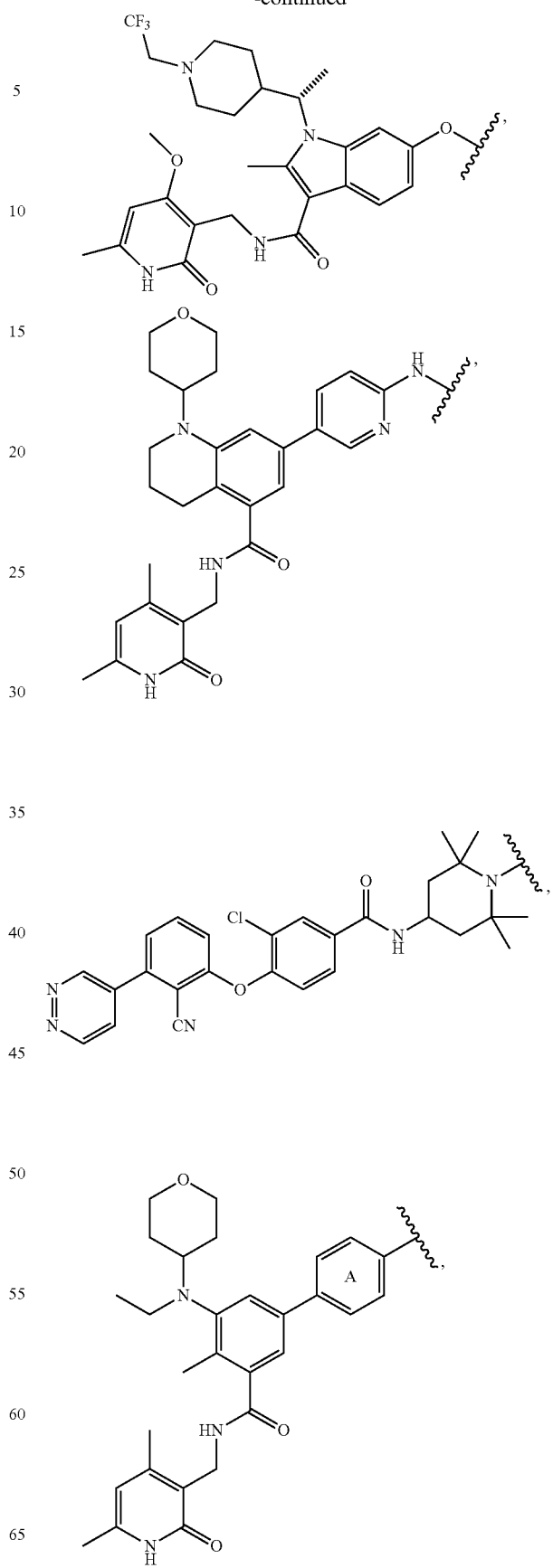

715
-continued
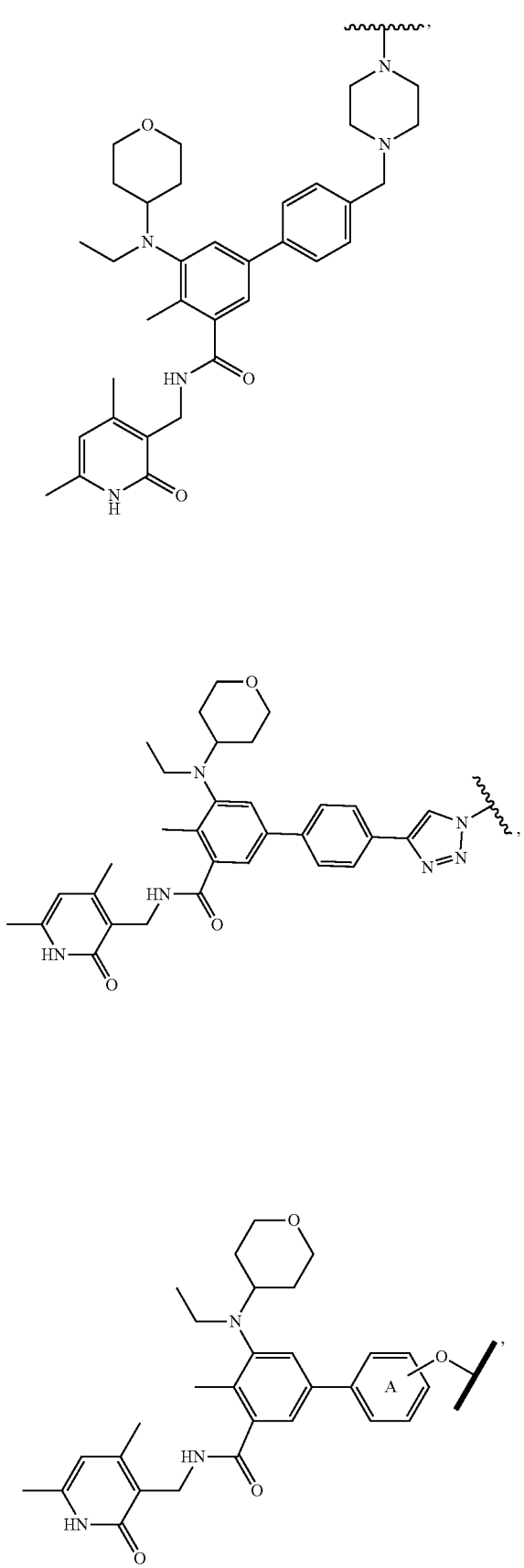
716
-continued
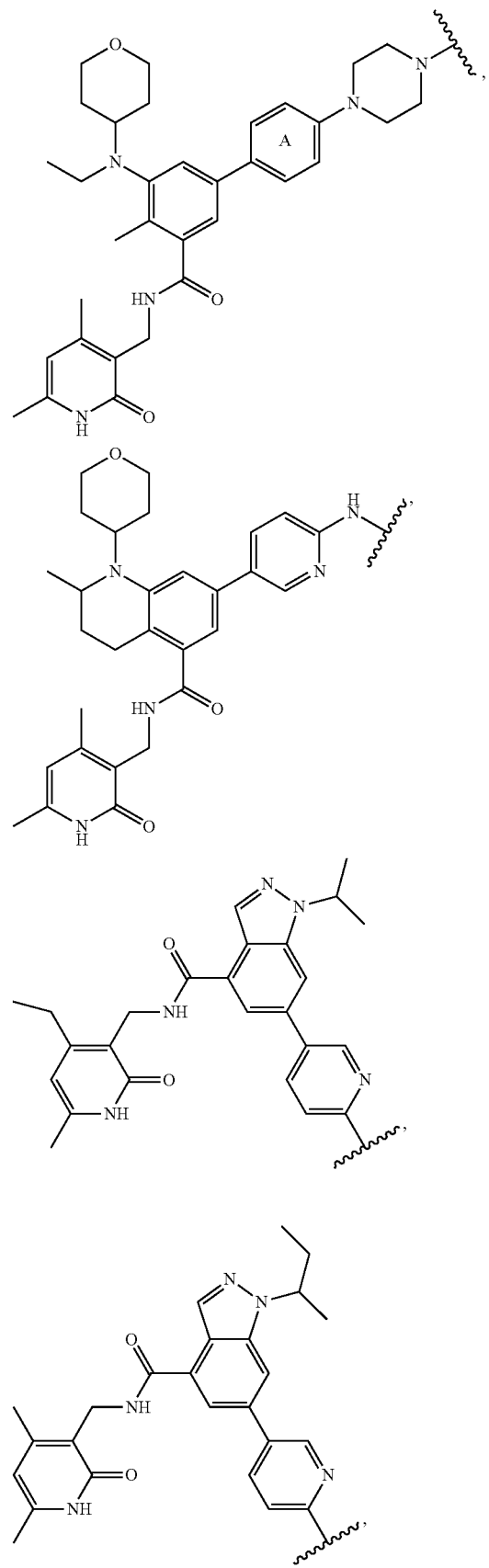

or a combination thereof, wherein

may be N-substituted.

In any aspect or embodiment described herein, the linker (L) comprises a chemical structural unit represented by the formula:

$-(A^L)_q-$, wherein:
(A$^L$)q is a group which is connected to at least one of a ULM moiety, a PTM moiety, or a combination thereof;
q is an integer greater than or equal to 1;
each A$^L$ is independently selected from the group consisting of, a bond, CR$^{L1}$R$^{L2}$, S, SO, SO$_2$, NR$^{L3}$, SO$_2$NR$^{L3}$, SONR$^{L3}$, CONR$^{L3}$, NR$^{L3}$CONR$^{L4}$, NR$^{L3}$SO$_2$NR$^{L4}$, CO, CR$^{L1}$=CR$^{L2}$, C≡C, SiR$^{L1}$R$^{L2}$, P(O)R$^{L1}$, P(O)OR$^{L1}$, NR$^{L3}$C(=NCN)NR$^{L4}$, NR$^{L3}$C(=NCN), NR$^{L3}$C(=CNO$_2$)NR$^{L4}$, C$_{3-11}$cycloalkyl optionally substituted with 0-6 R$^{L1}$ and/or R$^{L2}$ groups, C$_{3-11}$heterocyclyl optionally substituted with 0-6 R$^{L1}$ and/or R$^{L2}$ groups, aryl optionally substituted with 0-6 R$^{L1}$ and/or R$^{L2}$ groups, heteroaryl optionally substituted with 0-6 R$^{L1}$ and/or R$^{L2}$ groups, where R$^{L1}$ or R$^{L2}$, each independently are optionally linked to other groups to form cycloalkyl and/or heterocyclyl moiety, optionally substituted with 0-4 R$^{L5}$ groups; and
R$^{L1}$, R$^{L2}$, R$^{L3}$, R$^{L4}$ and R$^{L5}$ are, each independently, H, halo, C$_{1-8}$alkyl, OC$_{1-8}$alkyl, SC$_{1-8}$alkyl, NHC$_{1-8}$alkyl, N(C$_{1-8}$alkyl)$_2$, C$_{3-11}$cycloalkyl, aryl, heteroaryl, C$_{3-11}$heterocyclyl, OC$_{1-8}$ cycloalkyl, SC$_{1-8}$cycloalkyl, NHC$_{1-8}$cycloalkyl, N(C$_{1-8}$cycloalkyl)$_2$, N(C$_{1-8}$cycloalkyl)(C$_{1-8}$alkyl), OH, NH$_2$, SH, SO$_2$C$_{1-8}$alkyl, P(O)(OC$_{1-8}$alkyl)(C$_{1-8}$alkyl), P(O)(OC$_{1-8}$alkyl)$_2$, CC—C$_{1-8}$alkyl, CCH, CH=CH(C$_{1-8}$alkyl), C(C$_{1-8}$alkyl)=CH(C$_{1-8}$alkyl), C(C$_{1-8}$alkyl)=C(C$_{1-8}$alkyl)2, Si(OH)$_3$, Si(C$_{1-8}$alkyl)$_3$, Si(OH)(C$_{1-8}$alkyl)$_2$, COC$_{1-8}$alkyl, CO$_2$H, halogen, CN, CF$_3$, CHF$_2$, CH$_2$F, NO$_2$, SF$_5$, SO$_2$NHC$_{1-8}$alkyl, SO$_2$N(C$_{1-8}$alkyl)$_2$, SONHC$_{1-8}$alkyl, SON(C$_{1-8}$alkyl)$_2$, CONHC$_{1-8}$alkyl, CON(C$_{1-8}$alkyl)$_2$, N(C$_{1-8}$alkyl)CONH(C$_{1-8}$alkyl), N(C$_1$-8alkyl)CON(C$_{1-8}$alkyl)$_2$, NHCONH(C$_{1-8}$alkyl), NHCON(C$_{1-8}$alkyl)$_2$, NHCONH$_2$, N(C$_{1-8}$alkyl)SO$_2$NH(C$_{1-8}$alkyl), N(C$_{1-8}$alkyl) SO$_2$N(C$_{1-8}$alkyl)$_2$, NH SO$_2$NH(C$_{1-8}$alkyl), NH SO$_2$N(C$_{1-8}$alkyl)$_2$, NH SO$_2$NH$_2$.

In any aspect or embodiment describe herein, the linker (L) is selected from

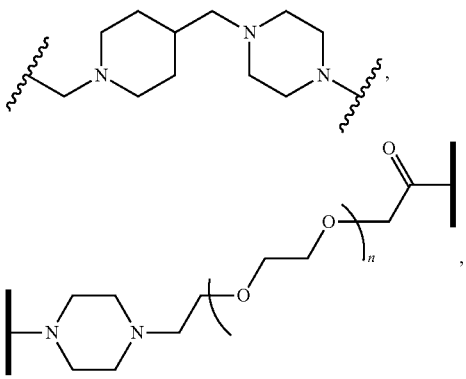

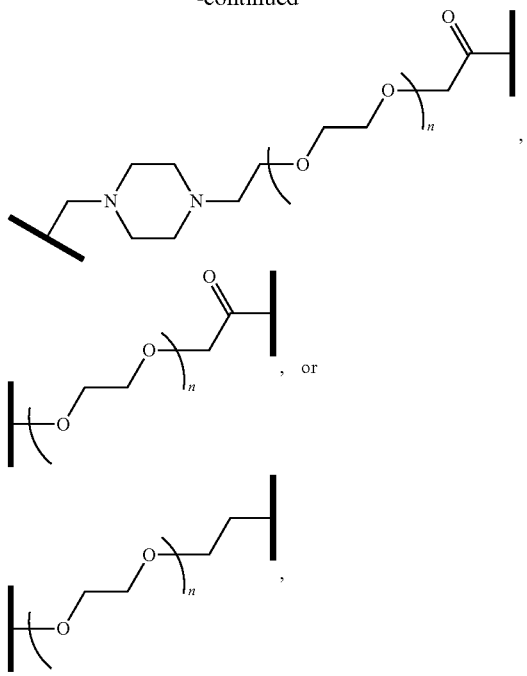

wherein n is 0, 1, 2, 3, 4, 5, 6, 7, 8, 9, or 10.

In any aspect or embodiment described herein, the linker (L) comprises a group represented by a general structure selected from the group consisting of: —N(R)—(CH$_2$)$_m$—O(CH$_2$)$_n$—O(CH$_2$)$_o$—O(CH$_2$)$_p$—O(CH$_2$)$_q$—O(CH$_2$)$_r$—OCH$_2$—, —O—(CH$_2$)$_m$—O(CH$_2$)$_n$—O(CH$_2$)$_o$O(CH$_2$)$_p$—O(CH$_2$)$_q$—O(CH$_2$)$_r$—OCH$_2$—, —O—(CH$_2$)$_m$—O(CH$_2$)$_n$—O(CH$_2$)$_o$—O(CH$_2$)$_p$—O(CH$_2$)$_q$—O(CH$_2$)$_r$—O—; —N(R)—(CH$_2$)$_m$—O(CH$_2$)$_n$—O(CH$_2$)$_o$—O(CH$_2$)$_p$—O(CH$_2$)$_q$—O(CH$_2$)$_r$—O—; —(CH$_2$)$_m$—O(CH$_2$)$_n$—O(CH$_2$)$_o$—O(CH$_2$)$_p$—O(CH$_2$)$_q$—O(CH$_2$)$_r$—O—; —(CH$_2$)$_m$—O(CH$_2$)$_n$—O(CH$_2$)$_o$—O(CH$_2$)$_p$—O(CH$_2$)$_q$—O(CH$_2$)$_r$—OCH$_2$—;

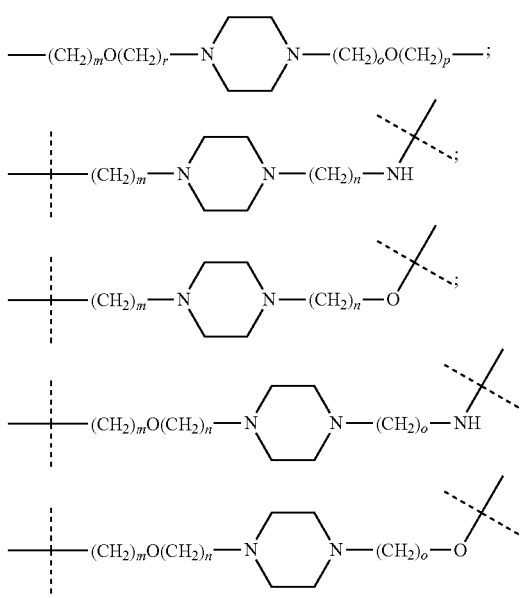

719
-continued
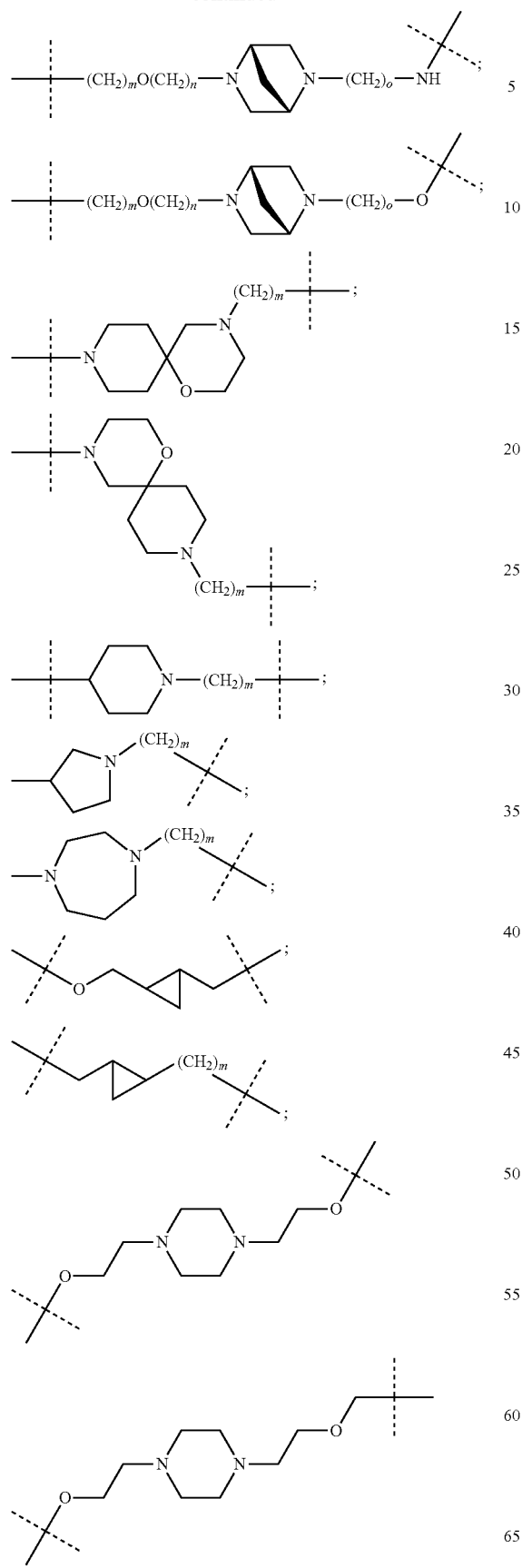
720
-continued
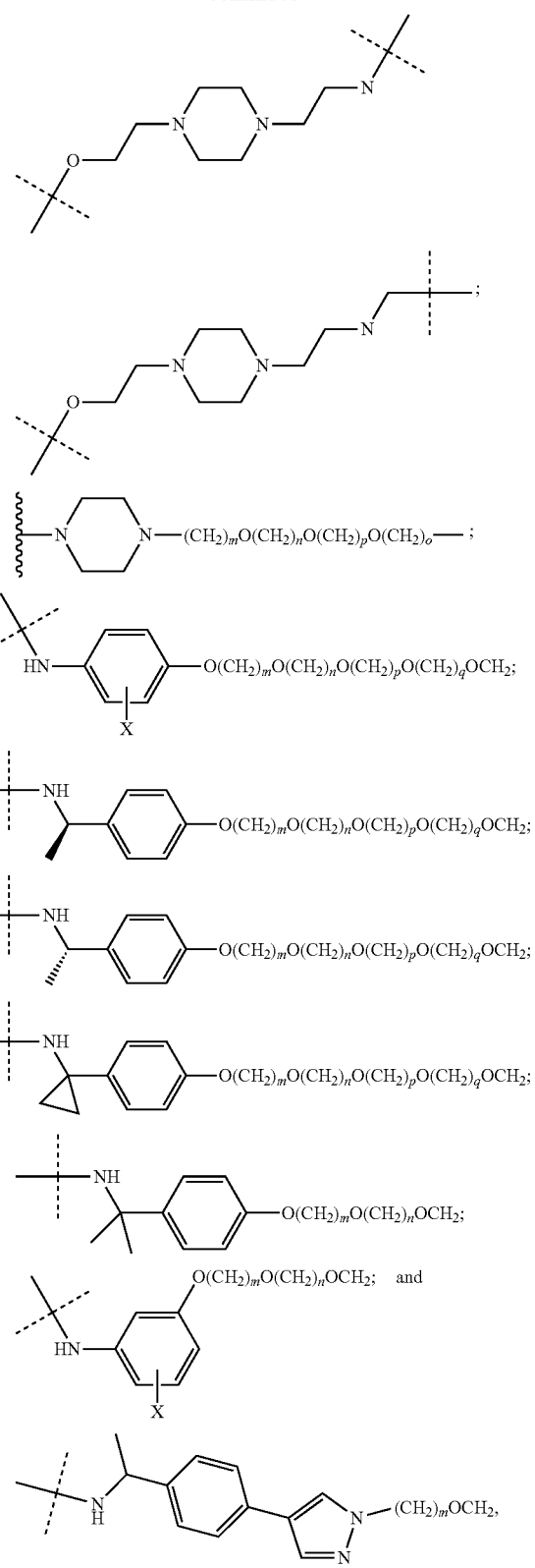
wherein m, n, o, p, q, and r, are independently 0, 1, 2, 3, 4, 5, 6, with the proviso that when the number is zero, there is no N—O or O—O bond, R is selected from the group H, methyl and ethyl, and X is selected from the group H and F;

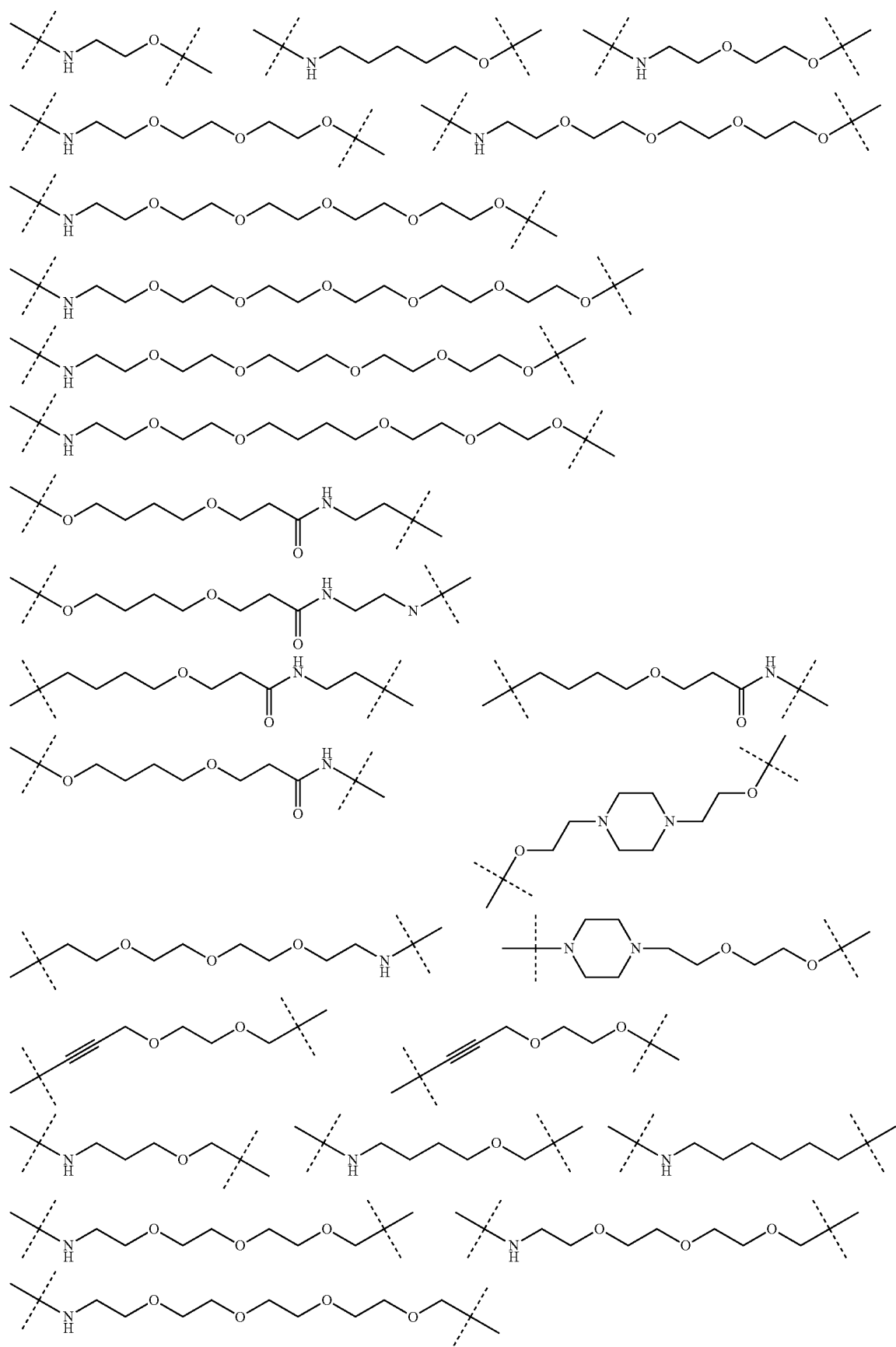

-continued
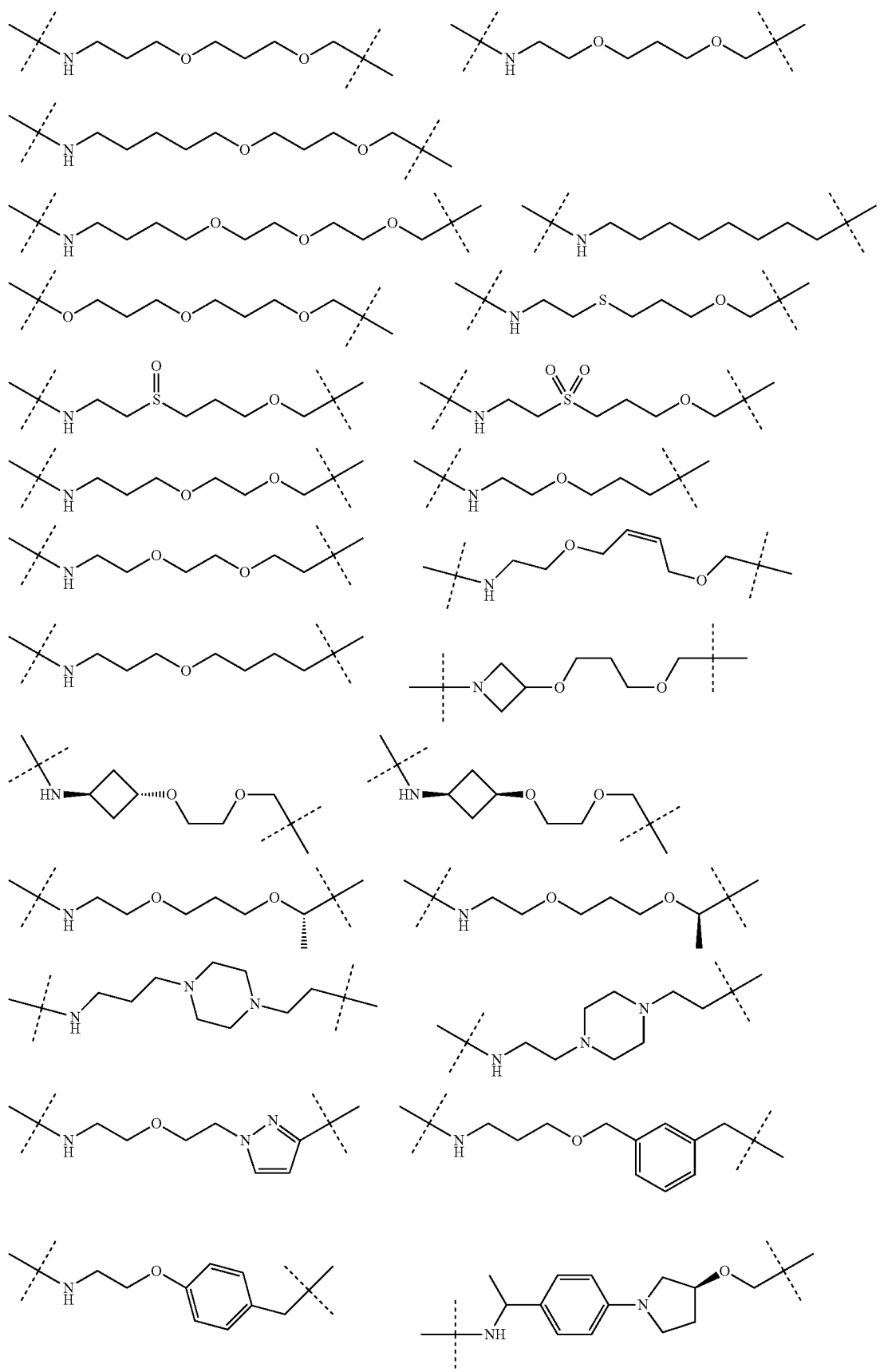

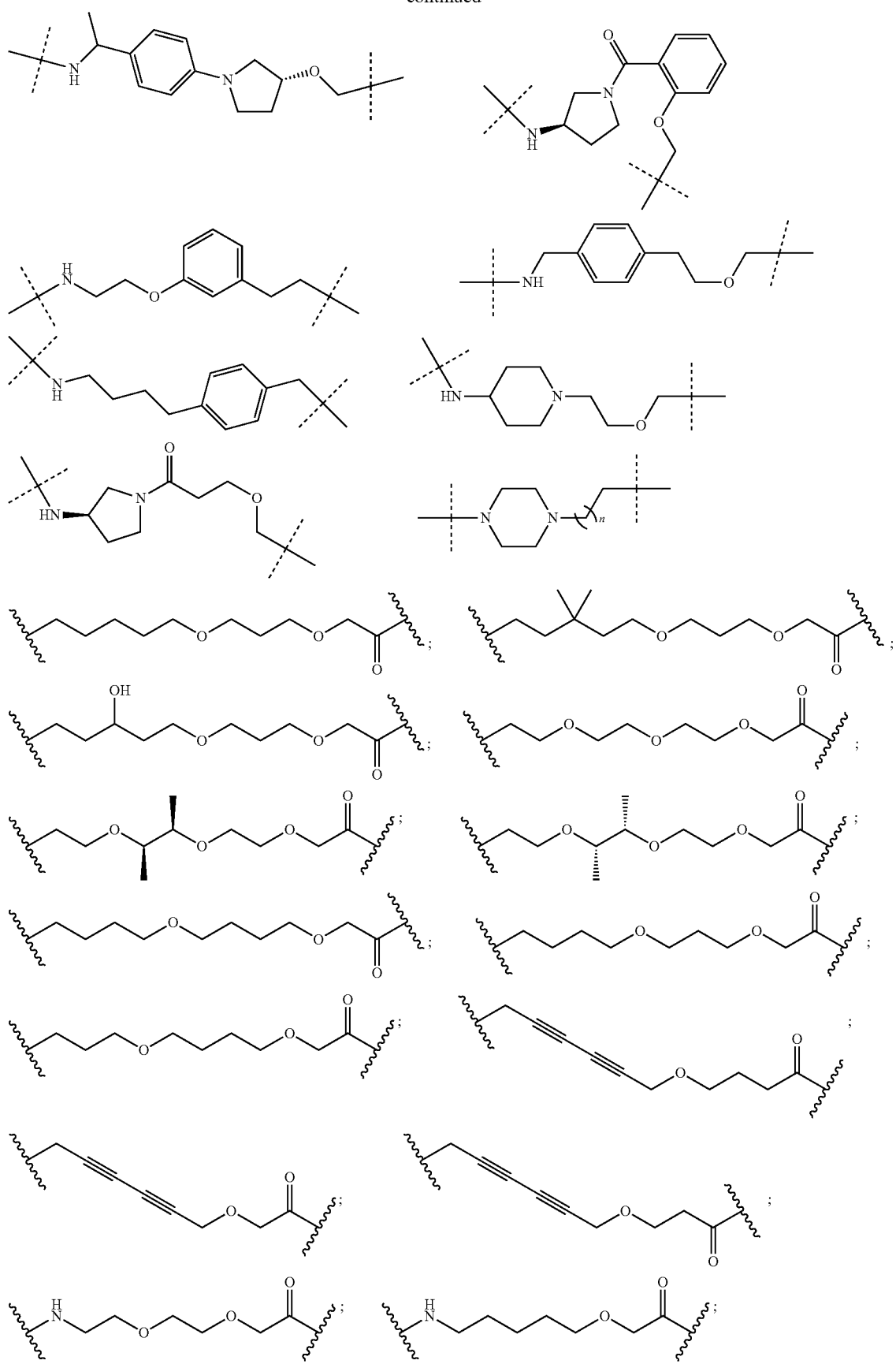

-continued
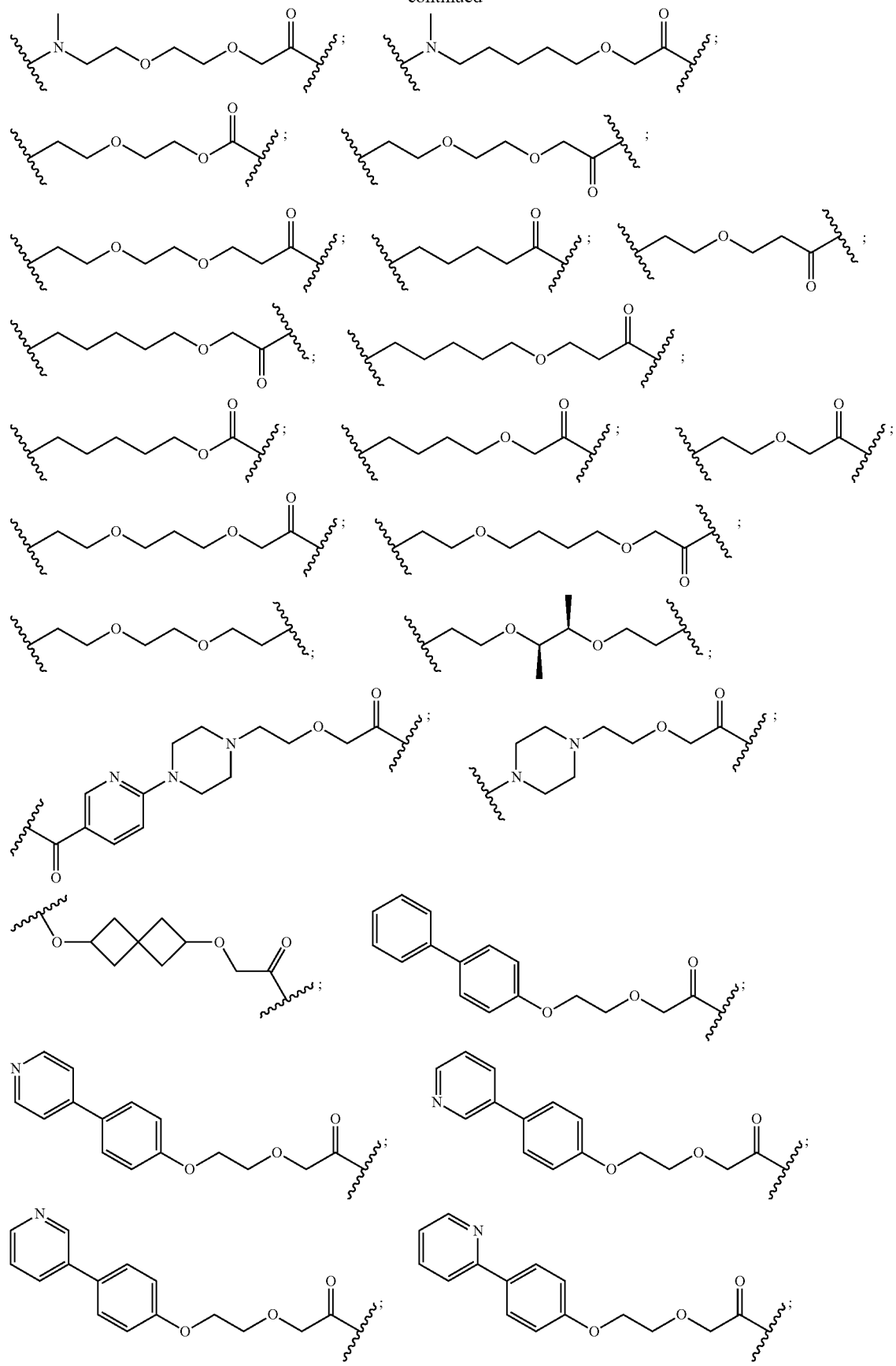

729 730
-continued
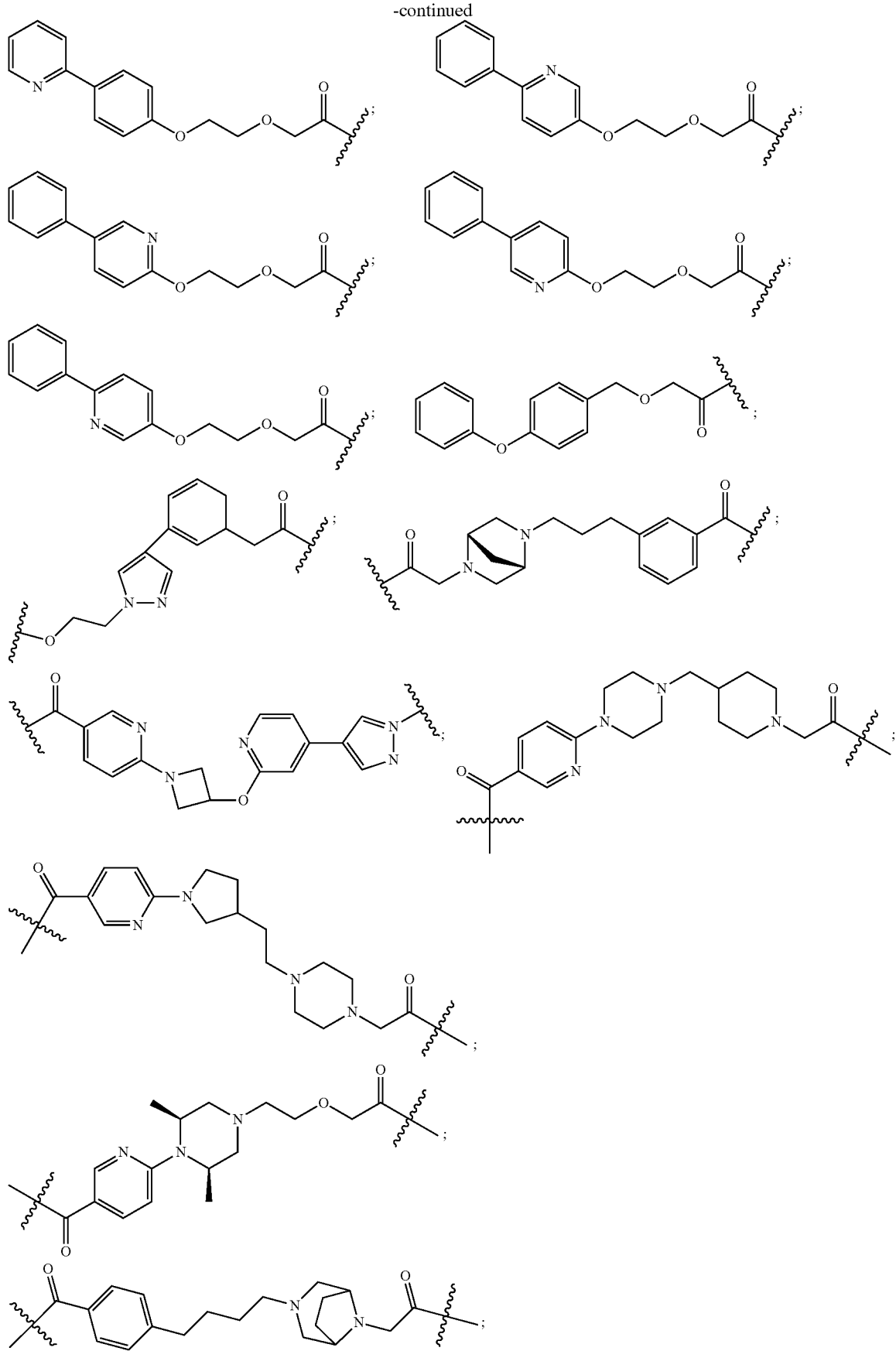

-continued
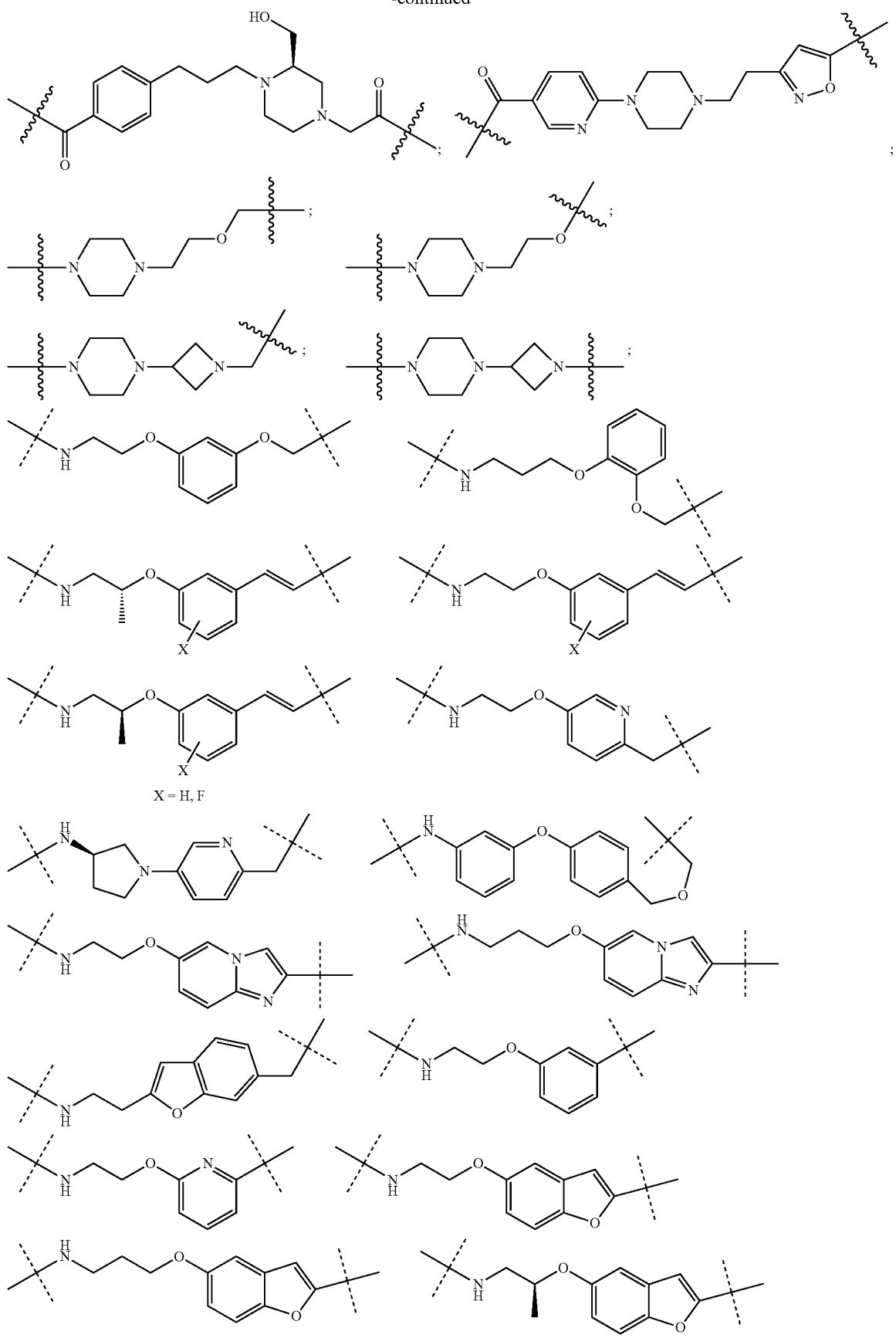

733
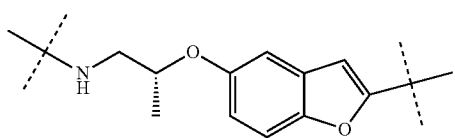
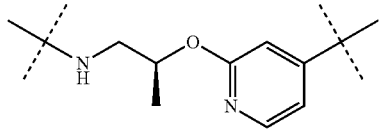
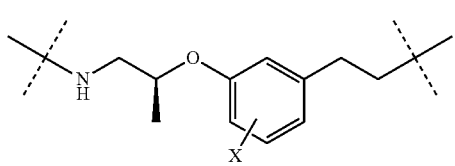
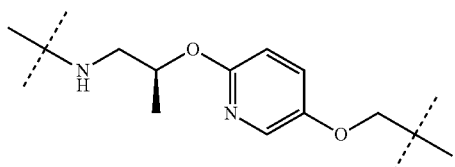
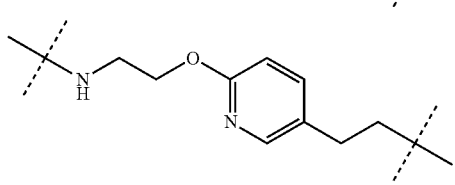
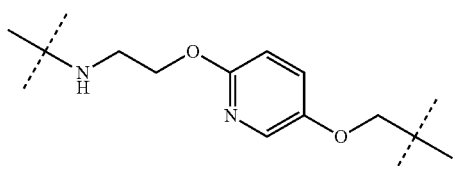
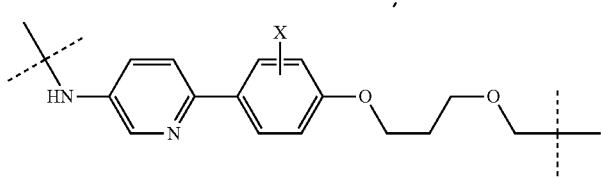
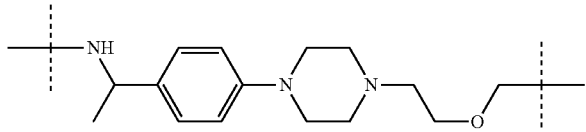
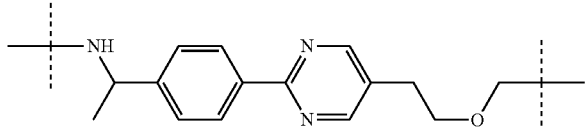
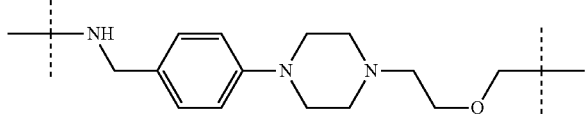
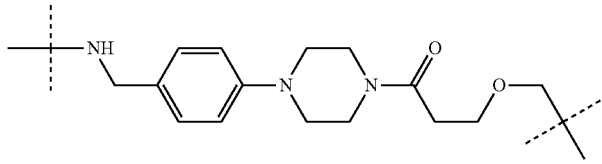
734
-continued
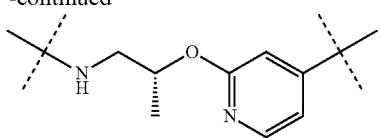
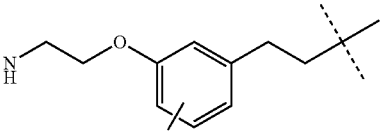
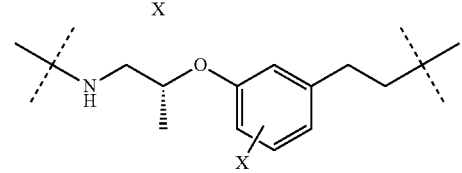
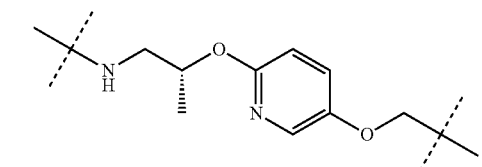
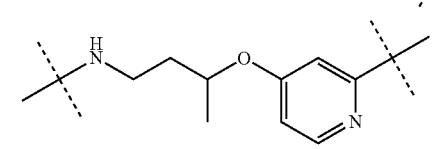
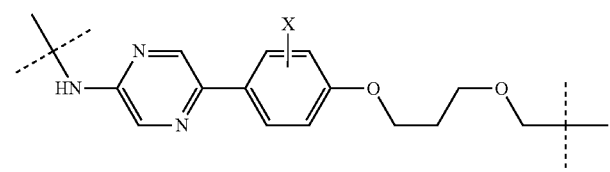

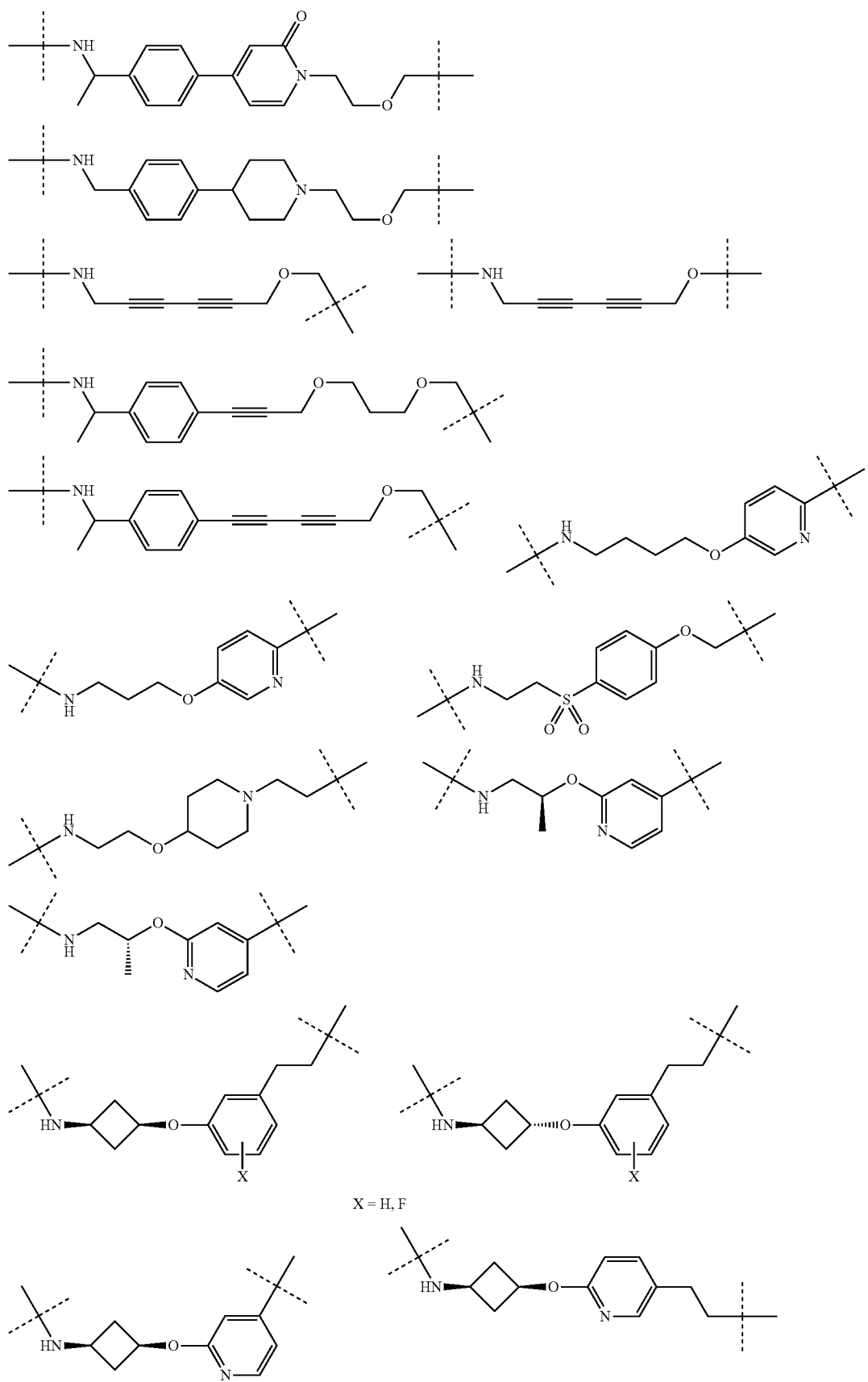

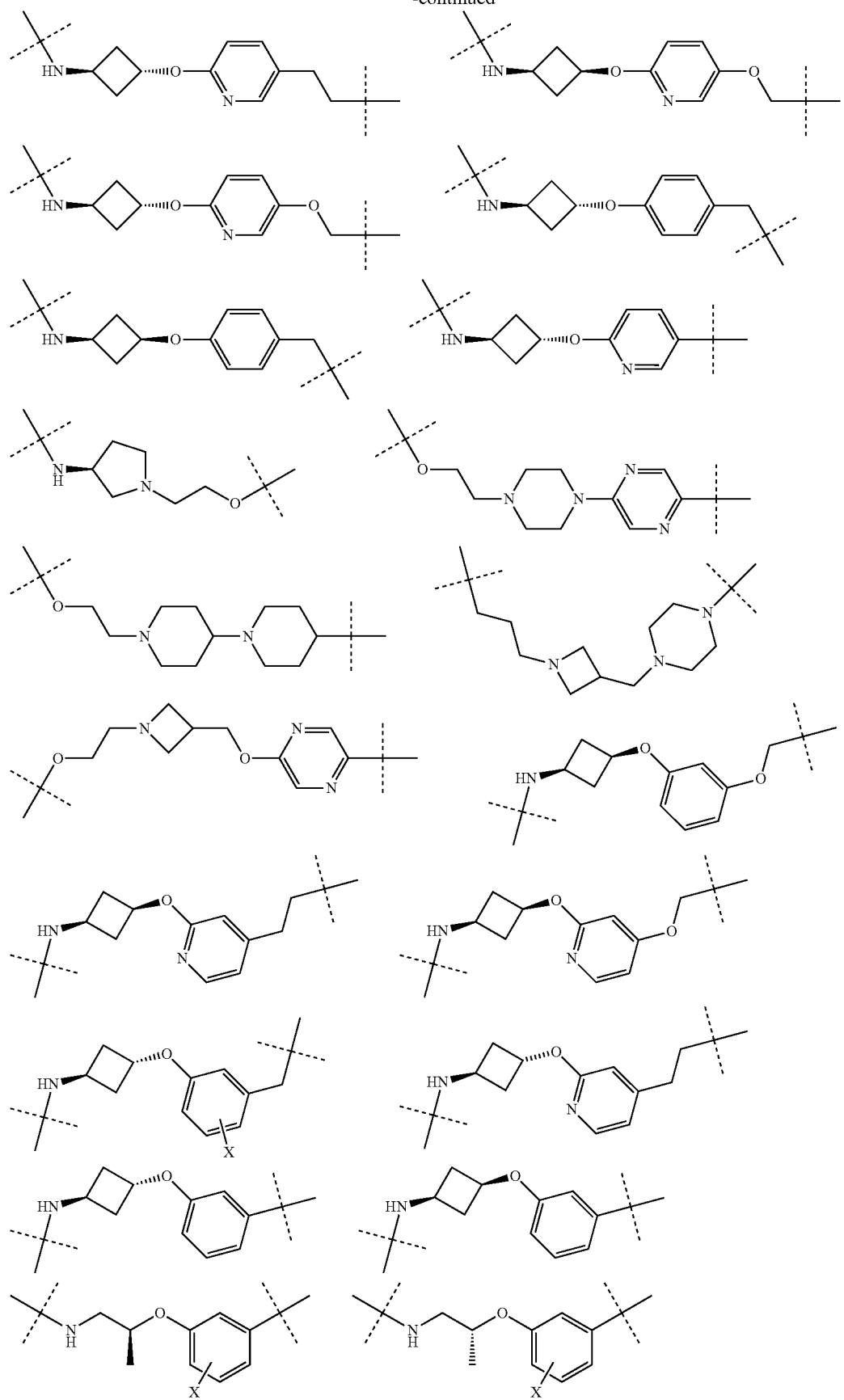

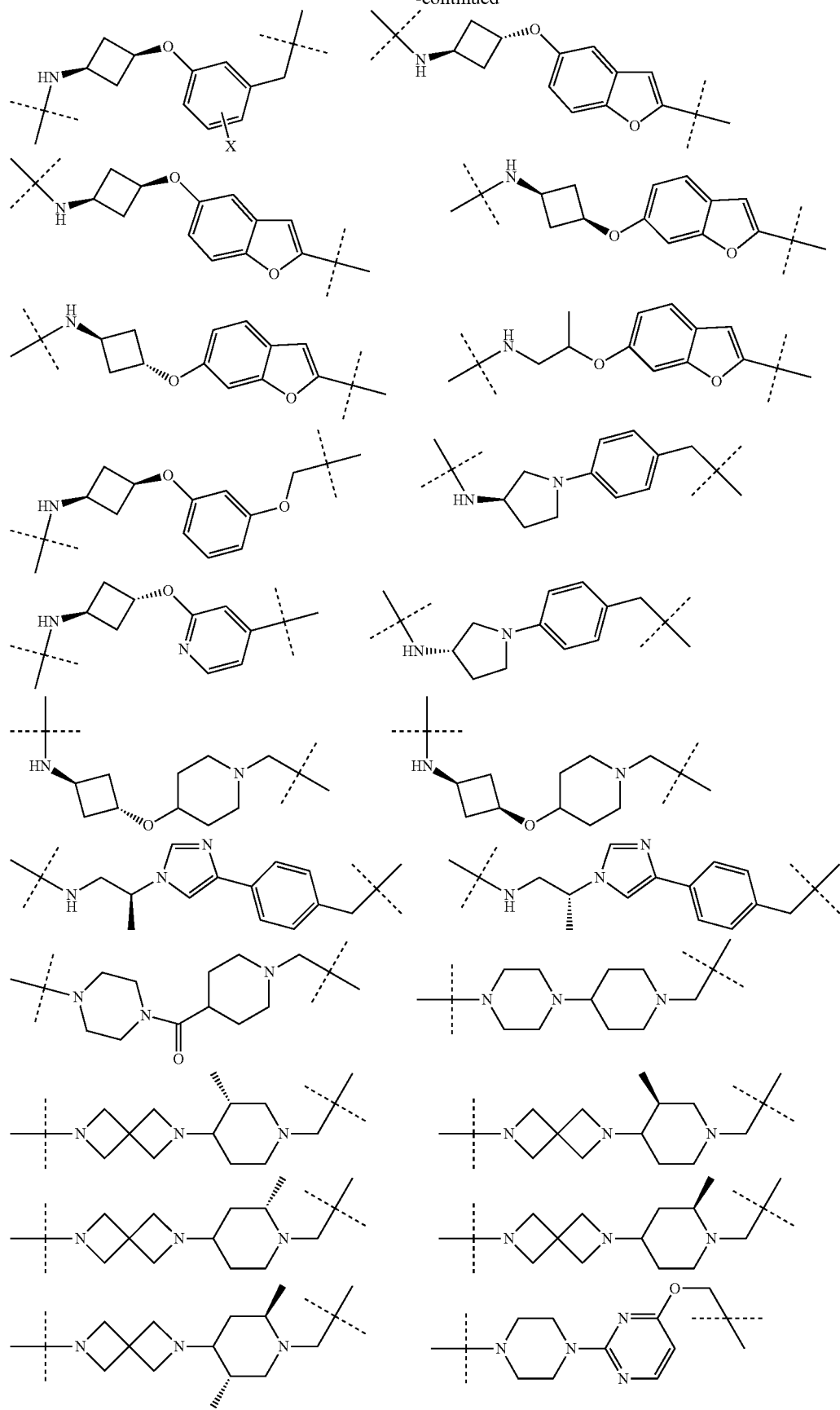

741
742
-continued
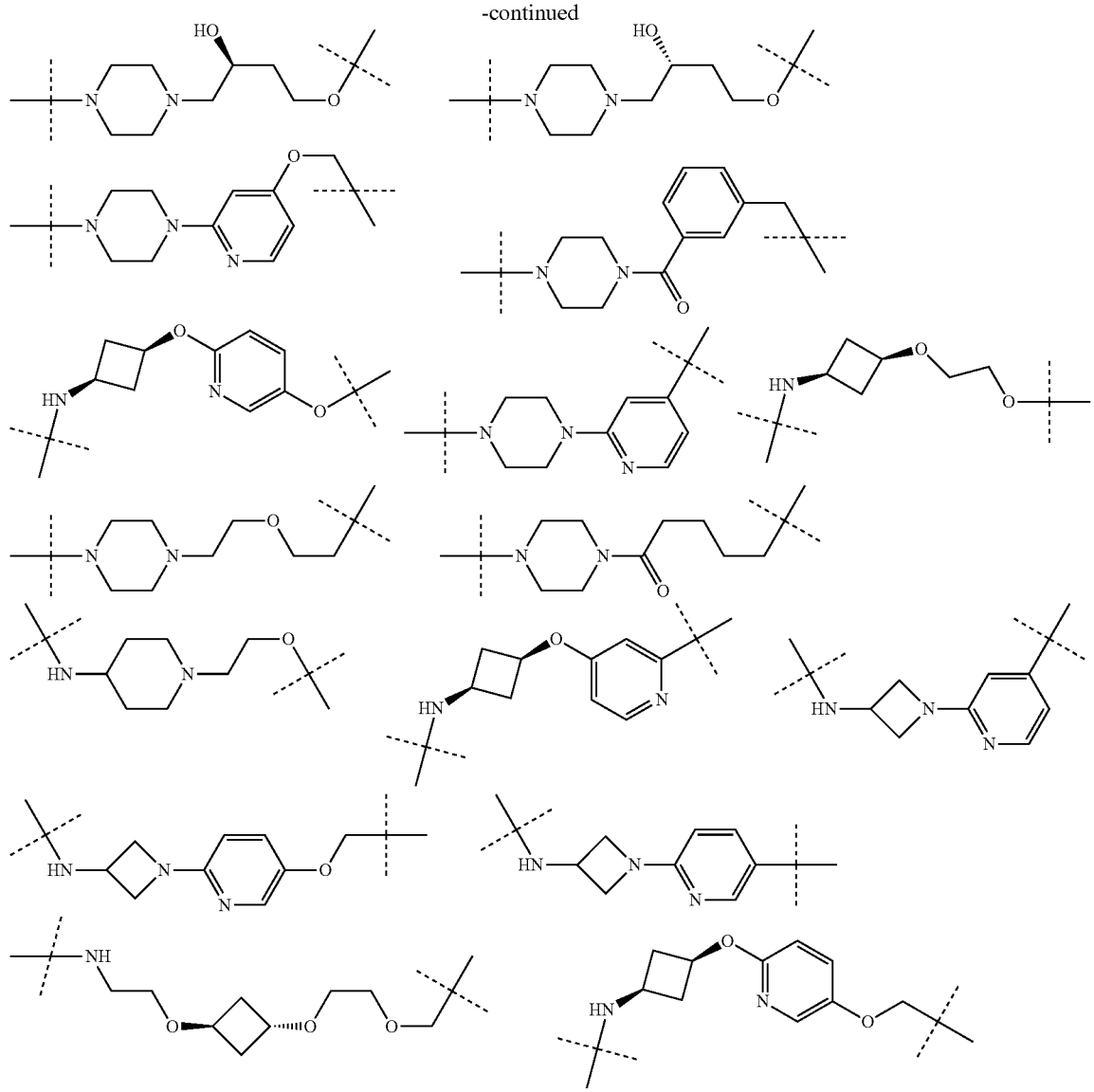
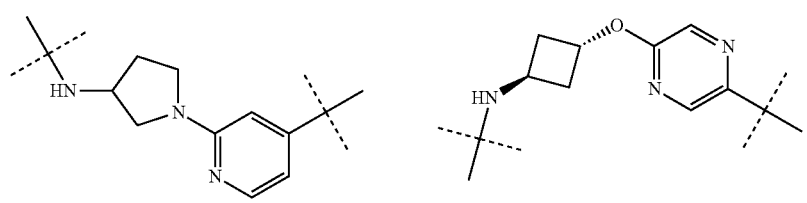
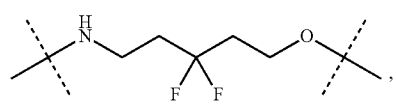
wherein each n and m of the linker can independently be 0, 1, 2, 3, 4, 5, 6.

In any aspect or embodiment described herein, the linker (L) is selected from the group consisting of:
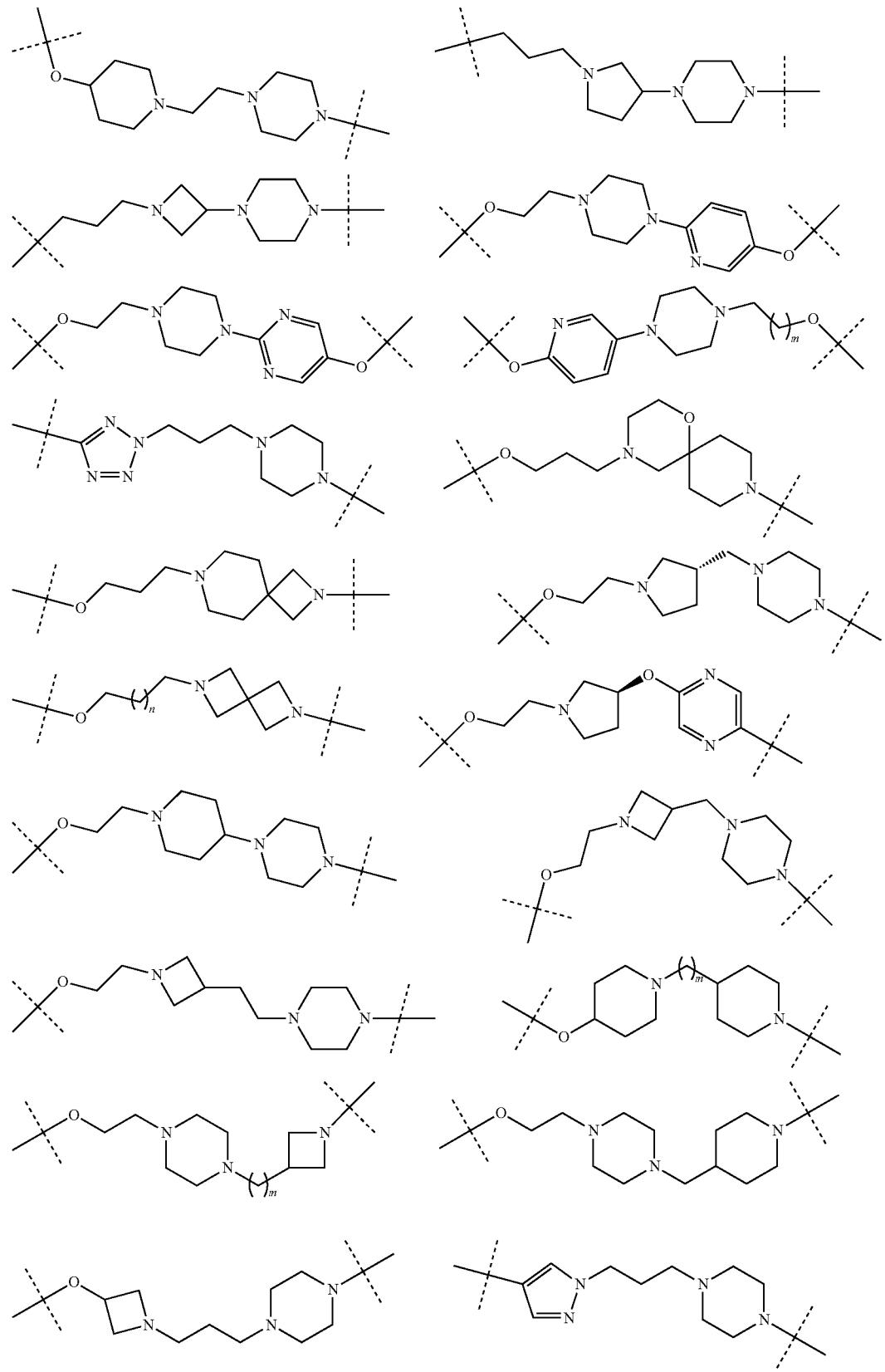

745 746
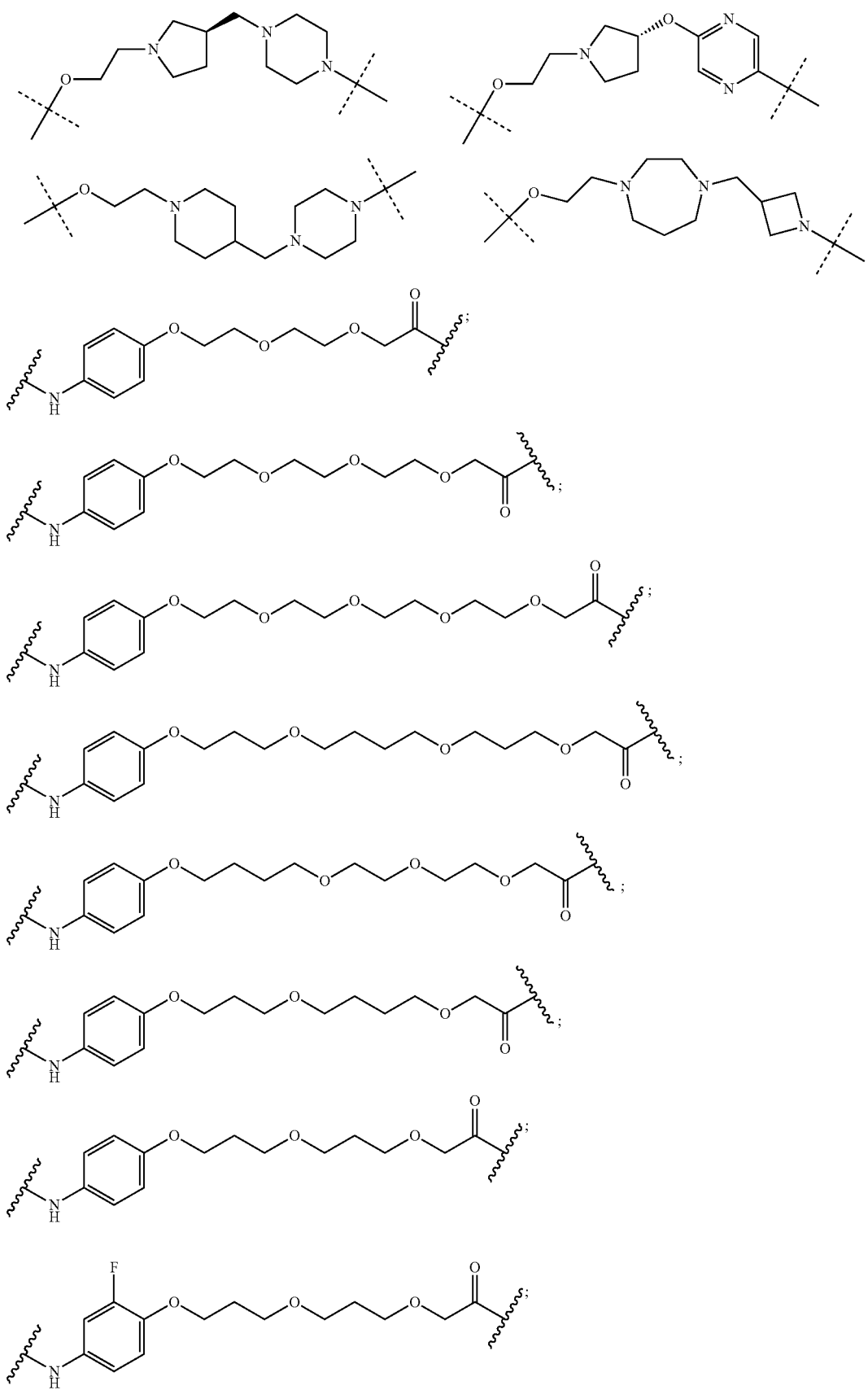

-continued
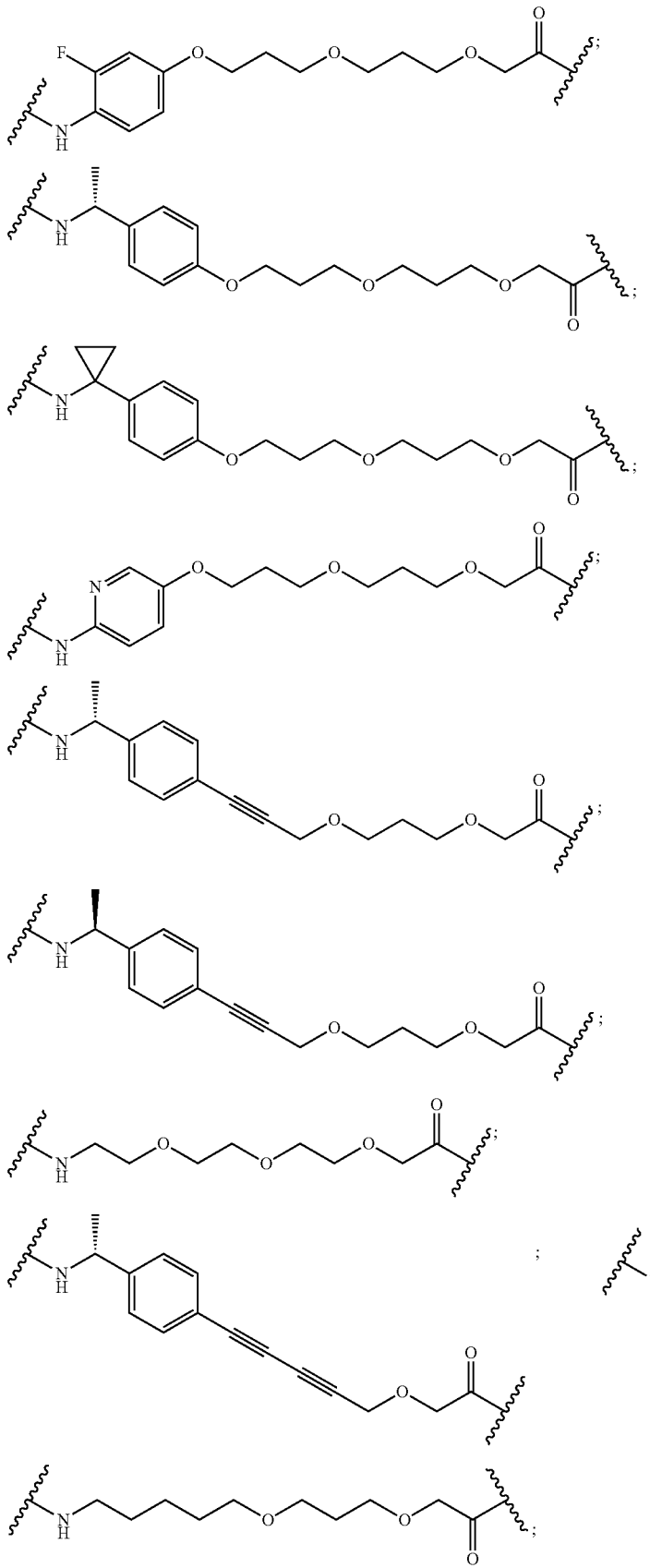

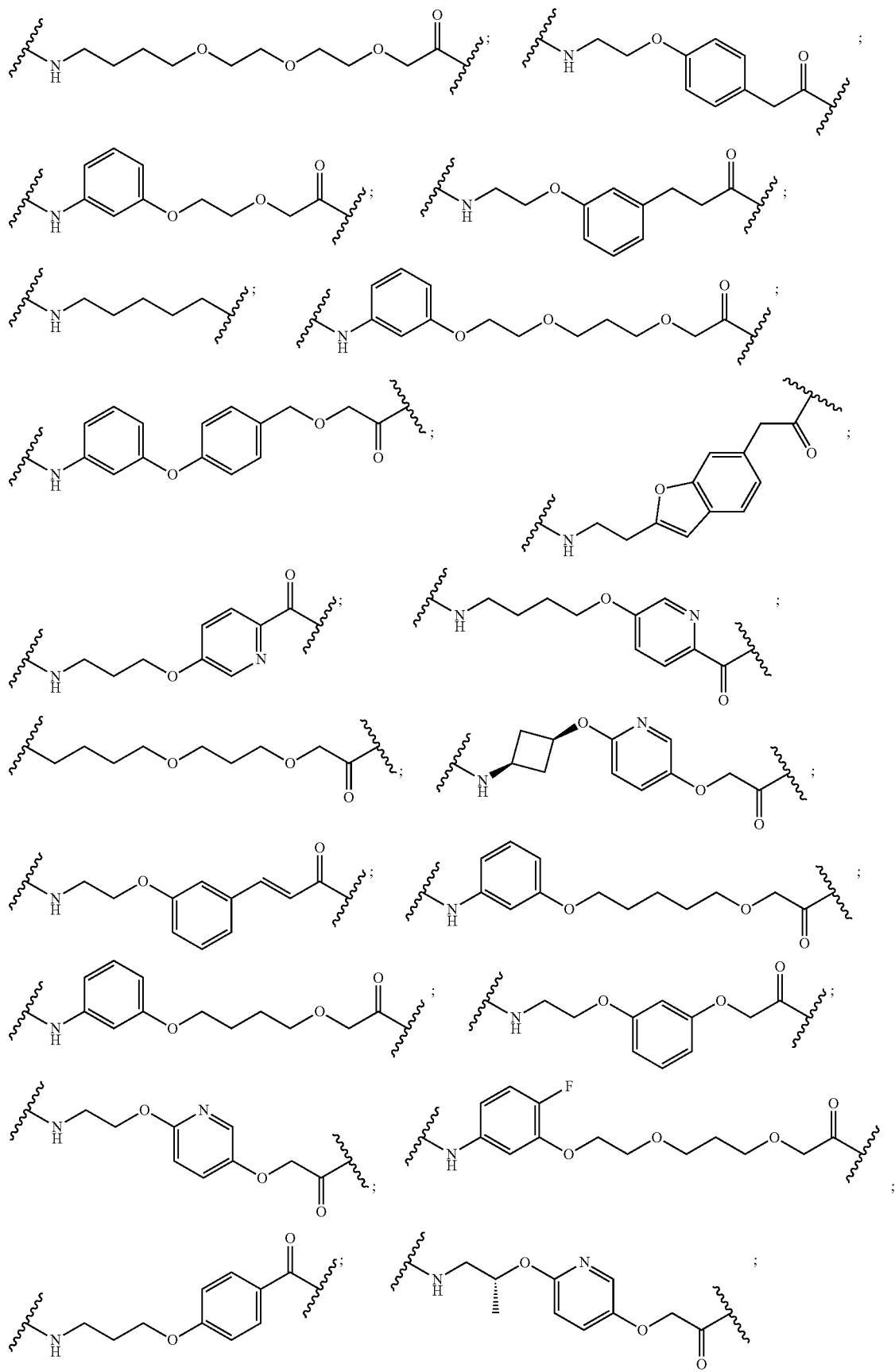

751
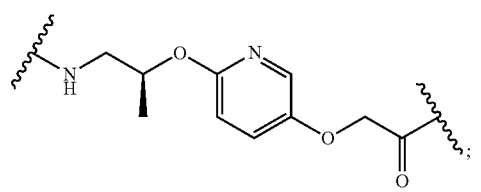
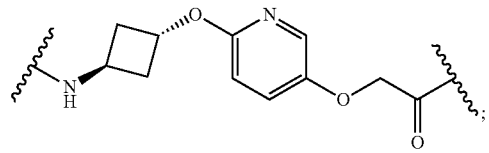
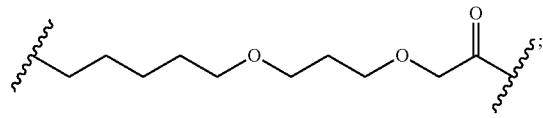
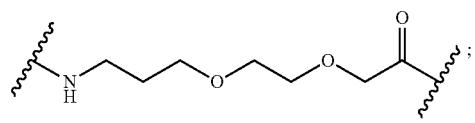
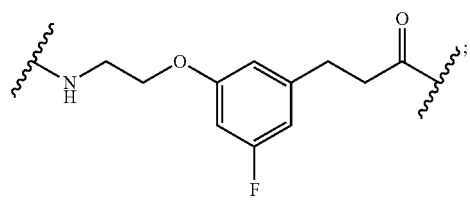
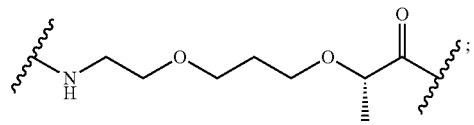
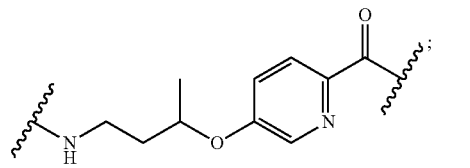
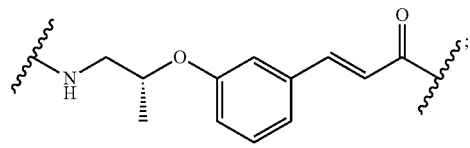
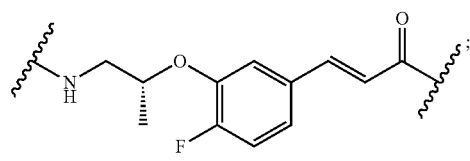
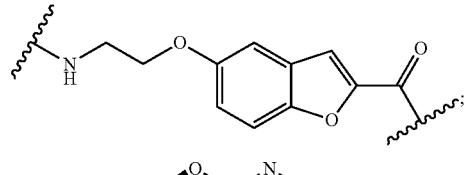
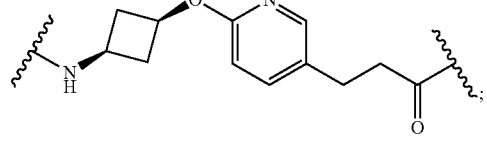
-continued
752
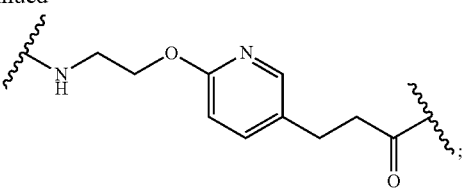
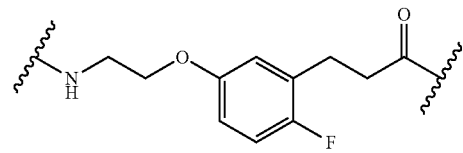
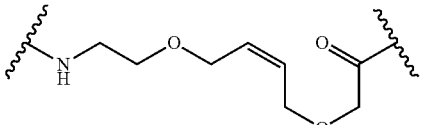
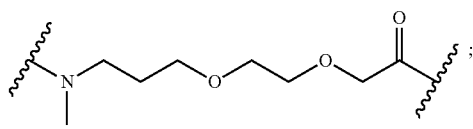
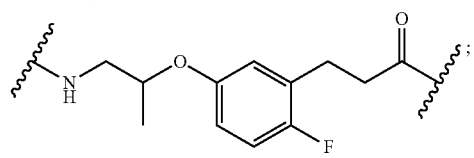
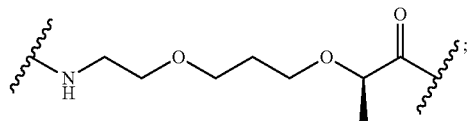
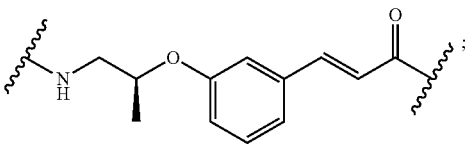
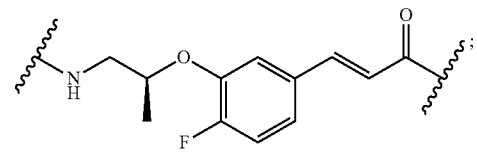
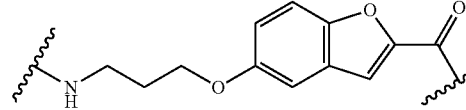
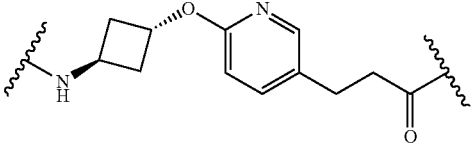

-continued
753
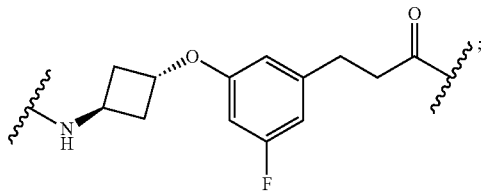
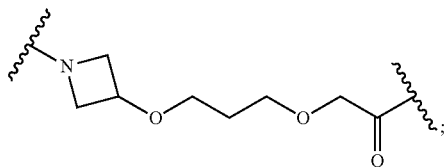
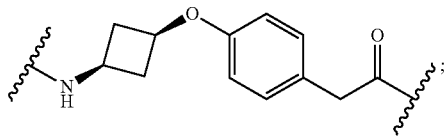
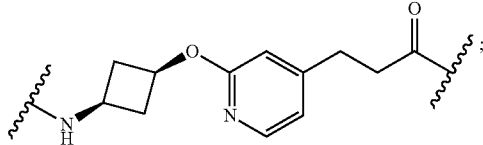
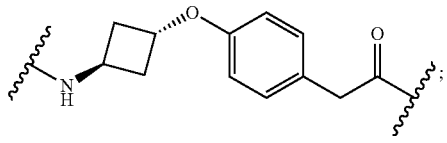
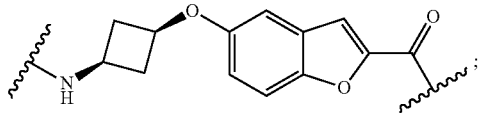
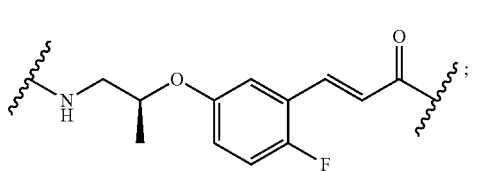
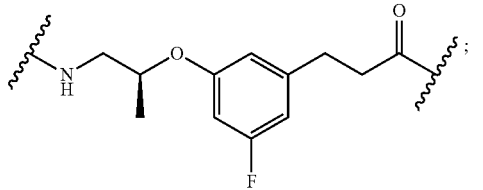
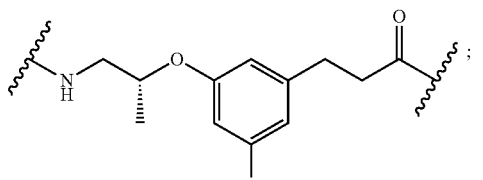
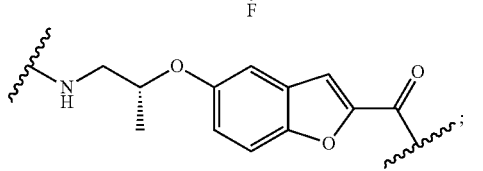
754
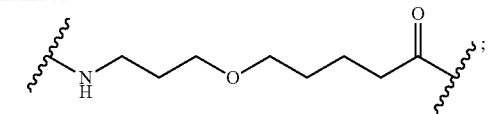
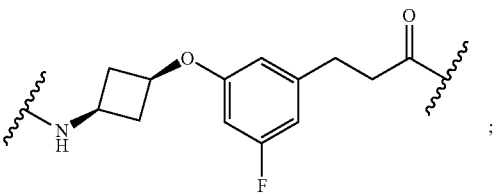
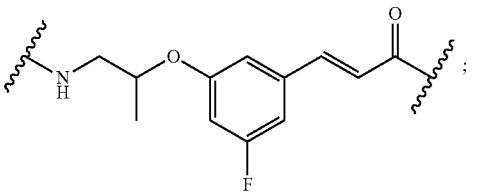
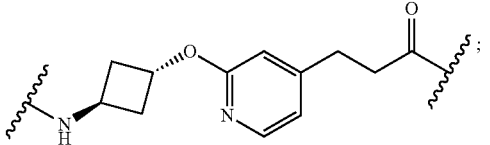
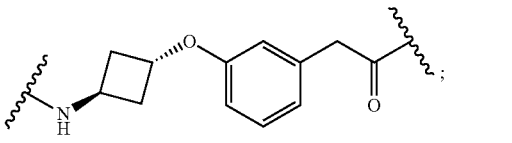
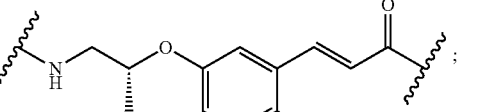
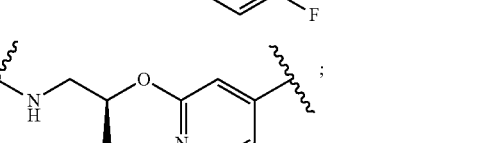
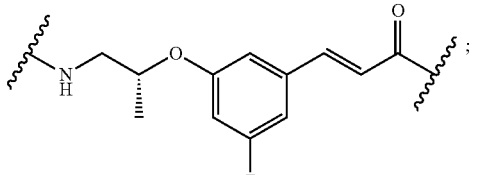
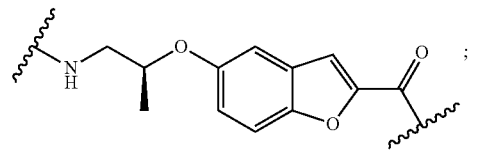
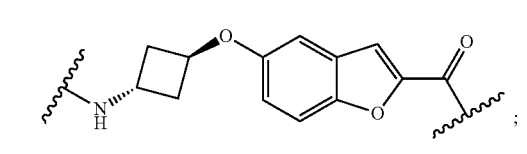

-continued
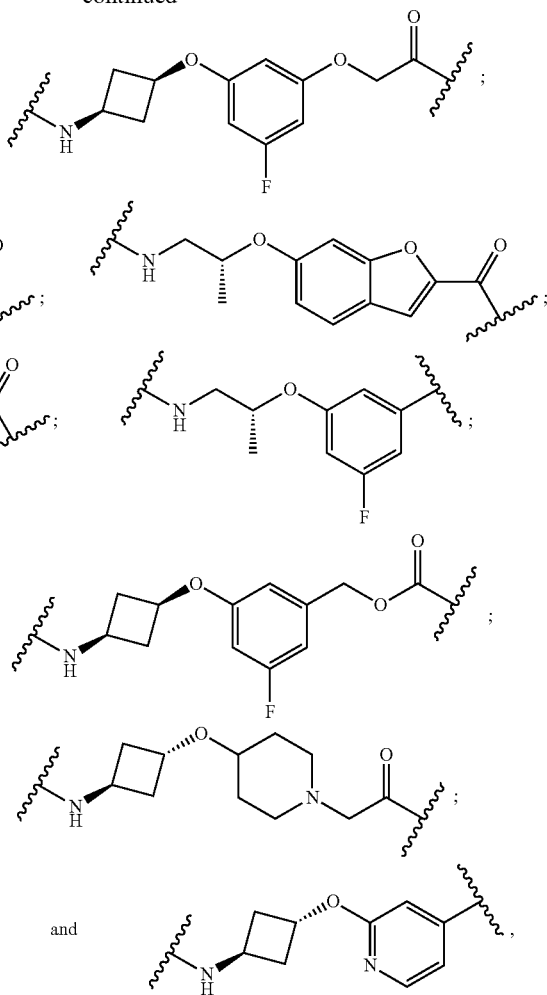
wherein each m and n is independently 0, 1, 2, 3, 4, 5, or 6.
In any aspect or embodiment described herein, the linker (L) is selected from the group consisting of:
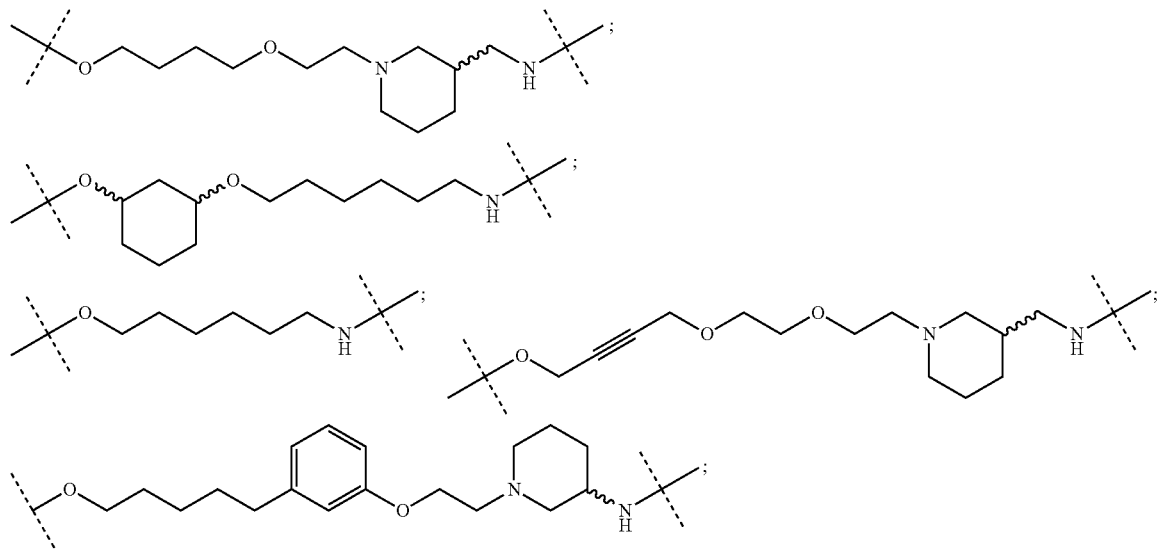

-continued
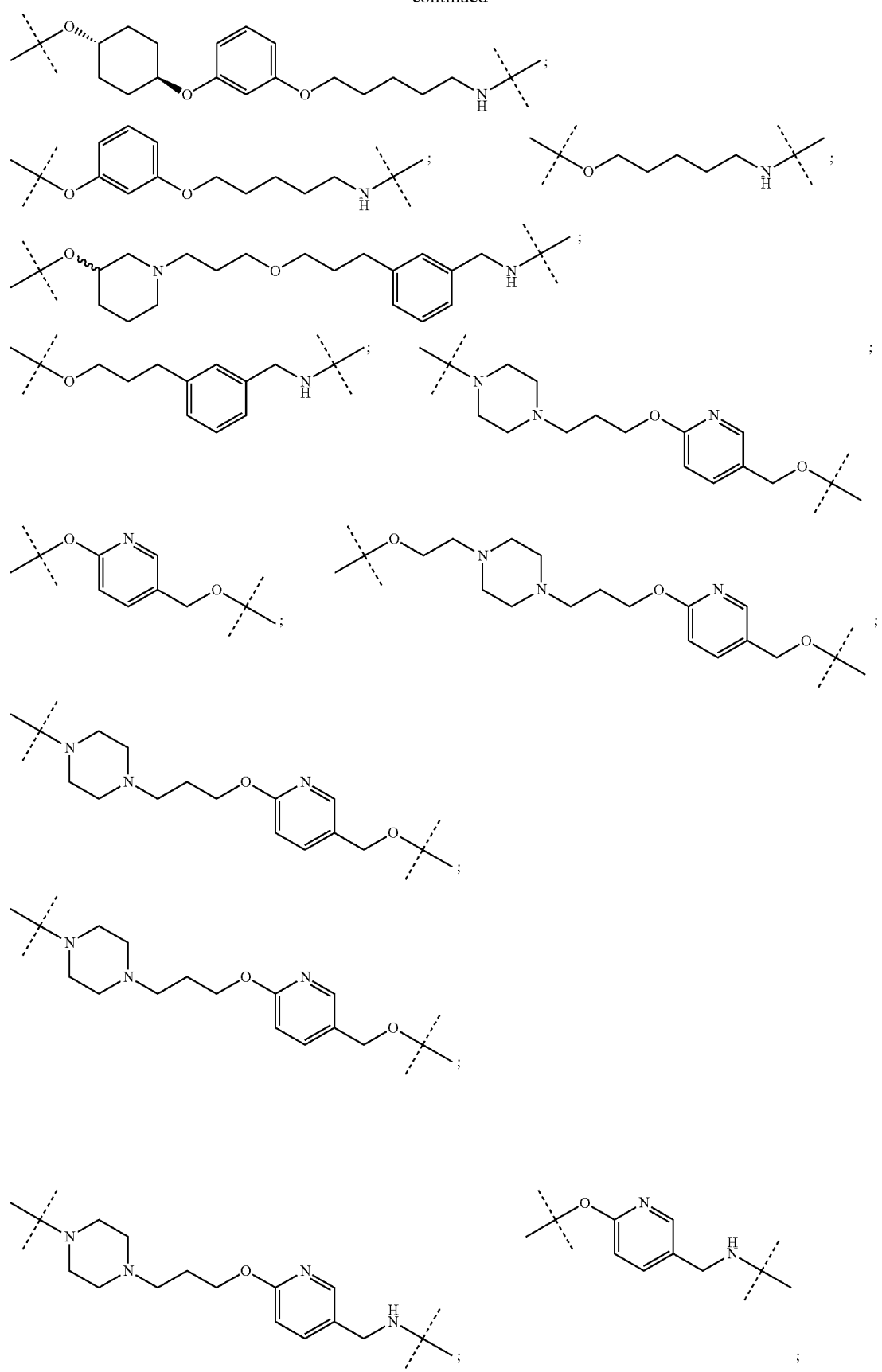

759 760
-continued
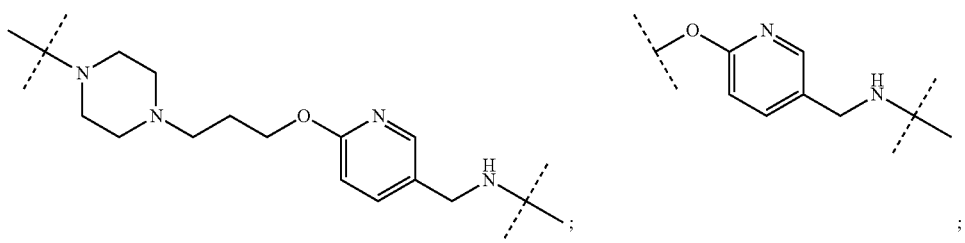
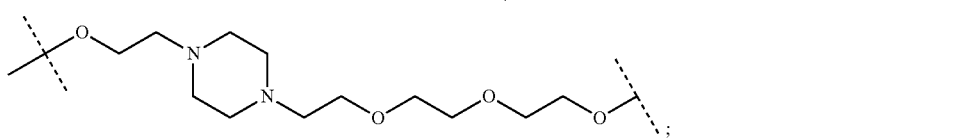
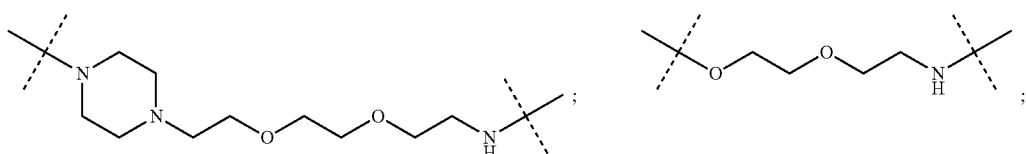
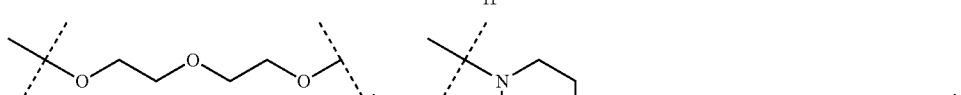
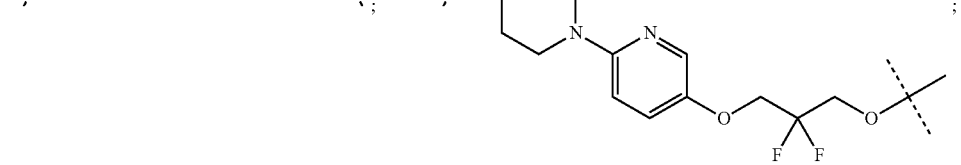
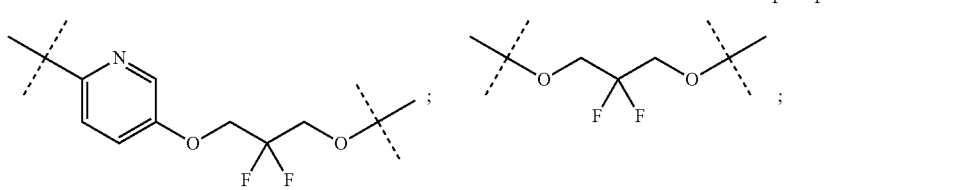
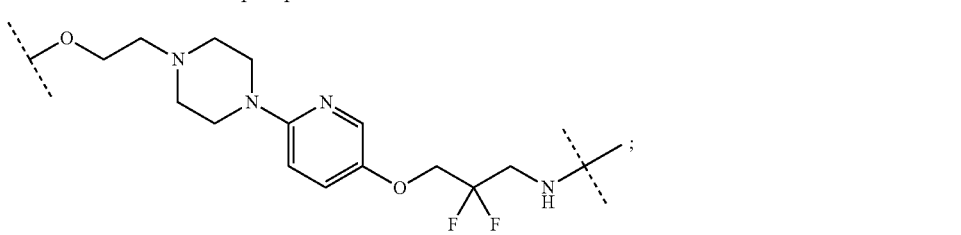
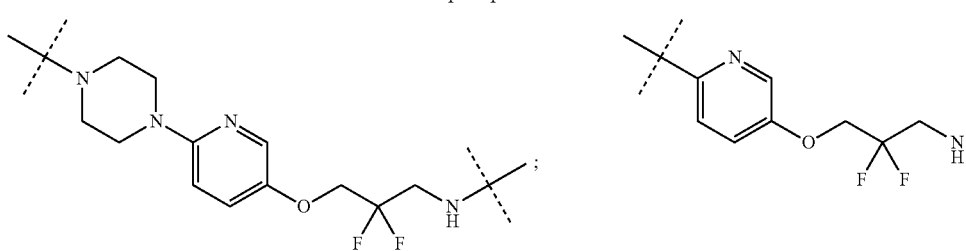
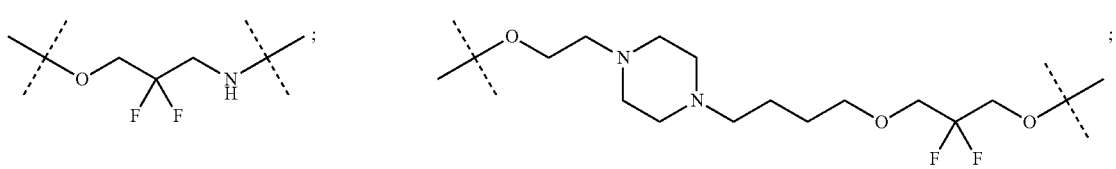

-continued
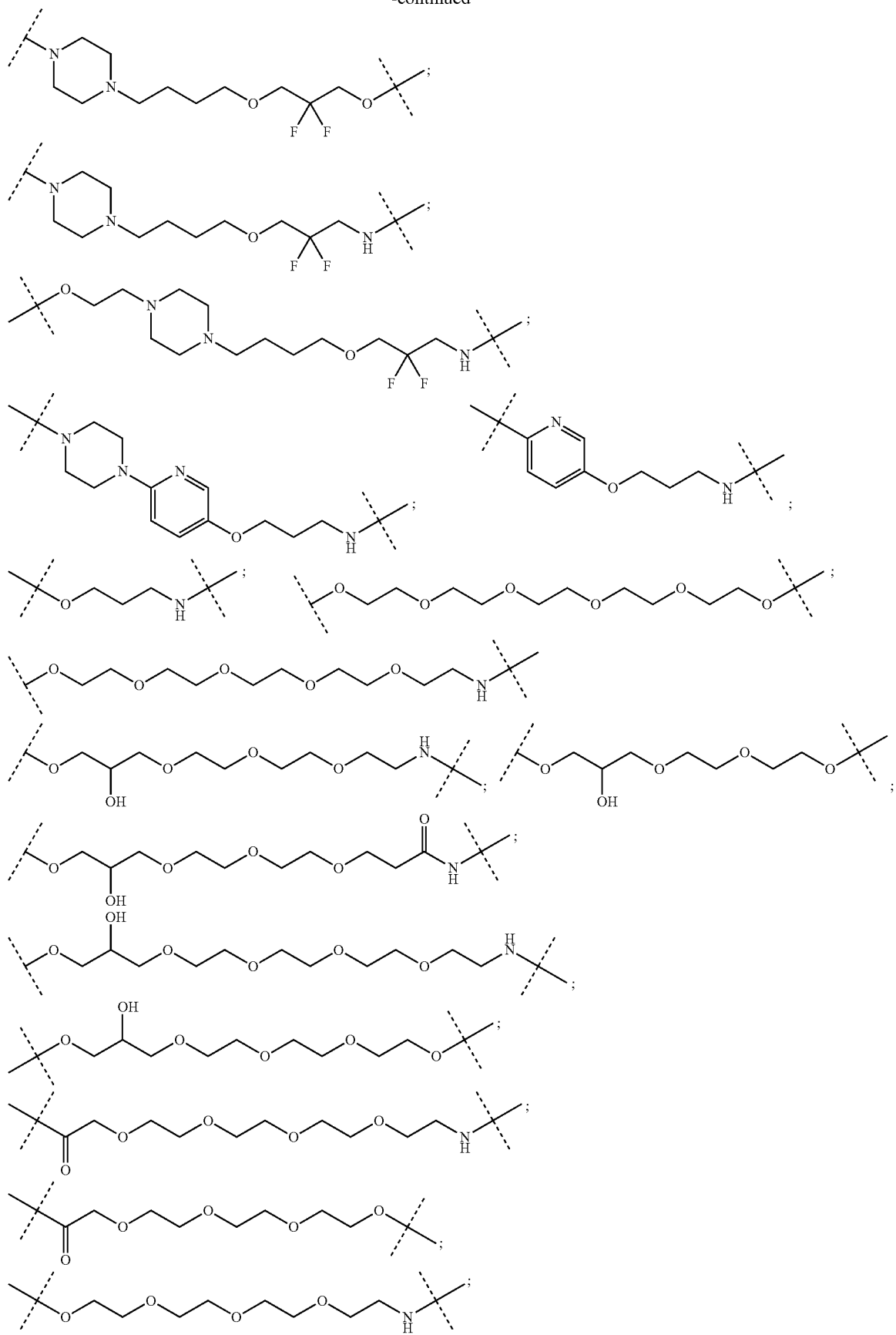

763 764
-continued
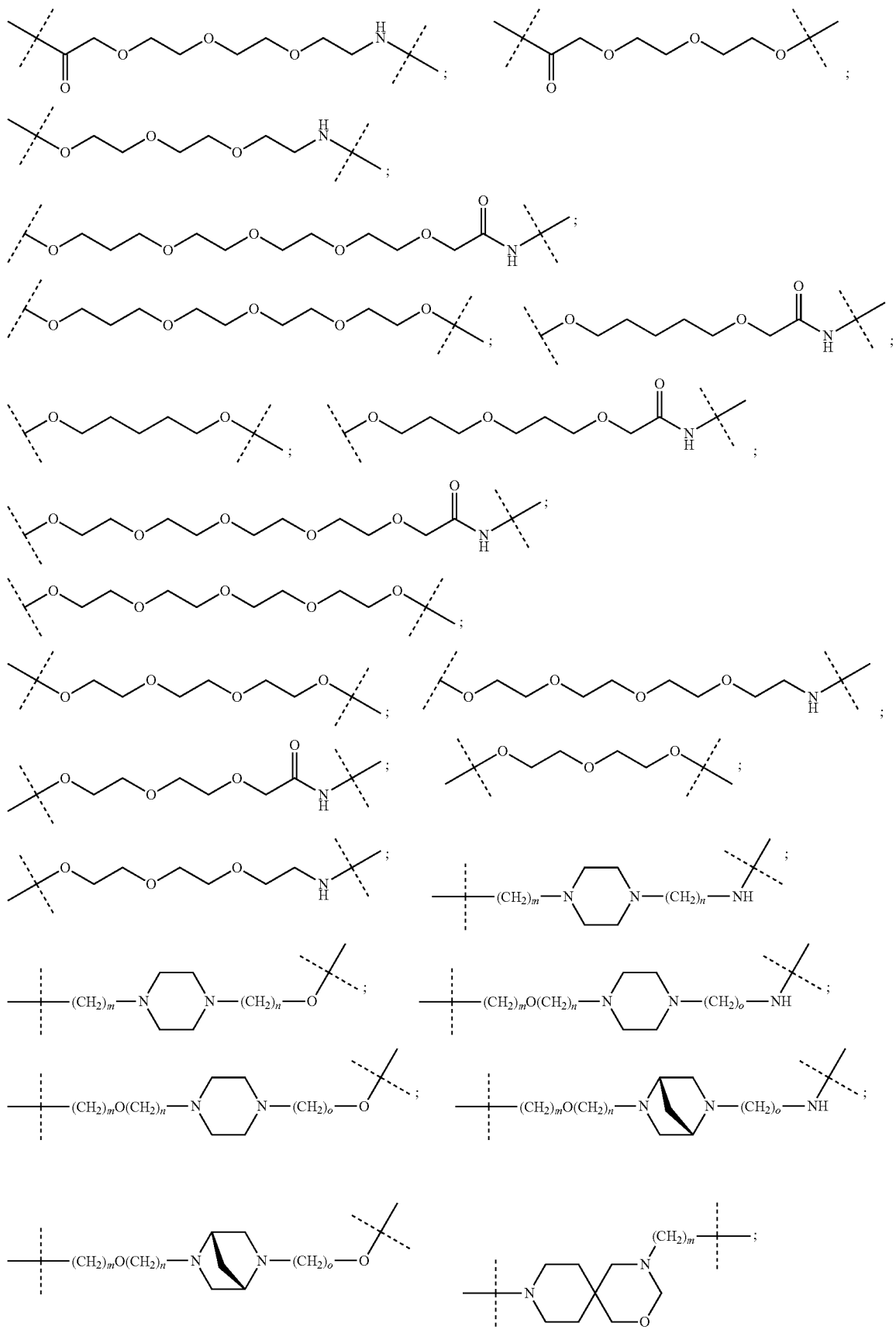

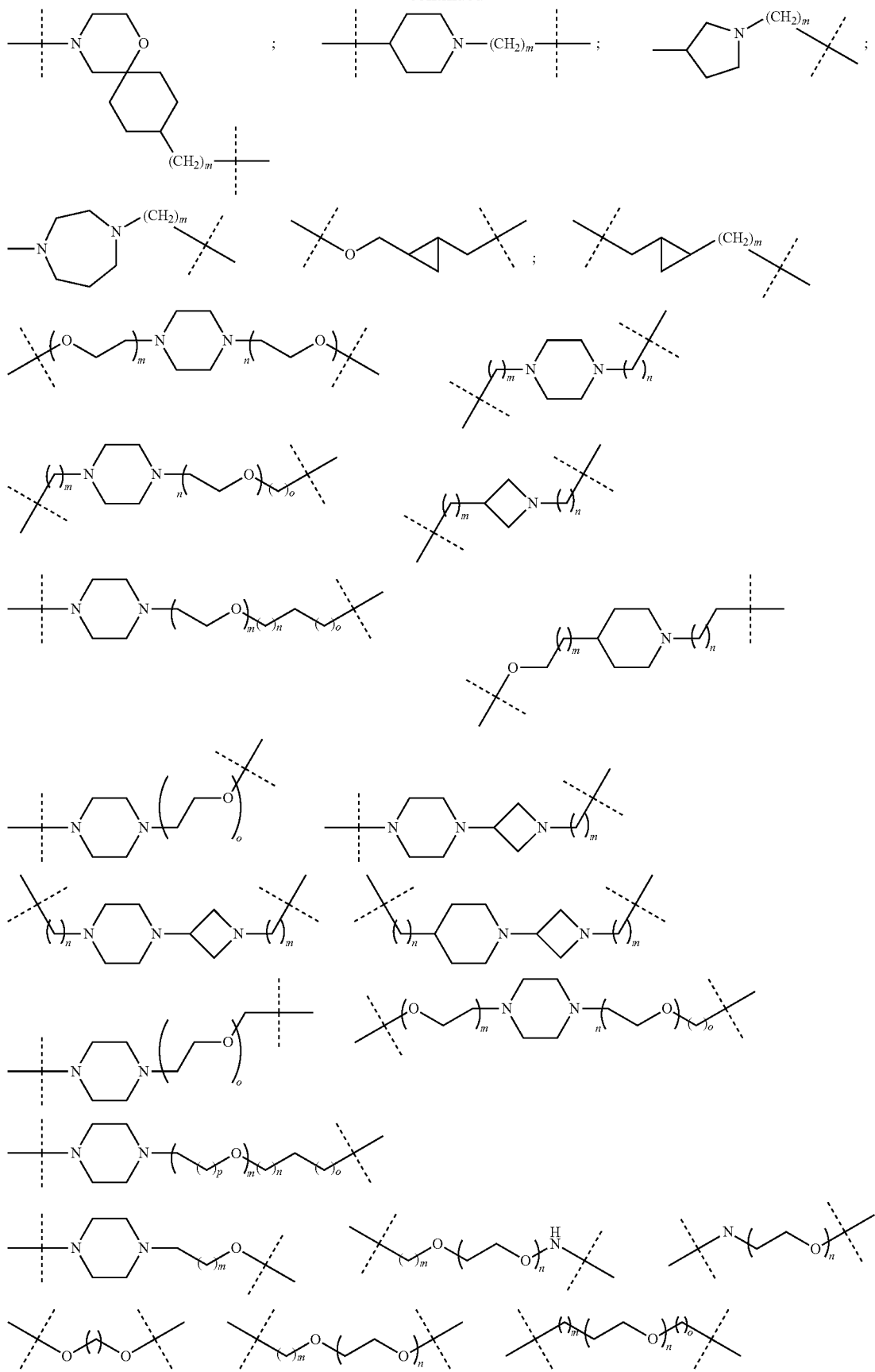

767                    -continued                    768
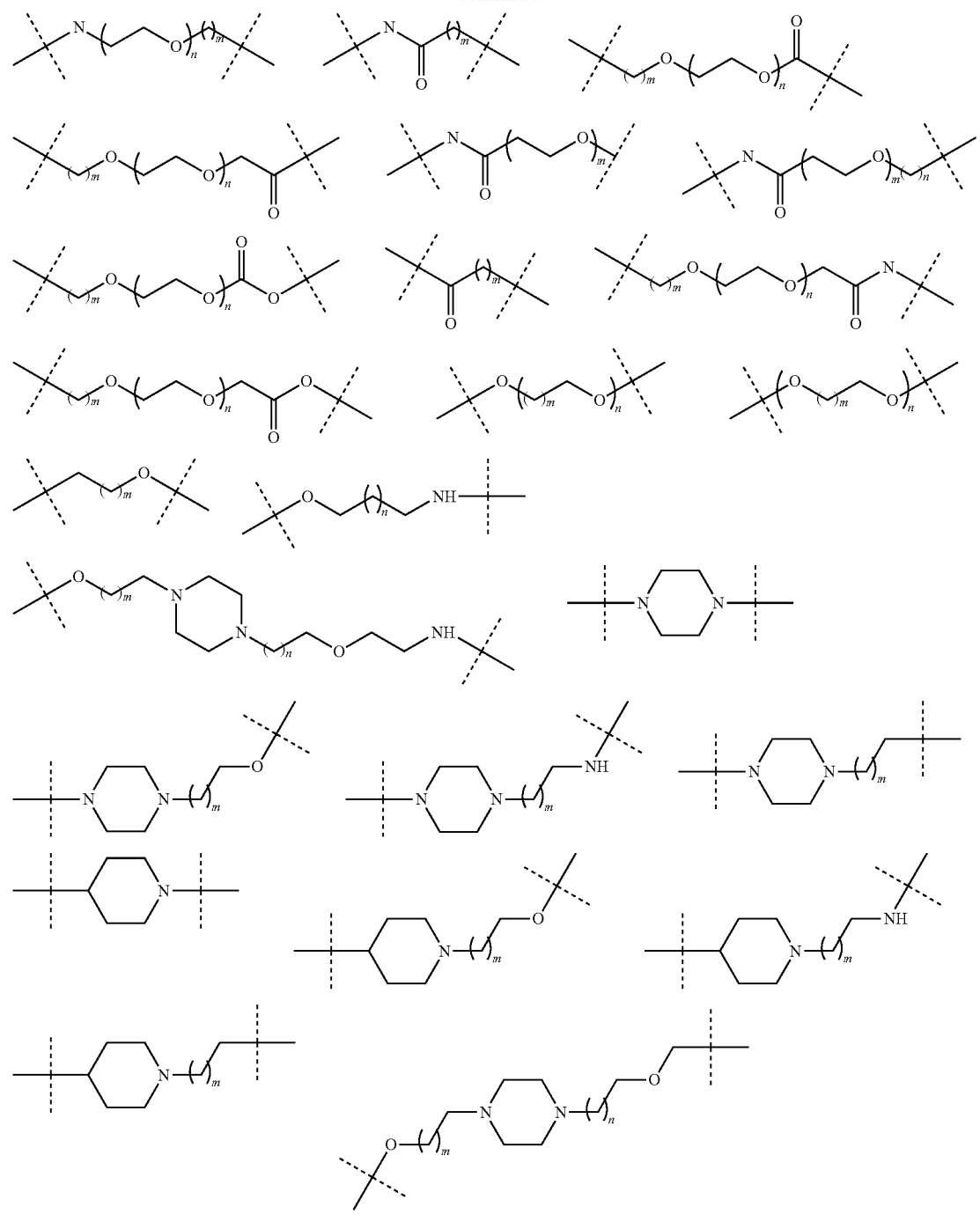
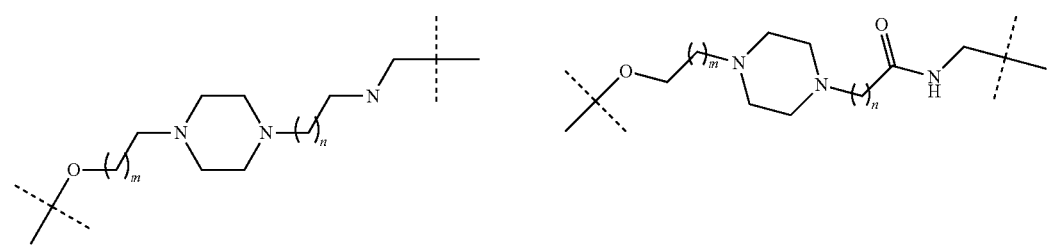

-continued
769
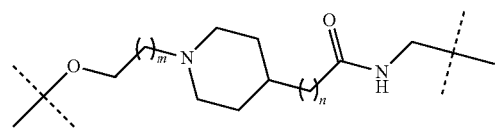
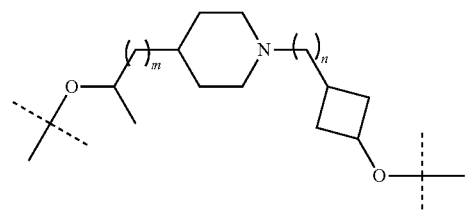
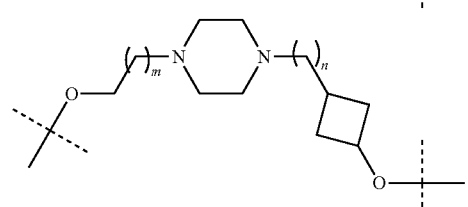
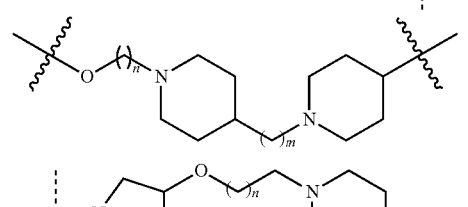
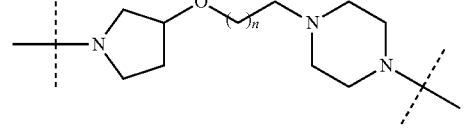
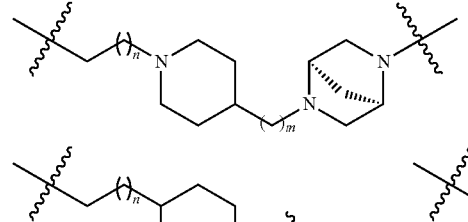
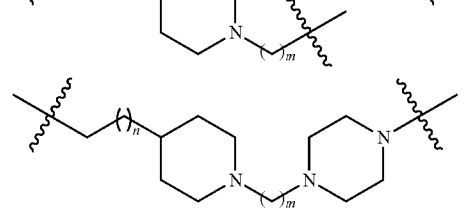
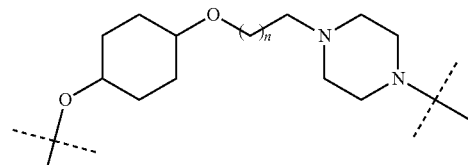
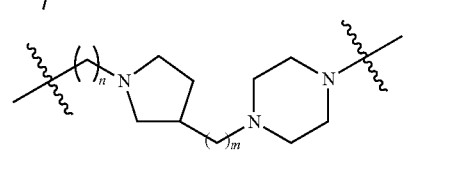
770
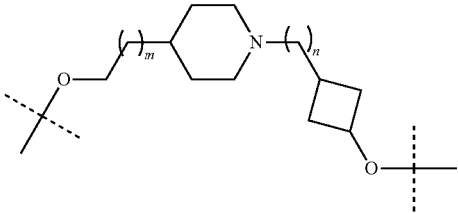
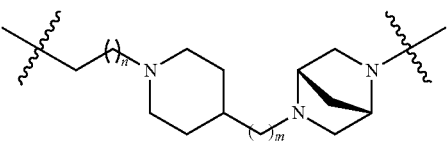
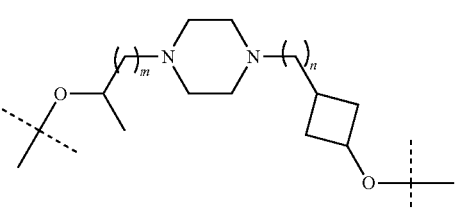
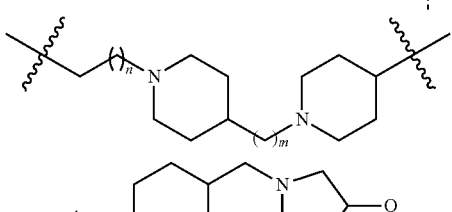
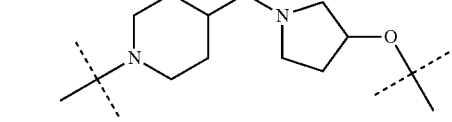
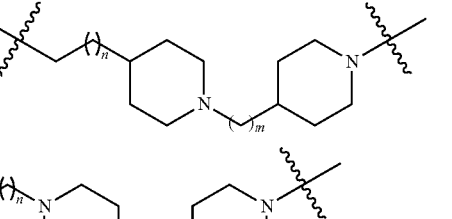
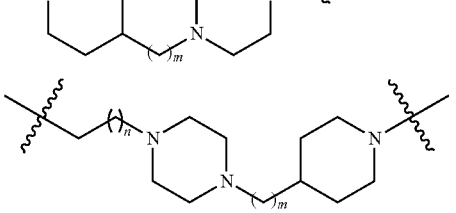
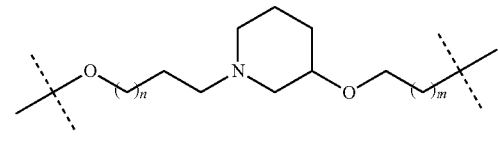
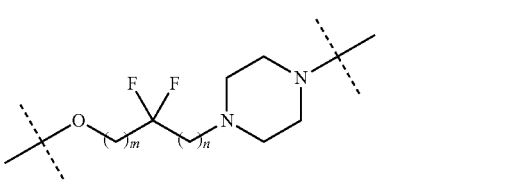

-continued
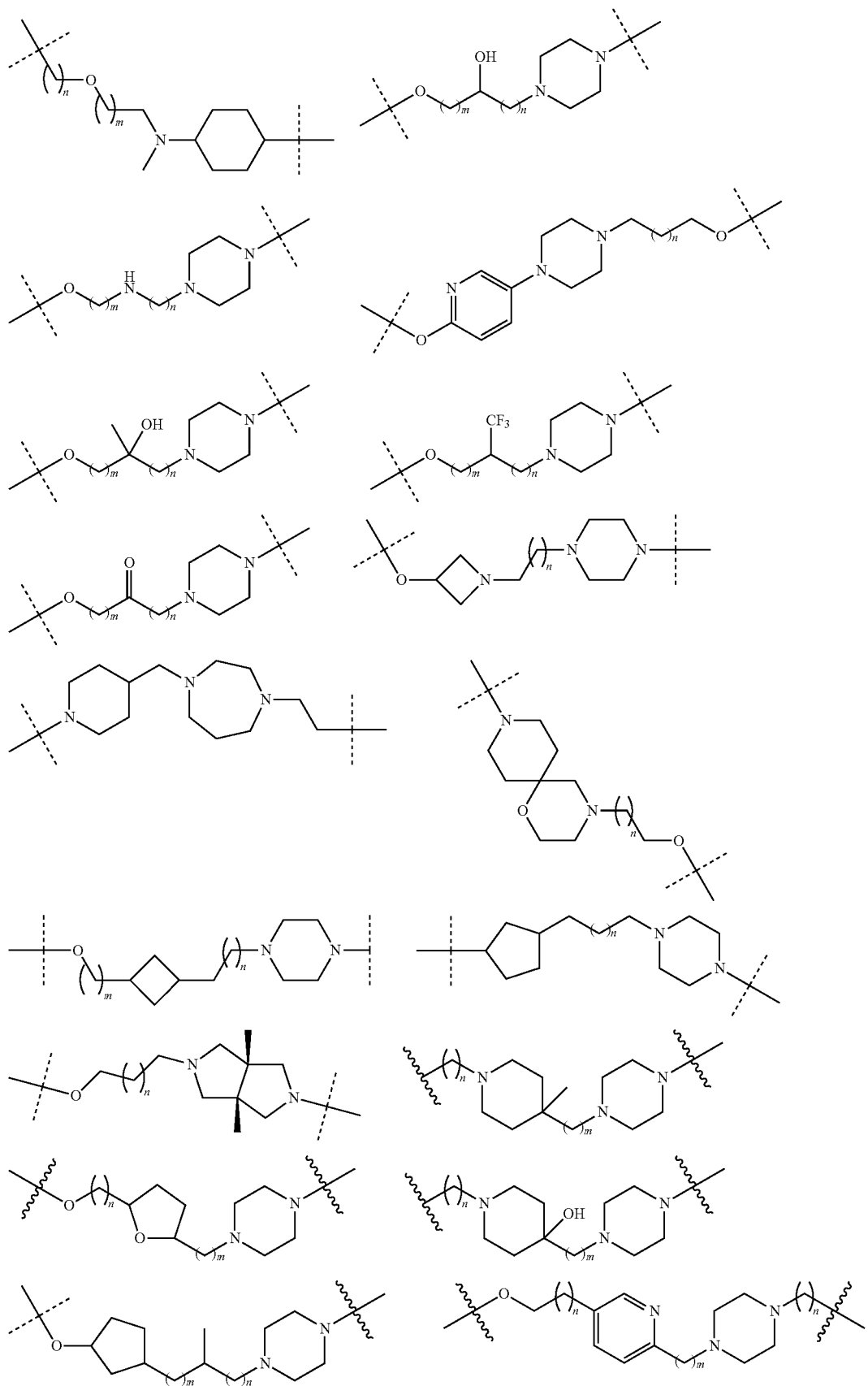

773 774
-continued
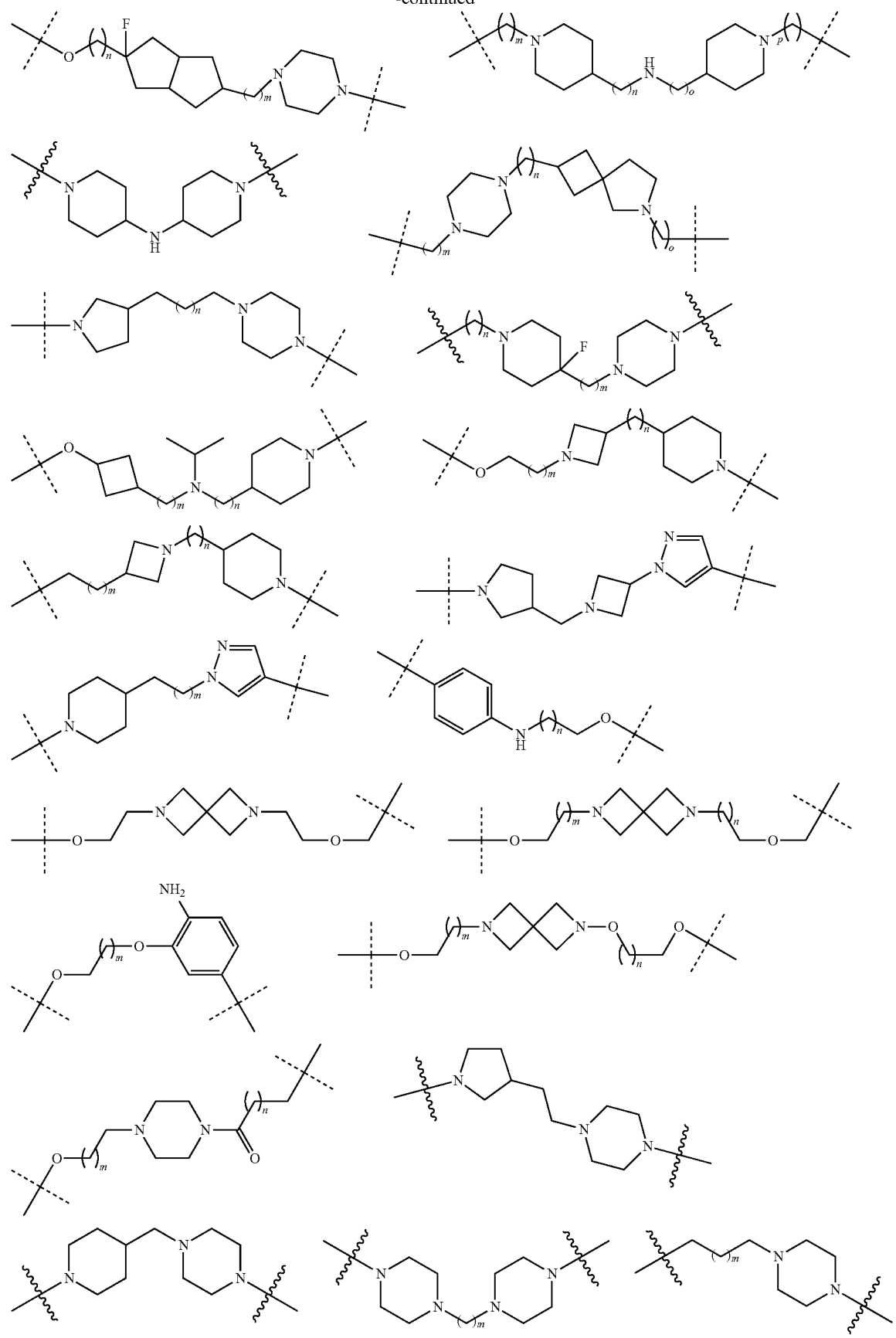

-continued
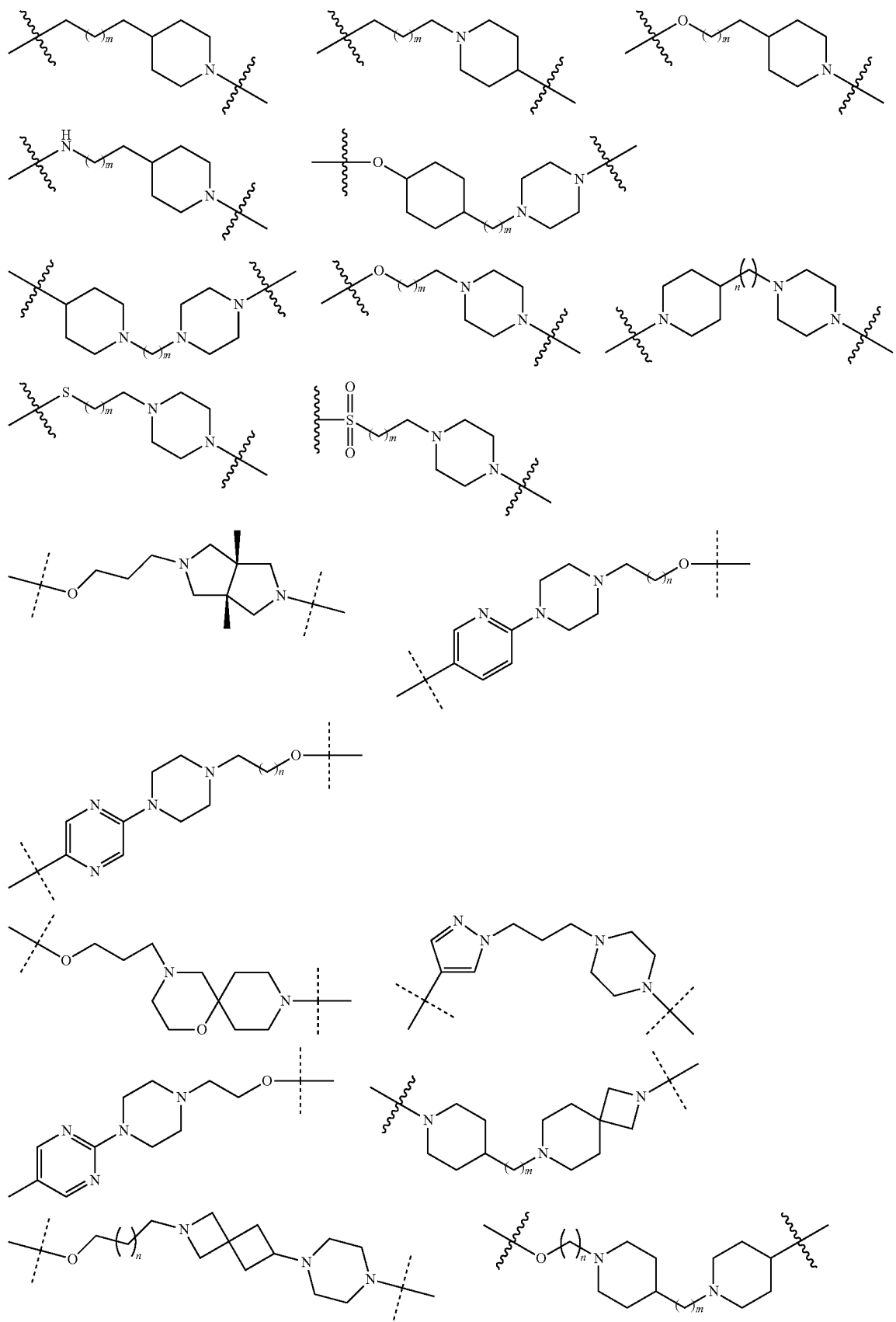

-continued
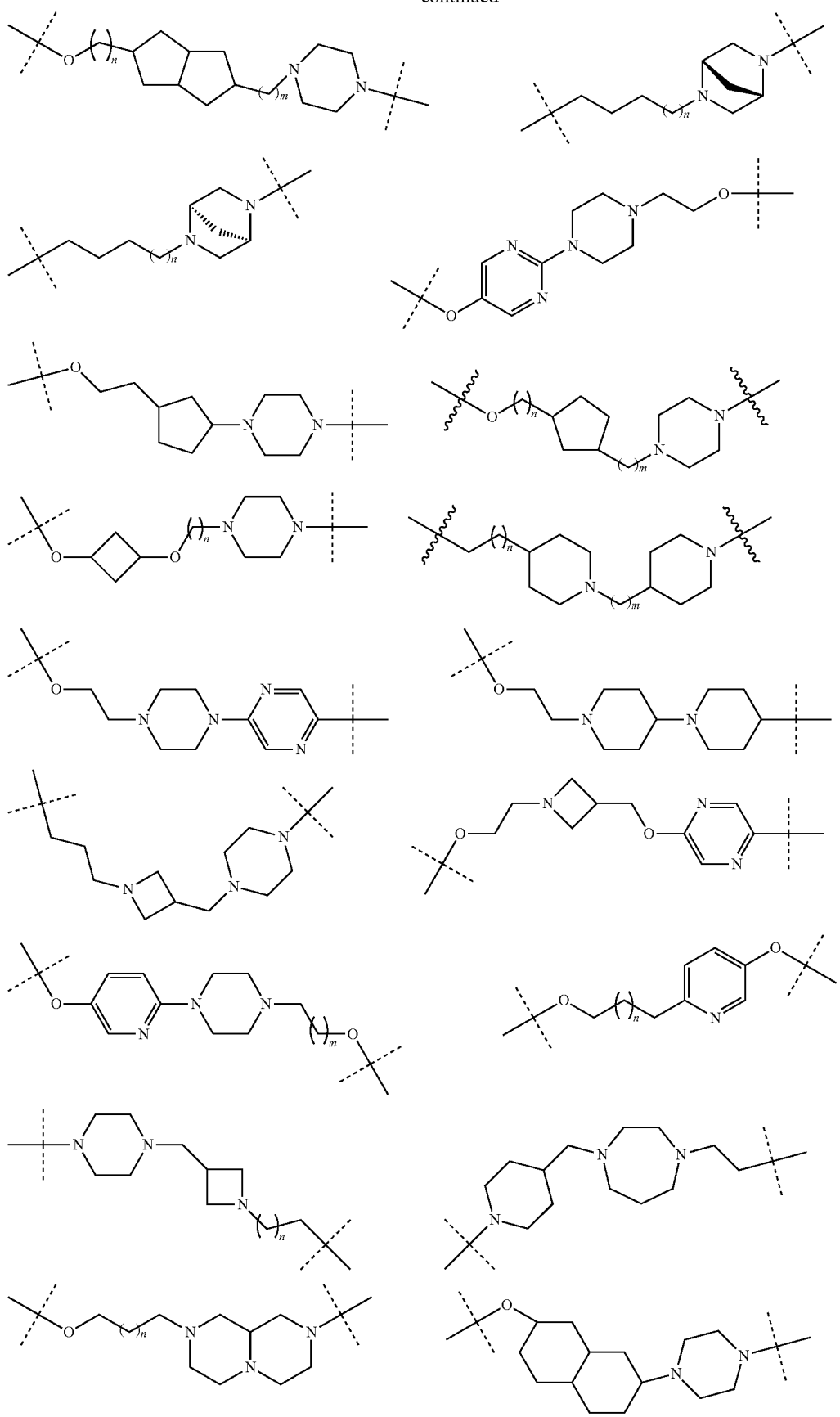

-continued
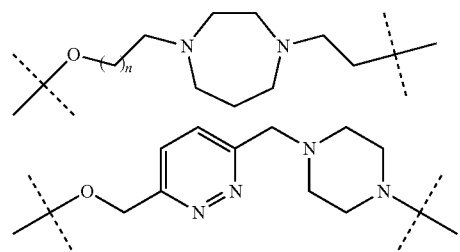
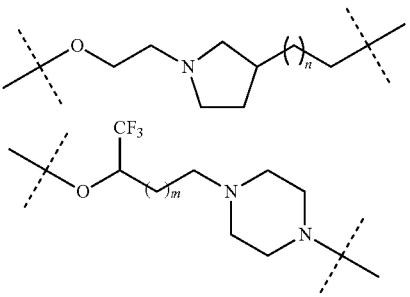
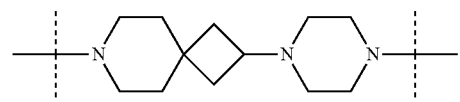
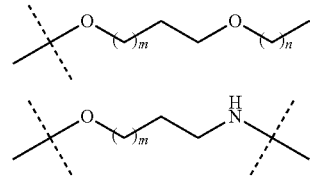
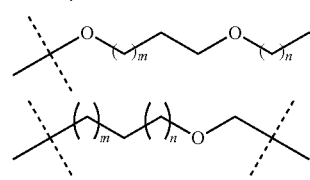
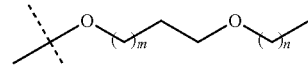
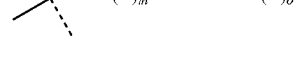
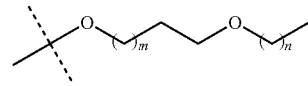
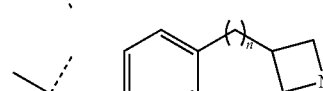
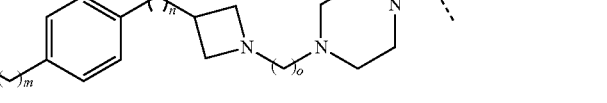

781 782
-continued
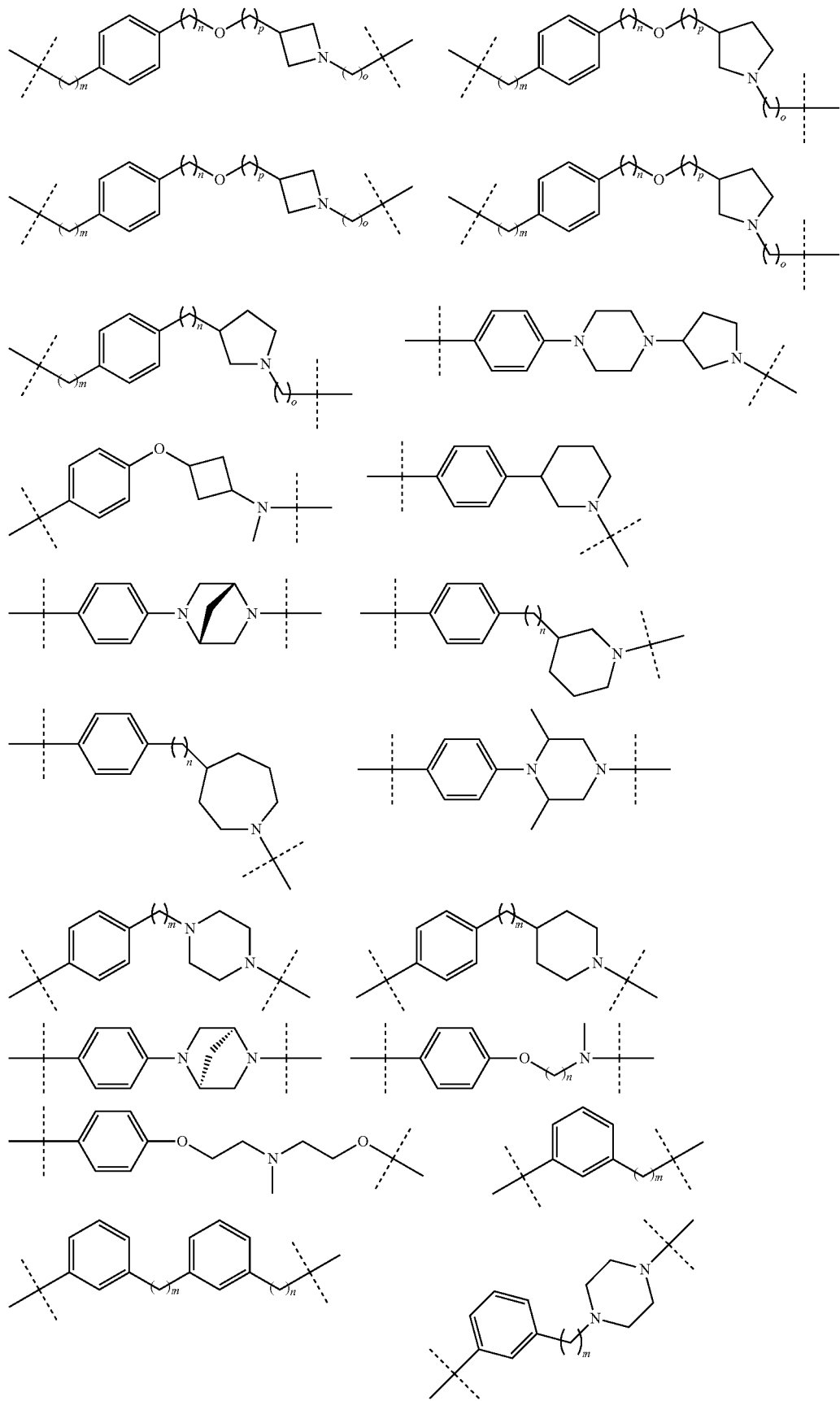

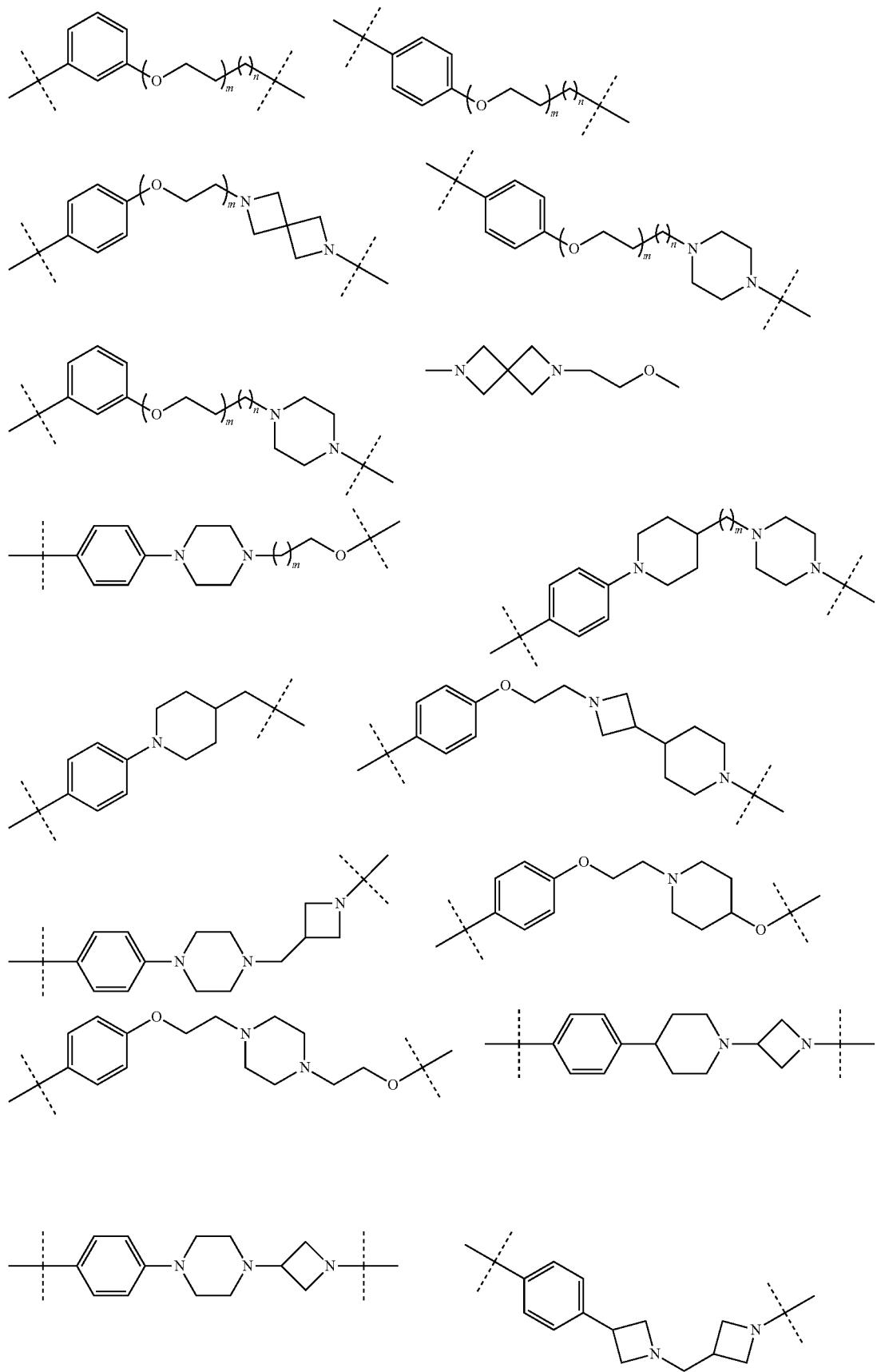

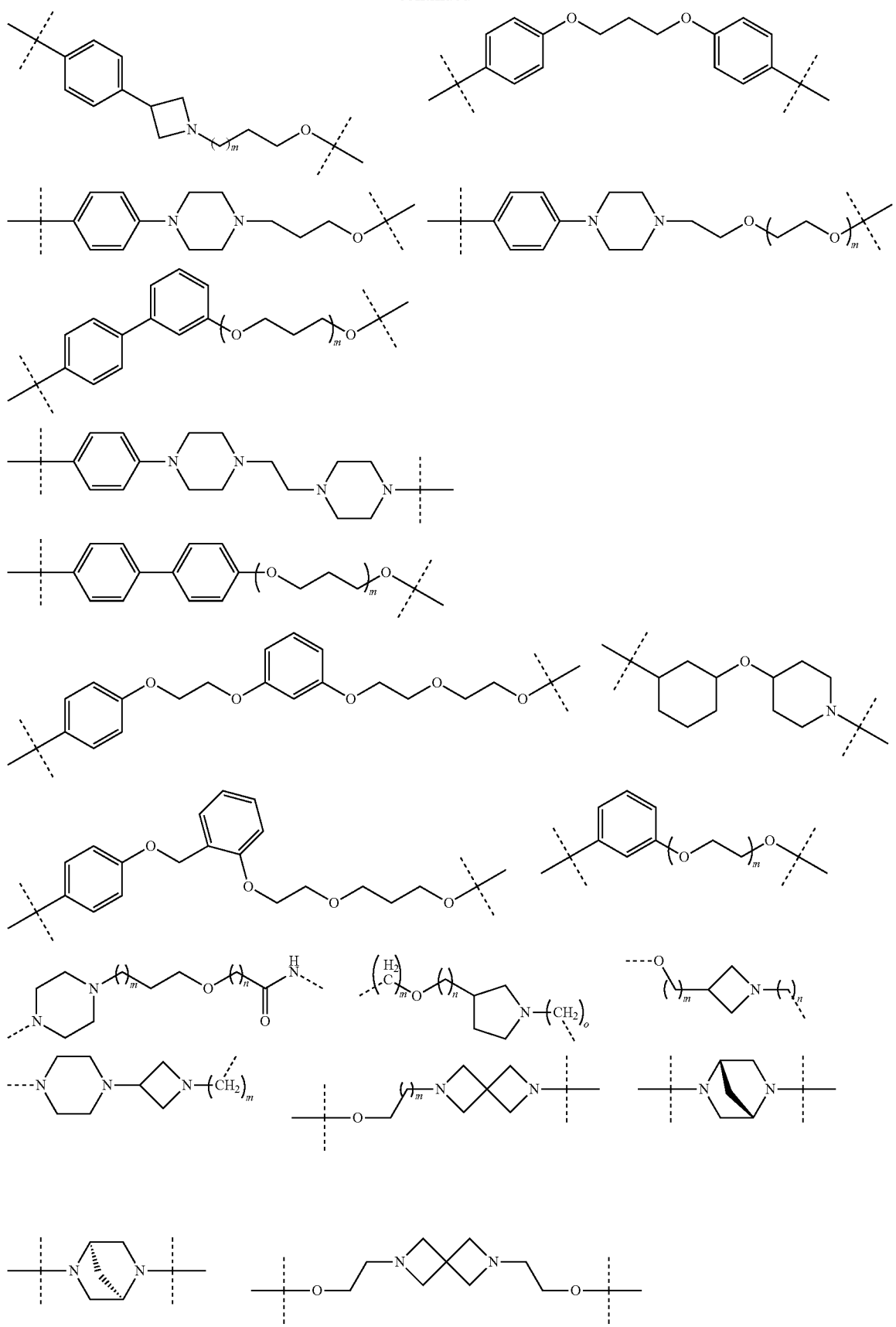

787 788
-continued
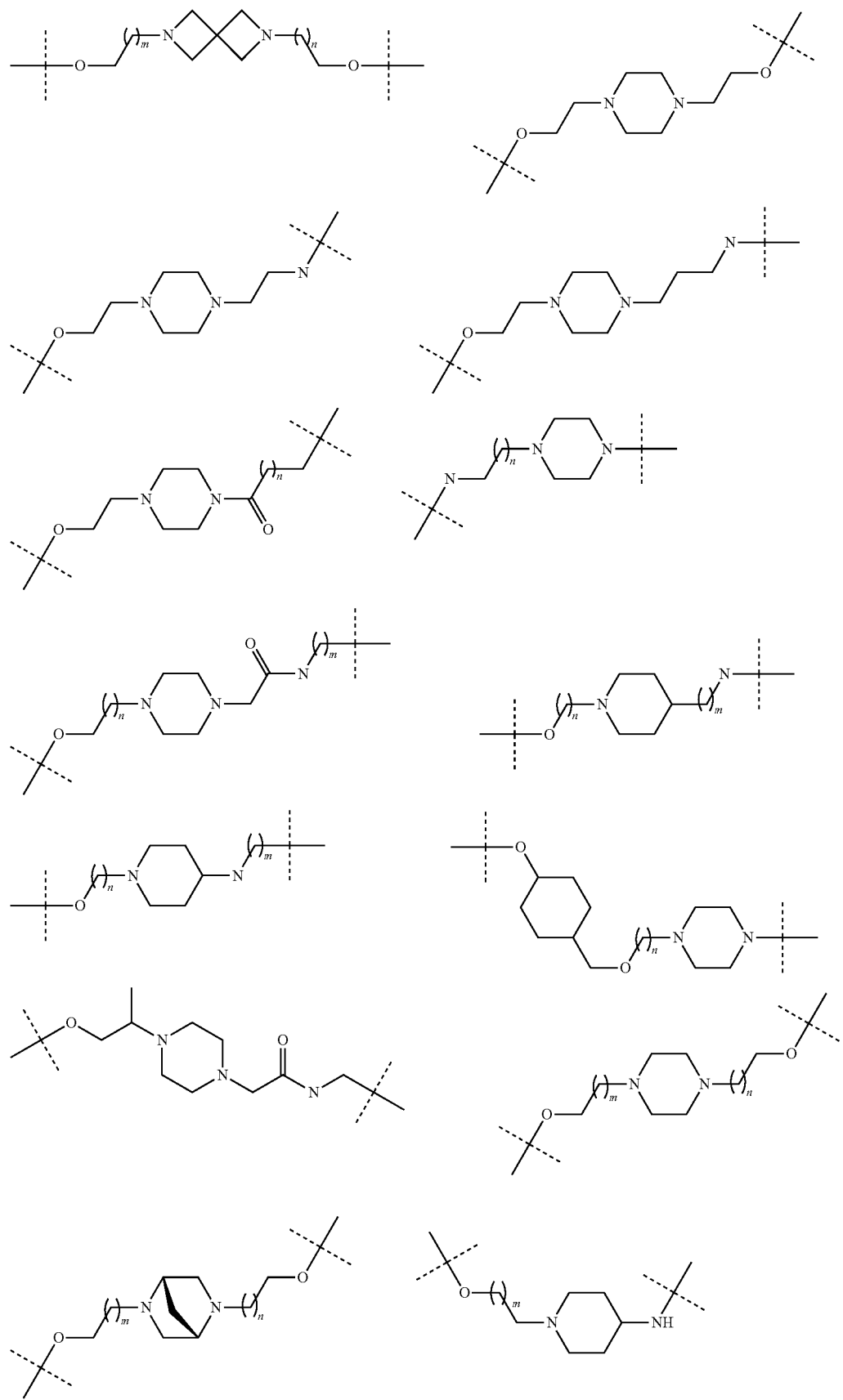

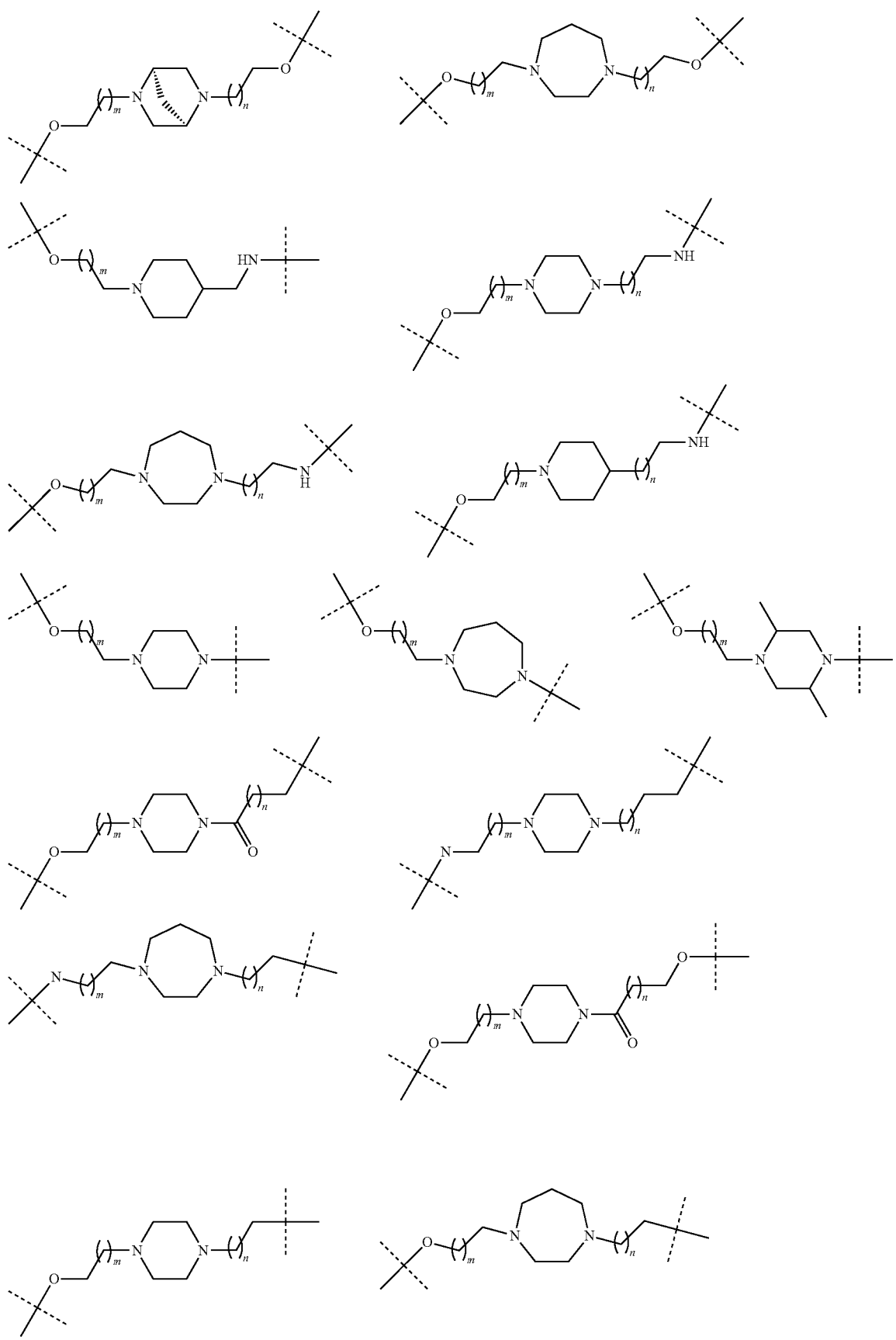

-continued
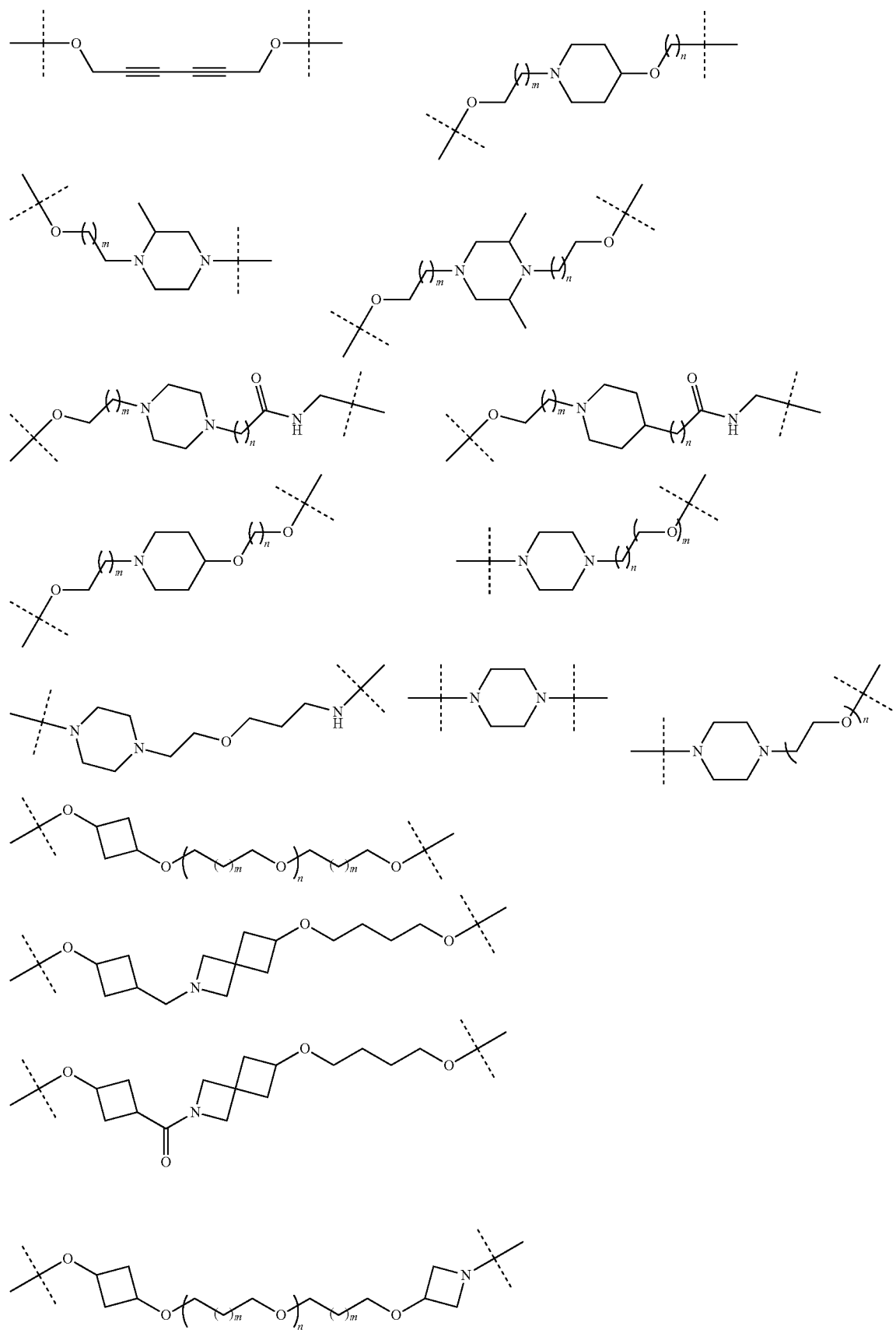

-continued
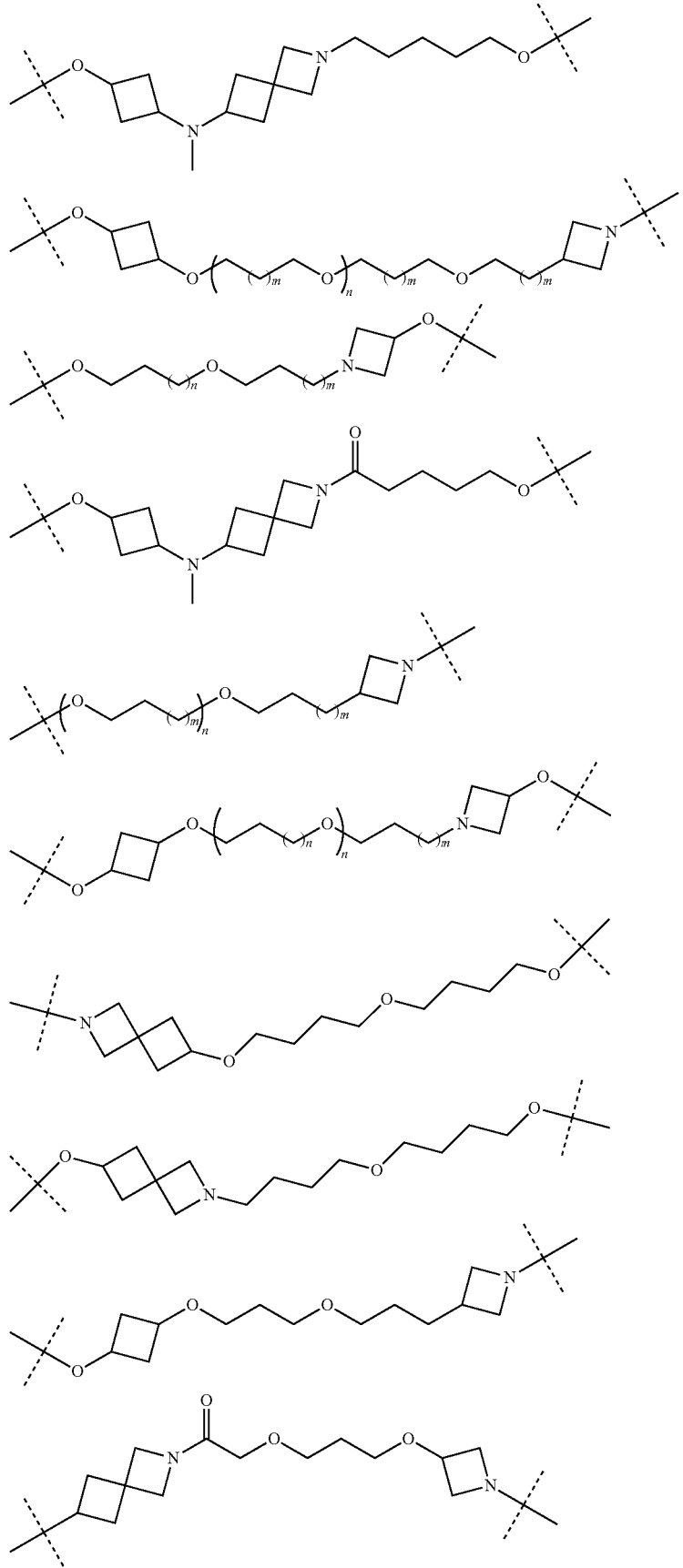

-continued
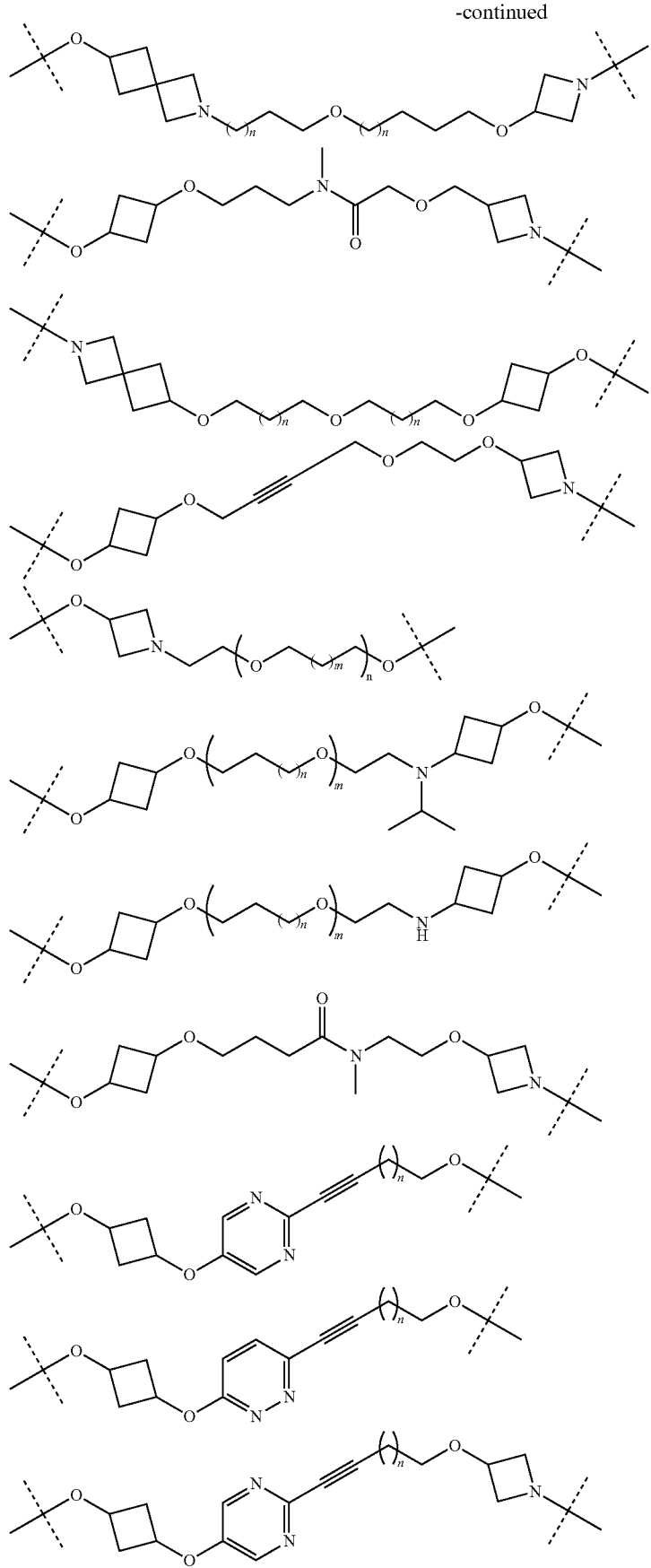

-continued
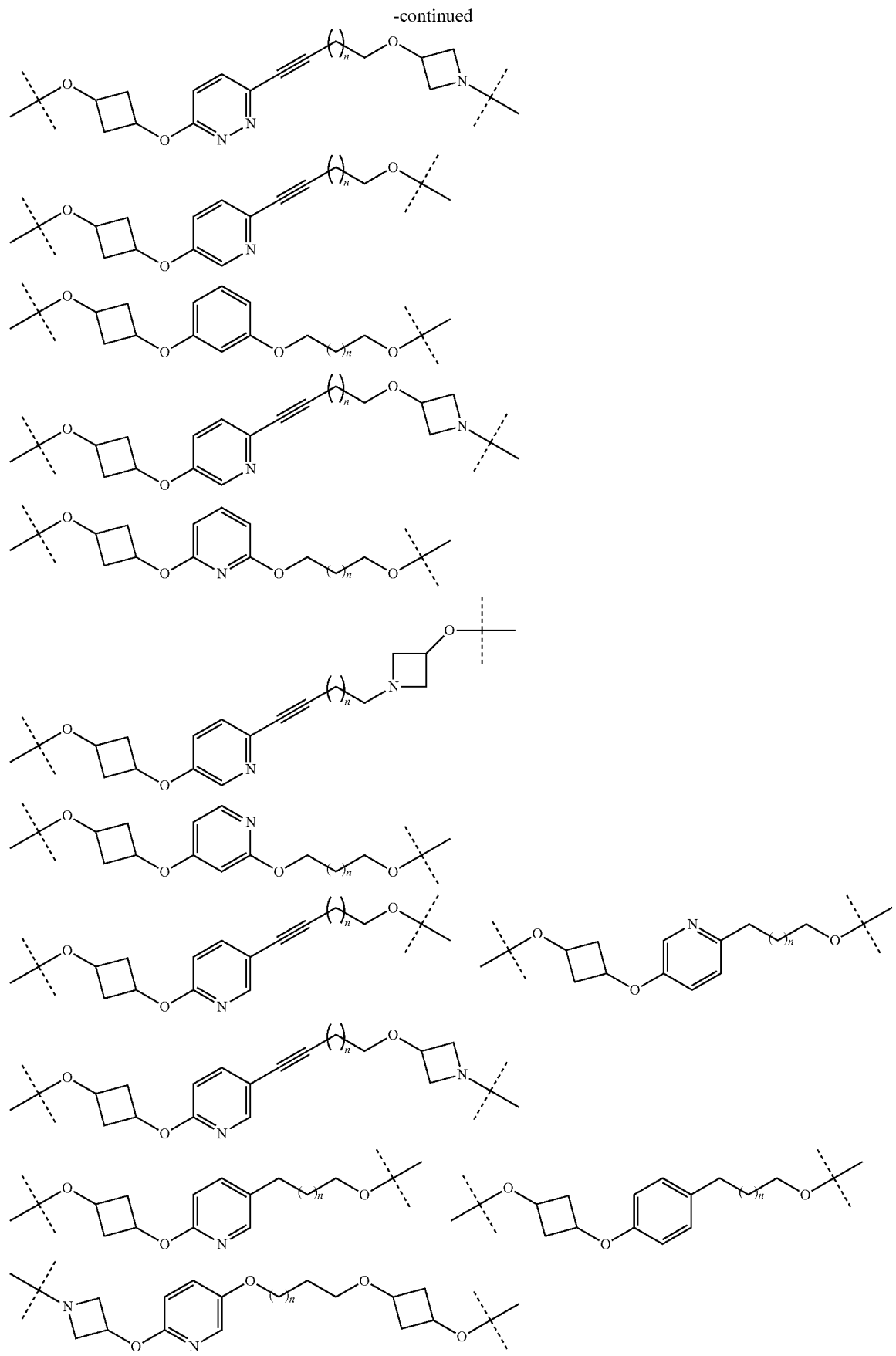

-continued
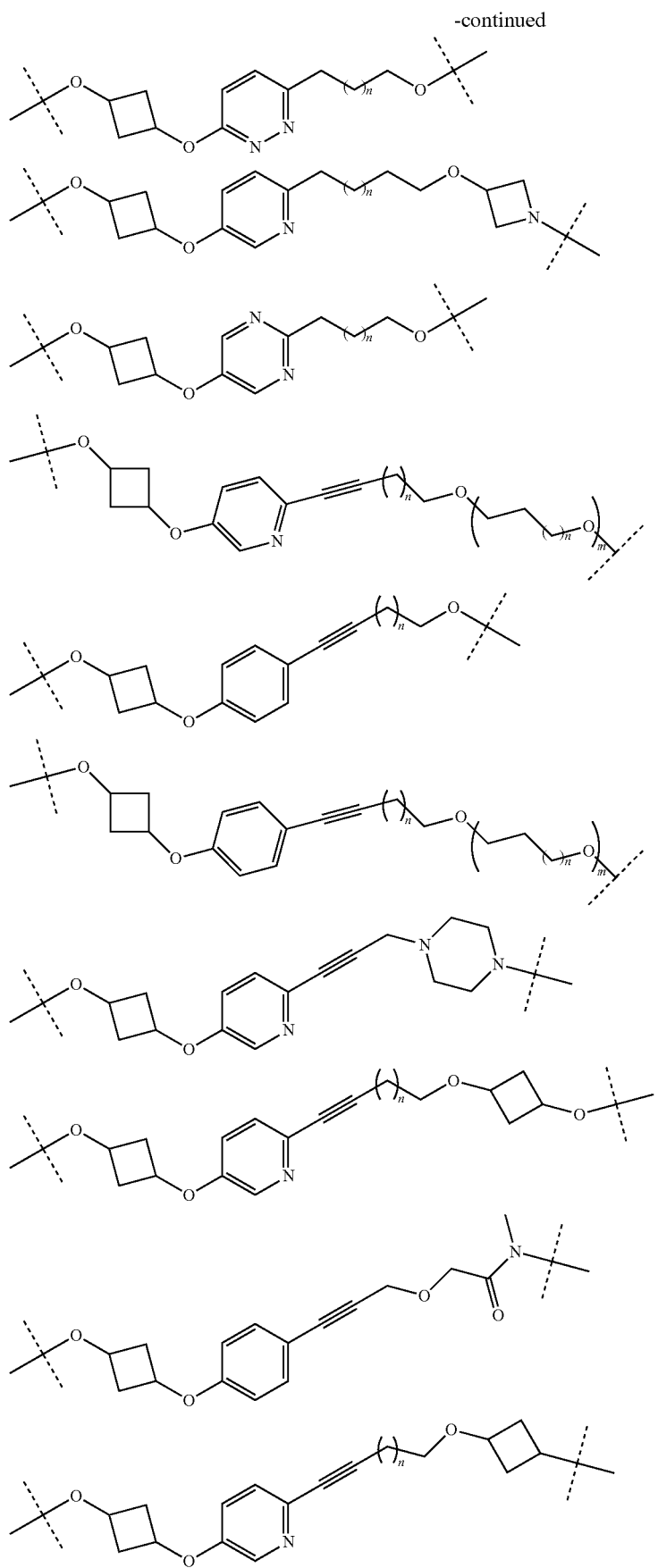

-continued
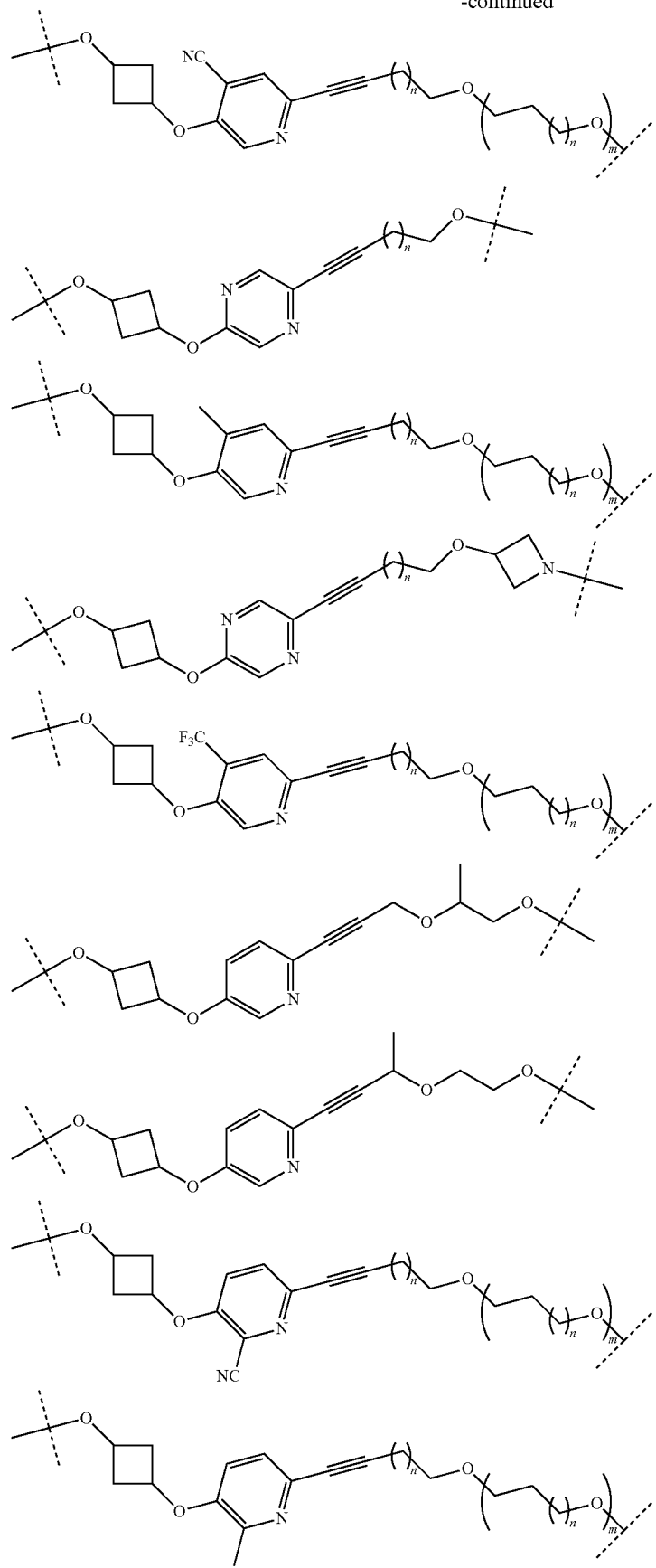

-continued
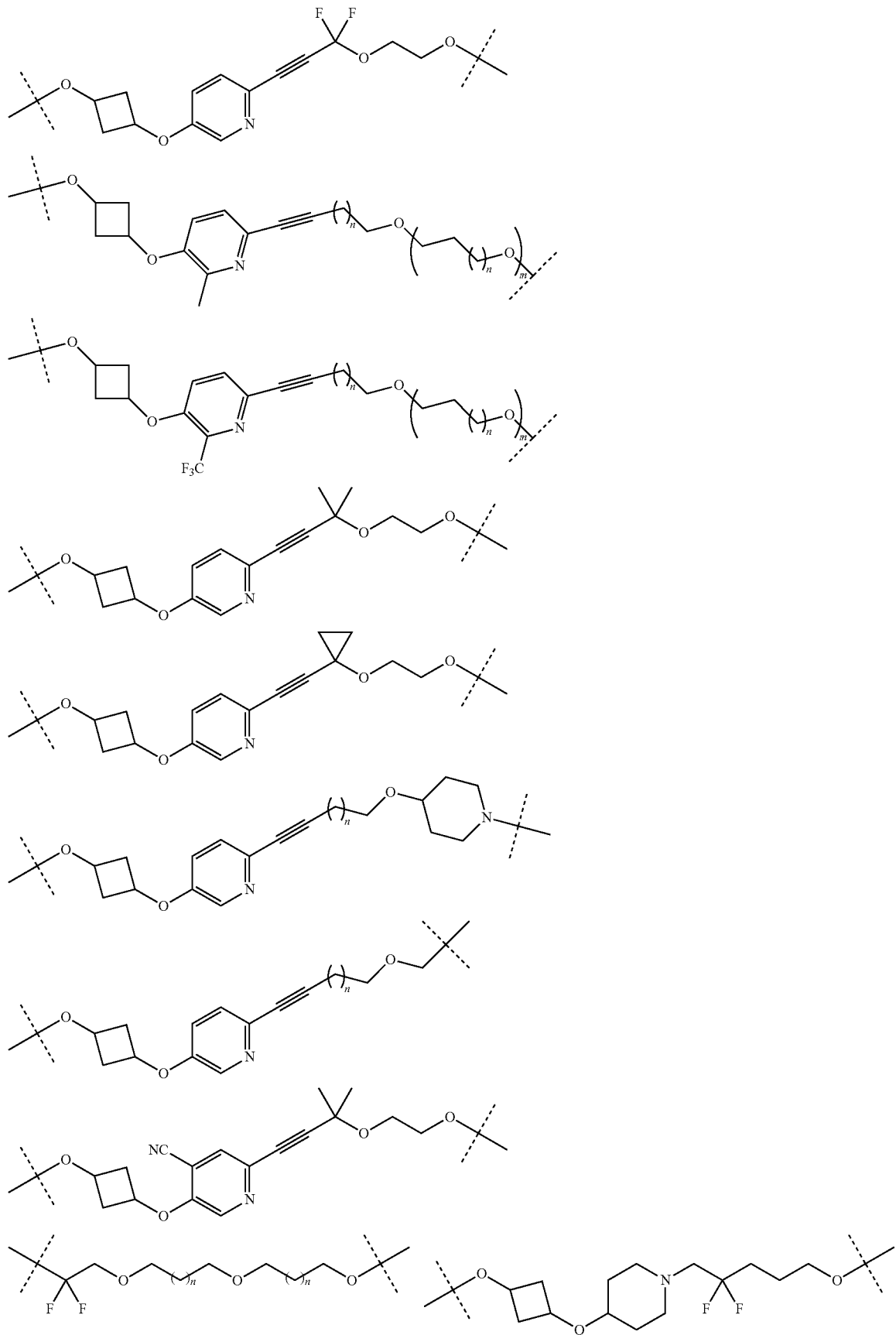

-continued
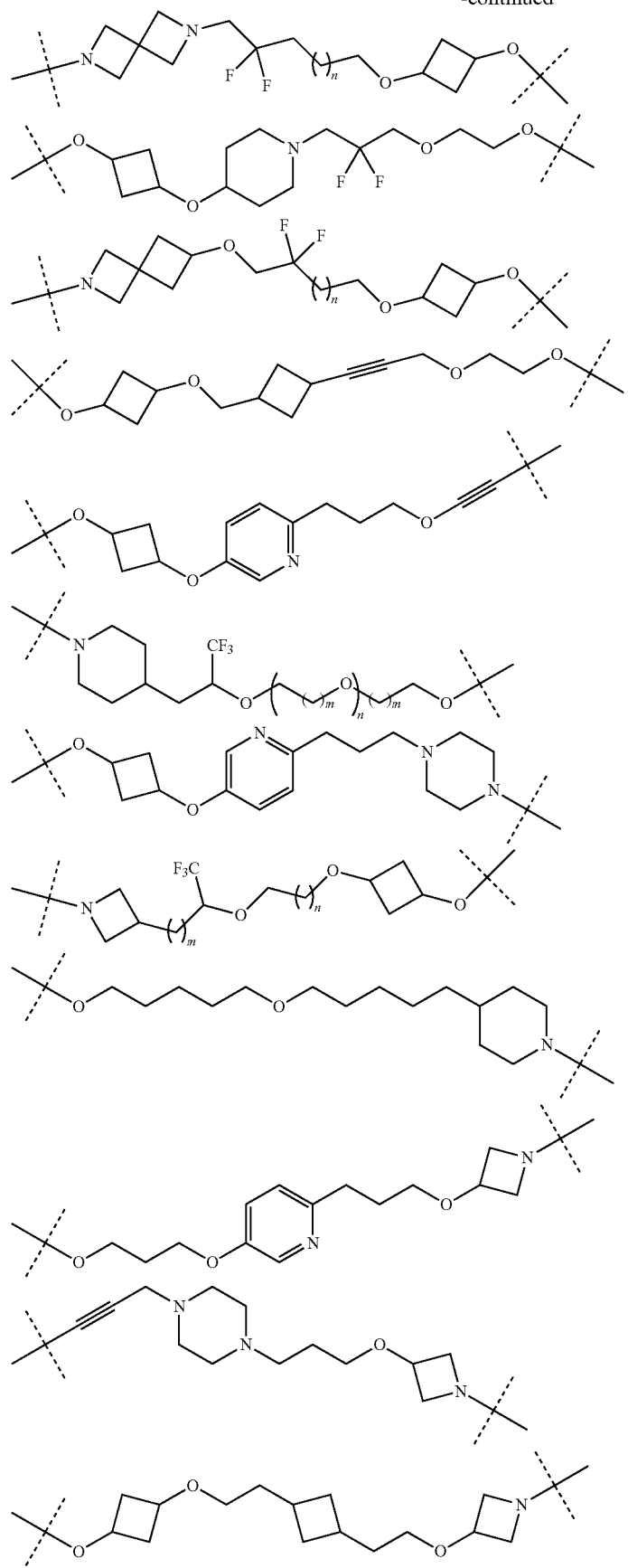

-continued
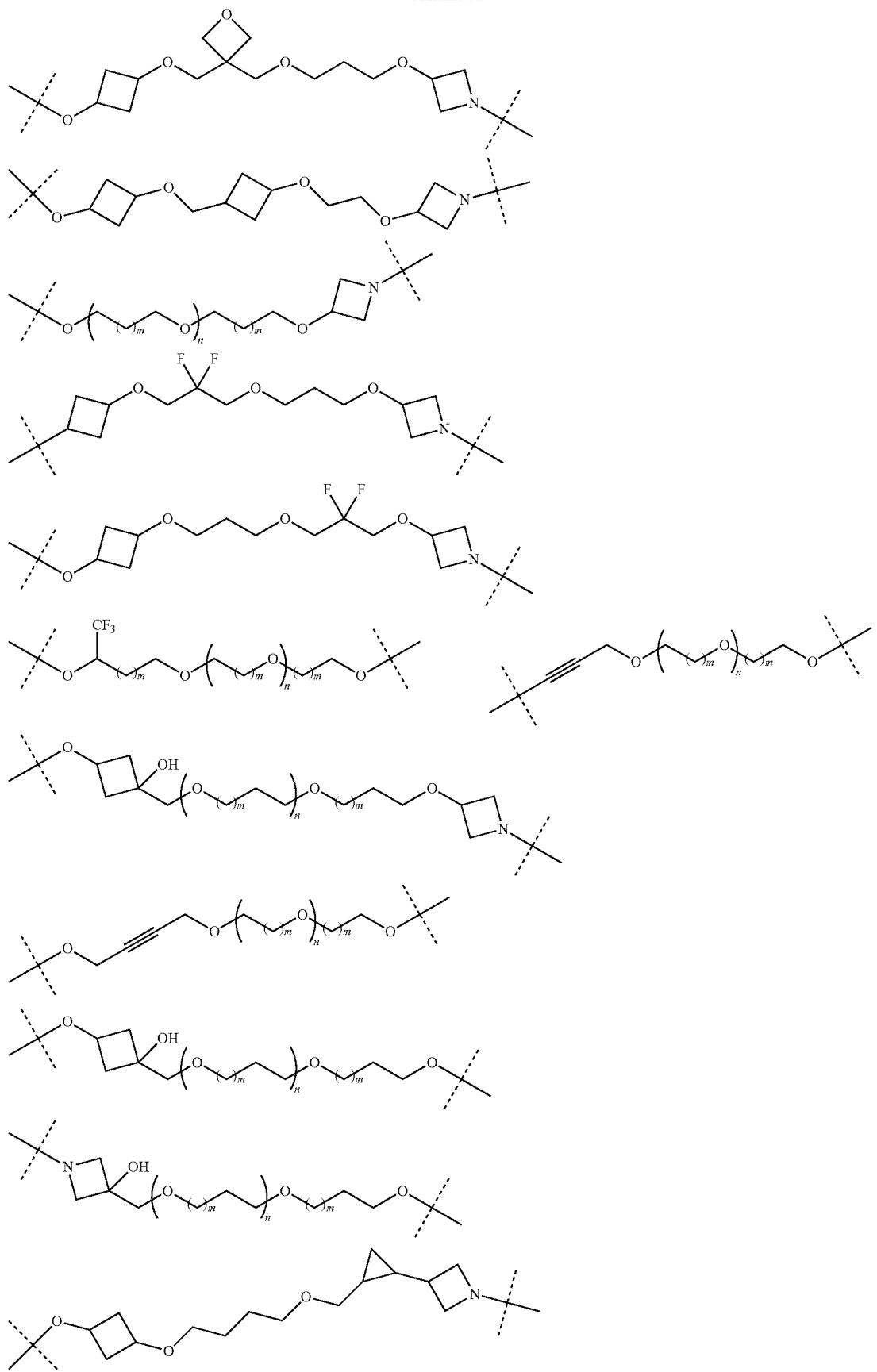

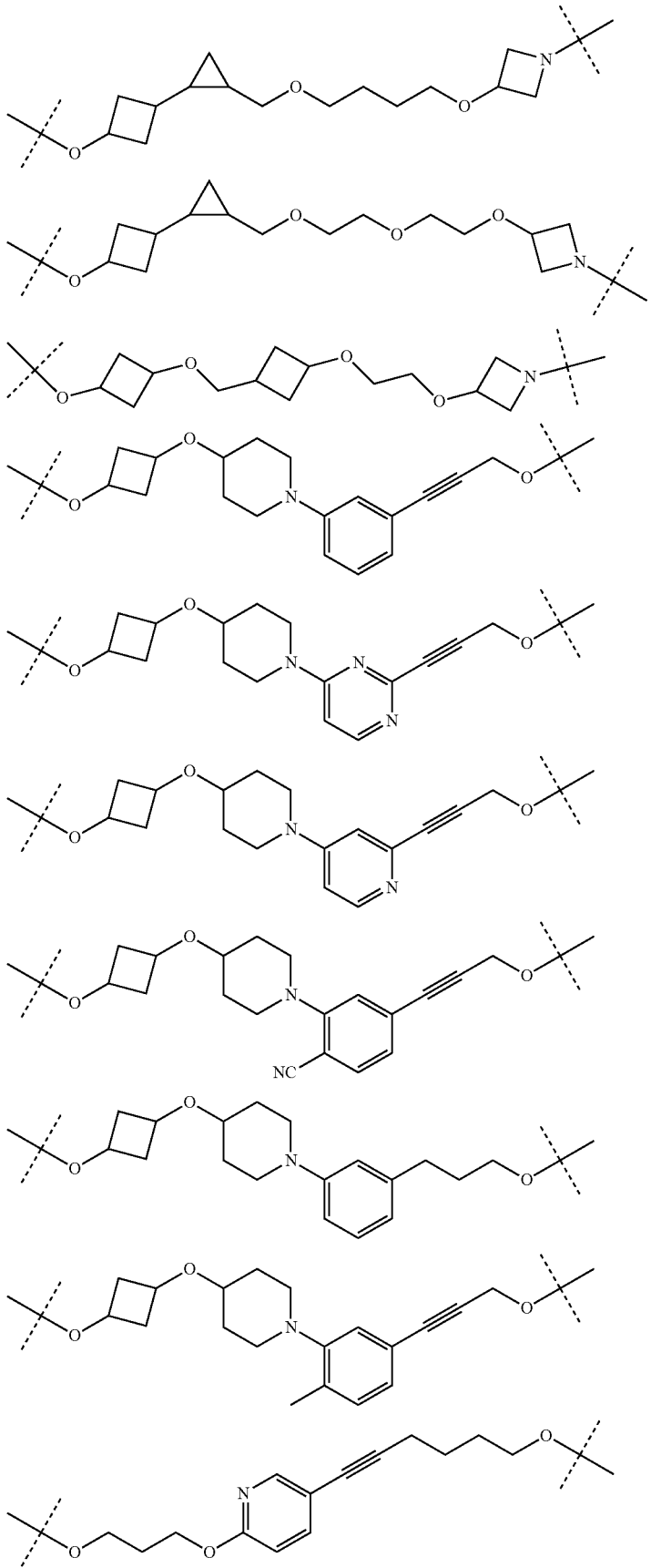

811
-continued
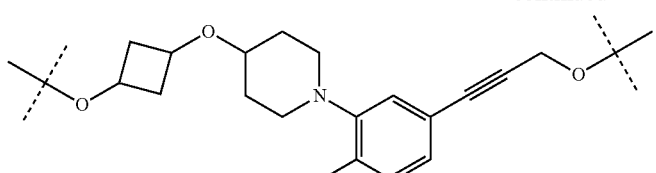
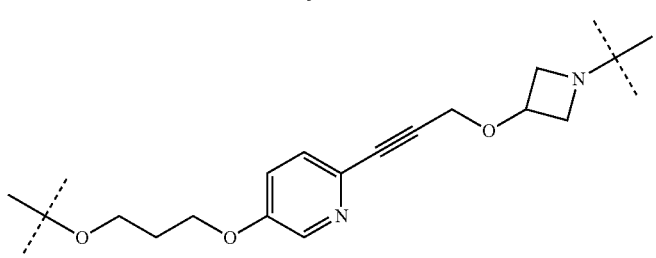
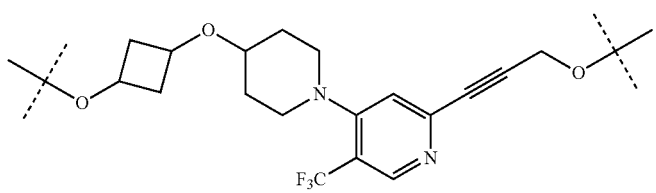
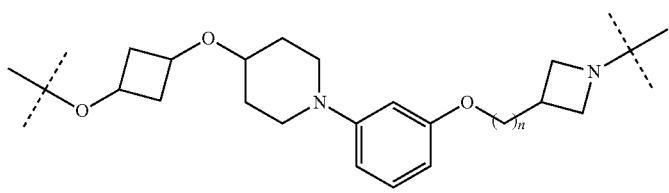
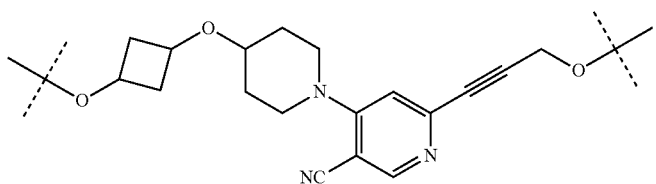
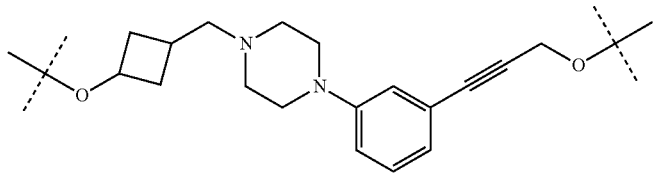
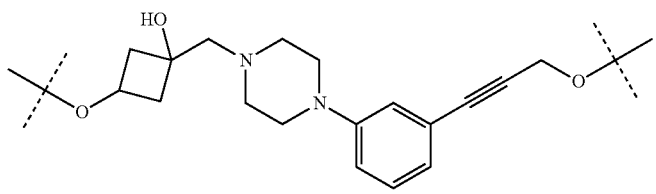
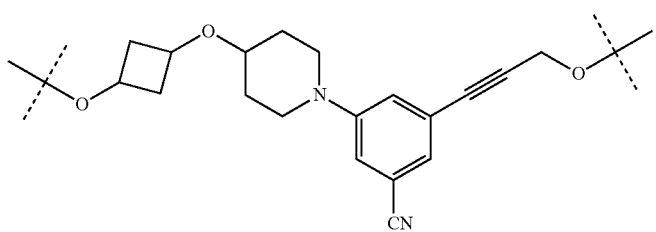

813
814
-continued
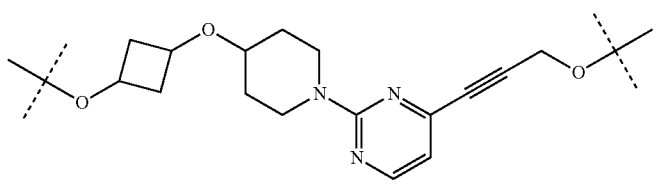
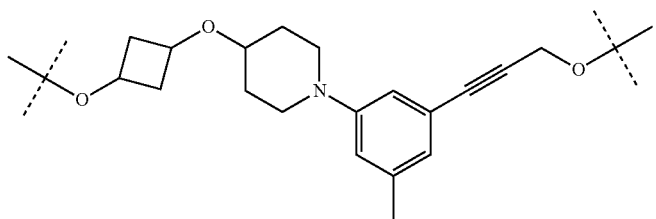
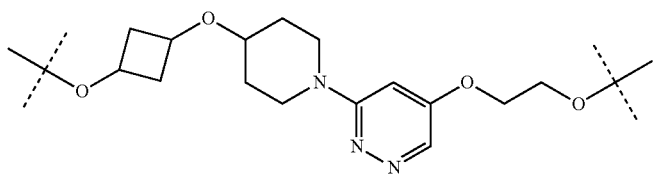
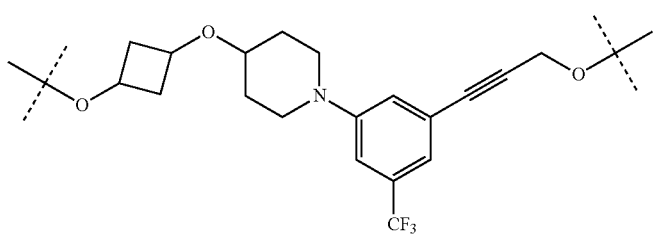
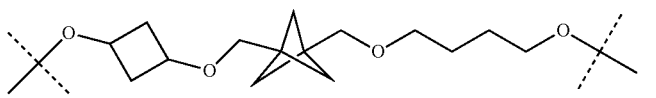
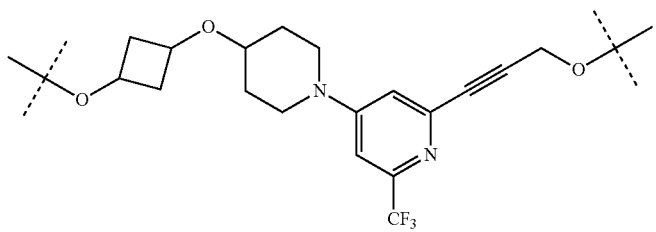
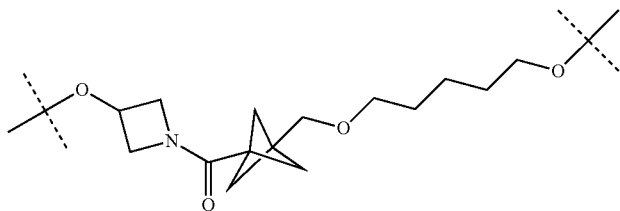
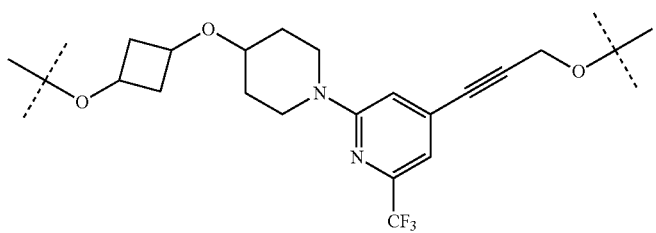

815
816
-continued
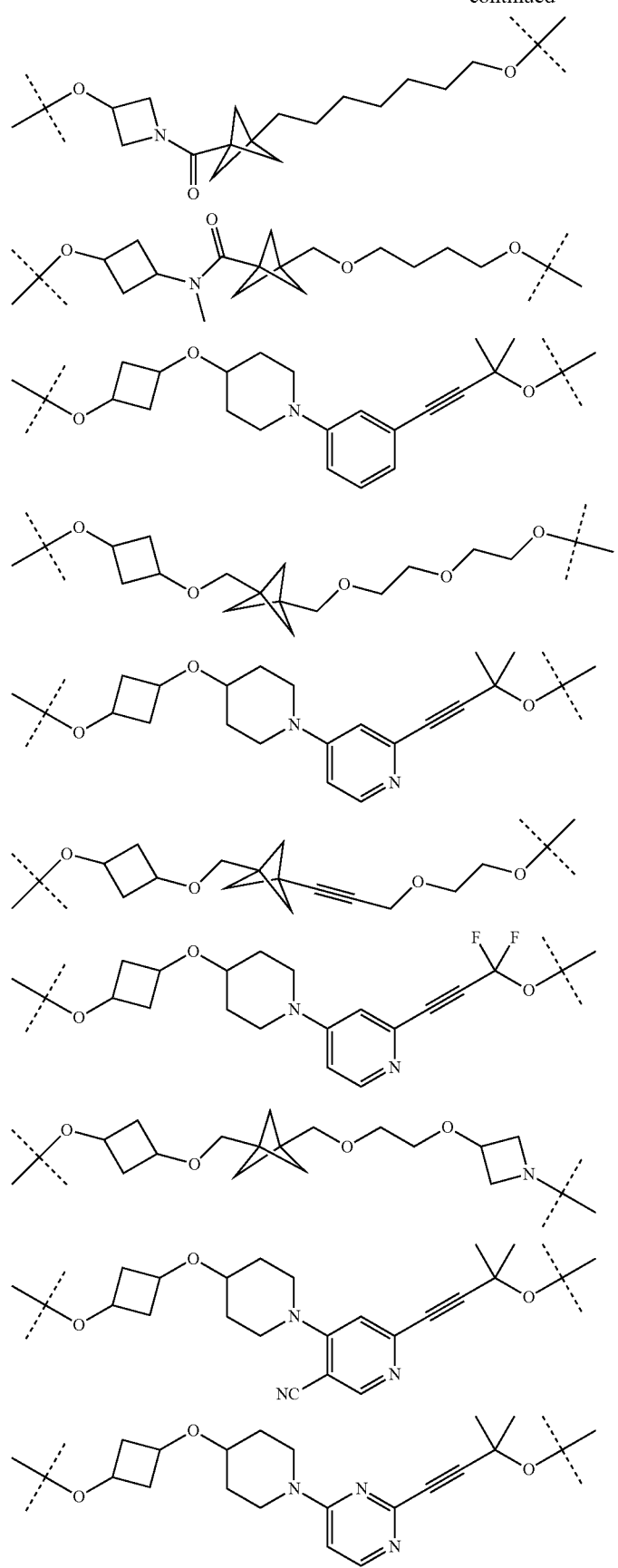

-continued
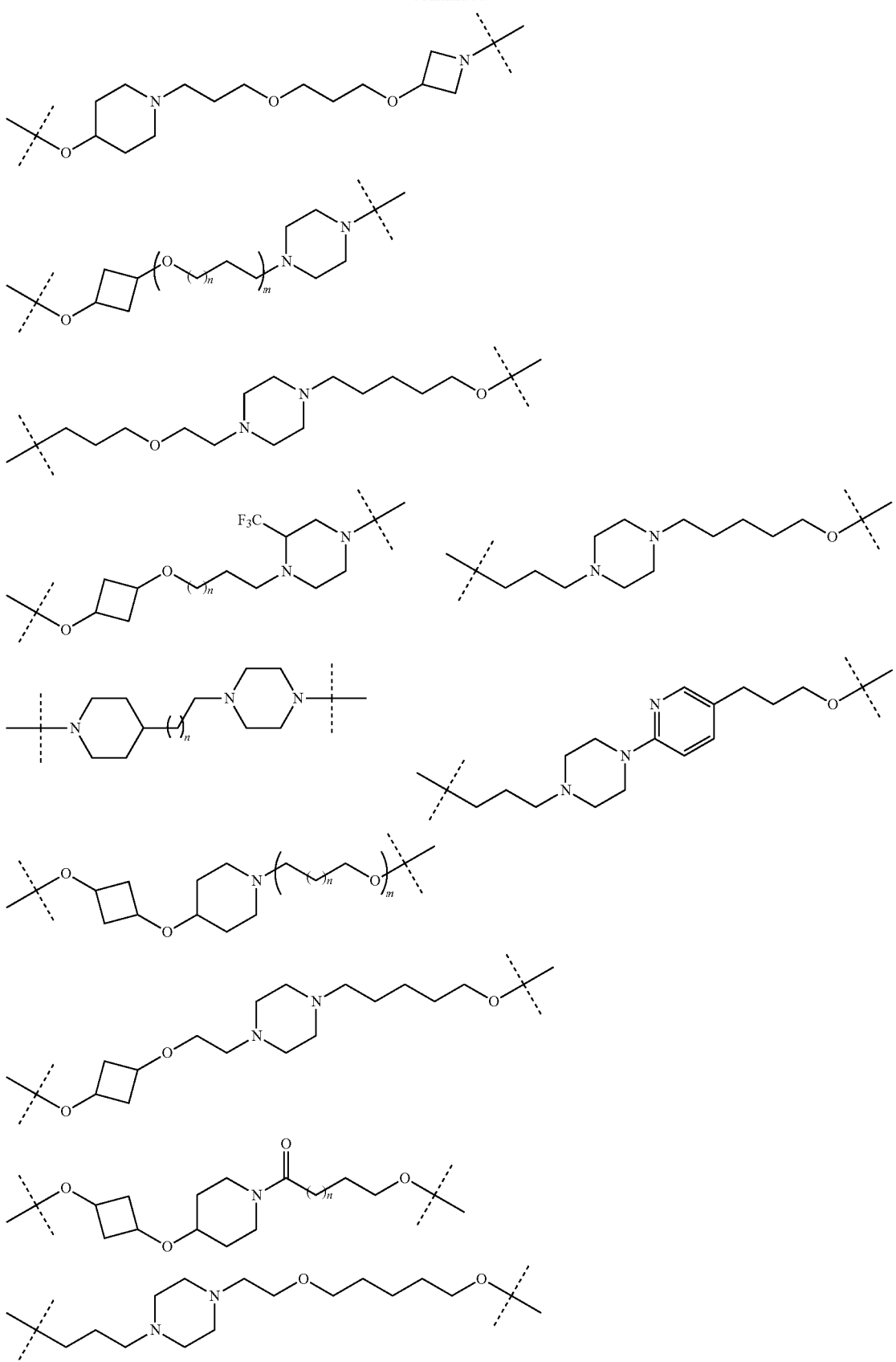

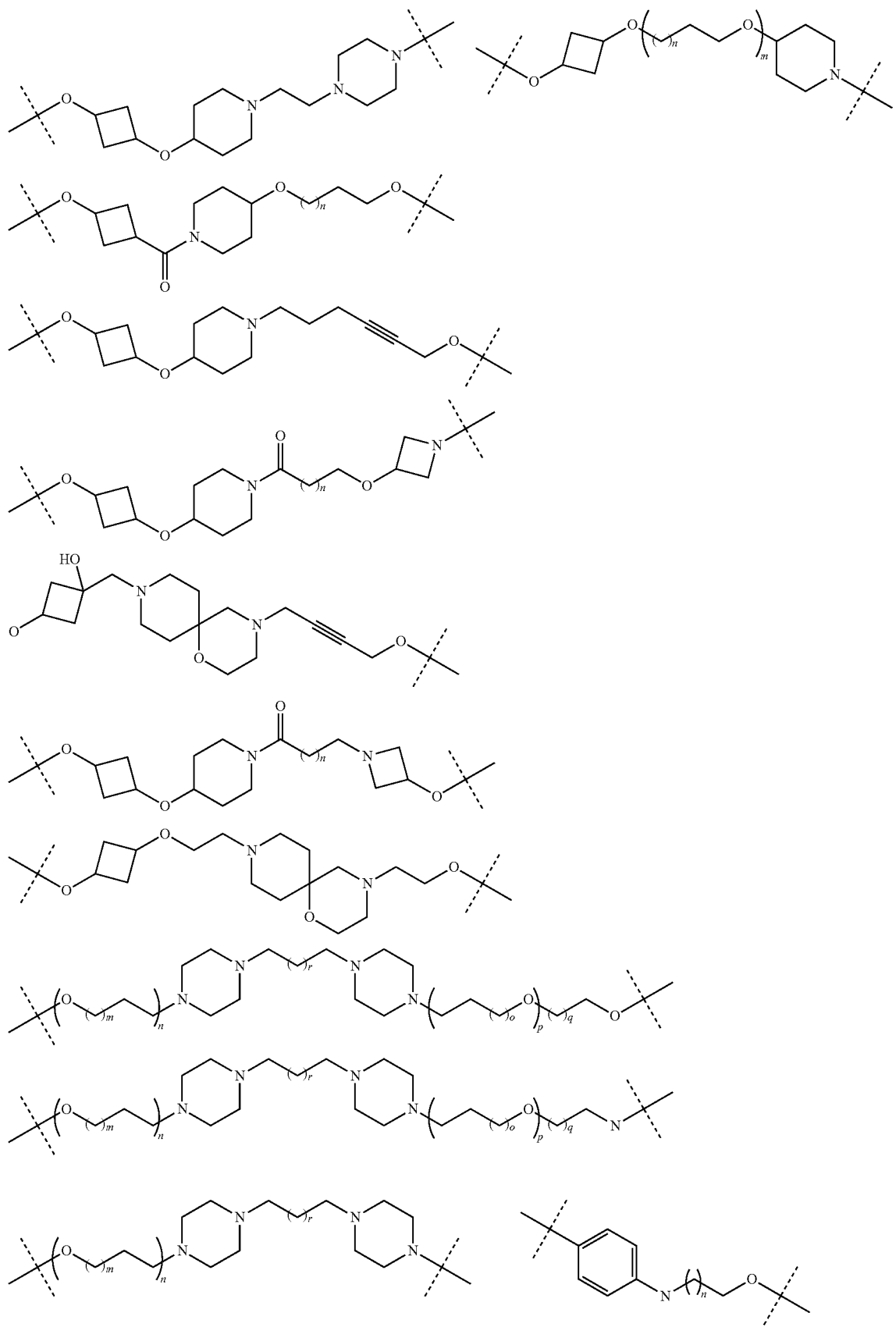

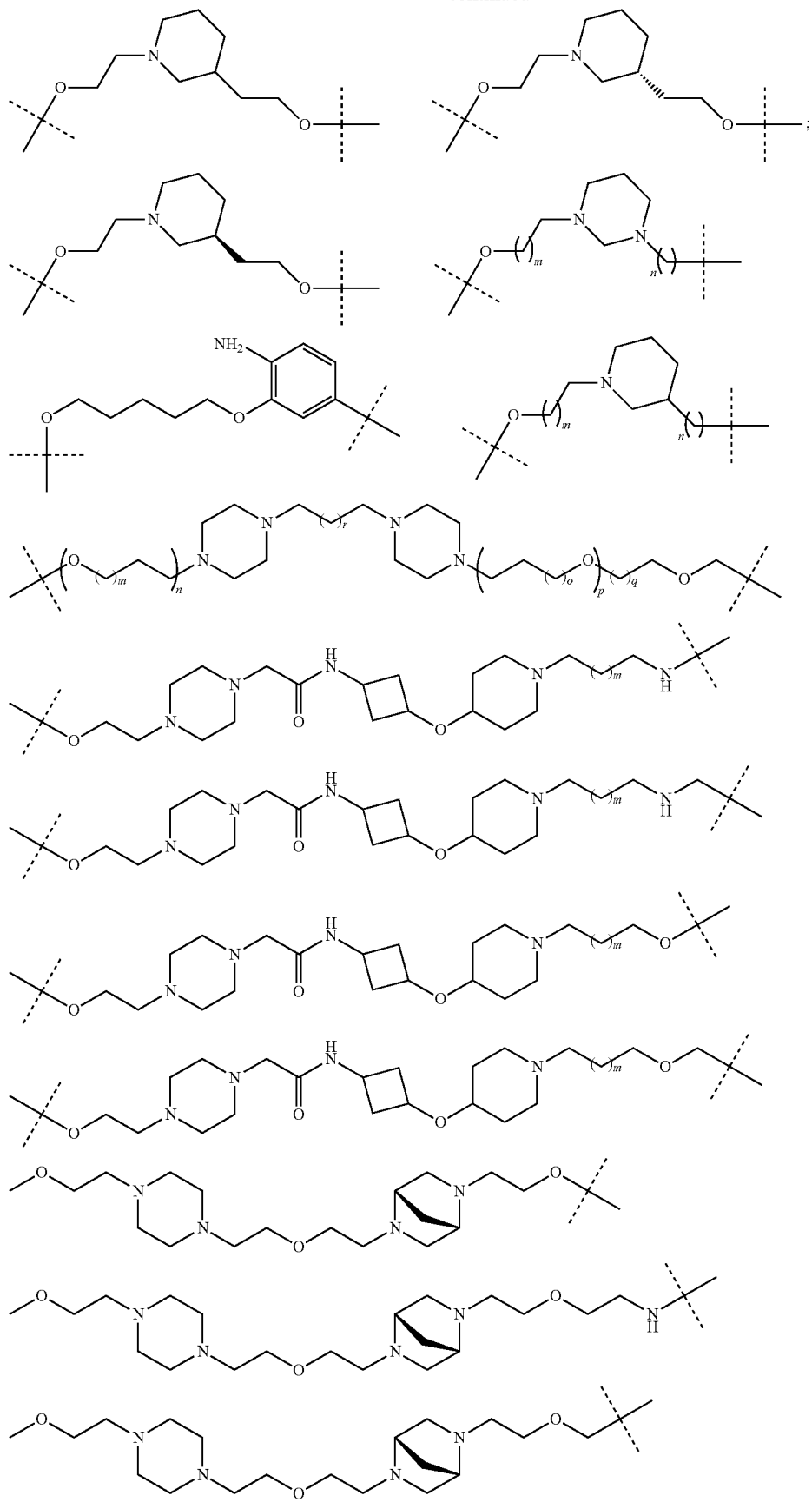

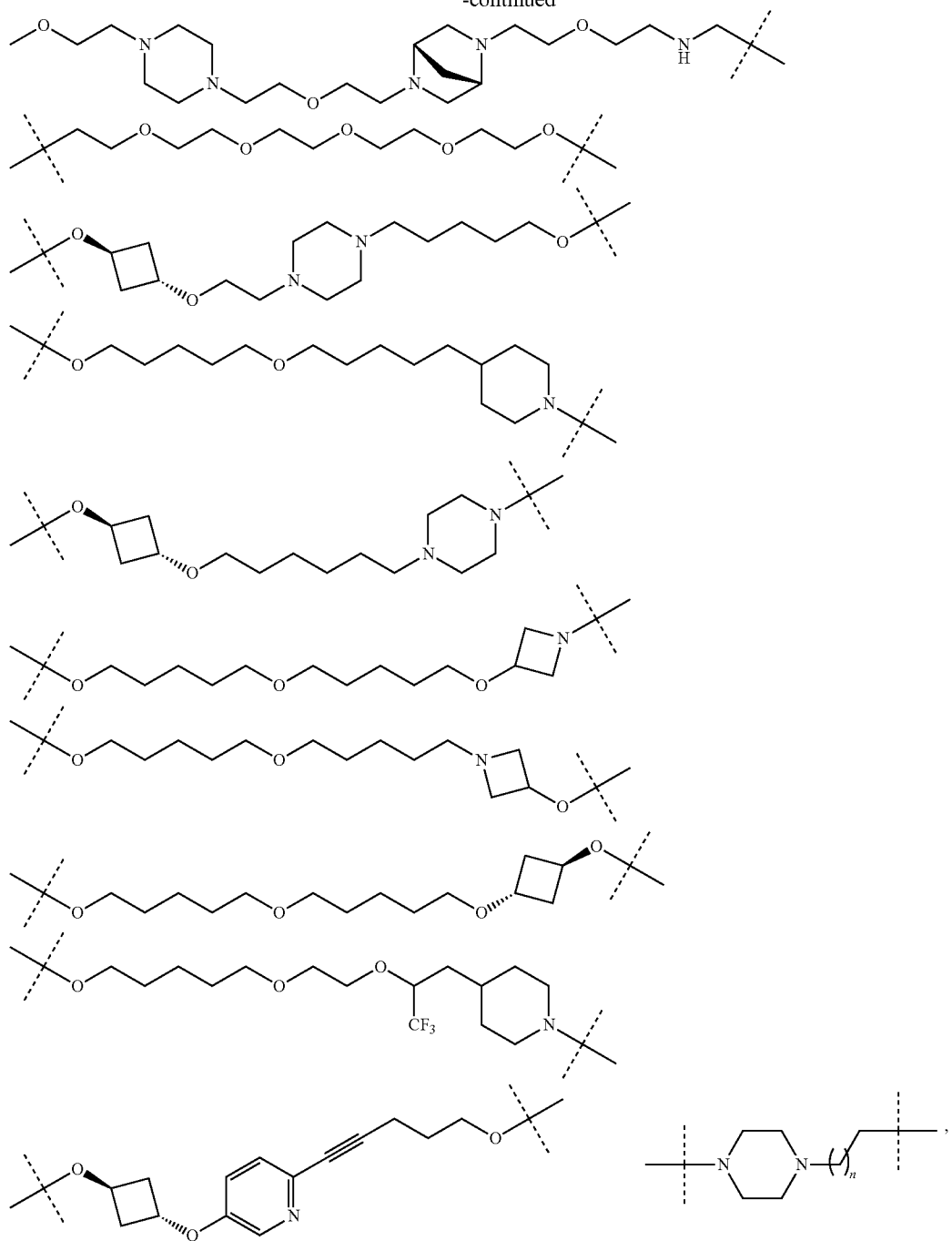
wherein each m, n, o, p, q, and r is independently 0, 1, 2, 3, 4, 5, 6, or 7.
In any aspect or embodiment described herein, L is selected from the group consisting of:
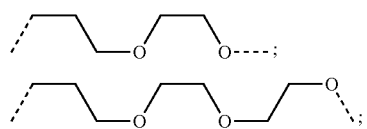
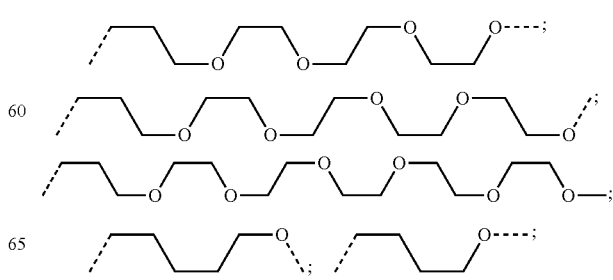

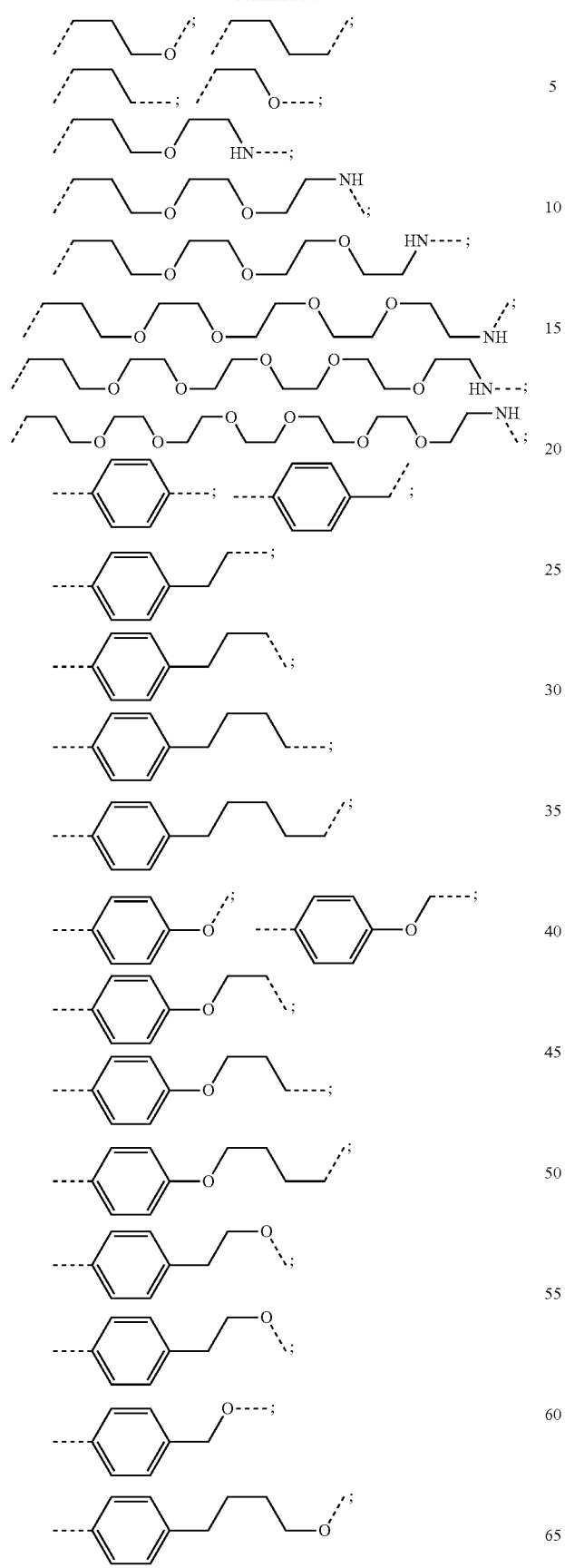
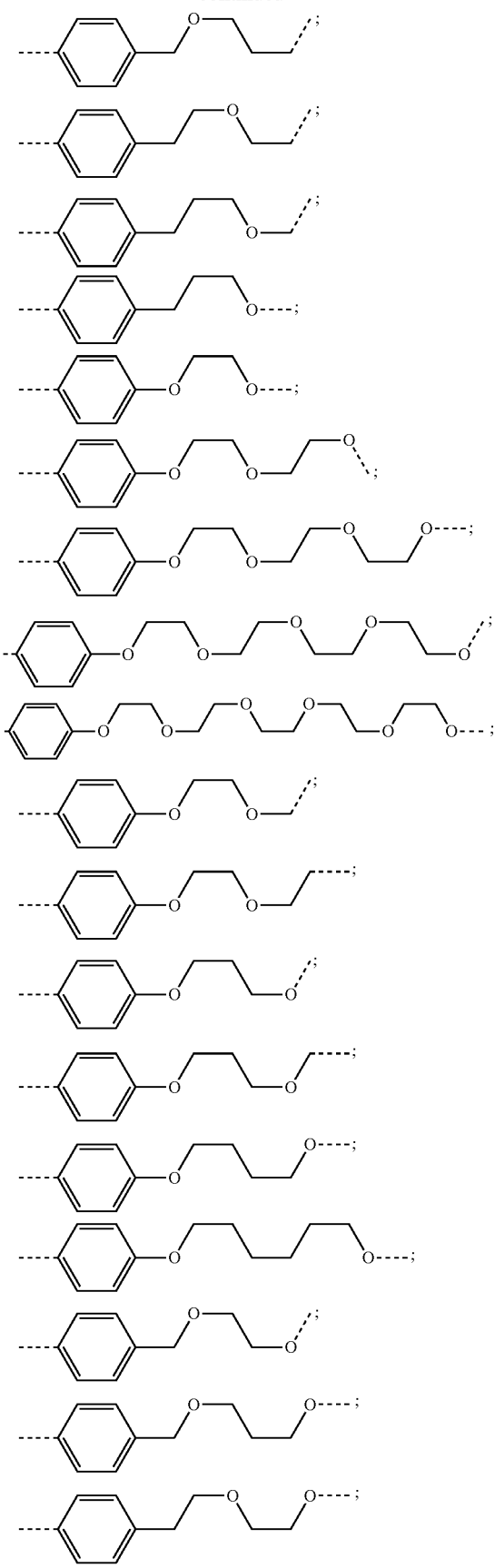

827
-continued
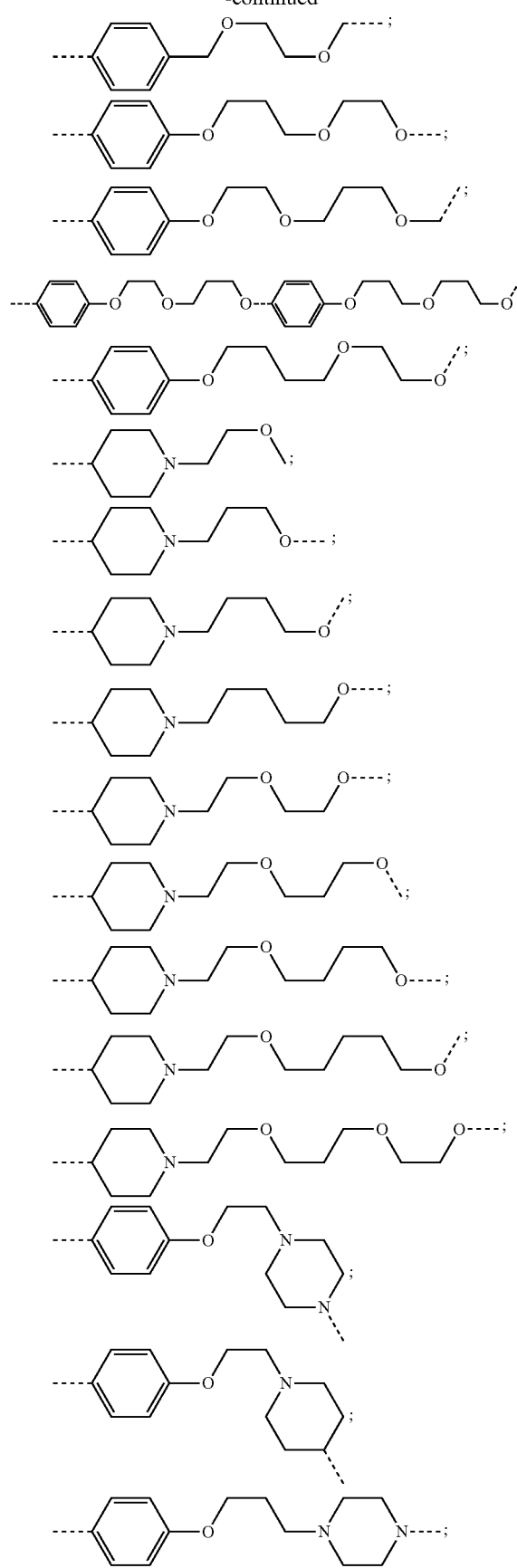
828
-continued
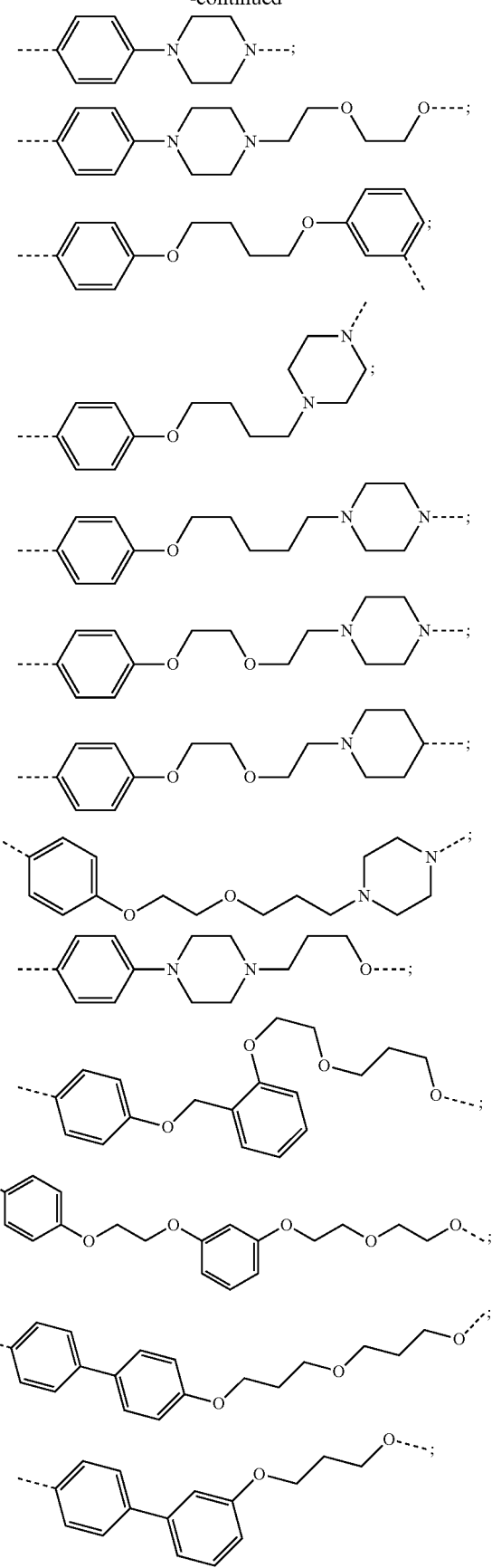

829
-continued
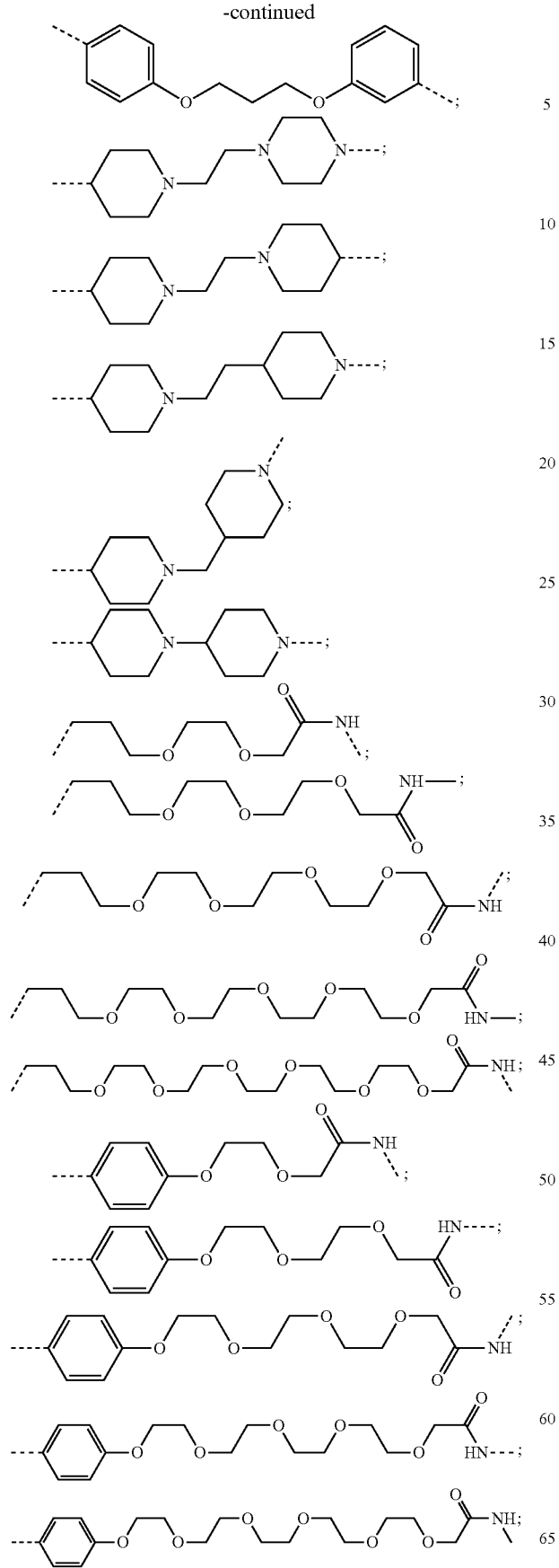
830
-continued
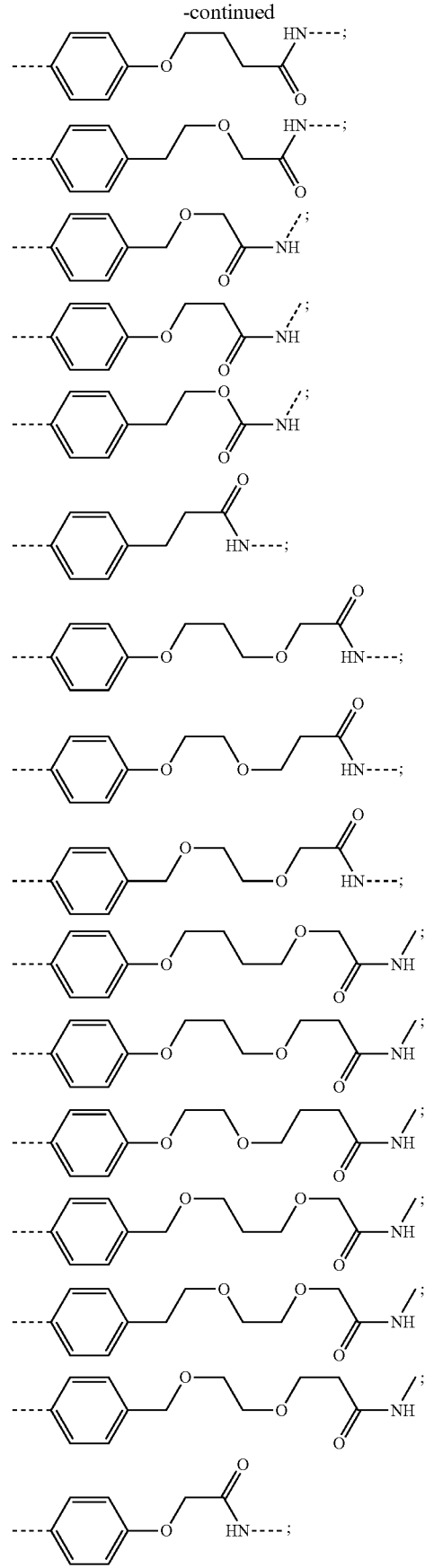

831
-continued
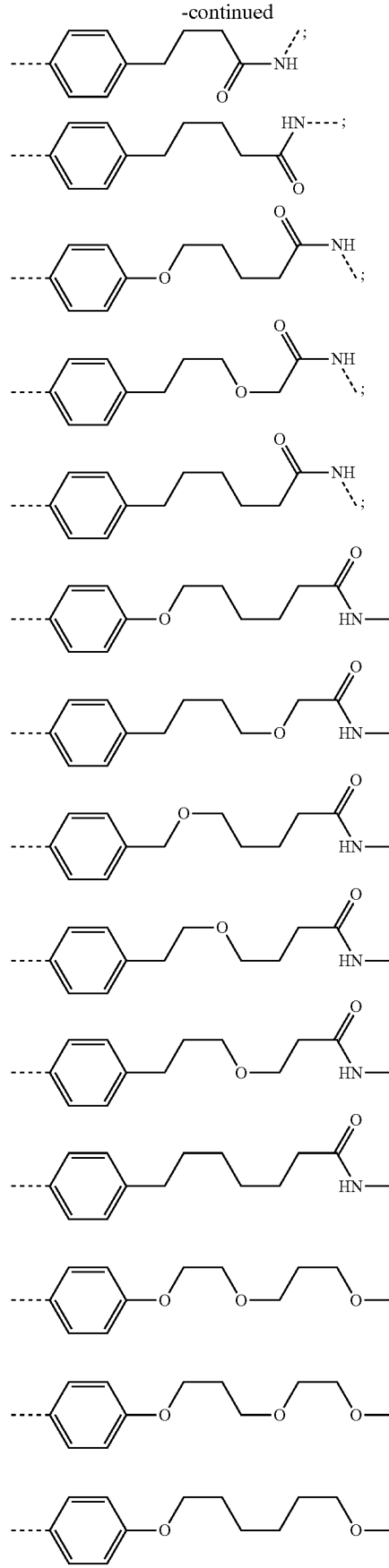
832
-continued
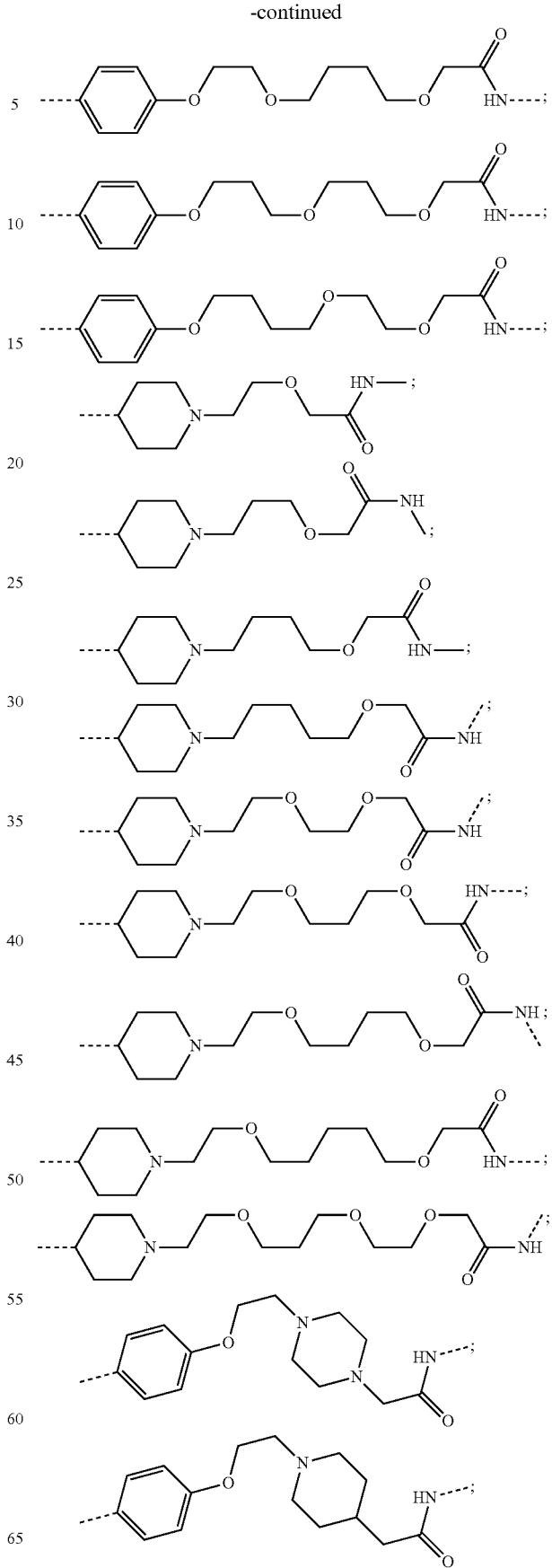

833
-continued
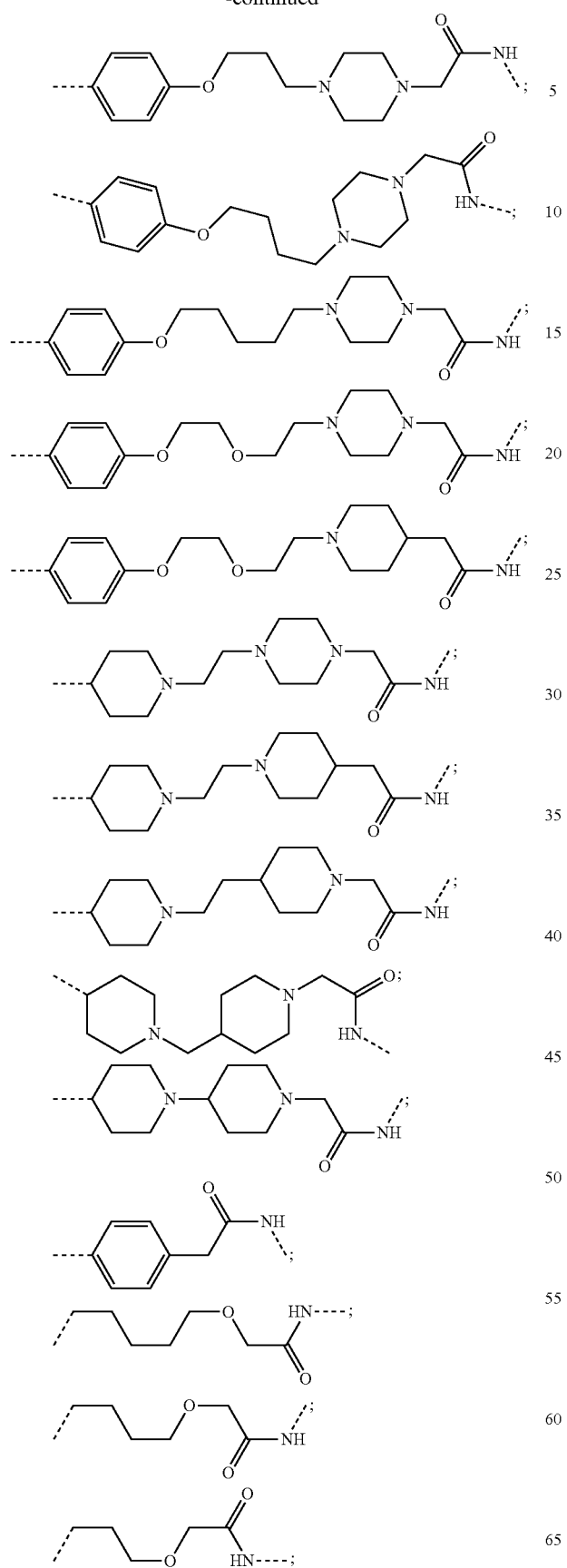
834
-continued
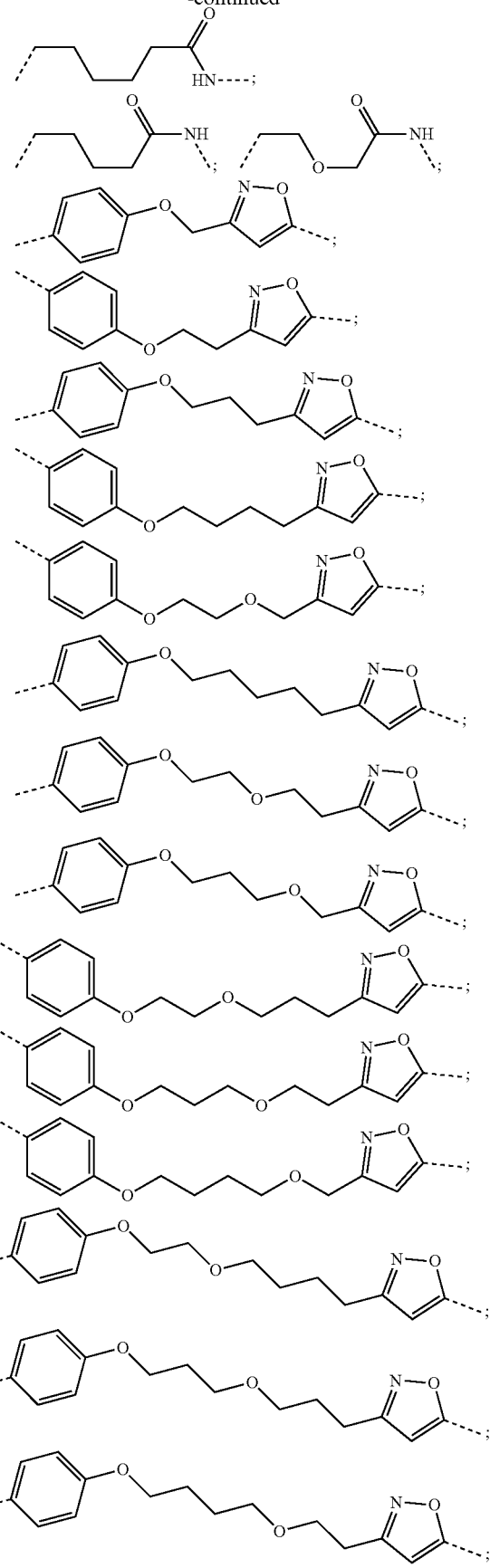

835
-continued
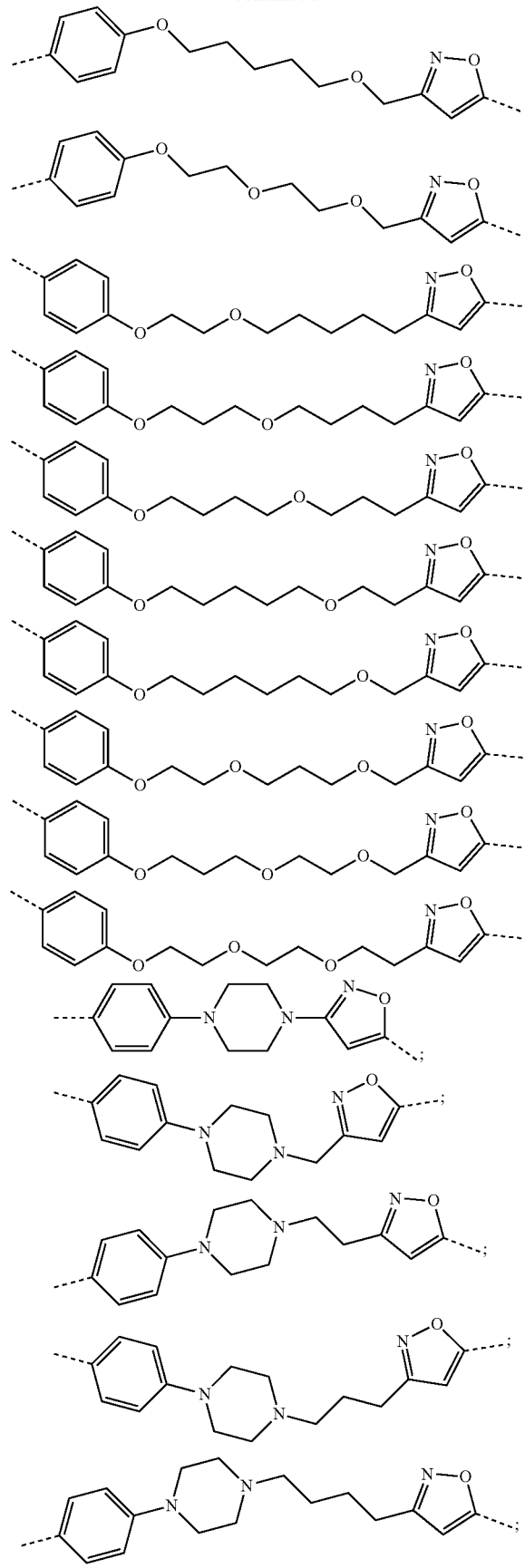
836
-continued
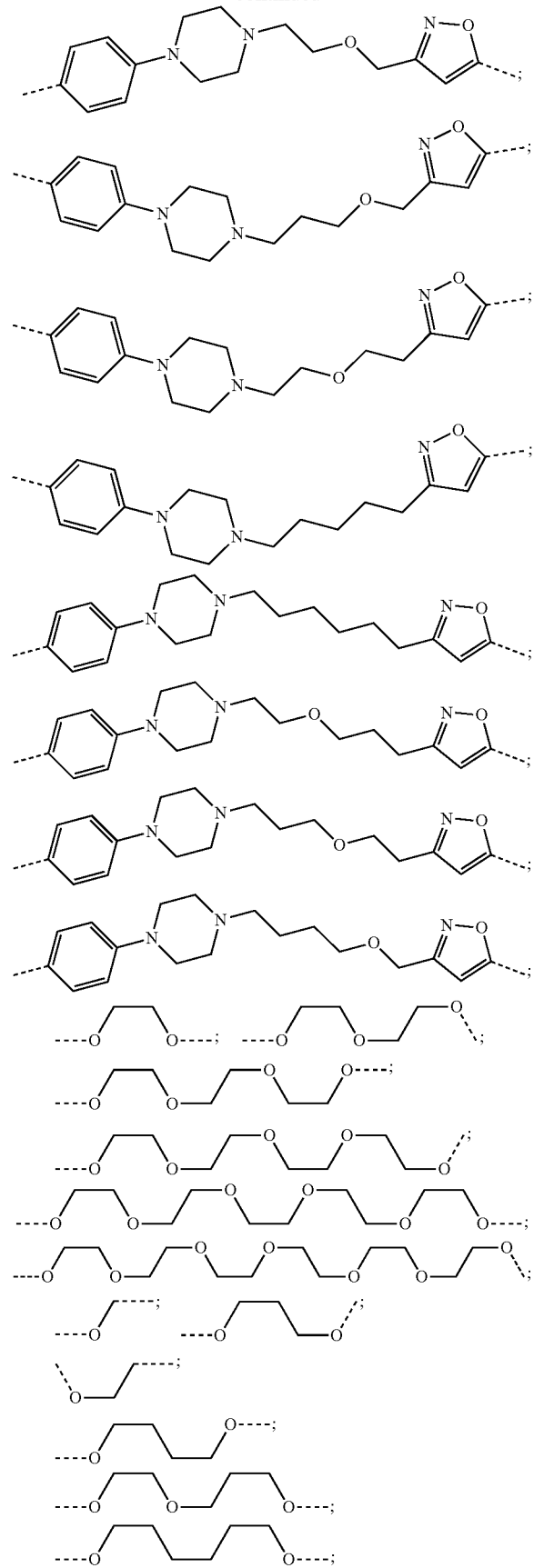

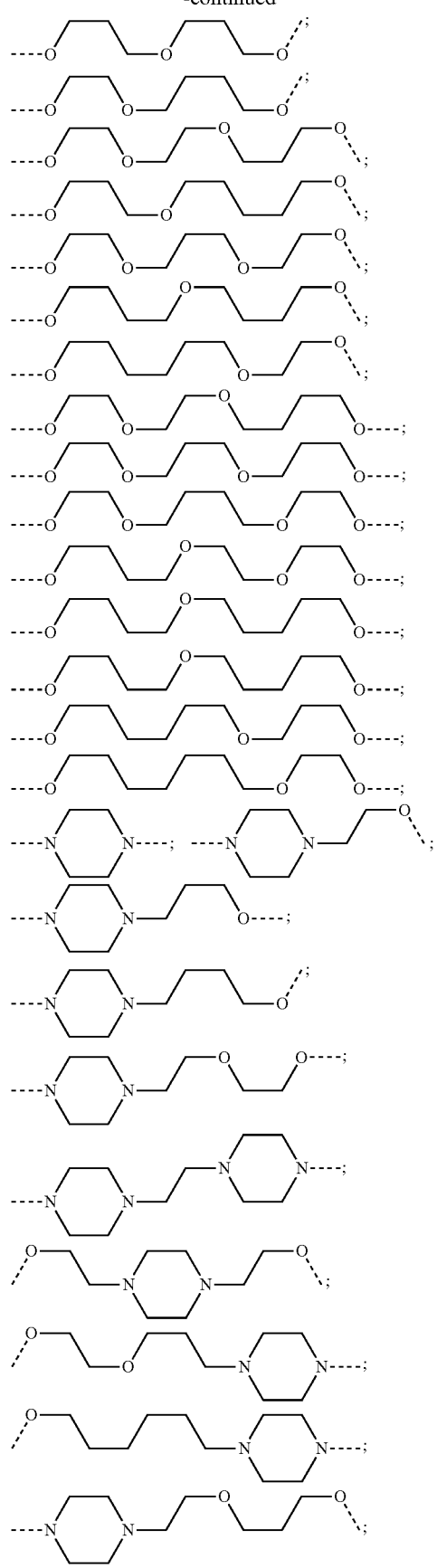
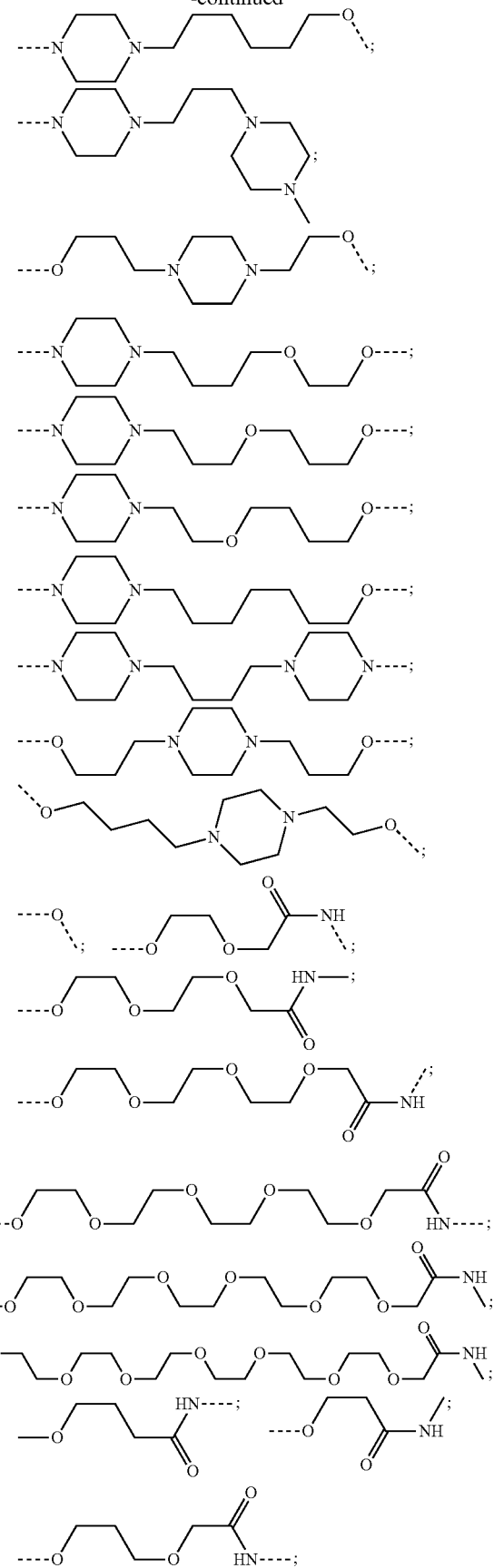

839
-continued
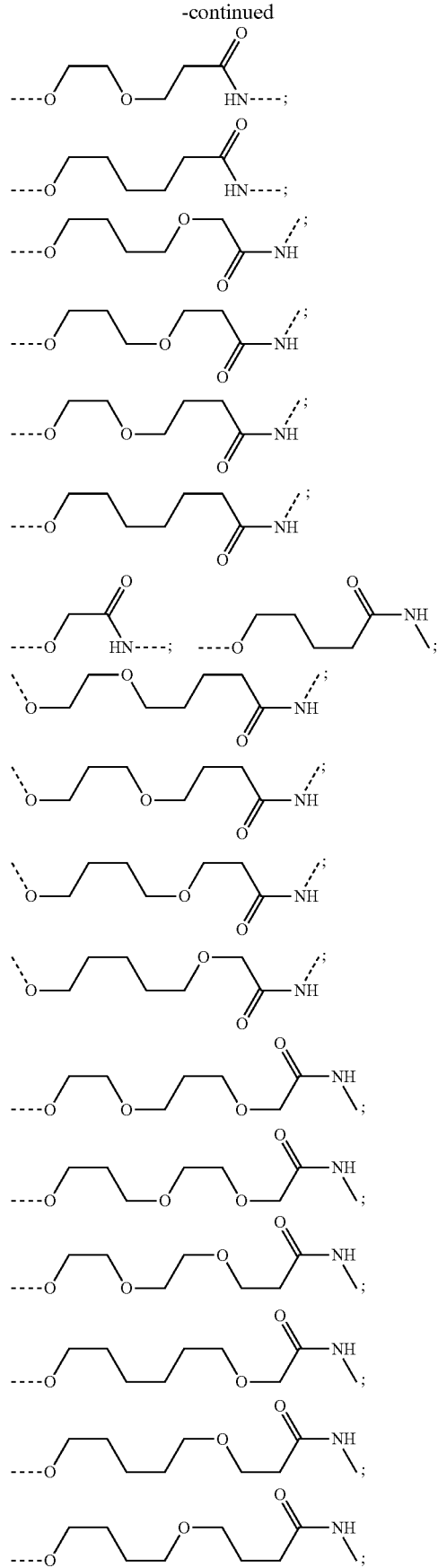
840
-continued
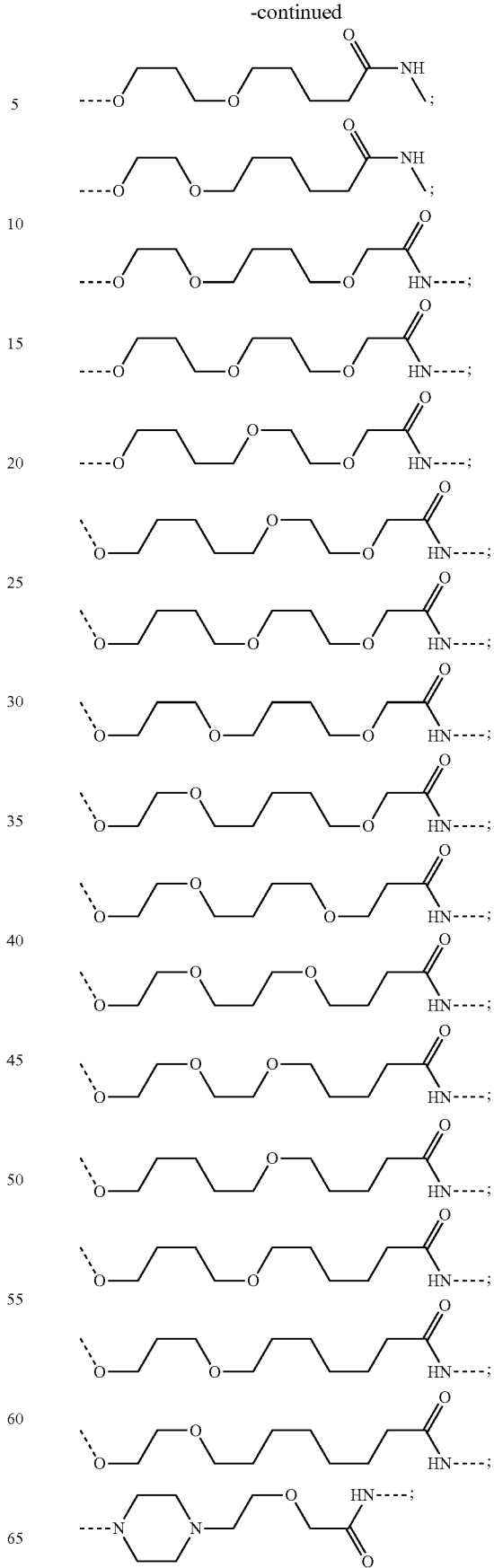

-continued
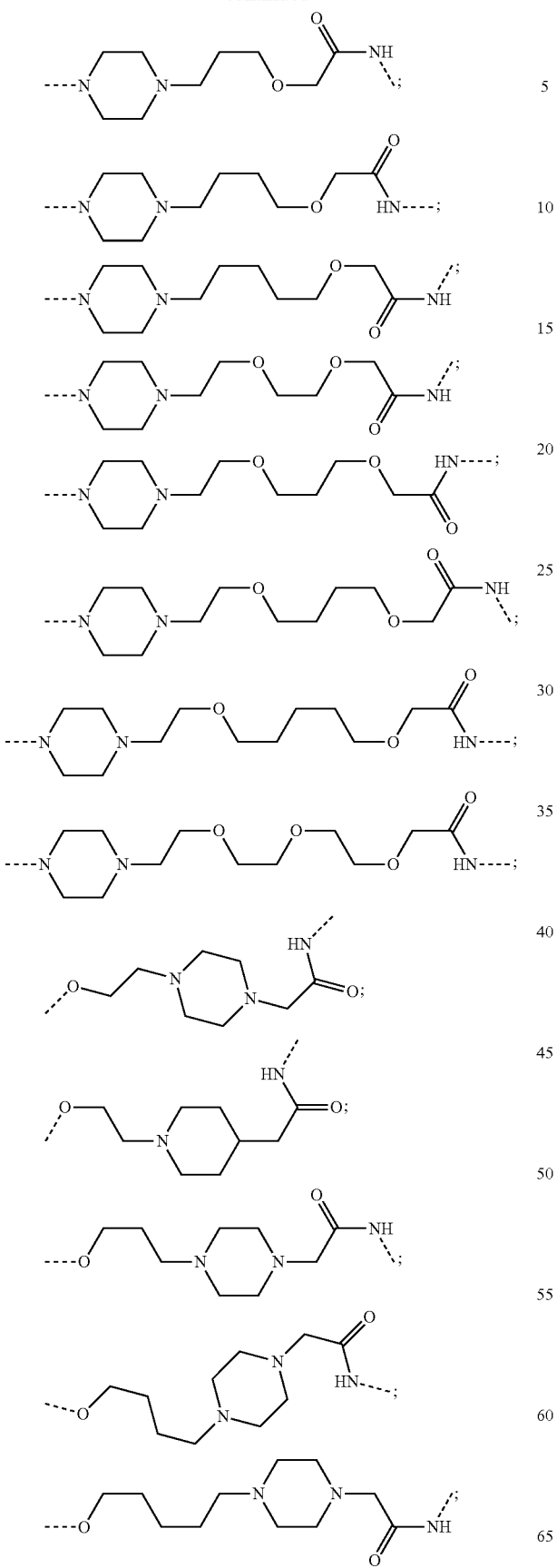
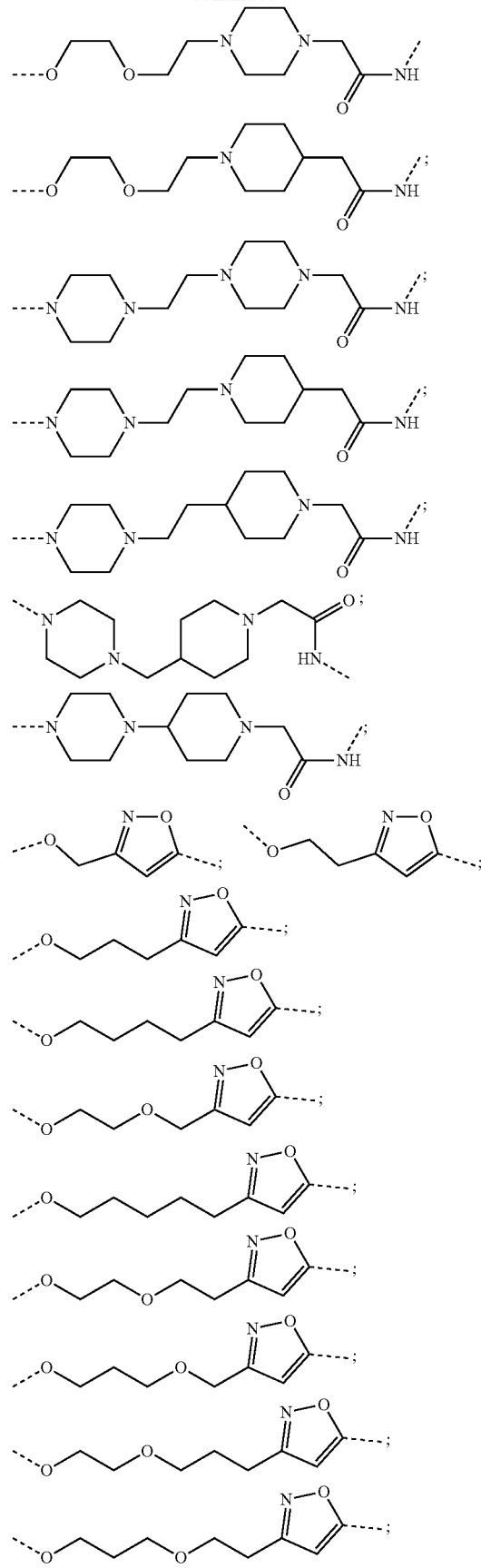

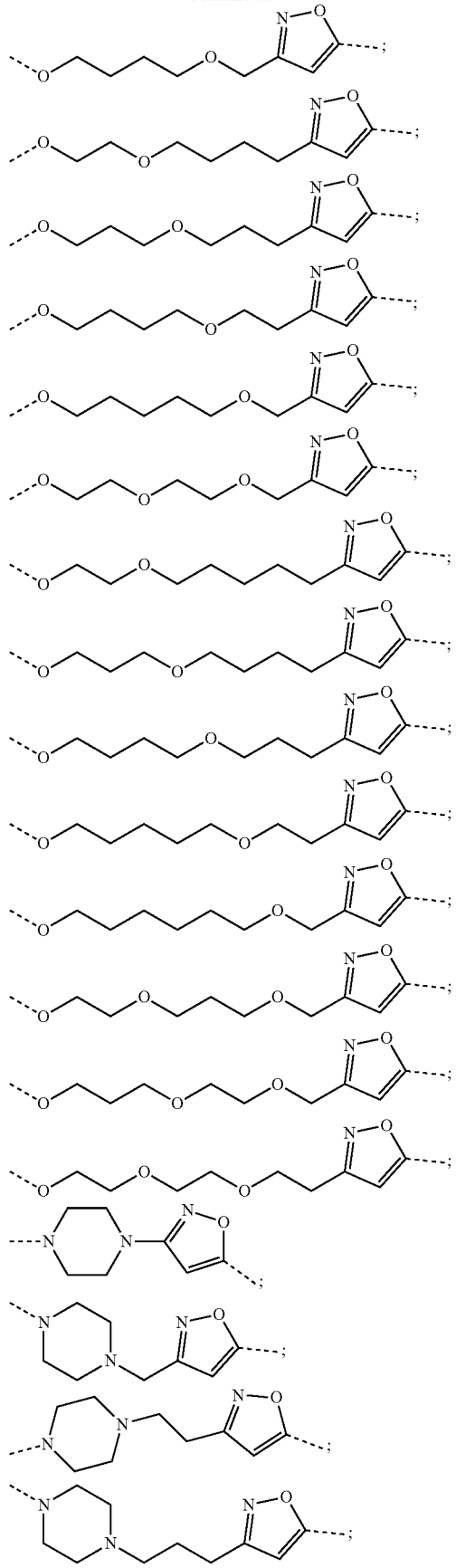

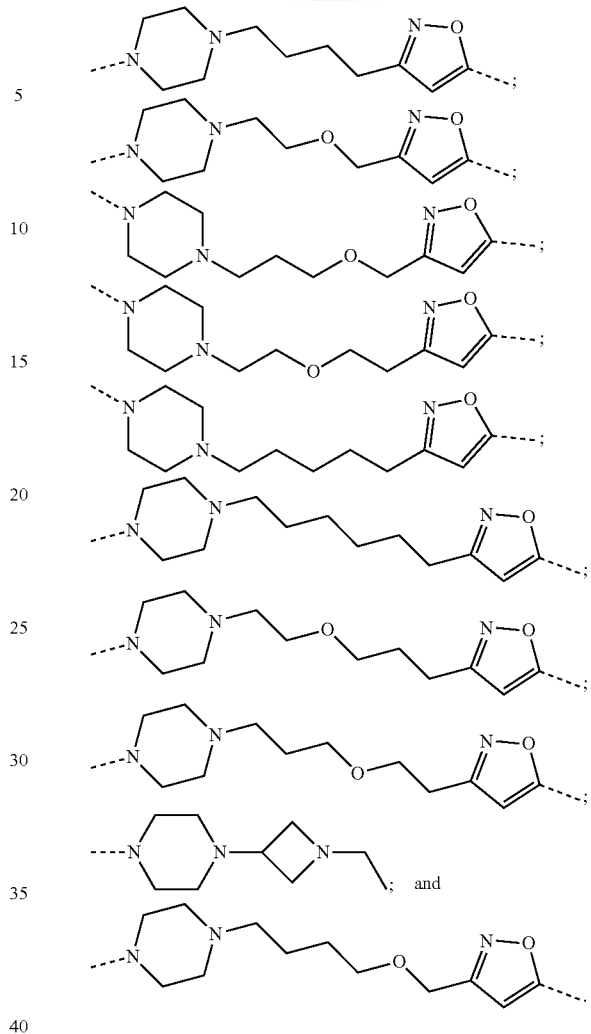

In additional embodiments, the linker (L) comprises a structure selected from, but not limited to the structure shown below, where a dashed line indicates the attachment point to the PTM or ULM moieties.

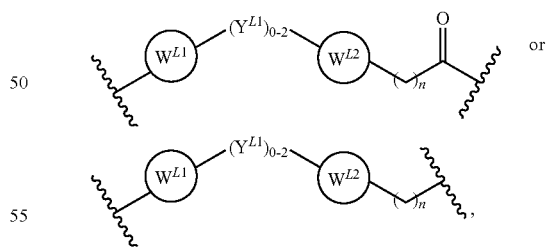

wherein:

$W^{L1}$ and $W^{L2}$ are each independently a 4-8 membered ring with 0-4 heteroatoms, optionally substituted with $R^Q$, each $R^Q$ is independently a H, halo, OH, CN, $CF_3$, $C_1$-$C_6$ alkyl (linear, branched, optionally substituted), $C_1$-$C_6$ alkoxy (linear, branched, optionally substituted), or 2 $R^Q$ groups taken together with the atom they are attached to, form a 4-8 membered ring system containing 0-4 heteroatoms;

$Y^{L1}$ is each independently a bond, $C_1$-$C_6$ alkyl (linear, branched, optionally substituted) and optionally one or more C atoms are replaced with O; or $C_1$-$C_6$ alkoxy (linear, branched, optionally substituted);

n is 0-10; and a dashed line indicates the attachment point to the PTM or ULM moieties.

In additional embodiments, the linker (L) comprises a structure selected from, but not limited to the structure shown below, where a dashed line indicates the attachment point to the PTM or ULM moieties.

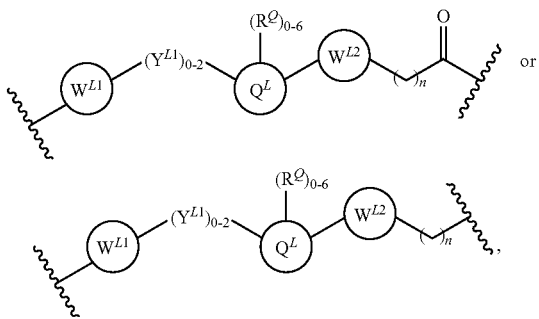

wherein:
$W^{L1}$ and $W^{L2}$ are each independently aryl, heteroaryl, cyclic, heterocyclic, $C_{1-6}$ alkyl, bicyclic, biaryl, biheteroaryl, or biheterocyclic, each optionally substituted with $R^Q$, each $R^Q$ is independently a H, halo, OH, CN, $CF_3$, hydroxyl, nitro, C≡CH, $C_{2-6}$ alkenyl, $C_{2-6}$ alkynyl, $C_1$-$C_6$ alkyl (linear, branched, optionally substituted), $C_1$-$C_6$ alkoxy (linear, branched, optionally substituted), $OC_{1-3}$alkyl (optionally substituted by 1 or more —F), OH, $NH_2$, $NR^{Y1}R^{Y2}$, CN, or 2 $R^Q$ groups taken together with the atom they are attached to, form a 4-8 membered ring system containing 0-4 heteroatoms;

$Y^{L1}$ is each independently a bond, $NR^{YL1}$, O, S, $NR^{YL2}$, $CR^{YL1}R^{YL2}$, C=O, C=S, SO, $SO_2$, $C_1$-$C_6$alkyl (linear, branched, optionally substituted) and optionally one or more C atoms are replaced with O; $C_1$-$C_6$ alkoxy (linear, branched, optionally substituted);

$Q^L$ is a 3-6 membered alicyclic or aromatic ring with 0-4 heteroatoms, optionally bridged, optionally substituted with 0-6 $R^Q$, each $R^Q$ is independently H, $C_{1-6}$ alkyl (linear, branched, optionally substituted by 1 or more halo, $C_{1-6}$ alkoxyl), or 2 $R^Q$ groups taken together with the atom they are attached to, form a 3-8 membered ring system containing 0-2 heteroatoms);

$R^{YL1}$, $R^{YL2}$ are each independently H, OH, $C_{1-6}$ alkyl (linear, branched, optionally substituted by 1 or more halo, $C_{1-6}$ alkoxyl), or $R^1$, $R^2$ together with the atom they are attached to, form a 3-8 membered ring system containing 0-2 heteroatoms);

n is 0-10; and a dashed line indicates the attachment point to the PTM or ULM moieties.

In any aspect or embodiment described herein, the linker (L) is a polyethylenoxy group optionally substituted with aryl or phenyl comprising from 1 to 10 ethylene glycol units.

In any aspect or embodiment described herein, the compound comprises multiple ULMs, multiple PTMs, multiple linkers or any combinations thereof.

In any aspect or embodiment described herein, the compound is has a chemical structure selected from exemplary compounds 1-119 (i.e., a compound of Table 1 or 2), including salts, prodrugs, polymorphs, analogs, derivatives, and deuterated forms thereof.

In another aspect, the present disclosure provides a composition that comprises an effective amount of a bifunctional compound of the present disclosure, and a pharmaceutically acceptable carrier.

In any aspect or embodiment described herein, the composition further comprises at least one of additional bioactive agent or another bifunctional compound of the present disclosure.

In any aspect or embodiment described herein, the additional bioactive agent is anti-cancer agent.

In a further aspect, the present disclosure provides a composition that comprises a pharmaceutically acceptable carrier and an effective amount of at least one compound of the present disclosure for treating a disease or disorder in a subject, the method comprising administering the composition to a subject in need thereof, wherein the compound is effective in treating or ameliorating at least one symptom of the disease or disorder.

In any aspect or embodiment described herein, the disease or disorder is associated with EZH2 accumulation and aggregation.

In any aspect or embodiment described herein, the disease or disorder is cancer associated with EZH2 accumulation and aggregation.

In any aspect or embodiment described herein, the disease or disorder is cancer.

What is claimed is:

1. A compound having the chemical structure:

ULM-L-PTM, or a pharmaceutically acceptable salt thereof, wherein:
(a) the ULM is:

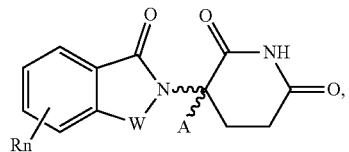

wherein:
W is $CH_2$ or C=O;
A is H;
⁓⁓⁓ represents a bond that may be stereospecific or non-stereospecific;
n is 1; and
R is a bond to the chemical linking moiety or NHR' covalently joined to the chemical linking moiety;
R' is alkyl;
(b) the L is a chemical linking moiety connecting the ULM and the PTM which comprises (1) a chemical structural unit represented by the formula:
—$(CH_2)$m-O$(CH_2)$n-O$(CH_2)$o-O$(CH_2)$p-O$(CH_2)$q-O$(CH_2)$r-O—, —NH—$(CH_2)$m-O$(CH_2)$n-O$(CH_2)$o-O$(CH_2)$p-O$(CH_2)$q-O$(CH_2)$r-O—;

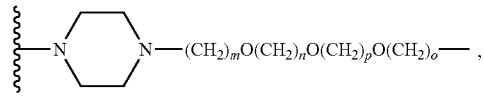

-continued

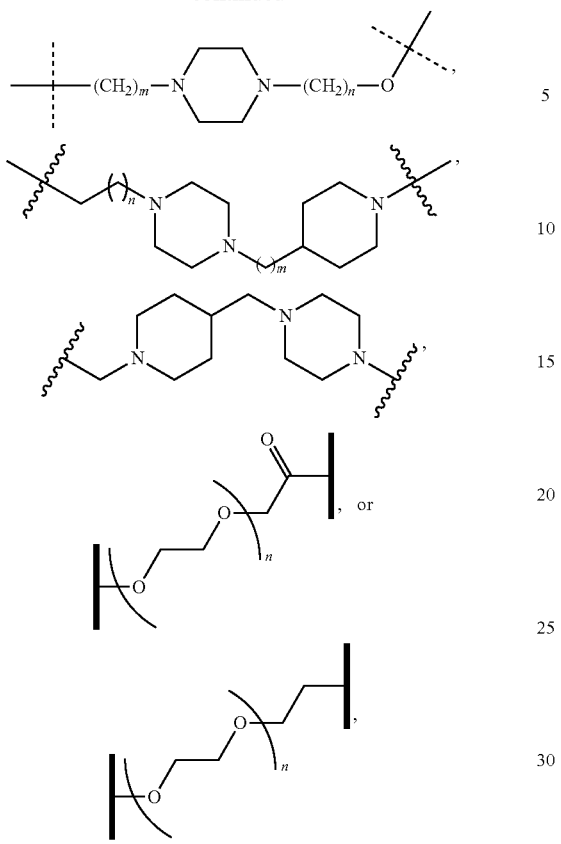

wherein:
each m, o, p, q, and r of the chemical linking moiety are independently 0, 1, 2, 3, 4, 5, 6, with the proviso that when the number is zero, there is no N—O or O—O bond;
n of the chemical linking moiety is 0, 1, 2, 3, 4, 5, 6, 7, 8, 9, or 10; or
(2) a polyethylenoxy group comprising 1, 2, 3, 4, 5, 6, 7, 8, 9, or 10 ethylene glycol units; and
(c) the PTM is PTM-I-1, PTM-IVa-1, or PTM-IVb-1:

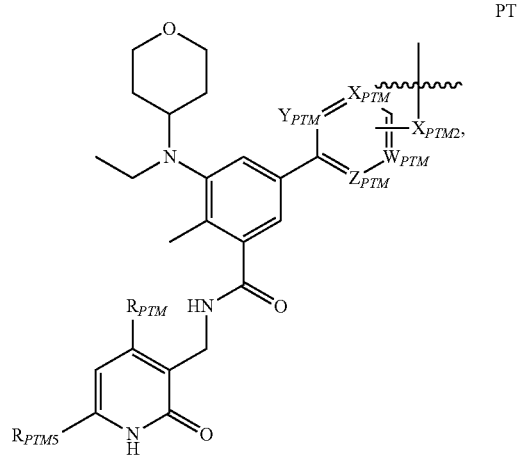

PTM-I-1

-continued

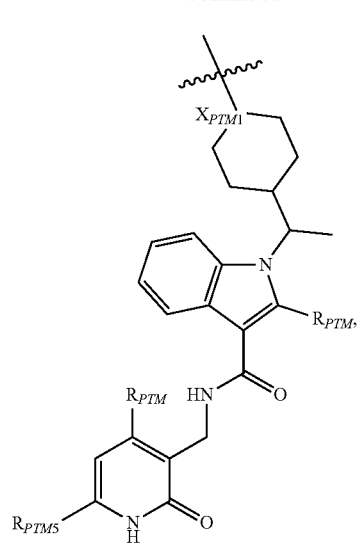

PTM-IVa-1

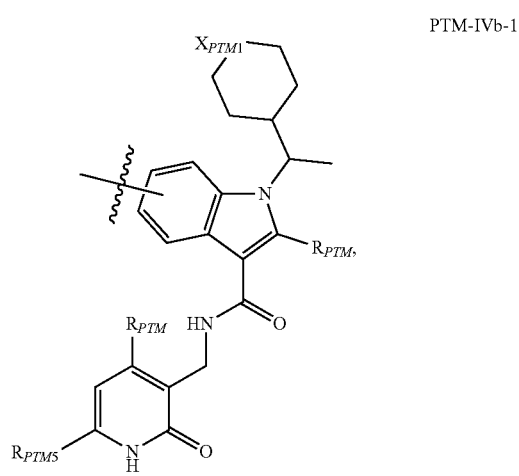

PTM-IVb-1 wherein:
$W_{PTM}$ and $X_{PTM}$ are independently C or N;
$Y_{PTM}$ and $Z_{PTM}$ are CH;
$X_{PTM1}$ is NH or O;
$X_{PTM2}$ is absent;
$R_{PTM}$ is methyl or methoxy;
$R_{PTM5}$ is methyl; and
- - - - indicates a covalent linkage to the chemical linking moiety.

2. The compound according to claim 1, wherein L is:
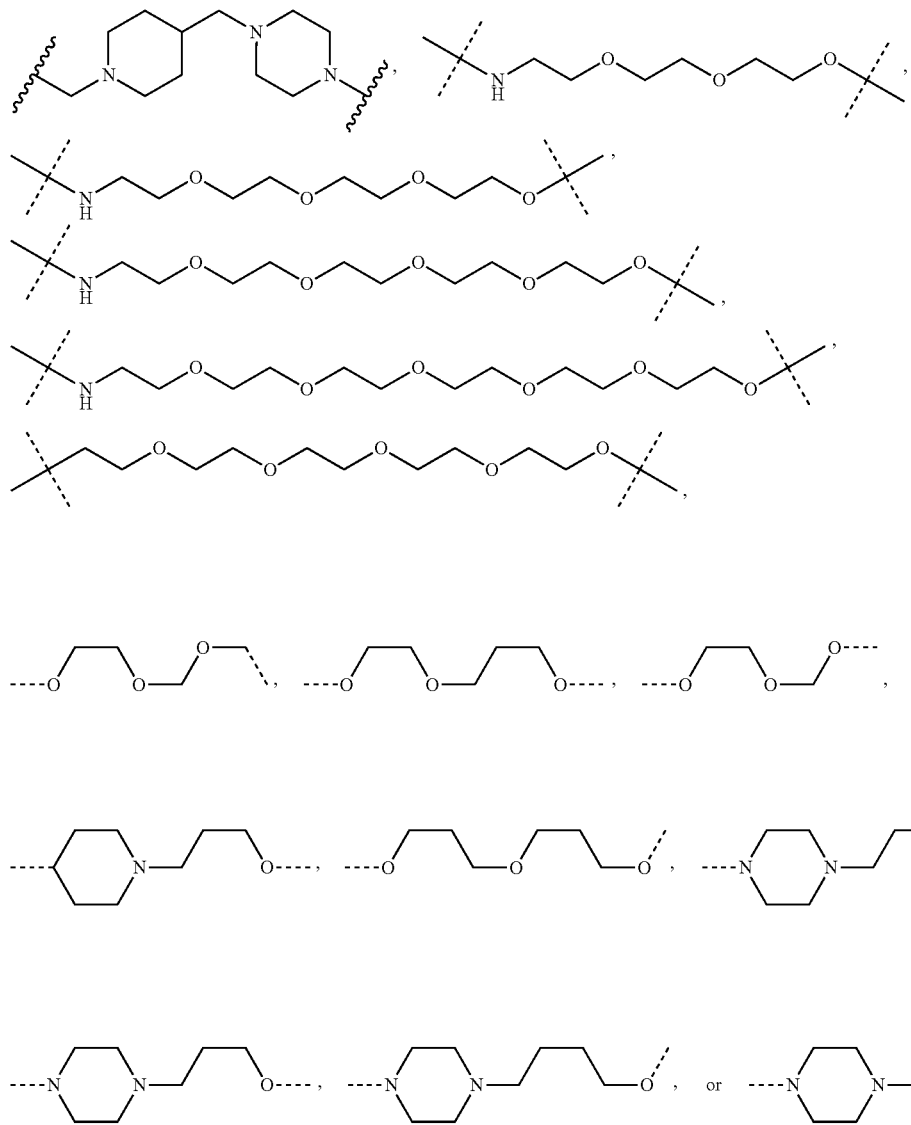
3. The compound according to claim 1, wherein the chemical linking moiety (L) is a polyethylenoxy group comprising 1, 2, 3, 4, 5, 6, 7, 8, 9, or 10 ethylene glycol units.
4. A compound, wherein the compound is:
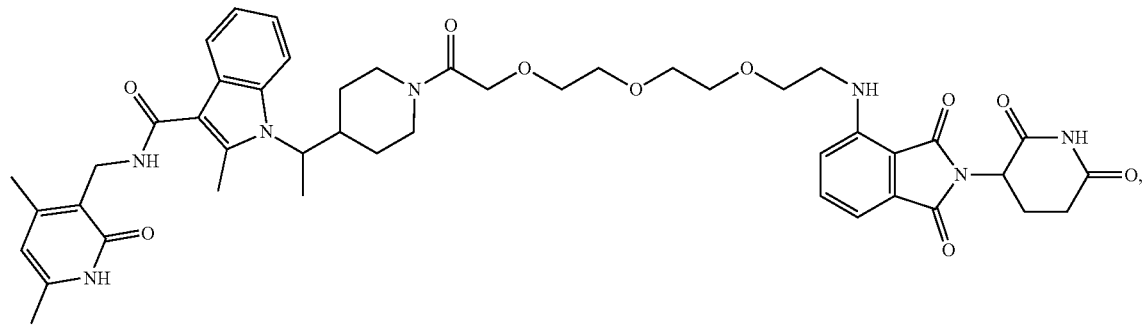

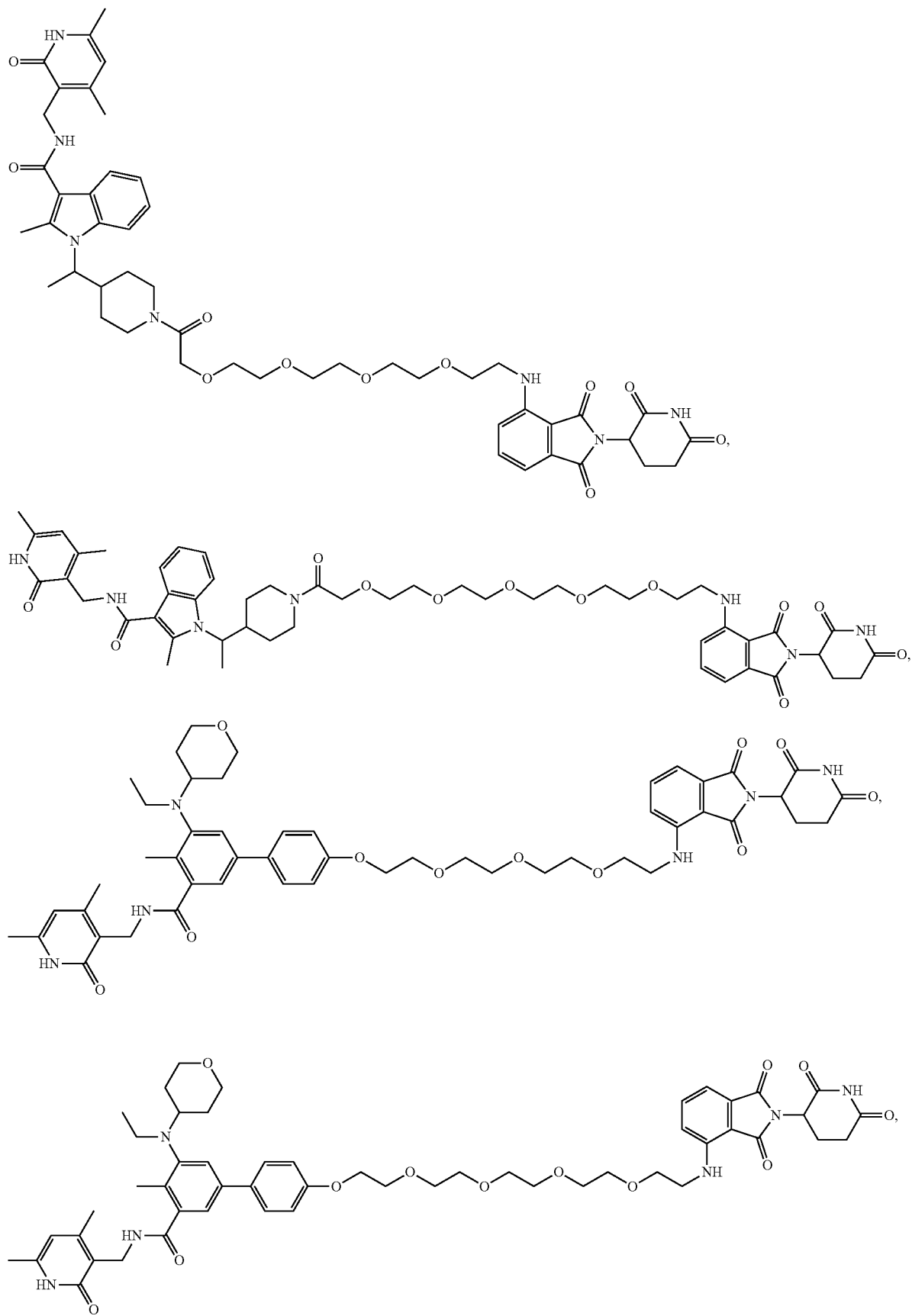

853 854
-continued
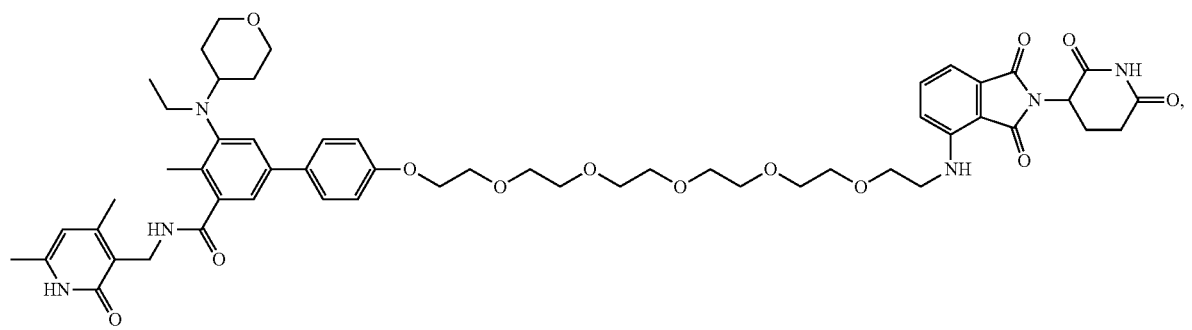
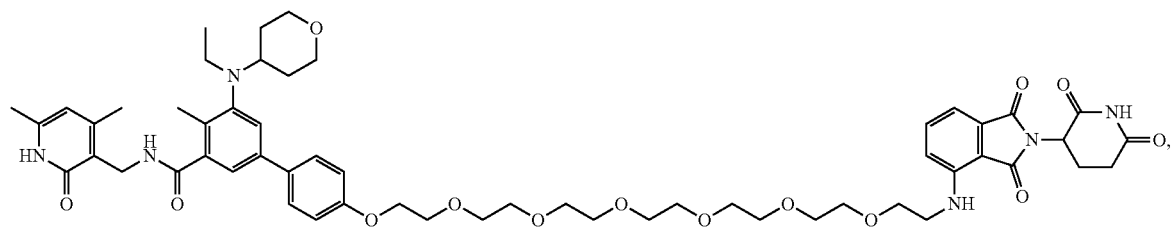
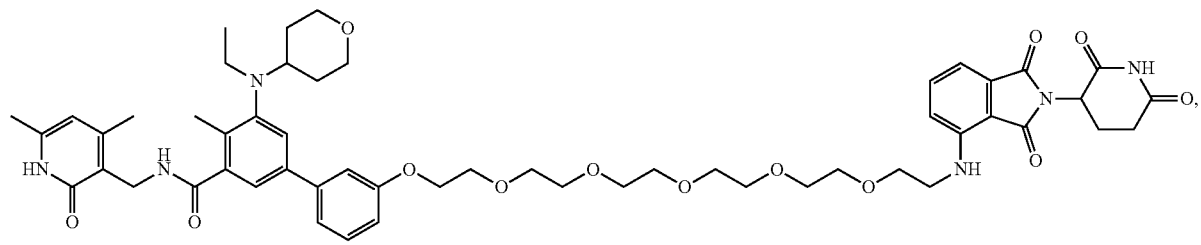
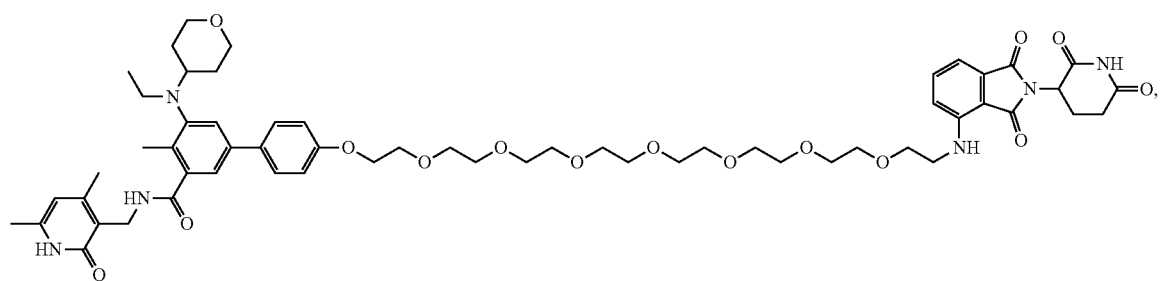
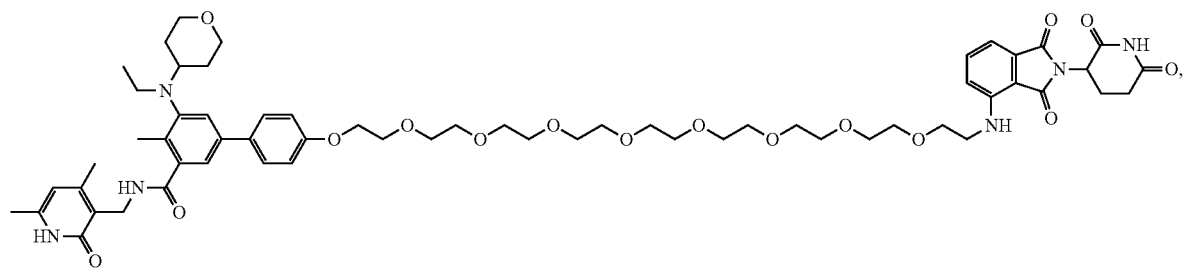

855 856
-continued
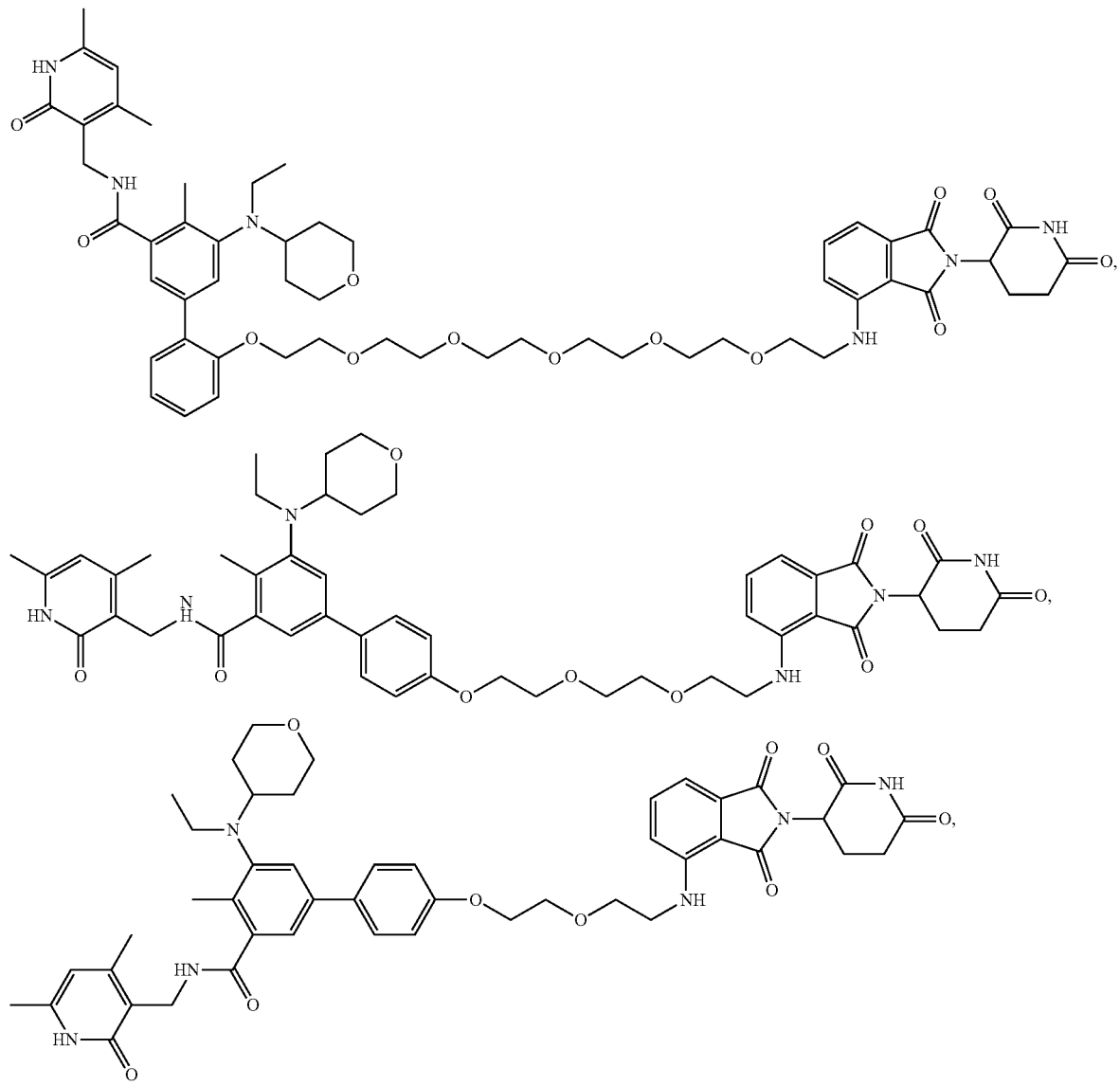
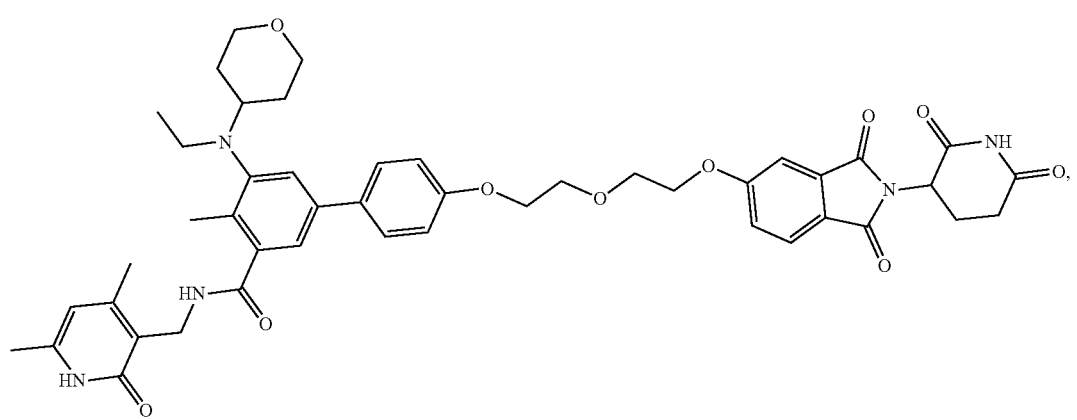

857
858
-continued
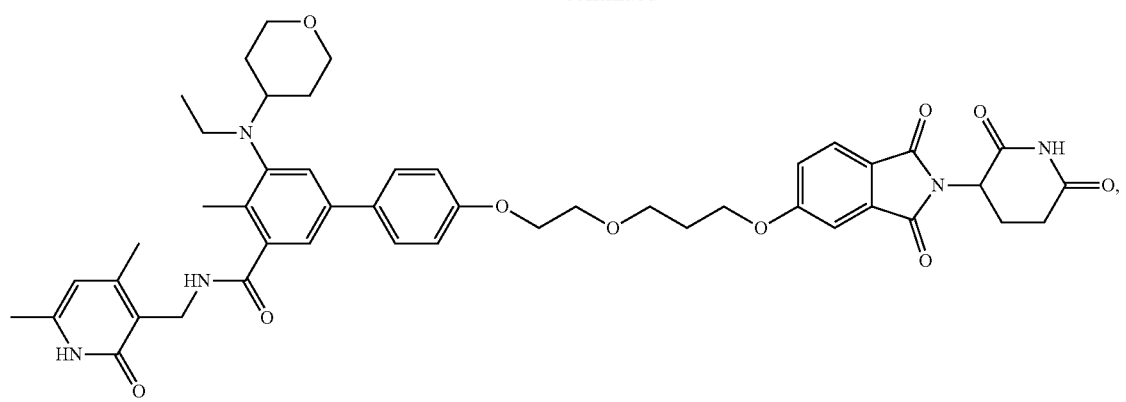
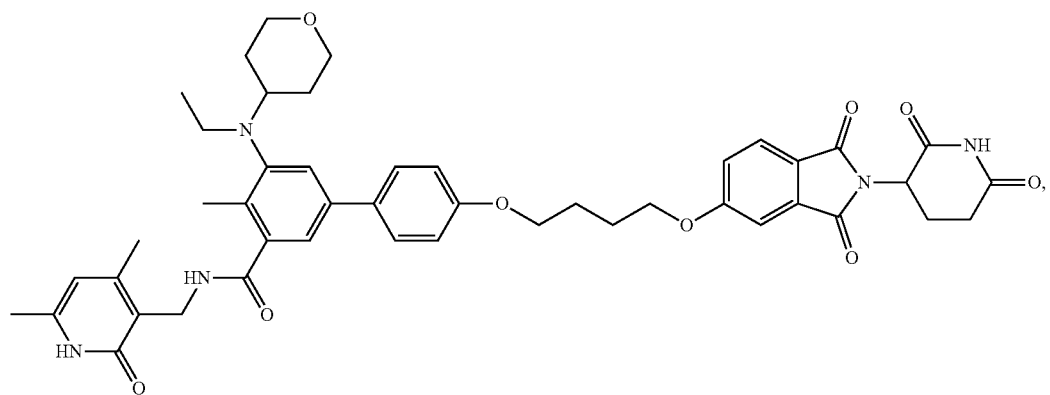
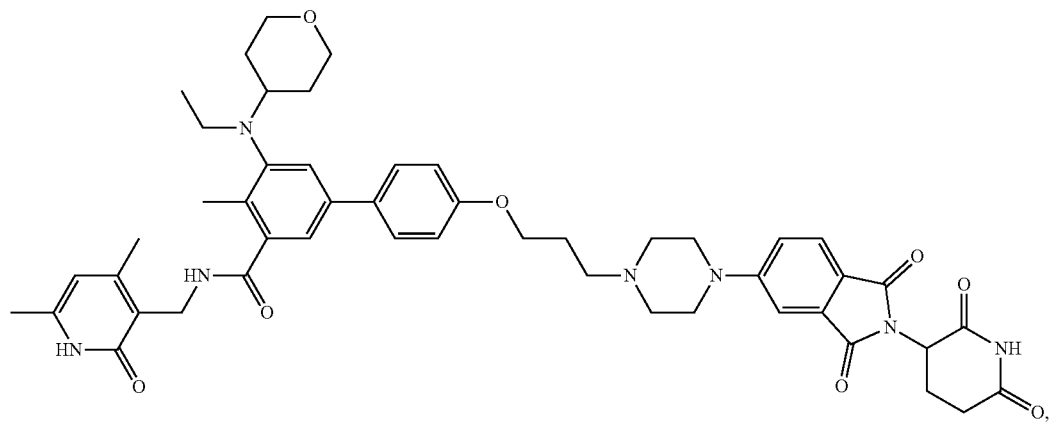
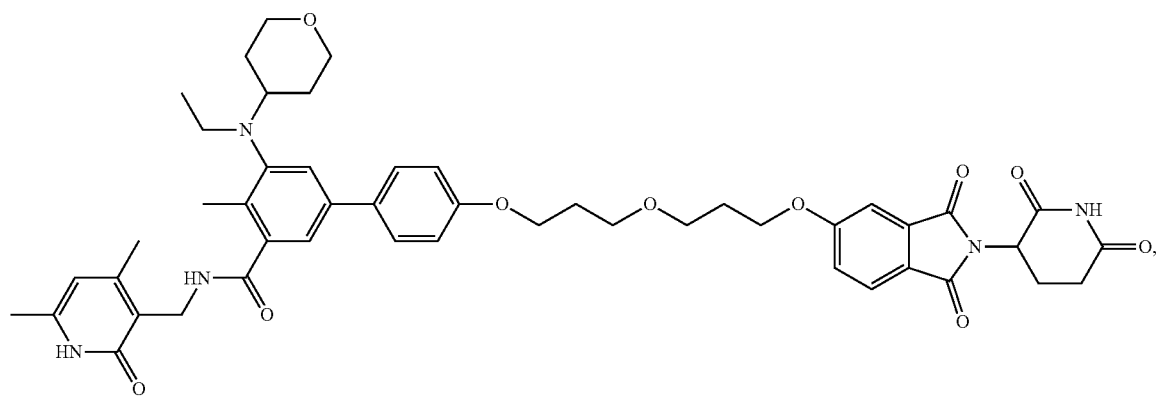

-continued
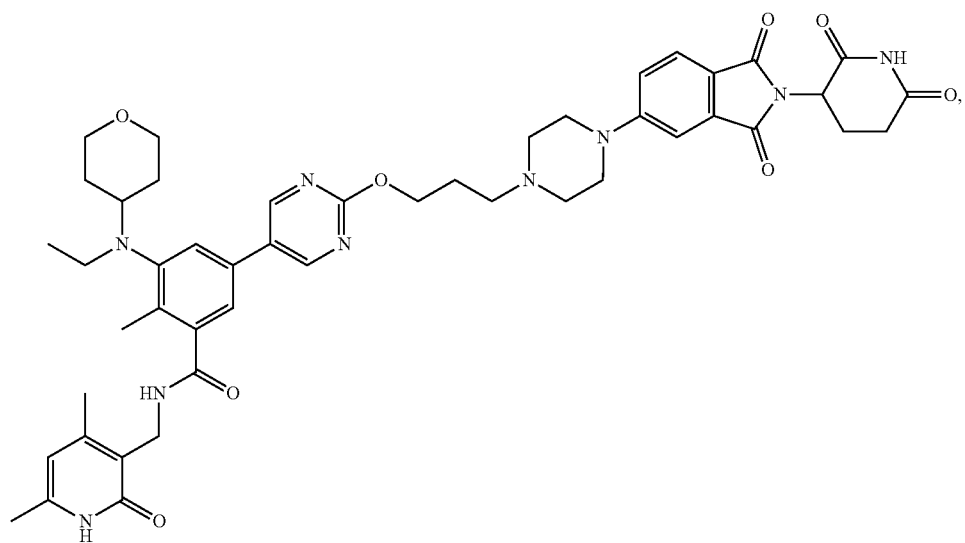
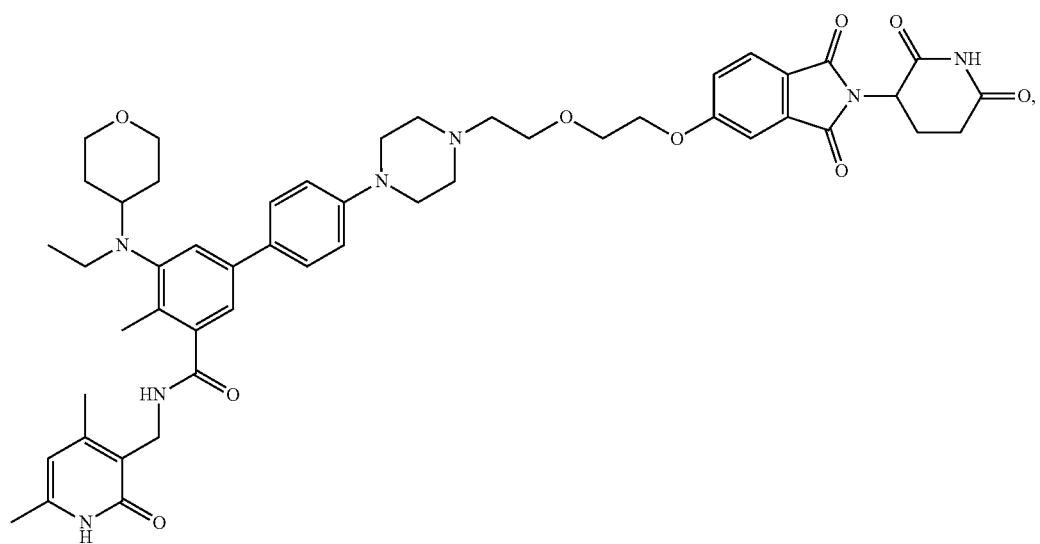
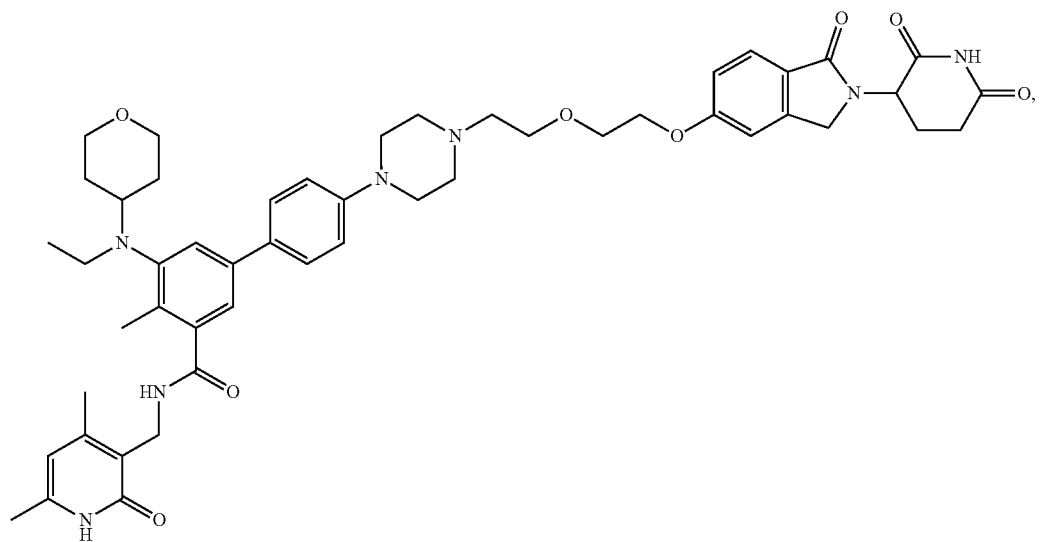

861
862
-continued
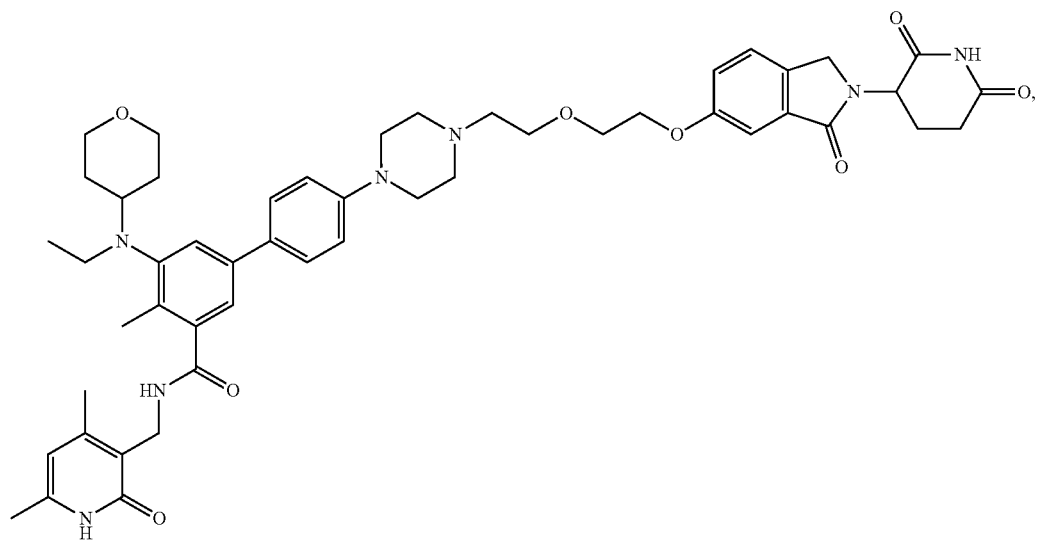
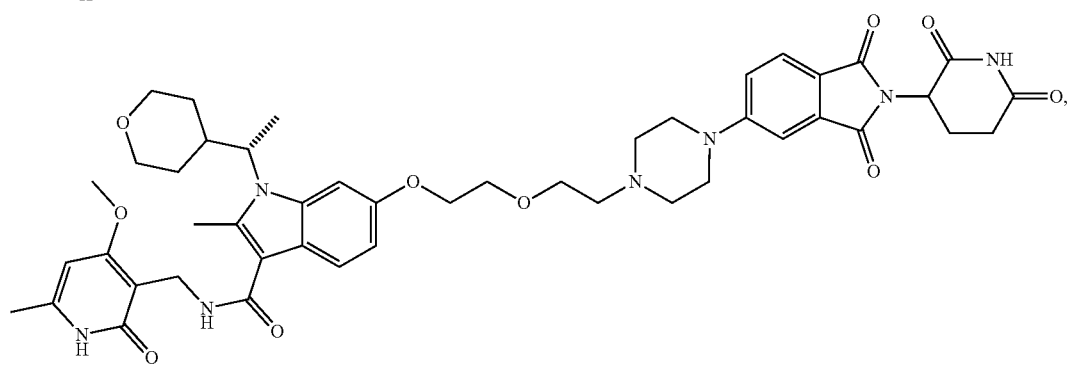
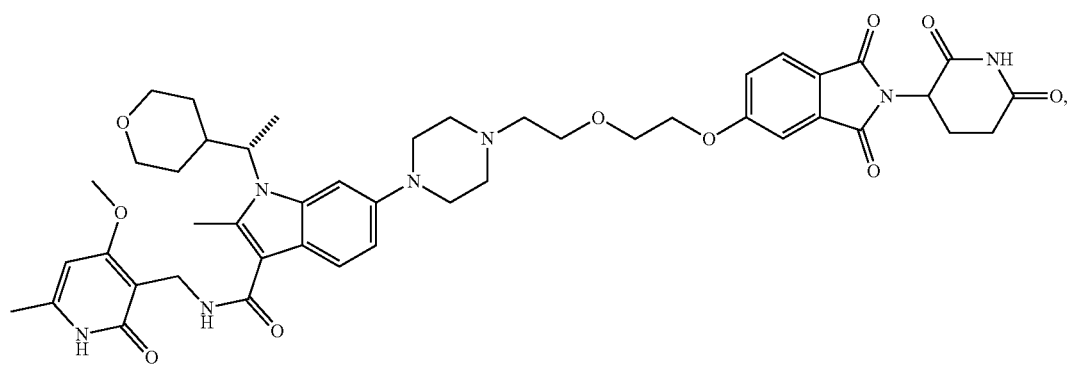
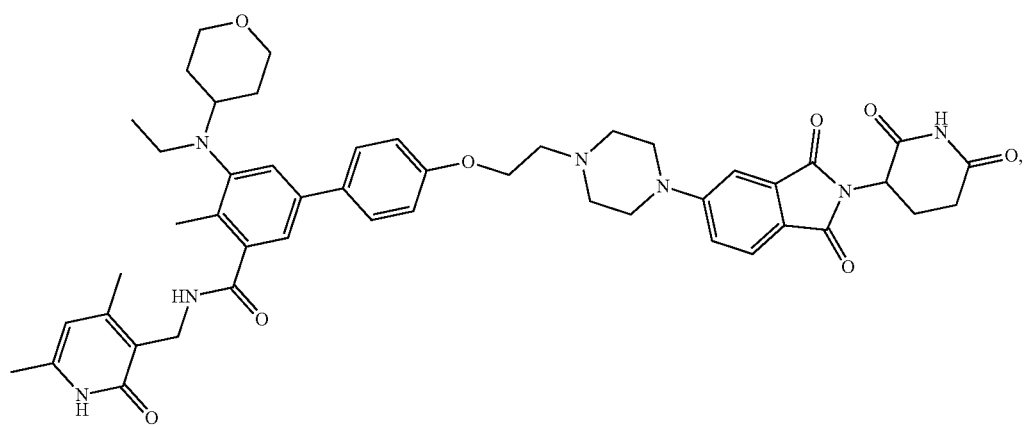

-continued

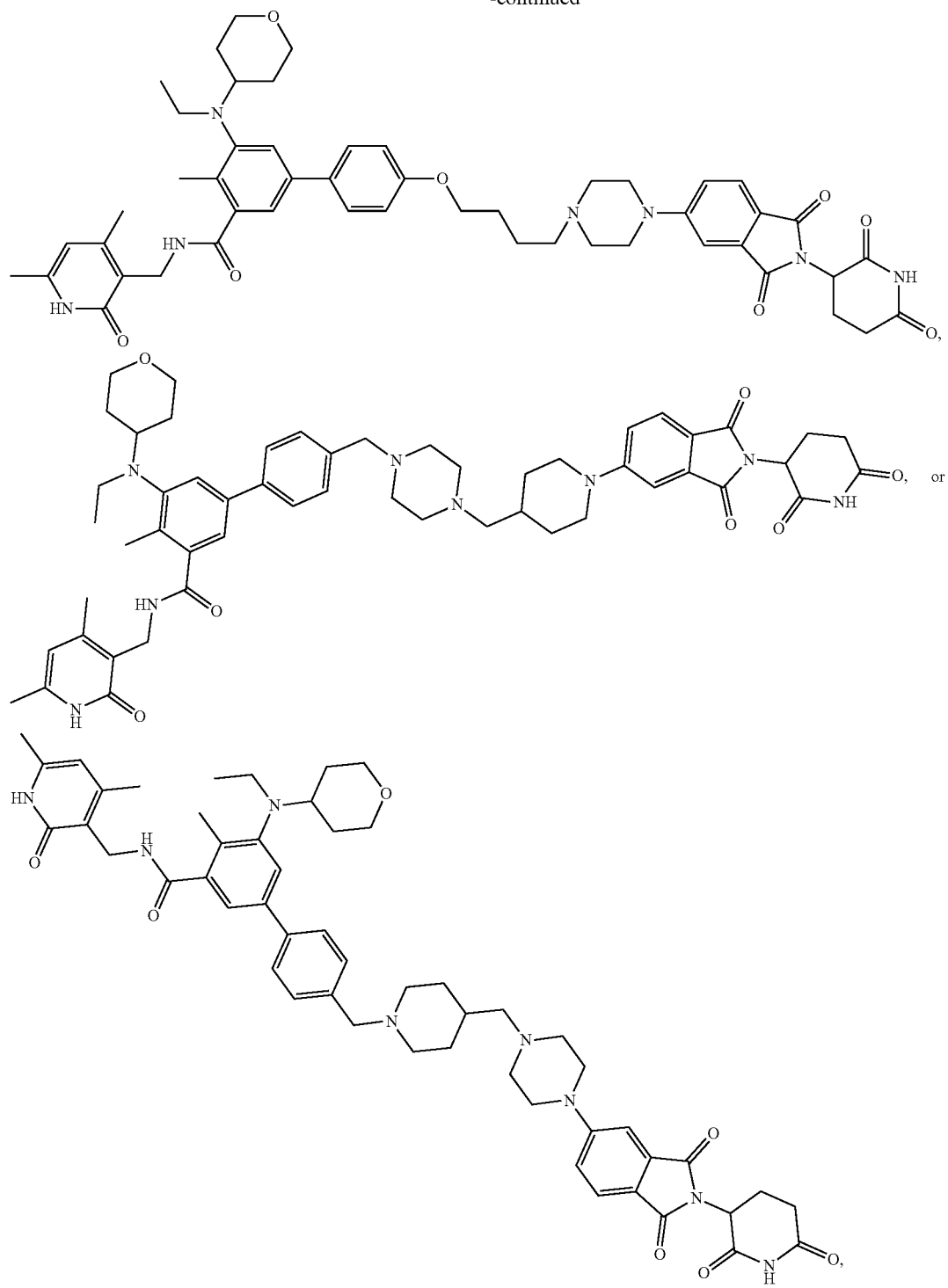

or a pharmaceutically acceptable salt thereof.

5. A pharmaceutical composition comprising a compound of claim 1, and a pharmaceutically acceptable carrier.

6. The pharmaceutical composition of claim 5, wherein the composition further comprises at least one additional bioactive agent.

7. The pharmaceutical composition of claim 6, wherein the additional bioactive agent is an anti-cancer agent.

8. A method of treating a disease or disorder, associated with EZH2 accumulation and aggregation the method comprising administering a compound of claim 1 to a subject.

9. The method of claim 8, wherein the disease or disorder is cancer.

10. The method of claim 8, wherein the disease or disorder is breast cancer, prostate cancer, bladder cancer, uterine cancer, renal cancer, melanoma, and/or lymphoma.

11. A pharmaceutical composition comprising a compound of claim 4, and a pharmaceutically acceptable carrier.

12. The pharmaceutical composition of claim 11, wherein the composition further comprises at least one additional bioactive agent.

13. The pharmaceutical composition of claim 12, wherein the additional bioactive agent is an anti-cancer agent.

14. A method of treating a disease or disorder, associated with EZH2 accumulation and aggregation the method comprising administering a compound of claim 4 to a subject.

15. The method of claim 14, wherein the disease or disorder is cancer.

16. The method of claim 14, wherein the disease or disorder is breast cancer, prostate cancer, bladder cancer, uterine cancer, renal cancer, melanoma, and/or lymphoma.

* * * * *